(12) United States Patent
Zhou et al.

(10) Patent No.: US 7,589,167 B2
(45) Date of Patent: Sep. 15, 2009

(54) ZA LOOPS OF BROMODOMAINS

(75) Inventors: Ming-Ming Zhou, Greenwich, CT (US); Aneel K. Aggarwal, Edgewater, NJ (US); Eric Verdin, San Francisco, CA (US); Melanie Ott, San Francisco, CA (US)

(73) Assignees: J. David Gladstone Institutes, Irvine, CA (US); Mt. Sinai School of Medicine, New York, NY (US)

( * ) Notice: Subject to any disclaimer, the term of this patent is extended or adjusted under 35 U.S.C. 154(b) by 0 days.

(21) Appl. No.: 09/784,553

(22) Filed: Feb. 16, 2001

(65) Prior Publication Data
US 2004/0043378 A1 Mar. 4, 2004

Related U.S. Application Data

(63) Continuation-in-part of application No. 09/510,314, filed on Feb. 22, 2000.

(51) Int. Cl.
*C07K 2/00* (2006.01)
*C07K 7/00* (2006.01)
*C07K 14/00* (2006.01)

(52) U.S. Cl. .................. 530/300; 530/333; 530/350

(58) Field of Classification Search .............. 530/300, 530/324, 325, 350; 514/2; 435/69.1
See application file for complete search history.

(56) References Cited

U.S. PATENT DOCUMENTS 5,837,840 A * 11/1998 Crabtree et al. ............ 536/23.4
5,858,686 A    1/1999 Schlessinger et al.

OTHER PUBLICATIONS

Stedman's Online Medical Dictionary, 27th Edition, definition for "peptide", www.stedman's.com.*
Zeng et al., FEBS Letters,. vol. 513 No. 1, pp. 124-128 (Feb. 2002).*
Yang et al., Nature, vol. 382 No. 6589, pp. 319-324 (Jul. 1996).*
Platt et al., Journal of Virology, vol. 73 No. 12, 9789-95 (Dec. 1999).*
Denis and Green, Genes and Development, vol. 10 No. 3, pp. 261-271 (Feb. 1996).*
Thorpe et al., Immunogenetics, vol. 44 No. 5, pp. 391-396 (1996).*
Taniguchi et al., Genomics, vol. 51 No. 1, pp. 114-123 (Jul. 1998).*
Denis et al., Cell Growth & Differentiation, vol. 11, pp. 417-424 (Aug. 2000).*
Guo et al., Journal of Cell Science, vol. 113, pp. 3085-3091 (Sep. 2000).*
Jeanmougin et al., Trends in Biochemical Sciences, vol. 22, pp. 151-153 (May 1997).*
Marcus et al., Intervirology, vol. 45, pp. 260-266 (Jul.-Dec. 2002).*
Molla et al., Current Opinion in Biotechnology, vol. 14, pp. 634-640 (Dec. 2003).*
Archer and Hodin, *Curr. Opin. Genet. Biol.*, 9:171-174 (1999).
Clore et al., *Meth. Enzymol.*, 239:349-363 (1994).
Dhalluin et al., *Nature*, 399:491-496 (1999).
Fu et al., *J. Biol. Chem.*, 274(49):34527-34530 (1999).
Garber et al., Mol. Cell. Biol., 20(18):6958-6969 (2000).
Grunstein et al., *Nature*, 389:349-352 (1997).
Jeanmougin et al., *Trends in Biochemical Sciences*, 22:151-153 (1997).
Kiernan et al., *EMBO Journal*, 18:6106-6118 (1999).
Sattler et al., *Prog. In Nuclear Magnetic Resonance Spec.*, 4:93-158 (1999).
Shuker et al., *Science*, 274:1531-1534 (1996).
Sobulo et al., *Proc. Natl. Acad. Sci. USA*, 94:8732-8737 (1997).
Struhl, *Genes Dev.* 12:599-606 (1998).
Yamazaki et al., *J. Am. Chem. Soc.*, 116:11655-11666 (1994).
Zhou et al., *J. Biol. Chem.*, 270:31119-31123 (1995).

* cited by examiner

*Primary Examiner*—Zachariah Lucas
(74) *Attorney, Agent, or Firm*—Klauber & Jackson, LLC

(57) ABSTRACT

The present invention provides the structural determination of a bromodomain determined by NMR spectroscopy. The present invention also provides binding partners for the bromodomain. The present invention further provides the structural determination of the Tat-P/CAF binding complex determined by NMR spectroscopy. In addition, the present invention provides methodology for related drug discovery using high throughput drug screening or structure based rational drug design using the three-dimensional data.

2 Claims, 17 Drawing Sheets

Three-Dimensional Structure of the P/CAF Bromodomain

Nε-acetyl-lysine

Nω-acetyl-histamine

Nα-acetyl-histidine

HIV-1 Tat Peptide: SYGR-AcK-KRRQRC

A

B

1. Control
2. Tat_K50 (aa 46-55)          SYGR-K-KRRQRC
3. Tat_AcK50                    SYGR-AcK-KRRQRC
4. Tat_AcK50_Y47A               SAGR-AcK-KRRQRC
5. Tat_AcK50_R49A               SYGA-AcK-KRRQRC
6. Tat_AcK50_K51A               SYGR-AcK-ARRQRC
7. Tat_AcK50_R52A               SYGR-AcK-KARQRC
8. Tat_AcK50_R53A               SYGR-AcK-KRAQRC
9. Tat_AcK50_Q54A               SYGR-AcK-KRRARC
10. Tat_AcK51                   SYGRK-AcK-RRQRC
11. Tat_AcK28 (aa 23-33)        TNCYCK-AcK-CCFH
12. Histone H4_AcK16            SGRGKGGKGLGKGGA-AcK-RHRK Where:

$R_1$, $R_2$, $R_3$ = H, $CH_3$, X (halogen: F, Cl, Br, I), OH, SH, or $NH_3^+$ $R_4$ = alkyl, aryl

SEQUENCE LISTING

<160> NUMBER OF SEQ ID NOS: 63

<210> SEQ ID NO 1
<211> LENGTH: 3014
<212> TYPE: DNA
<213> ORGANISM: Homo sapiens

<400> SEQUENCE: 1

```
ggggccgcgt cgacgcggaa aagaggccgt gggggggcctc ccagcgctgg cagacaccgt     60
gaggctggca gccgccggca cgcacaccta gtccgcagtc ccgaggaaca tgtccgcagc    120
cagggcgcgg agcagagtcc cgggcaggag aaccaaggga gggcgtgtgc tgtggcggcg    180
gcggcagcgg cagcggagcc gctagtcccc tccctcctgg gggagcagct gccgccgctg    240
ccgccgccgc caccaccatc agcgcgcggg gcccggccag agcgagccgg gcgagcggcg    300
cgctaggggg agggcggggg cggggagggg ggtgggcgaa ggggggcggga gggcgtgggg    360 ggagggtctc gctctcccga ctaccagagc ccgagggaga ccctggcggc ggcggcggcg    420
cctgacactc ggcgcctcct gccgtgctcc ggggcggcat gtccgaggct ggcggggccg    480
ggccgggcgg ctgcggggca ggagccgggg caggggccgg gccggggcg ctgcccccgc    540 agcctgcggc gcttccgccc gcgccccgc agggctcccc ctgcgccgct gccgccgggg    600
gctcgggcgc ctgcggtccg gcgacggcag tggctgcagc gggcacggcc gaaggaccgg    660
gaggcggtgg ctcggcccga atcgccgtga agaaagcgca actacgctcc gctccgcggg    720
ccaagaaact ggagaaactc ggagtgtact ccgcctgcaa ggccgaggag tcttgtaaat    780
gtaatggctg gaaaaacccct aacccctcac ccactccccc cagagccgac ctgcagcaaa    840
taattgtcag tctaacagaa tcctgtcgga gttgtagcca tgccctagct gctcatgttt    900
cccacctgga gaatgtgtca gaggaagaaa tgaacagact cctgggaata gtattggatg    960
tggaatatct ctttacctgt gtccacaagg aagaagatgc agataccaaa caagtttatt   1020
tctatctatt taagctcttg agaaagtcta ttttacaaag aggaaaacct gtggttgaag   1080
gctcttggga aaagaaaccc ccatttgaaa aacctagcat tgaacagggt gtgaataact   1140
ttgtgcagta caaatttagt cacctgccag caaaagaaag gcaaacaata gttgagttgg   1200
```

-continued

```
caaaaatgtt cctaaaccgc atcaactatt ggcatctgga ggcaccatct caacgaagac    1260
tgcgatctcc caatgatgat atttctggat acaaagagaa ctacacaagg tggctgtgtt    1320
actgcaacgt gccacagttc tgcgacagtc tacctcggta cgaaaccaca caggtgtttg    1380
ggagaacatt gcttcgctcg gtcttcactg ttatgaggcg acaactcctg aacaagcaa     1440 gacaggaaaa agataaactg cctcttgaaa acgaactct aatcctcact catttcccaa     1500
aatttctgtc catgctagaa gaagaagtat atagtcaaaa ctctcccatc tgggatcagg    1560
attttctctc agcctcttcc agaaccagcc agctaggcat ccaaacagtt atcaatccac    1620
ctcctgtggc tgggacaatt tcatacaatt caacctcatc ttcccttgag cagccaaacg    1680
cagggagcag cagtcctgcc tgcaaagcct cttctggact tgaggcaaac ccaggagaaa    1740
agaggaaaat gactgattct catgttctgg aggaggccaa gaaacccccga gttatggggg   1800 atattccgat ggaattaatc aacgaggtta tgtctaccat cacggaccct gcagcaatgc    1860
ttggaccaga gaccaatttt ctgtcagcac actcggccag ggatgaggcg gcaaggttgg    1920
aagagcgcag gggtgtaatt gaatttcacg tggttggcaa ttccctcaac cagaaaccaa    1980
acaagaagat cctgatgtgg ctggttggcc tacagaacgt tttctcccac cagctgcccc    2040
gaatgccaaa agaatacatc acacggctcg tctttgaccc gaaacacaaa acccttgctt    2100
taattaaaga tggccgtgtt attggtggta tctgtttccg tatgttccca tctcaaggat    2160
tcacagagat tgtcttctgt gctgtaacct caaatgagca agtcaagggc tatggaacac    2220
acctgatgaa tcatttgaaa gaatatcaca taaagcatga catcctgaac ttcctcacat    2280
atgcagatga atatgcaatt ggatacttta agaaacaggg tttctccaaa gaaattaaaa    2340
tacctaaaac caaatatgtt ggctatatca aggattatga aggagccact ttaatgggat    2400
gtgagctaaa tccacggatc ccgtacacag aattttctgt catcattaaa aagcagaagg    2460
agataattaa aaaactgatt gaagaaaac aggcacaaat tcgaaaagtt taccctggac     2520
tttcatgttt taaagatgga gttcgacaga ttcctataga aagcattcct ggaattagag    2580
agacaggctg gaaccgagt ggaaaagaga aagtaaaga gcccagagac cctgaccagc      2640
tttacagcac gctcaagagc atcctccagc aggtgaagag ccatcaaagc gcttggccct    2700
tcatggaacc tgtgaagaga acagaagctc aggatatta tgaagttata aggttcccca    2760
tggatctgaa aaccatgagt gaacgcctca gaataggta ctacgtgtct aagaaattat     2820
tcatggcaga cttacagcga gtctttacca attgcaaaga gtacaacgcc gctgagagtg    2880
aatactacaa atgtgccaat atcctggaga aattcttctt cagtaaaatt aaggaagctg    2940
gattaattga caagtgattt ttttccccc tctgcttctt agaaactcac caagcagtgt      3000
gcctaaagca aggt                                                        3014
```

<210> SEQ ID NO 2
<211> LENGTH: 832
<212> TYPE: PRT
<213> ORGANISM: Homo sapiens

<400> SEQUENCE: 2

```
Met Ser Glu Ala Gly Gly Ala Gly Pro Gly Gly Cys Gly Ala Gly Ala
1               5                   10                  15

Gly Ala Gly Ala Gly Pro Gly Ala Leu Pro Pro Gln Pro Ala Ala Leu
            20                  25                  30

Pro Pro Ala Pro Pro Gln Gly Ser Pro Cys Ala Ala Ala Ala Gly Gly
        35                  40                  45
```

```
Ser Gly Ala Cys Gly Pro Ala Thr Ala Val Ala Ala Gly Thr Ala
    50                  55                  60

Glu Gly Pro Gly Gly Gly Ser Ala Arg Ile Ala Val Lys Lys Ala
65                  70                  75                  80

Gln Leu Arg Ser Ala Pro Arg Ala Lys Lys Leu Glu Lys Leu Gly Val
                85                  90                  95

Tyr Ser Ala Cys Lys Ala Glu Glu Ser Cys Lys Cys Asn Gly Trp Lys
                100                 105                 110

Asn Pro Asn Pro Ser Pro Thr Pro Pro Arg Ala Asp Leu Gln Gln Ile
                115                 120                 125

Ile Val Ser Leu Thr Glu Ser Cys Arg Ser Cys Ser His Ala Leu Ala
                130                 135                 140

Ala His Val Ser His Leu Glu Asn Val Ser Glu Glu Met Asn Arg
145                 150                 155                 160

Leu Leu Gly Ile Val Leu Asp Val Glu Tyr Leu Phe Thr Cys Val His
                165                 170                 175

Lys Glu Glu Asp Ala Asp Thr Lys Gln Val Tyr Phe Tyr Leu Phe Lys
                180                 185                 190

Leu Leu Arg Lys Ser Ile Leu Gln Arg Gly Lys Pro Val Val Glu Gly
            195                 200                 205

Ser Leu Glu Lys Lys Pro Pro Phe Glu Lys Pro Ser Ile Glu Gln Gly
    210                 215                 220

Val Asn Asn Phe Val Gln Tyr Lys Phe Ser His Leu Pro Ala Lys Glu
225                 230                 235                 240

Arg Gln Thr Ile Val Glu Leu Ala Lys Met Phe Leu Asn Arg Ile Asn
                245                 250                 255

Tyr Trp His Leu Glu Ala Pro Ser Gln Arg Arg Leu Arg Ser Pro Asn
                260                 265                 270

Asp Asp Ile Ser Gly Tyr Lys Glu Asn Tyr Thr Arg Trp Leu Cys Tyr
            275                 280                 285

Cys Asn Val Pro Gln Phe Cys Asp Ser Leu Pro Arg Tyr Glu Thr Thr
    290                 295                 300

Gln Val Phe Gly Arg Thr Leu Leu Arg Ser Val Phe Thr Val Met Arg
305                 310                 315                 320

Arg Gln Leu Leu Glu Gln Ala Arg Gln Glu Lys Asp Lys Leu Pro Leu
                325                 330                 335

Glu Lys Arg Thr Leu Ile Leu Thr His Phe Pro Lys Phe Leu Ser Met
                340                 345                 350

Leu Glu Glu Glu Val Tyr Ser Gln Asn Ser Pro Ile Trp Asp Gln Asp
                355                 360                 365

Phe Leu Ser Ala Ser Arg Thr Ser Gln Leu Gly Ile Gln Thr Val
    370                 375                 380

Ile Asn Pro Pro Val Ala Gly Thr Ile Ser Tyr Asn Ser Thr Ser
385                 390                 395                 400

Ser Ser Leu Glu Gln Pro Asn Ala Gly Ser Ser Pro Ala Cys Lys
                405                 410                 415

Ala Ser Ser Gly Leu Glu Ala Asn Pro Gly Glu Lys Arg Lys Met Thr
                420                 425                 430

Asp Ser His Val Leu Glu Glu Ala Lys Lys Pro Arg Val Met Gly Asp
            435                 440                 445

Ile Pro Met Glu Leu Ile Asn Glu Val Met Ser Thr Ile Thr Asp Pro
    450                 455                 460
```

```
Ala Ala Met Leu Gly Pro Glu Thr Asn Phe Leu Ser Ala His Ser Ala
465                 470                 475                 480

Arg Asp Glu Ala Ala Arg Leu Glu Glu Arg Gly Val Ile Glu Phe
            485                 490                 495

His Val Val Gly Asn Ser Leu Asn Gln Lys Pro Asn Lys Lys Ile Leu
            500                 505                 510

Met Trp Leu Val Gly Leu Gln Asn Val Phe Ser His Gln Leu Pro Arg
        515                 520                 525

Met Pro Lys Glu Tyr Ile Thr Arg Leu Val Phe Asp Pro Lys His Lys
        530                 535                 540

Thr Leu Ala Leu Ile Lys Asp Gly Arg Val Ile Gly Gly Ile Cys Phe
545                 550                 555                 560

Arg Met Phe Pro Ser Gln Gly Phe Thr Glu Ile Val Phe Cys Ala Val
                565                 570                 575

Thr Ser Asn Glu Gln Val Lys Gly Tyr Gly Thr His Leu Met Asn His
            580                 585                 590

Leu Lys Glu Tyr His Ile Lys His Asp Ile Leu Asn Phe Leu Thr Tyr
        595                 600                 605

Ala Asp Glu Tyr Ala Ile Gly Tyr Phe Lys Lys Gln Gly Phe Ser Lys
        610                 615                 620

Glu Ile Lys Ile Pro Lys Thr Lys Tyr Val Gly Tyr Ile Lys Asp Tyr
625                 630                 635                 640

Glu Gly Ala Thr Leu Met Gly Cys Glu Leu Asn Pro Arg Ile Pro Tyr
            645                 650                 655

Thr Glu Phe Ser Val Ile Ile Lys Lys Gln Lys Glu Ile Ile Lys Lys
                660                 665                 670

Leu Ile Glu Arg Lys Gln Ala Gln Ile Arg Lys Val Tyr Pro Gly Leu
        675                 680                 685

Ser Cys Phe Lys Asp Gly Val Arg Gln Ile Pro Ile Glu Ser Ile Pro
        690                 695                 700

Gly Ile Arg Glu Thr Gly Trp Lys Pro Ser Gly Lys Glu Lys Ser Lys
705                 710                 715                 720

Glu Pro Arg Asp Pro Asp Gln Leu Tyr Ser Thr Leu Lys Ser Ile Leu
                725                 730                 735

Gln Gln Val Lys Ser His Gln Ser Ala Trp Pro Phe Met Glu Pro Val
            740                 745                 750

Lys Arg Thr Glu Ala Pro Gly Tyr Tyr Glu Val Ile Arg Phe Pro Met
        755                 760                 765

Asp Leu Lys Thr Met Ser Glu Arg Leu Lys Asn Arg Tyr Tyr Val Ser
        770                 775                 780

Lys Lys Leu Phe Met Ala Asp Leu Gln Arg Val Phe Thr Asn Cys Lys
785                 790                 795                 800

Glu Tyr Asn Ala Ala Glu Ser Glu Tyr Tyr Lys Cys Ala Asn Ile Leu
                805                 810                 815

Glu Lys Phe Phe Phe Ser Lys Ile Lys Glu Ala Gly Leu Ile Asp Lys
            820                 825                 830

<210> SEQ ID NO 3
<211> LENGTH: 25
<212> TYPE: PRT
<213> ORGANISM: Artificial Sequence
<220> FEATURE:
<223> OTHER INFORMATION: synthetic bromodomain peptide
<220> FEATURE:
<221> NAME/KEY: MOD_RES
<222> LOCATION: (2)..(4)
```

```
<223> OTHER INFORMATION: Any amino acid; this range may encompass 2-3
      residues
<220> FEATURE:
<221> NAME/KEY: MOD_RES
<222> LOCATION: (6)..(13)
<223> OTHER INFORMATION: Any amino acid; this range may encompass 5-8
      residues
<220> FEATURE:
<221> NAME/KEY: MOD_RES
<222> LOCATION: (14)
<223> OTHER INFORMATION: Pro, Lys or His
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (17)
<223> OTHER INFORMATION: Pro, Lys or His
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)
<223> OTHER INFORMATION: Met, Ile or Val

<400> SEQUENCE: 3

Phe Xaa Xaa Xaa Pro Xaa Xaa Xaa Xaa Xaa Xaa Xaa Xaa Xaa Tyr
1               5                   10                  15

Xaa Xaa Xaa Xaa Xaa Xaa Pro Xaa Asp
            20                  25

<210> SEQ ID NO 4
<211> LENGTH: 12
<212> TYPE: PRT
<213> ORGANISM: Artificial Sequence
<220> FEATURE:
<223> OTHER INFORMATION: synthetic bromodomain peptide
<220> FEATURE:
<221> NAME/KEY: MOD_RES
<222> LOCATION: (6)..(6)
<223> OTHER INFORMATION: acetyl lysine

<400> SEQUENCE: 4

Ile Ser Tyr Gly Arg Xaa Lys Arg Arg Gln Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic bromodomain peptide
<220> FEATURE:
<221> NAME/KEY: MOD_RES
<222> LOCATION: (8)..(8)
<223> OTHER INFORMATION: acetyl lysine

<400> SEQUENCE: 5

Ala Arg Lys Ser Thr Gly Gly Xaa Ala Pro Arg Lys Gln Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic bromodomain peptide
<220> FEATURE:
<221> NAME/KEY: MOD_RES
```

```
<222> LOCATION: (8)..(8)
<223> OTHER INFORMATION: acetyl lysine

<400> SEQUENCE: 6

Gln Ser Thr Ser Arg His Lys Xaa Leu Met Phe Lys Thr Glu
1               5                   10

<210> SEQ ID NO 7
<211> LENGTH: 110
<212> TYPE: PRT
<213> ORGANISM: Homo sapiens
<220> FEATURE:
<223> OTHER INFORMATION: bromodomain peptide

<400> SEQUENCE: 7

Ser Lys Glu Pro Arg Asp Pro Asp Gln Leu Tyr Ser Thr Leu Lys Ser
1               5                   10                  15

Ile Leu Gln Gln Val Lys Ser His Gln Ser Ala Trp Pro Phe Met Glu
                20                  25                  30

Pro Val Lys Arg Thr Glu Ala Pro Gly Tyr Tyr Glu Val Ile Arg Ser
            35                  40                  45

Pro Met Asp Leu Lys Thr Met Ser Glu Arg Leu Lys Asn Arg Tyr Tyr
        50                  55                  60

Val Ser Lys Lys Leu Phe Met Ala Asp Leu Gln Arg Val Phe Thr Asn
65                  70                  75                  80

Cys Lys Glu Tyr Asn Ala Pro Glu Ser Glu Tyr Tyr Lys Cys Ala Asn
                85                  90                  95

Ile Leu Glu Lys Phe Phe Phe Ser Lys Ile Lys Glu Ala Gly
            100                 105                 110

<210> SEQ ID NO 8
<211> LENGTH: 110
<212> TYPE: PRT
<213> ORGANISM: Homo sapiens

<400> SEQUENCE: 8

Gly Lys Glu Leu Lys Asp Pro Asp Gln Leu Tyr Thr Thr Leu Lys Asn
1               5                   10                  15

Leu Leu Ala Gln Ile Lys Ser His Pro Ser Ala Trp Pro Phe Met Glu
                20                  25                  30

Pro Val Lys Lys Ser Glu Ala Pro Asp Tyr Tyr Glu Val Ile Arg Phe
            35                  40                  45

Pro Ile Asp Leu Lys Thr Met Thr Glu Arg Leu Arg Ser Arg Tyr Tyr
        50                  55                  60

Val Thr Arg Lys Leu Phe Val Ala Asp Leu Gln Arg Val Ile Ala Asn
65                  70                  75                  80

Cys Arg Glu Tyr Asn Pro Pro Asp Ser Glu Tyr Cys Arg Cys Ala Ser
                85                  90                  95

Ala Leu Glu Lys Phe Phe Tyr Phe Lys Leu Lys Glu Gly Gly
            100                 105                 110

<210> SEQ ID NO 9
<211> LENGTH: 109
<212> TYPE: PRT
<213> ORGANISM: Tetrahymena thermophila

<400> SEQUENCE: 9

Leu Lys Lys Ser Lys Glu Arg Ser Phe Asn Leu Gln Cys Ala Asn Val
1               5                   10                  15
```

-continued

```
Ile Glu Asn Met Lys Arg His Lys Gln Ser Trp Pro Phe Leu Asp Pro
            20                  25                  30

Val Asn Lys Asp Asp Val Pro Asp Tyr Tyr Asp Val Ile Thr Asp Pro
        35                  40                  45

Ile Asp Ile Lys Ala Ile Glu Lys Lys Leu Gln Asn Asn Gln Tyr Val
50                  55                  60

Asp Lys Asp Gln Phe Ile Lys Asp Val Lys Arg Ile Phe Thr Asn Ala
65                  70                  75                  80

Lys Ile Tyr Asn Gln Pro Asp Thr Ile Tyr Tyr Lys Ala Ala Lys Glu
                85                  90                  95

Leu Glu Asp Phe Val Glu Pro Tyr Leu Thr Lys Leu Lys
            100                 105
```

<210> SEQ ID NO 10
<211> LENGTH: 109
<212> TYPE: PRT
<213> ORGANISM: Saccharomyces cerevisiae

<400> SEQUENCE: 10

```
Ala Gln Arg Pro Lys Arg Gly Pro His Asp Ala Ala Ile Gln Asn Ile
1               5                   10                  15

Leu Thr Glu Leu Gln Asn His Ala Ala Ala Trp Pro Phe Leu Gln Pro
            20                  25                  30

Val Asn Lys Glu Glu Val Pro Asp Tyr Tyr Asp Phe Ile Lys Glu Pro
        35                  40                  45

Met Asp Leu Ser Thr Met Glu Ile Lys Leu Glu Ser Asn Lys Tyr Gln
50                  55                  60

Lys Met Glu Asp Phe Ile Tyr Asp Ala Arg Leu Val Phe Asn Asn Cys
65                  70                  75                  80

Arg Met Tyr Asn Gly Glu Asn Thr Ser Tyr Tyr Lys Tyr Ala Asn Arg
                85                  90                  95

Leu Glu Lys Phe Phe Asn Asn Lys Val Lys Glu Ile Pro
            100                 105
```

<210> SEQ ID NO 11
<211> LENGTH: 112
<212> TYPE: PRT
<213> ORGANISM: Homo sapiens

<400> SEQUENCE: 11

```
Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
            20                  25                  30

Pro Val Asp Pro Gln Leu Leu Gly Ile Pro Asp Tyr Phe Asp Ile Val
        35                  40                  45

Lys Ser Pro Met Asp Leu Ser Thr Ile Lys Arg Lys Leu Asp Thr Gly
50                  55                  60

Gln Tyr Gln Glu Pro Trp Gln Tyr Val Asp Asp Ile Trp Leu Met Phe
65                  70                  75                  80

Asn Asn Ala Trp Leu Tyr Asn Arg Lys Thr Ser Arg Val Tyr Lys Tyr
                85                  90                  95

Cys Ser Lys Leu Ser Glu Val Phe Glu Gln Glu Ile Asp Pro Val Met
            100                 105                 110
```

<210> SEQ ID NO 12
<211> LENGTH: 112

```
<212> TYPE: PRT
<213> ORGANISM: Homo sapiens

<400> SEQUENCE: 12

Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
            20                  25                  30

Pro Val Asp Pro Gln Leu Leu Gly Ile Pro Asp Tyr Phe Asp Ile Val
        35                  40                  45

Lys Asn Pro Met Asp Leu Ser Thr Ile Lys Arg Lys Leu Asp Thr Gly
    50                  55                  60

Gln Tyr Gln Glu Pro Trp Gln Tyr Val Asp Asp Val Trp Leu Met Phe
65                  70                  75                  80

Asn Asn Ala Trp Leu Tyr Asn Arg Lys Thr Ser Arg Val Tyr Lys Phe
                85                  90                  95

Cys Ser Lys Leu Ala Glu Val Phe Glu Gln Glu Ile Asp Pro Val Met
            100                 105                 110

<210> SEQ ID NO 13
<211> LENGTH: 112
<212> TYPE: PRT
<213> ORGANISM: Mus musculus

<400> SEQUENCE: 13

Lys Lys Ile Phe Lys Pro Glu Glu Leu Arg Gln Ala Leu Met Pro Thr
1               5                   10                  15

Leu Glu Ala Leu Tyr Arg Gln Asp Pro Glu Ser Leu Pro Phe Arg Gln
            20                  25                  30

Pro Val Asp Pro Gln Leu Leu Gly Ile Pro Asp Tyr Phe Asp Ile Val
        35                  40                  45

Lys Asn Pro Met Asp Leu Ser Thr Ile Lys Arg Lys Leu Asp Thr Gly
    50                  55                  60

Gln Tyr Gln Glu Pro Trp Gln Tyr Val Asp Asp Val Arg Leu Met Phe
65                  70                  75                  80

Asn Asn Ala Trp Leu Tyr Asn Arg Lys Thr Ser Arg Val Tyr Lys Phe
                85                  90                  95

Cys Ser Lys Leu Ala Glu Val Phe Glu Gln Glu Ile Asp Pro Val Met
            100                 105                 110

<210> SEQ ID NO 14
<211> LENGTH: 111
<212> TYPE: PRT
<213> ORGANISM: Caenorhabditis elegans

<400> SEQUENCE: 14

Asp Thr Val Phe Ser Gln Glu Asp Leu Ile Lys Phe Leu Leu Pro Val
1               5                   10                  15

Trp Glu Lys Leu Asp Lys Ser Glu Asp Ala Ala Pro Phe Arg Val Pro
            20                  25                  30

Val Asp Ala Lys Leu Leu Asn Ile Pro Asp Tyr His Glu Ile Ile Lys
        35                  40                  45

Arg Pro Met Asp Leu Glu Thr Val His Lys Lys Leu Tyr Ala Gly Gln
    50                  55                  60

Tyr Gln Asn Ala Gly Gln Phe Cys Asp Asp Ile Trp Leu Met Leu Asp
65                  70                  75                  80

Asn Ala Trp Leu Tyr Asn Arg Lys Asn Ser Lys Val Tyr Lys Tyr Gly
```

-continued

```
                85                  90                  95
Leu Lys Leu Ser Glu Met Phe Val Ser Glu Met Asp Pro Val Met
            100                 105                 110

<210> SEQ ID NO 15
<211> LENGTH: 110
<212> TYPE: PRT
<213> ORGANISM: Homo sapiens

<400> SEQUENCE: 15

Arg Arg Arg Thr Asp Pro Met Val Thr Leu Ser Ser Ile Leu Glu Ser
1               5                   10                  15

Ile Ile Asn Asp Met Arg Asp Leu Pro Asn Thr Tyr Pro Phe His Thr
            20                  25                  30

Pro Val Asn Ala Lys Val Val Lys Asp Tyr Tyr Lys Ile Ile Thr Arg
        35                  40                  45

Pro Met Asp Leu Gln Thr Leu Arg Glu Asn Val Arg Lys Arg Leu Tyr
    50                  55                  60

Pro Ser Arg Glu Glu Phe Arg Glu His Leu Glu Leu Ile Val Lys Asn
65                  70                  75                  80

Ser Ala Thr Tyr Asn Gly Pro Lys His Ser Leu Thr Gln Ile Ser Gln
                85                  90                  95

Ser Met Leu Asp Leu Cys Asp Glu Lys Leu Lys Glu Lys Glu
            100                 105                 110

<210> SEQ ID NO 16
<211> LENGTH: 110
<212> TYPE: PRT
<213> ORGANISM: Mesocricetus auratus

<400> SEQUENCE: 16

Arg Arg Arg Thr Asp Pro Met Val Thr Leu Ser Ser Ile Leu Glu Ser
1               5                   10                  15

Ile Ile Asn Asp Met Arg Asp Leu Pro Asn Thr Tyr Pro Phe His Thr
            20                  25                  30

Pro Val Asn Ala Lys Val Val Lys Asp Tyr Tyr Lys Ile Ile Thr Arg
        35                  40                  45

Pro Met Asp Leu Gln Thr Leu Arg Glu Asn Val Arg Lys Arg Leu Tyr
    50                  55                  60

Pro Ser Arg Glu Glu Phe Arg Glu His Leu Glu Leu Ile Val Lys Asn
65                  70                  75                  80

Ser Ala Thr Tyr Asn Gly Pro Lys His Ser Leu Thr Gln Ile Ser Gln
                85                  90                  95

Ser Met Leu Asp Leu Cys Asp Glu Lys Leu Lys Glu Lys Glu
            100                 105                 110

<210> SEQ ID NO 17
<211> LENGTH: 111
<212> TYPE: PRT
<213> ORGANISM: Homo sapiens

<400> SEQUENCE: 17

Leu Leu Asp Asp Asp Asp Gln Val Ala Phe Ser Phe Ile Leu Asp Asn
1               5                   10                  15

Ile Val Thr Gln Lys Met Met Ala Val Pro Asp Ser Trp Pro Phe His
            20                  25                  30

His Pro Val Asn Lys Lys Phe Val Pro Asp Tyr Tyr Lys Val Ile Val
        35                  40                  45
```

```
Asn Pro Met Asp Leu Glu Thr Ile Arg Lys Asn Ile Ser Lys His Lys
        50                  55                  60

Tyr Gln Ser Arg Glu Ser Phe Leu Asp Asp Val Asn Leu Ile Leu Ala
65                  70                  75                  80

Asn Ser Val Lys Tyr Asn Gly Pro Glu Ser Gln Tyr Thr Lys Thr Ala
                85                  90                  95

Gln Glu Ile Val Asn Val Cys Tyr Gln Thr Leu Thr Glu Tyr Asp
                100                 105                 110

<210> SEQ ID NO 18
<211> LENGTH: 111
<212> TYPE: PRT
<213> ORGANISM: Mesocricetus auratus

<400> SEQUENCE: 18

Leu Leu Asp Asp Asp Gln Val Ala Phe Ser Phe Ile Leu Asp Asn
1               5                   10                  15

Ile Val Thr Gln Lys Met Met Ala Val Pro Asp Ser Trp Pro Phe His
                20                  25                  30

His Pro Val Asn Lys Lys Phe Val Pro Asp Tyr Tyr Lys Val Ile Val
                35                  40                  45

Ser Pro Met Asp Leu Glu Thr Ile Arg Lys Asn Ile Ser Lys His Lys
        50                  55                  60

Tyr Gln Ser Arg Glu Ser Phe Leu Asp Asp Val Asn Leu Ile Leu Ala
65                  70                  75                  80

Asn Ser Val Lys Tyr Asn Gly Ser Glu Ser Gln Tyr Thr Lys Thr Ala
                85                  90                  95

Gln Glu Ile Val Asn Val Cys Tyr Gln Thr Leu Thr Glu Tyr Asp
                100                 105                 110

<210> SEQ ID NO 19
<211> LENGTH: 111
<212> TYPE: PRT
<213> ORGANISM: Homo sapiens

<400> SEQUENCE: 19

Lys Pro Gly Arg Val Thr Asn Gln Leu Gln Tyr Leu His Lys Val Val
1               5                   10                  15

Met Lys Ala Leu Trp Lys His Gln Phe Ala Trp Pro Phe Arg Gln Pro
                20                  25                  30

Val Asp Ala Val Lys Leu Gly Leu Pro Asp Tyr His Lys Ile Ile Lys
                35                  40                  45

Gln Pro Met Asp Met Gly Thr Ile Lys Arg Arg Leu Glu Asn Asn Tyr
        50                  55                  60

Tyr Trp Ala Ala Ser Glu Cys Met Gln Asp Phe Asn Thr Met Phe Thr
65                  70                  75                  80

Asn Cys Tyr Ile Tyr Asn Lys Pro Thr Asp Asp Ile Val Leu Met Ala
                85                  90                  95

Gln Thr Leu Glu Lys Ile Phe Leu Gln Lys Val Ala Ser Met Pro
                100                 105                 110

<210> SEQ ID NO 20
<211> LENGTH: 111
<212> TYPE: PRT
<213> ORGANISM: Homo sapiens

<400> SEQUENCE: 20
```

```
Lys Pro Gly Arg Lys Thr Asn Gln Leu Gln Tyr Met Gln Asn Val Val
1               5                   10                  15

Val Lys Thr Leu Trp Lys His Gln Phe Ala Trp Pro Phe Tyr Gln Pro
            20                  25                  30

Val Asp Ala Ile Lys Leu Asn Leu Pro Asp Tyr His Lys Ile Ile Lys
            35                  40                  45

Asn Pro Met Asp Met Gly Thr Ile Lys Lys Arg Leu Glu Asn Asn Tyr
        50                  55                  60

Tyr Trp Ser Ala Ser Glu Cys Met Gln Asp Phe Asn Thr Met Phe Thr
65              70                  75                  80

Asn Cys Tyr Ile Tyr Asn Lys Pro Thr Asp Ile Val Leu Met Ala
                85                  90                  95

Gln Ala Leu Glu Lys Ile Phe Leu Gln Lys Val Ala Gln Met Pro
                100                 105                 110
```

<210> SEQ ID NO 21
<211> LENGTH: 111
<212> TYPE: PRT
<213> ORGANISM: Drosophila melanogaster

<400> SEQUENCE: 21

```
Arg Pro Gly Arg Asn Thr Asn Gln Leu Gln Tyr Leu Ile Lys Thr Val
1               5                   10                  15

Met Lys Val Ile Trp Lys His His Phe Ser Trp Pro Phe Gln Gln Pro
            20                  25                  30

Val Asp Ala Lys Lys Leu Asn Leu Pro Asp Tyr His Lys Ile Ile Lys
            35                  40                  45

Gln Pro Met Asp Met Gly Thr Ile Lys Lys Arg Leu Glu Asn Asn Tyr
        50                  55                  60

Tyr Trp Ser Ala Lys Glu Thr Ile Gln Asp Phe Asn Thr Met Phe Asn
65              70                  75                  80

Asn Cys Tyr Val Tyr Asn Lys Pro Gly Glu Asp Val Val Val Met Ala
                85                  90                  95

Gln Thr Leu Glu Lys Val Phe Leu Gln Lys Ile Glu Ser Met Pro
                100                 105                 110
```

<210> SEQ ID NO 22
<211> LENGTH: 109
<212> TYPE: PRT
<213> ORGANISM: Saccharomyces cerevisiae

<400> SEQUENCE: 22

```
Asn Pro Ile Pro Lys His Gln Gln Lys His Ala Leu Leu Ala Ile Lys
1               5                   10                  15

Ala Val Lys Arg Leu Lys Asp Ala Arg Pro Phe Leu Gln Pro Val Asp
            20                  25                  30

Pro Val Lys Leu Asp Ile Pro Phe Tyr Phe Asn Tyr Ile Lys Arg Pro
            35                  40                  45

Met Asp Leu Ser Thr Ile Glu Arg Lys Leu Asn Val Gly Ala Tyr Glu
        50                  55                  60

Val Pro Glu Gln Ile Thr Glu Asp Phe Asn Leu Met Val Asn Asn Ser
65              70                  75                  80

Ile Lys Phe Asn Gly Pro Asn Ala Gly Ile Ser Gln Met Ala Arg Asn
                85                  90                  95

Ile Gln Ala Ser Phe Glu Lys His Met Leu Asn Met Pro
                100                 105
```

```
<210> SEQ ID NO 23
<211> LENGTH: 113
<212> TYPE: PRT
<213> ORGANISM: Homo sapiens

<400> SEQUENCE: 23

Lys Lys Gly Lys Leu Ser Glu Gln Leu Lys His Cys Asn Gly Ile Leu
1               5                   10                  15

Lys Glu Leu Leu Ser Lys Lys His Ala Ala Tyr Ala Trp Pro Phe Tyr
            20                  25                  30

Lys Pro Val Asp Ala Ser Ala Leu Gly Leu His Asp Tyr His Asp Ile
        35                  40                  45

Ile Lys His Pro Met Asp Leu Ser Thr Val Lys Arg Lys Met Glu Asn
    50                  55                  60

Arg Asp Tyr Arg Asp Ala Gln Glu Phe Ala Ala Asp Val Arg Leu Met
65                  70                  75                  80

Phe Ser Asn Cys Tyr Lys Tyr Asn Pro Pro Asp His Asp Val Val Ala
                85                  90                  95

Met Ala Arg Lys Leu Gln Asp Val Phe Glu Phe Arg Tyr Ala Lys Met
            100                 105                 110

Pro

<210> SEQ ID NO 24
<211> LENGTH: 113
<212> TYPE: PRT
<213> ORGANISM: Homo sapiens

<400> SEQUENCE: 24

Lys Lys Gly Lys Leu Ser Glu His Leu Arg Tyr Cys Asp Ser Ile Leu
1               5                   10                  15

Arg Glu Met Leu Ser Lys Lys His Ala Ala Tyr Ala Trp Pro Phe Tyr
            20                  25                  30

Lys Pro Val Asp Ala Glu Ala Leu Glu Leu His Asp Tyr His Asp Ile
        35                  40                  45

Ile Lys His Pro Met Asp Leu Ser Thr Val Lys Arg Lys Met Asp Gly
    50                  55                  60

Arg Glu Tyr Pro Asp Ala Gln Gly Phe Ala Ala Asp Val Arg Leu Met
65                  70                  75                  80

Phe Ser Asn Cys Tyr Lys Tyr Asn Pro Pro Asp His Glu Val Val Ala
                85                  90                  95

Met Ala Arg Lys Leu Gln Asp Val Phe Glu Met Arg Phe Ala Lys Met
            100                 105                 110

Pro

<210> SEQ ID NO 25
<211> LENGTH: 113
<212> TYPE: PRT
<213> ORGANISM: Drosophila melanogaster

<400> SEQUENCE: 25

Asn Lys Glu Lys Leu Ser Asp Ala Leu Lys Ser Cys Asn Glu Ile Leu
1               5                   10                  15

Lys Glu Leu Phe Ser Lys Lys His Ser Gly Tyr Ala Trp Pro Phe Tyr
            20                  25                  30

Lys Pro Val Asp Ala Glu Met Leu Gly Leu His Asp Tyr His Asp Ile
        35                  40                  45
```

-continued

Ile Lys Lys Pro Met Asp Leu Gly Thr Val Lys Arg Lys Met Asp Asn
 50                  55                  60

Arg Glu Tyr Lys Ser Ala Pro Glu Phe Ala Ala Asp Val Arg Leu Ile
 65                  70                  75                  80

Phe Thr Asn Cys Tyr Lys Tyr Asn Pro Pro Asp His Asp Val Val Ala
                 85                  90                  95

Met Gly Arg Lys Leu Gln Asp Val Phe Glu Met Arg Tyr Ala Asn Ile
            100                 105                 110

Pro

<210> SEQ ID NO 26
<211> LENGTH: 113
<212> TYPE: PRT
<213> ORGANISM: Saccharomyces cerevisiae

<400> SEQUENCE: 26

Lys Ser Lys Arg Leu Gln Gln Ala Met Lys Phe Cys Gln Ser Val Leu
 1               5                  10                  15

Lys Glu Leu Met Ala Lys Lys His Ala Ser Tyr Asn Tyr Pro Phe Leu
                20                  25                  30

Glu Pro Val Asp Pro Val Ser Met Asn Leu Pro Thr Tyr Phe Asp Tyr
             35                  40                  45

Val Lys Glu Pro Met Asp Leu Gly Thr Ile Ala Lys Lys Leu Asn Asp
 50                  55                  60

Trp Gln Tyr Gln Thr Met Glu Asp Phe Glu Arg Glu Val Arg Leu Val
 65                  70                  75                  80

Phe Lys Asn Cys Tyr Thr Phe Asn Pro Asp Gly Thr Ile Val Asn Met
                 85                  90                  95

Met Gly His Arg Leu Glu Glu Val Phe Asn Ser Lys Trp Ala Asp Arg
            100                 105                 110

Pro

<210> SEQ ID NO 27
<211> LENGTH: 108
<212> TYPE: PRT
<213> ORGANISM: Homo sapiens

<400> SEQUENCE: 27

Met Glu Met Gln Leu Thr Pro Phe Leu Ile Leu Leu Arg Lys Thr Leu
 1               5                  10                  15

Glu Gln Leu Gln Glu Lys Asp Thr Gly Asn Ile Phe Ser Glu Pro Val
                20                  25                  30

Pro Leu Ser Glu Val Pro Asp Tyr Leu Asp His Ile Lys Lys Pro Met
             35                  40                  45

Asp Phe Phe Thr Met Lys Gln Asn Leu Glu Ala Tyr Arg Tyr Leu Asn
 50                  55                  60

Phe Asp Asp Phe Glu Glu Asp Phe Asn Leu Ile Val Ser Asn Cys Leu
 65                  70                  75                  80

Lys Tyr Asn Ala Lys Asp Thr Ile Phe Tyr Arg Ala Ala Val Arg Leu
                 85                  90                  95

Arg Glu Gln Gly Gly Ala Val Val Arg Gln Ala Arg
            100                 105

<210> SEQ ID NO 28
<211> LENGTH: 113
<212> TYPE: PRT
<213> ORGANISM: Homo sapiens -continued

```
<400> SEQUENCE: 28

Ser Glu Asp Gln Glu Ala Ile Gln Ala Gln Lys Ile Trp Lys Lys Ala
1               5                   10                  15

Ile Met Leu Val Trp Arg Ala Ala Asn His Arg Tyr Ala Asn Val
            20                  25                  30

Phe Leu Gln Pro Val Thr Asp Asp Ile Ala Pro Gly Tyr His Ser Ile
        35                  40                  45

Val Gln Arg Pro Met Asp Leu Ser Thr Ile Lys Lys Asn Ile Glu Asn
    50                  55                  60

Gly Leu Ile Arg Ser Thr Ala Glu Phe Gln Arg Asp Ile Met Leu Met
65                  70                  75                  80

Phe Gln Asn Ala Val Met Tyr Asn Ser Ser Asp His Asp Val Tyr His
                85                  90                  95

Met Ala Val Glu Met Gln Arg Asp Val Leu Glu Gln Ile Gln Gln Phe
                100                 105                 110

Leu

<210> SEQ ID NO 29
<211> LENGTH: 106
<212> TYPE: PRT
<213> ORGANISM: Gallus gallus

<400> SEQUENCE: 29

Asn Leu Pro Thr Val Asp Pro Ile Ala Val Cys His Glu Leu Tyr Asn
1               5                   10                  15

Thr Ile Arg Asp Tyr Lys Asp Glu Gln Gly Arg Leu Leu Cys Glu Leu
            20                  25                  30

Phe Ile Arg Ala Pro Lys Arg Arg Asn Gln Pro Asp Tyr Tyr Glu Val
        35                  40                  45

Val Ser Gln Pro Ile Asp Leu Met Lys Ile Gln Gln Lys Leu Lys Met
    50                  55                  60

Glu Glu Tyr Asp Asp Val Asn Val Leu Thr Ala Asp Phe Gln Leu Leu
65                  70                  75                  80

Phe Asn Asn Ala Lys Ala Tyr Tyr Lys Pro Asp Ser Pro Glu Tyr Lys
                85                  90                  95

Ala Ala Cys Lys Leu Trp Glu Leu Tyr Leu
                100                 105

<210> SEQ ID NO 30
<211> LENGTH: 112
<212> TYPE: PRT
<213> ORGANISM: Gallus gallus

<400> SEQUENCE: 30

Ser Ser Pro Gly Tyr Leu Lys Glu Ile Leu Glu Gln Leu Leu Glu Ala
1               5                   10                  15

Val Ala Val Ala Thr Asn Pro Ser Gly Arg Leu Ile Ser Glu Leu Phe
            20                  25                  30

Gln Lys Leu Pro Ser Lys Val Gln Tyr Pro Asp Tyr Ala Ile Ile
        35                  40                  45

Lys Glu Pro Ile Asp Leu Lys Thr Ile Ala Gln Arg Ile Gln Asn Gly
    50                  55                  60

Thr Tyr Lys Ser Ile His Ala Met Ala Lys Asp Ile Asp Leu Leu Ala
65                  70                  75                  80

Lys Asn Ala Lys Thr Tyr Asn Glu Pro Gly Ser Gln Val Phe Lys Asp
```

```
                85                  90                  95
Ala Asn Ala Ile Lys Lys Ile Phe Asn Met Lys Lys Ala Glu Ile Glu
            100                 105                 110

<210> SEQ ID NO 31
<211> LENGTH: 112
<212> TYPE: PRT
<213> ORGANISM: Gallus gallus

<400> SEQUENCE: 31

Thr Ser Phe Met Asp Thr Ser Asn Pro Leu Tyr Gln Leu Tyr Asp Thr
1               5                   10                  15

Val Arg Ser Cys Arg Asn Asn Gln Gly Gln Leu Ile Ser Glu Pro Phe
            20                  25                  30

Phe Gln Leu Pro Ser Lys Lys Tyr Pro Asp Tyr Tyr Gln Gln Ile
        35                  40                  45

Lys Thr Pro Ile Ser Leu Gln Gln Ile Arg Ala Lys Leu Lys Asn His
50                  55                  60

Glu Tyr Glu Thr Leu Asp Gln Leu Glu Ala Asp Leu Asn Leu Met Phe
65                  70                  75                  80

Glu Asn Ala Lys Arg Tyr Asn Val Pro Asn Ser Ala Ile Tyr Lys Arg
                85                  90                  95

Val Leu Lys Met Gln Gln Val Met Gln Ala Lys Lys Glu Leu Ala
            100                 105                 110

<210> SEQ ID NO 32
<211> LENGTH: 113
<212> TYPE: PRT
<213> ORGANISM: Gallus gallus

<400> SEQUENCE: 32

Ser Lys Lys Asn Met Arg Lys Gln Arg Met Lys Ile Leu Tyr Asn Ala
1               5                   10                  15

Val Leu Glu Ala Arg Glu Ser Gly Thr Gln Arg Arg Leu Cys Asp Leu
            20                  25                  30

Phe Met Val Lys Pro Ser Lys Lys Asp Tyr Pro Asp Tyr Lys Ile
        35                  40                  45

Ile Leu Glu Pro Met Asp Leu Lys Met Ile Glu His Asn Ile Arg Asn
50                  55                  60

Asp Lys Tyr Val Gly Glu Ala Met Ile Asp Met Lys Leu Met
65                  70                  75                  80

Phe Arg Asn Ala Arg His Tyr Asn Glu Glu Gly Ser Gln Val Tyr Asn
                85                  90                  95

Asp Ala His Met Leu Glu Lys Ile Leu Lys Glu Lys Arg Lys Glu Leu
            100                 105                 110

Gly

<210> SEQ ID NO 33
<211> LENGTH: 115
<212> TYPE: PRT
<213> ORGANISM: Gallus gallus

<400> SEQUENCE: 33

Lys Lys Ser Lys Tyr Met Thr Pro Met Gln Gln Lys Leu Asn Glu Val
1               5                   10                  15

Tyr Glu Ala Val Lys Asn Tyr Thr Asp Lys Arg Gly Arg Arg Leu Ser
            20                  25                  30
```

```
Ala Ile Phe Leu Arg Leu Pro Ser Arg Ser Glu Leu Pro Asp Tyr Tyr
            35                  40                  45

Ile Thr Ile Lys Lys Pro Val Asp Met Glu Lys Ile Arg Ser His Met
 50                  55                  60

Met Ala Asn Lys Tyr Gln Asp Ile Asp Ser Met Val Glu Asp Phe Val
 65                  70                  75                  80

Met Met Phe Asn Asn Ala Cys Thr Tyr Asn Glu Pro Glu Ser Leu Ile
                 85                  90                  95

Tyr Lys Asp Ala Leu Val Leu His Lys Val Leu Leu Glu Thr Arg Arg
                100                 105                 110

Glu Ile Glu
        115

<210> SEQ ID NO 34
<211> LENGTH: 112
<212> TYPE: PRT
<213> ORGANISM: Unknown Organism
<220> FEATURE:
<223> OTHER INFORMATION: Description of Unknown Organism: see
      Jeanmougin et al., Trends in Biochem. Sci. 22:151-153 (1997)

<400> SEQUENCE: 34

His Asn Ala Pro Phe Asp Lys Thr Lys Phe Asp Glu Val Leu Glu Ala
 1               5                  10                  15

Leu Val Gly Leu Lys Asp Asn Glu Gly Asn Pro Phe Asp Asp Ile Phe
                20                  25                  30

Glu Glu Leu Pro Ser Lys Arg Tyr Phe Pro Asp Tyr Tyr Gln Ile Ile
            35                  40                  45

Gln Lys Pro Ile Cys Tyr Lys Met Met Arg Asn Lys Ala Lys Thr Gly
 50                  55                  60

Lys Tyr Leu Ser Met Gly Asp Phe Tyr Asp Asp Ile Arg Leu Met Val
 65                  70                  75                  80

Ser Asn Ala Gln Thr Tyr Asn Met Pro Gly Ser Leu Val Tyr Glu Cys
                 85                  90                  95

Ser Val Leu Ile Ala Asn Thr Ala Asn Ser Leu Glu Ser Lys Asp Gly
                100                 105                 110

<210> SEQ ID NO 35
<211> LENGTH: 113
<212> TYPE: PRT
<213> ORGANISM: Unknown Organism
<220> FEATURE:
<223> OTHER INFORMATION: Description of Unknown Organism: see Jeanmougin
      et al., Trends in Biochem. Sci. 22:151-153 (1997)

<400> SEQUENCE: 35

Gly Thr Asn Glu Ile Asp Val Pro Lys Val Ile Gln Asn Ile Leu Asp
 1               5                  10                  15

Ala Leu His Glu Glu Lys Asp Glu Gln Gly Arg Phe Leu Ile Asp Ile
                20                  25                  30

Phe Ile Asp Leu Pro Ser Lys Arg Leu Tyr Pro Asp Tyr Tyr Glu Ile
            35                  40                  45

Ile Lys Ser Pro Met Thr Ile Lys Met Leu Glu Lys Arg Phe Lys Lys
 50                  55                  60

Gly Glu Tyr Thr Thr Leu Glu Ser Phe Val Lys Asp Leu Asn Gln Met
 65                  70                  75                  80

Phe Ile Asn Ala Lys Thr Tyr Asn Ala Pro Gly Ser Phe Val Tyr Glu
                 85                  90                  95
```

```
Asp Ala Glu Lys Leu Ser Gln Leu Ser Ser Ser Leu Ile Ser Ser Phe
                100                 105                 110
Ser

<210> SEQ ID NO 36
<211> LENGTH: 113
<212> TYPE: PRT
<213> ORGANISM: Homo sapiens

<400> SEQUENCE: 36

Gly Thr Asn Glu Ile Asp Val Pro Lys Val Ile Gln Asn Ile Leu Asp
1               5                   10                  15

Ala Leu His Glu Glu Lys Asp Glu Gln Gly Arg Phe Leu Ile Asp Ile
                20                  25                  30

Phe Ile Asp Leu Pro Ser Lys Arg Leu Tyr Pro Asp Tyr Tyr Glu Ile
                35                  40                  45

Ile Lys Ser Pro Met Thr Ile Lys Met Leu Glu Lys Arg Phe Lys Lys
            50                  55                  60

Gly Glu Tyr Thr Thr Leu Glu Ser Phe Val Lys Asp Leu Asn Gln Met
65                  70                  75                  80

Phe Ile Asn Ala Lys Thr Tyr Asn Ala Pro Gly Ser Phe Val Tyr Glu
                85                  90                  95

Asp Ala Glu Lys Leu Ser Gln Leu Ser Ser Ser Leu Ile Ser Ser Phe
                100                 105                 110
Ser

<210> SEQ ID NO 37
<211> LENGTH: 114
<212> TYPE: PRT
<213> ORGANISM: Homo sapiens

<400> SEQUENCE: 37

Ser Pro Asn Pro Pro Asn Leu Thr Lys Lys Met Lys Lys Ile Val Asp
1               5                   10                  15

Ala Val Ile Lys Tyr Lys Asp Ser Ser Ser Gly Arg Gln Leu Ser Glu
                20                  25                  30

Val Phe Ile Gln Leu Pro Ser Arg Lys Glu Leu Pro Glu Tyr Tyr Glu
                35                  40                  45

Leu Ile Arg Lys Pro Val Asp Phe Lys Lys Ile Lys Glu Arg Ile Arg
            50                  55                  60

Asn His Lys Tyr Arg Ser Leu Asn Asp Leu Glu Lys Asp Val Met Leu
65                  70                  75                  80

Leu Cys Gln Asn Ala Gln Thr Phe Asn Leu Glu Gly Ser Leu Ile Tyr
                85                  90                  95

Glu Asp Ser Ile Val Leu Gln Ser Val Phe Thr Ser Val Arg Gln Lys
                100                 105                 110
Ile Glu

<210> SEQ ID NO 38
<211> LENGTH: 113
<212> TYPE: PRT
<213> ORGANISM: Gallus gallus

<400> SEQUENCE: 38

Ser Pro Asn Pro Pro Lys Leu Thr Lys Gln Met Asn Ala Ile Ile Asp
1               5                   10                  15

Thr Val Ile Asn Tyr Lys Asp Ser Ser Gly Arg Gln Leu Ser Glu Val
```

-continued

```
                20                  25                  30
Phe Ile Gln Leu Pro Ser Arg Lys Glu Leu Pro Glu Tyr Tyr Glu Leu
            35                  40                  45

Ile Arg Lys Pro Val Asp Phe Lys Lys Ile Lys Glu Arg Ile Arg Asn
 50                  55                  60

His Lys Tyr Arg Ser Leu Gly Asp Leu Glu Lys Asp Val Met Leu Leu
 65                  70                  75                  80

Cys His Asn Ala Gln Thr Phe Asn Leu Glu Gly Ser Gln Ile Tyr Glu
                85                  90                  95

Asp Ser Ile Val Leu Gln Ser Val Phe Lys Ser Ala Arg Gln Lys Ile
               100                 105                 110

Ala

<210> SEQ ID NO 39
<211> LENGTH: 114
<212> TYPE: PRT
<213> ORGANISM: Gallus gallus

<400> SEQUENCE: 39

Ser Pro Asn Pro Asn Leu Thr Lys Lys Met Lys Lys Ile Val Asp
 1               5                  10                  15

Ala Val Ile Lys Tyr Lys Asp Ser Ser Gly Arg Gln Leu Ser Glu
                20                  25                  30

Val Phe Ile Gln Leu Pro Ser Arg Lys Glu Leu Pro Glu Tyr Tyr Glu
                35                  40                  45

Leu Ile Arg Lys Pro Val Asp Phe Lys Lys Ile Lys Glu Arg Ile Arg
             50                  55                  60

Asn His Lys Tyr Arg Ser Leu Asn Asp Leu Glu Lys Asp Val Met Leu
 65                  70                  75                  80

Leu Cys Gln Asn Ala Gln Thr Phe Asn Leu Glu Val Ser Leu Ile Tyr
                85                  90                  95

Glu Asp Ser Ile Val Leu Gln Ser Val Phe Thr Ser Val Arg Gln Lys
               100                 105                 110

Ile Glu

<210> SEQ ID NO 40
<211> LENGTH: 105
<212> TYPE: PRT
<213> ORGANISM: Homo sapiens

<400> SEQUENCE: 40

Ala Lys Leu Ser Pro Ala Asn Gln Arg Lys Cys Glu Arg Val Leu Leu
 1               5                  10                  15

Ala Leu Phe Cys His Glu Pro Cys Arg Pro Leu His Gln Leu Ala Thr
                20                  25                  30

Asp Ser Thr Phe Ser Leu Asp Gln Pro Gly Gly Thr Leu Asp Leu Thr
             35                  40                  45

Leu Ile Arg Ala Arg Leu Gln Glu Lys Leu Ser Pro Pro Tyr Ser Ser
 50                  55                  60

Pro Gln Glu Phe Ala Gln Asp Val Gly Arg Met Phe Lys Gln Phe Asn
 65                  70                  75                  80

Lys Leu Thr Glu Asp Lys Ala Asp Val Gln Ser Ile Ile Gly Leu Gln
                85                  90                  95

Arg Phe Phe Glu Thr Arg Met Asn Glu
               100                 105
```

-continued

```
<210> SEQ ID NO 41
<211> LENGTH: 105
<212> TYPE: PRT
<213> ORGANISM: Mus musculus

<400> SEQUENCE: 41

Ala Lys Leu Ser Pro Ala Asn Gln Arg Lys Cys Glu Arg Val Leu Leu
1               5                   10                  15

Ala Leu Phe Cys His Glu Pro Cys Arg Pro Leu His Gln Leu Ala Thr
            20                  25                  30

Asp Ser Thr Phe Ser Met Glu Gln Pro Gly Gly Thr Leu Asp Leu Thr
        35                  40                  45

Leu Ile Arg Ala Arg Leu Gln Glu Lys Leu Ser Pro Pro Tyr Ser Ser
    50                  55                  60

Pro Gln Glu Phe Ala Gln Asp Val Gly Arg Met Phe Lys Gln Phe Asn
65                  70                  75                  80

Lys Leu Thr Glu Asp Lys Ala Asp Val Gln Ser Ile Ile Gly Leu Gln
                85                  90                  95

Arg Phe Phe Glu Thr Arg Met Asn Asp
            100                 105

<210> SEQ ID NO 42
<211> LENGTH: 108
<212> TYPE: PRT
<213> ORGANISM: Mus sp.

<400> SEQUENCE: 42

Thr Lys Leu Thr Pro Ile Asp Lys Arg Lys Cys Glu Arg Leu Leu Leu
1               5                   10                  15

Phe Leu Tyr Cys His Glu Met Ser Leu Ala Phe Gln Asp Pro Val Pro
            20                  25                  30

Leu Thr Val Pro Asp Tyr Tyr Lys Ile Ile Lys Asn Pro Met Asp Leu
        35                  40                  45

Ser Thr Ile Lys Lys Arg Leu Gln Glu Asp Tyr Cys Met Tyr Thr Lys
    50                  55                  60

Pro Glu Asp Phe Val Ala Asp Phe Arg Leu Ile Phe Gln Asn Cys Ala
65                  70                  75                  80

Glu Phe Asn Glu Pro Asp Ser Glu Val Ala Asn Ala Gly Ile Lys Leu
                85                  90                  95

Glu Ser Tyr Phe Glu Glu Leu Leu Lys Asn Leu Tyr
            100                 105

<210> SEQ ID NO 43
<211> LENGTH: 27
<212> TYPE: PRT
<213> ORGANISM: Artificial Sequence
<220> FEATURE:
<223> OTHER INFORMATION: synthetic bromodomain peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid; this range may encompass 2-3
      residues
<220> FEATURE:
<221> NAME/KEY: MOD_RES
<222> LOCATION: (8)..(15)
<223> OTHER INFORMATION: Any amino acid; this range may encompass 5-8
      residues
```

```
<220> FEATURE:
<221> NAME/KEY: MOD_RES
<222> LOCATION: (16)
<223> OTHER INFORMATION: Pro, Lys or His
<220> FEATURE:
<221> NAME/KEY: MOD_RES
<222> LOCATION: (17)
<223> OTHER INFORMATION: Any amino acid
<220> FEATURE:
<221> NAME/KEY: MOD_RES
<222> LOCATION: (19)
<223> OTHER INFORMATION: Tyr, Phe or His
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)
<223> OTHER INFORMATION: Met, Ile or Val

<400> SEQUENCE: 43

Xaa Xaa Phe Xaa Xaa Xaa Pro Xaa Xaa Xaa Xaa Xaa Xaa Xaa Xaa Xaa
1               5                   10                  15

Xaa Tyr Xaa Xaa Xaa Xaa Xaa Xaa Pro Xaa Asp
            20                  25

<210> SEQ ID NO 44
<211> LENGTH: 20
<212> TYPE: PRT
<213> ORGANISM: Artificial Sequence
<220> FEATURE:
<223> OTHER INFORMATION: synthetic bromodomain peptide

<400> SEQUENCE: 44

Trp Pro Phe Met Glu Pro Val Lys Arg Thr Glu Ala Pro Gly Tyr Tyr
1               5                   10                  15

Glu Val Ile Arg
            20

<210> SEQ ID NO 45
<211> LENGTH: 101
<212> TYPE: PRT
<213> ORGANISM: Human immunodeficiency virus type 1
<220> FEATURE:
<223> OTHER INFORMATION: Tat protein

<400> SEQUENCE: 45

Met Glu Pro Val Asp Pro Arg Leu Glu Pro Trp Lys His Pro Gly Ser
1               5                   10                  15

Gln Pro Lys Thr Ala Ser Asn Asn Cys Tyr Cys Lys Arg Cys Cys Leu
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Ala Pro Gln Asp Ser Lys Thr
    50                  55                  60

His Gln Val Ser Leu Ser Lys Gln Pro Ala Ser Gln Pro Arg Gly Asp
65                  70                  75                  80

Pro Thr Gly Pro Lys Glu Ser Lys Lys Val Glu Arg Glu Thr Glu
                85                  90                  95

Thr Asp Pro Glu Asp
            100

<210> SEQ ID NO 46
<211> LENGTH: 9
```

```
<212> TYPE: PRT
<213> ORGANISM: Artificial Sequence
<220> FEATURE:
<223> OTHER INFORMATION: Synthetic HIV-1 Tat peptide
<220> FEATURE:
<221> NAME/KEY: MOD_RES
<222> LOCATION: (5)..(7)
<223> OTHER INFORMATION: Any amino acid

<400> SEQUENCE: 46

Tyr Gly Arg Lys Xaa Xaa Xaa Arg Gln
  1               5

<210> SEQ ID NO 47
<211> LENGTH: 10
<212> TYPE: PRT
<213> ORGANISM: Artificial Sequence
<220> FEATURE:
<223> OTHER INFORMATION: synthetic HIV-1 Tat peptide

<400> SEQUENCE: 47

Ser Tyr Gly Arg Lys Lys Arg Arg Gln Arg
1               5                   10

<210> SEQ ID NO 48
<211> LENGTH: 21
<212> TYPE: PRT
<213> ORGANISM: Artificial Sequence
<220> FEATURE:
<223> OTHER INFORMATION: Synthetic HIV-1 Tat peptide
<220> FEATURE:
<221> NAME/KEY: MOD_RES
<222> LOCATION: (2)..(5)
<223> OTHER INFORMATION: Any amino acid; this range may encompass 2-4
      residues
<220> FEATURE:
<221> NAME/KEY: MOD_RES
<222> LOCATION: (7)..(10)
<223> OTHER INFORMATION: Any amino acid; this range may encompass 2-4
      residues
<220> FEATURE:
<221> NAME/KEY: MOD_RES
<222> LOCATION: (12)..(15)
<223> OTHER INFORMATION: Any amino acid; this range may encompass 2-4
      residues
<220> FEATURE:
<221> NAME/KEY: MOD_RES
<222> LOCATION: (17)..(19)
<223> OTHER INFORMATION: Any amino acid; this range may encompass 1-3
      residues
<220> FEATURE:
<221> NAME/KEY: MOD_RES
<222> LOCATION: (21)
<223> OTHER INFORMATION: Ile, Leu, Met or Val

<400> SEQUENCE: 48

Phe Xaa Xaa Xaa Xaa Val Xaa Xaa Xaa Xaa Glu Xaa Xaa Xaa Xaa Tyr
  1               5                  10                  15

Xaa Xaa Xaa Val Xaa
              20

<210> SEQ ID NO 49
<211> LENGTH: 62
<212> TYPE: PRT
<213> ORGANISM: Artificial Sequence
<220> FEATURE:
<223> OTHER INFORMATION: synthetic bromodomain peptide

<400> SEQUENCE: 49

Phe Met Glu Pro Val Lys Arg Thr Glu Ala Pro Gly Tyr Tyr Glu Val
1               5                  10                  15
```

-continued

```
Ile Arg Phe Pro Met Asp Leu Lys Thr Met Ser Glu Arg Leu Lys Asn
            20                  25                  30

Arg Tyr Tyr Val Ser Lys Lys Leu Phe Met Ala Asp Leu Gln Arg Val
        35                  40                  45

Phe Thr Asn Cys Lys Glu Tyr Asn Ala Ala Glu Ser Glu Tyr
    50                  55                  60

<210> SEQ ID NO 50
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 50

Ser Tyr Gly Arg Xaa Lys Arg Arg Gln Arg Cys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 51

Ser Ala Gly Arg Xaa Lys Arg Arg Gln Arg Cys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 52

Ser Tyr Gly Ala Xaa Lys Arg Arg Gln Arg Cys
1               5                   10

<210> SEQ ID NO 53
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 53

Ser Tyr Gly Arg Xaa Ala Arg Arg Gln Arg Cys
1               5                   10
```

```
<210> SEQ ID NO 54
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 54

Ser Tyr Gly Arg Xaa Lys Ala Arg Gln Arg Cys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 55

Ser Tyr Gly Arg Xaa Lys Arg Ala Gln Arg Cys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (5)..(5)
<223> OTHER INFORMATION: acetylated lysine

<400> SEQUENCE: 56

Ser Tyr Gly Arg Xaa Lys Arg Arg Ala Arg Cys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (6)..(6)
<223> OTHER INFORMATION: acetylated lysine

<400> SEQUENCE: 57

Ser Tyr Gly Arg Lys Xaa Arg Arg Gln Arg Cys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: synthetic HIV-1 Tat peptide
<220> FEATURE:
<221> NAME/KEY: MOD_RES
<222> LOCATION: (7)..(7)
<223> OTHER INFORMATION: acetylated lysine
```

```
<400> SEQUENCE: 58

Thr Asn Cys Tyr Cys Lys Xaa Cys Cys Phe His
1               5                   10

<210> SEQ ID NO 59
<211> LENGTH: 20
<212> TYPE: PRT
<213> ORGANISM: Artificial Sequence
<220> FEATURE:
<223> OTHER INFORMATION: synthetic histone H4 AcK16 peptide
<220> FEATURE:
<221> NAME/KEY: MOD_RES
<222> LOCATION: (16)..(16)
<223> OTHER INFORMATION: acetylated lysine

<400> SEQUENCE: 59

Ser Gly Arg Gly Lys Gly Gly Lys Gly Leu Gly Lys Gly Gly Ala Xaa
1               5                   10                  15

Arg His Arg Lys
            20

<210> SEQ ID NO 60
<211> LENGTH: 11
<212> TYPE: PRT
<213> ORGANISM: Artificial Sequence
<220> FEATURE:
<223> OTHER INFORMATION: synthetic HIV-1 Tat peptide

<400> SEQUENCE: 60

Ser Tyr Gly Arg Lys Lys Arg Arg Gln Arg Cys
1               5                   10

<210> SEQ ID NO 61
<211> LENGTH: 6
<212> TYPE: PRT
<213> ORGANISM: Artificial Sequence
<220> FEATURE:
<223> OTHER INFORMATION: hexahistidine tag

<400> SEQUENCE: 61

His His His His His His
1               5

<210> SEQ ID NO 62
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (8)
<223> OTHER INFORMATION: acetyl lysine

<400> SEQUENCE: 62

Ser Gly Arg Gly Lys Gly Gly Xaa Gly Leu Gly Lys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)
<223> OTHER INFORMATION: acetyl lysine
```

```
<400> SEQUENCE: 63

Arg Lys Ser Thr Gly Gly Xaa Ala Pro Arg Lys Gln
1               5                   10
```

ZA LOOPS OF BROMODOMAINS

CROSS-REFERENCE TO RELATED APPLICATIONS

The present application is a continuation-in-part application claiming the priority of copending U.S. Ser. No. 09/510,314 filed Feb. 22, 2000, the disclosure of which is hereby incorporated by reference in its entirety. Applicants claim the benefits of this application under 35 U.S.C. §120.

FIELD OF THE INVENTION

The present invention provides the three-dimensional structure of a histone acetyltransferase bromodomain. The three-dimensional structural information is included in the invention. The present invention also identifies for the first time, that bromodomains can bind to binding partners that comprise an acetylated lysine. The interaction between bromodomains and their binding partners play a crucial role in various cellular functions, including in the regulation/modulation of DNA transcription. Therefore, the present invention provides procedures for identifying agents that can modulate the interaction of bromodomains and their binding partners by high throughput drug screening and/or through the use of rational drug design based on the three-dimensional data provided herein.

BACKGROUND OF THE INVENTION

In recent years great strides have been made in the elucidation of the steps involved in intercellular and intracellular signaling. Indeed, the individual steps of the cascade of events involved in a number of cellular signal transduction processes have been determined. For example, intercellular signal transduction generally begins with an intercellular ligand binding the extracellular portion of a receptor of the plasma membrane. The bound receptor then either directly or indirectly initiates the activation of one or more cellular factors. An activated cellular factor may act as transcription factor by entering the nucleus to interact with its corresponding genomic response element, or alternatively, it may interact with other cellular factors depending on the complexity of the process. In either case, one or more transcription factors ultimately bind to one or more specific genomic response elements. This binding plays a crucial role in the up and/or down regulation of the transcription of the specific genes that are under the control of these genomic response elements. However, the process of re-organizing the chromatin of eukaryotic cells, which is a prerequisite for the binding of the transcription factor to the genomic response elements, has remained a mystery.

Chromatin contains several highly conserved histone proteins including: H3, H4, H2A, H2B, and H1. These histone proteins package eukaryotic DNA into repeating nucleosomal units that are folded into higher-order chromatin fibers [Luger and Richmond, Curr. Opin. Genet. Dev. 8:140-146 (1998)]. A portion of the histone that comprises roughly a quarter of the protein protrudes from the chromatin surface, and is thereby sensitive to proteolytic enzymes [van Holde, in Chromatin (Rich, A,. ed., Springer, New York) pages 111-148 (1988); Hect et al., Cell 80:583-592 (1995)]. This portion of the histone is known as the "histone tail". Histone tails tend to be free for protein-protein interaction, and are also the portion of the histone most prone to post-translational modification. Such post-translational modification includes acetylation, phosphorylation, methylation, ubiquitination, and ADP-ribosylation [van Holde, in Chromatin (Rich, A,. ed., Springer, New York) pages 111-148 (1988)].

Of all classes of proteins, histones are amongst the most susceptible to post-translational modification. Perhaps the best studied post-translational modification of histones is the acetylation of specific lysine residues [Grunstin, M., Nature, 389:349-352 (1997)]. Indeed, acetylation of histone lysine residues has been suggested to play a pivotal role in chromatin remodeling and gene activation. Consistently, distinct classes of enzymes, namely histone acetyltransferases (HATs) and histone deacetylases (HDACs), acetylate or de-acetylate specific histone lysine residues [Struhl, Genes Dev. 12:599-606 (1998)].

Nearly all known nuclear HATs contain an approximately 110 amino acid sequence known as the bromodomain [Jeanmougin et al., Trends in Biochemical Sciences, 22:151-153 (1997)], a protein motif that was initially discovered in Drosophila brahma protein. Bromodomains are found in a large number of chromatin-associated proteins and have now been identified in approximately 70 human proteins, often adjacent to other protein motifs [Jeanmougin et al., Trends in Biochemical Sciences, 22:151-153 (1997); Tamkun et al., Cell, 68:561-572 (1992): Hanes et al., Nucleic Acids Research, 20:2603 (1992)]. Proteins that contain a bromodomain often contain a second bromodomain. However, despite the wide occurrence of bromodomains and their likely role in chromatin regulation, their three-dimensional structure and binding partners heretofore have remained unknown.

Therefore, there is a need to identify a binding partner for a bromodomain. In addition, there is a need to identify agonists or antagonists to the bromodomain-binding partner complex. Since a preferred method of drug-screening relies on structure based drug design, there is also a need to determine the three-dimensional structure of a bromodomain. In this case, once the three dimensional structure of bromodomain is determined, potential agonists and/or potential antagonists can be designed with the aid of computer modeling [Bugg et al., Scientific American, December:92-98 (1993); West et al., TIPS, 16:67-74 (1995); Dunbrack et al., Folding & Design, 2:27-42 (1997)]. However, heretofore the three-dimensional structure of the bromodomain has remained unknown. Therefore, there is a need for obtaining a form of the bromodomain that is amenable for NMR analysis and/or X-ray crystallographic analysis. Furthermore, there is a need for the determination of the three-dimensional structure of the bromodomain. Finally, there is a need for procedures for related structural based drug design predicated on such structural data.

The citation of any reference herein should not be construed as an admission that such reference is available as "Prior Art" to the instant application.

SUMMARY OF THE INVENTION

The present invention provides, for the first time, that bromodomains bind to acetyl-lysine residues of proteins. The present invention also provides the three-dimensional structure of a bromodomain as well as the three-dimensional structure of a bromodomain-acetyl-histamine complex. The structural information provided can be employed in methods of identifying drugs that can modulate the cellular processes that involve bromodomain-acetyl-lysine interactions. These interactions include chromatin remodeling, which is a required step in eukaryotic transcription. In a particular embodiment, the three-dimensional structural information is used in the identification and/design of an inhibitor of leukemia. In another embodiment, the three-dimensional structural information is used in the identification and/design of an inhibitor of HIV-1 infection and/or AIDS.

The present invention provides an isolated nucleic acid that encodes a peptide consisting of about 21 to 40 amino acids that comprises a ZA loop of a bromodomain. In a preferred embodiment the peptide comprises about 23 to 34 amino acids. The isolated nucleic acid can further comprise a heterologous nucleotide sequence.

In a preferred embodiment the peptide comprises the amino acid sequence of SEQ ID NO:3. In another embodiment the peptide comprises the amino acid sequence of SEQ ID NO:43. In particular embodiments the ZA loop is obtained from the bromodomain having the amino acid sequence of SEQ ID NO:7, or SEQ ID NO:8, or SEQ ID NO:9, or SEQ ID NO:10, or SEQ ID NO:11, or SEQ ID NO: 12, or SEQ ID NO: 13, or SEQ ID NO: 14, or SEQ ID NO:15, or SEQ ID NO:16, or SEQ ID NO:17, or SEQ ID NO:18, or SEQ ID NO:19, or SEQ ID NO:20, or SEQ ID NO:21, or SEQ ID NO: 22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID) NO:39, or SEQ ID NO:40, or SEQ ID NO:41, or SEQ ID NO:42.

The present invention further provides a recombinant DNA molecule that comprises an isolated nucleic acid of the present invention, as described above, with or without a heterologous nucleotide sequence. Such a recombinant DNA molecule can be operatively linked to an expression control sequence and can be part of an expression vector. The present invention further provides a cell that comprises such an expression vector. The cell can be either a eukaryotic or a prokaryotic cell. The present invention further provides a method of expressing the peptides of the present invention or fragments thereof in this cell. One such method comprises culturing the cell in an appropriate cell culture medium under conditions that provide for expression of the peptide by the cell.

The present invention further provides a peptide consisting of about 21 to 40 amino acids that comprises a ZA loop of a bromodomain. In a preferred embodiment the peptide comprises about 23 to 34 amino acids. The present invention also provides fusion proteins or peptides comprising these peptides.

In a preferred embodiment the peptide comprises the amino acid sequence of SEQ ID NO:3. In another embodiment the peptide comprises the amino acid sequence of SEQ ID NO:43. In yet another preferred embodiment the peptide comprises the amino acid sequence of SEQ ID NO:48.

In particular embodiments the ZA loop is obtained from the bromodomain having the amino acid sequence of SEQ ID NO:7, or SEQ ID NO:8, or SEQ ID NO:9, or SEQ ID NO: 10, or SEQ ID NO: 11, or SEQ ID NO: 12, or SEQ ID NO: 13, or SEQ ID NO: 14, or SEQ ID NO:15, or SEQ ID NO:16, or SEQ ID NO:17, or SEQ ID NO:18, or SEQ ID NO:19, or SEQ ID NO:20, or SEQ ID NO:21, or SEQ ID NO: 22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID NO:39, or SEQ ID NO:40, or SEQ ID NO:41, or SEQ ID NO:42.

The present invention also provides antibodies raised against the peptides/proteins of the present invention, or raised against an antigenic fragment of these proteins/fragments. In a particular embodiment an antibody is raised against a fragment of the ZA loop of a bromodomain. In another embodiment an antibody is raised against a fragment of a protein or peptide that comprises an acetyl-lysine, wherein the protein or peptide can bind to a bromodomain. Such fragments can be conjugated to a carrier protein or be part of a fusion protein. In one embodiment the antibody is a polyclonal antibody. In another embodiment, the antibody is a monoclonal antibody. A hybridoma that makes the monoclonal antibody is also part of the present invention. In a particular embodiment the antibody is a chimeric antibody. Antibodies that can specifically recognize acetyl-lysine residues involved bromodomain binding are also part of the present invention.

In another aspect of the present invention a method is provided for identifying a compound that modulates the affinity of a bromodomain for a ligand (and/or protein) that comprises an acetylated lysine or an analog of an acetylated lysine (see FIG. 12). One such embodiment comprises contacting the bromodomain and the ligand in the presence of a compound under conditions that, the bromodomain and the ligand bind in the absence of the compound. The affinity of the bromodomain for the ligand is then determined (e.g., measured). A compound is identified as a compound that modulates the affinty of the bromodomain for the ligand when there is a change in the affinity of the bromodomain for the ligand in the presence of the compound. When the affinity of the bromodomain for the ligand increases in the presence of the compound, the compound is identified as a promoting agent for the bromodomain-ligand complex. When the affinity of the bromodomain for the ligand decreases in the presence of the compound, the compound is identified as an inhibitor of the bromodomain-ligand complex. In a preferred embodiment, the compound to be tested is pre-selected by performing rational drug design with the set of atomic coordinates obtained from one or more of Tables 1-6. More preferably the selecting is performed in conjunction with computer modeling. In a particular embodiment, the compound is selected by performing rational drug design with the set of atomic coordinates obtained from a set of atomic coordinates defining the three-dimensional structure of a bromodomain consisting of the amino acid sequence of SEQ ID NO:7 alone or with acetyl-histamine.

The present invention also provides a method of identifying a compound that modulates the stability of a bromodomain-ligand binding complex. Preferably the ligand comprises either an acetyl-lysine or an analog of acetyl-lysine. One such embodiment comprises contacting the bromodomain-ligand binding complex in the presence of the compound under conditions in which the bromodomain-ligand binding complex forms in the absence of the compound. The stability of the bromodomain-ligand binding complex is then determined (e.g., measured). A compound is identified as a compound that modulates the stability of the bromodomain-ligand binding complex when there is a change in the stability of the bromodomain-ligand binding complex in the presence of that compound. When the stability of the bromodomain-ligand binding complex increases in the presence of the compound, the compound is identified as a stabilizing agent. When the stability of the bromodomain-ligand binding complex decreases in the presence of the compound, the compound is identified as an inhibitor. In a preferred embodiment, the compound to be tested is pre-selected by performing rational drug design with the set of atomic coordinates obtained from one or more of Tables 1-6. More preferably the selecting is performed in conjunction with computer modeling. In a particular embodiment, the compound is selected by performing rational drug design with the set of atomic coordinates obtained from a set of atomic coordinates defining the three-dimensional structure of a bromodomain consisting of the amino acid sequence of SEQ ID NO:7 alone or with acetyl-histamine.

As anyone having skill in the art of drug development would readily understand, the potential drugs selected by the above methodologies can be refined by re-testing in appropriate drug assays, including those disclosed herein. Chemical analogs of such potential drugs can be obtained (either through chemical synthesis or drug libraries) and be analogously tested. Therefore, methods comprising successive iterations of the steps of the individual drug assays, as exemplified herein, using either repetitive or different binding studies, or transcription activation studies or other such studies are envisioned in the present invention. In addition, potential drugs may be identified first by rapid throughput drug screening, as described below, prior to performing computer modeling on a potential drug using the three-dimensional structure of the bromodomain.

The present invention further comprises all of the potential, selected, and putative compounds (drugs) identified by the methods of the present invention, as well as the final drugs themselves identified with the methods of the present invention.

The present invention further provides a method for identifying a potential binding partner for a protein (e.g., a histone) comprising an acetyl-lysine. One such embodiment comprises contacting the protein with a polypeptide comprising a bromodomain. In a preferred embodiment the bromodomain comprises the amino acid sequence of SEQ ID NO:3. In particular embodiments the bromodomain has the amino acid sequence of SEQ ID NO:7, or SEQ ID NO:8, or SEQ ID NO:9, or SEQ ID NO:10, or SEQ ID NO: 11, or SEQ ID NO: 12, or SEQ ID NO: 13, or SEQ ID NO: 14, or SEQ ID NO:15, or SEQ ID NO:16, or SEQ ID NO: 17, or SEQ ID NO:18, or SEQ ID NO:19, or SEQ ID NO:20, or SEQ ID NO:21, or SEQ ID NO: 22, or SEQ ID NO:23, or SEQ ID NO:24, or SEQ ID NO:25, or SEQ ID NO:26, or SEQ ID NO:27, or SEQ ID NO:28, or SEQ ID NO:29, or SEQ ID NO:30, or SEQ ID NO: or SEQ ID NO:31, or SEQ ID NO:32, or SEQ ID NO: 33, or SEQ ID NO:34, or SEQ ID NO:35, or SEQ ID NO:36, or SEQ ID NO:37, or SEQ ID NO:38, or SEQ ID NO: or SEQ ID NO:39, or SEQ ID NO:40, or SEQ ID NO:41, or SEQ ID NO:42.

The present invention further provides a method for identifying a protein having a bromodomain. One such embodiment comprises contacting a cellular extract with a peptide comprising an acetyl-lysine and/or an acetyl-lysine analog.

The present invention further provides agents that can inhibit the binding of a bromodomain with a protein comprising an acetyl-lysine. In one embodiment the agent is ISYGR-AcK-KRRQRR (SEQ ID NO:4). In another embodiment the agent is ARKSTGG-AcK-APRKQL (SEQ ID NO:5). In still another embodiment the agent is QSTSRHK-AcK-LMFKTE (SEQ ID NO:6). In yet another embodiment the agent is an analog of acetyl-lysine (see FIGS. 12 and 13). One particular analog of acetyl-lysine is acetyl-histamine. In still another embodiment the agent is an antibody that recognizes an acetyl-lysine of a protein binding partner of a bromodomain. In a preferred embodiment the agent is an antibody raised against a ZA loop of a bromodomain. These agents can be used as pharmaceuticals in compositions that contain a pharmaceutically acceptable carrier for example, or in the various drug assays of the present invention, serving as controls to demonstrate specificity.

The present invention further provides an apparatus that comprises a representation of a bromodomain or a bromodomain-ligand complex (e.g., the Tat-P/CAF complex). One such apparatus is a computer that comprises the representation of the bromodomain or a bromodomain-ligand complex in computer memory. In one embodiment, the computer comprises a machine-readable data storage medium which contains data storage material that is encoded with machine-readable data which comprises the atomic coordinates from a bromodomain or a bromodomain-ligand complex. Preferably the computer comprises a machine-readable data storage medium which contains data storage material that is encoded with machine-readable data which comprises a portion or all of the structural coordinates contained in Tables 1-6 and 10-14. In one embodiment, the computer comprises a machine-readable data storage medium which contains data storage material that is encoded with machine-readable data which comprises the structural coordinates for the Tat-P/CAF complex. More preferably the computer further comprises a working memory for storing instructions for processing the machine-readable data, a central processing unit coupled to both the working memory and to the machine-readable data storage medium for processing the machine readable data into a three-dimensional representation of the Tat-P/CAF complex, for example. In a preferred embodiment, the computer also comprises a display that is coupled to the central-processing unit for displaying the three-dimensional representation.

In addition, the present invention provides methods of identifying compounds that modulate the affinity of P/CAF for Tat that is acetylated at the lysine residue at position 50 of SEQ ID NO:45. In one such embodiment the method comprises contacting the bromodomain of P/CAF or a fragment thereof with a binding partner in the presence of the compound under conditions in which the bromodomain of P/CAF and the binding partner bind in the absence of the compound. The affinity of the bromodomain of P/CAF and the binding partner is then determined (e.g., measured). When there is a change in the affinity of the bromodomain of P/CAF for the binding partner in the presence of the compound, the compound is identified as a modulator. In one embodiment of this type the binding partner is Tat that is acetylated at the lysine residue at position 50 of SEQ ID NO:45. In a preferred embodiment the binding partner is a fragment of Tat comprising an acetyl-lysine at position 50. In still another embodiment the binding partner is an analog of the fragment of Tat comprising an acetyl-lysine at position 50. When the affinity of the bromodomain of P/CAF for the binding partner increases in the presence of the compound, the compound is identified as a Tat-P/CAF complex promoting agent, whereas when the affinity of the bromodomain of P/CAF for the binding partner decreases in the presence of the compound, the compound is identified as an inhibitor of the Tat-P/CAF complex.

In a preferred embodiment the compound is selected by performing rational drug design with the set of atomic coordinates obtained from one or more of Tables 1-5 and 10-14. More preferably the selection is performed in conjunction with computer modeling. Compounds selected by these methods are also part of the present invention. Preferably the compound is a small organic molecule. More preferably the compound is an analog of acetyl-lysine. Even more preferably, the compound is not included in Table 15-1 to 15-33.

The present invention also provides methods of identifying a compound that modulates the stability of the binding complex formed between P/CAF and Tat that is acetylated at the lysine residue at position 50 of SEQ ID NO:45. In one such embodiment the method comprises contacting the bromodomain of P/CAF or a fragment thereof with a binding partner in the presence of the compound under conditions in which the bromodomain of P/CAF and the binding partner bind in the absence of the compound. The stability of the bromodomain of P/CAF and the binding partner is then determined (e.g., measured). When there is a change in the stability of the binding complex between the bromodomain of P/CAF and the binding partner in the presence of the compound, the compound is identified as a modulator. In one embodiment of this type the binding partner is Tat that is acetylated at the lysine residue at position 50 of SEQ ID NO:45. In a preferred embodiment the binding partner is a fragment of Tat comprising an acetyl-lysine at position 50. In still another embodiment the binding partner is an analog of the fragment of Tat comprising an acetyl-lysine at position 50. When the stability of the bromodomain of P/CAF for the binding partner increases in the presence of the compound, the compound is identified as a stabilizing agent, whereas when the stability of the bromodomain of P/CAF for the binding partner decreases in the presence of the compound, the compound is identified as an inhibitor of the Tat-P/CAF complex. In a preferred embodiment the compound is selected by performing rational drug design with the set of atomic coordinates obtained from one or more of Tables 1-5 and 10-14. More preferably the selection is performed in conjunction with computer modeling. Compounds identified by these methods are also part of the present invention. Preferably the compound is an analog of acetyl-lysine. More preferably the compound is a small organic molecule not included in Table 15-1 to 15-33.

The present invention also provides agents that can modulate the binding of P/CAF and Tat. In a preferred embodiment the agent is a small organic molecule. Preferably the agent inhibits and/or destabilizes the binding of P/CAF with Tat. Preferably the agent is an analog of acetyl-lysine. More preferably the agent is not included in FIG. 13.

Another aspect of the present invention provides methods of preventing, and/or retarding the progression and/or treating HIV infection in an individual. One such method employs administering to the individual compounds that modulate the Tat-P/CAF complex selected by performing rational drug design with the set of atomic coordinates obtained from one or more of Tables 1-5 and 10-14. In a preferred embodiment the compound administered is an acetyl-lysine analog. In a particular embodiment this compound is a small organic molecule contained in Table 15-1 to 15-33. Preferably the compound either de-stabilizes or inhibits the Tat-P/CAF complex.

Accordingly, it is a principal object of the present invention to provide the three-dimensional coordinates of a bromodomain.

It is a further object of the present invention to provide the three-dimensional coordinates of a bromodomain complexed with acetyl-histamine.

It is a further object of the present invention to provide the three-dimensional coordinates of the Tat-P/CAF complex.

It is a further object of the present invention to provide an assay for identifying proteins that contain bromodomains that bind proteins that comprise acetyl-lysine.

It is a further object of the present invention to provide methods of identifying drugs that can modulate the bromodomain-acetyl-lysine binding complex.

It is a further object of the present invention to provide methods of identifying drugs that can inhibit the binding of a bromodomain to a protein containing acetyl-lysine.

It is a further object of the present invention to provide methods of identifying drugs that can modulate the Tat-P/CAF binding complex.

It is a further object of the present invention to provide methods of identifying drugs that can inhibit the binding/formation of the Tat-P/CAF binding complex.

It is a further object of the present invention to provide methods that incorporate the use of rational design for identifying such drugs.

It is a further object of the present invention to provide a method of identifying drugs that can treat leukemia.

It is a further object of the present invention to provide a method of identifying drugs that can treat, retard the progression, prevent and/or cure AIDS.

These and other aspects of the present invention will be better appreciated by reference to the following drawings and Detailed Description.

BRIEF DESCRIPTION OF THE DRAWINGS

FIGS. 2A-2B shows the stereoview of the $C_\alpha$ trace of 30 superimposed NMR-derived structures of the bromodomain (residues 722-830). The N-terminal four residues (SKEP) (residues 1-4 of SEQ ID NO: 7) which are structurally disordered are omitted for clarity. For the final 30 structures, the root-mean-square deviations (RMSDs) of the backbone and all heavy atoms are 0.63±0.11 Å and 1.15±0.12 Å for residues 723-830, respectively. The RMSDs of the backbone and all heavy atoms for the four α-helices (residues 727-743, 770-776, 785-802, and 807-827), are 0.34±0.04 Å and 0.87±0.06 Å, respectively. FIGS. 2C-2D show the stereoview of the bromodomain structures from the bottom of the protein, which is rotated approximately 90 from the orientation in FIGS. 2A-2B. FIG. 2E shows the Ribbons [Carson, M., *J. Appl. Crystallogr.* 24:958-961 (1991)] depiction of the averaged minimized NMR structure of the P/CAF bromodomain. The orientation of FIG. 2E is as shown in FIGS. 2A-2B. FIGS. 2F-2G are schematic representations of the overall topology of the up-and-down four-helix bundle folds with the opposite handedness. The left-handed fold is seen in bromodomain, cytochrome $b_5$, and T4 lysozyme (left, FIG. 2F), whereas the right-handed four-helix bundles are observed in proteins such as hemerythrin and cytochrome $b_{562}$ (right, FIG. 2G) [Richardson, J., *Adv. Protein Chem.*, 34:167-339 (1989); Presnell and Cohen, *Proc. Natl. Acad. Sci. USA* 86:6592-6596 (1989)]. FIG. 2H is a molecular surface representation of the electrostatic potential (blue=positive; red=negative) of the bromodomain calculated in GRASP [Nicholls et al., *Biophys. J.* 64:166-170 (1993)]. The hydrophobic and aromatic residues (Tyr809, Tyr802, Tyr760, Ala757, and Val752) located between the ZA and BC loops are indicated.

FIG. 3A shows the superimposed region of the 2D $^{15}$N-HSQC spectra of the bromodomain (approximately 0.5 mM) in its free form (red) and complexed to the AcK-containing H4 peptide (molar ratio 1:6) (black). FIG. 3B is the Ribbon and dotted-surface diagram of the bromodomain depicting the location of the lysine-acetylated H4 peptide binding site. The color coding reflects the chemical shift changes ($\Delta\delta$) of the backbone amide $^1$H and $^{15}$N resonances upon binding to the AcK peptide as observed in the $^{15}$N-HSQC spectra. The normalized weighted average of the chemical shift changes was calculated by $\Delta_{av}/\Delta_{max}=[\Delta\delta^2_{NH}+\Delta\delta^2_N/25)/2]^{1/2}/\Delta_{max}$, where $\Delta_{max}$ is the maximum weighted chemical shift difference observed for Tyr809 (0.16 ppm). The backbone atoms are color-coded in red, yellow, or green for residues that have $\alpha_{av}/\Delta_{max}$ of >0.6 (Tyr809, Glu808, Asn803, and Ala757), 0.2-0.6 (Ala813, Tyr802, Tyr760, and Val752), or <0.2 (Cys812, Ser807, Cys799, Phe796, and Phe748), respectively. The non-perturbed residues are shown in blue. FIG. 3C shows the chemical structures of acetyl-lysine, acetyl-histamine, and acetyl-histidine.

FIG. 6D shows the binding of the CBP of the bromodomain to the Tat AcK50 peptide. AcK is an acetyl-lysine residue

FIG. 10A shows the effects of the point mutation of the individual residues of the bromodomain to alanine on the protein binding to the lysine-acetylated Tat peptide. FIG. 10B is an assessment of the peptide residue mutation on its binding to the P/CAF bromodomain.

DETAILED DESCRIPTION OF THE INVENTION

The present invention identifies a general binding partner (ligand) for the protein motif known as the bromodomain. Indeed, by combining structural and site-directed mutagenesis studies the present invention demonstrates that bromodomains can interact specifically with acetyl-lysine (AcK), making them the first protein modules known to exhibit such interactions. Like other modular domains, such as Src homology-2 (SH2) and phosphotyrosine binding (PTB) domains, which specifically interact with phosphotyrosine-containing proteins, the bromodomain/acetyl-lysine recognition provides a means to regulate protein-protein interactions via protein lysine acetylation. The nature of the acetyl-lysine recognition by the bromodomain is similar to that of histone acetyltransferase interaction with acetyl-CoA. The present invention therefore couples for the first time, the functionality of the bromodomain with the HAT activity of coactivators in the regulation of gene transcription.

The present invention further provides both a nuclear magnetic resonance (NMR) structure of the bromodomain from the HAT coactivator P/CAF (p300/CBP-associated factor) as well as the structure for the P/CAF bromodomain in complex with acetyl-histamine. The structure reveals an unusual left-handed up-and-down four-helix bundle.

The results disclosed herein explain prior deletion experiments which showed that the bromodomain is indispensable for the function of GCN5 in yeast. Bromodomain-AcK binding also appears to be important for the assembly and activity of multiprotein complexes in transcriptional activation. The results reported herein therefore form the foundation for identifying specific biological ligands and for defining the molecular mechanisms by which the extensive family of bromodomains participate in chromatin remodeling and transcriptional activation As disclosed herein, the binding partner for the bromodomain is a peptide or protein comprising an acetyl-lysine (AcK). Interestingly, whereas a free acetyl-lysine does not appear to bind the bromodomain, an analog of the acetyl-lysine, acetyl-histamine, does. This is most likely due to the additional charge present in the free amino acid. Consistently, free acetyl-histidine also does not to bind the bromodomain.

In addition, as disclosed herein, the gene transactivation of HIV-1 Tat protein requires lysine-acetylation at amino acid residue 50 of Tat (see SEQ ID NO:45) by the transcription co-activator p300/CBP and the subsequent formation of a binding complex between the Tat having the acetylated lysine with P/CAF. The binding complex between P/CAF and Tat is mediated via the bromodomain of P/CAF and the acetylated lysine of Tat. Indeed, this binding is required for the gene transactivation activity of Tat and thus, for HV-1 expression and replication.

Figure 1:
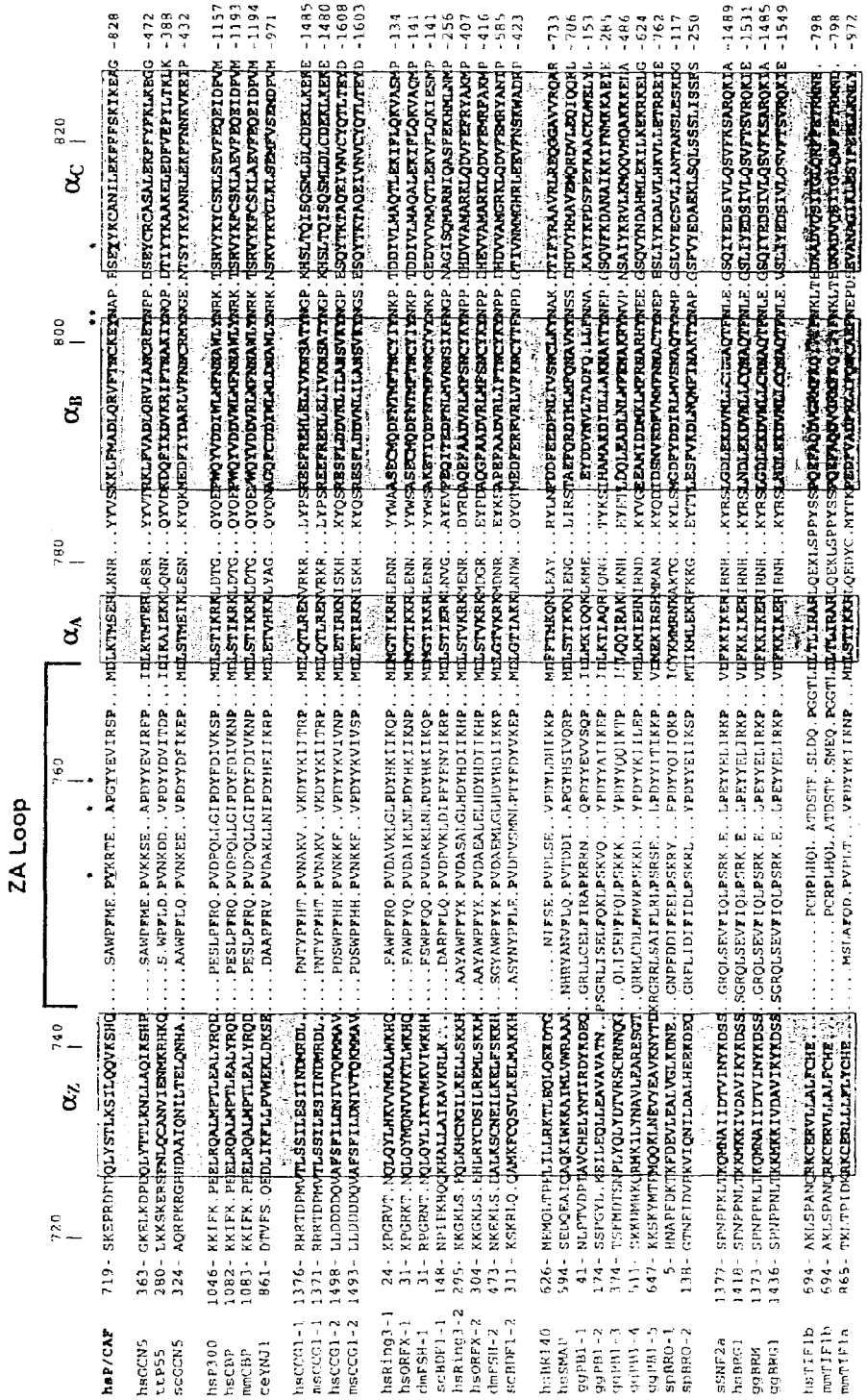
FIG. 1. Structure-based sequence alignment of a selected number of bromodomains. The sequences were aligned based on the NMR-derived structure of the P/CAF bromodomain, and the predicated four a-helices are shown in green boxes. Bromodomains are grouped on the basis of the sequence and/or functional similarities as described by Jeanmougin et al., [Trends in Biochemical Sciences, 22:151-153 (1997)]. Residue numbers of the P/CAF bromodomain are indicated above its sequence. Three absolutely conserved residues, corresponding to Pro751, Pro767, and Asn803 in the P/CAF bromodomain, are shown in red. Highly conserved residues are colored in blue. The residues of the P/CAF bromodomain that interact with acetyl-histamine, as determined by intermolecular NOEs, are indicated by asterisks. The ZA loop, which is critical for acetyl-lysine binding, for each of the indicated bromodomains is also identified. The underlined residues were changed individually by site-directed mutagenesis to Ala. Genbank accession numbers for the proteins are as indicated in Table 8, in the Example below, along with the SEQ ID NOs. for the bromodomain sequences. Specifically, hsp/CAF (SEQ ID NO:7) hsGCN5 (SEQ ID NO:8), ttP55 (SEQ ID NO:9), scGCN5 (SEQ ID NO:10), hsP300 (SEQ ID NO:11), hsCBP (SEQ ID:12), mmCBP (SEQ ID NO:13), ceYNJ1 (SEQ ID NO:14), hsCCG1 -1 (SEQ ID NO:15), msCCG1-1 (SEQ ID NO:16), hsCCG1-2 (SEQ ID NO:17), msCCG1-2 (SEQ ID NO:18), hsRing3-1 (SEQ ID NO:19), hsOREX1 (SEQ ID NO:20), dmFSH1 (SEQ ID NO:21) hsBR140(SEQ ID NO:27) hsSMAP (SEQ ID NO:28), ggPB1 (SEQ ID NO:29), ggPB1-2 (SEQ ID NO:30), ggPB1-3 (SEQ ID NO:31), ggPB1-4 (SEQ ID NO:32), ggPB1-5 (SEQ ID NO:33), spBRO-1 (SEQ ID NO: 34), spBRO-2 (SEQ ID NO:35 ), hsSNf2a (SEQ ID NO:36), hsBRGL (SEQ ID NO:37), ggBRM (SEQ ID NO:38), ggBRG1 (SEQ ID NO:39), hsTIF1b (SEQ ID NO:40), mmTIF1b (SEQ ID NO:41), and mmTIF1a (SEQ ID NO:42) are exemplified.
Figures 2A, 2B, 2C, 2D:
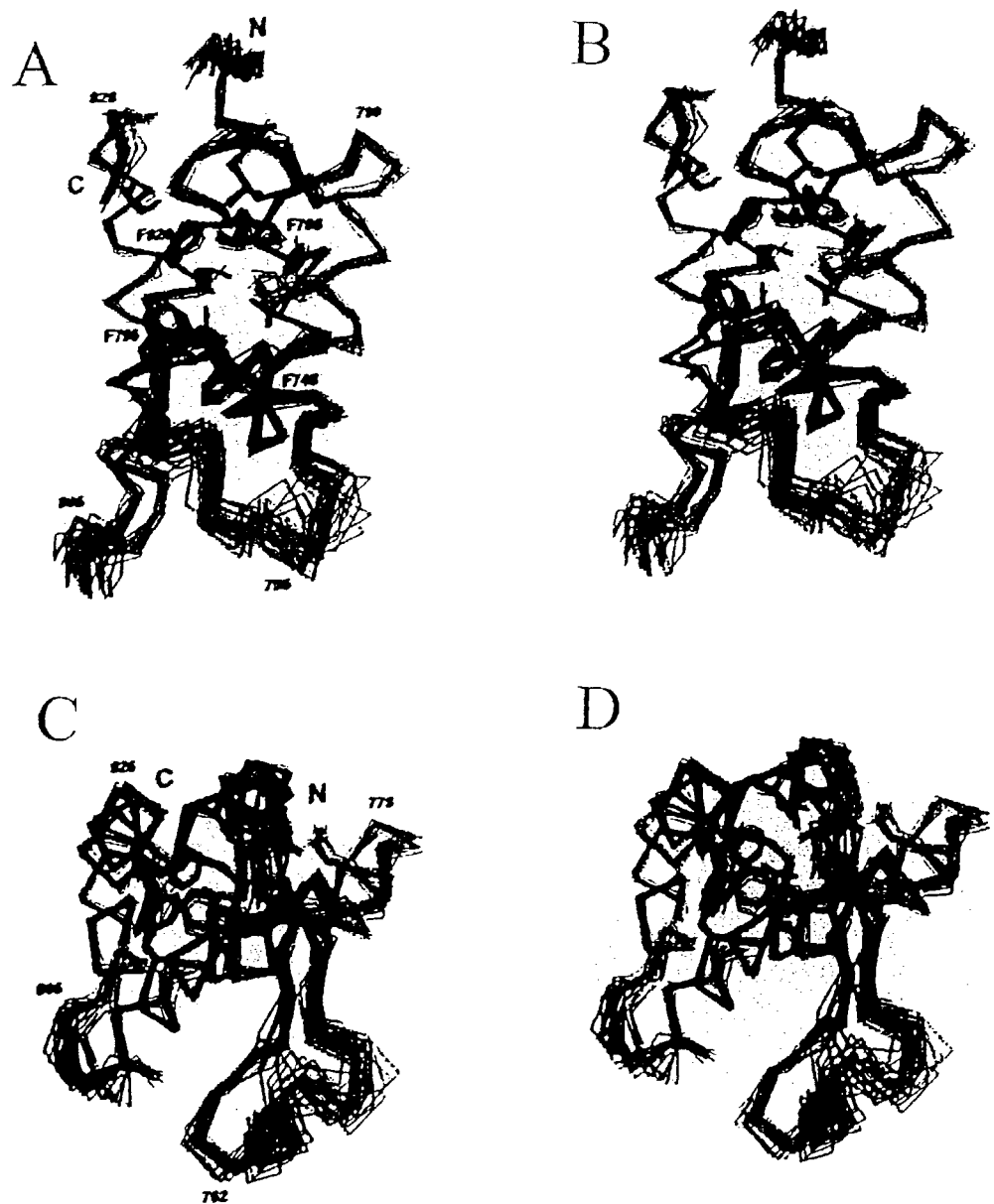
FIGS. 2A-2H depict the structure of the P/CAF bromodomain.

The present invention further provides a key region of the bromodomain for the interaction with its acetyl-lysine binding partner, the ZA loop. The amino acid sequence of the ZA loop is defined in FIG. 1 for a number of bromodomains and is depicted in FIG. 2A for P/CAF. In a particular embodiment, the ZA loop has between about 21 and 40 amino acid residues comprising the amino acid sequence:

$F\ X_{2-3}\ P\ X_{5-8}\ J_{P/K/H}\ X\ Y\ J_{Y/F/H}\ X_5\ P\ J_{M/I/V}\ D$ (SEQ ID NO:3)

more preferably the ZA loop has about 23 to 34 amino acid residues and comprises the amino acid sequence:

$X_2\ F\ X_{2-3}\ P\ X_{5-8}\ J_{P/K/H}\ X\ Y\ J_{Y/F/H}\ X_5\ P\ J_{M/I/V}\ D$ (SEQ ID NO:43)

In a specific embodiment, the ZA loop has between about 20 and 64 amino acid residues comprising the amino acid sequence:

$F\ X_{2-4}\ V\ X_{2-4}\ E\ X_{2-4}\ Y\ X_{1-3}\ V J_{I/L/M/V}$ (SEQ ID NO:48)

(1) The single letter amino acid code is used in this description, i.e., "F" for phenylalanine; "P" for proline; "Y" for tyrosine; and "D" for aspartic acid.

(2) "X" indicates any amino acid (an undesignated amino acid); and X, $X_2$, $X_{2-3}$, $X_5$, and $X_{5-8}$ indicates one undesignated amino acid, two consecutive undesignated amino acids, two or three consecutive undesignated amino acids, five consecutive undesignated amino acids, and five to eight consecutive undesignated amino acids respectively.

(3) "J" indicates that identity of the amino acid is restricted to a particular group, again the one letter code is used (i) $J_{P/K/H}$ is either proline, lysine or histidine.

(ii) $J_{Y/F/H}$ is either tyrosine, phenylalanine or histidine.

(iii) $J_{M/I/V}$ is either methionine, isoleucine, or valine.

(iv) $J_{I/L/M/V}$ is either isoleucine, leucine, methionine, or valine

Since this region of the bromodomain is important in binding its acetyl-lysine binding partner, antibodies specifically raised against this region are also included in the present invention. In a particular embodiment, the antibody is a humanized chimeric antibody that can be used in therapeutic treatment. Thus monoclonal, chimeric, and polyclonal antibodies raised against bromodomains, preferably against amino acid residues in the ZA loop region are part of the present invention. In a specific embodiment the antibody is raised against a peptide, fusion peptide or conjugated peptide consisting of amino acid residues 746 to 765 of SEQ ID NO:2, i.e., WPFMEPVKRTEAPGYYEVIR (SEQ ID NO:44). In another embodiment the antibody is raised against a peptide, fusion peptide or conjugated peptide consisting of amino acid residues 748 to 809 of SEQ ID NO:2 (which is SEQ ID NO:49).

Such antibodies can be used in the treatment of leukemia or AIDs for example. Alternatively, these antibodies can be used in drug discovery assays.

Analogously, the present invention provides peptides derived from the HIV-1 Tat protein. In one such embodiment the peptide comprises 7 to 21 amino acid residues comprising the amino acid sequence $YGRKX_{1-3}RQ$ (SEQ ID NO:46)

In a specific embodiment the peptide fragment of Tat has ten amino acid residues and the amino acid sequence:

SYGRKKRRQR (SEQ ID NO:47)

Preferably the lysine corresponding to lysine50 of Tat (see SEQ ID NO:45) is acetylated. These peptide fragments can be used in the drug assays of the present invention and/or as antigens for antibodies that specifically interfere with the interaction (e.g., binding) of Tat with P/CAF interaction.

The present invention provides the first detailed structural information regarding a bromodomain and a bromodomain complexed with its acetylated binding partner. The present invention therefore provides the three-dimensional structure of the bromodomain and abromodomain acetylated binding partner complex. Since the interaction of the bromodomain with a histone for example, can play a significant role in chromatin remodeling/regulation, the structural information provided herein can be employed in methods of identifying drugs that can modulate basic cell processes by modulating the transcription. In a particular embodiment, the three-dimensional structural information is used in the design of a small organic molecule for the treatment of cancer or as disclosed below, HIV-1 infection and/or AIDs. In addition, the present invention provides a critical structural feature for a class of inhibitors (acetyl-lysine analogs) of the interaction between bromodomains and their protein binding partners which contain an acetylated-lysine (e.g., Tat with P/CAF), see FIG. 12, as well as a compilation of compounds that share this critical feature, see Table 15-1 to 15-33.

Indeed, the bromodomain and lysine-acetylated protein interaction can now be implicated to play a causal role in the development of a number of diseases including cancers such as leukemia. For example, chromatin remodeling plays a central role in the etiology of viral infection and cancer [Archer and Hodin, Curr. Opin. Genet. Biol. 9:171-174 (1999); Jacobson and Pillus, Curr. Opin. Genet. Biol. 9:175-184 (1999)]. Both altered histone acetylation/deacetylation and aberrant forms of chromatin-remodeling complexes are associated with human diseases. Furthermore, chromosomal translocation of various cellular genes with those encoding HATs and subunits of chromatin remodeling complexes have been implicated in leukomogenesis. The MOZ (monocytic leukemia zinc finger) and MLL/ALL-1 genes are frequently fused to the gene encoding the co-activator HAT CBP [Sobulo et al., Proc. Natl. Acad. Sci. USA 94:8732-8737(1997)]. The resulting fusion protein MLL-CBP contains the tandem bromodomain-PHD finger-HAT domain of CBP. It also has been shown that both the bromodomain and HAT domain of CBP are required for leukomogenesis, because deletion of either the bromodomain or the HAT domain results in loss of the MLL-CBP fusion protein's ability for cell transform. These results indicate that the CBP bromodomain, and more particularly, the ZA loop of the CBP bromodomain, is an excellent target for developing drugs that interfere with the bromodomain acetyl-lysine interaction that can be used in the treatment of human acute leukemia. In addition, an antibody (e.g., a humanized antibody) raised specifically against a peptide from the ZA loop of the CBP bromodomain could also be effective for treating these conditions.

In addition, it now known that the human immunodeficiency virus type 1 (HIV-1) trans-activator protein, Tat, is tightly regulated by lysine acetylation [Kiernan et al., *EMBO Journal* 18:6106-6118 (1999)]. HIV-1 Tat transcriptional activity is absolutely required for productive HIV viral replication [Jeang and Gatignol, *Curr. Top. Microbiol. Immunol.*, 188:123-144(1994)]. Therefore, the interaction of the acetyl-lysine of Tat with one or more bromodomain-containing proteins associated with chromatin remodeling could mediate gene transcription. More particularly, it is disclosed herein that acetylated lysine50 of Tat specifically binds to the bromodomain of P/CAF. Therefore, this particular bromodomain/lysine-acetylated Tat interaction serves as a drug target for blocking HIV replication in cells. As indicated above, an antibody raised specifically against a peptide from the ZA loop of the P/CALF bromodomain could also be effective for treating and/or preventing HIV infections including those that lead to AIDs.

In addition, based on the new structural information disclosed herein, the key amino acid residues for the binding of a given bromodomain and its binding partner can be identified and further elucidated using basic mutagenesis and standard isothermal titration calorimetry, for example. Indeed, both the critical amino acids for the bromodomain and the binding partner (i.e., apart from the acetyl-lysine) can be readily determined and are also part of the present invention.

Therefore, the results obtained from the structural and functional studies disclosed herein provide the foundation for both high throughput drug screening and structure-based rational drug design. The agents identified by this procedure are useful for ameliorating conditions involving chromatin remodeling/regulation, and/or in the treatment of cancer and/or AIDS, as indicated above.

Structure based rational drug design is the most efficient method of drug development. However, heretofore, no information has been disclosed regarding the structure of the bromodomain or more importantly, its interaction with the acetyl-lysine of its binding partner. Obtaining detailed structural information requires an extensive NMR or X-ray crystallographic analysis. By determining and then exploiting the detailed structural information of the bromodomain and of the bromodomain/acetyl-histamine (exemplified by NMR analysis below) the present invention provides novel methods for developing new drugs through structure based rational drug design.

Figure 2E:
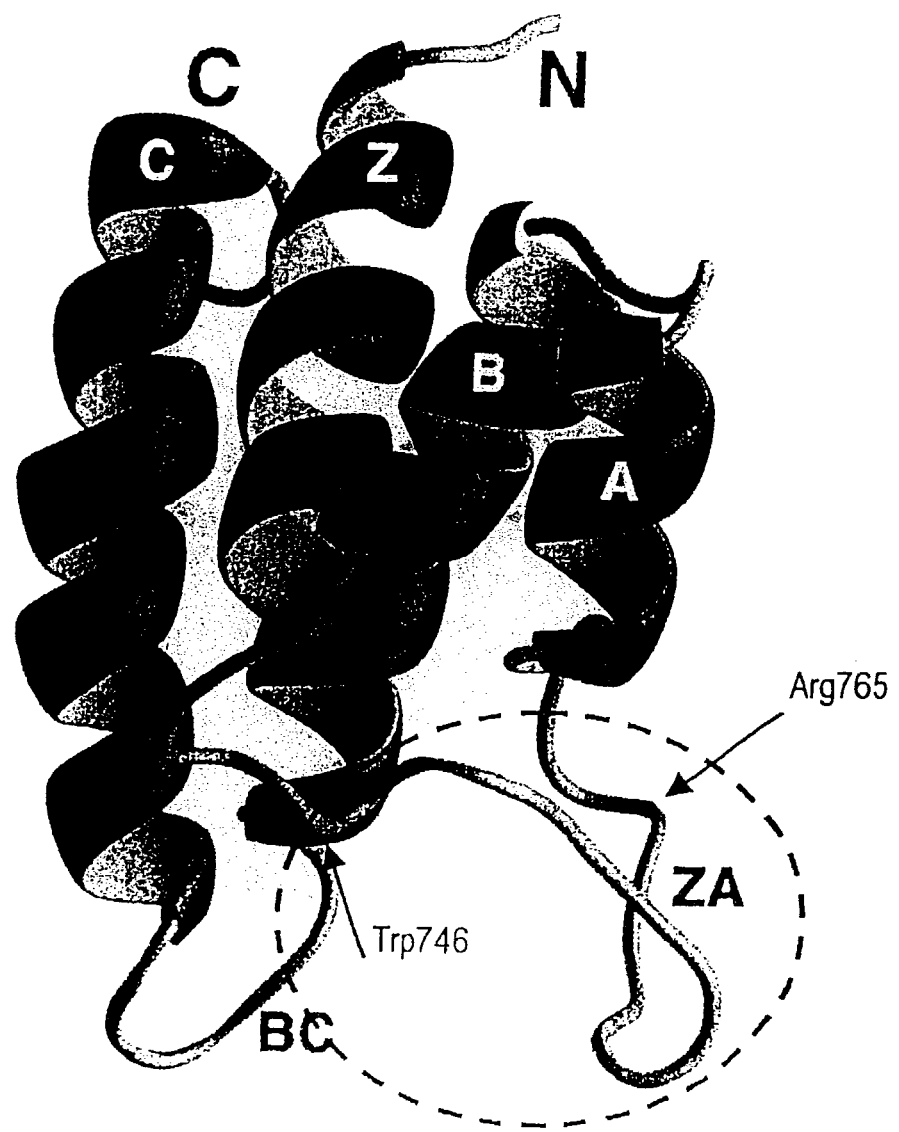
Figure 4:
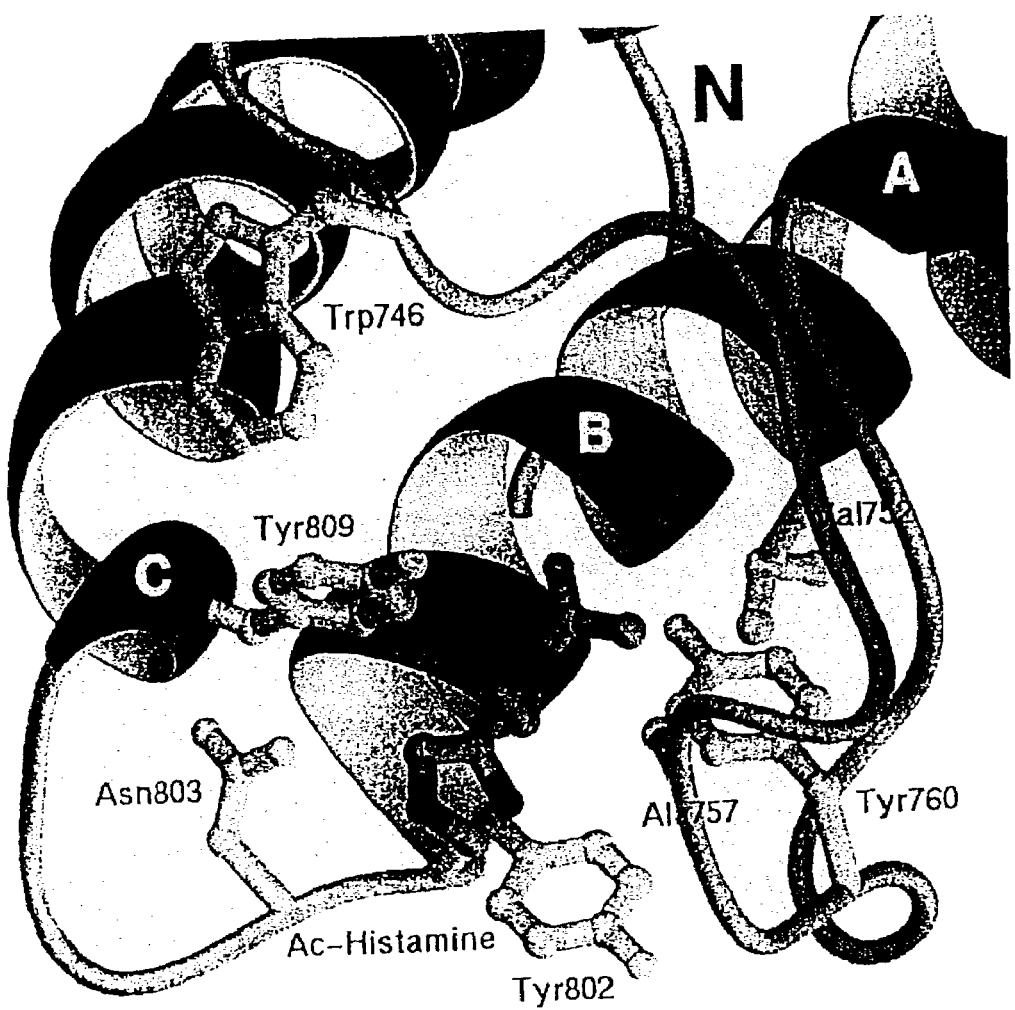
FIG. 4 depicts the acetyl-lysine binding pocket. This is the Ribbons [Carson, M., *J. Appl. Crystallogr.* 24:958-961 (1991)] depiction of a portion of the P/CAF bromodomain complexed with the acetyl-histamine. The ligand is color-coded by atom type.
Figure 9:
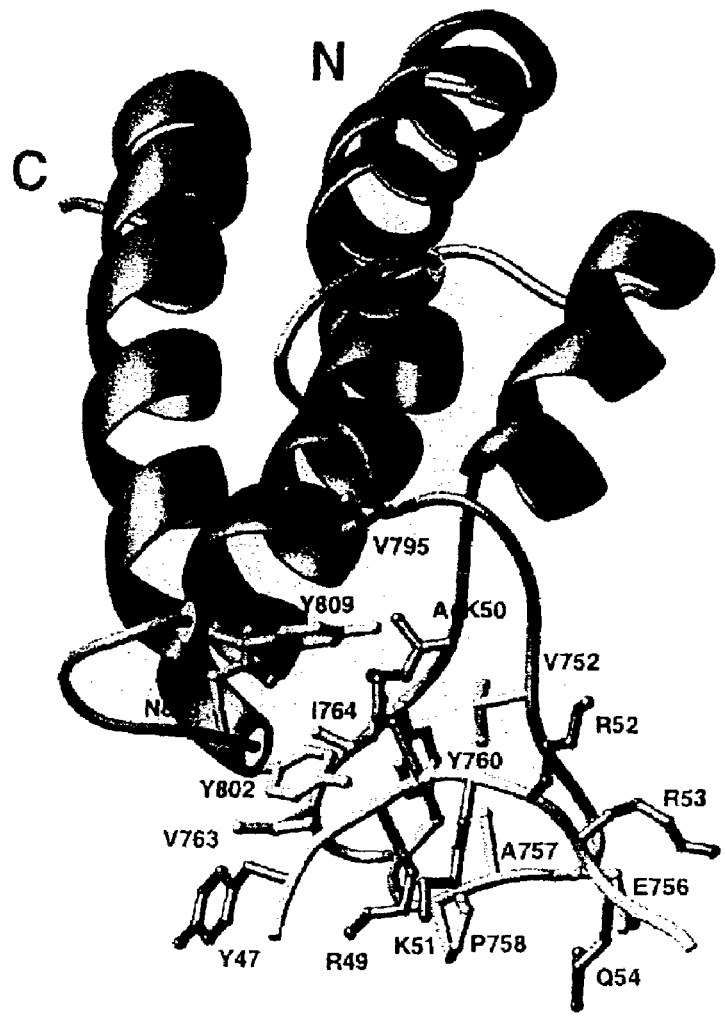
FIG. 9 depicts the structure of the P/CAF bromodomain in the complex with the lysine-acetylated Tat peptide (SYGR-AcK-KRRQRC, SEQ ID NO:50, where AcK is acetyl-lysine residue). The side chains of the amino acid residues on both the protein (green) and peptide (dark orange) that showed intermolecular NOEs in the NMR spectra are displayed.

Thus the present invention provides representative sets of the atomic structure coordinates of the free form of the P/CAF bromodomain (Table 5), of the P/CAF bromodomain-acetyl-histamine complex (Table 6) and of the Tat-P/CAF complex (Table 10) which were all obtained by NMR analysis. A Ribbon diagram of the three-dimensional structure of the P/CAF bromodomain is depicted in FIG. 2E, whereas the P/CAF bromodomain acetyl-lysine binding pocket is depicted in FIG. 4 and the Tat-P/CAF complex is depicted in FIG. 9. The present invention also provides the NOE-derived distance restraints, and NMR chemical shift assignments of the P/CAF bromodomain. and the Tat-P/CAF complex. The NMR chemical shift assignments of the P/CAF bromodomain are included in the chemical shift table (Table 1) for the $^1$H-$^{15}$N HSQC spectrum of P/CAF bromodomain. The unambiguous NOE-derived nter-proton Distance Restraints (Table 2), the ambiguous NOE-derived Inter-proton Distance Restraints (Table 3) and the $^1$H bonding restraints (Table 4) are also disclosed herein. The NMR chemical shift assignments of the Tat-P/CAF complex are included in the chemical shift table (Table 11) for the $^1$H—$^{15}$N HSQC spectrum of P/CAF bromodomain. The unambiguous NOE-derived Inter-proton Distance Restraints (Table 13), the ambiguous NOE-derived Inter-proton Distance Restraints (Table 14) and the $^1$H bonding restraints (Table 12) are also disclosed herein. The sample atomic coordinate data provided enable the skilled artisan to practice the invention.

In addition, Tables 1-6 and/or 10-14 are also capable of being placed into a computer readable form which is also part of the present invention. Furthermore, methods of using these coordinates and chemical shifts and related information (including in computer readable forms) either individually or together in drug assays are also provided. More particularly, such atomic coordinates can be used to identify potential ligands or drugs which will modulate the binding of a bromodomain with its binding partner.

In a particular aspect of the present invention, the lysine-acetylated Tat is shown herein to specifically bind to the bromodomain of the p300/CBP-associated factor (P/CAF) in vitro and in vivo. Structural and mutational analyses provides the identification of key amino acid residues on both the bromodomain and Tat that are important for the binding complex. The identification of these important amino acid residues further demonstrates the biological importance of this interaction for Tat transactivation activity. Together, the findings disclosed herein indicate a novel mechanism by which the lysine-acetylated Tat recruits P/CAF via a bromodomain interaction, leading to chromatin remodeling-mediated transcriptional activation of HIV-1. Furthermore, the extreme specificity of the Tat-P/CAF binding (see e.g., FIGS. 5A-5B and 10A-10B) indicates that compounds that interfere with this binding complex are not likely to interfere to otherwise related bromodomain-ligand interactions.

Therefore, the three-dimensional structural information provided by the present invention allows the identification and/or design of specific compounds that can act as modulators of crucial processes. In the case of the Tat-P/CAF interaction, such compounds can be used as drugs to inhibit HIV-1 expression in a cell and/or subsequent infection of other cells. Therefore, the inhibitors identified and/or designed by the methods disclosed can be used to prevent, treat, retard the progression, and potentially cure HIV-1 infections and AIDS.

Therefore, if appearing herein, the following terms shall have the definitions set out below.

As used herein a "bromodomain-acetyl-lysine binding complex" is a binding complex between a bromodomain or fragment thereof and either a peptide/polypeptide comprising an acetyl-lysine (or an analog of acetyl-lysine), or a free analog of acetyl-lysine, such as acetyl-histamine disclosed in the Example below. Preferably, the peptide comprises at least six amino acids in addition to the acetyl-lysine. A fragment of a bromodomain preferably comprises a ZA loop as defined below. The dissociation constant of a bromodomain-acetyl-lysine binding complex is dependent on whether the lysine residue or analog thereof is acetylated or not, such that the affinity for the bromodomain and the peptide comprising the lysine residue (for example) significantly decreases when that lysine residue is not acetylated. One example of a bromodomain-acetyl-lysine binding complex is that formed between P/CAF with Tat (the "Tat-P/CAF complex") as exemplified below.

Figure 12:
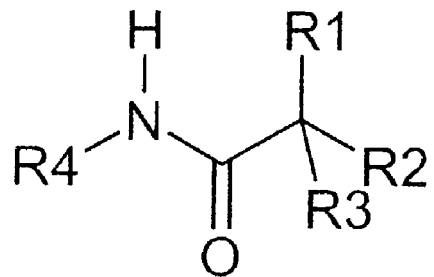
FIG. 12 depicts the chemical structure common to the acetyl-lysine analogs of the present invention. $R_1$, $R_2$, and $R_3$ can be H, $CH_3$, a halogen (e.g., F, Cl, Br, I etc.), OH, SH, or $NH_3^+$. R4 can be an alkyl (including a peptide/protein attached thereto such as a peptide comprising an acetyl-lysine in which the "N" of the structure depicted is the epsilon nitrogen (i.e., $N^\epsilon$) of a lysyl residue), or an aryl group. See also Tables 15-1 to 15-33 for examples.

As used herein the term "acetyl-lysine analog" is used interchangeably with the term "analog of acetyl-lysine" and is a compound that contains the acetyl-amine-like structure as depicted in FIG. 12. Examples of acetyl-lysine analogs are included in Table 15-1 to 15-33.

As used herein a "ZA loop" of a bromodomain is a key protion of a bromodomain that is involved in the binding of the bromodomain to the acetyl-lysine. The structure of the actual ZA loop of the bromodomain of P/CAF is depicted in FIG. 2A. As used herein, however, a ZA loop has between about 20 and 40 amino acids and preferably comprises the amino acid sequence of SEQ ID NO:3 and/or SEQ ID NO:48. More preferably the ZA loop comprises between about 23 to 34 amino acids. In a specific embodiment the ZA loop has the amino acid sequence SEQ ID NO:43. The amino acid sequence of the ZA loop for a representative number of individual bromodomains is shown in FIG. 1.

A "polypeptide" or "peptide" comprising a fragment of a bromodomain, such as the ZA loop, or a peptide or polypeptide comprising an acetyl-lysine, as used herein can be the "fragment" alone, or a larger chimeric or fusion peptide/protein which contains the "fragment".

As used herein the terms "fusion protein" and "fusion peptide" are used interchangeably and encompass "chimeric proteins and/or chimeric peptides" and fusion "intein proteins/peptides". A fusion protein comprises at least a portion of a protein or peptide of the present invention, e.g., a bromodomain, joined via a peptide bond to at least a portion of another protein or peptide including e.g., a second bromodomain in a chimeric fusion protein. In a particular embodiment the portion of the bromodomain is antigenic. Fusion proteins can comprise a marker protein or peptide, or a protein or peptide that aids in the isolation and/or purification of the protein, for example.

As used herein, and unless otherwise specified, the terms "agent", "potential drug", "compound", "test compound" or "potential compound" are used interchangeably, and refer to chemicals which potentially have a use as an inhibitor or activator/stabilizer of bromodomain-acetyl-lysine binding. Therefore, such "agents", "potential drugs", "compounds" and "potential compounds" may be used, as described herein, in drug assays and drug screens and the like.

As used herein a "small organic molecule" is an organic compound, including a peptide [or organic compound complexed with an inorganic compound (e.g., metal)] that has a molecular weight of less than 3 Kilodaltons. Such small organic molecules can be included as agents, etc. as defined above.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

As used herein the term "about" signifies that a value is within twenty percent of the indicated value i.e., a peptide containing "about" 20 amino acid residues can contain between 16 and 24 amino acid residues.

General Techniques for Constructing Nucleic Acids That Encode the Bromodomains and Fragments Thereof (Incuding, ZA Loops); and the Bromodomain Binding Partners of the Present Invention.

In accordance with the present invention there may be employed conventional molecular biology, microbiology, and recombinant DNA techniques within the skill of the art. Such techniques are explained fully in the literature. See, e.g., Sambrook and Russell *Molecular Cloning: A Laboratory Manual*, Third Edition (2001) Vols. I-E, Cold Spring Harbor Laboratory Press, Cold Spring Harbor, N.Y. (herein "Sambrook and Russell, 2001"), Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRE Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook et al., 1989 supra, Sambrook and Russell, 2001]. The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5×or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived [see Sambrook et al., 1989 supra, 9.50-10.51, Sambrook and Russell, 2001]. For hybridization with shorter nucleic acids, i.e., oligonucleotides, the position of mismatches becomes more important, and the length of the oligonucleotide determines its specificity [see Sambrook et al., 1989 supra, 11.7-11.8, Sambrook and Russell, 2001]. Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)]. Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

Two DNA sequences are "substantially homologous" when at least about 60% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art [See, e.g., Sambrook et al., 1989 supra; DNA Cloning, Vols. I & II, supra; Nucleic Acid Hybridization, supra., and Sambrook and Russell, 2001]

As used herein an amino acid sequence is 100% "homologous" to a second amino acid sequence if the two amino acid sequences are identical, and/or differ only by neutral or conservative substitutions as defined below. Accordingly, an amino acid sequence is 50% "homologous" to a second amino acid sequence if 50% of the two amino acid sequences are identical, and/or differ only by neutral or conservative substitutions.

As used herein, DNA and protein sequence percent identity can be determined using MacVector 6.0.1, Oxford Molecular Group PLC (1996) and the Clustal W algorithm with the alignment default parameters, and default parameters for identity. These commercially available programs can also be used to determine sequence similarity using the same or analogous default parameters.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein a "heterologous nucleotide sequence" is a nucleotide sequence that is added to a nucleotide sequence of the present invention by recombinant methods to form a nucleic acid which is not naturally formed in nature. Such nucleic acids can encode fusion proteins or peptides, including chimeric proteins and peptides. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing nucleic acids encoding analogs and derivatives of the bromodomains of the present invention and polypeptides/peptides that can bind a bromodomain when a lysine of the polypeptide/peptide is acetylated, including modified fragments, that have the same or homologous functional activity as the individual fragments, and homologs thereof. The production and use of derivatives and analogs related to the fragments are within the scope of the present invention.

Due to the degeneracy of nucleotide coding sequences, other DNA sequences which encode substantially the same amino acid sequence as a nucleic acid encoding a protein comprising bromodomain or bromodomain binding partner (i.e., when post-transcriptionally acetylated) of the present invention for example, may be used in the practice of the present invention. These include but are not limited to allelic genes, homologous genes from other species, which are altered by the substitution of different codons that encode the same amino acid residue within the sequence, thus producing a silent change. Likewise, the peptides and polypeptides of the present invention include, but are not limited to, those containing, as a primary amino acid sequence, analogous portions of their respective amino acid sequences including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained;
(e) Ile for Leu or for Val or vice versa as roughly equivalent hydrophobic amino acids; and
(f) Phe for Tyr or vice versa as roughly equivalent aromatic amino acids.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Specific amino acid residues for the P/CAF bromodomain have been identified that are important for binding, indicating a potential lower stringency for the substitution of the remaining amino acids residues.

All of the peptides/fragments of the present invention can be modified by being placed in a fusion or chimeric peptide or protein, or labeled e.g., to have an N-terminal FLAG-tag, or H6 (SEQ ID NO: 61) tag. In a particular embodiment the P/CAF bromodomain fragment can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The nucleic acids encoding peptides and protein fragments of the present invention and analogs thereof can be produced by various methods known in the art. The manipulations which result in their production can occur at the gene or protein level [Sambrook et al., 1989, supra; Sambrook and Russell, 2001, supra]. The nucleotide sequence can be cleaved at appropriate sites with restriction endonuclease(s), followed by further enzymatic modification if desired, isolated, and ligated in vitro. In addition a nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson et al., *J. Biol. Chem.*, 253:6551 (1978); Zoller and Smith, DNA, 3:479-488 (1984); Oliphant et al., *Gene,* 44:177 (1986); Hutchinson et al., *Proc. Natl. Acad. Sci. U.S.A.,* 83:710 (1986)], use of TAB® linkers (Pharmacia), etc. PCR techniques are preferred for site directed mutagenesis [see Higuchi, "Using PCR to Engineer DNA", in *PCR Technology: Principles and Applications for DNA Amplification*, H. Erlich, ed., Stockton Press, Chapter 6, pp. 61-70 (1989)].

The identified and isolated nucleic acids can then be inserted into an appropriate cloning vector. A large number of vector-host systems known in the art may be used.

Protein Expression and Purification

A bacterial protein expression system can be used to make various stable isotopically labeled ($^{13}C$, $^{15}N$, and $^{2}H$) protein samples that are useful for a three-dimensional NMR structural determination of a protein complex. For example a pET14b (Novagen) bacterial expression vector can be constructed which expresses the recombinant P/CAF bromodomain as an amino-terminal His-tagged fusion protein.

Protein expression and purification can be conducted using standard procedures for His-tagged proteins [Zhou et al., *J. Biol. Chem.* 270:31119-31123 (1995)]. To optimize the level of protein expression, various bacterial growth and expression conditions can be screened, which include different *E. Coli* cell lines, and growth and protein induction temperatures. Generally, it is preferred to obtain the maximum amount of soluble protein while still inducing protein expression with a relatively low IPTG concentration e.g., ~0.2 mM (final concentration) at 16° C. As exemplified below, the bromodomain of P/CAF (residues 719-832 of SEQ ID NO:2 which is SEQ ID NO:7) was subcloned into the pET14b expression vector (Novagen) and expressed in *Escherichia coli* BL21(DE3) cells. Uniformly $^{15}$N- and $^{15}$N/$^{13}$C-labeled proteins were prepared by growing bacteria in a minimal medium containing $^{15}$NH$_4$Cl with or without $^{13}$C$_6$-glucose. A uniformly $^{15}$N/$^{13}$C-labeled and fractionally deuterated protein sample was prepared by growing the cells in 75% $^2$H$_2$O. The bromodomain was purified by affinity chromatography on a nickel-IDA column (Invitrogen) followed by the removal of poly-His tag by thrombin cleavage. The final purification of the protein was achieved by size-exclusion chromatography. The acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation. NMR samples contained approximately 1 mM protein in 100 mM phosphate buffer of pH 6.5 and 5 mM perdeuterated DTT and 0.5 mM EDTA in H$_2$O/$^2$H$_2$O (9/1) or $^2$H$_2$O.

One major advantage of using the heteronuclear multidimensional approach, as exempled herein, is that the NMR resonance assignments of a protein are obtained in a sequence-specific manner which assures accuracy and greatly facilitates data analysis and structure determination [Clore and Gronenborn *Meth. Enzymol.* 239:249-363 (1994)]. In addition, the signal overlapping problems in the protein spectra are minimized by the use of multidimensional NMR spectra, which separates the proton signals according to the chemical shifts of their attached hetero-nuclei (such as $^{15}$N and $^{13}$C). This NMR approach has been proven very powerful for structural analysis of large proteins [Clore and Gronenbom *Meth. Enzymol.* 239:249-363 (1994)]. To facilitate sequence-specific resonance assignments for the structural study, a uniformly $^{13}$C, $^{15}$N-labeled and fractionally (75%) deuterated protein sample of the bromodomain can be prepared by growing bacterial cells in 75% $^2$H$_2$O as exemplified below. Such protein samples can be used for triple-resonance NMR experiments. A triple-labeled protein sample is useful for high-resolution NMR structural studies. Because of the favorable $^1$H, $^{13}$C, and $^{15}$N relaxation rates caused by the partial deuteration of the protein, constant-time triple-resonance NMR spectra can be acquired with higher digital resolution and sensitivity [Sattler, M. & Fesik, S. W. *Structure* 4:1245-1249 (1996)]. In addition, various stable-isotopically labeled ($^{15}$N and $^{13}$C/$^{15}$N) proteins can also be prepared using this procedure.

Synthetic Polypeptides

The term "polypeptide" is used in its broadest sense to refer to a compound of two or more subunit amino acids, amino acid analogs, or peptidomimetics. The subunits are linked by peptide bonds. The terms "polypeptide", "protein", and "peptide" are used interchangeably herein, though preferably as used herein a "peptide" refers to a compound of at least two but less than fifty subunit amino acids, and a polypeptide or protein refers to compound of fifty or more amino acids. The polypeptides of the present invention may be chemically synthesized or as detailed above, genetically engineered or isolated from natural sources.

In addition, potential drugs or agents that may be tested in the drug screening assays of the present invention may also be chemically synthesized. When the peptide is to be modified, e.g., acetylated, the modification can be at any time during the peptide synthesis, including using an acetyl-lysine as a starting material or acetylating a lysine residue of a peptide after the peptide has been synthesized. In the Example below, the acetyl-lysine-containing peptides were prepared on a Milli-Gen 9050 peptide synthesizer (Perkin Elmer) using Fmoc/HITU chemistry. Acetyl-lysine was incorporated using the reagent Fmoc-Ac-Lys with BBTUIDIPEA activation.

Thus, synthetic polypeptides, prepared using the well known techniques of solid phase, liquid phase, or peptide condensation techniques, or any combination thereof, can include natural and unnatural amino acids. Amino acids used for peptide synthesis may be standard Boc (N$^\alpha$-amino protected N$^\alpha$-t-butyloxycarbonyl) amino acid resin with the standard deprotecting, neutralization, coupling and wash protocols of the original solid phase procedure of Merrifield [*J. Am. Chem. Soc.*, 85:2149-2154 (1963)], or the base-labile N$^\alpha$-amino protected 9-fluorenylmethoxycarbonyl (Fmoc) amino acids first described by Carpino and Han [*J. Org. Chem.*, 37:3403-3409 (1972)]. Both Fmoc and Boc N$^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N$^\alpha$-protecting groups that are familiar to those skilled in this art. Solid phase peptide synthesis may be accomplished by techniques familiar to those in the art and provided, for example, in Stewart and Young [Solid Phase Synthesis, Second Edition, Pierce Chemical Co., Rockford, Ill. (1984)] and Fields and Noble [*Int. J. Pept. Protein Res.*, 35:161-214 (1990)], or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Alternative synthetic amino acids that can be used include ornithine for lysine, fluorophenylalanine for phenylalanine, and norleucine for leucine or isoleucine. Other synthetic amino acids include 2-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, 4-hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, and N-methylvaline. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., R$_1$—CH$_2$—NH—R$_2$, where R$_1$ and R$_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, Life Sciences, 31:189-199 (1982); Hruby et al., Biochem J., 268:249-262 (1990)]; the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson [Biophys. Biochem. Res. Commun., 94:1128-1132 (1980)]. A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, in The Peptides: Analysis, Synthesis, Biology, Vol. 3, Gross and Meienhofer, eds., Academic Press: New York, pp. 137-167 (1981); Ponsanti et al., Tetrahedron, 46:8255-8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate [Kazmierski et al., J. Am. Chem. Soc., 113:2275-2283 (1991)]; (2S,3S)-methyl-phenylalanine, (2S,3R)-methyl-phenylalanine, (2R,3S)-methyl-phenylalanine and (2R, 3R)-methyl-phenylalanine (Kazinierski and Hruby, Tetrahedron Lett. (1991)]; 2-aminotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al., J. Takeda Res. Labs., 43:53-76 (1989)]; β-carboline (D and L) [Kazmierski, Ph.D. Thesis, University of Arizona (1988)]; HIC (histidine isoquinoline carboxylic acid) [Zechel et al., Int. J. Pep. Protein Res., 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog [Kemp et al., J. Org. Chem., 50:5834-5838 (1985)]; β-sheet inducing analogs [Kemp et al., Tetrahedron Lett., 29:5081-5082 (1988); β-turn inducing analogs [Kemp et al., Tetrahedron Lett., 29:5057-5060 (1988)]; ∝-helix inducing analogs (Kemp et al., Tetrahedron Lett., 29:4935-4938 (1988)]; γ-turn inducing analogs [Kemp et al., J. Org. Chem., 54:109:115 (1989)]; and analogs provided by the following references: Nagai and Sato, Tetrahedron Lett., 26:647-650 (1985); DiMaio et al., J. Chem. Soc. Perkin Trans., p. 1687 (1989); also a Gly-Ala turn analog [Kahn et al., Tetrahedron Lett., 30:2317 (1989)]; amide bond isostere [Jones et al., Tetrahedron Lett., 29:3853-3856 (1988)]; tretrazol [Zabrocki et al., J. Am. Chem. Soc., 110:5875-5880 (1988)]; DTC [Samanen et al., Int. J. Protein Pep. Res., 35:501:509 (1990)]; and analogs taught in Olson et al., J. Am. Chem. Sci., 112:323-333 (1990) and Garvey et al., J. Org. Chem., 56:436 (1990). Conformationally restricted mimetics of beta turns and beta bulges, and peptides containing them, are described in U.S. Pat. No. 5,440,013, issued Aug. 8, 1995 to Kahn.

Structure-Based Mutation Analysis

Protein structural analysis using NMR spectroscopy has several unique advantages. In addition to high-resolution three-dimensional structural information, the chemical shift assignments for the protein obtained in the structural study further provides a map of the entire protein at the atomic level, which can be used for structure-based biochemical analysis of protein-protein interactions. For example, the information generated from the NMR structural analysis can also serve to identify specific amino acid residues in the peptide-binding site for complementary mutagenesis studies. Specific focus can be placed on those residues that display long-range NOEs (particularly the side-chain NOEs in the $^{13}$C-NOESY data) between the bromoomain and a peptide comprising an acetyl-lysine.

To ensure mutant proteins are valid for functional analysis, it can be determined as to whether a mutation results in any significant perturbation of the overall conformation of the bromodomain, particularly the effects of mutation on the acetyl-lysine binding sites. NMR spectroscopy is a powerful method for examining the effects of such a mutation on the conformation of the protein. One can readily obtain information about the global conformation of a mutant protein from the proton ($^1$H) ID spectrum, by examining the chemical shift dispersion and peak line-width of NMR signals of amide, aromatic and aliphatic protons. Moreover, 2D $^1$H-$^{15}$N HSQC spectra reveal details of the effects of a mutation on both local and global conformation of the protein, since every single $^1$H/$^{15}$N signal (both the chemical shift and line-shape) in the NMR spectrum is a "reporter" for a particular amino acid residue. Thus, to assess how mutations effect protein stability and the overall protein conformation, the $^{15}$N HSQC spectra of mutated proteins can be compared to that of the wild-type protein bromodomain.

Chemical-shift perturbations due to ligand binding have proven to be a reliable and sensitive probe for the ligand binding site of the protein. This is because the chemical-shift changes of the backbone amide groups are likely to reflect any changes in protein conformation and/or hydrogen bonding due to the peptide/ligand binding. To examine the effects of a mutation on the ligand binding (in this case the ligand is a peptide comprising an acetyl-lysine), peptide titration experiments can be conducted by following the changes of $^1$H/$^{15}$N signals of the mutant proteins as a function of the peptide concentration. These experiments indicate whether the acetyl-lysine binding site remains the same or changes in the mutants relative to the wild type protein. The effects of the mutation on the peptide binding affinity can also be examined by NMR spectroscopy. If the mutated proteins result in the reduction of the binding affinity, a change of the exchange phenomenon between the free and the ligand-bound signals should be observed in NMR spectrum. If the reduction in binding affinity causes the peptide binding to change from a slow exchange rate to a fast exchange rate, on the NMR time scale, then the peptide binding affinity can be determined from the NMR titration experiment. From these mutation analyses key amino acid residues that are important for binding a peptide comprising the acetyl-lysine can be identified. Such analysis has been exemplified below.

Protein Structure Determination by NMR Spectroscopy

The NMR results from the present invention are summarized by the atomic structure coordinates of the free form of the P/CAF bromodomain (Table 5), of the P/CAF bromodomain-acetyl-histamine complex (Table 6), and the Tat-P/CAF complex (Table 10). The NMR chemical shift assignments of the P/CAF bromodomain are included in the chemical shift table (Table 1) for the $^1$H-$^{15}$N HSQC spectrum of P/CAF bromodomain. The unambiguous NOE-derived Inter-proton Distance Restraints for the P/CAF bromodomain are in Table 2, the ambiguous NOE-derived Inter-proton Distance Restraints are in Table 3, and the $^1$H bonding restraints are disclosed in Table 4. The NMR chemical shift assignments of the Tat-P/CAF complex are included in the chemical shift table (Table 11) for the $^1$H-15N HSQC spectrum of Tat-P/CAF complex The unambiguous NOE-derived Inter-proton Distance Restraints for the Tat-P/CAF complex are in Table 13, the ambiguous NOE-derived Inter-proton Distance Restraints are in Table 14, and the $^1$H bonding restraints are disclosed in Table 12.

Backbone and Side-chain Assignments: Sequence-specific backbone assignment can be achieved by using a suite of deuterium-decoupled triple-resonance 3D NMR experiments which include UNCA, HN(CO)CA, HN(CA)CB, HN(CO-CA)CB, HNCO, and HN(CA)CO experiments [Yamazaki, et al., *J. Am. Chem. Soc.* 116:11655-11666 (1994)]. The water flip-back scheme is used in these NMR pulse programs to minimize amide signal attenuation from water exchange. Sequential side-chain assignments are typically accomplished from a series of 3D NMR experiments with alternative approaches to confirm the assignments. These experiments include 3D $^{15}$N TOCSY-HSQC, HCCH-TOCSY, (H)C(CO)NH-TOCSY, and H(C)(CO)NH-TOCSY [see Clore and Gronenborn *Meth. Enzymol.* 239:249-363 (1994); Sattler et al., *Prog. in Nuclear Magnetic Resonance Spec.* 4:93-158 (1999)].

Stereospecific Methyl Groups: Stereospecific assignments of methyl groups of Valine and Leucine residues can be obtained from an analysis of carbon signal multiplet splitting using a fractionally $^{13}$C-labeled protein sample, which can be readily prepared using M9 minimal medium containing 10% $^{13}$C-/90%$^{12}$C-glucose mixture [see Neri, et al., *Biochemistry* 28:7510-7516 (1989)].

Dihedral Angle Restraints: Backbone dihedral angle ($\Phi$) constraints can be generated from the $^3J_{HNH\alpha}$ coupling constants measured in a HNHA-J experiment [see Vuister, G. & Bax, A. *J. Am. Chem. Soc.* 115:7772-7777 (1993)]. Side-chain dihedral angles ($\chi$1) can be obtained from short mixing time $^{15}$N-edited 3D TOCSY-HSQC [see Clore, et al., *J, Biomol. NMR* 1:13-22 (1991)] and 3D HNH experiments [see Matson et al., *J. Biomol. NMR* 3:239-244 (1993)], which can also provide stereospecific assignments of β methylene protons.

Hydrogen Bonds Restraints: Amide protons that are involved in hydrogen bonds can be identified from an analysis of amide exchange rates measured from a series of 2D $^1$H/$^{15}$N HSQC spectra recorded after adding $^2$H$_2$O to the protein sample.

NOE Distance Restraints: Distance restraints are obtained from analysis of $^{15}$N, and $^{13}$C-edited 3D NOESY data, which can be collected with different mixing times to 30 minimize spin diffusion problems. The nuclear Overhauser effect (NOE)-derived restraints are categorized as strong (1.8-3 Å), medium (1.8-4 Å) or weak (1.8-5 Å) based on the observed NOE intensities. A recently developed procedure for the iterative automated NOE analysis by using ARIA [see Nilges et al., *Prog. NMR Spectroscopy* 32:107-139 (1998)] can be employed which integrates with X-PLOR [Brunger, *X-PLOR Version 3.1: A system for X-Ray crystallography and NMR*, Yale University Press, New Haven, Conn., (1993)] for structural calculations. To ensure the success of ARIA/X-PLOR-assisted NOE analysis and structure calculations, the ARIA assigned NOE peaks can be manually confirmed.

Intermolecular NOE Distance Restrains: For the structural determination of a protein/peptide complex, intermolecular NOE distance restraints can be obtained from a $^{13}$C-edited (F,) and $^{15}$N, and $^{13}$C-filtered (F$_3$) 3D NOESY data set collected for a sample containing isotope-labeled protein and non-labeled peptide.

Structure Calculations and Refinements: Structures of the protein can be generated using a distance geometry/simulated annealing protocol with the X-PLOR program [see Nilges,et al., *FEBS Lett.* 229:317-324 (1988); Kuszewski, et al., *J. Biolmol. NMR* 2:33-56 (1992); Brtinger, A. T. *X-PLOR Version 3.1: A system for X-Ray crystallography and NMR* (Yale University Press, New Haven, Conn., 1993)]. The structure calculations can employ inter-proton distance restraints obtained from $^{15}$N- and $^{13}$C-resolved NOESY spectra. The initial low-resolution structures can be used to facilitate NOE assignments, and help identify hydrogen bonding partners for slowly exchanging amide protons. The experimental restraints of dihedral angles and hydrogen bonds can be included in the distance restraints for structure refinements.

Protein-Structure Based Design of Agonists and Antagonists of the Bromodomain-Acetyl-Lysine Binding Complex Once the three-dimensional structure of the Bromodomain and the Bromodomain-acetyl-lysine binding complex are determined, a potential drug or agent (antagonist or agonist) can be examined through the use of computer modeling using a docking program such as GRAM, DOCK, or AUTODOCK [Dunbrack et al., 1997, supra]. This procedure can include computer fitting of potential agents to the bromodomain, for example, to ascertain how well the shape and the chemical structure of the potential ligand will complement or interfere with the interaction between the bromodomain and the acetyl-lysine [Bugg et al., *Scientific American*, December:92-98 (1993); West et al., *TIPS*, 16:67-74 (1995)]. Computer programs can also be employed to estimate the attraction, repulsion, and steric hindrance of the agent to the dimer-dimer binding site, for example. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with related proteins. This will minimize potential side-effects due to unwanted interactions with other proteins.

Initially a potential drug could be obtained by screening a random peptide library produced by recombinant bacteriophage for example, [Scott and Smith, *Science,* 249:386-390 (1990); Cwirla et al., *Proc. Natl. Acad. Sci.,* 87:6378-6382 (1990); Devlin et al., *Science,* 249:404-406 (1990)] or a chemical library. In particular, based on the NMR structural analysis provided herein, compounds that comprise an "acetyl-amine-like" structure as depicted in FIG. 12 are particularly good candidates. Examples of such "acetyl-lysine analogs" are included in Tabel 15-1 to 15-33.

An agent selected in this manner could be then be systematically modified (if necessary) by computer modeling programs until one or more promising potential drugs are identified. Such analysis has been shown to be effective in the development of HIV protease inhibitors [Lam et al., *Science* 263:380-384 (1994); Wlodawer et al., *Ann. Rev. Biochem.* 62:543-585 (1993); Appelt, *Perspectives in Drug Discovery and Design* 1:23-48 (1993); Erickson, *Perspectives in Drug Discovery and Design* 1:109-128 (1993)].

Such computer modeling allows the selection of a finite number of rational chemical modifications, as opposed to the countless number of essentially random chemical modifications that could be made, any one of which might lead to a useful drug. Each chemical modification requires additional chemical steps, which while being reasonable for the synthesis of a finite number of compounds, quickly becomes overwhelming if all possible modifications needed to be synthesized. Thus, through the use of the three-dimensional structural analysis disclosed herein and computer modeling, a large number of these compounds can be rapidly screened on the computer monitor screen, and a few likely candidates can be determined without the laborious synthesis of untold numbers of compounds.

Once a potential drug (agonist or antagonist) is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential drug may be synthesized de novo. As mentioned above, the de novo synthesis of one or even a relatively small group of specific compounds is reasonable in the art of drug design.

The potential drug can then be tested in any standard binding assay (including in high throughput binding assays) for its ability to bind to the ZA loop of a bromodomain. Alternatively the potential drug can be tested for its ability to modulate the binding of a bromodomain to acetylated histamine, for example. When a suitable potential drug is identified, a second NMR structural analysis can optionally be performed on the binding complex formed between the bromodomain-acetyl-lysine binding complex, or the bromodomain alone and the potential drug. Computer programs that can be used to aid in solving such three-dimensional structures include QUANTA, CHARMM, INSIGHT, SYBYL, MACROMODE, and ICM, MOLMOL, RASMOL, AND GRASP [Kraulis, *J. Appl Crystallogr.* 24:946-950 (1991)]. Most if not all of these programs and others as well can be also obtained from the WorldWideWeb through the internet.

Using the approach described herein and equipped with the structural analysis disclosed herein, the three-dimensional structures of other bromodomain-acetyl-lysine binding complexes can more readily be obtained and analyzed. Such analysis will, in turn, allow corresponding drug screening methodology to be performed using the three-dimensional structures of such related complexes.

For all of the drug screening assays described herein further refinements to the structure of the drug will generally be necessary and can be made by the successive iterations of any and/or all of the steps provided by the particular drug screening assay, including further structural analysis by NMR, for example.

Phage libraries for Drug Screening: Phage libraries have been constructed which when infected into host *E. coli* produce random peptide sequences of approximately 10 to 15 amino acids [Parmnley and Smith, *Gene* 73:305-318 (1988), Scott and Smith, *Science* 249:386-249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive bromodomain. After a specified incubation period, the filters can be thoroughly washed and developed for autoradiography. Plaques containing the phage that bind to the radioactive bromodomain can then be identified. These phages can be further cloned and then retested for their ability to bind to the bromodomain as before. Once the phage has been purified, the binding sequence contained within the phage can be determined by standard DNA sequencing techniques. Once the DNA sequence is known, synthetic peptides can be generated which are encoded by these sequences. These peptides can be tested, for example, for their ability to modulate the affinity of the bromodomain for its binding partner (e.g., Tat or a fragment of Tat containing the acetyl-lysine corresponding to position 50 of SEQ ID NO:45).

The effective peptide(s) can be synthesized in large quantities for use in in vivo models and eventually in humans to treat certain tumors. It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, *Vaccine,* 10:175-178 (1990)].

Drug Screening Assays

The drug screening assays of the present invention may use any of a number of means for determining the interaction between an agent/drug (e.g., an acetyl-lysine analog) and a peptide comprising an acetyl-lysine and/or a bromodomain. Thus, standard high throughput drug screening procedures can be employed using a library of low molecular weight compounds, for example that can be screened to identify a binding partner for the bromodoamin. Any such chemical library can be used including those discussed above.

In a particular assay, a bromodomain (e.g., from P/CAF) is placed on or coated onto a solid support. Methods for placing the peptides or proteins on the solid support are well known in the art and include such things as linking biotin to the protein and linking avidin to the solid support. An agent is allowed to equilibrate with the bromodomain to test for binding. Generally, the solid support is washed and agents that are retained are selected as potential drugs. Alternatively, a peptide comprising an acetyl-lysine is placed on or coated onto a solid support. In a particular embodiment of this type, the peptide comprises the amino acid sequence of SEQ ID NO:4. In a preferred embodiment, the peptide comprises the amino acid sequence of SEQ ID NO:46.

The agent may be labeled. For example, in one embodiment radiolabeled agents are used to measure the binding of the agent. In another embodiment the agents have fluorescent markers. In yet another embodiment, a Biocore chip (Pharmacia) coated with the bromodomain is used, for example and the change in surface conductivity can be measured.

In addition, since a number of proteins have been identified that contain bromodomains, and the binding partners of many of these proteins are known, the fact that the bromodomain specifically binds to an acetylated lysine as disclosed herein allows the identification and preparation of a number of potential modulators of the bromodomain-acetyl-lysine binding complex based on the amino acid sequences of the binding partners to the proteins. Such potential modulators include: ISYGR-AcK-KRRQRR (SEQ ID NO:4), ARK-STGG-AcK-APRKQL (SEQ ID NO:5) and QSTSRHK-AcK-LMFKTE (SEQ ID NO:6) which bind to the P/CAF bromodomain as shown in the Example, below. Such peptides also can be used, for example, as a starting point for the design of an inhibitor of the bromodomain-acetyl-lysine binding complex.

Alternatively, a drug can be specifically designed to bind to the ZA loop of a bromodomain for example, such as the P/CAF bromodomain, and be assayed through NMR based methodology [Shuker et al., *Science* 274:1531-1534 (1996) hereby incorporated by reference in its entirety.] In a particular embodiment, analogs of the binding partner of the bromodomain can be used in this analysis. One such peptide has the amino acid sequence of SEQ D NO:4. In another embodiment of this type, the peptide has the amino acid sequence of SEQ ID NO:5. In another such embodiment of this type, the peptide has the amino acid sequence of SEQ ID NO:6.

The assay begins with contacting a compound with a $^{15}$N-labeled bromodomain. Binding of the compound with the ZA loop of the bromodomain can be determined by monitoring the $^{15}$N- or $^{1}$H-amide chemical shift changes in two dimensional $^{15}$N-heteronuclear single-quantum correlation (15N-HSQC) spectra upon the addition of the compound to the $^{15}$N-labeled bromodomain. Since these spectra can be rapidly obtained, it is feasible to screen a large number of compounds [Shuker et al., *Science* 274:1531-1534 (1996)]. A compound is identified as a potential ligand if it binds to the ZA loop of the bromodomain. In a further embodiment, the potential ligand can then be used as a model structure, and analogs to the compound can be obtained (e.g, from the vast chemical libraries commercially available, or alternatively through de novo synthesis). The analogs are then screened for their ability to bind the ZA loop of the bromodomain thus to obtain a ligand. An analog of the potential ligand is chosen as a ligand when it binds to the ZA loop of the bromodomain with a higher binding affinity than the potential ligand. In a preferred embodiment of this type the analogs are screened by monitoring the $^{15}$N- or $^{1}$H-amide chemical shift changes in two dimensional $^{15}$N-heteronuclear single-quantum correlation ($^{15}$N-HSQC) spectra upon the addition of the analog to the $^{15}$N-labeled bromodomain as described above.

In another further embodiment, compounds are screened for binding to two nearby sites on the bromodomain. In this case, a compound that binds a first site of the bromodomain does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by NMR spectroscopy or X-ray crystallography. On the basis of this structural information, a linked compound is synthesized in which the ligand for the first site and the ligand for the second site are linked. In a preferred embodiment of this type the two ligands are covalently linked. This linked compound is tested to determine if it has a higher binding affinity for the bromodomain than either of the two individual ligands. A linked compound is selected as a ligand when it has a higher binding affinity for the bromodomain than either of the two ligands. In a preferred embodiment the affinity of the linked compound with the bromodomain is determined monitoring the $^{15}$N- or $^{1}$H-amide chemical shift changes in two dimensional $^{15}$N-heteronuclear single-quantum correlation (15N-HSQC) spectra upon the addition of the linked compound to the $^{15}$N-labeled bromodomain as described above.

A larger linked compound can be constructed in an analogous manner, e.g., linking three ligands which bind to three nearby sites on the bromodomain to form a multilinked compound that has an even higher affinity for the bromodomain than the linked compound.

Identification of New Bromodomains

By disclosing that protein bound acetyl-lysine is a binding partner for bromodomains, the present invention provides a method of identifying novel proteins that contain bromodomains. In short, a protein fragment or analog thereof comprising an acetyl-lysine or an acetyl-lysine analog can be used as bait to identify a binding partner that comprises a bromodomain. Any one of a number of procedures can be carried out to identify such a binding partner. One such assay comprises passing a cell extract over the bait peptide which is attached to a solid support. After washing the solid support to remove any non-specific binders, the bromodomain containing protein can be eluted from the solid support with an appropriate eluant. In a particular embodiment, the free bait peptide can be used in the elution. Other methodology includes the use of a yeast two-hybrid system, a GST pull down assay, ELISA, immunometric assays, and a modification of the CORT procedure of Schlessinger et al., (U.S. Pat. No. 5,858,686, Issued on Jan. 12, 1999 which is hereby incorporated by reference in its entirety) for use with the bromodomain-acetyl-lysine binding complex.

Labels

Suitable labels include enzymes, fluorophores (e.g., fluorescein isothiocyanate (FITC), phycoerythrin (PE), Texas red (TR), rhodamine, free or chelated lanthamide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419-439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

Three-Dimensional Representation of the Structure of the bromodomains

In addition, the present invention provides a computer that comprises a representation of a bromodomain (or a bromodomain-ligand complex, e.g., the Tat-P/CAF complex) in computer memory that can be used to screen for compounds that will or are likely to inhibit the bromodomain-ligand interaction. In a particular embodiment of the present invention the bromodomain-ligand complex is the Tat-P/CAF complex and the compound identified by the screen can used to prevent, retard the progression, treat and/or cure AIDS.

In a related embodiment, the computer can be used in the design of altered bromodomains that have either enhanced, or alternatively diminished binding activity activity. Preferably, the computer comprises portions of and/or all of the information contained in Tables 1-6 and 10-14. In a particular embodiment, the computer comprises: (i) a machine-readable data storage material encoded with machine-readable data, (ii) a working memory for storing instructions for processing the machine readable data, (iii) a central processing unit coupled to the working memory and the machine-readable data storage material for processing the machine-readable data into a three-dimensional representation, and (iv) a display coupled to the central processing unit for displaying the three-dimensional representation.

Figure 11:
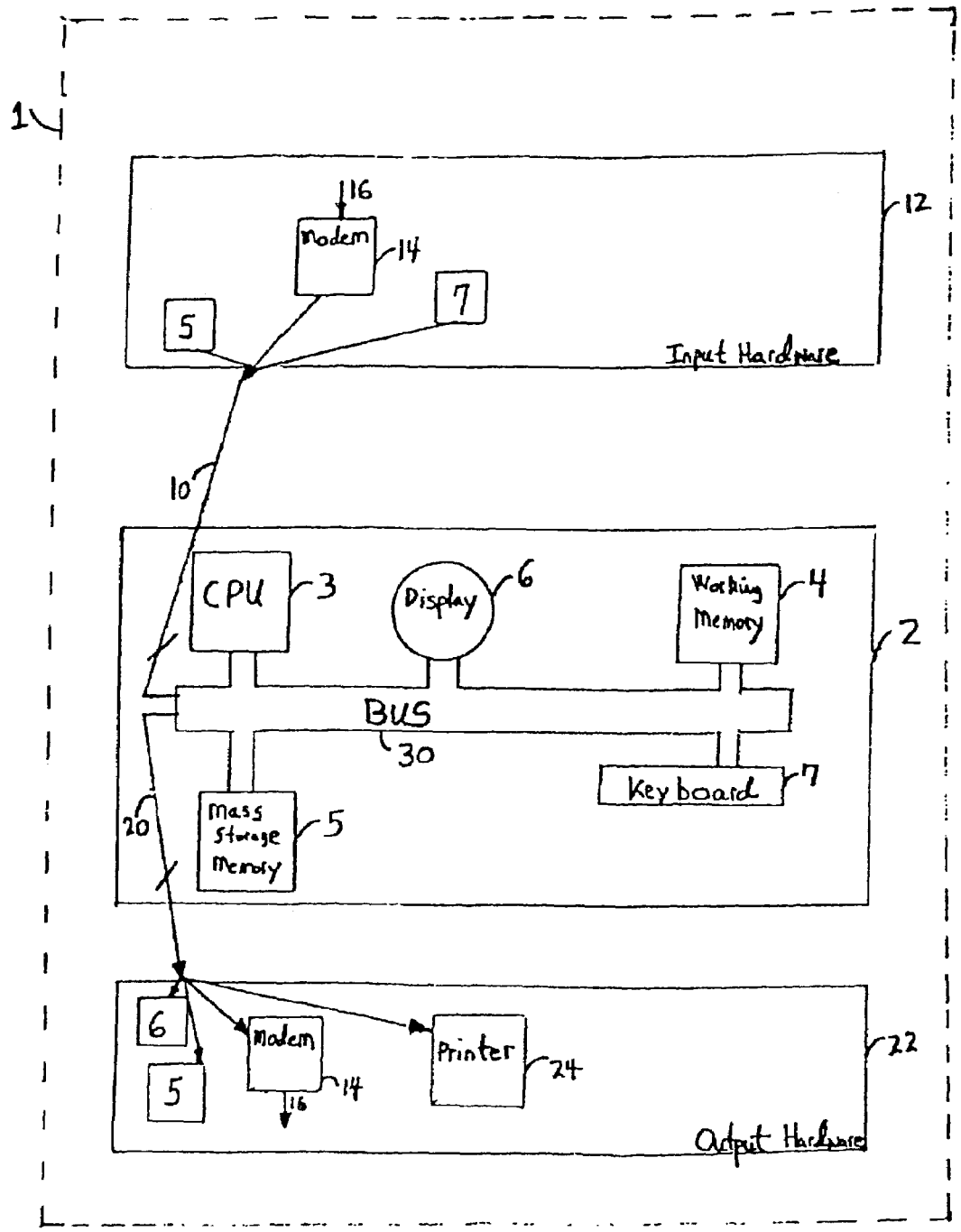
FIG. 11 depicts a schematic of a computer comprising a central processing unit ("CPU"), a working memory, a mass storage memory, a display terminal, and a keyboard that are interconnected by a conventional bidirectional system bus. The computer can be used to display and manipulate the structural data of the present invention.

Thus the machine-readable data storage medium comprises a data storage material encoded with machine readable data which can comprise portions and/or all of the structural information contained in Tables 1-6 and 10-14. One embodiment for manipulating and displaying the structural data provided by the present invention is schematically depicted in FIG. 11. As depicted, the System 1, includes a computer 2 comprising a central processing unit ("CPU") 3, a working memory 4 which may be random-access memory or "core" memory, mass storage memory 5 (e.g., one or more disk or CD-ROM drives), a display terminal 6 (e.g., a cathode-ray tube), one or more keyboards 7, one or more input lines 10, and one or more output lines 20, all of which are interconnected by a conventional bidirectional system bus 30.

Input hardware 12, coupled to the computer 2 by input lines 10, may be implemented in a variety of ways. Machine-readable data may be inputted via the use of one or more modems 14 connected by a telephone line or dedicated data line 16. Alternatively or additionally, the input hardware 12 may comprise CD-ROM or disk drives 5. In conjunction with the display terminal 6, the keyboard 7 may also be used as an input device. Output hardware 22, coupled to computer 2 by output lines 20, may similarly be implemented by conventional devices. Output hardware 22 may include a display terminal 6 for displaying the three dimensional data. Output hardware might also include a printer 24, so that a hard copy output may be produced, or a disk drive 5, to store system output for later use, see also U.S. Pat. No. 5,978,740, Issued Nov. 2, 1999, the contents of which are hereby incorporated by reference in their entireties.

In operation, the CPU 3 (i) coordinates the use of the various input and output devices 12 and 22; (ii) coordinates data accesses from mass storage 5 and accesses to and from working memory 4; and (iii) determines the sequence of data processing steps. Any of a number of programs may be used to process the machine-readable data of this invention.

Antibodies to Portions of the Bromodomain that Interact with Acetyl-Lysine

According to the present invention, the bromodomains, and more particularly the ZA loops of the bromodomains and fragments thereof can be produced by a recombinant source, or through chemical synthesis, or through the modification of these peptides and fragments; and derivatives or analogs thereof, including fusion proteins, may be used as an immunogen to generate antibodies that specifically interfere with the formation of the bromodomain-acetyl-lysine binding complex. Similarly, antibodies can be raised against peptides that comprise one or more acetyl-lysine residues which also interfere with the formation of the bromodomain-acetyl-lysine binding complex. Such antibodies include but are not limited to polyclonal, monoclonal, chimeric, single chain, Fab fragments, and a Fab expression library.

Various procedures known in the art may be used for the production of the polyclonal antibodies. For the production of antibody, various host animals can be immunized by injection with the peptide having the amino acid sequence of SEQ ID NO:3, for example, or a derivative (e.g., or fusion protein) thereof, including but not limited to rabbits, mice, rats, sheep, goats, etc. In one embodiment, the peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the peptides or protein fragments of the present invention, or analog, or derivative thereof, any technique that provides for the production of antibody molecules by continuous cell lines in culture may be used. These include but are not limited to the hybridoma technique originally developed by Kohler and Milstein [*Nature*, 256:495-497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals utilizing technology described in PCT/US90/02545. In fact, according to the invention, techniques developed for the production of "chimeric antibodies" [Morrison et al., *J. Bacteriol.,* 159:870 (1984); Neuberger et al., *Nature,* 312:604-608 (1984); Takeda et al., *Nature,* 314: 452-454 (1985)] by splicing the genes from a mouse antibody molecule specific for the peptide having the amino acid sequence of SEQ ID NO:3, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce specific single chain antibodies. An additional embodiment of the invention utilizes the techniques described for the construction of Fab expression libraries [Huse et al., *Science,* 246:1275-1281(1989)] to allow rapid and easy identification of monoclonal Fab fragments with the desired specificity.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a ZA loop of a bromodomain, for example, one may assay generated hybridomas for a product which binds to a bromodomain fragment containing such an epitope and choose those which do not cross-react with bromodomain fragments that do not include that epitope.

In a specific embodiment, antibodies that interfere with the formation of the bromodomain-acetyl-lysine complex can be generated. Such antibodies can be tested using the assays described and could potentially be used in anti-cancer therapies.

Administration

According to the invention, the component or components of a therapeutic composition, e.g., an agent of the invention that interferes with the bromodomain-acetyl-lysine binding complex such as the peptide having the amino acid sequence of SEQ ID NOs:4, 5, 6, 46, or 47, or an acetyl-lysine analog as defined by FIG. 12 and exemplified in Table 15-1 to 15-33, and a pharmaceutically acceptable carrier, may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In a preferred aspect, the agent of the present invention can cross cellular and nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to such an agent. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the $F(ab')_2$ fragment can be reduced, and crosslinked to the agent via the reduced sulfhydryl. Antibodies for use as targeting molecule are specific for a cell surface antigen.

In another embodiment, the therapeutic compound can be delivered in a vesicle, in particular a liposome [see Langer, *Science,* 249:1527-1533 (1990); Treat et al., in *Liposomes in the Therapy of Infectious Disease and Cancer,* Lopez-Berestein and Fidler (eds.), Liss: New York, pp. 353-365 (1989); Lopez-Berestein, ibid., pp. 317-327; see generally ibid.].

In yet another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.,* 14:201 (1987); Buchwald et al., *Surgery,* 88:507 (1980); Saudek et al., *N. Engl. J. Med.,* 321:574 (1989)]. In another embodiment, polymeric materials can be used [see *Medical Applications of Controlled Release,* Langer and Wise (eds.), CRC Press: Boca Raton, Fla. (1974); *Controlled Drug Bioavailability, Drug Product Design and Performance,* Smolen and Ball (eds.), Wiley: New York (1984); Ranger and Peppas, *J. Macromol. Sci. Rev. Macromol. Chem.,* 23:61 (1983); see also Levy et al., *Science,* 228:190 (1985); During et al., *Ann. Neurol.,* 25:351 (1989); Howard et al., *J. Neurosurg.,* 71:105 (1989)]. In yet another embodiment, a controlled release system can be placed in proximity of the therapeutic target, i.e., the bone marrow, thus requiring only a fraction of the systemic dose [see, e.g., Goodson, in *Medical Applications of Controlled Release,* supra, vol. 2, pp. 115-138 (1984)]. Other controlled release systems are discussed in the review by Langer [*Science,* 249:1527-1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435-1712 which are herein incorporated by reference. The compositions may be prepared in liquid form, or may be in dried powder, such as lyophilized form.

Oral Delivery. Contemplated for use herein are oral solid dosage forms, which are described generally in Remington's Pharmaceutical Sciences, 18th Ed.1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include an agent of the present invention (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. An example of such a moiety is polyethylene glycol.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of an agent of the present invention (or derivative) is also contemplated. Nasal delivery allows the passage of a peptide, for example, to the blood stream directly after administering the therapeutic product to the nose, without the necessity for deposition of the product in the lung. Formulations for nasal delivery include those with dextran or cyclodextran.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research*, 7:565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, Vol. 111, pp. 206-212 (1989) (α1-antitrypsin); Smith et al., *J. Clin. Invest.*, 84:1145-1146 (1989) (a-1-proteinase); Oswein et al., "Aerosolization of Proteins", *Proceedings of Symposium on Respiratory Drug Delivery II*, Keystone, Colorado, March, (1990) (recombinant human growth hormone); Debs et al., *J. Immunol.*, 140:3482-3488 (1988) (interferon-γ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

A subject in whom administration of an agent of the present invention is an effective therapeutic regiment for cancer, for example, is preferably a human, but can be any animal. Thus, as can be readily appreciated by one of ordinary skill in the art, the methods and pharmaceutical compositions of the present invention are particularly suited to administration to any animal, e.g., for veterinary medical use, particularly for a mammal, and including, but by no means limited to, domestic animals, such as feline or canine subjects, farm animals, including bovine, equine, caprine, ovine, and porcine subjects, wild animals (whether in the wild or in a zoological garden), research animals, such as mice, rats, rabbits, goats, sheep, pigs, dogs, cats, avian species, such as chickens, turkeys, and songbirds.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Structure and Ligand of a Histone Acetyltransferase Bromodomain

Introduction

The bromodomain is a protein motif comprising approximately 110 amino acids that is found in practically all nuclear histone acetyltransferases (HATs) [Jeanmougin et al., Trends in Biochemical *Sciences*, 22:151-153 (1997)]. However, despite the seemingly requisite occurrence of this motif in HATs, their role in these enzymes is unknown. Indeed, although this motif has also been identified in other chromatin proteins, heretofore not even one binding partner for a bromodomain had been identified.

Materials and Methods

Sample preparation: The bromodomain of P/CAF (residues 719-832 of SEQ ID NO:2) was subcloned into the pET14b expression vector (Novagen) and expressed in *Escherichia coli* BL21(DE3) cells. Uniformly $^{15}$N- and $^{15}$N/$^{13}$C-labelled proteins were prepared by growing bacteria in a minimal medium containing $^{15}$NH$_4$Cl with or without $^{13}$C$_6$-glucose. A uniformly $^{15}$N/$^{13}$C-labelled and fractionally deuterated protein sample was prepared by growing the cells in 75% $^2$H$_2$O. The bromodomain was purified by affinity chromatography on a nickel-IDA column (Invitrogen) followed by the removal of poly-His tag by thrombin cleavage. The final purification of the protein was achieved by size-exclusion chromatography. The acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation. NMR samples contained approximately 1 mM protein in 100 mM phosphate buffer of pH 6.5 and 5 mM perdeuterated DTT and 0.5 mM EDTA in H$_2$O/$^2$H$_2$O (9/1) or $^2$H$_2$O.

NMR spectroscopy: All NMR spectra were acquired at 30° C. on a Bruker DRX600 or DRX500 spectrometer. The backbone assignments of the $^1$H, $^{13}$C, and $^{15}$N resonances were achieved using deuterium-decoupled triple-resonance experiments of HNCACB and HN(CO)CACB [Yamazaki et al., *J. Am. Chem. Soc.* 116:11655-11666 (1994)] recorded using the uniformly $^{15}$N/$^{13}$C-labeled and fractionally deuterated protein. The side-chain atoms were assigned from 3D HCCH-TOCSY [Clore and Gronenbom, *Meth. Enzymol.* 239:249-363 (1994)] and (H)C(CO)NH-TOCSY [Logan et al., *J. Biolmol. NMR* 3:225-231 (1993)] data collected on the uniformly $^{15}$N/$^{13}$C-labeled protein. Stereospecific assignments of methyl groups of the Val and Leu residues were obtained using a fractionally $^{13}$C-labeled sample [Neri et al., *Biochemistry* 28:7510-7516 (1989)]. The NOE-derived distance restraints were obtained from $^{15}$N- or $^{13}$C-edited 3D NOESY spectra. φ-angle restraints were determined based on the $^3J_{Hn,H^\alpha}$ coupling constants measured in a 3D H spectrum [Clore and Gronenbom, *Meth. Enzymol.* 239:249-363 (1994)]. Slowly exchanging amide protons were identified from a series of 2D $^{15}$N-HSQC spectra recorded after the H$_2$O buffer was changed to a $^2$H$_2$O buffer. The intermolecular NOEs used in defining the structure of the bromodomain/Ac-histamine complex were detected in $^{13}$C-edited (F$_1$), $^{13}$C/$^{15}$N-filtered (F$_3$) 3D NOESY spectrum [Clore and Gronenbom, *Meth. Enzymol.* 239:249-363 (1994)]. All NMR spectra were processed with the NMRPipe/NMRDraw programs and analyzed using NMRView [Johnson and Blevins, *J. Biomol., NMR* 4:603-614 (1994)].

Structure calculations: Structures of the bromodomain were calculated with a distance geometry/simulated annealing protocol using the X-PLOR program [Brunger, *X-PLOR Version 3.1: A system for X-Ray crystallography and NMR*, Yale University Press, New Haven, Conn., (1993)]. A total of 1324 manually assigned NOE-derived distance restraints were obtained from the $^{15}$N—- and $^{13}$C-edited NOE spectra. Further analysis of the NOE spectra was carried out by the iterative automated assignment procedure using ARIA [Nilges and O'Donoghue, *Prog. NMR Spectroscopy* 32:107-139 (1998)], which integrates with X-PLOR for structure calculations. A total of 1519 unambiguous and 590 ambiguous distance restraints were identified from the NOE data by ARIA, many of which were checked and confirmed manually. The ARIA-assigned distance restraints were in agreement with the structures calculated using only the manually assigned NOE distance restraints, 28 hydrogen-bond distance restraints for 14 hydrogen bonds, and 54φ-angle restraints. The final structure calculations employed a total of 3515 NMR experimental restraints obtained from the manual and the ARIA-assisted assignments, 2843 of which were unambiguously assigned NOE-derived distance restraints that comprise of 1077 intra-residue, 621 sequential, 550 medium-range, and 595 long-range NOEs. For the ensemble of the final 30 structures, no distance and torsional angle restraints were violated by more than 0.3 Å and 5°, respectively. The total, distance violation, and dihedral violation energies were 178.7±2.4 kcal mol$^{-1}$, 41.6±0.9 kcal mol$^{-1}$, and 0.50±0.06 kcal mol$^{-1}$, respectively. The Lennard-Jones potential which was not used during any refinement stage, was −526.2±16.8 kcal mol$^{-1}$ for the final structures. Ramachandran plot analysis of the final structures (residues 727-828) with Procheck-NMR [Laskowski et al., *J. Biolmol. NMR* 8:477-486 (1996)] showed that 71.0±0.6%, 23.8±0.6%, 3.5±0.2%, and 1.7±0.2% of the non-Gly and non-Pro residues were in the most favorable, additionally allowed, generously allowed, and disallowed regions, respectively. The corresponding values for the residues in the four a-helices (residues 727-743, 770-776, 785-802, and 807-827) were 88.9±0.4%, 11.0±0.4%, 0.1±0.1%, and 0.0±0.0%, respectively. The structure of the bromodomain/acetyl-histamine complex was determined using the free form structure and additional 25 intermolecular and 5 intra-ligand NOE-derived distance restraints.

Site-directed mutagenesis: Mutant proteins were prepared using the QuickChange site-directed mutagenesis kit (Stratagene). The presence of appropriate mutations was confirmed by DNA sequencing.

Ligand titration: Ligand titration experiments were performed by recording a series of 2D $^{15}$N— and $^{13}$C-HSQC spectra on the uniformly $^{15}$N-, and $^{15}$N/$^{13}$C-labelled bromodomain (~0.3 mM), respectively, in the presence of different amounts of ligand concentration ranging from 0 to approximately 2.0 mM. The protein sample and the stock solutions of the ligands were all prepared in the same aqueous buffer containing 100 mM phosphate and 5 mM perdeuterated DTT at pH 6.5.

The full length nucleic acid sequence of the human p300/CBP-associated factor (P/CAF) was obtained from GenBank. Accession No: U57317.2 (SEQ ID NO: 1):

```
   1 ggggccgcgt cgacgcggaa aagaggccgt gggggcctc ccagcgctgg cagacaccgt
  61 gaggctggca gccgccggca cgcacaccta gtccgcagtc ccgaggaaca tgtccgcagc
 121 cagggcgcgg agcagagtcc cgggcaggag aaccaaggga gggcgtgtgc tgtggcggcg
 181 gcggcagcgg cagcggagcc gctagtcccc tccctcctgg gggagcagct gccgccgctg
 241 ccgccgccgc caccaccatc agcgcgcggg gcccggccag agcgagccgg gcgagcggcg
 301 cgctagggg agggcggggg cgggagggg ggtgggcgaa ggggcggga gggcgtgggg
 361 ggagggtctc gctctcccga ctaccagagc ccgagggaga ccctggcggc ggcggcggcg
 421 cctgacactc ggcgcctcct gccgtgctcc ggggcggcat gtccgagget ggcggggccg
 481 ggccgggcgg ctgcggggca ggagccgggg caggggccgg gcccggggcg ctgccccgc
 541 agcctgcggc gcttccgccc gcgccccgc agggctcccc ctgcgccgct gccgccgggg
 601 gctcgggcgc ctgcggtccg gcgacggcag tggctgcagc gggcacggcc gaaggaccgg
 661 gaggcggtgg ctcggcccga atcgccgtga agaaagcgca actacgctcc gctccgcggg
 721 ccaagaaact ggagaaactc ggagtgtact ccgcctgcaa ggccgaggag tcttgtaaat
 781 gtaatggctg gaaaacccct aaccctcac ccactccccc cagagccgac ctgcagcaaa
 841 taattgtcag tctaacagaa tcctgtcgga gttgtagcca tgccctagct gctcatgttt
 901 cccacctgga gaatgtgtca gaggaagaaa tgaacagact cctgggaata gtattggatg
 961 tggaatatct ctttacctgt gtccacaagg aagaagatgc agataccaaa caagtttatt
1021 tctatctatt taagctcttg agaaagtcta ttttacaaag aggaaaacct gtggttgaag
1081 gctctttgga aaagaaaccc ccatttgaaa aacctagcat tgaacagggt gtgaataact
1141 ttgtgcagta caaatttagt cacctgccag caaagaaag gcaaacaata gttgagttgg
1201 caaaaatgtt cctaaaccgc atcaactatt ggcatctgga ggcaccatct caacgaagac
1261 tgcgatctcc caatgatgat atttctggat acaaagagaa ctacacaagg tggctgtgtt
1321 actgcaacgt gccacagttc tgcgacagtc tacctcggta cgaaaccaca caggtgtttg
1381 ggagaacatt gcttcgctcg gtcttcactg ttatgaggcg acaactcctg gaacaagcaa
1441 gacaggaaaa agataaactg cctcttgaaa aacgaactct aatcctcact catttcccaa
1501 aatttctgtc catgctagaa gaagaagtat atagtcaaaa ctctcccatc tgggatcagg
1561 attttctctc agcctcttcc agaaccagcc agctaggcat ccaaacagtt atcaatccac
1621 ctcctgtggc tgggacaatt tcatacaatt caacctcatc ttcccttgag cagccaaacg
1681 cagggagcag cagtcctgcc tgcaaagcct cttctggact tgaggcaaac ccaggagaaa
```

-continued

```
1741 agaggaaaat gactgattct catgttctgg aggaggccaa gaaaccccga gttatggggg 1801 atattccgat ggaattaatc aacgaggtta tgtctaccat cacggaccct gcagcaatgc 1861 ttggaccaga gaccaatttt ctgtcagcac actcggccag ggatgaggcg gcaaggttgg 1921 aagagcgcag gggtgtaatt gaatttcacg tggttggcaa ttccctcaac cagaaaccaa 1981 acaagaagat cctgatgtgg ctggttggcc tacagaacgt tttctcccac cagctgcccc 2041 gaatgccaaa agaatacatc acacggctcg tctttgaccc gaaacacaaa acccttgctt 2101 taattaaaga tggccgtgtt attggtggta tctgtttccg tatgttccca tctcaaggat 2161 tcacagagat tgtcttctgt gctgtaacct caaatgagca agtcaagggc tatggaacac 2221 acctgatgaa tcatttgaaa gaatatcaca taaagcatga catcctgaac ttcctcacat 2281 atgcagatga atatgcaatt ggatacttta agaaacaggg tttctccaaa gaaattaaaa 2341 tacctaaaac caaatatgtt ggctatatca aggattatga aggagccact ttaatgggat 2401 gtgagctaaa tccacggatc ccgtacacag aattttctgt catcattaaa aagcagaagg 2461 agataattaa aaaactgatt gaaagaaaac aggcacaaat tcgaaaagtt taccctggac 2521 tttcatgttt taaagatgga gttcgacaga ttcctataga aagcattcct ggaattagag 2581 agacaggctg gaaaccgagt ggaaaagaga aagtaaaga gaccagagac cctgaccagc 2641 tttacagcac gctcaagagc atcctccagc aggtgaagag ccatcaaagc gcttggcct 2701 tcatggaacc tgtgaagaga acagaagctc caggatatta tgaagttata aggttcccca 2761 tggatctgaa aaccatgagt gaacgcctca gaataggta ctacgtgtct aagaaattat 2321 tcatggcaga cttacagcga gtctttacca attgcaaaga gtacaacgcc gctgagagtg 2881 aatactacaa atgtgccaat atcctggaga aattcttctt cagtaaaatt aaggaagctg 2941 gattaattga caagtgattt ttttccccc tctgcttctt agaaactcac caagcagtgt 3001 gcctaaagca aggt
```

The full length protein sequence of the human p300/CBP-associated factor (P/CAF) was obtained from GenBank. Accession No: U57317.2, (SEQ ID NO:2):

```
  1 MSEAGGAGPG GCGAGAGAGA GPGALPPQPA ALPPAPPQGS PCAAAAGGSC ACGPATAVAA

61 ACTAEGPGGG GSARTAVKKA QLRSAPRAKK LEKLGVYSAC KAEESCKCNG WKNPNPSPTP

121 PRADLQQIIV SLTESCRSCS HALAAHVSHL ENVSEEEMNR LLGTVLDVEY LFTCVHKEED

181 ADTKQVYFYL FKLLRKSILQ RGICPVVEGSL EKKPPFEKPS IEQGVNNFVQ YKFSHLPAKE

241 RQTIVELK(M FLNRINYWHL EAPSQRRLRS PNDDTSGYKE NYTRWLCYCN VPQFCDSLPR

301 YETTQVFGRT LLRSVFTV34R RQLLEQARQE KDKLPLEKRT LILTHFPKFL SMLEEEVYSQ

361 NSPTWDQDFL SASSRTSQLG IQTVINPPPV AGTISYNSTS SSLEQPNAGS SSPACKASSG

421 LEANPGEKRK MTDSHVLEEA KKPRVMGDIP MELINEVMST ITDPAAMLGP ETNFLSAHSA

481 RDEAARLEER RGVTEFHVVG NSLNQKPNKK ILMWLVGLQN VFSHQLPRMP KEYITRLVFD

541 PKHKTLALIK DGRVIGGICF RMFPSQGFTE IVFCAVTSNE QVKGYGTHLM NHLKEYHIKH

601 DILNFLTYAD EYAIGYFKKQ GFSKEIKIFK TKYVGYIKDY EGATLMGCEL NPRIPYTEFS

661 VIIKKQKEII KKLIERKQAQ IRKVYPGLSC FKDGVRQIPI ESIPGIRETG WKPSGKEKSK

721 EPRDPDQLYS TLKSILQQVK SHQSAWPFME PVKRTEAPGY YEVIRFPMDL KTMSERLKNR

781 YYVSKKLFMA DLQRVFTNCK EYNAAESEYY KCANILEKFF FSKIKEAGLI DK
```

Results

The P/CAF bromodomain represents an extensive family of bromodomains (FIG. 1). A large number of long-range nuclear Overhauser enhancement (NOE)-derived distance restraints were identified in the NMR data of the P/CAF bromodomain, yielding a well-defined three-dimensional structure (FIGS. 2A-2D). Table 1 shows the NMR chemical shift assignment of the P/CAF bromodomain. Table 2 shows the Unambiguous NOE-derived distance restraints. Table 3 shows the Ambiguous NOE-derived distance restraints. Table 4 shows the Hydrogen bond restraints. The NMR structure coordinates of the P/CAF bromodomain in the free and complexed to acetyl-histamine are shown in Tables 5 and 6, respectively.

Figures 2F, 2G:
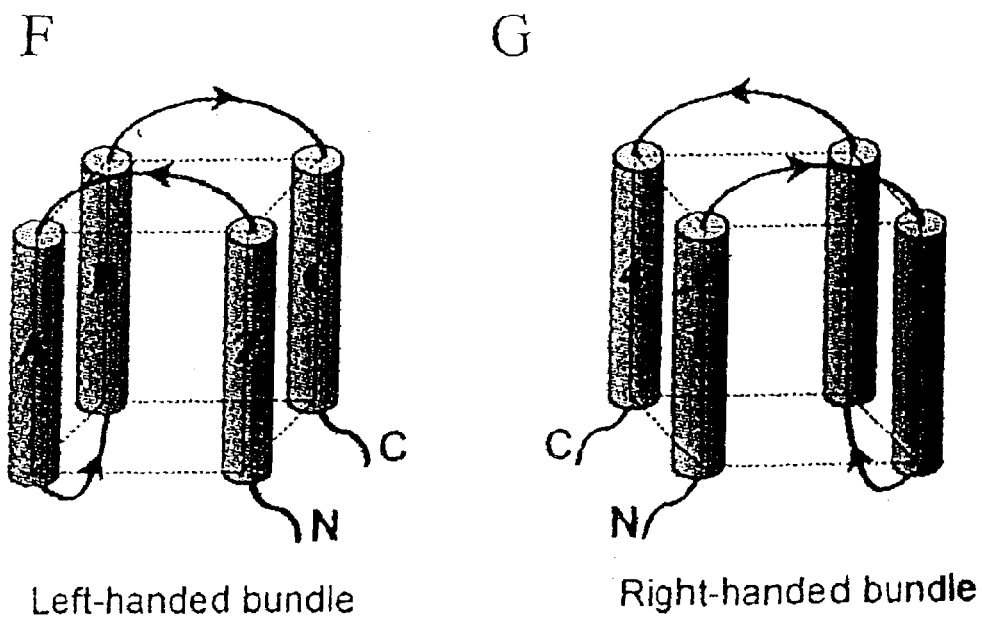
Figure 2H:
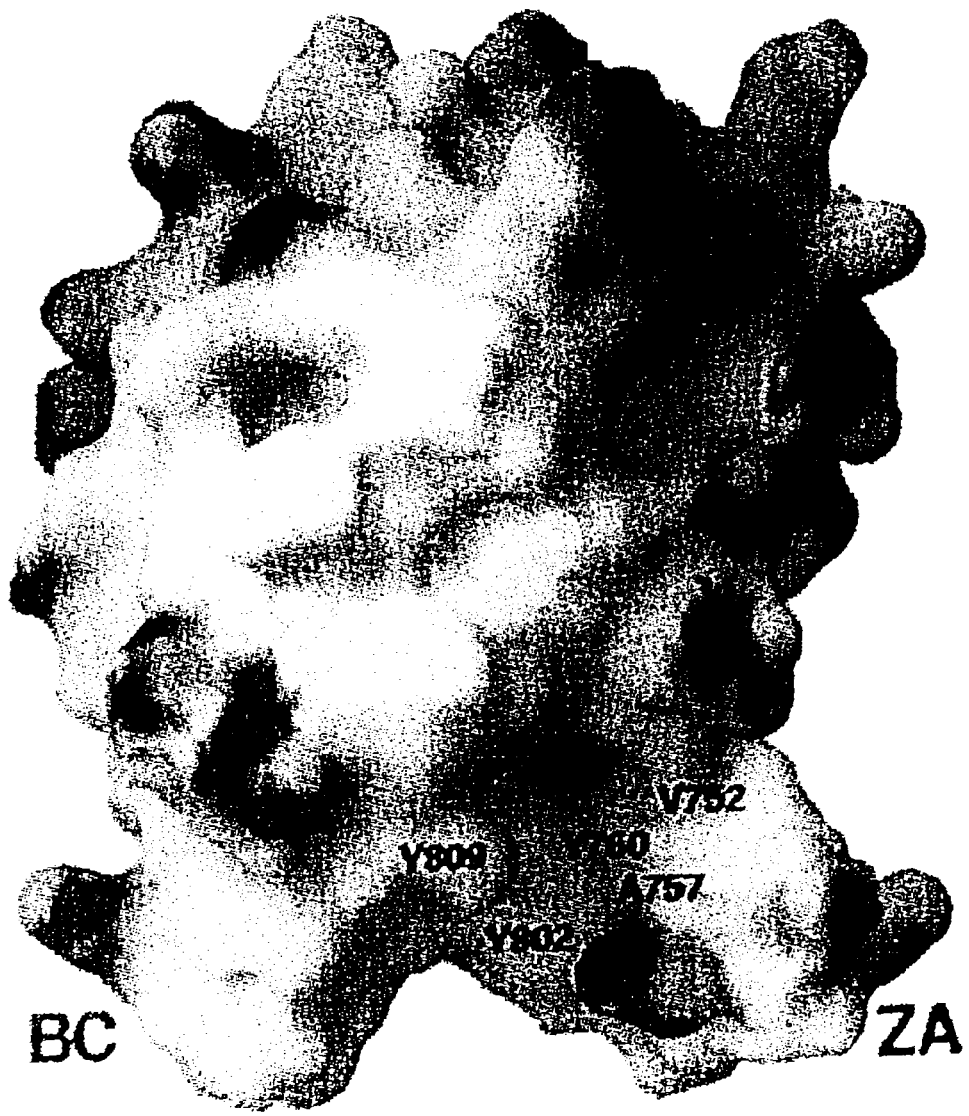

The structure consists of a four-helix bundle (helices $\alpha_Z$, $\alpha_A$, $\alpha_B$, and $\alpha_C$) with a left-handed twist, and a long intervening loop between helices $\alpha_Z$ and $\alpha_A$ (termed the ZA loop, FIG. 2E). The four amphipathic a-helices are packed tightly against one another in an antiparallel manner, with crossing angles for adjacent helices of ~16-20°. The up-and-down four-helix bundle can adapt two topological folds with opposite handedness (FIGS. 2F-2G). The right-handed four-helix bundle fold occurs more commonly and is seen in proteins such as hemerythrin and cytochrome $b_{562}$. The left-handed fold of the bromodomain structure is less common, but also observed in proteins such as cytochrome $b_5$ and T4 lysozyme [Richardson, J., *Adv. Protein Chem.*, 34:167-339 (1989); Presnell and Cohen, *Proc. Natl. Acad. Sci. USA* 86:6592-6596 (1989)]. This topological difference arises from the orientation of the loop between the first two helices (FIGS. 2F-2G). The right-handed four-helix bundle proteins have a relatively short hairpin-like connection between the first two helices, which makes the "preferred" turn to the right at the top of the first helix [Richardson, J., *Adv. Protein Chem.*, 34:167-339 (1989); Presnell and Cohen, *Proc. Natl. Acad. Sci. USA* 86:6592-6596 (1989); Weber and Salemme, *Nature* 287:82-84 (1980)]. In contrast, proteins with the left-handed fold usually have a long loop after the first helix and often contain additional secondary structural elements at the base of the helix bundle [Richardson, J., *Adv. Protein Chem.*, 34:167-339 (1989); Presnell and Cohen, *Proc. Natl. Acad. Sci. USA* 86:6592-6596 (1989)]. In the bromodomain structure, this long ZA loop has a defined conformation and is packed against the loop between helices $\alpha_B$ and $\alpha_C$ (termed the BC loop) to form a hydrophobic pocket. These tertiary interactions between the two loops appear to favor the left turn of the ZA loop, resulting in the left-handed four-helix bundle fold of the bromodomain. The hydrophobic pocket formed by loops ZA and BC is lined by residues Val752, Ala757, Tyr760, Val763, Tyr802 and Tyr809 (FIG. 2H), and appears to be a site for protein-protein interactions (see below). The pocket is located at one end of the four-helix bundle, opposite to the N- and C-termini of the protein. Interestingly, the ZA loop varies in length amongst different bromodomains, but almost always contains residues corresponding to Phe748, Pro751, Pro758, Tyr760, and Pro767 (FIG. 1). The conservation of these residues within the ZA loop as well as residues within the a-helical regions implies a similar left-handed four-helix bundle structure for the large family of bromodomains (FIG. 1).

Figure 3A:
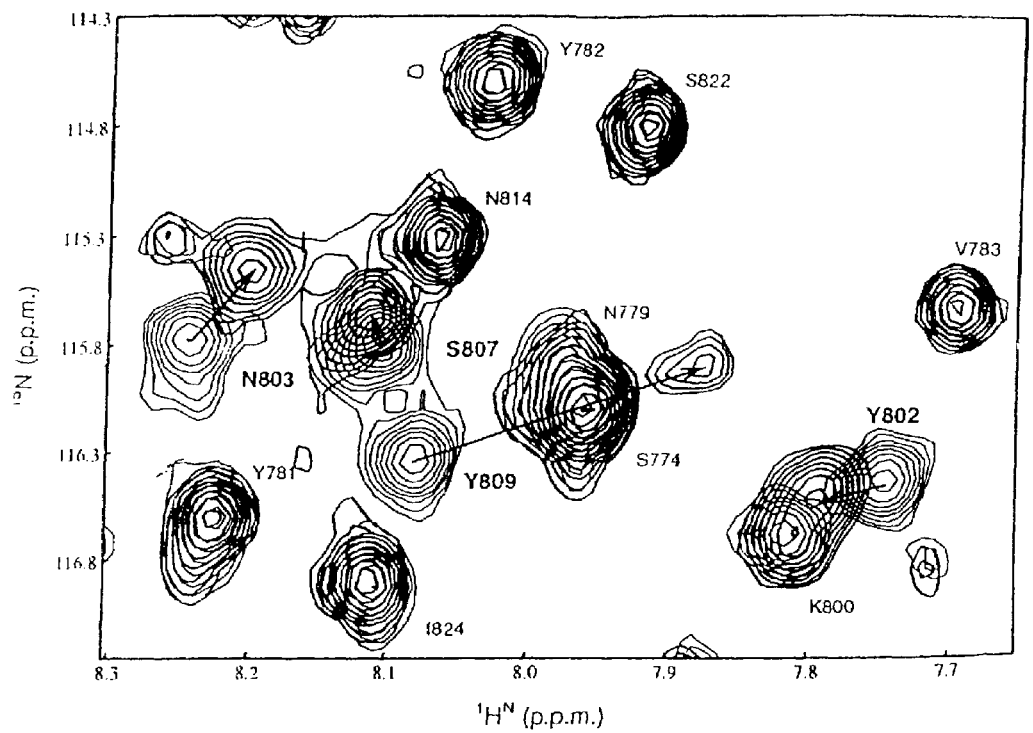
FIGS. 3A-3C show the binding of the P/CAF bromodomain to AcK.

The modular bromodomain structure supports the idea that bromodomain can act as a functional unit for protein-protein interactions. The observation that bromodomains are found in nearly all known nuclear HATs (A-type) that are known to promote transcription-related acetylation of histones on specific lysine residues, but not present in cytoplasmic HATs (B-type), prompted the determination of whether bromodomains can interact with acetyl-lysine (AcK). The NMR titration of the P/CAF bromodomain were performed with a peptide (SGRGKGG-$_{Ac}$K-GLGK) (SEQ ID NO: 62)derived from histone H4, in which Lys8 is acetylated (Lys8 is the major acetylation site in H4 for GCN5, a yeast homologue of P/CAF). Remarkably, the bromodomain could indeed bind the AcK peptide. Moreover, this interaction appeared to be specific, based on the $^{15}$N-HSQC spectra which showed that only a limited number of residues underwent chemical shift changes as a function of peptide concentration (FIG. 3A). Conversely, the NMR titration of the bromodomain with a non-acetylated, but otherwise identical H4 peptide, showed no noticeable chemical shift changes, demonstrating that the interaction between the bromodomain and the lysine-acetylated H4 peptide was dependent upon acetylation of lysine. The dissociation constant ($K_D$) for the AcK peptide was estimated to be 346±54 μM. This binding is likely reinforced through additional interactions between bromodomain-containing proteins and target proteins. Notably, many chromatin-associated proteins contain two or multiple bromodomains (FIG. 1). Indeed, binding with another lysine-acetylated peptide (RKSTGG-AcK-APRKQ) (SEQ ID NO: 63) derived from the major acetylation site on histone H3 (residues 9-20) was also observed. Together, these data demonstrate that the P/CAF bromodomain has the ability to bind AcK peptides in an acetylation dependent manner.

Figure 3B:
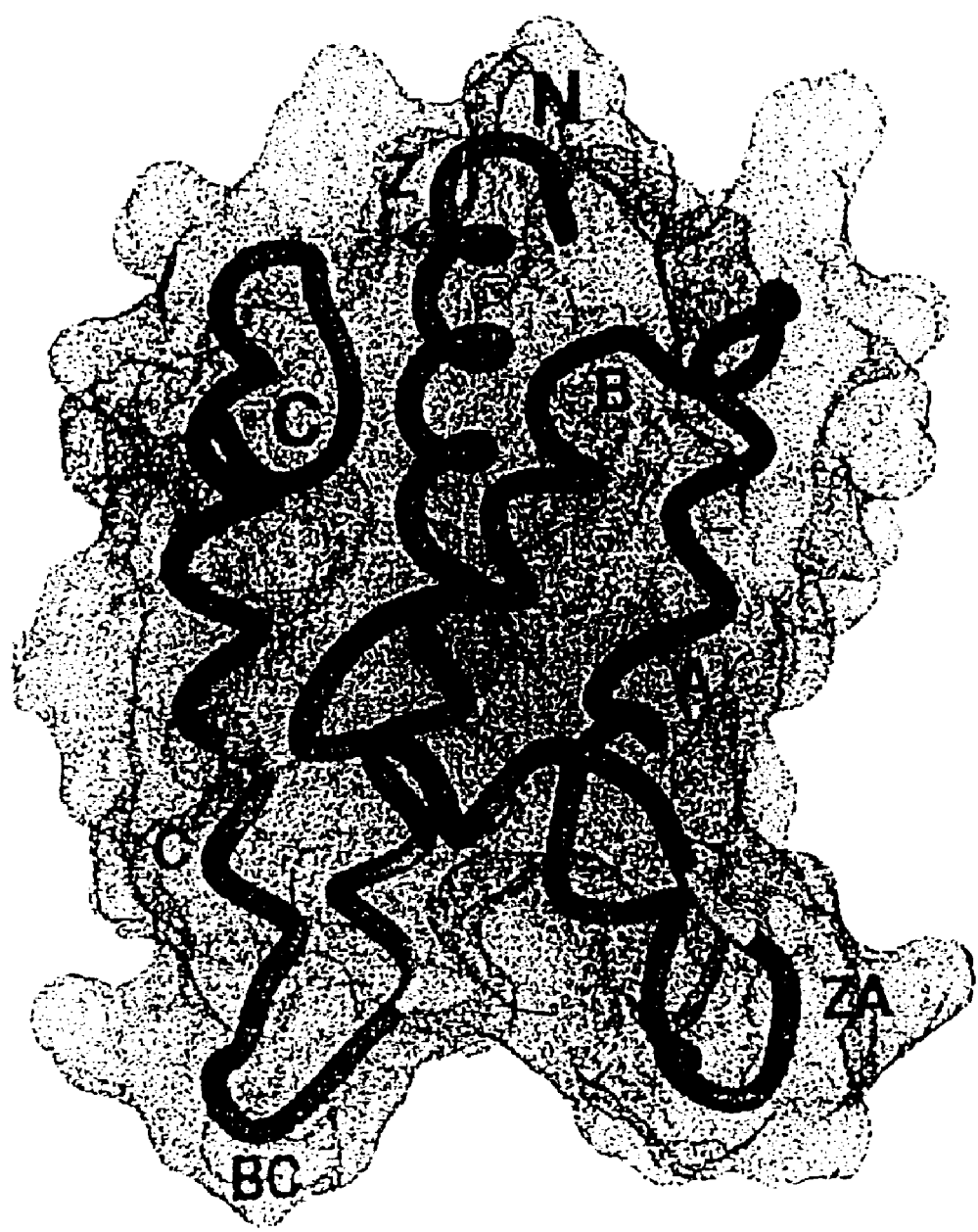
Figure 3C:
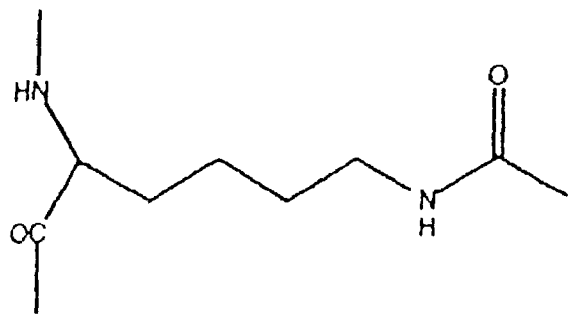
Figure 3C:
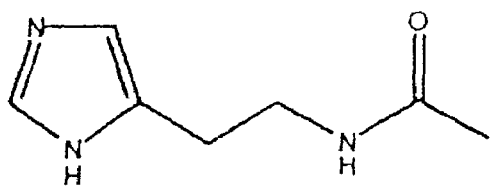
Figure 3C:
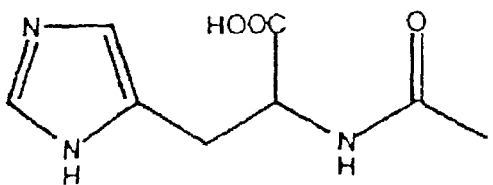

Intriguingly, the bromodomain residues that exhibited the most significant $^1$H and $^{15}$N chemical shift changes on peptide binding are located near the hydrophobic pocket between the ZA and BC loops (FIG. 3B). Because a similar pattern of amide chemical shift changes was observed with the two different AcK-containing peptides, it was surmised that the hydrophobic cavity is the primary binding site for AcK. This hypothesis was further supported by titration with acetyl-histamine, which mimics the chemical structure of the AcK side-chain (FIG. 3C). Both $^{15}$N— and $^{13}$C-HSQC spectra showed that interaction with acetyl-histamine was also acetylation-dependent, involving the same set of residues that showed chemical shift perturbations with similar concentration dependence. It should be noted that the bromodomain did not bind to the amino acids acetyl-lysine or acetyl-histidine alone, possibly due to the presence of the charged amino, carboxyl, or caboxylate group adjacent to the acetyl moiety (FIG. 3C). Taken together, these results strongly suggest that the P/CAF bromodomain can interact with acetyl-lysine-containing proteins in a specific manner, and that this interaction is localized to the bromodomain hydrophobic cavity.

To identify the key residues involved in bromodomain-AcK recognition, the NMR structure of the P/CAF bromodomain in complex with acetyl-histamine was elucidated. As anticipated, the acetylated moiety binds in the bromodomain hydrophobic pocket (FIG. 4). The intermolecular interactions are largely hydrophobic in nature, with the methyl group of acetyl-histamine making extensive contacts with the side-chains of Val752, Ala757, and Tyr760, and the methylene groups of acetyl-histamine displaying specific NOEs to Val752, Ala757, Tyr760, Tyr802, and Tyr809. No intermolecular NOEs were observed for the imidazole ring of acetyl-histamine. From the spectral analysis it is clear that the structure of the bromodomain is very similar in both the free and complex forms.

It is worth noting that the bromodomain-AcK recognition is reminiscent of the interactions between the histone acetyltransferase Hat1 and acetyl-CoA. Although the binding pockets of these two otherwise structurally unrelated proteins are composed of different secondary structural elements, the nature of acetyl-lysine recognition has striking similarities. In particular, Tyr809, Tyr802, Tyr760, and Val752 in the bromodomain appear to be related to Phe220, Phe261, Val254, and Ile217 of Hat1, respectively, in their interactions with the acetyl moiety. This observation may suggest an evolutionary convergent mechanism of acetyl-lysine recognition between bromodomains and histone acetyltransferases.

To determine the relative contributions of residues within the hydrophobic cavity in bromodomain-AcK binding, site-directed mutagenesis was used to alter residues Tyr809, Tyr802, Tyr760, and Val752 (Table 7).

TABLE 7

Structural and Functional Analysis of the P/CAF Bromodomain Mutants

| Bromodomain Proteins | Structural Integrity [a] | H4 AcK-Peptide Binding $K_D$ (µM) [b] |
|---|---|---|
| Wild-Type | ++++ | 346 ± 54 |
| Tyr809Ala | ++++ | No Binding [c] |
| Tyr802Ala | +++ | >10,000 [d] |
| Tyr760Ala | +++ | >10,000 |
| Val752Ala | ++ | >10,000 |

[a] The effects of mutations on the structural integrity of the bromodomain were assessed by using the $^{15}$N-HSQC spectra. The amide $^1$H/$^{15}$N resonances of the mutant proteins were compared to those of the wild-type bromodomain to determine if the particular mutations lead to global or local structure disruption. Severe line-broadening of the amide resonances would indicate protein conformational exchange due to a decrease of structure stability resulting from point mutations. Structural integrity of the mutant proteins is expressed here relative to that of the wild-type, using the signs of "++++" for as stable as the wild-type, "+++" for mildly destabilized, "++" for moderately destabilized, and "−" for completely unfolded.
[b] The ligand binding affinity ($K_D$) of the bromodomain proteins was estimated by following chemical shift changes of amide peaks in the $^{15}$N-HSQC spectra as a function of the ligand concentration.
[c] No detectable ligand binding observed in the NMR titration.
[d] Ligand binding affinity was significantly reduced and beyond the limit for reliable measurements by NMR titration.

Substitution of Ala for Tyr809 completely abrogated the bromodomain binding to the lysine-acetylated H4 peptide, while the Tyr802Ala, Tyr760Ala, and Val752Ala mutants had significantly reduced ligand binding affinity. To assess whether these mutations disrupted the overall bromodomain fold, the $^{15}$N-HSQC spectra of the mutants was compared to that of the wild-type protein. For the Tyr809Ala mutant, the amide chemical shifts were only affected for a few residues near the mutation site. However, mutations of the other residues in the hydrophobic binding pocket perturbed the local protein conformation to greater extents, particularly the ZA loop (Table 7). Thus, the NMR structural analysis and the mutagenesis studies show that Tyr809, which is structurally supported by Trp746 and Asn803 (FIG. 4), is essential for the bromodomain interaction with the acetyl group of acetyl-lysine, while residues of Tyr802, Tyr760, and Val752 likely play both structural and functional roles in the recognition. These residues are highly conserved throughout the bromodomain family (FIG. 1), suggesting that recognition of acetyl-lysine may be a feature of bromodomains, in general. Therefore, Val752, Ala757, Tyr760, Tyr802, Asn803, and Tyr809 are key amino acid residues for the P/CAF bromodomain binding to acetyl-lysine.

TABLE 8

Amino Acid Sequences of Bromodomains Identified in FIG. 1

| PROTEIN BD | SEQ ID NO: | GenBank Acc. No. |
|---|---|---|
| hsp/CAF | 7 | U57317 |
| hsGCN5 | 8 | U57136 |
| ttP55 | 9 | U47321 |
| scGCN5 | 10 | Q03330 |
| hsP300 | 11 | A54277 |
| hsCBP | 12 | S39162 |
| mmCBP | 13 | S39161 |
| ceYNJ1 | 14 | P34545 |
| hsCCG1-1 | 15 | P21675 |
| msCCG1-1 | 16 | D26114 |
| hsCCG1-2 | 17 | |
| msCCG1-2 | 18 | |
| hsRing3-1 | 19 | P25440 |
| hsOREX-1 | 20 | D26362 |
| dmFSH-1 | 21 | P13709 |
| scBDF1-1 | 22 | P35817 |
| hsRing3-2 | 23 | |
| hsORFX-2 | 24 | |
| dmFSH-2 | 25 | |
| scBDF1-2 | 26 | |
| hsBR140 | 27 | JC2069 |
| hsSMAP | 28 | X87613 |
| ggPB1-1 | 29 | X90849 |
| ggPB1-2 | 30 | |
| ggPB1-3 | 31 | |
| ggPB1-4 | 32 | |
| ggPB1-5 | 33 | |
| spBRO-1 | 34 | S54260 |
| spBRO-2 | 35 | |
| hsSNf2a | 36 | S45251 |
| hsBRGL | 37 | S39039 |
| ggBRM | 38 | X91638 |
| ggBRG1 | 39 | X91637 |
| hsTIF1b | 40 | X97548 |
| mmTIF1b | 41 | X99644 |
| mmTIF1a | 42 | S78219 |

Example 2

Structural Insights into HIV-1 TAT Transactivation via P/CAF

Introduction

Whereas the life cycle of HIV is still being elucidated, it is currently accepted that HIV binds to CD4 protein of a host T cell or macrophage and with the aid of a chemokine receptor (e.g., CCR5 or CXCR4) enters the host cell. Once in the host cell, the retrovirus, HV-1, is converted to a DNA by reverse transcriptase and the expression of the HIV-1 genome is dependent on a complex series of events that are believed to be under the control of two viral regulatory proteins, Tat and Rev [Romano et al., *J. Cell Biochem.* 75(3):357-368 (1999)]. Rev controls post-translational events, whereas, Tat (the trans-activator protein) functions to stimulate the production of full-length HIV transcripts and viral replication in infected cells.

The Tat protein transactivates the transcription of HIV-1 starting at the 5' long terminal repeat (LTR) [Romano et al., *J. Cell Biochem.* 75(3):357-368 (1999)] by recruiting one or more carboxyl-terminal domain kinases to the HIV-1 promoter. More specifically, Tat stimulates transcription from the LTR at a hairpin element, the transactivation responsive region (TAR) [Kiernan et al., *EMBO J.* 18:6106-6118 (1999)] at least in part by interacting with and thereby recruiting the carboxyl-terminal domain kinase, i.e., the positive transcriptional elongation factor (P-TEFb) to the TAR RNA element [Garber et al., *Mol. Cell. Biol.* 20(18):6958-6969 (2000)]. P-TEFb is a muti-subunit kinase that minimally comprises a heterodimer consisting of the regulatory cyclin T1and its corresponding catalytic subunit, cyclin-dependent kinase 9 (CDK9). P-TEFb acts by phosphorylating the carboxyl-terminal domain of RNA polymerase II [Peng et al., *J. Biol. Chem.* 274 (49):34527-34530 (1999); Romano et al., *J. Cell-Biochem.* 75(3):357-368 (1999)].

Recently, it has been shown that HIV-1 Tat transcription activity is regulated through lysine acetylation by, and association with the histone acetyltransferases (HATs) p300/CBP and the p300/CBP-associating factor (P/CAF), which specifically acetylate lysine 50 (K50) and Lysine 28 (K28) of the Tat protein, respectively [Kiernan et al., *EMBO J.* 18:6106-6118 (1999); Ott et al., *Curr. Biol.* 9:1489-1492 (1999)]. Notably, the acetylation of K50 by the transcriptional co-activator p300/CBP is on the C-terminal arginine-rich motif (ARM) of Tat, which is essential for its binding to the TAR RNA element and for nuclear localization, [Kiernan et al., *EMBO J.* 18:6106-6118 (1999); Ott et al., *Curr. Biol.* 9:1489-1492 (1999)]. Acetylation of K28 of Tat by P/CAF enhances Tat binding to P-TEFb, whereas acetylation of K50 of Tat by P300/CBP promotes the dissociation of Tat from the TAR RNA element. This dissociation of Tat from the TAR RNA element occurs during early transcription elongation [Kiernan et al., *EMBO J.* 18:6106-6118 (1999)]. However, heretofore, little else was known regarding the relationship of these HATs with Tat after the acetylation has occurred.

Methods

Sample preparation: The bromodomain of P/CAF (residues 719-832) was subcloned into the pET14b expression vector (Novagen) and expressed in *Escherichia coli* BL21 (DE3) cells. Uniformly $^{15}$N— and $^{15}$N/$^{13}$C-labeled proteins were prepared by growing bacteria in a minimal medium containing $^{15}$NH$_4$Cl with or without $^{13}$C$_6$-glucose. A uniformly $^{15}$N/$^{13}$C-labeled and fractionally deuterated protein sample was prepared by growing the cells in 75% $^2$H$_2$O. The bromodomain was purified by affinity chromatography on a nickel-IDA column (Invitrogen) followed by the removal of poly-His tag by thrombin cleavage. The final purification of the protein was achieved by size-exclusion chromatography. The acetyl-lysine-containing peptides were prepared on a MilliGen 9050 peptide synthesizer (Perkin Elmer) using Fmoc/HBTU chemistry. Acetyl-lysine was incorporated using the reagent Fmoc-Ac-Lys with HBTU/DIPEA activation. NMR samples contained ~0.5 mM protein in complex with the lysine-acetylated Tat peptide in 100 mM phosphate buffer of pH 6.5 and 5 mM perdeuterated DTT and 0.5 mM EDTA in H$_2$0/$^2$H$_2$O (9/1) or $^2$H$_2$O. The bromodomain-containing constructs from P/CAF, CBP and TIF-1β were cloned into pGEX4T-3 vector (Pharmacia). These recombinant GST-fusion proteins were expressed in BL21 (DE3) codon plus cell line, and purified by using glutathione sepharose column.

NMR spectroscopy: All NMR spectra were acquired at 30° C. on a Bruker DRX600 or DRX500 spectrometer. The backbone assignments of the $^1$H, $^{13}$C, and $^{15}$N resonances were achieved using deuterium-decoupled triple-resonance experiments of HNCACB and HN(CO)CACB [Yamazaki et al., *J. Am. Chem. Soc.* 116:11655-11666 (1994)] recorded using the uniformly $^{15}$N/$^{13}$C-labelled and fractionally deuterated protein. The side-chain atoms were assigned from 3D HCCH-TOCSY [Clore and Gronenbom, *Meth. Enzymol.* 239:249-363 (1994)] and (H)C(CO)NH-TOCSY [Logan et al., *J. Biolmol. NMR* 3:225-231 (1993)] data collected on the uniformly $^{15}$N/$^{13}$C-labeled protein. Stereospecific assignments of methyl groups of the valine and leucine residues were obtained using a fractionally $^{13}$C-labeled sample [Neri et al., *Biochemistry* 28:7510-7516 (1989)]. The NOE-derived distance restraints were obtained from $^{15}$N- or $^{13}$C-edited 3D NOESY spectra [Clore and Gronenbom, *Meth. Enzymol.* 239:249-363 (1994)]. φ-angle restraints were determined based on the $^3$J$_{HN,H}$ coupling constants measured in a 3D HNHA spectrum [Clore and Gronenbom, *Meth. Enzymol.* 239:249-363 (1994)]. Slowly exchanging amide protons were identified from a series of 2D $^{15}$N-HSQC spectra recorded after the H$_2$O buffer was changed to a $^2$H$_2$O buffer. The intermolecular NOEs used in defining the structure of the bromodomain/Ac-histamine complex were detected in $^{13}$C-edited (F$_1$), $^{13}$C/$^{15}$N-filtered (F$_3$) 3D NOESY spectrum [Clore and Gronenbom, *Meth. Enzymol.* 239:249-363 (1994)]. All NMR spectra were processed with the NMRPipe/NMRDraw programs and analyzed using NMRView [Johnson and Blevins, *J. Biomol., NMR* 4:603-614 (1994)].

Ligand titration experiments were performed by recording a series of 2D $^{15}$N-HSQC spectra on the uniformly $^{15}$N-labelled bromodomain (~0.3 mM), respectively, in the presence of different amounts of ligand concentration ranging from 0 to ~2.0 mM. The protein sample and the stock solutions of the ligands were all prepared in the same aqueous buffer containing 100 mM phosphate and 5 mM perdeuterated DTT at pH 6.5.

Structure calculations. Structures of the bromodomain were calculated with a distance geometry/simulated annealing protocol using the X-PLOR program [Brunger, *X-PLOR Version 3.1: A system for X-Ray crystallography* and NMR, Yale University Press, New Haven, Conn., (1993)]. A total of 1324 manually assigned NOE-derived distance restraints were obtained from the $^{15}$N- and $^{13}$C-edited NOE spectra. Further analysis of the NOE spectra was carried out by the iterative automated assignment procedure by using ARIA [Nilges and O'Donoghue, *Prog. NMR Spectroscopy* 32:107-139 (1998)], which integrates with X-PLOR for structure calculations. The ARIA-assigned distance restraints were in agreement with the structures calculated using only the manually assigned NOE distance restraints, hydrogen-bond distance restraints, and 54 φ-angle restraints. The final structure calculations employed a total of 2903 NMR experimental restraints obtained from the manual and the ARIA-assisted assignments. For the ensemble of the final 30 structures, no distance and torsional angle restraints were violated by more than 0.3 Å and 5 Å, respectively. The Lennard-Jones potential which was not used during any refinement stage, and stereochemistry of the final structures was validated with Ramachandran plot analysis by using Procheck-NMR [Laskowski et al., *J. Biolmol. NMR* 8:477-486 (1996)].

Site directed mutagenesis. Site directed mutagenesis was performed on selected residues of P/CAF Bromodomain using quick-change kit (Stratagene). The mutants were confirmed by sequencing and proteins were expressed and purified as above.

Peptide binding assay. Equal amount (10 μM) of GST, GST-P/CAF bromodomain and its mutant proteins, as well as various GST-fusion bromodomains from CBP and TIF1β were incubated for at least two hours at room temperature with the N-terminal biotinylated and lysine-acetylated Tat peptide (50 μM) in a 50 mM Tris buffer of pH 7.5, containing 50 mM NaCl, 0.1% BSA and 1 mMDTT. Streptavidin agarose (10 μL) was added to mixture and the beads were washed twice in the Tris buffer with 500 mM NaCl and 0.1% NP-40. Proteins were eluted from the argarose beads in SDS buffer and separated on a 14% SDS-PAGE. The resolved proteins were transferred onto nitrocellulose membrane (Pharmacia), and the membrane was blocked overnight with 5% non-fat milk in washing buffer of 20 mM Tris, pH 7.5, plus 150 mM NaCl and 0.1% Tween-20 at 4° C. Western blotting was performed with anti-GST antibody (Sigma) and goat anti-rabbit IgG conjugated with horseradish-peroxidase (Promega) and developed by chemiluminescence. Peptide competition experiments were performed by incubating various non-biotinylated and mutant Tat peptide with the P/CAF bromodomain and the biotinylated and wild type Tat peptide. The molar ratio of the wild type and mutant Tat peptides in the mixture were kept at 1:2. The binding results were analyses by using the procedure as described above.

The full length protein sequence of the Human Immunodeficiency Virus type 1

Tat was obtained from GenBank, Accession No: AAA83395:

1  MEPVDPRLEP WKHPGSQPKT ASNNCYCKRC CLHCQVCFTK KGLGISYGRK
   KRRQRRRAPQ
61 DSKTHQVSLS KQPASQPRGD PTGPKESKKK VERETETDPE D (SEQ ID NO:45)

Results

Figure 5:
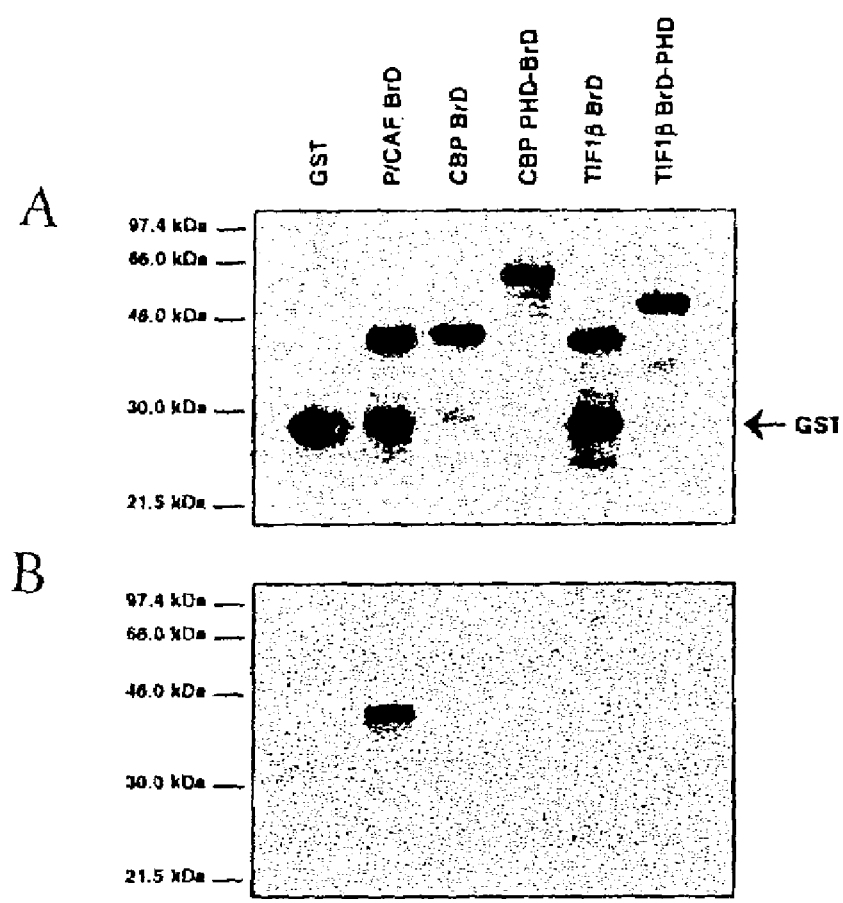
FIGS. 5A-5B show the binding of various bromodomains from P/CAF, CBP and TIF1b to the N-terminal biotinylated and lysine-acetylated Tat peptide that was immobilized on streptavidin agarose.
Figure 6:
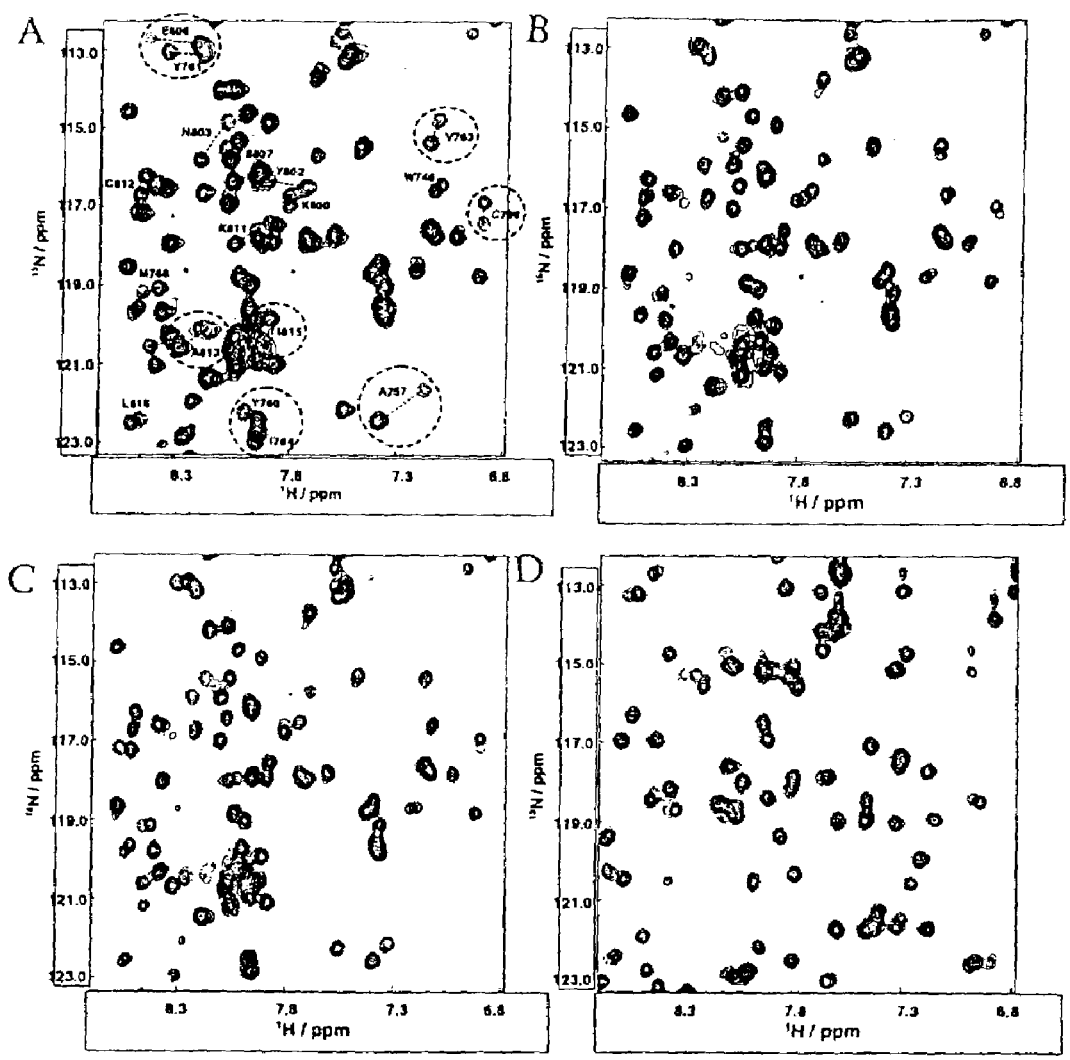
FIGS. 6A-6D shows the lysine-acetylated HIV-1 Tat protein interactions with bromodomains using 2D 1H-15N-HSQC spectra of the P/CAF or CBP bromodomain in the presence (red) or absence (black) of the lysine-acetylated peptides. Binding of the P/CAF bromodomain to the Tat AcK 50 peptide SYGR-AcK-KRRQRC (SEQ ID NO:50) is shown in FIG. 6A, to the Tat AcK 28 peptide TNCYCK-AcK-CCFH (SEQ IUD NO:58) is shown in FIG. 6B, and to histone H4 AcK16 peptide SGRGKGGKGLGKGGA-AcK-RHRK (SEQ ID NO:59) is shown in FIG. 6C.

To test whether or not the bromodomains of these HATs can bind to the lysine-acetylated Tat, in vitro binding assays were performed by using recombinant and purified bromodomains and lysine-acetylated peptides derived from the acetylation sites in Tat. While the bromodomains of CBP and TIF1β did not show any binding, the P/CAF bromodomain binds tightly only to the Tat peptide containing AcK50 (where AcK stands for an N$^\epsilon$-acetyl lysine residue) (FIGS. 5A-5B). NMR binding studies further confirmed the specific interaction of the P/CAF bromodomain and lysine-acetylated Tat peptide. Because NMR resonances of amide protons are highly sensitive to local chemical environment and conformational change in a protein, two-dimensional $^1$H-$^{15}$N heteronuclear single quantum correlation (HSQC) spectrum can be used to detect even weak but specific interactions between a protein and its binding ligand. As shown in 2D HSQC spectra (FIGS. 6A-6D), the bromodomain of P/CAF binds weakly to the lysine-acetylated peptides derived from known acetylation sites of K28 on Tat and of K16 on histone H4 by only interacting with the acetyl-lysine residue in the peptides ($K_d$<300 μM). This is reflected the relatively small chemical shift perturbation of the amide proton signals of the protein upon addition of ligand. On the other hand, the P/CAF bromodomain interacts strongly with the Tat AcK50 peptide, which involves many protein residues in addition to those for acetyl-lysine binding with an estimated $K_d$ of ~20 μM. Binding of peptide residues flanking the acetyl-lysine may explain the high specificity of the P/CAF bromodomain for the acetylated Tat. Furthermore, the p300/CBP bromodomain did not bind the lysine-acetylated Tat peptide in a specific manner except its weak interaction with the acetyl-lysine residue in the peptide (FIGS. 6A-6D). Together, these results demonstrate the P/CAF bromodomain can specifically recognize the lysine-acetylated Tat involving K50.

Figure 7:
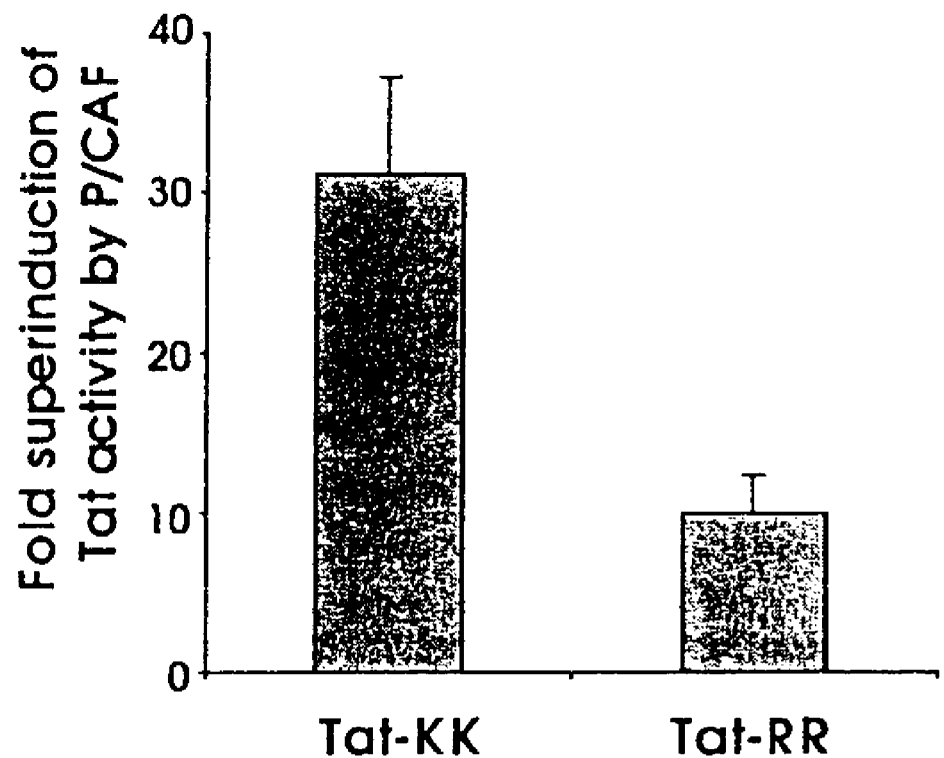
FIG. 7 is a bar graph of the measurement of superinduction of Tat transactivation activity by P/CAF. Tat-KK is the wild type Tat protein, and Tat-RR is the double mutant Tat carrying lysine to arginine mutations at K50 and K51 positions.
Figure 8:
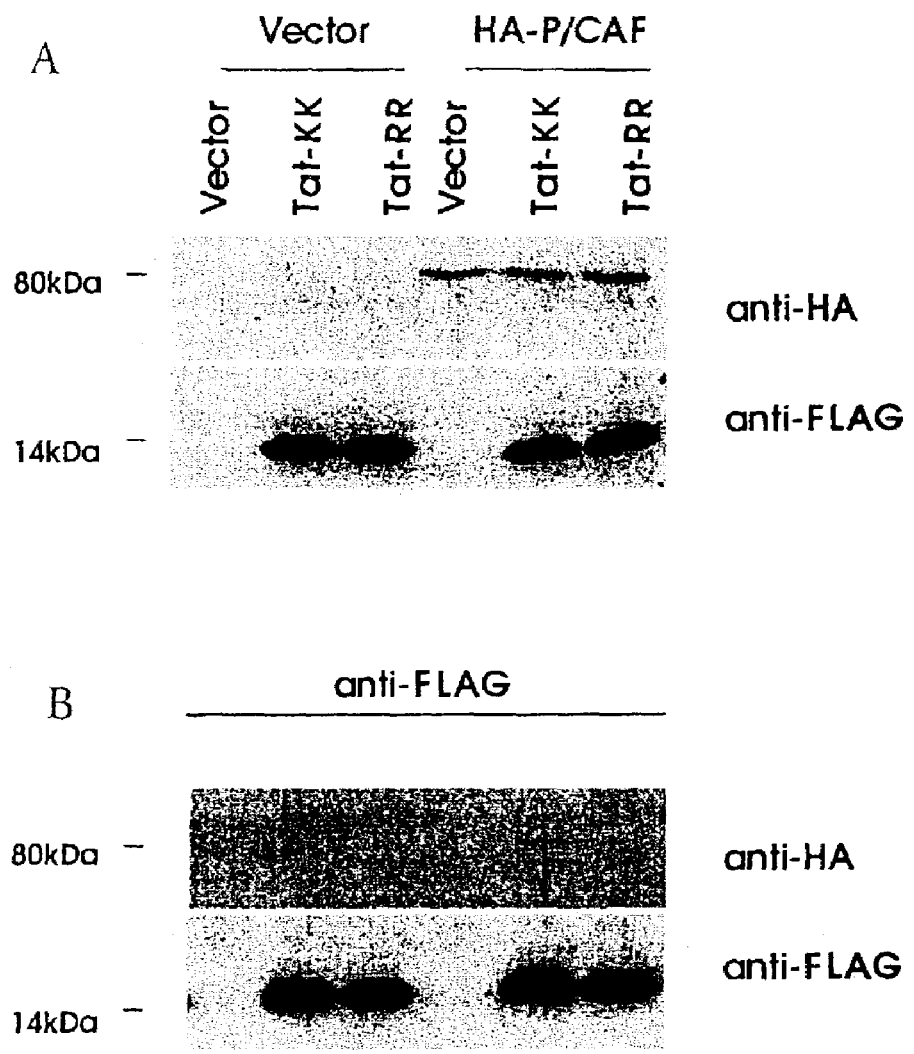
FIGS. 8A-8B show a western blot assay to detect P/CAF interaction with the Tat protein. Note that the protein-protein interaction was only observed with the wild type Tat but not with the Tat K50R/K51R mutant protein. The FLAG was joined to the Tat peptide, whereas the HA-tag was joined to P/CAF.

To determine how the P/CAF binding affects Tat function in vivo, transactivation activity of Tat was measured. Superinduction of Tat transactivation activity exhibited as much as a 30-fold increase upon P/CAF stimulation (FIG. 7). This profound P/CAF effect requires acetylation at K50 on Tat, as a double mutant of K50 and K51 substituted with arginines resulted in a nearly two-thirds reduction of the enhancement. Further, specific interaction between P/CAF and wild type Tat in cells was also detected, but not with the Tat double mutant containing K50R/K51R (FIGS. 8A-8B). Taken together, these results confirm that P/CAF can directly interact via its bromodomain with the lysine-acetylated Tat, which possibly regulates Tat transactivation activity.

To further understand the molecular basis of the P/CAF bromodomain recognition of the lysine-acetylated Tat, the three-dimensional structure was determined for the P/CAF bromodomain in complex with an 11-residue Tat peptide containing AcK50. A total of 2,903 NMR-derived distance and dihedral angle restraints were used. The structure of the bromodomain in the peptide-bound form consists of an up-and-down four-helix bundle (helices $\alpha_Z$, $\alpha_A$, $\alpha_B$, and $\alpha_C$) with a left-handed twist, and a long intervening loop between helices $\alpha_Z$ and $\alpha_A$ (termed the ZA loop) (FIG. 9). The overall structure of the complex is well defined (Table 9), and similar to the structure of the free bromodomain [Dhalluin et al., *Nature* 399:491-496 (1999); Example 1 above] except that the ZA and BC loops, which compose the acetyl-lysine binding pocket, undergo local conformational changes in order to accommodate their interactions with the peptide residues.

TABLE 9

NMR Structural Statistics of the P/CAF Bromodomain/Tat Peptide Complex

| | | |
|---|---|---|
| Total Experimental Restraints | | 2903 |
| Distance Restraints$^a$ | | 2822 |
| Total Ambiguous | | 122 |
| Total Unambiguous | | 2700 |
| Intra-residue | (i = j) | 1118 (41.40%) |
| Sequential | (\|i − j\| = 1) | 487 (18.04%) |
| Medium | (2 ≤ \|i − j\| ≤ 4) | 547 (20.26%) |
| Long range | (\|i − j\| > 4) | 478 (17.70%) |
| Intermolecular | | 78 (2.39%) |
| Hydrogen Bond Restraints | | 28 |
| Dihedral Angle Restraints | | 53 |

TABLE 9-continued

NMR Structural Statistics of the P/CAF Bromodomain/Tat Peptide Complex

Final Energies (kcalmol$^{-1}$)

| | |
|---|---|
| $E_{Total}$ | 366.35 ± 31.11 |
| $E_{NOE}$ | 58.05 ± 12.57 |
| $E_{Dihedral}$ | 0.57 ± 0.31 |
| $E_{L-J}$b | −569.47 ± 22.42 |

| Ramachandran Plot (%) | Protein/Peptide Complex | Secondary Structure |
|---|---|---|
| Most Favorable Region | 72.06 ± 2.29 | 91.95 ± 3.04 |
| Additionally Allowed Region | 22.91 ± 2.41 | 7.42 ± 3.08 |
| Generously Allowed Region | 3.64 ± 1.40 | 0.62 ± 0.82 |
| Disallowed Region | 1.33 ± 0.64 | 0.00 ± 0.0 |

| RMSDs of Atomic Coordinates (Å) | Protein/Peptide Complex | Secondary Structure |
|---|---|---|
| Protein (aa 9-116) | | |
| Backbone | 0.66 ± 0.14 | 0.39 ± 0.05 |
| Heavy atoms | 1.25 ± 0.18 | 0.96 ± 0.07 |
| Peptide (aa 202-206, 208-209) | | |
| Backbone | 0.50 ± 0.16 | |
| Heavy atoms | 1.83 ± 0.50 | |
| Complex (aa 9-116, 202-206, 208-209) | | |
| Backbone | 0.72 ± 0.15 | 0.54 ± 0.09 |
| Heavy atoms | 1.39 ± 0.20 | 1.24 ± 0.16 | aOf the total 2903 NOB-derived distance restraints, only 341 were obtained by using ARIA program, of which 122 are classified as ambiguous NOEs. The latter resonance signals in the spectra match with more than one proton atom in both the chemical shift assignment and the final NMR structures
bThe Lennard-Jones potential was not used during any refinement stage.
cNone of these final structures exhibit NOE-derived distance restraint violations greater than 0.5 Å or dihedral angle restraint violations greater than 5°.

The Tat AcK50 peptide adopts an extended conformation and lies between the ZA and BC loops (FIG. 9). The acetyl-lysine side-chain intercalates deep into a preformed hydrophobic and aromatic cavity located between the ZA and BC loops opposite to the N- and C-termini, and interacts extensively with residues V752, Y760, I764, Y802, and Y809. While the peptide residues S(AcK−4), K(AcK+1), R(AcK+2), R(AcK+5) do not interact directly with the protein, the residues Y(AcK−3), G(AcK−2), R(AcK−1), R(AcK+3), and Q(AcK+4) showed numerous intermolecular NOEs with the protein. Particularly, Y(AcK−3) and Q(AcK+4) form extensive contacts with V763 and E756, respectively, suggesting that these two residues contribute significantly to specificity of the bromodomain/Tat recognition.

Figure 10:
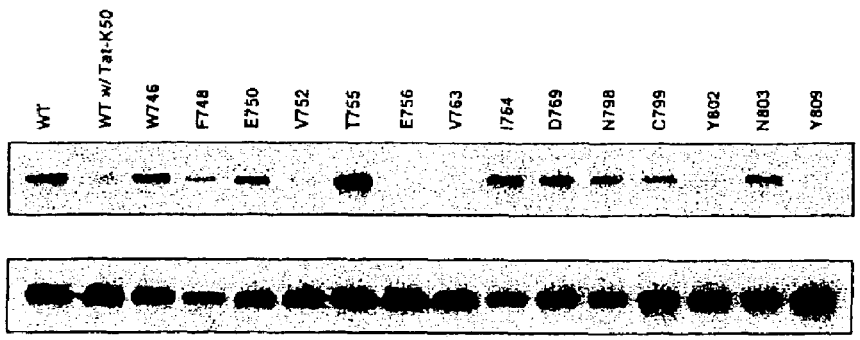
FIGS. 10A-10B shows the results of the mutational analyses of the P/CAF bromodomain binding to the HIV-1 Tat.
Figure 10:
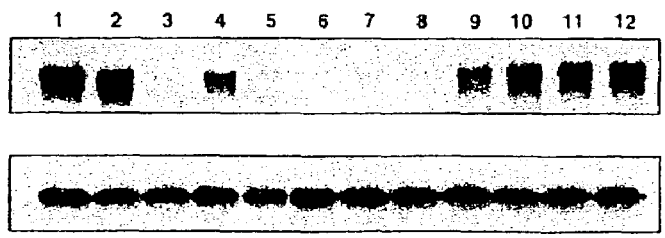

To identify the amino acid residues of the P/CAF bromodomain that are important for complex formation, mutant proteins were tested for binding to the biotinylated and lysine-acetylated Tat peptide that is immobilized onto streptavidin agarose (FIG. 10A). As expected, proteins containing alanine point mutation at the residue Y809, Y802, V752, or F748, which interact directly with the acetyl-lysine residue, showed nearly complete loss or significantly reduced binding to the Tat peptide. Moreover, when the residue V763 or E756 was mutated to alanine, a nearly complete loss in binding to the Tat AcK5O peptide was observed, indicating that these two amino acid residues provide essential contributions to the Tat recognition by interacting with the residues flanking the acetyl-lysine. The results from the mutational analysis agree with the observations of intermolecular NOEs in the NMR spectra.

To further determine Tat sequence preference for P/CAF interaction, various mutant peptides were synthesized and their binding to the P/CAF bromodomain tested in a competition assay by using a western blot with the antibody against the GST-fusion bromodomain (FIG. 10B). Because of high sensitivity of this detection method, the binding assay was performed at protein concentration (~10 μM) much lower than that in the NMR binding studies, which ensured specificity of protein-peptide interactions. In agreement with the binding results described above (e.g., see FIGS. 5A-5B, 6A-6D, 7, and 8A-8B), lysine-acetylated peptides derived from acetylation sites at K50 or K28 in Tat, or from histone H4 at K16 showed almost no competition with the Tat AcK50 peptide in binding to the P/CAF bromodomain, confirming that the latter interaction is tight and specific. Additionally, while substitution of residue R(AcK−1), K(AcK+1), R(AcK+2), or R(AcK+3) to alanine slightly weakened Tat peptide binding to the bromodomain, mutation of Y(AcK-3) or Q(AcK+4) resulted in significant loss in binding to the protein. These data can be explained by the observation of extensive pair-wise interactions between Y(AcK-3) and V763, and between Q(AcK+4) and E756, which agrees perfectly with the site-directed mutagenesis results obtained with the protein (FIG. 10A). Together, these results demonstrate that the specificity of P/CAF bromodomain and acetylated Tat complex formation is achieved through specific interactions with acetyl-lysine as well as amino acid residues at (AcK−3) and (AcK+4) positions.

The HIV-1 Tat is a versatile protein and elicits many cellular functions. In addition to its lysine-acetylation and interaction with P/CAF as disclosed herein, this portion of arginine-rich motif (named ARM) has also been shown to interact with the TAR RNA element as well as protein nuclear localization, particularly involving arginine52 and arginine53. The findings disclosed herein that are based on the detailed structural and mutational analyses indicate that the lysine-acetylated Tat specifically is associated with P/CAF via a bromodomain interaction in vivo, and that this interaction is important for transactivation activity of Tat in cells. Furthermore, the data disclosed herein reveal that in addition to the acetylated-lysine (K50) the flanking residues, tyrosine (AcK−3) and glutamine at (AcK+4) positions in Tat are also uniquely important for the specificity of the Tat and P/CAF bromodomain recognition, but not with its other functions. This new information is extremely useful in applying mutational analysis in vivo studies to further elucidate the biological importance of the Tat-P/CAF association in molecular mechanisms by which Tat transactivates gene transcription of HIV-1 via chromatin remodeling.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference herein in their entireties.

TABLE 1

NMR Chemical Shift Assignment of the P/CAF Bromodomain

| RES_ID | 715 | RES_ID | 775 | HD2 | 3.656000 | RES_ID | 779 |
|---|---|---|---|---|---|---|---|
| RES_TYPE | GLY | RES_TYPE | GLU | HD1 | 3.800000 | RES_TYPE | ASN |
| SPIN_SYSTEM_ID | 1 | SPIN_SYSTEM_ID | 61 | END_RES_DEF | | SPIN_SYSTEM_ID | 65 |
| HETEROGENEITY | 100 | HETEROGENEITY | 100 | RES_ID | 723 | HETEROGENEITY | 100 |
| END_RES_DEF | | N | 124.471000 | RES_TYPE | ARG | N | 116.108000 |
| RES_ID | 716 | HN | 8.150000 | SPIN_SYSTEM_ID | 9 | HN | 7.947000 |
| RES_TYPE | SER | CA | 59.570000 | HETEROGENEITY | 100 | CA | 53.510000 |
| SPIN_SYSTEM_ID | 2 | HA | 4.045000 | N | 121.192000 | HA | 4.771000 |
| HETEROGENEITY | 100 | CB | 29.280000 | HN | 8.416000 | CB | 38.095000 |
| END_RES_DEF | | HB1 | 2.246000 | CA | 63.430000 | HB1 | 3.019000 |
| RES_ID | 717 | HB2 | 2.063000 | HA | 4.331000 | HB2 | 2.773000 |
| RES_TYPE | HIS | CG | 36.443000 | CB | 30.930000 | ND2 | 112.665000 |
| SPIN_SYSTEM_ID | 3 | HG1 | 2.345000 | HB1 | 1.815000 | HD21 | 7.598000 |
| HETEROGENEITY | 100 | HG2 | 2.176000 | HB2 | 1.762000 | HD22 | 6.969000 |
| END_RES_DEF | | END_RES_DEF | | CG | 27.630000 | END_RES_DEF | |
| RES_ID | 718 | RES_ID | 776 | HG1 | 1.681000 | RES_ID | 780 |
| RES_TYPE | MET | RES_TYPE | ARG | CD | 43.603000 | RES_TYPE | ARG |
| SPIN_SYSTEM_ID | 4 | SPIN_SYSTEM_ID | 62 | HD1 | 3.161000 | SPIN_SYSTEM_ID | 66 |
| HETEROGENEITY | 100 | HETEROGENEITY | 100 | END_RES_DEF | | HETEROGENEITY | 100 |
| END_RES_DEF | | N | 120.372000 | RES_ID | 724 | N | 114.141000 |
| RES_ID | 719 | HN | 8.391000 | RES_TYPE | ASP | HN | 8.158000 |
| RES_TYPE | SER | CA | 60.676000 | SPIN_SYSTEM_ID | 10 | CA | 56.821000 |
| SPIN_SYSTEM_ID | 5 | HA | 3.869000 | HETEROGENEITY | 100 | HA | 4.405000 |
| HETEROGENEITY | 100 | CB | 30.385000 | N | 122.012000 | CB | 25.429000 |
| END_RES_DEF | | HB1 | 2.047000 | HN | 8.273000 | HB1 | 2.097000 |
| RES_ID | 720 | HB2 | 1.076000 | CA | 52.415000 | HB2 | 2.022000 |
| RES_TYPE | LYS | CG | 29.284000 | HA | 4.874000 | CG | 27.632000 |
| SPIN_SYSTEM_ID | 6 | HG1 | 1.722000 | CB | 41.400000 | HG1 | 1.539000 |
| HETEROGENEITY | 100 | HG2 | 0.877000 | HB1 | 2.754000 | HG2 | 1.534000 |
| CA | 56.296000 | CD | 44.154000 | HB2 | 2.692000 | CD | 43.050000 |
| HA | 4.361000 | HD1 | 2.578000 | END_RES_DEF | | HD1 | 3.060000 |
| CB | 33.140000 | HD2 | 2.051000 | RES_ID | 725 | HD2 | 3.024000 |
| HB1 | 1.882000 | END_RES_DEF | | RES_TYPE | PRO | END_RES_DEF | |
| HB2 | 1.684000 | RES_ID | 777 | SPIN_SYSTEM_ID | 11 | RES_ID | 781 |
| CG | 25.430000 | RES_TYPE | LEU | HETEROGENEITY | 100 | RES_TYPE | TYR |
| HG1 | 1.585000 | SPIN_SYSTEM_ID | 63 | CA | 65.080000 | SPIN_SYSTEM_ID | 67 |
| HG2 | 1.433000 | HETEROGENEITY | 100 | HA | 4.329000 | HETEROGENEITY | 100 |
| CD | 29.834000 | N | 120.208000 | CB | 32.590000 | N | 116.764000 |
| HD1 | 1.703000 | HN | 8.856000 | HB1 | 2.326000 | HN | 8.222000 |
| CE | 41.960000 | CA | 58.470000 | HB2 | 1.973000 | CA | 60.125000 |
| HE1 | 3.003000 | HA | 4.691000 | CG | 27.632000 | HA | 4.064000 |
| END_RES_DEF | | CB | 42.621000 | HG1 | 2.028000 | CB | 40.850000 |
| RES_ID | 721 | HB1 | 2.295000 | CD | 51.310000 | HB1 | 2.948000 |
| RES_TYPE | GLU | HB2 | 1.925000 | HD1 | 3.866000 | HB2 | 2.055000 |
| SPIN_SYSTEM_ID | 7 | CG | 27.080000 | END_HES_DEF | | CD1 | 134.350000 |
| HETEROGENEITY | 100 | HG | 1.832000 | RES_ID | 726 | HD1 | 6.285000 |
| N | 122.990000 | CD1 | 25.429000 | RES_TYPE | ASP | CE1 | 118.930000 |
| HN | 8.317000 | HD1# | 1.067000 | SPIN_SYSTEM_ID | 12 | HE1 | 6.709000 |
| CA | 54.620000 | CD2 | 27.081000 | HETEROGENEITY | 100 | END_RES_DEF | |
| HA | 4.540000 | HD2# | 0.871000 | N | 119.716000 | RES_ID | 782 |
| CB | 29.830000 | END_RES_DEF | | HN | 8.397000 | RES_TYPE | TYR |
| HB1 | 2.024000 | RES_ID | 778 | CA | 55.720000 | SPIN_SYSTEM_ID | 68 |
| HB2 | 1.893000 | RES_TYPE | LYS | HA | 4.692000 | HETEROGENEITY | 100 |
| CG | 35.893000 | SPIN_SYSTEM_ID | 64 | CB | 40.550000 | N | 114.633000 |
| HG1 | 2.271000 | HETEROGENEITY | 100 | HB1 | 2.792000 | HN | 8.014000 |
| END_RES_DEF | | N | 120.372000 | HB2 | 2.730000 | CA | 57.920000 |
| RES_ID | 722 | HN | 7.958000 | END_RES_DEF | | HA | 4.528000 |
| RES_TYPE | PRO | CA | 59.574000 | RES_ID | 727 | CB | 36.443000 |
| SPIN_SYSTEM_ID | 8 | HA | 4.333000 | RES_TYPE | GLN | HB1 | 3.062000 |
| HETEROGENEITY | 100 | CB | 32.588000 | SPIN_SYSTEM_ID | 13 | HB2 | 2.907000 |
| CA | 63.430000 | HB1 | 2.055000 | HETEROGENEITY | 100 | CD1 | 133.248000 |
| HA | 4.393000 | CG | 24.878000 | N | 121.356000 | HD1 | 7.175000 |
| CB | 32.030000 | HG1 | 1.596000 | HN | 8.196000 | CE1 | 120.582000 |
| HB1 | 2.224000 | CD | 29.835000 | CA | 55.920000 | HE1 | 7.286000 |
| HB2 | 1.880000 | HD1 | 1.804000 | HA | 4.163000 | END_RES_DEF | |
| CG | 27.630000 | CE | 41.951000 | CB | 28.730000 | RES_ID | 783 |
| HG1 | 2.028000 | HE1 | 2.990000 | HB1 | 2.148000 | RES_TYPE | VAL |
| CD | 50.760000 | END_RES_DEF | | CG | 34.240000 | SPIN_SYSTEM_ID | 69 |
| | | | | HG1 | 2.524000 | HETEROGENEITY | 100 |
| | | | | HG2 | 2.371000 | N | 115.780000 |
| | | | | END_RES_DEF | | HN | 7.698000 |

TABLE 1-continued

NMR Chemical Shift Assignment of the P/CAF Bromodomain

| Field | Value | Field | Value |
|---|---|---|---|
| RES_ID | 728 | CA | 62.330000 |
| RES_TYPE | LEU | HA | 4.083000 |
| SPIN_SYSTEM_ID | 14 | CB | 31.500000 |
| HETEROGENEITY | 100 | HB | 2.321000 |
| N | 121.356000 | CG1 | 21.570000 |
| HN | 8.210000 | HG1# | 0.944000 |
| CA | 58.473000 | CG2 | 18.820000 |
| HA | 4.045000 | HG2# | 0.823000 |
| CB | 41.400000 | END_RES_DEF | |
| HB1 | 1.847000 | RES_ID | 784 |
| HB2 | 1.555000 | RES_TYPE | SER |
| CG | 27.080000 | SPIN_SYSTEM_ID | 70 |
| HG | 1.480000 | HETEROGENEITY | 100 |
| CD1 | 25.970000 | N | 111.353000 |
| HD1# | 0.794000 | HN | 7.415000 |
| CD2 | 23.226000 | CA | 55.719000 |
| HD2# | 0.786000 | HA | 4.741000 |
| END_RES_DEF | | CB | 66.183000 |
| RES_ID | 729 | HB1 | 4.200000 |
| RES_TYPE | TYR | HB2 | 3.750000 |
| SPIN_SYSTEM_ID | 15 | END_RES_DEF | |
| HETEROGENEITY | 100 | RES_ID | 785 |
| N | 119.060000 | RES_TYPE | LYS |
| HN | 8.021000 | SPIN_SYSTEM_ID | 71 |
| CA | 62.320000 | HETEROGENEITY | 100 |
| HA | 4.038000 | CA | 59.030000 |
| CB | 38.640000 | HA | 4.021000 |
| HB1 | 3.211000 | CB | 31.590000 |
| HB2 | 3.024000 | END_RES_DEF | |
| CD1 | 134.350000 | RES_ID | 786 |
| HD1 | 7.053000 | RES_TYPE | LYS |
| CE1 | 119.481000 | SPIN_SYSTEM_ID | 72 |
| HE1 | 6.882000 | HETEROGENEITY | 100 |
| END_RES_DEF | | N | 120.208000 |
| RES_ID | 730 | HN | 8.244000 |
| RES_TYPE | SER | CA | 59.720000 |
| SPIN_SYSTEM_ID | 16 | HA | 4.062000 |
| HETEROGENEITY | 100 | CB | 30.385000 |
| N | 112.173000 | HB1 | 1.779000 |
| HN | 8.167000 | CG | 24.530000 |
| HA | 3.920000 | CD | 28.182000 |
| HB1 | 3.995000 | HD1 | 1.680000 |
| END_RES_DEF | | CE | 41.670000 |
| RES_ID | 731 | HE1 | 3.137000 |
| RES_TYPE | THR | HE2 | 3.045000 |
| SPIN_SYSTEM_ID | 17 | END_RES_DEF | |
| HETEROGENEITY | 100 | RES_ID | 787 |
| N | 120.372000 | RES_TYPE | LEU |
| HN | 8.059000 | SPIN_SYSTEM_ID | 73 |
| CA | 66.730000 | HETEROGENEITY | 100 |
| HA | 3.924000 | N | 118.732000 |
| CB | 68.930000 | HN | 7.422000 |
| HB | 4.247000 | CA | 57.922000 |
| CG2 | 21.570000 | HA | 4.213000 |
| HG2# | 1.142000 | CB | 43.603000 |
| END_RES_DEF | | HB1 | 1.996000 |
| RES_ID TYPE | 732 LEU | HB2 | 1.891000 |
| SPIN_SYSTEM_ID | 18 | CG | 27.632000 |
| HETEROGENEITY | 100 | HG | 1.794000 |
| N | 120.536000 | CD1 | 25.979000 |
| HN | 8.460000 | HD1# | 0.924000 |
| CA | 57.920000 | CD2 | 23.776000 |
| HA | 3.289000 | HD2# | 0.895000 |
| CB | 39.750000 | END_RES_DEF | |
| HB1 | 1.532000 | RES_ID | 788 |
| HB2 | 0.294000 | RES_TYPE | PHE |
| CG | 24.880000 | SPIN_SYSTEM_ID | 74 |
| HG | 1.683000 | HETEROGENEITY | 100 |
| CD1 | 25.429000 | N | 118.732000 |
| HD1# | 0.469000 | HN | 6.928000 |
| | | CA | 60.676000 |
| CD2 | 19.921000 | HA | 3.763000 |
| HD2# | −0.193000 | CB | 39.750000 |
| END_RES_DEF | | HB1 | 2.945000 |
| RES_ID | 733 | HB2 | 2.381000 |
| RES_TYPE | LYS | CD1 | 133.799000 |
| SPIN_SYSTEM_ID | 19 | HD1 | 6.400000 |
| HETEROGENEITY | 100 | CE1 | 131.596000 |
| N | 118.568000 | HE1 | 6.928000 |
| HN | 8.563000 | END_RES_DEF | |
| CA | 60.125000 | RES_ID | 789 |
| HA | 3.679000 | RES_TYPE | MET |
| CB | 32.588000 | SPIN_SYSTEM_ID | 75 |
| HB1 | 1.729000 | HETEROGENEITY | 100 |
| HB2 | 1.360000 | N | 116.272000 |
| CG | 24.880000 | HN | 8.489000 |
| HG1 | 1.280000 | CA | 59.020000 |
| CD | 29.835000 | HA | 3.911000 |
| HD1 | 1.585000 | CB | 32.590000 |
| CE | 41.960000 | HB1 | 2.318000 |
| HE1 | 2.918000 | HB2 | 2.208000 |
| END_RES_DEF | | CG | 33.140000 |
| RES_ID | 734 | HG1 | 2.942000 |
| RES_TYPE | SER | HG2 | 2.611000 |
| SPIN_SYSTEM_ID | 20 | CE | 17.168000 |
| HETEROGENEITY | 100 | HE# | 2.027000 |
| N | 113.157000 | END_RES_DEF | |
| HN | 7.540000 | RES_ID | 790 |
| CA | 61.227000 | RES_TYPE | ALA |
| HA | 4.281000 | SPIN_SYSTEM_ID | 76 |
| CB | 63.879000 | HETEROGENEITY | 100 |
| HB1 | 4.060000 | N | 119.716000 |
| END_RES_DEF | | HN | 8.000000 |
| RES_ID | 735 | CA | 55.170000 |
| RES_TYPE | ILE | HA | 4.084000 |
| SPIN_SYSTEM_ID | 21 | CB | 18.270000 |
| HETEROGENEITY | 100 | HB# | 1.485000 |
| N | 120.700000 | END_RES_DEF | |
| HN | 7.951000 | RES_ID | 791 |
| CA | 65.080000 | RES_TYPE | ASP |
| HA | 3.786000 | SPIN_SYSTEM_ID | 77 |
| CB | 38.095000 | HETEROGENEITY | 100 |
| HB | 1.879000 | N | 119.716000 |
| CG1 | 28.733000 | HN | 7.376000 |
| HG11 | 1.748000 | CA | 57.371000 |
| HG12 | 1.052000 | HA | 4.371000 |
| CG2 | 17.168000 | CB | 38.646000 |
| HG2# | 1.003000 | HB1 | 2.730000 |
| CD1 | 13.863000 | END_RES_DEF | |
| HD1# | 0.619000 | RES_ID | 792 |
| END_RES_DEF | | RES_TYPE | LEU |
| RES_ID | 736 | SPIN_SYSTEM_ID | 78 |
| RES_TYPE | LEU | HETEROGENEITY | 100 |
| SPIN_SYSTEM_ID | 22 | N | 119.550000 |
| HETEROGENEITY | 100 | HN | 7.363000 |
| N | 119.880000 | CA | 57.922000 |
| HN | 8.841000 | HA | 3.398000 |
| CA | 58.473000 | CB | 40.299000 |
| HA | 4.090000 | HB1 | 0.757000 |
| CB | 41.950000 | HB2 | 0.442000 |
| HB1 | 2.090000 | CG | 27.632000 |
| HB2 | 1.703000 | HG | 0.707000 |
| CG | 27.330000 | CD1 | 24.327000 |
| HG | 1.759000 | HD1# | 0.184000 |
| CD1 | 26.530000 | CD2 | 25.979000 |
| HD1# | 1.061000 | HD2# | 0.061000 |
| CD2 | 23.776000 | END_RES_DEF | |
| HD2# | 0.977000 | RES_ID | 793 |
| END_RES_DEF | | RES_TYPE | GLN |
| RES_ID | 737 | SPIN_SYSTEM_ID | 79 |
| RES_TYPE | GLN | HETEROGENEITY | 100 |
| SPIN_SYSTEM_ID | 23 | N | 114.141000 |

TABLE 1-continued

NMR Chemical Shift Assignment of the P/CAF Bromodomain

| Field | Value | Field | Value |
|---|---|---|---|
| HETEROGENEITY | 100 | HN | 8.069000 |
| N | 117.256000 | CA | 59.024000 |
| HN | 8.505000 | HA | 3.804000 |
| CA | 59.020000 | CB | 28.733000 |
| HA | 4.032000 | HB1 | 2.157000 |
| CB | 28.182000 | HB2 | 2.097000 |
| HB1 | 2.327000 | CG | 35.342000 |
| HB2 | 2.263000 | HG1 | 2.460000 |
| CG | 34.240000 | NE2 | 111.353000 |
| HG1 | 2.536000 | HE21 | 7.319000 |
| HG2 | 2.461000 | HE22 | 7.222000 |
| END_RES_DEF | | END_RES_DEF | |
| RES_ID | 738 | RES_ID | 794 |
| RES_TYPE | GLN | RES_TYPE | ARG |
| SPIN_SYSTEM_ID | 24 | SPIN_SYSTEM_ID | 80 |
| HETEROGENEITY | 100 | HETEROGENEITY | 100 |
| N | 118.896000 | N | 118.568000 |
| HN | 8.033000 | HN | 7.382000 |
| CA | 59.574000 | CA | 58.473000 |
| HA | 4.196000 | HA | 4.078000 |
| CB | 29.835000 | CB | 29.835000 |
| HB1 | 2.482000 | HB1 | 1.973000 |
| HB2 | 2.469000 | HB2 | 1.886000 |
| CG | 35.342000 | CG | 27.080000 |
| HG1 | 2.840000 | HG1 | 1.742000 |
| HG2 | 2.467000 | CD | 43.603000 |
| NE2 | 110.369000 | HD1 | 3.390000 |
| HE21 | 7.022000 | HD2 | 3.325000 |
| HE22 | 6.916000 | END_RES_DEF | |
| END_RES_DEF | | RES_ID | 795 |
| RES_ID | 739 | RES_TYPE | VAL |
| RES_ID TYPE | VAL | SPIN_SYSTEM_ID | 81 |
| SPIN_ SYSTEM_ | 25 | HETEROGENEITY | 100 |
| HETEROGENEITY | 100 | N | 117.912000 |
| N | 119.716000 | HN | 7.013000 |
| HN | 8.526000 | CA | 66.730000 |
| CA | 67.830000 | HA | 3.039000 |
| HA | 3.844000 | CB | 30.930000 |
| CB | 32.030000 | HB | 1.435000 |
| HB | 2.384000 | CG1 | 22.124000 |
| CG1 | 23.330000 | HG1# | 0.479000 |
| HG1# | 1.183000 | CG2 | 21.573000 |
| CG2 | 22.120000 | HG2# | 0.142000 |
| HG2# | 1.033000 | END_RES_DEF | |
| END_RES_DEF | | RES_ID | 796 |
| RES_ID | 740 | RES_TYPE | PHE |
| RES_TYPE | LYS | SPIN_SYSTEM_ID | 82 |
| SPIN_ SYSTEM_ | 26 | HETEROGENEITY | 100 |
| HETEROGENEITY | 100 | N | 116.928000 |
| N | 114.633000 | HN | 6.357000 |
| HN | 8.572000 | CA | 58.470000 |
| CA | 59.574000 | HA | 4.161000 |
| HA | 3.886000 | CB | 38.096000 |
| CB | 32.380000 | HB1 | 3.090000 |
| HB1 | 1.873000 | HB2 | 2.944000 |
| HG1 | 1.022000 | CD1 | 132.147000 |
| HD1 | 1.520000 | HD1 | 6.641000 |
| END_RES_DEF | | CE1 | 131.596000 |
| RES_ID | 741 | HE1 | 6.456000 |
| RES_TYPE | SER | CZ | 129.393000 |
| SPIN_ SYSTEM_ | 27 | HZ | 6.406000 |
| HETEROGENEITY | 100 | END_RES_DEF | |
| N | 110.369000 | RES_ID | 797 |
| HN | 7.557000 | RES_TYPE | THR |
| CA | 59.024000 | SPIN_SYSTEM_ID | 83 |
| HA | 4.448000 | HETEROGENEITY | 100 |
| CB | 63.980000 | N | 115.289000 |
| HB1 | 4.004000 | HN | 9.047000 |
| END_RES_DEF | | CA | 66.734000 |
| RES_ID | 742 | HA | 3.838000 |
| RES_TYPE | HIS | CB | 68.380000 |
| SPIN_ SYSTEM_ | 28 | HB | 4.210000 |
| HETEROGENEITY | 100 | CG2 | 22.120000 |
| N | 125.619000 | HG2# | 1.296000 |
| HN | 7.536000 | END_RES_DEF | |
| CA | 58.473000 | RES_ID | 798 |
| HA | 3.967000 | RES_TYPE | ASN |
| CB | 32.588000 | SPIN_SYSTEM_ID | 84 |
| HB1 | 2.990000 | HETEROGENEITY | 100 |
| HB2 | 2.799000 | N | 120.700000 |
| CD2 | 118.930000 | HN | 8.846000 |
| HD2 | 4.978000 | CA | 55.170000 |
| CE1 | 138.755000 | HA | 4.315000 |
| HE1 | 7.522000 | CB | 38.090000 |
| END_RES_DEF | | HB1 | 2.985000 |
| RES_ID | 743 | HB2 | 2.661000 |
| RES_TYPE | GLN | END_RES_DEF | |
| SPIN_ SYSTEM_ | 29 | RES_ID | 799 |
| HETEROGENEITY | 100 | RES_TYPE | CYS |
| N | 128.571000 | SPIN_SYSTEM_ID | 85 |
| HN | 8.543000 | HETEROGENEITY | 100 |
| CA | 59.125000 | N | 116.928000 |
| HA | 4.209000 | HN | 6.893000 |
| CB | 29.834000 | CA | 62.157000 |
| HB1 | 2.111000 | HA | 4.405000 |
| CG | 33.690000 | CB | 26.530000 |
| HG1 | 2.390000 | HB1 | 3.304000 |
| NE2 | 112.173000 | HB2 | 3.032000 |
| HE21 | 7.581000 | END_RES_DEF | |
| HE22 | 6.870000 | RES_ID | 800 |
| END_RES_DEF | | RES_TYPE | LYS |
| RES_ID | 744 | SPIN_SYSTEM_ID | 86 |
| RES_TYPE | SER | HETEROGENEITY | 100 |
| SPIN_ SYSTEM_ | 30 | N | 116.764000 |
| HETEROGENEITY | 100 | HN | 7.799000 |
| N | 119.060000 | CA | 58.473000 |
| HN | 11.668000 | HA | 4.204000 |
| CA | 60.125000 | CB | 32.588000 |
| HA | 4.838000 | HB1 | 1.743000 |
| CB | 63.980000 | CG | 25.429000 |
| HB1 | 4.334000 | HG1 | 1.313000 |
| HB2 | 3.926000 | HG2 | 0.138000 |
| END_RES_DEF | | CD | 29.835000 |
| RES_ID | 745 | HD1 | 1.291000 |
| RES_TYPE | ALA | CE | 41.400000 |
| SPIN_ SYSTEM_ | 31 | HE1 | 2.486000 |
| HETEROGENEITY | 100 | HE2 | 2.421000 |
| N | 117.584000 | END_RES_DEF | |
| HN | 7.868000 | RES_ID | 801 |
| CA | 53.510000 | RES_TYPE | GLU |
| HA | 4.396000 | SPIN_SYSTEM_ID | 87 |
| CB | 20.470000 | HETEROGENEITY | 100 |
| HB# | 1.688000 | N | 117.912000 |
| END_RES_DEF | | HN | 7.945000 |
| RES_ID | 746 | CA | 57.992000 |
| RES_TYPE | TRP | HA | 4.250000 |
| SPIN_ SYSTEM_ | 32 | CB | 30.385000 |
| HETEROGENEITY | 100 | HB1 | 2.172000 |
| N | 116.600000 | HB2 | 2.003000 |
| HN | 7.135000 | CG | 36.994000 |
| CA | 60.691000 | HG1 | 2.407000 |
| HA | 4.368000 | HG2 | 2.203000 |
| CB | 27.630000 | END_RES_DEF | |
| HB1 | 3.594000 | RES_ID | 802 |
| HB2 | 3.351000 | RES_TYPE | TYR |
| CD1 | 128.843000 | SPIN_SYSTEM_ID | 88 |
| HD1 | 7.897000 | HETEROGENEITY | 100 |
| NE1 | 110.861000 | N | 116.60000 |
| HE1 | 10.474000 | HN | 7.744000 |
| CE3 | 122.234000 | CA | 60.676000 |
| HE3 | 7.336000 | HA | 4.369000 |
| CZ2 | 116.177000 | CB | 41.400000 |
| HZ2 | 7.382000 | HB1 | 2.929000 |
| CZ3 | 123.336000 | CD1 | 134.901000 |
| HZ3 | 7.197000 | HD1 | 6.989000 |

TABLE 1-continued

NMR Chemical Shift Assignment of the P/CAF Bromodomain

| | | | |
|---|---|---|---|
| CH2 | 126.089000 | CE1 | 119.481000 |
| HH2 | 7.150000 | HE1 | 6.823000 |
| END_RES_DEF | | END_RES_DEF | |
| RES_ID | 747 | RES_ID | 803 |
| RES_TYPE | PRO | RES_TYPE | ASN |
| SPIN_SYSTEM_ID | 33 | SPIN_SYSTEM_ID | 89 |
| HETEROGENEITY | 100 | HETEROGENEITY | 100 |
| CA | 64.531000 | N | 115.944000 |
| HA | 3.756000 | HN | 8.241000 |
| CB | 29.835000 | CA | 51.864000 |
| HB1 | 0.487000 | HA | 5.024000 |
| HB2 | −0.783000 | CB | 40.849000 |
| CG | 26.530000 | HB1 | 3.069000 |
| HG1 | 0.233000 | HB2 | 2.907000 |
| HG2 | −0.931000 | ND2 | 118.732000 |
| CD | 50.212000 | HD21 | 8.316000 |
| HD2 | 1.567000 | HD22 | 7.809000 |
| HD1 | 2.177000 | END_RES_DEF | |
| END_RES_DEF | | RES_ID | 804 |
| RES_ID | 748 | RES_TYPE | ALA |
| RES_TYPE | PHE | SPIN_SYSTEM_ID | 90 |
| SPIN_SYSTEM_ID | 34 | HETEROGENEITY | 100 |
| HETEROGENEITY | 100 | END_RES_DEF | |
| N | 113.321000 | RES_ID | 805 |
| HN | 7.585000 | RES_TYPE | PRO |
| CA | 55.719000 | SPIN_SYSTEM_ID | 91 |
| HA | 4.930000 | HETEROGENEITY | 100 |
| CB | 39.202000 | CA | 63.980000 |
| HB1 | 3.491000 | HA | 2.422000 |
| HB2 | 2.532000 | HB1 | 1.949000 |
| CD1 | 133.248000 | HG1 | 1.648000 |
| HD1 | 7.099000 | HG2 | 1.558000 |
| HE1 | 7.174000 | CD | 50.762000 |
| HZ | 7.296000 | HD2 | 3.601000 |
| END_RES_DEF | | HD1 | 3.706000 |
| RES_ID | 749 | END_RES_DEF | |
| RES_TYPE | MET | RES_ID | 806 |
| SPIN_SYSTEM_ID | 35 | RES_TYPE | GLU |
| HETEROGENEITY | 100 | SPIN_SYSTEM_ID | 92 |
| N | 117.748000 | HETEROGENEITY | 100 |
| HN | 7.115000 | N | 112.993000 |
| CA | 56.820000 | HN | 8.246000 |
| HA | 4.286000 | CA | 56.820000 |
| CB | 32.590000 | HA | 4.185000 |
| HB1 | 2.233000 | CB | 28.733000 |
| HB2 | 2.174000 | HB1 | 2.095000 |
| CG | 33.140000 | HB2 | 1.973000 |
| HG1 | 2.851000 | CG | 36.270000 |
| CE | 17.168000 | HG1 | 2.200000 |
| HE# | 2.175000 | END_RES_DEF | |
| END_RES_DEF | | RES_ID | 807 |
| RES_ID | 750 | RES_TYPE | SER |
| RES_TYPE | GLU | SPIN_SYSTEM_ID | 93 |
| SPIN_SYSTEM_ID | 36 | HETEROGENEITY | 100 |
| HETEROGENEITY | 100 | N | 115.780000 |
| N | 113.813000 | HN | 8.112000 |
| HN | 7.709000 | CA | 58.473000 |
| CA | 53.516000 | HA | 4.406000 |
| HA | 4.849000 | CB | 66.183000 |
| CB | 31.487000 | HB1 | 4.393000 |
| HB1 | 2.091000 | HB2 | 4.157000 |
| HB2 | 1.730000 | END_RES_DEF | |
| CG | 35.893000 | RES_ID | 808 |
| HG1 | 2.164000 | RES_TYPE | GLU |
| END_RES_DEF | | SPIN_SYSTEM_ID | 94 |
| RES_ID | 751 | HETEROGENEITY | 100 |
| RES_TYPE | PRO | N | 123.488000 |
| SPIN_SYSTEM_ID | 37 | HN | 9.061000 |
| HETEROGENEITY | 100 | CA | 59.574000 |
| CA | 62.879000 | HA | 4.232000 |
| HA | 4.242000 | CB | 29.835000 |
| CB | 32.040000 | HB1 | 2.169000 |
| HB1 | 2.328000 | CG | 36.443000 |
| HB2 | 1.683000 | HG1 | 2.528000 |
| CG | 27.080000 | END_RES_DEF | |
| HG1 | 2.126000 | RES_ID | 809 |
| HG2 | 1.978000 | RES_TYPE | TYR |
| CD | 50.763000 | SPIN_SYSTEM_ID | 95 |
| HD1 | 3.670000 | HETEROGENEITY | 100 |
| END_RES_DEF | | N | 116.436000 |
| RES_ID | 752 | HN | 8.072000 |
| RES_ID TYPE | VAL | CA | 60.120000 |
| SPIN_SYSTEM_ID | 38 | HA | 3.834000 |
| HETEROGENEITY | 100 | CB | 37.550000 |
| N | 124.450000 | HB1 | 3.018000 |
| HN | 8.124000 | HB2 | 2.738000 |
| CA | 63.430000 | CD1 | 132.698000 |
| HA | 3.553000 | HD1 | 6.891000 |
| CB | 32.580000 | CE1 | 120.032000 |
| HB | 1.145000 | HE1 | 7.011000 |
| CG1 | 21.573000 | END_RES_DEF | |
| HG1# | 0.464000 | RES_ID | 810 |
| CG2 | 21.573000 | RES_TYPE | TYR |
| HG2# | 0.169000 | SPIN_SYSTEM_ID | 96 |
| END_RES_DEF | | HETEROGENEITY | 100 |
| RES_ID | 753 | N | 119.880000 |
| RES_TYPE | LYS | HN | 7.356000 |
| SPIN_SYSTEM_ID | 39 | CA | 61.777000 |
| HETEROGENEITY | 100 | HA | 3.819000 |
| N | 129.883000 | CB | 40.300000 |
| HN | 9.045000 | HB1 | 3.390000 |
| CA | 56.310000 | HB2 | 2.500000 |
| HA | 4.370000 | CD1 | 136.553000 |
| CB | 32.880000 | HD1 | 7.094000 |
| HB1 | 1.873000 | CE1 | 119.481000 |
| HG1 | 1.435000 | HE1 | 7.000000 |
| HD1 | 1.673000 | END_RES_DEF | |
| HE1 | 2.985000 | RES_ID | 811 |
| END_RES_DEF | | RES_TYPE | LYS |
| RES_ID | 754 | SPIN_SYSTEM_ID | 97 |
| RES_TYPE | ARG | HETEROGENEITY | 100 |
| SPIN_SYSTEM_ID | 40 | N | 118.076000 |
| HETEROGENEITY | 100 | HN | 8.072000 |
| N | 120.208000 | CA | 60.676000 |
| HN | 8.054000 | HA | 4.204000 |
| END_RES_DEF | | CB | 32.588000 |
| RES_ID | 755 | HB1 | 2.091000 |
| RES_TYPE | THR | CG | 25.979000 |
| SPIN_SYSTEM_ID | 41 | HG1 | 1.819000 |
| HETEROGENEITY | 100 | HG2 | 1.582000 |
| CA | 63.430000 | CD | 29.834000 |
| HA | 4.038000 | HD1 | 1.813000 |
| CB | 68.380000 | CE | 41.963000 |
| HB | 4.293000 | HE1 | 2.962000 |
| CG2 | 22.670000 | END_RES_DEF | |
| HG2# | 1.267000 | RES_ID | 812 |
| END_RES_DEF | | RES_TYPE | CYS |
| RES_ID | 756 | SPIN_SYSTEM_ID | 98 |
| RES_TYPE | GLU | HETEROGENEITY | 100 |
| SPIN_SYSTEM_ID | 42 | N | 116.764000 |
| HETEROGENEITY | 100 | HN | 8.520000 |
| N | 118.732000 | CA | 65.087000 |
| HN | 7.209000 | HA | 4.202000 |
| CA | 56.270000 | CB | 27.080000 |
| HA | 4.448000 | HB1 | 3.396000 |
| CB | 30.930000 | HB2 | 3.056000 |
| HB1 | 2.174000 | END_RES_DEF | |
| HB2 | 2.000000 | RES_ID | 813 |
| CG | 36.440000 | RES_TYPE | ALA |
| HG1 | 2.292000 | SPIN_SYSTEM_ID | 98 |
| END_RES_DEF | | HETEROGENEITY | 100 |
| RES_ID | 757 | N | 120.700000 |
| RES_TYPE | ALA | HN | 8.315000 |
| SPIN_ | 43 | CA | 55.563000 |

TABLE 1-continued

NMR Chemical Shift Assignment of the P/CAF Bromodomain

| | | | |
|---|---|---|---|
| SYSTEM_ID | | HB1 | 2.086000 |
| HETEROGENEITY | 100 | CG | 37.545000 |
| N | 122.504000 | HG1 | 2.325000 |
| HN | 7.379000 | HG2 | 2.265000 |
| CA | 50.220000 | END_RES_DEF | |
| HA | 4.937000 | RES_ID | 763 |
| CB | 19.370000 | RES_TYPE | VAL |
| HB# | 1.082000 | SPIN_SYSTEM_ID | 49 |
| END_RES_DEF | | HETEROGENEITY | 100 |
| RES_ID | 758 | N | 115.453000 |
| RES_TYPE | PRO | HN | 7.135000 |
| SPIN_SYSTEM_ID | 44 | CA | 63.430000 |
| HETEROGENEITY | 100 | HA | 4.077000 |
| CA | 65.080000 | CB | 33.690000 |
| HA | 4.496000 | HB | 2.015000 |
| CB | 31.487000 | CG1 | 21.020000 |
| HB1 | 2.374000 | HG1# | 1.045000 |
| HB2 | 2.027000 | CG2 | 21.574000 |
| CG | 27.632000 | HG2# | 0.991000 |
| HG1 | 2.122000 | END_RES_DEF | |
| HG2 | 2.038000 | RES_ID | 764 |
| CD | 50.212000 | RES_TYPE | ILE |
| HD2 | 3.515000 | SPIN_SYSTEM_ID | 50 |
| HD1 | 3.717000 | HETEROGENEITY | 100 |
| END_RES_DEF | | N | 122.832000 |
| RES_ID | 759 | HN | 7.947000 |
| RES_TYPE | GLY | CA | 57.920000 |
| SPIN_SYSTEM_ID | 45 | HA | 3.916000 |
| HETEROGENEITY | 100 | CB | 34.240000 |
| END_RES_DEF | | HB | 1.205000 |
| RES_ID | 760 | CG1 | 24.878000 |
| RES_TYPE | TYR | HG11 | 0.798000 |
| SPIN_SYSTEM_ID | 46 | HG12 | 0.216000 |
| HETEROGENEITY | 100 | CG2 | 16.617000 |
| N | 122.504000 | HG2# | 0.380000 |
| HN | 7.945000 | CD1 | 9.457000 |
| CA | 62.328000 | HD1# | 0.537000 |
| HA | 3.536000 | END_RES_DEF | |
| CB | 39.750000 | RES_ID | 765 |
| HB1 | 2.689000 | RES_TYPE | ARG |
| HB2 | 2.487000 | SPIN_SYSTEM_ID | 51 |
| CD1 | 133.799000 | HETEROGENEITY | 100 |
| HD1 | 5.120000 | N | 125.291000 |
| CE1 | 118.379000 | HN | 7.749000 |
| HE1 | 6.070000 | CA | 57.371000 |
| END_RES_DEF | | HA | 3.875000 |
| RES_ID | 761 | CB | 30.936000 |
| RES_TYPE | TYR | HB1 | 1.388000 |
| SPIN_SYSTEM_ID | 47 | HB2 | 1.211000 |
| HETEROGENEITY | 100 | CG | 27.080000 |
| N | 113.157000 | HG1 | 1.319000 |
| HN | 8.225000 | HG2 | 1.173000 |
| CA | 60.676000 | CD | 43.052000 |
| HA | 4.101000 | HD1 | 2.971000 |
| CB | 37.550000 | END_RES_DEF | |
| HB1 | 3.189000 | RES_ID | 766 |
| HB2 | 2.801000 | RES_TYPE | SER |
| CD1 | 134.901000 | SPIN_SYSTEM_ID | 52 |
| HD1 | 7.342000 | HETEROGENEITY | 100 |
| CE1 | 118.930000 | N | 116.600000 |
| HE1 | 6.646000 | HN | 8.387000 |
| END_RES_DEF | | CA | 54.618000 |
| RES_ID | 762 | HA | 4.984000 |
| RES_TYPE | GLU | CB | 38.640000 |
| SPIN_SYSTEM_ID | 48 | HB1 | 3.034000 |
| HETEROGENEITY | 100 | HB2 | 2.907000 |
| N | 117.912000 | END_RES_DEF | |
| HN | 7.702000 | RES_ID | 767 |
| CA | 57.922000 | RES_TYPE | PRO |
| HA | 4.209000 | SPIN_SYSTEM_ID | 53 |
| CB | 29.480000 | HETEROGENEITY | 100 |

| | | | |
|---|---|---|---|
| HETEROGENEITY | 100 | | |
| N | 117.584000 | | |
| HN | 7.145000 | | |
| CA | 59.688000 | | |
| HA | 4.075000 | | |
| CB | 32.588000 | | |
| HB1 | 1.929000 | | |
| CG | 25.644000 | | |
| HG1 | 1.492000 | | |
| CD | 29.284000 | | |
| HD1 | 1.681000 | | |
| CE | 41.963000 | | |
| HE1 | 2.964000 | | |
| END_RES_DEF | | | |
| RES_ID | 819 | | |
| RES_TYPE | PHE | | |
| SPIN_SYSTEM_ID | 105 | | |
| HETEROGENEITY | 100 | | |
| N | 121.028000 | | |
| HN | 7.869000 | | |
| CA | 61.230000 | | |
| HA | 4.328000 | | |
| CB | 39.200000 | | |
| HB1 | 3.133000 | | |
| HB2 | 3.047000 | | |
| CD1 | 133.800000 | | |
| HD1 | 7.180000 | | |
| END_RES_DEF | | | |
| RES_ID | 820 | | |
| RES_TYPE | PHE | | |
| SPIN_SYSTEM_ID | 106 | | |
| HETEROGENEITY | 100 | | |
| N | 120.700000 | | |
| HN | 9.126000 | | |
| CA | 60.691000 | | |
| HA | 3.961000 | | |
| CB | 38.640000 | | |
| HB1 | 3.289000 | | |
| HB2 | 3.067000 | | |
| CD1 | 133.248000 | | |
| HD1 | 6.904000 | | |
| CE1 | 132.698000 | | |
| HE1 | 7.011000 | | |
| END_RES_DEF | | | |
| RES_ID | 821 | | |
| RES_TYPE | PHE | | |
| SPIN_SYSTEM_ID | 107 | | |
| HETEROGENEITY | 100 | | |
| N | 118.076000 | | |
| HN | 8.359000 | | |
| CA | 61.770000 | | |
| HA | 3.840000 | | |
| CB | 38.090000 | | |
| HB1 | 3.064000 | | |
| CD1 | 133.248000 | | |
| HD1 | 7.175000 | | |
| CE1 | 132.698000 | | |
| HE1 | 7.294000 | | |
| CZ | 131.596000 | | |
| HZ | 7.430000 | | |
| END_RES_DEF | | | |
| RES_ID | 822 | | |
| RES_TYPE | SER | | |
| SPIN_SYSTEM_ID | 108 | | |
| HETEROGENEITY | 100 | | |
| N | 114.961000 | | |
| HN | 7.906000 | | |
| CA | 61.773000 | | |
| HA | 4.200000 | | |
| CB | 62.879000 | | |
| SYSTEM_ID | | | |
| HETEROGENEITY | 100 | | |
| HB1 | 4.007000 | | |

TABLE 1-continued

NMR Chemical Shift Assignment of the P/CAF Bromodomain

| | | | |
|---|---|---|---|
| CA | 63.429000 | END_RES_DEF | |
| HA | 4.083000 | RES_ID | 823 |
| CB | 32.588000 | RES_TYPE | LYS |
| HB1 | 2.209000 | SPIN_SYSTEM_ID | 109 |
| CG | 28.180000 | HETEROGENEITY | 100 |
| HG1 | 2.177000 | N | 120.864000 |
| HG2 | 1.883000 | HN | 7.938000 |
| CD | 50.763000 | CA | 56.820000 |
| HD2 | 3.390000 | HA | 4.008000 |
| HD1 | 3.623000 | CB | 31.487000 |
| END_RES_DEF | | HB1 | 1.730000 |
| RES_ID | 768 | HB2 | 1.567000 |
| RES_TYPE | MET | CG | 23.226000 |
| SPIN_SYSTEM_ID | 54 | HG1 | 0.833000 |
| HETEROGENEITY | 100 | CD | 27.080000 |
| N | 119.060000 | HD1 | 1.403000 |
| HN | 8.430000 | CE | 42.501000 |
| CA | 54.067000 | HE1 | 2.569000 |
| HA | 4.935000 | HE2 | 2.422000 |
| CB | 31.487000 | END_RES_DEF | |
| HB1 | 1.989000 | RES_ID | 824 |
| HB2 | 1.353000 | RES_TYPE | ILE |
| CG | 30.930000 | SPIN_SYSTEM_ID | 110 |
| HG1 | 2.690000 | HETEROGENEITY | 100 |
| CE | 14.414000 | N | 116.928000 |
| HE# | 1.929000 | HN | 8.101000 |
| END_RES_DEF | | CA | 64.530000 |
| RES_ID | 769 | HA | 3.818000 |
| RES_TYPE | ASP | CB | 36.990000 |
| SPIN_SYSTEM_ID | 55 | HB | 1.746000 |
| HETEROGENEITY | 100 | CG1 | 26.530000 |
| N | 119.060000 | HG11 | 1.140000 |
| HN | 7.365000 | HG12 | 1.073000 |
| CA | 53.516000 | CG2 | 18.820000 |
| HA | 4.745000 | HG2# | 0.654000 |
| CB | 44.154000 | CD1 | 13.312000 |
| HB1 | 2.371000 | HD1# | 0.541000 |
| END_RES_DEF | | END_RES_DEF | |
| RES_ID | 770 | RES_ID | 825 |
| RES_TYPE | LEU | RES_TYPE | LYS |
| SPIN_SYSTEM_ID | 56 | SPIN_SYSTEM_ID | 111 |
| HETEROGENEITY | 100 | HETEROGENEITY | 100 |
| N | 116.272000 | N | 122.176000 |
| HN | 9.055000 | HN | 7.546000 |
| CA | 57.922000 | CA | 59.024000 |
| HA | 4.036000 | HA | 4.043000 |
| CB | 41.400000 | CB | 32.360000 |
| HB1 | 2.095000 | HB1 | 1.879000 |
| HB2 | 1.395000 | HB2 | 1.757000 |
| CG | 27.080000 | CG | 24.878000 |
| HG | 1.713000 | HG1 | 1.390000 |
| CD1 | 27.080000 | HG2 | 1.302000 |
| HD1# | 0.940000 | CD | 29.284000 |
| CD2 | 22.675000 | HD1 | 1.633000 |
| HD2# | 0.628000 | CE | 41.400000 |
| END_RES_DEF | | HE1 | 2.913000 |
| RES_ID | 771 | END_RES_DEF | |
| RES_TYPE | LYS | RES_ID | 826 |
| SPIN_SYSTEM_ID | 57 | RES_TYPE | GLU |
| HETEROGENEITY | 100 | SPIN_SYSTEM_ID | 112 |
| N | 128.079000 | HETEROGENEITY | 100 |
| HN | 8.738000 | N | 121.192000 |
| CA | 60.676000 | HN | 8.063000 |
| HA | 4.198000 | CA | 59.024000 |
| CB | 32.037000 | HA | 3.995000 |
| HB1 | 2.330000 | CB | 29.834000 |
| HB2 | 2.224000 | HB1 | 2.058000 |
| CG | 25.280000 | CG | 36.050000 |
| HG1 | 1.483000 | HG1 | 2.342000 |
| HG2 | 1.403000 | HG2 | 2.205000 |
| CD | 30.385000 | END_RES_DEF | |
| HD1 | 1.793000 | RES_ID | 827 |
| HD2 | 1.696000 | RES_TYPE | ALA |
| CE | 41.950000 | SPIN_SYSTEM_ID | 113 |
| HE1 | 2.965000 | HETEROGENEITY | 100 |
| END_RES_DEF | | N | 117.748000 |
| RES_ID | 772 | HN | 7.620000 |
| RES_TYPE | THR | CA | 52.410000 |
| SPIN_SYSTEM_ID | 58 | HA | 4.291000 |
| HETEROGENEITY | 100 | CB | 19.920000 |
| N | 122.176000 | HB# | 1.358000 |
| HN | 9.445000 | END_RES_DEF | |
| CA | 67.040000 | RES_ID | 828 |
| HA | 3.845000 | RES_TYPE | GLY |
| CB | 67.835000 | SPIN_SYSTEM_ID | 114 |
| HB | 4.090000 | HETEROGENEITY | 100 |
| CG2 | 22.124000 | N | 126.767000 |
| HG2# | 1.058000 | HN | 7.744000 |
| END_RES_DEF | | CA | 45.902000 |
| RES_ID | 773 | HA1 | 4.019000 |
| RES_TYPE | MET | HA2 | 3.935000 |
| SPIN_SYSTEM_ID | 59 | END_RES_DEF | |
| HETEROGENEITY | 100 | RES_ID | 829 |
| N | 117.912000 | RES_TYPE | LEU |
| HN | 7.882000 | SPIN_SYSTEM_ID | 115 |
| CA | 60.676000 | HETEROGENEITY | 100 |
| HA | 4.319000 | N | 117.912000 |
| CB | 33.342000 | HN | 7.742000 |
| HB1 | 2.093000 | CA | 55.719000 |
| HB2 | 1.915000 | HA | 4.215000 |
| CG | 33.139000 | CB | 43.052000 |
| HG1 | 2.621000 | HB1 | 1.562000 |
| HG2 | 2.496000 | CG | 27.632000 |
| CE | 16.620000 | HG | 1.536000 |
| HE# | 1.241000 | CD1 | 23.776000 |
| END_RES_DEF | | HD1# | 0.711000 |
| RES_ID | 774 | END_RES_DEF | |
| RES_TYPE | SER | RES_ID | 830 |
| SPIN_SYSTEM_ID | 60 | RES_TYPE | ILE |
| HETEROGENEITY | 100 | SPIN_SYSTEM_ID | 116 |
| N | 116.108000 | HETEROGENEITY | 100 |
| HN | 7.958000 | N | 115.453000 |
| CA | 62.879000 | HN | 7.458000 |
| HA | 4.200000 | CA | 60.676000 |
| CB | 62.879000 | HA | 4.232000 |
| HB1 | 4.368000 | CB | 39.748000 |
| HB2 | 4.040000 | HB | 1.810000 |
| END_RES_DEF | | CG1 | 27.080000 |
| | | HG11 | 1.314000 |
| | | HG12 | 0.918000 |
| | | CG2 | 17.718000 |
| | | HG2# | 0.815000 |
| | | CD1 | 13.312000 |
| | | HD1# | 0.794000 |
| | | END_RES_DEF | |
| | | RES_ID | 831 |
| | | RES_TYPE | ASP |
| | | SPIN_SYSTEM_ID | 117 |
| | | HETEROGENEITY | 100 |
| | | N | 123.488000 |
| | | HN | 8.270000 |
| | | CA | 54.620000 |
| | | HA | 4.571000 |
| | | CB | 41.400000 |
| | | HB1 | 2.693000 |
| | | HB2 | 2.540000 |
| | | END_RES_DEF | |
| | | RES_ID | 832 |
| | | RES_TYPE | LYS |
| | | SPIN_SYSTEM_ID | 118 |
| | | HETEROGENEITY | 100 |
| | | N | 125.450000 |
| | | HN | 7.774000 |

TABLE 1-continued

NMR Chemical Shift Assignment of the P/CAF Bromodomain

| | |
|---|---|
| CA | 57.720000 |
| HA | 4.08200e0 |

TABLE 1-continued

NMR Chemical Shift Assignment of the P/CAF Bromodomain

| | |
|---|---|
| CB | 33.410000 |
| END_RES_DEF | |

TABLE 2

Unambiguous NOE-derived Inter-proton Distance Restraints

```
ASSI {2141}
((segid "BrD" and resid 89 and name HN))
(segid "BrD" and resid 96 and name HD %)
 4.200  4.200 1.300 peak      2141 weight 0.11000E+01 volume 0.36756E+02 ppm1   8.857 ppm2 7.704
ASSI {13261}
((segid "BrD" and resid 89 and name HD22))
(segid "BrD" and resid 95 and name HE %)
 3.900  3.800 1.600 peak     13261 weight 0.11000E+01 volume 0.50220E+02 ppm1   8.416 ppm2 7.624
ASSI {13271}
((segid "BrD" and resid 89 and name HD21))
(segid "BrD" and resid 95 and name HE %)
 4.000  4.000 1.500 peak     13271 weight 0.11000E+01 volume 0.43992E+02 ppm1   8.924 ppm2 7.624
ASSI {8521}
((segid "BrD" and resid 46 and name HN))
(segid "BrD" and resid 47 and name HD %)
 3.500  3.100 2.000 peak      8521 weight 0.11000E+01 volume 0.10017E+03 ppm1   8.562 ppm2 7.960
ASSI {14401}
((segid "BrD" and resid 87 and name HN))
((segid "BrD" and resid 88 and name HB1))
 3.700  3.400 1.800 peak     14401 weight 0.11000E+01 volume 0.72183E+02 ppm1   8.572 ppm2 3.532
OR {14401}
((segid "BrD" and resid 87 and name HN))
((segid "BrD" and resid 88 and name HB2))
ASSI {15611}
((segid "BrD" and resid 32 and name HE1))
((segid "BrD" and resid 94 and name HG2))
 4.500  4.500 1.000 peak     15611 weight 0.11000E+01 volume 0.23846E+02 ppm1  11.082 ppm2 3.143
OR {15611}
((segid "BrD" and resid 32 and name HE1))
((segid "BrD" and resid 94 and name HG1))
ASSI {1}
((segid "BrD" and resid 43 and name HN))
((segid "BrD" and resid 43 and name HA))
 2.700  1.800 1.800 peak         1 weight 0.11000E+01 volume 0.52965E+03 ppm1   8.001 ppm2 5.544
ASSI {11}
((segid "BrD" and resid 43 and name HN))
(segid "BrD" and resid 43 and name HB %)
 2.400  1.400 1.400 peak        11 weight 0.11000E+01 volume 0.93421E+03 ppm1   8.001 ppm2 1.689
ASSI {21}
((segid "BrD" and resid 43 and name HN))
((segid "BrD" and resid 42 and name HN))
 2.200  1.200 1.200 peak        21 weight 0.11000E+01 volume 0.18953E+04 ppm1   8.001 ppm2 7.816
ASSI {31}
((segid "BrD" and resid 42 and name HN))
((segid "BrD" and resid 41 and name HB))
 3.300  2.700 2.200 peak        31 weight 0.11000E+01 volume 0.14380E+03 ppm1   7.822 ppm2 4.900
ASSI {41}
((segid "BrD" and resid 42 and name HN))
((segid "BrD" and resid 42 and name HA))
 2.900  2.100 2.100 peak        41 weight 0.11000E+01 volume 0.30790E+03 ppm1   7.824 ppm2 5.053
ASSI {51}
((segid "BrD" and resid 42 and name HN))
((segid "BrD" and resid 42 and name HB2))
 2.700  1.800 1.800 peak        51 weight 0.11000E+01 volume 0.47343E+03 ppm1   7.821 ppm2 2.613
ASSI {61}
((segid "BrD" and resid 42 and name HN))
((segid "BrD" and resid 42 and name HG1))
 3.200  2.600 2.300 peak        61 weight 0.11000E+01 volume 0.16643E+03 ppm1   7.822 ppm2 2.899
ASSI {71}
((segid "BrD" and resid 42 and name HN))
((segid "BrD" and resid 42 and name HB1))
 3.400  2.900 2.100 peak        71 weight 0.11000E+01 volume 0.13090E+03 ppm1   7.821 ppm2 2.790
ASSI {91}
((segid "BrD" and resid 99 and name HN))
(segid "BrD" and resid 99 and name HB %)
```

TABLE 2-continued

| Unambiguous NOE-derived Inter-proton Distance Restraints |
|---|

```
  2.400  1.400  1.400 peak         91 weight  0.11000E+01 volume  0.90687E+03 ppm1    8.936 ppm2  2.208
ASSI {101}
((segid "BrD" and resid 99 and name HN))
((segid "BrD" and resid 99 and name HA))
  2.800  2.000  2.000 peak        101 weight  0.11000E+01 volume  0.42952E+03 ppm1    8.936 ppm2  4.441
ASSI {121}
((segid "BrD" and resid 99 and name HN))
((segid "BrD" and resid 98 and name HN))
  2.700  1.800  1.800 peak        121 weight  0.11000E+01 volume  0.45502E+03 ppm1    8.936 ppm2  9.112
ASSI {131}
((segid "BrD" and resid 98 and name HN))
((segid "BrD" and resid 98 and name HA))
  2.500  1.600  1.600 peak        131 weight  0.11000E+01 volume  0.72592E+03 ppm1    9.125 ppm2  4.811
ASSI {141}
((segid "BrD" and resid 98 and name HN))
((segid "BrD" and resid 98 and name HB1))
  3.300  2.700  2.200 peak        141 weight  0.11000E+01 volume  0.15487E+03 ppm1    9.125 ppm2  4.010
ASSI {151}
((segid "BrD" and resid 98 and name HN))
((segid "BrD" and resid 98 and name HB2))
  2.400  1.400  1.400 peak        151 weight  0.11000E+01 volume  0.95271E+03 ppm1    9.125 ppm2  3.656
ASSI {171}
((segid "BrD" and resid 30 and name HN))
((segid "BrD" and resid 30 and name HA))
  3.100  2.400  2.400 peak        171 weight  0.11000E+01 volume  0.20628E+03 ppm1   12.275 ppm2  5.451
ASSI {181}
((segid "BrD" and resid 30 and name HN))
((segid "BrD" and resid 30 and name HB1))
  3.200  2.600  2.300 peak        181 weight  0.11000E+01 volume  0.16806E+03 ppm1   12.275 ppm2  4.939
ASSI {191}
((segid "BrD" and resid 30 and name HN))
((segid "BrD" and resid 30 and name HB2))
  2.800  2.000  2.000 peak        191 weight  0.11000E+01 volume  0.40863E+03 ppm1   12.275 ppm2  4.538
ASSI {201}
((segid "BrD" and resid 30 and name HN))
((segid "BrD" and resid 29 and name HN))
  3.300  2.700  2.200 peak        201 weight  0.11000E+01 volume  0.15134E+03 ppm1   12.275 ppm2  9.150
ASSI {211}
((segid "BrD" and resid 29 and name HN))
((segid "BrD" and resid 29 and name HA))
  2.700  1.800  1.800 peak        211 weight  0.11000E+01 volume  0.44648E+03 ppm1    9.151 ppm2  4.818
ASSI {221}
((segid "BrD" and resid 29 and name HN))
((segid "BrD" and resid 29 and name HB1))
  2.800  2.000  2.000 peak        221 weight  0.11000E+01 volume  0.39478E+03 ppm1    9.152 ppm2  2.712
ASSI {231}
((segid "BrD" and resid 31 and name HN))
((segid "BrD" and resid 29 and name HA))
  3.400  2.900  2.100 peak        231 weight  0.11000E+01 volume  0.12405E+03 ppm1    8.479 ppm2  4.816
ASSI {241}
((segid "BrD" and resid 31 and name HN))
((segid "BrD" and resid 31 and name HA))
  3.300  2.700  2.200 peak        241 weight  0.11000E+01 volume  0.13933E+03 ppm1    8.479 ppm2  5.003
ASSI {251}
((segid "BrD" and resid 31 and name HN))
(segid "BrD" and resid 31 and name HB %)
  2.400  1.400  1.400 peak        251 weight  0.11000E+01 volume  0.88455E+03 ppm1    8.480 ppm2  2.307
ASSI {271}
((segid "BrD" and resid 28 and name HN))
((segid "BrD" and resid 28 and name HB2))
  2.500  1.600  1.600 peak        271 weight  0.11000E+01 volume  0.82952E+03 ppm1    8.166 ppm2  3.409
ASSI {281}
((segid "BrD" and resid 28 and name HN))
((segid "BrD" and resid 28 and name HB1))
  2.500  1.600  1.600 peak        281 weight  0.11000E+01 volume  0.71832E+03 ppm1    8.166 ppm2  3.596
ASSI {291}
((segid "BrD" and resid 28 and name HN))
((segid "BrD" and resid 28 and name HA))
  2.700  1.800  1.800 peak        291 weight  0.11000E+01 volume  0.51058E+03 ppm1    8.165 ppm2  4.598
ASSI {301}
((segid "BrD" and resid 28 and name HN))
((segid "BrD" and resid 29 and name HN))
  3.400  2.900  2.100 peak        301 weight  0.11000E+01 volume  0.11688E+03 ppm1    8.166 ppm2  9.164
ASSI {321}
((segid "BrD" and resid 32 and name HN))
((segid "BrD" and resid 32 and name HA))
  2.600  1.700  1.700 peak        321 weight  0.11000E+01 volume  0.66621E+03 ppm1    7.739 ppm2  4.977
```

TABLE 2-continued

Unambiguous NOE-derived Inter-proton Distance Restraints

ASSI {331}
((segid "BrD" and resid 32 and name HN))
((segid "BrD" and resid 32 and name HB1))
  2.900  2.100  2.100 peak        331 weight  0.11000E+01 volume  0.30872E+03 ppm1    7.740 ppm2  4.201
ASSI {341}
((segid "BrD" and resid 32 and name HN))
((segid "BrD" and resid 32 and name HB2))
  2.600  1.700  1.700 peak        341 weight  0.11000E+01 volume  0.59972E+03 ppm1    7.739 ppm2  3.958
ASSI {351}
((segid "BrD" and resid 30 and name HN))
((segid "BrD" and resid 31 and name HN))
  2.800  2.000  2.000 peak        351 weight  0.11000E+01 volume  0.41861E+03 ppm1   12.275 ppm2  8.477
ASSI {361}
((segid "BrD" and resid 105 and name HN))
((segid "BrD" and resid 105 and name HA))
  3.100  2.400  2.400 peak        361 weight  0.11000E+01 volume  0.22043E+03 ppm1    8.488 ppm2  4.934
ASSI {371}
((segid "BrD" and resid 105 and name HN))
((segid "BrD" and resid 105 and name HB1))
  2.800  2.000  2.000 peak        371 weight  0.11000E+01 volume  0.42542E+03 ppm1    8.487 ppm2  3.740
ASSI {401}
((segid "BrD" and resid 106 and name HN))
((segid "BrD" and resid 105 and name HN))
  2.700  1.800  1.800 peak        401 weight  0.11000E+01 volume  0.44987E+03 ppm1    9.740 ppm2  8.476
ASSI {411}
((segid "BrD" and resid 106 and name HN))
((segid "BrD" and resid 106 and name HA))
  2.600  1.700  1.700 peak        411 weight  0.11000E+01 volume  0.55394E+03 ppm1    9.740 ppm2  4.566
ASSI {421}
((segid "BrD" and resid 106 and name HN))
((segid "BrD" and resid 106 and name HB1))
  2.500  1.600  1.600 peak        421 weight  0.11000E+01 volume  0.71568E+03 ppm1    9.740 ppm2  3.895
ASSI {431}
((segid "BrD" and resid 106 and name HN))
((segid "BrD" and resid 106 and name HB2))
  2.300  1.300  1.300 peak        431 weight  0.11000E+01 volume  0.11998E+04 ppm1    9.740 ppm2  3.674
ASSI {451}
((segid "BrD" and resid 107 and name HN))
((segid "BrD" and resid 106 and name HN))
  2.300  2.100  2.100 peak        451 weight  0.11000E+01 volume  0.34851E+03 ppm1    8.981 ppm2  9.713
ASSI {461}
((segid "BrD" and resid 107 and name HN))
(segid "BrD" and resid 107 and name HD %)
  3.500  3.100  2.000 peak        461 weight  0.11000E+01 volume  0.11255E+03 ppm1    8.980 ppm2  7.783
ASSI {471}
((segid "BrD" and resid 107 and name HN))
((segid "BrD" and resid 107 and name HA))
  2.600  1.700  1.700 peak        471 weight  0.11000E+01 volume  0.57631E+03 ppm1    8.981 ppm2  4.443
ASSI {481}
((segid "BrD" and resid 107 and name HN))
((segid "BrD" and resid 107 and name HB1))
  3.200  2.600  2.300 peak        481 weight  0.11000E+01 volume  0.16715E+03 ppm1    8.980 ppm2  3.671
ASSI {501}
((segid "BrD" and resid 108 and name HN))
((segid "BrD" and resid 107 and name HN))
  2.600  1.700  1.700 peak        501 weight  0.11000E+01 volume  0.57313E+03 ppm1    8.529 ppm2  8.966
ASSI {511}
((segid "BrD" and resid 108 and name HN))
((segid "BrD" and resid 108 and name HA))
  2.700  1.800  1.800 peak        511 weight  0.11000E+01 volume  0.52916E+03 ppm1    8.526 ppm2  4.811
ASSI {521}
((segid "BrD" and resid 108 and name HN))
((segid "BrD" and resid 108 and name HB1))
  2.400  1.400  1.400 peak        521 weight  0.11000E+01 volume  0.97994E+03 ppm1    8.526 ppm2  4.583
ASSI {531}
((segid "BrD" and resid 109 and name HN))
((segid "BrD" and resid 109 and name HA))
  2.300  1.300  1.300 peak        531 weight  0.11000E+01 volume  0.11922E+04 ppm1    8.572 ppm2  4.615
ASSI {541}
((segid "BrD" and resid 110 and name HN))
((segid "BrD" and resid 109 and name HB2))
  2.900  2.100  2.100 peak        541 weight  0.11000E+02 volume  0.32815E+03 ppm1    8.714 ppm2  2.174
ASSI {551}
((segid "BrD" and resid 110 and name HN))
((segid "BrD" and resid 110 and name HA))
  2.800  2.000  2.000 peak        551 weight  0.11000E+01 volume  0.43619E+03 ppm1    8.714 ppm2  4.451

TABLE 2-continued

Unambiguous NOE-derived Inter-proton Distance Restraints

```
ASSI {561}
((segid "BrD" and resid 110 and name HN))
((segid "BrD" and resid 110 and name HB))
  2.500  1.600  1.600 peak        561 weight  0.11000E+01 volume  0.77600E+03 ppm1    8.714 ppm2  2.352
ASSI {581}
((segid "BrD" and resid 109 and name HN))
((segid "BrD" and resid 110 and name HN))
  2.800  2.000  2.000 peak        581 weight  0.11000E+01 volume  0.41482E+03 ppm1    8.572 ppm2  8.705
ASSI {591}
((segid "BrD" and resid 111 and name HN))
((segid "BrD" and resid 108 and name HA))
  3.200  2.600  2.300 peak        591 weight  0.11000E+01 volume  0.17690E+03 ppm1    8.168 ppm2  4.807
ASSI {601}
((segid "BrD" and resid 111 and name HN))
((segid "BrD" and resid 111 and name HA))
  2.500  1.600  1.600 peak        601 weight  0.11000E+01 volume  0.71549E+03 ppm1    8.168 ppm2  4.650
ASSI {621}
((segid "BrD" and resid 110 and name HN))
((segid "BrD" and resid 111 and name HN))
  2.800  2.000  2.000 peak        621 weight  0.11000E+01 volume  0.38661E+03 ppm1    8.714 ppm2  8.153
ASSI {631}
((segid "BrD" and resid 112 and name HN))
((segid "BrD" and resid 112 and name HA))
  2.300  1.300  1.300 peak        631 weight  0.11000E+01 volume  0.13944E+04 ppm1    8.667 ppm2  4.607
ASSI {641}
((segid "BrD" and resid 112 and name HN))
((segid "BrD" and resid 112 and name HG1))
  3.400  2.900  2.100 peak        642 weight  0.11000E+01 volume  0.12114E+03 ppm1    8.668 ppm2  2.956
ASSI {651}
((segid "BrD" and resid 112 and name HN))
((segid "BrD" and resid 112 and name HG2))
  3.500  3.100  2.000 peak        651 weight  0.11000E+01 volume  0.96511E+02 ppm1    8.668 ppm2  2.818
ASSI {661}
((segid "BrD" and resid 112 and name HN))
((segid "BrD" and resid 112 and name HB1))
  2.200  1.200  1.200 peak        661 weight  0.11000E+01 volume  0.15417E+04 ppm1    8.668 ppm2  2.667
ASSI {671}
((segid "BrD" and resid 113 and name HN))
((segid "BrD" and resid 113 and name HA))
  2.800  2.000  2.000 peak        671 weight  0.11000E+01 volume  0.42878E+03 ppm1    8.217 ppm2  4.904
ASSI {681}
((segid "BrD" and resid 113 and name HN))
(segid "BrD" and resid 113 and name HB %)
  2.400  1.400  1.400 peak        681 weight  0.11000E+01 volume  0.99017E+03 ppm1    8.219 ppm2  1.967
ASSI {701}
((segid "BrD" and resid 114 and name HN))
((segid "BrD" and resid 114 and name HA1))
  2.800  2.000  2.000 peak        701 weight  0.11000E+01 volume  0.42782E+03 ppm1    8.376 ppm2  4.619
ASSI {721}
((segid "BrD" and resid 113 and name HN))
((segid "BrD" and resid 114 and name HN))
  2.500  1.600  1.600 peak        721 weight  0.11000E+01 volume  0.73854E+03 ppm1    8.219 ppm2  8.351
ASSI {741}
((segid "BrD" and resid 100 and name HN))
((segid "BrD" and resid 100 and name HA))
  2.700  1.800  1.800 peak        741 weight  0.11000E+01 volume  0.49224E+03 ppm1    8.669 ppm2  4.938
ASSI {751}
((segid "BrD" and resid 100 and name HN))
((segid "BrD" and resid 100 and name H$$2))
  2.400  1.400  1.400 peak        751 weight  0.11000E+01 volume  0.10916E+04 ppm1    8.669 ppm2  3.422
ASSI {771}
((segid "BrD" and resid 99 and name HN))
((segid "BrD" and resid 100 and name HN))
  2.500  1.600  1.600 peak        771 weight  0.11000E+01 volume  0.76441E+03 ppm1    8.936 ppm2  8.664
ASSI {791}
((segid "BrD" and resid 97 and name HN))
((segid "BrD" and resid 97 and name HA))
  2.600  1.700  1.700 peak        791 weight  0.11000E+01 volume  0.58097E+03 ppm1    8.676 ppm2  4.809
ASSI {811}
((segid "BrD" and resid 97 and name HN))
((segid "BrD" and resid 98 and name HN))
  3.000  2.200  2.200 peak        811 weight  0.11000E+01 volume  0.25513E+03 ppm1    8.672 ppm2  9.124
ASSI {841}
((segid "BrD" and resid 96 and name HN))
((segid "BrD" and resid 96 and name HA))
  2.600  1.700  1.700 peak        841 weight  0.11000E+01 volume  0.65098E+03 ppm1    7.977 ppm2  4.433
```

TABLE 2-continued

Unambiguous NOE-derived Inter-proton Distance Restraints

ASSI {851}
((segid "BrD" and resid 96 and name HN))
((segid "BrD" and resid 96 and name HB1))
  2.800  2.000  2.000 peak       851 weight  0.11000E+01 volume  0.42091E+03 ppm1   7.976 ppm2  3.995
ASSI {861}
((segid "BrD" and resid 96 and name HN))
((segid "BrD" and resid 96 and name HB2))
  2.600  1.700  1.700 peak       861 weight  0.11000E+01 volume  0.56648E+03 ppm1   7.979 ppm2  3.112
ASSI {871}
((segid "BrD" and resid 96 and name HN))
((segid "BrD" and resid 97 and name HN))
  2.600  1.700  1.700 peak       871 weight  0.11000E+01 volume  0.67038E+03 ppm1   7.979 ppm2  8.678
ASSI {891}
((segid "BrD" and resid 95 and name HN))
((segid "BrD" and resid 95 and name HA))
  3.100  2.400  2.400 peak       891 weight  0.11000E+01 volume  0.22376E+03 ppm1   8.669 ppm2  4.443
ASSI {901}
((segid "BrD" and resid 95 and name HN))
((segid "BrD" and resid 95 and name HB1))
  2.800  2.000  2.000 peak       901 weight  0.11000E+01 volume  0.37061E+03 ppm1   8.669 ppm2  3.598
ASSI {911}
((segid "BrD" and resid 95 and name HN))
((segid "BrD" and resid 95 and name HB2))
  2.700  1.800  1.800 peak       911 weight  0.11000E+01 volume  0.54351E+03 ppm1   8.669 ppm2  3.346
ASSI {921}
((segid "BrD" and resid 94 and name HN))
((segid "BrD" and resid 94 and name HA))
  3.300  2.700  2.200 peak       921 weight  0.11000E+01 volume  0.13528E+03 ppm1   9.679 ppm2  4.846
ASSI {941}
((segid "BrD" and resid 94 and name HN))
((segid "BrD" and resid 95 and name HN))
  3.500  3.100  2.000 peak       941 weight  0.11000E+01 volume  0.95054E+02 ppm1   9.679 ppm2  8.670
ASSI {971}
((segid "BrD" and resid 93 and name HN))
((segid "BrD" and resid 93 and name HA))
  3.200  2.600  2.300 peak       971 weight  0.11000E+01 volume  0.16612E+03 ppm1   8.713 ppm2  5.037
ASSI {981}
((segid "BrD" and resid 93 and name HN))
((segid "BrD" and resid 93 and name HB2))
  3.300  2.700  2.200 peak       981 weight  0.11000E+01 volume  0.15761E+03 ppm1   8.713 ppm2  4.753
ASSI {1001}
((segid "BrD" and resid 92 and name HN))
((segid "BrD" and resid 92 and name HA))
  2.500  1.600  1.600 peak      1001 weight  0.11000E+01 volume  0.71435E+03 ppm1   8.873 ppm2  4.802
ASSI {1011}
((segid "BrD" and resid 92 and name HN))
((segid "BrD" and resid 93 and name HN))
  2.500  1.600  1.600 peak      1011 weight  0.11000E+01 volume  0.69883E+03 ppm1   8.871 ppm2  8.719
ASSI {1031}
((segid "BrD" and resid 76 and name HN))
((segid "BrD" and resid 76 and name HA))
  2.500  1.600  1.600 peak      1031 weight  0.11000E+01 volume  0.86678E+03 ppm1   8.611 ppm2  4.688
ASSI {1041}
((segid "BrD" and resid 76 and name HN))
(segid "BrD" and resid 76 and name HB %)
  2.200  1.200  1.200 peak      1041 weight  0.11000E+01 volume  0.16592E+04 ppm1   8.612 ppm2  2.102
ASSI {1061}
((segid "BrD" and resid 77 and name HN))
((segid "BrD" and resid 77 and name HA))
  2.700  1.800  1.800 peak      1061 weight  0.11000E+01 volume  0.53554E+03 ppm1   7.996 ppm2  4.980
ASSI {1071}
((segid "BrD" and resid 77 and name HN))
((segid "BrD" and resid 77 and name HB1))
  2.100  1.100  1.100 peak      1071 weight  0.11000E+01 volume  0.22098E+04 ppm1   7.996 ppm2  3.337
ASSI {1091}
((segid "BrD" and resid 76 and name HN))
((segid "BrD" and resid 77 and name HN))
  2.600  1.700  1.700 peak      1091 weight  0.11000E+01 volume  0.57823E+03 ppm1   8.612 ppm2  7.983
ASSI {1111}
((segid "BrD" and resid $$ and name HN))
((segid "BrD" and resid 75 and name HA))
  2.800  2.000  2.000 peak      1111 weight  0.11000E+01 volume  0.40919E+03 ppm1   9.106 ppm2  4.527
ASSI {1121}
((segid "BrD" and resid 75 and name HN))
((segid "BrD" and resid 75 and name HG1))
  2.600  1.700  1.700 peak      1121 weight  0.11000E+01 volume  0.66185E+03 ppm1   9.106 ppm2  3.549

TABLE 2-continued

Unambiguous NOE-derived Inter-proton Distance Restraints

ASSI {1131}
((segid "BrD" and resid 75 and name HN))
((segid "BrD" and resid 75 and name HG2))
 2.900 2.100 2.100 peak    1131 weight 0.11000E+01 volume 0.30957E+03 ppm1    9.106 ppm2 3.221
ASSI {1141}
((segid "BrD" and resid 75 and name HN))
((segid "BrD" and resid 75 and name HB1))
 3.100 2.400 2.400 peak    1141 weight 0.11000E+01 volume 0.19539E+03 ppm1    9.106 ppm2 2.919
ASSI {1151}
((segid "BrD" and resid 75 and name HN))
((segid "BrD" and resid 75 and name HB2))
 2.500 1.600 1.600 peak    1151 weight 0.11000E+01 volume 0.72202E+03 ppm1    9.106 ppm2 2.816
ASSI {1171}
((segid "BrD" and resid 76 and name HN))
((segid "BrD" and resid 75 and name HN))
 2.700 1.800 1.800 peak    1171 weight 0.11000E+01 volume 0.51792E+03 ppm1    8.613 ppm2 9.085
ASSI {1181}
((segid "BrD" and resid 74 and name HN))
(segid "BrD" and resid 74 and name HD %)
 3.000 2.200 2.200 peak    1181 weight 0.11000E+01 volume 0.24258E+03 ppm1    7.536 ppm2 7.004
ASSI {1191}
((segid "BrD" and resid 74 and name HN))
((segid "BrD" and resid 74 and name HA))
 3.000 2.200 2.200 peak    1191 weight 0.11000E+01 volume 0.27313E+03 ppm1    7.536 ppm2 4.368
ASSI {1201}
((segid "BrD" and resid 74 and name HN))
((segid "BrD" and resid 74 and name HB1))
 2.800 2.000 2.000 peak    1201 weight 0.11000E+01 volume 0.42552E+03 ppm1    7.5$$5 ppm2 1.552
ASSI {1211}
((segid "BrD" and resid 74 and name HN))
((segid "BrD" and resid 74 and name HB2))
 2.700 1.800 1.800 peak    1211 weight 0.11000E+01 volume 0.47386E+03 ppm1    7.536 ppm2 2.983
ASSI {1231}
((segid "BrD" and resid 75 and name HN))
((segid "BrD" and resid 74 and name HN))
 2.800 2.000 2.000 peak    1231 weight 0.11000E+01 volume 0.42446E+03 ppm1    9.105 ppm2 7.535
ASSI {1241}
((segid "BrD" and resid 70 and name HN))
((segid "BrD" and resid 70 and name HA))
 2.500 1.600 1.600 peak    1241 weight 0.11000E+01 volume 0.78559E+03 ppm1    8.040 ppm2 5.348
ASSI {1251}
((segid "BrD" and resid 70 and name HN))
((segid "BrD" and resid 70 and name HB2))
 2.900 2.100 2.100 peak    1251 weight 0.11000E+01 volume 0.29096E+03 ppm1    8.039 ppm2 4.357
ASSI {1261}
((segid "BrD" and resid 69 and name HN))
((segid "BrD" and resid 69 and name HA))
 2.800 2.000 2.000 peak    1261 weight 0.11000E+01 volume 0.43807E+03 ppm1    8.306 ppm2 4.690
ASSI {1271}
((segid "BrD" and resid 69 and name HN))
((segid "BrD" and resid 69 and name HB))
 3.300 2.700 2.200 peak    1271 weight 0.11000E+01 volume 0.13733E+03 ppm1    8.306 ppm2 2.921
ASSI {1281}
((segid "BrD" and resid 69 and name HN))
(segid "BrD" and resid 69 and name HG1 %)
 2.800 2.000 2.000 peak    1281 weight 0.11000E+01 volume 0.40608E+03 ppm1    8.306 ppm2 1.549
ASSI {1291}
((segid "BrD" and resid 69 and name HN))
(segid "BrD" and resid 69 and name HG2 %)
 3.000 2.200 2.200 peak    1291 weight 0.11000E+01 volume 0.24335E+03 ppm1    8.306 ppm2 1.430
ASSI {1301}
((segid "BrD" and resid 69 and name HN))
((segid "BrD" and resid 70 and name HN))
 2.800 2.000 2.000 peak    1301 weight 0.11000E+01 volume 0.40402E+03 ppm1    8.306 ppm2 8.022
ASSI {1321}
((segid "BrD" and resid 68 and name HN))
(segid "BrD" and resid 68 and name HD %)
 2.900 2.100 2.100 peak    1321 weight 0.11000E+01 volume 0.34716E+03 ppm1    8.626 ppm2 7.778
ASSI {1331}
((segid "BrD" and resid 68 and name HN))
((segid "BrD" and resid 68 and name HA))
 3.200 2.600 2.300 peak    1331 weight 0.11000E+01 volume 0.16288E+03 ppm1    8.626 ppm2 5.142
ASSI {1341}
((segid "BrD" and resid 68 and name HN))
((segid "BrD" and resid 68 and name HB1))
 3.000 2.200 2.200 peak    1341 weight 0.11000E+01 volume 0.26781E+03 ppm1    8.625 ppm2 3.669

TABLE 2-continued

Unambiguous NOE-derived Inter-proton Distance Restraints

ASSI {1351}
((segid "BrD" and resid 68 and name HN))
((segid "BrD" and resid 68 and name HB2))
  2.700  1.800  1.800 peak      1351 weight  0.11000E+01 volume  0.52551E+03 ppm1     8.627  ppm2  3.516
ASSI {1361}
((segid "BrD" and resid 68 and name HN))
((segid "BrD" and resid 69 and name HN))
  3.500  3.100  2.000 peak      1361 weight  0.11000E+01 volume  0.11066E+03 ppm1     8.622  ppm2  8.304
ASSI {1381}
((segid "BrD" and resid 67 and name HN))
(segid "BrD" and resid 67 and name HD %)
  3.100  2.400  2.400 peak      1381 weight  0.11000E+01 volume  0.20078E+03 ppm1     8.832  ppm2  6.888
ASSI {1391}
((segid "BrD" and resid 67 and name HN))
((segid "BrD" and resid 67 and name HA))
  2.800  2.000  2.000 peak      1391 weight  0.11000E+01 volume  0.36081E+03 ppm1     8.832  ppm2  4.671
ASSI {1401}
((segid "BrD" and resid 67 and name HN))
((segid "BrD" and resid 67 and name HB1))
  2.900  2.100  2.100 peak      1401 weight  0.11000E+01 volume  0.31437E+03 ppm1     8.832  ppm2  3.549
ASSI {1411}
((segid "BrD" and resid 67 and name HN))
((segid "BrD" and resid 67 and name HB2))
  2.400  1.400  1.400 peak      1411 weight  0.11000E+01 volume  0.92322E+03 ppm1     8.833  ppm2  2.661
ASSI {1431}
((segid "BrD" and resid 68 and name HN))
((segid "BrD" and resid 67 and name HN))
  2.500  1.600  1.600 peak      1431 weight  0.11000E+01 volume  0.76621E+03 ppm1     8.622  ppm2  8.829
ASSI {1441}
((segid "BrD" and resid 68 and name HN))
(segid "BrD" and resid 67 and name HD %)
  3.200  2.600  2.300 peak      1441 weight  0.11000E+01 volume  0.16656E+03 ppm1     8.626  ppm2  6.892
ASSI {1451}
((segid "BrD" and resid 66 and name HN))
((segid "BrD" and resid 66 and name HA))
  2.200  1.200  1.200 peak      1451 weight  0.11000E+01 volume  0.17604E+04 ppm1     8.763  ppm2  5.001
ASSI {1461}
((segid "BrD" and resid 65 and name HN))
((segid "BrD" and resid 65 and name HA))
  2.500  1.600  1.600 peak      1461 weight  0.11000E+01 volume  0.81596E+03 ppm1     8.564  ppm2  5.375
ASSI {1471}
((segid "BrD" and resid 65 and name HN))
((segid "BrD" and resid 65 and name HB1))
  2.600  1.700  1.700 peak      1471 weight  0.11000E+01 volume  0.66517E+03 ppm1     8.566  ppm2  3.627
ASSI {1481}
((segid "BrD" and resid 65 and name HN))
((segid "BrD" and resid 65 and name HB2))
  2.400  1.400  1.400 peak      1481 weight  0.11000E+01 volume  0.98393E+03 ppm1     8.564  ppm2  3.382
ASSI {1491}
((segid "BrD" and resid 65 and name HN))
((segid "BrD" and resid 64 and name HB1))
  2.400  1.400  1.400 peak      1491 weight  0.11000E+01 volume  0.10161E+04 ppm1     8.565  ppm2  2.659
ASSI {1501}
((segid "BrD" and resid 65 and name HN))
((segid "BrD" and resid 66 and name HN))
  2.300  1.300  1.300 peak      1501 weight  0.11000E+01 volume  0.13482E+04 ppm1     8.565  ppm2  8.765
ASSI {1521}
((segid "BrD" and resid 20 and name HN))
((segid "BrD" and resid 16 and name HA))
  2.700  1.800  1.800 peak      1521 weight  0.11000E+01 volume  0.44067E+03 ppm1     8.146  ppm2  4.527
ASSI {1531}
((segid "BrD" and resid 20 and name HN))
((segid "BrD" and resid 20 and name HA))
  2.500  1.600  1.600 peak      1531 weight  0.11000E+01 volume  0.84286E+03 ppm1     8.146  ppm2  4.895
ASSI {1541}
((segid "BrD" and resid 20 and name HN))
((segid "BrD" and resid 20 and name HB1))
  2.300  1.300  1.300 peak      1541 weight  0.11000E+01 volume  0.13472E+04 ppm1     8.147  ppm2  4.669
ASSI {1561}
((segid "BrD" and resid 21 and name HN))
((segid "BrD" and resid 21 and name HA))
  2.900  2.100  2.100 peak      1561 weight  0.11000E+01 volume  0.31054E+03 ppm1     8.546  ppm2  4.367
ASSI {1571}
((segid "BrD" and resid 101 and name HN))
((segid "BrD" and resid 101 and name H$$))
  2.700  1.800  1.800 peak      1571 weight  0.11000E+01 volume  0.51528E+03 ppm1     8.514  ppm2  2.538

TABLE 2-continued

Unambiguous NOE-derived Inter-proton Distance Restraints

ASSI {1581}
((segid "BrD" and resid 22 and name HN))
((segid "BrD" and resid 22 and name HA))
  2.700  1.800  1.800 peak       1581 weight  0.11000E+01 volume  0.45405E+03 ppm1      9.456 ppm2  4.712
ASSI {1591}
((segid "BrD" and resid 23 and name HN))
((segid "BrD" and resid 21 and name HB))
  3.300  2.700  2.200 peak       1591 weight  0.11000E+01 volume  0.13959E+03 ppm1      9.122 ppm2  2.486
ASSI {1601}
((segid "BrD" and resid 23 and name HN))
((segid "BrD" and resid 23 and name HA))
  2.600  1.700  1.700 peak       1601 weight  0.11000E+01 volume  0.61098E+03 ppm1      9.118 ppm2  4.645
ASSI {1611}
((segid "BrD" and resid 23 and name HN))
((segid "BrD" and resid 23 and name HG1))
  3.400  2.900  2.100 peak       1611 weight  0.11000E+01 volume  0.11565E+03 ppm1      9.119 ppm2  3.143
ASSI {1621}
((segid "BrD" and resid 23 and name HN))
((segid "BrD" and resid 23 and name HB1))
  2.900  2.100  2.100 peak       1621 weight  0.11000E+01 volume  0.34650E+03 ppm1      9.118 ppm2  2.939
ASSI {1641}
((segid "BrD" and resid 22 and name HN))
((segid "BrD" and resid 23 and name HN))
  2.600  1.700  1.700 peak       1641 weight  0.11000E+01 volume  0.57061E+03 ppm1      9.456 ppm2  9.123
ASSI {1651}
((segid "BrD" and resid 15 and name HN))
(segid "BrD" and resid 15 and name HD %)
  3.100  2.400  2.400 peak       1651 weight  0.11000E+01 volume  0.20888E+03 ppm1      8.598 ppm2  7.663
ASSI {1661}
((segid "BrD" and resid 24 and name HN))
((segid "BrD" and resid 24 and name HA))
  2.800  2.000  2.000 peak       1661 weight  0.11000E+01 volume  0.43492E+03 ppm1      8.661 ppm2  4.775
ASSI {1671}
((segid "BrD" and resid 24 and name HN))
((segid "BrD" and resid 24 and name HG1))
  2.800  2.000  2.000 peak       1671 weight  0.11000E+01 volume  0.42365E+03 ppm1      8.660 ppm2  3.454
ASSI {1681}
((segid "BrD" and resid 24 and name HN))
((segid "BrD" and resid 24 and name HB1))
  2.800  2.000  2.000 peak       1681 weight  0.11000E+01 volume  0.37096E+03 ppm1      8.654 ppm2  3.089
ASSI {1691}
((segid "BrD" and resid 24 and name HN))
((segid "BrD" and resid 23 and name HN))
  2.300  1.300  1.300 peak       1691 weight  0.11000E+01 volume  0.12196E+04 ppm1      8.659 ppm2  9.112
ASSI {1711}
((segid "BrD" and resid 25 and name HN))
((segid "BrD" and resid 27 and name HN))
  3.600  3.200  1.900 peak       1711 weight  0.11000E+01 volume  0.81722E+02 ppm1      9.134 ppm2  8.155
ASSI {1721}
((segid "BrD" and resid 25 and name HN))
((segid "BrD" and resid 25 and name HA))
  3.200  2.600  2.300 peak       1721 weight  0.11000E+01 volume  0.16529E+03 ppm1      9.134 ppm2  4.443
ASSI {1731}
((segid "BrD" and resid 25 and name HN))
((segid "BrD" and resid 25 and name HB))
  2.800  2.000  2.000 peak       1731 weight  0.11000E+01 volume  0.35564E+03 ppm1      9.132 ppm2  2.984
ASSI {1741}
((segid "BrD" and resid 25 and name HN))
(segid "BrD" and resid 25 and name HG1 %)
  2.600  1.700  1.700 peak       1741 weight  0.11000E+01 volume  0.61322E+03 ppm1      9.133 ppm2  1.799
ASSI {1751}
((segid "BrD" and resid 25 and name HN))
(segid "BrD" and resid 25 and name HG2 %)
  2.800  2.000  2.000 peak       1751 weight  0.11000E+01 volume  0.35918E+03 ppm1      9.133 ppm2  1.627
ASSI {1771}
((segid "BrD" and resid 24 and name HN))
((segid "BrD" and resid 25 and name HN))
  2.400  1.400  1.400 peak       1771 weight  0.11000E+01 volume  0.91823E+03 ppm1      8.661 ppm2  9.133
ASSI {1791}
((segid "BrD" and resid 26 and name HN))
((segid "BrD" and resid 26 and name HA))
  3.000  2.200  2.200 peak       1791 weight  0.11000E+01 volume  0.24601E+03 ppm1      9.196 ppm2  4.488
ASSI {1801}
((segid "BrD" and resid 27 and name HN))
((segid "BrD" and resid 26 and name HB1))
  2.700  1.800  1.800 peak       1801 weight  0.11000E+01 volume  0.50197E+03 ppm1      8.169 ppm2  2.480

TABLE 2-continued

Unambiguous NOE-derived Inter-proton Distance Restraints

ASSI {1811}
((segid "BrD" and resid 27 and name HN))
((segid "BrD" and resid 27 and name HA))
  2.700  1.800  1.800 peak      1811 weight  0.11000E+01 volume  0.49453E+03 ppm1     8.170 ppm2  5.055
ASSI {1821}
((segid "BrD" and resid 27 and name HN))
((segid "BrD" and resid 27 and name HB1))
  2.500  1.600  1.600 peak      1821 weight  0.11000E+01 volume  0.78563E+03 ppm1     8.170 ppm2  4.611
ASSI {1831}
((segid "BrD" and resid 27 and name HN))
((segid "BrD" and resid 26 and name HN))
  2.600  1.700  1.700 peak      1831 weight  0.11000E+01 volume  0.56681E+03 ppm1     8.169 ppm2  9.179
ASSI {1851}
((segid "BrD" and resid 19 and name HN))
((segid "BrD" and resid 15 and name HA))
  3.100  2.400  2.400 peak      1851 weight  0.11000E+01 volume  0.20055E+03 ppm1     9.187 ppm2  4.645
ASSI {1861}
((segid "BrD" and resid 19 and name HN))
((segid "BrD" and resid 19 and name HA))
  2.800  2.000  2.000 peak      1861 weight  0.11000E+01 volume  0.37223E+03 ppm1     9.189 ppm2  4.285
ASSI {1881}
((segid "BrD" and resid 20 and name HN))
((segid "BrD" and resid 19 and name HN))
  2.800  2.000  2.000 peak      1881 weight  0.11000E+01 volume  0.39357E+03 ppm1     8.146 ppm2  9.170
ASSI {1901}
((segid "BrD" and resid 83 and name HN))
((segid "BrD" and resid 83 and name HA))
  2.800  2.000  2.000 peak      1901 weight  0.11000E+01 volume  0.35792E+03 ppm1     9.658 ppm2  4.447
ASSI {1911}
((segid "BrD" and resid 83 and name HN))
((segid "BrD" and resid 83 and name HB))
  2.700  1.800  1.800 peak      1911 weight  0.11000E+01 volume  0.45140E+03 ppm1     9.659 ppm2  4.817
ASSI {1921}
((segid "BrD" and resid 83 and name HN))
(segid "BrD" and resid 83 and name HG2 %)
  3.000  2.200  2.200 peak      1921 weight  0.11000E+01 volume  0.28097E+03 ppm1     9.659 ppm2  1.910
ASSI {1931}
((segid "BrD" and resid 84 and name HN))
((segid "BrD" and resid 84 and name HA))
  2.800  2.000  2.000 peak      1931 weight  0.11000E+01 volume  0.37490E+03 ppm1     9.464 ppm2  4.901
ASSI {1941}
((segid "BrD" and resid 84 and name HN))
((segid "BrD" and resid 84 and name HB1))
  2.800  2.000  2.000 peak      1941 weight  0.11000E+01 volume  0.42690E+03 ppm1     9.463 ppm2  3.592
ASSI {1951}
((segid "BrD" and resid 84 and name HN))
((segid "BrD" and resid 84 and name HB2))
  3.000  2.200  2.200 peak      1951 weight  0.11000E+01 volume  0.26963E+03 ppm1     9.463 ppm2  3.268
ASSI {1971}
((segid "BrD" and resid 83 and name HN))
((segid "BrD" and resid 84 and name HN))
  2.600  1.700  1.700 peak      1971 weight  0.11000E+01 volume  0.61276E+03 ppm1     9.658 ppm2  9.450
ASSI {1981}
((segid "BrD" and resid 85 and name HN))
((segid "BrD" and resid 85 and name HA))
  2.900  2.100  2.100 peak      1981 weight  0.11000E+01 volume  0.32851E+03 ppm1     7.516 ppm2  5.014
ASSI {1991}
((segid "BrD" and resid 85 and name HN))
((segid "BrD" and resid 85 and name HB1))
  2.800  2.000  2.000 peak      1991 weight  0.11000E+01 volume  0.39507E+03 ppm1     7.516 ppm2  3.919
ASSI {2011}
((segid "BrD" and resid 84 and name HN))
((segid "BrD" and resid 85 and name HN))
  2.800  2.000  2.000 peak      2011 weight  0.11000E+01 volume  0.37475E+03 ppm1     9.464 ppm2  7.497
ASSI {2021}
((segid "BrD" and resid 86 and name HN))
((segid "BrD" and resid 85 and name HB1))
  3.200  2.600  2.300 peak      2021 weight  0.11000E+01 volume  0.17051E+03 ppm1     8.423 ppm2  3.911
ASSI {2031}
((segid "BrD" and resid 86 and name HN))
((segid "BrD" and resid 86 and name HA))
  2.800  2.000  2.000 peak      2031 weight  0.11000E+01 volume  0.42952E+03 ppm1     8.423 ppm2  4.809
ASSI {2051}
((segid "BrD" and resid 85 and name HN))
((segid "BrD" and resid 86 and name HN))
  2.800  2.000  2.000 peak      2051 weight  0.11000E+01 volume  0.39765E+03 ppm1     7.516 ppm2  8.406

TABLE 2-continued

Unambiguous NOE-derived Inter-proton Distance Restraints

ASSI {2061}
((segid "BrD" and resid 87 and name HN))
((segid "BrD" and resid 86 and name HB1))
 3.400  2.900  2.100 peak      2061 weight  0.11000E+01 volume  0.11283E+03 ppm1    8.570 ppm2  2.350
ASSI {2071}
((segid "BrD" and resid 87 and name HN))
((segid "BrD" and resid 87 and name HA))
 2.600  1.700  1.700 peak      2071 weight  0.11000E+01 volume  0.62404E+03 ppm1    8.572 ppm2  4.889
ASSI {2081}
((segid "BrD" and resid 87 and name HN))
((segid "BrD" and resid 87 and name HG1))
 3.000  2.200  2.200 peak      2081 weight  0.11000E+01 volume  0.28244E+03 ppm1    8.572 ppm2  3.014
ASSI {2091}
((segid "BrD" and resid 87 and name HN))
((segid "BrD" and resid 87 and name HG2))
 3.000  2.200  2.200 peak      2091 weight  0.11000E+01 volume  0.28579E+03 ppm1    8.570 ppm2  2.810
ASSI {2101}
((segid "BrD" and resid 87 and name HN))
((segid "BrD" and resid 87 and name HB2))
 2.700  1.800  1.800 peak      2101 weight  0.11000E+01 volume  0.46735E+03 ppm1    8.571 ppm2  2.607
ASSI {2111}
((segid "BrD" and resid 88 and name HN))
(segid "BrD" and resid 88 and name HD %)
 3.300  2.700  2.200 peak      2111 weight  0.11000E+01 volume  0.15320E+03 ppm1    8.355 ppm2  7.595
ASSI {2121}
((segid "BrD" and resid 88 and name HN))
((segid "BrD" and resid 88 and name HA))
 3.100  2.400  2.400 peak      2121 weight  0.11000E+01 volume  0.22276E+03 ppm1    8.356 ppm2  4.976
ASSI {2131}
((segid "BrD" and resid 88 and name HN))
((segid "BrD" and resid 88 and name HB1))
 2.500  1.600  1.600 peak      2131 weight  0.11000E+01 volume  0.72297E+03 ppm1    8.354 ppm2  3.536
ASSI {2151}
((segid "BrD" and resid 89 and name HN))
((segid "BrD" and resid 89 and name HA))
 3.000  2.200  2.200 peak      2151 weight  0.11000E+01 volume  0.26347E+03 ppm1    8.858 ppm2  5.631
ASSI {2161}
((segid "BrD" and resid 89 and name HN))
((segid "BrD" and resid 89 and name HB1))
 3.000  2.200  2.200 peak      2161 weight  0.11000E+01 volume  0.26996E+03 ppm1    8.858 ppm2  3.671
ASSI {2171}
((segid "BrD" and resid 89 and name HN))
((segid "BrD" and resid 89 and name HB2))
 2.400  1.400  1.400 peak      2171 weight  0.11000E+01 volume  0.10141E+04 ppm1    8.858 ppm2  3.508
ASSI {2191}
((segid "BrD" and resid 88 and name HN))
((segid "BrD" and resid 89 and name HN))
 2.600  1.700  1.700 peak      2191 weight  0.11000E+01 volume  0.62488E+03 ppm1    8.335 ppm2  9.848
ASSI {2201}
((segid "BrD" and resid 46 and name HN))
((segid "BrD" and resid 47 and name HN))
 2.800  2.000  2.000 peak      2201 weight  0.11000E+01 volume  0.38079E+03 ppm1    8.562 ppm2  8.836
ASSI {2211}
((segid "BrD" and resid 46 and name HN))
((segid "BrD" and resid 46 and name HA))
 2.700  1.800  1.800 peak      2211 weight  0.11000E+01 volume  0.49246E+03 ppm1    8.562 ppm2  4.125
ASSI {2221}
((segid "BrD" and resid 46 and name HN))
((segid "BrD" and resid 46 and name HB1))
 2.500  1.600  1.600 peak      2221 weight  0.11000E+01 volume  0.82312E+03 ppm1    8.561 ppm2  3.293
ASSI {2231}
((segid "BrD" and resid 46 and name HN))
((segid "BrD" and resid 46 and name HB2))
 2.500  1.600  1.600 peak      2231 weight  0.11000E+01 volume  0.72605E+03 ppm1    8.562 ppm2  3.095
ASSI {2241}
((segid "BrD" and resid 47 and name HN))
(segid "BrD" and resid 47 and name HE %)
 3.700  3.400  1.800 peak      2241 weight  0.11000E+01 volume  0.71965E+02 ppm1    8.832 ppm2  7.253
ASSI {2251}
((segid "BrD" and resid 47 and name HN))
((segid "BrD" and resid 47 and name HA))
 2.900  2.100  2.100 peak      2251 weight  0.11000E+01 volume  0.34426E+03 ppm1    8.831 ppm2  4.708
ASSI {2261}
((segid "BrD" and resid 47 and name HN))
((segid "BrD" and resid 47 and name HB1))
 2.800  2.000  2.000 peak      2261 weight  0.11000E+01 volume  0.37083E+03 ppm1    8.833 ppm2  3.807

TABLE 2-continued

Unambiguous NOE-derived Inter-proton Distance Restraints

ASSI {2271}
((segid "BrD" and resid 47 and name HN))
((segid "BrD" and resid 47 and name HB2))
  2.900  2.100  2.100 peak    2271 weight  0.11000E+01 volume  0.34763E+03 ppm1  8.632 ppm2  3.391
ASSI {2281}
((segid "BrD" and resid 48 and name HN))
((segid "BrD" and resid 48 and name HA))
  2.800  2.000  2.000 peak    2281 weight  0.11000E+01 volume  0.37621E+03 ppm1  8.307 ppm2  4.815
ASSI {2291}
((segid "BrD" and resid 48 and name HN))
((segid "BrD" and resid 48 and name HG2))
  3.300  2.700  2.200 peak    2291 weight  0.11000E+01 volume  0.14081E+03 ppm1  8.308 ppm2  2.857
ASSI {2301}
((segid "BrD" and resid 48 and name HN))
((segid "BrD" and resid 48 and name HB1))
  2.400  1.400  1.400 peak    2301 weight  0.11000E+01 volume  0.11018E+04 ppm1  8.308 ppm2  2.698
ASSI {2321}
((segid "BrD" and resid 47 and name HN))
((segid "BrD" and resid 48 and name HN))
  2.700  1.800  1.800 peak    2321 weight  0.11000E+01 volume  0.47004E+03 ppm1  8.832 ppm2  8.310
ASSI {2341}
((segid "BrD" and resid 49 and name HN))
((segid "BrD" and resid 49 and name HA))
  2.800  1.700  1.700 peak    2341 weight  0.11000E+01 volume  0.63035E+03 ppm1  7.762 ppm2  4.690
ASSI {2351}
((segid "BrD" and resid 49 and name HN))
((segid "BrD" and resid 49 and name HB))
  3.100  2.400  2.400 peak    2351 weight  0.11000E+01 volume  0.22961E+03 ppm1  7.762 ppm2  2.611
ASSI {2361}
((segid "BrD" and resid 49 and name HN))
(segid "BrD" and resid 49 and name HG2 %)
  3.300  2.700  2.200 peak    2361 weight  0.11000E+01 volume  0.15115E+03 ppm1  7.762 ppm2  1.586
ASSI {2381}
((segid "BrD" and resid 48 and name HN))
((segid "BrD" and resid 49 and name HN))
  2.400  1.400  1.400 peak    2381 weight  0.11000E+01 volume  0.95252E+03 ppm1  8.308 ppm2  7.742
ASSI {2391}
((segid "BrD" and resid 50 and name HN))
((segid "BrD" and resid 51 and name HN))
  2.600  1.700  1.700 peak    2391 weight  0.11000E+01 volume  0.55801E+03 ppm1  8.559 ppm2  8.318
ASSI {2401}
((segid "BrD" and resid 50 and name HN))
((segid "BrD" and resid 50 and name HA))
  2.700  1.800  1.800 peak    2401 weight  0.11000E+01 volume  0.45800E+03 ppm1  8.564 ppm2  4.525
ASSI {2421}
((segid "BrD" and resid 49 and name HN))
((segid "BrD" and resid 50 and name HN))
  2.400  1.400  1.400 peak    2421 weight  0.11000E+01 volume  0.91502E+03 ppm1  7.762 ppm2  8.554
ASSI {2431}
((segid "BrD" and resid 115 and name HN))
((segid "BrD" and resid 114 and name HA2))
  3.100  2.400  2.400 peak    2431 weight  0.11000E+01 volume  0.20145E+03 ppm1  8.355 ppm2  4.542
ASSI {2441}
((segid "BrD" and resid 115 and name HN))
((segid "BrD" and resid 115 and name HA))
  2.800  2.000  2.000 peak    2441 weight  0.11000E+01 volume  0.38387E+03 ppm1  8.355 ppm2  4.822
ASSI {2451}
((segid "BrD" and resid 116 and name HN))
((segid "BrD" and resid 115 and name HB1))
  2.700  1.800  1.800 peak    2451 weight  0.11000E+01 volume  0.51528E+03 ppm1  8.086 ppm2  2.169
ASSI {2461}
((segid "BrD" and resid 116 and name HN))
((segid "BrD" and resid 116 and name HA))
  2.500  1.600  1.600 peak    2461 weight  0.11000E+01 volume  0.81456E+03 ppm1  8.087 ppm2  4.828
ASSI {2471}
((segid "BrD" and resid 116 and name HN))
((segid "BrD" and resid 116 and name HB))
  2.600  1.700  1.700 peak    2471 weight  0.11000E+01 volume  0.58085E+03 ppm1  8.086 ppm2  2.419
ASSI {2481}
((segid "BrD" and resid 117 and name HN))
((segid "BrD" and resid 117 and name HA))
  3.300  2.700  2.200 peak    2481 weight  0.11000E+01 volume  0.15334E+03 ppm1  8.880 ppm2  5.171
ASSI {2491}
((segid "BrD" and resid 117 and name HN))
((segid "BrD" and resid 117 and name HB1))
  3.300  2.700  2.200 peak    2491 weight  0.11000E+01 volume  0.14660E+03 ppm1  8.879 ppm2  3.300

TABLE 2-continued

Unambiguous NOE-derived Inter-proton Distance Restraints

ASSI {2501}
((segid "BrD" and resid 117 and name HN))
((segid "BrD" and resid 117 and name HB2))
 2.800  2.000  2.000 peak     2501 weight  0.11000E+01 volume  0.41931E+03 ppm1   8.879 ppm2  3.147
ASSI {2511}
((segid "BrD" and resid 51 and name HN))
((segid "BrD" and resid 51 and name HA))
 2.300  1.300  1.300 peak     2511 weight  0.11000E+01 volume  0.13843E+04 ppm1   8.377 ppm2  4.475
ASSI {2521}
((segid "BrD" and resid 51 and name HN))
((segid "BrD" and resid 51 and name HG1))
 2.900  2.100  2.100 peak     2521 weight  0.11000E+01 volume  0.29957E+03 ppm1   8.375 ppm2  1.933
ASSI {2531}
((segid "BrD" and resid 17 and name HN))
((segid "BrD" and resid 17 and name HB))
 3.000  2.200  2.200 peak     2531 weight  0.11000E+01 volume  0.26023E+03 ppm1   8.679 ppm2  4.860
ASSI {2541}
((segid "BrD" and resid 17 and name HN))
((segid "BrD" and resid 17 and name HA))
 2.400  1.400  1.400 peak     2541 weight  0.11000E+01 volume  0.10062E+04 ppm1   8.678 ppm2  4.571
ASSI {2551}
((segid "BrD" and resid 17 and name HN))
(segid "BrD" and resid 17 and name HG2 %)
 3.100  2.400  2.400 peak     2551 weight  0.11000E+01 volume  0.20185E+03 ppm1   8.670 ppm2  1.745
ASSI {2561}
((segid "BrD" and resid 101 and name HN))
((segid "BrD" and resid 100 and name HB2))
 2.800  2.000  2.000 peak     2561 weight  0.11000E+01 volume  0.3$$3E+03 ppm1    8.513 ppm2  3.441
ASSI {2571}
((segid "BrD" and resid 101 and name HN))
((segid "BrD" and resid 101 and name HA))
 2.800  2.000  2.000 peak     2571 weight  0.11000E+01 volume  0.37743E+03 ppm1   8.513 ppm2  4.264
ASSI {2591}
((segid "BrD" and resid 100 and name HN))
((segid "BrD" and resid 101 and name HN))
 2.600  1.700  1.700 peak     2591 weight  0.11000E+01 volume  0.62929E+03 ppm1   8.669 ppm2  8.521
ASSI {2601}
((segid "BrD" and resid 102 and name HN))
((segid "BrD" and resid 102 and name HA))
 2.900  2.100  2.100 peak     2601 weight  0.11000E+01 volume  0.34745E+03 ppm1   9.156 ppm2  4.280
ASSI {2611}
((segid "BrD" and resid 102 and name HN))
((segid "BrD" and resid 101 and name HN))
 2.700  1.800  1.800 peak     2611 weight  0.11000E+01 volume  0.52631E+03 ppm1   9.156 ppm2  8.513
ASSI {2641}
((segid "BrD" and resid 103 and name HN))
((segid "BrD" and resid 103 and name HA))
 2.800  2.000  2.000 peak     2641 weight  0.11000E+01 volume  0.41836E+03 ppm1   8.695 ppm2  3.800
ASSI {2651}
((segid "BrD" and resid 103 and name HN))
((segid "BrD" and resid 103 and name HB2))
 2.800  2.000  2.000 peak     2651 weight  0.11000E+01 volume  0.35593E+03 ppm1   8.696 ppm2  1.928
ASSI {2661}
((segid "BrD" and resid 103 and name HN))
((segid "BrD" and resid 103 and name HB1))
 2.500  1.600  1.600 peak     2661 weight  0.11000E+01 volume  0.72768E+03 ppm1   8.695 ppm2  2.353
ASSI {2671}
((segid "BrD" and resid 103 and name HN))
((segid "BrD" and resid 103 and name HG2))
 3.200  2.600  2.300 peak     2671 weight  0.11000E+01 volume  0.18331E+03 ppm1   8.695 ppm2  2.529
ASSI {2681}
((segid "BrD" and resid 103 and name HN))
((segid "BrD" and resid 102 and name HN))
 2.600  1.700  1.700 peak     2681 weight  0.11000E+01 volume  0.68597E+03 ppm1   8.694 ppm2  9.157
ASSI {2711}
((segid "BrD" and resid 104 and name HN))
((segid "BrD" and resid 104 and name HA))
 2.600  1.700  1.700 peak     2711 weight  0.11000E+01 volume  0.66065E+03 ppm1   7.763 ppm2  4.690
ASSI {2731}
((segid "BrD" and resid 104 and name HN))
((segid "BrD" and resid 103 and name HN))
 2.800  2.000  2.000 peak     2731 weight  0.11000E+01 volume  0.40496E+03 ppm1   7.763 ppm2  8.680
ASSI {2751}
((segid "BrD" and resid 104 and name HN))
((segid "BrD" and resid 105 and name HN))
 2.700  1.800  1.800 peak     2751 weight  0.11000E+01 volume  0.54532E+03 ppm1   7.763 ppm2  8.475

TABLE 2-continued

Unambiguous NOE-derived Inter-proton Distance Restraints

ASSI {2771}
((segid "BrD" and resid 79 and name HN))
(segid "BrD" and resid 78 and name HD1 %)
 3.900  3.800 1.600 peak       2771 weight  0.11000E+01 volume  0.50980E+02 ppm1      8.685 ppm2  0.788
ASSI {2781}
((segid "BrD" and resid 81 and name HN))
((segid "BrD" and resid 81 and name HA))
 3.300  2.700 2.200 peak       2781 weight  0.11000E+01 volume  0.15663E+03 ppm1      7.640 ppm2  3.711
ASSI {2791}
((segid "BrD" and resid 81 and name HN))
((segid "BrD" and resid 81 and name HB))
 2.500  1.400 1.600 peak       2791 weight  0.11000E+01 volume  0.72728E+03 ppm1      7.640 ppm2  2.037
ASSI {2801}
((segid "BrD" and resid 81 and name HN))
(segid "BrD" and resid 81 and name HG1 %)
 2.500  1.600 1.600 peak       2801 weight  0.11000E+01 volume  0.82553E+03 ppm1      7.640 ppm2  1.071
ASSI {2811}
((segid "BrD" and resid 81 and name HN))
(segid "BrD" and resid 81 and name HG2 %)
 3.100  2.400 2.400 peak       2811 weight  0.11000E+01 volume  0.22921E+03 ppm1      7.640 ppm2  0.751
ASSI {2821}
((segid "BrD" and resid 82 and name HN))
(segid "BrD" and resid 82 and name HD %)
 3.000  2.200 2.200 peak       2821 weight  0.11000E+01 volume  0.28368E+03 ppm1      6.981 ppm2  7.258
ASSI {2831}
((segid "BrD" and resid 82 and name HN))
((segid "BrD" and resid 82 and name HA))
 2.800  2.000 2.000 peak       2831 weight  0.11000E+01 volume  0.42147E+03 ppm1      6.981 ppm2  4.738
ASSI {2841}
((segid "BrD" and resid 82 and name HN))
((segid "BrD" and resid 82 and name HB1))
 3.000  2.200 2.200 peak       2841 weight  0.11000E+01 volume  0.27134E+03 ppm1      6.981 ppm2  3.706
ASSI {2851}
((segid "BrD" and resid 82 and name HN))
((segid "BrD" and resid 82 and name HB2))
 2.600  1.700 1.700 peak       2851 weight  0.11000E+01 volume  0.58897E+03 ppm1      6.981 ppm2  3.556
ASSI {2871}
((segid "BrD" and resid 81 and name HN))
((segid "BrD" and resid 82 and name HN))
 2.800  2.000 2.000 peak       2871 weight  0.11000E+01 volume  0.36428E+03 ppm1      7.640 ppm2  6.966
ASSI {2891}
((segid "BrD" and resid 82 and name HN))
((segid "BrD" and resid 83 and name HN))
 2.800  2.000 2.000 peak       2891 weight  0.11000E+01 volume  0.41793E+03 ppm1      6.981 ppm2  9.658
ASSI {2901}
((segid "BrD" and resid 79 and name HN))
(segid "BrD" and resid 78 and name HD2 %)
 3.900  3.800 1.600 peak       2901 weight  0.11000E+01 volume  0.52951E+02 ppm1      5.684 ppm2  0.666
ASSI {2911}
((segid "BrD" and resid 80 and name HN))
((segid "BrD" and resid 80 and name HA))
 2.500  1.600 1.600 peak       2911 weight  0.11000E+01 volume  0.82068E+03 ppm1      8.005 ppm2  4.678
ASSI {2921}
((segid "BrD" and resid 80 and name HN))
((segid "BrD" and resid 81 and name HN))
 2.700  1.800 1.800 peak       2921 weight  0.11000E+01 volume  0.47132E+03 ppm1      8.006 ppm2  7.632
ASSI {2941}
((segid "BrD" and resid 83 and name HN))
(segid "BrD" and resid 82 and name HD %)
 3.400  2.900 2.100 peak       2941 weight  0.11000E+01 volume  0.12712E+03 ppm1      9.658 ppm2  7.248
ASSI {2951}
((segid "BrD" and resid 79 and name HN))
((segid "BrD" and resid 79 and name HA))
 2.600  2.700 1.700 peak       2951 weight  0.11000E+01 volume  0.57656E+03 ppm1      8.681 ppm2  4.406
ASSI {2961}
((segid "BrD" and resid 79 and name HN))
((segid "BrD" and resid 79 and name HG1))
 2.900  2.100 2.100 peak       2961 weight  0.11000E+01 volume  0.30890E+03 ppm1      8.681 ppm2  3.055
ASSI {2971}
((segid "BrD" and resid 79 and name HN))
((segid "BrD" and resid 79 and name HB2))
 2.500  1.600 1.600 peak       2971 weight  0.11000E+01 volume  0.75107E+03 ppm1      8.679 ppm2  2.684
ASSI {2981}
((segid "BrD" and resid 80 and name HN))
((segid "BrD" and resid 79 and name HN))
 2.700  1.800 1.800 peak       2981 weight  0.11000E+01 volume  0.45960E+03 ppm1      8.006 ppm2  8.676

TABLE 2-continued

| Unambiguous NOE-derived Inter-proton Distance Restraints |

ASSI {3001}
((segid "BrD" and resid 74 and name HN))
((segid "BrD" and resid 72 and name HA))
 3.500  3.100  2.000 peak     3001 weight  0.11000E+01 volume  0.98034E+02 ppm1   7.536 ppm2  4.666
ASSI {3011}
((segid "BrD" and resid 73 and name HN))
((segid "BrD" and resid 73 and name HA))
 2.600  1.700  1.700 peak     3011 weight  0.11000E+01 volume  0.57896E+03 ppm1   8.045 ppm2  4.811
ASSI {3021}
((segid "BrD" and resid 73 and name HN))
((segid "BrD" and resid 74 and name HN))
 2.800  2.000  2.000 peak     3021 weight  0.11000E+01 volume  0.42186E+03 ppm1   8.049 ppm2  7.542
ASSI {3041}
((segid "BrD" and resid 64 and name HN))
((segid "BrD" and resid 63 and name HA))
 3.100  2.400  2.400 peak     3041 weight  0.11000E+01 volume  0.20596E+03 ppm1   8.584 ppm2  5.298
ASSI {3051}
((segid "BrD" and resid 64 and name HN))
((segid "BrD" and resid 64 and name HA))
 2.600  1.700  1.700 peak     3051 weight  0.11000E+01 volume  0.63768E+03 ppm1   8.584 ppm2  4.940
ASSI {3061}
((segid "BrD" and resid 63 and name HN))
((segid "BrD" and resid 63 and name HA))
 2.900  2.100  2.100 peak     3061 weight  0.11000E+01 volume  0.33289E+03 ppm1   9.473 ppm2  5.302
ASSI {3071}
((segid "BrD" and resid 63 and name HN))
((segid "BrD" and resid 64 and name HN))
 2.600  1.700  1.700 peak     3071 weight  0.11000E+01 volume  0.68875E+03 ppm1   9.478 ppm2  8.565
ASSI {3091}
((segid "BrD" and resid 38 and name HN))
((segid "BrD" and resid 38 and name HA))
 3.100  2.400  2.400 peak     3091 weight  0.11000E+01 volume  0.21794E+03 ppm1   6.732 ppm2  4.166
ASSI {3101}
((segid "BrD" and resid 38 and name HN))
((segid "BrD" and resid 38 and name HB))
 2.500  1.600  1.600 peak     3101 weight  0.11000E+01 volume  0.76036E+03 ppm1   8.731 ppm2  1.767
ASSI {3111}
((segid "BrD" and resid 38 and name HN))
(segid "BrD" and resid 38 and name HG1 %)
 2.400  1.400  1.400 peak     3111 weight  0.11000E+01 volume  0.94284E+03 ppm1   8.733 ppm2  1.071
ASSI {3121}
((segid "BrD" and resid 38 and name HN))
(segid "BrD" and resid 38 and name HG2 %)
 4.000  4.000  1.500 peak     3121 weight  0.11000E+01 volume  0.47989E+02 ppm1   8.732 ppm2  0.784
ASSI {3131}
((segid "BrD" and resid 39 and name HN))
((segid "BrD" and resid 39 and name HA))
 3.600  3.200  1.900 peak     3131 weight  0.11000E+01 volume  0.90084E+02 ppm1   9.653 ppm2  4.977
ASSI {3141}
((segid "BrD" and resid 58 and name HN))
((segid "BrD" and resid 58 and name HA))
 2.900  2.100  2.100 peak     3141 weight  0.11000E+01 volume  0.34424E+03 ppm1  10.051 ppm2  4.451
ASSI {3151}
((segid "BrD" and resid 58 and name HN))
((segid "BrD" and resid 58 and name HB))
 2.900  2.100  2.100 peak     3151 weight  0.11000E+01 volume  0.30448E+03 ppm1  10.052 ppm2  4.686
ASSI {3161}
((segid "BrD" and resid 58 and name HN))
(segid "BrD" and resid 58 and name HG2 %)
 3.700  3.400  1.800 peak     3161 weight  0.11000E+01 volume  0.68430E+02 ppm1  10.051 ppm2  1.674
ASSI {3171}
((segid "BrD" and resid 57 and name HN))
((segid "BrD" and resid 57 and name HA))
 2.700  1.800  1.800 peak     3171 weight  0.11000E+01 volume  0.45739E+03 ppm1   9.359 ppm2  4.809
ASSI {3191}
((segid "BrD" and resid 58 and name HN))
((segid "BrD" and resid 57 and name HN))
 2.600  1.700  1.700 peak     3191 weight  0.11000E+01 volume  0.55403E+03 ppm1  10.051 ppm2  9.351
ASSI {3201}
((segid "BrD" and resid 56 and name HN))
((segid "BrD" and resid 56 and name HA))
 3.100  2.400  2.400 peak     3201 weight  0.11000E+01 volume  0.22011E+03 ppm1   9.678 ppm2  4.622
ASSI {3221}
((segid "BrD" and resid 57 and name HN))
((segid "BrD" and resid 56 and name HN))
 3.100  2.400  2.400 peak     3221 weight  0.11000E+01 volume  0.21874E+03 ppm1   9.359 ppm2  9.662

TABLE 2-continued

| Unambiguous NOE-derived Inter-proton Distance Restraints |
|---|

ASSI {3231}
((segid "BrD" and resid 79 and name HN))
((segid "BrD" and resid 78 and name HB2))
  3.200  2.600  2.300 peak       3231  weight  0.11000E+01 volume  0.19421E+03 ppm1      8.680  ppm2  1.049
ASSI {3241}
((segid "BrD" and resid 55 and name HN))
((segid "BrD" and resid 55 and name HA))
  2.600  1.700  1.700 peak       3241  weight  0.11000E+01 volume  0.57256E+03 ppm1      7.973  ppm2  5.343
ASSI {3251}
((segid "BrD" and resid 55 and name HN))
((segid "BrD" and resid 55 and name HB1))
  3.200  2.600  2.300 peak       3251  weight  0.11000E+01 volume  0.19260E+03 ppm1      7.975  ppm2  2.971
ASSI {3271}
((segid "BrD" and resid 16 and name HN))
((segid "BrD" and resid 16 and name HA))
  2.500  1.600  1.600 peak       3271  weight  0.11000E+01 volume  0.81267E+03 ppm1      8.792  ppm2  4.514
ASSI {3281}
((segid "BrD" and resid 15 and name HN))
((segid "BrD" and resid 11 and name HA))
  3.600  3.200  1.900 peak       3281  weight  0.11000E+01 volume  0.88613E+02 ppm1      8.599  ppm2  4.936
ASSI {3291}
((segid "BrD" and resid 15 and name HN))
((segid "BrD" and resid 15 and name HA))
  3.000  2.200  2.200 peak       3291  weight  0.11000E+01 volume  0.23859E+03 ppm1      8.599  ppm2  4.615
ASSI {3301}
((segid "BrD" and resid 15 and name HN))
((segid "BrD" and resid 15 and name HB1))
  2.600  1.700  1.700 peak       3301  weight  0.11000E+01 volume  0.66455E+03 ppm1      8.598  ppm2  3.809
ASSI {3311}
((segid "BrD" and resid 15 and name HN))
((segid "BrD" and resid 15 and name HB2))
  2.500  1.600  1.600 peak       3311  weight  0.11000E+01 volume  0.74771E+03 ppm1      8.598  ppm2  3.634
ASSI {3331}
((segid "BrD" and resid 16 and name HN))
((segid "BrD" and resid 15 and name HN))
  2.500  1.600  1.600 peak       3331  weight  0.11000E+01 volume  0.87721E+03 ppm1      8.793  ppm2  8.628
ASSI {3341}
((segid "BrD" and resid 13 and name HN))
((segid "BrD" and resid 13 and name HA))
  3.200  2.600  2.300 peak       3341  weight  0.11000E+01 volume  0.16876E+03 ppm1      8.801  ppm2  4.773
ASSI {3351}
((segid "BrD" and resid 14 and name HN))
((segid "BrD" and resid 14 and name HA))
  3.300  2.700  2.200 peak       3351  weight  0.11000E+01 volume  0.15715E+03 ppm1      8.811  ppm2  4.651
ASSI {3381}
((segid "BrD" and resid 13 and name HN))
((segid "BrD" and resid 13 and name HB1))
  2.300  1.300  1.300 peak       3381  weight  0.11000E+01 volume  0.12106E+04 ppm1      8.807  ppm2  2.758
ASSI {3391}
((segid "BrD" and resid 14 and name HN))
((segid "BrD" and resid 11 and name HA))
  3.300  2.700  2.200 peak       3391  weight  0.11000E+01 volume  0.15172E+03 ppm1      8.809  ppm2  4.939
ASSI {3412}
((segid "BrD" and resid 34 and name HN))
((segid "BrD" and resid 34 and name HA))
  2.800  2.000  2.000 peak       3411  weight  0.11000E+01 volume  0.39310E+03 ppm1      8.176  ppm2  5.542
ASSI {3421}
((segid "BrD" and resid 34 and name HN))
((segid "BrD" and resid 34 and name HB1))
  3.600  3.200  2.900 peak       3421  weight  0.11000E+01 volume  0.86584E+02 ppm1      8.182  ppm2  4.098
ASSI {3431}
((segid "BrD" and resid 34 and name HN))
((segid "BrD" and resid 34 and name HB2))
  2.700  1.800  1.800 peak       3431  weight  0.11000E+01 volume  0.51957E+03 ppm1      8.182  ppm2  3.143
ASSI {3441}
((segid "BrD" and resid 35 and name HN))
((segid "BrD" and resid 34 and name HB2))
  3.300  2.700  2.200 peak       3441  weight  0.11000E+01 volume  0.14464E+03 ppm1      7.735  ppm2  3.139
ASSI {3451}
((segid "BrD" and resid 35 and name HN))
((segid "BrD" and resid 35 and name HA))
  2.800  2.000  2.000 peak       3451  weight  0.11000E+01 volume  0.42792E+03 ppm1      7.734  ppm2  4.899
ASSI {3461}
((segid "BrD" and resid 35 and name HN))
((segid "BrD" and resid 35 and name HG1)
  2.700  1.800  1.800 peak       3461  weight  0.11000E+01 volume  0.54517E+03 ppm1      7.734  ppm2  3.436

TABLE 2-continued

Unambiguous NOE-derived Inter-proton Distance Restraints

```
ASSI {3471}
((segid "BrD" and resid 35 and name HN))
((segid "BrD" and resid 35 and name HB2))
  3.300  2.700  2.200 peak      3471 weight  0.11000E+01 volume  0.15293E+03 ppm1    7.733 ppm2  2.781
ASSI {3491}
((segid "BrD" and resid 34 and name HN))
((segid "BrD" and resid 35 and name HN))
  2.200  1.200  1.200 peak      3491 weight  0.11000E+01 volume  0.15285E+04 ppm1    8.176 ppm2  7.714
ASSI {3501}
((segid "BrD" and resid 36 and name HN))
((segid "BrD" and resid 36 and name HA))
  2.600  1.700  1.700 peak      3501 weight  0.11000E+01 volume  0.56896E+03 ppm1    8.310 ppm2  5.456
ASSI {3511}
((segid "BrD" and resid 36 and name HN))
((segid "BrD" and resid 36 and name HG1))
  3.700  3.400  1.800 peak      3511 weight  0.11000E+01 volume  0.72744E+02 ppm1    8.308 ppm2  2.771
ASSI {3521}
((segid "BrD" and resid 36 and name HN))
((segid "BrD" and resid 36 and name HB2))
  2.600  1.700  1.700 peak      3521 weight  0.11000E+01 volume  0.65455E+03 ppm1    8.311 ppm2  2.337
ASSI {3541}
((segid "BrD" and resid 35 and name HN))
((segid "BrD" and resid 36 and name HN))
  2.700  1.800  1.800 peak      3541 weight  0.11000E+01 volume  0.54251E+03 ppm1    7.734 ppm2  8.316
ASSI {3561}
((segid "BrD" and resid 12 and name HN))
((segid "BrD" and resid 12 and name HA))
  2.100  1.100  1.100 peak      3561 weight  0.11000E+01 volume  0.19935E+04 ppm1    9.021 ppm2  5.292
ASSI {3571}
((segid "BrD" and resid 12 and name HN))
((segid "BrD" and resid 12 and name HB1))
  2.700  1.800  1.800 peak      3571 weight  0.11000E+01 volume  0.46239E+03 ppm1    9.020 ppm2  3.428
ASSI {3581}
((segid "BrD" and resid 10 and name HN))
((segid "BrD" and resid 10 and name HA))
  3.500  3.100  2.000 peak      3581 weight  0.11000E+01 volume  0.10021E+03 ppm1    8.885 ppm2  5.481
ASSI {3591}
((segid "BrD" and resid 10 and name HN))
((segid "BrD" and resid 10 and name HB1))
  3.000  2.200  2.200 peak      3591 weight  0.11000E+01 volume  0.27522E+03 ppm1    8.885 ppm2  3.3$$1
ASSI {3611}
((segid "BrD" and resid 9 and name HN))
((segid "BrD" and resid 9 and name HB1))
  2.900  2.100  2.100 peak      3611 weight  0.11000E+01 volume  0.31864E+03 ppm1    9.054 ppm2  2.444
ASSI {3621}
((segid "BrD" and resid 9 and name HN))
((segid "BrD" and resid 10 and name HN))
  3.500  3.100  2.000 peak      3621 weight  0.11000E+01 volume  0.11024E+03 ppm1    9.054 ppm2  8.880
ASSI {3641}
((segid "BrD" and resid 62 and name HN))
((segid "BrD" and resid 62 and name HD1))
  3.400  2.900  2.100 peak      3641 weight  0.11000E+01 volume  0.12186E+03 ppm1    8.998 ppm2  3.185
ASSI {3651}
((segid "BrD" and resid 62 and name HN))
((segid "BrD" and resid 61 and name HG2))
  3.000  2.200  2.200 peak      3651 weight  0.11000E+01 volume  0.24395E+03 ppm1    8.999 ppm2  2.783
ASSI {3661}
((segid "BrD" and resid 62 and name HN))
((segid "BrD" and resid 62 and name HG1))
  2.600  1.700  1.700 peak      3661 weight  0.11000E+01 volume  0.63487E+03 ppm1    8.997 ppm2  2.329
ASSI {3681}
((segid "BrD" and resid 7 and name HN))
((segid "BrD" and resid 7 and name HA))
  3.100  2.400  2.400 peak      3681 weight  0.11000E+01 volume  0.21276E+03 ppm1    8.924 ppm2  5.147
ASSI {3691}
((segid "BrD" and resid 7 and name HN))
((segid "BrD" and resid 7 and name HG1))
  3.400  2.900  2.100 peak      3691 weight  0.11000E+01 volume  0.12947E+03 ppm1    8.923 ppm2  2.878
ASSI {3701}
((segid "BrD" and resid 7 and name HN))
((segid "BrD" and resid 7 and name HB1))
  3.100  2.400  2.400 peak      3701 weight  0.11000E+01 volume  0.20103E+03 ppm1    8.923 ppm2  2.631
ASSI {3711}
((segid "BrD" and resid 7 and name HN))
((segid "BrD" and resid 7 and name HB2))
  2.700  1.800  1.800 peak      3711 weight  0.11000E+01 volume  0.54229E+03 ppm1    8.924 ppm2  2.500
```

TABLE 2-continued

Unambiguous NOE-derived Inter-proton Distance Restraints

ASSI {3721}
((segid "BrD" and resid 79 and name HN))
((segid "BrD" and resid 78 and name HG))
 2.800  2.000  2.000 peak       3721 weight  0.11000E+01 volume  0.38659E+03 ppm1    8.681 ppm2  1.314
ASSI {3731}
((segid "BrD" and resid 78 and name HN))
((segid "BrD" and resid 78 and name HA))
 2.500  1.600  1.600 peak       3731 weight  0.11000E+01 volume  0.73125E+03 ppm1    7.996 ppm2  4.004
ASSI {3741}
((segid "BrD" and resid 118 and name HN))
((segid "BrD" and resid 118 and name HA))
 2.900  2.100  2.100 peak       3741 weight  0.11000E+01 volume  0.30830E+03 ppm1    8.381 ppm2  4.689
ASSI {3761}
((segid "BrD" and resid 54 and name HN))
((segid "BrD" and resid 54 and name HA))
 2.900  2.100  2.100 peak       3761 weight  0.11000E+01 volume  0.30432E+03 ppm1    9.036 ppm2  5.546
ASSI {3771}
((segid "BrD" and resid 54 and name HN))
((segid "BrD" and resid 54 and name HB1))
 3.400  2.900  2.100 peak       3771 weight  0.11000E+01 volume  0.12504E+03 ppm1    9.036 ppm2  2.596
ASSI {3781}
((segid "BrD" and resid 54 and name HN))
((segid "BrD" and resid 54 and name HB2))
 3.600  3.200  1.900 peak       3781 weight  0.11000E+01 volume  0.92666E+02 ppm1    9.037 ppm2  1.960
ASSI {3791}
((segid "BrD" and resid 62 and name HN))
((segid "BrD" and resid 59 and name HA))
 3.200  2.600  2.300 peak       3791 weight  0.11000E+01 volume  0.18605E+03 ppm1    8.998 ppm2  4.900
ASSI {3801}
((segid "BrD" and resid 62 and name HN))
((segid "BrD" and resid 62 and name HA))
 2.800  2.000  2.000 peak       3801 weight  0.11000E+01 volume  0.36964E+03 ppm1    8.998 ppm2  4.467
ASSI {3811}
((segid "BrD" and resid 72 and name HN))
(segid "BrD" and resid 72 and name HA))
 3.000  2.200  2.200 peak       3811 weight  0.11000E+01 volume  0.24473E+03 ppm1    8.858 ppm2  4.648
ASSI {3821}
((segid "BrD" and resid 72 and name HN))
((segid "BrD" and resid 73 and name HN))
 3.700  3.400  1.800 peak       3821 weight  0.11000E+01 volume  0.74895E+02 ppm1    8.858 ppm2  8.033
ASSI {3851}
((segid "BrD" and resid 61 and name HN))
((segid "BrD" and resid 61 and name HA))
 2.500  1.600  1.600 peak       3851 weight  0.11000E+01 volume  0.82145E+03 ppm1    8.748 ppm2  4.652
ASSI {3861}
((segid "BrD" and resid 65 and name HN))
((segid "BrD" and resid 62 and name HA))
 3.100  2.400  2.400 peak       3861 weight  0.11000E+01 volume  0.22227E+03 ppm1    8.568 ppm2  4.476
ASSI {3871}
((segid "BrD" and resid 60 and name HN))
((segid "BrD" and resid 60 and name HA))
 2.400  1.400  1.400 peak       3871 weight  0.11000E+01 volume  0.10791E+04 ppm1    8.569 ppm2  4.808
ASSI {3881}
((segid "BrD" and resid 60 and name HN))
((segid "BrD" and resid 60 and name HB2))
 2.400  1.400  1.400 peak       3881 weight  0.11000E+01 volume  0.10099E+04 ppm1    8.569 ppm2  4.647
ASSI {3891}
((segid "BrD" and resid 60 and name HN))
((segid "BrD" and resid 60 and name HB1))
 2.600  1.700  1.700 peak       3891 weight  0.11000E+01 volume  0.65212E+03 ppm1    8.560 ppm2  4.975
ASSI {3901}
((segid "BrD" and resid 59 and name HN))
((segid "BrD" and resid 59 and name HA))
 3.200  2.600  2.300 peak       3901 weight  0.11000E+01 volume  0.16755E+03 ppm1    8.497 ppm2  4.893
ASSI {3921}
((segid "BrD" and resid 7 and name HN))
((segid "BrD" and resid 6 and name HA))
 2.600  1.700  1.700 peak       3921 weight  0.11000E+01 volume  0.63166E+03 ppm1    8.924 ppm2  4.968
ASSI {3931}
((segid "BrD" and resid 10 and name HN))
((segid "BrD" and resid 9 and name HA))
 2.600  1.700  1.700 peak       3931 weight  0.11000E+01 volume  0.55346E+03 ppm1    8.884 ppm2  4.938
ASSI {3941}
((segid "BrD" and resid 13 and name HN))
((segid "BrD" and resid 12 and name HA))
 3.200  2.600  2.300 peak       3941 weight  0.11000E+01 volume  0.18205E+03 ppm1    8.809 ppm2  5.299

TABLE 2-continued

| Unambiguous NOE-derived Inter-proton Distance Restraints |
|---|

ASSI {3951}
((segid "BrD" and resid 16 and name HN))
((segid "BrD" and resid 15 and name HB1))
  3.300  2.700  2.200 peak      3951  weight  0.11000E+01 volume  0.13722E+03 ppm1      8.793  ppm2  3.818
ASSI {3961}
((segid "BrD" and resid 16 and name HN))
((segid "BrD" and resid 15 and name HB2))
  2.500  1.600  1.600 peak      3961  weight  0.11000E+01 volume  0.74092E+03 ppm1      8.793  ppm2  3.631
ASSI {3971}
((segid "BrD" and resid 17 and name HN))
((segid "BrD" and resid 16 and name HA))
  2.500  1.600  1.600 peak      3971  weight  0.11000E+01 volume  0.82695E+03 ppm1      8.669  ppm2  4.516
ASSI {3991}
((segid "BrD" and resid 18 and name HN))
((segid "BrD" and resid 18 and name HA))
  3.000  2.200  2.200 peak      3991  weight  0.11000E+01 volume  0.24581E+03 ppm1      9.072  ppm2  3.878
ASSI {4001}
((segid "BrD" and resid 18 and name HN))
((segid "BrD" and resid 17 and name HB))
  2.800  2.000  2.000 peak      4001  weight  0.11000E+01 volume  0.36663E+03 ppm1      9.072  ppm2  4.854
ASSI {4011}
((segid "BrD" and resid 14 and name HN))
((segid "BrD" and resid 17 and name HA))
  3.200  2.600  2.300 peak      4011  weight  0.11000E+01 volume  0.18724E+03 ppm1      9.072  ppm2  4.531
ASSI {4021}
((segid "BrD" and resid 18 and name HN))
(segid "BrD" and resid 17 and name HG2 %)
  3.100  2.400  2.400 peak      4021  weight  0.11000E+01 volume  0.23212E+03 ppm1      9.073  ppm2  1.749
ASSI {4041}
((segid "BrD" and resid 17 and name HN))
((segid "BrD" and resid 18 and name HN))
  2.600  1.700  1.700 peak      4041  weight  0.11000E+01 volume  0.57514E+03 ppm1      8.669  ppm2  9.062
ASSI {4051}
((segid "BrD" and resid 19 and name HN))
((segid "BrD" and resid 18 and name HA))
  3.500  3.100  2.000 peak      4051  weight  0.11000E+01 volume  0.95460E+02 ppm1      9.187  ppm2  3.878
ASSI {4061}
((segid "BrD" and resid 20 and name HN))
((segid "BrD" and resid 19 and name HA))
  3.200  2.600  2.300 peak      4061  weight  0.11000E+01 volume  0.17148E+03 ppm1      8.146  ppm2  4.288
ASSI {4071}
((segid "BrD" and resid 21 and name HN))
((segid "BrD" and resid 20 and name HA))
  3.400  2.900  2.100 peak      4071  weight  0.11000E+01 volume  0.11425E+03 ppm1      8.545  ppm2  4.889
ASSI {4081}
((segid "BrD" and resid 22 and name HN))
((segid "BrD" and resid 21 and name HA))
  3.300  2.700  2.200 peak      4081  weight  0.11000E+01 volume  0.15238E+03 ppm1      9.457  ppm2  4.361
ASSI {4091}
((segid "BrD" and resid 23 and name HN))
((segid "BrD" and resid 22 and name HA))
  3.600  3.200  1.900 peak      4091  weight  0.11000E+01 volume  0.91130E+02 ppm1      9.118  ppm2  4.734
ASSI {4101}
((segid "BrD" and resid 24 and name HN))
((segid "BrD" and resid 23 and name HA))
  3.500  3.100  2.000 peak      4101  weight  0.11000E+01 volume  0.11008E+03 ppm1      8.661  ppm2  4.640
ASSI {4111}
((segid "BrD" and resid 25 and name HN))
((segid "BrD" and resid 24 and name HA))
  3.300  2.700  2.200 peak      4111  weight  0.11000E+01 volume  0.14843E+03 ppm1      9.133  ppm2  4.753
ASSI {4121}
((segid "BrD" and resid 25 and name HN))
((segid "BrD" and resid 24 and name HG2))
  2.500  1.600  1.600 peak      4121  weight  0.11000E+01 volume  0.87462E+03 ppm1      9.131  ppm2  3.059
ASSI {4141}
((segid "BrD" and resid 27 and name HN))
((segid "BrD" and resid 26 and name HA))
  3.200  2.600  2.300 peak      4141  weight  0.11000E+01 volume  0.18491E+03 ppm1      8.171  ppm2  4.493
ASSI {4151}
((segid "BrD" and resid 28 and name HN))
((segid "BrD" and resid 27 and name HA))
  3.300  2.700  2.300 peak      4151  weight  0.11000E+01 volume  0.14739E+03 ppm1      8.166  ppm2  5.055
ASSI {4161}
((segid "BrD" and resid 29 and name HN))
((segid "BrD" and resid 28 and name HA))
  2.400  1.400  1.400 peak      4161  weight  0.11000E+01 volume  0.91502E+03 ppm1      9.151  ppm2  4.574

TABLE 2-continued

Unambiguous NOE-derived Inter-proton Distance Restraints

ASSI {4171}
((segid "BrD" and resid 29 and name HN))
((segid "BrD" and resid 28 and name HB1))
  3.400  2.900  2.100 peak      4171  weight  0.11000E+01  volume  0.11906E+03 ppm1     9.151  ppm2  3.597
ASSI {4181}
((segid "BrD" and resid 29 and name HN))
((segid "BrD" and resid 28 and name HB2))
  3.800  3.600  1.700 peak      4181  weight  0.11000E+01  volume  0.65813E+02 ppm1     9.152  ppm2  3.406
ASSI {4191}
((segid "BrD" and resid 30 and name HN))
((segid "BrD" and resid 29 and name HA))
  3.600  3.200  1.900 peak      4191  weight  0.11000E+01  volume  0.88464E+02 ppm1    12.275  ppm2  4.819
ASSI {4201}
((segid "BrD" and resid 30 and name HN))
((segid "BrD" and resid 29 and name HB1))
  3.400  2.900  2.100 peak      4201  weight  0.11000E+01  volume  0.11541E+03 ppm1    12.275  ppm2  2.718
ASSI {4211}
((segid "BrD" and resid 30 and name HN))
((segid "BrD" and resid 29 and name HG1))
  3.600  3.200  1.900 peak      4211  weight  0.11000E+01  volume  0.88536E+02 ppm1    12.275  ppm2  3.024
ASSI {4221}
((segid "BrD" and resid 31 and name HN))
((segid "BrD" and resid 30 and name HA))
  3.600  3.200  1.900 peak      4221  weight  0.11000E+01  volume  0.86531E+02 ppm1     8.481  ppm2  5.449
ASSI {4231}
((segid "BrD" and resid 31 and name HN))
((segid "BrD" and resid 30 and name HB1))
  3.000  2.200  2.200 peak      4231  weight  0.11000E+01  volume  0.23699E+03 ppm1     8.480  ppm2  4.941
ASSI {4241}
((segid "BrD" and resid 31 and name HN))
((segid "BrD" and resid 30 and name HB2))
  3.500  3.100  2.000 peak      4241  weight  0.11000E+01  volume  0.10932E+03 ppm1     8.480  ppm2  4.533
ASSI {4251}
((segid "BrD" and resid 68 and name HN))
((segid "BrD" and resid 67 and name HB1))
  2.700  1.800  2.800 peak      4251  weight  0.11000E+01  volume  0.47519E+03 ppm1     8.627  ppm2  3.555
ASSI {4261}
((segid "BrD" and resid 32 and name HN))
(segid "BrD" and resid 31 and name HB %)
  2.900  2.100  2.100 peak      4261  weight  0.11000E+01  volume  0.35188E+03 ppm1     7.739  ppm2  2.295
ASSI {4271}
((segid "BrD" and resid 32 and name HN))
((segid "BrD" and resid 31 and name HN))
  2.300  1.300  1.300 peak      4271  weight  0.11000E+01  volume  0.11812E+04 ppm1     7.739  ppm2  8.475
ASSI {4291}
((segid "BrD" and resid 35 and name HN))
((segid "BrD" and resid 34 and name HA))
  3.200  2.600  2.300 peak      4291  weight  0.11000E+01  volume  0.17960E+03 ppm1     7.734  ppm2  5.537
ASSI {4301}
((segid "BrD" and resid 36 and name HN))
((segid "BrD" and resid 37 and name HD1))
  3.500  3.100  2.000 peak      4301  weight  0.11000E+01  volume  0.97101E+02 ppm1     8.309  ppm2  4.277
ASSI {4311}
((segid "BrD" and resid 36 and name HN))
((segid "BrD" and resid 35 and name HA))
  3.300  2.700  2.200 peak      4311  weight  0.11000E+01  volume  0.16106E+03 ppm1     8.308  ppm2  4.893
ASSI {4321}
((segid "BrD" and resid 36 and name HN))
((segid "BrD" and resid 35 and name HG1))
  3.700  3.400  1.800 peak      4321  weight  0.11000E+01  volume  0.78555E+02 ppm1     8.307  ppm2  3.458
ASSI {4331}
((segid "BrD" and resid 39 and name HN))
((segid "BrD" and resid 38 and name HA))
  2.200  1.200  1.200 peak      4331  weight  0.11000E+01  volume  0.15683E+04 ppm1     9.652  ppm2  4.160
ASSI {4341}
((segid "BrD" and resid 39 and name HN))
((segid "BrD" and resid 38 and name HB))
  3.400  2.900  2.100 peak      4341  weight  0.11000E+01  volume  0.11939E+03 ppm1     9.652  ppm2  1.752
ASSI {4351}
((segid "BrD" and resid 39 and name HN))
(segid "BrD" and resid 38 and name HG1 %)
  3.600  3.200  1.900 peak      4351  weight  0.11000E+01  volume  0.93234E+02 ppm1     9.652  ppm2  1.071
ASSI {4361}
((segid "BrD" and resid 39 and name HN))
(segid "BrD" and resid 38 and name HG2 %)
  3.100  2.400  2.400 peak      4361  weight  0.11000E+01  volume  0.20061E+03 ppm1     9.652  ppm2  0.776

TABLE 2-continued

Unambiguous NOE-derived Inter-proton Distance Restraints

ASSI {4381}
((segid "BrD" and resid 43 and name HN))
((segid "BrD" and resid 42 and name HA))
 2.900  2.100  2.100 peak      4381  weight  0.11000E+01 volume  0.31481E+03 ppm1    8.001  ppm2  5.055
ASSI {4391}
((segid "BrD" and resid 43 and name HN))
((segid "BrD" and resid 42 and name HB2))
 2.800  2.000  2.000 peak      4391  weight  0.11000E+01 volume  0.36989E+03 ppm1    8.001  ppm2  2.607
ASSI {4401}
((segid "BrD" and resid 43 and name HN))
((segid "BrD" and resid 42 and name HB1))
 2.900  2.100  2.100 peak      4401  weight  0.11000E+01 volume  0.32280E+03 ppm1    8.001  ppm2  2.781
ASSI {4411}
((segid "BrD" and resid 36 and name HN))
((segid "BrD" and resid 36 and name HB1))
 2.800  2.000  2.000 peak      4411  weight  0.11000E+01 volume  0.42122E+03 ppm1    8.308  ppm2  2.698
ASSI {4421}
((segid "BrD" and resid 47 and name HN))
((segid "BrD" and resid 46 and name HA))
 3.300  2.700  2.200 peak      4421  weight  0.11000E+01 volume  0.14320E+03 ppm1    8.832  ppm2  4.139
ASSI {4431}
((segid "BrD" and resid 47 and name HN))
((segid "BrD" and resid 46 and name HB1)
 3.500  3.100  2.000 peak      4431  weight  0.11000E+01 volume  0.11013E+03 ppm1    8.832  ppm2  3.296
ASSI {4441}
((segid "BrD" and resid 47 and name HN))
((segid "BrD" and resid 46 and name HB2))
 3.100  2.400  2.400 peak      4441  weight  0.11000E+01 volume  0.20297E+03 ppm1    8.833  ppm2  3.094
ASSI {4451}
((segid "BrD" and resid 48 and name HN))
((segid "BrD" and resid 47 and name HA))
 3.200  2.600  2.300 peak      4451  weight  0.11000E+01 volume  0.16849E+03 ppm1    8.307  ppm2  4.708
ASSI {4461}
((segid "BrD" and resid 49 and name HN))
((segid "BrD" and resid 48 and name HA))
 3.000  2.200  2.200 peak      4461  weight  0.11000E+01 volume  0.24376E+03 ppm1    7.762  ppm2  4.816
ASSI {4471}
((segid "BrD" and resid 49 and name HN))
((segid "BrD" and resid 48 and name HG2))
 4.000  4.000  1.500 peak      4471  weight  0.11000E+01 volume  0.45441E+02 ppm1    7.762  ppm2  2.872
ASSI {4481}
((segid "BrD" and resid 49 and name HN))
((segid "BrD" and resid 48 and name HB1))
 3.200  2.600  2.300 peak      4481  weight  0.11000E+01 volume  0.17937E+03 ppm1    7.762  ppm2  2.693
ASSI {4491}
((segid "BrD" and resid 50 and name HN))
((segid "BrD" and resid 49 and name HA))
 2.600  1.700  1.700 peak      4491  weight  0.11000E+01 volume  0.60014E+03 ppm1    8.564  ppm2  4.693
ASSI {4501}
((segid "BrD" and resid 50 and name HN))
((segid "BrD" and resid 49 and name HB))
 2.900  2.100  2.100 peak      4501  weight  0.11000E+01 volume  0.31627E+03 ppm1    8.564  ppm2  2.622
ASSI {4511}
((segid "BrD" and resid 50 and name HN))
((segid "BrD" and resid 49 and name HG2 %))
 3.700  3.400  1.800 peak      4511  weight  0.11000E+01 volume  0.77577E+02 ppm1    8.564  ppm2  1.598
ASSI {4521}
((segid "BrD" and resid 55 and name HN))
((segid "BrD" and resid 54 and name HA))
 2.300  1.300  1.300 peak      4521  weight  0.11000E+01 volume  0.11556E+04 ppm1    7.974  ppm2  5.542
ASSI {4531}
((segid "BrD" and resid 55 and name HN))
((segid "BrD" and resid 54 and name HB1))
 3.700  3.400  1.800 peak      4531  weight  0.11000E+01 volume  0.71474E+02 ppm1    7.975  ppm2  2.572
ASSI {4541}
((segid "BrD" and resid 55 and name HN))
((segid "BrD" and resid 54 and name HB2))
 3.100  2.400  2.400 peak      4541  weight  0.11000E+01 volume  0.20173E+03 ppm1    7.975  ppm2  1.956
ASSI {4551}
((segid "BrD" and resid 56 and name HN))
((segid "BrD" and resid 55 and name HA))
 2.800  2.000  2.000 peak      4551  weight  0.11000E+01 volume  0.38353E+03 ppm1    9.676  ppm2  5.352
ASSI {4561}
((segid "BrD" and resid 56 and name HN))
((segid "BrD" and resid 55 and name HB1))
 2.400  1.400  1.400 peak      4561  weight  0.11000E+01 volume  0.92127E+03 ppm1    9.679  ppm2  2.978

TABLE 2-continued

Unambiguous NOE-derived Inter-proton Distance Restraints

ASSI {4571}
((segid "BrD" and resid 57 and name HN))
((segid "BrD" and resid 56 and name HA))
 3.200  2.600  2.300 peak       4571 weight  0.11000E+01 volume  0.16116E+03 ppm1   9.359 ppm2  4.648
ASSI {4581}
((segid "BrD" and resid 58 and name HN))
((segid "BrD" and resid 57 and name HA))
 3.400  2.900  2.100 peak       4581 weight  0.11000E+01 volume  0.12185E+03 ppm1  10.050 ppm2  4.805
ASSI {4591}
((segid "BrD" and resid 59 and name HN))
((segid "BrD" and resid 58 and name HA))
 3.400  2.900  2.100 peak       4591 weight  0.11000E+01 volume  0.13191E+03 ppm1   8.498 ppm2  4.449
ASSI {4601}
((segid "BrD" and resid 59 and name HN))
((segid "BrD" and resid 58 and name HB))
 3.200  2.600  2.300 peak       4601 weight  0.11000E+01 volume  0.18613E+03 ppm1   8.498 ppm2  4.697
ASSI {4611}
((segid "BrD" and resid 59 and name HN))
(segid "BrD" and resid 58 and name HG2 %)
 3.100  2.400  2.400 peak       4611 weight  0.11000E+01 volume  0.21128E+03 ppm1   8.496 ppm2  1.665
ASSI {4631}
((segid "BrD" and resid 58 and name HN))
((segid "BrD" and resid 59 and name HN))
 3.200  2.600  2.300 peak       4631 weight  0.11000E+01 volume  0.17034E+03 ppm1  10.051 ppm2  8.489
ASSI {4641}
((segid "BrD" and resid 61 and name HN))
((segid "BrD" and resid 61 and name HG1))
 2.400  1.400  1.400 peak       4641 weight  0.11000E+01 volume  0.89496E+03 ppm1   8.743 ppm2  2.974
ASSI {4651}
((segid "BrD" and resid 61 and name HN))
((segid "BrD" and resid 61 and name HB2))
 2.500  1.600  1.600 peak       4651 weight  0.11000E+01 volume  0.72876E+03 ppm1   8.743 ppm2  2.670
ASSI {4661}
((segid "BrD" and resid 61 and name HN))
((segid "BrD" and resid 60 and name HA))
 3.300  2.700  2.200 peak       4661 weight  0.11000E+01 volume  0.14220E+03 ppm1   8.749 ppm2  4.816
ASSI {4691}
((segid "BrD" and resid 60 and name HN))
((segid "BrD" and resid 61 and name HN))
 2.400  1.400  1.400 peak       4691 weight  0.11000E+01 volume  0.96369E+03 ppm1   8.566 ppm2  8.734
ASSI {4701}
((segid "BrD" and resid 62 and name HN))
((segid "BrD" and resid 61 and name HA))
 3.200  2.600  2.300 peak       4701 weight  0.11000E+01 volume  0.17192E+03 ppm1   8.997 ppm2  4.656
ASSI {4711}
((segid "BrD" and resid 63 and name HN))
((segid "BrD" and resid 62 and name HN))
 2.800  2.000  2.000 peak       4711 weight  0.11000E+01 volume  0.35764E+03 ppm1   9.477 ppm2  8.998
ASSI {4731}
((segid "BrD" and resid 63 and name HN))
((segid "BrD" and resid 62 and name HA))
 3.600  3.200  1.900 peak       4731 weight  0.11000E+01 volume  0.90728E+02 ppm1   9.472 ppm2  4.481
ASSI {4741}
((segid "BrD" and resid 65 and name HD21))
((segid "BrD" and resid 65 and name HB1))
 3.500  3.100  2.000 peak       4741 weight  0.11000E+01 volume  0.10454E+03 ppm1   8.206 ppm2  3.637
ASSI {4751}
((segid "BrD" and resid 65 and name HD22))
((segid "BrD" and resid 65 and name HB1))
 3.500  3.100  2.000 peak       4751 weight  0.11000E+01 volume  0.97769E+02 ppm1   7.576 ppm2  3.637
ASSI {4761}
((segid "BrD" and resid 65 and name HD21))
((segid "BrD" and resid 65 and name HB2))
 3.200  2.600  2.300 peak       4761 weight  0.11000E+01 volume  0.17538E+03 ppm1   8.205 ppm2  3.393
ASSI {4771}
((segid "BrD" and resid 65 and name HD22))
((segid "BrD" and resid 65 and name HB2))
 3.400  2.900  2.100 peak       4771 weight  0.11000E+01 volume  0.13182E+03 ppm1   7.576 ppm2  3.393
ASSI {4781}
((segid "BrD" and resid 24 and name HE21))
((segid "BrD" and resid 24 and name HG1))
 3.400  2.900  2.100 peak       4781 weight  0.11000E+01 volume  0.11561E+03 ppm1   7.634 ppm2  3.459
ASSI {4791}
((segid "BrD" and resid 24 and name HE22))
((segid "BrD" and resid 24 and name HG1))
 3.600  3.200  1.900 peak       4791 weight  0.11000E+01 volume  0.90206E+02 ppm1   7.523 ppm2  3.474

TABLE 2-continued

Unambiguous NOE-derived Inter-proton Distance Restraints

ASSI {4801}
((segid "BrD" and resid 66 and name HN))
((segid "BrD" and resid 65 and name HA))
  2.700  1.800  1.800 peak      4801 weight  0.11000E+01 volume  0.48168E+03 ppm1   8.762 ppm2  5.378
ASSI {4811}
((segid "BrD" and resid 66 and name HN))
((segid "BrD" and resid 65 and name HB1))
  3.400  2.900  2.100 peak      4811 weight  0.11000E+01 volume  0.11537E+03 ppm1   8.759 ppm2  3.608
ASSI {4821}
((segid "BrD" and resid 66 and name HN))
((segid "BrD" and resid 65 and name HB2))
  3.300  2.700  2.200 peak      4821 weight  0.11000E+01 volume  0.13853E+03 ppm1   8.763 ppm2  3.381
ASSI {4831}
((segid "BrD" and resid 67 and name HN))
((segid "BrD" and resid 66 and name HA))
  2.800  2.000  2.000 peak      4831 weight  0.11000E+01 volume  0.41855E+03 ppm1   8.832 ppm2  5.009
ASSI {4841}
((segid "BrD" and resid 68 and name HN))
((segid "BrD" and resid 67 and name HA))
  3.400  2.900  2.100 peak      4841 weight  0.11000E+01 volume  0.12732E+03 ppm1   8.627 ppm2  4.671
ASSI {4851}
((segid "BrD" and resid 68 and name HN))
((segid "BrD" and resid 67 and name HB2))
  3.300  2.700  2.200 peak      4851 weight  0.11000E+01 volume  0.15213E+03 ppm1   8.626 ppm2  2.662
ASSI {4861}
((segid "BrD" and resid 69 and name HN))
((segid "BrD" and resid 68 and name HA))
  2.400  1.400  1.400 peak      4861 weight  0.11000E+01 volume  0.95815E+03 ppm1   8.305 ppm2  5.141
ASSI {4871}
((segid "BrD" and resid 69 and name HN))
((segid "BrD" and resid 68 and name HB1))
  4.500  4.$00  1.000 peak      4871 weight  0.11000E+01 volume  0.22391E+03 ppm1   8.306 ppm2  3.669
ASSI {4881}
((segid "BrD" and resid 69 and name HN))
((segid "BrD" and resid 68 and name HB2))
  3.300  2.700  2.200 peak      4881 weight  0.11000E+01 volume  0.15981E+03 ppm1   8.306 ppm2  3.514
ASSI {4891}
((segid "BrD" and resid 70 and name HN))
((segid "BrD" and resid 69 and name HA))
  3.000  2.200  2.200 peak      4891 weight  0.11000E+01 volume  0.24443E+03 ppm1   8.039 ppm2  4.690
ASSI {4901}
((segid "BrD" and resid 70 and name HN))
((segid "BrD" and resid 69 and name HB))
  3.400  2.900  2.100 peak      4901 weight  0.11000E+01 volume  0.12954E+03 ppm1   8.040 ppm2  2.928
ASSI {4911}
((segid "BrD" and resid 70 and name HN))
(segid "BrD" and resid 69 and name HG1 %)
  3.800  3.600  1.700 peak      4911 weight  0.11000E+01 volume  0.61869E+02 ppm1   8.041 ppm2  1.551
ASSI {4921}
((segid "BrD" and resid 70 and name HN))
(segid "BrD" and resid 69 and name HG2 %)
  2.700  1.800  1.800 peak      4921 weight  0.11000E+01 volume  0.48346E+03 ppm1   8.040 ppm2  1.430
ASSI {4931}
((segid "BrD" and resid 73 and name HN))
((segid "BrD" and resid 72 and name HA))
  2.900  2.100  2.100 peak      4931 weight  0.11000E+01 volume  0.30696E+03 ppm1   8.045 ppm2  4.654
ASSI {4941}
((segid "BrD" and resid 74 and name HN))
((segid "BrD" and resid 73 and name HA))
  3.500  3.100  2.000 peak      4941 weight  0.11000E+01 volume  0.10430E+03 ppm1   7.536 ppm2  4.812
ASSI {4951}
((segid "BrD" and resid 75 and name HN))
((segid "BrD" and resid 74 and name HA))
  3.500  3.100  2.000 peak      4951 weight  0.11000E+01 volume  0.10099E+03 ppm1   9.106 ppm2  4.361
ASSI {4961}
((segid "BrD" and resid 76 and name HN))
((segid "BrD" and resid 75 and name HA))
  3.400  2.900  2.100 peak      4961 weight  0.11000E+01 volume  0.11734E+03 ppm1   8.611 ppm2  4.525
ASSI {4971}
((segid "BrD" and resid 76 and name HN))
(segid "BrD" and resid 75 and name HG1))
  3.000  2.200  2.200 peak      4971 weight  0.11000E+01 volume  0.28328E+03 ppm1   8.611 ppm2  3.549
ASSI {4981}
((segid "BrD" and resid 76 and name HN))
((segid "BrD" and resid 75 and name HG2))
  3.200  2.600  2.300 peak      4981 weight  0.11000E+01 volume  0.18815E+03 ppm1   8.610 ppm2  3.218

TABLE 2-continued

| Unambiguous NOE-derived Inter-proton Distance Restraints |
|---|

ASSI {4991}
((segid "BrD" and resid 76 and name HN))
((segid "BrD" and resid 75 and name HB2))
  2.600  1.700  1.700 peak      4991 weight  0.11000E+01 volume  0.61964E+03 ppm1    8.611 ppm2  2.815
ASSI {5001}
((segid "BrD" and resid 76 and name HN))
((segid "BrD" and resid 75 and name HB1))
  2.600  1.700  1.700 peak      5001 weight  0.11000E+01 volume  0.59739E+03 ppm1    8.611 ppm2  2.925
ASSI {5011}
((segid "BrD" and resid 77 and name HN))
((segid "BrD" and resid 76 and name HA))
  3.000  2.200  2.200 peak      5011 weight  0.11000E+01 volume  0.25554E+03 ppm1    7.996 ppm2  4.695
ASSI {5021}
((segid "BrD" and resid 77 and name HN))
(segid "BrD" and resid 76 and name HB %)
  2.500  1.600  1.600 peak      5021 weight  0.11000E+01 volume  0.86259E+03 ppm1    7.996 ppm2  2.092
ASSI {5031}
((segid "BrD" and resid 79 and name HN))
((segid "BrD" and resid 78 and name HA))
  3.300  2.700  2.200 peak      5031 weight  0.11000E+01 volume  0.14659E+03 ppm1    8.681 ppm2  3.995
ASSI {5041}
((segid "BrD" and resid 78 and name HN))
((segid "BrD" and resid 79 and name HN))
  2.400  1.400  1.400 peak      5041 weight  0.11000E+01 volume  0.10403E+04 ppm1    7.996 ppm2  8.687
ASSI {5061}
((segid "BrD" and resid 80 and name HN))
((segid "BrD" and resid 80 and name HD1))
  5.300  5.300  0.200 peak      5061 weight  0.11000E+01 volume  0.85899E+01 ppm1    8.006 ppm2  3.997
ASSI {5071}
((segid "BrD" and resid 80 and name HN))
((segid "BrD" and resid 79 and name HA))
  3.300  2.700  2.200 peak      5071 weight  0.11000E+01 volume  0.15955E+03 ppm1    8.006 ppm2  4.404
ASSI {5091}
((segid "BrD" and resid 80 and name HN))
((segid "BrD" and resid 79 and name HB2))
  3.200  2.600  2.300 peak      5091 weight  0.11000E+01 volume  0.16421E+03 ppm1    8.006 ppm2  2.704
ASSI {5101}
((segid "BrD" and resid 81 and name HN))
((segid "BrD" and resid 80 and name HA))
  3.700  3.400  1.800 peak      5101 weight  0.11000E+01 volume  0.77456E+02 ppm1    7.639 ppm2  4.685
ASSI {5111}
((segid "BrD" and resid 82 and name HN))
((segid "BrD" and resid 81 and name HB))
  2.500  1.600  1.600 peak      5111 weight  0.11000E+01 volume  0.81882E+03 ppm1    6.981 ppm2  2.042
ASSI {5121}
((segid "BrD" and resid 82 and name HN))
(segid "BrD" and resid 81 and name HG1 %)
  3.200  2.600  2.300 peak      5121 weight  0.11000E+01 volume  0.17066E+03 ppm1    6.981 ppm2  1.086
ASSI {5131}
((segid "BrD" and resid 82 and name HN))
(segid "BrD" and resid 81 and name HG2 %)
  3.400  2.900  2.100 peak      5131 weight  0.11000E+01 volume  0.12101E+03 ppm1    6.981 ppm2  0.749
ASSI {5141}
((segid "BrD" and resid 83 and name HN))
((segid "BrD" and resid 82 and name HA))
  3.400  2.900  2.100 peak      5141 weight  0.11000E+01 volume  0.11364E+03 ppm1    9.658 ppm2  4.743
ASSI {5151}
((segid "BrD" and resid 83 and name HN))
((segid "BrD" and resid 82 and name HB1))
  3.500  3.100  2.000 peak      5151 weight  0.11000E+01 volume  0.10752E+03 ppm1    9.660 ppm2  3.697
ASSI {5161}
((segid "BrD" and resid 83 and name HN))
((segid "BrD" and resid 82 and name HB2))
  2.800  2.000  2.000 peak      5161 weight  0.11000E+01 volume  0.41394E+03 ppm1    9.658 ppm2  3.551
ASSI {5171}
((segid "BrD" and resid 84 and name HN))
((segid "BrD" and resid 83 and name HB))
  3.200  2.600  2.300 peak      5171 weight  0.11000E+01 volume  0.19086E+03 ppm1    9.466 ppm2  4.817
ASSI {5181}
((segid "BrD" and resid 84 and name HN))
((segid "BrD" and resid 83 and name HA))
  3.600  3.200  1.900 peak      5181 weight  0.11000E+01 volume  0.83498E+02 ppm1    9.463 ppm2  4.449
ASSI {5191}
((segid "BrD" and resid 84 and name HN))
(segid "BrD" and resid 83 and name HG2 %)
  3.500  3.100  2.000 peak      5191 weight  0.11000E+01 volume  0.11050E+03 ppm1    9.463 ppm2  1.903

TABLE 2-continued

Unambiguous NOE-derived Inter-proton Distance Restraints

ASSI {5201}
((segid "BrD" and resid 85 and name HN))
((segid "BrD" and resid 84 and name HA))
  3.700  3.400  1.800 peak      5201 weight  0.11000E+01 volume  0.79848E+02 ppm1    7.515 ppm2  4.921
ASSI {5211}
((segid "BrD" and resid 85 and name HN))
((segid "BrD" and resid 84 and name HB2))
  3.400  2.900  2.100 peak      5211 weight  0.11000E+01 volume  0.12439E+03 ppm1    7.516 ppm2  3.268
ASSI {5221}
((segid "BrD" and resid 86 and name HN))
((segid "BrD" and resid 85 and name HA))
  3.900  3.800  1.600 peak      5221 weight  0.11000E+01 volume  0.50221E+02 ppm1    8.423 ppm2  5.012
ASSI {5231}
((segid "BrD" and resid 86 and name HN))
((segid "BrD" and resid 85 and name HB2))
  3.300  2.700  2.200 peak      5231 weight  0.11000E+01 volume  0.14503E+03 ppm1    8.423 ppm2  3.639
ASSI {5241}
((segid "BrD" and resid 87 and name HN))
((segid "BrD" and resid 86 and name HA))
  3.600  3.200  1.900 peak      5241 weight  0.11000E+01 volume  0.84494E+02 ppm1    8.572 ppm2  4.815
ASSI {5251}
((segid "BrD" and resid 88 and name HN))
((segid "BrD" and resid 87 and name HA))
  3.600  3.200  1.900 peak      5251 weight  0.11000E+01 volume  0.87457E+02 ppm1    8.357 ppm2  4.857
ASSI {5261}
((segid "BrD" and resid 88 and name HN))
((segid "BrD" and resid 87 and name HB1))
  3.100  2.400  2.400 peak      5261 weight  0.11000E+01 volume  0.23454E+03 ppm1    8.354 ppm2  2.782
ASSI {5271}
((segid "BrD" and resid 88 and name HN))
((segid "BrD" and resid 87 and name HB2))
  3.200  2.600  2.300 peak      5271 weight  0.11000E+01 volume  0.19424E+03 ppm1    8.354 ppm2  2.614
ASSI {5281}
((segid "BrD" and resid 88 and name HN))
((segid "BrD" and resid 87 and name HN))
  2.400  1.700  1.700 peak      5281 weight  0.11000E+01 volume  0.67695E+03 ppm1    8.355 ppm2  8.552
ASSI {5301}
((segid "BrD" and resid 89 and name HN))
((segid "BrD" and resid 88 and name HA))
  3.400  2.900  2.100 peak      5301 weight  0.11000E+01 volume  0.12542E+03 ppm1    8.858 ppm2  4.976
ASSI {5311}
((segid "BrD" and resid 89 and name HD21))
((segid "BrD" and resid 89 and name HB2))
  3.900  3.800  1.600 peak      5311 weight  0.11000E+01 volume  0.54504E+02 ppm1    8.923 ppm2  3.516
ASSI {5321}
((segid "BrD" and resid 89 and name HD22))
((segid "BrD" and resid 89 and name HB2))
  3.300  2.700  2.200 peak      5321 weight  0.11000E+01 volume  0.13631E+03 ppm1    8.416 ppm2  3.514
ASSI {5331}
((segid "BrD" and resid 89 and name HD21))
((segid "BrD" and resid 89 and name HB1))
  5.100  5.100  0.400 peak      5331 weight  0.11000E+01 volume  0.10399E+02 ppm1    8.923 ppm2  3.679
ASSI {5341}
((segid "BrD" and resid 89 and name HD22))
((segid "BrD" and resid 89 and name HB1))
  3.900  3.800  1.600 peak      5341 weight  0.11000E+01 volume  0.50137E+02 ppm1    8.416 ppm2  3.676
ASSI {5351}
((segid "BrD" and resid 92 and name HN))
((segid "BrD" and resid 92 and name HG1))
  2.700  1.800  1.800 peak      5351 weight  0.11000E+01 volume  0.53011E+03 ppm1    8.876 ppm2  2.818
ASSI {5361}
((segid "BrD" and resid 92 and name HN))
((segid "BrD" and resid 92 and name HB1))
  3.600  3.200  1.900 peak      5361 weight  0.11000E+01 volume  0.93326E+02 ppm1    8.875 ppm2  2.697
ASSI {5371}
((segid "BrD" and resid 92 and name HN))
((segid "BrD" and resid 92 and name HB2))
  2.500  1.600  1.600 peak      5371 weight  0.11000E+01 volume  0.87608E+03 ppm1    8.875 ppm2  2.576
ASSI {5381}
((segid "BrD" and resid 93 and name HN))
((segid "BrD" and resid 92 and name HG1))
  3.500  3.100  2.000 peak      5381 weight  0.11000E+01 volume  0.10524E+03 ppm1    8.714 ppm2  2.807
ASSI {5391}
((segid "BrD" and resid 93 and name HN))
((segid "BrD" and resid 92 and name HB1))
  3.200  2.600  2.300 peak      5391 weight  0.11000E+01 volume  0.16925E+03 ppm1    8.714 ppm2  2.702

TABLE 2-continued

| Unambiguous NOE-derived Inter-proton Distance Restraints |
|---|

ASSI {5401}
((segid "BrD" and resid 93 and name HN))
((segid "BrD" and resid 92 and name HB2))
  3.300  2.700  2.200 peak      5401  weight  0.11000E+01 volume  0.13613E+03 ppm1      8.714  ppm2  2.580
ASSI {5411}
((segid "BrD" and resid 94 and name HN))
((segid "BrD" and resid 94 and name HB1))
  2.700  1.800  1.800 peak      5411  weight  0.11000E+01 volume  0.51785E+03 ppm1      9.677  ppm2  2.777
ASSI {5421}
((segid "BrD" and resid 94 and name HN))
((segid "BrD" and resid 94 and name HG1))
  3.600  3.200  1.900 peak      5421  weight  0.11000E+01 volume  0.85031E+02 ppm1      9.679  ppm2  3.144
ASSI {5431}
((segid "BrD" and resid 94 and name HN))
((segid "BrD" and resid 93 and name HA))
  3.300  2.700  2.200 peak      5431  weight  0.11000E+01 volume  0.15989E+03 ppm1      9.678  ppm2  5.042
ASSI {5441}
((segid "BrD" and resid 94 and name HN))
((segid "BrD" and resid 93 and name HB2))
  3.000  2.200  2.200 peak      5441  weight  0.11000E+01 volume  0.25357E+03 ppm1      9.680  ppm2  4.764
ASSI {5451}
((segid "BrD" and resid 95 and name HN))
((segid "BrD" and resid 94 and name HA))
  3.600  3.200  1.900 peak      5451  weight  0.11000E+01 volume  0.81131E+02 ppm1      8.669  ppm2  4.839
ASSI {5461}
((segid "BrD" and resid 95 and name HN))
((segid "BrD" and resid 94 and name HG1))
  3.400  2.900  2.100 peak      5461  weight  0.11000E+01 volume  0.12127E+03 ppm1      8.669  ppm2  3.135
ASSI {5471}
((segid "BrD" and resid 95 and name HN))
((segid "BrD" and resid 94 and name HB1))
  2.800  2.000  2.000 peak      5471  weight  0.11000E+01 volume  0.41579E+03 ppm1      8.670  ppm2  2.776
ASSI {5481}
((segid "BrD" and resid 96 and name HN))
((segid "BrD" and resid 95 and name HN))
  2.400  1.400  1.400 peak      5481  weight  0.11000E+01 volume  0.91814E+03 ppm1      7.979  ppm2  8.679
ASSI {5501}
((segid "BrD" and resid 97 and name HN))
((segid "BrD" and resid 96 and name HA))
  3.300  2.700  2.200 peak      5501  weight  0.11000E+01 volume  0.15786E+03 ppm1      8.677  ppm2  4.426
ASSI {5511}
((segid "BrD" and resid 97 and name HN))
((segid "BrD" and resid 96 and name HB1))
  3.200  2.600  2.300 peak      5511  weight  0.11000E+01 volume  0.17339E+03 ppm1      8.674  ppm2  3.997
ASSI {5521}
((segid "BrD" and resid 97 and name HN))
((segid "BrD" and resid 96 and name HB2))
  3.000  2.200  2.200 peak      5521  weight  0.11000E+01 volume  0.24048E+03 ppm1      8.674  ppm2  3.107
ASSI {5531}
((segid "BrD" and resid 99 and name HN))
((segid "BrD" and resid 98 and name HA))
  3.200  2.600  2.300 peak      5531  weight  0.11000E+01 volume  0.16985E+03 ppm1      8.936  ppm2  4.813
ASSI {5541}
((segid "BrD" and resid 99 and name HN))
((segid "BrD" and resid 98 and name HB1))
  3.200  2.600  2.300 peak      5541  weight  0.11000E+01 volume  0.16699E+03 ppm1      8.936  ppm2  4.003
ASSI {5551}
((segid "BrD" and resid 99 and name HN))
((segid "BrD" and resid 98 and name HB2))
  2.900  2.100  2.100 peak      5551  weight  0.11000E+01 volume  0.29941E+03 ppm1      8.936  ppm2  3.663
ASSI {5561}
((segid "BrD" and resid 100 and name HN))
((segid "BrD" and resid 99 and name HA))
  3.300  2.700  2.200 peak      5561  weight  0.11000E+01 volume  0.14856E+03 ppm1      8.669  ppm2  4.438
ASSI {5571}
((segid "BrD" and resid 100 and name HN))
(segid "BrD" and resid 99 and name HB %)
  2.600  1.700  1.700 peak      5571  weight  0.11000E+01 volume  0.56660E+03 ppm1      8.669  ppm2  2.204
ASSI {5581}
((segid "BrD" and resid 101 and name HN))
((segid "BrD" and resid 100 and name HA))
  3.500  3.100  2.000 peak      5581  weight  0.11000E+01 volume  0.99135E+02 ppm1      8.513  ppm2  4.940
ASSI {5591}
((segid "BrD" and resid 101 and name HN))
((segid "BrD" and resid 100 and name HB1))
  3.200  2.600  2.300 peak      5591  weight  0.11000E+01 volume  0.18321E+03 ppm1      8.513  ppm2  3.484

TABLE 2-continued

Unambiguous NOE-derived Inter-proton Distance Restraints

ASSI {5601}
((segid "BrD" and resid 102 and name HN))
((segid "BrD" and resid 101 and name HA))
  3.500  3.100  2.000 peak     5601  weight  0.11000E+01 volume  0.10380E+03 ppm1    9.156  ppm2  4.256
ASSI {5611}
((segid "BrD" and resid 103 and name HN))
((segid "BrD" and resid 102 and name HA))
  3.500  3.100  2.000 peak     5611  weight  0.11000E+01 volume  0.10037E+03 ppm1    8.696  ppm2  4.277
ASSI {5621}
((segid "BrD" and resid 104 and name HN))
((segid "BrD" and resid 103 and name HA))
  3.200  2.600  2.300 peak     5621  weight  0.11000E+01 volume  0.16539E+03 ppm1    7.763  ppm2  3.792
ASSI {5631}
((segid "BrD" and resid 104 and name HN))
((segid "BrD" and resid 103 and name HB1))
  2.800  2.000  2.000 peak     5631  weight  0.11000E+01 volume  0.39404E+03 ppm1    7.762  ppm2  2.327
ASSI {5641}
((segid "BrD" and resid 104 and name HN))
((segid "BrD" and resid 103 and name HB2))
  3.200  2.600  2.300 peak     5641  weight  0.11000E+01 volume  0.16250E+03 ppm1    7.763  ppm2  1.917
ASSI {5651}
((segid "BrD" and resid 105 and name HN))
((segid "BrD" and resid 104 and name HA))
  3.200  2.600  2.300 peak     5651  weight  0.11000E+01 volume  0.16160E+03 ppm1    8.488  ppm2  4.688
ASSI {5661}
((segid "BrD" and resid 106 and name HN))
((segid "BrD" and resid 105 and name HA))
  3.600  3.200  1.900 peak     5661  weight  0.11000E+01 volume  0.94653E+02 ppm1    9.740  ppm2  4.934
ASSI {5671}
((segid "BrD" and resid 107 and name HN))
((segid "BrD" and resid 106 and name HA))
  3.500  3.100  2.000 peak     5671  weight  0.11000E+01 volume  0.10620E+03 ppm1    8.981  ppm2  4.568
ASSI {5681}
((segid "BrD" and resid 107 and name HN))
((segid "BrD" and resid 106 and name HB1))
  3.000  2.200  2.200 peak     5681  weight  0.11000E+01 volume  0.25814E+03 ppm1    8.980  ppm2  3.896
ASSI {5691}
((segid "BrD" and resid 108 and name HN))
((segid "BrD" and resid 107 and name HA))
  3.200  2.600  2.300 peak     5691  weight  0.11000E+01 volume  0.17635E+03 ppm1    8.526  ppm2  4.447
ASSI {5701}
((segid "BrD" and resid 108 and name HN))
((segid "BrD" and resid 107 and name HB1))
  2.600  1.700  1.700 peak     5701  weight  0.11000E+01 volume  0.68256E+03 ppm1    8.526  ppm2  3.671
ASSI {5711}
((segid "BrD" and resid 109 and name HN))
((segid "BrD" and resid 108 and name HA))
  3.700  3.400  1.800 peak     5711  weight  0.11000E+01 volume  0.77637E+02 ppm1    8.574  ppm2  4.818
ASSI {5721}
((segid "BrD" and resid 110 and name HN))
((segid "BrD" and resid 109 and name HA))
  3.700  3.400  1.800 peak     5721  weight  0.11000E+01 volume  0.78233E+02 ppm1    8.714  ppm2  4.615
ASSI {5731}
((segid "BrD" and resid 111 and name HN))
((segid "BrD" and resid 110 and name HA))
  3.000  2.200  2.200 peak     5731  weight  0.11000E+01 volume  0.28368E+03 ppm1    8.168  ppm2  4.428
ASSI {5741}
((segid "BrD" and resid 111 and name HN))
((segid "BrD" and resid 110 and name HB))
  2.300  1.300  1.300 peak     5741  weight  0.11000E+01 volume  0.13983E+04 ppm1    8.170  ppm2  2.353
ASSI {5751}
((segid "BrD" and resid 111 and name HN))
((segid "BrD" and resid 112 and name HN))
  2.800  2.000  2.000 peak     5751  weight  0.11000E+01 volume  0.38572E+03 ppm1    8.168  ppm2  8.665
ASSI {5761}
((segid "BrD" and resid 113 and name HN))
((segid "BrD" and resid 112 and name HA))
  2.700  1.800  1.800 peak     5761  weight  0.11000E+01 volume  0.46496E+03 ppm1    8.217  ppm2  4.602
ASSI {5771}
((segid "BrD" and resid 113 and name HN))
((segid "BrD" and resid 112 and name HG1))
  3.800  3.600  1.700 peak     5771  weight  0.11000E+01 volume  0.63604E+02 ppm1    8.216  ppm2  2.949
ASSI {5781}
((segid "BrD" and resid 113 and name HN))
((segid "BrD" and resid 112 and name HG2))
  4.100  4.100  1.400 peak     5781  weight  0.11000E+01 volume  0.37977E+02 ppm1    8.217  ppm2  2.812

TABLE 2-continued

Unambiguous NOE-derived Inter-proton Distance Restraints

ASSI {5791}
((segid "BrD" and resid 113 and name HN))
((segid "BrD" and resid 112 and name HB1))
  2.500  1.600  1.600 peak      5791 weight  0.11000E+01 volume  0.72974E+03 ppm1   8.217 ppm2  2.665
ASSI {5801}
((segid "BrD" and resid 112 and name HN))
((segid "BrD" and resid 113 and name HN))
  2.500  1.600  1.600 peak      5801 weight  0.11000E+01 volume  0.81801E+03 ppm1   8.668 ppm2  8.185
ASSI {5811}
((segid "BrD" and resid 114 and name HN))
((segid "BrD" and resid 113 and name HA))
  3.400  2.900  2.100 peak      5811 weight  0.11000E+01 volume  0.12247E+03 ppm1   8.376 ppm2  4.898
ASSI {5821}
((segid "BrD" and resid 114 and name HN))
(segid "BrD" and resid 113 and name HB %)
  3.000  2.200  2.200 peak      5821 weight  0.11000E+01 volume  0.28680E+03 ppm1   8.377 ppm2  1.965
ASSI {5831}
((segid "BrD" and resid 115 and name HN))
((segid "BrD" and resid 114 and name HA1))
  3.500  3.100  2.000 peak      5831 weight  0.11000E+01 volume  0.95188E+02 ppm1   8.355 ppm2  4.626
ASSI {5851}
((segid "BrD" and resid 115 and name HN))
((segid "BrD" and resid 116 and name HN))
  3.700  3.400  1.800 peak      5851 weight  0.11000E+01 volume  0.76519E+02 ppm1   8.355 ppm2  8.065
ASSI {5861}
((segid "BrD" and resid 117 and name HN))
((segid "BrD" and resid 116 and name HA))
  2.600  1.700  1.700 peak      5861 weight  0.11000E+01 volume  0.60302E+03 ppm1   8.884 ppm2  4.839
ASSI {5871}
((segid "BrD" and resid 117 and name HN))
((segid "BrD" and resid 116 and name HB))
  3.100  2.400  2.400 peak      5871 weight  0.11000E+01 volume  0.21223E+03 ppm1   8.876 ppm2  2.417
ASSI {5881}
((segid "BrD" and resid 118 and name HN))
((segid "BrD" and resid 117 and name HA))
  2.500  1.600  1.600 peak      5881 weight  0.11000E+01 volume  0.81728E+03 ppm1   8.381 ppm2  5.178
ASSI {5891}
((segid "BrD" and resid 79 and name HE21))
((segid "BrD" and resid 79 and name HG1))
  3.900  3.800  1.600 peak      5891 weight  0.11000E+01 volume  0.58235E+02 ppm1   7.926 ppm2  3.067
ASSI {5901}
((segid "BrD" and resid 79 and name HE22))
((segid "BrD" and resid 79 and name HG1))
  3.500  3.100  2.000 peak      5901 weight  0.11000E+01 volume  0.10842E+03 ppm1   7.829 ppm2  3.067
ASSI {5911}
((segid "BrD" and resid 29 and name HE21))
((segid "BrD" and resid 29 and name HG1))
  4.200  4.200  1.300 peak      5911 weight  0.11000E+01 volume  0.35552E+02 ppm1   8.188 ppm2  3.028
ASSI {5921}
((segid "BrD" and resid 29 and name HE22))
((segid "BrD" and resid 29 and name HG1))
  3.800  3.600  1.700 peak      5921 weight  0.11000E+01 volume  0.59289E+02 ppm1   7.477 ppm2  3.028
ASSI {5931}
((segid "BrD" and resid 70 and name HN))
((segid "BrD" and resid 70 and name HB1))
  3.300  2.700  2.200 peak      5931 weight  0.11000E+01 volume  0.15569E+03 ppm1   8.039 ppm2  4.807
ASSI {5941}
((segid "BrD" and resid 18 and name HN))
((segid "BrD" and resid 18 and name HB1))
  2.700  1.800  1.800 peak      5941 weight  0.11000E+01 volume  0.45519E+03 ppm1   9.072 ppm2  2.113
ASSI {5951}
((segid "BrD" and resid 18 and name HN))
((segid "BrD" and resid 18 and name HG))
  2.600  1.700  1.700 peak      5951 weight  0.11000E+01 volume  0.60681E+03 ppm1   9.072 ppm2  2.279
ASSI {5961}
((segid "BrD" and resid 18 and name HN))
(segid "BrD" and resid 18 and name HD2 %)
  3.000  2.200  2.200 peak      5961 weight  0.11000E+01 volume  0.24628E+03 ppm1   9.076 ppm2  0.416
ASSI {5971}
((segid "BrD" and resid 78 and name HN))
((segid "BrD" and resid 78 and name HB1))
  3.000  2.200  2.200 peak      5971 weight  0.11000E+01 volume  0.24153E+03 ppm1   7.996 ppm2  1.360
ASSI {5981}
((segid "BrD" and resid 78 and name HN))
((segid "BrD" and resid 78 and name HB2))
  2.600  1.700  1.700 peak      5981 weight  0.11000E+01 volume  0.64225E+03 ppm1   7.996 ppm2  1.048

TABLE 2-continued

Unambiguous NOE-derived Inter-proton Distance Restraints

ASSI {5991}
((segid "BrD" and resid 78 and name HN))
((segid "BrD" and resid 78 and name HD2 %)
  3.500  3.100  2.000 peak     5991  weight  0.11000E+01  volume  0.10124E+03  ppm1    7.994  ppm2  0.667
ASSI {6001}
((segid "BrD" and resid 78 and name HN))
((segid "BrD" and resid 78 and name HG))
  3.000  2.200  2.200 peak     6001  weight  0.11000E+01  volume  0.26923E+03  ppm1    7.996  ppm2  1.293
ASSI {6011}
((segid "BrD" and resid 78 and name HN))
(segid "BrD" and resid 78 and name HD1 %)
  3.500  3.100  2.000 peak     6011  weight  0.11000E+01  volume  0.10789E+03  ppm1    7.996  ppm2  0.790
ASSI {6021}
((segid "BrD" and resid 115 and name HN))
((segid "BrD" and resid 115 and name HB1))
  3.200  2.600  2.300 peak     6021  weight  0.11000E+01  volume  0.18336E+03  ppm1    8.355  ppm2  2.167
ASSI {6031}
((segid "BrD" and resid 115 and name HN))
(segid "BrD" and resid 115 and name HD1 %)
  2.800  2.000  2.200 peak     6031  weight  0.11000E+01  volume  0.43402E+03  ppm1    4.354  ppm2  1.318
ASSI {6041}
((segid "BrD" and resid 116 and name HN))
((segid "BrD" and resid 116 and name HG11))
  2.900  2.100  2.100 peak     6041  weight  0.11000E+01  volume  0.29943E+03  ppm1    8.086  ppm2  1.921
ASSI {6051}
((segid "BrD" and resid 116 and name HN))
((segid "BrD" and resid 116 and name HG12))
  3.000  2.200  2.200 peak     6051  weight  0.11000E+01  volume  0.27021E+03  ppm1    8.083  ppm2  1.525
ASSI {6061}
((segid "BrD" and resid 116 and name HN))
(segid "BrD" and resid 116 and name HG2 %)
  2.500  1.600  1.600 peak     6061  weight  0.11000E+01  volume  0.86711E+03  ppm1    8.084  ppm2  1.420
ASSI {6071}
((segid "BrD" and resid 110 and name HN))
((segid "BrD" and resid 110 and name HG12))
  3.000  2.200  2.200 peak     6071  weight  0.11000E+01  volume  0.25527E+03  ppm1    8.714  ppm2  1.679
ASSI {6081}
((segid "BrD" and resid 110 and name HN))
(segid "BrD" and resid 110 and name HG2 %)
  2.800  2.000  2.000 peak     6081  weight  0.11000E+01  volume  0.43268E+03  ppm1    8.714  ppm2  1.261
ASSI {6091}
((segid "BrD" and resid 110 and name HN))
(segid "BrD" and resid 110 and name HD1 %))
  3.400  2.900  2.100 peak     6091  weight  0.11000E+01  volume  0.13013E+03  ppm1    8.714  ppm2  1.116
ASSI {6101}
((segid "BrD" and resid 50 and name HN))
((segid "BrD" and resid 50 and name HB))
  2.400  1.400  1.400 peak     6101  weight  0.11000E+01  volume  0.10564E+04  ppm1    8.564  ppm2  1.812
ASSI {6111}
((segid "BrD" and resid 50 and name HN))
(segid "BrD" and resid 50 and name HD1 %)
  3.200  2.600  2.300 peak     6111  weight  0.11000E+01  volume  0.17790E+03  ppm1    8.564  ppm2  1.144
ASSI {6121}
((segid "BrD" and resid 50 and name HN))
((segid "BrD" and resid 50 and name HG12))
  3.300  2.700  2.200 peak     6121  weight  0.11000E+01  volume  0.13759E+03  ppm1    8.564  ppm2  0.823
ASSI {6131}
((segid "BrD" and resid 50 and name HN))
(segid "BrD" and resid 50 and name HG2 %)
  3.000  2.200  2.200 peak     6131  weight  0.11000E+01  volume  0.27674E+03  ppm1    8.564  ppm2  0.991
ASSI {6141}
((segid "BrD" and resid 50 and name HN))
((segid "BrD" and resid 50 and name HG11))
  4.100  4.100  1.400 peak     6141  weight  0.11000E+01  volume  0.38065E+02  ppm1    8.564  ppm2  1.405
ASSI {6151}
((segid "BrD" and resid 21 and name HN))
((segid "BrD" and resid 20 and name HB1))
  2.600  1.700  1.700 peak     6151  weight  0.11000E+01  volume  0.62145E+03  ppm1    8.544  ppm2  4.667
ASSI {6161}
((segid "BrD" and resid 20 and name HN))
((segid "BrD" and resid 21 and name HN))
  2.800  2.000  2.000 peak     6161  weight  0.11000E+01  volume  0.39694E+03  ppm1    8.146  ppm2  8.547
ASSI {6191}
((segid "BrD" and resid 22 and name HN))
((segid "BrD" and resid 21 and name HN))
  2.800  2.000  2.000 peak     6191  weight  0.11000E+01  volume  0.40962E+03  ppm1    9.455  ppm2  8.532

TABLE 2-continued

Unambiguous NOE-derived Inter-proton Distance Restraints

```
ASSI {6201}
((segid "BrD" and resid 101 and name HN))
((segid "BrD" and resid 101 and name HG11))
  2.400  1.400  1.400 peak      6201 weight  0.11000E+01 volume  0.10700E+04 ppm1   8.514 ppm2  2.489
ASSI {6211}
((segid "BrD" and resid 101 and name HN))
((segid "BrD" and resid 101 and name HG12))
  2.800  2.000  2.000 peak      6211 weight  0.11000E+01 volume  0.39771E+03 ppm1   8.513 ppm2  1.808
ASSI {6221}
((segid "BrD" and resid 101 and name HN))
(segid "BrD" and resid 101 and name HG2 %))
  2.700  1.800  1.800 peak      6221 weight  0.11000E+01 volume  0.49123E+03 ppm1   8.513 ppm2  1.596
ASSI {6231}
((segid "BrD" and resid 21 and name HN))
((segid "BrD" and resid 21 and name HB))
  2.600  1.700  1.700 peak      6231 weight  0.11000E+01 volume  0.63964E+03 ppm1   8.545 ppm2  2.495
ASSI {6241}
((segid "BrD" and resid 21 and name HN))
((segid "BrD" and resid 21 and name HG11))
  2.300  1.300  1.300 peak      6241 weight  0.11000E+01 volume  0.13646E+04 ppm1   8.545 ppm2  2.355
ASSI {6251}
((segid "BrD" and resid 21 and name HN))
(segid "BrD" and resid 21 and name HG12))
  3.100  2.400  2.400 peak      6251 weight  0.11000E+01 volume  0.22794E+03 ppm1   8.556 ppm2  1.659
ASSI {6261}
((segid "BrD" and resid 21 and name HN))
(segid "BrD" and resid 21 and name HG2 %))
  2.600  1.700  1.700 peak      6261 weight  0.11000E+01 volume  0.60538E+03 ppm1   8.556 ppm2  1.605
ASSI {6271}
((segid "BrD" and resid 21 and name HN))
(segid "BrD" and resid 21 and name HD1 %)
  2.800  2.100  2.100 peak      6271 weight  0.11000E+01 volume  0.30098E+03 ppm1   8.545 ppm2  1.226
ASSI {6281}
((segid "BrD" and resid 87 and name HN))
((segid "BrD" and resid 87 and name HB1))
  2.800  2.000  2.000 peak      6281 weight  0.11000E+01 volume  0.39163E+03 ppm1   8.570 ppm2  2.771
ASSI {6291}
((segid "BrD" and resid 79 and name HN))
((segid "BrD" and resid 79 and name HB1))
  2.500  1.600  1.600 peak      6291 weight  0.11000E+01 volume  0.73947E+03 ppm1   8.681 ppm2  2.771
ASSI {6301}
((segid "BrD" and resid 80 and name HN))
((segid "BrD" and resid 79 and name HB1))
  3.500  3.100  2.000 peak      6301 weight  0.11000E+01 volume  0.10437E+03 ppm1   8.006 ppm2  2.764
ASSI {6311}
((segid "BrD" and resid 23 and name HN))
((segid "BrD" and resid 23 and name HG2))
  3.200  2.600  2.300 peak      6311 weight  0.11000E+01 volume  0.19029E+03 ppm1   9.120 ppm2  3.068
ASSI {6321}
((segid "BrD" and resid 80 and name HN))
((segid "BrD" and resid 80 and name HG1))
  3.400  2.900  2.100 peak      6321 weight  0.11000E+01 volume  0.12866E+03 ppm1   8.006 ppm2  2.336
ASSI {6331}
((segid "BrD" and resid 80 and name HN))
((segid "BrD" and resid 80 and name HB1))
  2.800  2.000  2.000 peak      6331 weight  0.11000E+01 volume  0.38416E+03 ppm1   8.006 ppm2  2.579
ASSI {6341}
((segid "BrD" and resid 80 and name HN))
((segid "BrD" and resid 80 and name HB2))
  2.600  1.700  1.700 peak      6341 weight  0.11000E+01 volume  0.55298E+03 ppm1   8.006 ppm2  2.497
ASSI {6351}
((segid "BrD" and resid 66 and name HN))
((segid "BrD" and resid 66 and name HB2))
  3.400  2.900  2.100 peak      6351 weight  0.11000E+01 volume  0.12971E+03 ppm1   8.763 ppm2  2.629
ASSI {6361}
((segid "BrD" and resid 66 and name HN))
((segid "BrD" and resid 66 and name HG1))
  2.700  1.800  1.800 peak      6361 weight  0.11000E+01 volume  0.45372E+03 ppm1   8.764 ppm2  2.155
ASSI {6371}
((segid "BrD" and resid 9 and name HN))
((segid "BrD" and resid 9 and name HG1))
  3.600  3.200  1.900 peak      6371 weight  0.11000E+01 volume  0.84495E+02 ppm1   9.053 ppm2  2.254
ASSI {6381}
((segid "BrD" and resid 9 and name HN))
((segid "BrD" and resid 9 and name HB2))
  3.400  2.900  2.100 peak      6381 weight  0.11000E+01 volume  0.12497E+03 ppm1   9.055 ppm2  2.369
```

TABLE 2-continued

Unambiguous NOE-derived Inter-proton Distance Restraints

ASSI {6391}
((segid "BrD" and resid 102 and name HN))
(segid "BrD" and resid 102 and name HD1 %)
  3.100  2.400  2.400  peak      6391  weight  0.11000E+01  volume  0.19704E+03  ppm1      9.156  ppm2   1.310
ASSI {6401}
((segid "BrD" and resid 102 and name HN))
((segid "BrD" and resid 102 and name HB2))
  2.400  1.400  1.400  peak      6401  weight  0.11000E+01  volume  0.88089E+03  ppm1      9.155  ppm2   1.808
ASSI {6411}
((segid "BrD" and resid 102 and name HN))
((segid "BrD" and resid 102 and name HB1))
  2.700  1.800  1.800  peak      6411  weight  0.11000E+01  volume  0.47200E+03  ppm1      9.155  ppm2   2.002
ASSI {6421}
((segid "BrD" and resid 102 and name HN))
((segid "BrD" and resid 102 and name HG))
  3.200  2.600  2.300  peak      6421  weight  0.11000E+01  volume  0.16630E+03  ppm1      9.157  ppm2   2.152
ASSI {6431}
((segid "BrD" and resid 73 and name HN))
((segid "BrD" and resid 73 and name HB2))
  2.800  2.000  2.000  peak      6431  weight  0.11000E+01  volume  0.37491E+03  ppm1      8.045  ppm2   2.495
ASSI {6441}
((segid "BrD" and resid 73 and name HN))
((segid "BrD" and resid 73 and name HG))
  3.400  2.900  2.100  peak      6441  weight  0.11000E+01  volume  0.13407E+03  ppm1      8.045  ppm2   2.376
ASSI {6451}
((segid "BrD" and resid 73 and name HN))
(segid "BrD" and resid 73 and name HD2 %)
  3.600  3.200  1.900  peak      6451  weight  0.11000E+01  volume  0.91167E+02  ppm1      8.049  ppm2   1.491
ASSI {6461}
((segid "BrD" and resid 56 and name HN))
(segid "BrD" and resid 56 and name HD1 %)
  3.200  2.600  2.300  peak      6461  weight  0.11000E+01  volume  0.17282E+03  ppm1      9.679  ppm2   1.521
ASSI {6471}
((segid "BrD" and resid 56 and name HN))
((segid "BrD" and resid 56 and name HG))
  2.500  1.600  1.600  peak      6471  weight  0.11000E+01  volume  0.74688E+03  ppm1      9.680  ppm2   2.320
ASSI {6481}
((segid "BrD" and resid 56 and name HN))
((segid "BrD" and resid 56 and name HB2))
  3.100  2.400  2.400  peak      6481  weight  0.11000E+01  volume  0.21719E+03  ppm1      9.680  ppm2   2.002
ASSI {6491}
((segid "BrD" and resid 22 and name HN))
(segid "BrD" and resid 22 and name HD1 %)
  3.200  2.600  2.300  peak      6491  weight  0.11000E+01  volume  0.16857E+03  ppm1      9.456  ppm2   1.668
ASSI {6501}
((segid "BrD" and resid 22 and name HN))
((segid "BrD" and resid 22 and name HB2))
  2.400  1.400  1.400  peak      6501  weight  0.11000E+01  volume  0.10653E+04  ppm1      9.455  ppm2   2.292
ASSI {6511}
((segid "BrD" and resid 22 and name HN))
((segid "BrD" and resid 22 and name HB1))
  2.700  1.800  1.800  peak      6511  weight  0.11000E+01  volume  0.47530E+03  ppm1      9.455  ppm2   2.693
ASSI {6521}
((segid "BrD" and resid 22 and name HN))
((segid "BrD" and resid 22 and name HG))
  3.700  3.400  1.800  peak      6521  weight  0.11000E+01  volume  0.69056E+02  ppm1      9.455  ppm2   2.366
ASSI {6531}
((segid "BrD" and resid 63 and name HN))
(segid "BrD" and resid 63 and name HG2 %)
  3.200  2.600  2.300  peak      6531  weight  0.11000E+01  volume  0.19269E+03  ppm1      9.473  ppm2   1.478
ASSI {6541}
((segid "BrD" and resid 63 and name HN))
(segid "BrD" and resid 63 and name HD1 %)
  3.100  2.400  2.400  peak      6541  weight  0.11000E+01  volume  0.21627E+03  ppm1      9.472  ppm2   1.674
ASSI {6561}
((segid "BrD" and resid 63 and name HN))
((segid "BrD" and resid 63 and name HB2))
  2.500  1.600  1.600  peak      6561  weight  0.11000E+01  volume  0.86099E+03  ppm1      9.473  ppm2   2.532
ASSI {6571}
((segid "BrD" and resid 63 and name HN))
((segid "BrD" and resid 63 and name HG))
  3.000  2.200  2.200  peak      6571  weight  0.11000E+01  volume  0.26899E+03  ppm1      9.472  ppm2   2.439
ASSI {6581}
((segid "BrD" and resid 14 and name HN))
((segid "BrD" and resid 14 and name HB1))
  2.500  1.600  1.600  peak      6581  weight  0.11000E+01  volume  0.80229E+03  ppm1      8.809  ppm2   2.453

TABLE 2-continued

| Unambiguous NOE-derived Inter-proton Distance Restraints |
|---|

ASSI {6591}
((segid "BrD" and resid 14 and name HN))
((segid "BrD" and resid 14 and name HG))
 3.000  2.200  2.200 peak       6591  weight  0.11000E+01 volume  0.24747E+03 ppm1    8.809  ppm2  2.064
ASSI {6601}
((segid "BrD" and resid 14 and name HN))
((segid "BrD" and resid 14 and name HB2))
 2.500  1.600  1.600 peak       6601  weight  0.11000E+01 volume  0.85081E+03 ppm1    8.809  ppm2  2.164
ASSI {6611}
((segid "BrD" and resid 14 and name HN))
(segid "BrD" and resid 14 and name HD1 %)
 3.200  2.600  2.300 peak       6611  weight  0.11000E+01 volume  0.18673E+03 ppm1    8.809  ppm2  1.401
ASSI {6621}
((segid "BrD" and resid 24 and name HN))
((segid "BrD" and resid 24 and name HG2))
 2.300  1.300  1.300 peak       6621  weight  0.11000E+01 volume  0.12087E+04 ppm1    8.654  ppm2  3.032
ASSI {6631}
((segid "BrD" and resid 49 and name HN))
(segid "BrD" and resid 49 and name HG1 %)
 3.100  2.400  2.400 peak       6631  weight  0.11000E+01 volume  0.20533E+03 ppm1    7.762  ppm2  1.652
ASSI {6641}
((segid "BrD" and resid 50 and name HN))
(segid "BrD" and resid 49 and name HG1 %)
 3.400  2.900  2.100 peak       6641  weight  0.11000E+01 volume  0.12406E+03 ppm1    8.564  ppm2  1.652
ASSI {6651}
((segid "BrD" and resid 64 and name HN))
((segid "BrD" and resid 64 and name HB1))
 2.400  1.400  1.400 peak       6651  weight  0.11000E+01 volume  0.10941E+04 ppm1    8.584  ppm2  2.661
ASSI {6661}
((segid "BrD" and resid 64 and name HN))
((segid "BrD" and resid 64 and name HG1))
 2.700  1.800  1.800 peak       6661  weight  0.11000E+01 volume  0.45034E+03 ppm1    8.584  ppm2  2.210
ASSI {6671}
((segid "BrD" and resid 64 and name HN))
((segid "BrD" and resid 64 and name HD1))
 3.600  3.200  1.900 peak       6671  weight  0.11000E+01 volume  0.82950E+02 ppm1    8.584  ppm2  2.411
ASSI {6681}
((segid "BrD" and resid 104 and name HN))
((segid "BrD" and resid 104 and name HB1))
 2.600  1.700  1.700 peak       6681  weight  0.11000E+01 volume  0.59758E+03 ppm1    7.763  ppm2  2.537
ASSI {6691}
((segid "BrD" and resid 104 and name HN))
((segid "BrD" and resid 104 and name HG1))
 3.000  2.200  2.200 peak       6691  weight  0.11000E+01 volume  0.24911E+03 ppm1    7.763  ppm2  2.099
ASSI {6701}
((segid "BrD" and resid 104 and name HN))
((segid "BrD" and resid 104 and name HD1))
 2.900  2.100  2.100 peak       6701  weight  0.11000E+01 volume  0.30408E+03 ppm1    7.763  ppm2  2.288
ASSI {6711}
((segid "BrD" and resid 111 and name HN))
((segid "BrD" and resid 111 and name HB1))
 2.600  1.700  1.700 peak       6711  weight  0.11000E+01 volume  0.66813E+03 ppm1    8.168  ppm2  2.482
ASSI {6721}
((segid "BrD" and resid 111 and name HN))
((segid "BrD" and resid 111 and name HB2))
 2.400  1.400  1.400 peak       6721  weight  0.11000E+01 volume  0.98067E+03 ppm1    8.170  ppm2  2.376
ASSI {6731}
((segid "BrD" and resid 111 and name HN))
((segid "BrD" and resid 111 and name HG2))
 3.600  3.200  1.900 peak       6731  weight  0.11000E+01 volume  0.88731E+02 ppm1    8.168  ppm2  1.922
ASSI {6741}
((segid "BrD" and resid 111 and name HN))
((segid "BrD" and resid 111 and name HG1))
 3.200  2.600  2.300 peak       6741  weight  0.11000E+01 volume  0.16392E+03 ppm1    8.168  ppm2  2.002
ASSI {6761}
((segid "BrD" and resid 19 and name HN))
((segid "BrD" and resid 19 and name HB1))
 2.700  1.800  1.800 peak       6761  weight  0.11000E+01 volume  0.53478E+03 ppm1    9.187  ppm2  2.325
ASSI {6771}
((segid "BrD" and resid 19 and name HN))
((segid "BrD" and resid 19 and name HG1))
 4.000  4.000  1.500 peak       6771  weight  0.11000E+01 volume  0.45358E+02 ppm1    9.188  ppm2  1.879
ASSI {6781}
((segid "BrD" and resid 19 and name HN))
((segid "BrD" and resid 18 and name HG))
 2.800  2.000  2.000 peak       6781  weight  0.11000E+01 volume  0.38484E+03 ppm1    9.187  ppm2  2.271

TABLE 2-continued

| Unambiguous NOE-derived Inter-proton Distance Restraints |
|---|

ASSI {6791}
((segid "BrD" and resid 12 and name HN))
((segid "BrD" and resid 11 and name HA))
  3.000  2.200  2.200 peak      6791 weight  0.11000E+01 volume  0.26617E+03 ppm1      9.021  ppm2  4.940
ASSI {6801}
((segid "BrD" and resid 97 and name HN))
((segid "BrD" and resid 97 and name HB1))
  2.300  1.300  1.300 peak      6801 weight  0.11000E+01 volume  0.12859E+04 ppm1      8.674  ppm2  2.708
ASSI {6811}
((segid "BrD" and resid 97 and name HN))
((segid "BrD" and resid 97 and name HG2))
  2.900  2.100  2.100 peak      6811 weight  0.11000E+01 volume  0.32919E+03 ppm1      8.674  ppm2  2.193
ASSI {6821}
((segid "BrD" and resid 109 and name HN))
((segid "BrD" and resid 109 and name HB1))
  2.300  1.300  1.300 peak      6821 weight  0.11000E+01 volume  0.11797E+04 ppm1      8.573  ppm2  2.336
ASSI {6831}
((segid "BrD" and resid 109 and name HN))
((segid "BrD" and resid 109 and name HB2))
  3.200  2.600  2.300 peak      6831 weight  0.11000E+01 volume  0.19151E+03 ppm1      8.573  ppm2  2.173
ASSI {6841}
((segid "BrD" and resid 109 and name HN))
((segid "BrD" and resid 109 and name HG1))
  3.700  3.400  1.800 peak      6841 weight  0.11000E+01 volume  0.70793E+02 ppm1      8.574  ppm2  1.439
ASSI {6881}
((segid "BrD" and resid 86 and name HN))
((segid "BrD" and resid 86 and name HB1))
  2.700  1.800  1.800 peak      6881 weight  0.11000E+01 volume  0.51142E+03 ppm1      8.422  ppm2  2.359
ASSI {6891}
((segid "BrD" and resid 86 and name HN))
((segid "BrD" and resid 86 and name HG2))
  3.400  2.900  2.100 peak      6891 weight  0.11000E+01 volume  0.13112E+03 ppm1      8.423  ppm2  0.745
ASSI {6901}
((segid "BrD" and resid 86 and name HN))
((segid "BrD" and resid 86 and name HD1))
  3.800  3.600  1.700 peak      6901 weight  0.11000E+01 volume  0.59192E+02 ppm1      8.423  ppm2  1.862
ASSI {6921}
((segid "BrD" and resid 103 and name HN))
((segid "BrD" and resid 103 and name HG1))
  3.000  2.200  2.200 peak      6921 weight  0.11000E+01 volume  0.24153E+03 ppm1      8.695  ppm2  2.613
ASSI {6931}
((segid "BrD" and resid 104 and name HN))
((segid "BrD" and resid 103 and name HG1))
  3.200  2.600  2.300 peak      6931 weight  0.11000E+01 volume  0.18108E+03 ppm1      7.763  ppm2  2.608
ASSI {6941}
((segid "BrD" and resid 48 and name HN))
((segid "BrD" and resid 48 and name HG1))
  3.300  2.700  2.200 peak      6941 weight  0.11000E+01 volume  0.14027E+03 ppm1      8.307  ppm2  2.909
ASSI {6951}
((segid "BrD" and resid 49 and name HN))
((segid "BrD" and resid 48 and name HG1))
  4.100  4.100  1.400 peak      6951 weight  0.11000E+01 volume  0.41580E+02 ppm1      7.762  ppm2  2.932
ASSI {6961}
((segid "BrD" and resid 66 and name HN))
((segid "BrD" and resid 66 and name HB1))
  3.200  2.600  2.300 peak      6961 weight  0.11000E+01 volume  0.17814E+03 ppm1      8.763  ppm2  2.704
ASSI {6971}
((segid "BrD" and resid 35 and name HN))
((segid "BrD" and resid 35 and name HB1))
  2.900  2.100  2.100 peak      6971 weight  0.11000E+01 volume  0.32270E+03 ppm1      7.734  ppm2  2.850
ASSI {6981}
((segid "BrD" and resid 54 and name HN))
((segid "BrD" and resid 53 and name HA))
  2.500  1.600  1.600 peak      6981 weight  0.11000E+01 volume  0.78564E+03 ppm1      9.036  ppm2  4.690
ASSI {6991}
((segid "BrD" and resid 38 and name HN))
((segid "BrD" and resid 37 and name HA))
  2.200  1.200  1.200 peak      6991 weight  0.11000E+01 volume  0.16736E+04 ppm1      8.731  ppm2  4.849
ASSI {7001}
((segid "BrD" and resid 51 and name HN))
((segid "BrD" and resid 51 and name HB1))
  2.500  2.100  2.100 peak      7001 weight  0.11000E+01 volume  0.35413E+03 ppm1      8.375  ppm2  1.980
ASSI {7011}
((segid "BrD" and resid 51 and name HN))
((segid "BrD" and resid 51 and name HB2))
  3.000  2.200  2.200 peak      7011 weight  0.11000E+01 volume  0.24666E+03 ppm1      8.375  ppm2  1.818

TABLE 2-continued

Unambiguous NOE-derived Inter-proton Distance Restraints

ASSI {7021}
((segid "BrD" and resid 51 and name HN))
((segid "BrD" and resid 51 and name HG2))
 3.000  2.200  2.200 peak       7021 weight  0.11000E+01 volume  0.24666E+03 ppm1     8.375 ppm2  1.786
ASSI {7041}
((segid "BrD" and resid 52 and name HN))
((segid "BrD" and resid 52 and name HA))
 2.900  2.100  2.100 peak       7041 weight  0.11000E+01 volume  0.32203E+03 ppm1     9.004 ppm2  5.591
ASSI {7051}
((segid "BrD" and resid 52 and name HN))
((segid "BrD" and resid 52 and name HB1))
 2.700  1.800  1.800 peak       7051 weight  0.11000E+01 volume  0.48728E+03 ppm1     9.004 ppm2  3.641
ASSI {7061}
((segid "BrD" and resid 52 and name HN))
((segid "BrD" and resid 52 and name HB2))
 2.500  1.600  1.600 peak       7061 weight  0.11000E+01 volume  0.72550E+03 ppm1     9.003 ppm2  3.514
ASSI {7071}
((segid "BrD" and resid 52 and name HN))
((segid "BrD" and resid 51 and name HN))
 2.600  1.700  1.700 peak       7071 weight  0.11000E+01 volume  0.63507E+03 ppm1     9.004 ppm2  8.356
ASSI {7091}
((segid "BrD" and resid 52 and name HN))
((segid "BrD" and resid 51 and name HA))
 3.000  2.200  2.200 peak       7091 weight  0.11000E+01 volume  0.26640E+03 ppm1     9.004 ppm2  4.482
ASSI {7101}
((segid "BrD" and resid 52 and name HN))
((segid "BrD" and resid 53 and name HD1))
 3.500  3.100  2.000 peak       7101 weight  0.11000E+01 volume  0.10263E+03 ppm1     9.004 ppm2  4.230
ASSI {7111}
((segid "BrD" and resid 52 and name HN))
((segid "BrD" and resid 53 and name HD2))
 3.900  3.800  1.600 peak       7111 weight  0.11000E+01 volume  0.57287E+02 ppm1     9.003 ppm2  3.997
ASSI {7141}
((segid "BrD" and resid 59 and name HN))
((segid "BrD" and resid 59 and name HG2))
 3.300  2.700  2.200 peak       7141 weight  0.11000E+01 volume  0.14900E+03 ppm1     8.496 ppm2  3.103
ASSI {7151}
((segid "BrD" and resid 59 and name HN))
((segid "BrD" and resid 59 and name HG1))
 3.400  2.900  2.100 peak       7151 weight  0.11000E+01 volume  0.12335E+03 ppm1     8.498 ppm2  3.228
ASSI {7161}
((segid "BrD" and resid 59 and name HN))
((segid "BrD" and resid 59 and name HB1))
 3.400  2.900  2.100 peak       7161 weight  0.11000E+01 volume  0.11956E+03 ppm1     8.498 ppm2  2.700
ASSI {7171}
((segid "BrD" and resid 59 and name HN))
((segid "BrD" and resid 59 and name HB2))
 3.200  2.600  2.300 peak       7171 weight  0.11000E+01 volume  0.17215E+03 ppm1     8.499 ppm2  2.504
ASSI {7181}
((segid "BrD" and resid 57 and name HN))
((segid "BrD" and resid 57 and name HB1))
 2.400  1.400  1.400 peak       7181 weight  0.11000E+01 volume  0.94732E+03 ppm1     9.359 ppm2  2.947
ASSI {7191}
((segid "BrD" and resid 57 and name HN))
((segid "BrD" and resid 57 and name HB2))
 2.500  1.600  1.600 peak       7191 weight  0.11000E+01 volume  0.75718E+03 ppm1     9.358 ppm2  2.827
ASSI {7201}
((segid "BrD" and resid 57 and name HN))
((segid "BrD" and resid 57 and name HG1))
 3.600  3.200  1.900 peak       7201 weight  0.11000E+01 volume  0.93147E+02 ppm1     9.359 ppm2  2.088
ASSI {7211}
((segid "BrD" and resid 57 and name HN))
((segid "BrD" and resid 57 and name HD1))
 4.300  4.300  1.200 peak       7211 weight  0.11000E+01 volume  0.28923E+02 ppm1     9.358 ppm2  2.411
ASSI {7221}
((segid "BrD" and resid 57 and name HN))
((segid "BrD" and resid 57 and name HD2))
 3.400  2.900  2.100 peak       7221 weight  0.11000E+01 volume  0.13023E+03 ppm1     9.359 ppm2  2.292
ASSI {7231}
((segid "BrD" and resid 26 and name HN))
((segid "BrD" and resid 26 and name HB1))
 3.300  2.700  2.200 peak       7231 weight  0.11000E+01 volume  0.15703E+03 ppm1     9.195 ppm2  2.463
ASSI {7241}
((segid "BrD" and resid 26 and name HN))
((segid "BrD" and resid 26 and name HD1))
 3.500  3.100  2.000 peak       7241 weight  0.11000E+01 volume  0.99010E+02 ppm1     9.196 ppm2  2.092

TABLE 2-continued

Unambiguous NOE-derived Inter-proton Distance Restraints

ASSI {7261}
((segid "BrD" and resid 10 and name HN))
((segid "BrD" and resid 11 and name HD1))
   4.600  4.600  0.900 peak       7261  weight  0.11000E+01 volume    0.20621E+02 ppm1        8.885  ppm2  4.475
ASSI {7271}
((segid "BrD" and resid 10 and name HN))
((segid "BrD" and resid 9 and name HB1))
   3.400  2.900  2.100 peak       7271  weight  0.11000E+01 volume    0.12456E+03 ppm1        8.883  ppm2  2.422
ASSI {7281}
((segid "BrD" and resid 13 and name HN))
((segid "BrD" and resid 12 and name HB1))
   3.500  3.100  2.000 peak       7281  weight  0.11000E+01 volume    0.11107E+03 ppm1        8.802  ppm2  3.399
ASSI {7301}
((segid "BrD" and resid 15 and name HN))
((segid "BrD" and resid 14 and name HN))
   2.900  2.100  2.100 peak       7301  weight  0.11000E+01 volume    0.2$$9E+03 ppm1        8.597  ppm2  8.817
ASSI {7311}
((segid "BrD" and resid 16 and name HN))
((segid "BrD" and resid 13 and name HA))
   3.600  3.100  2.000 peak       7311  weight  0.11000E+01 volume    0.96679E+02 ppm1        8.794  ppm2  4.770
ASSI {7321}
((segid "BrD" and resid 15 and name HN))
(segid "BrD" and resid 14 and name HD2 %)
   3.600  3.200  1.900 peak       7321  weight  0.11000E+01 volume    0.89979E+02 ppm1        8.598  ppm2  1.393
ASSI {7331}
((segid "BrD" and resid 15 and name HN))
((segid "BrD" and resid 14 and name HB1))
   2.600  1.700  1.700 peak       7331  weight  0.11000E+01 volume    0.55160E+03 ppm1        8.599  ppm2  2.454
ASSI {7341}
((segid "BrD" and resid 15 and name HN))
((segid "BrD" and resid 14 and name HB2))
   3.600  3.200  1.900 peak       7341  weight  0.11000E+01 volume    0.85197E+02 ppm1        8.598  ppm2  2.162
ASSI {7351}
((segid "BrD" and resid 18 and name HN))
((segid "BrD" and resid 14 and name HA))
   3.500  3.100  2.000 peak       7351  weight  0.11000E+01 volume    0.10770E+03 ppm1        9.071  ppm2  4.652
ASSI {7361}
((segid "BrD" and resid 21 and name HN))
((segid "BrD" and resid 18 and name HA))
   3.200  2.600  2.300 peak       7361  weight  0.11000E+01 volume    0.16933E+03 ppm1        8.544  ppm2  3.874
ASSI {7371}
((segid "BrD" and resid 22 and name HN))
((segid "BrD" and resid 18 and name HA))
   3.700  3.400  1.800 peak       7371  weight  0.11000E+01 volume    0.72924E+02 ppm1        9.456  ppm2  3.896
ASSI {7381}
((segid "BrD" and resid 19 and name HN))
((segid "BrD" and resid 18 and name HB1))
   2.800  2.000  2.000 peak       7381  weight  0.11000E+01 volume    0.40235E+03 ppm1        9.186  ppm2  2.139
ASSI {7391}
((segid "BrD" and resid 19 and name HN))
(segid "BrD" and resid 18 and name HD1 %)
   3.800  3.600  1.700 peak       7391  weight  0.11000E+01 volume    0.63600E+02 ppm1        9.189  ppm2  1.084
ASSI {7401}
((segid "BrD" and resid 19 and name HN))
(segid "BrD" and resid 18 and name HD2 %)
   3.700  3.400  1.800 peak       7401  weight  0.11000E+01 volume    0.71915E+02 ppm1        9.187  ppm2  0.414
ASSI {7411}
((segid "BrD" and resid 20 and name HN))
((segid "BrD" and resid 19 and name HB1))
   3.200  2.600  2.300 peak       7411  weight  0.11000E+01 volume    0.16507E+03 ppm1        8.146  ppm2  2.336
ASSI {7421}
((segid "BrD" and resid 20 and name HN))
((segid "BrD" and resid 19 and name HB2))
   3.400  2.900  2.100 peak       7421  weight  0.11000E+01 volume    0.13044E+03 ppm1        8.147  ppm2  1.967
ASSI {7431}
((segid "BrD" and resid 23 and name HN))
((segid "BrD" and resid 19 and name HA))
   3.600  3.200  1.900 peak       7431  weight  0.11000E+01 volume    0.90645E+02 ppm1        9.120  ppm2  4.286
ASSI {7441}
((segid "BrD" and resid 23 and name HN))
((segid "BrD" and resid 20 and name HA))
   3.400  2.900  2.100 peak       7441  weight  0.11000E+01 volume    0.11524E+03 ppm1        9.118  ppm2  4.895
ASSI {7451}
((segid "BrD" and resid 20 and name HN))
((segid "BrD" and resid 22 and name HN))
   3.600  3.200  1.900 peak       7451  weight  0.11000E+01 volume    0.81392E+02 ppm1        8.147  ppm2  9.450

TABLE 2-continued

Unambiguous NOE-derived Inter-proton Distance Restraints

ASSI {7471}
((segid "BrD" and resid 21 and name HN))
((segid "BrD" and resid 23 and name HN))
  4.100  4.100  1.400 peak       7471  weight  0.11000E+01 volume  0.42834E+02 ppm1     8.545  ppm2  9.130
ASSI {7491}
((segid "BrD" and resid 24 and name HN))
((segid "BrD" and resid 21 and name HA))
  3.200  2.600  2.300 peak       7491  weight  0.11000E+01 volume  0.16448E+03 ppm1     8.661  ppm2  4.371
ASSI {7501}
((segid "BrD" and resid 26 and name HN))
((segid "BrD" and resid 23 and name HA))
  3.400  2.900  2.100 peak       7501  weight  0.11000E+01 volume  0.12059E+03 ppm1     9.196  ppm2  4.639
ASSI {7511}
((segid "BrD" and resid 27 and name HN))
((segid "BrD" and resid 24 and name HA))
  3.200  2.600  2.300 peak       7511  weight  0.11000E+01 volume  0.17746E+03 ppm1     8.170  ppm2  4.777
ASSI {7521}
((segid "BrD" and resid 26 and name HN))
((segid "BrD" and resid 25 and name HA))
  3.600  3.200  1.900 peak       7521  weight  0.11000E+01 volume  0.92661E+02 ppm1     8.166  ppm2  4.449
ASSI {7531}
((segid "BrD" and resid 26 and name HN))
((segid "BrD" and resid 25 and name HB))
  2.600  1.700  1.700 peak       7531  weight  0.11000E+01 volume  0.67212E+03 ppm1     9.196  ppm2  2.991
ASSI {7541}
((segid "BrD" and resid 26 and name HN))
(segid "BrD" and resid 25 and name HG2 %)
  2.900  2.100  2.100 peak       7541  weight  0.11000E+01 volume  0.31151E+03 ppm1     9.196  ppm2  1.640
ASSI {7551}
((segid "BrD" and resid 26 and name HN))
(segid "BrD" and resid 25 and name HG1 %)
  3.100  2.400  2.400 peak       7551  weight  0.11000E+01 volume  0.21302E+03 ppm1     9.197  ppm2  1.790
ASSI {7561}
((segid "BrD" and resid 43 and name HN))
((segid "BrD" and resid 44 and name HD1))
  3.400  2.900  2.100 peak       7561  weight  0.11000E+01 volume  0.11281E+03 ppm1     8.001  ppm2  4.324
ASSI {7571}
((segid "BrD" and resid 43 and name HN))
((segid "BrD" and resid 44 and name HD2))
  3.100  2.400  2.400 peak       7571  weight  0.11000E+01 volume  0.21754E+03 ppm1     8.001  ppm2  4.122
ASSI {7581}
((segid "BrD" and resid 49 and name HN))
((segid "BrD" and resid 46 and name HA))
  3.900  3.800  1.600 peak       7581  weight  0.11000E+01 volume  0.54216E+02 ppm1     7.763  ppm2  4.143
ASSI {7591}
((segid "BrD" and resid 56 and name HN))
((segid "BrD" and resid 56 and name HB1))
  2.700  1.800  1.800 peak       7591  weight  0.11000E+01 volume  0.48254E+03 ppm1     9.679  ppm2  2.693
ASSI {7601}
((segid "BrD" and resid 61 and name HN))
((segid "BrD" and resid 58 and name HA))
  2.900  2.100  2.100 peak       7601  weight  0.11000E+01 volume  0.30089E+03 ppm1     8.749  ppm2  4.452
ASSI {7611}
((segid "BrD" and resid 64 and name HN))
((segid "BrD" and resid 60 and name HA))
  3.400  2.900  2.100 peak       7611  weight  0.11000E+01 volume  0.11932E+03 ppm1     8.584  ppm2  4.807
ASSI {7621}
((segid "BrD" and resid 66 and name HN))
((segid "BrD" and resid 66 and name HD1))
  2.900  2.100  2.100 peak       7421  weight  0.11000E+01 volume  0.29994E+03 ppm1     8.759  ppm2  3.667
ASSI {7631}
((segid "BrD" and resid 75 and name HN))
((segid "BrD" and resid 72 and name HA))
  3.400  2.900  2.100 peak       7631  weight  0.11000E+01 volume  0.13400E+03 ppm1     9.106  ppm2  4.669
ASSI {7651}
((segid "BrD" and resid 79 and name HN))
((segid "BrD" and resid 76 and name HA))
  3.200  2.600  2.300 peak       7651  weight  0.11000E+01 volume  0.16410E+03 ppm1     8.680  ppm2  4.691
ASSI {7661}
((segid "BrD" and resid 80 and name HN))
((segid "BrD" and resid 77 and name HA))
  3.700  3.400  1.800 peak       7661  weight  0.11000E+01 volume  0.79484E+02 ppm1     8.006  ppm2  4.969
ASSI {7671}
((segid "BrD" and resid 81 and name HN))
((segid "BrD" and resid 78 and name HA))
  3.300  2.700  2.200 peak       7671  weight  0.11000E+01 volume  0.15049E+03 ppm1     7.619  ppm2  3.989

TABLE 2-continued

| Unambiguous NOE-derived Inter-proton Distance Restraints |
|---|

ASSI {7681}
((segid "BrD" and resid 82 and name HN))
((segid "BrD" and resid 79 and name HA))
  3.600  3.200  1.900 peak      7681  weight  0.11000E+01 volume  0.80779E+02 ppm1      6.981  ppm2  4.411
ASSI {7701}
((segid "BrD" and resid 84 and name HN))
(segid "BrD" and resid 81 and name HA)
  3.500  3.100  2.000 peak      7701  weight  0.11000E+01 volume  0.10576E+03 ppm1      9.463  ppm2  3.705
ASSI {7711}
((segid "BrD" and resid 85 and name HN))
((segid "BrD" and resid 82 and name HA))
  3.300  2.700  2.200 peak      7711  weight  0.11000E+01 volume  0.13652E+03 ppm1      7.516  ppm2  4.768
ASSI {7721}
((segid "BrD" and resid 89 and name HN))
((segid "BrD" and resid 86 and name HA))
  3.500  3.100  2.000 peak      7721  weight  0.11000E+01 volume  0.10495E+03 ppm1      8.858  ppm2  4.811
ASSI {7731}
((segid "BrD" and resid 93 and name HN))
((segid "BrD" and resid 92 and name HA))
  3.600  3.200  1.900 peak      7731  weight  0.11000E+01 volume  0.94491E+02 ppm1      8.713  ppm2  4.796
ASSI {7741}
((segid "BrD" and resid 98 and name HN))
((segid "BrD" and resid 95 and name HA))
  3.300  2.700  2.200 peak      7741  weight  0.11000E+01 volume  0.14245E+03 ppm1      9.125  ppm2  4.441
ASSI {7751}
((segid "BrD" and resid 77 and name HN))
((segid "BrD" and resid 75 and name HN))
  3.500  3.100  2.000 peak      7751  weight  0.11000E+01 volume  0.10255E+03 ppm1      7.985  ppm2  9.096
ASSI {7761}
((segid "BrD" and resid 98 and name HN))
((segid "BrD" and resid 96 and name HN))
  3.900  3.800  1.600 peak      7761  weight  0.11000E+01 volume  0.51137E+02 ppm1      9.125  ppm2  7.963
ASSI {7771}
((segid "BrD" and resid 102 and name HN))
((segid "BrD" and resid 98 and name HA))
  3.500  3.100  2.000 peak      7771  weight  0.11000E+01 volume  0.10795E+03 ppm1      9.156  ppm2  4.809
ASSI {7781}
((segid "BrD" and resid 102 and name HN))
((segid "BrD" and resid 99 and name HA))
  3.500  3.100  2.000 peak      7781  weight  0.11000E+01 volume  0.10223E+03 ppm1      9.156  ppm2  4.443
ASSI {7791}
((segid "BrD" and resid 103 and name HN))
((segid "BrD" and resid 100 and name HA))
  3.000  2.200  2.200 peak      7791  weight  0.11000E+01 volume  0.26822E+03 ppm1      8.696  ppm2  4.932
ASSI {7801}
((segid "BrD" and resid 104 and name HN))
((segid "BrD" and resid 101 and name HA))
  3.000  2.200  2.200 peak      7801  weight  0.11000E+01 volume  0.25521E+03 ppm1      7.763  ppm2  4.275
ASSI {7811}
((segid "BrD" and resid 102 and name HN))
((segid "BrD" and resid 104 and name HN))
  4.300  4.300  1.200 peak      7811  weight  0.11000E+01 volume  0.28976E+02 ppm1      9.156  ppm2  7.772
ASSI {7831}
((segid "BrD" and resid 105 and name HN))
((segid "BrD" and resid 102 and name HA))
  3.300  2.700  2.200 peak      7831  weight  0.11000E+01 volume  0.14640E+03 ppm1      $$  ppm2  4.290
ASSI {7841}
((segid "BrD" and resid 108 and name HN))
((segid "BrD" and resid 105 and name HA))
  3.600  3.200  1.900 peak      7841  weight  0.11000E+01 volume  0.82783E+02 ppm1      8.526  ppm2  4.936
ASSI {7851}
((segid "BrD" and resid 16 and name HN))
((segid "BrD" and resid 16 and name HB1))
  2.900  2.100  2.100 peak      7851  weight  0.11000E+01 volume  0.35014E+03 ppm1      8.794  ppm2  4.587
ASSI {7861
((segid "BrD" and resid 24 and name HE22))
((segid "BrD" and resid 24 and name HG2))
  4.100  4.100  1.400 peak      7861  weight  0.11000E+01 volume  0.40620E+02 ppm1      7.523  ppm2  3.068
ASSI {7871}
((segid "BrD" and resid 24 and name HE21))
((segid "BrD" and resid 24 and name HG2))
  3.500  3.100  2.000 peak      7871  weight  0.11000E+01 volume  0.10084E+03 ppm1      7.629  ppm2  3.067
ASSI {7881}
((segid "BrD" and resid 25 and name HN))
((segid "BrD" and resid 24 and name HG1))
  3.400  2.900  2.100 peak      7881  weight  0.11000E+01 volume  0.11666E+03 ppm1      9.133  ppm2  3.447

TABLE 2-continued

Unambiguous NOE-derived Inter-proton Distance Restraints

```
ASSI {7891}
((segid "BrD" and resid 18 and name HN))
(segid "BrD" and resid 18 and name HD1 %)
  2.900  2.100  2.100 peak      7891 weight  0.11000E+01 volume  0.29964E+03 ppm1    9.072 ppm2  1.068
ASSI {7901}
((segid "BrD" and resid 73 and name HN))
(segid "BrD" and resid 73 and name HD1 %)
  3.300  2.700  2.200 peak      7901 weight  0.11000E+01 volume  0.15507E+03 ppm1    8.049 ppm2  1.540
ASSI {7911}
((segid "BrD" and resid 73 and name HN))
((segid "BrD" and resid 73 and name HB1))
  2.800  2.000  2.000 peak      7911 weight  0.11000E+01 volume  0.38621E+03 ppm1    8.045 ppm2  2.590
ASSI {7921}
((segid "BrD" and resid 56 and name HN))
(segid "BrD" and resid 56 and name HD2 %)
  3.100  2.400  2.400 peak      7921 weight  0.11000E+01 volume  0.19974E+03 ppm1    9.679 ppm2  1.235
ASSI {7931}
((segid "BrD" and resid 22 and name HN))
(segid "BrD" and resid 22 and name HD2 %)
  3.000  2.200  2.200 peak      7931 weight  0.11000E+01 volume  0.25836E+03 ppm1    9.455 ppm2  1.584
ASSI {7941}
((segid "BrD" and resid 110 and name HN))
((segid "BrD" and resid 110 and name HG11))
  2.900  2.100  2.100 peak      7941 weight  0.11000E+01 volume  0.31947E+03 ppm1    8.715 ppm2  1.745
ASSI {7951}
((segid "BrD" and resid 29 and name HN))
((segid "BrD" and resid 29 and name HG1))
  3.100  2.400  2.400 peak      7951 weight  0.11000E+01 volume  0.23530E+03 ppm1    9.152 ppm2  3.021
ASSI {7961}
((segid "BrD" and resid 23 and name HN))
((segid "BrD" and resid 23 and name HB2))
  2.400  1.400  1.400 peak      7961 weight  0.11000E+01 volume  0.91388E+03 ppm1    9.120 ppm2  2.851
ASSI {7971}
((segid "BrD" and resid 80 and name HN))
((segid "BrD" and resid 80 and name HD2))
  4.400  4.400  1.100 peak      7971 weight  0.11000E+01 volume  0.24560E+03 ppm1    8.007 ppm2  3.932
ASSI {7981}
((segid "BrD" and resid 100 and name HN))
((segid "BrD" and resid 100 and name HB1))
  2.800  2.000  2.000 peak      7981 weight  0.11000E+01 volume  0.39419E+03 ppm1    8.669 ppm2  3.493
ASSI {7991}
((segid "BrD" and resid 19 and name HN))
((segid "BrD" and resid 19 and name HB2))
  3.000  2.200  2.200 peak      7991 weight  0.11000E+01 volume  0.28394E+03 ppm1    9.187 ppm2  1.971
ASSI {8001}
((segid "BrD" and resid 97 and name HN))
((segid "BrD" and resid 97 and name HG1))
  2.500  1.600  1.600 peak      8001 weight  0.11000E+01 volume  0.82725E+03 ppm1    8.674 ppm2  2.415
ASSI {8011}
((segid "BrD" and resid 105 and name HN))
((segid "BrD" and resid 105 and name HB2))
  3.100  2.400  2.400 peak      8011 weight  0.11000E+01 volume  0.23309E+03 ppm1    8.487 ppm2  3.654
ASSI {8021}
((segid "BrD" and resid 12 and name HN))
((segid "BrD" and resid 12 and name HB2))
  3.100  2.400  2.400 peak      8021 weight  0.11000E+01 volume  0.23285E+03 ppm1    9.021 ppm2  3.337
ASSI {8031}
((segid "BrD" and resid 10 and name HN))
((segid "BrD" and resid 10 and name HB2))
  3.000  2.200  2.200 peak      8031 weight  0.11000E+01 volume  0.26676E+03 ppm1    8.886 ppm2  3.299
ASSI {8041}
((segid "BrD" and resid 114 and name HN))
((segid "BrD" and resid 114 and name HA2))
  2.800  2.000  2.000 peak      8041 weight  0.11000E+01 volume  0.43718E+03 ppm1    8.375 ppm2  4.531
ASSI {8051}
((segid "BrD" and resid 85 and name HN))
((segid "BrD" and resid 85 and name HB2))
  3.100  2.400  2.400 peak      8051 weight  0.11000E+01 volume  0.21741E+03 ppm1    7.517 ppm2  3.603
ASSI {8101}
((segid "BrD" and resid 39 and name HN))
((segid "BrD" and resid 39 and name HB1))
  2.800  2.000  2.000 peak      8101 weight  0.11000E+01 volume  0.36178E+03 ppm1    9.651 ppm2  3.480
ASSI {8111}
((segid "BrD" and resid 39 and name HN))
((segid "BrD" and resid 39 and name HD1))
  2.500  1.600  1.600 peak      8111 weight  0.11000E+01 volume  0.74538E+03 ppm1    9.653 ppm2  2.280
```

TABLE 2-continued

Unambiguous NOE-derived Inter-proton Distance Restraints

ASSI {8121}
((segid "BrD" and resid 39 and name HN))
((segid "BrD" and resid 39 and name HG1))
  3.100  2.400  2.400 peak       8121  weight  0.11000E+01 volume  0.20991E+03 ppm1     9.651  ppm2  2.042
ASSI {8131}
((segid "BrD" and resid 57 and name HN))
((segid "BrD" and resid 59 and name HN))
  3.700  3.400  1.800 peak       8131  weight  0.11000E+01 volume  0.75880E+02 ppm1     9.355  ppm2  8.478
ASSI {8171}
((segid "BrD" and resid 57 and name HN))
((segid "BrD" and resid 56 and name HB1))
  2.800  2.000  2.000 peak       8171  weight  0.11000E+01 volume  0.40297E+03 ppm1     9.359  ppm2  2.702
ASSI {8191}
((segid "BrD" and resid 57 and name HN))
(segid "BrD" and resid 56 and name HD1 %)
  3.700  3.400  1.800 peak       8191  weight  0.11000E+01 volume  0.68904E+02 ppm1     9.358  ppm2  1.547
ASSI {8201}
((segid "BrD" and resid 57 and name HN))
((segid "BrD" and resid 57 and name HG2))
  3.700  3.400  1.800 peak       8201  weight  0.11000E+01 volume  0.72644E+02 ppm1     9.361  ppm2  2.011
ASSI {8241}
((segid "BrD" and resid 28 and name HN))
((segid "BrD" and resid 24 and name HA))
  3.600  3.200  1.900 peak       8241  weight  0.11000E+01 volume  0.82533E+02 ppm1     8.166  ppm2  4.803
ASSI {8251}
((segid "BrD" and resid 28 and name HN))
((segid "BrD" and resid 28 and name HD2))
  3.800  3.600  1.700 peak       8251  weight  0.11000E+01 volume  0.64220E+02 ppm1     8.166  ppm2  5.585
ASSI {8351}
((segid "BrD" and resid 51 and name HN))
(segid "BrD" and resid 50 and name HD2 %)
  3.000  2.200  2.200 peak       8351  weight  0.11000E+01 volume  0.27507E+03 ppm1     8.379  ppm2  0.982
ASSI {8431}
((segid "BrD" and resid 117 and name HN))
(segid "BrD" and resid 116 and name HG2 %)
  3.700  3.400  1.800 peak       8431  weight  0.11000E+01 volume  0.73143E+02 ppm1     8.877  ppm2  1.422
ASSI {8471}
((segid "BrD" and resid 102 and name HN))
((segid "BrD" and resid 101 and name HB))
  3.000  2.200  2.200 peak       8471  weight  0.11000E+01 volume  0.25477E+03 ppm1     9.156  ppm2  2.531
ASSI {8491}
((segid "BrD" and resid 102 and name HN))
(segid "BrD" and resid 101 and name HG2 %)
  3.300  2.700  2.200 peak       8491  weight  0.11000E+01 volume  0.14766E+03 ppm1     9.156  ppm2  1.598
ASSI {8541}
((segid "BrD" and resid 46 and name HN))
(segid "BrD" and resid 46 and name HD %)
  3.500  3.100  2.000 peak       8541  weight  0.11000E+01 volume  0.10722E+03 ppm1     8.562  ppm2  5.719
ASSI {8591}
((segid "BrD" and resid 43 and name HN))
((segid "BrD" and resid 41 and name HA))
  3.000  2.200  2.200 peak       8591  weight  0.11000E+01 volume  0.24489E+03 ppm1     8.001  ppm2  4.645
ASSI {8671}
((segid "BrD" and resid 111 and name HN))
((segid "BrD" and resid 110 and name HG11))
  3.600  3.200  1.900 peak       8671  weight  0.11000E+01 volume  0.81338E+02 ppm1     8.168  ppm2  1.747
ASSI {8701}
((segid "BrD" and resid 111 and name HN))
(segid "BrD" and resid 110 and name HD1 %)
  4.000  4.000  1.500 peak       8701  weight  0.11000E+01 volume  0.48240E+02 ppm1     8.168  ppm2  1.148
ASSI {8731}
((segid "BrD" and resid 58 and name HN))
((segid "BrD" and resid 57 and name HB1))
  3.100  2.400  2.400 peak       8731  weight  0.11000E+01 volume  0.22478E+03 ppm1    10.051  ppm2  2.937
ASSI {8741}
((segid "BrD" and resid 58 and name HN))
((segid "BrD" and resid 57 and name HB2))
  3.100  2.400  2.400 peak       8741  weight  0.11000E+01 volume  0.21450E+03 ppm1    10.051  ppm2  2.831
ASSI {8761}
((segid "BrD" and resid 58 and name HN))
((segid "BrD" and resid 57 and name HD1))
  4.300  4.300  1.200 peak       8761  weight  0.11000E+01 volume  0.29553E+02 ppm1    10.051  ppm2  2.400
ASSI {8771}
((segid "BrD" and resid 58 and name HN))
((segid "BrD" and resid 57 and name HD2))
  3.800  3.600  1.700 peak       8771  weight  0.11000E+01 volume  0.60769E+02 ppm1    10.051  ppm2  2.303

TABLE 2-continued

Unambiguous NOE-derived Inter-proton Distance Restraints

ASSI {8781}
((segid "BrD" and resid 58 and name HN))
((segid "BrD" and resid 57 and name HG1))
  3.800  3.600  1.700 peak        8781  weight  0.11000E+01 volume  0.60094E+02 ppm1      10.051  ppm2  2.090
ASSI {8791}
((segid "BrD" and resid 58 and name HN))
((segid "BrD" and resid 57 and name HG2))
  3.800  3.600  1.700 peak        8791  weight  0.11000E+01 volume  0.67776E+02 ppm1      10.051  ppm2  2.010
ASSI {8821}
((segid "BrD" and resid 10 and name HN))
((segid "BrD" and resid 9 and name HG1))
  4.100  4.100  1.400 peak        8821  weight  0.11000E+01 volume  0.38664E+02 ppm1       8.885  ppm2  2.288
ASSI {8831}
((segid "BrD" and resid 11 and name HN))
((segid "BrD" and resid 12 and name HB2))
  3.400  2.900  2.100 peak        8831  weight  0.11000E+01 volume  0.11575E+03 ppm1       8.803  ppm2  3.337
ASSI {8841}
((segid "BrD" and resid 14 and name HN))
((segid "BrD" and resid 12 and name HN))
  2.600  1.700  1.700 peak        8841  weight  0.11000E+01 volume  0.58119E+03 ppm1       8.803  ppm2  9.004
ASSI {8921}
((segid "BrD" and resid 112 and name HN))
((segid "BrD" and resid 111 and name HB1))
  2.700  1.800  1.800 peak        8921  weight  0.11000E+01 volume  0.53559E+03 ppm1       8.666  ppm2  2.473
ASSI {8931}
((segid "BrD" and resid 112 and name HN))
((segid "BrD" and resid 111 and name HB2))
  3.100  2.400  2.400 peak        8931  weight  0.11000E+01 volume  0.20903E+03 ppm1       8.667  ppm2  3.363
ASSI {8951}
((segid "BrD" and resid 112 and name HN))
((segid "BrD" and resid 111 and name HG1))
  3.800  3.600  1.700 peak        8951  weight  0.11000E+01 volume  0.46936E+02 ppm1       8.668  ppm2  1.997
ASSI {9001}
((segid "BrD" and resid 109 and name HN))
((segid "BrD" and resid 104 and name HB1))
  2.600  1.700  1.700 peak        9001  weight  0.11000E+01 volume  0.67760E+03 ppm1       8.487  ppm2  2.536
ASSI {9021}
((segid "BrD" and resid 105 and name HN))
((segid "BrD" and resid 104 and name HG1))
  4.800  4.800  0.700 peak        9021  weight  0.11000E+01 volume  0.16288E+02 ppm1       8.485  ppm2  2.099
ASSI {9081}
((segid "BrD" and resid 109 and name HN))
((segid "BrD" and resid 108 and name HB1))
  2.500  1.600  1.600 peak        9081  weight  0.11000E+01 volume  0.75253E+03 ppm1       8.573  ppm2  4.614
ASSI {9141}
((segid "BrD" and resid 106 and name HN))
(segid "BrD" and resid 106 and name HD %))
  3.700  3.400  1.800 peak        9141  weight  0.11000E+01 volume  0.76595E+02 ppm1       9.740  ppm2  7.511
ASSI {9151}
((segid "BrD" and resid 106 and name HN))
((segid "BrD" and resid 102 and name HA))
  3.700  3.400  1.800 peak        9151  weight  0.11000E+01 volume  0.78592E+02 ppm1       9.740  ppm2  4.277
ASSI {9301}
((segid "BrD" and resid 63 and name HN))
((segid "BrD" and resid 60 and name HA))
  3.800  3.600  1.700 peak        9301  weight  0.11000E+01 volume  0.67510E+02 ppm1       9.471  ppm2  4.809
ASSI {9321}
((segid "BrD" and resid 63 and name HN))
((segid "BrD" and resid 62 and name HB1))
  2.200  1.200  1.200 peak        9321  weight  0.11000E+01 volume  0.14701E+04 ppm1       9.472  ppm2  2.654
ASSI {9331}
((segid "BrD" and resid 63 and name HN))
((segid "BrD" and resid 61 and name HN))
  3.500  3.100  2.000 peak        9331  weight  0.11000E+01 volume  0.10977E+03 ppm1       9.475  ppm2  8.757
ASSI {9351}
((segid "BrD" and resid 22 and name HN))
((segid "BrD" and resid 20 and name HA))
  4.100  4.100  1.400 peak        9351  weight  0.11000E+01 volume  0.39214E+02 ppm1       9.458  ppm2  4.872
ASSI {9361}
((segid "BrD" and resid 22 and name HN))
((segid "BrD" and resid 19 and name HA))
  3.600  3.200  1.900 peak        9361  weight  0.11000E+01 volume  0.85958E+02 ppm1       9.457  ppm2  4.286
ASSI {9391}
((segid "BrD" and resid 22 and name HN))
((segid "BrD" and resid 21 and name HB))
  2.700  1.800  1.800 peak        9391  weight  0.11000E+01 volume  0.51430E+03 ppm1       9.457  ppm2  2.491

TABLE 2-continued

Unambiguous NOE-derived Inter-proton Distance Restraints

ASSI {9551}
((segid "BrD" and resid 103 and name HN))
((segid "BrD" and resid 99 and name HA))
 4.600  4.600  0.900 peak      9551 weight  0.11000E+01 volume  0.21373E+02 ppm1   8.695 ppm2  4.441
ASSI {9571}
((segid "BrD" and resid 103 and name HN))
((segid "BrD" and resid 102 and name HG))
 3.200  2.600  2.300 peak      9571 weight  0.11000E+01 volume  0.17364E+03 ppm1   8.695 ppm2  2.187
ASSI {9581}
((segid "BrD" and resid 103 and name HN))
(segid "BrD" and resid 101 and name HG2 %)
 3.000  2.200  2.200 peak      9581 weight  0.11000E+01 volume  0.23656E+03 ppm1   8.695 ppm2  1.624
ASSI {9591}
((segid "BrD" and resid 103 and name HN))
(segid "BrD" and resid 102 and name HD1 %)
 3.600  3.200  1.900 peak      9591 weight  0.11000E+01 volume  0.85679E+02 ppm1   8.695 ppm2  1.308
ASSI {9601}
((segid "BrD" and resid 103 and name HN))
((segid "BrD" and resid 102 and name HB2))
 3.200  2.600  2.300 peak      9401 weight  0.11000E+01 volume  0.18049E+03 ppm1   8.695 ppm2  1.086
ASSI {9691}
((segid "BrD" and resid 18 and name HN))
((segid "BrD" and resid 18 and name HB2))
 2.800  2.000  2.000 peak      9691 weight  0.11000E+01 volume  0.37426E+03 ppm1   9.073 ppm2  0.909
ASSI {9701}
((segid "BrD" and resid 64 and name HN))
((segid "BrD" and resid 61 and name HA))
 3.100  2.400  2.400 peak      9701 weight  0.11000E+01 volume  0.22483E+03 ppm1   8.584 ppm2  4.652
ASSI {9711}
((segid "BrD" and resid 64 and name HN))
((segid "BrD" and resid 62 and name HA))
 3.900  3.800  1.600 peak      9711 weight  0.11000E+01 volume  0.56508E+02 ppm1   8.583 ppm2  4.488
ASSI {9741}
((segid "BrD" and resid 64 and name HN))
((segid "BrD" and resid 63 and name HB1))
 2.600  1.700  1.700 peak      9741 weight  0.11000E+01 volume  0.57592E+03 ppm1   8.585 ppm2  2.902
ASSI {9931}
((segid "BrD" and resid 62 and name HN))
((segid "BrD" and resid 62 and name HB2))
 2.900  2.100  2.100 peak      9931 weight  0.11000E+01 volume  0.30063E+03 ppm1   8.998 ppm2  1.683
ASSI {9941}
((segid "BrD" and resid 62 and name HN))
((segid "BrD" and resid 62 and name HG2))
 3.700  3.400  1.800 peak      9941 weight  0.11000E+01 volume  0.71463E+02 ppm1   8.998 ppm2  1.484
ASSI {9961}
((segid "BrD" and resid 12 and name HN))
((segid "BrD" and resid 11 and name HD1))
 2.800  2.000  2.000 peak      9961 weight  0.11000E+01 volume  0.35721E+03 ppm1   9.021 ppm2  4.473
ASSI {10011}
((segid "BrD" and resid 25 and name HN))
((segid "BrD" and resid 22 and name HA))
 3.300  2.700  2.200 peak     10011 weight  0.11000E+01 volume  0.14084E+03 ppm1   9.133 ppm2  4.697
ASSI {10041}
((segid "BrD" and resid 24 and name HN))
((segid "BrD" and resid 23 and name HB1))
 2.600  1.700  1.700 peak     10041 weight  0.11000E+01 volume  0.58902E+03 ppm1   8.655 ppm2  2.934
ASSI {10051}
((segid "BrD" and resid 24 and name HN))
(segid "BrD" and resid 21 and name HD2 %)
 3.600  3.200  1.900 peak     10051 weight  0.11000E+01 volume  0.85488E+02 ppm1   8.656 ppm2  1.610
ASSI {10071}
((segid "BrD" and resid 24 and name HN))
((segid "BrD" and resid 20 and name HA))
 3.800  3.600  1.700 peak     10071 weight  0.11000E+01 volume  0.60003E+02 ppm1   8.659 ppm2  4.888
ASSI {10101}
((segid "BrD" and resid 15 and name HN))
((segid "BrD" and resid 13 and name HB1))
 3.500  3.100  3.000 peak     10101 weight  0.11000E+01 volume  0.10487E+03 ppm1   8.599 ppm2  2.755
ASSI {10161}
((segid "BrD" and resid 16 and name HN))
((segid "BrD" and resid 15 and name HA))
 2.800  2.000  2.000 peak     10161 weight  0.11000E+01 volume  0.35770E+03 ppm1   8.796 ppm2  4.637
ASSI {10171}
((segid "BrD" and resid 16 and name HN))
(segid "BrD" and resid 15 and name HD %)
 3.500  3.100  2.000 peak     10171 weight  0.11000E+01 volume  0.11249E+03 ppm1   8.792 ppm2  7.660

TABLE 2-continued

Unambiguous NOE-derived Inter-proton Distance Restraints

ASSI {10211}
((segid "BrD" and resid 75 and name HN))
((segid "BrD" and resid 73 and name HA))
  3.900  3.800  1.600 peak      10211  weight  0.11000E+01 volume  0.50909E+02 ppm1     9.106  ppm2  4.820
ASSI {10271}
((segid "BrD" and resid 75 and name HN))
(segid "BrD" and resid 74 and name HD %)
  3.200  2.600  2.300 peak      10271  weight  0.11000E+01 volume  0.18529E+03 ppm1     9.107  ppm2  7.007
ASSI {10321}
((segid "BrD" and resid 96 and name HN))
((segid "BrD" and resid 95 and name HB2))
  2.600  1.700  1.700 peak      10321  weight  0.11000E+01 volume  0.63650E+03 ppm1     7.979  ppm2  3.345
ASSI {10341}
((segid "BrD" and resid 95 and name HN))
((segid "BrD" and resid 92 and name HA))
  3.400  2.900  2.100 peak      10341  weight  0.11000E+01 volume  0.12625E+03 ppm1     8.669  ppm2  4.792
ASSI {10361}
((segid "BrD" and resid 95 and name HN))
(segid "BrD" and resid 95 and name HD %)
  3.400  2.900  2.100 peak      10361  weight  0.11000E+01 volume  0.13077E+03 ppm1     8.670  ppm2  7.500
ASSI {10371}
((segid "BrD" and resid 96 and name HN))
(segid "BrD" and resid 96 and name HD %)
  3.300  2.700  2.200 peak      10371  weight  0.11000E+01 volume  0.14891E+03 ppm1     7.979  ppm2  7.701
ASSI {10481}
((segid "BrD" and resid 78 and name HN))
((segid "BrD" and resid 75 and name HA))
  3.100  2.400  2.400 peak      10481  weight  0.11000E+01 volume  0.20590E+03 ppm1     7.996  ppm2  4.532
ASSI {10491}
((segid "BrD" and resid 78 and name HN))
((segid "BrD" and resid 74 and name HA))
  2.800  2.000  2.000 peak      10491  weight  0.11000E+01 volume  0.36339E+03 ppm1     7.996  ppm2  4.370
ASSI {10511}
((segid "BrD" and resid 54 and name HN))
((segid "BrD" and resid 53 and name HB1))
  2.800  2.000  2.000 peak      10511  weight  0.11000E+01 volume  0.43885E+03 ppm1     9.037  ppm2  2.816
ASSI {10521}
((segid "BrD" and resid 54 and name HN))
(segid "BrD" and resid 50 and name HG2 %)
  3.400  2.900  2.100 peak      10521  weight  0.11000E+01 volume  0.12606E+03 ppm1     9.036  ppm2  0.987
ASSI {10671}
((segid "BrD" and resid 82 and name HN))
((segid "BrD" and resid 78 and name HA))
  3.900  3.800  1.600 peak      10671  weight  0.11000E+01 volume  0.53978E+02 ppm1     6.981  ppm2  4.005
ASSI {10691}
((segid "BrD" and resid 81 and name HN))
((segid "BrD" and resid 80 and name HG1))
  3.600  3.200  1.900 peak      10691  weight  0.11000E+01 volume  0.91821E+02 ppm1     7.640  ppm2  2.349
ASSI {10701}
((segid "BrD" and resid 81 and name HN))
((segid "BrD" and resid 80 and name HB1))
  3.700  3.400  1.800 peak      10701  weight  0.11000E+01 volume  0.72987E+02 ppm1     7.640  ppm2  2.580
ASSI {10711}
((segid "BrD" and resid 81 and name HN))
((segid "BrD" and resid 80 and name HB2))
  3.700  3.400  1.800 peak      10711  weight  0.11000E+01 volume  0.72825E+02 ppm1     7.640  ppm2  2.493
ASSI {10731}
((segid "BrD" and resid 81 and name HN))
((segid "BrD" and resid 79 and name HA))
  3.900  3.800  1.600 peak      10731  weight  0.11000E+01 volume  0.55498E+02 ppm1     7.640  ppm2  4.412
ASSI {10791}
((segid "BrD" and resid 80 and name HN))
(segid "BrD" and resid 78 and name HD2 %)
  5.500  5.500  0.000 peak      10791  weight  0.11000E+01 volume  0.61252E+00 ppm1     8.014  ppm2  0.668
ASSI {10801}
((segid "BrD" and resid 80 and name HN))
(segid "BrD" and resid 78 and name HD1 %)
  4.400  4.400  1.100 peak      10801  weight  0.11000E+01 volume  0.27938E+02 ppm1     8.014  ppm2  0.791
ASSI {10831}
((segid "BrD" and resid 79 and name HN))
((segid "BrD" and resid 78 and name HB1))
  3.300  2.700  2.200 peak      10831  weight  0.11000E+01 volume  0.14525E+03 ppm1     8.680  ppm2  1.364
ASSI {10911}
((segid "BrD" and resid 86 and name HN))
((segid "BrD" and resid 83 and name HA))
  3.300  2.700  2.200 peak      10911  weight  0.11000E+01 volume  0.16077E+03 ppm1     8.423  ppm2  4.445

TABLE 2-continued

Unambiguous NOE-derived Inter-proton Distance Restraints

ASSI {10951}
((segid "BrD" and resid 87 and name HN))
((segid "BrD" and resid 86 and name HD1))
   3.500  3.100  2.000 peak    10951 weight  0.11000E+01 volume  0.10535E+03 ppm1   8.571 ppm2  1.898
ASSI {10961}
((segid "BrD" and resid 86 and name HN))
((segid "BrD" and resid 87 and name HN))
   3.100  2.400  2.400 peak    10961 weight  0.11000E+01 volume  0.19900E+03 ppm1   8.424 ppm2  8.553
ASSI {10971}
((segid "BrD" and resid 87 and name HN))
((segid "BrD" and resid 83 and name HA))
   4.200  4.200  1.300 peak    10971 weight  0.11000E+01 volume  0.36593E+02 ppm1   8.572 ppm2  4.445
ASSI {11061}
((segid "BrD" and resid 89 and name HN))
(segid "BrD" and resid 88 and name HD %)
   3.200  2.600  2.300 peak    11061 weight  0.11000E+01 volume  0.19134E+03 ppm1   8.858 ppm2  7.596
ASSI {11071}
((segid "BrD" and resid 89 and name HN))
((segid "BrD" and resid 91 and name HD1))
   5.300  5.300  0.200 peak    11071 weight  0.11000E+01 volume  0.89575E+01 ppm1   8.858 ppm2  4.559
ASSI {11081}
((segid "BrD" and resid 89 and name HN))
((segid "BrD" and resid 91 and name HD2))
   3.800  3.600  1.700 peak    11081 weight  0.11000E+01 volume  0.66703E+02 ppm1   8.858 ppm2  4.400
ASSI {11101}
((segid "BrD" and resid 89 and name HN))
((segid "BrD" and resid 87 and name HB1))
   3.800  3.600  1.700 peak    11101 weight  0.11000E+01 volume  0.67773E+02 ppm1   8.858 ppm2  2.779
ASSI {11111}
((segid "BrD" and resid 89 and name HN))
((segid "BrD" and resid 87 and name HB2))
   4.200  4.200  1.300 peak    11111 weight  0.11000E+01 volume  0.36189E+02 ppm1   8.865 ppm2  2.610
ASSI {11121}
((segid "BrD" and resid 92 and name HN))
((segid "BrD" and resid 91 and name HB1))
   3.200  2.600  2.300 peak    11121 weight  0.11000E+01 volume  0.16770E+03 ppm1   8.876 ppm2  3.069
ASSI {11221}
((segid "BrD" and resid 30 and name HN))
((segid "BrD" and resid 28 and name HN))
   4.100  4.100  1.400 peak    11221 weight  0.11000E+01 volume  0.38088E+02 ppm1  12.275 ppm2  8.143
ASSI {11261}
((segid "BrD" and resid 31 and name HN))
((segid "BrD" and resid 29 and name HG1))
   5.100  5.100  0.400 peak    11261 weight  0.11000E+01 volume  0.11011E+02 ppm1   8.486 ppm2  2.997
ASSI {11311}
((segid "BrD" and resid 31 and name HN))
(segid "BrD" and resid 102 and name HD1 %)
   3.300  2.700  2.200 peak    11311 weight  0.11000E+01 volume  0.14151E+03 ppm1   8.480 ppm2  1.314
ASSI {11331}
((segid "BrD" and resid 32 and name HN))
((segid "BrD" and resid 33 and name HD1))
   3.900  3.800  1.600 peak    11331 weight  0.11000E+01 volume  0.57286E+02 ppm1   7.738 ppm2  2.782
ASSI {11341}
((segid "BrD" and resid 32 and name HN))
((segid "BrD" and resid 33 and name HD2))
   2.500  1.600  1.600 peak    11341 weight  0.11000E+01 volume  0.82617E+03 ppm1   7.739 ppm2  2.174
ASSI {11381}
((segid "BrD" and resid 34 and name HN))
((segid "BrD" and resid 32 and name HA))
   4.200  4.200  1.300 peak    11381 weight  0.11000E+01 volume  0.36612E+02 ppm1   8.183 ppm2  4.975
ASSI {11411}
((segid "BrD" and resid 34 and name HN))
((segid "BrD" and resid 33 and name HG1))
   2.600  1.700  1.700 peak    11411 weight  0.11000E+01 volume  0.60528E+03 ppm1   8.181 ppm2  2.784
ASSI {11421}
((segid "BrD" and resid 34 and name HN))
((segid "BrD" and resid 33 and name HD2))
   3.300  2.700  2.200 peak    11421 weight  0.11000E+01 volume  0.15559E+03 ppm1   8.184 ppm2  2.174
ASSI {11461}
((segid "BrD" and resid 34 and name HN))
((segid "BrD" and resid 33 and name HB1))
   3.500  3.100  2.000 peak    11461 weight  0.11000E+01 volume  0.11065E+03 ppm1   8.178 ppm2  1.094
ASSI {11471}
((segid "BrD" and resid 34 and name HN))
((segid "BrD" and resid 33 and name HG1))
   4.100  4.100  1.400 peak    11471 weight  0.11000E+01 volume  0.41672E+02 ppm1   8.177 ppm2  0.840

TABLE 2-continued

Unambiguous NOE-derived Inter-proton Distance Restraints

ASSI {11481}
((segid "BrD" and resid 34 and name HN))
((segid "BrD" and resid 33 and name HA))
  3.200  2.600  2.300 peak      11481  weight  0.11000E+01 volume  0.17351E+03 ppm1    8.182  ppm2    4.363
ASSI {11501}
((segid "BrD" and resid 36 and name HN))
((segid "BrD" and resid 35 and name HB1))
  4.000  4.000  1.500 peak      11501  weight  0.11000E+01 volume  0.43329E+02 ppm1    8.308  ppm2    2.840
ASSI {11611}
((segid "BrD" and resid 67 and name HN))
((segid "BrD" and resid 65 and name HB2))
  3.800  3.600  1.700 peak      11611  weight  0.11000E+01 volume  0.63235E+02 ppm1    8.832  ppm2    3.380
ASSI {11621}
((segid "BrD" and resid 67 and name HN))
((segid "BrD" and resid 66 and name HG1))
  3.700  3.400  1.800 peak      11621  weight  0.11000E+01 volume  0.76792E+02 ppm1    8.832  ppm2    2.146
ASSI {11641}
((segid "BrD" and resid 68 and name HN))
((segid "BrD" and resid 66 and name HA))
  2.500  1.600  1.600 peak      11641  weight  0.11000E+01 volume  0.80687E+03 ppm1    8.626  ppm2    5.012
ASSI {11681}
((segid "BrD" and resid 68 and name HN))
(segid "BrD" and resid 69 and name HG2 %)
  3.400  2.900  2.100 peak      11681  weight  0.11000E+01 volume  0.13257E+03 ppm1    8.626  ppm2    1.437
ASSI {11691}
((segid "BrD" and resid 68 and name HN))
(segid "BrD" and resid 69 and name HG1 %)
  3.700  3.400  1.800 peak      11691  weight  0.11000E+01 volume  0.73874E+02 ppm1    8.626  ppm2    1.562
ASSI {11721}
((segid "BrD" and resid 69 and name HN))
(segid "BrD" and resid 68 and name HD %)
  3.500  3.100  2.000 peak      11721  weight  0.11000E+01 volume  0.11106E+03 ppm1    8.306  ppm2  $$.782
ASSI {11781}
((segid "BrD" and resid 70 and name HN))
((segid "BrD" and resid 68 and name HA))
  3.200  2.600  2.300 peak      11781  weight  0.11000E+01 volume  0.19118E+03 ppm1    8.039  ppm2    5.135
ASSI {11791}
((segid "BrD" and resid 74 and name HN))
(segid "BrD" and resid 73 and name HD2 %)
  4.400  4.400  1.100 peak      11791  weight  0.11000E+01 volume  0.24720E+02 ppm1    7.536  ppm2    1.502
ASSI {11801}
((segid "BrD" and resid 74 and name HN))
(segid "BrD" and resid 73 and name HD1 %)
  4.100  4.100  1.400 peak      11801  weight  0.11000E+01 volume  0.39673E+02 ppm1    7.536  ppm2    1.531
ASSI {11811}
((segid "BrD" and resid 74 and name HN))
((segid "BrD" and resid 73 and name HG))
  3.100  2.400  2.400 peak      11811  weight  0.11000E+01 volume  0.21474E+03 ppm1    7.537  ppm2    2.401
ASSI {11821}
((segid "BrD" and resid 74 and name HN))
((segid "BrD" and resid 73 and name HB2))
  2.900  2.100  2.100 peak      11821  weight  0.11000E+01 volume  0.29959E+03 ppm1    7.536  ppm2    2.498
ASSI {11831}
((segid "BrD" and resid 74 and name HN))
((segid "BrD" and resid 73 and name HB1))
  3.000  2.200  2.200 peak      11831  weight  0.11000E+01 volume  0.27375E+03 ppm1    7.537  ppm2    2.603
ASSI {11871}
((segid "BrD" and resid 73 and name HN))
(segid "BrD" and resid 76 and name HB %)
  3.300  2.700  2.200 peak      11871  weight  0.11000E+01 volume  0.13672E+03 ppm1    8.046  ppm2    2.116
ASSI {11901}
((segid "BrD" and resid 74 and name HN))
((segid "BrD" and resid 18 and name HD1 %)
  3.700  3.400  1.800 peak      11901  weight  0.11000E+01 volume  0.74433E+02 ppm1    7.536  ppm2    1.076
ASSI {11981}
((segid "BrD" and resid 98 and name HN))
((segid "BrD" and resid 97 and name HB1))
  2.500  1.600  1.600 peak      11981  weight  0.11000E+01 volume  0.78973E+03 ppm1    9.125  ppm2    2.698
ASSI {11991}
((segid "BrD" and resid 98 and name HN))
((segid "BrD" and resid 97 and name HG1))
  3.100  2.400  2.400 peak      11991  weight  0.11000E+01 volume  0.20137E+03 ppm1    9.125  ppm2    2.426
ASSI {12001}
((segid "BrD" and resid 98 and name HN))
((segid "BrD" and resid 97 and name HG2))
  3.100  2.400  2.400 peak      12001  weight  0.11000E+01 volume  0.20070E+03 ppm1    9.124  ppm2    2.189

TABLE 2-continued

Unambiguous NOE-derived Inter-proton Distance Restraints

```
ASSI {12171}
((segid "BrD" and resid 101 and name HN))
((segid "BrD" and resid 99 and name HA))
   4.000  4.000  1.500 peak       12171  weight  0.11000E+01 volume  0.46069E+02 ppm1    8.513  ppm2  4.447
ASSI {12181}
((segid "BrD" and resid 101 and name HN))
((segid "BrD" and resid 97 and name HA))
   3.100  2.400  2.400 peak       12181  weight  0.11000E+01 volume  0.20943E+03 ppm1    8.513  ppm2  4.811
ASSI {12191}
((segid "BrD" and resid 103 and name HN))
((segid "BrD" and resid 102 and name HB1))
   2.800  2.000  2.000 peak       12191  weight  0.11000E+01 volume  0.37773E+03 ppm1    8.696  ppm2  2.012
ASSI {12201}
((segid "BrD" and resid 104 and name HN))
((segid "BrD" and resid 100 and name HA))
   3.200  2.600  2.300 peak       12201  weight  0.11000E+01 volume  0.18477E+03 ppm1    7.763  ppm2  4.936
ASSI {12231}
((segid "BrD" and resid 107 and name HN))
((segid "BrD" and resid 104 and name HA))
   3.000  2.200  2.200 peak       12231  weight  0.11000E+01 volume  0.26295E+03 ppm1    8.981  ppm2  4.682
ASSI {12321}
((segid "BrD" and resid 110 and name HN))
((segid "BrD" and resid 109 and name HD1))
   3.500  3.100  2.000 peak       12321  weight  0.11000E+01 volume  0.10959E+03 ppm1    8.714  ppm2  2.010
ASSI {12331}
((segid "BrD" and resid 110 and name HN))
((segid "BrD" and resid 109 and name HB1))
   2.700  1.800  1.800 peak       12331  weight  0.11000E+01 volume  0.48783E+03 ppm1    8.714  ppm2  2.337
ASSI {12341}
((segid "BrD" and resid 110 and name HN))
((segid "BrD" and resid 109 and name HG1))
   3.000  2.200  2.200 peak       12341  weight  0.11000E+01 volume  0.26294E+03 ppm1    8.714  ppm2  1.440
ASSI {12351}
((segid "BrD" and resid 111 and name HN))
((segid "BrD" and resid 110 and name HG12))
   3.000  2.200  2.200 peak       12351  weight  0.11000E+01 volume  0.27526E+03 ppm1    8.168  ppm2  1.680
ASSI {12361}
((segid "BrD" and resid 112 and name HN))
((segid "BrD" and resid 111 and name HG2))
   3.200  2.600  2.300 peak       12361  weight  0.11000E+01 volume  0.16739E+03 ppm1    8.668  ppm2  1.909
ASSI {12371}
((segid "BrD" and resid 113 and name HN))
((segid "BrD" and resid 110 and name HA))
   3.600  3.200  1.900 peak       12371  weight  0.11000E+01 volume  0.80563E+02 ppm1    8.217  ppm2  4.425
ASSI {12381}
((segid "BrD" and resid 113 and name HN))
((segid "BrD" and resid 111 and name HB1))
   3.900  3.800  1.600 peak       12381  weight  0.11000E+01 volume  0.57596E+02 ppm1    8.219  ppm2  2.486
ASSI {12391}
((segid "BrD" and resid 111 and name HN))
((segid "BrD" and resid 111 and name HB2))
   3.800  3.600  1.700 peak       12391  weight  0.11000E+01 volume  0.67480E+02 ppm1    8.218  ppm2  2.364
ASSI {12531}
((segid "BrD" and resid 48 and name HN))
((segid "BrD" and resid 47 and name HB1))
   4.300  4.300  1.200 peak       12531  weight  0.11000E+01 volume  0.28319E+02 ppm1    8.307  ppm2  3.796
ASSI {12541}
((segid "BrD" and resid 48 and name HN))
((segid "BrD" and resid 46 and name HA))
   4.000  4.000  1.500 peak       12541  weight  0.11000E+01 volume  0.44246E+02 ppm1    8.307  ppm2  4.152
ASSI {12551}
((segid "BrD" and resid 48 and name HN))
((segid "BrD" and resid 47 and name HB2))
   4.200  4.200  1.300 peak       12551  weight  0.11000E+01 volume  0.35395E+02 ppm1    8.307  ppm2  3.406
ASSI {12561}
((segid "BrD" and resid 47 and name HN))
(segid "BrD" and resid 46 and name HD %)
   3.500  3.100  2.000 peak       12561  weight  0.11000E+01 volume  0.10097E+03 ppm1    8.832  ppm2  5.727
ASSI {12571}
((segid "BrD" and resid 47 and name HN))
(segid "BrD" and resid 47 and name HD %)
   3.100  2.400  2.400 peak       12571  weight  0.11000E+01 volume  0.23274E+03 ppm1    8.833  ppm2  7.944
ASSI {12631}
((segid "BrD" and resid 51 and name HN))
((segid "BrD" and resid 50 and name HA))
   2.600  1.700  1.700 peak       12631  weight  0.11000E+01 volume  0.65616E+03 ppm1    8.377  ppm2  4.523
```

TABLE 2-continued

Unambiguous NOE-derived Inter-proton Distance Restraints

ASSI {12641}
((segid "BrD" and resid 52 and name HN))
((segid "BrD" and resid 51 and name HB1))
  3.400  2.900  2.100 peak       12641 weight  0.11000E+01 volume  0.11270E+03 ppm1     9.003  ppm2  1.995
ASSI {12651}
((segid "BrD" and resid 52 and name HN))
((segid "BrD" and resid 51 and name HG1))
  5.500  5.500  0.000 peak       12651 weight  0.11000E+01 volume  0.88686E+00 ppm1     9.003  ppm2  1.926
ASSI {12661}
((segid "BrD" and resid 52 and name HN))
((segid "BrD" and resid 51 and name HG2))
  3.400  2.900  2.100 peak       12661 weight  0.11000E+01 volume  0.11315E+03 ppm1     9.003  ppm2  1.780
ASSI {12671}
((segid "BrD" and resid 52 and name HN))
((segid "BrD" and resid 51 and name HB2))
  3.200  2.600  2.300 peak       12671 weight  0.11000E+01 volume  0.16847E+03 ppm1     9.004  ppm2  1.818
ASSI {12681}
((segid "BrD" and resid 52 and name HN))
(segid "BrD" and resid 50 and name HG2 %)
  2.800  2.000  2.000 peak       12681 weight  0.11000E+01 volume  0.38955E+03 ppm1     9.002  ppm2  0.991
ASSI {12731}
((segid "BrD" and resid 42 and name HN))
((segid "BrD" and resid 41 and name HA))
  3.400  2.900  2.100 peak       12731 weight  0.11000E+01 volume  0.12554E+03 ppm1     7.822  ppm2  4.650
ASSI {12771}
((segid "BrD" and resid 42 and name HN))
(segid "BrD" and resid 41 and name HG2 %)
  4.200  4.200  1.300 peak       12771 weight  0.11000E+01 volume  0.34295E+02 ppm1     7.821  ppm2  1.874
ASSI {12781}
((segid "BrD" and resid 97 and name HN))
(segid "BrD" and resid 96 and name HD %)
  3.300  2.700  2.200 peak       12781 weight  0.11000E+01 volume  0.13710E+03 ppm1     8.674  ppm2  7.701
ASSI {12791}
((segid "BrD" and resid 20 and name HN))
((segid "BrD" and resid 19 and name HG1))
  3.400  2.900  2.100 peak       12791 weight  0.11000E+01 volume  0.11346E+03 ppm1     8.146  ppm2  1.687
ASSI {12801}
((segid "BrD" and resid 19 and name HN))
((segid "BrD" and resid 18 and name HB2))
  3.400  2.900  2.100 peak       12801 weight  0.11000E+01 volume  0.11595E+03 ppm1     9.186  ppm2  0.901
ASSI {12811}
((segid "BrD" and resid 19 and name HN))
(segid "BrD" and resid 63 and name HD1 %)
  3.100  2.400  2.400 peak       12811 weight  0.11000E+01 volume  0.22952E+03 ppm1     9.186  ppm2  1.642
ASSI {12821}
((segid "BrD" and resid 19 and name HN))
(segid "BrD" and resid 63 and name HD2 %)
  3.000  2.200  2.200 peak       12821 weight  0.11000E+01 volume  0.27823E+03 ppm1     9.187  ppm2  1.476
ASSI {12831}
((segid "BrD" and resid 19 and name HN))
((segid "BrD" and resid 16 and name HA))
  3.000  2.200  2.200 peak       12831 weight  0.11000E+01 volume  0.27123E+03 ppm1     9.187  ppm2  4.516
ASSI {12871}
((segid "BrD" and resid 20 and name HN))
((segid "BrD" and resid 18 and name HG))
  3.800  3.600  1.700 peak       12871 weight  0.11000E+01 volume  0.64336E+02 ppm1     8.247  ppm2  2.290
ASSI {12931}
((segid "BrD" and resid 23 and name HN))
((segid "BrD" and resid 22 and name HB1))
  2.600  1.700  1.700 peak       12931 weight  0.11000E+01 volume  0.65708E+03 ppm1     9.120  ppm2  2.697
ASSI {12941}
((segid "BrD" and resid 23 and name HN))
((segid "BrD" and resid 22 and name HB2))
  2.800  2.000  2.000 peak       12941 weight  0.11000E+01 volume  0.39331E+03 ppm1     9.122  ppm2  2.310
ASSI {13051}
((segid "BrD" and resid 27 and name HN))
((segid "BrD" and resid 26 and name HD1))
  2.700  1.800  1.800 peak       13051 weight  0.11000E+01 volume  0.47384E+03 ppm1     8.168  ppm2  2.127
ASSI {13071}
((segid "BrD" and resid 27 and name HN))
((segid "BrD" and resid 24 and name HG1))
  3.500  3.100  2.000 peak       13071 weight  0.11000E+01 volume  0.10804E+03 ppm1     8.170  ppm2  3.447
ASSI {13081}
((segid "BrD" and resid 27 and name HN))
((segid "BrD" and resid 24 and name HG2))
  3.700  3.400  1.800 peak       13081 weight  0.11000E+01 volume  0.74378E+02 ppm1     8.170  ppm2  3.074

TABLE 2-continued

Unambiguous NOE-derived Inter-proton Distance Restraints

ASSI {13141}
((segid "BrD" and resid 60 and name HN))
((segid "BrD" and resid 59 and name HB2))
  2.900  2.100  2.100  peak    13141  weight  0.11000E+01  volume  0.32659E+03  ppm1  8.565  ppm2  2.522
ASSI {13151}
((segid "BrD" and resid 65 and name HN))
((segid "BrD" and resid 64 and name HG1))
  3.300  2.700  2.200  peak    13151  weight  0.11000E+01  volume  0.34156E+03  ppm1  8.565  ppm2  2.203
ASSI {13211}
((segid "BrD" and resid 15 and name HN))
((segid "BrD" and resid 14 and name HG))
  3.700  3.400  1.800  peak    13211  weight  0.11000E+01  volume  0.73008E+02  ppm1  8.597  ppm2  2.087
ASSI {13281}
(segid "BrD" and resid 65 and name HD2 %)
((segid "BrD" and resid 64 and name HB1))
  3.600  3.200  1.900  peak    13281  weight  0.11000E+01  volume  0.89819E+02  ppm1  8.205  ppm2  2.662
ASSI {13291}
((segid "BrD" and resid 65 and name HD22))
((segid "BrD" and resid 64 and name HB1))
  3.600  3.200  1.900  peak    13291  weight  0.11000E+01  volume  0.84418E+02  ppm1  7.576  ppm2  2.662
ASSI {13321}
((segid "BrD" and resid 93 and name HN))
((segid "BrD" and resid 93 and name HB1))
  4.100  4.100  1.400  peak    13321  weight  0.11000E+01  volume  0.42284E+02  ppm1  8.713  ppm2  5.009
ASSI {13331}
((segid "BrD" and resid 94 and name HN))
((segid "BrD" and resid 93 and name HB1))
  3.700  3.400  1.800  peak    13331  weight  0.11000E+01  volume  0.78957E+02  ppm1  9.679  ppm2  5.000
ASSI {13341}
((segid "BrD" and resid 17 and name HN))
((segid "BrD" and resid 16 and name HB1))
  3.400  2.900  2.100  peak    13341  weight  0.11000E+01  volume  0.11732E+03  ppm1  8.670  ppm2  4.602
ASSI {13351}
((segid "BrD" and resid 62 and name HN))
((segid "BrD" and resid 62 and name HD2))
  2.700  1.800  1.800  peak    13351  weight  0.11000E+01  volume  0.44005E+03  ppm1  8.998  ppm2  2.658
ASSI {13361}
((segid "BrD" and resid 86 and name HN))
((segid "BrD" and resid 86 and name HG1))
  4.100  4.100  1.400  peak    13361  weight  0.11000E+01  volume  0.42972E+02  ppm1  8.423  ppm2  1.920
ASSI {13371}
((segid "BrD" and resid 17 and name HN))
((segid "BrD" and resid 14 and name HA))
  2.600  1.700  1.700  peak    13371  weight  0.11000E+01  volume  0.66944E+03  ppm1  8.670  ppm2  4.652
ASSI {13381}
((segid "BrD" and resid 18 and name HN))
((segid "BrD" and resid 15 and name HA))
  3.800  3.600  1.700  peak    13381  weight  0.11000E+01  volume  0.66429E+02  ppm1  9.073  ppm2  8.620
ASSI {13391}
((segid "BrD" and resid 19 and name HN))
((segid "BrD" and resid 18 and name HN))
  2.300  1.300  1.300  peak    13391  weight  0.11000E+01  volume  0.12618E+04  ppm1  9.186  ppm2  9.067
ASSI {13401}
((segid "BrD" and resid 59 and name HN))
((segid "BrD" and resid 56 and name HA))
  3.100  2.400  2.400  peak    13401  weight  0.11000E+01  volume  0.22047E+03  ppm1  8.498  ppm2  4.643
ASSI {13421}
((segid "BrD" and resid 79 and name HN))
((segid "BrD" and resid 75 and name HA))
  4.000  4.000  1.500  peak    13421  weight  0.11000E+01  volume  0.47743E+02  ppm1  8.680  ppm2  4.518
ASSI {13431}
((segid "BrD" and resid 81 and name HN))
((segid "BrD" and resid 77 and name HA))
  4.500  4.500  1.000  peak    13431  weight  0.11000E+01  volume  0.23511E+02  ppm1  7.639  ppm2  4.978
ASSI {13441}
((segid "BrD" and resid 85 and name HN))
((segid "BrD" and resid 83 and name HA))
  3.600  3.200  1.900  peak    13441  weight  0.11000E+01  volume  0.85635E+02  ppm1  7.519  ppm2  4.441
ASSI {13451}
((segid "BrD" and resid 85 and name HN))
((segid "BrD" and resid 81 and name HA))
  2.500  1.600  1.600  peak    13451  weight  0.11000E+01  volume  0.75325E+03  ppm1  7.517  ppm2  3.646
ASSI {13461}
((segid "BrD" and resid 88 and name HN))
((segid "BrD" and resid 84 and name HA))
  2.800  2.000  2.000  peak    13461  weight  0.11000E+01  volume  0.40309E+03  ppm1  8.357  ppm2  4.922

TABLE 2-continued

Unambiguous NOE-derived Inter-proton Distance Restraints

ASSI {13481}
((segid "BrD" and resid 81 and name HN))
((segid "BrD" and resid 83 and name HN))
  3.900  3.800  1.600 peak       13481  weight  0.11000E+01 volume  0.50469E+02 ppm1      7.640  ppm2  9.655
ASSI {13491}
((segid "BrD" and resid 96 and name HN))
((segid "BrD" and resid 93 and name HA))
  3.700  3.400  1.800 peak       13491  weight  0.11000E+01 volume  0.70852E+02 ppm1      7.981  ppm2  5.013
ASSI {13501}
((segid "BrD" and resid 109 and name HN))
((segid "BrD" and resid 105 and name HA))
  4.600  4.600  0.900 peak       13501  weight  0.11000E+01 volume  0.18885E+02 ppm1      8.574  ppm2  4.935
ASSI {13511}
((segid "BrD" and resid 110 and name HN))
((segid "BrD" and resid 108 and name HA))
  3.500  3.100  2.000 peak       13511  weight  0.11000E+01 volume  0.11146E+03 ppm1      8.714  ppm2  4.816
ASSI {13521}
((segid "BrD" and resid 92 and name HN))
((segid "BrD" and resid 91 and name HA))
  3.200  2.600  2.300 peak       13521  weight  0.11000E+01 volume  0164567E+03 ppm1      8.873  ppm2  5.343
ASSI {13541}
((segid "BrD" and resid 98 and name HN))
((segid "BrD" and resid 100 and name HN))
  2.900  2.100  2.100 peak       13541  weight  0.11000E+01 volume  0.30894E+03 ppm1      9.125  ppm2  8.653
ASSI {13551}
((segid "BrD" and resid 103 and name HN))
((segid "BrD" and resid 101 and name HN))
  2.900  2.100  2.100 peak       13551  weight  0.11000E+01 volume  0.34725E+03 ppm1      8.696  ppm2  8.519
ASSI {13561}
((segid "BrD" and resid 32 and name HN))
((segid "BrD" and resid 30 and name HA))
  4.400  4.400  1.100 peak       13561  weight  0.11000E+01 volume  0.25941E+02 ppm1      7.739  ppm2  5.445
ASSI {13571}
((segid "BrD" and resid 24 and name HN))
((segid "BrD" and resid 23 and name HB2))
  2.800  2.000  2.000 peak       13571  weight  0.11000E+01 volume  0.42825E+03 ppm1      8.655  ppm2  2.870
ASSI {13581}
((segid "BrD" and resid 73 and name HN))
((segid "BrD" and resid 75 and name HN))
  4.000  4.000  1.500 peak       13581  weight  0.11000E+01 volume  0.46662E+02 ppm1      8.045  ppm2  9.084
ASSI {13591}
((segid "BrD" and resid 62 and name HN))
((segid "BrD" and resid 61 and name HG1))
  3.900  3.800  1.600 peak       13591  weight  0.11000E+01 volume  0.54843E+02 ppm1      8.999  ppm2  2.952
ASSI {13611}
((segid "BrD" and resid 67 and name HN))
((segid "BrD" and resid 65 and name HB1))
  2.800  2.000  2.000 peak       13611  weight  0.11000E+01 volume  0.36617E+03 ppm1      8.832  ppm2  3.626
ASSI {13621}
((segid "BrD" and resid 75 and name HN))
((segid "BrD" and resid 74 and name HB2))
  3.200  2.600  2.300 peak       13621  weight  0.11000E+01 volume  0.17250E+03 ppm1      9.106  ppm2  2.988
ASSI {13641}
((segid "BrD" and resid 104 and name HN))
((segid "BrD" and resid 106 and name HN))
  4.900  4.900  0.600 peak       13641  weight  0.11000E+01 volume  0.14134E+02 ppm1      7.763  ppm2  9.736
ASSI {13671}
((segid "BrD" and resid 74 and name HN))
(segid "BrD" and resid 18 and name HD2 %)
  3.900  2.800  1.600 peak       13671  weight  0.11000E+01 volume  0.56031E+02 ppm1      7.545  ppm2  0.414
ASSI {13701}
((segid "BrD" and resid 61 and name HN))
((segid "BrD" and resid 61 and name HB1))
  2.800  2.000  2.000 peak       13701  weight  0.11000E+01 volume  0.41690E+03 ppm1      8.743  ppm2  2.837
ASSI {13711}
((segid "BrD" and resid 62 and name HN))
((segid "BrD" and resid 61 and name HB1))
  2.800  2.000  2.000 peak       13711  weight  0.11000E+01 volume  0.40898E+03 ppm1      8.990  ppm2  2.853
ASSI {13731}
((segid "BrD" and resid 25 and name HN))
((segid "BrD" and resid 21 and name HA))
  2.900  2.100  2.100 peak       13731  weight  0.11000E+01 volume  0.30325+03 ppm1      9.134  ppm2  4.393
ASSI {13741}
((segid "BrD" and resid 63 and name HN))
((segid "BrD" and resid 59 and name HA))
  3.200  2.600  2.300 peak       13741  weight  0.11000E+01 volume  0.16317E+03 ppm1      9.472  ppm2  4.926

TABLE 2-continued

Unambiguous NOE-derived Inter-proton Distance Restraints

ASSI {13761}
((segid "BrD" and resid 74 and name HN))
((segid "BrD" and resid 71 and name HA))
 3.200 2.600 2.300 peak    13761 weight 0.11000E+01 volume 0.19208E+03 ppm1  7.536 ppm2 4.622
ASSI {13771}
((segid "BrD" and resid 75 and name HN))
((segid "BrD" and resid 71 and name HA))
 3.100 2.400 2.400 peak    13771 weight 0.11000E+01 volume 0.21726E+03 ppm1  9.106 ppm2 4.628
ASSI {13781}
((segid "BrD" and resid 77 and name HN))
((segid "BrD" and resid 74 and name HA))
 3.200 2.600 2.300 peak    13781 weight 0.11000E+01 volume 0.16504E+03 ppm1  7.996 ppm2 4.371
ASSI {13791}
((segid "BrD" and resid 105 and name HN))
((segid "BrD" and resid 101 and name HA))
 3.200 2.600 2.300 peak    13791 weight 0.11000E+01 volume 0.19414E+03 ppm1  8.487 ppm2 4.253
ASSI {13801}
((segid "BrD" and resid 26 and name HN))
((segid "BrD" and resid 24 and name HA))
 3.900 3.800 1.600 peak    13801 weight 0.11000E+01 volume 0.52793E+02 ppm1  9.196 ppm2 4.755
ASSI {13811}
((segid "BrD" and resid 26 and name HN))
((segid "BrD" and resid 25 and name HA))
 3.800 3.600 1.700 peak    13811 weight 0.11000E+01 volume 0.62704E+02 ppm1  9.196 ppm2 4.415
ASSI {13821}
((segid "BrD" and resid 29 and name HN))
((segid "BrD" and resid 25 and name HA))
 5.500 5.500 0.000 peak    13821 weight 0.11000E+01 volume 0.27795E+01 ppm1  9.152 ppm2 4.451
ASSI {13831}
((segid "BrD" and resid 54 and name HN))
((segid "BrD" and resid 55 and name HN))
 2.900 2.100 2.100 peak    13831 weight 0.11000E+01 volume 0.31830E+03 ppm1  9.037 ppm2 7.972
ASSI {13851}
((segid "BrD" and resid 48 and name HN))
(segid "BrD" and resid 47 and name HD %)
 3.900 3.800 1.600 peak    13851 weight 0.11000E+01 volume 0.57580E+02 ppm1  8.307 ppm2 7.949
ASSI {13861}
((segid "BrD" and resid 96 and name HN))
(segid "BrD" and resid 95 and name HD %)
 3.500 3.100 2.000 peak    13861 weight 0.11000E+01 volume 0.10869E+03 ppm1  7.979 ppm2 7.498
ASSI {14011}
((segid "BrD" and resid 108 and name HN))
(segid "BrD" and resid 107 and name HD %)
 4.300 4.300 1.200 peak    14011 weight 0.11000E+01 volume 0.30492E+02 ppm1  8.526 ppm2 7.782
ASSI {14881}
((segid "BrD" and resid 54 and name HN))
((segid "BrD" and resid 54 and name HG1))
 4.500 4.500 1.000 peak    14881 weight 0.11000E+01 volume 0.23600E+02 ppm1  9.038 ppm2 3.297
ASSI {15591}
((segid "BrD" and resid 32 and name HE1))
((segid "BrD" and resid 32 and name HB2))
 4.000 4.000 1.500 peak    15591 weight 0.11000E+01 volume 0.47456E+02 ppm1 11.081 ppm2 3.958
ASSI {15601}
((segid "BrD" and resid 32 and name HE1))
((segid "BrD" and resid 32 and name HB1))
 5.200 5.200 0.300 peak    15601 weight 0.11000E+01 volume 0.94290E+01 ppm1 11.081 ppm2 4.201
ASSI {111}
((segid "BrD" and resid 99 and name HN))
((segid "BrD" and resid 34 and name HZ))
 3.100 2.400 2.400 peak      111 weight 0.10000E+01 volume 0.20460E+03 ppm1  8.936 ppm2 7.899
ASSI {801}
((segid "BrD" and resid 97 and name HN))
((segid "BrD" and resid 97 and name HE1))
 4.000 4.000 1.500 peak      801 weight 0.10000E+01 volume 0.47904E+02 ppm1  8.673 ppm2 3.572
ASSI {931}
((segid "BrD" and resid 117 and name HN))
((segid "BrD" and resid 116 and name HN))
 3.600 3.100 2.000 peak      931 weight 0.10000E+01 volume 0.10704E+03 ppm1  8.883 ppm2 8.075
ASSI {1891}
((segid "BrD" and resid 83 and name HN))
((segid "BrD" and resid 85 and name HN))
 4.000 4.000 1.500 peak     1891 weight 0.10000E+01 volume 0.44105E+02 ppm1  9.660 ppm2 7.505
ASSI {2331}
((segid "BrD" and resid 49 and name HN))
((segid "BrD" and resid 50 and name HA))
 4.000 4.000 1.500 peak     2331 weight 0.10000E+01 volume 0.49544E+02 ppm1  7.761 ppm2 4.525

TABLE 2-continued

Unambiguous NOE-derived Inter-proton Distance Restraints

ASSI {2631}
((segid "BrD" and resid 103 and name HN))
(segid "BrD" and resid 82 and name HD %)
  3.800  3.600  1.700 peak         2631  weight  0.10000E+01 volume  0.64814E+02 ppm1      8.695 ppm2  7.246
ASSI {3601}
((segid "BrD" and resid 9 and name HN))
((segid "BrD" and resid 9 and name HA))
  2.900  2.100  2.100 peak         3601  weight  0.10000E+01 volume  0.32855E+03 ppm1      9.052 ppm2  4.936
ASSI {3751}
((segid "BrD" and resid 56 and name HN))
((segid "BrD" and resid 35 and name HA))
  3.200  2.600  2.300 peak         3751  weight  0.10000E+01 volume  0.18743E+03 ppm1      9.678 ppm2  4.895
ASSI {4371}
((segid "BrD" and resid 40 and name HN))
((segid "BrD" and resid 42 and name HA))
  3.400  2.900  2.100 peak         4371  weight  0.10000E+01 volume  0.12104E+03 ppm1      8.662 ppm2  5.021
ASSI {4671}
((segid "BrD" and resid 61 and name HN))
((segid "BrD" and resid 60 and name HB1))
  2.900  2.100  2.100 peak         4671  weight  0.10000E+01 volume  0.31176E+03 ppm1      8.746 ppm2  4.992
ASSI {5081}
((segid "BrD" and resid 73 and name HN))
((segid "BrD" and resid 74 and name HB2))
  3.100  2.400  2.400 peak         5081  weight  0.10000E+01 volume  0.21337E+03 ppm1      8.007 ppm2  3.018
ASSI {7641}
((segid "BrD" and resid 76 and name HN))
((segid "BrD" and resid 73 and name HA))
  3.500  3.100  2.000 peak         7641  weight  0.10000E+01 volume  0.97995E+02 ppm1      8.611 ppm2  4.812
ASSI {7691}
((segid "BrD" and resid 83 and name HN))
((segid "BrD" and resid 80 and name HA))
  2.800  2.000  2.000 peak         7691  weight  0.10000E+01 volume  0.35765E+03 ppm1      9.660 ppm2  4.675
ASSI {8061}
((segid "BrD" and resid 39 and name HN))
((segid "BrD" and resid 38 and name HN))
  4.300  4.300  1.200 peak         8061  weight  0.10000E+01 volume  0.29321E+02 ppm1      9.651 ppm2  8.726
ASSI {8071}
((segid "BrD" and resid 39 and name HN))
((segid "BrD" and resid 42 and name HG1))
  4.100  4.100  1.400 peak         8071  weight  0.10000E+01 volume  0.37403E+02 ppm1      9.657 ppm2  2.891
ASSI {8081}
((segid "BrD" and resid 39 and name HN))
((segid "BrD" and resid 42 and name HB1))
  3.900  3.600  1.600 peak         8081  weight  0.10000E+01 volume  0.55108E+02 ppm1      9.658 ppm2  2.784
ASSI {8091}
((segid "BrD" and resid 39 and name HN))
((segid "BrD" and resid 42 and name HB2))
  4.200  4.200  1.300 peak         8091  weight  0.10000E+01 volume  0.33585E+02 ppm1      9.651 ppm2  2.607
ASSI {8141}
((segid "BrD" and resid 57 and name HN))
((segid "BrD" and resid 36 and name HA))
  3.100  2.400  2.400 peak         8141  weight  0.10000E+01 volume  0.21622E+03 ppm1      9.359 ppm2  5.440
ASSI {8151}
((segid "BrD" and resid 57 and name HN))
((segid "BrD" and resid 58 and name HA))
  4.100  4.100  1.400 peak         8151  weight  0.10000E+01 volume  0.38316E+02 ppm1      9.359 ppm2  4.453
ASSI {8161}
((segid "BrD" and resid 57 and name HN))
((segid "BrD" and resid 37 and name HD1))
  3.700  3.400  1.800 peak         8161  weight  0.10000E+01 volume  0.78885E+02 ppm1      9.359 ppm2  4.288
ASSI {8221}
((segid "BrD" and resid 114 and name HN))
((segid "BrD" and resid 115 and name HG))
  3.800  3.600  1.700 peak         8221  weight  0.10000E+01 volume  0.68239E+02 ppm1      8.377 ppm2  2.169
OR {8221}
((segid "BrD" and resid 114 and name HN))
((segid "BrD" and resid 115 and name HB1))
ASSI {8231}
((segid "BrD" and resid 114 and name HN))
(segid "BrD" and resid 115 and name HD1 %)
  3.700  3.400  1.800 peak         8231  weight  0.10000E+01 volume  0.72638E+02 ppm1      8.375 ppm2  1.308
ASSI {8271}
((segid "BrD" and resid 28 and name HN))
(segid "BrD" and resid 31 and name HB %)
  3.400  2.900  2.100 peak         8271  weight  0.10000E+01 volume  0.12341E+03 ppm1      8.166 ppm2  2.308

TABLE 2-continued

Unambiguous NOE-derived Inter-proton Distance Restraints

ASSI {8281}
((segid "BrD" and resid 28 and name HN))
((segid "BrD" and resid 26 and name HB1))
  3.700  3.400  1.800 peak       8281  weight  0.10000E+01 volume  0.69844E+02 ppm1    8.166  ppm2  2.476
ASSI {8301}
((segid "BrD" and resid 28 and name HN))
(segid "BrD" and resid 102 and name HD1 %)
  3.400  2.900  2.100 peak       8301  weight  0.10000E+01 volume  0.11542E+03 ppm1    8.166  ppm2  1.318
ASSI {8311}
((segid "BrD" and resid 118 and name HN))
((segid "BrD" and resid 116 and name HG12))
  3.200  2.600  2.300 peak       8311  weight  0.10000E+01 volume  0.19156E+03 ppm1    8.381  ppm2  1.558
ASSI {8321}
((segid "BrD" and resid 118 and name HN))
(segid "BrD" and resid 116 and name HD1 %)
  4.100  4.100  1.400 peak       8321  weight  0.10000E+01 volume  0.39844E+02 ppm1    8.380  ppm2  1.394
OR {8321}
((segid "BrD" and resid 118 and name HN))
(segid "BrD" and resid 116 and name HG2 %)
ASSI {8331}
((segid "BrD" and resid 118 and name HN))
(segid "BrD" and resid 110 and name HG2 %)
  3.400  2.900  2.100 peak       8331  weight  0.10000E+01 volume  0.11494E+03 ppm1    8.381  ppm2  1.296
ASSI {8341}
((segid "BrD" and resid 51 and name HN))
(segid "BrD" and resid 50 and name HD1 %)
  4.000  4.000  1.500 peak       8341  weight  0.10000E+01 volume  0.45762E+02 ppm1    8.381  ppm2  1.156
ASSI {8401}
((segid "BrD" and resid 38 and name HN))
((segid "BrD" and resid 37 and name HB2))
  3.000  2.200  2.200 peak       8401  weight  0.10000E+01 volume  0.24692E+03 ppm1    8.733  ppm2  2.290
ASSI {8411}
((segid "BrD" and resid 117 and name HN))
((segid "BrD" and resid 118 and name HN))
  3.900  3.800  1.600 peak       8411  weight  0.10000E+01 volume  0.55844E+02 ppm1    8.880  ppm2  8.368
ASSI {8421}
((segid "BrD" and resid 117 and name HN))
((segid "BrD" and resid 116 and name HG11))
  3.900  3.800  1.600 peak       8421  weight  0.10000E+01 volume  0.57435E+02 ppm1    8.876  ppm2  1.915
ASSI {8441}
((segid "BrD" and resid 7 and name HN))
((segid "BrD" and resid 6 and name HD1))
  3.800  3.600  1.700 peak       8441  weight  0.10000E+01 volume  0.67409E+02 ppm1    8.923  ppm2  2.338
ASSI {8451}
((segid "BrD" and resid 102 and name HN))
((segid "BrD" and resid 28 and name HE1))
  3.900  3.800  1.600 peak       8451  weight  0.10000E+01 volume  0.51665E+02 ppm1    9.156  ppm2  8.153
ASSI {8461}
((segid "BrD" and resid 102 and name HN))
(segid "BrD" and resid 82 and name HE %)
  4.100  4.100  1.400 peak       8461  weight  0.10000E+01 volume  0.42485E+02 ppm1    9.156  ppm2  7.050
OR {8461}
((segid "BrD" and resid 102 and name HN))
((segid "BrD" and resid 82 and name HZ))
ASSI {8481}
((segid "BrD" and resid 102 and name HN))
((segid "BrD" and resid 103 and name HB1))
  3.600  3.200  1.900 peak       8481  weight  0.10000E+01 volume  0.86913E+02 ppm1    9.156  ppm2  2.348
ASSI {8501}
((segid "BrD" and resid 50 and name HN))
((segid "BrD" and resid 48 and name HA))
  5.100  5.100  0.400 peak       8501  weight  0.10000E+01 volume  0.11267E+02 ppm1    8.564  ppm2  4.822
ASSI {8551}
((segid "BrD" and resid 46 and name HN))
((segid "BrD" and resid 44 and name HA))
  4.000  4.000  1.500 peak       8551  weight  0.10000E+01 volume  0.43724E+02 ppm1    8.562  ppm2  5.119
ASSI {8581}
((segid "BrD" and resid 46 and name HN))
(segid "BrD" and resid 43 and name HB %)
  2.800  2.000  2.000 peak       8581  weight  0.10000E+01 volume  0.40920E+03 ppm1    8.562  ppm2  1.692
ASSI {8601}
((segid "BrD" and resid 43 and name HN))
((segid "BrD" and resid 39 and name HB1))
  4.100  4.100  1.400 peak       8601  weight  0.10000E+01 volume  0.39702E+02 ppm1    8.001  ppm2  2.497

TABLE 2-continued

Unambiguous NOE-derived Inter-proton Distance Restraints

ASSI {8611}
((segid "BrD" and resid 43 and name HN))
((segid "BrD" and resid 39 and name HD1))
  3.500  3.100  2.000 peak       8611  weight  0.10000E+01 volume  0.96093E+02 ppm1      8.001  ppm2  2.292
ASSI {8621}
((segid "BrD" and resid 43 and name HN))
(segid "BrD" and resid 41 and name HG2 %)
  4.200  4.200  1.300 peak       8621  weight  0.10000E+01 volume  0.33897E+02 ppm1      8.001  ppm2  1.887
ASSI {8631}
((segid "BrD" and resid 43 and name HN))
(segid "BrD" and resid 38 and name HG1 %)
  4.300  4.300  1.200 peak       8631  weight  0.10000E+01 volume  0.32108E+02 ppm1      8.002  ppm2  1.058
ASSI {8641}
((segid "BrD" and resid 43 and name HN))
(segid "BrD" and resid 38 and name HG2 %)
  3.900  3.800  1.600 peak       8641  weight  0.10000E+01 volume  0.57231E+02 ppm1      8.001  ppm2  0.778
ASSI {8661}
((segid "BrD" and resid 111 and name HN))
((segid "BrD" and resid 112 and name HB1))
  3.800  3.600  1.700 peak       8661  weight  0.10000E+01 volume  0.66898E+02 ppm1      8.167  ppm2  2.659
ASSI {8681}
((segid "BrD" and resid 111 and name HN))
(segid "BrD" and resid 110 and name HG2 %)
  3.000  2.200  2.200 peak       8681  weight  0.10000E+01 volume  0.28506E+03 ppm1      8.169  ppm2  1.250
ASSI {8691}
((segid "BrD" and resid 111 and name HN))
(segid "BrD" and resid 116 and name HD1 %)
  3.400  2.900  2.100 peak       8691  weight  0.10000E+01 volume  0.11425E+03 ppm1      8.168  ppm2  1.396
ASSI {8711}
((segid "BrD" and resid 58 and name HN))
((segid "BrD" and resid 37 and name HD1))
  3.700  3.400  1.800 peak       8711  weight  0.10000E+01 volume  0.73156E+02 ppm1     10.051  ppm2  4.255
ASSI {8721}
((segid "BrD" and resid 58 and name HN))
((segid "BrD" and resid 59 and name HG2))
  5.500  5.500  0.000 peak       8721  weight  0.10000E+01 volume  0.48442E+00 ppm1     10.051  ppm2  3.087
ASSI {8801}
((segid "BrD" and resid 58 and name HN))
(segid "BrD" and resid 54 and name HE %)
  4.600  4.600  0.900 peak       8801  weight  0.10000E+01 volume  0.21191E+02 ppm1     10.050  ppm2  2.534
ASSI {8971}
((segid "BrD" and resid 112 and name HN))
(segid "BrD" and resid 110 and name HG2 %)
  3.600  3.600  1.700 peak       8971  weight  0.10000E+01 volume  0.60828E+02 ppm1      8.669  ppm2  1.263
ASSI {8991}
((segid "BrD" and resid 105 and name HN))
((segid "BrD" and resid 106 and name HB1))
  3.500  3.100  2.000 peak       8991  weight  0.10000E+01 volume  0.10888E+03 ppm1      8.487  ppm2  3.870
ASSI {9041}
((segid "BrD" and resid 105 and name HN))
(segid "BrD" and resid 102 and name HD2 %)
  3.700  3.400  1.800 peak       9041  weight  0.10000E+01 volume  0.76403E+02 ppm1      8.486  ppm2  1.320
OR {9041}
((segid "BrD" and resid 105 and name HN))
(segid "BrD" and resid 102 and name HD1 %)
ASSI {9051}
((segid "BrD" and resid 105 and name HN))
(segid "BrD" and resid 101 and name HG2 %)
  3.900  3.800  1.600 peak       9051  weight  0.10000E+01 volume  0.50603E+02 ppm1      8.486  ppm2  1.602
ASSI {9131}
((segid "BrD" and resid 21 and name HN))
((segid "BrD" and resid 21 and name HG12))
  3.200  2.600  2.300 peak       9131  weight  0.10000E+01 volume  0.17190E+03 ppm1      8.574  ppm2  1.620
OR {9131}
(segid "BrD" and resid 21 and name HN))
(segid "BrD" and resid 21 and name HG2 %)
ASSI {9211}
((segid "BrD" and resid 106 and name HN))
(segid "BrD" and resid 102 and name HD2 %)
  3.800  3.600  1.700 peak       9211  weight  0.10000E+01 volume  0.58744E+02 ppm1      9.740  ppm2  1.314
ASSI {9221}
((segid "BrD" and resid 106 and name HN))
(segid "BrD" and resid 82 and name HE %)
  4.600  4.600  0.900 peak       9221  weight  0.10000E+01 volume  0.19539E+02 ppm1      9.740  ppm2  7.033
OR {9221}
((segid "BrD" and resid 106 and name HN))
((segid "BrD" and resid 82 and name HZ))

TABLE 2-continued

Unambiguous NOE-derived Inter-proton Distance Restraints

ASSI {9231}
((segid "BrD" and resid 84 and name HN))
((segid "BrD" and resid 80 and name HA))
  2.400  1.400  1.400 peak      9231  weight  0.10000E+01 volume  0.97923E+03 ppm1     9.464  ppm2  4.674
ASSI {9261}
((segid "BrD" and resid 84 and name HN))
(segid "BrD" and resid 50 and name HD1 %)
  4.700  4.700  0.800 peak      9261  weight  0.10000E+01 volume  0.17291E+02 ppm1     9.463  ppm2  1.136
ASSI {9271}
((segid "BrD" and resid 84 and name HN))
(segid "BrD" and resid 50 and name HG2 %)
  4.800  4.800  0.700 peak      9271  weight  0.10000E+01 volume  0.16063E+02 ppm1     9.464  ppm2  0.994
ASSI {9381}
((segid "BrD" and resid 63 and name HN))
((segid "BrD" and resid 63 and name HB1))
  2.800  2.000  2.000 peak      9381  weight  0.10000E+01 volume  0.41354E+03 ppm1     9.456  ppm2  2.904
ASSI {9411}
((segid "BrD" and resid 22 and name HN))
(segid "BrD" and resid 25 and name HG1 %)
  3.600  3.200  1.900 peak      9411  weight  0.10000E+01 volume  0.92991E+02 ppm1     9.456  ppm2  1.797
ASSI {9421}
((segid "BrD" and resid 22 and name HN))
(segid "BrD" and resid 21 and name HD1 %)
  3.700  3.400  1.800 peak      9421  weight  0.10000E+01 volume  0.76602E+02 ppm1     9.456  ppm2  1.228
ASSI {9431}
((segid "BrD" and resid 63 and name HN))
(segid "BrD" and resid 68 and name HD %)
  3.800  3.600  1.700 peak      9431  weight  0.10000E+01 volume  0.63643E+02 ppm1     9.456  ppm2  7.806
ASSI {9481}
((segid "BrD" and resid 109 and name HN))
((segid "BrD" and resid 109 and name HD1))
  3.100  2.400  2.400 peak      9481  weight  0.10000E+01 volume  0.19915E+03 ppm1     8.556  ppm2  2.031
ASSI {9521}
((segid "BrD" and resid 103 and name HN))
(segid "BrD" and resid 82 and name HE %)
  3.300  2.700  2.200 peak      9521  weight  0.10000E+01 volume  0.14688E+03 ppm1     8.695  ppm2  7.050
OR {9521}
((segid "BrD" and resid 103 and name HN))
((segid "BrD" and resid 82 and name HZ))
ASSI {9541}
((segid "BrD" and resid 112 and name HN))
((segid "BrD" and resid 111 and name HA))
  4.900  4.900  0.600 peak      9541  weight  0.10000E+01 volume  0.13131E+02 ppm1     8.696  ppm2  4.682
ASSI {9611}
((segid "BrD" and resid 99 and name HN))
(segid "BrD" and resid 34 and name HE %)
  3.500  3.100  2.000 peak      9611  weight  0.10000E+01 volume  0.10701E+03 ppm1     8.936  ppm2  7.772
ASSI {9671}
((segid "BrD" and resid 99 and name HN))
((segid "BrD" and resid 30 and name HB2))
  4.300  4.300  1.200 peak      9671  weight  0.10000E+01 volume  0.29603E+02 ppm1     8.936  ppm2  4.568
ASSI {9681}
((segid "BrD" and resid 18 and name HN))
(segid "BrD" and resid 14 and name HD2 %)
  3.600  3.200  1.900 peak      9681  weight  0.10000E+01 volume  0.80801E+02 ppm1     9.074  ppm2  1.390
OR {9681}
((segid "BrD" and resid 18 and name HN))
(segid "BrD" and resid 14 and name HD1 %)
ASSI {9751}
((segid "BrD" and resid 64 and name HN))
((segid "BrD" and resid 63 and name HB2))
  2.400  1.400  1.400 peak      9751  weight  0.10000E+01 volume  0.10265E+04 ppm1     8.585  ppm2  2.532
ASSI {9761}
((segid "BrD" and resid 64 and name HN))
(segid "BrD" and resid 63 and name HD2 %)
  3.300  2.700  2.200 peak      9761  weight  0.10000E+01 volume  0.14024E+03 ppm1     8.585  ppm2  1.489
ASSI {9811}
((segid "BrD" and resid 17 and name HN))
((segid "BrD" and resid 15 and name HB1))
  4.300  4.300  1.200 peak      9811  weight  0.10000E+01 volume  0.29691E+02 ppm1     8.669  ppm2  3.842
ASSI {9851}
((segid "BrD" and resid 40 and name HN))
(segid "BrD" and resid 41 and name HG2 %)
  2.500  1.600  1.600 peak      9851  weight  0.10000E+01 volume  0.73405E+03 ppm1     8.669  ppm2  1.866

TABLE 2-continued

Unambiguous NOE-derived Inter-proton Distance Restraints

ASSI {9871}
((segid "BrD" and resid 17 and name HN))
(segid "BrD" and resid 14 and name HD2 %)
  4.000  4.000  1.500 peak        9871  weight  0.10000E+01 volume  0.46134E+02 ppm1    8.668  ppm2  1.379
OR {9871}
((segid "BrD" and resid 17 and name HN))
(segid "BrD" and resid 14 and name HD1 %)
ASSI {9881}
((segid "BrD" and resid 17 and name HN))
(segid "BrD" and resid 18 and name HD2 %)
  4.600  4.600  0.900 peak        9881  weight  0.10000E+01 volume  0.20602E+02 ppm1    8.669  ppm2  0.394
ASSI {9911}
((segid "BrD" and resid 72 and name HN))
((segid "BrD" and resid 73 and name HB2))
  3.000  2.200  2.200 peak        9911  weight  0.10000E+01 volume  0.24469E+03 ppm1    8.858  ppm2  2.503
ASSI {9951}
((segid "BrD" and resid 12 and name HN))
((segid "BrD" and resid 13 and name HA))
  3.800  3.600  1.700 peak        9951  weight  0.10000E+01 volume  0.59337E+02 ppm1    9.021  ppm2  4.770
ASSI {9971}
((segid "BrD" and resid 12 and name HN))
((segid "BrD" and resid 15 and name HB2))
  4.100  4.100  1.400 peak        9971  weight  0.10000E+01 volume  0.38398E+02 ppm1    9.021  ppm2  3.618
ASSI {9981}
((segid "BrD" and resid 12 and name HN))
((segid "BrD" and resid 11 and name HB1))
  3.200  2.600  2.300 peak        9981  weight  0.10000E+01 volume  0.16530E+03 ppm1    9.021  ppm2  2.971
ASSI {9991}
((segid "BrD" and resid 12 and name HN))
((segid "BrD" and resid 11 and name HB2))
  3.300  2.700  2.200 peak        9991  weight  0.10000E+01 volume  0.13633E+03 ppm1    9.022  ppm2  2.611
OR {9991}
((segid "BrD" and resid 12 and name HN))
((segid "BrD" and resid 11 and name HG1))
ASSI {10021}
((segid "BrD" and resid 25 and name HN))
((segid "BrD" and resid 26 and name HD1))
  3.700  3.400  1.800 peak       10021  weight  0.10000E+01 volume  0.71669E+02 ppm1    9.134  ppm2  2.092
ASSI {10031}
((segid "BrD" and resid 25 and name HN))
(segid "BrD" and resid 102 and name HD1 %)
  3.800  3.600  1.700 peak       10031  weight  0.10000E+01 volume  0.60868E+02 ppm1    9.133  ppm2  1.295
OR {10031}
((segid "BrD" and resid 25 and name HN))
(segid "BrD" and resid 102 and name HD2 %)
ASSI {10061}
((segid "BrD" and resid 24 and name HN))
(segid "BrD" and resid 25 and name HG1 %)
  3.600  3.200  1.900 peak       10061  weight  0.10000E+01 volume  0.91063E+02 ppm1    8.657  ppm2  1.798
ASSI {10191}
((segid "BrD" and resid 16 and name HN))
((segid "BrD" and resid 18 and name HG))
  3.700  3.400  1.800 peak       10191  weight  0.10000E+01 volume  0.73953E+02 ppm1    8.792  ppm2  2.295
ASSI {10221}
((segid "BrD" and resid 76 and name HN))
((segid "BrD" and resid 74 and name HN))
  3.300  2.700  2.200 peak       10221  weight  0.10000E+01 volume  0.15827E+03 ppm1    8.611  ppm2  7.532
ASSI {10251}
((segid "BrD" and resid 75 and name HN))
(segid "BrD" and resid 18 and name HD1 %)
  4.200  4.200  1.300 peak       10251  weight  0.10000E+01 volume  0.32785E+02 ppm1    9.105  ppm2  1.056
ASSI {10261}
((segid "BrD" and resid 75 and name HN))
(segid "BrD" and resid 76 and name HB %)
  3.400  2.900  2.100 peak       10261  weight  0.10000E+01 volume  0.13102E+03 ppm1    9.406  ppm2  2.099
ASSI {10291}
((segid "BrD" and resid 75 and name HN))
(segid "BrD" and resid 75 and name HE %)
  3.800  3.600  1.700 peak       10291  weight  0.10000E+01 volume  0.67546E+02 ppm1    9.108  ppm2  2.654
ASSI {10301}
((segid "BrD" and resid 75 and name HN))
(segid "BrD" and resid 18 and name HD2 %)
  3.900  3.800  1.600 peak       10301  weight  0.10000E+01 volume  0.57563E+02 ppm1    9.106  ppm2  0.429
ASSI {10351}
((segid "BrD" and resid 95 and name HN))
((segid "BrD" and resid 93 and name HB1))
  2.900  2.100  2.100 peak       10351  weight  0.10000E+01 volume  0.35043E+03 ppm1    8.669  ppm2  5.018

TABLE 2-continued

| Unambiguous NOE-derived Inter-proton Distance Restraints |
|---|

ASSI {10401}
((segid "BrD" and resid 55 and name HN))
((segid "BrD" and resid 37 and name HB2))
  3.600  3.200  1.900 peak      10401  weight  0.10000E+01 volume  0.94850E+02 ppm1      7.996  ppm2    2.295
ASSI {10421}
((segid "BrD" and resid 55 and name HN))
((segid "BrD" and resid 37 and name HG2))
  2.700  1.800  1.800 peak      10421  weight  0.10000E+01 volume  0.46013E+03 ppm1      7.996  ppm2    2.578
ASSI {10441}
((segid "BrD" and resid 96 and name HN))
((segid "BrD" and resid 95 and name HB1))
  3.300  2.700  2.200 peak      10441  weight  0.10000E+01 volume  0.14200E+03 ppm1      7.988  ppm2    3.587
ASSI {10571}
((segid "BrD" and resid 80 and name HN))
((segid "BrD" and resid 79 and name HG1))
  2.400  1.400  1.400 peak      10571  weight  0.10000E+01 volume  0.10119E+04 ppm1      7.975  ppm2    3.105
ASSI {10581}
((segid "BrD" and resid 78 and name HN))
((segid "BrD" and resid 77 and name HB1))
  3.000  2.200  2.200 peak      10581  weight  0.10000E+01 volume  0.26376E+03 ppm1      7.974  ppm2    3.301
ASSI {10591}
((segid "BrD" and resid 55 and name HN))
((segid "BrD" and resid 58 and name HN))
  4.100  4.100  1.400 peak      10591  weight  0.10000E+01 volume  0.42990E+02 ppm1      7.972  ppm2   10.062
ASSI {10621}
((segid "BrD" and resid 56 and name HN))
((segid "BrD" and resid 34 and name HB1))
  3.700  3.400  1.800 peak      10621  weight  0.10000E+01 volume  0.69879E+02 ppm1      9.674  ppm2    4.100
ASSI {10641}
((segid "BrD" and resid 82 and name HN))
((segid "BrD" and resid 80 and name HB1))
  4.200  4.200  1.300 peak      10641  weight  0.10000E+01 volume  0.33240E+02 ppm1      6.981  ppm2    2.603
ASSI {10651}
((segid "BrD" and resid 82 and name HN))
((segid "BrD" and resid 84 and name HB2))
  4.300  4.300  1.200 peak      10651  weight  0.10000E+01 volume  0.31962E+02 ppm1      6.981  ppm2    3.230
ASSI {10661}
((segid "BrD" and resid 82 and name HN))
(segid "BrD" and resid 99 and name HB %)
  4.100  4.100  1.400 peak      10661  weight  0.10000E+01 volume  0.41756E+02 ppm1      6.981  ppm2    2.202
ASSI {10721}
((segid "BrD" and resid 81 and name HN))
((segid "BrD" and resid 77 and name HB1))
  3.900  3.800  1.600 peak      10721  weight  0.10000E+01 volume  0.54085E+02 ppm1      7.641  ppm2    3.310
ASSI {10751}
((segid "BrD" and resid 80 and name HN))
((segid "BrD" and resid 77 and name HB1))
  4.400  4.400  1.100 peak      10751  weight  0.10000E+01 volume  0.26321E+02 ppm1      8.005  ppm2    3.322
ASSI {10771}
((segid "BrD" and resid 80 and name HN))
((segid "BrD" and resid 81 and name HB))
  3.700  3.400  1.800 peak      10771  weight  0.10000E+01 volume  0.71103E+02 ppm1      8.006  ppm2    2.049
ASSI {10841}
((segid "BrD" and resid 79 and name HN))
(segid "BrD" and resid 76 and name HB %)
  3.500  3.100  2.000 peak      10841  weight  0.10000E+01 volume  0.10580E+03 ppm1      8.681  ppm2    2.096
ASSI {10881}
((segid "BrD" and resid 85 and name HN))
(segid "BrD" and resid 99 and name HB %)
  3.900  3.800  1.600 peak      10881  weight  0.10000E+01 volume  0.56660E+02 ppm1      7.515  ppm2    2.208
ASSI {10891}
((segid "BrD" and resid 85 and name HN))
(segid "BrD" and resid 81 and name HG2 %)
  4.100  4.100  1.400 peak      10891  weight  0.10000E+01 volume  0.42261E+02 ppm1      7.522  ppm2    0.765
ASSI {10921}
((segid "BrD" and resid 86 and name HN))
((segid "BrD" and resid 47 and name HB1))
  3.800  3.600  1.700 peak      10921  weight  0.10000E+01 volume  0.59880E+02 ppm1      8.423  ppm2    2.779
OR {10921}
((segid "BrD" and resid 86 and name HN))
((segid "BrD" and resid 87 and name HG2))
ASSI {10931}
((segid "BrD" and resid 86 and name HN))
((segid "BrD" and resid 87 and name HB2))
  3.800  3.600  1.700 peak      10931  weight  0.10000E+01 volume  0.59561E+02 ppm1      8.423  ppm2    2.577
ASSI {10941}
((segid "BrD" and resid 86 and name HN))

TABLE 2-continued

Unambiguous NOE-derived Inter-proton Distance Restraints (segid "BrD" and resid 99 and name HB %)
 3.600  3.200  1.900 peak       10941 weight  0.10000E+01 volume  0.93545E+02 ppm1   8.423 ppm2  2.210
ASSI {11001}
((segid "BrD" and resid 87 and name HN))
(segid "BrD" and resid 50 and name HD1 %)
 3.800  3.600  1.700 peak       11001 weight  0.10000E+01 volume  0.61476E+02 ppm1   8.570 ppm2  1.148
ASSI {11021}
((segid "BrD" and resid 87 and name HN))
((segid "BrD" and resid 86 and name HG2))
 4.500  4.500  1.000 peak       11021 weight  0.10000E+01 volume  0.22088E+02 ppm1   8.571 ppm2  0.780
ASSI {11031}
((segid "BrD" and resid 88 and name HN))
(segid "BrD" and resid 50 and name HD1 %)
 3.600  3.200  1.900 peak       11031 weight  0.10000E+01 volume  0.90228E+02 ppm1   8.354 ppm2  1.146
ASSI {11041}
((segid "BrD" and resid 88 and name HN))
((segid "BrD" and resid 84 and name HB2))
 4.000  4.000  1.500 peak       11041 weight  0.10000E+01 volume  0.46284E+02 ppm1   8.354 ppm2  3.299
ASSI {11051}
((segid "BrD" and resid 88 and name HN))
((segid "BrD" and resid 87 and name HG1))
 4.600  4.600  0.900 peak       11051 weight  0.10000E+01 volume  0.19886E+02 ppm1   8.354 ppm2  3.018
ASSI {11161}
((segid "BrD" and resid 93 and name HN))
((segid "BrD" and resid 91 and name HD2))
 3.700  3.400  1.800 peak       11161 weight  0.10000E+01 volume  0.78354E+02 ppm1   8.714 ppm2  4.410
ASSI {11171}
((segid "BrD" and resid 93 and name HN))
((segid "BrD" and resid 96 and name HB1))
 3.300  2.700  2.200 peak       11171 weight  0.10000E+01 volume  0.14983E+03 ppm1   8.714 ppm2  4.004
ASSI {11191}
((segid "BrD" and resid 30 and name HN))
((segid "BrD" and resid 28 and name HB2))
 4.400  4.400  1.100 peak       11191 weight  0.10000E+01 volume  0.26154E+02 ppm1  12.276 ppm2  3.392
ASSI {11201}
((segid "BrD" and resid 30 and name HN))
((segid "BrD" and resid 28 and name HB1))
 3.300  2.700  2.200 peak       11201 weight  0.10000E+01 volume  0.15024E+03 ppm1  12.275 ppm2  3.594
ASSI {11211}
((segid "BrD" and resid 30 and name HN))
((segid "BrD" and resid 32 and name HN))
 3.600  3.200  1.900 peak       11211 weight  0.10000E+01 volume  0.82022E+02 ppm1  12.276 ppm2  7.741
ASSI {11241}
((segid "BrD" and resid 31 and name HN))
((segid "BrD" and resid 28 and name HB1))
 3.600  3.200  1.900 peak       11241 weight  0.10000E+01 volume  0.94605E+02 ppm1   8.480 ppm2  3.594
ASSI {11251}
((segid "BrD" and resid 31 and name HN))
((segid "BrD" and resid 28 and name HB2))
 3.800  3.600  1.700 peak       11251 weight  0.10000E+01 volume  0.64760E+02 ppm1   8.481 ppm2  3.389
ASSI {11361}
((segid "BrD" and resid 32 and name HN))
(segid "BrD" and resid 102 and name HD1 %)
 4.500  4.500  1.000 peak       11361 weight  0.10000E+01 volume  0.23592E+02 ppm1   7.738 ppm2  1.310
ASSI {11391}
((segid "BrD" and resid 34 and name HN))
((segid "BrD" and resid 35 and name HG1))
 3.200  2.600  2.300 peak       11391 weight  0.10000E+01 volume  0.18521E+03 ppm1   8.182 ppm2  3.447
ASSI {11431}
((segid "BrD" and resid 34 and name HN))
(segid "BrD" and resid 31 and name HB %)
 2.900  2.100  2.100 peak       11431 weight  0.10000E+01 volume  0.29794E+03 ppm1   8.179 ppm2  2.301
ASSI {11441}
((segid "BrD" and resid 34 and name HN))
(segid "BrD" and resid 56 and name HD1 %)
 3.400  2.900  2.100 peak       11441 weight  0.10000E+01 volume  0.12961E+03 ppm1   8.184 ppm2  1.527
ASSI {11451}
((segid "BrD" and resid 34 and name HN))
(segid "BrD" and resid 102 and name HD1 %)
 3.600  3.200  1.900 peak       11451 weight  0.10000E+01 volume  0.84106E+02 ppm1   8.185 ppm2  1.305
ASSI {11521}
((segid "BrD" and resid 35 and name HN))
(segid "BrD" and resid 56 and name HD1 %)
 4.500  4.500  1.000 peak       11521 weight  0.10000E+01 volume  0.22012E+02 ppm1   7.734 ppm2  1.553
ASSI {11561}
((segid "BrD" and resid 36 and name HN))
((segid "BrD" and resid 57 and name HB1))

TABLE 2-continued

Unambiguous NOE-derived Inter-proton Distance Restraints

| | | | | | | | | | | |
|---|---|---|---|---|---|---|---|---|---|---|
| 3.400 | 2.900 | 2.100 peak | 11561 | weight | 0.10000E+01 | volume | 0.11642E+03 | ppm1 | 8.308 ppm2 | 2.953 |

ASSI {11571}
((segid "BrD" and resid 66 and name HN))
(segid "BrD" and resid 63 and name HD1 %)

| | | | | | | | | | | |
|---|---|---|---|---|---|---|---|---|---|---|
| 4.200 | 4.200 | 1.300 peak | 11571 | weight | 0.10000E+01 | volume | 0.34773E+02 | ppm1 | 8.763 ppm2 | 1.640 |

ASSI {11601}
((segid "BrD" and resid 67 and name HN))
(segid "BrD" and resid 68 and name HD %)

| | | | | | | | | | | |
|---|---|---|---|---|---|---|---|---|---|---|
| 4.400 | 4.400 | 1.100 peak | 11601 | weight | 0.10000E+01 | volume | 0.26280E+02 | ppm1 | 8.832 ppm2 | 7.780 |

ASSI {11651}
((segid "BrD" and resid 68 and name HN))
((segid "BrD" and resid 69 and name HB))

| | | | | | | | | | | |
|---|---|---|---|---|---|---|---|---|---|---|
| 3.700 | 3.400 | 1.600 peak | 11651 | weight | 0.10000E+01 | volume | 0.74566E+02 | ppm1 | 8.626 ppm2 | 2.947 |

ASSI {11661}
((segid "BrD" and resid 68 and name HN))
(segid "BrD" and resid 18 and name HD1 %)

| | | | | | | | | | | |
|---|---|---|---|---|---|---|---|---|---|---|
| 5.500 | 5.500 | 0.000 peak | 11661 | weight | 0.10000E+01 | volume | 0.40212E+01 | ppm1 | 8.626 ppm2 | 1.090 |

ASSI {11731}
((segid "BrD" and resid 70 and name HN))
((segid "BrD" and resid 68 and name HB1))

| | | | | | | | | | | |
|---|---|---|---|---|---|---|---|---|---|---|
| 3.600 | 3.200 | 1.900 peak | 11731 | weight | 0.10000E+01 | volume | 0.91804E+02 | ppm1 | 8.040 ppm2 | 3.689 |

ASSI {11741}
((segid "BrD" and resid 70 and name HN))
((segid "BrD" and resid 74 and name HB1))

| | | | | | | | | | | |
|---|---|---|---|---|---|---|---|---|---|---|
| 3.400 | 2.900 | 2.100 peak | 11741 | weight | 0.10000E+01 | volume | 0.13333E+03 | ppm1 | 8.039 ppm2 | 3.544 |

ASSI {11771}
((segid "BrD" and resid 70 and name HN))
((segid "BrD" and resid 73 and name HB2))

| | | | | | | | | | | |
|---|---|---|---|---|---|---|---|---|---|---|
| 3.700 | 3.400 | 1.800 peak | 11771 | weight | 0.10000E+01 | volume | 0.79558E+02 | ppm1 | 8.040 ppm2 | 2.491 |

ASSI {11841}
((segid "BrD" and resid 73 and name HN))
((segid "BrD" and resid 70 and name HB2))

| | | | | | | | | | | |
|---|---|---|---|---|---|---|---|---|---|---|
| 3.200 | 2.600 | 2.300 peak | 11841 | weight | 0.10000E+01 | volume | 0.16883E+03 | ppm1 | 8.047 ppm2 | 4.361 |

ASSI {11891}
((segid "BrD" and resid 74 and name HN))
((segid "BrD" and resid 75 and name HB2))

| | | | | | | | | | | |
|---|---|---|---|---|---|---|---|---|---|---|
| 4.700 | 4.700 | 0.800 peak | 11891 | weight | 0.10000E+01 | volume | 0.18157E+02 | ppm1 | 7.536 ppm2 | 2.851 |

ASSI {11911}
((segid "BrD" and resid 74 and name HN))
(segid "BrD" and resid 76 and name HB %)

| | | | | | | | | | | |
|---|---|---|---|---|---|---|---|---|---|---|
| 4.400 | 4.400 | 1.100 peak | 11911 | weight | 0.10000E+01 | volume | 0.27875E+02 | ppm1 | 7.536 ppm2 | 2.088 |

ASSI {12031}
((segid "BrD" and resid 99 and name HN))
((segid "BrD" and resid 100 and name HB2))

| | | | | | | | | | | |
|---|---|---|---|---|---|---|---|---|---|---|
| 3.800 | 3.600 | 1.700 peak | 12031 | weight | 0.10000E+01 | volume | 0.61845E+02 | ppm1 | 8.936 ppm2 | 3.439 |

ASSI {12041}
((segid "BrD" and resid 99 and name HN))
((segid "BrD" and resid 97 and name HB1))

| | | | | | | | | | | |
|---|---|---|---|---|---|---|---|---|---|---|
| 3.400 | 2.900 | 2.100 peak | 12041 | weight | 0.10000E+01 | volume | 0.12562E+03 | ppm1 | 8.936 ppm2 | 2.721 |

ASSI {12061}
((segid "BrD" and resid 100 and name HN))
((segid "BrD" and resid 101 and name HA))

| | | | | | | | | | | |
|---|---|---|---|---|---|---|---|---|---|---|
| 4.000 | 4.000 | 1.500 peak | 12061 | weight | 0.10000E+01 | volume | 0.47923E+02 | ppm1 | 8.669 ppm2 | 4.255 |

ASSI {12091}
((segid "BrD" and resid 100 and name HN))
((segid "BrD" and resid 101 and name HG11))

| | | | | | | | | | | |
|---|---|---|---|---|---|---|---|---|---|---|
| 4.100 | 4.100 | 1.400 peak | 12091 | weight | 0.10000E+01 | volume | 0.39843E+02 | ppm1 | 8.669 ppm2 | 2.519 |

OR {12091}
((segid "BrD" and resid 100 and name HN))
((segid "BrD" and resid 101 and name HB))
ASSI {12151}
((segid "BrD" and resid 101 and name HN))
((segid "BrD" and resid 104 and name HD1))

| | | | | | | | | | | |
|---|---|---|---|---|---|---|---|---|---|---|
| 3.500 | 3.100 | 2.000 peak | 12151 | weight | 0.10000E+01 | volume | 0.11138E+03 | ppm1 | 8.513 ppm2 | 2.282 |

ASSI {12221}
((segid "BrD" and resid 107 and name HN))
(segid "BrD" and resid 106 and name HD %)

| | | | | | | | | | | |
|---|---|---|---|---|---|---|---|---|---|---|
| 3.300 | 2.700 | 2.200 peak | 12221 | weight | 0.10000E+01 | volume | 0.14273E+03 | ppm1 | 8.981 ppm2 | 7.515 |

ASSI {12241}
((segid "BrD" and resid 107 and name HN))
((segid "BrD" and resid 103 and name HG2))

| | | | | | | | | | | |
|---|---|---|---|---|---|---|---|---|---|---|
| 3.400 | 2.900 | 2.100 peak | 12241 | weight | 0.10000E+01 | volume | 0.11969E+03 | ppm1 | 8.980 ppm2 | 2.547 |

ASSI {12271}
((segid "BrD" and resid 107 and name HN))
((segid "BrD" and resid 110 and name HG12))

| | | | | | | | | | | |
|---|---|---|---|---|---|---|---|---|---|---|
| 4.000 | 4.000 | 1.500 peak | 12271 | weight | 0.10000E+01 | volume | 0.48486E+02 | ppm1 | 8.980 ppm2 | 1.678 |

TABLE 2-continued

Unambiguous NOE-derived Inter-proton Distance Restraints

ASSI {12291}
((segid "BrD" and resid 108 and name HN))
((segid "BrD" and resid 109 and name HB2))
  5.500  5.500  0.000 peak       12291  weight  0.10000E+01  volume  0.20202E+00  ppm1        8.522  ppm2  2.195
ASSI {12411}
((segid "BrD" and resid 113 and name HN))
(segid "BrD" and resid 17 and name HG2 %)
  4.300  4.300  1.200 peak       12411  weight  0.10000E+01  volume  0.28750E+02  ppm1        8.218  ppm2  1.728
ASSI {12431}
((segid "BrD" and resid 113 and name HN))
(segid "BrD" and resid 110 and name HG2 %)
  3.400  2.900  2.100 peak       12431  weight  0.10000E+01  volume  0.12771E+03  ppm1        8.218  ppm2  1.275
ASSI {12441}
((segid "BrD" and resid 115 and name HN))
(segid "BrD" and resid 113 and name HB %)
  3.400  2.900  2.100 peak       12441  weight  0.10000E+01  volume  0.11633E+03  ppm1        8.355  ppm2  1.969
ASSI {12451}
((segid "BrD" and resid 115 and name HN))
((segid "BrD" and resid 116 and name HG12))
  5.500  5.500  0.000 peak       12451  weight  0.10000E+01  volume  0.47664E+01  ppm1        8.355  ppm2  1.556
ASSI {12461}
((segid "BrD" and resid 115 and name HN))
(segid "BrD" and resid 110 and name HD1 %)
  4.400  4.400  1.100 peak       12461  weight  0.10000E+01  volume  0.26420E+02  ppm1        8.356  ppm2  1.163
ASSI {12471}
((segid "BrD" and resid 115 and name HN))
((segid "BrD" and resid 110 and name HB))
  3.700  3.400  1.800 peak       12471  weight  0.10000E+01  volume  0.76081E+02  ppm1        8.355  ppm2  2.346
ASSI {12481}
((segid "BrD" and resid 117 and name HN))
(segid "BrD" and resid 116 and name HG12 %)
  4.700  4.700  0.800 peak       12481  weight  0.10000E+01  volume  0.17262E+02  ppm1        8.883  ppm2  1.544
ASSI {12491}
((segid "BrD" and resid 116 and name HN))
(segid "BrD" and resid 110 and name HG2 %)
  3.200  2.600  2.300 peak       12491  weight  0.10000E+01  volume  0.16590E+03  ppm1        8.063  ppm2  1.277
ASSI {12521}
((segid "BrD" and resid 116 and name HN))
(segid "BrD" and resid 110 and name HD1 %)
  3.200  2.600  2.300 peak       12521  weight  0.10000E+01  volume  0.17496E+03  ppm1        8.086  ppm2  1.156
ASSI {12591}
((segid "BrD" and resid 47 and name HN))
((segid "BrD" and resid 48 and name HG2))
  4.200  4.200  1.300 peak       12591  weight  0.10000E+01  volume  0.33544E+02  ppm1        8.832  ppm2  2.861
ASSI {12611}
((segid "BrD" and resid 47 and name HN))
(segid "BrD" and resid 43 and name HB %)
  3.800  3.600  1.700 peak       12611  weight  0.10000E+01  volume  0.60519E+02  ppm1        8.832  ppm2  1.700
ASSI {12621}
((segid "BrD" and resid 49 and name HN))
((segid "BrD" and resid 50 and name HB))
  3.600  3.200  1.900 peak       12621  weight  0.10000E+01  volume  0.90984E+02  ppm1        7.762  ppm2  1.797
ASSI {12701}
((segid "BrD" and resid 52 and name HN))
((segid "BrD" and resid 53 and name HG1))
  3.900  3.800  1.600 peak       12701  weight  0.10000E+01  volume  0.53690E+02  ppm1        9.004  ppm2  2.820
OR {12701}
((segid "BrD" and resid 52 and name HN))
((segid "BrD" and resid 53 and name HB1))
ASSI {12741}
((segid "BrD" and resid 42 and name HN))
((segid "BrD" and resid 39 and name HB1))
  3.100  2.400  2.400 peak       12741  weight  0.10000E+01  volume  0.21408E+03  ppm1        7.820  ppm2  2.491
ASSI {12751}
((segid "BrD" and resid 42 and name HN))
((segid "BrD" and resid 39 and name HD1))
  3.000  2.200  2.200 peak       12751  weight  0.10000E+01  volume  0.25898E+03  ppm1        7.821  ppm2  1.286
ASSI {12761}
((segid "BrD" and resid 42 and name HN))
(segid "BrD" and resid 43 and name HB %)
  3.500  3.100  2.000 peak       12761  weight  0.10000E+01  volume  0.10310E+03  ppm1        7.820  ppm2  1.706
ASSI {12851}
((segid "BrD" and resid 20 and name HN))
((segid "BrD" and resid 19 and name HD1))
  3.600  3.200  1.900 peak       12851  weight  0.10000E+01  volume  0.82185E+02  ppm1        8.145  ppm2  2.189

TABLE 2-continued

Unambiguous NOE-derived Inter-proton Distance Restraints

ASSI {12881}
((segid "BrD" and resid 20 and name HN))
((segid "BrD" and resid 21 and name HG12))
  3.900  3.800  1.600 peak      12881 weight  0.10000E+01 volume  0.55288E+02 ppm1      8.147  ppm2  1.639
OR {12881}
((segid "BrD" and resid 20 and name HN))
(segid "BrD" and resid 21 and name HG2 %)
ASSI {12891}
((segid "BrD" and resid 20 and name HN))
(segid "BrD" and resid 63 and name HD2 %)
  3.500  3.100  2.000 peak      12891 weight  0.10000E+01 volume  0.11141E+03 ppm1      8.146  ppm2  1.480
ASSI {12901}
((segid "BrD" and resid 20 and name HN))
(segid "BrD" and resid 17 and name HG2 %)
  3.900  3.800  1.600 peak      12901 weight  0.10000E+01 volume  0.53573E+02 ppm1      8.146  ppm2  1.762
ASSI {12991}
((segid "BrD" and resid 23 and name HN))
((segid "BrD" and resid 20 and name HN))
  3.800  3.600  1.700 peak      12991 weight  0.10000E+01 volume  0.61946E+02 ppm1      9.119  ppm2  8.121
ASSI {13021}
((segid "BrD" and resid 26 and name HN))
((segid "BrD" and resid 28 and name HB2))
  4.200  4.200  1.300 peak      13021 weight  0.10000E+01 volume  0.33211E+02 ppm1      9.196  ppm2  3.393
ASSI {13031}
((segid "BrD" and resid 26 and name HN))
((segid "BrD" and resid 35 and name HG1))
  4.500  4.500  1.000 peak      13031 weight  0.10000E+01 volume  0.21672E+02 ppm1      9.195  ppm2  3.493
ASSI {13041}
((segid "BrD" and resid 26 and name HN))
(segid "BrD" and resid 56 and name HD2 %)
  4.100  4.100  1.400 peak      13041 weight  0.10000E+01 volume  0.41596E+02 ppm1      9.196  ppm2  1.250
ASSI {13061}
((segid "BrD" and resid 27 and name HN))
((segid "BrD" and resid 26 and name HG1))
  3.800  3.600  1.700 peak      13061 weight  0.10000E+01 volume  0.66585E+02 ppm1      8.169  ppm2  1.596
ASSI {13091}
((segid "BrD" and resid 27 and name HN))
(segid "BrD" and resid 35 and name HE %)
  3.600  3.200  1.900 peak      13091 weight  0.10000E+01 volume  0.88198E+02 ppm1      8.169  ppm2  2.809
ASSI {13111}
((segid "BrD" and resid 59 and name HN))
(segid "BrD" and resid 59 and name HE %)
  3.300  2.700  2.200 peak      13111 weight  0.10000E+01 volume  0.15860E+03 ppm1      8.498  ppm2  1.864
ASSI {13131}
((segid "BrD" and resid 59 and name HN))
(segid "BrD" and resid 56 and name HD2 %)
  4.300  4.300  1.200 peak      13131 weight  0.10000E+01 volume  0.28520E+02 ppm1      8.499  ppm2  1.239
ASSI {13161}
((segid "BrD" and resid 60 and name HN))
((segid "BrD" and resid 59 and name HG1))
  3.600  3.200  1.900 peak      13161 weight  0.10000E+01 volume  0.93397E+02 ppm1      8.565  ppm2  3.213
ASSI {13221}
((segid "BrD" and resid 32 and name HE1))
((segid "BrD" and resid 32 and name HD1))
  2.300  1.300  1.300 peak      13221 weight  0.10000E+01 volume  0.12506E+04 ppm1    11.082  ppm2  8.475
ASSI {13231}
((segid "BrD" and resid 32 and name HE1))
((segid "BrD" and resid 32 and name HN))
  3.200  2.600  2.300 peak      13231 weight  0.10000E+01 volume  0.18835E+03 ppm1    11.082  ppm2  7.742
OR {13231}
((segid "BrD" and resid 32 and name HE1))
((segid "BrD" and resid 32 and name HH2))
ASSI {13241}
((segid "BrD" and resid 32 and name HE1))
((segid "BrD" and resid 32 and name HZ2))
  2.500  1.600  1.600 peak      13241 weight  0.10000E+01 volume  0.70734E+03 ppm1    11.082  ppm2  7.984
ASSI {13251}
((segid "BrD" and resid 32 and name HE1))
((segid "BrD" and resid 30 and name HA))
  3.100  2.400  2.400 peak      13251 weight  0.10000E+01 volume  0.22949E+03 ppm1    11.082  ppm2  5.450
ASSI {13301}
((segid "BrD" and resid 76 and name HN))
((segid "BrD" and resid 77 and name HA))
  4.200  4.200  1.300 peak      13301 weight  0.10000E+01 volume  0.33586E+02 ppm1      8.610  ppm2  4.967

TABLE 2-continued

Unambiguous NOE-derived Inter-proton Distance Restraints

ASSI {13311}
((segid "BrD" and resid 76 and name HN))
((segid "BrD" and resid 77 and name HB1))
  4.100  4.100  1.400 peak      13311  weight  0.10000E+01 volume  0.37785E+02 ppm1      8.623  ppm2  3.344
ASSI {13651}
((segid "BrD" and resid 56 and name HN))
(segid "BrD" and resid 81 and name HG1 %)
  4.100  4.100  1.400 peak      13651  weight  0.10000E+01 volume  0.38100E+02 ppm1      9.680  ppm2  1.077
ASSI {13661}
((segid "BrD" and resid 56 and name HN))
(segid "BrD" and resid 81 and name HG2 %)
  4.200  4.200  1.300 peak      13661  weight  0.10000E+01 volume  0.33875E+02 ppm1      9.681  ppm2  0.743
ASSI {13681}
((segid "BrD" and resid 74 and name HN))
(segid "BrD" and resid 14 and name HD1 %)
  4.700  4.700  0.800 peak      13681  weight  0.10000E+01 volume  0.17399E+03 ppm1      7.536  ppm2  1.405
OR {13681}
((segid "BrD" and resid 74 and name HN))
(segid "BrD" and resid 14 and name HD2 %)
ASSI {13721}
((segid "BrD" and resid 16 and name HN))
((segid "BrD" and resid 17 and name HB))
  4.400  4.400  1.100 peak      13721  weight  0.10000E+01 volume  0.26713E+02 ppm1      8.794  ppm2  4.874
ASSI {13751}
((segid "BrD" and resid 74 and name HN))
((segid "BrD" and resid 68 and name HA))
  5.300  5.300  0.200 peak      13751  weight  0.10000E+01 volume  0.81254E+01 ppm1      7.537  ppm2  5.140
ASSI {13881}
((segid "BrD" and resid 46 and name HN))
(segid "BrD" and resid 38 and name HG1 %)
  4.600  4.600  0.900 peak      13881  weight  0.10000E+01 volume  0.18836E+02 ppm1      8.562  ppm2  1.082
ASSI {13891}
((segid "BrD" and resid 62 and name HN))
((segid "BrD" and resid 67 and name HB1))
  4.100  4.100  1.400 peak      13891  weight  0.10000E+01 volume  0.40043E+02 ppm1      8.998  ppm2  3.557
ASSI {13931}
((segid "BrD" and resid 116 and name HN))
(segid "BrD" and resid 75 and name HE %)
  5.000  5.000  0.500 peak      13931  weight  0.10000E+01 volume  0.12168E+02 ppm1      8.086  ppm2  2.640
ASSI {13941}
((segid "BrD" and resid 115 and name HN))
((segid "BrD" and resid 110 and name HA))
  4.100  4.100  1.400 peak      13941  weight  0.10000E+01 volume  0.38338E+02 ppm1      8.355  ppm2  4.419
ASSI {13951}
((segid "BrD" and resid 114 and name HN))
(segid "BrD" and resid 112 and name HN))
  4.000  4.000  1.500 peak      13951  weight  0.10000E+01 volume  0.49230E+02 ppm1      8.375  ppm2  8.642
ASSI {13961}
((segid "BrD" and resid 114 and name HN))
((segid "BrD" and resid 112 and name HB1))
  5.200  5.200  0.300 peak      13961  weight  0.10000E+01 volume  0.99997E+01 ppm1      8.377  ppm2  2.665
ASSI {14001}
((segid "BrD" and resid 108 and name HN))
((segid "BrD" and resid 106 and name HN))
  4.900  4.900  0.600 peak      14001  weight  0.10000E+01 volume  0.12922E+02 ppm1      8.529  ppm2  9.745
ASSI {14021}
((segid "BrD" and resid 108 and name HN))
((segid "BrD" and resid 104 and name HA))
  2.700  1.800  1.800 peak      14021  weight  0.10000E+01 volume  0.54819E+03 ppm1      8.526  ppm2  4.663
ASSI {14032}
((segid "BrD" and resid 108 and name HN))
((segid "BrD" and resid 110 and name HG12))
  5.200  5.200  0.300 peak      14031  weight  0.10000E+01 volume  0.95149E+03 ppm1      8.521  ppm2  1.696
ASSI {14051}
((segid "BrD" and resid 107 and name HN))
((segid "BrD" and resid 108 and name HA))
  4.500  4.500  1.000 peak      14051  weight  0.10000E+01 volume  0.23253E+02 ppm1      8.980  ppm2  4.798
ASSI {14081}
((segid "BrD" and resid 106 and name HN))
(segid "BrD" and resid 21 and name HG2 %)
  4.600  4.600  0.900 peak      14081  weight  0.10000E+01 volume  0.21267E+02 ppm1      9.740  ppm2  1.640
ASSI {14091}
((segid "BrD" and resid 105 and name HN))
((segid "BrD" and resid 106 and name HA))
  4.500  4.500  1.000 peak      14091  weight  0.10000E+01 volume  0.22194E+02 ppm1      8.487  ppm2  4.568

TABLE 2-continued

Unambiguous NOE-derived Inter-proton Distance Restraints

ASSI {14101}
((segid "BrD" and resid 105 and name HN))
((segid "BrD" and resid 103 and name HB2))
  5.000  5.000  0.500 peak      14101 weight  0.10000E+01 volume  0.11917E+02 ppm1      8.487  ppm2  1.881
ASSI {14181}
((segid "BrD" and resid 100 and name HN))
((segid "BrD" and resid 34 and name HZ))
  4.400  4.700  0.800 peak      14181 weight  0.10000E+01 volume  0.18067E+02 ppm1      8.675  ppm2  7.907
ASSI {14211}
((segid "BrD" and resid 100 and name HN))
((segid "BrD" and resid 97 and name HB1))
  4.400  4.400  1.100 peak      14211 weight  0.10000E+01 volume  0.25437E+02 ppm1      8.669  ppm2  2.715
ASSI {14331}
((segid "BrD" and resid 99 and name HN))
((segid "BrD" and resid 101 and name HN))
  4.300  4.300  1.200 peak      14231 weight  0.10000E+01 volume  0.28380E+02 ppm1      8.936  ppm2  8.500
ASSI {14261}
((segid "BrD" and resid 99 and name HN))
((segid "BrD" and resid 33 and name HG1))
  5.500  5.500  0.000 peak      14261 weight  0.10000E+01 volume  0.32802E+02 ppm1      8.936  ppm2  0.866
ASSI {14271}
((segid "BrD" and resid 98 and name HN))
((segid "BrD" and resid 101 and name HN))
  4.400  4.400  1.100 peak      14271 weight  0.10000E+01 volume  0.25780E+02 ppm1      9.125  ppm2  8.515
ASSI {14291}
((segid "BrD" and resid 97 and name HN))
((segid "BrD" and resid 93 and name HB1))
  5.500  5.500  0.000 peak      14291 weight  0.10000E+01 volume  0.62831E+01 ppm1      8.677  ppm2  5.016
OR {14291}
((segid "BrD" and resid 97 and name HN))
((segid "BrD" and resid 93 and name HA))
ASSI {14321}
((segid "BrD" and resid 95 and name HN))
((segid "BrD" and resid 32 and name HH2))
  3.700  3.400  1.800 peak      14321 weight  0.10000E+01 volume  0.76926E+02 ppm1      8.669  ppm2  7.739
ASSI {14331}
((segid "BrD" and resid 93 and name HN))
((segid "BrD" and resid 96 and name HN))
  4.500  4.500  1.000 peak      14331 weight  0.10000E+01 volume  0.22598E+02 ppm1      8.713  ppm2  7.963
ASSI {14351}
((segid "BrD" and resid 93 and name HN))
((segid "BrD" and resid 95 and name HB1))
  4.600  4.600  0.900 peak      14351 weight  0.10000E+01 volume  0.20643E+02 ppm1      8.714  ppm2  3.617
ASSI {14361}
((segid "BrD" and resid 87 and name HN))
((segid "BrD" and resid 89 and name HD21))
  3.900  3.800  1.600 peak      14381 weight  0.10000E+01 volume  0.54969E+02 ppm1      8.568  ppm2  8.959
ASSI {14391}
((segid "BrD" and resid 87 and name HN))
((segid "BrD" and resid 89 and name HN))
  3.600  3.200  1.900 peak      14391 weight  0.10000E+01 volume  0.81305E+02 ppm1      8.568  ppm2  8.838
ASSI {14431}
((segid "BrD" and resid 85 and name HN))
((segid "BrD" and resid 87 and name HN))
  4.100  4.200  1.400 peak      14431 weight  0.10000E+01 volume  0.43435E+02 ppm1      7.516  ppm2  8.557
ASSI {14471}
((segid "BrD" and resid 82 and name HN))
((segid "BrD" and resid 80 and name HN))
  4.800  4.800  0.700 peak      14471 weight  0.10000E+01 volume  0.16164E+02 ppm1      6.979  ppm2  7.979
ASSI {14521}
((segid "BrD" and resid 79 and name HN))
((segid "BrD" and resid 77 and name HA))
  4.800  4.800  0.700 peak      14521 weight  0.10000E+01 volume  0.15931E+02 ppm1      8.679  ppm2  4.968
ASSI {14531}
((segid "BrD" and resid 79 and name HN))
(segid "BrD" and resid 59 and name HE %)
  4.000  4.000  1.500 peak      14531 weight  0.10000E+01 volume  0.45701E+02 ppm1      8.680  ppm2  1.876
ASSI {14561}
((segid "BrD" and resid 76 and name HN))
((segid "BrD" and resid 74 and name HA))
  4.300  4.300  1.200 peak      14561 weight  0.10000E+01 volume  0.31541E+02 ppm1      8.611  ppm2  4.361
ASSI {14601}
((segid "BrD" and resid 72 and name HN))
((segid "BrD" and resid 75 and name HB2))
  4.600  4.600  0.900 peak      14601 weight  0.10000E+01 volume  0.21235E+02 ppm1      8.859  ppm2  2.805
ASSI {14611}
((segid "BrD" and resid 72 and name HN))

TABLE 2-continued

Unambiguous NOE-derived Inter-proton Distance Restraints ((segid "BrD" and resid 9 and name HB1))
  3.600  3.200  1.900 peak    14611  weight  0.10000E+01 volume    0.90159E+02 ppm1    8.859 ppm2  2.443
ASSI {14661}
((segid "BrD" and resid 64 and name HN))
((segid "BrD" and resid 62 and name HN))
  4.100  4.100  1.400 peak    14661  weight  0.10000E+01 volume    0.40125E+02 ppm1    8.585 ppm2  8.966
ASSI {14681}
((segid "BrD" and resid 64 and name HN))
((segid "BrD" and resid 65 and name HB2))
  4.800  4.800  0.700 peak    14681  weight  0.10000E+01 volume    0.16509E+02 ppm1    8.584 ppm2  3.383
ASSI {14711}
((segid "BrD" and resid 63 and name HN))
(segid "BrD" and resid 74 and name HD %)
  4.600  4.600  0.900 peak    14711  weight  0.10000E+01 volume    0.18909E+02 ppm1    9471 ppm2  7.007
ASSI {14741}
((segid "BrD" and resid 62 and name HN))
((segid "BrD" and resid 61 and name HN))
  2.600  1.700  1.700 peak    14741  weight  0.10000E+01 volume    0.63142E+03 ppm1    8.997 ppm2  8.742
ASSI {14771}
((segid "BrD" and resid 62 and name HN))
((segid "BrD" and resid 65 and name HB2))
  4.200  4.200  1.300 peak    14771  weight  0.10000E+01 volume    0.33744E+02 ppm1    8.999 ppm2  3.355
ASSI {14841}
((segid "BrD" and resid 57 and name HN))
((segid "BrD" and resid 35 and name HA))
  3.200  2.600  2.300 peak    14841  weight  0.10000E+01 volume    0.16187E+03 ppm1    9.359 ppm2  4.904
ASSI {14861}
((segid "BrD" and resid 55 and name HN))
((segid "BrD" and resid 59 and name HN))
  3.900  3.800  1.600 peak    14861  weight  0.10000E+01 volume    0.53302E+03 ppm1    7.974 ppm2  8.496
ASSI {14891}
((segid "BrD" and resid 54 and name HN))
((segid "BrD" and resid 84 and name HB1))
  4.600  4.600  0.900 peak    14891  weight  0.10000E+01 volume    0.21172E+02 ppm1    9.037 ppm2  3.597
ASSI {14981}
((segid "BrD" and resid 48 and name HN))
((segid "BrD" and resid 46 and name HB2))
  4.300  4.300  1.200 peak    14981  weight  0.10000E+01 volume    0.30250E+02 ppm1    8.306 ppm2  3.090
ASSI {14991}
((segid "BrD" and resid 48 and name HN))
(segid "BrD" and resid 49 and name HG1 %)
  3.700  3.400  1.800 peak    14991  weight  0.10000E+01 volume    0.71559E+02 ppm1    8.305 ppm2  1.639
ASSI {15001}
((segid "BrD" and resid 92 and name HN))
(segid "BrD" and resid 89 and name HD22))
  4.900  4.900  0.600 peak    15001  weight  0.10000E+01 volume    0.14588E+02 ppm1    8.632 ppm2  8.433
ASSI {15011}
((segid "BrD" and resid 47 and name HN))
((segid "BrD" and resid 49 and name HN))
  4.000  4.000  1.500 peak    15011  weight  0.10000E+01 volume    0.44203E+02 ppm1    8.632 ppm2  7.759
ASSI {15041}
((segid "BrD" and resid 43 and name HN))
((segid "BrD" and resid 42 and name HG2))
  4.000  4.000  1.500 peak    15041  weight  0.10000E+01 volume    0.44922E+02 ppm1    8.000 ppm2  2.889
ASSI {15071}
((segid "BrD" and resid 35 and name HN))
((segid "BrD" and resid 33 and name HA))
  4.300  4.300  1.200 peak    15071  weight  0.10000E+01 volume    0.32086E+02 ppm1    7.735 ppm2  4.346
ASSI {15081}
((segid "BrD" and resid 35 and name HN))
((segid "BrD" and resid 34 and name HB1))
  3.800  3.600  1.700 peak    15081  weight  0.10000E+01 volume    0.61308E+02 ppm1    7.734 ppm2  4.079
ASSI {15111}
((segid "BrD" and resid 34 and name HN))
(segid "BrD" and resid 81 and name HG2 %)
  4.700  4.700  0.800 peak    15111  weight  0.10000E+01 volume    0.17971E+02 ppm1    8.178 ppm2  0.756
ASSI {15131}
((segid "BrD" and resid 32 and name HN))
((segid "BrD" and resid 33 and name HG1))
  4.400  5.400  0.100 peak    15131  weight  0.10000E+01 volume    0.80093E+01 ppm1    7.739 ppm2  0.859
ASSI {15141}
((segid "BrD" and resid 31 and name HN))
((segid "BrD" and resid 28 and name HN))
  3.200  2.600  2.300 peak    15141  weight  0.10000E+01 volume    0.16166E+03 ppm1    8.480 ppm2  8.159
OR {15141}
((segid "BrD" and resid 31 and name HN))
((segid "BrD" and resid 28 and name HE1))

TABLE 2-continued

Unambiguous NOE-derived Inter-proton Distance Restraints

ASSI {15161}
((segid "BrD" and resid 30 and name HN))
(segid "BrD" and resid 31 and name HB %)
  3.800  3.600  1.700 peak      15161 weight  0.10000E+01 volume  0.65201E+02 ppm1    12.276  ppm2  2.299
ASSI {15171}
((segid "BrD" and resid 30 and name HN))
(segid "BrD" and resid 102 and name HD1 %)
  3.900  3.800  1.600 peak      15171 weight  0.10000E+01 volume  0.51602E+02 ppm1    12.275  ppm2  1.315
ASSI {15191}
((segid "BrD" and resid 29 and name HN))
((segid "BrD" and resid 31 and name HN))
  5.000  5.000  0.500 peak      15191 weight  0.10000E+01 volume  0.12673E+02 ppm1     9.152  ppm2  5.470
ASSI {15201}
((segid "BrD" and resid 29 and name HN))
((segid "BrD" and resid 30 and name HB1))
  4.300  4.300  1.200 peak      15201 weight  0.10000E+01 volume  0.29023E+02 ppm1     9.151  ppm2  4.941
ASSI {15211}
((segid "BrD" and resid 29 and name HN))
((segid "BrD" and resid 101 and name HD1 %)
  5.000  5.000  0.500 peak      15211 weight  0.10000E+01 volume  0.12825E+02 ppm1     9.153  ppm2  1.558
ASSI {15261}
((segid "BrD" and resid 27 and name HN))
((segid "BrD" and resid 28 and name HB1))
  4.400  4.400  1.100 peak      15261 weight  0.10000E+01 volume  0.27022E+02 ppm1     8.169  ppm2  3.575
ASSI {15291}
((segid "BrD" and resid 26 and name HN))
((segid "BrD" and resid 24 and name HN))
  3.500  3.100  2.000 peak      15291 weight  0.10000E+01 volume  0.10602E+03 ppm1     9.196  ppm2  8.655
ASSI {15311}
((segid "BrD" and resid 25 and name HN))
((segid "BrD" and resid 24 and name HE22))
  4.900  4.900  0.600 peak      15311 weight  0.10000E+01 volume  0.14311E+02 ppm1     9.133  ppm2  7.489
ASSI {15361}
((segid "BrD" and resid 24 and name HN))
((segid "BrD" and resid 24 and name HE21))
  4.000  4.000  1.500 peak      15361 weight  0.10000E+01 volume  0.49074E+02 ppm1     8.659  ppm2  7.616
ASSI {15381}
((segid "BrD" and resid 19 and name HN))
(segid "BrD" and resid 75 and name HE %)
  5.500  5.500  0.000 peak      15381 weight  0.10000E+01 volume  0.38565E+01 ppm1     9.187  ppm2  2.654
ASSI {15391}
((segid "BrD" and resid 19 and name HN))
((segid "BrD" and resid 63 and name HG))
  4.500  4.500  1.000 peak      15391 weight  0.10000E+01 volume  0.24115E+02 ppm1     9.188  ppm2  2.454
ASSI {15401}
((segid "BrD" and resid 18 and name HN))
((segid "BrD" and resid 21 and name HN))
  3.900  3.800  2.600 peak      15401 weight  0.10000E+01 volume  0.53379E+02 ppm1     9.072  ppm2  8.558
ASSI {15421}
((segid "BrD" and resid 17 and name HN))
((segid "BrD" and resid 16 and name HN))
  2.800  2.000  2.000 peak      15421 weight  0.10000E+01 volume  0.36762E+03 ppm1     8.669  ppm2  8.780
ASSI {15441}
((segid "BrD" and resid 17 and name HN))
((segid "BrD" and resid 20 and name HN))
  3.500  3.100  2.000 peak      15441 weight  0.10000E+01 volume  0.95968E+02 ppm1     8.668  ppm2  8.184
ASSI {15481}
((segid "BrD" and resid 15 and name HN))
(segid "BrD" and resid 18 and name HD1 %)
  5.500  5.500  0.000 peak      15481 weight  0.10000E+01 volume  0.62753E+01 ppm1     8.599  ppm2  1.069
ASSI {15511}
((segid "BrD" and resid 12 and name HN))
((segid "BrD" and resid 10 and name HA))
  3.900  3.800  1.600 peak      15511 weight  0.10000E+01 volume  0.54637E+02 ppm1     9.023  ppm2  5.464
ASSI {15531}
((segid "BrD" and resid 10 and name HN))
((segid "BrD" and resid 8 and name HD2))
  5.200  5.200  0.300 peak      15531 weight  0.10000E+01 volume  0.99597E+01 ppm1     8.885  ppm2  4.288
ASSI {15551}
((segid "BrD" and resid 7 and name HN))
((segid "BrD" and resid 8 and name HD2))
  4.900  4.900  0.600 peak      15551 weight  0.10000E+01 volume  0.14339E+02 ppm1     8.924  ppm2  4.281
ASSI {15631}
((segid "BrD" and resid 32 and name HE1))
((segid "BrD" and resid 33 and name HD2))
  3.800  3.600  1.700 peak      15631 weight  0.10000E+01 volume  0.61547E+02 ppm1    11.082  ppm2  2.167

TABLE 2-continued

Unambiguous NOE-derived Inter-proton Distance Restraints

ASSI {15641}
((segid "BrD" and resid 67 and name HN))
((segid "BrD" and resid 62 and name HA))
  4.600  4.600  0.900 peak      15641 weight  0.10000E+01 volume  0.20420E+02 ppm1    8.832 ppm2  4.471
ASSI {27052}
((segid "BrD" and resid 89 and name HB1))
((segid "BrD" and resid 91 and name HD1))
  3.600  3.200  1.900 peak      27052 weight  0.11000E+01 volume  0.39185E+02 ppm1    3.669 ppm2  4.556
ASSI {27062}
((segid "BrD" and resid 89 and name HB2))
((segid "BrD" and resid 91 and name HD1))
  3.700  3.400  1.800 peak      27062 weight  0.11000E+01 volume  0.32055E+02 ppm1    3.473 ppm2  4.556
ASSI {27072}
((segid "BrD" and resid 89 and name HB2))
((segid "BrD" and resid 91 and name HD2))
  3.400  2.900  2.100 peak      27072 weight  0.11000E+01 volume  0.54263E+02 ppm1    3.473 ppm2  4.411
ASSI {26992}
((segid "BrD" and resid 89 and name HA))
((segid "BrD" and resid 91 and name HG1))
  3.400  2.900  2.100 peak      26992 weight  0.11000E+01 volume  0.54091E+02 ppm1    5.642 ppm2  2.792
OR {26992}
((segid "BrD" and resid 89 and name HA))
((segid "BrD" and resid 91 and name HG2))
ASSI {26732}
((segid "BrD" and resid 94 and name HG1))
(segid "BrD" and resid 95 and name HD %)
  3.300  2.700  2.200 peak      26732 weight  0.11000E+01 volume  0.57563E+02 ppm1    3.127 ppm2  7.505
OR {26732}
((segid "BrD" and resid 94 and name HG2))
(segid "BrD" and resid 95 and name HD %)
ASSI {26822}
((segid "BrD" and resid 94 and name HB2))
(segid "BrD" and resid 95 and name HD %)
  3.000  2.200  2.200 peak      26822 weight  0.11000E+01 volume  0.10961E+03 ppm1    2.733 ppm2  7.506
OR {26822}
((segid "BrD" and resid 94 and name HB1))
(segid "BrD" and resid 95 and name HD %)
ASSI {19122}
(segid "BrD" and resid 43 and name HB %)
(segid "BrD" and resid 47 and name HE %)
  3.900  3.800  1.600 peak      19122 weight  0.11000E+01 volume  0.23047E+02 ppm1    1.697 ppm2  7.267
ASSI {2}
((segid "BrD" and resid 93 and name HA))
((segid "BrD" and resid 93 and name HB2))
  2.100  1.100  1.100 peak        2 weight  0.11000E+01 volume  0.10291E+04 ppm1    5.003 ppm2  4.766
ASSI {22}
((segid "BrD" and resid 108 and name HB1))
((segid "BrD" and resid 108 and name HA))
  1.800  0.800  0.800 peak        22 weight  0.11000E+01 volume  0.21120E+04 ppm1    4.603 ppm2  4.801
ASSI {32}
((segid "BrD" and resid 70 and name HA))
((segid "BrD" and resid 70 and name HB1))
  2.500  1.600  1.600 peak        32 weight  0.11000E+01 volume  0.29221E+03 ppm1    5.344 ppm2  4.786
ASSI {62}
((segid "BrD" and resid 70 and name HB2))
((segid "BrD" and resid 70 and name HA))
  2.500  1.600  1.600 peak        62 weight  0.11000E+01 volume  0.30042E+03 ppm1    4.360 ppm2  5.360
ASSI {72}
((segid "BrD" and resid 20 and name HA))
((segid "BrD" and resid 20 and name HB1))
  2.200  1.100  1.100 peak        72 weight  0.11000E+01 volume  0.10650E+04 ppm1    4.901 ppm2  4.670
ASSI {92}
((segid "BrD" and resid 27 and name HA))
((segid "BrD" and resid 27 and name HB1))
  2.100  1.100  1.100 peak        92 weight  0.11000E+01 volume  0.83585E+03 ppm1    5.050 ppm2  4.617
ASSI {112}
((segid "BrD" and resid 38 and name HA))
(segid "BrD" and resid 38 and name HG2 %)
  2.600  1.700  1.700 peak      112 weight  0.11000E+01 volume  0.24356E+03 ppm1    4.162 ppm2  0.792
ASSI {132}
((segid "BrD" and resid 38 and name HB))
(segid "BrD" and resid 38 and name HG1 %)
  2.400  1.400  1.400 peak      132 weight  0.11000E+01 volume  0.41156E+03 ppm1    1.751 ppm2  1.076
ASSI {152}
(segid "BrD" and resid 38 and name HG2 %)
((segid "BrD" and resid 38 and name HB))
  2.300  1.300  1.300 peak      152 weight  0.11000E+01 volume  0.59973E+03 ppm1    0.808 ppm2  1.776

TABLE 2-continued

Unambiguous NOE-derived Inter-proton Distance Restraints

ASSI {232}
((segid "BrD" and resid 81 and name HB))
(segid "BrD" and resid 81 and name HG1 %)
  2.400  1.400  1.400 peak        232 weight  0.11000E+01 volume   0.37056E+03 ppm1   2.042 ppm2  1.079
ASSI {242}
((segid "BrD" and resid 81 and name HB))
(segid "BrD" and resid 81 and name HG2 %)
  2.300  1.300  1.300 peak        242 weight  0.11000E+01 volume   0.47548E+03 ppm1   2.042 ppm2  0.759
ASSI {262}
((segid "BrD" and resid 15 and name HA))
((segid "BrD" and resid 15 and name HB1))
  2.700  1.800  1.800 peak        262 weight  0.11000E+01 volume   0.20830E+03 ppm1   4.607 ppm2  3.811
ASSI {322}
((segid "BrD" and resid 46 and name HB1))
((segid "BrD" and resid 46 and name HA))
  2.700  1.800  1.800 peak        322 weight  0.11000E+01 volume   0.21305E+03 ppm1   3.274 ppm2  4.143
ASSI {332}
((segid "BrD" and resid 46 and name HB2))
((segid "BrD" and resid 46 and name HA))
  2.700  1.800  1.800 peak        332 weight  0.11000E+01 volume   0.21514E+03 ppm1   3.077 ppm2  4.143
ASSI {352}
((segid "BrD" and resid 47 and name HA))
((segid "BrD" and resid 47 and name HB2))
  2.700  1.800  1.800 peak        352 weight  0.11000E+01 volume   0.22249E+03 ppm1   4.704 ppm2  3.395
ASSI {362}
((segid "BrD" and resid 47 and name HB1))
((segid "BrD" and resid 47 and name HA))
  2.600  1.700  1.700 peak        362 weight  0.11000E+01 volume   0.23254E+03 ppm1   3.815 ppm2  4.721
ASSI {382}
((segid "BrD" and resid 67 and name HA))
((segid "BrD" and resid 67 and name HB1))
  2.400  1.400  1.400 peak        382 weight  0.11000E+01 volume   0.45818E+03 ppm1   4.654 ppm2  3.572
ASSI {392}
((segid "BrD" and resid 67 and name HA))
((segid "BrD" and resid 67 and name HB2))
  2.500  1.600  1.600 peak        392 weight  0.11000E+01 volume   0.31584E+03 ppm1   4.653 ppm2  2.669
ASSI {422}
((segid "BrD" and resid 68 and name HB1))
((segid "BrD" and resid 68 and name HA))
  3.100  2.400  2.400 peak        422 weight  0.11000E+01 volume   0.94493E+02 ppm1   3.669 ppm2  5.143
ASSI {432}
((segid "BrD" and resid 68 and name HB2))
((segid "BrD" and resid 68 and name HA))
  2.700  1.800  1.800 peak        432 weight  0.11000E+01 volume   0.18471E+03 ppm1   3.522 ppm2  5.143
ASSI {472}
((segid "BrD" and resid 88 and name HB1))
((segid "BrD" and resid 88 and name HA))
  2.600  1.700  1.700 peak        472 weight  0.11000E+01 volume   0.28741E+03 ppm1   3.522 ppm2  4.989
ASSI {492}
((segid "BrD" and resid 95 and name HA))
((segid "BrD" and resid 95 and name HB2))
  2.600  1.700  1.700 peak        492 weight  0.11000E+01 volume   0.23932E+03 ppm1   4.459 ppm2  3.361
ASSI {502}
((segid "BrD" and resid 95 and name HB1))
((segid "BrD" and resid 95 and name HA))
  2.600  1.700  1.700 peak        502 weight  0.11000E+01 volume   0.28555E+03 ppm1   3.619 ppm2  4.444
ASSI {522}
((segid "BrD" and resid 96 and name HA))
((segid "BrD" and resid 96 and name HB1))
  2.800  2.000  2.000 peak        522 weight  0.11000E+01 volume   0.17185E+03 ppm1   4.409 ppm2  3.998
ASSI {532}
((segid "BrD" and resid 96 and name HA))
((segid "BrD" and resid 96 and name HB2))
  2.800  2.000  2.000 peak        532 weight  0.11000E+01 volume   0.16898E+03 ppm1   4.409 ppm2  3.118
ASSI {562}
((segid "BrD" and resid 31 and name HA))
(segid "BrD" and resid 31 and name HB %)
  2.500  1.600  1.600 peak        562 weight  0.11000E+01 volume   0.36354E+03 ppm1   5.000 ppm2  2.315
ASSI {592}
(segid "BrD" and resid 43 and name HB %)
((segid "BrD" and resid 43 and name HA))
  2.200  1.200  1.200 peak        592 weight  0.11000E+01 volume   0.76123E+03 ppm1   1.700 ppm2  5.539
ASSI {612}
(segid "BrD" and resid 76 and name HB %)
((segid "BrD" and resid 76 and name HA))
  2.100  1.100  1.100 peak        612 weight  0.11000E+01 volume   0.87848E+03 ppm1   2.093 ppm2  4.687

TABLE 2-continued

| Unambiguous NOE-derived Inter-proton Distance Restraints |
|---|

ASSI {632}
(segid "BrD" and resid 99 and name HB %)
((segid "BrD" and resid 99 and name HA))
  2.000  1.000  1.000 peak       632 weight  0.11000E+01 volume  0.10742E+04 ppm1    2.190  ppm2  4.440
ASSI {642}
((segid "BrD" and resid 113 and name HA))
(segid "BrD" and resid 113 and name HB %)
  2.100  1.100  1.100 peak       642 weight  0.11000E+01 volume  0.84264 E+03 ppm1    4.901  ppm2  1.979
ASSI {662}
((segid "BrD" and resid 34 and name HA))
((segid "BrD" and resid 34 and name HB1))
  2.600  1.700  1.700 peak       662 weight  0.11000E+01 volume  0.27701E+03 ppm1    5.542  ppm2  4.107
ASSI {672}
((segid "BrD" and resid 34 and name HA))
((segid "BrD" and resid 34 and name HB2))
  2.800  2.000  2.000 peak       672 weight  0.11000E+01 volume  0.16922E+03 ppm1    5.542  ppm2  3.146
ASSI {702}
((segid "BrD" and resid 74 and name HA))
((segid "BrD" and resid 74 and name HB1))
  3.000  2.200  2.200 peak       702 weight  0.11000E+01 volume  0.10996E+03 ppm1    4.359  ppm2  3.563
ASSI {712}
((segid "BrD" and resid 74 and name HA))
((segid "BrD" and resid 74 and name HB2))
  3.100  2.400  2.400 peak       712 weight  0.11000E+01 volume  0.88126E+02 ppm1    4.361  ppm2  3.000
ASSI {742}
((segid "BrD" and resid 82 and name HA))
((segid "BrD" and resid 82 and name HB1)
  2.800  2.000  2.000 peak       742 weight  0.11000E+01 volume  0.15835E+03 ppm1    4.755  ppm2  3.695
ASSI {752}
((segid "BrD" and resid 82 and name HA))
((segid "BrD" and resid 82 and name HB2))
  2.700  1.800  1.800 peak       752 weight  0.11000E+01 volume  0.18532E+03 ppm1    4.755  ppm2  3.573
ASSI {792}
((segid "BrD" and resid 106 and name HA))
((segid "BrD" and resid 106 and name HB1))
  2.700  1.800  1.800 peak       792 weight  0.11000E+01 volume  0.19130E+03 ppm1    4.558  ppm2  3.916
ASSI {802}
((segid "BrD" and resid 106 and name HA))
((segid "BrD" and resid 106 and name HB2))
  2.600  1.700  1.700 peak       802 weight  0.11000E+01 volume  0.25966E+03 ppm1    4.557  ppm2  3.702
ASSI {842}
((segid "BrD" and resid 107 and name HB1))
((segid "BrD" and resid 107 and name HA))
  2.200  1.200  1.200 peak       842 weight  0.11000E+01 volume  0.64742E+03 ppm1    3.671  ppm2  4.435
ASSI {872}
((segid "BrD" and resid 65 and name HA))
((segid "BrD" and resid 65 and name HB1))
  2.600  1.700  1.700 peak       872 weight  0.11000E+01 volume  0.23368E+03 ppm1    5.398  ppm2  3.621
ASSI {882}
((segid "BrD" and resid 65 and name HA))
((segid "BrD" and resid 65 and name HB2))
  2.900  2.100  2.100 peak       882 weight  0.11000E+01 volume  0.14380E+03 ppm1    5.396  ppm2  3.369
ASSI {892}
((segid "BrD" and resid 84 and name HA))
((segid "BrD" and resid 84 and name HB1))
  2.700  1.800  1.800 peak       892 weight  0.11000E+01 volume  0.20950E+03 ppm1    4.904  ppm2  3.606
ASSI {902}
((segid "BrD" and resid 84 and name HA))
((segid "BrD" and resid 84 and name HB2))
  2.600  1.700  1.700 peak       902 weight  0.11000E+01 volume  0.23639E+03 ppm1    4.904  ppm2  3.272
ASSI {942}
((segid "BrD" and resid 100 and name HB2))
((segid "BrD" and resid 100 and name HA))
  2.300  1.300  1.300 peak       942 weight  0.11000E+01 volume  0.53744E+03 ppm1    3.424  ppm2  4.949
ASSI {952}
((segid "BrD" and resid 10 and name HA))
((segid "BrD" and resid 10 and name HB1))
  3.200  2.600  2.300 peak       952 weight  0.11000E+01 volume  0.81254E+02 ppm1    5.478  ppm2  3.354
ASSI {972}
((segid "BrD" and resid 12 and name HA))
((segid "BrD" and resid 12 and name HB1))
  2.700  1.800  1.800 peak       972 weight  0.11000E+01 volume  0.22766E+03 ppm1    5.297  ppm2  3.434
ASSI {992}
((segid "BrD" and resid 77 and name HA))
((segid "BrD" and resid 77 and name HB1))
  2.600  1.600  1.600 peak       992 weight  0.11000E+01 volume  0.33274E+03 ppm1    4.951  ppm2  3.319

TABLE 2-continued

| Unambiguous NOE-derived Inter-proton Distance Restraints |
|---|

ASSI {1032}
((segid "BrD" and resid 117 and name HB2))
((segid "BrD" and resid 117 and name HA))
  2.700  1.800  1.800 peak        1032 weight  0.11000E+01 volume    0.21830E+03 ppm1        3.127  ppm2  5.167
ASSI {1042}
((segid "BrD" and resid 117 and name HB1))
((segid "BrD" and resid 117 and name HA))
  2.600  1.700  1.700 peak        1042 weight  0.11000E+01 volume    0.23430E+03 ppm1        3.301  ppm2  5.167
ASSI {1052}
((segid "BrD" and resid 89 and name HA))
((segid "BrD" and resid 89 and name HB1))
  2.900  2.100  2.100 peak        1052 weight  0.11000E+01 volume    0.12958E+03 ppm1        5.641  ppm2  3.668
ASSI {1062}
((segid "BrD" and resid 89 and name HA))
((segid "BrD" and resid 89 and name HB2))
  2.800  2.000  2.000 peak        1062 weight  0.11000E+01 volume    0.16727E+03 ppm1        5.641  ppm2  3.491
ASSI {1092}
((segid "BrD" and resid 18 and name HA))
((segid "BrD" and resid 18 and name HG))
  3.100  2.400  2.400 peak        1092 weight  0.11000E+01 volume    0.85824E+02 ppm1        3.866  ppm2  2.277
ASSI {1132}
(segid "BrD" and resid 18 and name HD2 %)
((segid "BrD" and resid 18 and name HA))
  2.100  1.100  1.100 peak        1132 weight  0.11000E+01 volume    0.86347E+03 ppm1        0.415  ppm2  3.883
ASSI {1142}
(segid "BrD" and resid 18 and name HD2 %)
((segid "BrD" and resid 18 and name HG))
  2.500  1.600  1.600 peak        1142 weight  0.11000E+01 volume    0.31482E+03 ppm1        0.419  ppm2  2.274
ASSI {1162}
((segid "BrD" and resid 78 and name HA))
((segid "BrD" and resid 78 and name HB2))
  2.500  1.600  1.600 peak        1162 weight  0.11000E+01 volume    0.33654E+03 ppm1        3.968  ppm2  1.044
ASSI {1172}
((segid "BrD" and resid 78 and name HA))
((segid "BrD" and resid 78 and name HG))
  2.900  2.100  2.100 peak        1172 weight  0.11000E+01 volume    0.14454E+03 ppm1        3.967  ppm2  1.270
ASSI {1202}
((segid "BrD" and resid 78 and name HB1))
((segid "BrD" and resid 78 and name HA))
  2.700  1.800  1.800 peak        1202 weight  0.11000E+01 volume    0.21843E+03 ppm1        1.305  ppm2  4.001
ASSI {1212}
((segid "BrD" and resid 78 and name HB1))
(segid "BrD" and resid 78 and name HD1 %)
  2.900  2.100  2.100 peak        1212 weight  0.11000E+01 volume    0.13310E+03 ppm1        1.305  ppm2  0.776
ASSI {1222}
((segid "BrD" and resid 78 and name HB1))
(segid "BrD" and resid 78 and name HD2 %)
  2.700  1.800  1.800 peak        1222 weight  0.11000E+01 volume    0.22009E+03 ppm1        1.305  ppm2  0.673
ASSI {1262}
((segid "BrD" and resid 78 and name HG))
((segid "BrD" and resid 78 and name HB2))
  2.400  1.400  1.400 peak        1262 weight  0.11000E+01 volume    0.41554E+03 ppm1        1.254  ppm2  1.043
ASSI {1282}
(segid "BrD" and resid 78 and name HD1 %)
((segid "BrD" and resid 78 and name HA))
  2.400  1.400  1.400 peak        1282 weight  0.11000E+01 volume    0.38399E+03 ppm1        0.761  ppm2  3.998
ASSI {1302}
(segid "BrD" and resid 78 and name HD1 %)
((segid "BrD" and resid 78 and name HB2))
  2.600  1.700  1.700 peak        1302 weight  0.11000E+01 volume    0.25846E+03 ppm1        0.761  ppm2  1.038
ASSI {1312}
(segid "BrD" and resid 78 and name HD1 %)
((segid "BrD" and resid 78 and name HG))
  2.200  1.200  1.200 peak        1312 weight  0.11000E+01 volume    0.70030E+03 ppm1        0.761  ppm2  1.270
ASSI {1322}
((segid "BrD" and resid 115 and name HA))
((segid "BrD" and resid 115 and name HB1))
  2.200  1.200  1.200 peak        1322 weight  0.11000E+01 volume    0.70481E+03 ppm1        4.807  ppm2  2.182
ASSI {1352}
(segid "BrD" and resid 115 and name HD1 %)
((segid "BrD" and resid 115 and name HA))
  3.300  2.700  2.200 peak        1352 weight  0.11000E+01 volume    0.57522E+02 ppm1        1.352  ppm2  4.829
ASSI {1362}
(segid "BrD" and resid 115 and name HD1 %)
((segid "BrD" and resid 115 and name HG))
  2.400  1.400  1.400 peak        1362 weight  0.11000E+01 volume    0.44618E+03 ppm1        1.352  ppm2  2.148

TABLE 2-continued

Unambiguous NOE-derived Inter-proton Distance Restraints

ASSI {1382}
((segid "BrD" and resid 116 and name HB))
((segid "BrD" and resid 116 and name HA))
 2.700 1.800 1.800 peak       1382 weight 0.11000E+01 volume 0.19754E+03 ppm1  2.411 ppm2 4.823
ASSI {1402}
((segid "BrD" and resid 116 and name HB))
((segid "BrD" and resid 116 and name HG12))
 2.200 1.200 1.200 peak       1402 weight 0.11000E+01 volume 0.69345E+03 ppm1  2.409 ppm2 1.555
ASSI {1422}
((segid "BrD" and resid 116 and name HG11))
((segid "BrD" and resid 116 and name HB))
 2.500 1.600 1.600 peak       1422 weight 0.11000E+01 volume 0.30727E+03 ppm1  1.920 ppm2 2.418
ASSI {1432}
(segid "BrD" and resid 116 and name HG2 %)
((segid "BrD" and resid 116 and name HA))
 2.500 1.600 1.600 peak       1432 weight 0.11000E+01 volume 0.32118E+03 ppm1  1.403 ppm2 4.823
ASSI {1442}
(segid "BrD" and resid 116 and name HG2 %)
((segid "BrD" and resid 116 and name HB))
 2.300 1.300 1.300 peak       1442 weight 0.11000E+01 volume 0.50062E+03 ppm1  1.403 ppm2 2.419
ASSI {1452}
(segid "BrD" and resid 116 and name HD1 %)
((segid "BrD" and resid 116 and name HG12))
 2.100 1.100 1.100 peak       1452 weight 0.11000E+01 volume 0.85569E+03 ppm1  1.399 ppm2 1.554
ASSI {1462}
(segid "BrD" and resid 116 and name HD1 %)
((segid "BrD" and resid 116 and name HG11))
 2.500 1.600 1.600 peak       1462 weight 0.11000E+01 volume 0.33669E+03 ppm1  1.399 ppm2 1.919
ASSI {1512}
((segid "BrD" and resid 110 and name HB))
((segid "BrD" and resid 110 and name HA))
 2.400 1.400 1.400 peak       1512 weight 0.11000E+01 volume 0.40202E+03 ppm1  2.338 ppm2 4.418
ASSI {1542}
(segid "BrD" and resid 110 and name HG2 %)
((segid "BrD" and resid 110 and name HA))
 2.200 1.200 1.200 peak       1542 weight 0.11000E+01 volume 0.74299E+03 ppm1  1.251 ppm2 4.418
ASSI {1552}
(segid "BrD" and resid 110 and name HG2 %)
((segid "BrD" and resid 110 and name HB))
 2.200 1.200 1.200 peak       1552 weight 0.11000E+01 volume 0.70453E+03 ppm1  1.252 ppm2 2.361
ASSI {1562}
(segid "BrD" and resid 110 and name HG2 %)
((segid "BrD" and resid 110 and name HG11))
 2.600 1.700 1.700 peak       1562 weight 0.11000E+01 volume 0.27736E+03 ppm1  1.253 ppm2 1.718
ASSI {1572}
(segid "BrD" and resid 110 and name HG2 %)
(segid "BrD" and resid 110 and name HD1 %)
 2.000 1.000 1.000 peak       2572 weight 0.11000E+01 volume 0.13448E+04 ppm1  1.254 ppm2 1.141
ASSI {1602}
(segid "BrD" and resid 110 and name HD1 %)
((segid "BrD" and resid 110 and name HA))
 2.200 1.200 1.200 peak       1602 weight 0.11000E+01 volume 0.74125E+03 ppm1  1.154 ppm2 4.420
ASSI {1612}
(segid "BrD" and resid 110 and name HD1 %)
((segid "BrD" and resid 110 and name HB))
 2.200 1.200 1.200 peak       1612 weight 0.11000E+01 volume 0.75209E+03 ppm1  1.154 ppm2 2.361
ASSI {1622}
(segid "BrD" and resid 110 and name HD1 %)
((segid "BrD" and resid 110 and name HG11))
 2.300 1.300 1.300 peak       1622 weight 0.11000E+01 volume 0.59823E+03 ppm1  1.154 ppm2 1.718
ASSI {1682}
(segid "BrD" and resid 50 and name HD1 %)
((segid "BrD" and resid 50 and name HB))
 2.800 2.000 2.000 peak       1682 weight 0.11000E+01 volume 0.14989E+03 ppm1  1.154 ppm2 1.826
ASSI {1692}
(segid "BrD" and resid 50 and name HD1 %)
((segid "BrD" and resid 50 and name HG11))
 2.300 1.300 1.300 peak       1692 weight 0.11000E+01 volume 0.49711E+03 ppm1  1.154 ppm2 1.408
ASSI {1702}
(segid "BrD" and resid 50 and name HD1 %)
((segid "BrD" and resid 50 and name HG12))
 2.400 1.400 1.400 peak       1702 weight 0.11000E+01 volume 0.46662E+03 ppm1  1.155 ppm2 0.838
ASSI {1712}
(segid "BrD" and resid 50 and name HD1 %)
(segid "BrD" and resid 50 and name HG2 %)
 2.400 1.400 1.400 peak       1712 weight 0.11000E+01 volume 0.45248E+03 ppm1  1.154 ppm2 0.994

TABLE 2-continued

Unambiguous NOE-derived Inter-proton Distance Restraints

ASSI {1742}
(segid "BrD" and resid 50 and name HG2 %)
((segid "BrD" and resid 50 and name HA))
  2.400  1.400  1.400 peak      1742 weight  0.11000E+01 volume  0.43004E+03 ppm1   1.006 ppm2  4.518
ASSI {1752}
(segid "BrD" and resid 50 and name HG2 %)
((segid "BrD" and resid 50 and name HB))
  2.200  1.200  1.200 peak      1752 weight  0.11000E+01 volume  0.61685E+03 ppm1   1.006 ppm2  1.825
ASSI {1762}
(segid "BrD" and resid 50 and name HG2 %)
((segid "BrD" and resid 50 and name HG11))
  2.800  2.000  2.000 peak      1762 weight  0.11000E+01 volume  0.16808E+03 ppm1   1.008 ppm2  1.409
ASSI {1772}
(segid "BrD" and resid 50 and name HG2 %)
((segid "BrD" and resid 50 and name HG12))
  2.400  1.400  1.400 peak      1772 weight  0.11000E+01 volume  0.40990E+03 ppm1   1.006 ppm2  0.838
ASSI {1792}
((segid "BrD" and resid 101 and name HA))
(segid "BrD" and resid 101 and name HD1 %)
  2.700  1.800  1.800 peak      1792 weight  0.11000E+01 volume  0.20691E+03 ppm1   4.261 ppm2  1.578
ASSI {1812}
((segid "BrD" and resid 101 and name HB))
(segid "BrD" and resid 101 and name HD1 %)
  2.300  1.300  1.300 peak      1812 weight  0.11000E+01 volume  0.50350E+03 ppm1   2.537 ppm2  1.578
ASSI {1852}
((segid "BrD" and resid 101 and name HG11))
(segid "BrD" and resid 101 and name HG2 %)
  2.600  1.700  1.700 peak      1852 weight  0.11000E+01 volume  0.23958E+03 ppm1   2.444 ppm2  1.609
ASSI {1872}
(segid "BrD" and resid 101 and name HG2 %)
((segid "BrD" and resid 101 and name HA))
  2.400  1.400  1.400 peak      1872 weight  0.11000E+01 volume  0.44349E+03 ppm1   1.596 ppm2  4.265
ASSI {1882}
(segid "BrD" and resid 101 and name HG2 %)
((segid "BrD" and resid 101 and name HB))
  2.200  1.200  1.200 peak      1882 weight  0.11000E+01 volume  0.72150E+03 ppm1   1.600 ppm2  2.536
ASSI {1892}
(segid "BrD" and resid 101 and name HG2 %)
((segid "BrD" and resid 101 and name HG12))
  2.300  1.300  1.300 peak      1892 weight  0.11000E+01 volume  0.60307E+03 ppm1   1.598 ppm2  1.806
ASSI {1922}
(segid "BrD" and resid 101 and name HD1 %)
((segid "BrD" and resid 101 and name HG11))
  2.300  1.300  1.300 peak      1922 weight  0.11000E+01 volume  0.50142E+03 ppm1   1.550 ppm2  2.467
ASSI {1932}
(segid "BrD" and resid 101 and name HD1 %)
((segid "BrD" and resid 101 and name HG12))
  2.200  1.200  1.200 peak      1932 weight  0.11000E+01 volume  0.71179E+03 ppm1   1.550 ppm2  1.806
ASSI {1952}
((segid "BrD" and resid 21 and name HA))
(segid "BrD" and resid 21 and name HD1 %)
  2.800  2.000  2.000 peak      1952 weight  0.11000E+01 volume  0.16491E+03 ppm1   4.359 ppm2  1.221
ASSI {1962}
((segid "BrD" and resid 21 and name HB))
(segid "BrD" and resid 21 and name HG2 %)
  3.100  2.400  2.400 peak      1962 weight  0.11000E+01 volume  0.84008E+02 ppm1   2.487 ppm2  1.588
ASSI {1982}
((segid "BrD" and resid 21 and name HG12))
(segid "BrD" and resid 21 and name HD1 %)
  2.500  1.600  1.600 peak      1982 weight  0.11000E+01 volume  0.32478E+03 ppm1   1.648 ppm2  1.222
ASSI {2012}
(segid "BrD" and resid 21 and name HG2 %)
((segid "BrD" and resid 21 and name HG11))
  2.600  1.700  1.700 peak      2012 weight  0.11000E+01 volume  0.24142E+03 ppm1   1.598 ppm2  2.357
ASSI {2022}
(segid "BrD" and resid 21 and name HD1 %)
((segid "BrD" and resid 21 and name HB))
  2.500  1.600  1.600 peak      2022 weight  0.11000E+01 volume  0.29587E+03 ppm1   1.206 ppm2  2.508
ASSI {2032}
(segid "BrD" and resid 21 and name HD1 %)
((segid "BrD" and resid 21 and name HG11))
  2.400  1.400  1.400 peak      2032 weight  0.11000E+01 volume  0.44094E+03 ppm1   1.205 ppm2  2.355
ASSI {2042}
(segid "BrD" and resid 21 and name HD1 %)
(segid "BrD" and resid 21 and name HG2 %)
  2.300  1.300  1.300 peak      2042 weight  0.11000E+01 volume  0.49870E+03 ppm1   1.205 ppm2  1.588

TABLE 2-continued

Unambiguous NOE-derived Inter-proton Distance Restraints

ASSI {2052}
((segid "BrD" and resid 112 and name HA))
((segid "BrD" and resid 112 and name HG1))
  2.700  1.800  1.800 peak      2052 weight  0.11000E+01 volume  0.21076E+03 ppm1   4.607 ppm2  2.942
ASSI {2072}
((segid "BrD" and resid 112 and name HB1))
((segid "BrD" and resid 112 and name HG1))
  2.300  1.300  1.300 peak      2072 weight  0.11000E+01 volume  0.51152E+03 ppm1   2.684 ppm2  2.947
ASSI {2092}
((segid "BrD" and resid 94 and name HA))
((segid "BrD" and resid 94 and name HG1))
  2.700  1.800  1.800 peak      2092 weight  0.11000E+01 volume  0.21281E+03 ppm1   4.830 ppm2  3.127
ASSI {2112}
((segid "BrD" and resid 92 and name HG1))
((segid "BrD" and resid 92 and name HA))
  2.400  1.400  1.400 peak      2112 weight  0.11000E+01 volume  0.46860E+03 ppm1   2.816 ppm2  4.798
ASSI {2142}
((segid "BrD" and resid 87 and name HG1))
((segid "BrD" and resid 87 and name HA))
  2.900  2.100  2.100 peak      2142 weight  0.11000E+01 volume  0.13435E+03 ppm1   3.030 ppm2  4.874
ASSI {2152}
((segid "BrD" and resid 87 and name HG2))
((segid "BrD" and resid 87 and name HA))
  2.500  1.600  1.600 peak      2152 weight  0.11000E+01 volume  0.35437E+03 ppm1   2.782 ppm2  4.875
ASSI {2172}
((segid "BrD" and resid 61 and name HG1))
((segid "BrD" and resid 61 and name HA))
  2.300  1.300  1.300 peak      2172 weight  0.11000E+01 volume  0.47499E+03 ppm1   2.980 ppm2  4.670
ASSI {2182}
((segid "BrD" and resid 61 and name HG2))
((segid "BrD" and resid 61 and name HA))
  2.800  2.000  2.000 peak      2182 weight  0.11000E+01 volume  0.17452E+03 ppm1   2.832 ppm2  4.670
ASSI {2202}
((segid "BrD" and resid 42 and name HG1))
((segid "BrD" and resid 42 and name HA))
  2.400  1.400  1.400 peak      2202 weight  0.11000E+01 volume  0.43794E+03 ppm1   2.880 ppm2  5.049
ASSI {2222}
((segid "BrD" and resid 36 and name HG1))
((segid "BrD" and resid 36 and name HA))
  2.600  1.700  1.700 peak      2222 weight  0.11000E+01 volume  0.28226E+03 ppm1   2.781 ppm2  5.445
ASSI {2252}
((segid "BrD" and resid 79 and name HG1))
((segid "BrD" and resid 79 and name HA))
  2.600  1.700  1.700 peak      2252 weight  0.11000E+01 volume  0.27675E+03 ppm1   3.033 ppm2  4.417
ASSI {2262}
((segid "BrD" and resid 29 and name HA))
((segid "BrD" and resid 29 and name HB1))
  2.000  1.000  1.000 peak      2262 weight  0.11000E+01 volume  0.11521E+04 ppm1   4.810 ppm2  2.738
ASSI {2272}
((segid "BrD" and resid 29 and name HG1))
((segid "BrD" and resid 29 and name HA))
  2.600  1.700  1.700 peak      2272 weight  0.11000E+01 volume  0.24467E+03 ppm1   2.980 ppm2  4.810
ASSI {2302}
((segid "BrD" and resid 23 and name HG1))
((segid "BrD" and resid 23 and name HA))
  2.500  1.600  1.600 peak      2302 weight  0.11000E+01 volume  0.32948E+03 ppm1   3.124 ppm2  4.638
ASSI {2312}
((segid "BrD" and resid 23 and name HG2))
((segid "BrD" and resid 23 and name HA))
  2.400  1.400  1.400 peak      2312 weight  0.11000E+01 volume  0.37520E+03 ppm1   3.068 ppm2  4.638
ASSI {2322}
((segid "BrD" and resid 80 and name HD2))
((segid "BrD" and resid 80 and name HG1))
  2.500  1.600  1.600 peak      2322 weight  0.11000E+01 volume  0.34874E+03 ppm1   3.913 ppm2  2.347
ASSI {2342}
((segid "BrD" and resid 80 and name HD2))
((segid "BrD" and resid 80 and name HB1))
  2.800  2.000  2.000 peak      2342 weight  0.11000E+01 volume  0.17327E+03 ppm1   3.913 ppm2  2.573
ASSI {2372}
((segid "BrD" and resid 66 and name HA))
((segid "BrD" and resid 66 and name HD1))
  2.700  1.800  1.800 peak      2372 weight  0.11000E+01 volume  0.22458E+03 ppm1   5.000 ppm2  3.670
ASSI {2382}
((segid "BrD" and resid 66 and name HG2))
((segid "BrD" and resid 66 and name HD1))
  2.500  1.600  1.600 peak      2382 weight  0.11000E+01 volume  0.35872E+03 ppm1   2.140 ppm2  3.670

TABLE 2-continued

Unambiguous NOE-derived Inter-proton Distance Restraints

ASSI {2392}
((segid "BrD" and resid 9 and name HD1))
((segid "BrD" and resid 9 and name HG1))
  2.300  1.300  1.300 peak      2392 weight  0.11000E+01 volume  0.81278E+03 ppm1    3.769 ppm2  2.279
ASSI {2432}
((segid "BrD" and resid 35 and name HG1))
((segid "BrD" and resid 35 and name HA))
  2.900  2.100  2.100 peak      2432 weight  0.11000E+01 volume  0.13495E+03 ppm1    3.422 ppm2  4.901
ASSI {2442}
((segid "BrD" and resid 102 and name HB1))
((segid "BrD" and resid 102 and name HA))
  2.700  1.800  1.800 peak      2442 weight  0.11000E+01 volume  0.22859E+03 ppm1    1.994 ppm2  4.282
ASSI {2452}
((segid "BrD" and resid 102 and name HB2))
((segid "BrD" and resid 102 and name HA))
  2.700  1.800  1.800 peak      2452 weight  0.11000E+01 volume  0.18482E+03 ppm1    1.848 ppm2  4.280
ASSI {2462}
((segid "BrD" and resid 102 and name HB1))
(segid "BrD" and resid 102 and name HD1 %)
  2.500  1.600  1.600 peak      2462 weight  0.11000E+01 volume  0.28966E+03 ppm1    1.992 ppm2  1.325
ASSI {2472}
((segid "BrD" and resid 102 and name HB2))
(segid "BrD" and resid 102 and name HD1 %)
  2.500  1.600  1.600 peak      2472 weight  0.11000E+01 volume  0.33733E+03 ppm1    1.842 ppm2  1.325
ASSI {2532}
((segid "BrD" and resid 73 and name HA))
((segid "BrD" and resid 73 and name HB2))
  2.500  1.600  1.600 peak      2532 weight  0.11000E+01 volume  0.31007E+03 ppm1    4.805 ppm2  2.482
ASSI {2542}
((segid "BrD" and resid 73 and name HA))
((segid "BrD" and resid 73 and name HG))
  2.600  1.700  1.700 peak      2542 weight  0.11000E+01 volume  0.27034E+03 ppm1    4.805 ppm2  2.368
ASSI {2572}
((segid "BrD" and resid 73 and name HB2))
(segid "BrD" and resid 73 and name HD1 %)
  2.400  1.400  1.400 peak      2572 weight  0.11000E+01 volume  0.37597E+03 ppm1    2.487 ppm2  1.539
ASSI {2582}
(segid "BrD" and resid 73 and name HD2 %)
((segid "BrD" and resid 73 and name HA))
  2.200  1.200  1.200 peak      2582 weight  0.11000E+01 volume  0.64867E+03 ppm1    1.499 ppm2  4.827
ASSI {2592}
(segid "BrD" and resid 73 and name HD2 %)
((segid "BrD" and resid 73 and name HG))
  2.100  1.100  1.100 peak      2592 weight  0.11000E+01 volume  0.88262E+03 ppm1    1.500 ppm2  2.367
ASSI {2602}
(segid "BrD" and resid 56 and name HD2 %)
((segid "BrD" and resid 56 and name HG))
  2.200  1.200  1.200 peak      2602 weight  0.11000E+01 volume  0.64971E+03 ppm1    1.254 ppm2  2.328
ASSI {2612}
(segid "BrD" and resid 56 and name HD2 %)
((segid "BrD" and resid 56 and name HB1))
  2.700  1.800  1.800 peak      2612 weight  0.11000E+01 volume  0.20000E+03 ppm1    1.254 ppm2  2.703
ASSI {2622}
(segid "BrD" and resid 56 and name HD2 %)
((segid "BrD" and resid 56 and name HA))
  2.200  1.200  1.200 peak      2622 weight  0.11000E+01 volume  0.63602E+03 ppm1    1.253 ppm2  4.630
ASSI {2652}
((segid "BrD" and resid 22 and name HB1))
((segid "BrD" and resid 22 and name HA))
  2.400  1.400  1.400 peak      2652 weight  0.11000E+01 volume  0.44257E+03 ppm1    2.682 ppm2  4.723
ASSI {2662}
((segid "BrD" and resid 22 and name HB2))
((segid "BrD" and resid 22 and name HA))
  2.400  1.400  1.400 peak      2662 weight  0.11000E+01 volume  0.37194E+03 ppm1    2.287 ppm2  4.723
ASSI {2682}
(segid "BrD" and resid 22 and name HD2 %)
((segid "BrD" and resid 22 and name HA))
  2.200  1.200  1.200 peak      2682 weight  0.11000E+01 volume  0.64884E+03 ppm1    1.599 ppm2  4.723
ASSI {2702}
((segid "BrD" and resid 63 and name HA))
((segid "BrD" and resid 63 and name HB1))
  2.900  2.100  2.100 peak      2702 weight  0.11000E+01 volume  0.13727E+03 ppm1    5.296 ppm2  2.907
ASSI {2712}
((segid "BrD" and resid 63 and name HA))
((segid "BrD" and resid 63 and name HB2))
  2.700  1.800  1.800 peak      2712 weight  0.11000E+01 volume  0.18645E+03 ppm1    5.296 ppm2  2.535

TABLE 2-continued

Unambiguous NOE-derived Inter-proton Distance Restraints

ASSI {2722}
((segid "BrD" and resid 63 and name HA))
((segid "BrD" and resid 63 and name HG))
 2.900  2.100  2.100 peak       2722 weight  0.11000E+01 volume  0.13509E+03 ppm1   5.293 ppm2  2.423
ASSI {2732}
((segid "BrD" and resid 63 and name HA))
(segid "BrD" and resid 63 and name HD1 %)
 2.700  1.800  1.800 peak       2732 weight  0.11000E+01 volume  0.22485E+03 ppm1   5.296 ppm2  1.649
ASSI {2742}
((segid "BrD" and resid 63 and name HA))
(segid "BrD" and resid 63 and name HD2 %)
 3.300  2.700  2.200 peak       2742 weight  0.11000E+01 volume  0.65439E+02 ppm1   5.296 ppm2  1.490
ASSI {2752}
((segid "BrD" and resid 63 and name HB2))
(segid "BrD" and resid 63 and name HD1 %)
 2.500  1.600  1.600 peak       2752 weight  0.11000E+01 volume  0.34992E+03 ppm1   2.538 ppm2  1.653
ASSI {2762}
((segid "BrD" and resid 63 and name HB2))
(segid "BrD" and resid 63 and name HD2 %)
 2.700  1.800  1.800 peak       2762 weight  0.11000E+01 volume  0.19887E+03 ppm1   2.538 ppm2  1.491
ASSI {2772}
((segid "BrD" and resid 63 and name HB1))
(segid "BrD" and resid 63 and name HD1 %)
 2.600  1.700  1.700 peak       2772 weight  0.11000E+01 volume  0.26127E+03 ppm1   2.883 ppm2  1.653
ASSI {2782}
((segid "BrD" and resid 63 and name HB1))
(segid "BrD" and resid 63 and name HD2 %)
 2.600  1.700  1.700 peak       2782 weight  0.11000E+01 volume  0.25187E+03 ppm1   2.883 ppm2  1.491
ASSI {2852}
(segid "BrD" and resid 14 and name HD2 %)
((segid "BrD" and resid 14 and name HA))
 3.100  2.400  2.400 peak       2852 weight  0.11000E+01 volume  0.89872E+02 ppm1   1.400 ppm2  4.655
ASSI {2862}
(segid "BrD" and resid 14 and name HD2 %)
((segid "BrD" and resid 14 and name HG))
 2.700  1.800  1.800 peak       2862 weight  0.11000E+01 volume  0.20094E+03 ppm1   1.401 ppm2  2.061
ASSI {2872}
((segid "BrD" and resid 24 and name HA))
((segid "BrD" and resid 24 and name HG1))
 2.700  1.800  1.800 peak       2872 weight  0.11000E+01 volume  0.22636E+03 ppm1   4.783 ppm2  3.454
ASSI {2892}
((segid "BrD" and resid 24 and name HG2))
((segid "BrD" and resid 24 and name HA))
 2.400  1.400  1.400 peak       2892 weight  0.11000E+01 volume  0.36992E+03 ppm1   3.076 ppm2  4.784
ASSI {2902}
((segid "BrD" and resid 83 and name HB))
((segid "BrD" and resid 83 and name HA))
 2.300  1.300  1.300 peak       2902 weight  0.11000E+01 volume  0.54241E+03 ppm1   4.804 ppm2  4.460
ASSI {2912}
((segid "BrD" and resid 17 and name HA))
((segid "BrD" and resid 17 and name HB))
 2.500  1.600  1.600 peak       2912 weight  0.11000E+01 volume  0.32083E+03 ppm1   4.542 ppm2  4.860
ASSI {2932}
(segid "BrD" and resid 25 and name HG2 %)
((segid "BrD" and resid 25 and name HB))
 2.300  1.300  1.300 peak       2932 weight  0.11000E+01 volume  0.60381E+03 ppm1   1.650 ppm2  3.005
ASSI {2942}
(segid "BrD" and resid 25 and name HG1 %)
((segid "BrD" and resid 25 and name HB))
 2.200  1.200  1.200 peak       2942 weight  0.11000E+01 volume  0.72430E+03 ppm1   1.795 ppm2  3.006
ASSI {2972}
((segid "BrD" and resid 49 and name HA))
((segid "BrD" and resid 49 and name HB))
 2.500  1.600  1.600 peak       2972 weight  0.11000E+01 volume  0.32061E+03 ppm1   4.658 ppm2  2.620
ASSI {2992}
((segid "BrD" and resid 49 and name HA))
(segid "BrD" and resid 49 and name HG2 %)
 2.900  2.100  2.100 peak       2992 weight  0.11000E+01 volume  0.13480E+03 ppm1   4.658 ppm2  1.570
ASSI {3012}
((segid "BrD" and resid 49 and name HB))
(segid "BrD" and resid 49 and name HG2 %)
 2.500  1.600  1.600 peak       3012 weight  0.11000E+01 volume  0.36520E+03 ppm1   2.634 ppm2  1.570
ASSI {3022}
(segid "BrD" and resid 49 and name HG1 %)
((segid "BrD" and resid 49 and name HB))
 2.500  1.600  1.600 peak       3022 weight  0.11000E+01 volume  0.34642E+03 ppm1   1.647 ppm2  2.615

TABLE 2-continued

Unambiguous NOE-derived Inter-proton Distance Restraints

ASSI {3042}
(segid "BrD" and resid 49 and name HG1 %)
((segid "BrD" and resid 49 and name HA))
  2.700  1.800  1.800 peak      3042  weight  0.11000E+01  volume  0.21850E+03  ppm1      1.647  ppm2  4.679
ASSI {3052}
(segid "BrD" and resid 69 and name HG1 %)
((segid "BrD" and resid 69 and name HA))
  2.100  1.100  1.100 peak      3052  weight  0.11000E+01  volume  0.91954E+03  ppm1      1.550  ppm2  4.695
ASSI {3072}
((segid "BrD" and resid 58 and name HA))
((segid "BrD" and resid 58 and name HB))
  2.200  1.200  1.200 peak      3072  weight  0.11000E+01  volume  0.67241E+03  ppm1      4.456  ppm2  4.703
ASSI {3102}
((segid "BrD" and resid 28 and name HB2))
((segid "BrD" and resid 28 and name HA))
  2.800  2.000  2.000 peak      3102  weight  0.11000E+01  volume  0.15370E+03  ppm1      3.372  ppm2  4.582
ASSI {3112}
((segid "BrD" and resid 28 and name HB1))
((segid "BrD" and resid 28 and name HA))
  2.800  2.000  2.000 peak      3112  weight  0.11000E+01  volume  0.16666E+03  ppm1      3.571  ppm2  4.582
ASSI {3142}
((segid "BrD" and resid 64 and name HA))
((segid "BrD" and resid 64 and name HD1))
  3.000  2.200  2.200 peak      3142  weight  0.11000E+01  volume  0.11363E+03  ppm1      4.950  ppm2  2.373
ASSI {3162}
((segid "BrD" and resid 64 and name HB1))
((segid "BrD" and resid 64 and name HA))
  2.200  1.200  1.200 peak      3162  weight  0.11000E+01  volume  0.77951E+03  ppm1      2.636  ppm2  4.940
ASSI {3172}
((segid "BrD" and resid 64 and name HG1))
((segid "BrD" and resid 64 and name HA))
  2.500  1.600  1.600 peak      3172  weight  0.11000E+01  volume  0.29624E+03  ppm1      2.190  ppm2  4.938
ASSI {3182}
((segid "BrD" and resid 64 and name HG1))
((segid "BrD" and resid 64 and name HB1))
  2.300  1.300  1.300 peak      3182  weight  0.11000E+01  volume  0.60420E+03  ppm1      2.190  ppm2  2.662
ASSI {3192}
((segid "BrD" and resid 64 and name HG1))
((segid "BrD" and resid 64 and name HE1))
  2.500  1.600  1.600 peak      3192  weight  0.11000E+01  volume  0.31904E+03  ppm1      2.190  ppm2  3.597
ASSI {3202}
((segid "BrD" and resid 6 and name HB1))
((segid "BrD" and resid 6 and name HA))
  2.400  1.400  1.400 peak      3202  weight  0.11000E+01  volume  0.45358E+03  ppm1      2.489  ppm2  4.969
ASSI {3212}
((segid "BrD" and resid 6 and name HD1))
((segid "BrD" and resid 6 and name HA))
  2.800  2.000  2.000 peak      3212  weight  0.11000E+01  volume  0.15911E+03  ppm1      2.310  ppm2  4.972
ASSI {3222}
((segid "BrD" and resid 6 and name HG2))
((segid "BrD" and resid 6 and name HA))
  2.900  2.100  2.100 peak      3222  weight  0.11000E+01  volume  0.13404E+03  ppm1      2.040  ppm2  4.973
ASSI {3232}
((segid "BrD" and resid 104 and name HG1))
((segid "BrD" and resid 104 and name HA))
  2.400  1.400  1.400 peak      3232  weight  0.11000E+01  volume  0.41964E+03  ppm1      2.140  ppm2  4.672
ASSI {3242}
((segid "BrD" and resid 104 and name HA))
((segid "BrD" and resid 104 and name HB1))
  2.100  1.100  1.100 peak      3242  weight  0.11000E+01  volume  0.87442E+03  ppm1      4.657  ppm2  2.537
ASSI {3272}
((segid "BrD" and resid 104 and name HA))
((segid "BrD" and resid 107 and name HB1))
  2.500  1.600  1.600 peak      3272  weight  0.11000E+01  volume  0.31692E+03  ppm1      4.656  ppm2  3.663
ASSI {3292}
((segid "BrD" and resid 111 and name HB2))
((segid "BrD" and resid 111 and name HA))
  2.100  1.100  1.100 peak      3292  weight  0.11000E+01  volume  0.10458E+04  ppm1      2.366  ppm2  4.656
ASSI {3112}
((segid "BrD" and resid 111 and name HA))
((segid "BrD" and resid 111 and name HG2))
  2.800  2.000  2.000 peak      3312  weight  0.11000E+01  volume  0.17232E+03  ppm1      4.656  ppm2  1.918
ASSI {3332}
((segid "BrD" and resid 111 and name HA))
((segid "BrD" and resid 111 and name HB1))
  2.100  1.100  1.100 peak      3332  weight  0.11000E+01  volume  0.97545E+03  ppm1      4.656  ppm2  2.473

TABLE 2-continued

Unambiguous NOE-derived Inter-proton Distance Restraints

ASSI {3362}
((segid "BrD" and resid 19 and name HA))
((segid "BrD" and resid 19 and name HD1))
 3.100  2.400  2.400 peak      3362 weight  0.11000E+01 volume   0.91418E+02 ppm1    4.310  ppm2  2.214
ASSI {3372}
((segid "BrD" and resid 19 and name HB1))
((segid "BrD" and resid 19 and name HA))
 2.500  1.600  1.600 peak      3372 weight  0.11000E+01 volume   0.34161E+03 ppm1    2.290  ppm2  4.297
ASSI {3382}
((segid "BrD" and resid 19 and name HB1))
((segid "BrD" and resid 16 and name HA))
 3.900  3.800  1.600 peak      3382 weight  0.11000E+01 volume   0.22305E+02 ppm1    2.290  ppm2  4.507
ASSI {3392}
((segid "BrD" and resid 19 and name HG1))
((segid "BrD" and resid 19 and name HA))
 2.400  1.400  1.400 peak      3392 weight  0.11000E+01 volume   0.37229E+03 ppm1    1.895  ppm2  4.296
ASSI {3402}
((segid "BrD" and resid 19 and name HG1))
((segid "BrD" and resid 19 and name HE1))
 2.600  1.700  1.700 peak      3402 weight  0.11000E+01 volume   0.28547E+03 ppm1    1.895  ppm2  3.526
ASSI {3412}
((segid "BrD" and resid 19 and name HD1))
((segid "BrD" and resid 19 and name HE1))
 1.800  0.800  0.800 peak      3412 weight  0.11000E+01 volume   0.21730E+04 ppm1    2.192  ppm2  3.522
ASSI {3422}
((segid "BrD" and resid 60 and name HA))
((segid "BrD" and resid 60 and name HB1))
 1.700  0.700  0.700 peak      3422 weight  0.11000E+01 volume   0.29577E+04 ppm1    4.805  ppm2  4.995
ASSI {3452}
((segid "BrD" and resid 11 and name HB1))
((segid "BrD" and resid 11 and name HA))
 2.300  1.300  1.300 peak      3452 weight  0.11000E+01 volume   0.52164E+03 ppm1    2.933  ppm2  4.942
ASSI {3462}
((segid "BrD" and resid 11 and name HB2))
((segid "BrD" and resid 11 and name HA))
 2.300  1.300  1.300 peak      3462 weight  0.11000E+01 volume   0.61125E+03 ppm1    2.586  ppm2  4.943
ASSI {3492}
((segid "BrD" and resid 97 and name HA))
((segid "BrD" and resid 97 and name HB1))
 2.300  1.300  1.300 peak      3492 weight  0.11000E+01 volume   0.52974E+03 ppm1    4.805  ppm2  2.704
ASSI {3532}
((segid "BrD" and resid 109 and name HE2))
((segid "BrD" and resid 109 and name HD1))
 2.500  1.600  1.600 peak      3532 weight  0.11000E+01 volume   0.30326E+03 ppm1    3.029  ppm2  1.994
ASSI {3542}
((segid "BrD" and resid 109 and name HE2))
((segid "BrD" and resid 109 and name HG1))
 2.700  1.800  1.800 peak      3542 weight  0.11000E+01 volume   0.22719E+03 ppm1    3.027  ppm2  1.411
ASSI {3552}
((segid "BrD" and resid 109 and name HE1))
((segid "BrD" and resid 109 and name HG1))
 2.600  1.700  1.700 peak      3552 weight  0.11000E+01 volume   0.23490E+03 ppm1    3.176  ppm2  1.411
ASSI {3562}
((segid "BrD" and resid 109 and name HD1))
((segid "BrD" and resid 109 and name HE1))
 2.700  1.800  1.800 peak      3562 weight  0.11000E+01 volume   0.22693E+03 ppm1    1.994  ppm2  3.195
ASSI {3602}
((segid "BrD" and resid 86 and name HE1))
((segid "BrD" and resid 86 and name HG2))
 2.900  2.100  2.100 peak      3602 weight  0.11000E+01 volume   0.13036E+03 ppm1    3.080  ppm2  0.766
ASSI {3612}
((segid "BrD" and resid 86 and name HD1))
((segid "BrD" and resid 86 and name HG2))
 2.300  1.300  1.300 peak      3612 weight  0.11000E+01 volume   0.49629E+03 ppm1    1.896  ppm2  0.765
ASSI {3622}
((segid "BrD" and resid 86 and name HD1))
((segid "BrD" and resid 86 and name HE1))
 2.600  1.700  1.700 peak      3622 weight  0.11000E+01 volume   0.24556E+03 ppm1    1.892  ppm2  3.093
ASSI {3632}
((segid "BrD" and resid 86 and name HA))
((segid "BrD" and resid 86 and name HG1))
 2.800  2.000  2.000 peak      3632 weight  0.11000E+01 volume   0.14893E+03 ppm1    4.806  ppm2  1.895
ASSI {3682}
((segid "BrD" and resid 8 and name HG1))
((segid "BrD" and resid 8 and name HD1))
 2.000  1.000  1.000 peak      3682 weight  0.11000E+01 volume   0.11498E+04 ppm1    2.635  ppm2  4.436

TABLE 2-continued

Unambiguous NOE-derived Inter-proton Distance Restraints

ASSI {3692}
((segid "BrD" and resid 8 and name HG1))
((segid "BrD" and resid 8 and name HD2))
 2.100  1.100  1.100 peak    3692 weight  0.11000E+01 volume  0.87712E+03 ppm1    2.635 ppm2  4.286
ASSI {3702}
((segid "BrD" and resid 8 and name HB2))
((segid "BrD" and resid 8 and name HA))
 2.600  1.700  1.700 peak    3702 weight  0.11000E+01 volume  0.24482E+03 ppm1    2.487 ppm2  5.021
ASSI {3712}
((segid "BrD" and resid 8 and name HB1))
((segid "BrD" and resid 8 and name HA))
 2.400  1.400  1.400 peak    3712 weight  0.11000E+01 volume  0.36862E+03 ppm1    2.831 ppm2  5.021
ASSI {3722}
((segid "BrD" and resid 8 and name HD1))
((segid "BrD" and resid 7 and name HA))
 2.100  1.100  1.100 peak    3722 weight  0.11000E+01 volume  0.89203E+03 ppm1    4.407 ppm2  5.144
ASSI {3732}
((segid "BrD" and resid 8 and name HD2))
((segid "BrD" and resid 7 and name HA))
 2.100  1.100  1.100 peak    3732 weight  0.11000E+01 volume  0.93259E+03 ppm1    4.263 ppm2  5.144
ASSI {3752}
((segid "BrD" and resid 44 and name HA))
((segid "BrD" and resid 44 and name HB1))
 2.400  1.400  1.400 peak    3752 weight  0.11000E+01 volume  0.42716E+03 ppm1    5.098 ppm2  2.973
ASSI {3762}
((segid "BrD" and resid 44 and name HA))
((segid "BrD" and resid 44 and name HB2))
 2.600  1.700  1.700 peak    3762 weight  0.11000E+01 volume  0.27621E+03 ppm1    5.098 ppm2  2.636
ASSI {3792}
((segid "BrD" and resid 44 and name HB2))
((segid "BrD" and resid 44 and name HD1))
 2.800  2.000  2.000 peak    3792 weight  0.11000E+01 volume  0.16780E+03 ppm1    2.631 ppm2  4.337
ASSI {3802}
((segid "BrD" and resid 44 and name HB1))
((segid "BrD" and resid 44 and name HD1))
 3.200  2.600  2.300 peak    3802 weight  0.11000E+01 volume  0.70033E+02 ppm1    2.981 ppm2  4.337
ASSI {3822}
((segid "BrD" and resid 44 and name HG1))
((segid "BrD" and resid 44 and name HA))
 2.900  2.100  2.100 peak    3822 weight  0.11000E+01 volume  0.14259E+03 ppm1    2.729 ppm2  5.114
ASSI {3832}
((segid "BrD" and resid 44 and name HG2))
((segid "BrD" and resid 44 and name HA))
 2.700  1.800  1.800 peak    3832 weight  0.11000E+01 volume  0.22601E+03 ppm1    2.645 ppm2  5.114
ASSI {3842}
((segid "BrD" and resid 41 and name HA))
((segid "BrD" and resid 41 and name HB))
 1.900  0.900  0.900 peak    3842 weight  0.11000E+01 volume  0.19310E+04 ppm1    4.657 ppm2  4.899
ASSI {3882}
((segid "BrD" and resid 103 and name HG2))
((segid "BrD" and resid 103 and name HA2))
 2.800  2.000  2.000 peak    3882 weight  0.11000E+01 volume  0.14970E+03 ppm1    2.519 ppm2  3.789
ASSI {3892}
((segid "BrD" and resid 103 and name HG1))
((segid "BrD" and resid 103 and name HA))
 2.900  2.100  2.100 peak    3892 weight  0.11000E+01 volume  0.14619E+03 ppm1    2.598 ppm2  3.789
ASSI {3912}
((segid "BrD" and resid 103 and name HG2))
((segid "BrD" and resid 103 and name HB1))
 3.000  2.200  2.200 peak    3912 weight  0.11000E+01 volume  0.10641E+03 ppm1    2.519 ppm2  2.346
ASSI {3922}
((segid "BrD" and resid 103 and name HG1))
((segid "BrD" and resid 103 and name HB1))
 3.200  2.600  2.300 peak    3922 weight  0.11000E+01 volume  0.80668E+03 ppm1    2.598 ppm2  2.346
ASSI {3942}
((segid "BrD" and resid 48 and name HA))
((segid "BrD" and resid 48 and name HG1))
 3.100  2.400  2.400 peak    3942 weight  0.11000E+01 volume  0.93117E+02 ppm1    4.803 ppm2  2.940
ASSI {3952}
((segid "BrD" and resid 48 and name HA))
((segid "BrD" and resid 48 and name HG2))
 3.000  2.200  2.200 peak    3952 weight  0.11000E+01 volume  0.10971E+03 ppm1    4.803 ppm2  2.851
ASSI {3982}
(segid "BrD" and resid 50 and name HD1 %)
((segid "BrD" and resid 50 and name HA))
 2.300  1.300  1.300 peak    3982 weight  0.11000E+01 volume  0.51678E+03 ppm1    1.155 ppm2  4.518

TABLE 2-continued

Unambiguous NOE-derived Inter-proton Distance Restraints

ASSI {4012}
(segid "BrD" and resid 110 and name HD1 %)
((segid "BrD" and resid 110 and name HG12))
  2.600  1.700  1.700 peak    4012 weight  0.11000E+01 volume  0.27804E+03 ppm1    1.154 ppm2  1.652
ASSI {4022}
(segid "BrD" and resid 110 and name HG2 %)
((segid "BrD" and resid 110 and name HG12))
  2.500  1.600  1.600 peak    4022 weight  0.11000E+01 volume  0.35399E+03 ppm1    1.253 ppm2  1.651
ASSI {4032}
((segid "BrD" and resid 110 and name HB))
((segid "BrD" and resid 110 and name HG12))
  3.300  2.700  2.200 peak    4032 weight  0.11000E+01 volume  0.60399E+02 ppm1    2.338 ppm2  1.651
ASSI {4052}
((segid "BrD" and resid 24 and name HB1))
((segid "BrD" and resid 24 and name HG1))
  2.600  1.700  1.700 peak    4052 weight  0.11000E+01 volume  0.27715E+03 ppm1    3.076 ppm2  3.453
ASSI {4062}
((segid "BrD" and resid 80 and name HD1))
((segid "BrD" and resid 80 and name HG1))
  2.400  1.400  1.400 peak    4062 weight  0.11000E+01 volume  0.37330E+03 ppm1    3.956 ppm2  2.347
ASSI {4072}
((segid "BrD" and resid 80 and name HD1))
((segid "BrD" and resid 80 and name HB1))
  2.700  1.800  1.800 peak    4072 weight  0.11000E+01 volume  0.22342E+03 ppm1    3.956 ppm2  2.573
ASSI {4112}
((segid "BrD" and resid 101 and name HA))
((segid "BrD" and resid 101 and name HB))
  2.600  1.700  1.700 peak    4112 weight  0.11000E+01 volume  0.25152E+03 ppm1    4.263 ppm2  2.535
ASSI {4122}
((segid "BrD" and resid 101 and name HA))
((segid "BrD" and resid 101 and name HG11))
  2.600  1.700  1.700 peak    4122 weight  0.11000E+01 volume  0.23036E+03 ppm1    4.263 ppm2  2.469
ASSI {4132}
((segid "BrD" and resid 101 and name HA))
((segid "BrD" and resid 101 and name HG12))
  2.500  1.600  1.600 peak    4132 weight  0.11000E+01 volume  0.31941E+03 ppm1    4.261 ppm2  1.806
ASSI {4142}
(segid "BrD" and resid 38 and name HG1 %)
((segid "BrD" and resid 38 and name HA))
  2.300  1.300  1.300 peak    4142 weight  0.11000E+01 volume  0.50428E+03 ppm1    1.058 ppm2  4.168
ASSI {4162}
(segid "BrD" and resid 81 and name HG2 %)
((segid "BrD" and resid 81 and name HA))
  2.400  1.400  1.400 peak    4162 weight  0.11000E+01 volume  0.38926E+03 ppm1    0.761 ppm2  3.716
ASSI {4182}
(segid "BrD" and resid 81 and name HG1 %)
((segid "BrD" and resid 81 and name HA))
  2.400  1.400  1.400 peak    4182 weight  0.11000E+01 volume  0.43496E+03 ppm1    1.059 ppm2  3.716
ASSI {4212}
((segid "BrD" and resid 69 and name HB))
((segid "BrD" and resid 69 and name HA))
  2.200  1.200  1.200 peak    4212 weight  0.11000E+01 volume  0.67869E+03 ppm1    2.929 ppm2  4.696
ASSI {4222}
((segid "BrD" and resid 18 and name HA))
((segid "BrD" and resid 18 and name HB1))
  2.800  2.000  2.000 peak    4222 weight  0.11000E+01 volume  0.15123E+03 ppm1    3.866 ppm2  2.131
ASSI {4272}
((segid "BrD" and resid 116 and name HB))
(segid "BrD" and resid 116 and name HD1 %)
  2.500  1.600  1.600 peak    4272 weight  0.11000E+01 volume  0.31982E+03 ppm1    2.409 ppm2  1.399
ASSI {4282}
((segid "BrD" and resid 110 and name HB))
((segid "BrD" and resid 110 and name HG11))
  3.100  2.400  2.400 peak    4282 weight  0.11000E+01 volume  0.90397E+02 ppm1    2.338 ppm2  1.718
ASSI {4302}
((segid "BrD" and resid 50 and name HA))
((segid "BrD" and resid 50 and name HG11))
  2.600  1.700  1.700 peak    4302 weight  0.11000E+01 volume  0.24102E+03 ppm1    4.506 ppm2  1.409
ASSI {4322}
((segid "BrD" and resid 50 and name HB))
((segid "BrD" and resid 50 and name HG12))
  2.700  1.800  1.800 peak    4322 weight  0.11000E+01 volume  0.20938E+03 ppm1    1.797 ppm2  0.840
ASSI {4332}
((segid "BrD" and resid 50 and name HB))
((segid "BrD" and resid 50 and name HG11))
  2.700  1.800  1.800 peak    4332 weight  0.11000E+01 volume  0.20876E+03 ppm1    1.797 ppm2  1.407

TABLE 2-continued

Unambiguous NOE-derived Inter-proton Distance Restraints

ASSI {4342}
((segid "BrD" and resid 50 and name HB))
((segid "BrD" and resid 50 and name HA))
  3.000  2.200  2.200 peak      4342 weight  0.11000E+01 volume  0.11875E+03 ppm1    1.797 ppm2  4.516
ASSI {4382}
((segid "BrD" and resid 21 and name HA))
((segid "BrD" and resid 21 and name HB))
  2.700  1.800  1.800 peak      4382 weight  0.11000E+01 volume  0.19816E+03 ppm1    4.359 ppm2  2.515
ASSI {4392}
((segid "BrD" and resid 21 and name HA))
((segid "BrD" and resid 21 and name HG12))
  2.600  1.700  1.700 peak      4392 weight  0.11000E+01 volume  0.25295E+03 ppm1    4.358 ppm2  1.653
ASSI {4402}
((segid "BrD" and resid 21 and name HA))
((segid "BrD" and resid 21 and name HG11))
  2.600  1.700  1.700 peak      4402 weight  0.11000E+01 volume  0.24995E+03 ppm1    4.358 ppm2  2.357
ASSI {4412}
((segid "BrD" and resid 21 and name HB))
((segid "BrD" and resid 21 and name HG11))
  2.900  2.100  2.100 peak      4412 weight  0.11000E+01 volume  0.13199E+03 ppm1    2.487 ppm2  2.356
ASSI {4472}
((segid "BrD" and resid 21 and name HG12))
((segid "BrD" and resid 21 and name HB))
  2.800  2.000  2.000 peak      4472 weight  0.11000E+01 volume  1.7027E+03 ppm1     1.642 ppm2  2.511
ASSI {4482}
((segid "BrD" and resid 21 and name HG12))
((segid "BrD" and resid 21 and name HG11))
  2.200  1.200  1.200 peak      4482 weight  0.11000E+01 volume  0.65087E+03 ppm1    1.642 ppm2  2.357
ASSI {4502}
(segid "BrD" and resid 21 and name HG2 %)
((segid "BrD" and resid 21 and name HA))
  2.400  1.400  1.400 peak      4502 weight  0.11000E+01 volume  0.39582E+03 ppm1    1.596 ppm2  4.369
ASSI {4512}
((segid "BrD" and resid 36 and name HG1))
((segid "BrD" and resid 36 and name HB2))
  2.100  1.100  1.100 peak      4512 weight  0.11000E+01 volume  0.10618E+04 ppm1    2.781 ppm2  2.342
ASSI {4562}
((segid "BrD" and resid 9 and name HG1))
((segid "BrD" and resid 9 and name HA))
  2.800  2.000  2.000 peak      4562 weight  0.11000E+01 volume  0.15274E+03 ppm1    2.236 ppm2  4.940
ASSI {4582}
((segid "BrD" and resid 9 and name HA))
((segid "BrD" and resid 9 and name HB2))
  2.400  1.400  1.400 peak      4582 weight  0.11000E+01 volume  0.39636E+03 ppm1    4.953 ppm2  2.385
ASSI {4592}
((segid "BrD" and resid 35 and name HB2))
((segid "BrD" and resid 35 and name HG1))
  2.600  1.700  1.700 peak      4592 weight  0.11000E+01 volume  0.27554E+03 ppm1    2.781 ppm2  3.447
ASSI {4602}
((segid "BrD" and resid 35 and name HB1))
((segid "BrD" and resid 35 and name HG1))
  3.000  2.200  2.200 peak      4602 weight  0.11000E+01 volume  0.10522E+03 ppm1    2.838 ppm2  3.447
ASSI {4632}
(segid "BrD" and resid 73 and name HD1 %)
((segid "BrD" and resid 73 and name HG))
  2.100  1.100  1.100 peak      4632 weight  0.11000E+01 volume  0.81939E+03 ppm1    1.549 ppm2  2.368
ASSI {4642}
((segid "BrD" and resid 56 and name HA))
((segid "BrD" and resid 56 and name HB1))
  2.500  1.600  1.600 peak      4642 weight  0.11000E+01 volume  0.31507E+03 ppm1    4.606 ppm2  2.694
ASSI {4652}
((segid "BrD" and resid 22 and name HD2 %))
((segid "BrD" and resid 22 and name HB %))
  2.500  1.600  1.600 peak      4652 weight  0.11000E+01 volume  0.35307E+03 ppm1    1.600 ppm2  2.702
ASSI {4662}
((segid "BrD" and resid 22 and name HA))
((segid "BrD" and resid 22 and name HG))
  2.400  1.400  1.400 peak      4662 weight  0.11000E+01 volume  0.43065E+03 ppm1    4.704 ppm2  2.360
ASSI {4722}
((segid "BrD" and resid 14 and name HA))
((segid "BrD" and resid 14 and name HB1))
  2.400  1.400  1.400 peak      4722 weight  0.11000E+01 volume  0.40350E+03 ppm1    4.655 ppm2  2.464
ASSI {4732}
((segid "BrD" and resid 14 and name HA))
((segid "BrD" and resid 14 and name HB2))
  2.500  1.600  1.600 peak      4732 weight  0.11000E+01 volume  0.34201E+03 ppm1    4.655 ppm2  2.159

TABLE 2-continued

Unambiguous NOE-derived Inter-proton Distance Restraints

ASSI {4742}
((segid "BrD" and resid 14 and name HA))
((segid "BrD" and resid 14 and name HG))
  2.800  2.000  2.000 peak     4742 weight  0.11000E+01 volume  0.16298E+03 ppm1    4.655  ppm2  2.062
ASSI {4752}
(segid "BrD" and resid 14 and name HD2 %)
((segid "BrD" and resid 14 and name HB2))
  2.900  2.100  2.100 peak     4752 weight  0.11000E+01 volume  0.12176E+03 ppm1    1.401  ppm2  2.155
ASSI {4762}
(segid "BrD" and resid 14 and name HD2 %)
((segid "BrD" and resid 14 and name HB1))
  2.200  1.200  1.200 peak     4762 weight  0.11000E+01 volume  0.78049E+03 ppm1    1.401  ppm2  2.466
ASSI {4782}
((segid "BrD" and resid 24 and name HB2)
((segid "BrD" and resid 24 and name HG1))
  2.700  1.800  1.800 peak     4782 weight  0.11000E+01 volume  0.20235E+03 ppm1    2.989  ppm2  1.453
ASSI {4812}
((segid "BrD" and resid 25 and name HA)
(segid "BrD" and resid 25 and name HG2 %)
  2.600  1.700  1.700 peak     4812 weight  0.11000E+01 volume  0.28433E+03 ppm1    4.412  ppm2  1.637
ASSI {4822}
(segid "BrD" and resid 25 and name HG1 %)
((segid "BrD" and resid 25 and name HA))
  2.300  1.300  1.300 peak     4822 weight  0.11000E+01 volume  0.50491E+03 ppm1    1.796  ppm2  4.427
ASSI {4832}
((segid "BrD" and resid 30 and name HB1))
((segid "BrD" and resid 30 and name HA))
  2.700  1.800  1.800 peak     4832 weight  0.11000E+01 volume  0.18839E+03 ppm1    4.907  ppm2  5.445
ASSI {4852}
((segid "BrD" and resid 30 and name HA))
((segid "BrD" and resid 30 and name HB2))
  2.900  2.100  2.100 peak     4.852 weight  0.11000E+01 volume  0.13412E+03 ppm1    5.444  ppm2  4.533
ASSI {4862}
((segid "BrD" and resid 104 and name HE1))
((segid "BrD" and resid 104 and name HD1))
  1.900  0.900  0.900 peak     4862 weight  0.11000E+01 volume  0.17529E+04 ppm1    3.571  ppm2  2.290
ASSI {4912}
((segid "BrD" and resid 57 and name HG1))
((segid "BrD" and resid 57 and name HA))
  2.400  1.400  1.400 peak     4912 weight  0.11000E+01 volume  0.42230E+03 ppm1    2.110  ppm2  4.800
ASSI {4922}
((segid "BrD" and resid 97 and name HE1))
((segid "BrD" and resid 97 and name HG2))
  2.200  1.200  1.200 peak     4922 weight  0.11000E+01 volume  0.69710E+03 ppm1    3.569  ppm2  2.172
ASSI {4932}
((segid "BrD" and resid 109 and name HA))
((segid "BrD" and resid 109 and name HB2))
  2.000  1.000  1.000 peak     4932 weight  0.11000E+01 volume  0.10760E+04 ppm1    4.653  ppm2  2.149
ASSI {4942}
((segid "BrD" and resid 109 and name HA))
((segid "BrD" and resid 109 and name HB1)
  2.000  1.000  1.000 peak     4942 weight  0.11000E+01 volume  0.13416E+04 ppm1    4.653  ppm2  2.321
ASSI {4962}
((segid "BrD" and resid 109 and name HB2))
((segid "BrD" and resid 109 and name HG1))
  2.500  1.600  1.600 peak     4962 weight  0.11000E+01 volume  0.29632E+03 ppm1    2.141  ppm2  1.417
ASSI {4972}
((segid "BrD" and resid 109 and name HB1))
((segid "BrD" and resid 109 and name HG1))
  2.500  1.600  1.600 peak     4972 weight  0.11000E+01 volume  0.36408E+03 ppm1    2.334  ppm2  1.417
ASSI {4982}
((segid "BrD" and resid 109 and name HG1))
((segid "BrD" and resid 109 and name HA))
  2.700  1.600  1.800 peak     4982 weight  0.11000E+01 volume  0.22259E+03 ppm1    1.399  ppm2  4.639
ASSI {5002}
((segid "BrD" and resid 109 and name HE2))
((segid "BrD" and resid 109 and name HA))
  2.800  2.000  2.000 peak     5002 weight  0.11000E+01 volume  0.16510E+03 ppm1    3.029  ppm2  4.639
ASSI {5012}
((segid "BrD" and resid 86 and name HG2))
((segid "BrD" and resid 86 and name HA))
  2.800  2.000  2.000 peak     5012 weight  0.11000E+01 volume  0.18063E+03 ppm1    0.761  ppm2  4.812
ASSI {5022}
(segid "BrD" and resid 41 and name HG2 %)
((segid "BrD" and resid 41 and name HA))
  2.200  1.200  1.200 peak     5022 weight  0.11000E+01 volume  0.76022E+03 ppm1    1.844  ppm2  4.671

TABLE 2-continued

Unambiguous NOE-derived Inter-proton Distance Restraints

ASSI {5032}
(segid "BrD" and resid 41 and name HG2 %)
((segid "BrD" and resid 41 and name HB))
  2.000  1.000  1.000 peak      5032 weight  0.11000E+01 volume  0.12138E+04 ppm1    1.845 ppm2  4.901
ASSI {5042}
(segid "BrD" and resid 58 and name HG2 %)
((segid "BrD" and resid 58 and name HA))
  2.000  1.000  1.000 peak      5042 weight  0.11000E+01 volume  0.10640E+04 ppm1    1.649 ppm2  4.451
ASSI {5052}
(segid "BrD" and resid 58 and name HG2 %)
((segid "BrD" and resid 58 and name HB))
  1.900  0.900  0.900 peak      5052 weight  0.11000E+01 volume  0.14547E+04 ppm1    1.649 ppm2  4.705
ASSI {5062}
(segid "BrD" and resid 17 and name HG2 %)
((segid "BrD" and resid 17 and name HA))
  2.300  1.300  1.300 peak      5062 weight  0.11000E+01 volume  0.54601E+03 ppm1    1.747 ppm2  4.542
ASSI {5072}
(segid "BrD" and resid 17 and name HG2 %)
((segid "BrD" and resid 17 and name HB))
  2.100  1.100  1.100 peak      5072 weight  0.11000E+01 volume  0.92706E+03 ppm1    1.745 ppm2  4.861
ASSI {5082}
(segid "BrD" and resid 83 and name HG2 %)
((segid "BrD" and resid 83 and name HB))
  2.100  1.100  1.100 peak      5082 weight  0.11000E+01 volume  0.10099E+04 ppm1    1.893 ppm2  4.805
ASSI {5092}
(segid "BrD" and resid 83 and name HG2 %)
((segid "BrD" and resid 83 and name HA))
  2.200  1.200  1.200 peak      5092 weight  0.11000E+01 volume  0.64890E+03 ppm1    1.894 ppm2  4.460
ASSI {5122}
((segid "BrD" and resid 37 and name HA))
((segid "BrD" and resid 37 and name HG1))
  2.000  2.000  2.000 peak      5122 weight  0.11000E+01 volume  0.14935E+03 ppm1    4.853 ppm2  2.725
ASSI {5132}
((segid "BrD" and resid 37 and name HA))
((segid "BrD" and resid 37 and name HG2))
  3.200  2.600  2.300 peak      5132 weight  0.11000E+01 volume  0.80336E+02 ppm1    4.853 ppm2  2.587
ASSI {5162}
((segid "BrD" and resid 37 and name HG2))
((segid "BrD" and resid 37 and name HD1))
  2.300  1.300  1.300 peak      5162 weight  0.11000E+01 volume  0.49428E+03 ppm1    2.585 ppm2  4.291
ASSI {5172}
((segid "BrD" and resid 37 and name HG1))
((segid "BrD" and resid 37 and name HD1))
  2.500  1.600  1.600 peak      5172 weight  0.11000E+01 volume  0.34945E+03 ppm1    2.733 ppm2  4.290
ASSI {5182}
((segid "BrD" and resid 37 and name HG1))
((segid "BrD" and resid 37 and name HB1))
  2.300  1.300  1.300 peak      5182 weight  0.11000E+01 volume  0.51291E+03 ppm1    2.733 ppm2  2.961
ASSI {5192}
((segid "BrD" and resid 37 and name HG2))
((segid "BrD" and resid 37 and name HB1))
  2.300  1.300  1.300 peak      5192 weight  0.11000E+01 volume  0.56233E+03 ppm1    2.584 ppm2  2.961
ASSI {5202}
((segid "BrD" and resid 37 and name HB1))
((segid "BrD" and resid 37 and name HA))
  2.200  1.200  1.200 peak      5202 weight  0.11000E+01 volume  0.64791E+03 ppm1    2.935 ppm2  4.858
ASSI {5212}
((segid "BrD" and resid 37 and name HB2))
((segid "BrD" and resid 37 and name HA))
  2.400  1.400  1.400 peak      5212 weight  0.11000E+01 volume  0.38926E+03 ppm1    2.290 ppm2  4.858
ASSI {5222}
((segid "BrD" and resid 37 and name HB1))
((segid "BrD" and resid 37 and name HD1))
  3.600  3.200  1.900 peak      5222 weight  0.11000E+01 volume  0.35026E+02 ppm1    2.935 ppm2  4.298
ASSI {5272}
((segid "BrD" and resid 53 and name HD1))
((segid "BrD" and resid 52 and name HA))
  3.300  2.700  2.200 peak      5272 weight  0.11000E+01 volume  0.65454E+02 ppm1    4.214 ppm2  5.504
ASSI {5282}
((segid "BrD" and resid 53 and name HB1))
((segid "BrD" and resid 53 and name HA))
  2.200  1.200  1.200 peak      5282 weight  0.11000E+01 volume  0.77735E+03 ppm1    2.780 ppm2  4.686
ASSI {5292}
((segid "BrD" and resid 53 and name HG2))
((segid "BrD" and resid 53 and name HA))
  2.900  2.100  2.100 peak      5292 weight  0.11000E+01 volume  0.13443E+03 ppm1    2.487 ppm2  4.687

TABLE 2-continued

Unambiguous NOE-derived Inter-proton Distance Restraints

```
ASSI {5302}
((segid "BrD" and resid 51 and name HA))
((segid "BrD" and resid 51 and name HG2))
  2.300  1.300  1.300 peak       5302 weight 0.11000E+01 volume  0.54723E+03 ppm1    4.459 ppm2  1.796
ASSI {5312}
((segid "BrD" and resid 51 and name HA))
((segid "BrD" and resid 51 and name HG1))
  2.400  1.400  1.400 peak       5312 weight 0.11000E+01 volume  0.30019E+03 ppm1    4.459 ppm2  1.946
ASSI {5332}
((segid "BrD" and resid 51 and name HB1))
((segid "BrD" and resid 51 and name HA))
  2.700  1.800  1.800 peak       5332 weight 0.11000E+01 volume  0.20757E+03 ppm1    1.945 ppm2  4.468
ASSI {5342}
((segid "BrD" and resid 51 and name HB2))
((segid "BrD" and resid 51 and name HA))
  2.400  1.400  1.400 peak       5342 weight 0.11000E+01 volume  0.37628E+03 ppm1    1.795 ppm2  4.468
ASSI {5372}
((segid "BrD" and resid 51 and name HG1))
((segid "BrD" and resid 51 and name HD1))
  2.800  2.000  2.000 peak       5372 weight 0.11000E+01 volume  0.26452E+03 ppm1    1.946 ppm2  3.606
ASSI {5362}
((segid "BrD" and resid 51 and name HG2))
((segid "BrD" and resid 51 and name HD1))
  2.400  1.400  1.400 peak       5382 weight 0.11000E+01 volume  0.40660E+03 ppm1    1.796 ppm2  3.606
ASSI {5392}
((segid "BrD" and resid 51 and name HD1))
((segid "BrD" and resid 51 and name HD1))
  2.500  1.600  1.600 peak       5392 weight 0.11000E+01 volume  0.36659E+03 ppm1    3.577 ppm2  1.945
ASSI {5402}
((segid "BrD" and resid 51 and name HD1))
((segid "BrD" and resid 51 and name HB2))
  2.400  1.400  1.400 peak       5402 weight 0.11000E+01 volume  0.38417E+03 ppm1    3.577 ppm2  1.795
ASSI {5412}
((segid "BrD" and resid 51 and name HD1))
((segid "BrD" and resid 51 and name HA))
  2.700  1.800  1.800 peak       5412 weight 0.11000E+01 volume  0.20141E+03 ppm1    3.578 ppm2  4.463
ASSI {5422}
((segid "BrD" and resid 52 and name HA))
((segid "BrD" and resid 52 and name HB1))
  2.500  1.600  1.600 peak       5422 weight 0.11000E+01 volume  0.31370E+03 ppm1    5.592 ppm2  3.654
ASSI {5432}
((segid "BrD" and resid 52 and name HA))
((segid "BrD" and resid 52 and name HB2))
  2.800  2.000  2.000 peak       5432 weight 0.11000E+01 volume  0.16779E+03 ppm1    5.592 ppm2  3.533
ASSI {5462}
((segid "BrD" and resid 75 and name HG2))
((segid "BrD" and resid 75 and name HA))
  2.700  1.800  1.600 peak       5462 weight 0.11000E+01 volume  0.19830E+03 ppm1    3.226 ppm2  4.517
ASSI {5482}
((segid "BrD" and resid 75 and name HG2))
((segid "BrD" and resid 75 and name HB2))
  2.600  1.700  1.700 peak       5482 weight 0.11000E+01 volume  0.27353E+03 ppm1    3.227 ppm2  2.847
ASSI {5492}
((segid "BrD" and resid 75 and name HG1))
((segid "BrD" and resid 75 and name HB2))
  2.300  1.300  1.300 peak       5492 weight 0.11000E+01 volume  0.44028E+03 ppm1    3.523 ppm2  2.847
ASSI {5502}
((segid "BrD" and resid 75 and name HG1))
((segid "BrD" and resid 75 and name HB1))
  2.700  1.800  1.800 peak       5502 weight 0.11000E+01 volume  0.21586E+03 ppm1    3.523 ppm2  2.931
ASSI {5512}
((segid "BrD" and resid 75 and name HG2))
((segid "BrD" and resid 75 and name HB1))
  2.700  1.800  1.800 peak       5512 weight 0.11000E+01 volume  1.21836E+03 ppm1    3.227 ppm2  2.931
ASSI {5522}
((segid "BrD" and resid 75 and name HA))
((segid "BrD" and resid 75 and name HG1))
  2.600  2.000  2.000 peak       5522 weight 0.11000E+01 volume  0.16121E+03 ppm1    4.509 ppm2  3.530
ASSI {5542}
((segid "BrD" and resid 19 and name HB2))
((segid "BrD" and resid 16 and name HA))
  2.900  2.100  2.100 peak       5542 weight 0.11000E+01 volume  0.12463E+03 ppm1    1.989 ppm2  4.507
ASSI {5552}
((segid "BrD" and resid 19 and name HB2))
((segid "BrD" and resid 19 and name HA))
  2.600  1.700  1.700 peak       5552 weight 0.11000E+01 volume  0.27005E+03 ppm1    1.989 ppm2  4.297
```

TABLE 2-continued

| Unambiguous NOE-derived Inter-proton Distance Restraints |

ASSI {5582}
((segid "BrD" and resid 54 and name HA))
((segid "BrD" and resid 54 and name HB2))
  3.000  2.200  2.200 peak     5582  weight  0.11000E+01  volume  0.10290E+03 ppm1     5.543  ppm2  1.964
ASSI {5592}
((segid "BrD" and resid 97 and name HG1))
((segid "BrD" and resid 97 and name HE1))
  3.100  2.400  2.400 peak     5592  weight  0.11000E+01  volume  0.89029E+03 ppm1     2.436  ppm2  3.572
ASSI {5622}
((segid "BrD" and resid 59 and name HG2))
((segid "BrD" and resid 59 and name HA))
  2.400  1.400  1.400 peak     5622  weight  0.11000E+01  volume  039103E+03 ppm1     3.137  ppm2  4.911
ASSI {5632}
((segid "BrD" and resid 59 and name HG1))
((segid "BrD" and resid 59 and name HA))
  3.000  2.200  2.200 peak     5632  weight  0.11000E+01  volume  0.11482E+03 ppm1     3.228  ppm2  4.911
ASSI {5642}
((segid "BrD" and resid 13 and name HG2))
((segid "BrD" and resid 13 and name HA))
  2.300  1.300  1.300 peak     5642  weight  0.11000E+01  volume  0.56353E+03 ppm1     2.978  ppm2  4.775
ASSI {5652}
((segid "BrD" and resid 13 and name HG1))
((segid "BrD" and resid 13 and name HA))
  2.800  2.000  2.000 peak     5652  weight  0.11000E+01  volume  0.18150E+03 ppm1     3.131  ppm2  4.775
ASSI {5672}
((segid "BrD" and resid 57 and name HA))
((segid "BrD" and resid 57 and name HD1))
  2.600  1.700  1.700 peak     5672  weight  0.11000E+01  volume  0.27608E+03 ppm1     4.805  ppm2  2.387
ASSI {5682}
((segid "BrD" and resid 57 and name HA))
((segid "BrD" and resid 57 and name HG2))
  2.900  2.100  2.100 peak     5682  weight  0.11000E+01  volume  0.12195E+03 ppm1     4.805  ppm2  2.016
ASSI {5712}
((segid "BrD" and resid 57 and name HB2))
((segid "BrD" and resid 57 and name HA))
  2.500  1.600  1.600 peak     5712  weight  0.11000E+01  volume  0.35277E+03 ppm1     2.843  ppm2  4.600
ASSI {5722}
((segid "BrD" and resid 57 and name HB1))
((segid "BrD" and resid 57 and name HA))
  2.400  1.400  1.400 peak     5722  weight  0.11000E+01  volume  0.42344E+03 ppm1     2.935  ppm2  4.798
ASSI {5732}
((segid "BrD" and resid 57 and name HE1))
((segid "BrD" and resid 57 and name HG2))
  2.300  1.200  1.200 peak     5732  weight  0.11000E+01  volume  0.67766E+03 ppm1     3.572  ppm2  2.017
ASSI {5752}
((segid "BrD" and resid 57 and name HD2))
((segid "BrD" and resid 57 and name HA))
  2.600  1.700  1.700 peak     5753  weight  0.11000E+01  volume  0.24171E+03 ppm1     2.295  ppm2  4.800
ASSI {5762}
((segid "BrD" and resid 57 and name HD1))
((segid "BrD" and resid 57 and name HE1))
  2.100  1.100  1.100 peak     5762  weight  0.11000E+01  volume  0.83932E+03 ppm1     2.387  ppm2  3.591
ASSI {5772}
((segid "BrD" and resid 57 and name HD2))
((segid "BrD" and resid 57 and name HE1))
  2.100  1.100  1.100 peak     5772  weight  0.11000E+01  volume  0.96087E+03 ppm1     2.289  ppm2  3.591
ASSI {5792}
((segid "BrD" and resid 12 and name HA))
((segid "BrD" and resid 12 and name HB2))
  2.700  1.800  1.800 peak     5792  weight  0.11000E+01  volume  0.22035E+03 ppm1     5.297  ppm2  3.338
ASSI {5812}
((segid "BrD" and resid 57 and name HG1))
((segid "BrD" and resid 57 and name HE1))
  2.600  1.700  1.700 peak     5812  weight  0.11000E+01  volume  0.23002E+03 ppm1     2.099  ppm2  3.590
ASSI {5822}
((segid "BrD" and resid 26 and name HA))
((segid "BrD" and resid 26 and name HB1))
  2.100  1.100  1.100 peak     5822  weight  0.11000E+01  volume  0.10358E+04 ppm1     4.509  ppm2  2.482
ASSI {5832}
((segid "BrD" and resid 26 and name HA))
((segid "BrD" and resid 26 and name HD1))
  2.700  1.800  1.800 peak     5832  weight  0.11000E+01  volume  0.18918E+03 ppm1     4.509  ppm2  2.109
ASSI {5842}
((segid "BrD" and resid 26 and name HA))
((segid "BrD" and resid 26 and name HG1))
  3.200  2.600  2.300 peak     5842  weight  0.11000E+01  volume  0.75991E+02 ppm1     4.509  ppm2  1.629

TABLE 2-continued

Unambiguous NOE-derived Inter-proton Distance Restraints

ASSI {5852}
((segid "BrD" and resid 10 and name HA))
((segid "BrD" and resid 10 and name HB2))
  2.800  2.000  2.000 peak      5852  weight  0.11000E+01 volume  0.18381E+03 ppm1     5.478  ppm2  3.300
ASSI {5862}
((segid "BrD" and resid 56 and name HA))
((segid "BrD" and resid 56 and name HB2))
  2.800  2.000  2.000 peak      5862  weight  0.11000E+01 volume  0.18369E+03 ppm1     4.607  ppm2  2.003
ASSI {5872}
(segid "BrD" and resid 56 and name HD2 %)
((segid "BrD" and resid 56 and name HB2))
  2.600  1.700  1.700 peak      5872  weight  0.11000E+01 volume  0.24752E+03 ppm1     1.254  ppm2  2.004
ASSI {5882}
(segid "BrD" and resid 69 and name HG1 %)
((segid "BrD" and resid 69 and name HB))
  2.100  1.100  1.100 peak      5882  weight  0.11000E+01 volume  0.96122E+03 ppm1     1.548  ppm2  2.922
ASSI {5892}
(segid "BrD" and resid 69 and name HG2 %)
((segid "BrD" and resid 69 and name HB))
  2.100  1.100  1.100 peak      5892  weight  0.11000E+01 volume  0.91489E+03 ppm1     1.424  ppm2  2.919
ASSI {5902}
(segid "BrD" and resid 69 and name HG2 %)
((segid "BrD" and resid 69 and name HA))
  2.600  1.700  1.700 peak      5902  weight  0.11000E+01 volume  0.28227E+03 ppm1     1.425  ppm2  4.696
ASSI {5912}
(segid "BrD" and resid 78 and name HD2 %)
((segid "BrD" and resid 78 and name HA))
  2.800  2.000  2.000 peak      5912  weight  0.11000E+01 volume  0.18293E+03 ppm1     0.662  ppm2  3.999
ASSI {5922}
(segid "BrD" and resid 78 and name HD2 %)
((segid "BrD" and resid 78 and name HB2))
  2.600  1.700  1.700 peak      5922  weight  0.11000E+01 volume  0.24706E+03 ppm1     0.662  ppm2  1.039
ASSI {5932}
(segid "BrD" and resid 78 and name HD2 %)
((segid "BrD" and resid 78 and name HG))
  2.300  1.300  1.300 peak      5932  weight  0.11000E+01 volume  0.60283E+03 ppm1     0.662  ppm2  1.270
ASSI {5962}
((segid "BrD" and resid 18 and name HA))
(segid "BrD" and resid 18 and name HD1 %)
  2.600  1.700  1.700 peak      5962  weight  0.11000E+01 volume  0.27810E+03 ppm1     3.867  ppm2  1.079
ASSI {5982}
(segid "BrD" and resid 18 and name HD1 %)
((segid "BrD" and resid 18 and name HG))
  2.700  1.800  1.800 peak      5982  weight  0.11000E+01 volume  0.22916E+03 ppm1     1.057  ppm2  2.278
ASSI {5992}
(segid "BrD" and resid 18 and name HD2 %)
((segid "BrD" and resid 18 and name HB1))
  2.600  1.700  1.700 peak      5992  weight  0.11000E+01 volume  0.25721E+03 ppm1     0.418  ppm2  2.137
ASSI {6002}
((segid "BrD" and resid 102 and name HG))
(segid "BrD" and resid 102 and name HD1 %)
  2.300  1.300  1.300 peak      6002  weight  0.11000E+01 volume  0.47853E+03 ppm1     2.141  ppm2  1.324
ASSI {6012}
((segid "BrD" and resid 73 and name HB2))
(segid "BrD" and resid 73 and name HD2 %)
  2.300  1.300  1.300 peak      6012  weight  0.11000E+01 volume  0.54334E+03 ppm1     2.583  ppm2  1.483
ASSI {6052}
((segid "BrD" and resid 73 and name HA))
((segid "BrD" and resid 73 and name HB1))
  2.400  1.400  1.400 peak      6052  weight  0.11000E+01 volume  0.44904E+03 ppm1     4.803  ppm2  2.364
ASSI {6074}
(segid "BrD" and resid 73 and name HD1 %)
((segid "BrD" and resid 73 and name HA))
  2.500  1.600  1.600 peak      6072  weight  0.11000E+01 volume  0.30560E+03 ppm1     1.549  ppm2  4.825
ASSI {6112}
((segid "BrD" and resid 56 and name HB1))
(segid "BrD" and resid 56 and name HD1 %)
  2.700  1.800  1.800 peak      6112  weight  0.11000E+01 volume  0.20480E+03 ppm1     2.685  ppm2  1.538
ASSI {6122}
((segid "BrD" and resid 56 and name HB2))
(segid "BrD" and resid 56 and name HD1 %)
  2.900  2.100  2.100 peak      6122  weight  0.11000E+01 volume  0.13067E+03 ppm1     1.994  ppm2  1.538
ASSI {6162}
((segid "BrD" and resid 56 and name HG))
(segid "BrD" and resid 56 and name HD1 %)
  2.300  1.300  1.300 peak      6162  weight  0.11000E+01 volume  0.52968E+03 ppm1     2.339  ppm2  1.539

TABLE 2-continued

| Unambiguous NOE-derived Inter-proton Distance Restraints |
|---|

ASSI {6212}
((segid "BrD" and resid 22 and name HA))
(segid "BrD" and resid 22 and name HD1 %)
  2.500  1.600  1.600 peak      6212  weight  0.11000E+01  volume    0.33531E+03  ppm1      4.706  ppm2   1.648
ASSI {6232}
(segid "BrD" and resid 22 and name HD1 %)
((segid "BrD" and resid 22 and name HB1))
  2.400  1.400  1.400 peak      6232  weight  0.11000E+01  volume    0.37274E+03  ppm1      1.648  ppm2   2.702
ASSI {6242}
(segid "BrD" and resid 22 and name HD1 %)
((segid "BrD" and resid 22 and name HG))
  2.200  1.200  1.200 peak      6242  weight  0.11000E+01  volume    0.77165E+03  ppm1      1.648  ppm2   2.361
ASSI {6272}
(segid "BrD" and resid 63 and name HD2 %)
((segid "BrD" and resid 63 and name HG))
  2.600  1.700  1.700 peak      6272  weight  0.11000E+01  volume    0.24631E+03  ppm1      1.498  ppm2   2.424
ASSI {6282}
(segid "BrD" and resid 63 and name HD1 %)
((segid "BrD" and resid 63 and name HG))
  2.700  1.800  1.800 peak      6282  weight  0.11000E+01  volume    0.31403E+03  ppm1      1.649  ppm2   2.424
ASSI {6322}
((segid "BrD" and resid 66 and name HG2))
((segid "BrD" and resid 66 and name HD2))
  2.500  1.600  1.600 peak      6322  weight  0.11000E+01  volume    0.35570E+03  ppm1      2.140  ppm2   3.637
ASSI {6352}
((segid "BrD" and resid 66 and name HD2))
((segid "BrD" and resid 66 and name HA))
  2.500  1.600  1.600 peak      6352  weight  0.11000E+01  volume    0.30900E+03  ppm1      3.631  ppm2   4.998
ASSI {6392}
((segid "BrD" and resid 100 and name HB1))
((segid "BrD" and resid 100 and name HA))
  2.100  1.100  1.100 peak      6192  weight  0.11000E+01  volume    0.94220E+03  ppm1      3.455  ppm2   4.949
ASSI {6412}
((segid "BrD" and resid 114 and name HA1))
((segid "BrD" and resid 114 and name HA2)
  2.100  1.100  1.100 peak      6412  weight  0.11000E+01  volume    0.97579E+03  ppm1      4.600  ppm2   4.522
ASSI {6432}
((segid "BrD" and resid 85 and name HA))
((segid "BrD" and resid 85 and name HB1))
  2.700  1.800  1.800 peak      6432  weight  0.11000E+01  volume    0.21987E+03  ppm1      5.001  ppm2   3.906
ASSI {6442}
((segid "BrD" and resid 85 and name HA))
((segid "BrD" and resid 85 and name HB2))
  2.800  2.000  2.000 peak      6442  weight  0.11000E+01  volume    0.16015E+03  ppm1      5.000  ppm2   3.621
ASSI {6492}
((segid "BrD" and resid 98 and name HA))
((segid "BrD" and resid 98 and name HB1))
  2.800  2.000  2.000 peak      6492  weight  0.11000E+01  volume    0.16821E+03  ppm1      4.804  ppm2   4.014
ASSI {6502}
((segid "BrD" and resid 98 and name HA))
((segid "BrD" and resid 98 and name HB2))
  2.700  1.800  1.800 peak      6502  weight  0.11000E+01  volume    0.19206E+03  ppm1      4.804  ppm2   3.660
ASSI {6512}
((segid "BrD" and resid 32 and name HA))
((segid "BrD" and resid 32 and name HB2))
  2.700  1.800  1.800 peak      6512  weight  0.11000E+01  volume    0.22946E+03  ppm1      4.953  ppm2   3.965
ASSI {6522}
((segid "BrD" and resid 32 and name HA))
((segid "BrD" and resid 32 and name HB1))
  2.700  1.800  1.800 peak      6522  weight  0.11000E+01  volume    0.20617E+03  ppm1      4.954  ppm2   4.206
ASSI {6552}
((segid "BrD" and resid 11 and name HA))
((segid "BrD" and resid 11 and name HG1))
  2.600  1.700  1.700 peak      6552  weight  0.11000E+01  volume    0.23807E+03  ppm1      4.951  ppm2   2.635
ASSI {6562}
((segid "BrD" and resid 53 and name HG1))
((segid "BrD" and resid 53 and name HA))
  2.100  2.800  1.800 peak      6562  weight  0.11000E+01  volume    0.10893E+03  ppm1      2.784  ppm2   4.687
ASSI {6572}
((segid "BrD" and resid 31 and name HA))
(segid "BrD" and resid 102 and name HD1 %)
  2.500  1.600  1.600 peak      6572  weight  0.11000E+01  volume    0.36090E+03  ppm1      5.000  ppm2   1.323
ASSI {6612}
(segid "BrD" and resid 31 and name HB %)
(segid "BrD" and resid 102 and name HD1 %)
  2.500  1.600  1.600 peak      6612  weight  0.11000E+01  volume    0.31261E+03  ppm1      2.289  ppm2   1.320

TABLE 2-continued

Unambiguous NOE-derived Inter-proton Distance Restraints

ASSI {6642}
((segid "BrD" and resid 43 and name HA))
((segid "BrD" and resid 44 and name HD2))
  2.400  1.400  1.400 peak      6642  weight  0.11000E+01 volume  0.39497E+03 ppm1     5.547  ppm2  $$
ASSI {6662}
(segid "BrD" and resid 43 and name HB %)
((segid "BrD" and resid 44 and name HD2))
  2.700  1.800  1.800 peak      6662  weight  0.11000E+01 volume  0.20471E+03 ppm1     1.700  ppm2  4.135
ASSI {6672}
(segid "BrD" and resid 43 and name HB %)
((segid "BrD" and resid 46 and name HB1))
  2.600  1.700  1.700 peak      6672  weight  0.11000E+01 volume  0.27100E+03 ppm1     1.697  ppm2  3.295
ASSI {6682}
(segid "BrD" and resid 43 and name HB %)
((segid "BrD" and resid 46 and name HB2))
  2.700  1.800  1.800 peak      6682  weight  0.11000E+01 volume  0.19809E+03 ppm1     1.697  ppm2  3.100
ASSI {6732}
((segid "BrD" and resid 76 and name HA))
((segid "BrD" and resid 79 and name HB1))
  2.800  2.000  2.000 peak      6732  weight  0.11000E+01 volume  0.16513E+03 ppm1     4.658  ppm2  2.774
ASSI {6872}
(segid "BrD" and resid 113 and name HB %)
(segid "BrD" and resid 17 and name HG2 %)
  2.500  1.600  1.600 peak      6872  weight  0.11000E+01 volume  0.31889E+03 ppm1     1.994  ppm2  1.750
ASSI {6882}
((segid "BrD" and resid 79 and name HA))
((segid "BrD" and resid 79 and name HB1))
  2.700  1.800  1.800 peak      6882  weight  0.11000E+01 volume  0.19089E+03 ppm1     4.409  ppm2  2.781
ASSI {6892}
((segid "BrD" and resid 79 and name HA))
((segid "BrD" and resid 79 and name HB2))
  2.200  1.200  1.200 peak      6892  weight  0.11000E+01 volume  0.79324E+03 ppm1     4.409  ppm2  2.678
ASSI {6912}
(segid "BrD" and resid 43 and name HB %)
((segid "BrD" and resid 44 and name HD1))
  2.900  2.100  2.100 peak      6912  weight  0.11000E+01 volume  0.13650E+03 ppm1     1.700  ppm2  4.337
ASSI {6942}
(segid "BrD" and resid 25 and name HG1 %)
(segid "BrD" and resid 102 and name HD1 %)
  2.700  1.800  1.800 peak      6942  weight  0.11000E+01 volume  0.21235E+03 ppm1     1.795  ppm2  1.323
ASSI {6962}
(segid "BrD" and resid 25 and name HG1 %)
(segid "BrD" and resid 78 and name HD1 %)
  3.000  2.200  2.200 peak      6962  weight  0.11000E+01 volume  0.99662E+02 ppm1     1.798  ppm2  0.774
ASSI {6972}
(segid "BrD" and resid 25 and name HG1 %)
(segid "BrD" and resid 78 and name HD2 %)
  2.800  2.000  2.000 peak      6972  weight  0.11000E+01 volume  0.15213E+03 ppm1     1.797  ppm2  0.673
ASSI {6992}
(segid "BrD" and resid 25 and name HG2 %)
(segid "BrD" and resid 102 and name HD1 %)
  2.200  1.200  1.200 peak      6992  weight  0.11000E+01 volume  0.77265E+03 ppm1     1.646  ppm2  1.324
ASSI {7002}
(segid "BrD" and resid 25 and name HG2 %)
(segid "BrD" and resid 78 and name HD1 %)
  2.800  2.000  2.000 peak      7002  weight  0.11000E+01 volume  0.16697E+03 ppm1     1.646  ppm2  0.775
ASSI {7022}
((segid "BrD" and resid 38 and name HB))
((segid "BrD" and resid 38 and name HA))
  2.800  2.000  2.000 peak      7022  weight  0.11000E+01 volume  0.17527E+03 ppm1     1.751  ppm2  4.170
ASSI {7032}
(segid "BrD" and resid 38 and name HG2 %)
(segid "BrD" and resid 43 and name HB %)
  2.200  1.200  1.200 peak      7032  weight  0.11000E+01 volume  0.74974E+03 ppm1     0.808  ppm2  1.715
ASSI {7092}
((segid "BrD" and resid 81 and name HA))
((segid "BrD" and resid 81 and name HB))
  2.800  2.000  2.000 peak      7092  weight  0.11000E+01 volume  0.15194E+01 ppm1     3.718  ppm2  2.037
ASSI {7102}
((segid "BrD" and resid 81 and name HB))
((segid "BrD" and resid 78 and name HA))
  3.100  2.400  2.400 peak      7102  weight  0.11000E+01 volume  0.98817E+02 ppm1     2.042  ppm2  4.000
ASSI {7122}
(segid "BrD" and resid 81 and name HG1 %)
((segid "BrD" and resid 78 and name HA))
  2.600  1.700  1.700 peak      7122  weight  0.11000E+01 volume  0.25254E+03 ppm1     1.059  ppm2  3.999

TABLE 2-continued

Unambiguous NOE-derived Inter-proton Distance Restraints

ASSI {7172}
(segid "BrD" and resid 81 and name HG2 %)
((segid "BrD" and resid 34 and name HB1))
 2.600 1.700 1.700 peak     7172 weight 0.11000E+01 volume 0.27152E+03 ppm1     0.755 ppm2 4.106
ASSI {7192}
((segid "BrD" and resid 17 and name HA))
((segid "BrD" and resid 20 and name HB1))
 3.200 2.600 2.300 peak     7192 weight 0.11000E+01 volume 0.76028E+02 ppm1     4.542 ppm2 4.671
ASSI {7252}
(segid "BrD" and resid 17 and name HG2 %)
(segid "BrD" and resid 102 and name HD2 %)
 5.500 5.500 0.000 peak     7252 weight 0.11000E+01 volume 0.56051E+00 ppm1     1.745 ppm2 1.320
ASSI {7272}
(segid "BrD" and resid 17 and name HG2 %)
(segid "BrD" and resid 18 and name HD2 %)
 2.800 2.000 2.000 peak     7272 weight 0.11000E+01 volume 0.14970E+03 ppm1     1.747 ppm2 0.409
ASSI {7352}
(segid "BrD" and resid 58 and name HG2 %)
(segid "BrD" and resid 54 and name HE %)
 2.400 1.400 1.400 peak     7352 weight 0.11000E+01 volume 0.41514E+03 ppm1     1.649 ppm2 2.563
ASSI {7482}
((segid "BrD" and resid 32 and name HA))
((segid "BrD" and resid 33 and name HD1))
 2.900 2.100 2.100 peak     7482 weight 0.11000E+01 volume 0.12205E+03 ppm1        $$ ppm2 3.451
ASSI {7492}
((segid "BrD" and resid 32 and name HA))
((segid "BrD" and resid 33 and name HG1))
 2.900 2.100 2.100 peak     7492 weight 0.11000E+01 volume 0.14430E+03 ppm1     4.952 ppm2 2.776
ASSI {7502}
((segid "BrD" and resid 62 and name HA))
((segid "BrD" and resid 62 and name HB1))
 2.700 1.800 1.800 peak     7502 weight 0.11000E+01 volume 0.21435E+03 ppm1     4.457 ppm2 2.657
ASSI {7522}
((segid "BrD" and resid 62 and name HA))
((segid "BrD" and resid 62 and name HG2))
 2.800 2.000 2.000 peak     7522 weight 0.11000E+01 volume 0.15009E+03 ppm1     4.457 ppm2 1.478
ASSI {7532}
((segid "BrD" and resid 62 and name HA))
((segid "BrD" and resid 62 and name HB2))
 3.000 2.200 2.200 peak     7532 weight 0.11000E+01 volume 0.10361E+03 ppm1     4.457 ppm2 1.681
ASSI {7652}
((segid "BrD" and resid 74 and name HA))
(segid "BrD" and resid 59 and name HE %))
 3.100 2.400 2.400 peak     7652 weight 0.11000E+01 volume 0.93787E+02 ppm1     4.361 ppm2 1.879
ASSI {7662}
((segid "BrD" and resid 74 and name HB1))
((segid "BrD" and resid 71 and name HA))
 3.100 2.400 2.400 peak     7662 weight 0.11000E+01 volume 0.98803E+02 ppm1     3.576 ppm2 4.627
ASSI {7722}
((segid "BrD" and resid 105 and name HA))
((segid "BrD" and resid 108 and name HB1))
 3.100 2.400 2.400 peak     7722 weight 0.11000E+01 volume 0.93160E+02 ppm1     4.902 ppm2 4.582
ASSI {7752}
((segid "BrD" and resid 107 and name HA))
((segid "BrD" and resid 110 and name HB))
 2.800 2.000 2.000 peak     7752 weight 0.11000E+01 volume 0.15544E+03 ppm1     4.410 ppm2 2.360
ASSI {7762}
((segid "BrD" and resid 96 and name HA))
(segid "BrD" and resid 99 and name HB %)
 3.400 2.900 2.100 peak     7762 weight 0.11000E+01 volume 0.54211E+02 ppm1     4.409 ppm2 2.206
ASSI {7772}
((segid "BrD" and resid 107 and name HA))
((segid "BrD" and resid 110 and name HG11))
 3.100 2.400 2.400 peak     7772 weight 0.11000E+01 volume 0.86608E+02 ppm1     4.408 ppm2 1.715
ASSI {7782}
((segid "BrD" and resid 107 and name HA))
((segid "BrD" and resid 110 and name HG12))
 2.900 2.100 2.100 peak     7782 weight 0.11000E+01 volume 0.14800E+03 ppm1     4.408 ppm2 1.661
ASSI {7792}
((segid "BrD" and resid 107 and name HA))
(segid "BrD" and resid 110 and name HG2 %)
 3.100 2.400 2.400 peak     7792 weight 0.11000E+01 volume 0.86153E+02 ppm1     4.408 ppm2 1.261
ASSI {7802}
((segid "BrD" and resid 107 and name HA))
((segid "BrD" and resid 110 and name HD1 %)
 3.000 2.200 2.200 peak     7802 weight 0.11000E+01 volume 0.11960E+03 ppm1     4.408 ppm2 1.141

TABLE 2-continued

Unambiguous NOE-derived Inter-proton Distance Restraints

ASSI {7872}
((segid "BrD" and resid 49 and name HA))
((segid "BrD" and resid 91 and name HD2))
  2.700  1.800  1.800 peak       7872  weight  0.11000E+01 volume  0.22343E+03 ppm1     5.641  ppm2  4.407
ASSI {7892}
((segid "BrD" and resid 100 and name HA))
((segid "BrD" and resid 103 and name HB2))
  2.900  2.100  2.100 peak       7892  weight  0.11000E+01 volume  0.12930E+03 ppm1     4.952  ppm2  1.897
ASSI {7922}
((segid "BrD" and resid 100 and name HB2))
((segid "BrD" and resid 97 and name HA))
  2.600  1.700  1.700 peak       7922  weight  0.11000E+01 volume  0.24354E+03 ppm1     3.455  ppm2  4.798
ASSI {7932}
((segid "BrD" and resid 100 and name HB2))
((segid "BrD" and resid 97 and name HA))
  2.600  1.700  1.700 peak       7932  weight  0.11000E+01 volume  0.23409E+03 ppm1     3.424  ppm2  4.799
ASSI {7962}
((segid "BrD" and resid 12 and name HA))
((segid "BrD" and resid 15 and name HB2))
  2.900  2.100  2.100 peak       7962  weight  0.11000E+01 volume  0.12451E+03 ppm1     5.298  ppm2  3.646
ASSI {7972}
((segid "BrD" and resid 12 and name HA))
((segid "BrD" and resid 15 and name HB1))
  3.100  2.400  2.400 peak       7972  weight  0.11000E+01 volume  0.81954E+02 ppm1     5.297  ppm2  3.812
ASSI {8032}
((segid "BrD" and resid 77 and name HA))
((segid "BrD" and resid 80 and name HG1))
  3.000  2.200  2.200 peak       8032  weight  0.11000E+01 volume  0.10885E+03 ppm1     4.952  ppm2  2.347
ASSI {8062}
((segid "BrD" and resid 85 and name HB2))
((segid "BrD" and resid 82 and name HA))
  3.000  2.200  2.200 peak       8062  weight  0.11000E+01 volume  0.10120E+03 ppm1     3.621  ppm2  4.753
ASSI {8072}
((segid "BrD" and resid 98 and name HB2))
((segid "BrD" and resid 95 and name HA))
  3.100  2.400  2.400 peak       8072  weight  0.11000E+01 volume  0.94016E+02 ppm1     3.667  ppm2  4.447
ASSI {8102}
((segid "BrD" and resid 63 and name HB1))
((segid "BrD" and resid 60 and name HA))
  2.600  1.700  1.700 peak       8102  weight  0.11000E+01 volume  0.27762E+03 ppm1     2.883  ppm2  4.808
ASSI {8112}
((segid "BrD" and resid 63 and name HB2))
((segid "BrD" and resid 60 and name HA))
  2.700  1.800  1.800 peak       8112  weight  0.11000E+01 volume  0.20887E+03 ppm1     2.538  ppm2  4.809
ASSI {8142}
(segid "BrD" and resid 63 and name HD1 %)
((segid "BrD" and resid 18 and name HB2))
  2.800  2.000  2.000 peak       8142  weight  0.11000E+01 volume  0.16157E+03 ppm1     1.649  ppm2  0.919
ASSI {8152}
(segid "BrD" and resid 63 and name HD1 %)
(segid "BrD" and resid 18 and name HD1 %)
  2.700  1.800  1.800 peak       8152  weight  0.11000E+01 volume  0.20633E+03 ppm1     1.646  ppm2  1.085
ASSI {8162}
(segid "BrD" and resid 63 and name HD1 %)
((segid "BrD" and resid 18 and name HB1))
  2.400  1.400  1.400 peak       8162  weight  0.11000E+01 volume  0.38153E+03 ppm1     1.649  ppm2  2.139
ASSI {8172}
(segid "BrD" and resid 63 and name HD2 %)
((segid "BrD" and resid 19 and name HA))
  2.400  1.400  1.400 peak       8172  weight  0.11000E+01 volume  0.45741E+03 ppm1     1.501  ppm2  4.295
ASSI {8182}
((segid "BrD" and resid 14 and name HB2))
((segid "BrD" and resid 14 and name HG))
  3.100  2.400  2.400 peak       8182  weight  0.11000E+01 volume  0.92156E+02 ppm1     2.145  ppm2  2.059
ASSI {8192}
((segid "BrD" and resid 14 and name HB1))
((segid "BrD" and resid 14 and name HG))
  2.600  1.700  1.700 peak       8192  weight  0.11000E+01 volume  0.23309E+03 ppm1     2.444  ppm2  2.059
ASSI {8222}
(segid "BrD" and resid 14 and name HD2 %)
(segid "BrD" and resid 18 and name HD2 %)
  2.500  1.600  1.600 peak       8222  weight  0.11000E+01 volume  0.31711E+03 ppm1     1.401  ppm2  0.409
ASSI {8232}
(segid "BrD" and resid 14 and name HD2 %)
(segid "BrD" and resid 18 and name HD1 %)
  2.400  1.400  1.400 peak       8232  weight  0.11000E+01 volume  0.46026E+03 ppm1     1.401  ppm2  1.085

TABLE 2-continued

Unambiguous NOE-derived Inter-proton Distance Restraints

ASSI {8302}
((segid "BrD" and resid 18 and name HA))
((segid "BrD" and resid 18 and name HB2))
  2.700  1.800  1.800 peak      8302  weight  0.11000E+01  volume  0.20320E+03  ppm1      3.867  ppm2  0.920
ASSI {8392}
(segid "BrD" and resid 18 and name HD1 %)
((segid "BrD" and resid 18 and name HB2))
  2.400  1.400  1.400 peak      8392  weight  0.11000E+01  volume  0.39910E+03  ppm1      1.057  ppm2  0.925
ASSI {8402}
(segid "BrD" and resid 18 and name HD1 %)
((segid "BrD" and resid 74 and name HW1))
  1.000  2.200  2.200 peak      8402  weight  0.11000E+01  volume  0.10291E+03  ppm1      1.056  ppm2  3.563
ASSI {8412}
(segid "BrD" and resid 18 and name HD1 %)
((segid "BrD" and resid 74 and name HB2))
  2.900  2.100  2.100 peak      8412  weight  0.11000E+01  volume  0.13686E+03  ppm1      1.057  ppm2  2.998
ASSI {8442}
(segid "BrD" and resid 18 and name HD2 %)
(segid "BrD" and resid 14 and name HD1 %)
  2.900  2.100  2.100 peak      8442  weight  0.11000E+01  volume  0.12935E+03  ppm1      0.412  ppm2  1.417
ASSI {8452}
(segid "BrD" and resid 18 and name HD2 %)
((segid "BrD" and resid 18 and name HB2))
  2.800  2.000  2.000 peak      8452  weight  0.11000E+01  volume  0.15454E+03  ppm1      0.415  ppm2  0.917
ASSI {8442}
(segid "BrD" and resid 18 and name HD2 %)
(segid "BrD" and resid 102 and name HD2 %)
  5.500  5.500  0.000 peak      8462  weight  0.11000E+01  volume  0.22428E+01  ppm1      0.414  ppm2  1.320
ASSI {8552}
((segid "BrD" and resid 22 and name HB1))
((segid "BrD" and resid 19 and name HA))
  2.600  1.700  1.700 peak      8552  weight  0.11000E+01  volume  0.27759E+03  ppm1      2.682  ppm2  4.295
ASSI {8562}
((segid "BrD" and resid 22 and name HB2))
(segid "BrD" and resid 22 and name HD1 %)
  2.500  1.600  1.600 peak      8562  weight  0.11000E+01  volume  0.30282E+03  ppm1      2.286  ppm2  1.671
ASSI {8602}
((segid "BrD" and resid 22 and name HA))
((segid "BrD" and resid 25 and name HB))
  2.600  1.700  1.700 peak      8602  weight  0.11000E+01  volume  0.25484E+03  ppm1      4.706  ppm2  2.980
ASSI {8652}
(segid "BrD" and resid 56 and name HD1 %)
((segid "BrD" and resid 56 and name HA))
  2.500  1.600  1.600 peak      8652  weight  0.11000E+01  volume  0.34489E+03  ppm1      1.544  ppm2  4.638
ASSI {8672}
(segid "BrD" and resid 56 and name HD2 %)
(segid "BrD" and resid 78 and name HD2 %)
  2.900  2.100  2.100 peak      8672  weight  0.11000E+01  volume  0.14779E+03  ppm1      1.253  ppm2  0.674
ASSI {8682}
(segid "BrD" and resid 56 and name HD2 %)
(segid "BrD" and resid 78 and name HD1 %)
  2.300  1.300  1.300 peak      8682  weight  0.11000E+01  volume  0.48347E+03  ppm1      1.254  ppm2  0.767
ASSI {8722}
((segid "BrD" and resid 73 and name HA))
(segid "BrD" and resid 76 and name HB %)
  2.700  1.800  1.800 peak      8722  weight  0.11000E+01  volume  0.22156E+03  ppm1      4.805  ppm2  2.101
ASSI {8742}
(segid "BrD" and resid 73 and name HD1 %)
((segid "BrD" and resid 73 and name HB1))
  2.400  1.400  1.400 peak      8742  weight  0.11000E+01  volume  0.42630E+03  ppm1      1.549  ppm2  2.594
ASSI {8752}
((segid "BrD" and resid 78 and name HA))
(segid "BrD" and resid 59 and name HE %)
  3.300  2.700  2.200 peak      8752  weight  0.11000E+01  volume  0.67002E+02  ppm1      3.967  ppm2  1.876
ASSI {8782}
((segid "BrD" and resid 78 and name HB1))
(segid "BrD" and resid 59 and name HE %)
  3.200  2.600  2.300 peak      8782  weight  0.11000E+01  volume  0.75592E+02  ppm1      1.307  ppm2  1.876
ASSI {8792}
((segid "BrD" and resid 78 and name HB2))
(segid "BrD" and resid 59 and name HE %)
  2.900  2.100  2.100 peak      8792  weight  0.11000E+01  volume  0.13248E+03  ppm1      1.054  ppm2  1.876
ASSI {8802}
((segid "BrD" and resid 78 and name HB1))
((segid "BrD" and resid 75 and name HA))
  3.100  2.400  2.400 peak      8802  weight  0.11000E+01  volume  0.93675E+02  ppm1      1.305  ppm2  4.520

TABLE 2-continued

Unambiguous NOE-derived Inter-proton Distance Restraints

ASSI {8812}
((segid "BrD" and resid 78 and name HG))
(segid "BrD" and resid 59 and name HE %)
3.200  2.600  2.300 peak      8812 weight  0.11000E+01 volume  0.81269E+02 ppm1      1.254 ppm2  1.878
ASSI {8822}
(segid "BrD" and resid 78 and name HD1 %)
(segid "BrD" and resid 81 and name HG1 %)
2.600  1.700  1.700 peak      8822 weight  0.11000E+01 volume  0.25375E+03 ppm1      0.761 ppm2  1.078
ASSI {8852}
(segid "BrD" and resid 78 and name HD1 %)
(segid "BrD" and resid 59 and name HE %)
2.900  2.100  2.100 peak      8852 weight  0.11000E+01 volume  0.13937E+03 ppm1      0.761 ppm2  1.875
ASSI {8872}
(segid "BrD" and resid 78 and name HD2 %)
(segid "BrD" and resid 25 and name HG2 %)
2.600  1.700  1.700 peak      8872 weight  0.11000E+01 volume  0.25847E+03 ppm1      0.662 ppm2  1.637
ASSI {8892}
(segid "BrD" and resid 78 and name HD2 %)
(segid "BrD" and resid 81 and name HG1 %)
2.800  2.000  2.000 peak      8892 weight  0.11000E+01 volume  0.17974E+03 ppm1      0.662 ppm2  1.078
ASSI {8912}
(segid "BrD" and resid 78 and name HD2 %)
(segid "BrD" and resid 59 and name HE %)
2.600  1.700  1.700 peak      8912 weight  0.11000E+01 volume  0.24075E+03 ppm1      0.662 ppm2  1.875
ASSI {8922}
((segid "BrD" and resid 102 and name HA))
((segid "BrD" and resid 105 and name HB1))
2.800  2.000  2.000 peak      8922 weight  0.11000E+01 volume  0.18319E+03 ppm1      4.263 ppm2  1.742
ASSI {8932}
((segid "BrD" and resid 102 and name HA))
((segid "BrD" and resid 105 and name HB2))
2.700  1.800  1.800 peak      8932 weight  0.11000E+01 volume  0.21483E+03 ppm1      4.263 ppm2  3.674
ASSI {8952}
((segid "BrD" and resid 102 and name HB1))
((segid "BrD" and resid 99 and name HA))
2.900  2.100  2.100 peak      8952 weight  0.11000E+01 volume  0.14144E+03 ppm1      1.993 ppm2  4.442
ASSI {8972}
(segid "BrD" and resid 102 and name HD1 %)
((segid "BrD" and resid 25 and name HA))
2.700  1.800  1.800 peak      8972 weight  0.11000E+01 volume  0.20447E+03 ppm1      1.303 ppm2  4.434
ASSI {8982}
(segid "BrD" and resid 102 and name HD1 %)
((segid "BrD" and resid 105 and name HB1))
3.000  2.200  2.200 peak      8982 weight  0.11000E+01 volume  0.11841E+03 ppm1      1.303 ppm2  3.740
ASSI {8992}
(segid "BrD" and resid 102 and name HD1 %)
((segid "BrD" and resid 105 and name HB2))
2.800  2.000  2.000 peak      8992 weight  0.11000E+01 volume  0.16956E+03 ppm1      1.303 ppm2  3.689
ASSI {9002}
(segid "BrD" and resid 102 and name HD1 %)
((segid "BrD" and resid 28 and name HB1))
2.600  1.700  1.700 peak      9002 weight  0.11000E+01 volume  0.27744E+03 ppm1      1.303 ppm2  3.603
ASSI {9012}
(segid "BrD" and resid 102 and name HD1 %)
((segid "BrD" and resid 28 and name HB2))
2.800  2.000  2.000 peak      9012 weight  0.11000E+01 volume  0.15194E+03 ppm1      1.303 ppm2  3.402
ASSI {9062}
((segid "BrD" and resid 115 and name HB1))
(segid "BrD" and resid 115 and name HD1 %)
2.300  1.300  1.300 peak      9062 weight  0.11000E+01 volume  0.58334E+03 ppm1      2.190 ppm2  1.348
ASSI {9082}
((segid "BrD" and resid 21 and name HA))
((segid "BrD" and resid 24 and name HB1))
3.000  2.200  2.200 peak      9082 weight  0.11000E+01 volume  0.11815E+03 ppm1      4.360 ppm2  3.074
ASSI {9092}
((segid "BrD" and resid 31 and name HB))
((segid "BrD" and resid 18 and name HA))
2.800  2.000  2.000 peak      9092 weight  0.11000E+01 volume  0.16218E+03 ppm1      2.488 ppm2  3.884
ASSI {9182}
(segid "BrD" and resid 21 and name HD1 %)
(segid "BrD" and resid 18 and name HD2 %)
2.900  2.100  2.100 peak      9182 weight  0.11000E+01 volume  0.13133E+03 ppm1      1.203 ppm2  0.410
ASSI {9222}
(segid "BrD" and resid 21 and name HD1 %)
((segid "BrD" and resid 18 and name HA))
2.900  2.100  2.100 peak      9222 weight  0.11000E+01 volume  0.13713E+03 ppm1      1.205 ppm2  3.883

TABLE 2-continued

Unambiguous NOE-derived Inter-proton Distance Restraints

ASSI {9242}
((segid "BrD" and resid 50 and name HG11))
((segid "BrD" and resid 50 and name HG12))
  2.500  1.600  1.600 peak      9242 weight  0.11000E+01 volume  0.31586E+03 ppm1    1.397  ppm2  0.834
ASSI {9292}
(segid "BrD" and resid 50 and name HG2 %)
((segid "BrD" and resid 53 and name HB1))
  2.700  1.800  1.800 peak      9292 weight  0.11000E+01 volume  0.22449E+03 ppm1    1.006  ppm2  2.820
ASSI {9302}
(segid "BrD" and resid 50 and name HG2 %)
((segid "BrD" and resid 53 and name HG2))
  3.100  2.400  2.400 peak      9302 weight  0.11000E+01 volume  0.95431E+02 ppm1    1.006  ppm2  2.500
ASSI {9312}
(segid "BrD" and resid 50 and name HG2 %)
((segid "BrD" and resid 84 and name HB2))
  2.800  2.000  2.000 peak      9312 weight  0.11000E+01 volume  0.16689E+03 ppm1    1.004  ppm2  3.271
ASSI {9322}
(segid "BrD" and resid 50 and name HG2 %)
((segid "BrD" and resid 53 and name HA))
  2.500  1.600  1.600 peak      9322 weight  0.11000E+01 volume  0.33859E+03 ppm1    1.008  ppm2  4.690
ASSI {9332}
((segid "BrD" and resid 101 and name HA))
((segid "BrD" and resid 104 and name HD1))
  3.000  2.200  2.200 peak      9332 weight  0.11000E+01 volume  0.11803E+03 ppm1    4.265  ppm2  2.302
ASSI {9342}
((segid "BrD" and resid 101 and name HB))
((segid "BrD" and resid 98 and name HA))
  2.500  1.600  1.600 peak      9342 weight  0.11000E+01 volume  0.31366E+03 ppm1    2.533  ppm2  4.810
ASSI {9372}
((segid "BrD" and resid 101 and name HG11))
((segid "BrD" and resid 101 and name HG12))
  2.300  1.300  1.300 peak      9372 weight  0.11000E+01 volume  0.48997E+03 ppm1    2.444  ppm2  1.807
ASSI {9422}
(segid "BrD" and resid 101 and name HD1 %)
((segid "BrD" and resid 98 and name HA))
  2.600  1.700  1.700 peak      9422 weight  0.11000E+01 volume  0.26958E+03 ppm1    1.547  ppm2  4.810
ASSI {9432}
((segid "BrD" and resid 110 and name HA))
((segid "BrD" and resid 110 and name HG12))
  3.000  2.200  2.200 peak      9432 weight  0.11000E+01 volume  0.11168E+03 ppm1    4.411  ppm2  1.651
ASSI {9442}
((segid "BrD" and resid 110 and name HA))
(segid "BrD" and resid 113 and name HB %)
  2.700  1.800  1.800 peak      9442 weight  0.11000E+01 volume  0.20383E+03 ppm1    4.411  ppm2  1.976
ASSI {9712}
((segid "BrD" and resid 24 and name HA))
((segid "BrD" and resid 24 and name HB2))
  2.500  1.600  1.600 peak      9712 weight  0.11000E+01 volume  0.30771E+03 ppm1    4.784  ppm2  2.989
ASSI {9762}
((segid "BrD" and resid 23 and name HA))
((segid "BrD" and resid 23 and name HB2))
  2.300  1.300  1.300 peak      9762 weight  0.11000E+01 volume  0.47366E+03 ppm1    4.653  ppm2  2.857
ASSI {9772}
((segid "BrD" and resid 23 and name HA))
((segid "BrD" and resid 23 and name HB1))
  2.400  1.400  1.400 peak      9772 weight  0.11000E+01 volume  0.38829E+03 ppm1    4.653  ppm2  2.930
ASSI {9782}
((segid "BrD" and resid 13 and name HB1))
((segid "BrD" and resid 13 and name HA))
  2.900  2.100  2.100 peak      9782 weight  0.11000E+01 volume  0.14088E+03 ppm1    2.733  ppm2  4.775
ASSI {9802}
((segid "BrD" and resid 103 and name HA))
((segid "BrD" and resid 103 and name HB2))
  2.900  2.100  2.100 peak      9802 weight  0.11000E+01 volume  0.13225E+03 ppm1    3.769  ppm2  1.897
ASSI {9812}
((segid "BrD" and resid 103 and name HA))
((segid "BrD" and resid 103 and name HB1))
  2.800  2.000  2.000 peak      9812 weight  0.11000E+01 volume  0.16112E+03 ppm1    3.769  ppm2  2.346
ASSI {9822}
((segid "BrD" and resid 103 and name HA))
((segid "BrD" and resid 106 and name HB1))
  2.800  2.000  2.000 peak      9822 weight  0.11000E+01 volume  0.15761E+03 ppm1    3.769  ppm2  3.917
ASSI {9832}
((segid "BrD" and resid 103 and name HA))
((segid "BrD" and resid 106 and name HB2))
  2.800  2.000  2.000 peak      9832 weight  0.11000E+01 volume  0.15186E+03 ppm1    3.769  ppm2  3.702

TABLE 2-continued

Unambiguous NOE-derived Inter-proton Distance Restraints

ASSI {9862}
((segid "BrD" and resid 10 and name HA))
((segid "BrD" and resid 11 and name HD1))
  3.000  2.200  2.200 peak        9862 weight  0.11000E+01 volume  0.11074E+03 ppm1     5.479  ppm2  4.464
ASSI {9872}
((segid "BrD" and resid 22 and name HB2))
((segid "BrD" and resid 19 and name HA))
  2.800  2.000  2.000 peak        9872 weight  0.11000E+01 volume  0.16684E+03 ppm1     2.286  ppm2  4.297
ASSI {9912}
((segid "BrD" and resid 36 and name HB1))
((segid "BrD" and resid 36 and name HA))
  2.700  1.800  1.800 peak        9912 weight  0.11000E+01 volume  0.21618E+03 ppm1     2.685  ppm2  5.445
ASSI {9922}
((segid "BrD" and resid 36 and name HB2))
((segid "BrD" and resid 36 and name HA))
  2.800  2.000  2.000 peak        9922 weight  0.11000E+01 volume  0.17054E+03 ppm1     2.340  ppm2  5.444
ASSI {9932}
((segid "BrD" and resid 36 and name HB1))
((segid "BrD" and resid 37 and name HD1))
  5.500  5.500  0.000 peak        9932 weight  0.11000E+01 volume  0.21944E+00 ppm1     2.686  ppm2  4.296
ASSI {9942}
((segid "BrD" and resid 36 and name HB2))
((segid "BrD" and resid 37 and name HD1))
  3.900  3.800  1.600 peak        9942 weight  0.11000E+01 volume  0.23373E+02 ppm1     2.341  ppm2  4.296
ASSI {9952}
((segid "BrD" and resid 36 and name HG1))
((segid "BrD" and resid 37 and name HD1))
  2.600  1.700  1.700 peak        9952 weight  0.11000E+01 volume  0.23785E+03 ppm1     2.781  ppm2  4.289
ASSI {9962}
((segid "BrD" and resid 54 and name HB1))
((segid "BrD" and resid 54 and name HA))
  2.900  2.100  2.100 peak        9962 weight  0.11000E+01 volume  0.14616E+03 ppm1     2.585  ppm2  5.542
ASSI {9982}
((segid "BrD" and resid 54 and name HB2))
((segid "BrD" and resid 54 and name HG1))
  2.900  2.100  2.100 peak        9982 weight  0.11000E+01 volume  0.13342E+03 ppm1     1.947  ppm2  3.304
ASSI {10042}
((segid "BrD" and resid 54 and name HA))
((segid "BrD" and resid 54 and name HG1))
  3.400  2.900  2.100 peak      10042 weight  0.11000E+01 volume  0.51922E+02 ppm1     5.541  ppm2  3.304
ASSI {10062}
((segid "BrD" and resid 35 and name HA))
((segid "BrD" and resid 35 and name HB2))
  3.000  2.200  2.200 peak      10062 weight  0.11000E+01 volume  0.10268E+03 ppm1     4.904  ppm2  2.781
ASSI {10072}
((segid "BrD" and resid 35 and name HA))
((segid "BrD" and resid 35 and name HB1))
  3.100  2.400  2.400 peak      10072 weight  0.11000E+01 volume  0.86087E+02 ppm1     4.904  ppm2  2.831
ASSI {10112}
((segid "BrD" and resid 70 and name HB1))
(segid "BrD" and resid 69 and name HG2 %)
  4.700  4.700  0.800 peak      10112 weight  0.11000E+01 volume  0.77364E+01 ppm1     4.756  ppm2  1.427
ASSI {10122}
((segid "BrD" and resid 70 and name HB2))
(segid "BrD" and resid 69 and name HG2 %)
  4.800  4.800  0.700 peak      10122 weight  0.11000E+01 volume  0.67595E+01 ppm1     4.359  ppm2  1.428
ASSI {10132}
((segid "BrD" and resid 70 and name HB2))
(segid "BrD" and resid 69 and name HG1 %)
  3.200  2.600  2.300 peak      10132 weight  0.11000E+01 volume  0.71828E+02 ppm1     4.360  ppm2  1.543
ASSI {10232}
((segid "BrD" and resid 7 and name HB1))
((segid "BrD" and resid 7 and name HA))
  2.800  2.000  2.000 peak      10232 weight  0.11000E+01 volume  0.15716E+03 ppm1     2.634  ppm2  5.143
ASSI {10242}
((segid "BrD" and resid 7 and name HB2))
((segid "BrD" and resid 7 and name HA))
  2.900  2.100  2.100 peak      10242 weight  0.11000E+01 volume  0.13922E+03 ppm1     2.501  ppm2  5.143
ASSI {10252}
((segid "BrD" and resid 42 and name HA))
((segid "BrD" and resid 42 and name HB1))
  2.400  1.400  1.400 peak      10252 weight  0.11000E+01 volume  0.37492E+03 ppm1     5.051  ppm2  2.784
ASSI {10292}
((segid "BrD" and resid 42 and name HB2))
((segid "BrD" and resid 42 and name HA))
  2.300  1.300  1.300 peak      10292 weight  0.11000E+01 volume  0.49547E+03 ppm1     2.586  ppm2  5.046

TABLE 2-continued

Unambiguous NOE-derived Inter-proton Distance Restraints

```
ASSI {10312}
((segid "BrD" and resid 87 and name HA))
((segid "BrD" and resid 87 and name HB2))
 2.400  1.400 1.400 peak        10312 weight  0.11000E+01 volume   0.37181E+03 ppm1     4.858 ppm2  2.881
ASSI {10322}
((segid "BrD" and resid 87 and name HA))
((segid "BrD" and resid 87 and name HB1))
 2.500  1.600 1.600 peak        10322 weight  0.11000E+01 volume   0.30668E+03 ppm1     4.854 ppm2  2.780
ASSI {10332}
((segid "BrD" and resid 87 and name HB1))
((segid "BrD" and resid 84 and name HA))
 2.600  1.700 1.700 peak        10332 weight  0.11000E+01 volume   0.28367E+03 ppm1     2.779 ppm2  4.873
ASSI {10342}
((segid "BrD" and resid 87 and name HB2))
((segid "BrD" and resid 84 and name HA))
 2.100  1.100 1.100 peak        10342 weight  0.11000E+01 volume   0.80939E+03 ppm1     2.585 ppm2  4.873
ASSI {10352}
((segid "BrD" and resid 87 and name HB2))
((segid "BrD" and resid 87 and name HG1))
 2.300  1.300 1.300 peak        10352 weight  0.11000E+01 volume   0.47273E+03 ppm1     2.585 ppm2  3.021
ASSI {10392}
((segid "BrD" and resid 87 and name HG2))
(segid "BrD" and resid 50 and name HD14))
 3.500  3.200 2.000 peak        10392 weight  0.11000E+01 volume   0.42729E+02 ppm1     2.782 ppm2  1.145
ASSI {10402}
((segid "BrD" and resid 48 and name HA))
((segid "BrD" and resid 48 and name HB1))
 2.400  1.400 1.400 peak        10402 weight  0.11000E+01 volume   0.46141E+03 ppm1     4.803 ppm2  2.729
ASSI {10422}
((segid "BrD" and resid 94 and name HA))
((segid "BrD" and resid 94 and name HB1))
 2.300  1.300 1.300 peak        10422 weight  0.11000E+01 volume   0.56402E+03 ppm1     4.831 ppm2  2.731
ASSI {10452}
((segid "BrD" and resid 92 and name HB2))
((segid "BrD" and resid 92 and name HA))
 2.300  1.300 1.300 peak        10452 weight  0.11000E+01 volume   0.48724E+03 ppm1     2.570 ppm2  4.798
ASSI {10462}
((segid "BrD" and resid 92 and name HB1))
((segid "BrD" and resid 92 and name HA))
 2.000  1.000 1.000 peak        10462 weight  0.11000E+01 volume   0.12901E+04 ppm1     2.694 ppm2  4.798
ASSI {10482}
((segid "BrD" and resid 112 and name HB1))
((segid "BrD" and resid 109 and name HA))
 2.400  1.400 1.400 peak        10482 weight  0.11000E+01 volume   0.44320E+03 ppm1     2.684 ppm2  4.638
ASSI {10492}
((segid "BrD" and resid 112 and name HB1))
((segid "BrD" and resid 112 and name HA))
 2.400  1.400 1.400 peak        10492 weight  0.11000E+01 volume   0.38447E+03 ppm1     2.684 ppm2  4.587
ASSI {10532}
((segid "BrD" and resid 75 and name HA))
((segid "BrD" and resid 75 and name HB1))
 2.500  1.600 1.600 peak        10532 weight  0.11000E+01 volume   0.36144E+03 ppm1     4.509 ppm2  2.931
ASSI {10542}
((segid "BrD" and resid 75 and name HA))
((segid "BrD" and resid 75 and name HB2))
 2.400  1.400 1.400 peak        10542 weight  0.11000E+01 volume   0.39358E+03 ppm1     4.509 ppm2  2.847
ASSI {10552}
((segid "BrD" and resid 75 and name HG1))
(segid "BrD" and resid 75 and name HE %))
 2.600  1.700 1.700 peak        10552 weight  0.11000E+01 volume   0.23961E+03 ppm1     3.523 ppm2  2.662
ASSI {10562}
((segid "BrD" and resid 75 and name HG2))
(segid "BrD" and resid 75 and name HE %))
 2.600  1.700 1.700 peak        10562 weight  0.11000E+01 volume   0.23485E+03 ppm1     3.227 ppm2  2.662
ASSI {10632}
((segid "BrD" and resid 66 and name HA))
((segid "BrD" and resid 66 and name HG1))
 2.600  1.700 1.700 peak        10632 weight  0.11000E+01 volume   0.25166E+03 ppm1     5.000 ppm2  2.181
ASSI {10642}
((segid "BrD" and resid 66 and name HG2))
((segid "BrD" and resid 66 and name HA))
 2.500  1.600 1.600 peak        10642 weight  0.11000E+01 volume   0.30460E+03 ppm1     2.141 ppm2  4.998
ASSI {10652}
((segid "BrD" and resid 66 and name HA))
((segid "BrD" and resid 66 and name HB1))
 2.300  1.300 1.300 peak        10652 weight  0.11000E+01 volume   0.48749E+03 ppm1     5.000 ppm2  2.702
```

TABLE 2-continued

Unambiguous NOE-derived Inter-proton Distance Restraints

ASSI {10662}
((segid "BrD" and resid 66 and name HA))
((segid "BrD" and resid 66 and name HB2))
2.100   1.100 1.100 peak        10662  weight  0.11000E+01 volume   0.87656E+03 ppm1    5.000 ppm2   2.608
ASSI {10672}
((segid "BrD" and resid 80 and name HB2))
((segid "BrD" and resid 77 and name HA))
2.600   1.700 1.700 peak        10672  weight  0.11000E+01 volume   0.24800E+03 ppm1    2.536 ppm2   4.951
ASSI {10682}
((segid "BrD" and resid 80 and name HB1))
((segid "BrD" and resid 77 and name HA))
2.600   1.700 1.700 peak        10682  weight  0.11000E+01 volume   0.24031E+03 ppm1    2.583 ppm2   4.951
ASSI {10692}
((segid "BrD" and resid 80 and name HB2))
((segid "BrD" and resid 80 and name HA))
3.000   2.200 2.200 peak        10692  weight  0.11000E+01 volume   0.11905E+03 ppm1    2.536 ppm2   4.671
ASSI {10702}
((segid "BrD" and resid 80 and name HB1))
((segid "BrD" and resid 80 and name HA))
2.900   2.100 2.100 peak        10702  weight  0.11000E+01 volume   0.13820E+03 ppm1    2.584 ppm2   4.672
ASSI {10752}
((segid "BrD" and resid 80 and name HA))
((segid "BrD" and resid 80 and name HG1))
2.300   1.300 1.300 peak        10752  weight  0.11000E+01 volume   0.52255E+03 ppm1    4.655 ppm2   2.339
ASSI {10762}
((segid "BrD" and resid 80 and name HA))
(segid "BrD" and resid 83 and name HG2 %)
3.200   2.600 2.300 peak        10762  weight  0.11000E+01 volume   0.74419E+02 ppm1    4.655 ppm2   1.901
ASSI {10792}
((segid "BrD" and resid 9 and name HA))
((segid "BrD" and resid 9 and name HB1))
2.500   1.600 1.600 peak        10792  weight  0.11000E+01 volume   0.30562E+03 ppm1    4.953 ppm2   2.434
ASSI {10802}
((segid "BrD" and resid 20 and name HA))
((segid "BrD" and resid 23 and name HB1))
2.800   2.000 2.000 peak        10802  weight  0.11000E+01 volume   0.14886E+03 ppm1    4.901 ppm2   2.931
ASSI {10812}
((segid "BrD" and resid 20 and name HA))
((segid "BrD" and resid 23 and name HB2))
2.900   2.100 2.100 peak        10812  weight  0.11000E+01 volume   0.14118E+03 ppm1    4.901 ppm2   2.857
ASSI {10822}
((segid "BrD" and resid 27 and name HB1))
((segid "BrD" and resid 24 and name HA))
2.500   1.600 1.600 peak        10822  weight  0.11000E+01 volume   0.34604E+03 ppm1    4.608 ppm2   4.768
ASSI {10932}
((segid "BrD" and resid 108 and name HA))
((segid "BrD" and resid 111 and name HB1))
2.900   2.100 2.100 peak        10932  weight  0.11000E+01 volume   0.13575E+03 ppm1    4.801 ppm2   2.475
ASSI {10942}
((segid "BrD" and resid 108 and name HA))
((segid "BrD" and resid 111 and name HB2))
3.000   2.200 2.200 peak        10942  weight  0.11000E+01 volume   0.11676E+03 ppm1    4.803 ppm2   2.351
ASSI {10952}
((segid "BrD" and resid 108 and name HA))
((segid "BrD" and resid 111 and name HD1))
3.200   2.600 2.300 peak        10952  weight  0.11000E+01 volume   0.76235E+02 ppm1    4.803 ppm2   2.237
ASSI {11002}
((segid "BrD" and resid 44 and name HG2))
((segid "BrD" and resid 44 and name HD1))
2.300   1.300 1.300 peak        11002  weight  0.11000E+01 volume   0.53477E+03 ppm1    2.645 ppm2   4.337
ASSI {11032}
((segid "BrD" and resid 44 and name HD1))
((segid "BrD" and resid 43 and name HA))
2.300   1.300 1.300 peak        11032  weight  0.11000E+01 volume   0.59437E+03 ppm1    4.312 ppm2   5.541
ASSI {11092}
((segid "BrD" and resid 11 and name HA))
((segid "BrD" and resid 14 and name HB1))
3.000   2.200 2.200 peak        11092  weight  0.11000E+01 volume   0.11894E+03 ppm1    4.951 ppm2   2.471
ASSI {11112}
((segid "BrD" and resid 11 and name HD1))
((segid "BrD" and resid 10 and name HB2))
2.800   2.000 2.000 peak        11112  weight  0.11000E+01 volume   0.15710E+03 ppm1    4.457 ppm2   3.300
ASSI {11122}
((segid "BrD" and resid 11 and name HD1))
((segid "BrD" and resid 10 and name HB1))
3.000   2.200 2.200 peak        11122  weight  0.11000E+01 volume   0.11776E+03 ppm1    4.457 ppm2   3.355

TABLE 2-continued

Unambiguous NOE-derived Inter-proton Distance Restraints

```
ASSI {11152}
((segid "BrD" and resid 37 and name HD1))
((segid "BrD" and resid 36 and name HA))
3.400   2.900 2.100 peak        11152  weight  0.11000E+01 volume  0.48585E+02 ppm1    4.262  ppm2  5.446
ASSI {11182}
((segid "BrD" and resid 53 and name HD2))
(segid "BrD" and resid 50 and name HG2 %)
3.400   2.900 2.100 peak        11182  weight  0.11000E+01 volume  0.47917E+02 ppm1    4.015  ppm2  0.993
ASSI {11212}
((segid "BrD" and resid 53 and name HG1))
((segid "BrD" and resid 53 and name HD1))
2.800   2.000 2.000 peak        11212  weight  0.11000E+01 volume  0.15118E+03 ppm1    2.784  ppm2  4.209
ASSI {11222}
((segid "BrD" and resid 53 and name HG2))
((segid "BrD" and resid 53 and name HD1))
2.800   2.000 2.000 peak        11222  weight  0.11000E+01 volume  0.15165E+03 ppm1    2.490  ppm2  4.210
ASSI {11232}
((segid "BrD" and resid 53 and name HG2))
((segid "BrD" and resid 53 and name HD2))
2.900   2.100 2.100 peak        11232  weight  0.11000E+01 volume  0.12572E+03 ppm1    2.484  ppm2  4.011
ASSI {11242}
((segid "BrD" and resid 53 and name HG1))
((segid "BrD" and resid 53 and name HD2))
3.100   2.400 2.400 peak        11242  weight  0.11000E+01 volume  0.94017E+02 ppm1    2.784  ppm2  4.011
ASSI {11252}
((segid "BrD" and resid 53 and name HG1))
(segid "BrD" and resid 50 and name HG2 %)
4.300   4.300 1.200 peak        11252  weight  0.11000E+01 volume  0.13261E+02 ppm1    2.784  ppm2  0.993
ASSI {11272}
((segid "BrD" and resid 19 and name HB1))
(segid "BrD" and resid 63 and name HD2 %)
3.000   2.200 2.200 peak        11272  weight  0.11000E+01 volume  0.10292E+03 ppm1    2.290  ppm2  1.492
ASSI {11292}
((segid "BrD" and resid 19 and name HB1))
(segid "BrD" and resid 63 and name HD1 %)
3.300   2.700 2.200 peak        11292  weight  0.11000E+01 volume  0.56479E+02 ppm1    2.290  ppm2  1.655
ASSI {11302}
((segid "BrD" and resid 19 and name HB2))
(segid "BrD" and resid 63 and name HD1 %)
3.400   2.900 2.100 peak        11302  weight  0.11000E+01 volume  0.52899E+02 ppm1    1.988  ppm2  1.656
ASSI {11392}
((segid "BrD" and resid 97 and name HA))
((segid "BrD" and resid 97 and name HG1))
2.400   1.400 1.400 peak        11392  weight  0.11000E+01 volume  0.40873E+03 ppm1    4.805  ppm2  2.438
ASSI {11422}
((segid "BrD" and resid 97 and name HB1))
((segid "BrD" and resid 94 and name HA))
2.200   1.200 1.200 peak        11422  weight  0.11000E+01 volume  0.64841E+03 ppm1    2.685  ppm2  4.830
ASSI {11442}
((segid "BrD" and resid 97 and name HD1))
((segid "BrD" and resid 97 and name HA))
3.600   3.200 1.900 peak        11442  weight  0.11000E+01 volume  0.36224E+02 ppm1    2.420  ppm2  4.800
ASSI {11472}
((segid "BrD" and resid 86 and name HB1))
((segid "BrD" and resid 86 and name HA))
2.400   1.400 1.400 peak        11472  weight  0.11000E+01 volume  0.38167E+03 ppm1    2.340  ppm2  4.807
ASSI {11482}
((segid "BrD" and resid 86 and name HB1))
((segid "BrD" and resid 86 and name HG2))
2.900   2.100 2.100 peak        11482  weight  0.11000E+01 volume  0.12261E+03 ppm1    2.340  ppm2  0.766
ASSI {11612}
((segid "BrD" and resid 64 and name HB1))
((segid "BrD" and resid 61 and name HA))
2.300   1.300 1.300 peak        11612  weight  0.11000E+01 volume  0.48201E+03 ppm1    2.636  ppm2  4.667
ASSI {11622}
((segid "BrD" and resid 64 and name HG1))
((segid "BrD" and resid 61 and name HA))
2.600   1.700 1.700 peak        11622  weight  0.11000E+01 volume  0.27263E+03 ppm1    2.190  ppm2  4.667
ASSI {11692}
((segid "BrD" and resid $$ and name HA))
((segid "BrD" and resid $$ and name HB2))
2.400   1.400 1.400 peak        11692  weight  0.11000E+01 volume  0.40526E+03 ppm1    4.972  ppm2  2.291
ASSI {11702}
((segid "BrD" and resid 72 and name HD1))
((segid "BrD" and resid 72 and name HA))
2.600   1.700 1.700 peak        11702  weight  0.11000E+01 volume  0.26243E+03 ppm1    2.291  ppm2  4.646
```

TABLE 2-continued

Unambiguous NOE-derived Inter-proton Distance Restraints

ASSI {11712}
((segid "BrD" and resid 62 and name HD1))
((segid "BrD" and resid 62 and name HG1))
2.700  1.800 1.800 peak       11732  weight  0.11000E+01 volume  0.19040E+03 ppm1    3.177 ppm2   2.323
ASSI {11732}
((segid "BrD" and resid 62 and name HD2))
((segid "BrD" and resid 62 and name HG2))
3.200  2.600 2.300 peak       11732  weight  0.11000E+01 volume  0.69523E+02 ppm1    2.629 ppm2   1.480
ASSI {11742}
((segid "BrD" and resid 62 and name HD1))
((segid "BrD" and resid 59 and name HA))
3.100  2.400 2.400 peak       11742  weight  0.11000E+01 volume  0.81736E+02 ppm1    3.177 ppm2   4.911
ASSI {11782}
((segid "BrD" and resid 91 and name HG1))
((segid "BrD" and resid 91 and name HD2))
3.000  2.200 2.200 peak       11782  weight  0.11000E+01 volume  0.11953E+03 ppm1    2.779 ppm2   4.406
ASSI {11802}
((segid "BrD" and resid 91 and name HA))
((segid "BrD" and resid 91 and name HB1))
2.700  1.800 1.800 peak       11802  weight  0.11000E+01 volume  0.18443E+03 ppm1    5.347 ppm2   2.978
ASSI {11812}
((segid "BrD" and resid 91 and name HA))
((segid "BrD" and resid 91 and name HG1))
3.700  3.400 1.800 peak       11812  weight  0.11000E+01 volume  0.32384E+02 ppm1    5.347 ppm2   2.788
ASSI {11852}
((segid "BrD" and resid 91 and name HD1))
((segid "BrD" and resid 89 and name HA))
2.700  1.800 1.800 peak       11852  weight  0.11000E+01 volume  0.19122E+03 ppm1    4.559 ppm2   5.642
ASSI {11882}
((segid "BrD" and resid 91 and name HD2))
((segid "BrD" and resid 89 and name HB1))
2.800  2.000 2.000 peak       11882  weight  0.11000E+01 volume  0.16587E+03 ppm1    4.410 ppm2   3.668
ASSI {11912}
((segid "BrD" and resid 91 and name HB2))
((segid "BrD" and resid 91 and name HD1))
3.700  3.400 1.800 peak       11912  weight  0.11000E+01 volume  0.31825E+02 ppm1    2.730 ppm2   4.559
ASSI {11922}
((segid "BrD" and resid 91 and name HB1))
((segid "BrD" and resid 91 and name HD1))
3.400  2.900 2.100 peak       11922  weight  0.11000E+01 volume  0.50256E+02 ppm1    2.978 ppm2   4.559
ASSI {11942}
((segid "BrD" and resid 91 and name HB2))
((segid "BrD" and resid 91 and name HA))
2.600  2.000 2.000 peak       11942  weight  0.11000E+01 volume  0.17033E+03 ppm1    2.725 ppm2   5.378
ASSI {11952}
((segid "BrD" and resid 33 and name HA))
((segid "BrD" and resid 33 and name HG2))
3.000  2.200 2.200 peak       11952  weight  0.11000E+01 volume  0.10731E+03 ppm1    4.361 ppm2  −0.319
ASSI {11962}
((segid "BrD" and resid 33 and name HA))
((segid "BrD" and resid 33 and name HB2))
2.700  1.800 1.800 peak       11962  weight  0.11000E+01 volume  0.20069E+03 ppm1    4.361 ppm2  −0.166
ASSI {11972}
((segid "BrD" and resid 33 and name HA))
((segid "BrD" and resid 33 and name HB1))
2.700  1.800 1.800 peak       11972  weight  0.11000E+01 volume  0.18669E+03 ppm1    4.360 ppm2   1.083
ASSI {12032}
((segid "BrD" and resid 33 and name HG1))
((segid "BrD" and resid 33 and name HB2))
2.900  2.100 2.100 peak       12032  weight  0.11000E+01 volume  0.13883E+03 ppm1    0.858 ppm2  −0.165
ASSI {12042}
((segid "BrD" and resid 33 and name HG2))
((segid "BrD" and resid 33 and name HB2))
2.900  2.100 2.100 peak       12042  weight  0.11000E+01 volume  0.12386E+03 ppm1   −0.124 ppm2  −0.169
ASSI {12062}
((segid "BrD" and resid 33 and name HD1))
((segid "BrD" and resid 33 and name HG1))
3.000  2.200 2.200 peak       12062  weight  0.11000E+01 volume  0.11534E+03 ppm1    2.780 ppm2   0.864
ASSI {12072}
((segid "BrD" and resid 33 and name HD2))
((segid "BrD" and resid 33 and name HG1))
3.100  2.400 2.400 peak       12072  weight  0.11000E+01 volume  0.97683E+02 ppm1    2.189 ppm2   0.864
ASSI {12082}
((segid "BrD" and resid 33 and name HD1))
((segid "BrD" and resid 33 and name HG2))
2.900  2.100 2.100 peak       12082  weight  0.11000E+01 volume  0.13243E+03 ppm1    2.780 ppm2  −0.319

TABLE 2-continued

Unambiguous NOE-derived Inter-proton Distance Restraints

ASSI {12092}
((segid "BrD" and resid 33 and name HD2))
((segid "BrD" and resid 33 and name HG2))
2.900  2.100 2.100 peak      12092 weight 0.11000E+01 volume 0.13995E+03 ppm1   2.189 ppm2 −0.319
ASSI {12102}
((segid "BrD" and resid 33 and name HB1))
((segid "BrD" and resid 33 and name HG2))
2.900  2.100 2.100 peak      12102 weight 0.11000E+01 volume 0.14146E+03 ppm1   1.051 ppm2 −0.326
ASSI {12132}
((segid "BrD" and resid 33 and name HB1))
((segid "BrD" and resid 33 and name HG1))
3.100  2.400 2.400 peak      12132 weight 0.11000E+01 volume 0.94205E+02 ppm1   1.055 ppm2  0.859
ASSI {12182}
((segid "BrD" and resid 35 and name HA))
((segid "BrD" and resid 36 and name HB1))
4.100  4.100 1.400 peak      12182 weight 0.11000E+01 volume 0.16299E+02 ppm1   4.904 ppm2  2.685
ASSI {12222}
((segid "BrD" and resid 59 and name HG2))
(segid "BrD" and resid 59 and name HB1)
2.300  1.300 1.300 peak      12222 weight 0.11000E+01 volume 0.52760E+03 ppm1   3.137 ppm2  1.875
ASSI {12242}
((segid "BrD" and resid 59 and name HB2))
(segid "BrD" and resid 59 and name HE %)
2.700  1.800 1.800 peak      12242 weight 0.11000E+01 volume 0.19334E+03 ppm1   2.487 ppm2  1.876
ASSI {12252}
((segid "BrD" and resid 59 and name HA))
((segid "BrD" and resid 59 and name HB2))
3.300  2.700 2.200 peak      12252 weight 0.11000E+01 volume 0.59031E+02 ppm1   4.903 ppm2  2.487
ASSI {12262}
((segid "BrD" and resid 59 and name HA))
((segid "BrD" and resid 62 and name HB1))
3.100  2.400 2.400 peak      12262 weight 0.11000E+01 volume 0.90574E+02 ppm1   4.903 ppm2  2.657
ASSI {12272}
((segid "BrD" and resid 59 and name HA))
((segid "BrD" and resid 62 and name HB2))
2.900  2.100 2.100 peak      12272 weight 0.11000E+01 volume 0.13057E+03 ppm1   4.903 ppm2  1.670
ASSI {12312}
((segid "BrD" and resid 61 and name HB1))
((segid "BrD" and resid 61 and name HA))
2.500  1.600 1.600 peak      12312 weight 0.11000E+01 volume 0.30078E+03 ppm1   2.826 ppm2  4.673
ASSI {12322}
((segid "BrD" and resid 61 and name HB1))
((segid "BrD" and resid 58 and name HA))
3.000  2.200 2.200 peak      12322 weight 0.11000E+01 volume 0.10826E+03 ppm1   2.826 ppm2  4.451
ASSI {12332}
((segid "BrD" and resid 61 and name HB2))
((segid "BrD" and resid 58 and name HA))
2.400  1.400 1.400 peak      12332 weight 0.11000E+01 volume 0.42931E+03 ppm1   2.679 ppm2  4.453
ASSI {12342}
((segid "BrD" and resid 61 and name HB2))
((segid "BrD" and resid 61 and name HA))
2.100  1.100 1.100 peak      12342 weight 0.11000E+01 volume 0.81117E+03 ppm1   2.679 ppm2  4.473
ASSI {12392}
(segid "BrD" and resid 102 and name HD2 %)
((segid "BrD" and resid 102 and name HG))
2.000  1.000 1.000 peak      12392 weight 0.11000E+01 volume 0.13862E+04 ppm1   1.304 ppm2  2.159
ASSI {12402}
(segid "BrD" and resid 102 and name HD2 %)
((segid "BrD" and resid 102 and name HB1))
2.400  1.400 1.400 peak      12402 weight 0.11000E+01 volume 0.42022E+03 ppm1   1.304 ppm2  2.020
ASSI {12422}
(segid "BrD" and resid 102 and name HD2 %)
(segid "BrD" and resid 31 and name $$)
3.500  3.100 2.000 peak      12422 weight 0.11000E+01 volume 0.40319E+02 ppm1   1.305 ppm2  2.315
ASSI {12432}
(segid "BrD" and resid 14 and name HD1 %)
((segid "BrD" and resid 14 and name HG))
2.400  1.400 1.400 peak      12432 weight 0.11000E+01 volume 0.38368E+03 ppm1   1.402 ppm2  2.062
ASSI {12442}
(segid "BrD" and resid 14 and name HD1 %)
((segid "BrD" and resid 14 and name HB2))
2.300  1.300 1.300 peak      12442 weight 0.11000E+01 volume 0.51224E+03 ppm1   1.402 ppm2  2.155
ASSI {12452}
(segid "BrD" and resid 14 and name HD1 %)
((segid "BrD" and resid 14 and name HB1))
2.300  1.300 1.300 peak      12452 weight 0.11000E+01 volume 0.51311E+03 ppm1   1.402 ppm2  2.468

TABLE 2-continued

Unambiguous NOE-derived Inter-proton Distance Restraints

ASSI {12462}
(segid "BrD" and resid 14 and name HD1 %)
((segid "BrD" and resid 14 and name HA))
2.600  1.700 1.700 peak       12642 weight  0.11000E+01 volume  0.23971E+03 ppm1    1.401 ppm2  4.655
ASSI {12472}
(segid "BrD" and resid 14 and name HD1 %)
(segid "BrD" and resid 18 and name HD1 %)
2.500  1.600 1.600 peak       12472 weight  0.11000E+01 volume  0.29352E+03 ppm1    1.402 ppm2  1.084
ASSI {12602}
(segid "BrD" and resid 59 and name HE %)
((segid "BrD" and resid 59 and name HB1))
2.700  1.800 1.800 peak       12602 weight  0.11000E+01 volume  0.21211E+03 ppm1    1.847 ppm2  2.707
ASSI {12622}
(segid "BrD" and resid 59 and name HE %)
((segid "BrD" and resid 59 and name HG1))
3.100  2.400 2.400 peak       12622 weight  0.11000E+01 volume  0.88634E+02 ppm1    1.848 ppm2  3.230
ASSI {12662}
(segid "BrD" and resid 54 and name HE %)
((segid "BrD" and resid 54 and name HB2))
2.700  1.800 1.800 peak       12662 weight  0.11000E+01 volume  0.21213E+03 ppm1    2.535 ppm2  1.964
ASSI {12682}
(segid "BrD" and resid 54 and name HE %)
((segid "BrD" and resid 54 and name HG1))
2.500  1.600 1.600 peak       12682 weight  0.11000E+01 volume  0.35414E+03 ppm1    2.535 ppm2  3.307
ASSI {12772}
(segid "BrD" and resid 50 and name HG2 %)
((segid "BrD" and resid 84 and name HB1))
2.900  2.100 2.100 peak       12772 weight  0.11000E+01 volume  0.14057E+03 ppm1    1.004 ppm2  3.605
ASSI {12802}
((segid "BrD" and resid 74 and name HB2))
((segid "BrD" and resid 75 and name HA))
3.300  2.700 2.200 peak       12802 weight  0.11000E+01 volume  0.66311E+02 ppm1    1.054 ppm2  4.517
ASSI {12902}
(segid "BrD" and resid 38 and name HG1 %)
(segid "BrD" and resid 43 and name HB %)
2.800  2.000 2.000 peak       12902 weight  0.11000E+01 volume  0.17186E+03 ppm1    1.059 ppm2  1.715
ASSI {12912}
((segid "BrD" and resid 25 and name HA))
((segid "BrD" and resid 28 and name HB2))
3.400  2.900 2.100 peak       12912 weight  0.11000E+01 volume  0.50976E+02 ppm1    4.412 ppm2  3.406
ASSI {12922}
((segid "BrD" and resid 25 and name HA))
((segid "BrD" and resid 28 and name HB1))
3.400  2.900 2.100 peak       12922 weight  0.11000E+01 volume  0.50633E+02 ppm1    4.412 ppm2  3.607
ASSI {12932}
((segid "BrD" and resid 25 and name HB))
((segid "BrD" and resid 25 and name HA))
2.600  1.700 1.700 peak       12932 weight  0.11000E+01 volume  0.25503E+03 ppm1    2.979 ppm2  4.436
ASSI {12942}
((segid "BrD" and resid 99 and name HA))
(segid "BrD" and resid 102 and name HD1 %)
3.500  3.100 2.000 peak       12942 weight  0.11000E+01 volume  0.42963E+02 ppm1    4.458 ppm2  1.321
ASSI {12952}
(segid "BrD" and resid 17 and name HG2 %)
(segid "BrD" and resid 18 and name HD1 %)
3.100  2.400 2.400 peak       12952 weight  0.11000E+01 volume  0.90746E+02 ppm1    1.745 ppm2  1.083
ASSI {12982}
((segid "BrD" and resid 98 and name HB1))
((segid "BrD" and resid 95 and name HA))
3.200  2.600 2.300 peak       12982 weight  0.11000E+01 volume  0.76248E+02 ppm1    4.013 ppm2  4.445
ASSI {13062}
(segid "BrD" and resid 56 and name HD1 %)
((segid "BrD" and resid 34 and name HB2))
2.900  2.100 2.100 peak       13062 weight  0.11000E+01 volume  0.13096E+03 ppm1    1.546 ppm2  3.143
ASSI {13152}
((segid "BrD" and resid 81 and name HA))
((segid "BrD" and resid 84 and name HB2))
3.300  2.700 2.200 peak       13152 weight  0.11000E+01 volume  0.59764E+02 ppm1    3.718 ppm2  3.278
ASSI {13162}
((segid "BrD" and resid 85 and name HA))
((segid "BrD" and resid 88 and name HB1))
3.400  2.900 2.100 peak       13162 weight  0.11000E+01 volume  0.52965E+02 ppm1    5.003 ppm2  3.532
ASSI {13172}
((segid "BrD" and resid 86 and name HB1))
((segid "BrD" and resid 83 and name HA))
3.700  3.400 1.800 peak       13172 weight  0.11000E+01 volume  0.32755E+02 ppm1    2.340 ppm2  4.462

TABLE 2-continued

Unambiguous NOE-derived Inter-proton Distance Restraints

ASSI {13182}
(segid "BrD" and resid 54 and name HE %)
((segid "BrD" and resid 54 and name HA))
2.300   1.300  1.300 peak       13182  weight  0.11000E+01 volume  0.48303E+03 ppm1    2.535  ppm2  5.543
ASSI {13212}
((segid "BrD" and resid 47 and name HA))
((segid "BrD" and resid 50 and name HB))
3.600   3.200  1.900 peak       13212  weight  0.11000E+01 volume  0.37838E+02 ppm1    4.704  ppm2  1.823
ASSI {13222}
(segid "BrD" and resid 81 and name HG2 %)
((segid "BrD" and resid 34 and name HB2))
2.800   2.000  2.000 peak       13222  weight  0.11000E+01 volume  0.16892E+03 ppm1    0.756  ppm2  1.149
ASSI {13252}
((segid "BrD" and resid 34 and name HB2))
((segid "BrD" and resid 56 and name HG))
3.100   2.400  2.400 peak       13252  weight  0.11000E+01 volume  0.87944E+02 ppm1    3.127  ppm2  2.323
ASSI {13262}
((segid "BrD" and resid 34 and name HB1))
((segid "BrD" and resid 56 and name HG))
3.200   2.600  2.300 peak       13262  weight  0.11000E+01 volume  0.75137E+02 ppm1    4.108  ppm2  2.322
ASSI {13362}
(segid "BrD" and resid 14 and name HD1 %)
((segid "BrD" and resid 18 and name HB1))
2.300   1.300  1.300 peak       13362  weight  0.11000E+01 volume  0.50793E+03 ppm1    1.058  ppm2  2.128
ASSI {13372}
((segid "BrD" and resid 14 and name HB1))
(segid "BrD" and resid 18 and name HD1 %)
4.000   4.000  1.500 peak       13372  weight  0.11000E+01 volume  0.18693E+02 ppm1    2.441  ppm2  1.084
ASSI {13382}
(segid "BrD" and resid 25 and name HG1 %)
((segid "BrD" and resid 22 and name HA))
2.600   1.700  1.700 peak       13382  weight  0.11000E+01 volume  0.28894E+03 ppm1    1.795  ppm2  4.720
ASSI {13402}
((segid "BrD" and resid 102 and name HB2))
((segid "BrD" and resid 99 and name HA))
2.600   1.700  1.700 peak       13402  weight  0.11000E+01 volume  0.26245E+03 ppm1    1.842  ppm2  4.441
ASSI {13422}
((segid "BrD" and resid 21 and name HB))
(segid "BrD" and resid 18 and name HD2 %)
3.700   3.400  1.800 peak       13422  weight  0.11000E+01 volume  0.29780E+02 ppm1    2.487  ppm2  0.409
ASSI {13432}
((segid "BrD" and resid 57 and name HA))
((segid "BrD" and resid 60 and name HB2))
2.700   1.800  1.800 peak       13432  weight  0.11000E+01 volume  0.19090E+03 ppm1    4.805  ppm2  4.625
ASSI {13442}
((segid "BrD" and resid 57 and name HA))
((segid "BrD" and resid 60 and name HB1))
2.900   2.100  2.100 peak       13442  weight  0.11000E+01 volume  0.14250E+03 ppm1    4.805  ppm2  5.000
ASSI {13482}
(segid "BrD" and resid 58 and name HG2 %)
((segid "BrD" and resid 62 and name HD2))
2.800   2.000  2.000 peak       13482  weight  0.11000E+01 volume  0.17578E+03 ppm1    1.651  ppm2  2.644
ASSI {13492}
((segid "BrD" and resid 61 and name HB1))
(segid "BrD" and resid 58 and name HG2 %)
3.600   3.200  1.900 peak       13492  weight  0.11000E+01 volume  0.34592E+02 ppm1    2.826  ppm2  1.662
ASSI {13512}
(segid "BrD" and resid 59 and name HE %)
((segid "BrD" and resid 59 and name HA))
3.100   2.400  2.400 peak       13512  weight  0.11000E+01 volume  0.83827E+02 ppm1    1.848  ppm2  4.913
ASSI {13522}
(segid "BrD" and resid 59 and name HE %)
((segid "BrD" and resid 56 and name HD2 %)
3.400   2.900  2.100 peak       13522  weight  0.11000E+01 volume  0.55813E+02 ppm1    1.848  ppm2  1.271
ASSI {13542}
((segid "BrD" and resid 21 and name HA))
((segid "BrD" and resid 24 and name HB2))
3.200   2.600  2.300 peak       13542  weight  0.11000E+01 volume  0.69544E+02 ppm1    4.360  ppm2  2.989
ASSI {13552}
((segid "BrD" and resid 74 and name HB2))
((segid "BrD" and resid 71 and name HA))
3.300   2.700  2.200 peak       13552  weight  0.11000E+01 volume  0.56669E+02 ppm1    2.974  ppm2  4.624
ASSI {13652}
(segid "BrD" and resid 58 and name HG2 %)
((segid "BrD" and resid 62 and name HD1))
2.800   2.000  2.000 peak       13652  weight  0.11000E+01 volume  0.18084E+03 ppm1    1.649  ppm2  3.182

TABLE 2-continued

Unambiguous NOE-derived Inter-proton Distance Restraints

ASSI {13662}
((segid "BrD" and resid 32 and name HA))
(segid "BrD" and resid 31 and name $$)
3.700  3.400 1.800 peak       13662 weight  0.11000E+01 volume   0.29321E+02 ppm1    4.952 ppm2  2.312
ASSI {13702}
((segid "BrD" and resid 42 and name HB1))
(segid "BrD" and resid 43 and name HB %)
3.800  3.600 1.700 peak       13702 weight  0.11000E+01 volume   0.26752E+02 ppm1    2.785 ppm2  1.712
ASSI {13722}
((segid "BrD" and resid 59 and name HA))
((segid "BrD" and resid 62 and name HD2))
2.600  1.700 1.700 peak       13722 weight  0.11000E+01 volume   0.25810E+03 ppm1    4.903 ppm2  2.634
ASSI {13742}
((segid "BrD" and resid 63 and name HG))
((segid "BrD" and resid 63 and name HB1))
2.300  1.300 1.300 peak       13742 weight  0.11000E+01 volume   0.59564E+03 ppm1    2.437 ppm2  2.905
ASSI {13902}
((segid "BrD" and resid 70 and name HB1))
(segid "BrD" and resid 69 and name HG1 %)
3.700  3.400 1.800 peak       13902 weight  0.11000E+01 volume   0.30896E+02 ppm1    4.756 ppm2  1.544
ASSI {13912}
(segid "BrD" and resid 101 and name HG2 %)
((segid "BrD" and resid 98 and name HA))
2.800  2.000 2.000 peak       13912 weight  0.11000E+01 volume   0.17496E+03 ppm1    1.596 ppm2  4.810
ASSI {13932}
((segid "BrD" and resid 101 and name HG12))
(segid "BrD" and resid 98 and name HA))
3.400  2.900 2.100 peak       13932 weight  0.11000E+01 volume   0.55145E+02 ppm1    1.797 ppm2  4.808
ASSI {13942}
((segid "BrD" and resid 98 and name HA))
((segid "BrD" and resid 101 and name HG11))
3.300  2.700 2.200 peak       13942 weight  0.11000E+01 volume   0.65568E+02 ppm1    4.804 ppm2  2.469
ASSI {14002}
((segid "BrD" and resid 53 and name HB1))
((segid "BrD" and resid 53 and name HD1))
2.400  2.000 2.000 peak       14002 weight  0.11000E+01 volume   0.16043E+03 ppm1    2.781 ppm2  4.208
ASSI {14012}
((segid "BrD" and resid 53 and name HB1))
((segid "BrD" and resid 53 and name HD2))
3.000  2.200 2.200 peak       14012 weight  0.11000E+01 volume   0.10929E+03 ppm1    2.781 ppm2  4.010
ASSI {14072}
((segid "BrD" and resid 79 and name HA))
((segid "BrD" and resid 82 and name HB2))
3.000  2.200 2.200 peak       14072 weight  0.11000E+01 volume   0.11123E+03 ppm1    4.409 ppm2  3.606
ASSI {14082}
((segid "BrD" and resid 79 and name HA))
((segid "BrD" and resid 82 and name HB1))
3.300  2.700 2.200 peak       14082 weight  0.11000E+01 volume   0.67314E+02 ppm1    4.409 ppm2  3.697
ASSI {14092}
((segid "BrD" and resid 79 and name HB2))
((segid "BrD" and resid 76 and name HA))
2.400  1.400 1.400 peak       14092 weight  0.11000E+01 volume   0.38186E+03 ppm1    2.680 ppm2  4.683
ASSI {14182}
((segid "BrD" and resid 94 and name HA))
((segid "BrD" and resid 97 and name HD1))
3.200  2.600 2.300 peak       14182 weight  0.11000E+01 volume   0.68636E+02 ppm1    4.830 ppm2  2.434
ASSI {14252}
((segid "BrD" and resid 113 and name HA))
(segid "BrD" and resid 17 and name HG2 %)
3.600  3.200 1.900 peak       14252 weight  0.11000E+01 volume   0.37471E+02 ppm1    4.901 ppm2  1.750
ASSI {14552}
((segid "BrD" and resid 11 and name HB2))
((segid "BrD" and resid 11 and name HD1))
2.700  1.800 1.800 peak       14552 weight  0.11000E+01 volume   0.21551E+03 ppm1    2.580 ppm2  4.460
ASSI {14572}
((segid "BrD" and resid 14 and name HB2))
((segid "BrD" and resid 11 and name HA))
3.300  2.700 2.200 peak       14572 weight  0.11000E+01 volume   0.58722E+02 ppm1    2.145 ppm2  4.942
ASSI {14592}
(segid "BrD" and resid 102 and name HD2 %)
((segid "BrD" and resid 31 and name HA))
3.400  2.900 2.100 peak       14592 weight  0.11000E+01 volume   0.51768E+02 ppm1    1.303 ppm2  4.984
ASSI {14612}
(segid "BrD" and resid 102 and name HD2 %)
(segid "BrD" and resid 25 and name HG2 %)
2.300  1.300 1.300 peak       14612 weight  0.11000E+01 volume   0.50747E+03 ppm1    1.305 ppm2  1.633

TABLE 2-continued

Unambiguous NOE-derived Inter-proton Distance Restraints

ASSI {14622}
(segid "BrD" and resid 102 and name HD2 %)
((segid "BrD" and resid 25 and name HA))
2.700  1.800  1.800 peak     14622  weight  0.11000E+01 volume  0.22785E+03 ppm1     1.303 ppm2  4.425
ASSI {14662}
((segid "BrD" and resid 18 and name HB2))
((segid "BrD" and resid 18 and name HG))
3.100  2.400  2.400 peak     14662  weight  0.11000E+01 volume  0.98423E+02 ppm1     0.911 ppm2  2.274
ASSI {14772}
((segid "BrD" and resid 36 and name HA))
((segid "BrD" and resid 37 and name HG2))
5.500  5.500  0.000 peak     14772  weight  0.11000E+01 volume  0.48374E+00 ppm1     5.447 ppm2  2.587
ASSI {14812}
((segid "BrD" and resid 42 and name HB2))
(segid "BrD" and resid 43 and name HB %)
3.200  2.600  2.300 peak     14812  weight  0.11000E+01 volume  0.74053E+02 ppm1     2.586 ppm2  1.710
ASSI {14822}
((segid "BrD" and resid 35 and name HA))
((segid "BrD" and resid 36 and name HB2))
3.800  3.600  1.700 peak     14822  weight  0.11000E+01 volume  0.27804E+02 ppm1     4.904 ppm2  2.340
ASSI {14942}
((segid "BrD" and resid 46 and name HA))
(segid "BrD" and resid 88 and name HE %)
2.700  1.800  1.800 peak     14942  weight  0.11000E+01 volume  0.19889E+03 ppm1     4.163 ppm2  7.421
ASSI {14962}
((segid "BrD" and resid 46 and name HA))
(segid "BrD" and resid 46 and name HE %)
3.600  3.200  1.900 peak     14962  weight  0.11000E+01 volume  0.36218E+02 ppm1     4.164 ppm2  6.689
ASSI {14992}
((segid "BrD" and resid 46 and name HB2))
(segid "BrD" and resid 46 and name HE %)
3.700  3.400  1.800 peak     14992  weight  0.11000E+01 volume  0.28675E+02 ppm1     3.078 ppm2  6.689
ASSI {15062}
((segid "BrD" and resid 28 and name HB2))
((segid "BrD" and resid 28 and name HD2))
3.100  2.400  2.400 peak     15062  weight  0.11000E+01 volume  0.98530E+02 ppm1     3.372 ppm2  5.575
ASSI {15072}
((segid "BrD" and resid 28 and name HB1))
((segid "BrD" and resid 28 and name HD2))
3.200  2.600  2.300 peak     15072  weight  0.11000E+01 volume  0.74212E+02 ppm1     3.570 ppm2  5.575
ASSI {15122}
((segid "BrD" and resid 67 and name HB1))
(segid "BrD" and resid 67 and name HE %)
4.100  4.100  1.400 peak     15122  weight  0.11000E+01 volume  0.17734E+02 ppm1     2.639 ppm2  7.315
ASSI {15292}
((segid "BrD" and resid 47 and name HA))
(segid "BrD" and resid 46 and name HD %)
4.100  4.100  1.400 peak     15292  weight  0.11000E+01 volume  0.16402E+02 ppm1     4.705 ppm2  5.762
ASSI {15322}
((segid "BrD" and resid 47 and name HB2))
(segid "BrD" and resid 47 and name HE %)
3.400  2.900  2.100 peak     15322  weight  0.11000E+01 volume  0.56146E+02 ppm1     3.375 ppm2  7.371
ASSI {15332}
((segid "BrD" and resid 47 and name HB1))
(segid "BrD" and resid 47 and name HE %)
3.200  2.600  2.300 peak     15332  weight  0.11000E+01 volume  0.74345E+02 ppm1     3.816 ppm2  7.371
ASSI {15352}
((segid "BrD" and resid 32 and name HB2))
((segid "BrD" and resid 32 and name HE3))
2.600  1.700  1.700 peak     15352  weight  0.11000E+01 volume  0.27498E+03 ppm1     3.962 ppm2  7.952
ASSI {15432}
((segid "BrD" and resid 74 and name HB1))
(segid "BrD" and resid 74 and name HD %)
2.900  2.100  2.100 peak     15432  weight  0.11000E+01 volume  0.14689E+03 ppm1     3.576 ppm2  6.998
ASSI {15482}
((segid "BrD" and resid 74 and name HB2))
(segid "BrD" and resid 74 and name HE %)
3.600  3.200  1.900 peak     15482  weight  0.11000E+01 volume  0.37941E+02 ppm1     2.985 ppm2  7.533
ASSI {15492}
((segid "BrD" and resid 74 and name HB1))
(segid "BrD" and resid 74 and name HE %)
2.800  2.000  2.000 peak     15492  weight  0.11000E+01 volume  0.16094E+03 ppm1     3.571 ppm2  7.535
ASSI {15602}
((segid "BrD" and resid 82 and name HB2))
(segid "BrD" and resid 82 and name HE %)
3.000  2.200  2.200 peak     15602  weight  0.11000E+01 volume  0.11655E+03 ppm1     3.573 ppm2  7.069

TABLE 2-continued

Unambiguous NOE-derived Inter-proton Distance Restraints

ASSI {15612}
((segid "BrD" and resid 82 and name HB1))
(segid "BrD" and resid 82 and name HE %)
2.800  2.000 2.000 peak      15612 weight  0.11000E+01 volume  0.15106E+03 ppm1    3.672 ppm2   7.069
ASSI {15732}
((segid "BrD" and resid 82 and name HA))
(segid "BrD" and resid 82 and name HE %)
3.200  2.600 2.300 peak      15732 weight  0.11000E+01 volume  0.68425E+02 ppm1    4.755 ppm2   7.063
ASSI {15742}
((segid "BrD" and resid 82 and name HA))
(segid "BrD" and resid 82 and name HD %)
2.100  1.100 1.100 peak      15742 weight  0.11000E+01 volume  0.82972E+03 ppm1    4.755 ppm2   7.259
ASSI {15792}
((segid "BrD" and resid 15 and name HA))
(segid "BrD" and resid 18 and name HD2 %)
4.600  4.600 0.900 peak      15792 weight  0.11000E+01 volume  0.83712E+01 ppm1    4.607 ppm2   0.408
ASSI {16522}
((segid "BrD" and resid 107 and name HA))
(segid "BrD" and resid 107 and name HE %)
2.700  1.800 1.800 peak      16522 weight  0.11000E+01 volume  0.21131E+03 ppm1    4.410 ppm2   7.901
ASSI {16532}
((segid "BrD" and resid 96 and name HA))
(segid "BrD" and resid 96 and name HE %)
2.800  2.000 2.000 peak      16532 weight  0.11000E+01 volume  0.16900E+03 ppm1    4.410 ppm2   7.607
ASSI {16692}
((segid "BrD" and resid 52 and name HA))
(segid "BrD" and resid 53 and name HG2))
5.500  5.500 0.000 peak      16692 weight  0.11000E+01 volume  0.97221E+00 ppm1    5.592 ppm2   2.494
ASSI {16822}
((segid "BrD" and resid 105 and name HB1))
(segid "BrD" and resid 105 and name HA))
2.600  1.700 1.700 peak      16822 weight  0.11000E+01 volume  0.25358E+03 ppm1    3.721 ppm2   4.932
ASSI {17182}
((segid "BrD" and resid 105 and name HB2))
(segid "BrD" and resid 105 and name HA))
2.400  1.400 1.400 peak      17182 weight  0.11000E+01 volume  0.43854E+03 ppm1    3.668 ppm2   4.932
ASSI {17202}
((segid "BrD" and resid 105 and name HB2))
(segid "BrD" and resid 105 and name HD %)
2.200  1.200 1.200 peak      17202 weight  0.11000E+01 volume  0.67242E+03 ppm1    3.720 ppm2   7.788
ASSI {17242}
((segid "BrD" and resid 105 and name HA))
(segid "BrD" and resid 105 and name HD %)
2.200  1.200 1.200 peak      17242 weight  0.11000E+01 volume  0.69463E+03 ppm1    4.903 ppm2   7.787
ASSI {17292}
((segid "BrD" and resid 116 and name HA))
((segid "BrD" and resid 116 and name HG12))
2.800  2.000 2.000 peak      17292 weight  0.11000E+01 volume  0.16843E+03 ppm1    4.804 ppm2   1.554
ASSI {17302}
((segid "BrD" and resid 116 and name HA))
((segid "BrD" and resid 116 and name HG11))
3.300  2.400 2.400 peak      17302 weight  0.11000E+01 volume  0.94615E+02 ppm1    4.804 ppm2   1.917
ASSI {17412}
((segid "BrD" and resid 34 and name HB2))
(segid "BrD" and resid 34 and name HD %)
2.900  2.100 2.100 peak      17412 weight  0.11000E+01 volume  0.12277E+03 ppm1    3.125 ppm2   7.705
ASSI {17652}
(segid "BrD" and resid 81 and name HG2 %)
((segid "BrD" and resid 34 and name HA))
2.500  1.600 1.600 peak      17652 weight  0.11000E+01 volume  0.31158E+03 ppm1    0.760 ppm2   5.542
ASSI {17662}
(segid "BrD" and resid 81 and name HG2 %)
((segid "BrD" and resid 55 and name HA))
2.600  1.700 1.700 peak      17662 weight  0.11000E+01 volume  0.23078E+03 ppm1    0.755 ppm2   5.366
ASSI {17722}
((segid "BrD" and resid 33 and name HG1))
((segid "BrD" and resid 33 and name HA))
3.100  2.400 2.400 peak      17722 weight  0.11000E+01 volume  0.93743E+02 ppm1    0.859 ppm2   4.354
ASSI {17812}
((segid "BrD" and resid 33 and name HD2))
((segid "BrD" and resid 33 and name HB2))
3.000  2.200 2.200 peak      17812 weight  0.11000E+01 volume  0.10412E+03 ppm1    2.190 ppm2  −0.162
ASSI {17822}
((segid "BrD" and resid 33 and name HD1))
((segid "BrD" and resid 33 and name HB2))
3.000  2.200 2.200 peak      17822 weight  0.11000E+01 volume  0.9990E+02 ppm1     2.782 ppm2  −0.362

TABLE 2-continued

| Unambiguous NOE-derived Inter-proton Distance Restraints |
|---|

ASSI {17832}
((segid "BrD" and resid 33 and name HD2))
((segid "BrD" and resid 33 and name HA))
3.900   3.800 1.600 peak        17832   weight  0.11000E+01 volume   0.24295E+02 ppm1        2.190  ppm2   4.354
ASSI {17842}
((segid "BrD" and resid 33 and name HD1))
((segid "BrD" and resid 33 and name HA))
3.800   3.600 1.700 peak        17842   weight  0.11000E+01 volume   0.26770E+02 ppm1        2.785  ppm2   4.353
ASSI {17862}
((segid "BrD" and resid 33 and name HD2))
((segid "BrD" and resid 32 and name HA))
3.300   2.700 2.200 peak        17862   weight  0.11000E+01 volume   0.62722E+02 ppm1        2.190  ppm2   4.981
ASSI {17872}
((segid "BrD" and resid 33 and name HD1))
((segid "BrD" and resid 32 and name HH2))
5.500   5.500 0.000 peak        17872   weight  0.11000E+01 volume   0.61193E+03 ppm1        2.783  ppm2   7.797
ASSI {17882}
((segid "BrD" and resid 33 and name HD2))
((segid "BrD" and resid 32 and name HH2))
5.500   5.500 0.000 peak        17882   weight  0.11000E+01 volume   0.56139E+03 ppm1        2.191  ppm2   7.797
ASSI {17912}
((segid "BrD" and resid 33 and name HB1))
((segid "BrD" and resid 33 and name HD2))
3.900   3.800 1.600 peak        17912   weight  0.11000E+01 volume   0.21009E+02 ppm1        1.056  ppm2   2.190
ASSI {17942}
((segid "BrD" and resid 33 and name HB1))
((segid "BrD" and resid 33 and name HD1))
3.300   2.700 2.200 peak        17942   weight  0.11000E+01 volume   0.67464E+02 ppm1        1.056  ppm2   2.792
ASSI {18062}
((segid "BrD" and resid 75 and name HG1))
(segid "BrD" and resid 110 and name HG2 %)
4.000   4.000 1.500 peak        18062   weight  0.11000E+01 volume   0.20766E+02 ppm1        3.522  ppm2   1.262
ASSI {18082}
((segid "BrD" and resid 75 and name HG2))
(segid "BrD" and resid 110 and name HD1 %)
3.400   2.900 2.100 peak        18082   weight  0.11000E+01 volume   0.48309E+02 ppm1        3.226  ppm2   1.140
ASSI {18092}
((segid "BrD" and resid 75 and name HG2))
(segid "BrD" and resid 110 and name HG2 %)
4.100   4.100 1.400 peak        18092   weight  0.11000E+01 volume   0.17226E+02 ppm1        3.226  ppm2   1.262
ASSI {18162}
((segid "BrD" and resid 53 and name HB1))
((segid "BrD" and resid 52 and name HA))
5.500   5.500 0.000 peak        18162   weight  0.11000E+01 volume   0.54558E+00 ppm1        2.784  ppm2   5.582
ASSI {18172}
((segid "BrD" and resid 53 and name HB1))
(segid "BrD" and resid 46 and name HE %)
2.400   1.700 1.700 peak        18172   weight  0.11000E+01 volume   0.27274E+03 ppm1        2.783  ppm2   6.688
ASSI {18182}
((segid "BrD" and resid 53 and name HB1))
(segid "BrD" and resid 47 and name HE %)
2.500   1.600 1.600 peak        18182   weight  0.11000E+01 volume   0.34975E+03 ppm1        2.783  ppm2   7.267
ASSI {18192}
((segid "BrD" and resid 53 and name HA))
(segid "BrD" and resid 47 and name HD %)
3.200   2.400 2.400 peak        18192   weight  0.11000E+01 volume   0.93621E+02 ppm1        2.777  ppm2   7.962
ASSI {18222}
(segid "BrD" and resid 35 and name HE %)
((segid "BrD" and resid 35 and name HG1))
2.300   1.300 1.300 peak        18222   weight  0.11000E+01 volume   0.50180E+03 ppm1        2.781  ppm2   3.448
ASSI {18292}
(segid "BrD" and resid 35 and name HE %)
((segid "BrD" and resid 35 and name HA))
2.700   1.800 1.800 peak        18292   weight  0.11000E+01 volume   0.21224E+03 ppm1        2.782  ppm2   4.901
ASSI {18452}
((segid "BrD" and resid 75 and name HG2))
(segid "BrD" and resid 74 and name HD %)
3.400   2.900 2.100 peak        18452   weight  0.11000E+01 volume   0.49200E+02 ppm1        3.227  ppm2   6.999
ASSI {18462}
((segid "BrD" and resid 75 and name HG1))
(segid "BrD" and resid 74 and name HD %)
3.100   2.400 2.400 peak        18462   weight  0.11000E+01 volume   0.92286E+02 ppm1        3.524  ppm2   7.001
ASSI {18512}
(segid "BrD" and resid 75 and name HE %)
((segid "BrD" and resid 75 and name HA))
2.900   2.100 2.100 peak        18512   weight  0.11000E+01 volume   0.12672E+03 ppm1        2.635  ppm2   4.518

TABLE 2-continued

Unambiguous NOE-derived Inter-proton Distance Restraints

ASSI {18752}
(segid "BrD" and resid 75 and name HE %)
(segid "BrD" and resid 18 and name HD2 %)
3.800  3.600 1.700 peak      18752  weight  0.11000E+01 volume   0.27479E+02 ppm1    2.634 ppm2   0.416
ASSI {18792}
(segid "BrD" and resid 75 and name HE %)
(segid "BrD" and resid 110 and name HG2 %)
2.700  1.800 1.800 peak      18792  weight  0.11000E+01 volume   0.21856E+03 ppm1    2.634 ppm2   1.262
ASSI {18802}
(segid "BrD" and resid 75 and name HE %)
(segid "BrD" and resid 110 and name HD1 %)
2.600  1.700 1.700 peak      18802  weight  0.11000E+01 volume   0.24635E+03 ppm1    2.634 ppm2   1.140
ASSI {19032}
((segid "BrD" and resid 75 and name HA))
(segid "BrD" and resid 74 and name HD %)
2.600  1.700 1.700 peak      19032  weight  0.11000E+01 volume   0.28302E+03 ppm1    4.508 ppm2   6.998
ASSI {19112}
(segid "BrD" and resid 43 and name HB %)
(segid "BrD" and resid 88 and name HE %)
2.900  2.100 2.100 peak      19112  weight  0.11000E+01 volume   0.13802E+03 ppm1    1.700 ppm2   7.414
ASSI {19132}
(segid "BrD" and resid 43 and name HB %)
(segid "BrD" and resid 88 and name HD %)
4.900  4.900 0.600 peak      19132  weight  0.11000E+01 volume   0.55356E+01 ppm1    1.697 ppm2   7.609
ASSI {19142}
(segid "BrD" and resid 43 and name HB %)
(segid "BrD" and resid 46 and name HE %)
3.400  2.900 2.100 peak      19142  weight  0.11000E+01 volume   0.52712E+02 ppm1    1.497 ppm2   4.449
ASSI {19162}
(segid "BrD" and resid 43 and name HB %)
(segid "BrD" and resid 46 and name HD %)
2.600  1.700 1.700 peak      19142  weight  0.11000E+01 volume   0.28846E+03 ppm1    1.697 ppm2   5.753
ASSI {19852}
((segid "BrD" and resid 102 and name HA))
((segid "BrD" and resid 102 and name HG))
2.700  1.800 1.800 peak      19852  weight  0.11000E+01 volume   0.19930E+03 ppm1    4.263 ppm2   2.157
ASSI {20082}
((segid "BrD" and resid 110 and name HA))
((segid "BrD" and resid 110 and name HG11))
2.400  1.400 1.400 peak      20082  weight  0.11000E+01 volume   0.38344E+03 ppm1    4.411 ppm2   1.718
ASSI {20232}
(segid "BrD" and resid 17 and name HG2 %)
((segid "BrD" and resid 18 and name HA))
3.100  2.400 2.400 peak      20232  weight  0.11000E+01 volume   0.91939E+02 ppm1    1.747 ppm2   $$
ASSI {20342}
((segid "BrD" and resid 53 and name HA))
((segid "BrD" and resid 53 and name HD1))
3.300  2.700 2.200 peak      20342  weight  0.11000E+01 volume   0.66608E+02 ppm1    4.696 ppm2   4.210
ASSI {20372}
((segid "BrD" and resid 53 and name HA))
(segid "BrD" and resid 47 and name HE %)
3.900  3.800 1.600 peak      20372  weight  0.11000E+01 volume   0.22477E+02 ppm1    4.696 ppm2   7.260
ASSI {20422}
((segid "BrD" and resid 53 and name HD2))
((segid "BrD" and resid 53 and name HA))
3.200  2.600 2.300 peak      20422  weight  0.11000E+01 volume   0.75265E+02 ppm1    4.015 ppm2   4.696
ASSI {20432}
((segid "BrD" and resid 53 and name HD1))
(segid "BrD" and resid 50 and name HG2 %)
3.400  2.900 2.100 peak      20432  weight  0.11000E+01 volume   0.50650E+02 ppm1    4.214 ppm2   0.993
ASSI {20462}
((segid "BrD" and resid 53 and name HG1))
(segid "BrD" and resid 46 and name HE %)
3.600  3.200 1.900 peak      20462  weight  0.11000E+01 volume   0.35265E+02 ppm1    2.$$4 ppm2   6.689
ASSI {20472}
((segid "BrD" and resid 53 and name HG1))
(segid "BrD" and resid 47 and name HE %)
2.500  1.600 1.600 peak      20472  weight  0.11000E+01 volume   0.29199E+03 ppm1    2.784 ppm2   7.267
ASSI {20482}
((segid "BrD" and resid 53 and name HG2))
(segid "BrD" and resid 47 and name HE %)
2.600  1.700 1.700 peak      20482  weight  0.11000E+01 volume   0.27122E+03 ppm1    2.484 ppm2   7.267
ASSI {20492}
((segid "BrD" and resid 53 and name HG2))
(segid "BrD" and resid 47 and name HD %)
2.400  1.400 1.400 peak      20492  weight  0.11000E+01 volume   0.38647E+03 ppm1    2.486 ppm2   7.958

TABLE 2-continued

| Unambiguous NOE-derived Inter-proton Distance Restraints |
|---|

ASSI {20502}
((segid "BrD" and resid 53 and name HG1))
(segid "BrD" and resid 47 and name HD %))
2.800  2.000 2.000 peak        20502 weight  0.11000E+01 volume   0.18213E+03 ppm1     2.784 ppm2  7.958
ASSI {20522}
((segid "BrD" and resid 53 and name HG1))
((segid "BrD" and resid 52 and name HA))
5.500  5.500 0.000 peak        20522 weight  0.11000E+01 volume   0.58337E+01 ppm1     2.784 ppm2  5.587
ASSI {20602}
((segid "BrD" and resid 61 and name HG2))
((segid "BrD" and resid 58 and name HA))
2.500  1.600 1.600 peak        20602 weight  0.11000E+01 volume   0.31153E+03 ppm1     2.831 ppm2  4.452
ASSI {20612}
((segid "BrD" and resid 61 and name HG1))
((segid "BrD" and resid 58 and name HA))
2.500  1.600 1.600 peak        20612 weight  0.11000E+01 volume   0.36307E+03 ppm1     2.980 ppm2  4.452
ASSI {20702}
((segid "BrD" and resid 80 and name HA))
((segid "BrD" and resid 83 and name HB))
1.400  0.500 0.800 peak        20702 weight  0.11000E+01 volume   0.11465E+05 ppm1     4.656 ppm2  4.804
ASSI {20772}
((segid "BrD" and resid 58 and name HB))
((segid "BrD" and resid 54 and name HA))
3.400  2.900 2.100 peak        20772 weight  0.21000E+01 volume   0.51113E+03 ppm1     4.702 ppm2  5.544
ASSI {20782}
(segid "BrD" and resid 58 and name HG2 %)
((segid "BrD" and resid 54 and name HA))
2.800  2.000 2.000 peak        20782 weight  0.11000E+01 volume   0.15234E+03 ppm1     1.644 ppm2  5.542
ASSI {20882}
((segid "BrD" and resid 62 and name HD1))
((segid "BrD" and resid 62 and name HA))
3.100  2.400 2.400 peak        20882 weight  0.11000E+01 volume   0.94082E+02 ppm1     3.177 ppm2  4.476
ASSI {20892}
((segid "BrD" and resid 62 and name HD2))
((segid "BrD" and resid 62 and name HA))
3.000  2.200 2.200 peak        20892 weight  0.11000E+01 volume   0.10112E+03 ppm1     2.634 ppm2  4.476
ASSI {20902}
((segid "BrD" and resid 62 and name HD1))
(segid "BrD" and resid 67 and name HE %)
4.400  4.400 1.100 peak        20902 weight  0.11000E+01 volume   0.11575E+02 ppm1     3.177 ppm2  7.316
ASSI {20912}
((segid "BrD" and resid 62 and name HD1))
(segid "BrD" and resid 67 and name HD %)
3.700  3.400 1.800 peak        20912 weight  0.11000E+01 volume   0.30541E+02 ppm1     3.177 ppm2  6.893
ASSI {20922}
((segid "BrD" and resid 62 and name HD2))
(segid "BrD" and resid 67 and name HD %)
3.400  2.900 2.100 peak        20922 weight  0.11000E+01 volume   0.54284E+02 ppm1     2.634 ppm2  6.893
ASSI {20932}
((segid "BrD" and resid 62 and name HD2))
(segid "BrD" and resid 67 and name HE %)
3.100  2.400 2.400 peak        20932 weight  0.11000E+01 volume   0.91289E+02 ppm1     2.634 ppm2  7.315
ASSI {20952}
((segid "BrD" and resid 62 and name HB1))
((segid "BrD" and resid 62 and name HD1))
3.200  2.600 2.300 peak        20952 weight  0.11000E+01 volume   0.71708E+02 ppm1     2.641 ppm2  3.183
ASSI {20962}
((segid "BrD" and resid 62 and name HB2))
((segid "BrD" and resid 62 and name HG1))
3.000  2.200 2.200 peak        20962 weight  0.11000E+01 volume   0.10075E+03 ppm1     1.699 ppm2  2.325
ASSI {20972}
((segid "BrD" and resid 62 and name HG2))
((segid "BrD" and resid 62 and name HB1))
2.700  1.800 1.800 peak        20972 weight  0.11000E+01 volume   0.20830E+03 ppm1     2.641 ppm2  1.479
ASSI {21012}
((segid "BrD" and resid 62 and name HG2))
((segid "BrD" and resid 62 and name HD1))
3.100  2.400 2.400 peak        21012 weight  0.11000E+01 volume   0.87215E+02 ppm1     1.501 ppm2  3.182
ASSI {21022}
((segid "BrD" and resid 62 and name HG1))
((segid "BrD" and resid 62 and name HA))
2.900  2.100 2.100 peak        21022 weight  0.11000E+01 volume   0.13858E+03 ppm1     2.340 ppm2  4.474
ASSI {21162}
((segid "BrD" and resid 83 and name HA))
((segid "BrD" and resid 86 and name HG2))
4.800  4.800 0.700 peak        21162 weight  0.11000E+01 volume   0.66244E+01 ppm1     4.459 ppm2  0.766

TABLE 2-continued

Unambiguous NOE-derived Inter-proton Distance Restraints

```
ASSI {21512}
((segid "BrD" and resid 38 and name HB))
(segid "BrD" and resid 46 and name HD %)
 3.400  2.900 2.100 peak      21512 weight 0.11000E+01 volume 0.54169E+02 ppm1  1.747 ppm2 5.745
ASSI {21522}
((segid "BrD" and resid 38 and name HB))
(segid "BrD" and resid 47 and name HE %)
 4.500  4.500 1.000 peak      21522 weight 0.11000E+01 volume 0.90841E+01 ppm1  1.751 ppm2 7.259
ASSI {21532}
((segid "BrD" and resid 38 and name HB))
(segid "BrD" and resid 46 and name HE %)
 4.500  4.500 1.000 peak      21532 weight 0.11000E+01 volume 0.94356E+01 ppm1  1.747 ppm2 6.689
ASSI {21602}
(segid "BrD" and resid 81 and name HG1 %)
((segid "BrD" and resid 34 and name HB2))
 3.300  2.700 2.200 peak      21602 weight 0.11000E+01 volume 0.56657E+02 ppm1  1.056 ppm2 3.146
ASSI {21622}
(segid "BrD" and resid 81 and name HG1 %)
((segid "BrD" and resid 55 and name HA))
 2.400  1.400 1.400 peak      21622 weight 0.11000E+01 volume 0.44267E+03 ppm1  1.056 ppm2 5.367
ASSI {21632}
(segid "BrD" and resid 81 and name HG1 %)
((segid "BrD" and resid 34 and name HA))
 2.800  2.000 2.000 peak      21632 weight 0.11000E+01 volume 0.15411E+03 ppm1  1.056 ppm2 5.542
ASSI {21762}
(segid "BrD" and resid 81 and name HG2 %)
((segid "BrD" and resid 78 and name HA))
 2.600  1.700 1.700 peak      21762 weight 0.11000E+01 volume 0.24983E+03 ppm1  0.760 ppm2 4.004
ASSI {21832}
(segid "BrD" and resid 50 and name HD1 %)
(segid "BrD" and resid 49 and name HG1 %)
 2.900  2.100 2.100 peak      21832 weight 0.11000E+01 volume 0.14668E+03 ppm1  1.155 ppm2 1.645
ASSI {21842}
(segid "BrD" and resid 50 and name HD1 %)
(segid "BrD" and resid 49 and name HG2 %)
 2.400  1.400 1.400 peak      21842 weight 0.11000E+01 volume 0.37404E+03 ppm1  1.155 ppm2 1.571
ASSI {21852}
((segid "BrD" and resid 49 and name HB))
(segid "BrD" and resid 88 and name HD %)
 3.400  2.900 2.100 peak      21852 weight 0.11000E+01 volume 0.48521E+02 ppm1  2.634 ppm2 7.606
ASSI {21862}
((segid "BrD" and resid 49 and name HB))
(segid "BrD" and resid 88 and name HE %)
 3.400  2.900 2.100 peak      21862 weight 0.11000E+01 volume 0.55049E+02 ppm1  2.634 ppm2 7.414
ASSI {21872}
((segid "BrD" and resid 49 and name HB))
((segid "BrD" and resid 46 and name HA))
 3.700  3.400 1.800 peak      21872 weight 0.11000E+01 volume 0.31537E+02 ppm1  2.634 ppm2 4.143
ASSI {21912}
(segid "BrD" and resid 50 and name HD1 %)
((segid "BrD" and resid 87 and name HB2))
 2.600  1.700 1.700 peak      21912 weight 0.11000E+01 volume 0.24085E+03 ppm1  1.155 ppm2 2.603
ASSI {21922}
(segid "BrD" and resid 50 and name HD1 %)
((segid "BrD" and resid 87 and name HB1))
 2.400  2.400 1.400 peak      21922 weight 0.11000E+01 volume 0.36901E+03 ppm1  1.155 ppm2 2.778
ASSI {21932}
(segid "BrD" and resid 50 and name HD1 %)
((segid "BrD" and resid 87 and name HG1))
 3.700  3.400 1.800 peak      21932 weight 0.11000E+01 volume 0.32396E+02 ppm1  1.155 ppm2 3.028
ASSI {21942}
(segid "BrD" and resid 50 and name HD1 %)
((segid "BrD" and resid 84 and name HB2))
 2.700  1.800 1.800 peak      21942 weight 0.11000E+01 volume 0.22842E+03 ppm1  1.155 ppm2 3.272
ASSI {21962}
(segid "BrD" and resid 50 and name HD1 %)
((segid "BrD" and resid 84 and name HB1))
 2.600  1.700 1.700 peak      21962 weight 0.11000E+01 volume 0.28478E+03 ppm1  1.155 ppm2 3.606
ASSI {21992}
(segid "BrD" and resid 50 and name HD1 %)
((segid "BrD" and resid 88 and name HA))
 2.700  1.800 1.800 peak      21992 weight 0.11000E+01 volume 0.19153E+03 ppm1  1.155 ppm2 4.988
ASSI {22002}
(segid "BrD" and resid 50 and name HD1 %)
((segid "BrD" and resid 84 and name HA))
 2.300  1.300 1.300 peak      22002 weight 0.11000E+01 volume 0.57384E+03 ppm1  1.155 ppm2 4.915
```

TABLE 2-continued

Unambiguous NOE-derived Inter-proton Distance Restraints

```
ASSI {22052}
((segid "BrD" and resid 50 and name HB))
(segid "BrD" and resid 46 and name HE %)
3.000  2.200 2.200 peak      22052  weight  0.11000E+01 volume  0.99146E+02 ppm1     1.797 ppm2  6.489
ASSI {22092}
(segid "BrD" and resid 50 and name HG2 %)
((segid "BrD" and resid 52 and name HA))
3.500  3.100 2.000 peak      22092  weight  0.11000E+01 volume  0.46395E+02 ppm1     1.006 ppm2  5.587
ASSI {22102}
(segid "BrD" and resid 50 and name HG2 %)
(segid "BrD" and resid 46 and name HD %)
3.700  3.400 1.800 peak      22102  weight  0.11000E+01 volume  0.30083E+02 ppm1     1.007 ppm2  5.745
ASSI {22152}
(segid "BrD" and resid 50 and name HG2 %)
(segid "BrD" and resid 47 and name HE %)
4.300  4.300 1.200 peak      22152  weight  0.11000E+01 volume  0.12530E+02 ppm1     1.007 ppm2  7.259
ASSI {22162}
(segid "BrD" and resid 50 and name HG2 %)
(segid "BrD" and resid 46 and name HE %)
2.500  1.600 1.600 peak      22162  weight  0.11000E+01 volume  0.31318E+03 ppm1     1.007 ppm2  6.689
ASSI {22172}
(segid "BrD" and resid 50 and name HG2 %)
((segid "BrD" and resid 84 and name HA))
2.900  2.100 2.100 peak      22172  weight  0.11000E+01 volume  0.14754E+03 ppm1     1.007 ppm2  4.915
ASSI {22192}
((segid "BrD" and resid 50 and name HG2 %)
((segid "BrD" and resid 49 and name HG2 %)
3.700  3.400 1.800 peak      22192  weight  0.11000E+01 volume  0.30274E+02 ppm1     1.006 ppm2  1.570
ASSI {22262}
((segid "BrD" and resid 50 and name HG12))
((segid "BrD" and resid 50 and name HA))
3.300  2.700 2.200 peak      22262  weight  0.11000E+01 volume  0.57888E+02 ppm1     0.809 ppm2  4.522
ASSI {22342}
(segid "BrD" and resid 69 and name HG2 %)
((segid "BrD" and resid 70 and name HA))
3.500  3.100 2.000 peak      22342  weight  0.11000E+01 volume  0.43395E+02 ppm1     1.427 ppm2  5.356
ASSI {22512}
(segid "BrD" and resid 49 and name HG1 %)
(segid "BrD" and resid 88 and name HE %)
2.300  1.300 1.300 peak      22517  weight  0.11000E+01 volume  0.52744E+03 ppm1     1.646 ppm2  7.419
ASSI {22522}
(segid "BrD" and resid 49 and name HG1 %)
(segid "BrD" and resid 88 and name HD %)
2.500  1.600 1.600 peak      22522  weight  0.11000E+01 volume  0.29406E+03 ppm1     1.646 ppm2  7.604
ASSI {22652}
((segid "BrD" and resid 7 and name HG1))
((segid "BrD" and resid 7 and name HA))
3.000  2.200 2.200 peak      22652  weight  0.11000E+01 volume  0.11329E+03 ppm1     2.880 ppm2  5.143
ASSI {22792}
((segid "BrD" and resid 104 and name HB1))
((segid "BrD" and resid 101 and name HA))
2.300  1.300 1.300 peak      24792  weight  0.11000E+01 volume  0.53105E+03 ppm1     2.537 ppm2  4.267
ASSI {22872}
((segid "BrD" and resid 6 and name HE1))
((segid "BrD" and resid 6 and name HA))
2.100  1.100 1.100 peak      22872  weight  0.11000E+01 volume  0.98321E+03 ppm1     3.610 ppm2  4.972
ASSI {22942}
((segid "BrD" and resid 44 and name HD2))
((segid "BrD" and resid 44 and name HA))
3.100  2.400 2.400 peak      22942  weight  0.11000E+01 volume  0.83098E+02 ppm1     4.114 ppm2  5.114
ASSI {23162}
((segid "BrD" and resid 8 and name HG1))
((segid "BrD" and resid 8 and name HA))
2.600  1.700 1.700 peak      23162  weight  0.11000E+01 volume  0.28012E+03 ppm1     2.635 ppm2  5.021
ASSI {23172}
((segid "BrD" and resid 11 and name HG1))
((segid "BrD" and resid 10 and name HA))
4.100  4.100 1.400 peak      23172  weight  0.11000E+01 volume  0.17156E+02 ppm1     2.635 ppm2  5.477
ASSI {23302}
((segid "BrD" and resid 9 and name HD1))
((segid "BrD" and resid 9 and name HA))
2.900  2.100 2.100 peak      23302  weight  0.11000E+01 volume  0.23154E+03 ppm1     3.768 ppm2  4.940
ASSI {23352}
((segid "BrD" and resid 9 and name HD1))
((segid "BrD" and resid 9 and name HB1))
2.400  1.400 1.400 peak      23352  weight  0.11000E+01 volume  0.39945E+03 ppm1     3.768 ppm2  2.434
```

TABLE 2-continued

Unambiguous NOE-derived Inter-proton Distance Restraints

ASSI {23362}
((segid "BrD" and resid 9 and name HD1))
((segid "BrD" and resid 9 and name HB2))
2.300  1.300 1.300 peak     23362 weight 0.11000E+01 volume 0.50335E+03 ppm1  3.768 pm2  2.385
ASSI {23542}
((segid "BrD" and resid 11 and name HA))
((segid "BrD" and resid 11 and name HD1))
2.600  1.700 1.700 peak     23542 weight 0.11000E+01 volume 0.23295E+03 ppm1  4.951 ppm2  4.459
ASSI {23552}
(segid "BrD" and resid 14 and name HD2 %)
((segid "BrD" and resid 11 and name HA))
2.500  1.600 1.600 peak     23552 weight 0.11000E+01 volume 0.34571E+03 ppm1  1.401 ppm2  4.947
ASSI {23692}
((segid "BrD" and resid 14 and name HB2))
(segid "BrD" and resid 18 and name HD1 %)
2.900  2.100 2.100 peak     23692 weight 0.11000E+01 volume 0.14113E+03 ppm1  2.143 ppm2  1.084
ASSI {23702}
((segid "BrD" and resid 14 and name HA))
(segid "BrD" and resid 17 and name HG2 %)
3.400  2.900 2.100 peak     23702 weight 0.11000E+01 volume 0.49626E+02 ppm1  4.656 ppm2  1.750
ASSI {23722}
((segid "BrD" and resid 14 and name HG))
(segid "BrD" and resid 18 and name HD2 %)
3.200  2.600 2.300 peak     23722 weight 0.11000E+01 volume 0.69871E+02 ppm1  2.044 ppm2  0.415
ASSI {23752}
((segid "BrD" and resid 14 and name HA))
((segid "BrD" and resid 17 and name HB))
2.100  1.100 1.100 peak     23752 weight 0.11000E+01 volume 0.89711E+03 ppm1  4.656 ppm2  4.854
ASSI {23852}
(segid "BrD" and resid 14 and name HD1 %)
((segid "BrD" and resid 11 and name HA))
2.200  1.200 1.200 peak     23852 weight 0.11000E+01 volume 0.75160E+03 ppm1  1.402 ppm2  4.947
ASSI {23952}
((segid "BrD" and resid 18 and name HB2))
((segid "BrD" and resid 15 and name HA))
3.200  3.600 2.300 peak     23952 weight 0.11000E+01 volume 0.79651E+02 ppm1  0.911 ppm2  4.630
ASSI {23962}
((segid "BrD" and resid 18 and name HB1))
((segid "BrD" and resid 15 and name HA))
3.100  2.400 2.400 peak     23962 weight 0.11000E+01 volume 0.98332E+02 ppm1  2.144 ppm2  4.626
ASSI {24042}
(segid "BrD" and resid 18 and name HD2 %)
((segid "BrD" and resid 17 and name HB))
2.900  2.100 2.100 peak     24042 weight 0.11000E+01 volume 0.13399E+03 ppm1  0.414 ppm2  4.860
ASSI {24052}
(segid "BrD" and resid 18 and name HD2 %)
(segid "BrD" and resid 74 and name HD %)
2.500  1.600 1.600 peak     24052 weight 0.11000E+01 volume 0.29789E+03 ppm1  0.415 ppm2  6.998
ASSI {24062}
(segid "BrD" and resid 18 and name HD2 %)
(segid "BrD" and resid 74 and name HE %)
2.700  1.800 1.800 peak     24062 weight 0.11000E+01 volume 0.22219E+03 ppm1  0.415 ppm2  7.534
ASSI {24072}
(segid "BrD" and resid 18 and name HD2 %)
((segid "BrD" and resid 74 and name HB1))
3.200  2.600 2.300 peak     24072 weight 0.11000E+01 volume 0.70185E+02 ppm1  0.419 ppm2  3.565
ASSI {24082}
(segid "BrD" and resid 18 and name HD2 %)
((segid "BrD" and resid 74 and name HB2))
2.900  2.100 2.100 peak     24082 weight 0.11000E+01 volume 0.13658E+03 ppm1  0.415 ppm2  2.995
ASSI {24092}
(segid "BrD" and resid 18 and name HD2 %)
(segid "BrD" and resid 63 and name HD1 %)
3.200  2.600 2.300 peak     24092 weight 0.11000E+01 volume 0.72579E+02 ppm1  0.414 ppm2  1.648
ASSI {24132}
(segid "BrD" and resid 18 and name HD2 %)
((segid "BrD" and resid 74 and name HA))
3.400  2.900 2.100 peak     24132 weight 0.11000E+01 volume 0.52592E+02 ppm1  0.414 ppm2  4.378
ASSI {24162}
(segid "BrD" and resid 18 and name HD1 %)
(segid "BrD" and resid 74 and name HE %)
3.000  2.200 2.200 peak     24162 weight 0.11000E+01 volume 0.10145E+03 ppm1  1.058 ppm2  7.536
ASSI {24182}
(segid "BrD" and resid 18 and name HD1 %)
(segid "BrD" and resid 74 and name HD %)
2.600  1.700 1.700 peak     24182 weight 0.11000E+01 volume 0.27877E+03 ppm1  1.056 ppm2  6.998

TABLE 2-continued

Unambiguous NOE-derived Inter-proton Distance Restraints

ASSI {24212}
(segid "BrD" and resid 18 and name HD1 %)
((segid "BrD" and resid 74 and name HA))
3.200  2.600  2.300 peak    24212 weight  0.11000E+01 volume  0.78587E+02 ppm1  1.056 ppm2  4.378
ASSI {24522}
(segid "BrD" and resid 63 and name HD1 %)
((segid "BrD" and resid 19 and name HA)
2.600  1.700  1.700 peak    24522 weight  0.11000E+01 volume  0.26998E+03 ppm1  1.647 ppm2  4.297
ASSI {24662}
(segid "BrD" and resid 63 and name HD2 %)
(segid "BrD" and resid 18 and name HD1 %)
2.700  1.800  1.800 peak    24662 weight  0.11000E+01 volume  0.19359E+03 ppm1  1.498 ppm2  1.090
ASSI {24672}
(segid "BrD" and resid 63 and name HD2 %)
((segid "BrD" and resid 18 and name HB2))
5.500  5.500  0.000 peak    24672 weight  0.11000E+01 volume  0.20842E+01 ppm1  1.498 ppm2  0.928
ASSI {24742}
((segid "BrD" and resid 19 and name HB2))
((segid "BrD" and resid 19 and name HE1))
4.000  4.000  1.500 peak    24742 weight  0.11000E+01 volume  0.20066E+02 ppm1  1.989 ppm2  3.525
ASSI {24752}
((segid "BrD" and resid 19 and name HB1))
((segid "BrD" and resid 19 and name HE1))
3.300  2.700  2.200 peak    24752 weight  0.11000E+01 volume  0.65557E+02 ppm1  2.290 ppm2  3.525
ASSI {24762}
((segid "BrD" and resid 19 and name HG1))
((segid "BrD" and resid 16 and name HA))
2.900  2.100  2.100 peak    24762 weight  0.11000E+01 volume  0.12763E+03 ppm1  1.894 ppm2  4.508
ASSI {24812}
((segid "BrD" and resid 19 and name HD1))
((segid "BrD" and resid 16 and name HA))
2.300  1.300  1.300 peak    24812 weight  0.11000E+01 volume  0.50116E+03 ppm1  2.192 ppm2  4.507
ASSI {24872}
((segid "BrD" and resid 23 and name HG1))
((segid "BrD" and resid 20 and name HA))
3.100  2.400  2.400 peak    24872 weight  0.11000E+01 volume  0.91712E+02 ppm1  3.124 ppm2  4.893
ASSI {24902}
((segid "BrD" and resid 24 and name HG1))
((segid "BrD" and resid 21 and name HA))
3.200  2.600  2.300 peak    24902 weight  0.11000E+01 volume  0.67606E+02 ppm1  3.469 ppm2  4.370
ASSI {24912}
((segid "BrD" and resid 24 and name HG2))
((segid "BrD" and resid 21 and name HA))
2.600  2.700  1.700 peak    24912 weight  0.11000E+01 volume  0.26410E+03 ppm1  3.076 ppm2  4.370
ASSI {24932}
((segid "BrD" and resid 24 and name HA))
((segid "BrD" and resid 24 and name HB1))
2.200  1.200  1.200 peak    24932 weight  0.11000E+01 volume  0.62910E+03 ppm1  4.784 ppm2  3.074
ASSI {25432}
((segid "BrD" and resid 85 and name HB1))
((segid "BrD" and resid 82 and name HA))
3.100  2.400  2.400 peak    25432 weight  0.11000E+01 volume  0.87929E+02 ppm1  3.917 ppm2  4.753
ASSI {25552}
((segid "BrD" and resid 101 and name HG12))
((segid "BrD" and resid 101 and name HB))
2.300  1.300  1.300 peak    25552 weight  0.11000E+01 volume  0.65437E+03 ppm1  2.797 ppm2  2.538
ASSI {25612}
(segid "BrD" and resid 21 and name HG2 %)
((segid "BrD" and resid 18 and name HA))
3.000  2.200  2.200 peak    25612 weight  0.11000E+01 volume  0.11187E+03 ppm1  1.599 ppm2  3.890
ASSI {26032}
(segid "BrD" and resid 110 and name HD1 %)
((segid "BrD" and resid 75 and name HG1))
3.400  2.900  2.100 peak    26032 weight  0.11000E+01 volume  0.51048E+02 ppm1  1.155 ppm2  3.524
ASSI {26172}
(segid "BrD" and resid 110 and name HG2 %)
(segid "BrD" and resid 18 and name HD2 %)
4.400  4.400  1.100 peak    26172 weight  0.11000E+01 volume  0.11733E+02 ppm1  1.254 ppm2  0.408
ASSI {26182}
(segid "BrD" and resid 110 and name HD1 %)
(segid "BrD" and resid 18 and name HD2 %)
3.000  2.200  2.200 peak    26182 weight  0.1100E+01 volume  0.11735E+03 ppm1  1.153 ppm2  0.410
ASSI {26302}
(segid "BrD" and resid 116 and name HD1 %)
((segid "BrD" and resid 116 and name HA))
2.500  1.600  1.600 peak    26302 weight  0.11000E+01 volume  0.31414E+03 ppm1  1.401 ppm2  4.826

TABLE 2-continued

Unambiguous NOE-derived Inter-proton Distance Restraints

ASSI {26562}
((segid "BrD" and resid 103 and name HA))
(segid "BrD" and resid 106 and name HD %)
3.100  2.400 2.400 peak      26562 weight  0.11000E+01 volume  0.97052E+02 ppm1   3.768 ppm2  7.514
ASSI {26592}
((segid "BrD" and resid 103 and name HB1))
((segid "BrD" and resid 100 and name HA))
2.700  1.800 1.800 peak      26592 weight  0.11000E+01 volume  0.20226E+03 ppm1   2.338 ppm2  4.946
ASSI {26642}
((segid "BrD" and resid 103 and name HB2))
((segid "BrD" and resid 103 and name HG2))
2.000  1.000 1.000 peak      26642 weight  0.11000E+01 volume  0.14101E+04 ppm1   1.891 ppm2  2.520
ASSI {26652}
((segid "BrD" and resid 103 and name HB2))
((segid "BrD" and resid 103 and name HG1))
2.200  1.200 1.200 peak      26652 weight  0.11000E+01 volume  0.62174E+03 ppm1   1.893 ppm2  2.598
ASSI {26662}
((segid "BrD" and resid 103 and name HG2))
((segid "BrD" and resid 100 and name HA))
3.500  3.100 2.000 peak      26662 weight  0.11000E+01 volume  0.45243E+02 ppm1   2.519 ppm2  4.947
ASSI {26672}
((segid "BrD" and resid 103 and name HG1))
((segid "BrD" and resid 100 and name HA))
3.900  3.800 1.600 peak      26672 weight  0.11000E+01 volume  0.23440E+02 ppm1   2.598 ppm2  4.947
ASSI {26722}
((segid "BrD" and resid 94 and name HG1))
((segid "BrD" and resid 32 and name HH2))
2.900  2.100 2.100 peak      26722 weight  0.11000E+01 volume  0.14855E+03 ppm1   3.129 ppm2  7.788
ASSI {26782}
((segid "BrD" and resid 94 and name HB1))
((segid "BrD" and resid 32 and name HZ2))
2.500  1.600 1.600 peak      26782 weight  0.11000E+01 volume  0.35938E+03 ppm1   2.735 ppm2  7.998
ASSI {26792}
((segid "BrD" and resid 94 and name HB1))
((segid "BrD" and resid 32 and name HH2))
3.000  2.200 2.200 peak      26792 weight  0.11000E+01 volume  0.10089E+03 ppm1   2.733 ppm2  7.785
ASSI {26842}
((segid "BrD" and resid 94 and name HG1))
((segid "BrD" and resid 94 and name HB1))
2.200  1.200 1.200 peak      26842 weight  0.11000E+01 volume  0.72439E+03 ppm1   3.123 ppm2  2.731
ASSI {26862}
((segid "BrD" and resid 87 and name HG2))
((segid "BrD" and resid 86 and name HD1))
3.600  3.200 1.900 peak      26862 weight  0.11000E+01 volume  0.34874E+02 ppm1   2.782 ppm2  1.900
ASSI {26882}
((segid "BrD" and resid 87 and name HB1))
((segid "BrD" and resid 87 and name HG1))
2.400  1.400 1.400 peak      26882 weight  0.11000E+01 volume  0.47090E+03 ppm1   2.779 ppm2  3.021
ASSI {27152}
((segid "BrD" and resid 80 and name HD2))
((segid "BrD" and resid 80 and name HA))
2.400  1.400 1.400 peak      27152 weight  0.11000E+01 volume  0.41973E+03 ppm1   3.912 ppm2  4.678
ASSI {27162}
((segid "BrD" and resid 80 and name HD1))
((segid "BrD" and resid 80 and name HA))
2.600  1.700 1.700 peak      27162 weight  0.11000E+01 volume  0.27730E+03 ppm1   3.962 ppm2  4.677
ASSI {27212}
((segid "BrD" and resid 77 and name HB1))
((segid "BrD" and resid 74 and name HA))
2.800  2.000 2.000 peak      27212 weight  0.11000E+01 volume  0.14302E+01 ppm1   1.325 ppm2  4.378
ASSI {27242}
((segid "BrD" and resid 80 and name HB2))
((segid "BrD" and resid 80 and name HD1))
2.900  2.100 2.100 peak      2.7242 weight  0.11000E+01 volume  0.12614E+03 ppm1   2.536 ppm2  3.955
ASSI {27252}
((segid "BrD" and resid 80 and name HB2))
((segid "BrD" and resid 80 and name HD2))
2.800  2.000 2.000 peak      27252 weight  0.11000E+01 volume  0.14981E+03 ppm1   2.536 ppm2  3.890
ASSI {27312}
((segid "BrD" and resid 56 and name HG))
((segid "BrD" and resid 34 and name HA))
5.500  5.500 0.000 peak      27312 weight  0.11000E+01 volume  0.47641E+00 ppm1   2.338 ppm2  5.542
ASSI {27352}
((segid "BrD" and resid 55 and name HB1))
((segid "BrD" and resid 55 and name HA))
2.200  1.200 1.200 peak      27352 weight  0.11000E+01 volume  0.72273E+03 ppm1   2.979 ppm2  5.366

TABLE 2-continued

Unambiguous NOE-derived Inter-proton Distance Restraints

ASSI {27412}
(segid "BrD" and resid 81 and name HG1 %)
((segid "BrD" and resid 34 and name HB1))
3.100  2.400 2.400 peak      27412 weight  0.11000E+01 volume  0.93003E+02 ppm1   1.058 ppm2  4.106
ASSI {27512}
(segid "BrD" and resid 22 and name HD2 %)
((segid "BrD" and resid 22 and name HG))
1.900  0.900 0.900 peak      27512 weight  0.11000E+01 volume  0.14735E+04 ppm1   1.599 ppm2  2.362
ASSI {27522}
(segid "BrD" and resid 22 and name HD2 %)
((segid "BrD" and resid 22 and name HB2))
2.200  1.200 1.200 peak      27522 weight  0.11000E+01 volume  0.70123E+03 ppm1   1.599 ppm2  2.286
ASSI {27682}
(segid "BrD" and resid 73 and name HD2 %)
((segid "BrD" and resid 73 and name HB2))
2.900  2.100 2.100 peak      27682 weight  0.11000E+01 volume  0.12667E+03 ppm1   1.600 ppm2  2.483
ASSI {27922}
(segid "BrD" and resid 78 and name HD1 %)
(segid "BrD" and resid 82 and name HD %)
3.600  3.200 1.900 peak      27922 weight  0.11000E+01 volume  0.39776E+02 ppm1   0.760 ppm2  7.259
ASSI {27972}
(segid "BrD" and resid 78 and name HD2 %)
(segid "BrD" and resid 82 and name HD %)
3.400  2.900 2.100 peak      27972 weight  0.11000E+01 volume  0.49710E+02 ppm1   0.662 ppm2  7.259
ASSI {28242}
(segid "BrD" and resid 56 and name HD1 %)
((segid "BrD" and resid 34 and name HB1))
3.000  2.200 2.200 peak      28242 weight  0.11000E+01 volume  0.10505E+03 ppm1   1.549 ppm2  4.110
ASSI {28282}
(segid "BrD" and resid 56 and name HD2 %)
((segid "BrD" and resid 34 and name HA))
3.800  3.600 1.700 peak      28282 weight  0.11000E+01 volume  0.25930E+02 ppm1   1.253 ppm2  5.540
ASSI {28312}
(segid "BrD" and resid 56 and name HD2 %)
((segid "BrD" and resid 34 and name HB1))
3.400  2.900 2.100 peak      28312 weight  0.11000E+01 volume  0.48455E+02 ppm1   1.253 ppm2  4.110
ASSI {28362}
(segid "BrD" and resid 56 and name HD2 %)
((segid "BrD" and resid 34 and name HB2))
3.200  2.600 2.300 peak      28362 weight  0.11000E+01 volume  0.68625E+02 ppm1   1.254 ppm2  3.134
ASSI {28672}
(segid "BrD" and resid 102 and name HD1 %)
((segid "BrD" and resid 102 and name HA))
2.100  1.100 1.100 peak      28672 weight  0.11000E+01 volume  0.89519E+03 ppm1   1.303 ppm2  4.282
ASSI {28712}
(segid "BrD" and resid 102 and name HD2 %)
((segid "BrD" and resid 102 and name HB2))
2.000  1.000 1.000 peak      28712 weight  0.11000E+01 volume  0.12274E+04 ppm1   1.303 ppm2  1.832
ASSI {28802}
((segid "BrD" and resid 115 and name HG))
((segid "BrD" and resid 115 and name HA))
2.400  1.400 1.400 peak      28802 weight  0.11000E+01 volume  0.40182E+03 ppm1   2.143 ppm2  4.828
ASSI {28962}
(segid "BrD" and resid 56 and name HD1 %)
((segid "BrD" and resid 34 and name HA))
3.200  2.600 2.300 peak      28962 weight  0.11000E+01 volume  0.68400E+02 ppm1   1.544 ppm2  5.540
ASSI {28982}
((segid "BrD" and resid 59 and name HG2))
((segid "BrD" and resid 56 and name HA))
2.400  1.400 1.400 peak      28982 weight  0.11000E+01 volume  0.37484E+03 ppm1   3.137 ppm2  4.636
ASSI {29062}
(segid "BrD" and resid 59 and name HE %)
((segid "BrD" and resid 56 and name HA))
3.100  2.400 2.400 peak      29062 weight  0.11000E+01 volume  0.84530E+02 ppm1   1.847 ppm2  4.636
ASSI {29122}
(segid "BrD" and resid 59 and name HE %)
(segid "BrD" and resid 74 and name HE %)
2.400  1.400 1.400 peak      29122 weight  0.11000E+01 volume  0.44730E+03 ppm1   1.548 ppm2  7.535
ASSI {29182}
(segid "BrD" and resid 54 and name HE %)
((segid "BrD" and resid 58 and name H$$))
3.000  2.200 2.200 peak      29182 weight  0.11000E+01 volume  0.12060E+03 ppm1   2.536 ppm2  4.696
ASSI {29282}
((segid "BrD" and resid 54 and name HB1))
((segid "BrD" and resid 54 and name HG1))
2.600  2.000 2.000 peak      29162 weight  0.11000E+01 volume  0.16180E+03 ppm1   2.545 ppm2  3.304

TABLE 2-continued

Unambiguous NOE-derived Inter-proton Distance Restraints

ASSI {29312}
((segid "BrD" and resid 44 and name HB2))
((segid "BrD" and resid 44 and name HD2))
3.500  3.100  2.000 peak      29312 weight  0.11000E+01 volume   0.45332E+02 ppm1   2.634 ppm2  4.126
ASSI {29342}
((segid "BrD" and resid 44 and name HG2))
((segid "BrD" and resid 43 and name HA))
3.600  3.200  1.900 peak      29342 weight  0.11000E+01 volume   0.36619E+02 ppm1   2.645 ppm2  5.542
ASSI {29362}
((segid "BrD" and resid 44 and name HD1))
((segid "BrD" and resid 44 and name HA))
3.200  2.600  2.300 peak      29362 weight  0.11000E+01 volume   0.69346E+02 ppm1   4.310 ppm2  5.114
ASSI {29422}
((segid "BrD" and resid 91 and name HB1))
((segid "BrD" and resid 91 and name HD2))
2.600  1.700  1.700 peak      29422 weight  0.11000E+01 volume   0.26299E+03 ppm1   2.978 ppm2  4.407
ASSI {29432}
((segid "BrD" and resid 91 and name HB2))
((segid "BrD" and resid 91 and name HD2))
2.800  2.000  2.000 peak      29432 weight  0.11000E+01 volume   0.15191E+03 ppm1   2.730 ppm2  4.407
ASSI {29492}
((segid "BrD" and resid 79 and name HG1))
((segid "BrD" and resid 76 and name HA))
2.400  1.400  1.400 peak      29492 weight  0.11000E+01 volume   0.46894E+03 ppm1   3.033 ppm2  4.680
ASSI {29612}
((segid "BrD" and resid 70 and name HA))
(segid "BrD" and resid 70 and name HG1 %)
4.000  4.000  1.500 peak      29612 weight  0.11000E+01 volume   0.20014E+02 ppm1   5.346 ppm2  1.547
ASSI {29932}
((segid "BrD" and resid 66 and name HB2))
((segid "BrD" and resid 66 and name HD2))
2.700  1.800  1.800 peak      29932 weight  0.11000E+01 volume   0.20564E+03 ppm1   2.641 ppm2  3.633
ASSI {29942}
((segid "BrD" and resid 66 and name HB1))
((segid "BrD" and resid 66 and name HD2))
2.600  1.700  1.700 peak      29942 weight  0.11000E+01 volume   0.23040E+03 ppm1   2.701 ppm2  3.636
ASSI {29952}
((segid "BrD" and resid 66 and name HB2))
((segid "BrD" and resid 66 and name HD1))
2.600  1.700  1.700 peak      29952 weight  0.11000E+01 volume   0.23393E+03 ppm1   2.633 ppm2  3.670
ASSI {29962}
((segid "BrD" and resid 66 and name HB1))
((segid "BrD" and resid 66 and name HD1))
2.700  1.800  1.800 peak      29962 weight  0.11000E+01 volume   0.22124E+03 ppm1   2.701 ppm2  3.669
ASSI {30032}
((segid "BrD" and resid 51 and name HA))
((segid "BrD" and resid 52 and name HA))
4.100  4.100  1.400 peak      30032 weight  0.11000E+01 volume   0.17278E+02 ppm1   4.459 ppm2  5.505
ASSI {30052}
((segid "BrD" and resid 86 and name HD1))
((segid "BrD" and resid 86 and name HA))
3.500  3.100  2.000 peak      30052 weight  0.11000E+01 volume   0.45207E+02 ppm1   1.895 ppm2  4.810
ASSI {30162}
((segid "BrD" and resid 64 and name HA))
(segid "BrD" and resid 15 and name HE %)
2.400  1.400  1.400 peak      30162 weight  0.11000E+01 volume   0.39656E+03 ppm1   4.950 ppm2  7.405
ASSI {30202}
(segid "BrD" and resid 64 and name HE1 %)
((segid "BrD" and resid 64 and name HA))
2.300  1.300  1.300 peak      30202 weight  0.11000E+01 volume   0.49260E+03 ppm1   3.597 ppm2  4.939
ASSI {30342}
((segid "BrD" and resid 86 and name HB1))
(segid "BrD" and resid 96 and name HD %)
2.700  1.800  1.800 peak      30342 weight  0.11000E+01 volume   0.18798E+03 ppm1   2.337 ppm2  7.722
ASSI {30352}
((segid "BrD" and resid 86 and name HB1))
(segid "BrD" and resid 96 and name HE %)
2.700  1.800  1.800 peak      30352 weight  0.1100E+01 volume    0.21345E+03 ppm1   2.338 ppm2  7.603
ASSI {30392}
((segid "BrD" and resid 86 and name HE1))
((segid "BrD" and resid 86 and name HA))
3.100  2.400  2.400 peak      30392 weight  0.11000E+01 volume   0.90505E+02 ppm1   3.080 ppm2  4.808
ASSI {30402}
((segid "BrD" and resid 86 and name HE1))
((segid "BrD" and resid 86 and name HB1))
2.200  1.200  1.200 peak      30402 weight  0.11000E+01 volume   0.64111E+03 ppm1   3.079 ppm2  2.370

TABLE 2-continued

Unambiguous NOE-derived Inter-proton Distance Restraints

```
ASSI {30412}
((segid "BrD" and resid 86 and name HE1))
((segid "BrD" and resid 86 and name HG1))
2.900   2.100 2.100 peak        30412  weight  0.11000E+01 volume   0.14017E+03 ppm1       3.079 ppm2    1.896
ASSI {30512}
((segid "BrD" and resid 109 and name HE1))
((segid "BrD" and resid 109 and name HA))
2.900   2.100 2.100 peak        30512  weight  0.11000E+01 volume   0.12187E+03 ppm1       3.176 ppm2    4.639
ASSI {30522}
((segid "BrD" and resid 109 and name HD1))
((segid "BrD" and resid 109 and name HA))
1.900   0.900 0.900 peak        30522  weight  0.11000E+01 volume   0.17943E+04 ppm1       1.994 ppm2    4.639
ASSI {30622}
((segid "BrD" and resid 109 and name HB2))
((segid "BrD" and resid 106 and name HA))
2.400   1.400 1.400 peak        30622  weight  0.11000E+01 volume   0.44758E+03 ppm1       2.334 ppm2    4.575
ASSI {30632}
((segid "BrD" and resid 109 and name HB2))
((segid "BrD" and resid 106 and name HA))
2.700   1.800 1.800 peak        30632  weight  0.11000E+01 volume   0.21060E+03 ppm1       2.339 pm2     4.573
ASSI {30732}
((segid "BrD" and resid 97 and name HG2))
((segid "BrD" and resid 97 and name HA))
2.400   1.400 1.400 peak        30732  weight  0.11000E+01 volume   0.42305E+03 ppm1       2.143 ppm2    4.800
ASSI {30802}
((segid "BrD" and resid 104 and name HD1))
((segid "BrD" and resid 104 and name HA))
1.700   0.700 0.700 peak        30802  weight  0.11000E+01 volume   0.32351E+04 ppm1       2.289 ppm2    4.671
ASSI {30862}
((segid "BrD" and resid 111 and name HG1))
((segid "BrD" and resid 111 and name HA))
2.000   1.600 1.600 peak        30862  weight  0.11000E+01 volume   0.32568E+03 ppm1       2.000 ppm2    4.670
ASSI {30872}
((segid "BrD" and resid 111 and name HD1))
((segid "BrD" and resid 111 and name HA))
2.500   1.600 1.600 peak        30872  weight  0.11000E+01 volume   0.34175E+03 ppm1       2.240 ppm2    4.656
ASSI {30912}
((segid "BrD" and resid 111 and name HE1))
((segid "BrD" and resid 111 and name HA))
2.200   1.200 1.200 peak        30912  weight  0.11000E+01 volume   0.72636E+03 ppm1       3.520 ppm2    4.656
ASSI {31022}
((segid "BrD" and resid 72 and name HD1))
((segid "BrD" and resid 72 and name HE2))
2.200   1.200 1.200 peak        31022  weight  0.11000E+01 volume   0.72521E+03 ppm1       2.287 ppm2    3.654
ASSI {31032}
((segid "BrD" and resid 72 and name HD1))
((segid "BrD" and resid 72 and name HE1))
2.300   1.300 1.300 peak        31032  weight  0.11000E+01 volume   0.50216E+03 ppm1       2.267 ppm2    3.744
ASSI {31042}
((segid "BrD" and resid 72 and name HB1))
((segid "BrD" and resid 72 and name HE1))
2.200   1.200 1.200 peak        31042  weight  0.11000E+01 volume   0.79378E+03 ppm1       2.387 ppm2    3.744
ASSI {31052}
((segid "BrD" and resid 72 and name HB1))
((segid "BrD" and resid 72 and name HE2))
1.900   0.900 0.900 peak        31052  weight  0.11000E+01 volume   0.15518E+04 ppm1       2.386 ppm2    3.652
ASSI {1632}
(segid "BrD" and resid 110 and name HD1 %)
((segid "BrD" and resid 78 and name HB1))
2.100   2.100 2.400 peak         1632  weight  0.10000E+01 volume   0.10163E+04 ppm1       1.154 ppm2    1.309
ASSI {4042}
((segid "BrD" and resid 79 and name HG1))
((segid "BrD" and resid 80 and name HG1))
3.700   3.400 1.800 peak         4042  weight  0.10000E+01 volume   0.30439E+02 ppm1       3.029 ppm2    2.351
ASSI {4882}
((segid "BrD" and resid 19 and name HD1))
(segid "BrD" and resid 63 and name HD2 %)
2.700   1.800 1.800 peak         4882  weight  0.10000E+01 volume   0.22363E+03 ppm1       2.191 ppm2    1.495
ASSI {4902}
((segid "BrD" and resid 97 and name HB1))
(segid "BrD" and resid 101 and name HD1 %)
3.000   2.200 2.200 peak         4902  weight  0.10000E+01 volume   0.10809E+03 ppm1       2.683 ppm2    1.580
ASSI {4992}
((segid "BrD" and resid 37 and name HG2))
((segid "BrD" and resid 55 and name HA))
4.200   4.200 1.300 peak         4992  weight  0.10000E+01 volume   0.14817E+02 ppm1       2.586 ppm2    5.380
```

TABLE 2-continued

Unambiguous NOE-derived Inter-proton Distance Restraints

ASSI {6092}
((segid "BrD" and resid 115 and name HG))
(segid "BrD" and resid 110 and name HG2 %)
3.700  3.400  1.800 peak        6092 weight  0.10000E+01 volume  0.29496E+02 ppm1    2.140  ppm2  1.222
ASSI {6222}
(segid "BrD" and resid 22 and name HD2 %)
(segid "BrD" and resid 56 and name HD2 %)
2.300  1.300  1.300 peak        6272 weight  0.10000E+01 volume  0.52799E+03 ppm1    1.599  ppm2  1.246
ASSI {6602}
(segid "BrD" and resid 31 and name HB %)
(segid "BrD" and resid 56 and name HD1 %)
2.500  1.600  1.600 peak        6602 weight  0.10000E+01 volume  0.34161E+03 ppm1    2.291  ppm2  1.539
ASSI {6792}
(segid "BrD" and resid 99 and name HB %)
((segid "BrD" and resid 82 and name HA))
3.000  2.200  2.200 peak        6792 weight  0.10000E+01 volume  0.12038E+03 ppm1    2.190  ppm2  4.752
ASSI {6832}
(segid "BrD" and resid 99 and name HB %)
((segid "BrD" and resid 86 and name HG2))
3.000  2.200  2.200 peak        6832 weight  0.10000E+01 volume  0.11935E+03 ppm1    2.191  ppm2  0.765
ASSI {6852}
(segid "BrD" and resid 113 and name HB %)
(segid "BrD" and resid 110 and name HG2 %)
2.800  2.000  2.000 peak        6852 weight  0.10000E+01 volume  0.15622E+03 ppm1    1.991  ppm2  1.221
ASSI {6862}
(segid "BrD" and resid 113 and name HB %)
(segid "BrD" and resid 18 and name HD1 %)
4.900  4.900  0.600 peak        6862 weight  0.10000E+01 volume  0.56980E+01 ppm1    1.991  ppm2  1.066
ASSI {6902}
((segid "BrD" and resid 31 and name HA))
((segid "BrD" and resid 33 and name HD1))
3.300  2.700  2.200 peak        6902 weight  0.10000E+01 volume  0.60152E+02 ppm1    5.000  ppm2  2.794
ASSI {6952}
(segid "BrD" and resid 25 and name HG2 %)
(segid "BrD" and resid 31 and name HB %)
2.500  1.600  1.600 peak        6952 weight  0.10000E+01 volume  0.32952E+03 ppm1    1.650  ppm2  2.320
ASSI {6982}
(segid "BrD" and resid 25 and name HG2 %)
(segid "BrD" and resid 56 and name HD2 %)
2.500  1.600  1.600 peak        6982 weight  0.10000E+01 volume  0.36117E+03 ppm1    1.646  ppm2  1.252
ASSI {7362}
(segid "BrD" and resid 25 and name HG2 %)
((segid "BrD" and resid 102 and name HG))
2.900  2.100  2.100 peak        7362 weight  0.10000E+01 volume  0.13044E+03 ppm1    1.647  ppm2  2.157
ASSI {7412}
((segid "BrD" and resid 46 and name HA))
(segid "BrD" and resid 49 and name HG1 %)
3.400  2.900  2.100 peak        7412 weight  0.10000E+01 volume  0.55913E+02 ppm1    4.164  ppm2  1.645
ASSI {7422}
((segid "BrD" and resid 46 and name HA))
(segid "BrD" and resid 43 and name HB %)
3.600  3.200  1.900 peak        7422 weight  0.10000E+01 volume  0.39252E+02 ppm1    4.164  ppm2  1.710
ASSI {7442}
((segid "BrD" and resid 68 and name HA))
(segid "BrD" and resid 63 and name HD1 %)
3.700  3.400  1.000 peak        7442 weight  0.10000E+01 volume  0.32100E+02 ppm1    5.146  ppm2  1.653
ASSI {7462}
((segid "BrD" and resid 68 and name HB2))
(segid "BrD" and resid 10 and name HD1 %)
3.100  2.400  2.400 peak        7462 weight  0.10000E+01 volume  0.95501E+02 ppm1    3.522  ppm2  1.083
ASSI {7472}
((segid "BrD" and resid 68 and name HB1))
(segid "BrD" and resid 10 and name HD1 %)
3.100  2.400  2.400 peak        7472 weight  0.10000E+01 volume  0.06786E+02 ppm1    3.669  ppm2  1.084
ASSI {8082}
((segid "BrD" and resid 98 and name HA))
((segid "BrD" and resid 30 and name HB2))
2.900  2.100  2.100 peak        8082 weight  0.10000E+01 volume  0.14301E+03 ppm1    4.803  ppm2  4.530
ASSI {8132}
(segid "BrD" and resid 63 and name HD1 %)
((segid "BrD" and resid 15 and name HA))
2.800  2.000  2.000 peak        8132 weight  0.10000E+01 volume  0.17717E+03 ppm1    1.646  ppm2  4.624
ASSI {8252}
((segid "BrD" and resid 109 and name HG1))
((segid "BrD" and resid 109 and name HD1))
2.700  1.500  1.600 peak        8252 weight  0.10000E+01 volume  0.20695E+03 ppm1    1.401  ppm2  1.989

TABLE 2-continued

Unambiguous NOE-derived Inter-proton Distance Restraints

```
ASSI {8282}
((segid "BrD" and resid 16 and name HA))
((segid "BrD" and resid 21 and name HG12))
3.300   2.700  2.200 peak        8282  weight  0.10000E+01 volume  0.61204E+02 ppm1    3.866 ppm2  1.640
ASSI {8362}
((segid "BrD" and resid 18 and name HG))
(segid "BrD" and resid 14 and name HD2 %)
3.100   2.400  2.400 peak        8362  weight  0.10000E+01 volume  0.89516E+02 ppm1    2.290 ppm2  1.415
OR {8362}
((segid "BrD" and resid 18 and name HG))
(segid "BrD" and resid 14 and name HD1 %)
ASSI {8422}
(segid "BrD" and resid 18 and name HD1 %)
((segid "BrD" and resid 14 and name HG))
2.700   1.800  1.800 peak        8422  weight  0.10000E+01 volume  0.21908E+02 ppm1    1.052 ppm2  2.070
ASSI {8432}
(segid "BrD" and resid 18 and name HD1 %)
((segid "BrD" and resid 15 and name HA))
2.700   1.800  1.800 peak        8432  weight  0.10000E+01 volume  0.20923E+03 ppm1    1.057 ppm2  4.626
ASSI {8512}
(segid "BrD" and resid 22 and name HD2 %)
(segid "BrD" and resid 78 and name HD2 %)
3.300   2.700  2.200 peak        8512  weight  0.10000E+01 volume  0.62220E+02 ppm1    1.599 ppm2  0.677
ASSI {8522}
(segid "BrD" and resid 22 and name HD2 %)
(segid "BrD" and resid 59 and name HE %)
2.900   2.100  2.100 peak        8522  weight  0.10000E+01 volume  0.12491E+03 ppm1    1.599 ppm2  1.871
ASSI {8532}
(segid "BrD" and resid 22 and name HD1 %)
((segid "BrD" and resid 60 and name HA))
2.600   1.700  1.700 peak        8532  weight  0.10000E+01 volume  0.23265E+03 ppm1    1.645 ppm2  4.809
ASSI {8582}
((segid "BrD" and resid 22 and name HB2))
(segid "BrD" and resid 63 and name HD2 %)
2.600   1.700  1.700 peak        8582  weight  0.10000E+01 volume  0.24738E+03 ppm1    2.286 ppm2  1.494
ASSI {8612}
((segid "BrD" and resid 56 and name HB1))
((segid "BrD" and resid 35 and name HA))
2.600   2.000  2.000 peak        8612  weight  0.10000E+01 volume  0.17130E+03 ppm1    2.685 ppm2  4.900
ASSI {8632}
(segid "BrD" and resid 56 and name HD1 %)
(segid "BrD" and resid 81 and name HG2 %)
3.800   3.600  1.700 peak        8632  weight  0.10000E+01 volume  0.24706E+02 ppm1    1.547 ppm2  0.758
ASSI {8642}
((segid "BrD" and resid 116 and name HG12))
((segid "BrD" and resid 116 and name HG11))
2.000   1.000  1.000 peak        8642  weight  0.10000E+01 volume  0.13013E+04 ppm1    1.540 ppm2  1.921
ASSI {8702}
(segid "BrD" and resid 56 and name HD2 %)
(segid "BrD" and resid 81 and name HG1 %)
2.400   1.400  1.400 peak        8702  weight  0.10000E+01 volume  0.46717E+03 ppm1    1.254 ppm2  1.080
ASSI {8832}
(segid "BrD" and resid 78 and name HD1 %)
((segid "BrD" and resid 18 and name HB2))
4.100   4.100  1.400 peak        8832  weight  0.10000E+01 volume  0.15698E+02 ppm1    0.761 ppm2  0.924
ASSI {8862}
(segid "BrD" and resid 76 and name HD2 %)
(segid "BrD" and resid 18 and name HD2 %)
3.000   2.200  2.200 peak        8862  weight  0.10000E+01 volume  0.10893E+03 ppm1    0.662 ppm2  0.427
ASSI {8942}
((segid "BrD" and resid 102 and name HA))
(segid "BrD" and resid 101 and name HG2 %)
3.100   2.400  2.400 peak        8942  weight  0.10000E+01 volume  0.83720E+02 ppm1    4.263 ppm2  1.612
ASSI {9102}
((segid "BrD" and resid 21 and name HG12))
(segid "BrD" and resid 102 and name HD2 %)
3.700   3.400  1.800 peak        9102  weight  0.10000E+01 volume  0.31128E+02 ppm1    1.648 ppm2  1.320
OR {9102}
(segid "BrD" and resid 21 and name HG2 %)
(segid "BrD" and resid 102 and name HD1 %)
ASSI {9122}
(segid "BrD" and resid 21 and name HG2 %)
(segid "BrD" and resid 110 and name HD1 %)
2.900   3.100  2.100 peak        9122  weight  0.10000E+01 volume  0.12723E+03 ppm1    1.600 ppm2  1.143
```

TABLE 2-continued

Unambiguous NOE-derived Inter-proton Distance Restraints

ASSI {9132}
(segid "BrD" and resid 21 and name HG2 %)
(segid "BrD" and resid 78 and name HD2 %)
3.400  2.900  2.100 peak      9132 weight  0.10000E+01 volume  0.52384E+02 ppm1   1.596 ppm2  0.670
ASSI {9172}
(segid "BrD" and resid 21 and name HD1 %)
(segid "BrD" and resid 17 and name HG2 %)
2.500  1.600  1.600 peak      9172 weight  0.10000E+01 volume  0.33280E+03 ppm1   1.205 ppm2  1.748
ASSI {9402}
(segid "BrD" and resid 21 and name HG2 %)
((segid "BrD" and resid 106 and name HA))
2.600  1.700  1.700 peak      9402 weight  0.10000E+01 volume  0.25016E+03 ppm1   1.597 ppm2  4.536
ASSI {9412}
(segid "BrD" and resid 101 and name HG2 %)
((segid "BrD" and resid 30 and name HB1))
2.800  2.000  2.000 peak      5412 weight  0.10000E+01 volume  0.17182E+03 ppm1   1.598 ppm2  4.928
ASSI {9462}
((segid "BrD" and resid 110 and name HB))
((segid "BrD" and resid 115 and name HB1))
3.000  2.200  2.200 peak      9462 weight  0.10000E+01 volume  0.11040E+03 ppm1   3.338 ppm2  2.182
ASSI {9502}
(segid "BrD" and resid 110 and name HG2 %)
((segid "BrD" and resid 115 and name HB1))
2.500  1.600  1.600 peak      9502 weight  0.10000E+01 volume  0.34762E+03 ppm1   1.252 ppm2  2.182
ASSI {9512}
(segid "BrD" and resid 110 and name HG2 %)
((segid "BrD" and resid 116 and name HG12))
2.500  1.600  1.600 peak      9512 weight  0.10000E+01 volume  0.33973E+03 ppm1   1.253 ppm2  1.586
ASSI {9572}
(segid "BrD" and resid 110 and name HD1 %)
(segid "BrD" and resid 78 and name HD1 %)
3.800  3.600  1.700 peak      9572 weight  0.10000E+01 volume  0.27664E+02 ppm1   1.154 ppm2  0.750
ASSI {9602}
(segid "BrD" and resid 110 and name HD1 %)
(segid "BrD" and resid 78 and name HD2 %)
3.400  2.900  2.100 peak      9602 weight  0.10000E+01 volume  0.49420E+02 ppm1   1.154 ppm2  0.676
ASSI {9622}
(segid "BrD" and resid 116 and name HG2 %)
(segid "BrD" and resid 110 and name HG2 %)
2.800  2.000  2.000 peak      9622 weight  0.10000E+01 volume  0.18357E+03 ppm1   1.401 ppm2  1.271
ASSI {9632}
(segid "BrD" and resid 116 and name HD1 %)
(segid "BrD" and resid 110 and name HD1 %)
2.100  1.100  1.100 peak      9632 weight  0.10000E+01 volume  0.89032E+03 ppm1   1.399 ppm2  1.152
ASSI {9992}
((segid "BrD" and resid 54 and name HB2))
((segid "BrD" and resid 59 and name HB2))
2.700  1.800  1.800 peak      9992 weight  0.10000E+01 volume  0.19570E+03 ppm1   1.947 ppm2  2.490
ASSI {10032}
((segid "BrD" and resid 54 and name HA))
((segid "BrD" and resid 59 and name HB2))
3.000  2.200  2.200 peak     10032 weight  0.10000E+01 volume  0.99741E+02 ppm1   5.541 ppm2  2.401
ASSI {10142}
((segid "BrD" and resid 70 and name HB2))
((segid "BrD" and resid 73 and name HB1))
4.100  4.100  1.400 peak     10142 weight  0.10000E+01 volume  0.17505E+02 ppm1   4.360 ppm2  2.597
ASSI {10172}
((segid "BrD" and resid 52 and name HB2))
((segid "BrD" and resid 80 and name HG1))
4.200  4.200  1.300 peak     10172 weight  0.10000E+01 volume  0.15368E+02 ppm1   3.522 ppm2  2.345
ASSI {10512}
((segid "BrD" and resid 61 and name HG1))
((segid "BrD" and resid 60 and name HB2))
2.700  1.800  1.800 peak     10512 weight  0.10000E+01 volume  0.19616E+03 ppm1   2.980 ppm2  4.588
ASSI {10832}
((segid "BrD" and resid 30 and name HB1))
(segid "BrD" and resid 102 and name HD1 %)
3.600  3.200  1.900 peak     10632 weight  0.10000E+01 volume  0.34957E+02 ppm1   4.907 ppm2  1.329
ASSI {10842}
((segid "BrD" and resid 30 and name HB2))
(segid "BrD" and resid 102 and name HD1 %)
3.200  2.600  2.300 peak     10842 weight  0.10000E+01 volume  0.80809E+02 ppm1   4.510 ppm2  1.320
ASSI {10912}
((segid "BrD" and resid 93 and name HB1))
((segid "BrD" and resid 91 and name HG1))
3.700  3.400  1.800 peak     10912 weight  0.10000E+01 volume  0.12594E+02 ppm1   5.000 ppm2  2.798

TABLE 2-continued

Unambiguous NOE-derived Inter-proton Distance Restraints

ASSI {10922}
((segid "BrD" and resid 93 and name HB2))
((segid "BrD" and resid 91 and name HG1))
3.700  3.400  1.800 peak    10922 weight  0.10000E+01 volume  0.31695E+02 ppm1    4.755 ppm2  2.799
ASSI {10962}
((segid "BrD" and resid 44 and name HA))
((segid "BrD" and resid 41 and name HA))
4.600  4.600  0.900 peak    10962 weight  0.10000E+01 volume  0.78869E+01 ppm1    5.099 ppm2  4.654
ASSI {11342}
((segid "BrD" and resid 19 and name HG1))
(segid "BrD" and resid 63 and name HD2 %)
3.100  2.400  2.400 peak    11342 weight  0.10000E+01 volume  0.91996E+02 ppm1    1.889 ppm2  1.493
ASSI {11372}
((segid "BrD" and resid 26 and name HA))
(segid "BrD" and resid 31 and name HB %)
2.200  1.200  1.200 peak    11372 weight  0.10000E+01 volume  0.67300E+03 ppm1    4.509 ppm2  2.311
ASSI {11382}
((segid "BrD" and resid 26 and name HA))
(segid "BrD" and resid 35 and name HE %)
2.400  2.000  2.000 peak    11382 weight  0.10000E+01 volume  0.18352E+03 ppm1    4.509 ppm2  2.783
ASSI {11502}
((segid "BrD" and resid 86 and name HE1))
((segid "BrD" and resid 83 and name HA))
2.900  2.100  2.100 peak    11502 weight  0.10000E+01 volume  0.14787E+03 ppm1    3.080 ppm2  4.460
ASSI {11572}
((segid "BrD" and resid 109 and name HB1))
(segid "BrD" and resid 21 and name HG2 %)
3.500  3.100  2.000 peak    21572 weight  0.10000E+01 volume  0.46116E+02 ppm1    2.334 ppm2  2.587
ASSI {11642}
((segid "BrD" and resid 6 and name HB2))
((segid "BrD" and resid 7 and name HG1))
3.100  2.400  2.400 peak    11642 weight  0.10000E+01 volume  0.90515E+02 ppm1    2.291 ppm2  2.876
ASSI {11752}
((segid "BrD" and resid 55 and name HB1))
((segid "BrD" and resid 37 and name HA))
2.800  2.000  2.000 peak    11752 weight  0.10000E+01 volume  0.16032E+03 ppm1    2.979 ppm2  4.860
ASSI {11832}
((segid "BrD" and resid 91 and name HA))
((segid "BrD" and resid 92 and name HB2))
3.500  3.100  2.000 peak    11832 weight  0.10000E+01 volume  0.43713E+02 ppm1    5.347 ppm2  2.571
ASSI {12292}
(segid "BrD" and resid 81 and name HG2 %)
((segid "BrD" and resid 56 and name HG))
3.300  2.700  2.200 peak    12292 weight  0.10000E+01 volume  0.58134E+02 ppm1    0.761 ppm2  2.323
ASSI {12502}
((segid "BrD" and resid 54 and name HG1))
((segid "BrD" and resid 59 and name HB2))
4.000  4.000  1.500 peak    12502 weight  0.10000E+01 volume  0.18992E+02 ppm1    3.288 ppm2  2.467
ASSI {12632}
(segid "BrD" and resid 59 and name HE %)
((segid "BrD" and resid 77 and name HB1))
2.500  1.600  1.600 peak    12632 weight  0.10000E+01 volume  0.30644E+03 ppm1    1.848 ppm2  3.321
ASSI {12732}
((segid "BrD" and resid 71 and name HA))
(segid "BrD" and resid 18 and name HD1 %)
3.700  3.400  1.800 peak    12732 weight  0.10000E+01 volume  0.29522E+02 ppm1    4.608 ppm2  1.084
ASSI {12752}
((segid "BrD" and resid 71 and name HA))
(segid "BrD" and resid 18 and name HD2 %)
3.300  2.700  2.200 peak    12752 weight  0.10000E+01 volume  0.66213E+02 ppm1    4.607 ppm2  0.403
ASSI {12872}
((segid "BrD" and resid 62 and name HD1))
((segid "BrD" and resid 59 and name HB2))
3.500  3.100  2.000 peak    12872 weight  0.10000E+01 volume  0.44554E+02 ppm1    3.177 ppm2  2.484
ASSI {13092}
((segid "BrD" and resid 54 and name HD1))
(segid "BrD" and resid 81 and name HD1 %)
3.400  2.900  2.100 peak    13092 weight  0.10000E+01 volume  0.51686E+02 ppm1    3.288 ppm2  1.075
ASSI {13112}
((segid "BrD" and resid 73 and name HB2))
((segid "BrD" and resid 68 and name HA))
3.000  2.200  2.200 peak    13112 weight  0.10000E+01 volume  0.10760E+03 ppm1    2.486 ppm2  5.142
ASSI {13122}
((segid "BrD" and resid 73 and name HB1))
((segid "BrD" and resid 68 and name HA))
2.900  2.100  2.100 peak    13122 weight  0.10000E+01 volume  0.13268E+03 ppm1    2.583 ppm2  5.141

TABLE 2-continued

| Unambiguous NOE-derived Inter-proton Distance Restraints |
|---|

ASSI {13232}
((segid "BrD" and resid 46 and name HB1))
(segid "BrD" and resid 38 and name HG2 %)
3.500   3.100   2.000 peak        13232  weight  0.10000E+01 volume   0.45934E+02 ppm1       3.275  ppm2   0.790
ASSI {13282}
((segid "BrD" and resid 56 and name HA)
(segid "BrD" and resid 22 and name HD2 %)
3.200   2.400   2.400 peak        13282  weight  0.10000E+01 volume   0.86016E+02 ppm1       4.607  ppm2   1.637
OR {13282}
((segid "BrD" and resid 56 and name HA))
(segid "BrD" and resid 22 and name HD1 %)
ASSI {13$$}
((segid "BrD" and resid 116 and name HG12))
(segid "BrD" and resid 110 and name HD1 %)
2.700   1.800   1.800 peak        13312  weight  0.10000E+01 volume   0.18778E+03 ppm1       1.548  ppm2   1.145
ASSI {13332}
(segid "BrD" and resid $$ and name HD1 %)
((segid "BrD" and resid 43 and name HB2))
2.500   1.400   1.400 peak        13332  weight  0.10000E+01 volume   0.34390E+03 ppm1       1.648  ppm2   2.516
ASSI {13412}
(segid "BrD" and resid 25 and name HG1 %)
(segid "BrD" and resid 56 and name HD2 %)
2.900   2.100   2.100 peak        13412  weight  0.10000E+01 volume   0.12726E+03 ppm1       1.795  ppm2   1.252
ASSI {13572}
((segid "BrD" and resid 49 and name HB))
((segid "BrD" and resid 50 and name HG11))
5.500   5.500   0.000 peak        13572  weight  0.10000E+01 volume   0.27123E+01 ppm1       2.634  ppm2   1.417
ASSI {13582}
((segid "BrD" and resid 49 and name HB))
(segid "BrD" and resid 50 and name HD1 %)
4.000   4.000   1.500 peak        13582  weight  0.10000E+01 volume   0.18896E+02 ppm1       2.634  ppm2   1.148
ASSI {13682}
(segid "BrD" and resid 54 and name HE %)
((segid "BrD" and resid 57 and name HG1))
3.600   3.200   1.900 peak        13682  weight  0.10000E+01 volume   0.37432E+02 ppm1       2.537  ppm2   2.101
ASSI {13732}
((segid "BrD" and resid 63 and name HA))
((segid "BrD" and resid 68 and name HB1))
3.500   3.100   2.000 peak        13732  weight  0.10000E+01 volume   0.44471E+02 ppm1       5.296  ppm2   3.662
ASSI {13752}
(segid "BrD" and resid 63 and name HD2 %)
((segid "BrD" and resid 19 and name HB2))
2.700   1.800   2.800 peak        13752  weight  0.10000E+01 volume   0.20264E+03 ppm1       1.498  ppm2   1.996
ASSI {13772}
((segid "BrD" and resid 64 and name HA))
(segid "BrD" and resid 63 and name HD2 %)
4.000   4.000   1.500 peak        13772  weight  0.10000E+01 volume   0.18294E+02 ppm1       4.951  ppm2   1.488
ASSI {13792}
(segid "BrD" and resid 49 and name HG1 %)
(segid "BrD" and resid 50 and name HG2 %)
3.800   3.600   1.700 peak        13792  weight  0.10000E+01 volume   0.26015E+02 ppm1       1.646  ppm2   1.009
ASSI {13812}
((segid "BrD" and resid 76 and name HA))
((segid "BrD" and resid 80 and name HB2))
4.200   4.200   1.300 peak        13812  weight  0.10000E+01 volume   0.14558E+02 ppm1       4.656  ppm2   2.508
ASSI {13832}
((segid "BrD" and resid 56 and name HB1))
((segid "BrD" and resid 34 and name HB2))
3.100   2.400   2.400 peak        13832  weight  0.10000E+01 volume   0.92421E+02 ppm1       2.685  ppm2   3.159
ASSI {13842}
((segid "BrD" and resid 67 and name HB2))
((segid "BrD" and resid 62 and name HA))
3.400   2.900   2.100 peak        13842  weight  0.10000E+01 volume   0.56015E+02 ppm1       2.636  ppm2   4.483
ASSI {13862}
(segid "BrD" and resid 69 and name HG2 %)
(segid "BrD" and resid 18 and name HD1 %)
3.600   3.200   1.900 peak        13862  weight  0.10000E+01 volume   0.35688E+02 ppm1       1.425  ppm2   1.030
ASSI {13872}
(segid "BrD" and resid 69 and name HG2 %)
((segid "BrD" and resid 18 and name HB2))
5.500   5.500   0.000 peak        13872  weight  0.10000E+01 volume   0.14355E+01 ppm1       1.425  ppm2   0.880
ASSI {13892}
((segid "BrD" and resid 12 and name HA))
(segid "BrD" and resid 14 and name HD2 %)
3.000   2.200   2.200 peak        13892  weight  0.10000E+01 volume   0.11539E+03 ppm1       5.298  ppm2   1.382

TABLE 2-continued

Unambiguous NOE-derived Inter-proton Distance Restraints

```
OR {13892}
((segid "BrD" and resid 12 and name HA))
(segid "BrD" and resid 14 and name HD1 %)
ASSI {13982}
((segid "BrD" and resid 74 and name HA))
((segid "BrD" and resid 68 and name HB2))
3.600   3.200 1.900 peak        13982 weight  0.10000E+01 volume   0.36366E+02 ppm1    4.360 ppm2  3.499
ASSI {14032}
(segid "BrD" and resid 76 and name HB %)
((segid "BrD" and resid 80 and name HG1))
2.800   2.000 2.000 peak        14032 weight  0.10000E+01 volume   0.17944E+03 ppm1    2.091 ppm2  2.344
ASSI {14052}
(segid "BrD" and resid 14 and name HD1 %)
((segid "BrD" and resid 70 and name HA))
2.700   1.800 1.800 peak        14052 weight  0.10000E+01 volume   0.21486E+03 ppm1    1.402 ppm2  5.362
ASSI {14112}
((segid "BrD" and resid 14 and name HA))
(segid "BrD" and resid 113 and name HB %)
3.100   2.400 2.400 peak        14112 weight  0.10000E+01 volume   0.82177E+02 ppm1    4.655 ppm2  1.987
ASSI {14212}
((segid "BrD" and resid 98 and name HB2))
((segid "BrD" and resid 30 and name HB1))
3.700   3.400 1.800 peak        14212 weight  0.10000E+01 volume   0.32251E+02 ppm1    1.667 ppm2  4.933
ASSI {14222}
((segid "BrD" and resid 99 and name HA))
((segid "BrD" and resid 102 and name HG))
3.400   2.900 2.100 peak        14222 weight  0.10000E+01 volume   0.54061E+02 ppm1    4.459 ppm2  2.136
ASSI {14242}
((segid "BrD" and resid 99 and name HA))
((segid "BrD" and resid 82 and name HB2))
3.000   2.200 2.200 peak        14242 weight  0.10000E+01 volume   0.10335E+03 ppm1    4.457 ppm2  3.581
ASSI {14262}
((segid "BrD" and resid 31 and name HA))
((segid "BrD" and resid 33 and name HD2))
3.300   2.700 2.200 peak        14$$ weight   0.10000E+01 volume   0.413$$E+03 ppm1    6.000 ppm2  2.318
ASSI {14272}
(segid "BrD" and resid 31 and name HB %)
((segid "BrD" and resid 25 and name HA))
3.000   2.200 2.200 peak        14272 weight  0.10000E+01 volume   0.10586E+03 ppm1    2.289 ppm2  4.437
ASSI {14292}
((segid "BrD" and resid 110 and name HB))
(segid "BrD" and resid 115 and name HD1 %)
5.500   5.500 0.000 peak        14292 weight  0.10000E+01 volume   0.49615E+00 ppm1    2.338 ppm2  2.318
ASSI {14302}
(segid "BrD" and resid 63 and name HD2 %)
((segid "BrD" and resid 22 and name HB1))
2.500   1.600 1.600 peak        14302 weight  0.10000E+01 volume   0.30120E+03 ppm1    1.498 ppm2  2.695
ASSI {14332}
((segid "BrD" and resid 103 and name HA))
(segid "BrD" and resid 102 and name HB2))
3.500   3.100 2.000 peak        14332 weight  0.10000E+01 volume   0.41084E+02 ppm1    3.769 ppm2  1.830
ASSI {14352}
((segid "BrD" and resid 106 and name HA))
((segid "BrD" and resid 109 and name HG1))
4.000   4.000 1.500 peak        14352 weight  0.10000E+01 volume   0.19913E+02 ppm1    4.555 ppm2  1.435
ASSI {14382}
((segid "BrD" and resid 15 and name HA))
((segid "BrD" and resid 14 and name HG))
3.800   3.600 1.700 peak        14382 weight  0.10000E+01 volume   0.25435E+02 ppm1    4.606 ppm2  2.042
ASSI {14442}
((segid "BrD" and resid 110 and name HA))
((segid "BrD" and resid 115 and name HB1))
2.800   2.000 2.000 peak        14442 weight  0.10000E+01 volume   0.18018E+03 ppm1    4.411 ppm2  2.181
OR {14442}
((segid "BrD" and resid 110 and name HA))
((segid "BrD" and resid 115 and name HG))
ASSI {14452}
(segid "BrD" and resid 110 and name HG2 %)
(segid "BrD" and resid 115 and name HD1 %)
2.600   1.700 1.700 peak        14452 weight  0.10000E+01 volume   0.23487E+03 ppm1    1.254 ppm2  1.330
ASSI {14512}
((segid "BrD" and resid 111 and name HG1))
(segid "BrD" and resid 110 and name HG2 %)
3.600   3.200 1.900 peak        14512 weight  0.10000E+01 volume   0.36391E+02 ppm1    1.989 ppm2  1.278
```

TABLE 2-continued

Unambiguous NOE-derived Inter-proton Distance Restraints

ASSI {14652}
((segid "BrD" and resid 18 and name HA))
((segid "BrD" and resid 21 and name HG11))
3.700  3.400 1.800 peak      14652 weight  0.10000E+01 volume  0.30202E+02 ppm1   3.866 ppm2  2.351
ASSI {14672}
(segid "BrD" and resid 18 and name HD1 %)
((segid "BrD" and resid 63 and name HG))
3.100  2.400 2.400 peak      14672 weight  0.10000E+01 volume  0.91159E+02 ppm1   1.057 ppm2  2.467
ASSI {14702}
(segid "BrD" and resid 21 and name HD1 %)
(segid "BrD" and resid 63 and name HD2 %)
2.300  2.300 2.200 peak      14702 weight  0.10000E+01 volume  0.60922E+03 ppm1   1.205 ppm2  1.458
ASSI {14752}
(segid "BrD" and resid 54 and name HE %)
(segid "BrD" and resid 81 and name HG1 %)
3.700  3.400 1.800 peak      14752 weight  0.10000E+01 volume  0.28669E+02 ppm1   2.535 ppm2  1.075
ASSI {14762}
((segid "BrD" and resid 51 and name HA))
((segid "BrD" and resid 53 and name HD1))
5.500  5.500 0.000 peak      14762 weight  0.10000E+01 volume  0.89215E+01 ppm1   4.460 ppm2  4.222
ASSI {14782}
((segid "BrD" and resid 36 and name HA))
((segid "BrD" and resid 57 and name HB1))
2.300  1.300 1.300 peak      14782 weight  0.10000E+01 volume  0.60416E+03 ppm1   5.446 ppm2  2.986
ASSI {15012}
((segid "BrD" and resid 46 and name HB1))
(segid "BrD" and resid 38 and name HG1 %)
4.000  4.000 1.500 peak      15012 weight  0.10000E+01 volume  0.20055E+02 ppm1   3.275 ppm2  1.075
ASSI {15032}
((segid "BrD" and resid 46 and name HB1))
(segid "BrD" and resid 47 and name HD %)
4.500  4.500 1.000 peak      15032 weight  0.10000E+01 volume  0.96365E+01 ppm1   3.276 ppm2  7.934
ASSI {15042}
((segid "BrD" and resid 46 and name HB2))
(segid "BrD" and resid 47 and name HD %)
3.200  2.600 2.300 peak      15042 weight  0.10000E+01 volume  0.71990E+02 ppm1   3.077 ppm2  7.933
ASSI {15052}
((segid "BrD" and resid 46 and name HA))
(segid "BrD" and resid 49 and name HG2 %)
3.600  3.200 1.900 peak      15052 weight  0.10000E+01 volume  0.38868E+02 ppm1   4.165 ppm2  1.571
ASSI {15092}
((segid "BrD" and resid 28 and name HB2))
(segid "BrD" and resid 31 and name HB %)
2.800  2.000 2.000 peak      15092 weight  0.10000E+01 volume  0.15966E+03 ppm1   3.374 ppm2  2.312
ASSI {15182}
((segid "BrD" and resid 67 and name HB1))
((segid "BrD" and resid 62 and name HB2))
4.000  4.000 1.500 peak      15182 weight  0.10000E+01 volume  0.19603E+02 ppm1   3.572 ppm2  1.693
ASSI {15192}
((segid "BrD" and resid 67 and name HB1))
((segid "BrD" and resid 62 and name HG2))
4.400  4.400 1.100 peak      15192 weight  0.10000E+01 volume  0.11033E+02 ppm1   3.572 ppm2  1.474
ASSI {15402}
((segid "BrD" and resid 82 and name HB2))
(segid "BrD" and resid 99 and name HB %)
3.000  2.200 2.200 peak      15402 weight  0.10000E+01 volume  0.10651E+03 ppm1   3.572 ppm2  2.206
ASSI {15412}
((segid "BrD" and resid 82 and name HB1))
(segid "BrD" and resid 99 and name HB %)
2.900  2.100 2.100 peak      15412 weight  0.10000E+01 volume  0.12753E+03 ppm1   3.672 ppm2  2.206
ASSI {15552}
((segid "BrD" and resid 82 and name HB2))
((segid "BrD" and resid 103 and name HB2))
3.700  3.400 1.800 peak      15552 weight  0.10000E+01 volume  0.31328E+02 ppm1   3.573 ppm2  1.897
ASSI {15592}
((segid "BrD" and resid 107 and name HB1))
((segid "BrD" and resid 103 and name HG2))
3.100  2.400 2.400 peak      15592 weight  0.10000E+01 volume  0.86957E+02 ppm1   3.670 ppm2  2.540
ASSI {15712}
((segid "BrD" and resid 107 and name HB1))
(segid "BrD" and resid 107 and name HD %)
2.200  1.200 1.200 peak      15712 weight  0.10000E+01 volume  0.63746E+03 ppm1   3.673 ppm2  7.827
ASSI {15812}
((segid "BrD" and resid 15 and name HA))
((segid "BrD" and resid 18 and name HA))
3.300  2.700 2.200 peak      15812 weight  0.10000E+01 volume  0.67333E+02 ppm1   4.606 ppm2  3.900

TABLE 2-continued

Unambiguous NOE-derived Inter-proton Distance Restraints

ASSI {15882}
((segid "BrD" and resid 15 and name HB1))
(segid "BrD" and resid 63 and name HD1 %)
4.000  4.000 1.500 peak      15882 weight 0.10000E+01 volume  0.19033E+02 ppm1    3.815 ppm2 1.652
ASSI {15932}
((segid "BrD" and resid 82 and name HB1))
((segid "BrD" and resid 107 and name HZ))
2.600  1.700 1.700 peak      15932 weight 0.10000E+01 volume  0.26167E+03 ppm1    3.670 ppm2 8.022
ASSI {16052}
((segid "BrD" and resid 68 and name HA))
((segid "BrD" and resid 73 and name HG))
4.000  4.000 1.500 peak      16052 weight 0.10000E+01 volume  0.20921E+02 ppm1    5.148 ppm2 2.367
ASSI {16062}
((segid "BrD" and resid 68 and name HB2))
(segid "BrD" and resid 74 and name HD %)
3.600  3.200 1.900 peak      16062 weight 0.10000E+01 volume  0.38285E+02 ppm1    3.522 ppm2 6.998
ASSI {16112}
((segid "BrD" and resid 68 and name HB1))
((segid "BrD" and resid 62 and name HD1))
4.500  4.500 1.000 peak      16112 weight 0.10000E+01 volume  0.90000E+01 ppm1    3.669 ppm2 3.148
ASSI {16122}
((segid "BrD" and resid 68 and name HB2))
((segid "BrD" and resid 62 and name HD1))
3.500  3.100 2.000 peak      16122 weight 0.10000E+01 volume  0.43825E+02 ppm1    3.522 ppm2 3.149
ASSI {16132}
((segid "BrD" and resid 68 and name HB1))
((segid "BrD" and resid 63 and name HB1))
 3.600  3.200 1.900 peak     16132 weight 0.10000E+01 volume  0.35724E+02 ppm1    3.669 ppm2 2.883
ASSI {16152}
((segid "BrD" and resid 68 and name HB2))
((segid "BrD" and resid 63 and name HB1))
3.500  3.100 2.000 peak      16152 weight 0.10000E+01 volume  0.44106E+02 ppm1    3.522 ppm2 2.884
ASSI {16162}
((segid "BrD" and resid 68 and name HB2))
((segid "BrD" and resid 62 and name HB1))
4.100  4.100 1.400 peak      16162 weight 0.10000E+01 volume  0.16622E+02 ppm1    3.522 ppm2 2.605
ASSI {16212}
((segid "BrD" and resid 88 and name HA))
(segid "BrD" and resid 49 and name HG2 %)
3.200  2.600 2.300 peak      16212 weight 0.10000E+01 volume  0.71276E+02 ppm1    4.999 ppm2 1.571
ASSI {16312}
((segid "BrD" and resid 88 and name HB1))
(segid "BrD" and resid 95 and name HD %)
3.500  3.100 2.000 peak      16312 weight 0.10000E+01 volume  0.47079E+02 ppm1    3.524 ppm2 7.496
ASSI {16382}
((segid "BrD" and resid 19 and name HE1))
(segid "BrD" and resid 63 and name HD2 %)
3.500  3.100 2.000 peak      16382 weight 0.10000E+01 volume  0.45471E+02 ppm1    3.522 ppm2 1.495
ASSI {16422}
((segid "BrD" and resid 66 and name HD2))
(segid "BrD" and resid 69 and name HG1 %)
4.900  4.900 0.600 peak      16422 weight 0.10000E+01 volume  0.59473E+01 ppm1    3.621 ppm2 1.562
ASSI {16432}
((segid "BrD" and resid 66 and name HD2))
(segid "BrD" and resid 63 and name HD1 %)
4.700  4.700 0.800 peak      16432 weight 0.10000E+01 volume  0.72449E+01 ppm1    3.620 ppm2 1.645
ASSI {16492}
((segid "BrD" and resid 96 and name HA))
((segid "BrD" and resid 86 and name HA))
2.200  1.200 1.200 peak      16492 weight 0.10000E+01 volume  0.78759E+03 ppm1    4.409 ppm2 4.802
ASSI {16502}
((segid "BrD" and resid 96 and name HA))
((segid "BrD" and resid 86 and name HG2))
4.100  4.100 1.400 peak      16502 weight 0.10000E+01 volume  0.17647E+02 ppm1    4.409 ppm2 0.75$$
ASSI {16612}
((segid "BrD" and resid 96 and name HB2))
(segid "BrD" and resid 96 and name HE %)
3.400  2.900 2.100 peak      16612 weight 0.10000E+01 volume  0.47985E+02 ppm1    3.134 ppm2 7.633
ASSI {16662}
((segid "BrD" and resid 96 and name HB1))
(segid "BrD" and resid 99 and name HB %)
4.200  4.200 1.300 peak      16662 weight 0.10000E+01 volume  0.14266E+02 ppm1    4.008 ppm2 2.227
ASSI {$$}
((segid "BrD" and resid 96 and name HB2))
(segid "BrD" and resid 99 and name HB %)
4.200  4.200 1.300 peak      16672 weight 0.10000E+01 volume  0.13986E+02 ppm1    3.125 ppm2 2.209

TABLE 2-continued

Unambiguous NOE-derived Inter-proton Distance Restraints

```
ASSI {16682}
((segid "BrD" and resid 52 and name HA))
((segid "BrD" and resid 53 and name HG1))
4.300   4.300 1.200 peak      16682 weight  0.10000E+01 volume  0.11894E+02 ppm1   5.589 ppm2  2.819
OR {16682}
((segid "BrD" and resid 52 and name HA))
((segid "BrD" and resid 53 and name HB1))
ASSI {16792}
((segid "BrD" and resid 95 and name HB2))
((segid "BrD" and resid 85 and name HA))
2.700   1.800 1.800 peak      16792 weight  0.10000E+01 volume  0.22870E+03 ppm1   3.375 ppm2  4.995
ASSI {16842}
((segid "BrD" and resid 15 and name HB2))
((segid "BrD" and resid 15 and name HA))
2.200   1.200 1.200 peak      16842 weight  0.10000E+01 volume  0.62256E+03 ppm1   1.677 ppm2  4.618
ASSI {16862}
((segid "BrD" and resid 106 and name HA))
(segid "BrD" and resid 82 and name HE %)
4.100   4.100 1.400 peak      16882 weight  0.10000E+01 volume  0.17840E+02 ppm1   4.557 ppm2  7.039
OR {16882}
((segid "BrD" and resid 106 and name HA))
((segid "BrD" and resid 82 and name HZ))
ASSI {16892}
((segid "BrD" and resid 106 and name HA))
(segid "BrD" and resid 106 and name HD %)
2.200   1.200 1.200 peak      16892 weight  0.10000E+01 volume  0.63095E+03 ppm1   4.556 ppm2  7.511
ASSI {16902}
((segid "BrD" and resid 106 and name HA))
(segid "BrD" and resid 106 and name HE %)
3.000   2.200 2.200 peak      16902 weight  0.10000E+01 volume  0.10621E+03 ppm1   4.558 ppm2  7.634
ASSI {16932}
((segid "BrD" and resid 57 and name HA))
((segid "BrD" and resid 36 and name HA))
5.500   5.500 0.000 peak      16932 weight  0.10000E+01 volume  0.15155E+01 ppm1   4.804 ppm2  5.444
ASSI {16972}
((segid "BrD" and resid 106 and name HB2))
(segid "BrD" and resid 82 and name HE %)
3.000   2.200 2.200 peak      16972 weight  0.10000E+01 volume  0.99455E+02 ppm1   3.676 ppm2  7.053
ASSI {17032}
((segid "BrD" and resid 62 and name HA))
((segid "BrD" and resid 67 and name HB1))
2.400   1.400 1.400 peak      17032 weight  0.10000E+01 volume  0.47084E+03 ppm1   4.462 ppm2  3.576
ASSI {17072}
((segid "BrD" and resid 95 and name HA))
((segid "BrD" and resid 32 and name HH2))
2.800   2.000 2.000 peak      17072 weight  0.10000E+01 volume  0.16966E+01 ppm1   4.462 ppm2  7.790
ASSI {17192}
((segid "BrD" and resid 20 and name HA))
((segid "BrD" and resid 23 and name HG2))
2.400   1.400 1.400 peak      17192 weight  0.10000E+01 volume  0.43323E+03 ppm1   4.903 ppm2  3.069
ASSI {17342}
((segid "BrD" and resid 97 and name HA))
(segid "BrD" and resid 96 and name HD %)
2.800   2.000 2.000 peak      17342 weight  0.10000E+01 volume  0.15398E+03 ppm1   4.807 ppm2  7.719
ASSI {17352}
((segid "BrD" and resid 34 and name HB2))
(segid "BrD" and resid 102 and name HD1 %)
3.900   3.800 1.600 peak      17352 weight  0.10000E+01 volume  0.22025E+02 ppm1   3.127 ppm2  1.319
OR {17352}
((segid "BrD" and resid 34 and name HB2))
(segid "BrD" and resid 102 and name HD2 %)
ASSI {17372}
((segid "BrD" and resid 34 and name HB1))
(segid "BrD" and resid 102 and name HD1 %)
4.300   4.300 1.200 peak      17372 weight  0.10000E+01 volume  0.12013E+02 ppm1   4.114 ppm2  1.317
OR {17372}
((segid "BrD" and resid 34 and name HB1))
(segid "BrD" and resid 102 and name HD2 %)
ASSI {17452}
((segid "BrD" and resid 34 and name HB2))
(segid "BrD" and resid 34 and name HE %)
3.800   3.600 1.700 peak      17452 weight  0.10000E+01 volume  0.24806E+02 ppm1   3.122 ppm2  7.774
ASSI {17502}
((segid "BrD" and resid 34 and name HA))
((segid "BrD" and resid 35 and name HA))
4.600   4.600 0.900 peak      17502 weight  0.10000E+01 volume  0.61169E+01 ppm1   5.544 ppm2  4.907
```

TABLE 2-continued

Unambiguous NOE-derived Inter-proton Distance Restraints

ASSI {17562}
(segid "BrD" and resid 81 and name HG2 %)
((segid "BrD" and resid 34 and name HZ))
3.500  3.100 2.000 peak      17562 weight 0.10000E+01 volume 0.45996E+02 ppm1    0.759 ppm2 7.903
ASSI {17572}
(segid "BrD" and resid 81 and name HG2 %)
(segid "BrD" and resid 34 and name HD %)
2.500  1.600 1.600 peak      17572 weight 0.10000E+01 volume 0.32265E+03 ppm1    0.761 ppm2 7.706
ASSI {17632}
(segid "BrD" and resid 81 and name HG2 %)
(segid "BrD" and resid 82 and name HD %)
2.300  1.300 1.300 peak      17632 weight 0.10000E+01 volume 0.40682E+03 ppm1    0.763 ppm2 7.263
ASSI {17642}
(segid "BrD" and resid 81 and name HG2 %)
(segid "BrD" and resid 82 and name HE %)
2.800  2.000 2.000 peak      17642 weight 0.10000E+01 volume 0.15950E+03 ppm1    0.760 ppm2 7.063
ASSI {17712}
((segid "BrD" and resid 33 and name HG1))
((segid "BrD" and resid 95 and name HA))
3.000  2.200 2.200 peak      17712 weight 0.10000E+01 volume 0.11633E+03 ppm1    0.859 ppm2 4.452
ASSI {17732}
((segid "BrD" and resid 33 and name HG1))
((segid "BrD" and resid 98 and name HB1))
3.400  2.900 2.100 peak      17732 weight 0.10000E+01 volume 0.51004E+02 ppm1    0.859 ppm2 4.020
ASSI {17742}
((segid "BrD" and resid 33 and name HG1))
((segid "BrD" and resid 98 and name HB2))
3.100  2.400 2.400 peak      17742 weight 0.10000E+01 volume 0.94735E+02 ppm1    0.859 ppm2 3.654
ASSI {17762}
((segid "BrD" and resid 33 and name HG2))
((segid "BrD" and resid 95 and name HA))
3.400  2.900 2.100 peak      17762 weight 0.10000E+01 volume 0.53516E+02 ppm1   −0.324 ppm2 4.444
ASSI {17782}
((segid "BrD" and resid 33 and name HD1))
(segid "BrD" and resid 31 and name HB %)
3.500  3.100 2.000 peak      17782 weight 0.10000E+01 volume 0.42246E+02 ppm1    2.782 ppm2 2.304
ASSI {17902}
((segid "BrD" and resid 33 and name HD2))
(segid "BrD" and resid 34 and name HD %)
3.900  3.800 1.600 peak      17902 weight 0.10000E+01 volume 0.21155E+02 ppm1    2.190 ppm2 7.707
ASSI {17952}
((segid "BrD" and resid 33 and name HB1))
((segid "BrD" and resid 95 and name HA))
3.800  3.600 1.700 peak      17952 weight 0.10000E+01 volume 0.26579E+02 ppm1    1.055 ppm2 4.443
ASSI {17962}
((segid "BrD" and resid 33 and name HB2))
((segid "BrD" and resid 95 and name HA))
3.900  3.800 1.600 peak      17962 weight 0.10000E+01 volume 0.22889E+02 ppm1   −0.176 ppm2 4.444
ASSI {17982}
((segid "BrD" and resid 33 and name HB2))
(segid "BrD" and resid 34 and name HD %)
3.700  3.400 1.800 peak      17982 weight 0.10000E+01 volume 0.30273E+02 ppm1   −0.174 ppm2 7.699
ASSI {18012}
((segid "BrD" and resid 75 and name HG1))
((segid "BrD" and resid 71 and name HA))
3.200  2.600 2.300 peak      18012 weight 0.10000E+01 volume 0.74474E+02 ppm1    3.524 ppm2 4.662
ASSI {18052}
((segid "BrD" and resid 59 and name HG1))
((segid "BrD" and resid 59 and name HB2))
2.600  1.700 1.700 peak      18052 weight 0.10000E+01 volume 0.28930E+03 ppm1    3.227 ppm2 2.482
OR {18052}
((segid "BrD" and resid 59 and name HG2))
((segid "BrD" and resid 59 and name HB2))
ASSI {18102}
((segid "BrD" and resid 75 and name HG2))
(segid "BrD" and resid 115 and name HD1 %)
4.400  4.400 1.100 peak      18102 weight 0.10000E+01 volume 0.10857E+02 ppm1    3.226 ppm2 1.327
ASSI {18112}
((segid "BrD" and resid 59 and name HG2))
(segid "BrD" and resid 22 and name HD1 %)
4.100  4.100 1.400 peak      18112 weight 0.10000E+01 volume 0.16621E+02 ppm1    3.226 ppm2 1.661
OR {18112}
((segid "BrD" and resid 59 and name HG1))
(segid "BrD" and resid 22 and name HD1 %)

TABLE 2-continued

Unambiguous NOE-derived Inter-proton Distance Restraints

ASSI {18122}
((segid "BrD" and resid 75 and name HG1))
((segid "BrD" and resid 115 and name HB1))
3.500  3.100  2.000  peak     14122  weight  0.10000E+01  volume  0.47142E+02  ppm1  3.522  ppm2  2.165
ASSI {18142}
((segid "BrD" and resid 75 and name HG1))
(segid "BrD" and resid 113 and name HB %)
3.900  3.800  1.600  peak     18142  weight  0.10000E+01  volume  0.23045E+02  ppm1  3.523  ppm2  1.996
ASSI {18282}
(segid "BrD" and resid 35 and name HE %)
((segid "BrD" and resid 60 and name HB1))
2.800  2.000  2.000  peak     18282  weight  0.10000E+01  volume  0.18338E+03  ppm1  2.782  ppm2  4.972
ASSI {18302}
(segid "BrD" and resid 35 and name HE %)
((segid "BrD" and resid 59 and name HG2))
3.400  2.900  2.100  peak     18302  weight  0.10000E+01  volume  0.50813E+02  ppm1  2.782  ppm2  3.248
OR {18302}
(segid "BrD" and resid 35 and name HE %)
((segid "BrD" and resid 59 and name HG1))
ASSI {18312}
(segid "BrD" and resid 35 and name HE %)
((segid "BrD" and resid 34 and name HB2))
3.000  2.200  2.200  peak     18312  weight  0.10000E+01  volume  0.11214E+03  ppm1  2.782  ppm2  3.101
ASSI {18352}
(segid "BrD" and resid 35 and name HE %)
(segid "BrD" and resid 56 and name HD1 %)
2.800  2.000  2.000  peak     18352  weight  0.10000E+01  volume  0.15609E+03  ppm1  2.782  ppm2  1.539
ASSI {18362}
(segid "BrD" and resid 35 and name HE %)
((segid "BrD" and resid 57 and name HB1))
2.400  1.400  1.400  peak     18362  weight  0.10000E+01  volume  0.43055E+03  ppm1  2.782  ppm2  2.938
ASSI {18382}
(segid "BrD" and resid 35 and name HE %)
((segid "BrD" and resid 26 and name HB1))
2.500  1.600  1.600  peak     18382  weight  0.10000E+01  volume  0.29206E+03  ppm1  2.781  ppm2  2.460
ASSI {18492}
((segid "BrD" and resid 59 and name HG1))
(segid "BrD" and resid 74 and name HE %)
5.000  5.000  0.500  peak     18492  weight  0.10000E+01  volume  0.50782E+01  ppm1  3.226  ppm2  7.552
OR {18492}
((segid "BrD" and resid 59 and name HG2))
(segid "BrD" and resid 74 and name HE %)
ASSI {18542}
(segid "BrD" and resid 75 and name HE %)
((segid "BrD" and resid 17 and name HB))
3.000  2.200  2.200  peak     18542  weight  0.10000E+01  volume  0.10304E+03  ppm1  2.634  ppm2  4.826
ASSI {18642}
(segid "BrD" and resid 75 and name HE %)
((segid "BrD" and resid 110 and name HA))
3.400  2.900  2.100  peak     18642  weight  0.10000E+01  volume  0.51911E+03  ppm1  2.634  ppm2  4.427
ASSI {18662}
(segid "BrD" and resid 75 and name HE %)
((segid "BrD" and resid 74 and name HB1))
2.900  2.100  2.100  peak     18662  weight  0.10000E+01  volume  0.13576E+03  ppm1  2.634  ppm2  3.597
ASSI {18682}
(segid "BrD" and resid 75 and name HE %)
((segid "BrD" and resid 74 and name HB2))
3.000  2.200  2.200  peak     18682  weight  0.10000E+01  volume  0.11929E+03  ppm1  2.634  ppm2  3.003
ASSI {18722}
(segid "BrD" and resid 75 and name HE %)
((segid "BrD" and resid 75 and name HB1))
3.700  3.400  1.800  peak     18722  weight  0.10000E+01  volume  0.33115E+02  ppm1  2.634  ppm2  2.906
ASSI {18732}
(segid "BrD" and resid 75 and name HE %)
((segid "BrD" and resid 75 and name HB2))
2.100  2.100  2.400  peak     18732  weight  0.10000E+01  volume  0.10446E+04  ppm1  2.634  ppm2  2.824
ASSI {18762}
(segid "BrD" and resid 75 and name HE %)
(segid "BrD" and resid 75 and name HD2 %)
4.900  4.900  0.600  peak     18762  weight  0.10000E+01  volume  0.60943E+01  ppm1  2.634  ppm2  0.676
ASSI {18772}
(segid "BrD" and resid 75 and name HE %)
(segid "BrD" and resid 14 and name HD1 %)
2.600  1.700  1.700  peak     18772  weight  0.10000E+01  volume  0.27797E+03  ppm1  2.634  ppm2  1.425
OR {18772}
(segid "BrD" and resid 75 and name HE %)
(segid "BrD" and resid 14 and name HD2 %)

TABLE 2-continued

Unambiguous NOE-derived Inter-proton Distance Restraints

```
ASSI {18782}
(segid "BrD" and resid 75 and name HE %)
(segid "BrD" and resid 115 and name HD1 %)
2.800   2.000 2.000 peak        18782  weight  0.10000E+01 volume   0.15408E+03 ppm1    2.634 ppm2  1.327
ASSI {18812}
(segid "BrD" and resid 75 and name HE %)
((segid "BrD" and resid 116 and name HG12))
3.600   3.200 1.900 peak        18812  weight  0.10000E+01 volume   0.36651E+02 ppm1    2.634 ppm2  1.547
ASSI {18862}
(segid "BrD" and resid 75 and name HE %)
((segid "BrD" and resid 116 and name HG11))
4.600   4.600 0.900 peak        18862  weight  0.10000E+01 volume   0.79723E+01 ppm1    2.635 ppm2  1.914
ASSI {18872}
(segid "BrD" and resid 75 and name HE %)
(segid "BrD" and resid 59 and name HE %)
3.500   3.100 2.000 peak        18872  weight  0.10000E+01 volume   0.40230E+02 ppm1    2.635 ppm2  1.865
ASSI {18882}
(segid "BrD" and resid 75 and name HE %)
(segid "BrD" and resid 113 and name HB %)
2.700   1.800 1.800 peak        18882  weight  0.10000E+01 volume   0.22570E+03 ppm1    2.634 ppm2  1.986
ASSI {18892}
(segid "BrD" and resid 75 and name HE %)
((segid "BrD" and resid 18 and name HG))
2.400   1.400 1.400 peak        18892  weight  0.10000E+01 volume   0.37764E+03 ppm1    2.636 ppm2  2.250
ASSI {18902}
(segid "BrD" and resid 75 and name HE %)
((segid "BrD" and resid 115 and name HB1))
2.400   1.600 1.600 peak        18902  weight  0.10000E+01 volume   0.35880E+03 ppm1    2.635 ppm2  2.199
ASSI {18932}
(segid "BrD" and resid 75 and name HE %)
((segid "BrD" and resid 14 and name HB1))
3.700   3.400 1.800 peak        18932  weight  0.10000E+01 volume   0.29255E+02 ppm1    2.636 ppm2  2.444
ASSI {18952}
((segid "BrD" and resid 57 and name HB2))
((segid "BrD" and resid 37 and name HD1))
3.200   2.600 2.300 peak        18952  weight  0.10000E+01 volume   0.68763E+02 ppm1    2.847 ppm2  4.289
ASSI {18992}
((segid "BrD" and resid 57 and name HB2))
((segid "BrD" and resid 36 and name HA))
3.700   3.400 1.800 peak        18992  weight  0.10000E+01 volume   0.28694E+02 ppm1    2.842 ppm2  5.444
ASSI {19072}
((segid "BrD" and resid 31 and name HA))
((segid "BrD" and resid 34 and name HZ))
3.100   2.400 2.400 peak        19072  weight  0.10000E+01 volume   0.98899E+02 ppm1    5.001 ppm2  7.893
ASSI {19092}
((segid "BrD" and resid 31 and name HA))
((segid "BrD" and resid 30 and name HA))
2.800   2.000 2.000 peak        19092  weight  0.10000E+01 volume   0.15610E+03 ppm1    5.001 ppm2  5.428
ASSI {19172}
((segid "BrD" and resid 43 and name HA))
(segid "BrD" and resid 88 and name HE %)
3.300   2.700 2.200 peak        19172  weight  0.10000E+01 volume   0.58244E+03 ppm1    6.847 ppm2  7.417
ASSI {19182}
((segid "BrD" and resid 43 and name HA))
((segid "BrD" and resid 44 and name HG1))
2.900   2.100 2.100 peak        19182  weight  0.10000E+01 volume   0.12258E+03 ppm1    5.544 ppm2  3.735
ASSI {19192}
((segid "BrD" and resid 43 and name HA))
((segid "BrD" and resid 44 and name HG2))
3.100   2.400 2.400 peak        19192  weight  0.10000E+01 volume   0.97301E+02 ppm1    5.544 ppm2  2.646
OR {19192}
((segid "BrD" and resid 43 and name HA))
((segid "BrD" and resid 44 and name HB2))
ASSI {19202}
((segid "BrD" and resid 43 and name HA))
(segid "BrD" and resid 38 and name HG2 %)
3.500   3.100 2.000 peak        19202  weight  0.10000E+01 volume   0.42319E+02 ppm1    5.544 ppm2  0.799
ASSI {19212}
(segid "BrD" and resid 43 and name HB %)
((segid "BrD" and resid 42 and name HG1))
3.600   3.200 1.900 peak        19212  weight  0.10000E+01 volume   0.35927E+02 ppm1    1.697 ppm2  2.898
ASSI {19242}
(segid "BrD" and resid 43 and name HB %)
(segid "BrD" and resid 50 and name HD1 %)
5.400   5.400 0.100 peak        19242  weight  0.10000E+01 volume   0.31463E+01 ppm1    1.697 ppm2  1.148
```

TABLE 2-continued

Unambiguous NOE-derived Inter-proton Distance Restraints

ASSI {19272}
(segid "BrD" and resid 43 and name HB %)
((segid "BrD" and resid 39 and name HG1))
3.300  2.700  2.200  peak       39272  weight  0.10000E+01  volume  0.60793E+02  ppm1      1.697  ppm2  2.032
ASSI {19282}
(segid "BrD" and resid 43 and name HB %)
((segid "BrD" and resid 38 and name HB))
3.000  2.200  2.200  peak       19282  weight  0.10000E+01  volume  0.12013E+03  ppm1      1.697  ppm2  1.790
ASSI {19312}
(segid "BrD" and resid 31 and name HB %)
(segid "BrD" and resid 25 and name HG1 %)
3.200  2.600  2.300  peak       19312  weight  0.10000E+01  volume  0.68019E+02  ppm1      2.289  ppm2  1.832
ASSI {19352}
(segid "BrD" and resid 31 and name HB %)
((segid "BrD" and resid 35 and name HB1))
3.400  2.900  2.100  peak       19352  weight  0.10000E+01  volume  0.48169E+02  ppm1      2.289  ppm2  2.841
ASSI {19362}
(segid "BrD" and resid 31 and name HB %)
((segid "BrD" and resid 28 and name HB1))
2.400  1.400  1.400  peak       19362  weight  0.10000E+01  volume  0.37768E+03  ppm1      2.289  ppm2  3.581
ASSI {19372}
(segid "BrD" and resid 31 and name HB %)
((segid "BrD" and resid 35 and name HG1))
2.500  1.600  1.600  peak       19372  weight  0.10000E+01  volume  0.30400E+ 03  ppm1      2.289  ppm2  3.427
ASSI {19382}
(segid "BrD" and resid 31 and name HB %)
((segid "BrD" and resid 34 and name HB2))
4.200  4.200  1.300  peak       19382  weight  0.10000E+01  volume  0.14651E+02  ppm1      2.289  ppm2  3.134
ASSI {19392}
(segid "BrD" and resid 31 and name HB %)
((segid "BrD" and resid 28 and name HA))
3.100  2.400  2.400  peak       19392  weight  0.10000E+01  volume  0.87183E+02  ppm1      2.289  ppm2  4.582
ASSI {19422}
(segid "BrD" and resid 31 and name HB %)
(segid "BrD" and resid 34 and name HE %)
3.500  3.100  2.000  peak       19422  weight  0.10000E+01  volume  0.44223E+02  ppm1      2.289  ppm2  7.803
ASSI {19482}
(segid "BrD" and resid 76 and name HB %)
((segid "BrD" and resid 79 and name HB2))
3.300  2.700  2.200  peak       19482  weight  0.10000E+01  volume  0.66817E+02  ppm1      2.092  ppm2  2.662
ASSI {19492}
(segid "BrD" and resid 76 and name HB %)
((segid "BrD" and resid 80 and name HB2))
2.800  2.000  2.000  peak       19492  weight  0.10000E+01  volume  0.15977E+03  ppm1      2.092  ppm2  2.564
OR {19492}
(segid "BrD" and resid 76 and name HB %)
((segid "BrD" and resid 80 and name HB1))
ASSI {19502}
(segid "BrD" and resid 76 and name HB %)
((segid "BrD" and resid 80 and name HB2))
2.700  1.800  1.800  peak       19502  weight  0.10000E+01  volume  0.21436E+03  ppm1      2.092  ppm2  2.507
ASSI {19522}
(segid "BrD" and resid 76 and name HB %)
((segid "BrD" and resid 77 and name HA))
2.800  2.000  2.000  peak       19522  weight  0.10000E+01  volume  0.15327E+03  ppm1      2.092  ppm2  4.963
ASSI {19552}
(segid "BrD" and resid 76 and name HB %)
((segid "BrD" and resid 51 and name HB2))
2.500  1.600  1.600  peak       19552  weight  0.10000E+01  volume  0.32487E+03  ppm1      2.092  ppm2  1.763
OR {19552}
(segid "BrD" and resid 76 and name HB %)
((segid "BrD" and resid 51 and name HG2))
ASSI {19572}
(segid "BrD" and resid 76 and name HB %)
(segid "BrD" and resid 116 and name HG2 %)
3.600  3.200  1.900  peak       19572  weight  0.10000E+01  volume  0.35020E+02  ppm1      2.092  ppm2  1.432
ASSI {19582}
(segid "BrD" and resid 73 and name HD2 %)
((segid "BrD" and resid 68 and name HA))
2.000  2.000  2.000  peak       19582  weight  0.10000E+01  volume  0.16601E+02  ppm1      1.600  ppm2  5.143
ASSI {19632}
((segid "BrD" and resid 76 and name HA))
((segid "BrD" and resid 80 and name HG1))
3.100  2.400  2.400  peak       19632  weight  0.10000E+01  volume  0.95067E+02  ppm1      4.656  ppm2  2.327

TABLE 2-continued

Unambiguous NOE-derived Inter-proton Distance Restraints

ASSI {19642}
(segid "BrD" and resid 99 and name HB %)
((segid "BrD" and resid 34 and name HZ))
2.200  2.200  2.300 peak      19642 weight  0.10000E+01 volume  0.65240E+03 ppm1   2.190 ppm2  7.903
ASSI {19652}
(segid "BrD" and resid 99 and name HB %)
(segid "BrD" and resid 34 and name HE %)
2.300  1.300  1.300 peak      19652 weight  0.10000E+01 volume  0.50164E+03 ppm1   2.190 ppm2  7.781
ASSI {19672}
(segid "BrD" and resid 99 and name HB %)
(segid "BrD" and resid 82 and name HD1)
2.500  1.600  1.600 peak      19672 weight  0.10000E+01 volume  0.36039E+03 ppm1   2.190 ppm2  7.259
ASSI {19692}
(segid "BrD" and resid 99 and name HB %)
((segid "BrD" and resid 85 and name HA))
3.100  2.400  2.400 peak      19692 weight  0.10000E+01 volume  0.92786E+02 ppm1   2.190 ppm2  5.005
ASSI {19702}
(segid "BrD" and resid 99 and name HB %)
((segid "BrD" and resid 100 and name HA))
3.000  2.200  2.200 peak      19702 weight  0.10000E+01 volume  0.10441E+03 ppm1   2.190 ppm2  4.948
ASSI {19752}
(segid "BrD" and resid 99 and name HB %)
((segid "BrD" and resid 103 and name HG1))
3.000  2.200  2.200 peak      19752 weight  0.10000E+01 volume  0.10256E+03 ppm1   2.190 ppm2  2.613
ASSI {19772}
(segid "BrD" and resid 76 and name HB %)
((segid "BrD" and resid 79 and name HB1))
3.500  3.100  2.000 peak      19772 weight  0.10000E+01 volume  0.45000E+02 ppm1   2.092 ppm2  2.784
ASSI {19792}
((segid "BrD" and resid 99 and name HA))
(segid "BrD" and resid 34 and name HZ))
2.600  1.700  1.700 peak      19792 weight  0.10000E+01 volume  0.26558E+03 ppm1   4.459 ppm2  7.901
ASSI {19802}
((segid "BrD" and resid 99 and name HA))
(segid "BrD" and resid 34 and name HE %)
2.700  1.800  1.800 peak      19802 weight  0.10000E+01 volume  0.21467E+03 ppm1   4.459 ppm2  7.771
ASSI {19812}
((segid "BrD" and resid 99 and name HA))
(segid "BrD" and resid 82 and name HE %)
3.200  2.600  2.300 peak      19812 weight  0.10000E+01 volume  0.71395E+02 ppm1   4.457 ppm2  7.073
ASSI {19822}
((segid "BrD" and resid 99 and name HA))
(segid "BrD" and resid 82 and name HD %)
2.800  2.000  2.000 peak      19822 weight  0.10000E+01 volume  0.15492E+03 ppm1   4.459 ppm2  7.259
ASSI {19832}
((segid "BrD" and resid 99 and name HA))
((segid "BrD" and resid 100 and name HA))
2.800  2.000  2.000 peak      19832 weight  0.10000E+01 volume  0.16591E+03 ppm1   4.458 ppm2  4.950
ASSI {19842}
((segid "BrD" and resid 99 and name HA))
((segid "BrD" and resid 103 and name HB2))
2.600  1.700  1.700 peak      19842 weight  0.10000E+01 volume  0.24667E+03 ppm1   4.458 ppm2  1.922
ASSI {19882}
((segid "BrD" and resid 113 and name HA))
(segid "BrD" and resid 110 and name HG2 %)
3.600  3.200  1.900 peak      19882 weight  0.10000E+01 volume  0.35803E+02 ppm1   4.903 ppm2  1.222
ASSI {19902}
((segid "BrD" and resid 113 and name HA))
((segid "BrD" and resid 112 and name HB1))
3.400  2.900  2.100 peak      19902 weight  0.10000E+01 volume  0.48759E+02 ppm1   4.903 ppm2  2.670
ASSI {19912}
((segid "BrD" and resid 113 and name HA))
((segid "BrD" and resid 110 and name HA))
3.500  3.100  2.000 peak      19912 weight  0.10000E+01 volume  0.44605E+02 ppm1   4.903 ppm2  4.419
ASSI {19922}
((segid "BrD" and resid 113 and name HA))
((segid "BrD" and resid 14 and name HA))
3.100  2.400  2.400 peak      19922 weight  0.10000E+01 volume  0.84488E+02 ppm1   4.903 ppm2  4.663
ASSI {19962}
((segid "BrD" and resid 113 and name HA))
(segid "BrD" and resid 115 and name HD1 %)
4.000  4.000  1.500 peak      19962 weight  0.10000E+01 volume  0.18572E+02 ppm1   4.899 ppm2  1.313
ASSI {19992}
(segid "BrD" and resid 113 and name HB %)
((segid "BrD" and resid 14 and name HB1))
3.300  2.700  2.200 peak      19992 weight  0.10000E+01 volume  0.60405E+02 ppm1   1.991 ppm2  2.442

TABLE 2-continued

Unambiguous NOE-derived Inter-proton Distance Restraints

ASSI {20032}
(segid "BrD" and resid 113 and name HB %)
((segid "BrD" and resid 14 and name HG))
2.100  2.100 2.400 peak    20032 weight  0.10000E+01 volume  0.86636E+03 ppm1    1.994 ppm2  2.059
ASSI {20042}
(segid "BrD" and resid 113 and name HB %)
(segid "BrD" and resid 18 and name HD2 %)
4.200  4.200 1.300 peak    20042 weight  0.10000E+01 volume  0.14101E+02 ppm1    1.993 ppm2  0.408
ASSI {20052}
(segid "BrD" and resid 113 and name HB %)
(segid "BrD" and resid 115 and name HD1 %)
2.400  1.400 1.400 peak    20052 weight  0.10000E+01 volume  0.47259E+03 ppm1    1.993 ppm2  1.319
ASSI {20072}
((segid "BrD" and resid 110 and name HA))
(segid "BrD" and resid 115 and name HD1 %)
$$     1.600 1.600 peak    20072 weight  0.10000E+01 volume  0.33630E+03 ppm1    4.409 ppm2  1.319
ASSI {20192}
((segid "BrD" and resid 17 and name HB))
(segid "BrD" and resid 115 and name HD1 %)
3.200  2.600 2.300 peak    20192 weight  0.10000E+01 volume  0.76060E+02 ppm1    4.854 ppm2  1.327
ASSI {20212}
((segid "BrD" and resid 17 and name HA))
(segid "BrD" and resid 21 and name HD1 %)
4.600  4.600 0.900 peak    20212 weight  0.10000E+01 volume  0.88717E+01 ppm1    4.542 ppm2  1.224
ASSI {20242}
(segid "BrD" and resid 17 and name HG2 %)
(segid "BrD" and resid 75 and name HE %)
2.600  1.700 1.700 peak    20242 weight  0.10000E+01 volume  0.27619E+03 ppm1    1.747 ppm2  2.619
ASSI {20252}
(segid "BrD" and resid 17 and name HG2 %)
((segid "BrD" and resid 21 and name HB))
3.000  2.200 2.200 peak    20252 weight  0.10000E+01 volume  0.10098E+03 ppm1    1.747 ppm2  2.507
ASSI {20272}
(segid "BrD" and resid 17 and name HG2 %)
((segid "BrD" and resid 115 and name HB1))
3.500  3.100 2.000 peak    20272 weight  0.10000E+01 volume  0.46134E+02 ppm1    1.747 ppm2  2.214
ASSI {20292}
(segid "BrD" and resid 17 and name HG2 %)
((segid "BrD" and resid 109 and name HB2))
2.600  1.700 1.700 peak    20292 weight  0.10000E+01 volume  0.25743E+03 ppm1    1.747 ppm2  2.149
ASSI {20302}
(segid "BrD" and resid 17 and name HG2 %)
((segid "BrD" and resid 18 and name HB2))
4.600  4.600 0.900 peak    20302 weight  0.10000E+01 volume  0.84610E+01 ppm1    1.747 ppm2  0.904
ASSI {20312}
((segid "BrD" and resid 41 and name HB))
((segid "BrD" and resid 39 and name HD1))
3.300  2.700 2.200 peak    20312 weight  0.10000E+01 volume  0.67487E+02 ppm1    4.903 ppm2  2.271
ASSI {20332}
((segid "BrD" and resid 41 and name HA))
((segid "BrD" and resid 44 and name HD2))
3.500  3.100 2.000 peak    20332 weight  0.10000E+01 volume  0.42717E+02 ppm1    4.656 ppm2  4.143
ASSI {20382}
((segid "BrD" and resid 41 and name HA))
((segid "BrD" and resid 44 and name HD1))
2.900  2.100 2.100 peak    20382 weight  0.10000E+01 volume  0.13674E+03 ppm1    4.656 ppm2  4.308
ASSI {20532}
(segid "BrD" and resid 41 and name HG2 %)
((segid "BrD" and resid 42 and name HA))
3.400  2.900 2.100 peak    20532 weight  0.10000E+01 volume  0.51387E+02 ppm1    1.845 ppm2  5.062
ASSI {20542}
(segid "BrD" and resid 41 and name HG2 %)
((segid "BrD" and resid 39 and name HD1))
2.600  1.700 1.700 peak    20542 weight  0.10000E+01 volume  0.28354E+03 ppm1    1.844 ppm2  2.019
ASSI {20562}
(segid "BrD" and resid 41 and name HG2 %)
((segid "BrD" and resid 39 and name HD1))
2.900  2.100 2.100 peak    20562 weight  0.10000E+01 volume  0.13596E+03 ppm1    1.844 ppm2  2.296
ASSI {20572}
(segid "BrD" and resid 41 and name HG2 %)
((segid "BrD" and resid 39 and name HB1))
3.200  2.600 2.300 peak    20572 weight  0.10000E+01 volume  0.75085E+02 ppm1    1.845 ppm2  2.466
ASSI {20592}
((segid "BrD" and resid 112 and name HG2))
((segid "BrD" and resid 112 and name HA))
2.400  1.400 1.400 peak    20592 weight  0.10000E+01 volume  0.44748E+03 ppm1    2.832 ppm2  4.585

TABLE 2-continued

Unambiguous NOE-derived Inter-proton Distance Restraints

ASSI {20712}
((segid "BrD" and resid 67 and name HA))
((segid "BrD" and resid 68 and name HA))
2.800   2.000 2.000 peak        20712 weight  0.10000E+01 volume   0.17530E+03 ppm1    4.656 ppm2  5.111
ASSI {20802}
(segid "BrD" and resid 25 and name HG2 %)
(segid "BrD" and resid 82 and name HE %)
2.900   2.100 2.100 peak        20802 weight  0.10000E+01 volume   0.13726E+03 ppm1    1.648 ppm2  7.026
OR {20802}
(segid "BrD" and resid 25 and name HG2 %)
((segid "BrD" and resid 82 and name HZ))
ASSI {20812}
(segid "BrD" and resid 58 and name HG2 %)
(segid "BrD" and resid 68 and name HE %)
3.200   2.600 2.300 peak        20812 weight  0.10000E+01 volume   0.69885E+02 ppm1    1.651 ppm2  7.920
ASSI {20852}
(segid "BrD" and resid 25 and name HG2 %)
((segid "BrD" and resid 31 and name HA))
3.400   2.900 2.100 peak        20852 weight  0.10000E+01 volume   0.55839E+02 ppm1    1.649 ppm2  4.980
ASSI {20862}
((segid "BrD" and resid 62 and name HD1))
((segid "BrD" and resid 62 and name HB2))
2.900   2.100 2.100 peak        20862 weight  0.10000E+01 volume   0.12367E+03 ppm1    3.175 ppm2  1.710
ASSI {20872}
((segid "BrD" and resid 62 and name HD2))
((segid "BrD" and resid 62 and name HB2))
3.000   2.200 2.200 peak        20872 weight  0.10000E+01 volume   0.11189E+03 ppm1    2.633 ppm2  1.711
ASSI {20992}
((segid "BrD" and resid 62 and name HB1))
(segid "BrD" and resid 68 and name HE %)
3.100   2.400 2.400 peak        20992 weight  0.10000E+01 volume   0.97455E+02 ppm1    2.638 ppm2  7.905
ASSI {21082}
(segid "BrD" and resid 83 and name $$)
((segid "BrD" and resid 87 and name HG2))
3.000   2.200 2.200 peak        21082 weight  0.10000E+01 volume   0.11102E+03 ppm1    1.895 ppm2  2.784
ASSI {21142}
((segid "BrD" and resid 83 and name HB))
((segid "BrD" and resid 80 and name HG1))
3.400   2.900 2.100 peak        21142 weight  0.10000E+01 volume   0.55703E+02 ppm1    4.803 ppm2  2.360
ASSI {21192}
(segid "BrD" and resid 83 and name HG2 %)
((segid "BrD" and resid 87 and name HG1))
2.100   1.100 1.100 peak        21192 weight  0.10000E+01 volume   0.10489E+04 ppm1    1.895 ppm2  3.028
ASSI {21202}
(segid "BrD" and resid 83 and name HG2 %)
((segid "BrD" and resid 87 and name HB2))
3.400   2.900 2.100 peak        21202 weight  0.10000E+01 volume   0.47826E+02 ppm1    1.899 ppm2  2.597
ASSI {21292}
(segid "BrD" and resid 25 and name HG1 %)
(segid "BrD" and resid 106 and name HD %)
2.500   2.500 2.000 peak        21292 weight  0.10000E+01 volume   0.35912E+03 ppm1    1.795 ppm2  7.515
ASSI {21322}
(segid "BrD" and resid 25 and name HG1 %)
(segid "BrD" and resid 82 and name HE %)
3.500   3.100 2.000 peak        21322 weight  0.10000E+01 volume   0.43989E+02 ppm1    1.795 ppm2  7.026
OR {21322}
(segid "BrD" and resid 25 and name HG1 %)
((segid "BrD" and resid 82 and name HZ))
ASSI {21392}
((segid "BrD" and resid 25 and name HB))
(segid "BrD" and resid 102 and name HD1 %)
3.600   3.200 1.900 peak        21392 weight  0.10000E+01 volume   0.35593E+02 ppm1    2.979 ppm2  1.327
OR {21392}
((segid "BrD" and resid 25 and name HB))
(segid "BrD" and resid 102 and name HD2 %)
ASSI {21402}
((segid "BrD" and resid 25 and name HB))
(segid "BrD" and resid 78 and name HD2 %)
4.400   4.400 1.100 peak        21402 weight  0.10000E+01 volume   0.11302E+02 ppm1    2.979 ppm2  0.676
ASSI {21422}
(segid "BrD" and resid 25 and name HG1 %)
((segid "BrD" and resid 102 and name HG))
3.500   3.100 2.000 peak        21422 weight  0.10000E+01 volume   0.43674E+02 ppm1    1.795 ppm2  2.157
ASSI {21452}
(segid "BrD" and resid 25 and name HG1 %)
((segid "BrD" and resid 104 and name HB1))
4.300   4.300 1.200 peak        21452 weight  0.10000E+01 volume   0.11856E+02 ppm1    1.796 ppm2  3.907

TABLE 2-continued

Unambiguous NOE-derived Inter-proton Distance Restraints

ASSI {21462}
(segid "BrD" and resid 25 and name HG1 %)
((segid "BrD" and resid 21 and name HA))
2.700  1.800  1.800 peak        21462  weight  0.10000E+01 volume  0.21023E+03 ppm1    1.797 ppm2  4.369
ASSI {21472}
(segid "BrD" and resid 25 and name HG1 %)
((segid "BrD" and resid 102 and name HA))
3.400  2.900  2.100 peak        21472  weight  0.10000E+01 volume  0.48930E+02 ppm1    1.796 ppm2  4.297
ASSI {21562}
(segid "BrD" and resid 81 and name HG2 %)
((segid "BrD" and resid 82 and name HA))
2.900  2.100  2.100 peak        21562  weight  0.10000E+01 volume  0.12612E+03 ppm1    0.760 ppm2  4.753
ASSI {21582}
(segid "BrD" and resid 38 and name HG1 %)
((segid "BrD" and resid 37 and name HA))
3.300  2.700  2.200 peak        21582  weight  0.10000E+01 volume  0.64039E+02 ppm1    1.056 ppm2  4.859
ASSI {21672}
(segid "BrD" and resid 81 and name HG1 %)
(segid "BrD" and resid 34 and name HD %)
3.400  2.900  2.100 peak        21672  weight  0.10000E+01 volume  0.52778E+02 ppm1    1.056 ppm2  7.706
ASSI {21702}
(segid "BrD" and resid 38 and name HG2 %)
((segid "BrD" and resid 41 and name HA))
4.900  4.900  0.600 peak        21702  weight  0.10000E+01 volume  0.56291E+01 ppm1    0.808 ppm2  4.646
ASSI {21732}
(segid "BrD" and resid 81 and name HG2 %)
(segid "BrD" and resid 56 and name HD2 %)
2.600  1.700  1.700 peak        21732  weight  0.10000E+01 volume  0.28103E+03 ppm1    0.760 ppm2  1.236
ASSI {21742}
(segid "BrD" and resid 81 and name HG2 %)
(segid "BrD" and resid 102 and name HD1 %)
3.900  3.800  1.600 peak        21742  weight  0.10000E+01 volume  0.21895E+02 ppm1    0.760 ppm2  1.319
OR {21742}
(segid "BrD" and resid 81 and name HG2 %)
(segid "BrD" and resid 102 and name HD2 %)
ASSI {21752}
(segid "BrD" and resid 81 and name HG2 %)
((segid "BrD" and resid 84 and name HB2))
3.000  2.200  2.200 peak        21752  weight  0.10000E+01 volume  0.11571E+03 ppm1    0.763 ppm2  3.296
ASSI {21772}
((segid "BrD" and resid 81 and name HB))
(segid "BrD" and resid 78 and name HD2 %)
3.200  2.600  2.300 peak        21772  weight  0.10000E+01 volume  0.80152E+02 ppm1    2.042 ppm2  0.683
ASSI {21802}
((segid "BrD" and resid 81 and name HA))
((segid "BrD" and resid 80 and name HB1))
3.900  3.800  1.600 peak        21802  weight  0.10000E+01 volume  0.23614E+02 ppm1    3.719 ppm2  2.564
OR {21802}
((segid "BrD" and resid 81 and name HA))
((segid "BrD" and resid 80 and name HB2))
ASSI {21812}
((segid "BrD" and resid 81 and name HA))
((segid "BrD" and resid 80 and name HB1))
3.600  3.200  1.900 peak        21812  weight  0.10000E+01 volume  0.37077E+02 ppm1    3.719 ppm2  2.597
ASSI {21902}
((segid "BrD" and resid 49 and name HA))
(segid "BrD" and resid 50 and name HD1 %)
4.100  4.100  1.400 peak        21902  weight  0.10000E+01 volume  0.17504E+02 ppm1    4.656 ppm2  1.140
ASSI {21952}
(segid "BrD" and resid 50 and name HD1 %)
((segid "BrD" and resid 68 and name HB1))
2.400  1.400  1.400 peak        21952  weight  0.10000E+01 volume  0.36864E+03 ppm1    1.155 ppm2  3.535
ASSI {21972}
(segid "BrD" and resid 50 and name HD1 %)
((segid "BrD" and resid 46 and name HA))
4.100  4.100  1.400 peak        21972  weight  0.10000E+01 volume  0.16984E+02 ppm1    1.155 ppm2  4.151
ASSI {22022}
(segid "BrD" and resid 50 and name HD1 %)
(segid "BrD" and resid 88 and name HD %)
3.100  2.400  2.400 peak        22022  weight  0.10000E+01 volume  0.52494E+02 ppm1    1.155 ppm2  7.606
ASSI {22042}
((segid "BrD" and resid 50 and name HB))
((segid "BrD" and resid 51 and name HB1))
4.800  4.800  0.700 peak        22042  weight  0.10000E+01 volume  0.67010E+01 ppm1    1.797 ppm2  1.966
OR {22042}
((segid "BrD" and resid 50 and name HB))
((segid "BrD" and resid 51 and name HG1))

TABLE 2-continued

Unambiguous NOE-derived Inter-proton Distance Restraints

ASSI {22132}
((segid "BrD" and resid 50 and name HA))
(segid "BrD" and resid 49 and name HG2 %)
2.500  1.600  1.600 peak      22132 weight  0.10000E+01 volume  0.30657E+03 ppm1      4.506 ppm2  1.570
ASSI {22142}
((segid "BrD" and resid 50 and name HA))
(segid "BrD" and resid 49 and name HG1 %)
3.800  3.600  1.700 peak      22142 weight  0.10000E+01 volume  0.27941E+02 ppm1      4.506 ppm2  1.646
ASSI {22212}
(segid "BrD" and resid 50 and name HG2 %)
((segid "BrD" and resid 51 and name HB1))
4.000  4.000  1.500 peak      22212 weight  0.10000E+01 volume  0.20287E+02 ppm1      1.007 ppm2  1.954
ASSI {22222}
((segid "BrD" and resid 84 and name HA))
(segid "BrD" and resid 83 and name HG2 %)
4.100  4.100  1.400 peak      22222 weight  0.10000E+01 volume  0.17290E+02 ppm1      4.903 ppm2  1.913
ASSI {22232}
((segid "BrD" and resid 84 and name HA))
((segid "BrD" and resid 87 and name HG1))
3.500  3.100  2.000 peak      22232 weight  0.10000E+01 volume  0.41523E+02 ppm1      4.904 ppm2  3.010
ASSI {22242}
((segid "BrD" and resid 84 and name HA))
((segid "BrD" and resid 88 and name HB1))
3.100  2.400  2.400 peak      22242 weight  0.10000E+01 volume  0.82426E+02 ppm1      4.904 ppm2  3.533
ASSI {22322}
(segid "BrD" and resid 69 and name HG1 %)
((segid "BrD" and resid 66 and name HA))
2.800  2.000  2.000 peak      22322 weight  0.10000E+01 volume  0.17920E+03 ppm1      1.551 ppm2  4.989
ASSI {22332}
(segid "BrD" and resid 69 and name HG1 %)
((segid "BrD" and resid 68 and name HA))
5.000  5.000  0.500 peak      22332 weight  0.10000E+01 volume  0.51283E+01 ppm1      1.551 ppm2  5.141
ASSI {22372}
(segid "BrD" and resid 69 and name HG2 %)
((segid "BrD" and resid 66 and name HB1))
4.000  4.000  1.800 peak      22372 weight  0.10000E+01 volume  0.19974E+02 ppm1      1.425 ppm2  2.726
ASSI {22382}
(segid "BrD" and resid 69 and name HG2 %)
((segid "BrD" and resid 11 and name HB2))
3.100  2.400  2.400 peak      22382 weight  0.10000E+01 volume  0.94687E+02 ppm1      1.425 ppm2  2.612
ASSI {22452}
(segid "BrD" and resid 69 and name HG2 %)
(segid "BrD" and resid 63 and name HD1 %)
2.400  1.400  1.400 peak      22452 weight  0.10000E+01 volume  0.42940E+03 ppm1      1.425 ppm2  1.659
ASSI {22482}
(segid "BrD" and resid 49 and name HG2 %)
((segid "BrD" and resid 50 and name HG12))
4.000  4.000  1.500 peak      22482 weight  0.10000E+01 volume  0.18478E+02 ppm1      1.548 ppm2  0.808
ASSI {22492}
(segid "BrD" and resid 49 and name HG2 %)
((segid "BrD" and resid 87 and name HA))
4.900  4.900  0.600 peak      22492 weight  0.10000E+01 volume  0.59811E+01 ppm1      1.549 ppm2  4.854
ASSI {22552}
(segid "BrD" and resid 49 and name HG1 %)
((segid "BrD" and resid 50 and name HG12))
4.800  4.800  0.700 peak      22552 weight  0.10000E+01 volume  0.66665E+01 ppm1      1.647 ppm2  0.835
ASSI {22592}
((segid "BrD" and resid 57 and name HG2))
((segid "BrD" and resid 36 and name HA))
3.500  3.100  2.000 peak      22592 weight  0.10000E+01 volume  0.41488E+02 ppm1      2.016 ppm2  5.446
ASSI {22612}
((segid "BrD" and resid 42 and name HA))
(segid "BrD" and resid 43 and name HB %)
4.300  4.300  1.200 peak      22612 weight  0.10000E+01 volume  0.12059E+02 ppm1      5.050 ppm2  1.710
ASSI {22632}
((segid "BrD" and resid 42 and name HA))
((segid "BrD" and resid 44 and name HD1))
4.200  4.200  1.300 peak      22632 weight  0.10000E+01 volume  0.14713E+02 ppm1      5.051 ppm2  4.337
ASSI {22642}
((segid "BrD" and resid 42 and name HA))
((segid "BrD" and resid 43 and name HA))
4.000  4.000  1.500 peak      22642 weight  0.10000E+01 volume  0.19305E+02 ppm1      5.051 ppm2  5.550
ASSI {22682}
((segid "BrD" and resid 117 and name HA))
((segid "BrD" and resid 116 and name HA))
3.200  2.600  2.300 peak      22682 weight  0.10000E+01 volume  0.76840E+02 ppm1      5.148 ppm2  4.826

TABLE 2-continued

Unambiguous NOE-derived Inter-proton Distance Restraints

ASSI {22722}
((segid "BrD" and resid 117 and name HA))
(segid "BrD" and resid 116 and name HD1 %)
4.300  4.300  1.200 peak      22722 weight  0.10000E+01 volume  0.13070E+02 ppm1    5.149 ppm2  1.409
OR {22722}
((segid "BrD" and resid 117 and name HA))
(segid "BrD" and resid 116 and name HG2 %)
ASSI {22732}
((segid "BrD" and resid 7 and name HB1))
((segid "BrD" and resid 8 and name HD2))
2.800  2.000  2.000 peak      22732 weight  0.10000E+01 volume  0.18127E+03 ppm1    2.636 ppm2  4.287
ASSI {22742}
((segid "BrD" and resid 37 and name HA))
((segid "BrD" and resid 38 and name HA))
3.900  3.800  1.600 peak      22742 weight  0.10000E+01 volume  0.21223E+02 ppm1    4.853 ppm2  4.167
ASSI {22752}
((segid "BrD" and resid 37 and name HA))
((segid "BrD" and resid 38 and name HB))
5.500  5.500  0.000 peak      22752 weight  0.10000E+01 volume  0.13492E+00 ppm1    4.853 ppm2  1.759
ASSI {22852}
((segid "BrD" and resid 59 and name HB2))
(segid "BrD" and resid 56 and name HD2 %)
3.100  2.700  2.200 peak      22852 weight  0.10000E+01 volume  0.58772E+02 ppm1    2.486 ppm2  1.246
ASSI {22882}
((segid "BrD" and resid 8 and name HD2))
((segid "BrD" and resid 8 and name HA))
3.300  2.700  2.200 peak      22882 weight  0.10000E+01 volume  0.65959E+02 ppm1    4.261 ppm2  5.021
ASSI {22892}
((segid "BrD" and resid 8 and name HD1))
((segid "BrD" and resid 8 and name HA))
2.800  2.000  2.000 peak      22892 weight  0.10000E+01 volume  0.15205E+03 ppm1    4.407 ppm2  5.019
ASSI {22932}
((segid "BrD" and resid 37 and name HD1))
((segid "BrD" and resid 37 and name HA))
3.000  2.200  2.200 peak      22932 weight  0.10000E+01 volume  0.11242E+03 ppm1    4.261 ppm2  4.859
ASSI {22952}
((segid "BrD" and resid 44 and name HD2))
((segid "BrD" and resid 42 and name HA))
3.600  3.200  1.900 peak      22952 weight  0.10000E+01 volume  0.34019E+02 ppm1    4.114 ppm2  5.046
ASSI {22962}
((segid "BrD" and resid 91 and name HD2))
((segid "BrD" and resid 93 and name HB2))
3.000  2.200  2.200 peak      22962 weight  0.10000E+01 volume  0.11249E+03 ppm1    4.409 ppm2  4.745
ASSI {22992}
((segid "BrD" and resid 11 and name HD1))
((segid "BrD" and resid 11 and name HB1))
2.500  1.600  1.600 peak      22992 weight  0.10000E+01 volume  0.33828E+03 ppm1    4.457 ppm2  2.945
ASSI {23012}
((segid "BrD" and resid 6 and name HD1))
((segid "BrD" and resid 6 and name HB1))
3.300  2.700  2.200 peak      23012 weight  0.10000E+01 volume  0.56548E+02 ppm1    4.409 ppm2  2.849
ASSI {23022}
((segid "BrD" and resid 44 and name HD1))
((segid "BrD" and resid 44 and name HG1))
2.100  1.100  1.100 peak      23022 weight  0.10000E+01 volume  0.84503E+03 ppm1    4.321 ppm2  2.727
ASSI {23062}
((segid "BrD" and resid 37 and name HD1))
((segid "BrD" and resid 37 and name HB2))
3.200  2.600  2.300 peak      23062 weight  0.10000E+01 volume  0.60384E+02 ppm1    4.261 ppm2  2.287
ASSI {23082}
((segid "BrD" and resid 91 and name HD1))
((segid "BrD" and resid 91 and name HG1))
2.600  1.700  1.700 peak      23082 weight  0.10000E+01 volume  0.26120E+03 ppm1    4.557 ppm2  2.784
ASSI {23092}
((segid "BrD" and resid 44 and name HD2))
((segid "BrD" and resid 44 and name HG1))
2.300  1.300  1.300 peak      23092 weight  0.10000E+01 volume  0.51719E+03 ppm1    4.114 ppm2  2.735
ASSI {23102}
((segid "BrD" and resid 44 and name HD2))
((segid "BrD" and resid 44 and name HG2))
2.300  1.300  1.300 peak      23102 weight  0.10000E+01 volume  0.54971E+03 ppm1    4.114 ppm2  2.654
ASSI {23112}
((segid "BrD" and resid 11 and name HD1))
((segid "BrD" and resid 11 and name HG1))
2.600  1.700  1.700 peak      23112 weight  0.10000E+01 volume  0.26059E+03 ppm1    4.454 ppm2  2.648

TABLE 2-continued

Unambiguous NOE-derived Inter-proton Distance Restraints

ASSI {23122}
((segid "BrD" and resid 44 and name HD2))
((segid "BrD" and resid 44 and name HB1))
2.700  1.800  1.800 peak       23122 weight  0.10000E+01 volume  0.21568E+03 ppm1        4.124 ppm2  2.973
ASSI {23202}
((segid "BrD" and resid 44 and name HG2))
((segid "BrD" and resid 41 and name HA))
3.200  2.600  2.300 peak       23202 weight  0.10000E+01 volume  0.75568E+02 ppm1        2.635 ppm2  4.666
ASSI {23242}
((segid "BrD" and resid 11 and name HG1))
(segid "BrD" and resid 69 and name HG1 %)
1.200  2.600  2.300 peak       23242 weight  0.10000E+01 volume  0.73085E+02 ppm1        2.635 ppm2  1.547
ASSI {23272}
((segid "BrD" and resid 11 and name HG1))
(segid "BrD" and resid 14 and name HD2 %)
3.500  3.100  2.000 peak       23272 weight  0.10000E+01 volume  0.45861E+02 ppm1        2.635 ppm2  1.376
OR {23272}
((segid "BrD" and resid 11 and name HG1))
(segid "BrD" and resid 14 and name HD1 %)
ASSI {23292}
((segid "BrD" and resid 91 and name HG1))
((segid "BrD" and resid 89 and name HA))
4.600  4.600  0.900 peak       23292 weight  0.10000E+01 volume  0.80378E+01 ppm1        2.784 ppm2  5.646
ASSI {23372}
((segid "BrD" and resid 9 and name HD1))
(segid "BrD" and resid 14 and name HD1 %)
3.700  3.400  1.800 peak       23372 weight  0.10000E+01 volume  0.32266E+02 ppm1        3.768 ppm2  1.425
OR {23372}
((segid "BrD" and resid 9 and name HD1))
(segid "BrD" and resid 14 and name HD2 %)
ASSI {23402}
((segid "BrD" and resid 100 and name HA))
((segid "BrD" and resid 86 and name HE1))
1.500  3.100  2.000 peak       23402 weight  0.10000E+01 volume  0.44085E+02 ppm1        4.952 ppm2  3.093
ASSI {23422}
((segid "BrD" and resid 9 and name HB2))
((segid "BrD" and resid 8 and name HA))
3.000  2.200  2.200 peak       23422 weight  0.10000E+01 volume  0.11322E+03 ppm1        2.388 ppm2  5.029
ASSI {23472}
((segid "BrD" and resid 6 and name HA))
((segid "BrD" and resid 6 and name HG1))
1.900  0.900  0.900 peak       23472 weight  0.10000E+01 volume  0.18609E+04 ppm1        4.952 ppm2  2.214
ASSI {23572}
((segid "BrD" and resid 11 and name HB2))
((segid "BrD" and resid 10 and name HA))
3.600  3.200  1.900 peak       23572 weight  0.10000E+01 volume  0.38586E+02 ppm1        2.585 ppm2  5.477
ASSI {23592}
((segid "BrD" and resid 12 and name HA))
((segid "BrD" and resid 11 and name HA))
4.600  4.600  0.900 peak       23592 weight  0.10000E+01 volume  0.79375E+01 ppm1        5.297 ppm2  4.948
ASSI {23602}
((segid "BrD" and resid 29 and name HG1))
((segid "BrD" and resid 27 and name HA))
3.900  3.800  1.600 peak       23602 weight  0.10000E+01 volume  0.21350E+02 ppm1        2.978 ppm2  5.022
ASSI {23632}
((segid "BrD" and resid 13 and name HB1))
((segid "BrD" and resid 113 and name HA))
2.700  1.800  1.800 peak       23632 weight  0.10000E+01 volume  0.21427E+03 ppm1        2.733 ppm2  4.920
ASSI {23642}
((segid "BrD" and resid 13 and name HG2))
((segid "BrD" and resid 113 and name HA))
3.200  2.600  2.300 peak       23642 weight  0.10000E+01 volume  0.71312E+02 ppm1        2.978 ppm2  4.920
ASSI {23652}
((segid "BrD" and resid 13 and name HB1))
((segid "BrD" and resid 12 and name HB2))
2.900  2.100  2.100 peak       23652 weight  0.10000E+01 volume  0.14282E+03 ppm1        2.732 ppm2  3.358
ASSI {23672}
((segid "BrD" and resid 14 and name HA))
(segid "BrD" and resid 18 and name HD2 %)
3.300  2.700  2.200 peak       23672 weight  0.10000E+01 volume  0.64900E+02 ppm1        4.654 ppm2  0.409
ASSI {23712}
((segid "BrD" and resid 111 and name HA))
(segid "BrD" and resid 110 and name HG2 %)
2.400  1.400  1.400 peak       23712 weight  0.10000E+01 volume  0.44849E+03 ppm1        4.656 ppm2  1.246

TABLE 2-continued

Unambiguous NOE-derived Inter-proton Distance Restraints

```
ASSI {23732}
((segid "BrD" and resid 14 and name HB2))
(segid "BrD" and resid 14 and name HD2 %)
2.200  1.200 1.200 peak      23732 weight 0.10000E+01 volume  0.70287E+03 ppm1   2.142 ppm2 1.402
OR {23732}
((segid "BrD" and resid 14 and name HB2))
(segid "BrD" and resid 14 and name HD1 %)
ASSI {23762}
(segid "BrD" and resid 14 and name HD2 %)
((segid "BrD" and resid 70 and name HA))
3.100  2.400 2.400 peak      23762 weight 0.10000E+01 volume  0.94978E+02 ppm1   1.401 ppm2 5.359
ASSI {23802}
(segid "BrD" and resid 14 and name HD2 %)
((segid "BrD" and resid 15 and name HB1))
3.800  3.600 1.700 peak      23802 weight 0.10000E+01 volume  0.26555E+02 ppm1   1.401 ppm2 3.785
ASSI {23842}
(segid "BrD" and resid 14 and name HD2 %)
(segid "BrD" and resid 75 and name HE %)
2.600  1.700 1.700 peak      23842 weight 0.10000E+01 volume  0.23698E+03 ppm1   1.401 ppm2 2.619
ASSI {23882}
((segid "BrD" and resid 18 and name HA))
((segid "BrD" and resid 17 and name HB))
3.500  3.100 2.000 peak      23882 weight 0.10000E+01 volume  0.41356E+02 ppm1   3.867 ppm2 4.867
ASSI {23922}
((segid "BrD" and resid 18 and name HB1))
(segid "BrD" and resid 63 and name HD2 %)
3.900  3.800 1.600 peak      23922 weight 0.10000E+01 volume  0.21833E+02 ppm1   2.144 ppm2 1.492
ASSI {23972}
((segid "BrD" and resid 18 and name HB2))
(segid "BrD" and resid 74 and name HE %)
3.200  2.400 2.300 peak      23972 weight 0.10000E+01 volume  0.77951E+02 ppm1   0.911 ppm2 7.513
ASSI {23982}
((segid "BrD" and resid 18 and name HB2))
(segid "BrD" and resid 74 and name HD %)
3.700  3.400 1.800 peak      23982 weight 0.10000E+01 volume  0.32246E+02 ppm1   0.911 ppm2 7.014
ASSI {24022}
((segid "BrD" and resid 18 and name HG))
(segid "BrD" and resid 115 and name HD1 %)
4.500  4.500 2.000 peak      24022 weight 0.10000E+01 volume  0.94731E+01 ppm1   2.290 ppm2 1.317
ASSI {24032}
(segid "BrD" and resid 18 and name HD2 %)
((segid "BrD" and resid 75 and name HA))
3.400  2.900 2.100 peak      24032 weight 0.10000E+01 volume  0.52852E+02 ppm1   0.415 ppm2 4.541
ASSI {24202}
(segid "BrD" and resid 18 and name HD1 %)
((segid "BrD" and resid 17 and name HB))
3.900  3.800 1.600 peak      24202 weight 0.10000E+01 volume  0.21965E+02 ppm1   1.056 ppm2 4.859
ASSI {24232}
(segid "BrD" and resid 18 and name HD1 %)
((segid "BrD" and resid 15 and name HB1))
3.700  3.400 1.800 peak      24232 weight 0.10000E+01 volume  0.32596E+02 ppm1   1.056 ppm2 3.401
ASSI {24262}
(segid "BrD" and resid 18 and name HD1 %)
(segid "BrD" and resid 78 and name HD2 %)
3.500  3.100 2.000 peak      24262 weight 0.10000E+01 volume  0.41978E+02 ppm1   1.056 ppm2 0.676
ASSI {24272}
(segid "BrD" and resid 18 and name HD1 %)
((segid "BrD" and resid 69 and name HA))
3.400  2.900 2.100 peak      24272 weight 0.10000E+01 volume  0.49516E+02 ppm1   1.057 ppm2 4.692
ASSI {24302}
((segid "BrD" and resid 63 and name HA))
((segid "BrD" and resid 68 and name HB2))
3.300  2.700 2.200 peak      24302 weight 0.10000E+01 volume  0.61304E+02 ppm1   5.294 ppm2 3.557
ASSI {24452}
((segid "BrD" and resid 63 and name HG))
((segid "BrD" and resid 68 and name HB2))
3.400  2.900 2.100 peak      24452 weight 0.10000E+01 volume  0.51423E+02 ppm1   2.437 ppm2 3.516
ASSI {24462}
((segid "BrD" and resid 63 and name HG))
((segid "BrD" and resid 15 and name HA))
2.500  2.500 2.000 peak      24462 weight 0.10000E+01 volume  0.29838E+03 ppm1   2.437 ppm2 4.645
ASSI {24482}
(segid "BrD" and resid 63 and name HD1 %)
((segid "BrD" and resid 18 and name HA))
3.600  3.200 1.900 peak      24482 weight 0.10000E+01 volume  0.38413E+02 ppm1   1.645 ppm2 3.878
```

TABLE 2-continued

Unambiguous NOE-derived Inter-proton Distance Restraints

ASSI {24512}
(segid "BrD" and resid 63 and name HD1 %)
((segid "BrD" and resid 68 and name HB2))
2.900  2.100  2.100 peak      24512 weight  0.10000E+01 volume  0.12238E+03 ppm1      1.649 ppm2  3.527
ASSI {24542}
(segid "BrD" and resid 63 and name HD1 %)
(segid "BrD" and resid 74 and name HD %)
3.200  2.600  2.300 peak      24542 weight  0.10000E+01 volume  0.76917E+02 ppm1      1.648 ppm2  7.006
ASSI {24682}
((segid "BrD" and resid 19 and name HA))
(segid "BrD" and resid 22 and name HD2 %)
3.100  2.400  2.400 peak      24682 weight  0.10000E+01 volume  0.84277E+02 ppm1      4.311 ppm2  1.588
ASSI {24702}
((segid "BrD" and resid 19 and name HA))
((segid "BrD" and resid 19 and name HE1))
3.100  2.400  2.400 peak      24702 weight  0.10000E+01 volume  0.84024E+02 ppm1      4.310 ppm2  3.544
ASSI {24782}
((segid "BrD" and resid 19 and name HG1))
(segid "BrD" and resid 15 and name HE %)
3.300  2.700  2.200 peak      24782 weight  0.10000E+01 volume  0.57590E+02 ppm1      1.895 ppm2  7.487
ASSI {24832}
((segid "BrD" and resid 19 and name HD1))
(segid "BrD" and resid 15 and name HE %)
2.400  1.400  1.400 peak      24832 weight  0.10000E+01 volume  0.37891E+03 ppm1      2.191 ppm2  7.469
ASSI {24842}
((segid "BrD" and resid 19 and name HD1))
(segid "BrD" and resid 63 and name HD1 %)
2.200  2.200  2.300 peak      24842 weight  0.10000E+01 volume  0.74438E+03 ppm1      2.191 ppm2  1.654
ASSI {24882}
((segid "BrD" and resid 23 and name HG1))
((segid "BrD" and resid 19 and name HG1))
2.600  1.700  1.700 peak      24882 weight  0.10000E+01 volume  0.24553E+03 ppm1      3.124 ppm2  1.888
ASSI {24892}
((segid "BrD" and resid 23 and name HG2))
((segid "BrD" and resid 19 and name HG1))
2.500  1.600  1.600 peak      24892 weight  0.10000E+01 volume  0.29588E+03 ppm1      3.068 ppm2  1.888
ASSI {25012}
((segid "BrD" and resid 21 and name HB))
(segid "BrD" and resid 106 and name HD %)
2.400  1.400  1.400 peak      25012 weight  0.10000E+01 volume  0.42303E+03 ppm1      2.486 ppm2  7.519
ASSI {25022}
((segid "BrD" and resid 21 and name HG12))
(segid "BrD" and resid 106 and name HD %)
4.300  4.300  1.200 peak      25022 weight  0.10000E+01 volume  0.12393E+02 ppm1      1.648 ppm2  7.511
ASSI {25072}
((segid "BrD" and resid 21 and name HG12))
(segid "BrD" and resid 17 and name HG2 %)
2.800  2.000  2.000 peak      25072 weight  0.10000E+01 volume  0.15768E+03 ppm1      1.648 ppm2  1.746
ASSI {25082}
((segid "BrD" and resid 21 and name HG11))
(segid "BrD" and resid 17 and name HG2 %)
2.200  1.200  1.200 peak      25082 weight  0.10000E+01 volume  0.65857E+03 ppm1      2.336 ppm2  1.746
ASSI {25092}
((segid "BrD" and resid 21 and name HG11))
(segid "BrD" and resid 102 and name HD2 %)
3.800  3.600  1.700 peak      25092 weight  0.10000E+01 volume  0.25380E+02 ppm1      2.338 ppm2  1.322
OR {25092}
((segid "BrD" and resid 21 and name HG11))
(segid "BrD" and resid 102 and name HD1 %)
ASSI {25102}
((segid "BrD" and resid 21 and name HG12))
((segid "BrD" and resid 20 and name HB1))
3.300  2.700  2.200 peak      25102 weight  0.10000E+01 volume  0.61127E+02 ppm1      1.648 ppm2  4.647
ASSI {25132}
((segid "BrD" and resid 62 and name HG1))
((segid "BrD" and resid 62 and name HG2))
2.200  1.200  1.200 peak      25132 weight  0.10000E+01 volume  0.61439E+03 ppm1      2.336 ppm2  1.498
ASSI {25192}
(segid "BrD" and resid 21 and name HD1 %)
(segid "BrD" and resid 102 and name HD2 %)
2.800  2.000  2.000 peak      25192 weight  0.10000E+01 volume  0.17249E+03 ppm1      1.205 ppm2  1.312
ASSI {25202}
(segid "BrD" and resid 21 and name HD1 %)
((segid "BrD" and resid 18 and name HB2))
3.400  2.900  2.100 peak      25202 weight  0.10000E+01 volume  0.54202E+02 ppm1      1.205 ppm2  0.902

TABLE 2-continued

Unambiguous NOE-derived Inter-proton Distance Restraints

ASSI {25272}
(segid "BrD" and resid 21 and name HG2 %)
(segid "BrD" and resid 106 and name HE %)
2.800   2.000 2.000 peak        25272 weight  0.10000E+01 volume   0.17480E+03 ppm1    1.599 ppm2  7.638
ASSI {25302}
(segid "BrD" and resid 21 and name HG2 %)
((segid "BrD" and resid 82 and name HZ))
3.500   3.100 2.000 peak        25302 weight  0.10000E+01 volume   0.42795E+02 ppm1    1.599 ppm2  6.998
ASSI {25312}
(segid "BrD" and resid 101 and name HG2 %)
((segid "BrD" and resid 30 and name HA))
3.500   3.100 2.000 peak        25312 weight  0.10000E+01 volume   0.43138E+02 ppm1    1.599 ppm2  5.444
ASSI {25322}
((segid "BrD" and resid 101 and name HA))
((segid "BrD" and resid 100 and name HA))
3.400   2.900 2.100 peak        25322 weight  0.10000E+01 volume   0.52950E+02 ppm1    4.261 ppm2  4.948
ASSI {25332}
((segid "BrD" and resid 101 and name HA))
((segid "BrD" and resid 100 and name HB1))
3.100   2.400 2.400 peak        25332 weight  0.10000E+01 volume   0.82741E+02 ppm1    4.261 ppm2  3.475
ASSI {25342}
((segid "BrD" and resid 101 and name HB))
((segid "BrD" and resid 30 and name HB2))
3.200   2.600 2.300 peak        25342 weight  0.10000E+01 volume   0.74692E+02 ppm1    2.536 ppm2  4.525
ASSI {25352}
((segid "BrD" and resid 101 and name HB))
((segid "BrD" and resid 30 and name HB1))
2.900   2.100 2.100 peak        25352 weight  0.10000E+01 volume   0.14018E+03 ppm1    2.536 ppm2  4.932
ASSI {25362}
((segid "BrD" and resid 101 and name HB))
(segid "BrD" and resid 102 and name HD1 %)
3.500   3.100 2.000 peak        25362 weight  0.10000E+01 volume   0.47210E+02 ppm1    2.536 ppm2  1.311
ASSI {25382}
((segid "BrD" and resid 98 and name HA))
(segid "BrD" and resid 102 and name HD1 %)
5.100   5.100 0.400 peak        25382 weight  0.10000E+01 volume   0.46968E+01 ppm1    4.804 ppm2  1.311
ASSI {25402}
((segid "BrD" and resid 98 and name HA))
((segid "BrD" and resid 30 and name HA))
3.300   2.700 2.200 peak        25402 weight  0.10000E+01 volume   0.66772E+02 ppm1    4.804 ppm2  5.444
ASSI {25412}
((segid "BrD" and resid 98 and name HA))
(segid "BrD" and resid 34 and name HE %)
3.700   3.400 1.800 peak        25412 weight  0.10000E+01 volume   0.30316E+02 ppm1    4.804 ppm2  7.779
ASSI {25422}
((segid "BrD" and resid 98 and name HB1))
((segid "BrD" and resid 30 and name HB2))
2.900   2.100 2.100 peak        25422 weight  0.10000E+01 volume   0.12678E+03 ppm1    4.013 ppm2  4.933
ASSI {25442}
((segid "BrD" and resid 98 and name HB1))
((segid "BrD" and resid 30 and name HB2))
3.300   2.700 2.200 peak        25442 weight  0.10000E+01 volume   0.62906E+02 ppm1    4.015 ppm2  4.533
ASSI {25452}
((segid "BrD" and resid 85 and name HB2))
(segid "BrD" and resid 99 and name HB %)
2.500   1.600 1.600 peak        25452 weight  0.10000E+01 volume   0.29534E+03 ppm1    1.620 ppm2  2.206
ASSI {25462}
((segid "BrD" and resid 85 and name HB1))
(segid "BrD" and resid 99 and name HB %)
2.800   2.000 2.000 peak        25462 weight  0.10000E+01 volume   0.15410E+03 ppm1    3.916 ppm2  2.206
ASSI {25502}
((segid "BrD" and resid 98 and name HB2))
((segid "BrD" and resid 34 and name HZ))
2.900   2.100 2.100 peak        25502 weight  0.10000E+01 volume   0.12121E+03 ppm1    3.470 ppm2  7.893
ASSI {25512}
((segid "BrD" and resid 85 and name HB2))
(segid "BrD" and resid 34 and name HE %)
2.400   1.400 1.400 peak        25512 weight  0.10000E+01 volume   0.45042E+03 ppm1    3.620 ppm2  7.779
ASSI {25522}
((segid "BrD" and resid 85 and name HB1))
(segid "BrD" and resid 34 and name HE %)
2.500   1.600 1.600 peak        25522 weight  0.10000E+01 volume   0.32323E+03 ppm1    3.917 ppm2  7.778
ASSI {25562}
(segid "BrD" and resid 101 and name HD1 %)
((segid "BrD" and resid 30 and name HB2))
3.500   3.100 2.000 peak        25562 weight  0.10000E+01 volume   0.41073E+02 ppm1    1.551 ppm2  4.532

TABLE 2-continued

Unambiguous NOE-derived Inter-proton Distance Restraints

ASSI {25572}
(segid "BrD" and resid 101 and name HD1 %)
((segid "BrD" and resid 30 and name HB1))
3.000  2.200  2.200 peak    25572 weight  0.10000E+01 volume  0.10658E+03 ppm1   1.549 ppm2  4.932
ASSI {25582}
(segid "BrD" and resid 21 and name HG2 %)
(segid "BrD" and resid 18 and name HD2 %)
3.600  3.200  1.900 peak    25582 weight  0.10000E+01 volume  0.38225E+02 ppm1   1.599 ppm2  0.408
ASSI {25642}
(segid "BrD" and resid 21 and name HG2 %)
((segid "BrD" and resid 24 and name HG2))
3.600  3.200  1.900 peak    25642 weight  0.10000E+01 volume  0.38422E+02 ppm1   1.599 ppm2  3.069
ASSI {25652}
(segid "BrD" and resid 21 and name HG2 %)
((segid "BrD" and resid 109 and name HE2))
4.000  4.000  1.500 peak    25652 weight  0.10000E+01 volume  0.20266E+02 ppm1   1.599 ppm2  3.012
ASSI {25722}
(segid "BrD" and resid 21 and name HG2 %)
((segid "BrD" and resid 109 and name HB2))
2.700  1.800  1.800 peak    25722 weight  0.10000E+01 volume  0.18743E+03 ppm1   1.599 ppm2  2.157
ASSI {25752}
(segid "BrD" and resid 101 and name HD1 %)
((segid "BrD" and resid 102 and name HB1))
3.100  2.400  2.400 peak    25752 weight  0.10000E+01 volume  0.84468E+02 ppm1   1.549 ppm2  1.970
ASSI {25812}
((segid "BrD" and resid 110 and name HB))
(segid "BrD" and resid 116 and name HD1 %)
2.300  1.300  1.300 peak    25812 weight  0.10000E+01 volume  0.55301E+03 ppm1   2.338 ppm2  1.410
ASSI {25822}
(segid "BrD" and resid 110 and name HG1 %)
(segid "BrD" and resid 78 and name HD2 %)
4.000  4.000  1.500 peak    25822 weight  0.10000E+01 volume  0.19996E+02 ppm1   1.697 ppm2  0.676
ASSI {25842}
(segid "BrD" and resid 110 and name HD1 %)
((segid "BrD" and resid 75 and name HA))
3.100  2.400  2.400 peak    25842 weight  0.10000E+01 volume  0.86474E+02 ppm1   1.154 ppm2  4.511
ASSI {25852}
(segid "BrD" and resid 110 and name HG2 %)
((segid "BrD" and resid 114 and name HA1))
4.200  4.200  1.300 peak    25852 weight  0.10000E+01 volume  0.14960E+02 ppm1   1.254 ppm2  4.569
ASSI {25952}
(segid "BrD" and resid 110 and name HG2 %)
(segid "BrD" and resid 107 and name HD %)
3.200  2.600  4.300 peak    25952 weight  0.10000E+01 volume  0.71378E+02 ppm1   1.251 ppm2  7.789
ASSI {26002}
(segid "BrD" and resid 110 and name HD1 %)
(segid "BrD" and resid 106 and name HE %)
2.500  1.600  1.600 peak    26002 weight  0.10000E+01 volume  0.29658E+03 ppm1   1.155 ppm2  7.638
ASSI {26012}
(segid "BrD" and resid 110 and name HD1 %)
(segid "BrD" and resid 106 and name HD %)
2.700  1.800  1.800 peak    26012 weight  0.10000E+01 volume  0.22034E+03 ppm1   1.155 ppm2  7.529
ASSI {26082}
(segid "BrD" and resid 110 and name HD1 %)
((segid "BrD" and resid 114 and name HB1))
2.300  1.300  1.300 peak    26082 weight  0.10000E+01 volume  0.31139E+03 ppm1   1.154 ppm2  2.182
ASSI {26092}
(segid "BrD" and resid 110 and name HG2 %)
((segid "BrD" and resid 111 and name HB1))
3.400  2.900  3.100 peak    26092 weight  0.10000E+01 volume  0.52641E+02 ppm1   3.254 ppm2  2.493
ASSI {26122}
(segid "BrD" and resid 110 and name HG2 %)
(segid "BrD" and resid 116 and name HG1 %)
3.700  3.400  1.800 peak    26122 weight  0.10000E+01 volume  0.30456E+02 ppm1   1.254 ppm2  1.918
ASSI {26132}
(segid "BrD" and resid 110 and name HD1 %)
(segid "BrD" and resid 116 and name HG1 %)
3.300  2.700  2.200 peak    26132 weight  0.10000E+01 volume  0.58180E+02 ppm1   1.154 ppm2  1.918
ASSI {26142}
(segid "BrD" and resid 110 and name HD1 %)
(segid "BrD" and resid 113 and name HB %)
2.400  1.400  1.400 peak    26142 weight  0.10000E+01 volume  0.40630E+03 ppm1   1.154 ppm2  1.978
ASSI {26212}
(segid "BrD" and resid 116 and name HG2 %)
((segid "BrD" and resid 117 and name HA))
4.200  4.200  1.300 peak    26212 weight  0.10000E+01 volume  0.13762E+02 ppm1   1.401 ppm2  5.168

TABLE 2-continued

Unambiguous NOE-derived Inter-proton Distance Restraints

ASSI {26222}
(segid "BrD" and resid 116 and name HG2 %)
((segid "BrD" and resid 79 and name HB2))
3.200   2.600 2.300 peak      26222 weight  0.10000E+01 volume   0.79045E+02 ppm1    1.401 ppm2  2.662
ASSI {26242}
(segid "BrD" and resid 116 and name HG2 %)
((segid "BrD" and resid 115 and name HB1))
3.800   3.600 1.700 peak      26242 weight  0.10000E+01 volume   0.25845E+02 ppm1    1.401 ppm2  2.175
ASSI {26252}
(segid "BrD" and resid 116 and name HG2 %)
(segid "BrD" and resid 116 and name HG1 %)
2.700   1.800 1.800 peak      26252 weight  0.10000E+01 volume   0.22212E+03 ppm1    1.401 ppm2  1.906
ASSI {26262}
(segid "BrD" and resid 116 and name HG2 %)
(segid "BrD" and resid 110 and name HD1 %)
2.400   2.400 2.100 peak      26262 weight  0.10000E+01 volume   0.45578E+03 ppm1    1.401 ppm2  1.140
ASSI {26322}
(segid "BrD" and resid 116 and name HD1 %)
((segid "BrD" and resid 107 and name HA))
3.200   2.600 2.300 peak      26322 weight  0.10000E+01 volume   0.76194E+02 ppm1    1.401 ppm2  4.427
ASSI {26372}
(segid "BrD" and resid 116 and name HD1 %)
((segid "BrD" and resid 75 and name HG1))
3.200   2.600 2.300 peak      26372 weight  0.10000E+01 volume   0.79388E+02 ppm1    1.401 ppm2  3.508
ASSI {26382}
(segid "BrD" and resid 116 and name HD1 %)
((segid "BrD" and resid 79 and name HB2))
3.400   2.900 2.100 peak      26382 weight  0.10000E+01 volume   0.54400E+02 ppm1    1.401 ppm2  2.662
ASSI {26402}
(segid "BrD" and resid 116 and name HD1 %)
((segid "BrD" and resid 110 and name HG11))
2.600   1.700 1.700 peak      26402 weight  0.10000E+01 volume   0.24061E+03 ppm1    1.401 ppm2  1.718
ASSI {26412}
(segid "BrD" and resid 116 and name HD1 %)
((segid "BrD" and resid 110 and name HG12))
2.100   1.100 1.100 peak      26412 weight  0.10000E+01 volume   0.93798E+03 ppm1    1.401 ppm2  1.637
ASSI {26432}
(segid "BrD" and resid 116 and name HD1 %)
((segid "BrD" and resid 78 and name HB2))
2.400   2.400 2.100 peak      26432 weight  0.10000E+01 volume   0.39159E+03 ppm1    1.399 ppm2  1.078
ASSI {26472}
(segid "BrD" and resid 116 and name HD1 %)
(segid "BrD" and resid 78 and name HD2 %)
4.900   4.900 0.600 peak      26472 weight  0.10000E+01 volume   0.55118E+01 ppm1    1.399 ppm2  0.680
ASSI {26482}
(segid "BrD" and resid 116 and name HD1 %)
(segid "BrD" and resid 110 and name HG2 %)
2.000   1.000 1.000 peak      26482 weight  0.10000E+01 volume   0.13707E+04 ppm1    1.399 ppm2  1.237
ASSI {26502}
(segid "BrD" and resid 63 and name HD2 %)
((segid "BrD" and resid 60 and name HA))
2.300   1.300 1.300 peak      26502 weight  0.10000E+01 volume   0.60749E+03 ppm1    1.501 ppm2  4.828
ASSI {26522}
((segid "BrD" and resid 116 and name HB))
((segid "BrD" and resid 115 and name HB1))
4.400   4.400 1.100 peak      26522 weight  0.10000E+01 volume   0.11059E+02 ppm1    2.432 ppm2  2.200
ASSI {26532}
((segid "BrD" and resid 116 and name HB))
(segid "BrD" and resid 110 and name HG2 %)
3.600   3.200 1.900 peak      26532 weight  0.10000E+01 volume   0.35446E+02 ppm1    2.409 ppm2  1.263
ASSI {26542}
((segid "BrD" and resid 116 and name HB))
(segid "BrD" and resid 110 and name HD1 %)
3.300   2.700 2.200 peak      26542 weight  0.10000E+01 volume   0.65125E+02 ppm1    2.409 ppm2  1.149
ASSI {26682}
((segid "BrD" and resid 103 and name HG2))
((segid "BrD" and resid 104 and name HA))
3.300   2.700 2.200 peak      26682 weight  0.10000E+01 volume   0.56609E+02 ppm1    2.519 ppm2  4.679
ASSI {26692}
((segid "BrD" and resid 94 and name HG1))
((segid "BrD" and resid 93 and name HB1))
5.400   5.400 0.100 peak      26692 weight  0.10000E+01 volume   0.32972E+01 ppm1    3.127 ppm2  5.038
OR {26692}
((segid "BrD" and resid 94 and name HG1))
((segid "BrD" and resid 93 and name HA))

TABLE 2-continued

Unambiguous NOE-derived Inter-proton Distance Restraints

ASSI {26702}
((segid "BrD" and resid 94 and name HG1))
((segid "BrD" and resid 95 and name HA))
3.700  3.400  1.800 peak      26702  weight  0.10000E+01 volume  0.33522E+02 ppm1      3.132 ppm2  4.448
ASSI {26752}
((segid "BrD" and resid 94 and name HG1))
((segid "BrD" and resid 97 and name HD1))
2.600  1.700  1.700 peak      26752  weight  0.10000E+01 volume  0.26306E+03 ppm1      3.127 ppm2  2.401
ASSI {26872}
((segid "BrD" and resid 86 and name HD1))
((segid "BrD" and resid 87 and name HG1))
2.700  1.800  1.800 peak      26872  weight  0.10000E+01 volume  0.22393E+03 ppm1      1.892 ppm2  3.028
ASSI {26902}
((segid "BrD" and resid 36 and name HG1))
((segid "BrD" and resid 57 and name HG2))
3.500  3.100  2.000 peak      26902  weight  0.10000E+01 volume  0.44296E+02 ppm1      2.781 ppm2  2.003
ASSI {26922}
((segid "BrD" and resid 37 and name HB1))
((segid "BrD" and resid 54 and name HA))
4.000  4.000  1.500 peak      26922  weight  0.10000E+01 volume  0.19758E+02 ppm1      2.930 ppm2  5.542
ASSI {26952}
((segid "BrD" and resid 37 and name HG1))
((segid "BrD" and resid 36 and name HA))
5.300  5.300  0.200 peak      26952  weight  0.10000E+01 volume  0.36066E+01 ppm1      2.733 ppm2  5.444
ASSI {26962}
((segid "BrD" and resid 112 and name HG2))
((segid "BrD" and resid 111 and name HG2))
3.400  2.900  2.100 peak      26962  weight  0.10000E+01 volume  0.56268E+02 ppm1      2.815 ppm2  1.898
ASSI {26972}
((segid "BrD" and resid 61 and name HB2))
(segid "BrD" and resid 58 and name HG2 %)
3.000  2.200  2.200 peak      26972  weight  0.10000E+01 volume  0.11517E+03 ppm1      2.684 ppm2  1.644
ASSI {27022}
((segid "BrD" and resid 89 and name HA))
((segid "BrD" and resid 93 and name HB2))
3.700  3.400  1.800 peak      27022  weight  0.10000E+01 volume  0.31951E+02 ppm1      5.642 ppm2  4.745
ASSI {27032}
((segid "BrD" and resid 89 and name HB1))
((segid "BrD" and resid 96 and name HB2))
3.300  2.700  2.200 peak      27032  weight  0.10000E+01 volume  0.59751E+02 ppm1      3.669 ppm2  3.117
ASSI {27082}
((segid "BrD" and resid 100 and name HB2))
(segid "BrD" and resid 101 and name HD1 %)
4.000  4.000  1.500 peak      27082  weight  0.10000E+01 volume  0.18249E+02 ppm1      3.421 ppm2  1.572
OR {27082}
((segid "BrD" and resid 100 and name HB2))
(segid "BrD" and resid 101 and name HG2 %)
ASSI {27092}
((segid "BrD" and resid 100 and name HB2))
((segid "BrD" and resid 101 and name HA))
4.000  4.000  1.500 peak      27092  weight  0.10000E+01 volume  0.18330E+02 ppm1      3.423 ppm2  4.265
ASSI {27102}
((segid "BrD" and resid 100 and name HB2))
((segid "BrD" and resid 101 and name HG11))
2.700  1.800  1.800 peak      27102  weight  0.10000E+01 volume  0.20958E+03 ppm1      3.423 ppm2  2.658
ASSI {27112}
((segid "BrD" and resid 100 and name HB2))
(segid "BrD" and resid 99 and name HB %)
3.400  2.900  2.100 peak      27112  weight  0.10000E+01 volume  0.49005E+02 ppm1      3.423 ppm2  2.206
ASSI {27142}
((segid "BrD" and resid 80 and name HD1))
((segid "BrD" and resid 77 and name HA))
3.100  2.400  2.400 peak      27142  weight  0.10000E+01 volume  0.85246E+02 ppm1      3.962 ppm2  4.963
ASSI {27172}
((segid "BrD" and resid 80 and name HD2))
((segid "BrD" and resid 84 and name HB2))
4.100  4.100  1.400 peak      27172  weight  0.10000E+01 volume  0.16098E+02 ppm1      3.913 ppm2  3.276
ASSI {27192}
((segid "BrD" and resid 80 and name HD2))
((segid "BrD" and resid 83 and name HB))
3.400  2.900  2.100 peak      27192  weight  0.10000E+01 volume  0.47687E+02 ppm1      3.912 ppm2  4.808
ASSI {27202}
((segid "BrD" and resid 80 and name HD2))
((segid "BrD" and resid 52 and name HA))
3.900  3.800  1.600 peak      27202  weight  0.10000E+01 volume  0.23078E+02 ppm1      3.902 ppm2  5.583

TABLE 2-continued

Unambiguous NOE-derived Inter-proton Distance Restraints

ASSI {27322}
((segid "BrD" and resid 56 and name HG))
(segid "BrD" and resid 81 and name HG1 %)
3.400  2.900  2.100 peak        27322 weight  0.10000E+01 volume  0.49600E+02 ppm1       2.339 ppm2  1.079
ASSI {27342}
((segid "BrD" and resid 55 and name HB1))
((segid "BrD" and resid 34 and name HA))
3.300  2.700  2.200 peak        27342 weight  0.10000E+01 volume  0.66937E+02 ppm1       2.979 ppm2  5.539
ASSI {27362}
((segid "BrD" and resid 55 and name HB1))
(segid "BrD" and resid 81 and name HG1 %)
3.900  3.800  1.600 peak        27362 weight  0.10000E+01 volume  0.24126E+02 ppm1       2.979 ppm2  1.075
ASSI {27372}
((segid "BrD" and resid 38 and name HA))
((segid "BrD" and resid 39 and name HA))
3.600  3.100  2.000 peak        27372 weight  0.10000E+01 volume  0.46121E+02 ppm1       4.163 ppm2  4.972
ASSI {27392}
((segid "BrD" and resid 55 and name HB1))
((segid "BrD" and resid 36 and name HA))
3.400  2.900  2.100 peak        27392 weight  0.10000E+01 volume  0.54954E+02 ppm1       2.979 ppm2  5.442
ASSI {27442}
(segid "BrD" and resid 69 and name HG1 %)
(segid "BrD" and resid 18 and name HD1 %)
2.400  2.400  2.100 peak        27442 weight  0.10000E+01 volume  0.37353E+03 ppm1       1.547 ppm2  1.091
ASSI {27452}
(segid "BrD" and resid 22 and name HD2 %)
(segid "BrD" and resid 25 and name HG1 %)
2.500  1.600  1.600 peak        27452 weight  0.10000E+01 volume  0.30318E+03 ppm1       1.599 ppm2  1.788
ASSI {27472}
(segid "BrD" and resid 22 and name HD2 %)
((segid "BrD" and resid 25 and name HB))
3.400  2.900  2.100 peak        27472 weight  0.10000E+01 volume  0.54052E+02 ppm1       1.599 ppm2  3.003
ASSI {27492}
(segid "BrD" and resid 22 and name HD2 %)
((segid "BrD" and resid 60 and name HA))
2.300  1.300  1.300 peak        27492 weight  0.10000E+01 volume  0.56630E+03 ppm1       1.599 ppm2  4.809
ASSI {27552}
(segid "BrD" and resid 22 and name HD2 %)
(segid "BrD" and resid 74 and name HE %)
2.300  2.300  2.200 peak        27552 weight  0.10000E+01 volume  0.54070E+03 ppm1       1.599 ppm2  7.529
ASSI {27572}
(segid "BrD" and resid 22 and name HD1 %)
((segid "BrD" and resid 60 and name HB1))
3.200  2.600  2.300 peak        27572 weight  0.10000E+01 volume  0.80681E+02 ppm1       1.645 ppm2  4.990
ASSI {27582}
(segid "BrD" and resid 22 and name HD1 %)
(segid "BrD" and resid 74 and name HE %)
3.200  1.200  1.200 peak        27582 weight  0.10000E+01 volume  0.62438E+03 ppm1       1.646 ppm2  7.529
ASSI {27632}
(segid "BrD" and resid 73 and name HD1 %)
((segid "BrD" and resid 68 and name HA))
2.500  1.600  1.600 peak        27632 weight  0.10000E+01 volume  0.31070E+03 ppm1       1.549 ppm2  5.143
ASSI {27662}
(segid "BrD" and resid 73 and name HD1 %)
((segid "BrD" and resid 70 and name HB2))
3.100  2.400  2.400 peak        27662 weight  0.10000E+01 volume  0.86052E+02 ppm1       1.549 ppm2  4.362
ASSI {27692}
(segid "BrD" and resid 73 and name HD2 %)
(segid "BrD" and resid 76 and name HB %)
2.800  2.000  2.000 peak        27692 weight  0.10000E+01 volume  0.17686E+03 ppm1       1.500 ppm2  2.106
ASSI {27712}
((segid "BrD" and resid 35 and name HA))
((segid "BrD" and resid 56 and name HB2))
2.100  1.100  1.100 peak        27712 weight  0.10000E+01 volume  0.10158E+04 ppm1       4.900 ppm2  2.004
ASSI {27722}
((segid "BrD" and resid 48 and name HA))
(segid "BrD" and resid 49 and name HG1 %)
3.000  2.200  2.200 peak        27722 weight  0.10000E+01 volume  0.11137E+03 ppm1       4.803 ppm2  1.652
ASSI {27772}
((segid "BrD" and resid 73 and name HB2))
((segid "BrD" and resid 70 and name HB2))
3.400  2.900  2.100 peak        27772 weight  0.10000E+01 volume  0.55069E+02 ppm1       2.487 ppm2  4.377
ASSI {27822}
((segid "BrD" and resid 78 and name HA))
((segid "BrD" and resid 77 and name HB1))
3.800  3.600  1.700 peak        27822 weight  0.10000E+01 volume  0.26285E+02 ppm1       3.967 ppm2  3.312

TABLE 2-continued

Unambiguous NOE-derived Inter-proton Distance Restraints

ASSI {27842}
((segid "BrD" and resid 78 and name HB2))
((segid "BrD" and resid 116 and name HG11))
3.700  3.400  1.800 peak      27842  weight  0.10000E+01 volume  0.31985E+02 ppm1     1.056 ppm2  1.954
ASSI {27872}
((segid "BrD" and resid 78 and name HB2))
((segid "BrD" and resid 79 and name HA))
4.100  4.100  1.400 peak      27872  weight  0.10000E+01 volume  0.17221E+02 ppm1     1.056 ppm2  4.411
ASSI {27882}
((segid "BrD" and resid 78 and name HG))
((segid "BrD" and resid 75 and name HA))
5.500  5.500  0.000 peak      27882  weight  0.10000E+01 volume  0.22274E+01 ppm1     1.254 ppm2  4.509
ASSI {27892}
((segid "BrD" and resid 78 and name HG))
((segid "BrD" and resid 82 and name HZ))
2.500  2.500  2.000 peak      27892  weight  0.10000E+01 volume  0.30077E+03 ppm1     1.254 ppm2  7.047
OR {27892}
((segid "BrD" and resid 78 and name HG))
(segid "BrD" and resid 82 and name HE %)
ASSI {27912}
((segid "BrD" and resid 78 and name HB2))
(segid "BrD" and resid 106 and name HD %)
3.600  3.200  1.900 peak      27912  weight  0.10000E+01 volume  0.34865E+02 ppm1     1.056 ppm2  7.532
ASSI {27942}
(segid "BrD" and resid 78 and name HD1 %)
(segid "BrD" and resid 106 and name HE %)
2.600  1.700  1.700 peak      27942  weight  0.10000E+01 volume  0.24618E+03 ppm1     0.760 ppm2  7.635
ASSI {27982}
(segid "BrD" and resid 78 and name HD2 %)
(segid "BrD" and resid 106 and name HD %)
2.200  1.200  1.200 peak      27982  weight  0.10000E+01 volume  0.76393E+03 ppm1     0.662 ppm2  7.528
ASSI {27992}
(segid "BrD" and resid 78 and name HD2 %)
((segid "BrD" and resid 83 and name HZ))
2.100  1.100  1.100 peak      27992  weight  0.10000E+01 volume  0.83417E+03 ppm1     0.662 ppm2  7.031
OR {27992}
(segid "BrD" and resid 78 and name HD2 %)
(segid "BrD" and resid 82 and name HE %)
ASSI {28012}
(segid "BrD" and resid 78 and name HD2 %)
(segid "BrD" and resid 106 and name HE %)
2.900  2.100  2.100 peak      28012  weight  0.10000E+01 volume  0.14234E+03 ppm1     0.662 ppm2  7.637
ASSI {28032}
(segid "BrD" and resid 78 and name HD1 %)
((segid "BrD" and resid 22 and name HA))
3.500  3.100  2.000 peak      28032  weight  0.10000E+01 volume  0.43609E+02 ppm1     0.761 ppm2  4.727
ASSI {28062}
(segid "BrD" and resid 78 and name HD1 %)
((segid "BrD" and resid 75 and name HA))
3.500  3.100  2.000 peak      28062  weight  0.10000E+01 volume  0.46405E+02 ppm1     0.761 ppm2  4.525
ASSI {28102}
(segid "BrD" and resid 78 and name HD1 %)
((segid "BrD" and resid 106 and name HB1))
4.700  4.700  0.800 peak      28102  weight  0.10000E+01 volume  0.77501E+01 ppm1     0.761 ppm2  3.918
ASSI {28122}
(segid "BrD" and resid 78 and name HD2 %)
((segid "BrD" and resid 106 and name HB2))
2.900  2.100  2.100 peak      28122  weight  0.10000E+01 volume  0.14435E+03 ppm1     0.662 ppm2  3.703
ASSI {28132}
(segid "BrD" and resid 78 and name HD2 %)
((segid "BrD" and resid 106 and name HB1))
2.900  2.100  2.100 peak      28132  weight  0.10000E+01 volume  0.12278E+03 ppm1     0.662 ppm2  3.919
ASSI {28192}
(segid "BrD" and resid 78 and name HD1 %)
((segid "BrD" and resid 81 and name HB))
2.700  1.800  1.800 peak      28192  weight  0.10000E+01 volume  0.18524E+03 ppm1     0.760 ppm2  2.043
ASSI {28202}
(segid "BrD" and resid 78 and name HD1 %)
(segid "BrD" and resid 22 and name HD2 %)
2.500  1.600  1.600 peak      28202  weight  0.10000E+01 volume  0.29008E+03 ppm1     0.761 ppm2  1.590
ASSI {28232}
(segid "BrD" and resid 78 and name HD1 %)
(segid "BrD" and resid 18 and name HD2 %)
3.300  2.700  2.200 peak      28232  weight  0.10000E+01 volume  0.64808E+02 ppm1     0.760 ppm2  0.424

TABLE 2-continued

Unambiguous NOE-derived Inter-proton Distance Restraints

```
ASSI {28262}
(segid "BrD" and resid 56 and name HD2 %)
(segid "BrD" and resid 74 and name HE %)
4.100  4.100 1.400 peak      28262  weight  0.10000E+01  volume  0.17777E+02 ppm1    1.254 ppm2  7.534
ASSI {28272}
(segid "BrD" and resid 56 and name HD2 %)
(segid "BrD" and resid 82 and name HE %)
3.400  2.900 2.100 peak      28272  weight  0.10000E+01  volume  0.54803E+02 ppm1    1.253 ppm2  7.041
OR {28272}
(segid "BrD" and resid 56 and name HD2 %)
((segid "BrD" and resid 82 and name HZ))
ASSI {28292}
(segid "BrD" and resid 56 and name HD2 %)
((segid "BrD" and resid 55 and name HA))
3.500  3.100 2.000 peak      28292  weight  0.10000E+01  volume  0.41030E+02 ppm1    1.254 ppm2  5.371
ASSI {28322}
(segid "BrD" and resid 56 and name HD2 %)
((segid "BrD" and resid 26 and name HA))
3.100  2.400 2.400 peak      28322  weight  0.10000E+01  volume  0.83493E+02 ppm1    1.254 ppm2  4.509
ASSI {28342}
(segid "BrD" and resid 56 and name HD2 %)
((segid "BrD" and resid 22 and name HA))
3.000  2.200 2.200 peak      28342  weight  0.10000E+01  volume  0.99805E+02 ppm1    1.251 ppm2  4.733
ASSI {28352}
(segid "BrD" and resid 56 and name HD2 %)
((segid "BrD" and resid 78 and name HA))
3.800  3.600 1.700 peak      28352  weight  0.10000E+01  volume  0.27666E+02 ppm1    1.254 ppm2  3.996
ASSI {28372}
(segid "BrD" and resid 56 and name HD2 %)
((segid "BrD" and resid 25 and name HB))
3.500  3.100 2.000 peak      28372  weight  0.10000E+01  volume  0.41722E+02 ppm1    1.254 ppm2  3.003
ASSI {28402}
((segid "BrD" and resid 56 and name HB1))
((segid "BrD" and resid 35 and name HG1))
3.800  3.600 1.700 peak      28402  weight  0.10000E+01  volume  0.28628E+02 ppm1    2.684 ppm2  3.451
ASSI {28412}
((segid "BrD" and resid 56 and name HB2))
((segid "BrD" and resid 35 and name HG1))
4.000  4.000 1.500 peak      28412  weight  0.10000E+01  volume  0.20241E+02 ppm1    1.993 ppm2  3.443
ASSI {28442}
((segid "BrD" and resid 102 and name HB1))
(segid "BrD" and resid 82 and name HE %)
2.900  2.100 2.100 peak      28442  weight  0.10000E+01  volume  0.13708E+03 ppm1    1.993 ppm2  7.064
ASSI {28472}
((segid "BrD" and resid 102 and name HB2))
(segid "BrD" and resid 34 and name HE %)
3.200  2.600 2.300 peak      28472  weight  0.10000E+01  volume  0.70904E+02 ppm1    $$ ppm2  7.774
ASSI {28502}
((segid "BrD" and resid 102 and name HB2))
(segid "BrD" and resid 81 and name HG2 %)
3.600  3.200 1.900 peak      28502  weight  0.10000E+01  volume  0.34445E+02 ppm1    $$ ppm2  0.766
ASSI {28532}
((segid "BrD" and resid 102 and name HG))
(segid "BrD" and resid 82 and name HE %)
2.500  1.600 1.600 peak      28532  weight  0.10000E+01  volume  0.29286E+03 ppm1    2.141 ppm2  7.041
ASSI {28562}
(segid "BrD" and resid 102 and name HD2 %)
(segid "BrD" and resid 82 and name HD %)
3.600  3.200 1.900 peak      28562  weight  0.10000E+01  volume  0.38923E+02 ppm1    1.303 ppm2  7.245
ASSI {28582}
(segid "BrD" and resid 102 and name HD2 %)
(segid "BrD" and resid 106 and name HD %)
3.100  2.400 2.400 peak      28582  weight  0.10000E+01  volume  0.86642E+02 ppm1    1.303 ppm2  7.514
ASSI {28622}
(segid "BrD" and resid 102 and name HD2 %)
((segid "BrD" and resid 28 and name HD2))
3.100  2.400 2.400 peak      28622  weight  0.10000E+01  volume  0.83600E+02 ppm1    1.303 ppm2  5.553
ASSI {28632}
(segid "BrD" and resid 102 and name HD2 %)
((segid "BrD" and resid 106 and name HA))
2.800  2.000 2.000 peak      28632  weight  0.10000E+01  volume  0.15974E+03 ppm1    1.303 ppm2  4.525
ASSI {28642}
(segid "BrD" and resid 102 and name HD2 %)
((segid "BrD" and resid 21 and name HA))
3.500  3.100 2.000 peak      28642  weight  0.10000E+01  volume  0.44750E+02 ppm1    1.303 ppm2  4.354
```

TABLE 2-continued

| Unambiguous NOE-derived Inter-proton Distance Restraints |
|---|

ASSI {28662}
(segid "BrD" and resid 102 and name HD1 %)
((segid "BrD" and resid 28 and name HD2))
3.200  2.600 2.300 peak      28662 weight  0.10000E+01 volume  0.73306E+02 ppm1   1.303 ppm2  5.574
ASSI {28702}
(segid "BrD" and resid 102 and name HD2 %)
((segid "BrD" and resid 106 and name HB1))
3.600  3.200 1.900 peak      28702 weight  0.10000E+01 volume  0.36289E+02 ppm1   1.303 ppm2  3.882
ASSI {28722}
(segid "BrD" and resid 102 and name HD2 %)
((segid "BrD" and resid 21 and name HB))
3.200  2.600 2.300 peak      28722 weight  0.10000E+01 volume  0.68526E+02 ppm1   1.305 ppm2  2.473
ASSI {28752}
(segid "BrD" and resid 102 and name HD2 %)
(segid "BrD" and resid 78 and name HD2 %)
3.400  2.900 2.100 peak      28752 weight  0.10000E+01 volume  0.55554E+02 ppm1   1.303 ppm2  0.676
ASSI {28782}
(segid "BrD" and resid 115 and name HD1 %)
(segid "BrD" and resid 17 and name HG2 %)
2.200  1.200 1.200 peak      28782 weight  0.10000E+01 volume  0.67664E+02 ppm1   1.352 ppm2  1.750
ASSI {28792}
(segid "BrD" and resid 66 and name HG2 %)
((segid "BrD" and resid 65 and name HA))
3.000  2.200 2.200 peak      28792 weight  0.10000E+01 volume  0.10599E+03 ppm1   2.141 ppm2  5.395
ASSI {28812}
(segid "BrD" and resid 115 and name HB1 %)
((segid "BrD" and resid 110 and name HA))
2.400  1.400 1.400 peak      28812 weight  0.10000E+01 volume  0.45932E+03 ppm1   2.190 ppm2  4.419
ASSI {28822}
((segid "BrD" and resid 115 and name HG)
((segid "BrD" and resid 110 and name HA))
2.800  2.000 2.000 peak      28822 weight  0.10000E+01 volume  0.18123E+03 ppm1   2.139 ppm2  4.426
ASSI {28842}
((segid "BrD" and resid 115 and name HG))
(segid "BrD" and resid 110 and name HA)
2.800  2.000 2.000 peak      28842 weight  0.10000E+01 volume  0.18123E+03 ppm1   2.139 ppm2  1.140
ASSI {28852}
(segid "BrD" and resid 115 and name HB1 %)
(segid "BrD" and resid 113 and name HB %)
3.600  3.200 1.900 peak      28852 weight  0.10000E+01 volume  0.39467E+02 ppm1   2.190 ppm2  1.978
ASSI {28872}
(segid "BrD" and resid 115 and name HB1 %)
((segid "BrD" and resid 110 and name HG12))
2.600  2.600 1.900 peak      28872 weight  0.10000E+01 volume  0.26332E+03 ppm1   2.190 ppm2  1.661
ASSI {28882}
(segid "BrD" and resid 115 and name HB1 %)
(segid "BrD" and resid 116 and name HD1 %)
2.200  1.200 1.200 peak      28882 weight  0.10000E+01 volume  0.69706E+03 ppm1   2.188 ppm2  1.424
OR {28882}
(segid "BrD" and resid 115 and name HB1 %)
(segid "BrD" and resid 116 and name HG2 %)
ASSI {28892}
(segid "BrD" and resid 115 and name HB1 %)
((segid "BrD" and resid 116 and name HG12))
4.000  4.000 1.600 peak      28892 weight  0.10000E+01 volume  0.19745E+02 ppm1   2.188 ppm2  1.583
ASSI {28912}
((segid "BrD" and resid 115 and name HA))
(segid "BrD" and resid 110 and name HG2 %)
3.400  2.900 2.100 peak      28912 weight  0.10000E+01 volume  0.51456E+02 ppm1   4.807 ppm2  1.263
ASSI {28932}
(segid "BrD" and resid 56 and name HD1 %)
((segid "BrD" and resid 35 and name HG1))
3.600  3.200 1.900 peak      28932 weight  0.10000E+01 volume  0.33849E+02 ppm1   1.549 ppm2  3.451
ASSI {28942}
(segid "BrD" and resid 56 and name HD1 %)
((segid "BrD" and resid 35 and name HG1))
2.800  2.000 2.000 peak      28942 weight  0.10000E+01 volume  0.16319E+03 ppm1   1.548 ppm2  4.900
ASSI {29012}
(segid "BrD" and resid 59 and name HE %)
((segid "BrD" and resid 81 and name HB))
2.500  2.500 2.000 peak      29012 weight  0.10000E+01 volume  0.32346E+03 ppm1   1.848 ppm2  2.018
ASSI {29042}
(segid "BrD" and resid 59 and name HE %)
((segid "BrD" and resid 54 and name HB2))
1.800  1.800 2.700 peak      29042 weight  0.10000E+01 volume  0.22344E+04 ppm1   1.848 ppm2  1.944

TABLE 2-continued

Unambiguous NOE-derived Inter-proton Distance Restraints

ASSI {29052}
(segid "BrD" and resid 59 and name HE %)
((segid "BrD" and resid 74 and name HB2))
3.900  3.800 1.600 peak     29052 weight 0.10000E+01 volume  0.23714E+02 ppm1      $$ ppm2 3.002
ASSI {29132}
(segid "BrD" and resid 59 and name HE %)
((segid "BrD" and resid 77 and name HA))
3.600  3.200 1.900 peak     29132 weight 0.10000E+01 volume  0.36305E+02 ppm1   1.847 ppm2 4.966
ASSI {29142}
(segid "BrD" and resid 59 and name HE %)
((segid "BrD" and resid 75 and name HA))
4.500  4.500 1.000 peak     29142 weight 0.10000E+01 volume  0.98620E+01 ppm1   1.847 ppm2 4.516
ASSI {29172}
(segid "BrD" and resid 54 and name HE %)
((segid "BrD" and resid 58 and name HA))
3.500  3.100 2.000 peak     29172 weight 0.10000E+01 volume  0.40557E+02 ppm1   2.536 ppm2 4.468
ASSI {29222}
(segid "BrD" and resid 54 and name HE %)
((segid "BrD" and resid 57 and name HB2))
2.800  2.000 2.000 peak     29222 weight 0.10000E+01 volume  0.17311E+03 ppm1   2.536 ppm2 2.881
ASSI {29232}
(segid "BrD" and resid 54 and name HE %)
((segid "BrD" and resid 59 and name HG2))
2.900  2.100 2.100 peak     29232 weight 0.10000E+01 volume  0.12717E+03 ppm1   2.535 ppm2 3.199
OR {29232}
(segid "BrD" and resid 54 and name HE %)
((segid "BrD" and resid 59 and name HG1))
ASSI {29292}
((segid "BrD" and resid 54 and name HB2))
(segid "BrD" and resid 81 and name HG1 %)
3.200  2.600 2.300 peak     29292 weight 0.10000E+01 volume  0.80321E+02 ppm1   1.947 ppm2 1.083
ASSI {29302}
(segid "BrD" and resid 54 and name HE %)
(segid "BrD" and resid 59 and name HE %)
3.000  2.200 2.200 peak     29302 weight 0.10000E+01 volume  0.10558E+03 ppm1   2.535 ppm2 1.863
ASSI {29382}
((segid "BrD" and resid 33 and name HA))
((segid "BrD" and resid 32 and name H23))
3.200  2.600 2.300 peak     29382 weight 0.10000E+01 volume  0.67859E+02 ppm1   4.361 ppm2 7.811
ASSI {29472}
((segid "BrD" and resid 91 and name HG1))
((segid "BrD" and resid 93 and name HB1))
3.700  3.400 1.800 peak     29472 weight 0.10000E+01 volume  0.32210E+02 ppm1   2.779 ppm2 5.018
OR {29472}
((segid "BrD" and resid 91 and name HG1))
((segid "BrD" and resid 93 and name HA))
ASSI {29602}
((segid "BrD" and resid 70 and name HA))
((segid "BrD" and resid 73 and name HB2))
3.600  3.200 1.900 peak     29602 weight 0.10000E+01 volume  0.37115E+02 ppm1   5.346 ppm2 2.483
ASSI {29622}
((segid "BrD" and resid 70 and name HB2))
((segid "BrD" and resid 9 and name HB1))
3.100  2.400 2.400 peak     29622 weight 0.10000E+01 volume  0.85748E+02 ppm1   4.360 ppm2 2.443
ASSI {29632}
((segid "BrD" and resid 70 and name HB1))
((segid "BrD" and resid 9 and name HB1))
3.600  3.200 1.900 peak     29632 weight 0.10000E+01 volume  0.38576E+02 ppm1   4.755 ppm2 2.442
ASSI {29642}
((segid "BrD" and resid 93 and name HB2))
((segid "BrD" and resid 91 and name HD1))
2.300  1.300 1.300 peak     29642 weight 0.10000E+01 volume  0.51818E+03 ppm1   4.755 ppm2 4.550
ASSI {29652}
((segid "BrD" and resid 93 and name HB1))
((segid "BrD" and resid 91 and name HD1))
2.900  2.100 2.100 peak     29652 weight 0.10000E+01 volume  0.14178E+03 ppm1   5.000 ppm2 4.550
ASSI {29662}
((segid "BrD" and resid 93 and name HB1))
((segid "BrD" and resid 94 and name HB1))
3.100  2.400 2.400 peak     29662 weight 0.10000E+01 volume  0.83013E+02 ppm1   5.000 ppm2 2.731
ASSI {29672}
((segid "BrD" and resid 93 and name HA))
((segid "BrD" and resid 91 and name HG1))
3.100  2.400 2.400 peak     29672 weight 0.10000E+01 volume  0.87723E+02 ppm1   5.003 ppm2 2.796

TABLE 2-continued

Unambiguous NOE-derived Inter-proton Distance Restraints

ASSI {29692}
((segid "BrD" and resid 108 and name HA))
((segid "BrD" and resid 111 and name HG2))
4.300   4.300  1.200 peak        29692  weight  0.10000E+01 volume   0.13111E+02 ppm1    4.804  ppm2   1.905
ASSI {29752}
((segid "BrD" and resid 30 and name HA))
(segid "BrD" and resid 102 and name HD1 %)
4.200   4.200  1.300 peak        29752  weight  0.10000E+01 volume   0.14252E+02 ppm1    5.445  ppm2   1.327
ASSI {29772}
((segid "BrD" and resid 30 and name HB2))
((segid "BrD" and resid 28 and name HE1))
3.300   2.700  2.200 peak        29772  weight  0.10000E+01 volume   0.60630E+02 ppm1    4.508  ppm2   8.090
ASSI {29782}
((segid "BrD" and resid 30 and name HB2))
(segid "BrD" and resid 101 and name HG2 %)
3.200   2.600  2.300 peak        29782  weight  0.10000E+01 volume   0.72004E+02 ppm1    4.507  ppm2   1.604
ASSI {29792}
((segid "BrD" and resid 27 and name HB1))
((segid "BrD" and resid 24 and name HB2))
3.400   2.900  2.100 peak        29792  weight  0.10000E+01 volume   0.52302E+02 ppm1    4.607  ppm2   3.077
OR {29792}
((segid "BrD" and resid 27 and name HB1))
((segid "BrD" and resid 24 and name HG2))
ASSI {29532}
((segid "BrD" and resid 66 and name HD2))
((segid "BrD" and resid 65 and name HA))
4.000   4.000  1.500 peak        29832  weight  0.10000E+01 volume   0.19067E+02 ppm1    3.631  ppm2   5.390
ASSI {29842}
((segid "BrD" and resid 66 and name HD1))
((segid "BrD" and resid 65 and name HA))
4.300   4.300  1.200 peak        29842  weight  0.10000E+01 volume   0.12737E+02 ppm1    3.673  ppm2   5.390
ASSI {29852}
((segid "BrD" and resid 66 and name HD1))
(segid "BrD" and resid 15 and name HE %)
2.800   2.000  2.000 peak        29852  weight  0.10000E+01 volume   0.17551E+03 ppm1    3.673  ppm2   7.488
ASSI {29882}
((segid "BrD" and resid 66 and name HD2))
(segid "BrD" and resid 15 and name HE %)
2.700   1.800  1.800 peak        29882  weight  0.10000E+01 volume   0.20920E+03 ppm1    3.631  ppm2   7.488
ASSI {29912}
((segid "BrD" and resid 66 and name HA))
((segid "BrD" and resid 65 and name HA))
3.500   3.100  2.000 peak        29912  weight  0.10000E+01 volume   0.40427E+02 ppm1    5.001  ppm2   5.387
ASSI {29922}
((segid "BrD" and resid 66 and name HB2))
((segid "BrD" and resid 65 and name HA))
4.700   4.700  0.800 peak        29922  weight  0.10000E+01 volume   0.75028E+01 ppm1    2.634  ppm2   5.395
ASSI {29982}
((segid "BrD" and resid 66 and name HB2))
(segid "BrD" and resid 69 and name HG1 %)
3.900   3.800  1.600 peak        29982  weight  0.10000E+01 volume   0.23433E+02 ppm1    2.633  ppm2   1.550
ASSI {29992}
((segid "BrD" and resid 66 and name HB1))
(segid "BrD" and resid 69 and name HG1 %)
3.900   3.800  1.600 peak        29992  weight  0.10000E+01 volume   0.22947E+02 ppm1    2.701  ppm2   1.551
ASSI {30022}
((segid "BrD" and resid 51 and name HA))
((segid "BrD" and resid 51 and name HD2))
5.500   5.500  0.000 peak        30022  weight  0.10000E+01 volume   0.72129E+01 ppm1    4.459  ppm2   4.011
ASSI {30062}
((segid "BrD" and resid 103 and name HB2))
((segid "BrD" and resid 82 and name HB1))
3.100   2.400  2.400 peak        30062  weight  0.10000E+01 volume   0.91298E+02 ppm1    1.896  ppm2   3.706
ASSI {30132}
((segid "BrD" and resid 116 and name HG11))
(segid "BrD" and resid 107 and name HE %)
2.900   2.100  2.100 peak        30132  weight  0.10000E+01 volume   0.12243E+03 ppm1    1.946  ppm2   7.491
ASSI {30142}
((segid "BrD" and resid 116 and name HG11))
(segid "BrD" and resid 107 and name HD %)
3.100   2.400  2.400 peak        30142  weight  0.10000E+01 volume   0.96863E+02 ppm1    1.946  ppm2   7.835
ASSI {30182}
((segid "BrD" and resid 64 and name HG1))
(segid "BrD" and resid 63 and name HD2 %)
3.500   3.100  2.000 peak        30182  weight  0.10000E+01 volume   0.45416E+02 ppm1    2.190  ppm2   1.489

TABLE 2-continued

Unambiguous NOE-derived Inter-proton Distance Restraints

ASSI {30262}
((segid "BrD" and resid 86 and name HG1))
((segid "BrD" and resid 96 and name HD %))
3.700  3.400  1.800 peak       30262 weight  0.10000E+01 volume  0.30501E+02 ppm1   1.891 ppm2  7.722
ASSI {30322}
((segid "BrD" and resid 86 and name HG2))
((segid "BrD" and resid 87 and name HG1))
3.400  2.900  2.100 peak       30322 weight  0.10000E+01 volume  0.52723E+02 ppm1   0.760 ppm2  3.028
ASSI {30362}
((segid "BrD" and resid 103 and name HB2))
(segid "BrD" and resid 99 and name HB %)
2.300  1.300  1.300 peak       30362 weight  0.10000E+01 volume  0.49767E+03 ppm1   1.892 ppm2  2.206
ASSI {30422}
((segid "BrD" and resid 86 and name HE1))
(segid "BrD" and resid 99 and name HB %)
2.500  1.600  1.600 peak       30422 weight  0.10000E+01 volume  0.29716E+03 ppm1   3.078 ppm2  2.206
ASSI {30492}
((segid "BrD" and resid 109 and name HE2))
((segid "BrD" and resid 106 and name HA))
3.000  2.200  2.200 peak       30492 weight  0.10000E+01 volume  0.11843E+03 ppm1   3.029 ppm2  4.591
ASSI {30502}
((segid "BrD" and resid 109 and name HE1))
((segid "BrD" and resid 106 and name HA))
3.800  3.600  1.700 peak       30502 weight  0.10000E+01 volume  0.25593E+02 ppm1   3.177 ppm2  4.590
ASSI {30532}
((segid "BrD" and resid 109 and name HD1))
((segid "BrD" and resid 112 and name HG1))
3.300  2.700  2.200 peak       30532 weight  0.10000E+01 volume  0.67000E+02 ppm1   1.994 ppm2  2.968
ASSI {30682}
((segid "BrD" and resid 109 and name HA))
(segid "BrD" and resid 21 and name HG2 %)
3.400  3.200  1.900 peak       30682 weight  0.10000E+01 volume  0.34166E+02 ppm1   4.656 ppm2  1.588
ASSI {30702}
((segid "BrD" and resid 109 and name HA)
((segid "BrD" and resid 112 and name HG1))
3.800  3.600  1.700 peak       30702 weight  0.10000E+01 volume  0.26014E+02 ppm1   4.653 ppm2  2.964
ASSI {30722}
((segid "BrD" and resid 109 and name HA))
((segid "BrD" and resid 112 and name HG2))
3.200  2.600  2.300 peak       30722 weight  0.10000E+01 volume  0.68767E+02 ppm1   4.653 ppm2  2.823
ASSI {30772}
((segid "BrD" and resid 104 and name HB1))
(segid "BrD" and resid 105 and name HD %)
3.200  2.600  2.300 peak       30772 weight  0.10000E+01 volume  0.81070E+02 ppm1   2.536 ppm2  7.819
ASSI {30922}
((segid "BrD" and resid 19 and name HB1))
(segid "BrD" and resid 16 and name HE %)
3.200  2.600  2.300 peak       30922 weight  0.10000E+01 volume  0.75523E+02 ppm1   2.289 ppm2  7.486
ASSI {30962}
((segid "BrD" and resid 59 and name HB2))
((segid "BrD" and resid 56 and name HA))
2.300  1.300  1.300 peak       30962 weight  0.10000E+01 volume  0.51425E+03 ppm1   2.486 ppm2  4.646
ASSI {31062}
((segid "BrD" and resid 22 and name HG))
(segid "BrD" and resid 74 and name HE %)
2.500  2.500  2.000 peak       31062 weight  0.10000E+01 volume  0.34749E+03 ppm1   2.388 ppm2  7.497
ASSI {31162}
((segid "BrD" and resid 54 and name HG1))
((segid "BrD" and resid 77 and name HA))
3.100  2.400  2.400 peak       31162 weight  0.10000E+01 volume  0.89147E+02 ppm1   3.388 ppm2  4.964
ASSI {13}
(segid "BrD" and resid 46 and name HD %)
(segid "BrD" and resid 88 and name HE %)
2.900  2.100  2.100 peak          13 weight  0.11000E+01 volume  0.62066E+02 ppm1   5.758 ppm2  7.421
ASSI {23}
(segid "BrD" and resid 47 and name HD %)
(segid "BrD" and resid 47 and name HE %)
3.200  2.600  2.300 peak          23 weight  0.11000E+01 volume  0.31210E+02 ppm1   5.758 ppm2  7.261
ASSI {43}
(segid "BrD" and resid 46 and name HE %)
(segid "BrD" and resid $$ and name HE %)
3.800  3.600  1.700 peak          43 weight  0.11000E+01 volume  0.11086E+02 ppm1   6.688 ppm2  7.421
ASSI {53}
(segid "BrD" and resid 46 and name HE %)
(segid "BrD" and resid 47 and name HE %)
4.000  4.000  1.500 peak          53 weight  0.11000E+01 volume  0.78634E+01 ppm1   6.688 ppm2  7.261

TABLE 2-continued

Unambiguous NOE-derived Inter-proton Distance Restraints

ASSI {93}
(segid "BrD" and resid 46 and name HD %)
((segid "BrD" and resid 46 and name HA))
2.600  1.700 1.700 peak        93 weight  0.11000E+01 volume  0.11748E+03 ppm1    5.758 ppm2  4.154
ASSI {103}
(segid "BrD" and resid 46 and name HE %)
((segid "BrD" and resid 88 and name HB1))
2.300  1.300 1.300 peak       103 weight  0.11000E+01 volume  0.25301E+03 ppm1    6.688 ppm2  3.527
ASSI {113}
(segid "BrD" and resid 46 and name HE %)
((segid "BrD" and resid 46 and name HB1))
3.300  2.700 2.200 peak       113 weight  0.11000E+01 volume  0.27341E+02 ppm1    6.688 ppm2  3.279
ASSI {133}
(segid "BrD" and resid 46 and name HD %)
((segid "BrD" and resid 46 and name HB2))
2.500  1.600 1.600 peak       133 weight  0.11000E+01 volume  0.14809E+03 ppm1    5.758 ppm2  3.104
ASSI {153}
(segid "BrD" and resid 46 and name HE %)
(segid "BrD" and resid 50 and name HD1 %)
3.000  2.200 2.200 peak       153 weight  0.11000E+01 volume  0.42674E+02 ppm1    6.685 ppm2  1.148
ASSI {273}
((segid "BrD" and resid 28 and name HE1))
((segid "BrD" and resid 28 and name HA))
3.600  3.200 1.900 peak       273 weight  0.11000E+01 volume  0.14248E+02 ppm1    6.129 ppm2  4.513
ASSI {333}
(segid "BrD" and resid 67 and name HD %)
(segid "BrD" and resid 68 and name HD %)
3.000  2.200 2.200 peak       333 weight  0.11000E+01 volume  0.41792E+02 ppm1    6.873 ppm2  7.772
ASSI {343}
(segid "BrD" and resid 67 and name HD %)
((segid "BrD" and resid 68 and name HA))
2.800  2.000 2.000 peak       343 weight  0.11000E+01 volume  0.67483E+02 ppm1    6.874 ppm2  5.146
ASSI {353}
(segid "BrD" and resid 67 and name HD %)
((segid "BrD" and resid 67 and name HA))
2.500  1.600 1.600 peak       353 weight  0.11000E+01 volume  0.12803E+03 ppm1    6.872 ppm2  4.678
ASSI {373}
(segid "BrD" and resid 67 and name HD %)
((segid "BrD" and resid 67 and name HB1))
2.300  1.300 1.300 peak       373 weight  0.11000E+01 volume  0.22980E+03 ppm1    6.874 ppm2  3.570
ASSI {383}
(segid "BrD" and resid 67 and name HE %)
(segid "BrD" and resid 68 and name HD %)
2.900  2.100 2.100 peak       383 weight  0.11000E+01 volume  0.60490E+03 ppm1    7.293 ppm2  7.780
ASSI {403}
(segid "BrD" and resid 67 and name HE %)
(segid "BrD" and resid 68 and name HE %)
2.400  1.400 1.400 peak       403 weight  0.11000E+01 volume  0.16842E+03 ppm1    7.293 ppm2  7.888
ASSI {433}
(segid "BrD" and resid 67 and name HE %)
((segid "BrD" and resid 67 and name HA))
3.000  2.200 2.200 peak       433 weight  0.11000E+01 volume  0.50708E+02 ppm1    7.292 ppm2  4.679
ASSI {463}
(segid "BrD" and resid 47 and name HE %)
(segid "BrD" and resid 46 and name HD %)
2.900  2.100 2.100 peak       463 weight  0.11000E+01 volume  0.56184E+02 ppm1    7.246 ppm2  5.744
ASSI {493}
(segid "BrD" and resid 47 and name HE %)
((segid "BrD" and resid 47 and name HA))
3.300  2.700 2.200 peak       493 weight  0.11000E+01 volume  0.27001E+02 ppm1    7.246 ppm2  4.711
ASSI {503}
(segid "BrD" and resid 47 and name HD %)
((segid "BrD" and resid 47 and name HA))
2.200  1.200 1.200 peak       503 weight  0.11000E+01 volume  0.29622E+03 ppm1    7.942 ppm2  4.693
ASSI {543}
((segid "BrD" and resid 32 and name HD1))
((segid "BrD" and resid 30 and name HA))
2.600  1.700 2.700 peak       543 weight  0.11000E+01 volume  0.10449E+03 ppm1    8.455 ppm2  5.452
ASSI {563}
((segid "BrD" and resid 32 and name HD1))
((segid "BrD" and resid 32 and name HB2))
2.900  2.100 2.100 peak       563 weight  0.11000E+01 volume  0.53265E+02 ppm1    8.456 ppm2  3.942
ASSI {603}
(segid "BrD" and resid 74 and name HD %)
((segid "BrD" and resid 74 and name HA))
2.500  1.600 1.600 peak       603 weight  0.11000E+01 volume  0.15470E+03 ppm1    7.013 ppm2  4.373

TABLE 2-continued

Unambiguous NOE-derived Inter-proton Distance Restraints

ASSI {843}
(segid "BrD" and resid 15 and name HD %)
((segid "BrD" and resid 15 and name HA))
1.900  0.900 0.900 peak       843 weight  0.11000E+01 volume  0.41725E+03 ppm1   7.664 ppm2  4.621
ASSI {863}
(segid "BrD" and resid 15 and name HD %)
((segid "BrD" and resid 15 and name HB1))
2.400  1.400 1.400 peak       863 weight  0.11000E+01 volume  0.19360E+03 ppm1   7.664 ppm2  3.818
ASSI {873}
(segid "BrD" and resid 15 and name HD %)
((segid "BrD" and resid 15 and name HB2))
2.000  1.000 1.000 PEAK       873 WEIGHT 0.11000E+01 volume  0.48925E+03 ppm1   7.644 ppm2  3.643
ASSI {693}
(segid "BrD" and resid 15 and name HE %)
((segid "BrD" and resid 15 and name HA))
3.500  3.100 2.000 peak       893 weight  0.11000E+01 volume  0.17907E+02 ppm1   7.478 ppm2  4.635
ASSI {903}
(segid "BrD" and resid 15 and name HE %)
((segid "BrD" and resid 15 and name HB2)
4.000  4.000 1.500 peak       903 weight  0.11000E+01 volume  0.77515E+01 ppm1   7.478 ppm2  3.643
ASSI {993}
(segid "BrD" and resid 68 and name HE %)
(segid "BrD" and resid 74 and name HD %)
3.100  2.400 2.400 peak       993 weight  0.11000E+01 volume  0.39808E+02 ppm1   7.850 ppm2  6.998
ASSI {1003}
(segid "BrD" and resid 68 and name HE %)
(segid "BrD" and resid 67 and name HD %)
2.900  2.100 2.100 peak      1003 weight  0.11000E+01 volume  0.57511E+02 ppm1   7.850 ppm2  6.896
ASSI {1063}
(segid "BrD" and resid 68 and name HE %)
((segid "BrD" and resid 68 and name HA))
2.900  2.100 2.100 peak      1063 weight  0.11000E+01 volume  0.51154E+02 ppm1   7.850 ppms  5.146
ASSI {1213}
(segid "BrD" and resid 68 and name HD %)
((segid "BrD" and resid 68 and name HB1))
2.000  1.000 1.000 peak      1213 weight  0.11000E+01 volume  0.59736E+03 ppm1   7.757 ppm2  3.673
ASSI {1263}
(segid "BrD" and resid 88 and name HD %)
(segid "BrD" and resid 46 and name HE %)
2.800  2.000 2.000 peak      1263 weight  0.11000E+01 volume  0.62764E+02 ppm1   7.618 ppm2  6.692
ASSI {1283}
(segid "BrD" and resid 88 and name HD %)
(segid "BrD" and resid 46 and name HD %)
3.100  2.400 2.400 peak      1283 weight  0.11000E+01 volume  0.38726E+02 ppm1   7.616 ppm2  5.745
ASSI {1303}
(segid "BrD" and resid 88 and name HD %)
((segid "BrD" and resid 88 and name HA))
2.200  1.200 1.200 peak      1103 weight  0.11000E+01 volume  31179E+03 ppm1    7.616 ppm2  4.999
ASSI {1313}
(segid "BrD" and resid 88 and name HE %)
((segid "BrD" and resid 88 and name HA))
2.800  2.000 2.000 peak      1313 weight  0.11000E+01 volume  0.64049E+02 ppm1   7.410 ppm2  4.999
ASSI {1323}
(segid "BrD" and resid 88 and name HD %)
((segid "BrD" and resid 46 and name HA))
3.100  2.400 2.400 peak      1123 weight  0.11000E+01 volume  0.36562E+02 ppm1   7.618 ppm2  4.154
ASSI {1363}
(segid "BrD" and resid 88 and name HD %)
((segid "BrD" and resid 88 and name HB1))
2.300  1.300 1.300 peak      1363 weight  0.11000E+01 volume  0.21010E+03 ppm1   7.616 ppm2  3.531
ASSI {1403}
(segid "BrD" and resid 96 and name HD %)
((segid "BrD" and resid 96 and name HA))
2.400  1.400 1.400 peak      1403 weight  0.11000E+01 volume  0.16299E+03 ppm1   7.711 ppm2  4.431
ASSI {1413}
(segid "BrD" and resid 96 and name HD %)
((segid "BrD" and resid 96 and name HB1))
2.400  1.400 1.400 peak      1413 weight  0.11000E+01 volume  0.19687E+03 ppm1   7.712 ppm2  3.996
ASSI {1503}
(segid "BrD" and resid 34 and name HD %)
((segid "BrD" and resid 31 and name HA))
2.200  1.200 1.200 peak      1503 weight  0.11000E+01 volume  0.26381E+03 ppm1   7.708 ppm2  4.985
ASSI {1583}
(segid "BrD" and resid 107 and name HE %)
((segid "BrD" and resid 107 and name HB1))
3.200  2.600 2.300 peak      1583 weight  0.11000E+01 volume  0.29123E+02 ppm1   7.896 ppm2  3.674

TABLE 2-continued

Unambiguous NOE-derived Inter-proton Distance Restraints

ASSI {1793}
(segid "BrD" and resid 95 and name HD %)
((segid "BrD" and resid 95 and name HB2))
3.400  2.900  2.100 peak      1793 weight  0.11000E+01 volume  0.22641E+02 ppm1   7.478 ppm2  3.352
ASSI {1833}
(segid "BrD" and resid 95 and name HD %)
((segid "BrD" and resid 95 and name HA))
2.100  1.100  1.100 peak      1833 weight  0.11000E+01 volume  0.35285E+03 ppm1   7.478 ppm2  4.446
ASSI {1883}
(segid "BrD" and resid 95 and name HE %)
((segid "BrD" and resid 95 and name HA))
3.400  2.900  2.100 peak      1883 weight  0.11000E+01 volume  0.23591E+02 ppm1   7.617 ppm2  4.446
ASSI {1943}
(segid "BrD" and resid 95 and name HE %)
((segid "BrD" and resid 32 and name HH2))
1.800  0.800  0.800 peak      1943 weight  0.11000E+01 volume  0.97461E+03 ppm1   7.619 ppm2  7.785
ASSI {1963}
(segid "BrD" and resid 95 and name HE %)
((segid "BrD" and resid 32 and name HZ2))
3.400  2.900  2.100 peak      1963 weight  0.11000E+01 volume  0.21009E+02 ppm1   7.618 ppm2  8.002
ASSI {2023}
((segid "BrD" and resid 32 and name HH2))
((segid "BrD" and resid 32 and name HZ2))
2.100  1.100  1.100 peak      2023 weight  0.11000E+01 volume  0.40155E+03 ppm1   7.757 ppm2  8.004
ASSI {2133}
((segid "BrD" and resid 82 and name HZ))
(segid "BrD" and resid 82 and name HD %)
2.600  1.700  1.700 peak      2133 weight  0.11000E+01 volume  0.10557E+03 ppm1   7.011 ppm2  7.361
ASSI {163}
(segid "BrD" and resid 46 and name HE %)
(segid "BrD" and resid 38 and name HG1 %)
3.000  2.200  2.200 peak       163 weight  0.10000E+01 volume  0.48608E+02 ppm1   4.688 ppm2  1.074
ASSI {183}
(segid "BrD" and resid 46 and name HD %)
((segid "BrD" and resid 50 and name HB))
3.100  2.400  2.400 peak       183 weight  0.10000E+01 volume  0.36832E+02 ppm1   5.758 ppm2  1.791
ASSI {253}
((segid "BrD" and resid 28 and name HE1))
(segid "BrD" and resid 101 and name HG2 %)
2.800  2.000  2.000 peak       253 weight  0.10000E+01 volume  0.66486E+02 ppm1   8.130 ppm2  1.601
ASSI {263}
((segid "BrD" and resid 28 and name HE1))
(segid "BrD" and resid 101 and name HD1 %)
2.600  1.700  1.700 peak       263 weight  0.10000E+01 volume  0.12057E+03 ppm1   8.129 ppm2  1.528
ASSI {283}
((segid "BrD" and resid 28 and name HE1))
((segid "BrD" and resid 30 and name HB1))
2.900  2.100  2.100 peak       283 weight  0.10000E+01 volume  0.53269E+02 ppm1   8.129 ppm2  4.927
ASSI {733}
(segid "BrD" and resid 74 and name HE %)
(segid "BrD" and resid 63 and name HD1 %)
3.700  3.400  1.800 peak       733 weight  0.10000E+01 volume  0.13584E+02 ppm1   7.524 ppm2  1.704
ASSI {793}
(segid "BrD" and resid 82 and name HE %)
(segid "BrD" and resid 106 and name HD %)
3.500  3.100  2.000 peak       793 weight  0.10000E+01 volume  0.18520E+02 ppm1   7.060 ppm2  7.494
ASSI {1113}
(segid "BrD" and resid 68 and name HD %)
((segid "BrD" and resid 62 and name HD2))
2.600  1.700  1.700 peak      1113 weight  0.10000E+01 volume  0.11215E+03 ppm1   7.758 ppm2  2.595
ASSI {1133}
(segid "BrD" and resid 68 and name HD %)
((segid "BrD" and resid 62 and name HB2))
2.800  2.000  2.000 peak      1133 weight  0.10000E+01 volume  0.66543E+02 ppm1   7.757 ppm2  1.718
ASSI {1173}
(segid "BrD" and resid 105 and name HD %)
(segid "BrD" and resid 102 and name HD2 %)
2.800  2.000  2.000 peak      1173 weight  0.10000E+01 volume  0.71257E+02 ppm1   7.758 ppm2  1.338
OR {1173}
(segid "BrD" and resid 105 and name HD %)
(segid "BrD" and resid 102 and name HD1 %)
ASSI {1353}
(segid "BrD" and resid 88 and name HE %)
((segid "BrD" and resid 88 and name HB1))
3.400  2.900  2.100 peak      1353 weight  0.10000E+01 volume  0.21121E+02 ppm1   7.413 ppm2  3.527

TABLE 2-continued

Unambiguous NOE-derived Inter-proton Distance Restraints

ASSI {1423}
(segid "BrD" and resid 96 and name HD %)
((segid "BrD" and resid 100 and name HB2))
3.100   2.400  2.400 peak         1423 weight  0.10000E+01 volume  0.40018E+03 ppm1   7.711 ppm2  3.454
OR {1423}
(segid "BrD" and resid 96 and name HD %)
((segid "BrD" and resid 100 and name HB2))
ASSI {1613}
(segid "BrD" and resid 107 and name HD %)
((segid "BrD" and resid 106 and name HB1))
3.600   3.200  1.900 peak         1613 weight  0.10000E+01 volume  0.14818E+02 ppm1   7.803 ppm2  3.953
ASSI {1663}
(segid "BrD" and resid 107 and name HD %)
((segid "BrD" and resid 103 and name HA))
3.100   2.400  2.400 peak         1663 weight  0.10000E+01 volume  0.38863E+02 ppm1   7.803 ppm2  3.804
ASSI {1753}
(segid "BrD" and resid 106 and name HE %)
((segid "BrD" and resid 75 and name HA))
3.700   3.400  1.800 peak         1753 weight  0.10000E+01 volume  0.13649E+02 ppm1   7.617 ppm2  4.534
ASSI {1803}
(segid "BrD" and resid 95 and name HD %)
((segid "BrD" and resid 85 and name HA))
3.300   2.700  2.200 peak         1803 weight  0.10000E+01 volume  0.27238E+02 ppm1   7.478 ppm2  4.985
ASSI {1853}
(segid "BrD" and resid 95 and name HD %)
((segid "BrD" and resid 85 and name HB1))
3.300   2.700  2.200 peak         1853 weight  0.10000E+01 volume  0.27537E+02 ppm1   7.479 ppm2  3.920
ASSI {1863}
(segid "BrD" and resid 95 and name HD %)
((segid "BrD" and resid 33 and name HB1))
3.200   2.600  2.300 peak         1863 weight  0.10000E+01 volume  0.30330E+02 ppm1   7.478 ppm2  2.047
ASSI {1903}
(segid "BrD" and resid 95 and name HE %)
((segid "BrD" and resid 33 and name HA))
3.500   3.100  2.000 peak         1903 weight  0.10000E+01 volume  0.17985E+02 ppm1   7.618 ppm2  4.343
ASSI {2003}
((segid "BrD" and resid 32 and name HH2))
(segid "BrD" and resid 95 and name HD %)
4.300   4.300  1.200 peak         2003 weight  0.10000E+01 volume  0.52192E+01 ppm1   7.757 ppm2  7.509
ASSI {2143}
((segid "BrD" and resid 82 and name HZ))
(segid "BrD" and resid 106 and name HD %)
3.400   3.600  1.700 peak         2143 weight  0.10000E+01 volume  0.11127E+02 ppm1   7.013 ppm2  7.509
ASSI {2183}
(segid "BrD" and resid 107 and name HE %)
((segid "BrD" and resid 79 and name HG1))
3.500   3.100  2.000 peak         2183 weight  0.10000E+01 volume  0.19805E+02 ppm1   7.897 ppm2  3.060
ASSI {54}
(segid "BrD" and resid 47 and name HD %)
((segid "BrD" and resid 47 and name HB1))
2.200   2.200  1.200 peak           54 weight  0.10000E+01 volume  0.95356E+03 ppm1   7.970 ppm2  3.806
ASSI {64}
(segid "BrD" and resid 47 and name HD %)
((segid "BrD" and resid 47 and name HB2))
2.300   2.300  2.300 peak           64 weight  0.10000E+01 volume  0.78871E+03 ppm1   7.970 ppm2  3.415
ASSI {144}
(segid "BrD" and resid 67 and name HD %)
(segid "BrD" and resid 67 and name HE %)
2.000   1.000  1.000 peak          144 weight  0.10000E+01 volume  0.18744E+04 ppm1   6.900 ppm2  7.321
ASSI {214}
(segid "BrD" and resid 67 and name HD %)
((segid "BrD" and resid 67 and name HB2))
2.200   1.200  1.200 peak          214 weight  0.10000E+01 volume  0.10973E+04 ppm1   6.899 ppm2  2.664
ASSI {274}
(segid "BrD" and resid 68 and name HD %)
((segid "BrD" and resid 68 and name HA))
2.400   1.400  1.400 peak          274 weight  0.10000E+01 volume  0.56412E+03 ppm1   7.778 ppm2  5.140
ASSI {294}
(segid "BrD" and resid 68 and name HD %)
((segid "BrD" and resid 68 and name HB2))
2.300   1.300  1.300 peak          294 weight  0.10000E+01 volume  0.81340E+03 ppm1   7.778 ppm2  3.546
ASSI {354}
(segid "BrD" and resid 88 and name HD %)
(segid "BrD" and resid 88 and name HE %)
2.000   1.000  1.000 peak          354 weight  0.10000E+01 volume  0.17752E+04 ppm1   7.612 ppm2  7.418

TABLE 2-continued

Unambiguous NOE-derived Inter-proton Distance Restraints

```
ASSI {454}
((segid "BrD" and resid 32 and name HD1))
((segid "BrD" and resid 32 and name HA))
3.000  2.200 2.200 peak         454 weight  0.10000E+01 volume  0.17821E+03 ppm1   8.491 ppm2  4.977
ASSI {474}
((segid "BrD" and resid 32 and name HD1))
((segid "BrD" and resid 32 and name HB1))
3.100  2.400 2.400 peak         424 weight  0.10000E+01 volume  0.14234E+03 ppm1   8.490 ppm2  4.213
ASSI {1694}
(segid "BrD" and resid 34 and name HE %)
((segid "BrD" and resid 34 and name HB1))
3.300  2.700 2.200 peak        1694 weight  0.10000E+01 volume  0.91431E+02 ppm1   7.781 ppm2  4.116
ASSI {1834}
(segid "BrD" and resid 96 and name HD %)
(segid "BrD" and resid 96 and name HE %)
1.900  0.900 0.900 peak        1834 weight  0.10000E+01 volume  0.29744E+04 ppm1   7.724 ppm2  7.614
ASSI {1914}
(segid "BrD" and resid 96 and name HD %)
((segid "BrD" and resid 96 and name HB2))
2.200  1.200 1.200 peak        1914 weight  0.10000E+01 volume  0.99570E+03 ppm1   7.726 ppm2  3.124
ASSI {2024}
(segid "BrD" and resid 34 and name HD %)
((segid "BrD" and resid 34 and name HB1))
2.500  1.600 1.600 peak        2024 weight  0.10000E+01 volume  0.48715E+03 ppm1   7.714 ppm2  4.115
ASSI {2084}
(segid "BrD" and resid 15 and name HD %)
(segid "BrD" and resid 15 and name HE %)
1.900  0.900 0.900 peak        2084 weight  0.10000E+01 volume  0.28924E+04 ppm1   7.689 ppm2  7.483
ASSI {2474}
(segid "BrD" and resid 96 and name HE %)
((segid "BrD" and resid 96 and name HB1))
3.300  2.700 2.200 peak        2474 weight  0.10000E+01 volume  0.86809E+02 ppm1   7.611 ppm2  4.001
ASSI {2554}
(segid "BrD" and resid 74 and name HE %)
(segid "BrD" and resid 74 and name HD %)
2.000  1.000 1.000 peak        2554 weight  0.10000E+01 volume  0.18278E+04 ppm1   7.539 ppm2  7.006
ASSI {3204
(segid "BrD" and resid 82 and name HD %)
((segid "BrD" and resid 82 and name HB1))
2.400  1.400 1.400 peak        3204 weight  0.10000E+01 volume  0.67788E+03 ppm1   7.265 ppm2  3.708
ASSI {3214}
(segid "BrD" and resid 82 and name HD %)
((segid "BrD" and resid 82 and name HB2))
2.300  1.300 1.300 peak        3214 weight  0.10000E+01 volume  0.77298E+03 ppm1   7.262 ppm2  3.572
ASSI {3304}
(segid "BrD" and resid 82 and name HD %)
(segid "BrD" and resid 82 and name HE %)
2.300  1.200 1.200 peak        3304 weight  0.10000E+01 volume  0.13642E+04 ppm1   7.262 ppm2  7.076
ASSI {3644}
(segid "BrD" and resid 74 and name HD %)
((segid "BrD" and resid 74 and name HB2))
2.400  1.400 1.400 peak        3644 weight  0.10000E+01 volume  0.64123E+03 ppm1   7.005 ppm2  3.007
ASSI {3894}
(segid "BrD" and resid 46 and name HD %)
(segid "BrD" and resid 46 and name HE %)
2.000  1.000 1.000 peak        3894 weight  0.10000E+01 volume  0.17599E+04 ppm1   5.743 ppm2  6.687
ASSI {3914}
(segid "BrD" and resid 46 and name HD %)
((segid "BrD" and resid 46 and name HB1))
2.400  1.400 1.400 peak        3914 weight  0.10000E+01 volume  0.61947E+03 ppm1   5.740 ppm2  3.304
ASSI {4064}
((segid "BrD" and resid 24 and name HD2))
((segid "BrD" and resid 24 and name HA))
3.000  2.200 2.200 peak        4064 weight  0.10000E+01 volume  0.15484E+03 ppm1   5.577 ppm2  4.586
ASSI {84}
(segid "BrD" and resid 82 and name HD %)
((segid "BrD" and resid 103 and name HA))
2.900  2.100 2.100 peak          84 weight  0.10000E+01 volume  0.22432E+03 ppm1   7.265 ppm2  1.790
ASSI {174}
(segid "BrD" and resid 67 and name HD %)
((segid "BrD" and resid 62 and name HA))
3.300  2.700 2.200 peak         174 weight  0.10000E+01 volume  0.89209E+02 ppm1   6.899 ppm2  4.490
ASSI {244}
(segid "BrD" and resid 67 and name HD %)
((segid "BrD" and resid 62 and name HB2))
2.900  2.100 2.100 peak         244 weight  0.10000E+01 volume  0.21286E+03 ppm1   6.899 ppm2  1.706
```

TABLE 2-continued

Unambiguous NOE-derived Inter-proton Distance Restraints

ASSI {254}
(segid "BrD" and resid 67 and name HD %)
(segid "BrD" and resid 73 and name HD1 %)
3.500  3.100  2.000 peak         254 weight  0.10000E+01 volume  0.64742E+02 ppm1   6.899 ppm2   1.545
ASSI {464}
((segid "BrD" and resid 32 and name HD1))
((segid "BrD" and resid 29 and name HA))
3.300  2.700  2.200 peak         464 weight  0.10000E+01 volume  0.97341E+02 ppm1   8.490 ppm2   4.814
ASSI {494}
((segid "BrD" and resid 32 and name HD1))
((segid "BrD" and resid 33 and name HD1))
5.500  5.500  0.000 peak         494 weight  0.10000E+01 volume  0.38880E+03 ppm1   8.490 ppm2   2.781
ASSI {504}
((segid "BrD" and resid 32 and name HD1))
((segid "BrD" and resid 33 and name HD2))
4.000  4.000  1.500 peak         504 weight  0.10000E+01 volume  0.30117E+02 ppm1   8.490 ppm2   2.211
ASSI {564}
((segid "BrD" and resid 107 and name HZ))
((segid "BrD" and resid 79 and name HB1))
3.100  2.400  2.400 peak         564 weight  0.10000E+01 volume  0.14239E+03 ppm1   8.008 ppm2   3.802
ASSI {624}
((segid "BrD" and resid 107 and name HZ))
((segid "BrD" and resid 79 and name HA))
3.000  2.200  2.200 peak         674 weight  0.10000E+01 volume  0.17938E+03 ppm1   8.058 ppm2   4.439
ASSI {634}
((segid "BrD" and resid 107 and name HZ))
(segid "BrD" and resid 107 and name HE %)
2.000  1.000  1.000 peak         634 weight  0.10000E+01 volume  0.19583E+04 ppm1   8.058 ppm2   7.927
ASSI {644}
((segid "BrD" and resid 107 and name HZ))
(segid "BrD" and resid 107 and name HD %)
2.500  2.500  2.000 peak         644 weight  0.10000E+01 volume  0.49678E+03 ppm1   8.058 ppm2   7.793
ASSI {664}
((segid "BrD" and resid 107 and name HZ))
((segid "BrD" and resid 79 and name HG1))
2.100  1.800  1.800 peak         664 weight  0.10000E+01 volume  0.34018E+03 ppm1   8.059 ppm2   2.994
ASSI {694}
((segid "BrD" and resid 32 and name HZ2))
((segid "BrD" and resid 94 and name HG1))
2.500  1.600  1.600 peak         694 weight  0.10000E+01 volume  0.45123E+03 ppm1   8.008 ppm2   3.154
ASSI {714}
((segid "BrD" and resid 32 and name HZ2))
((segid "BrD" and resid 32 and name HZ3))
2.100  2.100  2.400 peak         714 weight  0.10000E+01 volume  0.13157E+04 ppm1   8.004 ppm2   7.797
ASSI {724}
((segid "BrD" and resid 32 and name HE3))
((segid "BrD" and resid 33 and name HG2))
3.200  2.600  2.300 peak         724 weight  0.10000E+01 volume  0.11963E+03 ppm1   7.959 ppm2  −0.311
ASSI {804}
((segid "BrD" and resid 32 and name HZ2))
((segid "BrD" and resid 97 and name HB1))
2.700  1.800  1.800 peak         804 weight  0.10000E+01 volume  0.29399E+03 ppm1   7.961 ppm2   2.667
ASSI {854}
((segid "BrD" and resid 32 and name HE3))
((segid "BrD" and resid 32 and name HA))
2.900  2.100  2.100 peak         854 weight  0.10000E+01 volume  0.19220E+03 ppm1   7.957 ppm2   4.976
ASSI {864}
((segid "BrD" and resid 32 and name HE3))
((segid "BrD" and resid 33 and name HA))
2.600  1.700  1.700 peak         864 weight  0.10000E+01 volume  0.35337E+03 ppm1   7.956 ppm2   4.361
ASSI {874}
((segid "BrD" and resid 32 and name HE3))
((segid "BrD" and resid 32 and name HB1))
2.800  2.000  2.000 peak         874 weight  0.10000E+01 volume  0.24249E+03 ppm1   7.958 ppm2   3.966
ASSI {984}
(segid "BrD" and resid 107 and name HE %)
((segid "BrD" and resid 103 and name HA))
3.000  2.200  2.200 peak         984 weight  0.10000E+01 volume  0.17386E+03 ppm1   7.925 ppm2   3.742
ASSI {1024}
((segid "BrD" and resid 34 and name HZ))
((segid "BrD" and resid 102 and name HB2))
2.500  1.600  1.600 peak        1024 weight  0.10000E+01 volume  0.46463E+03 ppm1   7.926 ppm2   1.813
ASSI {1144}
((segid "BrD" and resid 34 and name HZ))
((segid "BrD" and resid 102 and name HB1))
2.900  2.100  2.100 peak        1144 weight  0.10000E+01 volume  0.21471E+03 ppm1   7.900 ppm2   1.967

TABLE 2-continued

Unambiguous NOE-derived Inter-proton Distance Restraints

ASSI {1154}
((segid "BrD" and resid 34 and name HZ))
((segid "BrD" and resid 98 and name HB1))
3.300  2.700  2.200 peak        1154 weight  0.10000E+01 volume  0.95962E+02 ppm1    7.899 ppm2  4.001
ASSI {1194}
(segid "BrD" and resid 107 and name HE %)
((segid "BrD" and resid 79 and name HA))
2.300  1.300  1.300 peak        1194 weight  0.10000E+01 volume  0.84240E+03 ppm1    7.889 ppm2  4.391
ASSI {1224}
(segid "BrD" and resid 60 and name HE %)
((segid "BrD" and resid 62 and name HD1))
3.100  2.400  2.400 peak        1224 weight  0.10000E+01 volume  0.13020E+03 ppm1    7.892 ppm2  3.172
ASSI {1314}
(segid "BrD" and resid 68 and name HE %)
(segid "BrD" and resid 73 and name HD2 %)
4.100  4.100  1.400 peak        1314 weight  0.10000E+01 volume  0.23932E+02 ppm1    7.892 ppm2  1.496
ASSI {1344}
((segid "BrD" and resid 32 and name HE3))
((segid "BrD" and resid 33 and name HD2))
3.200  2.600  2.300 peak        1344 weight  0.10000E+01 volume  0.10782E+03 ppm1    7.956 ppm2  2.212
ASSI {1434}
((segid "BrD" and resid 32 and name HZ3))
((segid "BrD" and resid 32 and name HE3))
1.800  0.800  0.800 peak        1434 weight  0.10000E+01 volume  0.39856E+04 ppm1    7.812 ppm2  7.954
ASSI {1454}
(segid "BrD" and resid 34 and name HE %)
(segid "BrD" and resid 102 and name HD1 %)
2.900  2.100  2.100 peak        1454 weight  0.10000E+01 volume  0.19468E+03 ppm1    7.808 ppm2  1.268
ASSI {1464}
(segid "BrD" and resid 107 and name HD %)
(segid "BrD" and resid 110 and name HD1 %)
2.800  2.000  2.000 peak        1464 weight  0.10000E+01 volume  0.23444E+03 ppm1    7.810 ppm2  1.153
ASSI {1474}
(segid "BrD" and resid 107 and name HD %)
(segid "BrD" and resid 116 and name HD1 %)
2.600  1.700  1.700 peak        1474 weight  0.10000E+01 volume  0.36349E+03 ppm1    7.406 ppm2  1.399
ASSI {1494}
(segid "BrD" and resid 107 and name HD %)
((segid "BrD" and resid 107 and name HA))
2.300  1.300  1.300 peak        1494 weight  0.10000E+01 volume  0.85611E+03 ppm1    7.803 ppm2  4.440
ASSI {1524}
(segid "BrD" and resid 105 and name HD %)
((segid "BrD" and resid 105 and name HB1))
2.300  1.300  1.300 peak        1524 weight  0.10000E+01 volume  0.86322E+03 ppm1    7.798 ppm2  3.741
ASSI {1564}
(segid "BrD" and resid 34 and name HE %)
((segid "BrD" and resid 28 and name HD2))
3.000  2.200  2.200 peak        1564 weight  0.10000E+01 volume  0.16881E+03 ppm1    7.794 ppm2  5.562
ASSI {1594}
((segid "BrD" and resid 32 and name HZ3))
(segid "BrD" and resid 95 and name HE %)
2.600  1.700  1.700 peak        1594 weight  0.10000E+01 volume  0.36507E+03 ppm1    7.791 ppm2  7.630
ASSI {1634}
(segid "BrD" and resid 34 and name HE %)
((segid "BrD" and resid 102 and name HB1))
3.200  2.600  2.300 peak        1634 weight  0.10000E+01 volume  0.12088E+03 ppm1    7.790 ppm2  2.032
ASSI {1644}
(segid "BrD" and resid 34 and name HE %)
((segid "BrD" and resid 98 and name HB1))
2.700  1.800  1.800 peak        1644 weight  0.10000E+01 volume  0.32157E+03 ppm1    7.784 ppm2  4.016
ASSI {1734}
(segid "BrD" and resid 107 and name HD %)
((segid "BrD" and resid 103 and name HG2))
2.400  2.400  2.100 peak        1724 weight  0.10000E+01 volume  0.57448E+03 ppm1    7.778 ppm2  2.487
ASSI {1754}
((segid "BrD" and resid 32 and name HZ3))
((segid "BrD" and resid 33 and name HB1))
2.700  1.800  1.800 peak        1754 weight  0.10000E+01 volume  0.30103E+03 ppm1    7.780 ppm2  1.088
ASSI {1764}
(segid "BrD" and resid 34 and name HE %)
(segid "BrD" and resid 81 and name HG2 %)
3.000  2.200  2.200 peak        1764 weight  0.10000E+01 volume  0.16442E+03 ppm1    7.781 ppm2  0.762
ASSI {1794}
(segid "BrD" and resid 68 and name HD %)
(segid "BrD" and resid 73 and name HD1 %)
2.600  1.700  1.700 peak        1794 weight  0.10000E+01 volume  0.42209E+03 ppm1    7.781 ppm2  1.543

TABLE 2-continued

Unambiguous NOE-derived Inter-proton Distance Restraints

ASSI {1904}
(segid "BrD" and resid 34 and name HD %)
((segid "BrD" and resid 34 and name HZ))
2.600  1.700 1.700 peak       1904  weight  0.10000E+01 volume  0.35420E+03 ppm1   7.719  ppm2  7.901
ASSI {1964}
(segid "BrD" and resid 34 and name HD %)
((segid "BrD" and resid 85 and name HB1))
3.000  2.200 2.200 peak       1954  weight  0.10000E+01 volume  0.18188E+03 ppm1   7.714  ppm2  3.920
ASSI {2124}
(segid "BrD" and resid 15 and name HD %)
(segid "BrD" and resid 63 and name HD1 %)
2.500  1.600 1.600 peak       2124  weight  0.10000E+01 volume  0.44171E+03 ppm1   7.689  ppm2  2.641
ASSI {2164}
(segid "BrD" and resid 15 and name HD %)
((segid "BrD" and resid 16 and name HA))
2.600  1.700 1.700 peak       2164  weight  0.10000E+01 volume  0.41516E+03 ppm1   7.650  ppm2  4.538
ASSI {2224}
(segid "BrD" and resid 106 and name HE %)
(segid "BrD" and resid 75 and name HE %)
3.000  2.200 2.200 peak       2224  weight  0.10000E+01 volume  0.17361E+03 ppm1   7.646  ppm2  3.666
ASSI {2234}
(segid "BrD" and resid 106 and name HE %)
((segid "BrD" and resid 78 and name HB1))
2.900  2.100 2.100 peak       2234  weight  0.10000E+01 volume  0.21480E+03 ppm1   7.647  ppm2  2.353
ASSI {2244}
(segid "BrD" and resid 106 and name HE %)
((segid "BrD" and resid 78 and name HB1))
2.600  1.700 1.700 peak       2244  weight  0.10000E+01 volume  0.42175E+03 ppm1   7.647  ppm2  1.268
OR {2244}
(segid "BrD" and resid 106 and name HE %)
((segid "BrD" and resid 78 and name HG))
ASSI {2264}
(segid "BrD" and resid 106 and name HE %)
((segid "BrD" and resid 106 and name HB1)
3.400  2.900 3.100 peak       2264  weight  0.10000E+01 volume  0.80420E+02 ppm1   7.644  ppm2  3.919
ASSI {2424}
(segid "BrD" and resid 106 and name HE %)
(segid "BrD" and resid 17 and name HG2 %)
4.000  4.000 1.500 peak       2414  weight  0.10000E+01 volume  0.29483E+02 ppm1   7.616  ppm2  1.706
ASSI {2484}
(segid "BrD" and resid 96 and name HE %)
((segid "BrD" and resid 86 and name HE1))
3.000  2.200 2.200 peak       2484  weight  0.10000E+01 volume  0.26268E+03 ppm1   7.611  ppm2  3.206
ASSI {2504}
(segid "BrD" and resid 106 and name HE %)
((segid "BrD" and resid 21 and name HG11))
2.500  1.600 1.600 peak       2504  weight  0.10000E+01 volume  0.54543E+03 ppm1   7.611  ppm2  2.374
ASSI {2514}
(segid "BrD" and resid 106 and name HE %)
((segid "BrD" and resid 18 and name HG))
2.600  1.700 1.700 peak       2514  weight  0.10000E+01 volume  0.40048E+03 ppm1   7.611  ppm2  3.374
ASSI {2574}
(segid "BrD" and resid 74 and name HE %)
(segid "BrD" and resid 63 and name HD24))
2.900  2.100 2.100 peak       2574  weight  0.10000E+01 volume  0.18991E+03 ppm1   7.539  ppm2  1.496
ASSI {2614}
(segid "BrD" and resid 106 and name HD %)
((segid "BrD" and resid 21 and name HG11))
3.200  2.600 2.300 peak       2614  weight  0.10000E+01 volume  0.10679E+03 ppm1   7.535  ppm2  2.308
ASSI {2654}
(segid "BrD" and resid 106 and name HD %)
(segid "BrD" and resid 21 and name HG2 %)
2.000  1.000 1.000 peak       3654  weight  0.10000E+01 volume  0.21819E+04 ppm1   7.541  ppm2  1.580
ASSI {2674}
(segid "BrD" and resid 74 and name HE %)
((segid "BrD" and resid 78 and name HG))
2.500  1.600 1.600 peak       2674  weight  0.10000E+01 volume  0.54850E+03 ppm1   7.529  ppm2  1.264
ASSI {2694}
(segid "BrD" and resid 74 and name HE %)
(segid "BrD" and resid 78 and name HD1 %)
2.500  1.600 1.600 peak       2694  weight  0.10000E+01 volume  0.46858E+03 ppm1   7.530  ppm2  0.780
ASSI {2754}
(segid "BrD" and resid 106 and name HD %)
((segid "BrD" and resid 106 and name HB1))
2.300  1.300 1.300 peak       2754  weight  0.10000E+01 volume  0.86816E+03 ppm1   7.524  ppm2  3.919

TABLE 2-continued

Unambiguous NOE-derived Inter-proton Distance Restraints

ASSI {2774}
(segid "BrD" and resid 106 and name HD %)
((segid "BrD" and resid 106 and name HB2))
2.400   1.400 1.400 peak           2774  weight  0.10000E+01 volume  0.63063E+03 ppm1    7.524 ppm2  3.708
ASSI {2834}
(segid "BrD" and resid 106 and name HD %)
(segid "BrD" and resid 107 and name HE %)
3.400   2.900 2.100 peak           2834  weight  0.10000E+01 volume  0.82229E+02 ppm1    7.513 ppm2  7.940
ASSI {3074}
(segid "BrD" and resid 67 and name HE %)
(segid "BrD" and resid 73 and name HD1 %)
4.000   4.000 1.500 peak           3074  weight  0.10000E+01 volume  0.26072E+02 ppm1    7.314 ppm2  1.545
ASSI {3144}
(segid "BrD" and resid 47 and name HE %)
(segid "BrD" and resid 46 and name HB2)
3.000   2.200 2.200 peak           3144  weight  0.10000E+01 volume  0.17782E+03 ppm1    7.270 ppm2  3.075
ASSI {3224}
(segid "BrD" and resid 82 and name HD %)
((segid "BrD" and resid 103 and name HG2))
3.100   2.400 2.400 peak           3224  weight  0.10000E+01 volume  0.12400E+03 ppm1    7.264 ppm2  2.595
ASSI {3234}
(segid "BrD" and resid 82 and name HD %)
((segid "BrD" and resid 103 and name HB1))
3.200   2.600 2.300 peak           3234  weight  0.10000E+01 volume  0.10914E+03 ppm1    7.266 ppm2  2.374
ASSI {3254}
(segid "BrD" and resid 82 and name HD %)
((segid "BrD" and resid 81 and name HB))
3.200   2.600 2.300 peak           3254  weight  0.10000E+01 volume  0.12188E+03 ppm1    7.266 ppm2  2.032
ASSI {3264}
(segid "BrD" and resid 82 and name HD %)
((segid "BrD" and resid 103 and name HB2))
3.100   2.400 2.400 peak           3264  weight  0.10000E+01 volume  0.13716E+03 ppm1    7.266 ppm2  1.902
ASSI {3314}
(segid "BrD" and resid 82 and name HD %)
(segid "BrD" and resid 102 and name HD2 %)
3.100   2.400 2.400 peak           3314  weight  0.10000E+01 volume  0.13023E+03 ppm1    7.261 ppm2  1.332
OR {3314}
(segid "BrD" and resid 82 and name HD %)
(segid "BrD" and resid 102 and name HD1 %)
ASSI {3354}
(segid "BrD" and resid 82 and name HE %)
((segid "BrD" and resid 106 and name HD1))
3.000   2.200 2.200 peak           3354  weight  0.10000E+01 volume  0.15234E+03 ppm1    7.069 ppm2  3.922
ASSI {3364}
(segid "BrD" and resid 82 and name HE %)
((segid "BrD" and resid 103 and name HA))
3.000   2.200 2.200 peak           $$    weight  0.10000E+01 volume  $$+03 ppm1          1.070 ppm2  3.789
ASSI {3404}
(segid "BrD" and resid 82 and name HE %)
((segid "BrD" and resid 102 and name HB2))
2.900   2.200 2.200 peak           3404  weight  0.10000E+01 volume  0.20703E+03 ppm1    7.070 ppm2  1.838
ASSI {3424}
(segid "BrD" and resid 82 and name HE %)
(segid "BrD" and resid 102 and name HD2 %)
2.400   1.400 1.400 peak           3424  weight  0.10000E+01 volume  0.67243E+03 ppm1    7.070 ppm2  1.333
ASSI {3444}
(segid "BrD" and resid 82 and name HE %)
(segid "BrD" and resid 107 and name HD %)
3.500   3.100 2.000 peak           3444  weight  0.10000E+01 volume  0.65231E+02 ppm1    7.069 ppm2  7.777
ASSI {3464}
(segid "BrD" and resid 82 and name HE %)
(segid "BrD" and resid 78 and name HD2 %)
2.900   2.100 2.100 peak           3464  weight  0.10000E+01 volume  0.20065E+03 ppm1    7.067 ppm2  0.680
ASSI {3614}
((segid "BrD" and resid 82 and name HZ))
(segid "BrD" and resid 102 and name HD2 %)
3.200   2.600 2.300 peak           3514  weight  0.10000E+01 volume  0.11748E+03 ppm1    7.021 ppm2  1.331
ASSI {3524}
((segid "BrD" and resid 82 and name HZ))
(segid "BrD" and resid 78 and name HD2 %)
2.800   2.000 2.000 peak           3524  weight  0.10000E+01 volume  0.25407E+03 ppm1    7.017 ppm2  0.681
ASSI {3674}
(segid "BrD" and resid 74 and name HD %)
(segid "BrD" and resid 68 and name HD %)
2.800   2.000 2.000 peak           3574  weight  0.10000E+01 volume  0.24275E+03 ppm1    7.005 ppm2  7.777

TABLE 2-continued

Unambiguous NOE-derived Inter-proton Distance Restraints

ASSI {3654}
(segid "BrD" and resid 74 and name HD %)
(segid "BrD" and resid 75 and name HE %)
3.300  2.700 2.200 peak        3654  weight  0.10000E+01 volume   0.90985E+02 ppm1    7.006 ppm2  2.667
ASSI {3684}
(segid "BrD" and resid 74 and name HD %)
(segid "BrD" and resid 59 and name HE %)
2.600  1.700 1.700 peak        3684  weight  0.10000E+01 volume   0.36097E+03 ppm1    7.005 ppm2  1.885
ASSI {3754}
(segid "BrD" and resid 67 and name HD %)
((segid "BrD" and resid 62 and name HG2))
3.400  2.900 2.100 peak        3754  weight  0.10000E+01 volume   0.78199E+02 ppm1    6.899 ppm2  1.496
ASSI {3804}
(segid "BrD" and resid 46 and name HE %)
((segid "BrD" and resid 53 and name HA))
3.100  2.400 2.400 peak        3804  weight  0.10000E+01 volume   0.13088E+03 ppm1    6.686 ppm2  4.701
ASSI {3944}
(segid "BrD" and resid 46 and name HD %)
(segid "BrD" and resid 38 and name HG1 %)
3.400  2.900 2.100 peak        3944  weight  0.10000E+01 volume   0.75575E+02 ppm1    5.740 ppm2  1.088
ASSI {4024}
((segid "BrD" and resid 52 and name HA))
((segid "BrD" and resid 53 and name HD2))
3.400  2.900 2.100 peak        4024  weight  0.10000E+01 volume   0.78758E+02 ppm1    5.589 ppm2  4.017
ASSI {4054}
((segid "BrD" and resid 28 and name HD2))
((segid "BrD" and resid 34 and name HZ))
2.800  2.000 2.000 peak        4054  weight  0.10000E+01 volume   0.24761E+03 ppm1    5.577 ppm2  7.924
ASSI {4124}
((segid "BrD" and resid 34 and name HA))
(segid "BrD" and resid 34 and name HD %)
2.300  1.300 1.300 peak        4114  weight  0.10000E+01 volume   0.78719E+03 ppm1    5.547 ppm2  7.713
ASSI {4204}
(segid "BrD" and resid 34 and name HD %)
(segid "BrD" and resid 56 and name HD1 %)
2.900  2.100 2.100 peak        4204  weight  0.10000E+01 volume   0.22356E+01 ppm1    7.714 ppm2  1.544
ASSI {4264}
(segid "BrD" and resid 34 and name HE %)
((segid "BrD" and resid 31 and name HA))
2.500  1.600 1.600 peak        4264  weight  0.10000E+01 volume   0.48557E+03 ppm1    7.781 ppm2  4.993
ASSI {4304}
(segid "BrD" and resid 107 and name HD %)
(segid "BrD" and resid 106 and name HD %)
2.800  2.000 2.000 peak        4304  weight  0.10000E+01 volume   0.27783E+03 ppm1    7.802 ppm2  7.517
ASSI {4324}
((segid "BrD" and resid 82 and name HZ))
((segid "BrD" and resid 103 and name HA))
3.300  2.700 2.200 peak        4324  weight  0.10000E+01 volume   0.96267E+02 ppm1    7.031 ppm2  3.790
ASSI {4364}
(segid "BrD" and resid 107 and name HE %)
((segid "BrD" and resid 78 and name HB2))
3.400  2.900 2.100 peak        4364  weight  0.10000E+01 volume   0.78224E+02 ppm1    7.8$$ ppm2  1.085
ASSI {5}
((segid "AcH" and resid 201 and name HA1))
(segid "BrD" and resid 38 and name HG1 %)
2.600  1.700 1.700 peak           5  weight  0.11000E+01 volume   0.16527E+03 ppm1    4.029 ppm2  1.081
OR {5}
((segid "AcH" and resid 201 and name HA2))
(segid "BrD" and resid 38 and name HG1 %)
ASSI {15}
((segid "AcH" and resid 201 and name HA1))
(segid "BrD" and resid 38 and name HG2 %)
2.600  1.700 1.700 peak          15  weight  0.11000E+01 volume   0.14933E+03 ppm1    4.026 ppm2  0.723
OR {15}
((segid "AcH" and resid 201 and name HA2))
(segid "Brd" and resid 38 and name HG2 %)
ASSI {25}
((segid "AcH" and resid 201 and name HA1))
(segid "BrD" and resid 43 and name HB %)
2.600  1.700 1.700 peak          25  weight  0.11000E+01 volume   0.16374E+03 ppm1    4.023 ppm2  1.609
ASSI {35}
((segid "AcH" and resid 201 and name HB2))
(segid "BrD" and resid 43 and name HB %)
2.600  1.700 1.700 peak          35  weight  0.11000E+01 volume   0.16831E+03 ppm1    3.428 ppm2  1.601

TABLE 2-continued

Unambiguous NOE-derived Inter-proton Distance Restraints

ASSI {45}
((segid "AcH" and resid 201 and name HB2))
(segid "BrD" and resid 38 and name HG1 %)
2.700  1.800 1.800 peak         45 weight  0.11000E+01 volume  0.14392E+03 ppm1    3.430 ppm2  1.074
OR {45}
((segid "AcH" and resid 201 and name HB1))
(segid "BrD" and resid 38 and name HG1 %)
ASSI {55}
((segid "AcH" and resid 201 and name HB2))
(segid "BrD" and resid 38 and name HG2 %)
2.600  1.700 1.700 peak         55 weight  0.11000E+01 volume  0.14742E+03 ppm1    3.430 ppm2  0.723
OR {55}
((segid "AcH" and resid 201 and name HB1))
(segid "BrD" and resid 38 and name HG2 %)
ASSI {65}
((segid "AcH" and resid 201 and name HD1))
(segid "BrD" and resid 43 and name HB %)
2.600  1.700 1.700 peak         65 weight  0.11000E+01 volume  0.15413E+03 ppm1    8.179 ppm2  1.608
ASSI {75}
((segid "AcH" and resid 201 and name HD2))
(segid "BrD" and resid 43 and name HB %)
2.700  1.800 1.800 peak         75 weight  0.11000E+01 volume  0.13471E+03 ppm1    7.683 ppm2  1.592
ASSI {85}
((segid "AcH" and resid 201 and name HD2))
(segid "BrD" and resid 38 and name HG1 %)
2.700  1.800 1.800 peak         85 weight  0.11000E+01 volume  0.12532E+03 ppm1    7.680 ppm2  1.066
ASSI {95}
((segid "AcH" and resid 201 and name HD2))
(segid "BrD" and resid 38 and name HG2 %)
2.700  1.800 1.800 peak         95 weight  0.11000E+01 volume  0.12585E+03 ppm1    7.690 ppm2  0.691
ASSI {105}
(segid "AcH" and resid 200 and name HA %)
(segid "BrD" and resid 38 and name HG2 %)
2.600  1.700 1.700 peak        105 weight  0.11000E+01 volume  0.16395E+01 ppm1    2.547 ppm2  0.727
ASSI {115}
(segid "AcH" and resid 200 and name HA %)
(segid "BrD" and resid 38 and name HG1 %)
2.400  1.400 1.400 peak        115 weight  0.11000E+01 volume  0.29029E+03 ppm1    2.548 ppm2  1.072
ASSI {125}
(segid "AcH" and resid 200 and name HA %)
(segid "BrD" and resid 43 and name HB %)
2.700  1.800 1.800 peak        125 weight  0.11000E+01 volume  0.13320E+03 ppm1    2.538 ppm2  1.603
ASSI {135}
(segid "AcH" and resid 200 and name HA %)
((segid "BrD" and resid 38 and name HA))
2.600  1.700 1.700 peak        135 weight  0.11000E+01 volume  0.17326E+03 ppm1    2.548 ppm2  4.209
ASSI {145}
(segid "AcH" and resid 200 and name HA %)
((segid "BrD" and resid 43 and name HA))
2.700  1.800 1.800 peak        145 weight  0.11000E+01 volume  0.12382E+03 ppm1    2.547 ppm2  5.520
ASSI {6}
((segid "AcH" and resid 201 and name HA1))
(segid "BrD" and resid 46 and name HE %)
2.700  1.800 1.800 peak          6 weight  0.11000E+01 volume  0.14312E+03 ppm1    4.007 ppm2  6.648
OR {6}
((segid "AcH" and resid 201 and name HA2))
(segid "BrD" and resid 46 and name HE %)
ASSI {16}
((segid "AcH" and resid 201 and name HA2))
(segid "BrD" and resid 95 and name HD %)
2.700  1.800 1.800 peak         16 weight  0.11000E+01 volume  0.13924E+03 ppm1    4.015 ppm2  7.481
OR {16}
((segid "AcH" and resid 201 and name HA1))
(segid "BrD" and resid 95 and name HD %)
ASSI {26}
((segid "AcH" and resid 201 and name HB1))
(segid "BrD" and resid 95 and name HD %)
2.600  1.700 1.700 peak         26 weight  0.11000E+01 volume  0.15229E+03 ppm1    3.429 ppm2  7.481
OR {26}
((segid "AcH" and resid 201 and name HB2))
(segid "BrD" and resid 95 and name HD %)
ASSI {36}
((segid "AcH" and resid 201 and name HA1))
(segid "BrD" and resid 88 and name HD %)
2.500  1.600 1.600 peak         36 weight  0.11000E+01 volume  0.18465E+03 ppm1    4.015 ppm2  7.637

TABLE 2-continued

Unambiguous NOE-derived Inter-proton Distance Restraints

```
OR {36}
((segid "AcH" and resid 201 and name HA2))
(segid "BrD" and resid 88 and name HD %)
ASSI {46}
((segid "AcH" and resid 201 and name HB2))
(segid "BrD" and resid 88 and name HD %)
2.700   1.800 1.800 peak          46 weight  0.11000E+01 volume   0.13938E+03 ppm1    3.429 ppm2  7.637
OR {46}
((segid "AcH" and resid 201 and name HB1))
(segid "BrD" and resid 88 and name HD %)
ASSI {56}
((segid "AcH" and resid 201 and name HA2))
(segid "BrD" and resid 95 and name HE %)
2.600   1.700 1.700 peak          56 weight  0.11000E+01 volume   0.16075E+03 ppm1    4.015 ppm2  7.585
OR {56}
((segid "AcH" and resid 201 and name HA1))
(segid "BrD" and resid 95 and name HE %)
ASSI {66}
((segid "AcH" and resid 201 and name HB1))
(segid "BrD" and resid 95 and name HE %)
2.600   1.700 1.700 peak          66 weight  0.11000E+01 volume   0.16293E+03 ppm1    3.429 ppm2  7.585
ASSI {76}
(segid "AcH" and resid 200 and name HA %)
(segid "BrD" and resid 95 and name HE %)
2.700   1.800 1.800 peak          76 weight  0.11000E+01 volume   0.14049E+03 ppm1    2.542 ppm2  7.585
ASSI {86}
((segid "AcH" and resid 201 and name HA1))
(segid "BrD" and resid 88 and name HE %)
2.600   1.700 1.700 peak          86 weight  0.11000E+01 volume   0.16796E+03 ppm1    4.019 ppm2  7.358
OR {86}
((segid "AcH" and resid 201 and name HA2))
(segid "BrD" and resid 88 and name HE %)
ASSI {96}
((segid "AcH" and resid 201 and name HB2))
(segid "BrD" and resid 88 and name HE %)
2.600   1.700 1.700 peak          96 weight  0.11000E+01 volume   0.16763E+03 ppm1    3.430 ppm2  7.358
OR {96}
((segid "AcH" and resid 201 and name HB1))
(segid "BrD" and resid 88 and name HE %)
ASSI {7}
(segid "AcH" and resid 200 and name HA %)
((segid "AcH" and resid 201 and name HN))
2.700   1.800 1.800 peak           7 weight  0.11000E+01 volume   0.12000E+03 ppm1    3.430 ppm2  7.358
ASSI {17}
(segid "AcH" and resid 200 and name HA %)
((segid "AcH" and resid 201 and name HA1))
2.700   1.800 1.800 peak          17 weight  0.11000E+01 volume   0.12000E+03 ppm1    3.430 ppm2  7.358
ASSI {27}
((segid "AcH" and resid 201 and name HB2))
((segid "AcH" and resid 201 and name HD1))
2.700   1.800 1.800 peak          27 weight  0.11000E+01 volume   0.12000E+03 ppm1    3.430 ppm2  7.358
OR {27}
((segid "AcH" and resid 201 and name HB1))
((segid "AcH" and resid 201 and name HD1))
ASSI {37}
((segid "AcH" and resid 201 and name HB1))
((segid "AcH" and resid 201 and name HN))
2.700   1.800 1.800 peak          37 weight  0.11000E+01 volume   0.12000E+03 ppm1    3.430 ppm2  7.358
OR {37}
((segid "AcH" and resid 201 and name HB2))
((segid "AcH" and resid 201 and name HN))
ASSI {47}
((segid "AcH" and resid 201 and name HA2))
((segid "AcH" and resid 201 and name HN))
2.700   1.800 1.800 peak          47 weight  0.11000E+01 volume   0.12000E+03 ppm1    3.430 ppm2  7.358
OR {47}
((segid "AcH" and resid 201 and name HA1))
((segid "AcH" and resid 201 and name HN))
```

TABLE 3

Ambiguous NOE-derived Inter-proton Distance Restraints

```
ASSI {311}
((segid "BrD" and resid 32 and name HN))
((segid "BrD" and resid 35 and name HO1))
 4.200  4.200 1.300 peak        311 weight  0.10000E+01 volume   0.35526E+02 ppm1      7.738 ppm2    3.430
OR {311}
((segid "BrD" and resid 32 and name HN))
((segid "BrD" and resid 28 and name HB2))
ASSI {391}
((segid "BrD" and resid 106 and name HN))
(segid "BrD" and resid 105 and name HD%))
 3.100  2.400 2.400 peak        391 weight  0.10000E+01 volume   0.20417E+03 ppm1      9.740 ppm2    7.778
OR {391}
((segid "BrD" and resid 106 and name HN))
((segid "BrD" and resid 104 and name HN))
OR {391}
((segid "BrD" and resid 106 and name HN))
((segid "BrD" and resid 107 and name HD%))
ASSI {731}
((segid "BrD" and resid 100 and name HN))
((segid "BrD" and resid 97 and name HA))
 3.300  2.700 2.200 peak        731 weight  0.10000E+01 volume   0.15089E+03 ppm1      8.669 ppm2    4.801
OR {731}
((segid "BrD" and resid 100 and name HN))
((segid "BrD" and resid 98 and name HA))
ASSI {781}
((segid "BrD" and resid 97 and name HN))
((segid "BrD" and resid 98 and name HB2))
 4.000  4.000 1.500 peak        781 weight  0.10000E+01 volume   0.45845E+02 ppm1      8.673 ppm2    3.671
OR {781}
((segid "BrD" and resid 97 and name HN))
((segid "BrD" and resid 85 and name HB2))
ASSI {831}
((segid "BrD" and resid 96 and name HN))
((segid "BrD" and resid 97 and name HB1))
 3.200  2.600 2.300 peak        831 weight  0.10000E+01 volume   0.17645E+03 ppm1      7.977 ppm2    2.728
OR {831}
((segid "BrD" and resid 78 and name HN))
((segid "BrD" and resid 79 and name HB2))
OR {831}
((segid "BrD" and resid 77 and name HN))
((segid "BrD" and resid 79 and name HB2))
OR {831}
((segid "BrD" and resid 96 and name HN))
((segid "BrD" and resid 92 and name HB1))
OR {831}
((segid "BrD" and resid 78 and name HN))
(segid "BrD" and resid 79 and name HB1))
ASSI {1051}
((segid "BrD" and resid 76 and name HN))
(segid "BrD" and resid 73 and name HB2))
 5.000  5.000 0.500 peak       1051 weight  0.10000E+01 volume   0.12021E+02 ppm1      6.612 ppm2    2.497
OR {1051}
((segid "BrD" and resid 76 and name HN))
((segid "BrD" and resid 80 and name HB2))
ASSI {1101}
((segid "BrD" and resid 75 and name HN))
((segid "BrD" and resid 18 and name HQ))
 5.500  5.500 0.000 peak       1101 weight  0.10000E+01 volume   0.63178E+01 ppm1      9.107 ppm2    2.294
OR {1101}
((segid "BrD" and resid 75 and name HN))
((segid "BrD" and resid 72 and name HD1))
OR {1101}
((segid "BrD" and resid 98 and name HN))
(segid "BrD" and resid 31 and name HB%))
ASSI {1551}
((segid "BrD" and resid 21 and name HN))
((segid "BrD" and resid 24 and name HE22))
 3.400  2.900 2.100 peak       1551 weight  0.10000E+01 volume   0.12608E+03 ppm1      8.544 ppm2    7.515
OR {1551}
((segid "BrD" and resid 21 and name HN))
(segid "BrD" and resid 106 and name HD%))
OR {1551}
((segid "BrD" and resid 109 and name HN))
(segid "BrD" and resid 106 and name HD%))
OR {1551}
((segid "BrD" and resid 64 and name HN))
(segid "BrD" and resid 15 and name HE%))
```

TABLE 3-continued

Ambiguous NOE-derived Inter-proton Distance Restraints

```
ASSI {1781}
((segid "BrD" and resid 26 and name HN))
((segid "BrD" and resid 22 and name HB1))
  3.400  2.900 2.100 peak       1781 weight  0.10000E+01 volume  0.12549E+03 ppm1    9.196 ppm2    2.672
OR {1781}
((segid "BrD" and resid 26 and name HN))
((segid "BrD" and resid 56 and name HB1))
ASSI {2721}
((segid "BrD" and resid 104 and name HN))
((segid "BrD" and resid 105 and name HB2))
  3.300  2.700 2.200 peak       2721 weight  0.10000E+01 volume  0.14753E+03 ppm1    7.763 ppm2    3.671
OR {2721}
((segid "BrD" and resid 104 and name HN))
((segid "BrD" and resid 107 and name HB1))
OR {2721 }
((segid "BrD" and resid 104 and name HN))
((segid "BrD" and resid 106 and name HB2))
ASSI {3261}
((segid "BrD" and resid 16 and name HN))
((segid "BrD" and resid 13 and name HG2))
  4.100  4.100 1.400 peak       3261 weight  0.10000E+01 volume  0.41938E+02 ppm1    8.794 ppm2    2.954
OR {3261}
((segid "BrD" and resid 16 and name HN))
((segid "BrD" and resid 11 and name HB1))
ASSI {3361}
((segid "BrD" and resid 13 and name HN))
((segid "BrD" and resid 13 and name HG1))
  4.100  4.100 1.400 peak       3361 weight  0.10000E+01 volume  0.40202E+02 ppm1    8.809 ppm2    3.103
OR {3361}
((segid "BrD" and resid 14 and name HN))
((segid "BrD" and resid 13 and name HG1))
ASSI {3371}
((segid "BrD" and resid 13 and name HN))
((segid "BrD" and resid 13 and name HG2))
  3.300  2.700 2.200 peak       3371 weight  0.10000E+01 volume  0.14859E+03 ppm1    8.802 ppm2    2.987
OR {3371}
((segid "BrD" and resid 14 and name HN))
((segid "BrD" and resid 13 and name HG2))
ASSI {3401}
((segid "BrD" and resid 13 and name HN))
((segid "BrD" and resid 11 and name HD1))
  3.800  3.600 1.700 peak       3401 weight  0.10000E+01 volume  0.67241E+02 ppm1    8.810 ppm2    4.485
OR {3401}
((segid "BrD" and resid 14 and name HN))
((segid "BrD" and resid 11 and name HD1))
OR {3401}
((segid "BrD" and resid 14 and name HN))
((segid "BrD" and resid 16 and name HA))
ASSI {3671}
((segid "BrD" and resid 102 and name HN))
((segid "BrD" and resid 30 and name HB1))
  3.800  3.600 1.700 peak       3671 weight  0.10000E+01 volume  0.58619E+02 ppm1    9.156 ppm2    4.934
OR {3671}
((segid "BrD" and resid 102 and name HN))
((segid "BrD" and resid 100 and name HA))
ASSI {3841}
((segid "BrD" and resid 103 and name HN))
((segid "BrD" and resid 100 and name HA))
  3.000  2.200 2.200 peak       3841 weight  0.10000E+01 volume  0.24821E+03 ppm1    8.661 ppm2    4.900
OR {3841}
((segid "BrD" and resid 40 and name HN))
((segid "BrD" and resid 41 and name HB))
ASSI {3911}
((segid "BrD" and resid 59 and name HN))
((segid "BrD" and resid 57 and name HB1))
  3.500  3.100 2.000 peak       3911 weight  0.10000E+01 volume  0.98690E+02 ppm1    8.496 ppm2    2.969
OR {3911}
((segid "BrD" and resid 59 and name HN))
((segid "BrD" and resid 61 and name HG1))
OR {3911}
((segid "BrD" and resid 31 and name HN))
((segid "BrD" and resid 29 and name HG1))
OR {3911}
((segid "BrD" and resid 59 and name HN))
((segid "BrD" and resid 55 and name HB1))
```

TABLE 3-continued

Ambiguous NOE-derived Inter-proton Distance Restraints

```
ASSI {4131}
((segid "BrD" and resid 25 and name HN))
((segid "BrD" and resid 21 and name HB))
  3.800  3.600  1.700 peak      4131 weight  0.10000E+01 volume  0.59139E+02 ppm1     9.133 ppm2    2.465
OR {4131}
((segid "BrD" and resid 25 and name HN))
((segid "BrD" and resid 26 and name HB1))
ASSI {6751}
((segid "BrD" and resid 111 and name HN))
((segid "BrD" and resid 111 and name HD1))
  3.200  2.600  2.300 peak      6751 weight  0.10000E+01 volume  0.16212E+03 ppm1     8.168 ppm2    2.204
OR {6751}
((segid "BrD" and resid 111 and name HN))
((segid "BrD" and resid 109 and name HB2))
ASSI {6861}
((segid "BrD" and resid 21 and name HN))
((segid "BrD" and resid 24 and name HG2))
  3.400  2.900  2.100 peak      6861 weight  0.10000E+01 volume  0.12194E+03 ppm1     8.574 ppm2    3.072
OR {6861}
((segid "BrD" and resid 21 and name HN))
((segid "BrD" and resid 24 and name HB2))
OR {6861}
((segid "BrD" and resid 21 and name HN))
((segid "BrD" and resid 23 and name HG2))
OR {6861}
((segid "BrD" and resid 21 and name HN))
((segid "BrD" and resid 24 and name HB1))
ASSI {6871}
((segid "BrD" and resid 21 and name HN))
((segid "BrD" and resid 22 and name HB1))
  3.300  2.700  2.200 peak      6871 weight  0.10000E+01 volume  0.15992E+03 ppm1     8.573 ppm2    2.702
OR {6871}
((segid "BrD" and resid 64 and name HN))
((segid "BrD" and resid 61 and name HB2))
OR {6871}
((segid "BrD" and resid 109 and name HN))
((segid "BrD" and resid 112 and name HB1))
OR {6871}
((segid "BrD" and resid 64 and name HN))
((segid "BrD" and resid 22 and name HB1))
ASSI {6911}
((segid "BrD" and resid 86 and name HN))
((segid "BrD" and resid 86 and name HE1))
  3.700  3.400  1.800 peak      6911 weight  0.10000E+01 volume  0.78171E+02 ppm1     8.423 ppm2    3.044
OR {6911}
((segid "BrD" and resid 86 and name HN))
((segid "BrD" and resid 87 and name HG1))
ASSI {7011}
((segid "BrD" and resid 52 and name HN))
((segid "BrD" and resid 80 and name HN))
  4.200  4.200  1.300 peak      7031 weight  0.10000E+01 volume  0.35356E+02 ppm1     9.003 ppm2    7.979
OR {7031}
((segid "BrD" and resid 52 and name HN))
((segid "BrD" and resid 77 and name HN))
OR {7031}
((segid "BrD" and resid 52 and name HN))
((segid "BrD" and resid 47 and name HD%))
ASSI {7121}
((segid "BrD" and resid 89 and name HD21))
((segid "BrD" and resid 85 and name HA))
  3.700  3.400  1.800 peak      7121 weight  0.10000E+01 volume  0.76700E+02 ppm1     8.923 ppm2    5.021
OR {7121}
((segid "BrD" and resid 89 and name HD21))
((segid "BrD" and resid 93 and name HB1))
ASSI {7131}
((segid "BrD" and resid 89 and name HD22))
((segid "BrD" and resid 85 and name HA))
  3.600  3.200  1.900 peak      7131 weight  0.10000E+01 volume  0.84076E+02 ppm1     8.416 ppm2    5.021
OR {7131}
((segid "BrD" and resid 89 and name HD22))
((segid "BrD" and resid 93 and name HB1))
ASSI {7251}
((segid "BrD" and resid 26 and name HN))
(segid "BrD" and resid 22 and name HD2%)
  3.000  2.200  2.200 peak      7251 weight  0.10000E+01 volume  0.24489E+03 ppm1     9.196 ppm2    1.549
```

TABLE 3-continued

Ambiguous NOE-derived Inter-proton Distance Restraints

```
OR {7251}
((segid "BrD" and resid 26 and name HN))
(segid "BrD" and resid 56 and name HD1%)
ASSI {8181}
((segid "BrD" and resid 57 and name HN))
(segid "BrD" and resid 25 and name HD2%)
 4.100  4.100 1.400 peak       8181 weight  0.10000E+01 volume   0.42960E+02 ppm1        9.359 ppm2    1.667
OR {8181}
((segid "BrD" and resid 57 and name HN))
(segid "BrD" and resid 58 and name HG2%)
OR {8181}
((segid "BrD" and resid 57 and name HN))
(segid "BrD" and resid 22 and name HD1%)
ASSI {8211}
((segid "BrD" and resid 114 and name HN))
((segid "BrD" and resid 111 and name HB2))
 4.000  4.000 1.500 peak       8211 weight  0.10000E+01 volume   0.47918E+02 ppm1        8.377 ppm2    2.177
OR {8211}
((segid "BrD" and resid 114 and name HN))
((segid "BrD" and resid 110 and name HB))
ASSI {8261}
((segid "BrD" and resid 28 and name HN))
((segid "BrD" and resid 25 and name HB))
 4.200  4.200 3.300 peak       8261 weight  0.10000E+01 volume   0.36987E+02 ppm1        8.166 ppm2    3.014
OR {8261}
((segid "BrD" and resid 28 and name HN))
((segid "BrD" and resid 29 and name HG1))
ASSI {8291}
((segid "BrD" and resid 28 and name HN))
(segid "BrD" and resid 25 and name HG2%)
 4.400  4.400 1.100 peak       8291 weight  0.10000E+01 volume   0.24897E+02 ppm1        8.164 ppm2    1.639
OR {8291}
((segid "BrD" and resid 28 and name HN))
((segid "BrD" and resid 26 and name HG1))
ASSI {8381}
((segid "BrD" and resid 61 and name HN))
(segid "BrD" and resid 58 and name HG2%)
 3.400  2.900 2.100 peak       8381 weight  0.10000E+01 volume   0.13119E+03 ppm1        8.743 ppm2    1.674
OR {8381}
((segid "BrD" and resid 61 and name HN))
(segid "BrD" and resid 22 and name HD2%)
OR {8381}
((segid "BrD" and resid 38 and name HN))
(segid "BrD" and resid 43 and name HB%)
ASSI {8391}
((segid "BrD" and resid 38 and name HN))
((segid "BrD" and resid 39 and name HG1))
 4.000  4.000 1.500 peak       8391 weight  0.10000E+01 volume   0.45211E+02 ppm1        8.743 ppm2    2.008
OR {8391}
((segid "BrD" and resid 61 and name HN))
((segid "BrD" and resid 57 and name HG2))
ASSI {8511}
((segid "BrD" and resid 50 and name HN))
((segid "BrD" and resid 53 and name HG1))
 3.700  3.400 1.800 peak       8511 weight  0.10000E+01 volume   0.70210E+02 ppm1        8.564 ppm2    2.814
OR {8511}
((segid "BrD" and resid 50 and name HN))
(segid "BrD" and resid 53 and name HB1))
OR {8511}
((segid "BrD" and resid 50 and name HN))
(segid "BrD" and resid 87 and name HB1))
OR {8511}
((segid "BrD" and resid 46 and name HN))
(segid "BrD" and resid 83 and name HG1))
OR {8511}
((segid "BrD" and resid 46 and name HN))
((segid "BrD" and resid 53 and name HB1))
ASSI {8751}
(segid "BrD" and resid 58 and name HN))
((segid "BrD" and resid 37 and name HG1))
 3.400  2.900 2.100 peak       8751 weight  0.10000E+01 volume   0.12911E+03 ppm1       10.051 ppm2    2.747
OR {8751}
((segid "BrD" and resid 58 and name HN))
(segid "BrD" and resid 35 and name HE%)
```

TABLE 3-continued

Ambiguous NOE-derived Inter-proton Distance Restraints

ASSI {8861}
((segid "BrD" and resid 9 and name HN))
((segid "BrD" and resid 8 and name HG1))
  3.600  3.200  1.900 peak       8861  weight  0.10000E+01 volume   0.86153E+02 ppm1      9.052 ppm2    2.631
OR {8861}
((segid "BrD" and resid 5 and name HN))
((segid "BrD" and resid 7 and name HB1))
ASSI {8891}
((segid "BrD" and resid 103 and name HN))
((segid "BrD" and resid 100 and name HA))
  4.000  4.000  1.500 peak       8891  weight  0.10000E+01 volume   0.44524E+02 ppm1      8.668 ppm2    4.917
OR {8891}
((segid "BrD" and resid 112 and name HN))
((segid "BrD" and resid 113 and name HA))
ASSI {8901}
((segid "BrD" and resid 112 and name HN))
((segid "BrD" and resid 108 and name HA))
  3.400  2.900  2.100 peak       8901  weight  0.10000E+01 volume   0.11279E+03 ppm1      8.668 ppm2    4.805
OR {8901}
((segid "BrD" and resid 103 and name HN))
((segid "BrD" and resid 82 and name HA))
OR {8901}
((segid "BrD" and resid 103 and name HN))
((segid "BrD" and resid 98 and name HA))
ASSI {8911}
((segid "BrD" and resid 103 and name HN))
((segid "BrD" and resid 99 and name HA))
  3.500  3.100  2.000 peak       8911  weight  0.10000E+01 volume   0.10762E+03 ppm1      8.668 ppm2    4.426
OR {8911}
((segid "BrD" and resid 112 and name HN))
((segid "BrD" and resid 110 and name HA))
ASSI {8941}
((segid "BrD" and resid 103 and name HN))
(segid "BrD" and resid 99 and name HB%)
  2.900  2.100  2.100 peak       8941  weight  0.10000E+01 volume   0.29817E+03 ppm1      8.667 ppm2    2.178
OR {8941}
((segid "BrD" and resid 103 and name HN))
((segid "BrD" and resid 102 and name HG))
OR {8941}
((segid "BrD" and resid 112 and name HN))
((segid "BrD" and resid 109 and name HB2))
ASSI {9011}
((segid "BrD" and resid 105 and name HN))
((segid "BrD" and resid 104 and name HD1))
  3.100  2.400  2.400 peak       9011  weight  0.10000E+01 volume   0.22428E+03 ppm1      8.487 ppm2    2.294
OR {9011}
((segid "BrD" and resid 105 and name HN))
((segid "BrD" and resid 103 and name HB1))
ASSI {9031}
((segid "BrD" and resid 105 and name HN))
((segid "BrD" and resid 102 and name HB2))
  3.800  3.600  1.700 peak       9031  weight  0.10000E+01 volume   0.62331E+02 ppm1      8.487 ppm2    1.805
OR {9031}
((segid "BrD" and resid 105 and name HN))
(segid "BrD" and resid 25 and name HG1%)
ASSI {9091}
((segid "BrD" and resid 109 and name HN))
((segid "BrD" and resid 106 and name HB2))
  3.800  3.600  1.700 peak       9091  weight  0.10000E+01 volume   0.66318E+02 ppm1      8.574 ppm2    3.678
OR {9091}
((segid "BrD" and resid 109 and name HN))
((segid "BrD" and resid 107 and name HB1))
OR {9091}
((segid "BrD" and resid 109 and name HN))
((segid "BrD" and resid 105 and name HB2))
OR {9091}
((segid "BrD" and resid 64 and name HN))
((segid "BrD" and resid 68 and name HB1))
ASSI {9101}
((segid "BrD" and resid 64 and name HN))
((segid "BrD" and resid 63 and name HB2))
  2.900  2.100  2.100 peak       9101  weight  0.10000E+01 volume   0.30416E+03 ppm1      8.573 ppm2    2.498
OR {9101}
((segid "BrD" and resid 21 and name HN))
((segid "BrD" and resid 21 and name HB))

TABLE 3-continued

Ambiguous NOE-derived Inter-proton Distance Restraints

```
ASSI {9111}
((segid "BrD" and resid 21 and name HN))
(segid "BrD" and resid 17 and name HG2%)
 3.500  3.100  2.000 peak       9111  weight  0.10000E+01 volume  0.10029E+03 ppm1       8.574 ppm2     1.725
OR {9111}
((segid "BrD" and resid 109 and name HN))
(segid "BrD" and resid 17 and name HG2%)
ASSI {9161}
((segid "BrD" and resid 106 and name HN))
((segid "BrD" and resid 104 and name HB1))
 3.900  3.800  1.600 peak       9161  weight  0.10000E+01 volume  0.56197E+02 ppm1       9.740 ppm2     2.560
OR {9161}
((segid "BrD" and resid 106 and name HN))
((segid "BrD" and resid 103 and name HG2))
ASSI {9171}
((segid "BrD" and resid 106 and name HN))
((segid "BrD" and resid 109 and name HB1))
 4.000  4.000  1.500 peak       9171  weight  0.10000E+01 volume  0.47295E+02 ppm1       9.739 ppm2     2.318
OR {9171}
((segid "BrD" and resid 106 and name HN))
((segid "BrD" and resid 103 and name HB1))
OR {9171}
((segid "BrD" and resid 106 and name HN))
((segid "BrD" and resid 104 and name HD1))
OR {9171}
((segid "BrD" and resid 106 and name HN))
((segid "BrD" and resid 21 and name HG11))
ASSI {9181}
((segid "BrD" and resid 106 and name HN))
((segid "BrD" and resid 102 and name HG))
 4.100  4.100  1.400 peak       9181  weight  0.10000E+01 volume  0.40041E+02 ppm1       9.742 ppm2     2.150
OR {9181}
((segid "BrD" and resid 106 and name HN))
((segid "BrD" and resid 109 and name HB2))
ASSI {9191}
((segid "BrD" and resid 106 and name HN))
((segid "BrD" and resid 102 and name HB1))
 4.200  4.200  1.300 peak       9191  weight  0.10000E+01 volume  0.35794E+02 ppm1       9.740 ppm2     2.002
OR {9191}
((segid "BrD" and resid 106 and name HN))
((segid "BrD" and resid 109 and name HD1))
ASSI {9201}
((segid "BrD" and resid 106 and name HN))
((segid "BrD" and resid 102 and name HB2))
 3.900  3.400  1.600 peak       9201  weight  0.10000E+01 volume  0.56492E+02 ppm1       9.739 ppm2     1.786
OR {9201}
((segid "BrD" and resid 106 and name HN))
(segid "BrD" and resid 25 and name HG1%)
ASSI {9241}
((segid "BrD" and resid 84 and name HN))
((segid "BrD" and resid 80 and name HD2))
 3.700  3.400  1.800 peak       9241  weight  0.10000E+01 volume  0.69670E+02 ppm1       9.464 ppm2     3.908
OR {9241}
((segid "BrD" and resid 84 and name HN))
((segid "BrD" and resid 85 and name HB1))
ASSI {9251}
((segid "BrD" and resid 63 and name HN))
((segid "BrD" and resid 62 and name HG1))
 3.700  3.400  1.800 peak       9251  weight  0.10000E+01 volume  0.78060E+02 ppm1       9.463 ppm2     2.352
OR {9251}
((segid "BrD" and resid 84 and name HN))
((segid "BrD" and resid 80 and name HG1))
OR {9251}
((segid "BrD" and resid 84 and name HN))
((segid "BrD" and resid 86 and name HB1))
ASSI {9281}
((segid "BrD" and resid 84 and name HN))
((segid "BrD" and resid 80 and name HN))
 3.300  2.700  2.200 peak       9281  weight  0.10000E+01 volume  0.13642E+03 ppm1       9.462 ppm2     8.001
OR {9281}
((segid "BrD" and resid 84 and name HN))
((segid "BrD" and resid 107 and name HZ))
OR {9281}
((segid "BrD" and resid 63 and name HN))
((segid "BrD" and resid 70 and name HN))
```

TABLE 3-continued

Ambiguous NOE-derived Inter-proton Distance Restraints

```
ASSI {9311}
((segid "BrD" and resid 22 and name HN))
((segid "BrD" and resid 22 and name HA))
 4.200  4.200  1.300 peak       9311  weight  0.10000E+01 volume  0.35671E+02 ppm1       9.472 ppm2       4.678
OR {9311}
((segid "BrD" and resid 84 and name HN))
((segid "BrD" and resid 80 and name HA))
ASSI {9341}
((segid "BrD" and resid 63 and name HN))
(segid "BrD" and resid 74 and name HE%)
 2.900  2.100  2.100 peak       9341  weight  0.10000E+01 volume  0.30219E+03 ppm1       9.456 ppm2       7.510
OR {9341}
((segid "BrD" and resid 22 and name HN))
(segid "BrD" and resid 106 and name HD%)
ASSI {9371}
((segid "BrD" and resid 22 and name HN))
((segid "BrD" and resid 24 and name HG2))
 3.400  2.900  2.100 peak       9371  weight  0.10000E+01 volume  0.12105E+03 ppm1       9.456 ppm2       3.066
OR {9371}
((segid "BrD" and resid 22 and name HN))
((segid "BrD" and resid 23 and name HG2))
OR {9371}
((segid "BrD" and resid 63 and name HN))
((segid "BrD" and resid 59 and name HG2))
ASSI {9441}
((segid "BrD" and resid 109 and name HN))
((segid "BrD" and resid 109 and name HB2))
 3.900  3.800  1.600 peak       9441  weight  0.10000E+01 volume  0.55505E+02 ppm1       8.557 ppm2       2.173
OR {9441}
((segid "BrD" and resid 64 and name HN))
((segid "BrD" and resid 64 and name HG1))
ASSI {9451}
((segid "BrD" and resid 21 and name HN))
((segid "BrD" and resid 24 and name HG2))
 3.900  3.800  1.600 peak       9451  weight  0.10000E+01 volume  0.53501E+02 ppm1       8.556 ppm2       3.108
OR {9451}
((segid "BrD" and resid 21 and name HN))
((segid "BrD" and resid 24 and name HB2))
OR {9451}
((segid "BrD" and resid 21 and name HN))
((segid "BrD" and resid 23 and name HG1))
OR {9451}
((segid "BrD" and resid 21 and name HN))
((segid "BrD" and resid 24 and name HB1))
ASSI {9461}
((segid "BrD" and resid 64 and name HN))
((segid "BrD" and resid 61 and name HB1))
 3.700  3.400  1.800 peak       9461  weight  0.10000E+01 volume  0.72347E+02 ppm1       8.544 ppm2       2.851
OR {9461}
((segid "BrD" and resid 21 and name HN))
((segid "BrD" and resid 23 and name HB2))
ASSI {9491}
((segid "BrD" and resid 21 and name HN))
((segid "BrD" and resid 19 and name HB2))
 3.300  2.700  2.200 peak       9491  weight  0.10000E+01 volume  0.14127E+03 ppm1       8.556 ppm2       1.929
OR {9491}
((segid "BrD" and resid 109 and name HN))
((segid "BrD" and resid 111 and name HG2))
OR {9491}
((segid "BrD" and resid 109 and name HN))
(segid "BrD" and resid 113 and name HB%)
OR {9491}
((segid "BrD" and resid 64 and name HN))
((segid "BrD" and resid 19 and name HB2))
ASSI {9501}
((segid "BrD" and resid 21 and name HN))
(segid "BrD" and resid 17 and name HG2%)
 3.300  2.700  2.200 peak       9501  weight  0.10000E+01 volume  0.14396E+03 ppm1       8.556 ppm2       1.762
OR {9501}
((segid "BrD" and resid 109 and name HN))
(segid "BrD" and resid 17 and name HG2%)
OR {9501}
((segid "BrD" and resid 21 and name HN))
(segid "BrD" and resid 25 and name HG1%)
```

TABLE 3-continued

Ambiguous NOE-derived Inter-proton Distance Restraints

ASSI {9531}
((segid "BrD" and resid 17 and name HN))
((segid "BrD" and resid 13 and name HA))
  3.600  3.200  1.900 peak        9531  weight  0.10000E+01 volume    0.86367E+02 ppm1        8.695 ppm2     4.805
OR {9531}
((segid "BrD" and resid 112 and name HN))
((segid "BrD" and resid 108 and name HA))
OR {9531}
((segid "BrD" and resid 103 and name HN))
((segid "BrD" and resid 82 and name HA))
ASSI {9561}
((segid "BrD" and resid 103 and name HN))
((segid "BrD" and resid 106 and name HB2))
  3.300  2.700  2.200 peak        9561  weight  0.10000E+01 volume    0.15504E+03 ppm1        8.696 ppm2     3.661
OR {9561}
((segid "BrD" and resid 103 and name HN))
((segid "BrD" and resid 82 and name HB1))
OR {9561}
((segid "BrD" and resid 103 and name HN))
((segid "BrD" and resid 105 and name HB2))
OR {9561}
((segid "BrD" and resid 103 and name HN))
((segid "BrD" and resid 107 and name HB1))
ASSI {9631}
((segid "BrD" and resid 99 and name HN))
((segid "BrD" and resid 100 and name HA))
  3.900  3.800  1.600 peak        9631  weight  0.10000E+01 volume    0.54041E+02 ppm1        8.936 ppm2     4.947
OR {9631}
((segid "BrD" and resid 99 and name HN))
((segid "BrD" and resid 30 and name HB1))
ASSI {9641}
((segid "BrD" and resid 99 and name HN))
((segid "BrD" and resid 101 and name HG11))
  3.900  3.800  1.600 peak        9641  weight  0.10000E+01 volume    0.56248E+02 ppm1        8.935 ppm2     2.460
OR {9641}
((segid "BrD" and resid 99 and name HN))
((segid "BrD" and resid 97 and name HG1))
ASSI {9651}
((segid "BrD" and resid 99 and name HN))
((segid "BrD" and resid 103 and name HB2))
  5.500  5.500  0.000 peak        9651  weight  0.10000E+01 volume    0.57216E+02 ppm1        8.936 ppm2     1.920
OR {9651}
((segid "BrD" and resid 99 and name HN))
((segid "BrD" and resid 86 and name HG1))
ASSI {9721}
((segid "BrD" and resid 64 and name HN))
((segid "BrD" and resid 64 and name HE1))
  4.000  4.000  1.500 peak        9721  weight  0.10000E+01 volume    0.46621E+02 ppm1        8.586 ppm2     3.626
OR {9721}
((segid "BrD" and resid 64 and name HN))
((segid "BrD" and resid 65 and name HB1))
ASSI {9731}
((segid "BrD" and resid 21 and name HN))
((segid "BrD" and resid 109 and name HE1))
  3.800  3.600  1.700 peak        9731  weight  0.10000E+01 volume    0.59335E+02 ppm1        8.584 ppm2     3.146
OR {9731}
((segid "BrD" and resid 21 and name HN))
((segid "BrD" and resid 23 and name HD1))
ASSI {9801}
((segid "BrD" and resid 103 and name HN))
((segid "BrD" and resid 106 and name HB2))
  4.600  4.600  0.900 peak        9801  weight  0.10000E+01 volume    0.19838E+02 ppm1        8.669 ppm2     3.659
OR {9801}
((segid "BrD" and resid 17 and name HN))
((segid "BrD" and resid 15 and name HB2))
OR {9801}
((segid "BrD" and resid 103 and name HN))
((segid "BrD" and resid 82 and name HB1))
OR {9801}
((segid "BrD" and resid 103 and name HN))
((segid "BrD" and resid 105 and name HB2))
ASSI {9821}
((segid "BrD" and resid 17 and name HN))
((segid "BrD" and resid 13 and name HD2))
  3.700  3.400  1.800 peak        9871  weight  0.10000E+01 volume    0.70791E+02 ppm1        8.668 ppm2     2.943

TABLE 3-continued

Ambiguous NOE-derived Inter-proton Distance Restraints

OR {9821}
((segid "BrD" and resid 17 and name HN))
((segid "BrD" and resid 13 and name HB1))
ASSI {9831}
((segid "BrD" and resid 17 and name HN))
((segid "BrD" and resid 18 and name HG))
　3.000　2.200　2.200 peak　　　　9831　weight　0.10000E+01 volume　0.24267E+03 ppm1　　8.669 ppm2　　2.284
OR {9831}
((segid "BrD" and resid 40 and name HN))
((segid "BrD" and resid 39 and name HD1))
OR {9831}
((segid "BrD" and resid 103 and name HN))
((segid "BrD" and resid 104 and name HD1))
ASSI {9841}
((segid "BrD" and resid 103 and name HN))
((segid "BrD" and resid 102 and name HB1))
　4.500　4.500　1.000 peak　　　　9841　weight　0.10000E+01 volume　0.24419E+02 ppm1　　8.669 ppm2　　1.973
OR {9841}
((segid "BrD" and resid 17 and name HN))
(segid "BrD" and resid 113 and name HB%)
ASSI {9861}
((segid "BrD" and resid 17 and name HN))
((segid "BrD" and resid 14 and name HB2))
　3.500　3.100　2.000 peak　　　　9861　weight　0.10000E+01 volume　0.99899E+02 ppm1　　8.668 ppm2　　2.135
OR {9861}
((segid "BrD" and resid 17 and name HN))
((segid "BrD" and resid 18 and name HB1))
OR {9861}
((segid "BrD" and resid 103 and name HN))
((segid "BrD" and resid 104 and name HG1))
ASSI {10081}
((segid "BrD" and resid 24 and name HN))
((segid "BrD" and resid 21 and name HB))
　4.300　4.300　1.200 peak　　　10081　weight　0.10000E+01 volume　0.28058E+02 ppm1　　8.666 ppm2　　2.481
OR {10081}
((segid "BrD" and resid 24 and name HN))
((segid "BrD" and resid 26 and name HB1))
ASSI {10181}
((segid "BrD" and resid 16 and name HN))
((segid "BrD" and resid 14 and name HB2))
　4.100　4.100　1.400 peak　　　10181　weight　0.10000E+01 volume　0.40626E+02 ppm1　　8.785 ppm2　　2.129
OR {10181}
((segid "BrD" and resid 16 and name HN))
((segid "BrD" and resid 18 and name HB1))
ASSI {10201}
((segid "BrD" and resid 16 and name HN))
((segid "BrD" and resid 19 and name HB2))
　3.900　3.800　1.600 peak　　　10201　weight　0.10000E+01 volume　0.57921E+02 ppm1　　8.791 ppm2　　1.963
OR {10201}
((segid "BrD" and resid 14 and name HN))
(segid "BrD" and resid 113 and nane HB%)
ASSI {10241}
((segid "BrD" and resid 75 and name HN))
((segid "BrD" and resid 78 and name HB1))
　3.900　3.800　1.600 peak　　　10241　weight　0.10000E+01 volume　0.50050E+02 ppm1　　9.106 ppm2　　1.347
OR {10241}
((segid "BrD" and resid 75 and name HN))
(segid "BrD" and resid 115 and name HD1%)
ASSI {10281}
((segid "BrD" and resid 98 and name HN))
((segid "BrD" and resid 97 and name HG1))
　4.000　4.000　1.500 peak　　　10281　weight　0.10000E+01 volume　0.43323E+02 ppm1　　9.106 ppm2　　2.456
OR {10281}
((segid "BrD" and resid 98 and name HN))
((segid "BrD" and resid 97 and name HD1))
OR {10281}
((segid "BrD" and resid 98 and name HN))
((segid "BrD" and resid 101 and name HG11))
ASSI {10331}
((segid "BrD" and resid 96 and name HN))
((segid "BrD" and resid 97 and name HG1))
　3.900　3.800　1.600 peak　　　10331　weight　0.10000E+01 volume　0.52285E+02 ppm1　　7.977 ppm2　　2.412
OR {10331}
((segid "BrD" and resid 77 and name HN))
((segid "BrD" and resid 73 and name HG))

TABLE 3-continued

Ambiguous NOE-derived Inter-proton Distance Restraints

```
OR {10331}
((segid "BrD" and resid 96 and name HN))
((segid "BrD" and resid 97 and name HD1))
OR {10331}
((segid "BrD" and resid 77 and name HN))
((segid "BrD" and resid 72 and name HB1))
ASSI {10381}
((segid "BrD" and resid 78 and name HN))
((segid "BrD" and resid 116 and name HG11))
  3.900  3.800  1.600 peak     10381 weight  0.10000E+01 volume   0.51654E+02 ppm1   7.996 ppm2   1.884
OR {10381}
((segid "BrD" and resid 77 and name HN))
((segid "BrD" and resid 116 and name HG11))
ASSI {10391}
((segid "BrD" and resid 78 and name HN))
(segid "BrD" and resid 22 and name HD2%)
  3.500  3.100  2.000 peak     10391 weight  0.10000E+01 volume   0.99200E+02 ppm1   7.996 ppm2   1.604
OR {10391}
((segid "BrD" and resid 55 and name HN))
(segid "BrD" and resid 22 and name HD2%)
OR {10391}
((segid "BrD" and resid 78 and name HN))
(segid "BrD" and resid 25 and name HG2%)
OR {10391}
((segid "BrD" and resid 77 and name HN))
(segid "BrD" and resid 22 and name HD2%)
OR {10391}
((segid "BrD" and resid 55 and name HN))
(segid "BrD" and resid 25 and name HG2%)
ASSI {10411}
((segid "BrD" and resid 77 and name HN))
((segid "BrD" and resid 80 and name HB2))
  2.800  2.000  2.000 peak     10411 weight  0.10000E+01 volume   0.43395E+03 ppm1   7.996 ppm2   2.456
OR {10411}
((segid "BrD" and resid 78 and name HN))
((segid "BrD" and resid 80 and name HG2))
ASSI {10431}
((segid "BrD" and resid 55 and name HN))
((segid "BrD" and resid 37 and name HG1))
  2.600  1.700  1.700 peak     10431 weight  0.10000E+01 volume   0.60264E+03 ppm1   7.996 ppm2   2.722
OR {10431}
((segid "BrD" and resid 78 and name HN))
((segid "BrD" and resid 79 and name HB2))
ASSI {10471}
((segid "BrD" and resid 96 and name HN))
((segid "BrD" and resid 94 and name HA))
  3.900  3.800  1.600 peak     10471 weight  0.10000E+01 volume   0.52287E+02 ppm1   7.984 ppm2   4.814
OR {10472}
((segid "BrD" and resid 96 and name HN))
((segid "BrD" and resid 86 and name HA))
OR {10471}
((segid "BrD" and resid 96 and name HN))
((segid "BrD" and resid 92 and name HA))
ASSI {10501}
((segid "BrD" and resid 80 and name HN))
((segid "BrD" and resid 80 and name HA))
  2.800  2.000  2.000 peak     10501 weight  0.10000E+01 volume   0.42726E+03 ppm1   7.974 ppm2   4.691
OR {10501}
((segid "BrD" and resid 80 and name HN))
((segid "BrD" and resid 76 and name HA))
ASSI {10541}
((segid "BrD" and resid 55 and name HN))
(segid "BrD" and resid 58 and name HG2%)
  3.500  3.100  2.000 peak     10541 weight  0.10000E+01 volume   0.11084E+03 ppm1   7.974 ppm2   1.670
OR {10541}
((segid "BrD" and resid 78 and name HN))
(segid "BrD" and resid 22 and name HD1%)
OR {10541}
((segid "BrD" and resid 78 and name HN))
(segid "BrD" and resid 110 and name HG12))
OR {10541}
((segid "BrD" and resid 55 and name HN))
(segid "BrD" and resid 43 and name HB%)
OR {10541}
((segid "BrD" and resid 78 and name HN))
(segid "BrD" and resid 25 and name HG2%)
```

TABLE 3-continued

Ambiguous NOE-derived Inter-proton Distance Restraints

OR {10541}
((segid "BrD" and resid 55 and name HN))
(segid "BrD" and resid 25 and name HG2%))
OR {10541}
((segid "BrD" and resid 78 and name HN))
(segid "BrD" and resid 63 and name HD1%)
OR {10541}
((segid "BrD" and resid 55 and name HN))
(segid "BrD" and resid 22 and name HD1%)
ASSI {10551}
((segid "BrD" and resid 78 and name HN))
((segid "BrD" and resid 78 and name HB2))
  3.400  2.900  2.100 peak      10551  weight  0.10000E+01 volume    0.13253E+03 ppm1    7.975 ppm2    1.068
OR {10551}
((segid "BrD" and resid 60 and name HN))
(segid "BrD" and resid 61 and name HG1%)
OR {10551}
((segid "BrD" and resid 78 and name HN))
(segid "BrD" and resid 81 and name HG1%)
OR {10551}
((segid "BrD" and resid 55 and name HN))
(segid "BrD" and resid 81 and name HG1%)
ASSI {10611}
((segid "BrD" and resid 56 and name HN))
((segid "BrD" and resid 34 and name HB2))
  3.100  2.400  2.400 peak      10611  weight  0.10000E+01 volume    0.21458E+03 ppm1    9.680 ppm2    3.116
OR {10611}
((segid "BrD" and resid 56 and name HN))
((segid "BrD" and resid 59 and name HG2))
ASSI {10631}
((segid "BrD" and resid 82 and name HN))
(segid "BrD" and resid 83 and name HG2%)
  3.500  3.100  2.000 peak      10631  weight  0.10000E+01 volume    0.97408E+02 ppm1    6.982 ppm2    1.909
OR {10631}
((segid "BrD" and resid 82 and name HN))
((segid "BrD" and resid 103 and name HB2))
ASSI {10781}
((segid "BrD" and resid 80 and name HN))
(segid "BrD" and resid 83 and name HG2%)
  3.900  3.800  1.600 peak      10781  weight  0.10000E+01 volume    0.57791E+02 ppm1    8.006 ppm2    1.932
OR {10781}
((segid "BrD" and resid 80 and name HN))
((segid "BrD" and resid 116 and name HG11))
OR {10781}
((segid "BrD" and resid 80 and name HN))
((segid "BrD" and resid 54 and name HB2))
ASSI {10811}
((segid "BrD" and resid 80 and name HN))
(segid "BrD" and resid 81 and name HG1%)
  3.600  3.300  1.900 peak      10811  weight  0.10000E+01 volume    0.94805E+02 ppm1    8.005 ppm2    1.064
OR {10811}
((segid "BrD" and resid 80 and name HN))
((segid "BrD" and resid 78 and name HB2))
ASSI {10901}
((segid "BrD" and resid 85 and name HN))
((segid "BrD" and resid 86 and name HG1))
  3.800  3.600  1.700 peak      10901  weight  0.10000E+01 volume    0.64876E+02 ppm1    7.516 ppm2    1.805
OR {10901}
((segid "BrD" and resid 85 and name HN))
(segid "BrD" and resid 83 and name HG2%)
ASSI {10981}
((segid "BrD" and resid 87 and name HN))
((segid "BrD" and resid 85 and name HA))
  3.900  3.600  1.600 peak      10981  weight  0.10000E+01 volume    0.57856E+02 ppm1    8.572 ppm2    5.005
OR {10981}
((segid "BrD" and resid 87 and name HN))
((segid "BrD" and resid 88 and name HA))
ASSI {10991}
((segid "BrD" and resid 87 and name HN))
((segid "BrD" and resid 85 and name HB2))
  3.200  2.600  2.300 peak      10991  weight  0.10000E+01 volume    0.17351E+03 ppm1    8.571 ppm2    3.639
OR {10991}
((segid "BrD" and resid 87 and name HN))
((segid "BrD" and resid 95 and name HB1))

TABLE 3-continued

Ambiguous NOE-derived Inter-proton Distance Restraints

```
ASSI {11181}
((segid "BrD" and resid 93 and name HN))
((segid "BrD" and resid 91 and name HB1))
 3.000  2.200  2.200 peak       11181  weight  0.10000E+01 volume  0.28245E+03 ppm1    8.714 ppm2    3.075
OR {11181}
((segid "BrD" and resid 93 and name HN))
((segid "BrD" and resid 96 and name HB2))
ASSI {11231}
((segid "BrD" and resid 31 and name HN))
((segid "BrD" and resid 98 and name HB1))
 3.900  3.800  1.600 peak       11231  weight  0.10000E+01 volume  0.56370E+02 ppm1    8.481 ppm2    3.992
OR {11231}
((segid "BrD" and resid 31 and name HN))
((segid "BrD" and resid 32 and name HB2))
ASSI {11271}
((segid "BrD" and resid 31 and name HN))
((segid "BrD" and resid 33 and name HD1))
 4.100  4.100  1.400 peak       11271  weight  0.10000E+01 volume  0.42900E+02 ppm1    8.480 ppm2    2.781
OR {11271}
((segid "BrD" and resid 59 and name HN))
((segid "BrD" and resid 61 and name HG2))
ASSI {11301}
((segid "BrD" and resid 31 and name HN))
(segid "BrD" and resid 101 and name HD1%)
 3.800  3.600  1.700 peak       11301  weight  0.10000E+01 volume  0.60718E+02 ppm1    8.479 ppm2    1.542
OR {11301}
((segid "BrD" and resid 31 and name HN))
(segid "BrD" and resid 56 and name HD1%)
ASSI {11321}
((segid "BrD" and resid 59 and name HN))
(segid "BrD" and resid 81 and name HG1%)
 4.200  4.200  1.300 peak       11321  weight  0.10000E+01 volume  0.33324E+02 ppm1    8.480 ppm2    2.110
OR {11321}
((segid "BrD" and resid 31 and name HN))
((segid "BrD" and resid 33 and name HB1))
ASSI {11531}
((segid "BrD" and resid 104 and name HN))
(segid "BrD" and resid 102 and name HD2%)
 4.700  4.700  0.800 peak       11531  weight  0.10000E+01 volume  0.18001E+02 ppm1    7.735 ppm2    1.282
OR {11531}
((segid "BrD" and resid 35 and name HN))
(segid "BrD" and resid 102 and name HD1%)
OR {11531}
((segid "BrD" and resid 104 and name HN))
(segid "BrD" and resid 102 and name HD1%)
ASSI {11541}
((segid "BrD" and resid 35 and name HN))
((segid "BrD" and resid 32 and name HB2))
 3.400  2.900  2.100 peak       11541  weight  0.10000E+01 volume  0.13237E+03 ppm1    7.734 ppm2    3.923
OR {11541}
((segid "BrD" and resid 104 and name HN))
((segid "BrD" and resid 106 and name HB1))
ASSI {11591}
((segid "BrD" and resid 66 and name HN))
((segid "BrD" and resid 69 and name HB))
 3.600  3.200  1.900 peak       11591  weight  0.10000E+01 volume  0.90637E+02 ppm1    8.764 ppm2    3.935
OR {11591}
((segid "BrD" and resid 66 and name HN))
((segid "BrD" and resid 63 and name HB1))
ASSI {11631}
((segid "BrD" and resid 67 and name HN))
(segid "BrD" and resid 63 and name HD1%)
 3.500  3.100  2.000 peak       11631  weight  0.10000E+01 volume  0.95713E+02 ppm1    8.832 ppm2    1.678
OR {11631}
((segid "BrD" and resid 67 and name HN))
((segid "BrD" and resid 62 and name HB2))
ASSI {11671}
((segid "BrD" and resid 68 and name HN))
(segid "BrD" and resid 63 and name HD1%)
 3.600  3.200  1.900 peak       11671  weight  0.10000E+01 volume  0.92729E+02 ppm1    8.626 ppm2    2.684
OR {11671}
((segid "BrD" and resid 68 and name HN))
((segid "BrD" and resid 62 and name HB2))
ASSI {11701}
((segid "BrD" and resid 69 and name HN))
((segid "BrD" and resid 63 and name HG))
 3.400  2.900  2.100 peak       11703  weight  0.10000E+01 volume  0.12326E+03 ppm1    8.306 ppm2    2.476
```

TABLE 3-continued

Ambiguous NOE-derived Inter-proton Distance Restraints

OR {11701}
((segid "BrD" and resid 69 and name HN))
((segid "BrD" and resid 71 and name HB2))
ASSI {11711}
((segid "BrD" and resid 69 and name HN))
((segid "BrD" and resid 66 and name HB2))
  3.800  3.600 1.700 peak      11711  weight  0.10000E+01 volume  0.68030E+02 ppm1      8.306 ppm2    2.614
OR {11711}
((segid "BrD" and resid 69 and name HN))
((segid "BrD" and resid 11 and name HB2))
OR {11711}
((segid "BrD" and resid 69 and name HN))
((segid "BrD" and resid 73 and name HB1))
ASSI {11751}
((segid "BrD" and resid 70 and name HN))
((segid "BrD" and resid 73 and name HG))
  4.200  4.200 1.300 peak      11751  weight  0.10000E+01 volume  0.36902E+02 ppm1      8.039 ppm2    2.374
OR {11751}
((segid "BrD" and resid 70 and name HN))
((segid "BrD" and resid 9 and name HB2))
ASSI {11761}
((segid "BrD" and resid 70 and name HN))
((segid "BrD" and resid 73 and name HB1))
  3.500  3.100 2.000 peak      11761  weight  0.10000E+01 volume  0.95470E+02 ppm1      8.040 ppm2    2.594
OR {11761}
((segid "BrD" and resid 70 and name HN))
((segid "BrD" and resid 11 and name HB2))
ASSI {11851}
((segid "BrD" and resid 73 and name HN))
((segid "BrD" and resid 74 and name HB1))
  3.600  3.200 1.900 peak      11851  weight  0.10000E+01 volume  0.82682E+02 ppm1      8.045 ppm2    3.572
OR {11851}
((segid "BrD" and resid 73 and name HN))
((segid "BrD" and resid 75 and name HG1))
ASSI {11931}
((segid "BrD" and resid 23 and name HN))
((segid "BrD" and resid 22 and name HA))
  3.800  3.600 1.700 peak      11931  weight  0.10000E+01 volume  0.64947E+02 ppm1      9.125 ppm2    4.688
OR {11931}
((segid "BrD" and resid 75 and name HN))
((segid "BrD" and resid 72 and name HA))
ASSI {11941}
((segid "BrD" and resid 98 and name HN))
((segid "BrD" and resid 100 and name HB2))
  4.000  4.000 1.500 peak      11941  weight  0.10000E+01 volume  0.47235E+02 ppm1      9.125 ppm2    3.411
OR {11941}
((segid "BrD" and resid 23 and name HN))
((segid "BrD" and resid 24 and name HG1))
ASSI {12011}
((segid "BrD" and resid 23 and name HN))
(segid "BrD" and resid 22 and name HD2%)
  3.800  3.600 1.700 peak      12011  weight  0.10000E+01 volume  0.60527E+02 ppm1      9.125 ppm2    1.594
OR {12011}
((segid "BrD" and resid 23 and name HN))
(segid "BrD" and resid 21 and name HG2%)
ASSI {12021}
((segid "BrD" and resid 98 and name HN))
((segid "BrD" and resid 30 and name HB1))
  4.000  4.000 1.500 peak      12021  weight  0.10000E+01 volume  0.46966E+02 ppm1      9.124 ppm2    4.936
OR {12021}
((segid "BrD" and resid 23 and name HN))
((segid "BrD" and resid 60 and name HB1))
OR {22021}
((segid "BrD" and resid 98 and name HN))
((segid "BrD" and resid 100 and name HA))
OR {12021}
((segid "BrD" and resid 23 and name HN))
((segid "BrD" and resid 64 and name HA))
ASSI {12071}
((segid "BrD" and resid 100 and name HN))
((segid "BrD" and resid 98 and name HB2))
  4.100  4.100 1.400 peak      12071  weight  0.10000E+01 volume  0.37827E+02 ppm1      8.669 ppm2    3.641
OR {12071}
((segid "BrD" and resid 100 and name HN))
((segid "BrD" and resid 85 and name HB2))

TABLE 3-continued

Ambiguous NOE-derived Inter-proton Distance Restraints

ASSI {12101}
((segid "BrD" and resid 100 and name HN))
((segid "BrD" and resid 103 and name HB1))
  2.000  2.000  2.500 peak      12101  weight  0.10000E+01 volume  0.26537E+04 ppm1      8.669 ppm2    2.323
OR {12101}
((segid "BrD" and resid 100 and name HN))
((segid "BrD" and resid 104 and name HD1))
ASSI {12111}
((segid "BrD" and resid 100 and name HN))
((segid "BrD" and resid 103 and name HB2))
  4.100  4.100  1.400 peak      12111  weight  0.10000E+01 volume  0.37921E+02 ppm1      8.669 ppm2    1.892
OR {12111}
((segid "BrD" and resid 100 and name HN))
((segid "BrD" and resid 86 and name HG1))
ASSI {12141}
((segid "BrD" and resid 100 and name HN))
(segid "BrD" and resid 96 and name HD%)
  4.300  4.300  1.200 peak      12141  weight  0.10000E+01 volume  0.30609E+02 ppm1      8.669 ppm2    7.737
OR {12141}
((segid "BrD" and resid 100 and name HN))
((segid "BrD" and resid 104 and name HN))
ASSI {12251}
((segid "BrD" and resid 107 and name HN))
((segid "BrD" and resid 110 and name HB))
  3.700  3.400  2.000 peak      12251  weight  0.10000E+01 volume  0.79191E+02 ppm1      8.980 ppm2    2.348
OR {12251}
((segid "BrD" and resid 107 and name HN))
((segid "BrD" and resid 103 and name HB1))
OR {12251}
((segid "BrD" and resid 107 and name HN))
((segid "BrD" and resid 109 and name HB1))
ASSI {12261}
((segid "BrD" and resid 107 and name HN))
((segid "BrD" and resid 102 and name HB2))
  5.500  5.500  0.000 peak      12261  weight  0.10000E+01 volume  0.35919E+00 ppm1      8.980 ppm2    1.797
OR {12261}
((segid "BrD" and resid 107 and name HN))
(segid "BrD" and resid 25 and name HG1%)
ASSI {12281}
((segid "BrD" and resid 108 and name HN))
((segid "BrD" and resid 103 and name HG2))
  4.100  4.100  1.400 peak      12281  weight  0.10000E+01 volume  0.42059E+02 ppm1      8.522 ppm2    2.529
OR {12281}
((segid "BrD" and resid 108 and name HN))
((segid "BrD" and resid 104 and name HB1))
ASSI {12301}
((segid "BrD" and resid 104 and name HN))
(segid "BrD" and resid 116 and name HD1%)
  3.900  3.800  1.600 peak      12301  weight  0.10000E+01 volume  0.52230E+02 ppm1      8.521 ppm2    1.422
OR {12301}
((segid "BrD" and resid 108 and name HN))
((segid "BrD" and resid 109 and name HG1))
ASSI {12311}
((segid "BrD" and resid 108 and name HN))
((segid "BrD" and resid 110 and name HB))
  4.100  4.100  1.400 peak      12311  weight  0.10000E+01 volume  0.41867E+02 ppm1      8.522 ppm2    2.331
OR {12311}
((segid "BrD" and resid 108 and name HN))
((segid "BrD" and resid 109 and name HB1))
ASSI {12401}
((segid "BrD" and resid 113 and name HN))
((segid "BrD" and resid 115 and name HG))
  3.300  2.700  2.200 peak      12401  weight  0.10000E+01 volume  0.16014E+03 ppm1      8.218 ppm2    2.152
OR {12401}
((segid "BrD" and resid 113 and name HN))
((segid "BrD" and resid 115 and name HB1))
OR {12401}
((segid "BrD" and resid 113 and name HN))
((segid "BrD" and resid 109 and name HB2))
ASSI {12501}
((segid "BrD" and resid 116 and name HN))
((segid "BrD" and resid 71 and name HA))
  4.300  4.300  1.200 peak      12501  weight  0.10000E+01 volume  0.28782E+02 ppm1      4.087 ppm2    4.664
OR {12501}
((segid "BrD" and resid 116 and name HN))
((segid "BrD" and resid 72 and name HA))

TABLE 3-continued

Ambiguous NOE-derived Inter-proton Distance Restraints

```
OR {12501}
((segid "BrD" and resid 116 and name HN))
((segid "BrD" and resid 114 and name HA1))
OR {12501}
((segid "BrD" and resid 116 and name HN))
((segid "BrD" and resid 76 and name HA))
ASSI {12511}
((segid "BrD" and resid 116 and name HN))
((segid "BrD" and resid 75 and name HA))
  3.600  3.200 1.900 peak      12511 weight  0.10000E+01 volume   0.81005E+02 ppm1    8.087 ppm2    4.526
OR {12511}
((segid "BrD" and resid 116 and name HN))
((segid "BrD" and resid 224 and name HA2))
ASSI {12601}
((segid "BrD" and resid 92 and name HN))
((segid "BrD" and resid 92 and name HB1))
  4.100  4.100 1.400 peak      12601 weight  0.10000E+01 volume   0.37922E+02 ppm1    8.831 ppm2    2.695
OR {12601}
((segid "BrD" and resid 92 and name HN))
((segid "BrD" and resid 91 and name HB2))
ASSI {12841}
((segid "BrD" and resid 19 and name HN))
((segid "BrD" and resid 17 and name HB))
  3.400  3.600 1.700 peak      12841 weight  0.10000E+01 volume   0.59211E+02 ppm1    9.187 ppm2    4.880
OR {12841}
((segid "BrD" and resid 19 and name HN))
((segid "BrD" and resid 20 and name HA))
ASSI {12861}
((segid "BrD" and resid 20 and name HN))
((segid "BrD" and resid 63 and name HG))
  4.000  4.000 1.500 peak      12861 weight  0.10000E+01 volume   0.43415E+02 ppm1    8.147 ppm2    2.471
OR {12861}
((segid "BrD" and resid 20 and name HN))
((segid "BrD" and resid 21 and name HB))
ASSI {12951}
((segid "BrD" and resid 23 and name HN))
(segid "BrD" and resid 25 and name HG1%)
  3.000  3.600 1.700 peak      12951 weight  0.10000E+01 volume   0.65898E+02 ppm1    9.119 ppm2    1.823
OR {12951}
((segid "BrD" and resid 98 and name HN))
((segid "BrD" and resid 101 and name HG12))
ASSI {12961}
((segid "BrD" and resid 23 and name HN))
(segid "BrD" and resid 22 and name HD1%)
  3.100  2.400 2.400 peak      12961 weight  0.10000E+01 volume   0.23452E+03 ppm1    9.120 ppm2    1.646
OR {12961}
((segid "BrD" and resid 23 and name HN))
((segid "BrD" and resid 21 and name HG12))
OR {12961}
((segid "BrD" and resid 23 and name HN))
(segid "BrD" and resid 21 and name HG2%)
OR {12961}
((segid "BrD" and resid 23 and name HN))
(segid "BrD" and resid 25 and name HG2%)
ASSI {12971}
((segid "BrD" and resid 98 and name HN))
(segid "BrD" and resid 101 and name HD1%)
  3.900  3.800 1.600 peak      12971 weight  0.10000E+01 volume   0.50522E+02 ppm1    9.119 ppm2    1.514
OR {12971}
((segid "BrD" and resid 23 and name HN))
(segid "BrD" and resid 63 and name HD2%)
ASSI {12981}
((segid "BrD" and resid 98 and name HN))
((segid "BrD" and resid 100 and name HB2))
  3.400  2.900 2.100 peak      12981 weight  0.10000E+01 volume   0.12055E+03 ppm1    9.119 ppm2    3.467
OR {12981}
((segid "BrD" and resid 23 and name HN))
((segid "BrD" and resid 24 and name HG1))
OR {12981}
((segid "BrD" and resid 98 and name HN))
((segid "BrD" and resid 100 and name HB1))
ASSI {13001}
((segid "BrD" and resid 98 and name HN))
(segid "BrD" and resid 95 and name HD%)
  3.900  3.800 1.600 peak      13001 weight  0.10000E+01 volume   0.54095E+02 ppm1    9.119 ppm2    7.520
```

TABLE 3-continued

Ambiguous NOE-derived Inter-proton Distance Restraints

OR {13001}
((segid "BrD" and resid 23 and name HN))
((segid "BrD" and resid 24 and name HE22))
OR {13001}
((segid "BrD" and resid 23 and name HN))
(segid "BrD" and resid 74 and name HE%)
ASSI {13011}
((segid "BrD" and resid 26 and name HN))
(segid "BrD" and resid 31 and name HB%)
  3.500  3.100  2.000 peak      13011  weight  0.10000E+01 volume    0.10060E+03 ppm1     9.196 ppm2    2.308
OR {13011}
((segid "BrD" and resid 26 and name HN))
((segid "BrD" and resid 22 and name HB2))
ASSI {13121}
((segid "BrD" and resid 59 and name HN))
((segid "BrD" and resid 56 and name HB2))
  3.800  3.600  1.700 peak      13121  weight  0.10000E+01 volume    0.59266E+02 ppm1     8.496 ppm2    2.008
OR {13121}
((segid "BrD" and resid 59 and name HN))
((segid "BrD" and resid 57 and name HG2))
OR {13121}
((segid "BrD" and resid 31 and name HN))
((segid "BrD" and resid 102 and name HB1))
ASSI {13171}
((segid "BrD" and resid 60 and name HN))
((segid "BrD" and resid 57 and name HB2))
  3.500  3.100  2.000 peak      13171  weight  0.10000E+01 volume    0.10295E+03 ppm1     8.564 ppm2    2.858
OR {13171}
((segid "BrD" and resid 60 and name HN))
((segid "BrD" and resid 61 and name HB1))
OR {13171}
((segid "BrD" and resid 65 and name HN))
((segid "BrD" and resid 61 and name HB1))
ASSI {13181}
((segid "BrD" and resid 60 and name HN))
((segid "BrD" and resid 22 and name HG))
  3.800  3.600  1.700 peak      13181  weight  0.10000E+01 volume    0.61364E+02 ppm1     8.565 ppm2    2.336
OR {13181}
((segid "BrD" and resid 65 and name HN))
((segid "BrD" and resid 62 and name HG1))
OR {13181}
((segid "BrD" and resid 60 and name HN))
(segid "BrD" and resid 56 and name HG))
OR {13181}
((segid "BrD" and resid 60 and name HN))
((segid "BrD" and resid 22 and name HB2))
OR {13181}
((segid "BrD" and resid 60 and name HN))
((segid "BrD" and resid 57 and name HD2))
ASSI {13191}
((segid "BrD" and resid 60 and name HN))
(segid "BrD" and resid 22 and name HD1%)
  3.200  2.600  2.300 peak      13191  weight  0.10000E+01 volume    0.17409E+03 ppm1     8.568 ppm2    1.666
OR {13191}
((segid "BrD" and resid 65 and name HN))
(segid "BrD" and resid 63 and name HD1%)
OR {13191}
((segid "BrD" and resid 60 and name HN))
(segid "BrD" and resid 58 and name HG2%)
ASSI {13201}
((segid "BrD" and resid 65 and name HN))
(segid "BrD" and resid 63 and name HD2%)
  3.600  3.200  1.900 peak      13201  weight  0.10000E+01 volume    0.81304E+02 ppm1     8.565 ppm2    1.497
OR {13201}
((segid "BrD" and resid 65 and name HN))
((segid "BrD" and resid 62 and name HD2))
OR {13201}
((segid "BrD" and resid 60 and name HN))
(segid "BrD" and resid 63 and name HD2%)
ASSI {13631}
((segid "BrD" and resid 84 and name HN))
((segid "BrD" and resid 82 and name HN))
  4.000  4.000  1.500 peak      13631  weight  0.10000E+01 volume    0.44090E+02 ppm1     9.463 ppm2    6.901
OR {13631}
((segid "BrD" and resid 63 and name HN))
(segid "BrD" and resid 74 and name HD%)

TABLE 3-continued

Ambiguous NOE-derived Inter-proton Distance Restraints

ASSI {13691}
((segid "BrD" and resid 22 and name HN))
((segid "BrD" and resid 22 and name HB2))
  3.700  3.400  1.800 peak      13691 weight  0.10000E+01 volume  0.68908E+02 ppm1      9.473 ppm2    2.333
OR {13691}
((segid "BrD" and resid 22 and name HN))
((segid "BrD" and resid 21 and name HG11))
OR {13691}
((segid "BrD" and resid 22 and name HN))
((segid "BrD" and resid 22 and name HG))
ASSI {13971}
((segid "BrD" and resid 114 and name HN))
((segid "BrD" and resid 112 and name HD2))
  4.900  4.900  0.600 peak      13971 weight  0.10000E+01 volume  0.14459E+02 ppm1      8.371 ppm2    2.786
OR {13971}
((segid "BrD" and resid 114 and name HN))
((segid "BrD" and resid 13 and name HB1))
ASSI {14061}
((segid "BrD" and resid 107 and name HN))
(segid "BrD" and resid 110 and name HG2%)
  4.800  4.800  0.700 peak      14061 weight  0.10000E+01 volume  0.15271E+02 ppm1      8.980 ppm2    1.260
OR {14061}
((segid "BrD" and resid 107 and name HN))
(segid "BrD" and resid 21 and name HD1%)
ASSI {14071}
((segid "BrD" and resid 106 and name HN))
((segid "BrD" and resid 107 and name HA))
  4.600  4.600  0.900 peak      14071 weight  0.10000E+01 volume  0.20679E+02 ppm1      9.742 ppm2    4.447
OR {14071}
((segid "BrD" and resid 106 and name HN))
((segid "BrD" and resid 99 and name HA))
ASSI {14131}
((segid "BrD" and resid 104 and name HN))
((segid "BrD" and resid 102 and name HB2))
  3.700  3.400  1.800 peak      14131 weight  0.10000E+01 volume  0.79648E+02 ppm1      7.763 ppm2    1.816
OR {14131}
((segid "BrD" and resid 104 and name HN))
((segid "BrD" and resid 101 and name HG12))
ASSI {14141}
((segid "BrD" and resid 103 and name HN))
((segid "BrD" and resid 106 and name HB1))
  3.600  3.200  1.900 peak      14141 weight  0.10000E+01 volume  0.92105E+02 ppm1      8.695 ppm2    3.908
OR {14141}
((segid "BrD" and resid 17 and name HN))
((segid "BrD" and resid 18 and name HA))
ASSI {14151}
((segid "BrD" and resid 102 and name HN))
((segid "BrD" and resid 105 and name HB2))
  4.000  4.000  1.500 peak      14151 weight  0.10000E+01 volume  0.49406E+02 ppm1      9.156 ppm2    3.635
OR {14151}
((segid "BrD" and resid 102 and name HN))
((segid "BrD" and resid 98 and name HB2))
OR {14151}
((segid "BrD" and resid 102 and name HN))
((segid "BrD" and resid 106 and name HB2))
ASSI {14161}
((segid "BrD" and resid 102 and name HN))
((segid "BrD" and resid 103 and name HA))
  5.000  5.000  0.500 peak      14161 weight  0.10000E+01 volume  0.12711E+02 ppm1      9.156 ppm2    3.753
OR {14161}
((segid "BrD" and resid 102 and name HN))
((segid "BrD" and resid 105 and name HB1))
ASSI {14171}
((segid "BrD" and resid 101 and name HN))
((segid "BrD" and resid 104 and name HN))
  4.300  4.300  1.200 peak      14171 weight  0.10000E+01 volume  0.29353E+02 ppm1      8.513 ppm2    7.761
OR {14171}
((segid "BrD" and resid 101 and name HN))
(segid "BrD" and resid 34 and name HE%)
ASSI {14201}
((segid "BrD" and resid 100 and name HN))
((segid "BrD" and resid 86 and name HE1))
  4.100  4.100  1.400 peak      14201 weight  0.10000E+01 volume  0.38990E+02 ppm1      8.667 ppm2    3.092
OR {14201}
((segid "BrD" and resid 100 and name HN))
((segid "BrD" and resid 96 and name HB2))

TABLE 3-continued

Ambiguous NOE-derived Inter-proton Distance Restraints

ASSI {14221}
((segid "BrD" and resid 100 and name HN))
((segid "BrD" and resid 101 and name HG12))
  4.800  4.800  0.700 peak      14221  weight  0.10000E+01 volume  0.14931E+02 ppm1      8.669 ppm2    1.806
OR {14221}
((segid "BrD" and resid 100 and name HN))
((segid "BrD" and resid 102 and name HB2))
ASSI {14241}
((segid "BrD" and resid 99 and name HN))
((segid "BrD" and resid 96 and name HB2))
  4.900  4.900  0.600 peak      14241  weight  0.10000E+01 volume  0.14325E+02 ppm1      8.940 ppm2    3.103
OR {14241}
((segid "BrD" and resid 99 and name HN))
((segid "BrD" and resid 94 and name HG1))
OR {14241}
((segid "BrD" and resid 99 and name HN))
((segid "BrD" and resid 86 and name HE1))
ASSI {14251}
((segid "BrD" and resid 99 and name HN))
(segid "BrD" and resid 60 and name HG2%)
  5.500  5.500  0.000 peak      14251  weight  0.10000E+01 volume  0.30696E+01 ppm1      8.934 ppm2    0.748
OR {14251}
((segid "BrD" and resid 99 and name HN))
((segid "BrD" and resid 86 and name HG2))
ASSI {14281}
((segid "BrD" and resid 96 and name HN))
((segid "BrD" and resid 32 and name HH2))
  3.800  3.600  1.700 peak      14281  weight  0.10000E+01 volume  0.66237E+02 ppm1      9.125 ppm2    7.750
OR {14281}
((segid "BrD" and resid 98 and name HN))
(segid "BrD" and resid 34 and name HE%)
OR {14281}
((segid "BrD" and resid 75 and name HN))
(segid "BrD" and resid 68 and name HD%)
ASSI {14301}
((segid "BrD" and resid 96 and name HN))
(segid "BrD" and resid 99 and name HB%)
  3.600  3.200  1.900 peak      14301  weight  0.10000E+01 volume  0.84940E+02 ppm1      7.977 ppm2    2.199
OR {14301}
((segid "BrD" and resid 96 and name HN))
((segid "BrD" and resid 97 and name HG2))
ASSI {14311}
((segid "BrD" and resid 77 and name HN))
(segid "BrD" and resid 73 and name HD1%)
  4.900  4.900  0.600 peak      14311  weight  0.10000E+01 volume  0.13346E+02 ppm1      7.981 ppm2    1.543
OR {14311}
((segid "BrD" and resid 78 and name HN))
((segid "BrD" and resid 116 and name HG12))
OR {14311}
((segid "BrD" and resid 78 and name HN))
(segid "BrD" and resid 56 and name HD1%)
OR {14311}
((segid "BrD" and resid 77 and name HN))
((segid "BrD" and resid 116 and name HG12))
OR {14311}
((segid "BrD" and resid 96 and name HN))
(segid "BrD" and resid 101 and name HD1%)
ASSI {14441}
((segid "BrD" and resid 83 and name HN))
((segid "BrD" and resid 79 and name HG1))
  4.600  4.600  0.900 peak      14441  weight  0.10000E+01 volume  0.19968E+02 ppm1      9.656 ppm2    1.046
OR {14441}
((segid "BrD" and resid 83 and name HN))
((segid "BrD" and resid 87 and name HG1))
ASSI {14451}
((segid "BrD" and resid 83 and name HN))
((segid "BrD" and resid 80 and name HG1))
  5.500  5.500  0.000 peak      14451  weight  0.10000E+01 volume  0.45437E+00 ppm1      9.658 ppm2    2.374
OR {14451}
((segid "BrD" and resid 83 and name HN))
((segid "BrD" and resid 86 and name HB1))
ASSI {14461}
((segid "BrD" and resid 83 and name HN))
((segid "BrD" and resid 86 and name HG2))
  5.000  5.000  0.500 peak      14461  weight  0.10000E+01 volume  0.12633E+02 ppm1      9.657 ppm2    0.743

TABLE 3-continued

Ambiguous NOE-derived Inter-proton Distance Restraints

```
OR {14461}
((segid "BrD" and resid 83 and name HN))
(segid "BrD" and resid 81 and name HG2%)
ASSI {14511}
((segid "BrD" and resid 79 and name HN))
(segid "BrD" and resid 106 and name HE%)
 3.600  3.200 1.900 peak      14511 weight 0.10000E+01 volume  0.86513E+02 ppm1    8.680 ppm2    7.621
OR {14511}
((segid "BrD" and resid 79 and name HN))
((segid "BrD" and resid 81 and name HN))
ASSI {14591}
((segid "BrD" and resid 72 and name HN))
((segid "BrD" and resid 73 and name HA))
 4.100  4.100 1.400 peak      14591 weight 0.10000E+01 volume  0.40514E+02 ppm1    8.858 ppm2    4.801
OR {14591}
((segid "BrD" and resid 72 and name HN))
((segid "BrD" and resid 70 and name HB1))
OR {14591}
((segid "BrD" and resid 72 and name HN))
((segid "BrD" and resid 115 and name HA))
ASSI {14631}
((segid "BrD" and resid 66 and name HN))
((segid "BrD" and resid 67 and name HA))
 4.400  4.400 1.100 peak      14631 weight 0.10000E+01 volume  0.25627E+02 ppm1    8.762 ppm2    4.678
OR {14631}
((segid "BrD" and resid 66 and name HN))
((segid "BrD" and resid 69 and name HA))
OR {14631}
((segid "BrD" and resid 66 and name HN))
((segid "BrD" and resid 61 and name HA))
ASSI {14641}
((segid "BrD" and resid 60 and name HN))
((segid "BrD" and resid 62 and name HN))
 4.200  4.200 1.300 peak      14641 weight 0.10000E+01 volume  0.32935E+02 ppm1    8.568 ppm2    8.968
OR {14641}
((segid "BrD" and resid 65 and name HN))
((segid "BrD" and resid 62 and name HN))
ASSI {14651}
((segid "BrD" and resid 65 and name HN))
((segid "BrD" and resid 65 and name HD22))
 4.200  4.200 1.300 peak      14651 weight 0.10000E+01 volume  0.33097E+02 ppm1    8.566 ppm2    7.569
OR {14651}
((segid "BrD" and resid 60 and name HN))
(segid "BrD" and resid 74 and name HE%)
ASSI {14751}
((segid "BrD" and resid 62 and name HN))
((segid "BrD" and resid 64 and name HN))
 2.800  2.000 2.000 peak      14751 weight 0.10000E+01 volume  0.39545E+03 ppm1    8.998 ppm2    8.576
OR {14751}
((segid "BrD" and resid 62 and name HN))
((segid "BrD" and resid 60 and name HN))
ASSI {14791}
((segid "BrD" and resid 38 and name HN))
((segid "BrD" and resid 37 and name HG2))
 3.900  3.800 1.600 peak      14791 weight 0.10000E+01 volume  0.52365E+02 ppm1    8.742 ppm2    2.547
OR {14791}
((segid "BrD" and resid 61 and name HN))
(segid "BrD" and resid 54 and name HE%)
OR {14791}
((segid "BrD" and resid 61 and name HN))
((segid "BrD" and resid 59 and name HB2))
OR {14791}
((segid "BrD" and resid 61 and name HN))
((segid "BrD" and resid 63 and name HB2))
ASSI {14801}
((segid "BrD" and resid 65 and name HN))
((segid "BrD" and resid 63 and name HN))
 4.400  4.400 1.100 peak      14801 weight 0.10000E+01 volume  0.24650E+02 ppm1    8.570 ppm2    9.470
OR {14801}
((segid "BrD" and resid 60 and name HN))
((segid "BrD" and resid 63 and name HN))
ASSI {14821}
((segid "BrD" and resid 59 and name HN))
((segid "BrD" and resid 55 and name HN))
 3.600  3.200 1.900 peak      14821 weight 0.10000E+01 volume  0.84273E+02 ppm1    8.498 ppm2    7.974
```

TABLE 3-continued

Ambiguous NOE-derived Inter-proton Distance Restraints

OR {14821}
((segid "BrD" and resid 31 and name HN))
((segid "BrD" and resid 32 and name HE3))
ASSI {14901}
((segid "BrD" and resid 54 and name HN))
((segid "BrD" and resid 55 and name HB1))
  4.400  4.400  1.100 peak        14901 weight  0.10000E+01 volume  0.25948E+02 ppm1        9.035 ppm2    2.965
OR {14901}
((segid "BrD" and resid 54 and name HN))
((segid "BrD" and resid 37 and name HB1))
ASSI {14921}
((segid "BrD" and resid 54 and name HN))
(segid "BrD" and resid 81 and name HG1%)
  4.000  4.000  1.500 peak        14921 weight  0.10000E+01 volume  0.46525E+02 ppm1        9.037 ppm2    1.081
OR {14921}
((segid "BrD" and resid 54 and name HN))
(segid "BrD" and resid 38 and name HG1%)
ASSI {14931}
((segid "BrD" and resid 52 and name HN))
(segid "BrD" and resid 50 and name HD1%)
  5.500  5.500  0.000 peak        14931 weight  0.10000E+01 volume  0.2319E+01 ppm1        9.004 ppm2    1.110
OR {14931}
((segid "BrD" and resid 52 and name HN))
(segid "BrD" and resid 81 and name HG1%)
ASSI {15021}
((segid "BrD" and resid 50 and name HN))
((segid "BrD" and resid 49 and name HB))
  3.400  2.900  2.100 peak        15021 weight  0.10000E+01 volume  0.11615E+03 ppm1        8.562 ppm2    2.642
OR {15021}
((segid "BrD" and resid 46 and name HN))
((segid "BrD" and resid 44 and name HB2))
ASSI {15091}
((segid "BrD" and resid 35 and name HN))
((segid "BrD" and resid 33 and name HB1))
  5.000  5.000  0.500 peak        15091 weight  0.10000E+01 volume  0.12753E+02 ppm1        7.735 ppm2    1.073
OR {15091}
((segid "BrD" and resid 35 and name HN))
(segid "BrD" and resid 41 and name HG1%)
ASSI {15181}
((segid "BrD" and resid 30 and name HN))
(segid "BrD" and resid 101 and name HG2%)
  3.900  3.800  1.800 peak        15181 weight  0.10000E+01 volume  0.50580E+02 ppm1      12.275 ppm2    1.601
OR {15181}
((segid "BrD" and resid 30 and name HN))
(segid "BrD" and resid 25 and name HG2%)
ASSI {15221}
((segid "BrD" and resid 28 and name HN))
((segid "BrD" and resid 32 and name HN))
  4.200  4.200  1.300 peak        15221 weight  0.10000E+01 volume  0.33692E+02 ppm1        8.166 ppm2    7.752
OR {15221}
((segid "BrD" and resid 28 and name HN))
(segid "BrD" and resid 34 and name HE%)
ASSI {15331}
((segid "BrD" and resid 25 and name HN))
(segid "BrD" and resid 31 and name HB%)
  4.500  4.500  1.000 peak        15331 weight  0.10000E+01 volume  0.22185E+02 ppm1        9.133 ppm2    2.295
OR {15331}
((segid "BrD" and resid 25 and name HN))
((segid "BrD" and resid 22 and name HB2))
ASSI {15341}
((segid "BrD" and resid 24 and name HN))
((segid "BrD" and resid 27 and name HN))
  3.700  3.400  1.800 peak        15341 weight  0.10000E+01 volume  0.78760E+02 ppm1        8.660 ppm2    8.147
OR {15341}
((segid "BrD" and resid 24 and name HN))
((segid "BrD" and resid 20 and name HN))
ASSI {15411}
((segid "BrD" and resid 18 and name HN))
((segid "BrD" and resid 21 and name HG12))
  4.300  4.300  1.200 peak        15411 weight  0.10000E+01 volume  0.29441E+02 ppm1        9.077 ppm2    1.642
OR {15411}
((segid "BrD" and resid 18 and name HN))
(segid "BrD" and resid 63 and name HD1%)
OR {15411}
((segid "BrD" and resid 18 and name HN))
(segid "BrD" and resid 21 and name HG2%)

TABLE 3-continued

Ambiguous NOE-derived Inter-proton Distance Restraints

ASSI {15451}
((segid "BrD" and resid 17 and name HN))
(segid "BrD" and resid 15 and name HD%)
  4.700  4.700  0.800 peak        15451 weight  0.10000E+01 volume  0.16799E+02 ppm1      8.669 ppm2      7.656
OR {15451}
((segid "BrD" and resid 17 and name HN))
(segid "BrD" and resid 106 and name HE%)
ASSI {15461}
((segid "BrD" and resid 16 and name HN))
(segid "BrD" and resid 14 and name HD2%)
  4.800  4.800  0.700 peak        15461 weight  0.10000E+01 volume  0.14734E+02 ppm1      8.791 ppm2      1.430
OR {15461}
((segid "BrD" and resid 16 and name HN))
(segid "BrD" and resid 69 and name HG2%)
OR {15461}
((segid "BrD" and resid 16 and name HN))
(segid "BrD" and resid 14 and name HD1%)
ASSI {15491}
((segid "BrD" and resid 14 and name HN))
((segid "BrD" and resid 15 and name HB1))
  5.000  5.000  0.500 peak        15491 weight  0.10000E+01 volume  0.11598E+02 ppm1      8.809 ppm2      3.823
OR {15491}
((segid "BrD" and resid 13 and name HN))
((segid "BrD" and resid 15 and name HB1))
ASSI {15501}
((segid "BrD" and resid 14 and name HN))
((segid "BrD" and resid 15 and name HB2))
  5.100  5.100  0.400 peak        15501 weight  0.10000E+01 volume  0.11421E+02 ppm1      8.809 ppm2      3.641
OR {15501}
((segid "BrD" and resid 13 and name HN))
((segid "BrD" and resid 15 and name HB2))
ASSI {15581}
((segid "BrD" and resid 32 and name HE1))
((segid "BrD" and resid 30 and name HB1))
  4.800  4.800  0.700 peak        15581 weight  0.10000E+01 volume  0.15339E+02 ppm1     11.082 ppm2      4.955
OR {15581}
((segid "BrD" and resid 32 and name HE1))
((segid "BrD" and resid 32 and name HA))
ASSI {15621}
((segid "BrD" and resid 32 and name HE1))
((segid "BrD" and resid 33 and name HD1))
  4.200  4.200  1.300 peak        15631 weight  0.10000E+01 volume  0.36353E+02 ppm1     11.082 ppm2      2.779
OR {15621}
((segid "BrD" and resid 32 and name HE1))
((segid "BrD" and resid 94 and name HB1))
ASSI {862}
((segid "BrD" and resid 95 and name HB2))
((segid "BrD" and resid 95 and name HA))
  2.900  2.100  2.100 peak          862 weight  0.10000E+01 volume  0.13207E+03 ppm1      3.373 ppm2      4.477
OR {862}
((segid "BrD" and resid 65 and name HB2))
((segid "BrD" and resid 62 and name HA))
ASSI {5972}
(segid "BrD" and resid 18 and name HD1%)
((segid "BrD" and resid 68 and name HB1))
  2.800  2.000  2.000 peak         5972 weight  0.10000E+01 volume  0.16386E+03 ppm1      1.057 ppm2      3.667
OR {5972}
(segid "BrD" and resid 18 and name HD1%)
((segid "BrD" and resid 15 and name HB2))
ASSI {6172}
(segid "BrD" and resid 56 and name HD1%)
((segid "BrD" and resid 26 and name HA))
  3.000  2.200  2.200 peak         6172 weight  0.10000E+01 volume  0.11879E+03 ppm1      1.546 ppm2      4.502
OR {6172}
((segid "BrD" and resid 116 and name HG12))
((segid "BrD" and resid 75 and name HA))
ASSI {6592}
(segid "BrD" and resid 31 and name HB%)
(segid "BrD" and resid 35 and name HE%)
  3.000  2.200  2.200 peak         6592 weight  0.10000E+01 volume  0.12050E+03 ppm1      2.289 ppm2      2.779
OR {6592}
(segid "BrD" and resid 31 and name HB%)
((segid "BrD" and resid 33 and name HD1))
ASSI {6622}
(segid "BrD" and resid 31 and name HB%)
((segid "BrD" and resid 56 and name HB2))
  3.200  2.600  2.300 peak         6622 weight  0.10000E+01 volume  0.78528E+02 ppm1      2.291 ppm2      1.994

TABLE 3-continued

Ambiguous NOE-derived Inter-proton Distance Restraints

```
OR {6622}
(segid "BrD" and resid 31 and name HB%)
((segid "BrD" and resid 102 and name HB1))
ASSI {6812}
(segid "BrD" and resid 99 and name HB%)
((segid "BrD" and resid 85 and name HB2))
  2.500  1.600 1.600 peak        6812 weight  0.10000E+01 volume  0.30669E+03 ppm1   2.190 ppm2   3.645
OR {6812}
(segid "BrD" and resid 99 and name HB%)
((segid "BrD" and resid 82 and name HB1))
ASSI {6822}
(segid "BrD" and resid 99 and name HB%)
((segid "BrD" and resid 103 and name HB2))
  2.900  2.100 2.100 peak        6822 weight  0.10000E+01 volume  0.12780E+03 ppm1   2.190 ppm2   1.903
OR {6822}
(segid "BrD" and resid 99 and name HB%)
((segid "BrD" and resid 86 and name HG1))
ASSI {7132}
(segid "BrD" and resid 38 and name HG1%)
((segid "BrD" and resid 46 and name HB1))
  2.600  1.700 1.700 peak        7132 weight  0.10000E+01 volume  0.23427E+03 ppm1   1.057 ppm2   3.306
OR {7132}
(segid "BrD" and resid 81 and name HG1%)
((segid "BrD" and resid 77 and name HB1))
ASSI {7142}
(segid "BrD" and resid 81 and name HG1%)
((segid "BrD" and resid 59 and name HB2))
  2.800  2.000 2.000 peak        7142 weight  0.10000E+01 volume  0.18258E+03 ppm1   1.058 ppm2   2.475
OR {7142}
(segid "BrD" and resid 38 and name HG1%)
((segid "BrD" and resid 53 and name HG2))
ASSI {7152}
(segid "BrD" and resid 81 and name HG1%)
((segid "BrD" and resid 54 and name HB2))
  2.800  2.000 2.000 peak        7152 weight  0.10000E+01 volume  0.17360E+03 ppm1   1.057 ppm2   1.962
OR {7152}
(segid "BrD" and resid 82 and name HG1%)
((segid "BrD" and resid 54 and name HB2))
ASSI {7222}
((segid "BrD" and resid 17 and name HB))
(segid "BrD" and resid 14 and name HD2%)
  3.200  2.600 2.300 peak        7222 weight  0.10000E+01 volume  0.77701E+02 ppm1   4.854 ppm2   1.424
OR {7222}
((segid "BrD" and resid 17 and name HB))
(segid "BrD" and resid 14 and name HD1%)
OR {7222}
((segid "BrD" and resid 17 and name HB))
((segid "BrD" and resid 109 and name and name HG1))
ASSI {7232}
((segid "BrD" and resid 17 and name HB))
(segid "BrD" and resid 115 and name HD1%)
  3.400  2.900 2.100 peak        7232 weight  0.10000E+01 volume  0.48663E+02 ppm1   4.854 ppm2   1.317
OR {7232}
((segid "BrD" and resid 17 and name HB))
(segid "BrD" and resid 14 and name HD2%)
ASSI {7262}
(segid "BrD" and resid 17 and name HG2%)
(segid "BrD" and resid 21 and name HD1%)
  2.400  1.400 1.400 peak        7262 weight  0.10000E+01 volume  0.43712E+03 ppm1   1.747 ppm2   1.221
OR {7262}
(segid "BrD" and resid 17 and name HG2%)
(segid "BrD" and resid 110 and name HG2%)
ASSI {7392}
((segid "BrD" and resid 15 and name HA))
((segid "BrD" and resid 16 and name HG))
  3.800  3.600 1.700 peak        7392 weight  0.10000E+01 volume  0.25131E+02 ppm1   4.605 ppm2   2.314
OR {7392}
((segid "BrD" and resid 15 and name HA))
((segid "BrD" and resid 19 and name HB1))
ASSI {7742}
((segid "BrD" and resid 106 and name HA))
(segid "BrD" and resid 25 and name HG1%)
  3.400  2.900 2.100 peak        7742 weight  0.10000E+01 volume  0.51959E+02 ppm1   4.557 ppm2   1.817
OR {7742}
((segid "BrD" and resid 106 and name HA))
((segid "BrD" and resid 102 and name HB2))
```

TABLE 3-continued

| Ambiguous NOE-derived Inter-proton Distance Restraints |
|---|

ASSI {8052}
((segid "BrD" and resid 77 and name HB1))
((segid "BrD" and resid 80 and name HB2))
  3.300  2.700  2.200 peak      8052 weight  0.10000E+01 volume  0.59988E+02 ppm1      3.325 ppm2    2.564
OR {8052}
((segid "BrD" and resid 77 and name HB1))
((segid "BrD" and resid 54 and name HB1))
OR {8052}
((segid "BrD" and resid 77 and name HB1))
(segid "BrD" and resid 54 and name HE%)
ASSI {8122}
((segid "BrD" and resid 63 and name HA))
((segid "BrD" and resid 62 and name HB1))
  3.700  3.400  1.800 peak      8122 weight  0.10000E+01 volume  0.30661E+02 ppm1      5.296 ppm2    2.660
OR {8122}
((segid "BrD" and resid 63 and name HA))
((segid "BrD" and resid 67 and name HB2))
OR {8122}
((segid "BrD" and resid 63 and name HA))
((segid "BrD" and resid 64 and name HB1))
ASSI {8212}
((segid "BrD" and resid 109 and name HG1))
((segid "BrD" and resid 109 and name HB1))
  2.200  1.200  1.200 peak      8212 weight  0.10000E+01 volume  0.72542E+03 ppm1      1.401 ppm2    2.310
OR {8212}
(segid "BrD" and resid 14 and name HD2%)
((segid "BrD" and resid 16 and name HG))
ASSI {8492}
(segid "BrD" and resid 18 and name HD2%)
((segid "BrD" and resid 14 and name HA))
  2.700  1.800  1.800 peak      8492 weight  0.10000E+01 volume  0.19700E+03 ppm1      0.414 ppm2    4.626
OR {8492}
(segid "BrD" and resid 18 and name HD2%)
((segid "BrD" and resid 15 and name HA))
OR {8492}
(segid "BrD" and resid 18 and name HD2%)
((segid "BrD" and resid 71 and name HA))
ASSI {8542}
(segid "BrD" and resid 22 and name HD1%)
((segid "BrD" and resid 60 and name HB2))
  2.600  1.700  1.700 peak      8542 weight  0.10000E+01 volume  0.14926E+03 ppm1      1.645 ppm2    4.629
OR {8542}
(segid "BrD" and resid 22 and name HD1%)
((segid "BrD" and resid 23 and name HA))
OR {8542}
(segid "BrD" and resid 22 and name HD1%)
((segid "BrD" and resid 56 and name HA))
OR {8542}
(segid "BrD" and resid 22 and name HD1%)
((segid "BrD" and resid 61 and name HA))
ASSI {8662}
(segid "BrD" and resid 56 and name HD2%)
(segid "BrD" and resid 22 and name HD2%)
  2.200  1.200  1.200 peak      8662 weight  0.10000E+01 volume  0.65442E+03 ppm1      1.254 ppm2    1.635
OR {8662}
(segid "BrD" and resid 56 and name HD2%)
(segid "BrD" and resid 25 and name HG2%)
ASSI {8712}
(segid "BrD" and resid 56 and name HD1%)
(segid "BrD" and resid 102 and name HD1%)
  2.600  1.700  1.700 peak      8712 weight  0.10000E+01 volume  0.26563E+01 ppm1      1.547 ppm2    1.321
OR {8712}
(segid "BrD" and resid 56 and name HD1%)
(segid "BrD" and resid 102 and name HD2%)
OR {8712}
((segid "BrD" and resid 116 and name HG12))
(segid "BrD" and resid 115 and name HD1%)
ASSI {8962}
((segid "BrD" and resid 56 and name HB2))
(segid "BrD" and resid 25 and name HG2%)
  3.700  3.400  1.800 peak      8962 weight  0.10000E+01 volume  0.31139E+02 ppm1      1.994 ppm2    1.427
OR {8962}
((segid "BrD" and resid 102 and name HB1))
(segid "BrD" and resid 101 and name HG2%)
OR {8962}
((segid "BrD" and resid 56 and name HB2))
(segid "BrD" and resid 22 and name HD2%)

TABLE 3-continued

Ambiguous NOE-derived Inter-proton Distance Restraints

ASSI {9112}
(segid "BrD" and resid 21 and name HG2%)
(segid "BrD" and resid 102 and name HD2%)
  2.600  1.700  1.700 peak      9112 weight  0.10000E+01 volume  0.28598E+03 ppm1      1.600 ppm2      1.324
OR {9112}
(segid "BrD" and resid 101 and name HG2%)
(segid "BrD" and resid 102 and name HD1%)
ASSI {9142}
(segid "BrD" and resid 21 and name HG2%)
(segid "BrD" and resid 78 and name HD1%)
  3.800  3.600  1.700 peak      9142 weight  0.10000E+01 volume  0.37968E+02 ppm1      1.596 ppm2      0.772
OR {9142}
(segid "BrD" and resid 21 and name HG2%)
(segid "BrD" and resid 81 and name HG2%)
ASSI {9192}
(segid "BrD" and resid 21 and name HD1%)
(segid "BrD" and resid 18 and name HD1%)
  2.500  1.600  1.600 peak      9192 weight  0.10000E+01 volume  0.36076E+03 ppm1      1.205 ppm2      1.068
OR {9192}
(segid "BrD" and resid 21 and name HD1%)
((segid "BrD" and resid 78 and name HB2))
ASSI {9662}
((segid "BrD" and resid 79 and name HG1))
(segid "BrD" and resid 83 and name HG2%)
  3.000  2.200  2.200 peak      9662 weight  0.10000E+01 volume  0.10300E+03 ppm1      1.031 ppm2      1.900
OR {9662}
((segid "BrD" and resid 79 and name HG1))
((segid "BrD" and resid 116 and name HG11))
ASSI {10002}
((segid "BrD" and resid 54 and name HB1))
(segid "BrD" and resid 81 and name HG1%)
  3.600  3.200  1.900 peak      10002 weight  0.10000E+01 volume  0.33897E+02 ppm1      2.585 ppm2      1.043
OR {10002}
((segid "BrD" and resid 42 and name HB2))
(segid "BrD" and resid 37 and name HG1%)
ASSI {10092}
((segid "BrD" and resid 35 and name HG1))
((segid "BrD" and resid 32 and name HA))
  3.100  2.400  2.400 peak      10092 weight  0.10000E+01 volume  0.97444E+02 ppm1      3.422 ppm2      4.972
OR {10092}
((segid "BrD" and resid 35 and name HG1))
((segid "BrD" and resid 31 and name HA))
ASSI {10182}
((segid "BrD" and resid 52 and name HB1))
((segid "BrD" and resid 80 and name HG1))
  4.100  4.100  1.400 peak      10182 weight  0.10000E+01 volume  0.17926E+02 ppm1      3.621 ppm2      2.345
OR {10182}
((segid "BrD" and resid 84 and name HB1))
((segid "BrD" and resid 80 and name HG1))
ASSI {10302}
((segid "BrD" and resid 42 and name HG1))
((segid "BrD" and resid 39 and name HD1))
  3.000  2.200  2.200 peak      10302 weight  0.10000E+01 volume  0.10808E+03 ppm1      2.880 ppm2      2.298
OR {10302}
((segid "BrD" and resid 7 and name HG1))
((segid "BrD" and resid 6 and name HB2))
ASSI {10412}
((segid "BrD" and resid 48 and name HA))
((segid "BrD" and resid 48 and name HB1))
  2.800  2.000  2.000 peak      10412 weight  0.10000E+01 volume  0.17461R+03 ppm1      4.831 ppm2      2.762
OR {10412}
((segid "BrD" and resid 67 and name HA))
((segid "BrD" and resid 87 and name HB1))
ASSI {10502}
((segid "BrD" and resid 112 and name HB1))
(segid "BrD" and resid 113 and name HB%)
  2.700  1.800  1.800 peak      1.502 weight  0.10000E+01 volume  0.19681E+03 ppm1      2.684 ppm2      1.985
OR {10502}
((segid "BrD" and resid 112 and name HB1))
(segid "BrD" and resid 109 and name HD1))
ASSI {10602}
((segid "BrD" and resid 23 and name HA))
((segid "BrD" and resid 19 and name HA))
  3.500  3.100  2.000 peak      10602 weight  0.10000E+01 volume  0.44566E+02 ppm1      4.656 ppm2      4.278
OR {10602}
((segid "BrD" and resid 104 and name HA))
((segid "BrD" and resid 101 and name HA))

TABLE 3-continued

Ambiguous NOE-derived Inter-proton Distance Restraints

```
ASSI {10902}
((segid "BrD" and resid 70 and name HB1))
((segid "BrD" and resid 11 and name HG1))
  3.200  2.600  2.300 peak      10902  weight  0.10000E+01 volume   0.71093E+02 ppm1      4.755 ppm2   2.646
OR {10902}
((segid "BrD" and resid 70 and name HB1))
(segid "BrD" and resid 75 and name HE%)
OR {10902}
((segid "BrD" and resid 93 and name HB2))
(segid "BrD" and resid 97 and name HB1))
OR {10902}
((segid "BrD" and resid 70 and name HB1))
((segid "BrD" and resid 62 and name HB1))
OR {10902}
((segid "BrD" and resid 70 and name HB1))
((segid "BrD" and resid 8 and name HG1))
ASSI {11592}
((segid "BrD" and resid 109 and name HB2))
(segid "BrD" and resid 21 and name HD1%)
  3.400  2.900  2.100 peak      11592  weight  0.10000E+01 volume   0.47549E+02 ppm1      2.141 ppm2   1.222
OR {11592}
((segid "BrD" and resid 109 and name HB2))
(segid "BrD" and resid 110 and name HG2%)
ASSI {11652}
((segid "BrD" and resid 59 and name HB2))
(segid "BrD" and resid 58 and name HG2%)
  2.900  2.100  2.100 peak      11652  weight  0.10000E+01 volume   0.12259E+03 ppm1      2.487 ppm2   1.660
OR {11652}
((segid "BrD" and resid 59 and name HB2))
(segid "BrD" and resid 22 and name HD1%)
ASSI {12162}
((segid "BrD" and resid 18 and name HA))
(segid "BrD" and resid 21 and name HG2%)
  3.600  3.200  1.900 peak      12162  weight  0.10000E+01 volume   0.38701E+02 ppm1      3.866 ppm2   1.591
OR {12162}
((segid "BrD" and resid 18 and name HA))
(segid "BrD" and resid 22 and name HD2%)
ASSI {12172}
((segid "BrD" and resid 6 and name HA))
((segid "BrD" and resid 6 and name HG2))
  2.500  1.600  1.600 peak      12172  weight  0.10000E+01 volume   0.31535E+03 ppm1      4.951 ppm2   2.033
OR {12172}
((segid "BrD" and resid 39 and name HA))
((segid "BrD" and resid 39 and name HG1))
ASSI {12302}
(segid "BrD" and resid 86 and name HG2%)
((segid "BrD" and resid 83 and name HA))
  3.600  3.200  1.900 peak      12302  weight  0.10000E+01 volume   0.36612E+02 ppm1      0.760 ppm2   4.450
OR {12302}
((segid "BrD" and resid 86 and name HG2))
((segid "BrD" and resid 96 and name HA))
ASSI {12572}
(segid "BrD" and resid 59 and name HE%)
(segid "BrD" and resid 22 and name HD1%)
  2.700  1.800  1.800 peak      12572  weight  0.10000E+01 volume   0.19213E+03 ppm1      1.848 ppm2   1.645
OR {12572}
(segid "BrD" and resid 59 and name HE%)
(segid "BrD" and resid 63 and name HD1%)
ASSI {12722}
(segid "BrD" and resid 18 and name HD1%)
((segid "BrD" and resid 68 and name HB2))
  3.400  2.900  2.100 peak      12722  weight  0.10000E+01 volume   0.56232E+02 ppm1      1.056 ppm2   3.513
OR {12722}
(segid "BrD" and resid 18 and name HD1%)
((segid "BrD" and resid 75 and name HG1))
ASSI {12742}
((segid "BrD" and resid 72 and name HA))
(segid "BrD" and resid 116 and name HG2%)
  3.000  2.200  2.200 peak      12742  weight  0.10000E+01 volume   0.10372E+03 ppm1      4.656 ppm2   1.414
OR {12742}
((segid "BrD" and resid 67 and name HA))
(segid "BrD" and resid 69 and name HG2%)
OR {12742}
((segid "BrD" and resid 111 and name HA))
(segid "BrD" and resid 116 and name HD1%)
```

TABLE 3-continued

Ambiguous NOE-derived Inter-proton Distance Restraints

ASSI {12862}
((segid "BrD" and resid 62 and name HD1))
(segid "BrD" and resid 54 and name HE%)
 3.000  2.200  2.200 peak      12862 weight 0.10000E+01 volume  0.10219E+03 ppm1      3.177 ppm2      3.569
OR {12862}
((segid "BrD" and resid 62 and name HD1))
((segid "BrD" and resid 63 and name HB2))
OR {12862}
((segid "BrD" and resid 62 and name HD1))
((segid "BrD" and resid 54 and name HB1))
ASSI {13242}
((segid "BrD" and resid 46 and name HB2))
(segid "BrD" and resid 38 and name HG2%)
 3.500  3.200  2.000 peak      13242 weight 0.10000E+01 volume  0.46826E+02 ppm1      3.080 ppm2      0.791
OR {13242}
((segid "BrD" and resid 46 and name HB2))
((segid "BrD" and resid 50 and name HG12))
ASSI {13322}
(segid "BrD" and resid 78 and name HD2%)
(segid "BrD" and resid 21 and name HG2%)
 2.700  3.600  1.800 peak      13322 weight 0.10000E+01 volume  0.21424E+03 ppm1      0.662 ppm2      1.590
OR {13322}
(segid "BrD" and resid 78 and name HD2%)
(segid "BrD" and resid 22 and name HD2%)
ASSI {13352}
(segid "BrD" and resid 18 and name HD2%)
(segid "BrD" and resid 14 and name HB1%)
 4.200  4.200  1.300 peak      13352 weight 0.10000E+01 volume  0.14748E+02 ppm1      0.415 ppm2      2.481
OR {13352}
(segid "BrD" and resid 18 and name HD2%)
((segid "BrD" and resid 21 and name HB))
ASSI {13392}
(segid "BrD" and resid 25 and name HG1%)
((segid "BrD" and resid 28 and name HA))
 2.600  2.000  2.000 peak      13392 weight 0.10000E+01 volume  0.16152E+03 ppm1      1.795 ppm2      4.566
OR {13392}
(segid "BrD" and resid 25 and name HG1%)
((segid "BrD" and resid 106 and name HA))
ASSI {13592}
(segid "BrD" and resid 56 and name HD2%)
((segid "BrD" and resid 59 and name HB2))
 2.600  1.700  1.700 peak      13592 weight 0.10000E+01 volume  0.24679E+03 ppm1      1.254 ppm2      3.499
OR {13592}
(segid "BrD" and resid 56 and name HD2%)
(segid "BrD" and resid 54 and name HE%)
OR {13592}
(segid "BrD" and resid 56 and name HD2%)
((segid "BrD" and resid 26 and name HB1))
ASSI {13602}
(segid "BrD" and resid 54 and name HE%)
((segid "BrD" and resid 37 and name HB2))
 2.500  1.600  1.600 peak      13602 weight 0.10000E+01 volume  0.34655E+03 ppm1      2.535 ppm2      2.323
OR {13602}
(segid "BrD" and resid 54 and name HE%)
((segid "BrD" and resid 56 and name HG))
ASSI {13762}
(segid "BrD" and resid 63 and name HD2%)
((segid "BrD" and resid 19 and name HB1))
 2.300  1.300  1.300 peak      13762 weight 0.10000E+01 volume  0.59623E+03 ppm1      1.498 ppm2      2.318
OR {13762}
(segid "BrD" and resid 63 and name HD2%)
((segid "BrD" and resid 22 and name HB2))
ASSI {13952}
(segid "BrD" and resid 14 and name HD1%)
((segid "BrD" and resid 14 and name HA))
 2.700  1.800  1.800 peak      13952 weight 0.10000E+01 volume  0.20695E+03 ppm1      1.402 ppm2      4.487
OR {13952}
(segid "BrD" and resid 14 and name HD1%)
((segid "BrD" and resid 69 and name HA))
ASSI {14042}
(segid "BrD" and resid 76 and name HB%)
(segid "BrD" and resid 73 and name HD1%)
 3.100  2.400  2.400 peak      14042 weight 0.10000E+01 volume  0.97985E+02 ppm1      2.092 ppm2      1.540
OR {14042}
(segid "BrD" and resid 76 and name HB%)
((segid "BrD" and resid 116 and name HG12))

TABLE 3-continued

Ambiguous NOE-derived Inter-proton Distance Restraints

ASSI {14162}
((segid "BrD" and resid 15 and name HA))
(segid "BrD" and resid 63 and name HD2%)
  3.600  3.200  1.900 peak      14162 weight  0.10000E+01 volume  0.37938E+02 ppm1      4.609 ppm2    1.490
OR {14162}
((segid "BrD" and resid 60 and name HB2))
(segid "BrD" and resid 63 and name HD2%)
ASSI {14192}
((segid "BrD" and resid 62 and name HA))
(segid "BrD" and resid 68 and name HB2))
  3.700  3.400  1.$$00 peak    14192 weight  0.10000E+01 volume  0.29612E+02 ppm1      4.459 ppm2    3.504
OR {14192}
((segid "BrD" and resid 95 and name HA))
((segid "BrD" and resid 89 and name HB2))
ASSI {14202}
((segid "BrD" and resid 95 and name HA))
((segid "BrD" and resid 98 and name HB2))
  3.200  2.600  2.300 peak      14202 weight  0.10000E+01 Volume  0.$$1269E+02 ppm1    4.462 ppm2    3.701
OR {14202}
((segid "BrD" and resid 62 and name HA))
((segid "BrD" and resid 68 and name HB1))
ASSI {14312}
(segid "BrD" and resid 22 and name HD2%)
((segid "BrD" and resid 59 and name HB2))
  2.700  1.800  1.800 peak      14312 weight  0.10000E+01 volume  0.21510E+03 ppm1      1.599 ppm2    2.501
OR {14312}
(segid "BrD" and resid 22 and name HD2%)
((segid "BrD" and resid 21 and name HB))
OR {14312}
(segid "BrD" and resid 22 and name HD2%)
(segid "BrD" and resid 63 and name HB2))
OR {14312}
(segid "BrD" and resid 22 and name HD2%)
((segid "BrD" and resid 26 and name HB1))
ASSI {14432}
(segid "BrD" and resid 21 and name HD1%)
((segid "BrD" and resid 18 and name HB1))
  2.700  1.$$00 1.800 peak     14432 weight  0.10000E+01 volume  0.19246E+03 ppm1      1.205 ppm2    2.148
OR {14432}
(segid "BrD" and resid 21 and name HD1%)
((segid "BrD" and resid 102 and name HG))
ASSI {14462}
(segid "BrD" and resid 110 and name HD1%)
(segid "BrD" and resid 116 and name HD1%)
  2.100  1.100  1.100 peak      14462 weight  0.10000E+01 volume  0.89267E+03 ppm1      1.154 ppm2    1.387
OR {14462}
(segid "BrD" and resid 110 and name HD1%)
(segid "BrD" and resid 115 and name HD1%)
ASSI {14602}
(segid "BrD" and resid 18 and name HD1%)
(segid "BrD" and resid 115 and name HD1%)
  3.500  3.100  2.000 peak      14602 weight  0.10000E+01 volume  0.42578E+02 ppm1      1.057 ppm2    1.327
OR {14602}
(segid "BrD" and resid 18 and name HD1%)
((segid "BrD" and resid 78 and name HB1))
ASSI {14642}
((segid "BrD" and resid 18 and name HA))
(segid "BrD" and resid 102 and name HD2%)
  4.400  4.400  1.100 peak      14642 weight  0.10000E+01 volume  0.11486E+02 ppm1      3.867 ppm2    1.320
OR {14642}
((segid "BrD" and resid 16 and name HA))
(segid "BrD" and resid 115 and name HD1%)
OR {14642}
((segid "BrD" and resid 18 and name HA))
(segid "BrD" and resid 78 and name HB1))
ASSI {14682}
(segid "BrD" and resid 22 and name HD1%)
((segid "BrD" and resid 64 and name HG1))
  3.000  2.200  2.200 peak      14682 weight  0.10000E+01 volume  0.10496E+03 ppm1      1.645 ppm2    2.186
OR {14682}
((segid "BrD" and resid 110 and name HG12))
((segid "BrD" and resid 115 and name HB1))
ASSI {14692}
(segid "BrD" and resid 63 and name HD2%)
((segid "BrD" and resid 19 and name HD1))
  2.300  1.300  1.300 peak      14692 weight  0.10000E+01 volume  0.59246E+03 ppm1      1.498 ppm2    2.191

TABLE 3-continued

Ambiguous NOE-derived Inter-proton Distance Restraints

```
OR {14692}
(segid "BrD" and resid 63 and name HD2%)
((segid "BrD" and resid 64 and name HG1))
ASSI {14792}
(segid "BrD" and resid 22 and name HD2%)
((segid "BrD" and resid 56 and name HA))
 2.600  1.700 1.700 peak       14792 weight  0.10000E+01 volume   0.26795E+03 ppm1     1.599 ppm2     4.639
OR {14792}
(segid "BrD" and resid 22 and name HD2%)
((segid "BrD" and resid 60 and name HB2))
ASSI {14802}
((segid "BrD" and resid 86 and name HD1))
((segid "BrD" and resid 83 and name HA))
 2.700  1.800 1.800 peak       14802 weight  0.10000E+01 volume   0.19483E+03 ppm1     1.896 ppm2     4.461
OR {14802}
((segid "BrD" and resid 103 and name HB2))
((segid "BrD" and resid 99 and name HA))
ASSI {14862}
((segid "BrD" and resid 54 and name HA))
(segid "BrD" and resid 81 and name HG1%)
 3.800  3.600 1.700 peak       14862 weight  0.10000E+01 volume   0.25126E+02 ppm1     5.543 ppm2     1.076
OR {14862}
((segid "BrD" and resid 54 and name HA))
(segid "BrD" and resid 38 and name HG1%)
ASSI {14872}
(segid "BrD" and resid 81 and name HG1%)
((segid "BrD" and resid 80 and name HB2))
 2.900  2.100 2.100 peak       14872 weight  0.10000E+01 volume   0.14378E+03 ppm1     1.058 ppm2     2.565
OR {14872}
(segid "BrD" and resid 81 and name HG1%)
((segid "BrD" and resid 80 and name HB1))
OR {14872}
(segid "BrD" and resid 81 and name HG1%)
(segid "BrD" and resid 54 and name HE%)
OR {14872}
(segid "BrD" and resid 81 and name HG1%)
((segid "BrD" and resid 54 and name HB1))
ASSI {14882}
(segid "BrD" and resid 81 and name HG1%)
((segid "BrD" and resid 56 and name HG))
 3.500  3.100 2.000 peak       14882 weight  0.10000E+01 volume   0.44935E+02 ppm1     1.058 ppm2     2.328
OR {14882}
(segid "BrD" and resid 38 and name HG1%)
((segid "BrD" and resid 37 and name HB2))
ASSI {15202}
((segid "BrD" and resid 72 and name HA))
((segid "BrD" and resid 75 and name HG2))
 4.000  4.000 1.500 peak       15202 weight  0.10000E+01 volume   0.18586E+02 ppm1     4.656 ppm2     3.224
OR {15202}
((segid "BrD" and resid 61 and name HA))
((segid "BrD" and resid 59 and name HG2))
OR {15202}
((segid "BrD" and resid 61 and name HA))
((segid "BrD" and resid 59 and name HG1))
ASSI {15382}
((segid "BrD" and resid 74 and name HA))
(segid "BrD" and resid 75 and name H$$%)
 3.200  2.600 2.300 peak       15382 weight  0.10000E+01 volume   0.70547E+02 ppm1     4.362 ppm2     2.653
OR {15382}
((segid "BrD" and resid 74 and name HA))
((segid "BrD" and resid 59 and name HB1))
ASSI {15392}
((segid "BrD" and resid 74 and name HB1))
((segid "BrD" and resid 73 and name HB2))
 3.200  2.600 2.300 peak       15392 weight  0.10000E+01 volume   0.74692E+02 ppm1     1.572 ppm2     2.471
OR {15392}
((segid "BrD" and resid 74 and name HB1))
((segid "BrD" and resid 63 and name HG))
ASSI {15532}
(segid "BrD" and resid 82 and name HB2))
((segid "BrD" and resid 103 and name HB1))
 3.100  2.400 2.400 peak       15532 weight  0.10000E+01 volume   0.91508E+02 ppm1     3.573 ppm2     1.344
OR {15532}
((segid "BrD" and resid 82 and name HB2))
((segid "BrD" and resid 86 and name HB1))
```

TABLE 3-continued

Ambiguous NOE-derived Inter-proton Distance Restraints

ASSI {15542}
((segid "BrD" and resid 82 and name HB1))
((segid "BrD" and resid 103 and name HB1))
 3.100  2.400  2.400 peak      15542 weight  0.10000E+01 volume  0.94295E+02 ppm1    3.672 ppm2    2.344
OR {15542}
((segid "BrD" and resid 107 and name HB1))
((segid "BrD" and resid 110 and name HB))
OR {15542}
((segid "BrD" and resid 107 and name HB1))
((segid "BrD" and resid 103 and name HB1))
OR {15542}
((segid "BrD" and resid 106 and name HB2))
((segid "BrD" and resid 21 and name HG11))
ASSI {15562}
((segid "BrD" and resid 82 and name HB1))
((segid "BrD" and resid 103 and name HB2))
 3.500  3.100  2.000 peak      15562 weight  0.10000E+01 volume  0.43748E+02 ppm1    3.671 ppm2    1.897
OR {15562}
((segid "BrD" and resid 82 and name HB1))
(segid "BrD" and resid 83 and name HG2%)
ASSI {15572}
((segid "BrD" and resid 106 and name HB2))
(segid "BrD" and resid 110 and name HG11))
 5.500  5.500  0.000 peak      15572 weight  0.10000E+01 volume  0.17071E+01 ppm1    3.671 ppm2    1.722
OR {15572}
((segid "BrD" and resid 107 and name HB1))
((segid "BrD" and resid 110 and name HG11))
OR {15572}
((segid "BrD" and resid 106 and name HB2))
(segid "BrD" and resid 17 and name HG2%)
ASSI {15582}
((segid "BrD" and resid 15 and name HB2))
(segid "BrD" and resid 63 and name HD1%)
 3.300  2.700  2.200 peak      15582 weight  0.10000E+01 volume  0.63452E+02 ppm1    3.671 ppm2    1.653
OR {15582}
((segid "BrD" and resid 106 and name HB2))
((segid "BrD" and resid 110 and name HG12))
OR {15582}
((segid "BrD" and resid 107 and name HB1))
((segid "BrD" and resid 110 and name HG12))
ASSI {15722}
((segid "BrD" and resid 52 and name HB1))
((segid "BrD" and resid 80 and name HB1))
 4.700  4.700  0.800 peak      15722 weight  0.10000E+01 volume  0.74610E+01 ppm1    3.620 ppm2    3.597
OR {15722}
((segid "BrD" and resid 84 and name HB1))
((segid "BrD" and resid 87 and name HB2))
OR {15722}
((segid "BrD" and resid 84 and name HB1))
((segid "BrD" and resid 80 and name HB1))
OR {15722}
((segid "BrD" and resid 65 and name HB1))
((segid "BrD" and resid 64 and name HB1))
ASSI {16012}
((segid "BrD" and resid 68 and name HA))
(segid "BrD" and resid 69 and name HG2%)
 3.700  3.400  1.800 peak      16012 weight  0.10000E+01 volume  0.30406E+02 ppm1    5.148 ppm2    1.433
OR {16012}
((segid "BrD" and resid 68 and name HA))
(segid "BrD" and resid 14 and name HD2%)
ASSI {16172}
((segid "BrD" and resid 68 and name HB1))
(segid "BrD" and resid 63 and name HD1%)
 3.600  3.200  1.900 peak      16172 weight  0.10000E+01 volume  0.37293E+02 ppm1    3.668 ppm2    1.645
OR {16172}
((segid "BrD" and resid 68 and name HB1))
(segid "BrD" and resid 22 and name HD1%)
ASSI {16182}
((segid "BrD" and resid 68 and name HB2))
(segid "BrD" and resid 63 and name HD1%)
 3.800  3.600  1.700 peak      16182 weight  0.10000E+01 volume  0.27740E+02 ppm1    3.522 ppm2    1.645
OR {16182}
((segid "BrD" and resid 68 and name HB2))
(segid "BrD" and resid 22 and name HD2%)

TABLE 3-continued

| Ambiguous NOE-derived Inter-proton Distance Restraints |

ASSI {16362}
((segid "BrD" and resid 97 and name HE1))
(segid "BrD" and resid 101 and name HD1%)
  3.000  2.200  2.200 peak      16362 weight  0.10000E+01 volume  0.11543E+03 ppm1      3.571 ppm2    1.580
OR {16362}
((segid "BrD" and resid 64 and name HE1))
(segid "BrD" and resid 22 and name HD2%)
OR {16362}
((segid "BrD" and resid 97 and name HE1))
(segid "BrD" and resid 101 and name HG2%)
ASSI {16372}
((segid "BrD" and resid 88 and name HB1))
((segid "BrD" and resid 50 and name HG11))
  2.900  2.100  2.100 peak      16372 weight  0.10000E+01 volume  0.13106E+03 ppm1      3.522 ppm2    1.401
OR {16372}
(segid "BrD" and resid 111 and name HE1%)
(segid "BrD" and resid 116 and name HD1%)
ASSI {16482}
((segid "BrD" and resid 96 and name HA))
((segid "BrD" and resid 85 and name HB1))
  3.800  3.600  1.700 peak      16482 weight  0.10000E+01 volume  0.24633E+02 ppm1      4.409 ppm2    3.891
OR {16482}
((segid "BrD" and resid 107 and name HA))
((segid "BrD" and resid 106 and name HB1))
ASSI {16572}
((segid "BrD" and resid 96 and name HB2))
((segid "BrD" and resid 86 and name HA))
  4.100  4.100  1.400 peak      16572 weight  0.10000E+01 volume  0.16756E+02 ppm1      3.132 ppm2    4.804
OR {16572}
((segid "BrD" and resid 96 and name HB2))
((segid "BrD" and resid 92 and name HA))
ASSI {16582}
((segid "BrD" and resid 96 and name HB1))
((segid "BrD" and resid 92 and name HA))
  3.800  3.600  1.700 peak      16582 weight  0.10000E+01 volume  0.28094E+02 ppm1      4.004 ppm2    4.808
OR {16582}
((segid "BrD" and resid 96 and name HB1))
((segid "BrD" and resid 97 and name HA))
OR {16582}
((segid "BrD" and resid 96 and name HB1))
((segid "BrD" and resid 94 and name HA))
ASSI {16782}
((segid "BrD" and resid 95 and name HB1))
((segid "BrD" and resid 85 and name HA))
  3.200  2.600  2.300 peak      16782 weight  0.10000E+01 volume  0.73175E+02 ppm1      3.620 ppm2    4.995
OR {16782}
((segid "BrD" and resid 95 and name HB1))
((segid "BrD" and resid 93 and name HB1))
OR {16782}
((segid "BrD" and resid 84 and name HB1))
((segid "BrD" and resid 85 and name HA))
ASSI {16852}
((segid "BrD" and resid 82 and name HB1))
(segid "BrD" and resid 107 and name HE%)
  3.000  2.200  2.200 peak      16852 weight  0.10000E+01 volume  0.10680E+03 ppm1      3.670 ppm2    7.896
OR {16852}
((segid "BrD" and resid 107 and name HB1))
(segid "BrD" and resid 107 and name HE%)
ASSI {17112}
((segid "BrD" and resid 95 and name HB2))
((segid "BrD" and resid 32 and name HH2))
  3.500  3.100  2.000 peak      17112 weight  0.10000E+01 volume  0.46090E+02 ppm1      3.366 ppm2    7.754
OR {17112}
((segid "BrD" and resid 95 and name HB2))
(segid "BrD" and resid 34 and name HE%)
OR {17112}
((segid "BrD" and resid 95 and name HB2))
(segid "BrD" and resid 96 and name HD%)
ASSI {17122}
((segid "BrD" and resid 105 and name HB1))
(segid "BrD" and resid 25 and name HG1%)
  3.400  2.900  2.100 peak      17122 weight  0.10000E+01 volume  0.47791E+02 ppm1      3.721 ppm2    1.824
OR {17122}
((segid "BrD" and resid 105 and name HB1))
((segid "BrD" and resid 102 and name HB2))

TABLE 3-continued

Ambiguous NOE-derived Inter-proton Distance Restraints

ASSI {17132}
((segid "BrD" and resid 106 and name HB2))
((segid "BrD" and resid 102 and name HB2))
 3.500  3.100  2.000 peak       17132 weight  0.10000E+01 volume   0.42104E+02 ppm1   3.668 ppm2   2.824
OR {17132}
((segid "BrD" and resid 105 and name HB2))
(segid "BrD" and resid 25 and name HG1%)
OR {17132}
((segid "BrD" and resid 106 and name HB2))
(segid "BrD" and resid 25 and name HG1%)
ASSI {17142}
((segid "BrD" and resid 106 and name HB2))
(segid "BrD" and resid 21 and name HG2%)
 3.700  3.400  1.800 peak       17142 weight  0.10000E+01 volume   0.28702E+02 ppm1   3.668 ppm2   1.612
OR {17142}
((segid "BrD" and resid 105 and name HB2))
(segid "BrD" and resid 101 and name HG2%)
OR {17142}
((segid "BrD" and resid 106 and name HB2))
(segid "BrD" and resid 21 and name HG2%)
ASSI {17272}
((segid "BrD" and resid 116 and name HA))
(segid "BrD" and resid 110 and name HG2%)
 4.000  4.000  1.500 peak       17272 weight  0.10000E+01 volume   0.18200E+02 ppm1   4.804 ppm2   1.262
OR {17272}
((segid "BrD" and resid 57 and name HA))
(segid "BrD" and resid 56 and name HD2%)
ASSI {17322}
((segid "BrD" and resid 59 and name HA))
((segid "BrD" and resid 62 and name HG2))
 4.200  4.200  1.300 peak       17322 weight  0.10000E+01 volume   0.13830E+02 ppm1   4.903 ppm2   1.490
OR {17322}
((segid "BrD" and resid 20 and name HA))
(segid "BrD" and resid 63 and name HD2%)
ASSI {17492}
((segid "BrD" and resid 34 and name HA))
((segid "BrD" and resid 31 and name HA))
 3.300  2.700  2.200 peak       17492 weight  0.10000E+01 volume   0.57702E+02 ppm1   5.544 ppm2   4.989
OR {17492}
((segid "BrD" and resid 34 and name HA))
((segid "BrD" and resid 32 and name HA))
ASSI {17522}
((segid "BrD" and resid 34 and name HA))
(segid "BrD" and resid 54 and name HE%)
 4.000  4.000  1.500 peak       17522 weight  0.10000E+01 volume   0.19574E+02 ppm1   5.544 ppm2   2.564
OR {17522}
((segid "BrD" and resid 34 and name HA))
((segid "BrD" and resid 37 and name HG2))
ASSI {17682}
((segid "BrD" and resid 33 and name HG1))
((segid "BrD" and resid 32 and name HE3))
 4.900  4.900  0.600 peak       17682 weight  0.10000E+01 volume   0.54467E+01 ppm1   0.859 ppm2   7.926
OR {17682}
((segid "BrD" and resid 33 and name HG1))
((segid "BrD" and resid 34 and name HZ))
ASSI {17692}
((segid "BrD" and resid 33 and name HG1))
((segid "BrD" and resid 32 and name HZ3))
 4.000  4.000  1.500 peak       17692 weight  0.10000E+01 volume   0.18980E+02 ppm1   0.859 ppm2   7.803
OR {17692}
((segid "BrD" and resid 33 and name HG1))
(segid "BrD" and resid 34 and name HE%)
ASSI {17702}
((segid "BrD" and resid 33 and name HG1))
((segid "BrD" and resid 32 and name HH2))
 4.100  4.100  1.400 peak       17702 weight  0.10000E+01 volume   0.16294E+02 ppm1   0.859 ppm2   7.745
OR {17702}
((segid "BrD" and resid 33 and name HG1))
(segid "BrD" and resid 34 and name HE%)
ASSI {17892}
((segid "BrD" and resid 33 and name HD1))
(segid "BrD" and resid 34 and name HD%)
 3.400  2.900  2.100 peak       17892 weight  0.10000E+01 volume   0.51743E+02 ppm1   2.783 ppm2   7.720
OR {17892}
((segid "BrD" and resid 33 and name HD1))
((segid "BrD" and resid 32 and name HH2))

TABLE 3-continued

Ambiguous NOE-derived Inter-proton Distance Restraints

```
ASSI {17972}
((segid "BrD" and resid 33 and name HB2))
((segid "BrD" and resid 32 and name HZ3))
  3.500  3.100  2.000 peak       17972 weight  0.10000E+01 volume  0.44678E+02 ppm1    −0.176 ppm2   7.789
OR {17972}
((segid "BrD" and resid 33 and name HB2))
(segid "BrD" and resid 34 and name HE%)
ASSI {18022}
((segid "BrD" and resid 59 and name HG2))
((segid "BrD" and resid 60 and name HB2))
  3.200  2.600  2.300 peak       18022 weight  0.10000E+01 volume  0.69853E+02 ppm1     3.227 ppm2   4.664
OR {18022}
((segid "BrD" and resid 75 and name HG2))
((segid "BrD" and resid 72 and name HA))
OR {18022}
((segid "BrD" and resid 59 and name HG1))
((segid "BrD" and resid 60 and name HB2))
OR {18022}
((segid "BrD" and resid 59 and name HG2))
((segid "BrD" and resid 58 and name HB))
OR {18022}
((segid "BrD" and resid 59 and name HG1))
((segid "BrD" and resid 58 and name HB))
ASSI {18032}
((segid "BrD" and resid 75 and name HG2))
((segid "BrD" and resid 74 and name HB1))
  3.400  2.900  2.100 peak       18032 weight  0.10000E+01 volume  0.48637E+02 ppm1     3.226 ppm2   3.597
OR {18032}
((segid "BrD" and resid 59 and name HG1))
((segid "BrD" and resid 74 and name HB1))
OR {18032}
((segid "BrD" and resid 59 and name HG2))
((segid "BrD" and resid 74 and name HB1))
OR {18032}
((segid "BrD" and resid 59 and name HG1))
((segid "BrD" and resid 67 and name HB1))
ASSI {18252}
(segid "BrD" and resid 35 and name HE%)
((segid "BrD" and resid 60 and name HB2))
  3.500  3.100  2.000 peak       18252 weight  0.10000E+01 volume  0.44998E+02 ppm1     2.782 ppm2   4.631
OR {18252}
(segid "BrD" and resid 35 and name HE%)
((segid "BrD" and resid 56 and name HA))
ASSI {18332}
(segid "BrD" and resid 35 and name HE%)
((segid "BrD" and resid 25 and name HB))
  3.700  3.400  1.800 peak       18332 weight  0.10000E+01 volume  0.33097E+02 ppm1     2.782 ppm2   3.003
OR {18332}
(segid "BrD" and resid 35 and name HE%)
((segid "BrD" and resid 55 and name HB1))
ASSI {18342}
(segid "BrD" and resid 35 and name HE%)
((segid "BrD" and resid 35 and name HB1))
  1.700  1.700  2.800 peak       18342 weight  0.10000E+01 volume  0.31606E+04 ppm1     2.781 ppm2   2.841
OR {18342}
(segid "BrD" and resid 35 and name HE%)
((segid "BrD" and resid 57 and name HB2))
ASSI {18392}
(segid "BrD" and resid 35 and name HE%)
((segid "BrD" and resid 57 and name HD1))
  2.500  1.600  1.600 peak       18392 weight  0.10000E+01 volume  0.33173E+03 ppm1     2.782 ppm2   2.361
OR {18392}
(segid "BrD" and resid 35 and name HE%)
((segid "BrD" and resid 56 and name HG))
ASSI {18402}
(segid "BrD" and resid 35 and name HE%)
(segid "BrD" and resid 31 and name HB%)
  2.300  1.300  1.300 peak       18402 weight  0.10000E+01 volume  0.54118E+03 ppm1     2.782 ppm2   2.312
OR {18402}
(segid "BrD" and resid 35 and name HE%)
((segid "BrD" and resid 57 and name HD2))
OR {18402}
(segid "BrD" and resid 35 and name HE%)
((segid "BrD" and resid 56 and name HG))
```

TABLE 3-continued

Ambiguous NOE-derived Inter-proton Distance Restraints

ASSI {18432}
(segid "BrD" and resid 35 and name HE%)
((segid "BrD" and resid 57 and name HG1))
  2.800  2.000  2.000 peak       18432  weight  0.10000E+01 volume  0.16595E+03 ppm1     2.780 ppm2     2.118
OR {18432}
(segid "BrD" and resid 35 and name HE%)
((segid "BrD" and resid 26 and name HD1))
ASSI {18522}
(segid "BrD" and resid 75 and name HE%)
((segid "BrD" and resid 71 and name HA))
  2.600  1.700  1.700 peak       18522  weight  0.10000E+01 volume  0.24378E+03 ppm1     2.635 ppm2     4.663
OR {18522}
(segid "BrD" and resid 75 and name HE%)
((segid "BrD" and resid 14 and name HA))
ASSI {18532}
(segid "BrD" and resid 75 and name HE%)
((segid "BrD" and resid 110 and name HA))
  4.200  4.200  1.300 peak       18532  weight  0.10000E+01 volume  0.13873E+02 ppm1     2.633 ppm2     4.383
OR {18532}
(segid "BrD" and resid 75 and name HE%)
((segid "BrD" and resid 74 and name HA))
ASSI {18592}
(segid "BrD" and resid 75 and name HE%)
(segid "BrD" and resid 74 and name HE%)
  3.600  3.200  1.900 peak       18592  weight  0.10000E+01 volume  0.36365E+02 ppm1     2.634 ppm2     7.552
OR {18592}
(segid "BrD" and resid 75 and name HE%)
(segid "BrD" and resid 106 and name HD%)
ASSI {18822}
(segid "BrD" and resid 75 and name HE%)
((segid "BrD" and resid 116 and name HG12))
  3.300  2.700  2.200 peak       18822  weight  0.10000E+01 volume  0.58075E+02 ppm1     2.635 ppm2     1.588
OR {18822}
(segid "BrD" and resid 75 and name HE%)
(segid "BrD" and resid 21 and name HG2%)
ASSI {18832}
(segid "BrD" and resid 75 and name HE%)
(segid "BrD" and resid 63 and name HD1%)
  3.400  2.900  2.100 peak       18832  weight  0.10000E+01 volume  0.54622E+02 ppm1     2.635 ppm2     1.657
OR {18832}
(segid "BrD" and resid 75 and name HE%)
((segid "BrD" and resid 110 and name HG12))
OR {18832}
(segid "BrD" and resid 75 and name HE%)
((segid "BrD" and resid 21 and name HG12))
ASSI {18912}
(segid "BrD" and resid 75 and name HE%)
((segid "BrD" and resid 14 and name HB2))
  2.700  1.800  1.800 peak       18912  weight  0.10000E+01 volume  0.20227E+03 ppm1     2.635 ppm2     2.126
OR {18912}
(segid "BrD" and resid 75 and name HE%)
((segid "BrD" and resid 115 and name HG))
ASSI {18942}
(segid "BrD" and resid 75 and name HE%)
((segid "BrD" and resid 21 and name HG11))
  3.700  3.400  1.800 peak       18942  weight  0.10000E+01 volume  0.30880E+02 ppm1     2.636 ppm2     2.344
OR {18942}
(segid "BrD" and resid 75 and name HE%)
((segid "BrD" and resid 110 and name HB))
OR {18942}
(segid "BrD" and resid 75 and name HE%)
((segid "BrD" and resid 109 and name HB1))
ASSI {18962}
((segid "BrD" and resid 57 and name HB1))
((segid "BrD" and resid 37 and name HD1))
  3.100  2.400  2.400 peak       18962  weight  0.10000E+01 volume  0.84483E+02 ppm1     2.931 ppm2     4.289
OR {18962}
((segid "BrD" and resid 37 and name HB1))
((segid "BrD" and resid 37 and name HD1))
ASSI {19022}
((segid "BrD" and resid 75 and name HA))
((segid "BrD" and resid 78 and name HB2))
  2.500  1.600  1.600 peak       19022  weight  0.10000E+01 volume  0.30551E+03 ppm1     4.508 ppm2     1.043
OR {19022}
((segid "BrD" and resid 75 and name HA))
(segid "BrD" and resid 18 and name HD1%)

TABLE 3-continued

Ambiguous NOE-derived Inter-proton Distance Restraints

ASSI {19222}
(segid "BrD" and resid 43 and name HB%)
((segid "BrD" and resid 42 and name HB1))
  4.500  4.500  1.000 peak      19222 weight  0.10000E+01 volume    0.92899E+01 ppm1     1.697 ppm2    2.768
OR {19222}
(segid "BrD" and resid 43 and name HB%)
((segid "BrD" and resid 44 and name HG1))
ASSI {19332}
(segid "BrD" and resid 31 and name HB%)
((segid "BrD" and resid 26 and name HB1))
  3.600  3.200  1.900 peak      19332 weight  0.10000E+01 volume    0.33671E+02 ppm1     2.289 ppm2    2.466
OR {19332}
(segid "BrD" and resid 31 and name HB%)
((segid "BrD" and resid 21 and name HB))
ASSI {19342}
(segid "BrD" and resid 31 and name HB%)
((segid "BrD" and resid 56 and name HB1))
  3.300  2.700  2.200 peak      19342 weight  0.10000E+01 volume    0.60076E+02 ppm1     2.289 ppm2    2.719
OR {19342}
(segid "BrD" and resid 31 and name HB%)
((segid "BrD" and resid 29 and name HB1))
ASSI {19402}
(segid "BrD" and resid 31 and name HB%)
((segid "BrD" and resid 29 and name HA))
  3.600  3.200  1.900 peak      19402 weight  0.1000E+01 volume     0.34186E+02 ppm1     2.289 ppm2    4.810
OR {19402}
(segid "BrD" and resid 31 and name HB%)
((segid "BrD" and resid 24 and name HA))
ASSI {19452}
((segid "BrD" and resid 73 and name HB2))
((segid "BrD" and resid 72 and name HA))
  3.800  3.600  1.700 peak      19452 weight  0.10000E+01 volume    0.27108E+02 ppm1     2.486 ppm2    4.672
OR {19452}
((segid "BrD" and resid 73 and name HB2))
((segid "BrD" and resid 69 and name HA))
ASSI {19462}
((segid "BrD" and resid 73 and name HB1))
((segid "BrD" and resid 72 and name HA))
  3.900  3.800  1.600 peak      19462 weight  0.10000E+01 volume    0.22158E+02 ppm1     2.583 ppm2    4.672
OR {19462}
((segid "BrD" and resid 73 and name HB1))
((segid "BrD" and resid 69 and name HA))
ASSI {19472}
(segid "BrD" and resid 99 and name HB%)
((segid "BrD" and resid 86 and name HB1))
  2.400  2.400  1.400 peak      19472 weight  0.10000E+01 volume    0.42620E+03 ppm1     2.190 ppm2    2.359
OR {19472}
(segid "BrD" and resid 99 and name HB%)
((segid "BrD" and resid 103 and name HB1))
ASSI {19562}
(segid "BrD" and resid 76 and name HB%)
((segid "BrD" and resid 51 and name HB1))
  1.800  1.800  2.700 peak      19562 weight  0.10000E+01 volume    0.21948E+04 ppm1     2.092 ppm2    3.946
OR {19562}
(segid "BrD" and resid 76 and name HB%)
((segid "BrD" and resid 116 and name HG11))
OR {19562}
(segid "BrD" and resid 76 and name HB%)
((segid "BrD" and resid 51 and name HG1))
ASSI {19712}
(segid "BrD" and resid 99 and name HB%)
((segid "BrD" and resid 98 and name HB1))
  3.300  2.700  2.200 peak      19712 weight  0.10000E+01 volume    0.62693E+02 ppm1     2.190 ppm2    3.988
OR {19712}
(segid "BrD" and resid 99 and name HB%)
((segid "BrD" and resid 96 and name HB1))
ASSI {19862}
((segid "BrD" and resid 102 and name HA))
((segid "BrD" and resid 105 and name HA))
  4.200  4.200  1.300 peak      19862 weight  0.10000E+01 volume    0.13941E+02 ppm1     4.261 ppm2    4.924
OR {19862}
((segid "BrD" and resid 102 and name HA))
((segid "BrD" and resid 30 and name HB1))
ASSI {19872}
((segid "BrD" and resid 102 and name HA))
(segid "BrD" and resid 105 and name HD%)
  2.700  1.800  1.800 peak      19872 weight  0.10000E+01 volume    0.22737E+03 ppm1     4.261 ppm2    7.779

TABLE 3-continued

Ambiguous NOE-derived Inter-proton Distance Restraints

OR {19872}
((segid "BrD" and resid 102 and name HA))
(segid "BrD" and resid 34 and name HE%)
ASSI {19892}
((segid "BrD" and resid 113 and name HA))
((segid "BrD" and resid 115 and name HG))
  3.600  3.200  1.900 peak      19892  weight  0.10000E+01 volume    0.36454E+02 ppm1        4.903 ppm2     2.133
OR {19892}
((segid "BrD" and resid 113 and name HA))
((segid "BrD" and resid 14 and name HB2))
ASSI {19932}
((segid "BrD" and resid 113 and name HA))
((segid "BrD" and resid 112 and name HA))
  3.400  2.900  2.100 peak      19932  weight  0.10000E+01 volume    0.55030E+02 ppm1        4.903 ppm2     4.598
OR {19932}
((segid "BrD" and resid 113 and name HA))
((segid "BrD" and resid 114 and name HA1))
ASSI {19972}
(segid "BrD" and resid 113 and name HB%)
(segid "BrD" and resid 75 and name HE%)
  3.400  2.900  2.100 peak      19972  weight  0.10000E+01 volume    0.53194E+02 ppm1        1.991 ppm2     2.662
OR {19972}
(segid "BrD" and resid 113 and name HB%)
((segid "BrD" and resid 112 and name HB1))
ASSI {20002}
(segid "BrD" and resid 113 and name HB%)
((segid "BrD" and resid 18 and name HG))
  2.700  1.800  1.800 peak      20002  weight  0.10000E+01 volume    0.18667E+03 ppm1        1.991 ppm2     2.304
OR {20002}
(segid "BrD" and resid 113 and name HB%)
((segid "BrD" and resid 110 and name HB))
OR {20002}
(segid "BrD" and resid 113 and name HB%)
((segid "BrD" and resid 109 and name HB1))
ASSI {20012}
(segid "BrD" and resid 113 and name HB%)
((segid "BrD" and resid 110 and name HB))
  3.900  3.800  1.600 peak      20012  weight  0.10000E+01 volume    0.22660E+02 ppm1        1.990 ppm2     2.369
OR {20012}
(segid "BrD" and resid 113 and name HB%)
((segid "BrD" and resid 109 and name HB1))
ASSI {20022}
(segid "BrD" and resid 113 and name HB%)
((segid "BrD" and resid 115 and name HG))
  3.300  2.700  2.200 peak      20022  weight  0.10000E+01 volume    0.61319E+02 ppm1        1.990 ppm2     2.135
OR {20022}
(segid "BrD" and resid 113 and name HB%)
((segid "BrD" and resid 14 and name HB2))
ASSI {20062}
((segid "BrD" and resid 110 and name HA))
(segid "BrD" and resid 116 and name HD1%)
  3.100  2.400  2.400 peak      20062  weight  0.10000E+01 volume    0.82911E+02 ppm1        4.411 ppm2     1.410
OR {20062}
((segid "BrD" and resid 110 and name HA))
((segid "BrD" and resid 109 and name HG1))
ASSI {20122}
(segid "BrD" and resid 113 and name HB%)
((segid "BrD" and resid 114 and name HA1))
  3.700  3.400  1.800 peak      20122  weight  0.10000E+01 volume    0.29578E+02 ppm1        1.994 ppm2     4.564
OR {20122}
(segid "BrD" and resid 113 and name HB%)
((segid "BrD" and resid 17 and name HA))
ASSI {20152}
(segid "BrD" and resid 113 and name HB%)
(segid "BrD" and resid 14 and name HD1%)
  2.700  1.800  1.800 peak      20152  weight  0.10000E+01 volume    0.21357E+03 ppm1        1.995 ppm2     1.425
OR {20152}
(segid "BrD" and resid 113 and name HB%)
(segid "BrD" and resid 14 and name HD2%)
OR {20152}
(segid "BrD" and resid 113 and name HB%)
((segid "BrD" and resid 109 and name HG1))
ASSI {20182}
((segid "BrD" and resid 17 and name HB))
((segid "BrD" and resid 14 and name HB2))
  3.400  2.900  2.100 peak      20182  weight  0.10000E+01 volume    0.54504E+02 ppm1        4.853 ppm2     2.149

TABLE 3-continued

Ambiguous NOE-derived Inter-proton Distance Restraints

```
OR {20182}
((segid "BrD" and resid 17 and name HB))
((segid "BrD" and resid 18 and name HB1))
OR {20182}
((segid "BrD" and resid 17 and name HB))
((segid "BrD" and resid 109 and name HB2))
ASSI {20202}
((segid "BrD" and resid 17 and name HB))
(segid "BrD" and resid 21 and name HD1%)
 4.300  4.300  1.200 peak     20202  weight  0.10000E+01 volume   0.12632E+02 ppm1    4.853 ppm2   1.222
OR {20202}
((segid "BrD" and resid 17 and name HB))
(segid "BrD" and resid 110 and name HG2%)
ASSI {20222}
(segid "BrD" and resid 17 and name HG2%)
((segid "BrD" and resid 14 and name HA))
 2.200  1.200  1.200 peak     20222  weight  0.10000E+01 volume   0.69704E+03 ppm1    1.747 ppm2   4.666
OR {20222}
(segid "BrD" and resid 17 and name HG2%)
((segid "BrD" and resid 109 and name HA))
OR {20222}
(segid "BrD" and resid 17 and name HG2%)
((segid "BrD" and resid 20 and name HB1))
ASSI {20262}
(segid "BrD" and resid 17 and name HG2%)
((segid "BrD" and resid 109 and name HB1))
 2.500  1.600  1.600 peak     20262  weight  0.10000E+01 volume   0.34655E+03 ppm1    1.747 ppm2   2.352
OR {20262}
(segid "BrD" and resid 17 and name HG2%)
((segid "BrD" and resid 21 and name HG11))
ASSI {20322}
((segid "BrD" and resid 20 and name HB1))
((segid "BrD" and resid 21 and name HG11))
 2.300  2.300  2.200 peak     20322  weight  0.10000E+01 volume   0.47335E+03 ppm1    4.656 ppm2   2.320
OR {20322}
((segid "BrD" and resid 20 and name HB1))
((segid "BrD" and resid 19 and name HB1))
OR {20322}
((segid "BrD" and resid 20 and name HB1))
((segid "BrD" and resid 109 and name HB1))
ASSI {20632}
((segid "BrD" and resid 112 and name HG2))
((segid "BrD" and resid 109 and name HD1))
 3.100  2.400  2.400 peak     20632  weight  0.10000E+01 volume   0.87177E+02 ppm1    2.832 ppm2   1.997
OR {20632}
((segid "BrD" and resid 112 and name HG2))
((segid "BrD" and resid 111 and name HG1))
OR {20632}
((segid "BrD" and resid 112 and name HG2))
(segid "BrD" and resid 113 and name HB%)
ASSI {20652}
((segid "BrD" and resid 111 and name HA))
(segid "BrD" and resid 115 and name HD1%)
 3.800  3.600  1.700 peak     20652  weight  0.10000E+01 volume   0.25940E+02 ppm1    4.656 ppm2   1.319
OR {20652}
((segid "BrD" and resid 104 and name HA))
(segid "BrD" and resid 102 and name HD2%)
OR {20652}
((segid "BrD" and resid 72 and name HA))
(segid "BrD" and resid 115 and name HD1%)
OR {20652}
((segid "BrD" and resid 104 and name HA))
(segid "BrD" and resid 102 and name HD1%)
OR {20652}
((segid "BrD" and resid 72 and name HA))
((segid "BrD" and resid 78 and name HB1))
ASSI {20662}
((segid "BrD" and resid 61 and name HA))
((segid "BrD" and resid 62 and name HB2))
 3.300  2.700  2.200 peak     20662  weight  0.10000E+01 volume   0.56653E+02 ppm1    4.656 ppm2   1.710
OR {20662}
((segid "BrD" and resid 67 and name HA))
((segid "BrD" and resid 62 and name HB2))
OR {20662}
((segid "BrD" and resid 111 and name HA))
((segid "BrD" and resid 110 and name HG11))
```

TABLE 3-continued

Ambiguous NOE-derived Inter-proton Distance Restraints

ASSI {20672}
((segid "BrD" and resid 23 and name HA))
((segid "BrD" and resid 26 and name HG1))
  3.300  2.700  2.200 peak      20672  weight  0.10000E+01  volume  0.58311E+02 ppm1    4.656 ppm2    1.661
OR {20672}
((segid "BrD" and resid 23 and name HA))
(segid "BrD" and resid 22 and name HD1%)
OR {20672}
((segid "BrD" and resid 61 and name HA))
(segid "BrD" and resid 22 and name HD1%)
OR {20672}
((segid "BrD" and resid 61 and name HA))
((segid "BrD" and resid 62 and name HB2))
OR {20672}
((segid "BrD" and resid 23 and name HA))
(segid "BrD" and resid 25 and name HG2%)
OR {20672}
((segid "BrD" and resid 61 and name HA))
(segid "BrD" and resid 58 and name HG2%)
OR {20672}
((segid "BrD" and resid 63 and name HA))
((segid "BrD" and resid 62 and name HB2))
ASSI {20682}
((segid "BrD" and resid 67 and name HA))
(segid "BrD" and resid 69 and name HG1%)
  2.700  1.800  1.800 peak      20682  weight  0.10000E+01  volume  0.18983E+03 ppm1    4.656 ppm2    1.547
OR {20682}
((segid "BrD" and resid 67 and name HA))
(segid "BrD" and resid 73 and name HD1%)
ASSI {20792}
(segid "BrD" and resid 25 and name HG2%)
(segid "BrD" and resid 74 and name HE%)
  3.100  2.400  2.400 peak      20792  weight  0.10000E+01  volume  0.98567E+02 ppm1    1.648 ppm2    7.517
OR {20792}
(segid "BrD" and resid 25 and name HG2%)
(segid "BrD" and resid 106 and name HD%)
OR {20792}
(segid "BrD" and resid 58 and name HG2%)
(segid "BrD" and resid 74 and name HE%)
ASSI {20822}
(segid "BrD" and resid 25 and name HG2%)
(segid "BrD" and resid 34 and name HE%)
  3.300  2.700  2.200 peak      20822  weight  0.10000E+01  volume  0.60371E+02 ppm1    1.650 ppm2    7.791
OR {20822}
(segid "BrD" and resid 58 and name HG2%)
(segid "BrD" and resid 68 and name HD%)
ASSI {20842}
(segid "BrD" and resid 25 and name HG2%)
((segid "BrD" and resid 102 and name HA))
  3.600  3.200  1.900 peak      20842  weight  0.10000E+01  volume  0.35063E+02 ppm1    1.649 ppm2    4.282
OR {20842}
(segid "BrD" and resid 58 and name HG2%)
((segid "BrD" and resid 37 and name HD1))
ASSI {21092}
(segid "BrD" and resid 58 and name HG2%)
((segid "BrD" and resid 61 and name HG2))
  2.600  1.700  1.700 peak      21092  weight  0.10000E+01  volume  0.23144E+03 ppm1    1.648 ppm2    2.833
OR {21092}
(segid "BrD" and resid 58 and name HG2%)
((segid "BrD" and resid 61 and name HB1))
OR {21092}
(segid "BrD" and resid 58 and name HG2%)
((segid "BrD" and resid 57 and name HB2))
ASSI {21102}
(segid "BrD" and resid 25 and name HG2%)
((segid "BrD" and resid 56 and name HB1))
  2.500  1.600  1.600 peak      21102  weight  0.10000E+01  volume  0.34384E+03 ppm1    1.649 ppm2    2.700
OR {21102}
(segid "BrD" and resid 58 and name HG2%)
((segid "BrD" and resid 61 and name HB2))
OR {21102}
(segid "BrD" and resid 58 and name HG2%)
((segid "BrD" and resid 37 and name HG1))
OR {21102}
(segid "BrD" and resid 25 and name HG2%)
((segid "BrD" and resid 22 and name HB1))

TABLE 3-continued

Ambiguous NOE-derived Inter-proton Distance Restraints

ASSI {21112}
(segid "BrD" and resid 58 and name HG2%)
(segid "BrD" and resid 54 and name HE%)
  2.500  1.600  1.600 peak      21112  weight  0.10000E+01 volume   0.32059E+03 ppm1     1.649 ppm2    2.508
OR {21112}
(segid "BrD" and resid 25 and name HG2%)
((segid "BrD" and resid 26 and name HB1))
ASSI {21132}
((segid "BrD" and resid 83 and name HB))
((segid "BrD" and resid 79 and name HG1))
  5.000  5.000  0.500 peak      21132  weight  0.10000E+01 volume   0.54051E+01 ppm1     4.504 ppm2    3.028
OR {21132}
((segid "BrD" and resid 83 and name HB))
((segid "BrD" and resid 87 and name HG1))
ASSI {21152}
((segid "BrD" and resid 58 and name HA))
(segid "BrD" and resid 54 and name HE%)
  3.500  3.100  2.000 peak      21152  weight  0.10000E+01 volume   0.43944E+02 ppm1     4.455 ppm2    2.572
OR {21152}
((segid "BrD" and resid 83 and name HA))
((segid "BrD" and resid 87 and name HB2))
ASSI {21222}
(segid "BrD" and resid 83 and name HG2%)
((segid "BrD" and resid 80 and name HG1))
  3.000  2.200  2.200 peak      21222  weight  0.10000E+01 volume   0.98918E+02 ppm1     1.894 ppm2    2.366
OR {21222}
(segid "BrD" and resid 83 and name HG2%)
((segid "BrD" and resid 86 and name HB1))
ASSI {21382}
((segid "BrD" and resid 25 and name HB))
(segid "Brd" and resid 102 and name HD1%)
  5.400  5.400  0.100 peak      21382  weight  0.10000E+01 volume   0.33579E+01 ppm1     2.980 ppm2    1.273
OR {21382}
((segid "BrD" and resid 25 and name HB))
(segid "BrD" and resid 56 and name HD2%)
ASSI {21412}
(segid "BrD" and resid 25 and name HG1%)
(segid "BrD" and resid 31 and name HB%)
  3.300  2.700  2.200 peak      21432  weight  0.10000E+01 volume   0.60830E+02 ppm1     1.795 ppm2    2.320
OR {21412}
(segid "BrD" and resid $$ and name HG1%)
((segid "BrD" and resid 21 and name HG11))
ASSI {21442}
(segid "BrD" and resid 25 and name HG1%)
((segid "BrD" and resid 105 and name HB1))
  2.600  1.700  1.700 peak      21442  weight  0.10000E+01 volume   0.23532E+03 ppm1     1.796 ppm2    3.695
OR {21442}
(segid "BrD" and resid 25 and name HG1%)
((segid "BrD" and resid 105 and name HB2))
OR {21442}
(segid "BrD" and resid 25 and name HG1%)
((segid "BrD" and resid 106 and name HB2))
ASSI {21502}
((segid "BrD" and resid 38 and name HA))
((segid "BrD" and resid 39 and name HD1))
  3.600  3.200  1.900 peak      21502  weight  0.10000E+01 volume   0.37412E+02 ppm1     4.163 ppm2    2.291
OR {21502}
((segid "BrD" and resid 38 and name HA))
((segid "BrD" and resid 37 and name HB2))
ASSI {21552}
(segid "BrD" and resid 81 and name HD2%)
((segid "BrD" and resid 31 and name HA))
  3.000  2.200  2.200 peak      21552  weight  0.10000E+01 volume   0.11144E+03 ppm1     0.760 ppm2    4.981
OR {21552}
(segid "BrD" and resid 81 and name HG2%)
((segid "BrD" and resid 85 and name HA))
OR {21552}
(segid "BrD" and resid 81 and name HG2%)
((segid "BrD" and resid 77 and name HA))
ASSI {21572}
(segid "BrD" and resid 81 and name HG1%)
((segid "BrD" and resid 77 and name HA))
  3.200  2.600  2.300 peak      21572  weight  0.10000E+01 volume   0.78059E+02 ppm1     1.056 ppm2    4.972
OR {21572}
(segid "BrD" and resid 38 and name HG1%)
((segid "BrD" and resid 39 and name HA))

TABLE 3-continued

Ambiguous NOE-derived Inter-proton Distance Restraints

ASSI {21592}
(segid "BrD" and resid 38 and name HG1%)
((segid "BrD" and resid 53 and name HA))
  3.100  2.400  2.400 peak      21592  weight  0.10000E+01 volume    0.93082E+02 ppm1     1.0562 ppm2    4.664
OR {21592}
(segid "BrD" and resid 81 and name HG1%)
((segid "BrD" and resid 80 and name HA))
OR {21592}
(segid "BrD" and resid 81 and name HG1%)
((segid "BrD" and resid 53 and name HA))
ASSI {21612}
(segid "BrD" and resid 38 and name HG1%)
((segid "BrD" and resid 37 and name HB1))
  3.800  3.600  1.700 peak      21612  weight  0.10000E+01 volume    0.25206E+02 ppm1     1.056 ppm2    2.966
OR {21612}
(segid "BrD" and resid 81 and name HG1%)
((segid "BrD" and resid 55 and name HB1))
ASSI {21652}
(segid "BrD" and resid 38 and name HG1%)
(segid "BrD" and resid 47 and name HE%)
  3.100  2.400  2.400 peak      21652  weight  0.10000E+01 volume    0.89355E+02 ppm1     1.056 ppm2    7.259
OR {21652}
(segid "BrD" and resid 81 and name HG1%)
(segid "BrD" and resid 82 and name HD%)
ASSI {21792}
((segid "BrD" and resid 81 and name HB))
(segid "BrD" and resid 82 and name HB2))
  3.900  3.800  1.600 peak      21792  weight  0.10000E+01 volume    0.21639E+02 ppm1     2.042 ppm2    3.573
OR {21792}
((segid "BrD" and resid 81 and name HB))
((segid "BrD" and resid 84 and name HB1))
ASSI {21982}
(segid "BrD" and resid 50 and name HD1%)
((segid "BrD" and resid 49 and name HA))
  3.000  2.200  2.200 peak      21982  weight  0.10000E+01 volume    0.11219E+03 ppm1     1.153 ppm2    4.692
OR {21982}
(segid "BrD" and resid 50 and name HD1%)
((segid "BrD" and resid 53 and name HA))
OR {21982}
(segid "BrD" and resid 50 and name HD1%)
(segid "BrD" and resid 47 and name HA))
ASSI {22072}
(segid "BrD" and resid 50 and name HD1%)
(segid "BrD" and resid 38 and name HG1%)
  3.800  3.600  1.700 peak      22072  weight  0.10000E+01 volume    0.25153E+02 ppm1     1.154 ppm2    1.078
OR {22072}
(segid "BrD" and resid 50 and name HD1%)
(segid "BrD" and resid 81 and name HG1%)
ASSI {22432}
(segid "BrD" and resid 69 and name HG2%)
((segid "BrD" and resid 19 and name HB2))
  5.500  5.500  0.000 peak      22432  weight  0.10000E+01 volume    0.5124$$E+00 ppm1     1.425 ppm2    1.993
OR {22432}
(segid "BrD" and resid 69 and name HG2%)
(segid "BrD" and resid 113 and name HB%)
ASSI {22502}
(segid "BrD" and resid 25 and name HG2%)
(segid "BrD" and resid 35 and name HE%)
  2.900  2.100  2.100 peak      22502  weight  0.10000E+01 volume    0.14480E+03 ppm1     1.633 ppm2    2.752
OR {22502}
(segid "BrD" and resid 49 and name HG1%)
((segid "BrD" and resid 48 and name HB1))
OR {22502}
(segid "BrD" and resid 58 and name HG2%)
((segid "BrD" and resid 37 and name HG1))
ASSI {22622}
((segid "BrD" and resid 42 and name HA))
((segid "BrD" and resid 44 and name HD2))
  4.000  4.000  1.500 peak      22622  weight  0.10000E+01 volume    0.20863E+02 ppm1     5.051 ppm2    4.133
OR {22622}
((segid "BrD" and resid 42 and name HA))
((segid "BrD" and resid 38 and name HA))
ASSI {22802}
((segid "BrD" and resid 104 and name HB1))
((segid "BrD" and resid 105 and name HB2))
  3.200  2.600  2.300 peak      22802  weight  0.10000E+01 volume    0.76681E+02 ppm1     2.536 ppm2    3.662

TABLE 3-continued

Ambiguous NOE-derived Inter-proton Distance Restraints

```
OR {22802}
((segid "BrD" and resid 104 and name HB1))
((segid "BrD" and resid 107 and name HB1))
ASSI {22862}
((segid "BrD" and resid 64 and name HE1))
((segid "BrD" and resid 19 and name HA))
   3.600  3.200  1.900 peak        22862  weight  0.10000E+01 volume   0.38596E+02 ppm1    3.573 ppm2    4.285
OR {22862}
((segid "BrD" and resid 57 and name HE1))
((segid "BrD" and resid 37 and name HD1))
ASSI {22912}
((segid "BrD" and resid 60 and name HB1))
((segid "BrD" and resid 22 and name HB2))
   4.100  4.100  1.400 peak        22912  weight  0.10000E+01 volume   0.16339E+02 ppm1    5.001 ppm2    2.312
OR {22912}
((segid "BrD" and resid 60 and name HB1))
((segid "BrD" and resid 56 and name HG))
ASSI {23002}
((segid "BrD" and resid 37 and name HD1))
((segid "BrD" and resid 57 and name HB1))
   3.100  2.400  2.400 peak        23002  weight  0.10000E+01 volume   0.82823E+02 ppm1    4.285 ppm2    2.966
OR {23002}
((segid "BrD" and resid 37 and name HD1))
((segid "BrD" and resid 37 and name HB1))
OR {23002}
((segid "BrD" and resid 44 and name HD1))
((segid "BrD" and resid 44 and name HB1))
ASSI {23042}
((segid "BrD" and resid 37 and name HD1))
((segid "BrD" and resid 37 and name HG2))
   2.000  1.000  1.000 peak        23042  weight  0.10000E+01 volume   0.14416E+04 ppm1    4.261 ppm2    2.621
OR {23042}
((segid "BrD" and resid 8 and name HD2))
((segid "BrD" and resid 8 and name HG1))
ASSI {23052}
((segid "BrD" and resid 8 and name HD1))
((segid "BrD" and resid 8 and name HB2))
   3.600  3.200  1.900 peak        23052  weight  0.10000E+01 volume   0.37937E+02 ppm1    4.409 ppm2    2.499
OR {23052}
((segid "BrD" and resid 8 and name HA1))
((segid "BrD" and resid 7 and name HB2))
ASSI {23212}
((segid "BrD" and resid 44 and name HG2))
((segid "BrD" and resid 44 and name HA))
   3.100  2.400  2.400 peak        23212  weight  0.10000E+01 volume   0.93859E+02 ppm1    2.635 ppm2    5.120
OR {23212}
((segid "BrD" and resid 8 and name HG1))
((segid "BrD" and resid 7 and name HA))
ASSI {23252}
((segid "BrD" and resid 11 and name HG1))
(segid "BrD" and resid 69 and name HG2%)
   3.000  2.200  2.200 peak        23252  weight  0.10000E+01 volume   0.10852E+03 ppm1    2.615 ppm2    1.417
OR {23252}
((segid "BrD" and resid 11 and name HG1))
(segid "BrD" and resid 14 and name HD2%)
ASSI {23382}
((segid "BrD" and resid 100 and name HA))
((segid "BrD" and resid 101 and name HA))
   5.500  5.500  0.000 peak        23382  weight  0.10000E+01 volume   0.24494E+01 ppm1    4.952 ppm2    4.256
OR {23382}
((segid "BrD" and resid 6 and name HA))
((segid "BrD" and resid 8 and name HD2))
ASSI {23392}
((segid "BrD" and resid 100 and name HA))
((segid "BrD" and resid 99 and name HA))
   3.200  2.600  2.300 peak        23392  weight  0.10000E+01 volume   0.72079E+02 ppm1    4.952 ppm2    4.444
OR {23392}
((segid "BrD" and resid 6 and name HA))
((segid "BrD" and resid 8 and name HD1))
ASSI {23512}
((segid "BrD" and resid 10 and name HA))
((segid "BrD" and resid 11 and name HA))
   3.400  2.900  2.100 peak        23512  weight  0.10000E+01 volume   0.53886E+02 ppm1    5.477 ppm2    4.939
OR {23512}
((segid "BrD" and resid 10 and name HA))
((segid "BrD" and resid 9 and name HA))
```

TABLE 3-continued

Ambiguous NOE-derived Inter-proton Distance Restraints

```
ASSI {23582}
((segid "BrD" and resid 12 and name HA))
((segid "BrD" and resid 16 and name HA))
  3.600  3.200  1.900 peak      23582 weight  0.10000E+01 volume  0.33831E+02 ppm1     5.297 ppm2     4.627
OR {23582}
((segid "BrD" and resid 12 and name HA))
((segid "BrD" and resid 16 and name HB1))
OR {23582}
((segid "BrD" and resid 12 and name HA))
((segid "BrD" and resid 14 and name HA))
ASSI {23682}
((segid "BrD" and resid 14 and name HA))
(segid "BrD" and resid 18 and name HD1%)
  3.300  2.700  2.200 peak      23682 weight  0.10000E+01 volume  0.67221E+02 ppm1     4.656 ppm2     1.083
OR {23682}
((segid "BrD" and resid 80 and name HA))
(segid "BrD" and resid 81 and name HG1%)
ASSI {23772}
(segid "BrD" and resid 14 and name HD2%)
((segid "BrD" and resid 15 and name HA))
  2.400  1.400  1.400 peak      23772 weight  0.10000E+01 volume  0.36871E+03 ppm1     1.400 ppm2     4.574
OR {23772}
((segid "BrD" and resid 109 and name HG1))
((segid "BrD" and resid 17 and name HA))
ASSI {23792}
(segid "BrD" and resid 14 and name HG2%)
((segid "BrD" and resid 18 and name HA))
  3.900  3.800  1.600 peak      23792 weight  0.10000E+01 volume  0.23831E+02 ppm1     1.401 ppm2     3.889
OR {23792}
((segid "BrD" and resid 109 and name HG1))
((segid "BrD" and resid 18 and name HA))
ASSI {23872}
((segid "BrD" and resid 18 and name HA))
(segid "BrD" and resid 74 and name HE%)
  2.900  2.100  2.100 peak      23872 weight  0.10000E+01 volume  0.13092E+03 ppm1     3.866 ppm2     7.534
OR {23872}
((segid "BrD" and resid 18 and name HA))
(segid "BrD" and resid 106 and name HD%)
ASSI {23892}
((segid "BrD" and resid 18 and name HA))
((segid "BrD" and resid 15 and name HA))
  2.900  2.100  2.100 peak      23892 weight  0.10000E+01 volume  0.13327E+01 ppm1     3.867 ppm2     4.631
OR {23892}
((segid "BrD" and resid 18 and name HA))
((segid "BrD" and resid 20 and name HB1))
OR {23892}
((segid "BrD" and resid 18 and name HA))
((segid "BrD" and resid 14 and name HA))
ASSI {23902}
((segid "BrD" and resid 18 and name HA))
((segid "BrD" and resid 17 and name HA))
  3.800  3.600  1.700 peak      23902 weight  0.10000E+01 volume  0.26018E+02 ppm1     3.867 ppm2     4.541
OR {23902}
((segid "BrD" and resid 18 and name HA))
((segid "BrD" and resid 106 and name HA))
ASSI {23912}
((segid "BrD" and resid 18 and name HB1))
(segid "BrD" and resid 14 and name HD2%)
  3.400  2.900  2.100 peak      23912 weight  0.10000E+01 volume  0.53948E+02 ppm1     2.140 ppm2     1.433
OR {23912}
((segid "BrD" and resid 18 and name HB1))
(segid "Brd" and resid 69 and name HG2%)
ASSI {23942}
((segid "BrD" and resid 18 and name HB2))
(segid "BrD" and resid 14 and name HD2%)
  4.100  4.100  1.400 peak      23942 weight  0.10000E+01 volume  0.16641E+02 ppm1     0.911 ppm2     1.415
OR {23942}
((segid "BrD" and resid 18 and name HB2))
(segid "BrD" and resid 69 and name HG2%)
ASSI {24102}
(segid "BrD" and resid 18 and name HD2%)
(segid "BrD" and resid 21 and name HG2%)
  5.500  5.500  0.000 peak      24102 weight  0.10000E+01 volume  0.18200E+00 ppm1     0.415 ppm2     1.596
OR {24102}
(segid "BrD" and resid 18 and name HD2%)
(segid "BrD" and resid 22 and name HD2%)
```

TABLE 3-continued

Ambiguous NOE-derived Inter-proton Distance Restraints

ASSI {24112}
(segid "BrD" and resid 18 and name HD2%)
(segid "BrD" and resid 115 and name HD1%)
 2.800  2.000  2.000 peak      24112  weight  0.10000E+01 volume  0.15952E+03 ppm1      0.416 ppm2    1.377
OR {24112}
(segid "BrD" and resid 18 and name HD2%)
(segid "BrD" and resid 14 and name HD2%)
OR {24112}
(segid "BrD" and resid 14 and name HD2%)
(segid "BrD" and resid 14 and name HD1%)
ASSI {24122}
(segid "BrD" and resid 18 and name HD2%)
(segid "BrD" and resid 115 and name HB%)
 3.900  3.800  1.600 peak      24122  weight  0.10000E+01 volume  0.21517E+02 ppm1      0.415 ppm2    1.986
OR {24122}
(segid "BrD" and resid 18 and name HD2%)
((segid "BrD" and resid 19 and name HB2))
ASSI {24292}
(segid "BrD" and resid 18 and name HD2%)
((segid "BrD" and resid 106 and name HB2))
 3.900  3.800  1.600 peak      24292  weight  0.10000E+01 volume  0.23222E+02 ppm1      0.416 ppm2    3.650
OR {24292}
(segid "BrD" and resid 18 and name HD2%)
((segid "BrD" and resid 68 and name HB1))
OR {24292}
(segid "BrD" and resid 18 and name HD2%)
((segid "BrD" and resid 15 and name HB2))
ASSI {24492}
(segid "BrD" and resid 63 and name HD1%)
((segid "BrD" and resid 68 and name HB1))
 2.800  2.000  2.000 peak      24492  weight  0.10000E+01 volume  0.15293E+03 ppm1      1.649 ppm2    3.671
OR {24492}
(segid "BrD" and resid 63 and name HD1%)
((segid "BrD" and resid 15 and name HB2))
ASSI {24502}
(segid "BrD" and resid 63 and name HD1%)
((segid "BrD" and resid 66 and name HD2))
 3.000  2.200  2.200 peak      24502  weight  0.10000E+01 volume  0.10614E+03 ppm1      1.649 ppm2    3.614
OR {24502}
(segid "BrD" and resid 63 and name HD1%)
((segid "BrD" and resid 64 and name HE1))
ASSI {24532}
(segid "BrD" and resid 63 and name HD1%)
((segid "BrD" and resid 16 and name HA))
 3.500  3.100  2.000 peak      24532  weight  0.10000E+01 volume  0.45951E+02 ppm1      1.649 ppm2    4.516
OR {24532}
(segid "BrD" and resid 63 and name HD1%)
((segid "BrD" and resid 17 and name HA))
ASSI {24602}
(segid "BrD" and resid 63 and name HD2%)
((segid "BrD" and resid 19 and name HE1))
 3.400  2.900  2.100 peak      24602  weight  0.10000E+01 volume  0.54742E+02 ppm1      1.500 ppm2    3.524
OR {24602}
(segid "BrD" and resid 63 and name HD2%)
((segid "BrD" and resid 68 and name HB2))
ASSI {24692}
((segid "BrD" and resid 19 and name HA))
((segid "BrD" and resid 22 and name HG))
 3.000  2.200  2.200 peak      24692  weight  0.10000E+01 volume  0.10672E+03 ppm1      4.310 ppm2    2.393
OR {24692}
((segid "BrD" and resid 19 and name HA))
((segid "BrD" and resid 64 and name HD1))
ASSI {24712}
((segid "BrD" and resid 19 and name HA))
((segid "BrD" and resid 23 and name HA))
 3.700  3.400  1.000 peak      24712  weight  0.10000E+01 volume  0.31255E+02 ppm1      4.310 ppm2    4.677
OR {24712}
((segid "BrD" and resid 19 and name HA))
((segid "BrD" and resid 22 and name HA))
OR {24712}
((segid "BrD" and resid 19 and name HA))
((segid "BrD" and resid 20 and name HB1))
ASSI {24722}
((segid "BrD" and resid 19 and name HB2))
((segid "BrD" and resid 15 and name HA))
 3.800  3.600  1.700 peak      24722  weight  0.10000E+01 volume  0.24706E+02 ppm1      1.989 ppm2    4.876

TABLE 3-continued

Ambiguous NOE-derived Inter-proton Distance Restraints

```
OR {24732}
((segid "BrD" and resid 19 and name HB2))
((segid "BrD" and resid 16 and name HB1))
ASSI {24732}
((segid "BrD" and resid 19 and name HB2))
((segid "BrD" and resid 15 and name HA))
  3.800  3.600  1.700 peak      24732  weight  0.10000E+01 volume  0.28161E+02 ppm1      1.989 ppm2   4.631
OR {24732}
((segid "BrD" and resid 19 and name HB2))
((segid "BrD" and resid 20 and name HB1))
ASSI {24772}
((segid "BrD" and resid 19 and name HG1))
((segid "BrD" and resid 20 and name HA))
  4.200  4.200  1.300 peak      24772  weight  0.10000E+01 volume  0.15236E+02 ppm1      1.895 ppm2   4.891
OR {24772}
((segid "BrD" and resid 86 and name HG1))
((segid "BrD" and resid 87 and name HA))
OR {24772}
((segid "BrD" and resid 19 and name HG1))
((segid "BrD" and resid 64 and name HA))
ASSI {24822}
((segid "BrD" and resid 19 and name HD1))
((segid "BrD" and resid 15 and name HA))
  4.100  4.100  1.400 peak      24822  weight  0.10000E+01 volume  0.16511E+02 ppm1      2.190 ppm2   4.643
OR {24822}
((segid "BrD" and resid 19 and name HD1))
((segid "BrD" and resid 20 and name HB1))
ASSI {24852}
((segid "BrD" and resid 97 and name HE1))
((segid "BrD" and resid 97 and name HA))
  2.000  2.000  2.500 peak      24852  weight  0.10000E+01 volume  0.10950E+04 ppm1      3.571 ppm2   4.802
OR {24852}
((segid "BrD" and resid 57 and name HE1))
((segid "BrD" and resid 57 and name HA))
ASSI {24982}
((segid "BrD" and resid 21 and name HA))
(segid "BrD" and resid 106 and name HD%)
  3.600  3.200  1.900 peak      24982  weight  0.10000E+01 volume  0.38794E+02 ppm1      4.358 ppm2   7.517
OR {24982}
((segid "BrD" and resid 33 and name HA))
(segid "BrD" and resid 95 and name HD%)
ASSI {24992}
((segid "BrD" and resid 21 and name HA))
((segid "BrD" and resid 22 and name HA))
  2.000  2.000  2.500 peak      24992  weight  0.10000E+01 volume  0.12806E+04 ppm1      4.360 ppm2   4.671
OR {24992}
((segid "BrD" and resid 21 and name HA))
((segid "BrD" and resid 20 and name HB1))
ASSI {25052}
((segid "BrD" and resid 21 and name HG12))
((segid "BrD" and resid 18 and name HB1))
  3.500  3.100  2.000 peak      25052  weight  0.10000E+01 volume  0.40558E+02 ppm1      1.648 ppm2   2.141
OR {25052}
((segid "BrD" and resid 21 and name HG12))
((segid "BrD" and resid 109 and name HB2))
ASSI {25112}
((segid "BrD" and resid 21 and name HG12))
((segid "BrD" and resid 109 and name HG1))
  3.900  3.800  1.600 peak      25112  weight  0.10000E+01 volume  0.24225E+02 ppm1      1.648 ppm2   1.387
OR {25112}
((segid "BrD" and resid 21 and name HG12))
(segid "BrD" and resid 115 and name HD1%)
OR {25112}
((segid "BrD" and resid 21 and name HG12))
(segid "BrD" and resid 14 and name HD2%)
ASSI {25152}
(segid "BrD" and resid 21 and name HD1%)
((segid "BrD" and resid 106 and name HA))
  2.600  1.700  1.700 peak      25152  weight  0.10000E+01 volume  0.24691E+03 ppm1      1.205 ppm2   4.545
OR {25152}
(segid "BrD" and resid 21 and name HD1%)
((segid "BrD" and resid 17 and name HA))
OR {25152}
(segid "BrD" and resid 21 and name HD1%)
((segid "BrD" and resid 75 and name HA))
```

TABLE 3-continued

Ambiguous NOE-derived Inter-proton Distance Restraints

```
ASSI {25162}
(segid "BrD" and resid 21 and name HD1%)
((segid "BrD" and resid 20 and name HA))
  5.500   5.500   0.000 peak        25162 weight  0.10000E+01 volume  0.644$$1E+01 ppm1   1.205 ppm2   4.907
OR {25162}
(segid "BrD" and resid 21 and name HD1%)
((segid "BrD" and resid 105 and name HA))
OR {25162}
(segid "BrD" and resid 21 and name HD1%)
((segid "BrD" and resid 59 and name HA))
ASSI {25172}
(segid "BrD" and resid 21 and name HD1%)
((segid "BrD" and resid 17 and name HB))
  3.100   2.400   2.400 peak        25172 weight  0.10000E+01 volume  0.95979E+02 ppm1   1.205 ppm2   4.863
OR {25172}
(segid "BrD" and resid 21 and name HD1%)
((segid "BrD" and resid 20 and name HA))
ASSI {25182}
(segid "BrD" and resid 21 and name HD1%)
(segid "BrD" and resid 74 and name HE%)
  2.600   1.700   1.700 peak        25182 weight  0.10000E+01 volume  0.25847E+03 ppm1   1.204 ppm2   7.536
OR {25182}
(segid "BrD" and resid 21 and name HD1%)
(segid "BrD" and resid 106 and name HD%)
ASSI {25392}
((segid "BrD" and resid 98 and name HA))
((segid "BrD" and resid 102 and name HA))
  3.400   2.900   2.100 peak        25392 weight  0.10000E+01 volume  0.50125E+02 ppm1   4.804 ppm2   4.265
OR {25392}
((segid "BrD" and resid 98 and name HA))
((segid "BrD" and resid 102 and name HA))
ASSI {25602}
(segid "BrD" and resid 21 and name HG2%)
((segid "BrD" and resid 20 and name HB1))
  3.400   2.900   2.100 peak        25602 weight  0.10000E+01 volume  0.54447E+02 ppm1   1.596 ppm2   4.657
OR {25602}
(segid "BrD" and resid 21 and name HG2%)
((segid "BrD" and resid 109 and name HA))
ASSI {25622}
(segid "BrD" and resid 21 and name HG2%)
((segid "BrD" and resid 105 and name HB1))
  3.400   2.900   2.100 peak        25622 weight  0.10000E+01 volume  0.55968E+02 ppm1   1.599 ppm2   3.736
OR {25622}
(segid "BrD" and resid 101 and name HG2%)
((segid "BrD" and resid 105 and name HB1))
ASSI {25632}
(segid "BrD" and resid 21 and name HG2%)
((segid "BrD" and resid 106 and name HB2))
  4.400   4.400   1.100 peak        25632 weight  0.10000E+01 volume  0.10843E+02 ppm1   1.599 ppm2   3.662
OR {25632}
(segid "BrD" and resid 21 and name HG2%)
((segid "BrD" and resid 105 and name HB2))
ASSI {25672}
(segid "BrD" and resid 101 and name HD1%)
((segid "BrD" and resid 97 and name HB1))
  3.100   2.400   2.400 peak        25672 weight  0.10000E+01 volume  0.84040E+02 ppm1   1.550 ppm2   2.702
OR {25672}
(segid "BrD" and resid 101 and name HD1%)
((segid "BrD" and resid 29 and name HB1))
ASSI {25692}
(segid "BrD" and resid 101 and name HD1%)
((segid "BrD" and resid 97 and name HG2))
  3.400   3.600   1.700 peak        25692 weight  0.10000E+01 volume  0.27614E+02 ppm1   1.550 ppm2   2.167
OR {25692}
(segid "BrD" and resid 101 and name HD1%)
(segid "BrD" and resid 99 and name HB%)
OR {25692}
(segid "BrD" and resid 101 and name HD1%)
((segid "BrD" and resid 33 and name HD2))
ASSI {25702}
(segid "BrD" and resid 21 and name HG2%)
(segid "BrD" and resid 75 and name HE%)
  4.300   4.300   1.200 peak        25702 weight  0.10000E+01 volume  0.11881E+02 ppm1   1.599 ppm2   2.654
OR {25702}
(segid "BrD" and resid 21 and name HG2%)
((segid "BrD" and resid 22 and name HB1))
```

TABLE 3-continued

Ambiguous NOE-derived Inter-proton Distance Restraints

```
OR {25702}
(segid "BrD" and resid 101 and name HG2%)
((segid "BrD" and resid 97 and name HB1))
ASSI {25732}
(segid "BrD" and resid 101 and name HG2%)
((segid "BrD" and resid 102 and name HB1))
 2.600  1.700 1.700 peak      25732 weight  0.10000E+01 volume  0.25581E+03 ppm1    1.599 ppm2   2.011
OR {25732}
(segid "BrD" and resid 21 and name HG2%)
((segid "BrD" and resid 109 and name HD1))
ASSI {25772}
(segid "BrD" and resid 21 and name HG2%)
(segid "BrD" and resid 18 and name HD1%)
 3.200  2.600 2.300 peak      25772 weight  0.10000E+01 volume  0.75349E+02 ppm1    1.599 ppm2   1.059
OR {25772}
(segid "BrD" and resid 21 and name HG2%)
((segid "BrD" and resid 78 and name HB2))
OR {25772}
(segid "BrD" and resid 21 and name HG2%)
(segid "BrD" and resid 81 and name HG1%)
ASSI {25832}
((segid "BrD" and resid 110 and name HB))
((segid "BrD" and resid 108 and name HA))
 3.800  3.600 1.700 peak      25832 weight  0.10000E+01 volume  0.26102E+02 ppm1    2.338 ppm2   4.823
OR {25832}
((segid "BrD" and resid 110 and name HB))
((segid "BrD" and resid 115 and name HA))
ASSI {25862}
(segid "BrD" and resid 110 and name HG2%)
((segid "BrD" and resid 114 and name HA2))
 3.100  2.400 2.400 peak      25862 weight  0.10000E+01 volume  0.90131E+02 ppm1    1.254 ppm2   4.509
OR {25862}
(segid "BrD" and resid 110 and name HG2%)
((segid "BrD" and resid 75 and name HA))
ASSI {25872}
(segid "BrD" and resid 110 and name HD1%)
((segid "BrD" and resid 14 and name HA))
 2.800  2.000 2.000 peak      25872 weight  0.10000E+01 volume  0.15266E+03 ppm1    1.154 ppm2   4.655
OR {25872}
(segid "BrD" and resid 110 and name HD1%)
((segid "BrD" and resid 71 and name HA))
OR {25872}
(segid "BrD" and resid 110 and name HD1%)
((segid "BrD" and resid 111 and name HA))
OR {25872}
(segid "BrD" and resid 110 and name HD1%)
((segid "BrD" and resid 109 and name HA))
ASSI {25882}
(segid "BrD" and resid 110 and name HG2%)
((segid "BrD" and resid 115 and name HA))
 2.800  2.000 2.000 peak      25882 weight  0.10000E+01 volume  0.15787E+03 ppm1    1.253 ppm2   4.824
OR {25882}
(segid "BrD" and resid 110 and name HG2%)
((segid "BrD" and resid 116 and name HA))
ASSI {25892}
(segid "BrD" and resid 110 and name HD1%)
((segid "BrD" and resid 17 and name HB))
 3.100  2.400 2.400 peak      25892 weight  0.10000E+01 volume  0.95882E+02 ppm1    1.154 ppm2   4.424
OR {25892}
(segid "BrD" and resid 110 and name HD1%)
((segid "BrD" and resid 115 and name HA))
ASSI {25902}
(segid "BrD" and resid 110 and name HD1%)
((segid "BrD" and resid 106 and name HA))
 3.000  2.200 2.200 peak      25902 weight  0.10000E+01 volume  0.11502E+03 ppm1    1.154 ppm2   4.568
OR {25902}
(segid "BrD" and resid 110 and name HD1%)
((segid "BrD" and resid 17 and name HA))
OR {25902}
(segid "BrD" and resid 110 and name HD1%)
((segid "BrD" and resid 114 and name HA1))
ASSI {26022}
(segid "BrD" and resid 110 and name HD1%)
((segid "BrD" and resid 106 and name HB2))
 3.200  2.600 2.300 peak      26022 weight  0.10000E+01 volume  0.70430E+02 ppm1    1.154 ppm2   3.670
```

TABLE 3-continued

Ambiguous NOE-derived Inter-proton Distance Restraints

```
OR {26022}
(segid "BrD" and resid 110 and name HD1%)
((segid "BrD" and resid 107 and name HB1))
ASSI {26042}
(segid "BrD" and resid 110 and name HG2%)
((segid "BrD" and resid 107 and name HB1))
   3.600  3.200  1.900 peak       26042  weight  0.10000E+01 volume  0.38059E+02 ppm1      1.251 ppm2     3.671
OR {26042}
(segid "BrD" and resid 110 and name HG2%)
((segid "BrD" and resid 106 and name HB2))
ASSI {26202}
(segid "BrD" and resid 116 and name HG2%)
((segid "BrD" and resid 76 and name HA))
   2.600  1.700  1.700 peak       26202  weight  0.10000E+01 volume  0.28885E+03 ppm1      1.401 ppm2     4.655
OR {26202}
(segid "BrD" and resid 116 and name HG2%)
((segid "BrD" and resid 72 and name HA))
ASSI {26312}
(segid "BrD" and resid 116 and name HD1%)
((segid "BrD" and resid 76 and name HA))
   3.800  3.600  1.700 peak       26312  weight  0.10000E+01 volume  0.26059E+02 ppm1      1.401 ppm2     4.655
OR {26312}
(segid "BrD" and resid 116 and name HD1%)
((segid "BrD" and resid 118 and name HA))
OR {26312}
(segid "BrD" and resid 116 and name HD1%)
((segid "BrD" and resid 111 and name HA))
OR {26312}
(segid "BrD" and resid 116 and name HD1%)
((segid "BrD" and resid 71 and name HA))
OR {26312}
(segid "BrD" and resid 116 and name HD1%)
((segid "BrD" and resid 72 and name HA))
ASSI {26352}
(segid "BrD" and resid 116 and name HG2%)
((segid "BrD" and resid 79 and name HA))
   3.600  3.200  1.900 peak       26352  weight  0.10000E+01 volume  0.36722E+02 ppm1      1.400 ppm2     4.428
OR {26352}
(segid "BrD" and resid 116 and name HG2%)
((segid "BrD" and resid 107 and name HA))
ASSI {26362}
(segid "BrD" and resid 116 and name HD1%)
((segid "BrD" and resid 107 and name HB1))
   3.800  3.600  1.700 peak       26362  weight  0.10000E+01 volume  0.28562E+02 ppm1      1.401 ppm2     3.662
OR {26362}
(segid "BrD" and resid 116 and name HD1%)
((segid "BrD" and resid 106 and name HB2))
ASSI {26512}
((segid "BrD" and resid 116 and name HB))
((segid "BrD" and resid 76 and name HA))
   3.300  2.700  2.200 peak       26532  weight  0.10000E+01 volume  0.66907E+02 ppm1      2.410 ppm2     4.655
OR {26512}
((segid "BrD" and resid 116 and name HB))
((segid "BrD" and resid 118 and name HA))
OR {26512}
((segid "BrD" and resid 116 and name HB))
((segid "BrD" and resid 72 and name HA))
ASSI {27012}
((segid "BrD" and resid 89 and name HA))
((segid "BrD" and resid 88 and name HA))
   3.600  3.200  1.900 peak       27012  weight  0.10000E+01 volume  0.33743E+02 ppm1      5.642 ppm2     5.005
OR {27012}
((segid "BrD" and resid 89 and name HA))
((segid "BrD" and resid 93 and name HB1))
ASSI {27292}
((segid "BrD" and resid 80 and name HG1))
((segid "BrD" and resid 52 and name HB1))
   3.300  2.700  2.200 peak       27292  weight  0.10000E+01 volume  0.61197E+02 ppm1      3.141 ppm2     1.649
OR {27292}
((segid "BrD" and resid 73 and name HG))
((segid "BrD" and resid 68 and name HB1))
ASSI {27302}
((segid "BrD" and resid 80 and name HG1))
((segid "BrD" and resid 77 and name HB1))
   4.600  4.600  0.900 peak       27302  weight  0.10000E+01 volume  0.87654E+01 ppm1      2.341 ppm2     3.311
```

TABLE 3-continued

Ambiguous NOE-derived Inter-proton Distance Restraints

```
OR {27302}
((segid "BrD" and resid 73 and name HG))
((segid "BrD" and resid 77 and name HB1))
OR {27302}
((segid "BrD" and resid 73 and name HG))
((segid "BrD" and resid 54 and name HG1))
OR {27302}
((segid "BrD" and resid 56 and name HG))
((segid "BrD" and resid 54 and name HG1))
OR {27302}
((segid "BrD" and resid 56 and name HG))
((segid "BrD" and resid 77 and name HB1))
ASSI {27332}
((segid "BrD" and resid 56 and name HG))
(segid "BrD" and resid 81 and name HG2%)
  3.600  3.200  1.900 peak        27332  weight  0.10000E+01 volume   0.35670E+02 ppm1     2.338 ppm2     0.758
OR {27332}
((segid "BrD" and resid 22 and name HG))
(segid "BrD" and resid 78 and name HD1%)
ASSI {27462}
(segid "BrD" and resid 22 and name HD1%)
((segid "BrD" and resid 25 and name HB))
  3.800  3.600  1.700 peak        27462  weight  0.10000E+01 volume   0.26281E+02 ppm1     1.648 ppm2     2.995
OR {27462}
(segid "BrD" and resid 22 and name HD1%)
((segid "BrD" and resid 61 and name HG1))
OR {27462}
(segid "BrD" and resid 22 and name HD1%)
((segid "BrD" and resid 74 and name HB2))
ASSI {27482}
(segid "BrD" and resid 22 and name HD2%)
((segid "BrD" and resid 26 and name HA))
  3.200  2.600  2.300 peak        27482  weight  0.10000E+01 volume   0.77977E+02 ppm1     1.599 ppm2     4.492
OR {27482}
(segid "BrD" and resid 22 and name HD2%)
((segid "BrD" and resid 58 and name HA))
ASSI {27502}
(segid "BrD" and resid 22 and name HD2%)
((segid "BrD" and resid 59 and name HA))
  3.200  2.600  2.300 peak        27502  weight  0.10000E+01 volume   0.74913E+02 ppm1     1.599 ppm2     4.901
OR {27502}
(segid "BrD" and resid 22 and name HD2%)
((segid "BrD" and resid 35 and name HA))
OR {27502}
(segid "BrD" and resid 22 and name HD2%)
((segid "BrD" and resid 20 and name HA))
ASSI {27542}
(segid "BrD" and resid 22 and name HD2%)
((segid "BrD" and resid 56 and name HB2))
  4.000  4.000  1.500 peak        27542  weight  0.10000E+01 volume   0.19846E+02 ppm1     1.599 ppm2     2.011
OR {27542}
(segid "BrD" and resid 22 and name HD2%)
((segid "BrD" and resid 81 and name HB))
ASSI {27562}
(segid "BrD" and resid 22 and name HD1%)
((segid "BrD" and resid 64 and name HA))
  3.300  2.700  2.200 peak        27562  weight  0.10000E+01 volume   0.62753E+02 ppm1     1.645 ppm2     4.911
OR {27562}
(segid "BrD" and resid 22 and name HD1%)
((segid "BrD" and resid 59 and name HA))
ASSI {27592}
((segid "BrD" and resid 110 and name HG12))
(segid "BrD" and resid 115 and name HD1%)
  3.300  2.700  2.200 peak        27592  weight  0.10000E+01 volume   0.61111E+02 ppm1     1.646 ppm2     1.321
OR {27592}
((segid "BrD" and resid 110 and name HG12))
((segid "BrD" and resid 78 and name HB1))
OR {27592}
(segid "BrD" and resid 22 and name HD1%)
(segid "BrD" and resid 102 and name HD2%)
OR {27592}
((segid "BrD" and resid 110 and name HG12))
(segid "BrD" and resid 102 and name HD2%)
ASSI {27622}
(segid "BrD" and resid 73 and name HD2%)
((segid "BrD" and resid 74 and name HA))
  3.000  2.200  2.200 peak        27622  weight  0.10000E+01 volume   0.10007E+03 ppm1     1.500 ppm2     4.362
```

TABLE 3-continued

Ambiguous NOE-derived Inter-proton Distance Restraints

```
OR {27622}
(segid "BrD" and resid 73 and name HD2%)
((segid "BrD" and resid 70 and name HB2))
ASSI {27832}
((segid "BrD" and resid 78 and name HA))
((segid "BrD" and resid 82 and name HZ))
  3.500  3.100  3.000 peak        27832  weight  0.10000E+01 volume  0.44344E+02 ppm1   3.966 ppm2   7.023
OR {27832}
((segid "BrD" and resid 78 and name HA))
(segid "BrD" and resid 74 and name HD%)
ASSI {27852}
((segid "BrD" and resid 78 and name HB2))
((segid "BrD" and resid 116 and name HG12))
  4.700  4.700  0.800 peak        27852  weight  0.10000E+01 volume  0.74365E+01 ppm1   1.056 ppm2   1.832
OR {27652}
((segid "BrD" and resid 78 and name HB2))
(segid "BrD" and resid 56 and name HD1%)
ASSI {27862}
((segid "BrD" and resid 78 and name HB2))
((segid "BrD" and resid 110 and name HG12))
  3.700  3.400  1.800 peak        27862  weight  0.10000E+01 volume  0.33112E+02 ppm1   1.054 ppm2   1.629
OR {27862}
((segid "BrD" and resid 78 and name HB2))
(segid "BrD" and resid 21 and name HG2%)
OR {27862}
((segid "BrD" and resid 78 and name HB2))
(segid "BrD" and resid 22 and name HD2%)
OR {27862}
((segid "BrD" and resid 78 and name HB2))
((segid "BrD" and resid 21 and name HG12))
ASSI {27962}
(segid "BrD" and resid 78 and name HD1%)
(segid "BrD" and resid 74 and name HD%)
  2.200  2.200  2.300 peak        27962  weight  0.10000E+01 volume  0.40433E+03 ppm1   0.761 ppm2   7.031
OR {27962}
(segid "BrD" and resid 78 and name HD1%)
(segid "BrD" and resid 82 and name HE%)
ASSI {28022}
(segid "BrD" and resid 78 and name HD2%)
((segid "BrD" and resid 22 and name HA))
  3.100  2.400  2.400 peak        28022  weight  0.10000E+01 volume  0.92248E+02 ppm1   0.862 ppm2   4.727
OR {28022}
(segid "BrD" and resid 78 and name HD2%)
((segid "BrD" and resid 82 and name HA))
ASSI {28042}
(segid "BrD" and resid 78 and name HD2%)
((segid "BrD" and resid 56 and name HA))
  3.600  3.200  1.900 peak        28042  weight  0.10000E+01 volume  0.33947E+02 ppm1   0.662 ppm2   4.631
OR {28042}
(segid "BrD" and resid 78 and name HD2%)
((segid "BrD" and resid 76 and name HA))
OR {28042}
(segid "BrD" and resid 78 and name HD2%)
((segid "BrD" and resid 80 and name HA))
OR {28042}
(segid "BrD" and resid 74 and name HD2%)
((segid "BrD" and resid 104 and name HA))
OR {28042}
(segid "BrD" and resid 78 and name HD2%)
((segid "BrD" and resid 20 and name HB1))
OR {28042}
(segid "BrD" and resid 78 and name HD2%)
((segid "BrD" and resid 109 and name HA))
OR {28042}
(segid "BrD" and resid 78 and name HD2%)
((segid "BrD" and resid 14 and name HA))
OR {28042}
(segid "BrD" and resid 78 and name HD2%)
((segid "BrD" and resid 71 and name HA))
OR {28042}
(segid "BrD" and resid 78 and name HD2%)
((segid "BrD" and resid 15 and name HA))
ASSI {28052}
(segid "BrD" and resid 78 and name HD1%)
((segid "BrD" and resid 56 and name HA))
  3.800  3.600  1.700 peak        28052  weight  0.10000E+01 volume  0.28600E+02 ppm1   0.761 ppm2   4.631
```

TABLE 3-continued

Ambiguous NOE-derived Inter-proton Distance Restraints

OR {28052}
(segid "BrD" and resid 78 and name HD1%)
((segid "BrD" and resid 76 and name HA))
OR {28052}
(segid "BrD" and resid 78 and name HD1%)
((segid "BrD" and resid 80 and name HA))
OR {28052}
(segid "BrD" and resid 78 and name HD1%)
((segid "BrD" and resid 60 and name HB2))
ASSI {28072}
(segid "BrD" and resid 78 and name HD1%)
((segid "BrD" and resid 79 and name HA))
  3.400  2.900  2.100 peak       28072 weight  0.10000E+01 volume     0.48389E+02 ppm1     0.762 ppm2    4.428
OR {28072}
(segid "BrD" and resid 78 and name HD1%)
((segid "BrD" and resid 25 and name HA))
OR {28072}
(segid "BrD" and resid 78 and name HD1%)
((segid "BrD" and resid 107 and name HA))
OR {28072}
(segid "BrD" and resid 78 and name HD1%)
((segid "BrD" and resid 99 and name HA))
ASSI {28082}
(segid "BrD" and resid 78 and name HD2%)
((segid "BrD" and resid 106 and name HA))
  3.000  2.200  2.200 peak       28082 weight  0.10000E+01 volume     0.10774E+03 ppm1     0.662 ppm2    4.525
OR {28082}
(segid "BrD" and resid 78 and name HD2%)
((segid "BrD" and resid 75 and name HA))
ASSI {28092}
(segid "BrD" and resid 78 and name HD2%)
((segid "BrD" and resid 79 and name HA))
  2.900  2.100  2.100 peak       28092 weight  0.10000E+01 volume     0.12398E+03 ppm1     0.662 ppm2    4.427
OR {28092}
(segid "BrD" and resid 78 and name HD2%)
((segid "BrD" and resid 107 and name HA))
ASSI {28112}
(segid "BrD" and resid 78 and name HD1%)
((segid "BrD" and resid 106 and name HB2))
  3.200  2.600  2.300 peak       28112 weight  0.10000E+01 volume     0.76864E+02 ppm1     0.760 ppm2    3.711
OR {28112}
(segid "BrD" and resid 78 and name HD1%)
((segid "BrD" and resid 81 and name HA))
ASSI {28142}
(segid "BrD" and resid 78 and name HD2%)
((segid "BrD" and resid 25 and name HB))
  3.900  3.800  1.600 peak       28142 weight  0.10000E+01 volume     0.22598E+02 ppm1     0.662 ppm2    3.005
OR {28142}
(segid "BrD" and resid 78 and name HD2%)
((segid "BrD" and resid 79 and name HG1))
OR {28142}
(segid "BrD" and resid 78 and name HD2%)
((segid "BrD" and resid 74 and name HB2))
ASSI {28152}
(segid "BrD" and resid 78 and name HD2%)
((segid "BrD" and resid 21 and name HG11))
  3.600  3.200  1.900 peak       28152 weight  0.10000E+01 volume     0.38156E+02 ppm1     0.662 ppm2    2.347
OR {28152}
(segid "BrD" and resid 78 and name HD2%)
((segid "BrD" and resid 56 and name HG))
OR {28152}
(segid "BrD" and resid 78 and name HD2%)
((segid "BrD" and resid 22 and name HG))
ASSI {28162}
(segid "BrD" and resid 78 and name HD2%)
(segid "BrD" and resid 75 and name HE%))
  4.300  4.300  1.200 peak       28162 weight  0.10000E+01 volume     0.12997E+02 ppm1     0.662 ppm2    2.670
OR {28162}
(segid "BrD" and resid 78 and name HD2%)
((segid "BrD" and resid 79 and name HB2))
OR {24162}
(segid "BrD" and resid 78 and name HD2%)
((segid "BrD" and resid 22 and name HB1))
ASSI {28172}
(segid "BrD" and resid 78 and name HD1%)
((segid "BrD" and resid 74 and name HB2))
  3.800  3.600  1.700 peak       28172 weight  0.10000E+01 volume     0.27394E+02 ppm1     0.760 ppm2    3.003

TABLE 3-continued

Ambiguous NOE-derived Inter-proton Distance Restraints

OR {28172}
(segid "BrD" and resid 78 and name HD1%)
((segid "BrD" and resid 25 and name HB))
ASSI {28302}
(segid "BrD" and resid 56 and name HD2%)
((segid "BrD" and resid 35 and name HA))
  2.600  1.700  1.700 peak       28302  weight  0.10000E+01 volume    0.27298E+03 ppm1       1.254 ppm2    4.907
OR {28302}
(segid "BrD" and resid 56 and name HD2%)
((segid "BrD" and resid 59 and name HA))
ASSI {28332}
(segid "BrD" and resid 56 and name HD2%)
((segid "BrD" and resid 25 and name HA))
  5.000  5.000  0.500 peak       28332  weight  0.10000E+01 volume    0.51532E+02 ppm1       1.253 ppm2    4.441
OR {28332}
(segid "BrD" and resid 56 and name HD2%)
((segid "BrD" and resid 58 and name HA))
ASSI {28482}
((segid "BrD" and resid 56 and name HB2))
(segid "BrD" and resid 81 and name HG2%)
  3.700  3.400  1.800 peak       28482  weight  0.10000E+01 volume    0.33282E+02 ppm1       1.993 ppm2    0.766
OR {28482}
((segid "BrD" and resid 102 and name HB1))
(segid "BrD" and resid 81 and name HG2%)
ASSI {28552}
((segid "BrD" and resid 102 and name HG))
(segid "BrD" and resid 25 and name HA))
  4.000  4.000  1.500 peak       28552  weight  0.10000E+01 volume    0.18876E+02 ppm1       2.141 ppm2    4.445
OR {28552}
((segid "BrD" and resid 102 and name HG))
((segid "BrD" and resid 99 and name HA))
OR {28552}
((segid "BrD" and resid 97 and name HG2))
((segid "BrD" and resid 96 and name HA))
ASSI {28592}
(segid "BrD" and resid 102 and name HD2%)
((segid "BrD" and resid 34 and name HZ))
  3.700  3.400  1.800 peak       28592  weight  0.10000E+01 volume    0.30371E+02 ppm1       1.303 ppm2    7.899
OR {28592}
(segid "BrD" and resid 102 and name HD2%)
(segid "BrD" and resid 107 and name HE%)
ASSI {28602}
(segid "BrD" and resid 102 and name HD2%)
(segid "BrD" and resid 34 and name HE%)
  2.000  2.000  2.500 peak       28602  weight  0.10000E+01 volume    0.10851E+04 ppm1       1.303 ppm2    7.771
OR {28602}
(segid "BrD" and resid 102 and name HD2%)
(segid "BrD" and resid 105 and name HD%)
ASSI {28682}
(segid "BrD" and resid 102 and name HD1%)
((segid "BrD" and resid 28 and name HA))
  4.000  4.000  1.500 peak       28682  weight  0.10000E+01 volume    0.20825E+02 ppm1       1.303 ppm2    4.583
OR {28682}
(segid "BrD" and resid 102 and name HD1%)
((segid "BrD" and resid 106 and name HA))
ASSI {28692}
(segid "BrD" and resid 102 and name HD1%)
((segid "BrD" and resid 30 and name HB2))
  2.700  1.800  1.800 peak       28692  weight  0.10000E+01 volume    0.20830E+03 ppm1       1.303 ppm2    4.536
OR {28692}
(segid "BrD" and resid 102 and name HD1%)
((segid "BrD" and resid 28 and name HA))
ASSI {28772}
(segid "BrD" and resid 102 and name HD2%)
(segid "BrD" and resid 78 and name HD1%)
  3.500  3.100  2.000 peak       28772  weight  0.10000E+01 volume    0.44195E+02 ppm1       1.304 ppm2    0.760
OR {28772}
(segid "BrD" and resid 102 and name HD2%)
(segid "BrD" and resid 81 and name HG2%)
ASSI {28862}
((segid "BrD" and resid 115 and name HB1))
((segid "BrD" and resid 110 and name HG11))
  3.300  2.700  2.200 peak       28862  weight  0.10000E+01 volume    0.61541E+02 ppm1       2.290 ppm2    1.742
OR {28862}
((segid "BrD" and resid 115 and name HB1))
(segid "BrD" and resid 17 and name HG2%)

TABLE 3-continued

Ambiguous NOE-derived Inter-proton Distance Restraints

ASSI {28952}
(segid "BrD" and resid 56 and name HD1%)
((segid "BrD" and resid 31 and name HA))
  3.300  2.400  2.400 peak     28952  weight  0.10000E+01 volume  0.92579E+02 ppm1     1.548 ppm2    4.984
OR {28952}
(segid "BrD" and resid 56 and name HD1%)
((segid "BrD" and resid 60 and name HB1))
ASSI {29002}
(segid "BrD" and resid 59 and name HE%)
(segid "BrD" and resid 76 and name HB%)
  3.500  3.200  2.000 peak     29002  weight  0.10000E+01 volume  0.43704E+02 ppm1     1.848 ppm2    2.108
OR {29002}
(segid "BrD" and resid 59 and name HE%)
((segid "BrD" and resid 18 and name HB1))
OR {29002}
(segid "BrD" and resid 59 and name HE%)
((segid "BrD" and resid 102 and name HG))
ASSI {29022}
(segid "BrD" and resid 59 and name HE%)
((segid "BrD" and resid 22 and name HB2))
  3.400  2.900  2.100 peak     29022  weight  0.10000E+01 volume  0.52140E+02 ppm1     1.848 ppm2    2.292
OR {29022}
(segid "BrD" and resid 59 and name HE%)
((segid "BrD" and resid 22 and name HG))
OR {29022}
(segid "BrD" and resid 59 and name HB%)
(segid "BrD" and resid 31 and name HB%)
ASSI {29032}
(segid "BrD" and resid 59 and name HE%)
((segid "BrD" and resid 56 and name HG))
  3.700  3.400  1.800 peak     29032  weight  0.10000E+01 volume  0.29631E+02 ppm1     1.848 ppm2    2.361
OR {29032}
(segid "BrD" and resid 59 and name HE%)
((segid "BrD" and resid 22 and name HG))
OR {29032}
(segid "BrD" and resid 59 and name HE%)
((segid "BrD" and resid 73 and name HG))
OR {29032}
(segid "BrD" and resid 59 and name HE%)
((segid "BrD" and resid 21 and name HG11))
ASSI {29072}
(segid "BrD" and resid 59 and name HE%)
((segid "BrD" and resid 22 and name HA))
  4.200  4.200  1.300 peak     29072  weight  0.10000E+01 volume  0.14615E+02 ppm1     1.848 ppm2    4.719
OR {29072}
(segid "BrD" and resid 59 and name HE%)
((segid "BrD" and resid 58 and name HB))
OR {29072}
(segid "BrD" and resid 59 and name HE%)
((segid "BrD" and resid 69 and name HA))
OR {29072}
(segid "BrD" and resid 59 and name HE%)
((segid "BrD" and resid 53 and name HA))
ASSI {29152}
(segid "BrD" and resid 59 and name HE%)
(segid "BrD" and resid 73 and name HD2%)
  3.600  3.200  1.900 peak     29152  weight  0.10000E+01 volume  0.18252E+02 ppm1     1.848 ppm2    1.462
OR {29152}
(segid "BrD" and resid 59 and name HE%)
(segid "BrD" and resid 63 and name HD2%)
OR {29152}
(segid "BrD" and resid 59 and name HE%)
((segid "BrD" and resid 62 and name HG2))
ASSI {29192}
(segid "BrD" and resid 54 and name HE%)
((segid "BrD" and resid 60 and name HB1))
  3.200  2.600  2.300 peak     29192  weight  0.10000E+01 volume  0.76364E+02 ppm1     2.536 ppm2    4.964
OR {29192}
(segid "BrD" and resid 54 and name HE%)
((segid "BrD" and resid 77 and name HA))
ASSI {29202}
(segid "BrD" and resid 54 and name HE%)
((segid "BrD" and resid 55 and name HB1))
  3.700  3.400  1.800 peak     29202  weight  0.10000E+01 volume  0.30281E+02 ppm1     2.535 ppm2    2.955
OR {29202}
(segid "BrD" and resid 54 and name HE%)
((segid "BrD" and resid 37 and name HB1))

TABLE 3-continued

Ambiguous NOE-derived Inter-proton Distance Restraints

ASSI {29252}
(segid "BrD" and resid 54 and name HE%)
(segid "BrD" and resid 35 and name HE%)
  2.500  2.500  2.000 peak      29252  weight  0.10000E+01 volume    0.29954E+03 ppm1      2.535 ppm2    2.801
OR {29252}
(segid "BrD" and resid 54 and name HE%)
((segid "BrD" and resid 53 and name HB1))
OR {29252}
(segid "BrD" and resid 54 and name HE%)
((segid "BrD" and resid 61 and name HG2))
OR {29252}
(segid "BrD" and resid 54 and name HE%)
((segid "BrD" and resid 36 and name HG1))
ASSI {29262}
(segid "BrD" and resid 54 and name HE%)
((segid "BrD" and resid 37 and name HG1))
  2.600  1.700  1.700 peak      29262  weight  0.10000E+01 volume    0.23100E+03 ppm1      2.535 ppm2    2.722
OR {29262}
(segid "BrD" and resid 54 and name HE%)
((segid "BrD" and resid 59 and name HB1))
ASSI {29582}
((segid "BrD" and resid 79 and name HA))
((segid "BrD" and resid 116 and name HG11))
  4.100  4.100  1.400 peak      29582  weight  0.10000E+01 volume    0.16991E+02 ppm1      4.409 ppm2    1.897
OR {29582}
((segid "BrD" and resid 79 and name HA))
((segid "BrD" and resid 103 and name HB2))
ASSI {29682}
((segid "BrD" and resid 108 and name HA))
((segid "BrD" and resid 111 and name HG1))
  4.100  4.100  1.400 peak      29682  weight  0.10000E+01 volume    0.16470E+02 ppm1      4.804 ppm2    2.003
OR {29682}
((segid "BrD" and resid 104 and name HA))
((segid "BrD" and resid 109 and name HD1))
ASSI {29702}
((segid "BrD" and resid 15 and name HA))
((segid "BrD" and resid 19 and name HB2))
  2.800  2.000  2.000 peak      29702  weight  0.10000E+01 volume    0.16051E+03 ppm1      4.607 ppm2    1.986
OR {29702}
((segid "BrD" and resid 104 and name HB1))
((segid "BrD" and resid 109 and name HD1))
OR {29702}
((segid "BrD" and resid 60 and name HB2))
((segid "BrD" and resid 56 and name HB2))
ASSI {29712}
((segid "BrD" and resid 15 and name HA))
((segid "BrD" and resid 18 and name HB1))
  3.100  2.400  2.400 peak      29712  weight  0.10000E+01 volume    0.92305E+02 ppm1      4.607 ppm2    2.182
OR {29712}
((segid "BrD" and resid 60 and name HB2))
((segid "BrD" and resid 64 and name HG1))
ASSI {29722}
((segid "BrD" and resid 15 and name HA))
(segid "BrD" and resid 14 and name HD2%)
  3.900  3.800  1.600 peak      29722  weight  0.10000E+01 volume    0.22638E+02 ppm1      4.607 ppm2    1.417
OR {29722}
((segid "BrD" and resid 15 and name HA))
(segid "BrD" and resid 69 and name HG2%)
ASSI {29732}
((segid "BrD" and resid 30 and name HA))
((segid "BrD" and resid 98 and name HA))
  2.600  1.700  1.700 peak      29732  weight  0.10000E+01 volume    0.26724E+03 ppm1      5.445 ppm2    4.810
OR {29732}
((segid "BrD" and resid 30 and name HA))
((segid "BrD" and resid 29 and name HA))
ASSI {30592}
((segid "BrD" and resid 109 and name HB1))
(segid "BrD" and resid 21 and name HD1%)
  3.700  3.400  1.800 peak      30592  weight  0.10000E+01 volume    0.31262E+02 ppm1      2.334 ppm2    1.222
OR {30592}
((segid "BrD" and resid 109 and name HB1))
(segid "BrD" and resid 110 and name HG2%)
ASSI {30672}
((segid "BrD" and resid 109 and name HB2))
((segid "BrD" and resid 110 and name HA))
  3.600  3.200  1.900 peak      30672  weight  0.10000E+01 volume    0.39278E+02 ppm1      2.141 ppm2    4.378

TABLE 3-continued

Ambiguous NOE-derived Inter-proton Distance Restraints

OR {30672}
((segid "BrD" and resid 109 and name HB2))
((segid "BrD" and resid 107 and name HA))
ASSI {30952}
(segid "BrD" and resid 75 and name HA))
((segid "BrD" and resid 78 and name HG))
  3.800  3.600  1.700 peak        30952 weight  0.10000E+01 volume    0.28077E+02 ppm1      4.509 ppm2    1.260
OR {30952}
((segid "BrD" and resid 26 and name HA))
(segid "BrD" and resid 56 and name HD2%)
ASSI {83}
(segid "BrD" and resid 46 and name HD%)
((segid "BrD" and resid 47 and name HA))
  2.300  2.300  2.200 peak          83 weight  0.10000E+01 volume    0.20163E+03 ppm1      5.756 ppm2    4.693
OR {83}
(segid "BrD" and resid 46 and name HD%)
((segid "BrD" and resid 53 and name HA))
ASSI {533}
(segid "BrD" and resid 47 and name HE%)
((segid "BrD" and resid 38 and name HB))
  3.200  2.600  2.300 peak         533 weight  0.10000E+01 volume    0.34245E+02 ppm1      7.246 ppm2    1.776
OR {533}
(segid "BrD" and resid 47 and name HE%)
((segid "BrD" and resid 50 and name HB))
ASSI {643}
(segid "BrD" and resid 74 and name HD%)
((segid "BrD" and resid 71 and name HA))
  3.100  2.400  2.400 peak         643 weight  0.10000E+01 volume    0.35398E+02 ppm1      7.012 ppm2    4.622
OR {643}
(segid "BrD" and resid 74 and name HD%)
((segid "BrD" and resid 15 and name HA))
OR {643}
(segid "BrD" and resid 74 and name HD%)
((segid "BrD" and resid 76 and name HA))
OR {643}
(segid "BrD" and resid 74 and name HD%)
((segid "BrD" and resid 56 and name HA))
OR {643}
(segid "BrD" and resid 74 and name HD%)
((segid "BrD" and resid 72 and name HA))
OR {643}
(segid "BrD" and resid 74 and name HD%)
((segid "BrD" and resid 14 and name HA))
ASSI {1143}
(segid "BrD" and resid 105 and name HD%)
(segid "BrD" and resid 101 and name HG2%)
  3.100  2.400  2.400 peak        1143 weight  0.10000E+01 volume    0.36890E+02 ppm1      7.758 ppm2    1.631
OR {1143}
(segid "BrD" and resid 105 and name HD%)
((segid "BrD" and resid 21 and name HG2%)
ASSI {1393}
(segid "BrD" and resid 96 and name HD%)
((segid "BrD" and resid 86 and name HA))
  2.200  2.200  2.300 peak        1393 weight  0.10000E+01 volume    0.26898E+03 ppm1      7.711 ppm2    4.810
OR {1393}
(segid "BrD" and resid 96 and name HD%)
((segid "BrD" and resid 92 and name HA))
ASSI {1763}
(segid "BrD" and resid 106 and name HE%)
((segid "BrD" and resid 107 and name HA))
  3.400  2.900  2.100 peak        1763 weight  0.10000E+01 volume    0.21871E+02 ppm1      7.617 ppm2    4.431
OR {1763}
(segid "BrD" and resid 106 and name HE%)
((segid "BrD" and resid 79 and name HA))
OR {1763}
(segid "BrD" and resid 106 and name HE%)
((segid "BrD" and resid 110 and name HA))
ASSI {1783}
(segid "BrD" and resid 106 and name HE%)
(segid "BrD" and resid 74 and name HD%)
  3.700  3.400  1.800 peak        1783 weight  0.10000E+01 volume    0.23872E+02 ppm1      7.617 ppm2    7.027
OR {1783}
(segid "BrD" and resid 106 and name HE%)
(segid "BrD" and resid 82 and name HE%)
OR {1783}
(segid "BrD" and resid 106 and name HE%)
((segid "BrD" and resid 82 and name HZ))

TABLE 3-continued

Ambiguous NOE-derived Inter-proton Distance Restraints

```
ASSI {1813}
(segid "BrD" and resid 95 and name HD%)
((segid "BrD" and resid 94 and name HA))
  3.300  2.700  2.200 peak        1813 weight  0.10000E+01 volume  0.28141E+02 ppm1    1.478 ppm2    4.810
OR {1813}
(segid "BrD" and resid 95 and name HD%)
((segid "BrD" and resid 86 and name HA))
ASSI {1893}
(segid "BrD" and resid 96 and name HE%)
((segid "BrD" and resid 96 and name HA))
  3.600  3.200  1.900 peak        1893 weight  0.10000E+01 volume  0.14793E+02 ppm1    7.618 ppm2    4.387
OR {1893}
(segid "BrD" and resid 95 and name HE%)
((segid "BrD" and resid 33 and name HA))
ASSI {2063}
((segid "BrD" and resid 32 and name HZ3))
((segid "BrD" and resid 32 and name HA))
  5.500  5.500  0.000 peak        2063 weight  0.10000E+01 volume  0.11153E+03 ppm1    7.804 ppm2    4.971
OR {2063}
((segid "BrD" and resid 32 and name HZ3))
((segid "BrD" and resid 93 and name HB1))
OR {2063}
((segid "BrD" and resid 32 and name HZ3))
((segid "BrD" and resid 85 and name HA))
ASSI {24}
(segid "BrD" and resid 46 and name HE%)
((segid "BrD" and resid 50 and name HB))
  3.600  3.200  1.900 peak          24 weight  0.10000E+01 volume  0.55296E+02 ppm1    6.687 ppm2    1.777
OR {24}
(segid "BrD" and resid 46 and name HE%)
((segid "BrD" and resid 38 and name HB))
ASSI {94}
(segid "BrD" and resid 82 and name HD%)
((segid "BrD" and resid 79 and name HA))
  2.200  1.200  1.200 peak          94 weight  0.10000E+01 volume  0.10359E+04 ppm1    7.266 ppm2    4.424
OR {94}
(segid "BrD" and resid 82 and name HD%)
((segid "BrD" and resid 99 and name HA))
ASSI {104}
(segid "BrD" and resid 47 and name HE%)
((segid "BrD" and resid 53 and name HG2))
  2.500  1.600  1.600 peak         104 weight  0.10000E+01 volume  0.51584E+03 ppm1    7.270 ppm2    2.504
OR {104}
(segid "BrD" and resid 82 and name HD%)
((segid "BrD" and resid 103 and name HG2))
ASSI {124}
(segid "BrD" and resid 47 and name HD%)
((segid "BrD" and resid 50 and name HG12))
  3.600  3.200  1.900 peak         124 weight  0.10000E+01 volume  0.55730E+02 ppm1    7.970 ppm2    0.780
OR {124}
(segid "BrD" and resid 47 and name HD%)
(segid "BrD" and resid 38 and name HG2%)
ASSI {134}
(segid "BrD" and resid 47 and name HD%)
((segid "BrD" and resid $$3 and name HD2))
  2.900  2.100  2.100 peak         134 weight  0.10000E+01 volume  0.18431E+03 ppm1    7.970 ppm2    4.007
OR {134}
((segid "BrD" and resid 32 and name HZ2)
((segid "BrD" and resid 98 and name HB1))
ASSI {554}
((segid "BrD" and resid 28 and name HE1))
((segid "BrD" and resid 30 and name HB2))
  2.900  2.100  2.100 peak         554 weight  0.10000E+01 volume  0.21924E+03 ppm1    8.158 ppm2    4.538
OR {554}
((segid "BrD" and resid 28 and name HE1))
((segid "BrD" and resid 28 and name HA))
ASSI {574}
(segid "BrD" and resid 68 and name HE%)
((segid "BrD" and resid 59 and name HA))
  3.200  2.600  2.300 peak         574 weight  0.10000E+01 volume  0.10500E+03 ppm1    7.921 ppm2    4.930
OR {574}
((segid "BrD" and resid 32 and name HE3))
((segid "BrD" and resid 32 and name HA))
ASSI {604}
((segid "BrD" and resid 107 and name HZ))
((segid "BrD" and resid 83 and name HB))
  3.500  3.100  2.000 peak         604 weight  0.10000E+01 volume  0.65660E+02 ppm1    8.063 ppm2    4.784
```

TABLE 3-continued

Ambiguous NOE-derived Inter-proton Distance Restraints

OR {604}
((segid "BrD" and resid 107 and name HZ))
((segid "BrD" and resid 82 and name HA))
ASSI {614}
((segid "BrD" and resid 107 and name HZ))
((segid "BrD" and resid 80 and name HA))
  3.300  2.700  2.200 peak        614  weight  0.10000E+01 volume    0.96219E+02 ppm1      8.062 ppm2    4.673
OR {614}
((segid "BrD" and resid 107 and name HZ))
((segid "BrD" and resid 118 and name HA))
OR {614}
((segid "BrD" and resid 107 and name HZ))
((segid "BrD" and resid 76 and name HA))
ASSI {704}
((segid "BrD" and resid 107 and name HZ))
((segid "BrD" and resid 79 and name HB1))
  2.800  2.000  2.000 peak        704  weight  0.10000E+01 volume    0.25291E+03 ppm1      8.009 ppm2    2.755
OR {704}
((segid "BrD" and resid 32 and name HZ2))
((segid "BrD" and resid 94 and name HB1))
ASSI {794}
((segid "BrD" and resid 32 and name HE3))
((segid "BrD" and resid 32 and name HB2))
  2.600  1.700  1.700 peak        794  weight  0.10000E+01 volume    0.39954E+03 ppm1      7.960 ppm2    4.212
OR {794}
(segid "BrD" and resid 47 and name HD%)
((segid "BrD" and resid 53 and name HD1))
ASSI {964}
((segid "BrD" and resid 34 and name HZ))
((segid "BrD" and resid 28 and name HD2))
  4.200  4.200  1.300 peak        964  weight  0.10000E+01 volume    0.22395E+02 ppm1      7.928 ppm2    5.579
OR {964}
((segid "BrD" and resid 34 and name HZ))
((segid "BrD" and resid 34 and name HA))
ASSI {974}
((segid "BrD" and resid 34 and name HZ))
((segid "BrD" and resid 98 and name HA))
  3.800  3.600  1.700 peak        974  weight  0.10000E+01 volume    0.41681E+02 ppm1      7.929 ppm2    4.791
OR {974}
((segid "BrD" and resid 34 and name HZ))
((segid "BrD" and resid 82 and name HA))
ASSI {1044}
(segid "BrD" and resid 107 and name HE%)
((segid "BrD" and resid 79 and name HA))
  2.300  1.300  1.300 peak      1044  weight  0.10000E+01 volume    0.86364E+03 ppm1      7.921 ppm2    4.440
OR {1044}
((segid "BrD" and resid 34 and name HZ))
((segid "BrD" and resid 99 and name HA))
ASSI {1074}
((segid "BrD" and resid 34 and name HZ))
(segid "BrD" and resid 102 and name HD1%)
  2.900  2.100  2.100 peak      1074  weight  0.10000E+01 volume    0.20962E+03 ppm1      7.924 ppm2    1.333
OR {1074}
(segid "BrD" and resid 107 and name HE%)
((segid "BrD" and resid 78 and name HB1))
ASSI {1084}
((segid "BrD" and resid 34 and name HZ))
((segid "BrD" and resid 98 and name HA))
  4.000  4.000  1.500 peak      1084  weight  0.10000E+01 volume    0.28521E+02 ppm1      7.913 ppm2    4.791
OR {1084}
((segid "BrD" and resid 34 and name HZ))
((segid "BrD" and resid 82 and name HA))
OR {1084}
(segid "BrD" and resid 68 and name HE%)
((segid "BrD" and resid 73 and name HA))
ASSI {1094}
(segid "BrD" and resid 107 and name HE%)
((segid "BrD" and resid 118 and name HA))
  3.200  2.600  2.300 peak      1094  weight  0.10000E+01 volume    0.10760E+03 ppm1      7.918 ppm2    4.683
OR {1094}
(segid "BrD" and resid 107 and name HE%)
((segid "BrD" and resid 76 and name HA))
OR {1094}
(segid "BrD" and resid 68 and name HE%)
((segid "BrD" and resid 58 and name HB))

TABLE 3-continued

Ambiguous NOE-derived Inter-proton Distance Restraints

OR {1094}
(segid "BrD" and resid 68 and name HE%)
((segid "BrD" and resid 67 and name HA))
OR {1094}
(segid "BrD" and resid 107 and name HE%)
((segid "BrD" and resid 104 and name HA))
OR {1094}
(segid "BrD" and resid 107 and name HE%)
((segid "BrD" and resid 80 and name HA))
OR {1094}
(segid "BrD" and resid 68 and name HE%)
((segid "BrD" and resid 69 and name HA))
ASSI {1104}
((segid "BrD" and resid 34 and name HZ))
(segid "BrD" and resid 99 and name HB%)
  2.400  1.400  1.400  peak        1104  weight  0.10000E+01  volume     0.63603E+03  ppm1       7.907  ppm2    2.212
OR {1104}
((segid "BrD" and resid 34 and name HZ))
((segid "BrD" and resid 33 and name HD2))
ASSI {1114}
(segid "BrD" and resid 68 and name HE%)
(segid "BrD" and resid 68 and name HD%)
  2.100  1.100  1.100  peak        1114  weight  0.10000E+01  volume     0.15243E+04  ppm1       7.904  ppm2    7.776
OR {1114}
(segid "BrD" and resid 107 and name HE%)
(segid "BrD" and resid 107 and name HD%)
OR {1114}
((segid "BrD" and resid 34 and name HZ))
(segid "BrD" and resid 34 and name HE%)
ASSI {1124}
((segid "BrD" and resid 34 and name HZ))
((segid "BrD" and resid 98 and name HB2))
  2.500  1.600  1.600  peak        1124  weight  0.10000E+01  volume     0.54441E+03  ppm1       7.898  ppm2    3.659
OR {1124}
(segid "BrD" and resid 107 and name HE%)
((segid "BrD" and resid 82 and name HB1))
OR {1124}
(segid "BrD" and resid 68 and name HE%)
((segid "BrD" and resid 68 and name HB1))
ASSI {1134}
(segid "BrD" and resid 68 and name HE%)
((segid "BrD" and resid 62 and name HG1))
  3.600  3.200  1.900  peak        1134  weight  0.10000E+01  volume     0.60159E+02  ppm1       7.900  ppm2    2.343
OR {1134}
(segid "BrD" and resid 68 and name HE%)
((segid "BrD" and resid 73 and name HG))
ASSI {1164}
(segid "BrD" and resid 68 and name HE%)
((segid "BrD" and resid 62 and name HG1))
  3.200  2.600  2.300  peak        1164  weight  0.10000E+01  volume     0.12306E+03  ppm1       7.896  ppm2    2.374
OR {1164}
(segid "BrD" and resid 68 and name HE%)
((segid "BrD" and resid 73 and name HG))
OR {1164}
(segid "BrD" and resid 107 and name HE%)
((segid "BrD" and resid 116 and name HB))
ASSI {1204}
(segid "BrD" and resid 68 and name HE%)
((segid "BrD" and resid 68 and name HB2))
  2.500  1.600  1.600  peak        1204  weight  0.10000E+01  volume     0.47618E+03  ppm1       7.892  ppm2    3.546
OR {1204}
(segid "BrD" and resid 68 and name HE%)
((segid "BrD" and resid 67 and name HB1))
OR {1204}
(segid "BrD" and resid 107 and name HE%)
((segid "BrD" and resid 82 and name HB2))
OR {1204}
((segid "BrD" and resid 34 and name HZ))
((segid "BrD" and resid 82 and name HB2))
ASSI {1244}
(segid "BrD" and resid 107 and name HE%)
((segid "BrD" and resid 79 and name HB2))
  2.500  1.600  1.600  peak        1244  weight  0.10000E+01  volume     0.54491E+03  ppm1       7.891  ppm2    2.644
OR {1244}
(segid "BrD" and resid 68 and name HE%)
((segid "BrD" and resid 62 and name HD2))

TABLE 3-continued

Ambiguous NOE-derived Inter-proton Distance Restraints

ASSI {1254}
(segid "BrD" and resid 107 and name HE%)
((segid "BrD" and resid 116 and name HG11)
 2.700  1.800  1.800 peak      1254  weight  0.10000E+01 volume  0.30083E+03 ppm1    7.891 ppm2    1.886
OR {1254}
(segid "BrD" and resid 68 and name HE%)
(segid "BrD" and resid 59 and name HE%)
OR {1254}
(segid "BrD" and resid 107 and name HE%)
((segid "BrD" and resid 103 and name HB2))
ASSI {1274}
((segid "BrD" and resid 34 and name HZ))
((segid "BrD" and resid 98 and name HA))
 3.400  2.900  2.100 peak      1274  weight  0.10000E+01 volume  0.84175E+02 ppm1    7.888 ppm2    4.815
OR {1274}
(segid "BrD" and resid 68 and name HE%)
((segid "BrD" and resid 73 and name HA))
ASSI {1284}
(segid "BrD" and resid 107 and name HE%)
((segid "BrD" and resid 103 and name HG2))
 2.500  1.600  1.600 peak      1284  weight  0.10000E+01 volume  0.45504E+03 ppm1    7.869 ppm2    2.554
OR {1284}
(segid "BrD" and resid 68 and name HE%)
((segid "BrD" and resid 54 and name HB1))
ASSI {1294}
(segid "BrD" and resid 107 and name HE%)
((segid "BrD" and resid 116 and name HB))
 3.300  2.700  2.200 peak      1294  weight  0.10000E+01 volume  0.10144E+03 ppm1    7.888 ppm2    2.422
OR {1294}
((segid "BrD" and resid 34 and name HZ))
((segid "BrD" and resid 101 and name HG11))
ASSI {1304}
(segid "BrD" and resid 68 and name HE%)
(segid "BrD" and resid 58 and name HG2%)
 2.600  1.700  1.700 peak      1304  weight  0.10000E+01 volume  0.38056E+03 ppm1    7.888 ppm2    1.656
OR {1304}
(segid "BrD" and resid 107 and name HE%)
((segid "BrD" and resid 110 and name HG12))
ASSI {1444}
(segid "BrD" and resid 107 and name HD%)
((segid "BrD" and resid 104 and name HA))
 2.900  2.100  2.100 peak      1444  weight  0.10000E+01 volume  0.19434E+03 ppm1    7.811 ppm2    4.684
OR {1444}
(segid "BrD" and resid 105 and name HD%)
((segid "BrD" and resid 104 and name HA))
OR {1444}
(segid "BrD" and resid 107 and name HD%)
((segid "BrD" and resid 118 and name HA))
OR {1444}
(segid "BrD" and resid 105 and name HD%)
((segid "BrD" and resid 109 and name HA))
ASSI {1504}
(segid "BrD" and resid 105 and name HD%)
((segid "BrD" and resid 105 and name HA))
 2.400  1.400  1.400 peak      1504  weight  0.10000E+01 volume  0.65395E+03 ppm1    7.798 ppm2    4.926
OR {1504}
(segid "BrD" and resid 68 and name HD%)
((segid "BrD" and resid 59 and name HA))
ASSI {1514}
(segid "BrD" and resid 107 and name HD%)
((segid "BrD" and resid 106 and name HA))
 2.800  2.000  2.000 peak      1514  weight  0.10000E+01 volume  0.27794E+03 ppm1    7.798 ppm2    4.572
OR {1514}
(segid "BrD" and resid 105 and name HD%)
((segid "BrD" and resid 106 and name HA))
OR {1514}
(segid "BrD" and resid 105 and name HD%)
((segid "BrD" and resid 108 and name HB1))
ASSI {1534}
(segid "BrD" and resid 105 and name HD%)
((segid "BrD" and resid 105 and name HB2))
 2.200  1.200  1.200 peak      1534  weight  0.10000E+01 volume  0.11824E+04 ppm1    7.799 ppm2    3.674
OR {1534}
(segid "BrD" and resid 107 and name HD%)
((segid "BrD" and resid 107 and name HB1))

TABLE 3-continued

Ambiguous NOE-derived Inter-proton Distance Restraints

ASSI {1534}
(segid "BrD" and resid 68 and name HD%)
((segid "BrD" and resid 68 and name HB1))
ASSI {1554}
(segid "BrD" and resid 34 and name HE%)
((segid "BrD" and resid 102 and name HB2))
  2.500  2.500 2.000 peak      1554  weight  0.10000E+01 volume   0.46212E+03 ppm1       7.799 ppm2    1.819
OR {1554}
(segid "BrD" and resid 68 and name HD%)
(segid "BrD" and resid 59 and name HE%)
ASSI {1574}
(segid "BrD" and resid 105 and name HD%)
((segid "BrD" and resid 102 and name HA))
  2.800  2.000 2.000 peak      1574  weight  0.10000E+01 volume   0.27340E+03 ppm1       7.797 ppm2    4.278
OR {1574}
(segid "BrD" and resid 105 and name HD%)
((segid "BrD" and resid 101 and name HA))
OR {1574}
(segid "BrD" and resid 34 and name HE%)
((segid "BrD" and resid 102 and name HA))
ASSI {1614}
(segid "BrD" and resid 68 and name HD%)
((segid "BrD" and resid 74 and name HB2))
  2.900  2.100 2.100 peak      1614  weight  0.10000E+01 volume   0.20510E+03 ppm1       7.790 ppm2    3.010
OR {1614}
(segid "BrD" and resid 105 and name HD%)
((segid "BrD" and resid 109 and name HE2))
ASSI {1624}
(segid "BrD" and resid 34 and name HE%)
((segid "BrD" and resid 33 and name HD1))
  2.800  2.000 2.000 peak      1624  weight  0.10000E+01 volume   0.23703E+03 ppm1       7.786 ppm2    2.796
OR {1624}
((segid "BrD" and resid 32 and name HZ3))
((segid "BrD" and resid 33 and name HD1))
OR {1624}
(segid "BrD" and resid 107 and name HD%)
((segid "BrD" and resid 79 and name HB1))
OR {1624}
((segid "BrD" and resid 32 and name HH2))
(segid "BrD" and resid 31 and name HB%)
ASSI {29032}
(segid "BrD" and resid 59 and name HE%)
((segid "BrD" and resid 56 and name HG))
  3.700  3.400 1.800 peak     29032  weight  0.10000E+01 volume   0.29631E+02 ppm1       1.848 ppm2    2.361
OR {29032}
(segid "BrD" and resid 59 and name HE%)
((segid "BrD" and resid 22 and name HG))
OR {29032}
(segid "BrD" and resid 59 and name HE%)
((segid "BrD" and resid 73 and name HG))
OR {29032}
(segid "BrD" and resid 59 and name HE%)
((segid "BrD" and resid 21 and name HG11))
ASSI {29072}
(segid "BrD" and resid 59 and name HE%)
((segid "BrD" and resid 22 and name HA))
  4.200  4.200 1.300 peak     29072  weight  0.10000E+01 volume   0.14615E+02 ppm1       1.848 ppm2    4.719
OR {29072}
(segid "BrD" and resid 59 and name HE%)
((segid "BrD" and resid 58 and name HB))
OR {29072}
(segid "BrD" and resid 59 and name HE%)
((segid "BrD" and resid 69 and name HA))
OR {29072}
(segid "BrD" and resid 59 and name HE%)
((segid "BrD" and resid 53 and name HA))
ASSI {29152}
(segid "BrD" and resid 59 and name HE%)
(segid "BrD" and resid 73 and name HD2%)
  3.600  3.200 1.900 peak     29152  weight  0.10000E+01 volume   0.18252E+02 ppm1       1.848 ppm2    1.462
OR {29152}
(segid "BrD" and resid 59 and name HE%)
(segid "BrD" and resid 63 and name HD2%)
OR {29152}
(segid "BrD" and resid 59 and name HE%)
((segid "BrD" and resid 62 and name HG2))

TABLE 3-continued

Ambiguous NOE-derived Inter-proton Distance Restraints

ASSI {29192}
(segid "BrD" and resid 54 and name HE%)
((segid "BrD" and resid 60 and name HB1))
  3.200  2.600  2.300 peak      29192  weight  0.10000E+01 volume    0.76364E+02 ppm1      2.536 ppm2    4.964
OR {29192}
(segid "BrD" and resid 54 and name HE%)
((segid "BrD" and resid 77 and name HA))
ASSI {29202}
(segid "BrD" and resid 54 and name HE%)
((segid "BrD" and resid 55 and name HB1))
  3.700  3.400  1.800 peak      29202  weight  0.10000E+01 volume    0.30281E+02 ppm1      2.535 ppm2    2.955
OR {29202}
(segid "BrD" and resid 54 and name HE%)
((segid "BrD" and resid 37 and name HB1))
ASSI {29252}
(segid "BrD" and resid 54 and name HE%)
(segid "BrD" and resid 35 and name HE%)
  2.500  2.500  2.000 peak      29252  weight  0.10000E+01 volume    0.29954E+03 ppm1      2.535 ppm2    2.801
OR {29252}
(segid "BrD" and resid 54 and name HE%)
((segid "BrD" and resid 53 and name HB1))
OR {29252}
(segid "BrD" and resid 54 and name HE%)
((segid "BrD" and resid 61 and name HG2))
OR {29252}
(segid "BrD" and resid 54 and name HE%)
((segid "BrD" and resid 36 and name HG1))
ASSI {29262}
(segid "BrD" and resid 54 and name HE%)
((segid "BrD" and resid 37 and name HG1))
  2.600  1.700  1.700 peak      29262  weight  0.10000E+01 volume    0.23100E+03 ppm1      2.535 ppm2    2.722
OR {29262}
(segid "BrD" and resid 54 and name HE%)
((segid "BrD" and resid 59 and name HB1))
ASSI {29582}
((segid "BrD" and resid 79 and name HA))
((segid "BrD" and resid 116 and name HG11))
  4.100  4.100  1.400 peak      29582  weight  0.10000E+01 volume    0.16991E+02 ppm1      4.409 ppm2    1.897
OR {29582}
((segid "BrD" and resid 79 and name HA))
((segid "BrD" and resid 103 and name HB2))
ASSI {29682}
((segid "BrD" and resid 108 and name HA))
((segid "BrD" and resid 111 and name HG1))
  4.100  4.100  1.400 peak      29682  weight  0.10000E+01 volume    0.16470E+02 ppm1      4.804 ppm2    2.003
OR {29682}
((segid "BrD" and resid 104 and name HA))
((segid "BrD" and resid 109 and name HD1))
ASSI {29702}
((segid "BrD" and resid 15 and name HA))
((segid "BrD" and resid 19 and name HB2))
  2.800  2.000  2.000 peak      29702  weight  0.10000E+01 volume    0.16051E+03 ppm1      4.607 ppm2    1.986
OR {29702}
((segid "BrD" and resid 104 and name HB1))
((segid "BrD" and resid 109 and name HD1))
OR {29702}
((segid "BrD" and resid 60 and name HB2))
((segid "BrD" and resid 56 and name HB2))
ASSI {29712}
((segid "BrD" and resid 15 and name HA))
((segid "BrD" and resid 18 and name HB1))
  3.100  2.400  2.400 peak      29712  weight  0.10000E+01 volume    0.92305E+02 ppm1      4.607 ppm2    2.182
OR {29712}
((segid "BrD" and resid 60 and name HB2))
((segid "BrD" and resid 64 and name HG1))
ASSI {29722}
((segid "BrD" and resid 15 and name HA))
(segid "BrD" and resid 14 and name HD2%)
  3.900  3.800  1.600 peak      29722  weight  0.10000E+01 volume    0.22638E+02 ppm1      4.607 ppm2    1.417
OR {29722}
((segid "BrD" and resid 15 and name HA))
(segid "BrD" and resid 69 and name HG2%)
ASSI {29732}
((segid "BrD" and resid 30 and name HA))
((segid "BrD" and resid 98 and name HA))
  2.600  1.700  1.700 peak      29732  weight  0.10000E+01 volume    0.26724E+03 ppm1      5.445 ppm2    4.810

TABLE 3-continued

Ambiguous NOE-derived Inter-proton Distance Restraints

OR {29732}
((segid "BrD" and resid 30 and name HA))
((segid "BrD" and resid 29 and name HA))
ASSI {30592}
((segid "BrD" and resid 109 and name HB1))
(segid "BrD" and resid 21 and name HD1%)
  3.700  3.400  1.800 peak      30592  weight  0.10000E+01 volume    0.31262E+02 ppm1      2.334 ppm2    1.222
OR {30592}
((segid "BrD" and resid 109 and name HB1))
(segid "BrD" and resid 110 and name HG2%)
ASSI {30672}
((segid "BrD" and resid 109 and name HB2))
((segid "BrD" and resid 110 and name HA))
  3.600  3.200  1.900 peak      30672  weight  0.10000E+01 volume    0.39278E+02 ppm1      2.141 ppm2    4.378
OR {30672}
((segid "BrD" and resid 109 and name HB2))
((segid "BrD" and resid 107 and name HA))
ASSI {30952}
(segid "BrD" and resid 75 and name HA))
((segid "BrD" and resid 78 and name HG))
  3.800  3.600  1.700 peak      30952  weight  0.10000E+01 volume    0.28077E+02 ppm1      4.509 ppm2    1.260
OR {30952}
((segid "BrD" and resid 26 and name HA))
(segid "BrD" and resid 56 and name HD2%)
ASSI {83}
(segid "BrD" and resid 46 and name HD%)
((segid "BrD" and resid 47 and name HA))
  2.300  2.300  2.200 peak         83  weight  0.10000E+01 volume    0.20163E+03 ppm1      5.756 ppm2    4.693
OR {83}
(segid "BrD" and resid 46 and name HD%)
((segid "BrD" and resid 53 and name HA))
ASSI {533}
(segid "BrD" and resid 47 and name HE%)
((segid "BrD" and resid 38 and name HB))
  3.200  2.600  2.300 peak       533  weight  0.10000E+01 volume    0.34245E+02 ppm1      7.246 ppm2    1.776
OR {533}
(segid "BrD" and resid 47 and name HE%)
((segid "BrD" and resid 50 and name HB))
ASSI {643}
(segid "BrD" and resid 74 and name HD%)
((segid "BrD" and resid 71 and name HA))
  3.100  2.400  2.400 peak       643  weight  0.10000E+01 volume    0.35398E+02 ppm1      7.012 ppm2    4.622
OR {643}
(segid "BrD" and resid 74 and name HD%)
((segid "BrD" and resid 15 and name HA))
OR {643}
(segid "BrD" and resid 74 and name HD%)
((segid "BrD" and resid 76 and name HA))
OR {643}
(segid "BrD" and resid 74 and name HD%)
((segid "BrD" and resid 56 and name HA))
OR {643}
(segid "BrD" and resid 74 and name HD%)
((segid "BrD" and resid 72 and name HA))
OR {643}
(segid "BrD" and resid 74 and name HD%)
((segid "BrD" and resid 14 and name HA))
ASSI {1143}
(segid "BrD" and resid 105 and name HD%)
(segid "BrD" and resid 101 and name HG2%)
  3.100  2.400  2.400 peak      1143  weight  0.10000E+01 volume    0.36890E+02 ppm1      7.758 ppm2    1.631
OR {1143}
(segid "BrD" and resid 105 and name HD%)
(segid "BrD" and resid 21 and name HG2%)
ASSI {1393}
(segid "BrD" and resid 96 and name HD%)
((segid "BrD" and resid 86 and name HA))
  2.200  2.200  2.300 peak      1393  weight  0.10000E+01 volume    0.26898E+03 ppm1      7.711 ppm2    4.810
OR {1393}
(segid "BrD" and resid 96 and name HD%)
((segid "BrD" and resid 92 and name HA))
ASSI {1763}
(segid "BrD" and resid 106 and name HE%)
((segid "BrD" and resid 107 and name HA))
  3.400  2.900  2.100 peak      1763  weight  0.10000E+01 volume    0.21871E+02 ppm1      7.617 ppm2    4.431

TABLE 3-continued

Ambiguous NOE-derived Inter-proton Distance Restraints

```
OR {1763}
(segid "BrD" and resid 106 and name HE%)
((segid "BrD" and resid 79 and name HA))
OR {1763}
(segid "BrD" and resid 106 and name HE%)
((segid "BrD" and resid 110 and name HA))
ASSI {1783}
(segid "BrD" and resid 106 and name HE%)
(segid "BrD" and resid 74 and name HD%)
   3.700  3.400  1.800 peak         1783  weight  0.10000E+01 volume    0.23872E+02 ppm1       7.617 ppm2    7.027
OR {1783}
(segid "BrD" and resid 106 and name HE%)
(segid "BrD" and resid 82 and name HE%)
OR {1783}
(segid "BrD" and resid 106 and name HE%)
((segid "BrD" and resid 82 and name HZ))
ASSI {1813}
(segid "BrD" and resid 95 and name HD%)
((segid "BrD" and resid 94 and name HA))
   3.300  2.700  2.200 peak         1813  weight  0.10000E+01 volume    0.28141E+02 ppm1       1.478 ppm2    4.810
OR {1813}
(segid "BrD" and resid 95 and name HD%)
((segid "BrD" and resid 86 and name HA))
ASSI {1893}
(segid "BrD" and resid 96 and name HE%)
((segid "BrD" and resid 96 and name HA))
   3.600  3.200  1.900 peak         1893  weight  0.10000E+01 volume    0.14793E+02 ppm1       7.618 ppm2    4.387
OR {1893}
(segid "BrD" and resid 95 and name HE%)
((segid "BrD" and resid 33 and name HA))
ASSI {2063}
((segid "BrD" and resid 32 and name HZ3))
((segid "BrD" and resid 32 and name HA))
   5.500  5.500  0.000 peak         2063  weight  0.10000E+01 volume    0.11153E+03 ppm1       7.804 ppm2    4.971
OR {2063}
((segid "BrD" and resid 32 and name HZ3))
((segid "BrD" and resid 93 and name HB1))
OR {2063}
((segid "BrD" and resid 32 and name HZ3))
((segid "BrD" and resid 85 and name HA))
ASSI {24}
(segid "BrD" and resid 46 and name HE%)
((segid "BrD" and resid 50 and name HB))
   3.600  3.200  1.900 peak           24  weight  0.10000E+01 volume    0.55296E+02 ppm1       6.687 ppm2    1.777
OR {24}
(segid "BrD" and resid 46 and name HE%)
((segid "BrD" and resid 38 and name HB))
ASSI {94}
(segid "BrD" and resid 82 and name HD%)
((segid "BrD" and resid 79 and name HA))
   2.200  1.200  1.200 peak           94  weight  0.10000E+01 volume    0.10359E+04 ppm1       7.266 ppm2    4.424
OR {94}
(segid "BrD" and resid 82 and name HD%)
((segid "BrD" and resid 99 and name HA))
ASSI {104}
(segid "BrD" and resid 47 and name HE%)
((segid "BrD" and resid 53 and name HG2))
   2.500  1.600  1.600 peak          104  weight  0.10000E+01 volume    0.51584E+03 ppm1       7.270 ppm2    2.504
OR {104}
(segid "BrD" and resid 82 and name HD%)
((segid "BrD" and resid 103 and name HG2))
ASSI {124}
(segid "BrD" and resid 47 and name HD%)
((segid "BrD" and resid 50 and name HG12))
   3.600  3.200  1.900 peak          124  weight  0.10000E+01 volume    0.55730E+02 ppm1       7.970 ppm2    0.780
OR {124}
(segid "BrD" and resid 47 and name HD%)
(segid "BrD" and resid 38 and name HG2%)
ASSI {134}
(segid "BrD" and resid 47 and name HD%)
((segid "BrD" and resid $$3 and name HD2))
   2.900  2.100  2.100 peak          134  weight  0.10000E+01 volume    0.18431E+03 ppm1       7.970 ppm2    4.007
OR {134}
((segid "BrD" and resid 32 and name HZ2)
((segid "BrD" and resid 98 and name HB1))
```

TABLE 3-continued

Ambiguous NOE-derived Inter-proton Distance Restraints

ASSI {554}
((segid "BrD" and resid 28 and name HE1))
((segid "BrD" and resid 30 and name HB2))
 2.900  2.100  2.100 peak        554  weight  0.10000E+01 volume   0.21924E+03 ppm1      8.158 ppm2    4.538
OR {554}
((segid "BrD" and resid 28 and name HE1))
((segid "BrD" and resid 28 and name HA))
ASSI {574}
(segid "BrD" and resid 68 and name HE%)
((segid "BrD" and resid 59 and name HA))
 3.200  2.600  2.300 peak        574  weight  0.10000E+01 volume   0.10500E+03 ppm1      7.921 ppm2    4.930
OR {574}
((segid "BrD" and resid 32 and name HE3))
((segid "BrD" and resid 32 and name HA))
ASSI {604}
((segid "BrD" and resid 107 and name HZ))
((segid "BrD" and resid 83 and name HB))
 3.500  3.100  2.000 peak        604  weight  0.10000E+01 volume   0.65660E+02 ppm1      8.063 ppm2    4.784
OR {604}
((segid "BrD" and resid 107 and name HZ))
((segid "BrD" and resid 82 and name HA))
ASSI {614}
((segid "BrD" and resid 107 and name HZ))
((segid "BrD" and resid 80 and name HA))
 3.300  2.700  2.200 peak        614  weight  0.10000E+01 volume   0.96219E+02 ppm1      8.062 ppm2    4.673
OR {614}
((segid "BrD" and resid 107 and name HZ))
((segid "BrD" and resid 118 and name HA))
OR {614}
((segid "BrD" and resid 107 and name HZ))
((segid "BrD" and resid 76 and name HA))
ASSI {704}
((segid "BrD" and resid 107 and name HZ))
((segid "BrD" and resid 79 and name HB1))
 2.800  2.000  2.000 peak        704  weight  0.10000E+01 volume   0.25291E+03 ppm1      8.009 ppm2    2.755
OR {704}
((segid "BrD" and resid 32 and name HZ2))
((segid "BrD" and resid 94 and name HB1))
ASSI {794}
((segid "BrD" and resid 32 and name HE3))
((segid "BrD" and resid 32 and name HB2))
 2.600  1.700  1.700 peak        794  weight  0.10000E+01 volume   0.39954E+03 ppm1      7.960 ppm2    4.212
OR {794}
(segid "BrD" and resid 47 and name HD%)
((segid "BrD" and resid 53 and name HD1))
ASSI {964}
((segid "BrD" and resid 34 and name HZ))
((segid "BrD" and resid 28 and name HD2))
 4.200  4.200  1.300 peak        964  weight  0.10000E+01 volume   0.22395E+02 ppm1      7.928 ppm2    5.579
OR {964}
((segid "BrD" and resid 34 and name HZ))
((segid "BrD" and resid 34 and name HA))
ASSI {974}
((segid "BrD" and resid 34 and name HZ))
((segid "BrD" and resid 98 and name HA))
 3.800  3.600  1.700 peak        974  weight  0.10000E+01 volume   0.41681E+02 ppm1      7.929 ppm2    4.791
OR {974}
((segid "BrD" and resid 34 and name HZ))
((segid "BrD" and resid 82 and name HA))
ASSI {1044}
(segid "BrD" and resid 107 and name HE%)
((segid "BrD" and resid 79 and name HA))
 2.300  1.300  1.300 peak       1044  weight  0.10000E+01 volume   0.86364E+03 ppm1      7.921 ppm2    4.440
OR {1044}
((segid "BrD" and resid 34 and name HZ))
((segid "BrD" and resid 99 and name HA))
ASSI {1074}
((segid "BrD" and resid 34 and name HZ))
(segid "BrD" and resid 102 and name HD1%)
 2.900  2.100  2.100 peak       1074  weight  0.10000E+01 volume   0.20962E+03 ppm1      7.924 ppm2    1.333
OR {1074}
(segid "BrD" and resid 107 and name HE%)
((segid "BrD" and resid 78 and name HB1))
ASSI {1084}
((segid "BrD" and resid 34 and name HZ))
((segid "BrD" and resid 98 and name HA))
 4.000  4.000  1.500 peak       1084  weight  0.10000E+01 volume   0.28521E+02 ppm1      7.913 ppm2    4.791

TABLE 3-continued

Ambiguous NOE-derived Inter-proton Distance Restraints

OR {1084}
((segid "BrD" and resid 34 and name HZ))
((segid "BrD" and resid 82 and name HA))
OR {1084}
(segid "BrD" and resid 68 and name HE%)
((segid "BrD" and resid 73 and name HA))
ASSI {1094}
(segid "BrD" and resid 107 and name HE%)
((segid "BrD" and resid 118 and name HA))
  3.200  2.600  2.300 peak      1094  weight  0.10000E+01 volume    0.10760E+03 ppm1    7.918 ppm2    4.683
OR {1094}
(segid "BrD" and resid 107 and name HE%)
((segid "BrD" and resid 76 and name HA))
OR {1094}
(segid "BrD" and resid 68 and name HE%)
((segid "BrD" and resid 58 and name HB))
OR {1094}
(segid "BrD" and resid 68 and name HE%)
((segid "BrD" and resid 67 and name HA))
OR {1094}
(segid "BrD" and resid 107 and name HE%)
((segid "BrD" and resid 104 and name HA))
OR {1094}
(segid "BrD" and resid 107 and name HE%)
((segid "BrD" and resid 80 and name HA))
OR {1094}
(segid "BrD" and resid 68 and name HE%)
((segid "BrD" and resid 69 and name HA))
ASSI {1104}
((segid "BrD" and resid 34 and name HZ))
(segid "BrD" and resid 99 and name HB%)
  2.400  1.400  1.400 peak      1104  weight  0.10000E+01 volume    0.63603E+03 ppm1    7.907 ppm2    2.212
OR {1104}
((segid "BrD" and resid 34 and name HZ))
((segid "BrD" and resid 33 and name HD2))
ASSI {1114}
(segid "BrD" and resid 68 and name HE%)
(segid "BrD" and resid 68 and name HD%)
  2.100  1.100  1.100 peak      1114  weight  0.10000E+01 volume    0.15243E+04 ppm1    7.904 ppm2    7.776
OR {1114}
(segid "BrD" and resid 107 and name HE%)
(segid "BrD" and resid 107 and name HD%)
OR {1114}
((segid "BrD" and resid 34 and name HZ))
(segid "BrD" and resid 34 and name HE%)
ASSI {1124}
((segid "BrD" and resid 34 and name HZ))
((segid "BrD" and resid 98 and name HB2))
  2.500  1.600  1.600 peak      1124  weight  0.10000E+01 volume    0.54441E+03 ppm1    7.898 ppm2    3.659
OR {1124}
(segid "BrD" and resid 107 and name HE%)
((segid "BrD" and resid 82 and name HB1))
OR {1124}
(segid "BrD" and resid 68 and name HE%)
((segid "BrD" and resid 68 and name HB1))
ASSI {1134}
(segid "BrD" and resid 68 and name HE%)
((segid "BrD" and resid 62 and name HG1))
  3.600  3.200  1.900 peak      1134  weight  0.10000E+01 volume    0.60159E+02 ppm1    7.900 ppm2    2.343
OR {1134}
(segid "BrD" and resid 68 and name HE%)
((segid "BrD" and resid 73 and name HG))
ASSI {1164}
(segid "BrD" and resid 68 and name HE%)
((segid "BrD" and resid 62 and name HG1))
  3.200  2.600  2.300 peak      1164  weight  0.10000E+01 volume    0.12306E+03 ppm1    7.896 ppm2    2.374
OR {1164}
(segid "BrD" and resid 68 and name HE%)
((segid "BrD" and resid 73 and name HG))
OR {1164}
(segid "BrD" and resid 107 and name HE%)
((segid "BrD" and resid 116 and name HB))
ASSI {1204}
(segid "BrD" and resid 68 and name HE%)
((segid "BrD" and resid 68 and name HB2))
  2.500  1.600  1.600 peak      1204  weight  0.10000E+01 volume    0.47618E+03 ppm1    7.892 ppm2    3.546

TABLE 3-continued

Ambiguous NOE-derived Inter-proton Distance Restraints

OR {1204}
(segid "BrD" and resid 68 and name HE%)
((segid "BrD" and resid 67 and name HB1))
OR {1204}
(segid "BrD" and resid 107 and name HE%)
((segid "BrD" and resid 82 and name HB2))
OR {1204}
((segid "BrD" and resid 34 and name HZ))
((segid "BrD" and resid 82 and name HB2))
ASSI {1244}
(segid "BrD" and resid 107 and name HE%)
((segid "BrD" and resid 79 and name HB2))
  2.500  1.600  1.600 peak      1244  weight  0.10000E+01 volume  0.54491E+03 ppm1      7.891 ppm2    2.644
OR {1244}
(segid "BrD" and resid 68 and name HE%)
((segid "BrD" and resid 62 and name HD2))
ASSI {1254}
(segid "BrD" and resid 107 and name HE%)
((segid "BrD" and resid 116 and name HG11)
  2.700  1.800  1.800 peak      1254  weight  0.10000E+01 volume  0.30083E+03 ppm1      7.891 ppm2    1.886
OR {1254}
(segid "BrD" and resid 68 and name HE%)
(segid "BrD" and resid 59 and name HE%)
OR {1254}
(segid "BrD" and resid 107 and name HE%)
((segid "BrD" and resid 103 and name HB2))
ASSI {1274}
((segid "BrD" and resid 34 and name HZ))
((segid "BrD" and resid 98 and name HA))
  3.400  2.900  2.100 peak      1274  weight  0.10000E+01 volume  0.84175E+02 ppm1      7.888 ppm2    4.815
OR {1274}
(segid "BrD" and resid 68 and name HE%)
((segid "BrD" and resid 73 and name HA))
ASSI {1284}
(segid "BrD" and resid 107 and name HE%)
((segid "BrD" and resid 103 and name HG2))
  2.500  1.600  1.600 peak      1284  weight  0.10000E+01 volume  0.45504E+03 ppm1      7.869 ppm2    2.554
OR {1284}
(segid "BrD" and resid 68 and name HE%)
((segid "BrD" and resid 54 and name HB1))
ASSI {1294}
(segid "BrD" and resid 107 and name HE%)
((segid "BrD" and resid 116 and name HB))
  3.300  2.700  2.200 peak      1294  weight  0.10000E+01 volume  0.10144E+03 ppm1      7.888 ppm2    2.422
OR {1294}
((segid "BrD" and resid 34 and name HZ))
((segid "BrD" and resid 101 and name HG11))
ASSI {1304}
(segid "BrD" and resid 68 and name HE%)
(segid "BrD" and resid 58 and name HG2%)
  2.600  1.700  1.700 peak      1304  weight  0.10000E+01 volume  0.38056E+03 ppm1      7.888 ppm2    1.656
OR {1304}
(segid "BrD" and resid 107 and name HE%)
((segid "BrD" and resid 110 and name HG12))
ASSI {1444}
(segid "BrD" and resid 107 and name HD%)
((segid "BrD" and resid 104 and name HA))
  2.900  2.100  2.100 peak      1444  weight  0.10000E+01 volume  0.19434E+03 ppm1      7.811 ppm2    4.684
OR {1444}
(segid "BrD" and resid 105 and name HD%)
((segid "BrD" and resid 104 and name HA))
OR {1444}
(segid "BrD" and resid 107 and name HD%)
((segid "BrD" and resid 118 and name HA))
OR {1444}
(segid "BrD" and resid 105 and name HD%)
((segid "BrD" and resid 109 and name HA))
ASSI {1504}
(segid "BrD" and resid 105 and name HD%)
((segid "BrD" and resid 105 and name HA))
  2.400  1.400  1.400 peak      1504  weight  0.10000E+01 volume  0.65395E+03 ppm1      7.798 ppm2    4.926
OR {1504}
(segid "BrD" and resid 68 and name HD%)
((segid "BrD" and resid 59 and name HA))

TABLE 3-continued

Ambiguous NOE-derived Inter-proton Distance Restraints

ASSI {1514}
(segid "BrD" and resid 107 and name HD%)
((segid "BrD" and resid 106 and name HA))
  2.800  2.000  2.000 peak      1514 weight  0.10000E+01 volume  0.27794E+03 ppm1      7.798 ppm2     4.572
OR {1514}
(segid "BrD" and resid 105 and name HD%)
((segid "BrD" and resid 106 and name HA))
OR {1514}
(segid "BrD" and resid 105 and name HD%)
((segid "BrD" and resid 108 and name HB1))
ASSI {1534}
(segid "BrD" and resid 105 and name HD%)
((segid "BrD" and resid 105 and name HB2))
  2.200  1.200  1.200 peak      1534 weight  0.10000E+01 volume  0.11824E+04 ppm1      7.799 ppm2     3.674
OR {1534}
(segid "BrD" and resid 107 and name HD%)
((segid "BrD" and resid 107 and name HB1))
ASSI {1534}
(segid "BrD" and resid 68 and name HD%)
((segid "BrD" and resid 68 and name HB1))
ASSI {1554}
(segid "BrD" and resid 34 and name HE%)
((segid "BrD" and resid 102 and name HB2))
  2.500  2.500  2.000 peak      1554 weight  0.10000E+01 volume  0.46212E+03 ppm1      7.799 ppm2     1.819
OR {1554}
(segid "BrD" and resid 68 and name HD%)
(segid "BrD" and resid 59 and name HE%)
ASSI {1574}
(segid "BrD" and resid 105 and name HD%)
((segid "BrD" and resid 102 and name HA))
  2.800  2.000  2.000 peak      1574 weight  0.10000E+01 volume  0.27340E+03 ppm1      7.797 ppm2     4.278
OR {1574}
(segid "BrD" and resid 105 and name HD%)
((segid "BrD" and resid 101 and name HA))
OR {1574}
(segid "BrD" and resid 34 and name HE%)
((segid "BrD" and resid 102 and name HA))
ASSI {1614}
(segid "BrD" and resid 68 and name HD%)
((segid "BrD" and resid 74 and name HB2))
  2.900  2.100  2.100 peak      1614 weight  0.10000E+01 volume  0.20510E+03 ppm1      7.790 ppm2     3.010
OR {1614}
(segid "BrD" and resid 105 and name HD%)
((segid "BrD" and resid 109 and name HE2))
ASSI {1624}
(segid "BrD" and resid 34 and name HE%)
((segid "BrD" and resid 33 and name HD1))
  2.800  2.000  2.000 peak      1624 weight  0.10000E+01 volume  0.23703E+03 ppm1      7.786 ppm2     2.796
OR {1624}
((segid "BrD" and resid 32 and name HZ3))
((segid "BrD" and resid 33 and name HD1))
OR {1624}
(segid "BrD" and resid 107 and name HD%)
(segid "BrD" and resid 79 and name HB1))
OR {1624}
((segid "BrD" and resid 32 and name HH2))
((segid "BrD" and resid 33 and name HD1))
ASSI {1654}
(segid "BrD" and resid 34 and name HE%)
((segid "BrD" and resid 85 and name HB1))
  2.600  1.700  1.700 peak      1654 weight  0.10000E+01 volume  0.16960E+03 ppm1      7.784 ppm2     3.920
OR {1654}
(segid "BrD" and resid 107 and name HD%)
((segid "BrD" and resid 106 and name HB1))
ASSI {1664}
(segid "BrD" and resid 34 and name HE%)
(segid "BrD" and resid 99 and name HB%)
  2.400  1.400  1.400 peak      1664 weight  0.10000E+01 volume  0.66064E+03 ppm1      7.786 ppm2     2.211
OR {1664}
(segid "BrD" and resid 34 and name HE%)
((segid "BrD" and resid 33 and name HD2))
ASSI {1674}
((segid "BrD" and resid 32 and name HH2))
((segid "BrD" and resid 33 and name HG1))
  3.300  2.700  2.200 peak      1674 weight  0.10000E+01 volume  0.96896E+02 ppm1      7.786 ppm2     0.876

TABLE 3-continued

Ambiguous NOE-derived Inter-proton Distance Restraints

OR {1674}
((segid "BrD" and resid 32 and name HZ3))
((segid "BrD" and resid 33 and name HG1))
OR {1674}
(segid "BrD" and resid 34 and name HE%)
((segid "BrD" and resid 33 and name HG1))
ASSI {1684}
(segid "BrD" and resid 34 and name HE%)
((segid "BrD" and resid 98 and name HA))
  3.400  2.900  2.100 peak        1684  weight  0.10000E+01 volume    0.73775E+02 ppm1    7.783 ppm2    4.815
OR {1684}
((segid "BrD" and resid 32 and name HH2))
((segid "BrD" and resid 94 and name HA))
OR {1684}
(segid "BrD" and resid 68 and name HD%)
((segid "BrD" and resid 73 and name HA))
OR {1684}
(segid "BrD" and resid 107 and name HD%)
((segid "BrD" and resid 108 and name HA))
OR {1684}
(segid "BrD" and resid 68 and name HD%)
((segid "BrD" and resid 60 and name HA))
OR {1684}
((segid "BrD" and resid 32 and name HH2))
((segid "BrD" and resid 98 and name HA))
OR {1684}
(segid "BrD" and resid 34 and name HE%)
((segid "BrD" and resid 86 and name HA))
OR {1684}
(segid "BrD" and resid 107 and name HD%)
((segid "BrD" and resid 116 and name HA))
OR {1684}
(segid "BrD" and resid 105 and name HD%)
((segid "BrD" and resid 108 and name HA))
OR {1684}
((segid "BrD" and resid 32 and name HZ3))
((segid "BrD" and resid 94 and name HA))
ASSI {1704}
(segid "BrD" and resid 68 and name HD%)
((segid "BrD" and resid 62 and name HD1))
  2.700  1.800  1.800 peak        1704  weight  0.10000E+01 volume    0.31213E+03 ppm1    7.787 ppm2    3.153
OR {1704}
(segid "BrD" and resid 105 and name HD%)
((segid "BrD" and resid 109 and name HE1))
ASSI {1714}
(segid "BrD" and resid 68 and name HD%)
((segid "BrD" and resid 62 and name HB1))
  2.300  1.300  1.300 peak        1714  weight  0.10000E+01 volume    0.79418E+03 ppm1    7.779 ppm2    2.602
OR {1714}
(segid "BrD" and resid 107 and name HD%)
((segid "BrD" and resid 103 and name HG1))
OR {1714}
(segid "BrD" and resid 68 and name HD%)
((segid "BrD" and resid 62 and name HD2))
ASSI {1734}
(segid "BrD" and resid 68 and name HD%)
((segid "BrD" and resid 62 and name HG1))
  2.900  2.100  2.100 peak        1734  weight  0.10000E+01 volume    0.18466E+03 ppm1    7.781 ppm2    2.324
OR {1734}
(segid "BrD" and resid 34 and name HE%)
((segid "BrD" and resid 31 and name HB%))
OR {1734}
(segid "BrD" and resid 107 and name HD%)
((segid "BrD" and resid 110 and name HB))
OR {1734}
(segid "BrD" and resid 68 and name HD%)
((segid "BrD" and resid 73 and name HG))
ASSI {1744}
(segid "BrD" and resid 107 and name HD%)
((segid "BrD" and resid 110 and name HG12))
  2.300  1.300  1.300 peak        1744  weight  0.10000E+01 volume    0.92480E+03 ppm1    7.781 ppm2    1.641
OR {1744}
(segid "BrD" and resid 34 and name HE%)
(segid "BrD" and resid 25 and name HG2%)

TABLE 3-continued

Ambiguous NOE-derived Inter-proton Distance Restraints

ASSI {1784}
(segid "BrD" and resid 68 and name HD%)
((segid "BrD" and resid 62 and name HG1))
  2.400  2.000  2.000 peak      1784  weight  0.10000E+01 volume    0.24728E+01 ppm1      7.781 ppm2    2.374
OR {1784}
(segid "BrD" and resid 107 and name HD%)
((segid "BrD" and resid 110 and name HB))
OR {1784}
(segid "BrD" and resid 68 and name HD%)
((segid "BrD" and resid 73 and name HG))
ASSI {1804}
(segid "BrD" and resid 68 and name HD%)
((segid "BrD" and resid 62 and name HG2))
  2.700  1.800  1.800 peak      18.4  weight  0.10000E+01 volume    0.30580E+03 ppm1      7.781 ppm2    1.503
OR {1804}
(segid "BrD" and resid 68 and name HD%)
(segid "BrD" and resid 73 and name HD2%)
ASSI {1884}
(segid "BrD" and resid 96 and name HD%)
((segid "BrD" and resid 92 and name HD1))
  2.900  2.100  2.100 peak      1884  weight  0.10000E+01 volume    0.22072E+03 ppm1      7.726 ppm2    2.666
OR {1884}
(segid "BrD" and resid 34 and name HD%)
((segid "BrD" and resid 56 and name HB1))
ASSI {1924}
(segid "BrD" and resid 96 and name HD%)
(segid "BrD" and resid 99 and name HB%)
  2.500  1.600  1.600 peak      1924  weight  0.10000E+01 volume    0.55504E+03 ppm1      7.721 ppm2    2.211
OR {1924}
(segid "BrD" and resid 34 and name HD%)
((segid "BrD" and resid 33 and name HD2))
ASSI {1964}
(segid "BrD" and resid 96 and name HD%)
((segid "BrD" and resid 92 and name HG1))
  2.800  2.000  2.000 peak      1964  weight  0.10000E+01 volume    0.22599E+03 ppm1      7.714 ppm2    2.796
OR {1964}
(segid "BrD" and resid 34 and name HD%)
((segid "BrD" and resid 33 and name HD1))
OR {1964}
(segid "BrD" and resid 34 and name HD%)
(segid "BrD" and resid 35 and name HE%)
ASSI {1974}
(segid "BrD" and resid 96 and name HD%)
((segid "BrD" and resid 86 and name HB1))
  2.300  2.300  3.200 peak      1974  weight  0.10000E+01 volume    0.79213E+03 ppm1      7.717 ppm2    2.321
OR {1974}
(segid "BrD" and resid 34 and name HD%)
(segid "BrD" and resid 31 and name HB%)
ASSI {1994}
(segid "BrD" and resid 34 and name HD%)
(segid "BrD" and resid 81 and name HG2%)
  2.400  1.400  1.400 peak      1994  weight  0.10000E+01 volume    0.69140E+03 ppm1      7.717 ppm2    0.762
OR {1994}
(segid "BrD" and resid 96 and name HD%)
((segid "BrD" and resid 84 and name HG2))
ASSI {2054}
(segid "BrD" and resid 34 and name HD%)
((segid "BrD" and resid 81 and name HB))
  2.900  2.100  2.100 peak      2.54  weight  0.10000E+01 volume    0.18901E+03 ppm1      7.709 ppm2    2.033
OR {2054}
(segid "BrD" and resid 34 and name HD%)
((segid "BrD" and resid 56 and name HB2))
ASSI {2064}
(segid "BrD" and resid 34 and name HD%)
((segid "BrD" and resid 33 and name HB1))
  2.800  2.000  2.000 peak      2064  weight  0.10000E+01 volume    0.24003E+03 ppm1      7.714 ppm2    1.088
OR {2064}
(segid "BrD" and resid 34 and name HD%)
(segid "BrD" and resid 81 and name HG1%)
ASSI {2134}
(segid "BrD" and resid 15 and name HD%)
((segid "BrD" and resid 19 and name HE1))
  4.000  4.000  1.500 peak      2134  weight  0.10000E+01 volume    0.29314E+02 ppm1      7.692 ppm2    3.512
OR {2134}
(segid "BrD" and resid 96 and name HD%)
((segid "BrD" and resid 89 and name HB2))

TABLE 3-continued

Ambiguous NOE-derived Inter-proton Distance Restraints

ASSI {2274}
(segid "BrD" and resid 106 and name HE%)
(segid "BrD" and resid 59 and name HE%)
  3.400  2.900  2.100 peak      2274  weight  0.10000E+01 volume    0.79128E+02 ppm1      7.640 ppm2    1.820
OR {2274}
(segid "BrD" and resid 106 and name HE%)
(segid "BrD" and resid 25 and name HG1%)
ASSI {2294}
(segid "BrD" and resid 106 and name HE%)
(segid "BrD" and resid 21 and name HG2%)
  2.600  1.700  1.700 peak      2294  weight  0.10000E+01 volume    0.41702E+03 ppm1      7.643 ppm2    1.593
OR {2294}
(segid "BrD" and resid 106 and name HE%)
((segid "BrD" and resid 116 and name HG12))
ASSI {2314}
(segid "BrD" and resid 106 and name HE%)
((segid "BrD" and resid 106 and name HB2))
  4.000  4.000  1.500 peak      2314  weight  0.10000E+01 volume    0.29399E+02 ppm1      7.633 ppm2    3.693
OR {2314}
(segid "BrD" and resid 95 and name HE%)
((segid "BrD" and resid 89 and name HB1))
OR {2314}
(segid "BrD" and resid 88 and name HD%)
((segid "BrD" and resid 89 and name HB1))
OR {2314}
(segid "BrD" and resid 106 and name HE%)
((segid "BrD" and resid 107 and name HB1))
ASSI {2324}
(segid "BrD" and resid 106 and name HE%)
(segid "BrD" and resid 21 and name HG2%)
  2.600  1.700  1.700 peak      2324  weight  0.10000E+01 volume    0.43383E+03 ppm1      7.616 ppm2    1.576
OR {2324}
(segid "BrD" and resid 88 and name HD%)
(segid "BrD" and resid 49 and name HG2%)
OR {2324}
(segid "BrD" and resid 106 and name HE%)
((segid "BrD" and resid 116 and name HG12))
ASSI {2334}
(segid "BrD" and resid 95 and name HE%)
((segid "BrD" and resid 33 and name HB1))
  2.900  2.100  2.100 peak      2334  weight  0.10000E+01 volume    0.19423E+03 ppm1      7.623 ppm2    1095
OR {2334}
(segid "BrD" and resid 106 and name HE%)
(segid "BrD" and resid 18 and name HD1%)
ASSI {2344}
(segid "BrD" and resid 95 and name HE%)
((segid "BrD" and resid 32 and name HZ2))
  3.300  2.700  2.200 peak      2344  weight  0.10000E+01 volume    0.91993E+02 ppm1      7.615 ppm2    8.004
OR {2344}
(segid "BrD" and resid 106 and name HE%)
((segid "BrD" and resid 107 and name HZ))
ASSI {2364}
(segid "BrD" and resid 95 and name HE%)
((segid "BrD" and resid 95 and name HA))
  3.000  2.200  2.200 peak      2354  weight  0.10000E+01 volume    0.18109E+03 ppm1      7.619 ppm2    4.448
OR {2354}
(segid "BrD" and resid 96 and name HE%)
((segid "BrD" and resid 96 and name HA))
OR {2354}
(segid "BrD" and resid 106 and name HE%)
((segid "BrD" and resid 107 and name HA))
OR {2354}
(segid "BrD" and resid 106 and name HE%)
((segid "BrD" and resid 79 and name HA))
ASSI {2364}
(segid "BrD" and resid 95 and name HE%)
((segid "BrD" and resid 33 and name HA))
  3.200  2.600  2.300 peak      2364  weight  0.10000E+01 volume    0.11374E+03 ppm1      7.617 ppm2    4.366
OR {2364}
(segid "BrD" and resid 106 and name HE%)
((segid "BrD" and resid 21 and name HA))
ASSI {2374}
(segid "BrD" and resid 88 and name HD%)
((segid "BrD" and resid 87 and name HB1))
  3.000  2.200  2.200 peak      2374  weight  0.10000E+01 volume    0.17346E+03 ppm1      7.619 ppm2    2.771

TABLE 3-continued

Ambiguous NOE-derived Inter-proton Distance Restraints

```
OR {2374}
(segid "BrD" and resid 106 and name HE%)
((segid "BrD" and resid 79 and name HB1))
OR {2374}
(segid "BrD" and resid 95 and name HE%)
((segid "BrD" and resid 33 and name HD1))
OR {2374}
(segid "BrD" and resid 88 and name HD%)
((segid "BrD" and resid 87 and name HG2))
ASSI {2404}
(segid "BrD" and resid 106 and name HE%)
(segid "BrD" and resid 75 and name HE%)
  2.800  2.000  2.000 peak       2404  weight  0.10000E+01 volume   0.24430E+03 ppm1    7.425 ppm2   2.618
OR {2404}
(segid "BrD" and resid 88 and name HD%)
((segid "BrD" and resid 49 and name HB))
ASSI {2424}
(segid "BrD" and resid 88 and name HD%)
(segid "BrD" and resid 49 and name HG1%)
  2.600  1.700  1.700 peak       2424  weight  0.10000E+01 volume   0.35330E+03 ppm1    7.616 ppm2   1.658
OR {2424}
(segid "BrD" and resid 106 and name HE%)
((segid "BrD" and resid 21 and name HG12))
ASSI {2454}
(segid "BrD" and resid 106 and name HE%)
((segid "BrD" and resid 17 and name HB))
  2.500  1.600  1.600 peak       2454  weight  0.10000E+01 volume   0.48101E+03 ppm1    7.611 ppm2   4.815
OR {2454}
(segid "BrD" and resid 96 and name HE%)
((segid "BrD" and resid 86 and name HA))
OR {2454}
(segid "BrD" and resid 96 and name HE%)
((segid "BrD" and resid 97 and name HA))
OR {2454}
(segid "BrD" and resid $$ and name HD%)
((segid "BrD" and resid 87 and name HA))
OR {2454}
(segid "BrD" and resid 96 and name HE%)
((segid "BrD" and resid 92 and name HA))
OR {2454}
(segid "BrD" and resid 95 and name HE%)
((segid "BrD" and resid 94 and name HA))
ASSI {2524}
(segid "BrD" and resid 106 and name HE%)
((segid "BrD" and resid 116 and name HG11))
  3.000  2.200  2.200 peak       2524  weight  0.10000E+01 volume   0.14273E+03 ppm1    7.611 ppm2   1.925
OR {2524}
(segid "BrD" and resid 96 and name HE%)
((segid "BrD" and resid 86 and name HG1))
OR {2524}
(segid "BrD" and resid 96 and name HE%)
(("BrD" and resid 86 and name HD1))
ASSI {2544}
(segid "BrD" and resid 106 and name HD%)
((segid "BrD" and resid 107 and name HA))
  3.100  2.400  2.400 peak       2544  weight  0.10000E+01 volume   0.12798E+03 ppm1    7.538 ppm2   4.390
OR {2544}
(segid "BrD" and resid 106 and name HD%)
((segid "BrD" and resid 79 and name HA))
OR {2544}
(segid "BrD" and resid 74 and name HE%)
((segid "BrD" and resid 74 and name HA))
ASSI {2604}
(segid "BrD" and resid 74 and name HE%)
((segid "BrD" and resid 59 and name HB1))
  2.500  1.600  1.600 peak       2604  weight  0.10000E+01 volume   0.55016E+03 ppm1    7.534 ppm2   2.695
OR {2604}
(segid "BrD" and resid 74 and name HE%)
((segid "BrD" and resid 22 and name HB1))
ASSI {2624}
(segid "BrD" and resid 106 and name HD%)
((segid "BrD" and resid 109 and name HB2))
  3.000  2.200  2.200 peak       2624  weight  0.10000E+01 volume   0.15519E+03 ppm1    7.534 ppm2   2.146
OR {2624}
(segid "BrD" and resid 74 and name HE%)
((segid "BrD" and resid 18 and name HB1))
```

TABLE 3-continued

Ambiguous NOE-derived Inter-proton Distance Restraints

ASSI {2644}
(segid "BrD" and resid 74 and name HE%)
((segid "BrD" and resid 63 and name HB2))
  2.300  1.300  1.300 peak      2644  weight  0.10000E+01 volume  0.82012E+01 ppm1      7.531 ppm2      2.521
OR {2644}
(segid "BrD" and resid 106 and name HD%)
((segid "BrD" and resid 21 and name HB))
ASSI {2644}
(segid "BrD" and resid 106 and name HD%)
(segid "BrD" and resid 102 and name HD2%)
  2.800  2.000  2.000 peak      2664  weight  0.10000E+01 volume  0.24374E+03 ppm1      7.530 ppm2      1.331
OR {2664}
(segid "BrD" and resid 74 and name HE%)
((segid "BrD" and resid 78 and name HB1))
ASSI {2784}
(segid "BrD" and resid 74 and name HE%)
((segid "BrD" and resid 68 and name HB2))
  2.900  2.100  2.100 peak      2784  weight  0.10000E+01 volume  0.21978E+03 ppm1      7.530 ppm2      3.559
OR {2784}
(segid "BrD" and resid 74 and name HE%)
((segid "BrD" and resid 74 and name HB1))
OR {2784}
(segid "BrD" and resid 95 and name HD%)
((segid "BrD" and resid 88 and name HB1))
ASSI {2804}
(segid "BrD" and resid 95 and name HD%)
((segid "BrD" and resid 32 and name HH2))
  2.800  2.000  2.000 peak      2804  weight  0.10000E+01 volume  0.23332E+03 ppm1      7.520 ppm2      1.793
OR {2804}
(segid "BrD" and resid 106 and name HD%)
(segid "BrD" and resid 107 and name HD%)
ASSI {2814}
(segid "BrD" and resid 106 and name HD%)
((segid "BrD" and resid 78 and name HB2))
  3.000  2.200  2.200 peak      2814  weight  0.10000E+01 volume  0.16253E+03 ppm1      7.520 ppm2      1.080
OR {2814}
(segid "BrD" and resid 74 and name HE%)
(segid "BrD" and resid 18 and name HD1%)
OR {2814}
(segid "BrD" and resid 95 and name HD%)
((segid "BrD" and resid 33 and name HE1))
ASSI {2914}
(segid "BrD" and resid 15 and name HE%)
((segid "BrD" and resid 19 and name HE1))
  2.900  2.100  2.100 peak      2914  weight  0.10000E+01 volume  0.20135E+03 ppm1      7.488 ppm2      3.545
OR {2914}
(segid "BrD" and resid 95 and name HD%)
((segid "BrD" and resid 88 and name HB1))
ASSI {3164}
(segid "BrD" and resid 62 and name HD%)
((segid "BrD" and resid 103 and name HB1))
  2.700  1.800  1.800 peak      3164  weight  0.10000E+01 volume  0.29307E+03 ppm1      7.270 ppm2      2.309
OR {3164}
(segid "BrD" and resid 47 and name HE%)
((segid "BrD" and resid 37 and name HB2))
ASSI {3284}
(segid "BrD" and resid 82 and name HD%)
(segid "BrD" and resid 34 and name HE%)
  2.800  2.000  2.000 peak      3284  weight  0.10000E+01 volume  0.24492E+03 ppm1      7.263 ppm2      7.800
OR {3284}
(segid "BrD" and resid 82 and name HD%)
(segid "BrD" and resid 107 and name HD%)
ASSI {3324}
(segid "BrD" and resid 82 and name HE%)
((segid "BrD" and resid 79 and name HA))
  2.900  2.100  2.100 peak      3324  weight  0.10000E+01 volume  0.20070E+03 ppm1      7.074 ppm2      4.440
OR {3324}
(segid "BrD" and resid 82 and name HE%)
((segid "BrD" and resid 107 and name HA))
ASSI {3394}
(segid "BrD" and resid 82 and name HE%)
((segid "BrD" and resid 81 and name HB))
  3.600  1.700  1.700 peak      3394  weight  0.10000E+01 volume  0.37424E+03 ppm1      7.069 ppm2      2.012
OR {3394}
(segid "BrD" and resid 82 and name HE%)
((segid "BrD" and resid 102 and name HB1))

TABLE 3-continued

| Ambiguous NOE-derived Inter-proton Distance Restraints |

ASSI {3414}
(segid "BrD" and resid 82 and name HE%)
(segid "BrD" and resid 25 and name HG2%)
 3.400  2.900  2.100 peak    3414  weight  0.10000E+01 volume   0.73603E+02 ppm1    7.067 ppm2    1.641
OR {3414}
(segid "BrD" and resid 82 and name HE%)
((segid "BrD" and resid 110 and name HG12))
ASSI {3474}
((segid "BrD" and resid 82 and name HZ))
((segid "BrD" and resid 102 and name HG))
 2.800  2.000  2.000 peak    3474  weight  0.10000E+01 volume   0.23859E+03 ppm1    7.025 ppm2    2.163
OR {3474}
(segid "BrD" and resid 74 and name HD%)
((segid "BrD" and resid 18 and name HB1))
ASSI {3484}
(segid "BrD" and resid 74 and name HD%)
(segid "BrD" and resid 78 and name HD1%)
 2.900  2.100  2.100 peak    3484  weight  0.10000E+01 volume   0.18792E+03 ppm1    7.023 ppm2    0.780
OR {3484}
((segid "BrD" and resid 82 and name HZ))
(segid "BrD" and resid 78 and name HD1%)
ASSI {3494}
(segid "BrD" and resid 74 and name HD%)
((segid "BrD" and resid 68 and name HB1))
 2.900  2.100  2.100 peak    3494  weight  0.10000E+01 volume   0.19853E+03 ppm1    7.022 ppm2    3.708
OR {3494}
((segid "BrD" and resid 82 and name HZ))
((segid "BrD" and resid 106 and name HB2))
ASSI {3504}
((segid "BrD" and resid 82 and name HZ))
((segid "BrD" and resid 81 and name HB))
 3.100  2.400  2.400 peak    3504  weight  0.10000E+01 volume   0.12383E+03 ppm1    7.023 ppm2    2.034
OR {3504}
(segid "BrD" and resid 74 and name HD%)
((segid "BrD" and resid 14 and name HG))
ASSI {3544}
(segid "BrD" and resid 74 and name HD%)
((segid "BrD" and resid 18 and name HG))
 3.400  2.900  2.100 peak    3544  weight  0.10000E+01 volume   0.82384E+02 ppm1    7.005 ppm2    2.307
OR {3544}
((segid "BrD" and resid 82 and name HZ))
((segid "BrD" and resid 103 and name HB1))
OR {3544}
(segid "BrD" and resid 74 and name HD%)
((segid "BrD" and resid 11 and name HG12))
OR {3544}
(segid "BrD" and resid 74 and name HD%)
((segid "BrD" and resid 62 and name HG1))
OR {3544}
(segid "BrD" and resid 74 and name HD%)
((segid "BrD" and resid 73 and name HG))
OR {3544}
((segid "BrD" and resid 82 and name HZ))
((segid "BrD" and resid 21 and name HG11))
ASSI {3554}
(segid "BrD" and resid 74 and name HD%)
(segid "BrD" and resid 63 and name HD1%)
 2.500  1.600  1.600 peak    3554  weight  0.10000E+01 volume   0.51806E+03 ppm1    7.009 ppm2    1.641
OR {3544}
(segid "BrD" and resid 74 and name HD%)
(segid "BrD" and resid 22 and name HD1%)
ASSI {3564}
(segid "BrD" and resid 74 and name HD%)
(segid "BrD" and resid 68 and name HE%)
 3.100  2.400  2.400 peak    3564  weight  0.10000E+01 volume   0.13987E+03 ppm1    7.005 ppm2    7.$$
OR {3564}
((segid "BrD" and resid 82 and name HZ))
(segid "BrD" and resid 107 and name HE%)
ASSI {3584}
(segid "BrD" and resid 74 and name HD%)
(segid "BrD" and resid 106 and name HE%)
 3.000  2.200  2.200 peak    3584  weight  0.10000E+01 volume   0.17632E+03 ppm1    7.005 ppm2    7.647
OR {3584}
((segid "BrD" and resid 82 and name HZ))
(segid "BrD" and resid 106 and name HE%)

TABLE 3-continued

Ambiguous NOE-derived Inter-proton Distance Restraints

ASSI {3604}
(segid "BrD" and resid 74 and name HD%)
((segid "BrD" and resid 71 and name HA))
  3.300  2.700  2.200 peak     3604  weight  0.10000E+01 volume  0.95504E+02 ppm1       7.005 ppm2    4.636
OR {3604}
(segid "BrD" and resid 74 and name HD%)
((segid "BrD" and resid 15 and name HA))
OR {3604}
(segid "BrD" and resid 74 and name HD%)
((segid "BrD" and resid 76 and name HA))
OR {3604}
(segid "BrD" and resid 74 and name HD%)
((segid "BrD" and resid 56 and name HA))
OR {3604}
(segid "BrD" and resid 74 and name HD%)
((segid "BrD" and resid 72 and name HA))
OR {3604}
(segid "BrD" and resid 74 and name HD%)
((segid "BrD" and resid 14 and name HA))
OR {3604}
(segid "BrD" and resid 74 and name HD%)
((segid "BrD" and resid 67 and name HA))
OR {3604}
(segid "BrD" and resid 74 and name HD%)
((segid "BrD" and resid 60 and name HB2))
OR {3604}
((segid "BrD" and resid 82 and name HZ))
((segid "BrD" and resid 104 and name HA))
ASSI {3634}
(segid "BrD" and resid 74 and name HD%)
((segid "BrD" and resid 75 and name HG2))
  3.100  2.400  2.400 peak     3634  weight  0.10000E+01 volume  0.12756E+03 ppm1       7.004 ppm2    3.221
OR {3634}
(segid "BrD" and resid 74 and name HD%)
((segid "BrD" and resid 59 and name HG1))
OR {3634}
(segid "BrD" and resid 74 and name HD%)
((segid "BrD" and resid 59 and name HG2))
ASSI {3664}
(segid "BrD" and resid 74 and name HD%)
((segid "BrD" and resid 63 and name HB2))
  3.600  3.200  1.900 peak     3664  weight  0.10000E+01 volume  0.57581E+02 ppm1       7.005 ppm2    2.520
OR {3664}
((segid "BrD" and resid 82 and name HZ))
((segid "BrD" and resid 21 and name HB))
ASSI {3674}
((segid "BrD" and resid 82 and name HZ))
((segid "BrD" and resid 21 and name HB))
  3.700  3.400  1.800 peak     3674  weight  0.10000E+01 volume  0.46728E+02 ppm1       7.004 ppm2    2.494
OR {3674}
(segid "BrD" and resid 74 and name HD%)
((segid "BrD" and resid 59 and name HB2))
OR {3674}
(segid "BrD" and resid 74 and name HD%)
((segid "BrD" and resid 73 and name HB2))
ASSI {3694}
(segid "BrD" and resid 74 and name HD%)
(segid "BrD" and resid 63 and name HD2%)
  3.500  3.100  2.000 peak     3694  weight  0.10000E+01 volume  0.62447E+02 ppm1       7.00$$ ppm2    1.496
OR {$$}
(segid "BrD" and resid 74 and name HD%)
(segid "BrD" and resid 73 and name HD2%)
ASSI {3854}
(segid "BrD" and resid 46 and name HE%)
((segid "BrD" and resid 50 and name HG12))
  2.700  1.800  1.800 peak     3854  weight  0.10000E+01 volume  0.29261E+03 ppm1       6.687 ppm2    0.795
OR {3854}
(segid "BrD" and resid 46 and name HE%)
(segid "BrD" and resid 38 and name HG2%)
ASSI {3954}
(segid "BrD" and resid 46 and name HD%)
((segid "BrD" and resid 50 and name HG12))
  3.200  2.600  2.300 peak     3954  weight  0.10000E+01 volume  0.11437E+03 ppm1       5.740 ppm2    0.796
OR {3954}
(segid "BrD" and resid 46 and name HD%)
(segid "BrD" and resid 38 and name HG2%)

TABLE 3-continued

Ambiguous NOE-derived Inter-proton Distance Restraints

ASSI {4144}
(segid "BrD" and resid 74 and name HD%)
((segid "BrD" and resid 78 and name HG))
  3.400  2.900  2.100 peak      4144  weight  0.10000E+01 volume    0.77150E+02 ppm1      7.005 ppm2      1.249
OR {4144}
((segid "BrD" and resid 82 and name HZ))
((segid "BrD" and resid 78 and name HG))
ASSI {4154}
(segid "BrD" and resid 74 and name HE%)
(segid "BrD" and resid 22 and name HD1%)
  2.400  1.400  1.400 peak      4154  weight  0.10000E+01 volume    0.70341E+03 ppm1      7.534 ppm2      1.676
OR {4154}
(segid "BrD" and resid 106 and name HD%)
((segid "BrD" and resid 21 and name HG12))
ASSI {4174}
(segid "BrD" and resid 96 and name HD%)
((segid "BrD" and resid 100 and name HA))
  3.100  2.400  2.400 peak      4174  weight  0.10000E+01 volume    0.13533E+03 ppm1      7.689 ppm2      4.927
OR {4174}
(segid "BrD" and resid 34 and name HD%)
((segid "BrD" and resid 35 and name HA))
OR {4174}
(segid "BrD" and resid 15 and name HD%)
((segid "BrD" and resid 64 and name HA))
OR {4174}
(segid "BrD" and resid 15 and name HD%)
((segid "BrD" and resid 11 and name HA))
OR {4174}
(segid "BrD" and resid 34 and name HD%)
((segid "BrD" and resid 32 and name HA))
ASSI {4224}
(segid "BrD" and resid 88 and name HD%)
((segid "BrD" and resid 50 and name HG12))
  3.200  2.400  2.400 peak      4224  weight  0.10000E+01 volume    0.12837E+03 ppm1      7.415 ppm2      0.845
OR {4224}
(segid "BrD" and resid 95 and name HE%)
((segid "BrD" and resid 33 and name HG1))
ASSI {4234}
(segid "BrD" and resid 96 and name HE%)
(segid "BrD" and resid 99 and name HB%)
  3.300  2.700  2.200 peak      4234  weight  0.10000E+01 volume    0.94963E+02 ppm1      7.611 ppm2      2.178
OR {4234}
(segid "BrD" and resid 106 and name HE%)
((segid "BrD" and resid 18 and name HB2))
OR {4234}
(segid "BrD" and resid 106 and name HE%)
((segid "BrD" and resid 109 and name HB2))
OR {4234}
(segid "BrD" and resid 106 and name HE%)
((segid "BrD" and resid 115 and name HB1))
OR {4234}
(segid "BrD" and resid 106 and name HE%)
((segid "BrD" and resid 115 and name HG))
ASSI {4244}
(segid "BrD" and resid 106 and name HE%)
(segid "BrD" and resid 78 and name HD1%)
  3.100  2.400  2.400 peak      4244  weight  0.10000E+01 volume    0.14012E+03 ppm1      7.616 ppm2      0.763
OR {4244}
(segid "BrD" and resid 96 and name HE%)
((segid "BrD" and resid 86 and name HG2))
ASSI {4284}
(segid "BrD" and resid 74 and name HE%)
((segid "BrD" and resid 74 and name HB2))
  3.000  2.200  2.200 peak      4284  weight  0.10000E+01 volume    0.18031E+03 ppm1      7.534 ppm2      3.010
OR {4284}
(segid "BrD" and resid 106 and name HD%)
((segid "BrD" and resid 109 and name HE2))
ASSI {4344}
((segid "BrD" and resid 34 and name HZ))
((segid "BrD" and resid 28 and name HD2))
  3.100  2.400  2.400 peak      4344  weight  0.10000E+01 volume    0.12962E+03 ppm1      7.904 ppm2      5.555
OR {4344}
(segid "BrD" and resid 68 and name HE%)
((segid "BrD" and resid 54 and name HA))

TABLE 3-continued

Ambiguous NOE-derived Inter-proton Distance Restraints

```
ASSI {4354}
(segid "BrD" and resid 106 and name HD%)
((segid "BrD" and resid 78 and name HB2))
 2.900  2.100  2.100 peak      4354  weight  0.10000E+01  volume  0.19182E+03  ppm1    7.539  ppm2    1.089
OR {4354}
(segid "BrD" and resid 74 and name HE%)
(segid "BrD" and resid 18 and name HD1%)
```

TABLE 4

Hydrogen Bonding Restraints

!Helix Z

| | | | |
|---|---|---|---|
| assign (residue 19 and name HN) (residue 15 and name O) | 1.80 | 0.0 | 0.40 |
| assign (residue 19 and name N) (residue 15 and name O) | 2.80 | 0.30 | 0.40 |
| assign (residue 22 and name HN) (residue 18 and name O) | 1.80 | 0.0 | 0.40 |
| assign (residue 22 and name N) (residue 18 and name O) | 2.80 | 0.30 | 0.40 |
| assign (residue 23 and name HN) (residue 19 and name O) | 1.80 | 0.0 | 0.40 |
| assign (residue 23 and name N) (residue 19 and name O) | 2.80 | 0.30 | 0.40 |
| assign (residue 24 and name HN) (residue 20 and name O) | 1.80 | 0.0 | 0.40 |
| assign (residue 24 and name N) (residue 20 and name O) | 2.80 | 0.30 | 0.40 |
| assign (residue 25 and name HN) (residue 21 and name O) | 1.80 | 0.0 | 0.40 |
| assign (residue 25 and name N) (residue 21 and name O) | 2.80 | 0.30 | 0.40 |

!Helix B

| | | | |
|---|---|---|---|
| assign (residue 75 and name HN) (residue 71 and name O) | 1.80 | 0.0 | 0.40 |
| assign (residue 75 and name N) (residue 71 and name O) | 2.80 | 0.30 | 0.40 |
| !assign (residue 77 and name HN) (residue 73 and name O) | 1.80 | 0.0 | 0.40 |
| !assign (residue 77 and name N) (residue 73 and name O) | 2.80 | 0.30 | 0.40 |
| assign (residue 78 and name HN) (residue 74 and name O) | 1.80 | 0.0 | 0.40 |
| assign (residue 78 and name N) (residue 74 and name O) | 2.80 | 0.30 | 0.40 |
| assign (residue 79 and name HN) (residue 75 and name O) | 1.80 | 0.0 | 0.40 |
| assign (residue 79 and name N) (residue 75 and name O) | 2.80 | 0.30 | 0.40 |
| !assign (residue 80 and name HN) (residue 76 and name O) | 1.80 | 0.0 | 0.40 |
| !assign (residue 80 and name N) (residue 76 and name O) | 2.80 | 0.30 | 0.40 |
| assign (residue 81 and name HN) (residue 77 and name O) | 1.80 | 0.0 | 0.40 |
| assign (residue 81 and name N) (residue 77 and name O) | 2.80 | 0.30 | 0.40 |
| assign (residue 82 and name HN) (residue 78 and name O) | 1.80 | 0.0 | 0.40 |
| assign (residue 82 and name N) (residue 78 and name O) | 2.80 | 0.30 | 0.40 |

!Helix C

| | | | |
|---|---|---|---|
| assign (residue 102 and name HN) (residue 98 and name O) | 1.80 | 0.0 | 0.40 |
| assign (residue 102 and name N) (residue 98 and name O) | 2.80 | 0.30 | 0.40 |
| assign (residue 103 and name HN) (residue 99 and name O) | 1.80 | 0.0 | 0.40 |
| assign (residue 103 and name N) (residue 99 and name O) | 2.80 | 0.30 | 0.40 |
| assign (residue 104 and name HN) (residue 100 and name O) | 1.80 | 0.0 | 0.40 |
| assign (residue 104 and name N) (residue 100 and name O) | 2.80 | 0.30 | 0.40 |
| assign (residue 104 and name HN) (residue 101 and name O) | 1.80 | 0.0 | 0.40 |
| assign (residue 104 and name N) (residue 101 and name O) | 2.80 | 0.30 | 0.40 |

TABLE 5

Atomic Structure Coordinates of the Free Form of the P/CAF Bromodomain

```
REMARK   FILENAME*'/bloch2/chris/BROMO_XPLOR_ARIA32/structures/it0/brd_187.pdb'
REMARK   initial random number seed: 1.342876E+11
REMARK   ****************************************************
REMARK          overall, bonds, angles, improper, vdw, noe, cd1h
REMARK   energies: 157.923, 9.30626, 73.1523, 0, 23.1819, 36.4277, 0.228429
REMARK   ****************************************************
REMARK          bonds, angles, improper, noe, cd1h
REMARK   rms-dev.: 2.164156E-03, 0.365011, 50.3111, 1.418985E-02, 0.263503
REMARK   ****************************************************
REMARK          noe, cd1h
REMARK   violations.: 2. 0
REMARK   ****************************************************
REMARK   DATE:29-Nov-98  06:51:33        created by user:
ATOM         1    CA     GLY    1    27.208   16.825   -6.349   1.00   0.00
ATOM         2    HA1    GLY    1    26.763   16.827   -5.365   1.00   0.00
ATOM         3    HA2    GLY    1    28.041   17.514   -6.357   1.00   0.00
```

TABLE 5-continued

Atomic Structure Coordinates of the
Free Form of the P/CAF Bromodomain

| ATOM | 4 | C | GLY | 1 | 27.723 | 15.432 | −6.650 | 1.00 | 0.00 |
|---|---|---|---|---|---|---|---|---|---|
| ATOM | 5 | O | GLY | 1 | 28.656 | 15.263 | −7.435 | 1.00 | 0.00 |
| ATOM | 6 | N | GLY | 1 | 26.194 | 17.285 | −7.337 | 1.00 | 0.00 |
| ATOM | 7 | HT1 | GLY | 1 | 26.586 | 18.049 | −7.923 | 1.00 | 0.00 |
| ATOM | 8 | HT2 | GLY | 1 | 25.350 | 17.641 | −6.843 | 1.00 | 0.00 |
| ATOM | 9 | HT3 | GLY | 1 | 25.914 | 16.490 | −7.955 | 1.00 | 0.00 |
| ATOM | 10 | N | SER | 2 | 27.113 | 14.432 | −6.024 | 1.00 | 0.00 |
| ATOM | 11 | HN | SER | 2 | 26.376 | 14.629 | −5.409 | 1.00 | 0.00 |
| ATOM | 12 | CA | SER | 2 | 27.516 | 13.044 | −6.226 | 1.00 | 0.00 |
| ATOM | 13 | HA | SER | 2 | 28.481 | 13.047 | −6.712 | 1.00 | 0.00 |
| ATOM | 14 | CB | SER | 2 | 27.638 | 12.329 | −4.878 | 1.00 | 0.00 |
| ATOM | 15 | HB1 | SER | 2 | 26.906 | 12.729 | −4.193 | 1.00 | 0.00 |
| ATOM | 16 | HB2 | SER | 2 | 27.462 | 11.273 | −5.017 | 1.00 | 0.00 |
| ATOM | 17 | CG | SER | 2 | 28.927 | 12.508 | −4.319 | 1.00 | 0.00 |
| ATOM | 18 | HG | SER | 2 | 29.571 | 12.014 | −4.832 | 1.00 | 0.00 |
| ATOM | 19 | C | SER | 2 | 26.519 | 12.308 | −7.114 | 1.00 | 0.00 |
| ATOM | 20 | O | SER | 2 | 25.320 | 12.288 | −6.835 | 1.00 | 0.00 |
| ATOM | 21 | N | HIS | 3 | 27.022 | 11.698 | −8.183 | 1.00 | 0.00 |
| ATOM | 22 | HN | HIS | 3 | 27.986 | 11.747 | −8.353 | 1.00 | 0.00 |
| ATOM | 23 | CA | HIS | 3 | 26.173 | 10.955 | −9.106 | 1.00 | 0.00 |
| ATOM | 24 | HA | HIS | 3 | 25.157 | 11.295 | −8.967 | 1.00 | 0.00 |
| ATOM | 25 | CB | HIS | 3 | 26.594 | 11.222 | −10.553 | 1.00 | 0.00 |
| ATOM | 26 | HB1 | HIS | 3 | 26.616 | 12.288 | −10.723 | 1.00 | 0.00 |
| ATOM | 27 | HB2 | HIS | 3 | 27.581 | 10.834 | −10.714 | 1.00 | 0.00 |
| ATOM | 28 | CG | HIS | 3 | 25.671 | 10.612 | −11.561 | 1.00 | 0.00 |
| ATOM | 29 | ND1 | HIS | 3 | 25.985 | 10.494 | −12.900 | 1.00 | 0.00 |
| ATOM | 30 | HD1 | HIS | 3 | 26.820 | 10.790 | −13.320 | 1.00 | 0.00 |
| ATOM | 31 | CD2 | HIS | 3 | 24.433 | 10.080 | −11.420 | 1.00 | 0.00 |
| ATOM | 32 | HD2 | HIS | 3 | 23.870 | 10.003 | −10.501 | 1.00 | 0.00 |
| ATOM | 33 | CE1 | HIS | 3 | 28.981 | 9.918 | −13.537 | 1.00 | 0.00 |
| ATOM | 34 | HE1 | HIS | 3 | 26.965 | 9.698 | −14.594 | 1.00 | 0.00 |
| ATOM | 35 | NE2 | HIS | 3 | 24.028 | 9.658 | −12.662 | 1.00 | 0.00 |
| ATOM | 36 | HE2 | HIS | 3 | 23.171 | 9.230 | −12.968 | 1.00 | 0.00 |
| ATOM | 37 | C | HIS | 3 | 26.233 | 9.459 | −8.817 | 1.00 | 0.00 |
| ATOM | 38 | O | HIS | 3 | 26.214 | 8.638 | −9.734 | 1.00 | 0.00 |
| ATOM | 39 | N | MET | 4 | 26.305 | 9.111 | −7.536 | 1.00 | 0.00 |
| ATOM | 40 | HN | MET | 4 | 26.314 | 9.811 | −6.850 | 1.00 | 0.00 |
| ATOM | 41 | CA | MET | 4 | 26.364 | 7.713 | −7.128 | 1.00 | 0.00 |
| ATOM | 42 | HA | MET | 4 | 26.164 | 7.105 | −7.998 | 1.00 | 0.00 |
| ATOM | 43 | CB | MET | 4 | 27.755 | 7.374 | −6.591 | 1.00 | 0.00 |
| ATOM | 44 | HB1 | MET | 4 | 28.456 | 8.117 | −6.944 | 1.00 | 0.00 |
| ATOM | 45 | HB2 | MET | 4 | 27.730 | 7.800 | −5.512 | 1.00 | 0.00 |
| ATOM | 46 | CG | MET | 4 | 28.254 | 6.005 | −7.024 | 1.00 | 0.00 |
| ATOM | 47 | HG1 | MET | 4 | 27.433 | 5.306 | −6.972 | 1.00 | 0.00 |
| ATOM | 48 | HG2 | MET | 4 | 28.606 | 6.071 | −8.043 | 1.00 | 0.00 |
| ATOM | 49 | SD | MET | 4 | 29.597 | 5.394 | −5.988 | 1.00 | 0.00 |
| ATOM | 50 | CE | MET | 4 | 28.922 | 3.825 | −5.449 | 1.00 | 0.00 |
| ATOM | 51 | HE1 | MET | 4 | 29.243 | 3.623 | −4.438 | 1.00 | 0.00 |
| ATOM | 52 | HE2 | MET | 4 | 29.273 | 3.039 | −6.102 | 1.00 | 0.00 |
| ATOM | 53 | HE3 | MET | 4 | 27.843 | 3.866 | −5.483 | 1.00 | 0.00 |
| ATOM | 54 | C | MET | 4 | 25.310 | 7.413 | −6.067 | 1.00 | 0.00 |
| ATOM | 55 | O | MET | 4 | 25.333 | 7.983 | −4.977 | 1.00 | 0.00 |
| ATOM | 56 | N | SER | 5 | 24.386 | 6.517 | −6.398 | 1.00 | 0.00 |
| ATOM | 57 | HN | SER | 5 | 24.422 | 6.098 | −7.283 | 1.00 | 0.00 |
| ATOM | 58 | CA | SER | 5 | 23.321 | 6.141 | −5.476 | 1.00 | 0.00 |
| ATOM | 59 | HA | SER | 5 | 23.780 | 5.750 | −4.580 | 1.00 | 0.00 |
| ATOM | 60 | CB | SER | 5 | 22.879 | 7.366 | −5.111 | 1.00 | 0.00 |
| ATOM | 61 | HB1 | SER | 5 | 22.188 | 7.882 | −6.014 | 1.00 | 0.00 |
| ATOM | 62 | HB2 | SER | 5 | 23.062 | 8.029 | −4.490 | 1.00 | 0.00 |
| ATOM | 63 | CG | SER | 5 | 21.309 | 6.990 | −4.405 | 1.00 | 0.00 |
| ATOM | 64 | HG | SER | 5 | 21.060 | 7.693 | −3.800 | 1.00 | 0.00 |
| ATOM | 65 | C | SER | 5 | 22.431 | 5.062 | −6.084 | 1.00 | 0.00 |
| ATOM | 66 | O | SER | 5 | 21.471 | 5.362 | −6.794 | 1.00 | 0.00 |
| ATOM | 67 | N | LYS | 6 | 22.756 | 3.805 | −5.800 | 1.00 | 0.00 |
| ATOM | 68 | HN | LYS | 6 | 23.532 | 3.630 | −5.228 | 1.00 | 0.00 |
| ATOM | 69 | CA | LYS | 6 | 21.987 | 2.680 | −4.319 | 1.00 | 0.00 |
| ATOM | 70 | HA | LYS | 6 | 21.642 | 2.942 | −7.308 | 1.00 | 0.00 |
| ATOM | 71 | CB | LYS | 6 | 22.869 | 1.433 | −6.409 | 1.00 | 0.00 |
| ATOM | 72 | HB1 | LYS | 6 | 22.266 | 0.563 | −6.192 | 1.00 | 0.00 |
| ATOM | 73 | HB2 | LYS | 6 | 22.255 | 1.508 | −5.673 | 1.00 | 0.00 |
| ATOM | 74 | CG | LYS | 6 | 23.510 | 1.238 | −7.773 | 1.00 | 0.00 |
| ATOM | 75 | HG1 | LYS | 6 | 24.045 | 2.138 | −8.041 | 1.00 | 0.00 |
| ATOM | 76 | HG2 | LYS | 6 | 24.201 | 0.409 | −7.721 | 1.00 | 0.00 |
| ATOM | 77 | CE | LYS | 6 | 22.469 | 0.947 | −8.842 | 1.00 | 0.00 |
| ATOM | 78 | HD1 | LYS | 6 | 21.794 | 1.787 | −8.911 | 1.00 | 0.00 |
| ATOM | 79 | HD2 | LYS | 6 | 22.970 | 0.804 | −9.788 | 1.00 | 0.00 |

TABLE 5-continued

Atomic Structure Coordinates of the
Free Form of the P/CAF Bromodomain

| ATOM | 80 | CE | LYS | 6 | 21.669 | −0.304 | −8.514 | 1.00 | 0.00 |
|---|---|---|---|---|---|---|---|---|---|
| ATOM | 81 | HE1 | LYS | 6 | 21.107 | −0.129 | −7.608 | 1.00 | 0.00 |
| ATOM | 82 | HE2 | LYS | 6 | 20.987 | −0.503 | −9.327 | 1.00 | 0.00 |
| ATOM | 83 | NZ | LYS | 6 | 22.548 | −1.489 | −8.317 | 1.00 | 0.00 |
| ATOM | 84 | HZ1 | LYS | 6 | 23.320 | −1.481 | −9.014 | 1.00 | 0.00 |
| ATOM | 85 | HZ2 | LYS | 6 | 21.999 | −2.365 | −8.435 | 1.00 | 0.00 |
| ATOM | 86 | HZ3 | LYS | 6 | 22.958 | −1.476 | −7.362 | 1.00 | 0.00 |
| ATOM | 87 | C | LYS | 6 | 20.776 | 2.397 | −5.436 | 1.00 | 0.00 |
| ATOM | 88 | O | LYS | 6 | 20.863 | 1.638 | −4.471 | 1.00 | 0.00 |
| ATOM | 89 | N | GLU | 7 | 19.646 | 3.011 | −5.773 | 1.00 | 0.00 |
| ATOM | 90 | HN | GLU | 7 | 19.637 | 3.606 | −6.552 | 1.00 | 0.00 |
| ATOM | 91 | CA | GLU | 7 | 18.420 | 2.825 | −5.005 | 1.00 | 0.00 |
| ATOM | 92 | HA | GLU | 7 | 18.531 | 1.926 | −4.418 | 1.00 | 0.00 |
| ATOM | 93 | CB | GLU | 7 | 18.200 | 4.011 | −4.064 | 1.00 | 0.00 |
| ATOM | 94 | HB1 | GLU | 7 | 18.505 | 4.916 | −4.567 | 1.00 | 0.00 |
| ATOM | 95 | HB2 | GLU | 7 | 17.148 | 4.078 | −3.828 | 1.00 | 0.00 |
| ATOM | 96 | CG | GLU | 7 | 18.975 | 3.904 | −2.762 | 1.00 | 0.00 |
| ATOM | 97 | HG1 | GLU | 7 | 19.746 | 3.156 | −2.876 | 1.00 | 0.00 |
| ATOM | 98 | HG2 | GLU | 7 | 19.430 | 4.860 | −2.548 | 1.00 | 0.00 |
| ATOM | 99 | CD | GLU | 7 | 18.095 | 3.515 | −1.589 | 1.00 | 0.00 |
| ATOM | 100 | OE1 | GLU | 7 | 17.118 | 4.243 | −1.312 | 1.00 | 0.00 |
| ATOM | 101 | OE2 | GLU | 7 | 18.383 | 2.483 | −0.947 | 1.00 | 0.00 |
| ATOM | 102 | C | GLU | 7 | 17.215 | 2.662 | −5.928 | 1.00 | 0.00 |
| ATOM | 103 | O | GLU | 7 | 16.278 | 3.461 | −5.886 | 1.00 | 0.00 |
| ATOM | 104 | N | PRO | 8 | 17.218 | 1.617 | −6.772 | 1.00 | 0.00 |
| ATOM | 105 | CA | PRO | 8 | 16.120 | 1.352 | −7.702 | 1.00 | 0.00 |
| ATOM | 106 | HA | PRO | 8 | 15.785 | 2.256 | −8.189 | 1.00 | 0.00 |
| ATOM | 107 | CB | PRO | 8 | 16.760 | 0.419 | −8.727 | 1.00 | 0.00 |
| ATOM | 108 | HB1 | PRO | 8 | 17.200 | 1.002 | −9.523 | 1.00 | 0.00 |
| ATOM | 109 | HB2 | PRO | 8 | 16.011 | −0.245 | −9.130 | 1.00 | 0.00 |
| ATOM | 110 | CG | PRO | 8 | 17.796 | −0.327 | −7.958 | 1.00 | 0.00 |
| ATOM | 111 | HG1 | PRO | 8 | 17.257 | −1.205 | −7.508 | 1.00 | 0.00 |
| ATOM | 112 | HG2 | PRO | 8 | 18.607 | −0.608 | −8.614 | 1.00 | 0.00 |
| ATOM | 113 | CD | PRO | 8 | 18.294 | 0.613 | −6.889 | 1.00 | 0.00 |
| ATOM | 114 | HD1 | PRO | 8 | 18.629 | 0.085 | −5.956 | 1.00 | 0.00 |
| ATOM | 115 | HD2 | PRO | 8 | 19.200 | 1.075 | −7.197 | 1.00 | 0.00 |
| ATOM | 116 | C | PRO | 8 | 14.938 | 0.669 | −7.021 | 1.00 | 0.00 |
| ATOM | 117 | O | PRO | 8 | 13.782 | 0.974 | −7.360 | 1.00 | 0.00 |
| ATOM | 118 | N | ARG | 9 | 15.236 | −0.196 | −6.057 | 1.00 | 0.00 |
| ATOM | 119 | HN | ARG | 9 | 14.176 | −0.357 | −5.833 | 1.00 | 0.00 |
| ATOM | 120 | CA | ARG | 9 | 14.199 | −0.917 | −5.328 | 1.00 | 0.00 |
| ATOM | 121 | HA | ARG | 9 | 13.522 | −0.189 | −4.906 | 1.00 | 0.00 |
| ATOM | 122 | CB | ARG | 9 | 13.431 | −1.830 | −6.279 | 1.00 | 0.00 |
| ATOM | 123 | HB1 | ARG | 9 | 12.822 | −2.504 | −5.695 | 1.00 | 0.00 |
| ATOM | 124 | HB2 | ARG | 9 | 12.778 | −1.222 | −6.898 | 1.00 | 0.00 |
| ATOM | 125 | CG | ARG | 9 | 14.313 | −2.661 | −7.188 | 1.00 | 0.00 |
| ATOM | 126 | HG1 | ARG | 9 | 14.295 | −2.236 | −8.181 | 1.00 | 0.00 |
| ATOM | 127 | HG2 | ARG | 9 | 15.322 | −2.640 | −6.803 | 1.00 | 0.00 |
| ATOM | 128 | CD | ARG | 9 | 13.843 | −4.106 | −7.263 | 1.00 | 0.00 |
| ATOM | 129 | HD1 | ARG | 9 | 13.831 | −4.518 | −6.264 | 1.00 | 0.00 |
| ATOM | 130 | HD2 | ARG | 9 | 12.844 | −4.125 | −7.671 | 1.00 | 0.00 |
| ATOM | 131 | NE | ARG | 9 | 14.714 | −4.926 | −8.102 | 1.00 | 0.00 |
| ATOM | 132 | HE | ARG | 9 | 13.302 | −4.464 | −8.735 | 1.00 | 0.00 |
| ATOM | 133 | CZ | ARG | 9 | 14.745 | −5.255 | −8.053 | 1.00 | 0.00 |
| ATOM | 134 | NH1 | ARG | 9 | 13.960 | −6.908 | −7.208 | 1.00 | 0.00 |
| ATOM | 135 | HH11 | ARG | 9 | 13.342 | −6.401 | −6.506 | 1.00 | 0.00 |
| ATOM | 136 | HH12 | ARG | 9 | 13.985 | −7.907 | −7.172 | 1.00 | 0.00 |
| ATOM | 137 | NH2 | ARG | 9 | 15.563 | −6.932 | −8.850 | 1.00 | 0.00 |
| ATOM | 138 | HH21 | ARG | 9 | 16.157 | −6.444 | −9.689 | 1.00 | 0.00 |
| ATOM | 139 | HH22 | ARG | 9 | 15.585 | −7.931 | −8.810 | 1.00 | 0.00 |
| ATOM | 140 | C | ARG | 9 | 14.800 | −1.744 | −4.196 | 1.00 | 0.00 |
| ATOM | 141 | O | ARG | 9 | 14.421 | −2.897 | −3.991 | 1.00 | 0.00 |
| ATOM | 142 | N | ASP | 10 | 15.732 | −1.144 | −1.458 | 1.00 | 0.00 |
| ATOM | 143 | HN | ASP | 10 | 15.988 | −0.223 | −3.673 | 1.00 | 0.00 |
| ATOM | 144 | CA | ASP | 10 | 16.393 | −1.824 | −2.345 | 1.00 | 0.00 |
| ATOM | 145 | HA | ASP | 10 | 17.087 | −2.450 | −2.760 | 1.00 | 0.00 |
| ATOM | 146 | CB | ASP | 10 | 17.169 | −0.813 | −1.497 | 1.00 | 0.00 |
| ATOM | 147 | HB1 | ASP | 10 | 17.594 | −0.041 | −2.146 | 1.00 | 0.00 |
| ATOM | 148 | HB2 | ASP | 10 | 16.490 | −0.341 | −0.802 | 1.00 | 0.00 |
| ATOM | 149 | CG | ASP | 10 | 18.292 | −1.457 | −0.708 | 1.00 | 0.00 |
| ATOM | 150 | OD1 | ASP | 10 | 18.771 | −2.532 | −1.126 | 1.00 | 0.00 |
| ATOM | 151 | OD2 | ASP | 10 | 18.692 | −0.886 | 0.328 | 1.00 | 0.00 |
| ATOM | 152 | C | ASP | 10 | 15.383 | −2.585 | −1.468 | 1.00 | 0.00 |
| ATOM | 153 | O | ASP | 10 | 14.728 | −1.961 | −0.619 | 1.00 | 0.00 |
| ATOM | 154 | N | PRO | 11 | 15.249 | −3.889 | −1.658 | 1.00 | 0.00 |
| ATOM | 155 | CA | PRO | 11 | 14.309 | −4.709 | −0.887 | 1.00 | 0.00 |

TABLE 5-continued

Atomic Structure Coordinates of the
Free Form of the P/CAF Bromodomain

| ATOM | 156 | HA | PRO | 11 | 13.311 | −4.297 | −0.920 | 1.00 | 0.00 |
|---|---|---|---|---|---|---|---|---|---|
| ATOM | 157 | CB | PRO | 11 | 14.326 | −6.068 | −1.607 | 1.00 | 0.00 |
| ATOM | 158 | HB1 | PRO | 11 | 13.311 | −6.399 | −1.772 | 1.00 | 0.00 |
| ATOM | 159 | HB2 | PRO | 11 | 14.849 | −6.791 | −0.999 | 1.00 | 0.00 |
| ATOM | 160 | CG | PRO | 11 | 15.036 | −5.829 | −2.899 | 1.00 | 0.00 |
| ATOM | 161 | HG1 | PRO | 11 | 15.582 | −6.715 | −3.288 | 1.00 | 0.00 |
| ATOM | 162 | HG2 | PRO | 11 | 14.324 | −5.561 | −3.666 | 1.00 | 0.00 |
| ATOM | 163 | CD | PRO | 11 | 15.981 | −4.692 | −2.646 | 1.00 | 0.00 |
| ATOM | 164 | HD1 | PRO | 11 | 16.155 | −4.133 | −3.552 | 1.00 | 0.00 |
| ATOM | 165 | HD2 | PRO | 11 | 16.911 | −5.056 | −2.237 | 1.00 | 0.00 |
| ATOM | 166 | C | PRO | 11 | 14.732 | −4.881 | 0.572 | 1.00 | 0.00 |
| ATOM | 167 | O | PRO | 11 | 11.991 | −5.446 | 1.375 | 1.00 | 0.00 |
| ATOM | 168 | N | ASP | 12 | 15.926 | −4.397 | 0.912 | 1.00 | 0.00 |
| ATOM | 169 | HN | ASP | 12 | 16.477 | −3.954 | 0.236 | 1.00 | 0.00 |
| ATOM | 170 | CA | ASP | 12 | 16.430 | −4.508 | 2.276 | 1.00 | 0.00 |
| ATOM | 171 | HA | ASP | 12 | 16.402 | −5.551 | 2.554 | 1.00 | 0.00 |
| ATOM | 172 | CB | ASP | 12 | 17.874 | −4.008 | 2.352 | 1.00 | 0.00 |
| ATOM | 173 | HB1 | ASP | 12 | 18.146 | −3.873 | 3.385 | 1.00 | 0.00 |
| ATOM | 174 | HB2 | ASP | 12 | 17.948 | −3.061 | 1.839 | 1.00 | 0.00 |
| ATOM | 175 | CG | ASP | 12 | 18.856 | −4.975 | 1.721 | 1.00 | 0.00 |
| ATOM | 176 | OD1 | ASP | 12 | 18.870 | −6.157 | 2.125 | 1.00 | 0.00 |
| ATOM | 177 | OD2 | ASP | 12 | 19.415 | −4.549 | 0.824 | 1.00 | 0.00 |
| ATOM | 178 | C | ASP | 12 | 15.555 | −3.719 | 3.243 | 1.00 | 0.00 |
| ATOM | 179 | O | ASP | 12 | 14.689 | −4.282 | 3.913 | 1.00 | 0.00 |
| ATOM | 180 | N | GLN | 13 | 15.785 | −2.412 | 3.309 | 1.00 | 0.00 |
| ATOM | 181 | HN | GLN | 13 | 16.486 | −2.020 | 2.748 | 1.00 | 0.00 |
| ATOM | 182 | CA | GLN | 13 | 15.012 | −1.546 | 4.191 | 1.00 | 0.00 |
| ATOM | 183 | HA | GLN | 13 | 15.115 | −1.923 | 5.197 | 1.00 | 0.00 |
| ATOM | 184 | CB | GLN | 13 | 15.550 | −0.115 | 4.134 | 1.00 | 0.00 |
| ATOM | 185 | HB1 | GLN | 13 | 15.055 | 0.411 | 3.331 | 1.00 | 0.00 |
| ATOM | 186 | HB2 | GLN | 13 | 16.610 | −0.149 | 3.931 | 1.00 | 0.00 |
| ATOM | 187 | CG | GLN | 13 | 15.336 | 0.669 | 5.420 | 1.00 | 0.00 |
| ATOM | 188 | HG1 | GLN | 13 | 15.288 | −0.025 | 6.248 | 1.00 | 0.00 |
| ATOM | 189 | HG2 | GLN | 13 | 14.403 | 1.208 | 5.347 | 1.00 | 0.00 |
| ATOM | 190 | CD | GLN | 13 | 16.450 | 1.662 | 5.681 | 1.00 | 0.00 |
| ATOM | 191 | OE1 | GLN | 13 | 16.875 | 2.391 | 4.790 | 1.00 | 0.00 |
| ATOM | 192 | NE2 | GLN | 13 | 16.930 | 1.695 | 6.925 | 1.00 | 0.00 |
| ATOM | 193 | HE21 | GLN | 13 | 17.651 | 2.328 | 7.125 | 1.00 | 0.00 |
| ATOM | 194 | HE22 | GLN | 13 | 16.543 | 1.085 | 7.507 | 1.00 | 0.00 |
| ATOM | 195 | C | GLN | 13 | 13.538 | −1.566 | 3.807 | 1.00 | 0.00 |
| ATOM | 196 | O | GLN | 13 | 12.658 | −1.099 | 4.666 | 1.00 | 0.00 |
| ATOM | 197 | N | LEU | 14 | 13.278 | −1.666 | 2.509 | 1.00 | 0.00 |
| ATOM | 198 | HN | LEU | 14 | 14.025 | −1.723 | 1.877 | 1.00 | 0.00 |
| ATOM | 199 | CA | LEU | 14 | 13.914 | −1.713 | 1.988 | 1.00 | 0.00 |
| ATOM | 200 | HA | LEU | 14 | 12.445 | −0.764 | 2.212 | 1.00 | 0.00 |
| ATOM | 201 | CB | LEU | 14 | 12.939 | −1.932 | 0.481 | 1.00 | 0.00 |
| ATOM | 202 | HB1 | LEU | 14 | 12.218 | −1.001 | 0.012 | 1.00 | 0.00 |
| ATOM | 203 | HB2 | LEU | 14 | 12.702 | −2.664 | 0.261 | 1.00 | 0.00 |
| ATOM | 204 | CG | LEU | 14 | 10.625 | −2.407 | −0.145 | 1.00 | 0.00 |
| ATOM | 205 | HG | LEU | 14 | 9.801 | −1.900 | 0.333 | 1.00 | 0.00 |
| ATOM | 206 | CD1 | LEU | 14 | 10.592 | −2.066 | −1.628 | 1.00 | 0.00 |
| ATOM | 207 | HD11 | LEU | 14 | 11.506 | −2.043 | −2.095 | 1.00 | 0.00 |
| ATOM | 208 | HD12 | LEU | 14 | 10.499 | −0.997 | −1.749 | 1.00 | 0.00 |
| ATOM | 209 | HD13 | LEU | 14 | 9.749 | −2.556 | −2.091 | 1.00 | 0.00 |
| ATOM | 210 | CD2 | LEU | 14 | 10.444 | −3.902 | 0.064 | 1.00 | 0.00 |
| ATOM | 211 | HD21 | LEU | 14 | 11.402 | −4.354 | 0.275 | 1.00 | 0.00 |
| ATOM | 212 | HD22 | LEU | 14 | 10.026 | −4.348 | −0.828 | 1.00 | 0.00 |
| ATOM | 213 | HD23 | LEU | 14 | 9.777 | −4.071 | 0.897 | 1.00 | 0.00 |
| ATOM | 214 | C | LEU | 14 | 11.121 | −2.822 | 2.689 | 1.00 | 0.00 |
| ATOM | 215 | O | LEU | 14 | 10.019 | −2.595 | 3.188 | 1.00 | 0.00 |
| ATOM | 216 | N | TYR | 15 | 11.697 | −4.018 | 2.715 | 1.00 | 0.00 |
| ATOM | 217 | HN | TYR | 15 | 12.579 | −4.131 | 2.303 | 1.00 | 0.00 |
| ATOM | 218 | CA | TYR | 15 | 11.063 | −5.167 | 3.350 | 1.00 | 0.00 |
| ATOM | 219 | HA | TYR | 15 | 10.125 | −5.357 | 2.843 | 1.00 | 0.00 |
| ATOM | 220 | CB | TYR | 15 | 11.964 | −6.394 | 3.218 | 1.00 | 0.00 |
| ATOM | 221 | HB1 | TYR | 15 | 12.163 | −6.569 | 2.173 | 1.00 | 0.00 |
| ATOM | 222 | HB2 | TYR | 15 | 12.896 | −6.200 | 3.728 | 1.00 | 0.00 |
| ATOM | 223 | CG | TYR | 15 | 12.374 | −7.659 | 3.798 | 1.00 | 0.00 |
| ATOM | 224 | CD1 | TYR | 15 | 12.076 | −8.808 | 4.734 | 1.00 | 0.00 |
| ATOM | 225 | HD1 | TYR | 15 | 13.051 | −8.070 | 5.053 | 1.00 | 0.00 |
| ATOM | 226 | CD2 | TYR | 15 | 10.321 | −8.111 | 3.402 | 1.00 | 0.00 |
| ATOM | 227 | HD2 | TYR | 15 | 9.564 | −7.543 | 2.671 | 1.00 | 0.00 |
| ATOM | 228 | CE1 | TYR | 15 | 11.542 | −9.565 | 5.268 | 1.00 | 0.00 |
| ATOM | 229 | HE1 | TYR | 15 | 12.102 | −10.132 | 5.998 | 1.00 | 0.00 |
| ATOM | 230 | CE2 | TYR | 15 | 9.582 | −9.269 | 3.921 | 1.00 | 0.00 |
| ATOM | 231 | HE2 | TYR | 15 | 8.606 | −9.604 | 3.610 | 1.00 | 0.00 |

TABLE 5-continued

Atomic Structure Coordinates of the
Free Form of the P/CAF Bromodomain

| ATOM | 232 | CZ | TYR | 15 | 10.296 | −9.993 | 4.860 | 1.00 | 0.00 |
|---|---|---|---|---|---|---|---|---|---|
| ATOM | 233 | OH | TYR | 15 | 9.761 | −11.145 | 5.383 | 1.00 | 0.00 |
| ATOM | 234 | HH | TYR | 15 | 10.392 | −11.863 | 5.295 | 1.00 | 0.00 |
| ATOM | 235 | C | TYR | 15 | 10.776 | −4.888 | 4.821 | 1.00 | 0.00 |
| ATOM | 236 | O | TYR | 15 | 9.750 | −5.307 | 5.358 | 1.00 | 0.00 |
| ATOM | 237 | N | SER | 16 | 11.694 | −4.181 | 5.471 | 1.00 | 0.00 |
| ATOM | 238 | HN | SER | 16 | 12.487 | −3.869 | 4.583 | 1.00 | 0.00 |
| ATOM | 239 | CA | SER | 16 | 11.535 | −3.836 | 6.878 | 1.00 | 0.00 |
| ATOM | 240 | HA | SER | 16 | 11.318 | −4.746 | 7.420 | 1.00 | 0.00 |
| ATOM | 241 | CB | SER | 16 | 12.824 | −3.220 | 7.425 | 1.00 | 0.00 |
| ATOM | 242 | HB1 | SER | 16 | 13.672 | −3.768 | 7.042 | 1.00 | 0.00 |
| ATOM | 243 | HB2 | SER | 16 | 12.889 | −2.189 | 7.111 | 1.00 | 0.00 |
| ATOM | 244 | CG | SER | 16 | 12.852 | −3.268 | 8.841 | 1.00 | 0.00 |
| ATOM | 245 | HG | SER | 16 | 13.743 | −3.471 | 9.137 | 1.00 | 0.00 |
| ATOM | 246 | C | SER | 16 | 10.373 | −2.867 | 7.061 | 1.00 | 0.00 |
| ATOM | 247 | O | SER | 16 | 9.748 | −2.824 | 8.120 | 1.00 | 0.00 |
| ATOM | 248 | N | THR | 17 | 10.087 | −2.096 | 6.017 | 1.00 | 0.00 |
| ATOM | 249 | HN | THR | 17 | 10.615 | −2.189 | 5.195 | 1.00 | 0.00 |
| ATOM | 250 | CA | THR | 17 | 8.983 | −1.146 | 6.049 | 1.00 | 0.00 |
| ATOM | 251 | HA | THR | 17 | 8.965 | −0.685 | 7.025 | 1.00 | 0.00 |
| ATOM | 252 | CB | THR | 17 | 9.102 | −0.961 | 4.982 | 1.00 | 0.00 |
| ATOM | 253 | HB | THR | 17 | 9.395 | −8.537 | 4.037 | 1.00 | 0.00 |
| ATOM | 254 | OG1 | THR | 17 | 10.278 | 0.771 | 5.316 | 1.00 | 0.00 |
| ATOM | 255 | HG1 | THR | 17 | 10.098 | 1.223 | 6.144 | 1.00 | 0.00 |
| ATOM | 256 | CG2 | THR | 17 | 7.971 | 0.832 | 4.783 | 1.00 | 0.00 |
| ATOM | 257 | HG21 | THR | 17 | 7.078 | 0.224 | 4.720 | 1.00 | 0.00 |
| ATOM | 258 | HG22 | THR | 17 | 8.088 | 1.395 | 3.867 | 1.00 | 0.00 |
| ATOM | 259 | HG23 | THR | 17 | 7.883 | 1.513 | 5.616 | 1.00 | 0.00 |
| ATOM | 260 | C | THR | 17 | 7.662 | −1.866 | 5.821 | 1.00 | 0.00 |
| ATOM | 261 | O | THR | 17 | 6.756 | −1.792 | 6.646 | 1.00 | 0.00 |
| ATOM | 262 | N | LEU | 18 | 7.574 | −2.569 | 4.697 | 1.00 | 0.00 |
| ATOM | 263 | HN | LEU | 18 | 8.339 | −2.578 | 4.083 | 1.00 | 0.00 |
| ATOM | 264 | CA | LEU | 18 | 6.369 | −3.302 | 4.330 | 1.00 | 0.00 |
| ATOM | 265 | HA | LEU | 18 | 5.555 | −2.597 | 4.289 | 1.00 | 0.00 |
| ATOM | 266 | CB | LEU | 18 | 6.550 | −3.928 | 2.955 | 1.00 | 0.00 |
| ATOM | 267 | HB1 | LEU | 18 | 7.307 | −4.694 | 1.026 | 1.00 | 0.00 |
| ATOM | 268 | HB2 | LEU | 18 | 5.619 | −4.389 | 2.661 | 1.00 | 0.00 |
| ATOM | 269 | CG | LEU | 18 | 6.964 | −2.940 | 1.875 | 1.00 | 0.00 |
| ATOM | 270 | HG | LEU | 18 | 7.969 | −2.603 | 2.075 | 1.00 | 0.00 |
| ATOM | 271 | CD1 | LEU | 18 | 6.950 | −3.607 | 0.510 | 1.00 | 0.00 |
| ATOM | 272 | HD11 | LEU | 18 | 7.945 | −3.943 | 0.274 | 1.00 | 0.00 |
| ATOM | 273 | HD12 | LEU | 18 | 6.540 | −2.894 | −0.236 | 1.00 | 0.00 |
| ATOM | 274 | HD13 | LEU | 18 | 6.270 | −4.442 | 0.574 | 1.00 | 0.00 |
| ATOM | 275 | CD2 | LEU | 18 | 6.048 | −1.722 | 1.899 | 1.00 | 0.00 |
| ATOM | 276 | HD21 | LEU | 18 | 3.138 | −1.963 | 2.630 | 1.00 | 0.00 |
| ATOM | 277 | HD22 | LEU | 18 | 5.811 | −1.428 | 0.889 | 1.00 | 0.00 |
| ATOM | 278 | HD23 | LEU | 18 | 6.549 | −0.908 | 2.401 | 1.00 | 0.00 |
| ATOM | 279 | C | LEU | 18 | 6.037 | −4.376 | 5.349 | 1.00 | 0.00 |
| ATOM | 280 | O | LEU | 18 | 4.961 | −4.372 | 5.947 | 1.00 | 0.00 |
| ATOM | 281 | N | LYS | 19 | 6.956 | −5.310 | 5.541 | 1.00 | 0.00 |
| ATOM | 282 | HN | LYS | 19 | 7.802 | −5.262 | 5.048 | 1.00 | 0.00 |
| ATOM | 283 | CA | LYS | 19 | 6.753 | −6.372 | 6.514 | 1.00 | 0.00 |
| ATOM | 284 | HA | LYS | 19 | 5.946 | −6.995 | 6.158 | 1.00 | 0.00 |
| ATOM | 285 | CB | LYS | 19 | 8.029 | −7.225 | 6.635 | 1.00 | 0.00 |
| ATOM | 286 | HB1 | LYS | 19 | 8.522 | −7.243 | 5.674 | 1.00 | 0.00 |
| ATOM | 287 | HB2 | LYS | 19 | 7.748 | −8.232 | 6.897 | 1.00 | 0.00 |
| ATOM | 288 | CG | LYS | 19 | 9.033 | −6.730 | 7.669 | 1.00 | 0.00 |
| ATOM | 289 | HG1 | LYS | 19 | 8.693 | −7.018 | 8.653 | 1.00 | 0.00 |
| ATOM | 290 | HG2 | LYS | 19 | 9.096 | −5.653 | 7.608 | 1.00 | 0.00 |
| ATOM | 291 | CD | LYS | 19 | 10.412 | −7.319 | 7.429 | 1.00 | 0.00 |
| ATOM | 292 | HD1 | LYS | 19 | 10.559 | −7.440 | 6.365 | 1.00 | 0.00 |
| ATOM | 293 | HD2 | LYS | 19 | 11.156 | −6.643 | 7.823 | 1.00 | 0.00 |
| ATOM | 294 | CE | LYS | 19 | 10.567 | −8.671 | 8.106 | 1.00 | 0.00 |
| ATOM | 295 | HE1 | LYS | 19 | 9.987 | −9.401 | 7.560 | 1.00 | 0.00 |
| ATOM | 296 | HE2 | LYS | 19 | 10.193 | −8.598 | 9.117 | 1.00 | 0.00 |
| ATOM | 297 | NZ | LYS | 19 | 11.988 | −9.115 | 8.146 | 1.00 | 0.00 |
| ATOM | 298 | HZ1 | LYS | 19 | 12.044 | −10.147 | 8.030 | 1.00 | 0.00 |
| ATOM | 299 | HZ2 | LYS | 19 | 12.418 | −8.855 | 9.057 | 1.00 | 0.00 |
| ATOM | 300 | HZ3 | LYS | 19 | 12.526 | −8.661 | 7.380 | 1.00 | 0.00 |
| ATOM | 301 | C | LYS | 19 | 6.349 | −5.772 | 7.862 | 1.00 | 0.00 |
| ATOM | 302 | O | LYS | 19 | 5.624 | −6.390 | 8.646 | 1.00 | 0.00 |
| ATOM | 303 | N | SER | 20 | 6.797 | −4.542 | 8.108 | 1.00 | 0.00 |
| ATOM | 304 | HN | SER | 20 | 7.366 | −4.092 | 7.419 | 1.00 | 0.00 |
| ATOM | 305 | CA | SER | 20 | 6.482 | −3.841 | 9.336 | 1.00 | 0.00 |
| ATOM | 306 | HA | SER | 20 | 6.568 | −4.551 | 10.141 | 1.00 | 0.00 |
| ATOM | 307 | CB | SER | 20 | 7.481 | −2.708 | 9.581 | 1.00 | 0.00 |

TABLE 5-continued

Atomic Structure Coordinates of the
Free Form of the P/CAF Bromodomain

| ATOM | 308 | HB1 | SER | 20 | 7.667 | −2.171 | 8.659 | 1.00 | 0.00 |
|---|---|---|---|---|---|---|---|---|---|
| ATOM | 309 | HB2 | SER | 20 | 8.416 | −3.123 | 9.929 | 1.00 | 0.00 |
| ATOM | 310 | CG | SER | 20 | 6.996 | −1.801 | 10.556 | 1.00 | 0.00 |
| ATOM | 311 | HG | SER | 20 | 7.552 | −1.841 | 11.337 | 1.00 | 0.00 |
| ATOM | 312 | C | SER | 20 | 5.070 | −3.288 | 9.292 | 1.00 | 0.00 |
| ATOM | 313 | O | SER | 20 | 4.184 | −3.752 | 10.016 | 1.00 | 0.00 |
| ATOM | 314 | N | ILE | 21 | 4.851 | −2.311 | 8.423 | 1.00 | 0.00 |
| ATOM | 315 | HN | ILE | 21 | 5.590 | −1.989 | 7.856 | 1.00 | 0.00 |
| ATOM | 316 | CA | ILE | 21 | 3.531 | −1.717 | 8.268 | 1.00 | 0.00 |
| ATOM | 317 | HA | ILE | 21 | 3.312 | −1.154 | 9.164 | 1.00 | 0.00 |
| ATOM | 318 | CB | ILE | 21 | 3.477 | −0.752 | 7.069 | 1.00 | 0.00 |
| ATOM | 319 | HB | ILE | 21 | 2.442 | −0.564 | 6.839 | 1.00 | 0.00 |
| ATOM | 320 | CG1 | ILE | 21 | 4.155 | −1.368 | 5.846 | 1.00 | 0.00 |
| ATOM | 321 | HG11 | ILE | 21 | 4.819 | −0.640 | 5.406 | 1.00 | 0.00 |
| ATOM | 322 | HG12 | ILE | 21 | 4.723 | −2.227 | 6.152 | 1.00 | 0.00 |
| ATOM | 323 | CG2 | ILE | 21 | 6.130 | 0.573 | 7.427 | 1.00 | 0.00 |
| ATOM | 324 | HG21 | ILE | 21 | 3.498 | 1.385 | 7.101 | 1.00 | 0.00 |
| ATOM | 325 | HG22 | ILE | 21 | 5.089 | 0.644 | 6.935 | 1.00 | 0.00 |
| ATOM | 326 | HG23 | ILE | 21 | 4.268 | 0.630 | 8.496 | 1.00 | 0.00 |
| ATOM | 327 | CD1 | ILE | 21 | 3.185 | −1.819 | 4.782 | 1.00 | 0.00 |
| ATOM | 328 | HD11 | ILE | 21 | 2.645 | −1.684 | 5.134 | 1.00 | 0.00 |
| ATOM | 329 | HD12 | ILE | 21 | 3.729 | −2.074 | 3.895 | 1.00 | 0.00 |
| ATOM | 330 | HD13 | ILE | 21 | 2.489 | −1.027 | 4.568 | 1.00 | 0.00 |
| ATOM | 331 | C | ILE | 21 | 2.472 | −2.801 | 8.095 | 1.00 | 0.00 |
| ATOM | 332 | O | ILE | 21 | 2.487 | −2.838 | 8.823 | 1.00 | 0.00 |
| ATOM | 333 | N | LEU | 22 | 2.710 | −3.715 | 7.164 | 1.00 | 0.00 |
| ATOM | 334 | HN | LEU | 22 | 3.520 | −3.646 | 6.622 | 1.00 | 0.00 |
| ATOM | 335 | CA | LEU | 22 | 1.785 | −4.812 | 6.920 | 1.00 | 0.00 |
| ATOM | 336 | HA | LEU | 22 | 0.864 | −4.390 | 6.544 | 1.00 | 0.00 |
| ATOM | 337 | CB | LEU | 22 | 2.361 | −5.772 | 5.874 | 1.00 | 0.00 |
| ATOM | 338 | HB1 | LEU | 22 | 1.785 | −6.685 | 5.900 | 1.00 | 0.00 |
| ATOM | 339 | HB2 | LEU | 22 | 3.379 | −6.000 | 6.147 | 1.00 | 0.00 |
| ATOM | 340 | CG | LEU | 22 | 2.360 | −5.245 | 4.439 | 1.00 | 0.00 |
| ATOM | 341 | HG | LEU | 22 | 3.054 | −4.421 | 4.365 | 1.00 | 0.00 |
| ATOM | 342 | CD1 | LEU | 22 | 2.815 | −6.329 | 3.474 | 1.00 | 0.00 |
| ATOM | 343 | HD11 | LEU | 22 | 2.102 | −6.416 | 2.668 | 1.00 | 0.00 |
| ATOM | 344 | HD12 | LEU | 22 | 2.885 | −7.371 | 3.997 | 1.00 | 0.00 |
| ATOM | 345 | HD13 | LEU | 22 | 3.783 | −6.069 | 3.071 | 1.00 | 0.00 |
| ATOM | 346 | CD2 | LEU | 22 | 0.980 | −4.733 | 4.057 | 1.00 | 0.00 |
| ATOM | 347 | HD21 | LEU | 22 | 0.926 | −3.671 | 4.243 | 1.00 | 0.00 |
| ATOM | 348 | HD22 | LEU | 22 | 0.234 | −5.242 | 4.647 | 1.00 | 0.00 |
| ATOM | 349 | HD23 | LEU | 22 | 0.803 | −4.926 | 3.008 | 1.00 | 0.00 |
| ATOM | 350 | C | LEU | 22 | 1.493 | −5.568 | 8.214 | 1.00 | 0.00 |
| ATOM | 351 | O | LEU | 22 | 0.340 | −5.862 | 8.525 | 1.00 | 0.00 |
| ATOM | 352 | N | GLN | 23 | 2.546 | −5.868 | 8.971 | 1.00 | 0.00 |
| ATOM | 353 | HN | GLN | 23 | 3.447 | −5.617 | 8.666 | 1.00 | 0.00 |
| ATOM | 354 | CA | GLN | 23 | 2.402 | −6.598 | 10.226 | 1.00 | 0.00 |
| ATOM | 355 | HA | GLN | 23 | 2.068 | −7.596 | 9.989 | 1.00 | 0.00 |
| ATOM | 356 | CB | GLN | 23 | 3.754 | −6.684 | 10.340 | 1.00 | 0.00 |
| ATOM | 357 | HB1 | GLN | 23 | 3.588 | −6.635 | 12.006 | 1.00 | 0.00 |
| ATOM | 358 | HB2 | GLN | 23 | 4.360 | −5.842 | 10.640 | 1.00 | 0.00 |
| ATOM | 359 | CG | GLN | 23 | 4.528 | −7.958 | 10.637 | 1.00 | 0.00 |
| ATOM | 360 | HG1 | GLN | 23 | 4.592 | −8.082 | 9.566 | 1.00 | 0.00 |
| ATOM | 361 | HG2 | GLN | 23 | 5.523 | −7.865 | 11.048 | 1.00 | 0.00 |
| ATOM | 362 | CD | GLN | 23 | 3.875 | −9.191 | 11.231 | 1.00 | 0.00 |
| ATOM | 363 | OE1 | GLN | 23 | 3.304 | −9.141 | 12.320 | 1.00 | 0.00 |
| ATOM | 364 | NE2 | GLN | 23 | 3.958 | −10.308 | 10.517 | 1.00 | 0.00 |
| ATOM | 365 | HE21 | GLN | 23 | 3.545 | −11.120 | 10.879 | 1.00 | 0.00 |
| ATOM | 366 | HE22 | GLN | 23 | 4.429 | −10.275 | 9.658 | 1.00 | 0.00 |
| ATOM | 367 | C | GLN | 23 | 1.374 | −5.941 | 11.151 | 1.00 | 0.00 |
| ATOM | 368 | O | GLN | 23 | 0.462 | −6.604 | 11.646 | 1.00 | 0.00 |
| ATOM | 369 | N | GLN | 24 | 1.542 | −4.645 | 11.404 | 1.00 | 0.00 |
| ATOM | 370 | HN | GLN | 24 | 2.303 | −4.175 | 11.002 | 1.00 | 0.00 |
| ATOM | 371 | CA | GLN | 24 | 0.659 | −3.920 | 12.317 | 1.00 | 0.00 |
| ATOM | 372 | HA | GLN | 24 | 0.434 | −4.580 | 13.142 | 1.00 | 0.00 |
| ATOM | 373 | CB | GLN | 24 | 1.369 | −2.679 | 12.863 | 1.00 | 0.00 |
| ATOM | 374 | HB1 | GLN | 24 | 2.330 | −2.973 | 13.260 | 1.00 | 0.00 |
| ATOM | 375 | HB2 | GLN | 24 | 0.774 | −2.258 | 13.659 | 1.00 | 0.00 |
| ATOM | 376 | CG | GLN | 24 | 1.596 | −1.602 | 11.817 | 1.00 | 0.00 |
| ATOM | 377 | HG1 | GLN | 24 | 0.680 | −1.044 | 11.689 | 1.00 | 0.00 |
| ATOM | 378 | HG2 | GLN | 24 | 1.860 | −2.077 | 10.885 | 1.00 | 0.00 |
| ATOM | 379 | CD | GLN | 24 | 2.702 | −0.638 | 12.200 | 1.00 | 0.00 |
| ATOM | 380 | OE1 | GLN | 24 | 3.210 | −0.671 | 13.320 | 1.00 | 0.00 |
| ATOM | 381 | NE2 | GLN | 24 | 3.082 | 0.227 | 11.266 | 1.00 | 0.00 |
| ATOM | 382 | HE21 | GLN | 24 | 2.633 | 0.195 | 10.395 | 1.00 | 0.00 |
| ATOM | 383 | HE22 | GLN | 24 | 3.795 | 0.862 | 11.486 | 1.00 | 0.00 |

TABLE 5-continued

Atomic Structure Coordinates of the
Free Form of the P/CAF Bromodomain

| ATOM | 384 | C | GLN | 24 | −0.658 | −3.511 | 11.654 | 1.00 | 0.00 |
|---|---|---|---|---|---|---|---|---|---|
| ATOM | 385 | O | GLN | 24 | −1.727 | −3.682 | 12.237 | 1.00 | 0.00 |
| ATOM | 386 | N | VAL | 25 | −0.577 | −2.936 | 10.456 | 1.00 | 0.00 |
| ATOM | 387 | HN | VAL | 25 | 0.298 | −2.811 | 10.047 | 1.00 | 0.00 |
| ATOM | 388 | CA | VAL | 25 | −1.769 | −2.477 | 9.743 | 1.00 | 0.00 |
| ATOM | 389 | HA | VAL | 25 | −2.139 | −1.597 | 10.251 | 1.00 | 0.00 |
| ATOM | 390 | CB | VAL | 25 | −1.454 | −2.085 | 8.285 | 1.00 | 0.00 |
| ATOM | 391 | HB | VAL | 25 | −2.344 | −1.670 | 7.845 | 1.00 | 0.00 |
| ATOM | 392 | CG1 | VAL | 25 | −0.364 | −1.025 | 8.239 | 1.00 | 0.00 |
| ATOM | 393 | HG11 | VAL | 25 | −0.774 | −0.102 | 7.858 | 1.00 | 0.00 |
| ATOM | 394 | HG12 | VAL | 25 | 0.434 | −1.358 | 7.591 | 1.00 | 0.00 |
| ATOM | 395 | HG13 | VAL | 25 | 0.024 | −0.863 | 9.234 | 1.00 | 0.00 |
| ATOM | 396 | CG2 | VAL | 25 | −1.061 | −3.301 | 7.473 | 1.00 | 0.00 |
| ATOM | 397 | HG21 | VAL | 25 | −1.924 | −3.934 | 7.330 | 1.00 | 0.00 |
| ATOM | 398 | HG22 | VAL | 25 | −0.295 | −3.848 | 7.997 | 1.00 | 0.00 |
| ATOM | 399 | HG23 | VAL | 25 | −0.684 | −2.982 | 6.511 | 1.00 | 0.00 |
| ATOM | 400 | C | VAL | 25 | −2.865 | −3.536 | 9.760 | 1.00 | 0.00 |
| ATOM | 401 | O | VAL | 25 | −4.042 | −3.213 | 9.907 | 1.00 | 0.00 |
| ATOM | 402 | N | LYS | 26 | −2.478 | −4.805 | 9.670 | 1.00 | 0.00 |
| ATOM | 403 | HN | LYS | 26 | −1.525 | −5.013 | 9.579 | 1.00 | 0.00 |
| ATOM | 404 | CA | LYS | 26 | −3.448 | −5.893 | 9.728 | 1.00 | 0.00 |
| ATOM | 405 | HA | LYS | 26 | −4.076 | −5.827 | 8.952 | 1.00 | 0.00 |
| ATOM | 406 | CB | LYS | 26 | −2.739 | −7.248 | 9.740 | 1.00 | 0.00 |
| ATOM | 407 | HB1 | LYS | 26 | −2.064 | −7.280 | 10.582 | 1.00 | 0.00 |
| ATOM | 408 | HB2 | LYS | 26 | −1.479 | −8.026 | 9.853 | 1.00 | 0.00 |
| ATOM | 409 | CG | LYS | 26 | −1.940 | −7.530 | 8.479 | 1.00 | 0.00 |
| ATOM | 410 | HG1 | LYS | 26 | −2.552 | −8.102 | 7.797 | 1.00 | 0.00 |
| ATOM | 411 | HG2 | LYS | 26 | −1.665 | −6.591 | 8.020 | 1.00 | 0.00 |
| ATOM | 412 | CD | LYS | 26 | −0.679 | −8.317 | 8.790 | 1.00 | 0.00 |
| ATOM | 413 | HD1 | LYS | 26 | −0.295 | −7.995 | 9.747 | 1.00 | 0.00 |
| ATOM | 414 | HD2 | LYS | 26 | 0.054 | −8.123 | 8.020 | 1.00 | 0.00 |
| ATOM | 415 | CE | LYS | 26 | −0.955 | −9.811 | 8.844 | 1.00 | 0.00 |
| ATOM | 416 | HE1 | LYS | 26 | −0.358 | −10.245 | 9.637 | 1.00 | 0.00 |
| ATOM | 417 | HE2 | LYS | 26 | −2.002 | −9.962 | 9.062 | 1.00 | 0.00 |
| ATOM | 418 | NZ | LYS | 26 | −0.625 | −10.486 | 7.558 | 1.00 | 0.00 |
| ATOM | 419 | HZ1 | LYS | 26 | 0.302 | −10.951 | 7.627 | 1.00 | 0.00 |
| ATOM | 420 | HZ2 | LYS | 26 | −0.595 | −9.790 | 6.787 | 1.00 | 0.00 |
| ATOM | 421 | HZ3 | LYS | 26 | −1.345 | −11.203 | 7.336 | 1.00 | 0.00 |
| ATOM | 422 | C | LYS | 26 | −4.319 | −5.750 | 10.973 | 1.00 | 0.00 |
| ATOM | 423 | O | LYS | 26 | −5.496 | −6.105 | 10.969 | 1.00 | 0.00 |
| ATOM | 424 | N | SER | 27 | −3.724 | −5.203 | 12.029 | 1.00 | 0.00 |
| ATOM | 425 | HN | SER | 27 | −2.783 | −4.928 | 11.957 | 1.00 | 0.00 |
| ATOM | 426 | CA | SER | 27 | −4.437 | −4.970 | 13.281 | 1.00 | 0.00 |
| ATOM | 427 | HA | SER | 27 | −5.407 | −5.436 | 13.209 | 1.00 | 0.00 |
| ATOM | 428 | CB | SER | 27 | −3.669 | −5.585 | 14.452 | 1.00 | 0.00 |
| ATOM | 429 | HB1 | SER | 27 | −2.861 | −4.927 | 14.735 | 1.00 | 0.00 |
| ATOM | 430 | HB2 | SER | 27 | −3.267 | −4.542 | 14.152 | 1.00 | 0.00 |
| ATOM | 431 | CG | SER | 27 | −4.514 | −5.777 | 15.573 | 1.00 | 0.00 |
| ATOM | 432 | HG | SER | 27 | −5.402 | −5.986 | 15.273 | 1.00 | 0.00 |
| ATOM | 433 | C | SER | 27 | −4.643 | −3.481 | 13.519 | 1.00 | 0.00 |
| ATOM | 434 | O | SER | 27 | −4.887 | −3.052 | 14.646 | 1.00 | 0.00 |
| ATOM | 435 | N | HIS | 28 | −4.516 | −2.692 | 12.457 | 1.00 | 0.00 |
| ATOM | 436 | HN | HIS | 28 | −4.367 | −3.088 | 11.578 | 1.00 | 0.00 |
| ATOM | 437 | CA | HIS | 28 | −4.753 | −1.267 | 12.552 | 1.00 | 0.00 |
| ATOM | 438 | HA | HIS | 28 | −4.393 | −0.936 | 13.515 | 1.00 | 0.00 |
| ATOM | 439 | CB | HIS | 28 | −4.006 | −0.512 | 11.456 | 1.00 | 0.00 |
| ATOM | 440 | HB1 | HIS | 28 | −2.948 | −0.628 | 11.622 | 1.00 | 0.00 |
| ATOM | 441 | HB2 | HIS | 28 | −4.266 | −0.930 | 10.496 | 1.00 | 0.00 |
| ATOM | 442 | CG | HIS | 28 | −4.292 | 0.956 | 11.417 | 1.00 | 0.00 |
| ATOM | 443 | ND1 | HIS | 28 | −4.264 | 1.759 | 12.538 | 1.00 | 0.00 |
| ATOM | 444 | HD1 | HIS | 28 | −4.083 | 1.459 | 13.454 | 1.00 | 0.00 |
| ATOM | 445 | CD2 | HIS | 28 | −4.569 | 1.777 | 10.377 | 1.00 | 0.00 |
| ATOM | 446 | HD2 | HIS | 28 | −4.665 | 1.487 | 9.340 | 1.00 | 0.00 |
| ATOM | 447 | CE1 | HIS | 28 | −4.533 | 3.006 | 12.191 | 1.00 | 0.00 |
| ATOM | 448 | HE1 | HIS | 28 | −4.507 | 3.852 | 12.859 | 1.00 | 0.00 |
| ATOM | 449 | HE2 | HIS | 28 | −4.719 | 3.042 | 10.886 | 1.00 | 0.00 |
| ATOM | 450 | NZ2 | HIS | 28 | −4.935 | 3.844 | 10.367 | 1.00 | 0.00 |
| ATOM | 451 | C | HIS | 28 | −6.246 | −1.009 | 12.480 | 1.00 | 0.00 |
| ATOM | 452 | O | HIS | 28 | −6.982 | −1.724 | 11.800 | 1.00 | 0.00 |
| ATOM | 453 | N | GLN | 29 | −6.690 | −0.037 | 13.241 | 1.00 | 0.00 |
| ATOM | 454 | HN | GLN | 29 | −6.048 | 0.472 | 13.775 | 1.00 | 0.00 |
| ATOM | 455 | CA | GLN | 29 | −8.109 | 0.272 | 13.334 | 1.00 | 0.00 |
| ATOM | 456 | HA | GLN | 29 | −8.680 | −0.668 | 13.358 | 1.00 | 0.00 |
| ATOM | 457 | CB | GLN | 29 | −8.371 | 1.007 | 14.638 | 1.00 | 0.00 |
| ATOM | 458 | HB1 | GLN | 29 | −9.433 | 1.028 | 14.832 | 1.00 | 0.00 |
| ATOM | 459 | HB2 | GLN | 29 | −8.012 | 2.021 | 14.552 | 1.00 | 0.00 |

TABLE 5-continued

Atomic Structure Coordinates of the
Free Form of the P/CAF Bromodomain

| ATOM | 460 | CG | GLN | 29 | −7.670 | 0.341 | 15.809 | 1.00 | 0.00 |
|---|---|---|---|---|---|---|---|---|---|
| ATOM | 461 | HG1 | GLN | 29 | −7.180 | −0.560 | 15.445 | 1.00 | 0.00 |
| ATOM | 462 | HG2 | GLN | 29 | −6.929 | 1.021 | 16.203 | 1.00 | 0.00 |
| ATOM | 463 | CD | GLN | 29 | −8.622 | −0.040 | 16.925 | 1.00 | 0.00 |
| ATOM | 464 | OE1 | GLN | 29 | −8.354 | 0.234 | 18.097 | 1.00 | 0.00 |
| ATOM | 465 | NE2 | GLN | 29 | −9.730 | −0.676 | 16.566 | 1.00 | 0.00 |
| ATOM | 466 | HE21 | GLN | 29 | −9.870 | −0.861 | 15.623 | 1.00 | 0.00 |
| ATOM | 467 | HE22 | GLN | 29 | −10.363 | −0.935 | 17.267 | 1.00 | 0.00 |
| ATOM | 468 | C | GLN | 29 | −8.607 | 1.069 | 12.132 | 1.00 | 0.00 |
| ATOM | 469 | O | GLN | 29 | −9.794 | 1.378 | 12.034 | 1.00 | 0.00 |
| ATOM | 470 | N | SER | 30 | −7.711 | 1.368 | 11.191 | 1.00 | 0.00 |
| ATOM | 471 | HN | SER | 30 | −6.785 | 1.056 | 11.306 | 1.00 | 0.00 |
| ATOM | 472 | CA | SER | 30 | −8.082 | 2.036 | 9.965 | 1.00 | 0.00 |
| ATOM | 473 | HA | SER | 30 | −9.149 | 2.199 | 9.989 | 1.00 | 0.00 |
| ATOM | 474 | CB | SER | 30 | −7.375 | 3.385 | 9.874 | 1.00 | 0.00 |
| ATOM | 475 | HB1 | SER | 30 | −6.453 | 3.269 | 9.324 | 1.00 | 0.00 |
| ATOM | 476 | HB2 | SER | 30 | −8.013 | 4.090 | 9.362 | 1.00 | 0.00 |
| ATOM | 477 | CG | SER | 30 | −7.079 | 3.891 | 11.163 | 1.00 | 0.00 |
| ATOM | 478 | HG | SER | 30 | −7.871 | 3.870 | 11.705 | 1.00 | 0.00 |
| ATOM | 479 | C | SER | 30 | −7.743 | 1.184 | 8.740 | 1.00 | 0.00 |
| ATOM | 480 | O | SER | 30 | −8.056 | 1.562 | 7.611 | 1.00 | 0.00 |
| ATOM | 481 | N | ALA | 31 | −7.089 | 0.039 | 8.962 | 1.00 | 0.00 |
| ATOM | 482 | HN | ALA | 31 | −6.867 | −0.224 | 9.880 | 1.00 | 0.00 |
| ATOM | 483 | CA | ALA | 31 | −6.726 | −0.855 | 7.868 | 1.00 | 0.00 |
| ATOM | 484 | HA | ALA | 31 | −6.413 | −0.246 | 7.034 | 1.00 | 0.00 |
| ATOM | 485 | CB | ALA | 31 | −5.553 | −1.732 | 8.272 | 1.00 | 0.00 |
| ATOM | 486 | HB1 | ALA | 31 | −5.218 | −2.301 | 7.417 | 1.00 | 0.00 |
| ATOM | 487 | HB2 | ALA | 31 | −5.865 | −2.047 | 9.054 | 1.00 | 0.00 |
| ATOM | 488 | HB3 | ALA | 31 | −4.746 | −1.321 | 8.629 | 1.00 | 0.00 |
| ATOM | 489 | C | ALA | 31 | −7.906 | −1.726 | 7.433 | 1.00 | 0.00 |
| ATOM | 490 | O | ALA | 31 | −7.795 | −2.496 | 6.480 | 1.00 | 0.00 |
| ATOM | 491 | N | TRP | 32 | −9.060 | −1.590 | 8.119 | 1.00 | 0.00 |
| ATOM | 492 | HN | TRP | 32 | −9.072 | −0.874 | 8.879 | 1.00 | 0.00 |
| ATOM | 493 | CA | TRP | 32 | −10.222 | −2.384 | 7.799 | 1.00 | 0.00 |
| ATOM | 494 | HA | TRP | 32 | −9.960 | −3.416 | 7.971 | 1.00 | 0.00 |
| ATOM | 495 | CB | TRP | 32 | −11.389 | −2.030 | 8.736 | 1.00 | 0.00 |
| ATOM | 496 | HB1 | TRP | 32 | −11.167 | −2.390 | 9.730 | 1.00 | 0.00 |
| ATOM | 497 | HB2 | TRP | 32 | −12.289 | −2.507 | 8.377 | 1.00 | 0.00 |
| ATOM | 498 | CG | TRP | 32 | −11.644 | −0.566 | 8.823 | 1.00 | 0.00 |
| ATOM | 499 | CD1 | TRP | 32 | −11.330 | 0.268 | 9.857 | 1.00 | 0.00 |
| ATOM | 500 | HD1 | TRP | 32 | −10.862 | −0.052 | 10.776 | 1.00 | 0.00 |
| ATOM | 501 | CD2 | TRP | 32 | −12.255 | 0.241 | 7.823 | 1.00 | 0.00 |
| ATOM | 502 | NE1 | TRP | 32 | −11.699 | 1.554 | 9.549 | 1.00 | 0.00 |
| ATOM | 503 | HE1 | TRP | 32 | −11.582 | 2.325 | 10.128 | 1.00 | 0.00 |
| ATOM | 504 | CE2 | TRP | 32 | −12.259 | 1.564 | 8.298 | 1.00 | 0.00 |
| ATOM | 505 | CE3 | TRP | 32 | −12.759 | −0.025 | 6.552 | 1.00 | 0.00 |
| ATOM | 506 | HE3 | TRP | 32 | −12.751 | −1.026 | 6.146 | 1.00 | 0.00 |
| ATOM | 507 | CZ2 | TRP | 32 | −12.780 | 2.612 | 7.553 | 1.00 | 0.00 |
| ATOM | 508 | HZ2 | TRP | 32 | −12.798 | 3.627 | 7.923 | 1.00 | 0.00 |
| ATOM | 509 | CZ3 | TRP | 32 | −13.278 | 1.012 | 5.816 | 1.00 | 0.00 |
| ATOM | 510 | HZ3 | TRP | 32 | −13.671 | 0.827 | 4.829 | 1.00 | 0.00 |
| ATOM | 511 | CH2 | TRP | 32 | −13.284 | 2.314 | 6.317 | 1.00 | 0.00 |
| ATOM | 512 | HH2 | TRP | 32 | −13.669 | 3.090 | 5.697 | 1.00 | 0.00 |
| ATOM | 513 | C | TRP | 32 | −10.647 | −2.251 | 6.323 | 1.00 | 0.00 |
| ATOM | 514 | O | TRP | 32 | −11.197 | −3.202 | 5.769 | 1.00 | 0.00 |
| ATOM | 515 | N | PRO | 33 | −10.400 | −1.102 | 5.633 | 1.00 | 0.00 |
| ATOM | 516 | CA | PRO | 33 | −10.776 | −0.964 | 4.229 | 1.00 | 0.00 |
| ATOM | 517 | HA | PRO | 33 | −11.746 | −1.400 | 4.038 | 1.00 | 0.00 |
| ATOM | 518 | CB | PRO | 33 | −10.842 | 0.530 | 3.996 | 1.00 | 0.00 |
| ATOM | 519 | HB1 | PRO | 33 | −10.273 | 0.798 | 3.113 | 1.00 | 0.00 |
| ATOM | 520 | HB2 | PRO | 33 | −11.870 | 0.844 | 3.852 | 1.00 | 0.00 |
| ATOM | 521 | CG | PRO | 33 | −10.257 | 1.205 | 5.213 | 1.00 | 0.00 |
| ATOM | 522 | HG1 | PRO | 33 | −9.438 | 1.839 | 4.913 | 1.00 | 0.00 |
| ATOM | 523 | HG2 | PRO | 33 | −11.008 | 1.791 | 5.713 | 1.00 | 0.00 |
| ATOM | 524 | CD | PRO | 33 | −9.749 | 0.125 | 6.125 | 1.00 | 0.00 |
| ATOM | 525 | HD1 | PRO | 33 | −8.693 | 0.063 | 6.031 | 1.00 | 0.00 |
| ATOM | 526 | HD2 | PRO | 33 | −10.014 | 0.330 | 7.146 | 1.00 | 0.00 |
| ATOM | 527 | C | PRO | 33 | −9.748 | −1.064 | 3.299 | 1.00 | 0.00 |
| ATOM | 528 | O | PRO | 33 | −10.097 | −2.161 | 2.259 | 1.00 | 0.00 |
| ATOM | 529 | N | PHE | 34 | −8.481 | −1.522 | 3.688 | 1.00 | 0.00 |
| ATOM | 530 | HN | PHE | 34 | −8.271 | −2.075 | 4.533 | 1.00 | 0.00 |
| ATOM | 531 | CA | PHE | 34 | −7.393 | −2.109 | 2.910 | 1.00 | 0.00 |
| ATOM | 532 | HA | PHE | 34 | −7.546 | −2.870 | 1.872 | 1.00 | 0.00 |
| ATOM | 533 | CB | PHE | 34 | −6.043 | −2.529 | 3.344 | 1.00 | 0.00 |
| ATOM | 534 | HB1 | PHE | 34 | −5.395 | −1.497 | 2.686 | 1.00 | 0.00 |
| ATOM | 535 | HB2 | PHE | 34 | −5.608 | −2.168 | 4.098 | 1.00 | 0.00 |

TABLE 5-continued

Atomic Structure Coordinates of the
Free Form of the P/CAF Bromodomain

| ATOM | 536 | CG | PHE | 34 | −5.120 | −0.134 | 3.900 | 1.00 | 0.00 |
|---|---|---|---|---|---|---|---|---|---|
| ATOM | 537 | CD1 | PHE | 34 | −6.997 | 0.798 | 3.361 | 1.00 | 0.00 |
| ATOM | 538 | HD1 | PHE | 34 | −7.638 | 0.503 | 2.542 | 1.00 | 0.00 |
| ATOM | 539 | CD2 | PHE | 34 | −5.300 | 0.255 | 4.946 | 1.00 | 0.00 |
| ATOM | 540 | HD2 | PHE | 34 | −4.611 | −0.459 | 5.373 | 1.00 | 0.00 |
| ATOM | 541 | CE1 | PHE | 34 | −7.069 | 2.077 | 3.868 | 1.00 | 0.00 |
| ATOM | 542 | HE1 | PHE | 34 | −7.761 | 2.789 | 3.443 | 1.00 | 0.00 |
| ATOM | 543 | CE2 | PHE | 34 | −5.368 | 1.536 | 5.459 | 1.00 | 0.00 |
| ATOM | 544 | HE2 | PHE | 34 | −4.728 | 1.824 | 6.279 | 1.00 | 0.00 |
| ATOM | 545 | CZ | PHE | 34 | −6.252 | 2.450 | 4.917 | 1.00 | 0.00 |
| ATOM | 546 | HZ | PHE | 34 | −6.304 | 3.453 | 5.314 | 1.00 | 0.00 |
| ATOM | 547 | C | PHE | 34 | −7.400 | −3.624 | 3.053 | 1.00 | 0.00 |
| ATOM | 548 | O | PHE | 34 | −7.293 | −4.349 | 2.065 | 1.00 | 0.00 |
| ATOM | 549 | N | MET | 35 | −7.543 | −4.100 | 4.215 | 1.00 | 0.00 |
| ATOM | 550 | HN | MET | 35 | −7.635 | −3.476 | 5.035 | 1.00 | 0.00 |
| ATOM | 551 | CA | MET | 35 | −7.587 | −5.534 | 4.541 | 1.00 | 0.00 |
| ATOM | 552 | HA | MET | 35 | −6.624 | −5.948 | 4.283 | 1.00 | 0.00 |
| ATOM | 553 | CB | MET | 35 | −7.868 | −5.802 | 6.021 | 1.00 | 0.00 |
| ATOM | 554 | HB1 | MET | 35 | −8.472 | −4.998 | 6.413 | 1.00 | 0.00 |
| ATOM | 555 | HB2 | MET | 35 | −8.415 | −6.729 | 6.110 | 1.00 | 0.00 |
| ATOM | 556 | CG | MET | 35 | −6.609 | −5.910 | 6.868 | 1.00 | 0.00 |
| ATOM | 557 | HG1 | MET | 35 | −5.714 | −5.267 | 7.730 | 1.00 | 0.00 |
| ATOM | 558 | HG2 | MET | 35 | −5.766 | −5.582 | 6.278 | 1.00 | 0.00 |
| ATOM | 559 | SD | MET | 35 | −6.296 | −7.591 | 7.437 | 1.00 | 0.00 |
| ATOM | 560 | CE | MET | 35 | −4.848 | −8.011 | 6.470 | 1.00 | 0.00 |
| ATOM | 561 | HE1 | MET | 35 | −4.248 | −8.726 | 7.013 | 1.00 | 0.00 |
| ATOM | 562 | HE2 | MET | 35 | −4.268 | −7.119 | 6.285 | 1.00 | 0.00 |
| ATOM | 563 | HE3 | MET | 35 | −5.157 | −8.441 | 5.529 | 1.00 | 0.00 |
| ATOM | 564 | C | MET | 35 | −8.656 | −6.194 | 3.674 | 1.00 | 0.00 |
| ATOM | 565 | O | MET | 35 | −9.847 | −5.924 | 3.827 | 1.00 | 0.00 |
| ATOM | 566 | N | GLU | 36 | −8.219 | −7.049 | 2.751 | 1.00 | 0.00 |
| ATOM | 567 | HN | GLU | 36 | −7.255 | −7.208 | 2.671 | 1.00 | 0.00 |
| ATOM | 568 | CA | GLU | 36 | −9.128 | −7.729 | 1.829 | 1.00 | 0.00 |
| ATOM | 569 | HA | GLU | 36 | −8.598 | −8.569 | 1.409 | 1.00 | 0.00 |
| ATOM | 570 | CB | GLU | 36 | −10.371 | −8.248 | 2.562 | 1.00 | 0.00 |
| ATOM | 571 | HB1 | GLU | 36 | −11.151 | −7.504 | 2.496 | 1.00 | 0.00 |
| ATOM | 572 | HB2 | GLU | 36 | −10.122 | −8.406 | 3.601 | 1.00 | 0.00 |
| ATOM | 573 | CG | GLU | 36 | −10.907 | −9.553 | 1.996 | 1.00 | 0.00 |
| ATOM | 574 | HG1 | GLU | 36 | −10.073 | −10.192 | 1.748 | 1.00 | 0.00 |
| ATOM | 575 | HG2 | GLU | 36 | −11.473 | −9.338 | 1.102 | 1.00 | 0.00 |
| ATOM | 576 | CD | GLU | 36 | −11.806 | −10.289 | 2.972 | 1.00 | 0.00 |
| ATOM | 577 | OE1 | GLU | 36 | −11.522 | −11.469 | 3.266 | 1.00 | 0.00 |
| ATOM | 578 | OE2 | GLU | 36 | −12.794 | −9.685 | 3.440 | 1.00 | 0.00 |
| ATOM | 579 | C | GLU | 36 | −9.543 | −6.792 | 0.696 | 1.00 | 0.00 |
| ATOM | 580 | O | GLU | 36 | −10.414 | −5.539 | 0.873 | 1.00 | 0.00 |
| ATOM | 581 | N | PRO | 37 | −8.913 | −6.929 | −0.486 | 1.00 | 0.00 |
| ATOM | 582 | CA | PRO | 37 | −9.200 | −6.075 | −1.644 | 1.00 | 0.00 |
| ATOM | 583 | HA | PRO | 37 | −9.135 | −5.029 | −1.386 | 1.00 | 0.00 |
| ATOM | 584 | CB | PRO | 37 | −8.087 | −6.425 | −2.646 | 1.00 | 0.00 |
| ATOM | 585 | HB1 | PRO | 37 | −7.650 | −5.515 | −3.031 | 1.00 | 0.00 |
| ATOM | 586 | HB2 | PRO | 37 | −8.504 | −6.999 | −3.451 | 1.00 | 0.00 |
| ATOM | 587 | CG | PRO | 37 | −7.087 | −7.224 | −1.876 | 1.00 | 0.00 |
| ATOM | 588 | HG1 | PRO | 37 | −6.627 | −7.957 | −2.522 | 1.00 | 0.00 |
| ATOM | 589 | HG2 | PRO | 37 | −6.338 | −6.570 | −1.455 | 1.00 | 0.00 |
| ATOM | 590 | CD | PRO | 37 | −7.857 | −7.904 | −0.784 | 1.00 | 0.00 |
| ATOM | 591 | HD1 | PRO | 37 | −7.229 | −8.071 | 0.077 | 1.00 | 0.00 |
| ATOM | 592 | HD2 | PRO | 37 | −8.276 | −8.834 | −1.137 | 1.00 | 0.00 |
| ATOM | 593 | C | PRO | 37 | −10.569 | −6.357 | −2.254 | 1.00 | 0.00 |
| ATOM | 594 | O | PRO | 37 | −11.467 | −6.866 | −1.586 | 1.00 | 0.00 |
| ATOM | 595 | N | VAL | 38 | −10.720 | −6.015 | −3.531 | 1.00 | 0.00 |
| ATOM | 596 | HN | VAL | 38 | −9.967 | −5.610 | −4.008 | 1.00 | 0.00 |
| ATOM | 597 | CA | VAL | 38 | −11.979 | −6.221 | −4.237 | 1.00 | 0.00 |
| ATOM | 598 | HA | VAL | 38 | −12.777 | −5.045 | −3.614 | 1.00 | 0.00 |
| ATOM | 599 | CB | VAL | 38 | −12.006 | −5.450 | −5.571 | 1.00 | 0.00 |
| ATOM | 600 | HB | VAL | 38 | −11.238 | −5.856 | −6.213 | 1.00 | 0.00 |
| ATOM | 601 | CG1 | VAL | 38 | −11.704 | −3.977 | −5.342 | 1.00 | 0.00 |
| ATOM | 602 | HG11 | VAL | 38 | −12.002 | −3.410 | −6.212 | 1.00 | 0.00 |
| ATOM | 603 | HG12 | VAL | 38 | −10.685 | −3.848 | −5.174 | 1.00 | 0.00 |
| ATOM | 604 | HG13 | VAL | 38 | −12.250 | −3.628 | −4.479 | 1.00 | 0.00 |
| ATOM | 605 | CG2 | VAL | 38 | −13.347 | −5.625 | −6.266 | 1.00 | 0.00 |
| ATOM | 606 | HG21 | VAL | 38 | −13.431 | −6.636 | −6.639 | 1.00 | 0.00 |
| ATOM | 607 | HG22 | VAL | 38 | −13.419 | −4.931 | −7.090 | 1.00 | 0.00 |
| ATOM | 608 | HG23 | VAL | 38 | −14.145 | −5.434 | −5.563 | 1.00 | 0.00 |
| ATOM | 609 | C | VAL | 38 | −12.222 | −7.700 | −4.513 | 1.00 | 0.00 |
| ATOM | 610 | O | VAL | 38 | −11.283 | −5.508 | −4.492 | 1.00 | 0.00 |
| ATOM | 611 | N | LYS | 39 | −13.477 | −8.047 | −4.775 | 1.00 | 0.00 |

TABLE 5-continued

Atomic Structure Coordinates of the
Free Form of the P/CAF Bromodomain

| ATOM | 612 | HN | LYS | 39 | −14.173 | −7.357 | −4.773 | 1.00 | 0.00 |
|---|---|---|---|---|---|---|---|---|---|
| ATOM | 613 | CA | LYS | 39 | −13.850 | −9.431 | −5.053 | 1.00 | 0.00 |
| ATOM | 614 | HA | LYS | 39 | −12.960 | −10.036 | −4.968 | 1.00 | 0.00 |
| ATOM | 615 | CB | LYS | 39 | −14.898 | −9.939 | −4.087 | 1.00 | 0.00 |
| ATOM | 616 | HB1 | LYS | 39 | −15.855 | −9.996 | −4.546 | 1.00 | 0.00 |
| ATOM | 617 | HB2 | LYS | 39 | −14.615 | −10.931 | −3.727 | 1.00 | 0.00 |
| ATOM | 618 | CG | LYS | 39 | −15.065 | −9.072 | −2.804 | 1.00 | 0.00 |
| ATOM | 619 | HG1 | LYS | 39 | −14.989 | −8.023 | −3.086 | 1.00 | 0.00 |
| ATOM | 620 | HG2 | LYS | 39 | −14.283 | −9.315 | −2.099 | 1.00 | 0.00 |
| ATOM | 621 | CD | LYS | 39 | −16.414 | −9.301 | −2.144 | 1.00 | 0.00 |
| ATOM | 622 | HD1 | LYS | 39 | −17.168 | −8.758 | −2.693 | 1.00 | 0.00 |
| ATOM | 623 | HD2 | LYS | 39 | −16.640 | −10.357 | −2.164 | 1.00 | 0.00 |
| ATOM | 624 | CE | LYS | 39 | −16.415 | −8.824 | −0.701 | 1.00 | 0.00 |
| ATOM | 625 | HE1 | LYS | 39 | −16.995 | −9.516 | −0.107 | 1.00 | 0.00 |
| ATOM | 626 | HE2 | LYS | 39 | −15.398 | −8.806 | −0.340 | 1.00 | 0.00 |
| ATOM | 627 | NZ | LYS | 39 | −17.002 | −7.462 | −0.567 | 1.00 | 0.00 |
| ATOM | 628 | HZ1 | LYS | 39 | −17.552 | −7.225 | −1.417 | 1.00 | 0.00 |
| ATOM | 629 | HZ2 | LYS | 39 | −16.246 | −6.758 | −0.448 | 1.00 | 0.00 |
| ATOM | 630 | HZ3 | LYS | 39 | −17.630 | −7.423 | 0.261 | 1.00 | 0.00 |
| ATOM | 631 | C | LYS | 39 | −14.399 | −9.563 | −6.469 | 1.00 | 0.00 |
| ATOM | 632 | O | LYS | 39 | −13.886 | −10.337 | −7.278 | 1.00 | 0.00 |
| ATOM | 633 | N | ARG | 40 | −15.448 | −8.801 | −6.759 | 1.00 | 0.00 |
| ATOM | 634 | HN | ARG | 40 | −15.810 | −8.206 | −6.070 | 1.00 | 0.00 |
| ATOM | 635 | CA | ARG | 40 | −16.078 | −8.326 | −8.074 | 1.00 | 0.00 |
| ATOM | 636 | HA | ARG | 40 | −15.147 | −8.504 | −8.800 | 1.00 | 0.00 |
| ATOM | 637 | CB | ARG | 40 | −16.534 | −10.246 | −8.417 | 1.00 | 0.00 |
| ATOM | 638 | HB1 | ARG | 40 | −15.676 | −10.822 | −8.729 | 1.00 | 0.00 |
| ATOM | 639 | HB2 | ARG | 40 | −17.260 | −10.197 | −9.234 | 1.00 | 0.00 |
| ATOM | 640 | CG | ARG | 40 | −17.198 | −10.968 | −7.256 | 1.00 | 0.00 |
| ATOM | 641 | HG1 | ARG | 40 | −18.190 | −10.585 | −7.115 | 1.00 | 0.00 |
| ATOM | 642 | HG2 | ARG | 40 | −16.612 | −10.809 | −6.363 | 1.00 | 0.00 |
| ATOM | 643 | CD | ARG | 40 | −17.305 | −12.462 | −7.516 | 1.00 | 0.00 |
| ATOM | 644 | HD1 | ARG | 40 | −16.418 | −12.788 | −8.038 | 1.00 | 0.00 |
| ATOM | 645 | HD2 | ARG | 40 | −18.173 | −12.645 | −8.133 | 1.00 | 0.00 |
| ATOM | 646 | NE | ARG | 40 | −17.434 | −13.225 | −6.277 | 1.00 | 0.00 |
| ATOM | 647 | HE | ARG | 40 | −17.683 | −12.735 | −5.466 | 1.00 | 0.00 |
| ATOM | 648 | CZ | ARG | 40 | −17.235 | −14.537 | −6.197 | 1.00 | 0.00 |
| ATOM | 649 | NH1 | ARG | 40 | −16.898 | −15.225 | −7.279 | 1.00 | 0.00 |
| ATOM | 650 | HH11 | ARG | 40 | −16.794 | −14.758 | −8.157 | 1.00 | 0.00 |
| ATOM | 651 | HH12 | ARG | 40 | −16.748 | −16.212 | −7.237 | 1.00 | 0.00 |
| ATOM | 652 | NH2 | ARG | 40 | −17.371 | −15.160 | −5.034 | 1.00 | 0.00 |
| ATOM | 653 | HH21 | ARG | 40 | −17.624 | −14.644 | −4.216 | 1.00 | 0.00 |
| ATOM | 654 | HH22 | ARG | 40 | −17.220 | −16.147 | −4.976 | 1.00 | 0.00 |
| ATOM | 655 | C | ARG | 40 | −17.268 | −7.874 | −8.116 | 1.00 | 0.00 |
| ATOM | 656 | O | ARG | 40 | −17.442 | −7.122 | −9.074 | 1.00 | 0.00 |
| ATOM | 657 | N | THR | 41 | −18.081 | −7.910 | −7.065 | 1.00 | 0.00 |
| ATOM | 658 | HN | THR | 41 | −17.886 | −8.530 | −6.332 | 1.00 | 0.00 |
| ATOM | 659 | CA | THR | 41 | −19.252 | −7.047 | −6.971 | 1.00 | 0.00 |
| ATOM | 660 | HA | THR | 41 | −19.528 | −6.751 | −7.973 | 1.00 | 0.00 |
| ATOM | 661 | CB | THR | 41 | −20.418 | −7.806 | −6.335 | 1.00 | 0.00 |
| ATOM | 662 | HB | THR | 41 | −20.623 | −8.689 | −6.922 | 1.00 | 0.00 |
| ATOM | 663 | OG1 | THR | 41 | −21.586 | −7.003 | −6.313 | 1.00 | 0.00 |
| ATOM | 664 | HG1 | THR | 41 | −21.499 | −6.331 | −5.634 | 1.00 | 0.00 |
| ATOM | 665 | CG2 | THR | 41 | −20.139 | −8.252 | −4.916 | 1.00 | 0.00 |
| ATOM | 666 | HG21 | THR | 41 | −19.793 | −7.409 | −4.335 | 1.00 | 0.00 |
| ATOM | 667 | HG22 | THR | 41 | −19.381 | −9.020 | −4.923 | 1.00 | 0.00 |
| ATOM | 668 | HG23 | THR | 41 | −21.045 | −9.644 | −4.477 | 1.00 | 0.00 |
| ATOM | 669 | C | THR | 41 | −18.940 | −5.797 | −6.155 | 1.00 | 0.00 |
| ATOM | 670 | O | THR | 41 | −19.562 | −4.751 | −6.338 | 1.00 | 0.00 |
| ATOM | 671 | N | GLU | 42 | −17.969 | −5.915 | −5.254 | 1.00 | 0.00 |
| ATOM | 672 | HN | GLU | 42 | −17.511 | −6.776 | −5.156 | 1.00 | 0.00 |
| ATOM | 673 | CA | GLU | 42 | −17.570 | −4.797 | −4.408 | 1.00 | 0.00 |
| ATOM | 674 | HA | GLU | 42 | −18.437 | −4.480 | −3.847 | 1.00 | 0.00 |
| ATOM | 675 | CB | GLU | 42 | −16.478 | −5.238 | −3.432 | 1.00 | 0.00 |
| ATOM | 676 | HB1 | GLU | 42 | −15.513 | −5.015 | −3.864 | 1.00 | 0.00 |
| ATOM | 677 | HB2 | GLU | 42 | −16.554 | −6.304 | −3.279 | 1.00 | 0.00 |
| ATOM | 678 | CG | GLU | 42 | −16.561 | −4.554 | −2.076 | 1.00 | 0.00 |
| ATOM | 679 | HG1 | GLU | 42 | −17.313 | −5.054 | −1.482 | 1.00 | 0.00 |
| ATOM | 680 | HG2 | GLU | 42 | −16.845 | −3.524 | −2.224 | 1.00 | 0.00 |
| ATOM | 681 | CD | GLU | 42 | −15.246 | −6.592 | −1.323 | 1.00 | 0.00 |
| ATOM | 682 | OE1 | GLU | 42 | −14.293 | −3.913 | −1.760 | 1.00 | 0.00 |
| ATOM | 683 | OE2 | GLU | 42 | −15.169 | −5.300 | −0.297 | 1.00 | 0.00 |
| ATOM | 684 | C | GLU | 42 | −17.072 | −3.624 | −5.249 | 1.00 | 0.00 |
| ATOM | 685 | O | GLU | 42 | −17.374 | −2.468 | −4.959 | 1.00 | 0.00 |
| ATOM | 686 | N | ALA | 43 | −16.304 | −3.935 | −6.288 | 1.00 | 0.00 |
| ATOM | 687 | HN | ALA | 43 | −16.098 | −4.877 | −6.467 | 1.00 | 0.00 |

TABLE 5-continued

Atomic Structure Coordinates of the
Free Form of the P/CAF Bromodomain

| ATOM | 688 | CA | ALA | 43 | −15.762 | −2.908 | −7.171 | 1.00 | 0.00 |
|------|-----|-----|-----|----|---------|--------|--------|------|------|
| ATOM | 689 | HA | ALA | 43 | −16.392 | −2.035 | −7.091 | 1.00 | 0.00 |
| ATOM | 690 | CB | ALA | 43 | −14.359 | −2.518 | −6.730 | 1.00 | 0.00 |
| ATOM | 691 | HB1 | ALA | 43 | −14.122 | −3.016 | −5.801 | 1.00 | 0.00 |
| ATOM | 692 | HB2 | ALA | 43 | −14.310 | −1.449 | −6.587 | 1.00 | 0.00 |
| ATOM | 693 | HB3 | ALA | 43 | −13.648 | −2.913 | −7.487 | 1.00 | 0.00 |
| ATOM | 694 | C | ALA | 43 | −15.753 | −3.381 | −8.623 | 1.00 | 0.00 |
| ATOM | 695 | O | ALA | 43 | −14.707 | −3.745 | −9.159 | 1.00 | 0.00 |
| ATOM | 696 | N | PRO | 44 | −16.925 | −3.378 | −9.280 | 1.00 | 0.00 |
| ATOM | 697 | CA | PRO | 44 | −17.051 | −3.815 | −10.673 | 1.00 | 0.00 |
| ATOM | 698 | HA | PRO | 44 | −16.545 | −4.754 | −10.841 | 1.00 | 0.00 |
| ATOM | 699 | CB | PRO | 44 | −18.558 | −4.006 | −10.840 | 1.00 | 0.00 |
| ATOM | 700 | HB1 | PRO | 44 | −18.862 | −3.787 | −11.859 | 1.00 | 0.00 |
| ATOM | 701 | HB2 | PRO | 44 | −18.824 | −5.024 | −10.597 | 1.00 | 0.00 |
| ATOM | 702 | CD | PRO | 44 | −19.165 | −3.039 | −9.884 | 1.00 | 0.00 |
| ATOM | 703 | HD1 | PRO | 44 | −19.259 | −2.070 | −10.352 | 1.00 | 0.00 |
| ATOM | 704 | HD2 | PRO | 44 | −20.133 | −3.397 | −9.564 | 1.00 | 0.00 |
| ATOM | 705 | CD | PRO | 44 | −18.224 | −2.963 | −8.711 | 1.00 | 0.00 |
| ATOM | 706 | HD1 | PRO | 44 | −18.173 | −1.953 | −8.334 | 1.00 | 0.00 |
| ATOM | 707 | HD2 | PRO | 44 | −18.537 | −3.642 | −7.932 | 1.00 | 0.00 |
| ATOM | 708 | C | PRO | 44 | −16.532 | −2.775 | −11.662 | 1.00 | 0.00 |
| ATOM | 709 | O | PRO | 44 | −16.263 | −3.090 | −12.821 | 1.00 | 0.00 |
| ATOM | 710 | N | GLY | 45 | −16.394 | −1.536 | −11.200 | 1.00 | 0.00 |
| ATOM | 711 | HN | GLY | 45 | −16.627 | −1.340 | −10.268 | 1.00 | 0.00 |
| ATOM | 712 | CA | GLY | 45 | −15.915 | −0.473 | −12.064 | 1.00 | 0.00 |
| ATOM | 713 | HA1 | GLY | 45 | −15.960 | −0.810 | −13.089 | 1.00 | 0.00 |
| ATOM | 714 | HA2 | GLY | 45 | −16.560 | 0.385 | −11.950 | 1.00 | 0.00 |
| ATOM | 715 | C | GLY | 45 | −14.491 | −0.059 | −11.747 | 1.00 | 0.00 |
| ATOM | 716 | O | GLY | 45 | −14.134 | 1.111 | −11.883 | 1.00 | 0.00 |
| ATOM | 717 | N | TYR | 46 | −13.676 | −1.020 | −11.327 | 1.00 | 0.00 |
| ATOM | 718 | HN | TYR | 46 | −14.019 | −1.934 | −11.241 | 1.00 | 0.00 |
| ATOM | 719 | CA | TYR | 46 | −12.282 | −0.748 | −10.995 | 1.00 | 0.00 |
| ATOM | 720 | HA | TYR | 46 | −12.343 | 0.205 | −10.488 | 1.00 | 0.00 |
| ATOM | 721 | CB | TYR | 46 | −11.739 | −1.832 | −10.062 | 1.00 | 0.00 |
| ATOM | 722 | HB1 | TYR | 46 | −10.765 | −2.142 | −10.411 | 1.00 | 0.00 |
| ATOM | 723 | HB2 | TYR | 46 | −12.408 | −2.680 | −10.078 | 1.00 | 0.00 |
| ATOM | 724 | CG | TYR | 46 | −11.585 | −1.382 | −8.625 | 1.00 | 0.00 |
| ATOM | 725 | CD1 | TYR | 46 | −10.623 | −1.931 | −7.799 | 1.00 | 0.00 |
| ATOM | 726 | HD1 | TYR | 46 | −9.964 | −2.690 | −8.196 | 1.00 | 0.00 |
| ATOM | 727 | CD2 | TYR | 46 | −12.432 | −0.408 | −8.095 | 1.00 | 0.00 |
| ATOM | 728 | HD2 | TYR | 46 | −13.194 | 0.029 | −8.724 | 1.00 | 0.00 |
| ATOM | 729 | CE1 | TYR | 46 | −10.487 | −1.522 | −6.486 | 1.00 | 0.00 |
| ATOM | 730 | HE1 | TYR | 46 | −9.725 | −1.960 | −5.859 | 1.00 | 0.00 |
| ATOM | 731 | CE2 | TYR | 46 | −12.303 | 0.007 | −6.783 | 1.00 | 0.00 |
| ATOM | 732 | HE2 | TYR | 46 | −12.964 | 0.766 | −6.389 | 1.00 | 0.00 |
| ATOM | 733 | CZ | TYR | 46 | −11.330 | −0.553 | −5.983 | 1.00 | 0.00 |
| ATOM | 734 | OH | TYR | 46 | −11.199 | −0.143 | −4.676 | 1.00 | 0.00 |
| ATOM | 735 | HH | TYR | 46 | −10.892 | −0.877 | −4.139 | 1.00 | 0.00 |
| ATOM | 736 | C | TYR | 46 | −11.427 | −0.671 | −12.256 | 1.00 | 0.00 |
| ATOM | 737 | O | TYR | 46 | −11.940 | −0.764 | −13.371 | 1.00 | 0.00 |
| ATOM | 738 | N | TYR | 47 | −10.120 | −0.506 | −12.072 | 1.00 | 0.00 |
| ATOM | 739 | HN | TYR | 47 | −9.772 | −0.440 | −11.159 | 1.00 | 0.00 |
| ATOM | 740 | CA | TYR | 47 | −9.189 | −0.421 | −13.195 | 1.00 | 0.00 |
| ATOM | 741 | HA | TYR | 47 | −8.188 | −0.506 | −12.800 | 1.00 | 0.00 |
| ATOM | 742 | CB | TYR | 47 | −9.433 | −1.567 | −14.181 | 1.00 | 0.00 |
| ATOM | 743 | HB1 | TYR | 47 | −10.224 | −1.285 | −14.860 | 1.00 | 0.00 |
| ATOM | 744 | HB2 | TYR | 47 | −8.529 | −1.748 | −14.743 | 1.00 | 0.00 |
| ATOM | 745 | CG | TYR | 47 | −9.833 | −2.862 | −13.514 | 1.00 | 0.00 |
| ATOM | 746 | CD1 | TYR | 47 | −10.758 | −3.715 | −14.105 | 1.00 | 0.00 |
| ATOM | 747 | HD1 | TYR | 47 | −11.188 | −3.443 | −15.057 | 1.00 | 0.00 |
| ATOM | 748 | CD2 | TYR | 47 | −9.290 | −3.229 | −12.290 | 1.00 | 0.00 |
| ATOM | 749 | HD2 | TYR | 47 | −8.572 | −2.574 | −11.810 | 1.00 | 0.00 |
| ATOM | 750 | CE1 | TYR | 47 | −11.124 | −4.899 | −13.496 | 1.00 | 0.00 |
| ATOM | 751 | HE1 | TYR | 47 | −11.843 | −5.550 | −13.971 | 1.00 | 0.00 |
| ATOM | 752 | CE2 | TYR | 47 | −9.653 | −4.411 | −11.674 | 1.00 | 0.00 |
| ATOM | 753 | HE2 | TYR | 47 | −9.219 | −4.679 | −10.722 | 1.00 | 0.00 |
| ATOM | 754 | CZ | TYR | 47 | −10.570 | −5.242 | −12.280 | 1.00 | 0.00 |
| ATOM | 755 | OH | TYR | 47 | −10.934 | −6.621 | −11.671 | 1.00 | 0.00 |
| ATOM | 756 | HH | TYR | 47 | −10.153 | −6.958 | −11.519 | 1.00 | 0.00 |
| ATOM | 757 | C | TYR | 47 | −9.318 | 0.917 | −13.916 | 1.00 | 0.00 |
| ATOM | 758 | O | TYR | 47 | −8.360 | 1.686 | −13.992 | 1.00 | 0.00 |
| ATOM | 759 | N | GLU | 48 | −10.504 | 1.184 | −14.451 | 1.00 | 0.00 |
| ATOM | 760 | HN | GLU | 48 | −11.227 | 0.529 | −14.362 | 1.00 | 0.00 |
| ATOM | 761 | CA | GLU | 48 | −10.754 | 2.425 | −15.175 | 1.00 | 0.00 |
| ATOM | 762 | HA | GLU | 48 | −10.103 | 2.441 | −16.037 | 1.00 | 0.00 |
| ATOM | 763 | CB | GLU | 48 | −12.209 | 2.478 | −15.618 | 1.00 | 0.00 |

TABLE 5-continued

Atomic Structure Coordinates of the
Free Form of the P/CAF Bromodomain

| ATOM | 764 | HB1 | GLU | 48 | −12.854 | 2.529 | −14.784 | 1.00 | 0.00 |
|---|---|---|---|---|---|---|---|---|---|
| ATOM | 765 | HB2 | GLU | 48 | −12.349 | 3.368 | −16.214 | 1.00 | 0.00 |
| ATOM | 766 | CG | GLU | 48 | −12.621 | 1.276 | −16.482 | 1.00 | 0.00 |
| ATOM | 767 | HG1 | GLU | 48 | −12.135 | 1.337 | −17.444 | 1.00 | 0.00 |
| ATOM | 768 | HG2 | GLU | 48 | −12.304 | 0.376 | −15.976 | 1.00 | 0.00 |
| ATOM | 769 | CD | GLU | 48 | −14.120 | 1.208 | −16.702 | 1.00 | 0.00 |
| ATOM | 770 | OE1 | GLU | 48 | −14.858 | 1.919 | −15.994 | 1.00 | 0.00 |
| ATOM | 771 | OE2 | GLU | 48 | −14.554 | 0.433 | −17.584 | 1.00 | 0.00 |
| ATOM | 772 | C | GLU | 48 | −10.445 | 3.639 | −14.306 | 1.00 | 0.00 |
| ATOM | 773 | O | GLU | 48 | −10.136 | 4.716 | −14.815 | 1.00 | 0.00 |
| ATOM | 774 | N | VAL | 49 | −10.529 | 3.459 | −12.992 | 1.00 | 0.00 |
| ATOM | 775 | HN | VAL | 49 | −10.781 | 2.578 | −12.684 | 1.00 | 0.00 |
| ATOM | 776 | CA | VAL | 49 | −10.261 | 4.545 | −12.055 | 1.00 | 0.00 |
| ATOM | 777 | HA | VAL | 49 | −9.905 | 5.392 | −12.624 | 1.00 | 0.00 |
| ATOM | 778 | CB | VAL | 49 | −11.542 | 4.971 | −11.313 | 1.00 | 0.00 |
| ATOM | 779 | HB | VAL | 49 | −12.308 | 5.171 | −12.047 | 1.00 | 0.00 |
| ATOM | 780 | CG1 | VAL | 49 | −12.033 | 3.853 | −10.407 | 1.00 | 0.00 |
| ATOM | 781 | HG11 | VAL | 49 | −11.630 | 3.991 | −9.414 | 1.00 | 0.00 |
| ATOM | 782 | HG12 | VAL | 49 | −11.705 | 2.901 | −10.799 | 1.00 | 0.00 |
| ATOM | 783 | HG13 | VAL | 49 | −13.112 | 3.872 | −10.364 | 1.00 | 0.00 |
| ATOM | 784 | CG2 | VAL | 49 | −11.301 | 6.246 | −10.518 | 1.00 | 0.00 |
| ATOM | 785 | HG21 | VAL | 49 | −10.706 | 6.020 | −9.646 | 1.00 | 0.00 |
| ATOM | 786 | HG22 | VAL | 49 | −12.249 | 6.661 | −10.209 | 1.00 | 0.00 |
| ATOM | 787 | HG23 | VAL | 49 | −10.779 | 6.963 | −11.135 | 1.00 | 0.00 |
| ATOM | 788 | C | VAL | 49 | −9.195 | 4.160 | −11.026 | 1.00 | 0.00 |
| ATOM | 789 | O | VAL | 49 | −8.861 | 4.956 | −10.148 | 1.00 | 0.00 |
| ATOM | 790 | N | ILE | 50 | −8.665 | 2.941 | −11.130 | 1.00 | 0.00 |
| ATOM | 791 | HN | ILE | 50 | −8.958 | 2.347 | −11.847 | 1.00 | 0.00 |
| ATOM | 792 | CA | ILE | 50 | −7.644 | 2.474 | −10.204 | 1.00 | 0.00 |
| ATOM | 793 | HA | ILE | 50 | −7.342 | 3.309 | −9.589 | 1.00 | 0.00 |
| ATOM | 794 | CB | ILE | 50 | −8.102 | 1.365 | −9.282 | 1.00 | 0.00 |
| ATOM | 795 | HB | ILE | 50 | −8.267 | 0.458 | −9.861 | 1.00 | 0.00 |
| ATOM | 796 | CG1 | ILE | 50 | −9.559 | 1.747 | −8.737 | 1.00 | 0.00 |
| ATOM | 797 | HG11 | ILE | 50 | −10.222 | 1.952 | −9.564 | 1.00 | 0.00 |
| ATOM | 798 | HG12 | ILE | 50 | −9.952 | 0.921 | −8.162 | 1.00 | 0.00 |
| ATOM | 799 | CG2 | ILE | 50 | −7.210 | 1.105 | −8.142 | 1.00 | 0.00 |
| ATOM | 800 | HG21 | ILE | 50 | −6.248 | 1.528 | −8.387 | 1.00 | 0.00 |
| ATOM | 801 | HG22 | ILE | 50 | −7.108 | 0.041 | −7.991 | 1.00 | 0.00 |
| ATOM | 802 | HG23 | ILE | 50 | −7.586 | 1.561 | −7.238 | 1.00 | 0.00 |
| ATOM | 803 | CD1 | ILE | 50 | −9.540 | 2.967 | −7.847 | 1.00 | 0.00 |
| ATOM | 804 | HD11 | ILE | 50 | −9.670 | 3.855 | −8.443 | 1.00 | 0.00 |
| ATOM | 805 | HD12 | ILE | 50 | −8.593 | 3.019 | −7.325 | 1.00 | 0.00 |
| ATOM | 806 | HD13 | ILE | 50 | −10.341 | 2.898 | −7.123 | 1.00 | 0.00 |
| ATOM | 807 | C | ILE | 50 | −6.428 | 1.945 | −10.953 | 1.00 | 0.00 |
| ATOM | 808 | O | ILE | 50 | −6.557 | 1.228 | −11.945 | 1.00 | 0.00 |
| ATOM | 809 | N | ARG | 51 | −5.248 | 2.301 | −10.466 | 1.00 | 0.00 |
| ATOM | 810 | HN | ARG | 51 | −5.216 | 2.877 | −9.676 | 1.00 | 0.00 |
| ATOM | 811 | CA | ARG | 51 | −4.000 | 1.873 | −11.085 | 1.00 | 0.00 |
| ATOM | 812 | HA | ARG | 51 | −4.014 | 2.198 | −12.114 | 1.00 | 0.00 |
| ATOM | 813 | CB | ARG | 51 | −2.811 | 2.519 | −10.373 | 1.00 | 0.00 |
| ATOM | 814 | HB1 | ARG | 51 | −3.181 | 3.123 | −9.557 | 1.00 | 0.00 |
| ATOM | 815 | HB2 | ARG | 51 | −2.177 | 1.740 | −9.975 | 1.00 | 0.00 |
| ATOM | 816 | CG | ARG | 51 | −1.967 | 3.403 | −11.277 | 1.00 | 0.00 |
| ATOM | 817 | HG1 | ARG | 51 | −2.041 | 3.037 | −12.291 | 1.00 | 0.00 |
| ATOM | 818 | HG2 | ARG | 51 | −0.939 | 3.358 | −10.960 | 1.00 | 0.00 |
| ATOM | 819 | CD | ARG | 51 | −2.433 | 4.849 | −11.240 | 1.00 | 0.00 |
| ATOM | 820 | HD1 | ARG | 51 | −2.996 | 5.010 | −10.332 | 1.00 | 0.00 |
| ATOM | 821 | HD2 | ARG | 51 | −1.566 | 5.493 | −11.244 | 1.00 | 0.00 |
| ATOM | 822 | NE | ARG | 51 | −3.275 | 5.184 | −12.385 | 1.00 | 0.00 |
| ATOM | 823 | HE | ARG | 51 | −4.217 | 5.390 | −12.212 | 1.00 | 0.00 |
| ATOM | 824 | CZ | ARG | 51 | −2.832 | 5.226 | −13.638 | 1.00 | 0.00 |
| ATOM | 825 | NH1 | ARG | 51 | −1.562 | 4.953 | −13.904 | 1.00 | 0.00 |
| ATOM | 826 | HH11 | ARG | 51 | −1.231 | 4.984 | −14.846 | 1.00 | 0.00 |
| ATOM | 827 | HH12 | ARG | 51 | −0.936 | 4.716 | −13.161 | 1.00 | 0.00 |
| ATOM | 828 | NH2 | ARG | 51 | −3.659 | 5.539 | −14.626 | 1.00 | 0.00 |
| ATOM | 829 | HH21 | ARG | 51 | −3.323 | 5.569 | −15.568 | 1.00 | 0.00 |
| ATOM | 830 | HH22 | ARG | 51 | −4.617 | 5.746 | −14.430 | 1.00 | 0.00 |
| ATOM | 831 | C | ARG | 51 | −3.864 | 0.354 | −11.056 | 1.00 | 0.00 |
| ATOM | 832 | O | ARG | 51 | −4.094 | −0.319 | −12.061 | 1.00 | 0.00 |
| ATOM | 833 | N | SER | 52 | −3.479 | −0.182 | −9.901 | 1.00 | 0.00 |
| ATOM | 834 | HN | SER | 52 | −3.310 | 0.401 | −9.134 | 1.00 | 0.00 |
| ATOM | 835 | CA | SER | 52 | −3.307 | −1.622 | −9.751 | 1.00 | 0.00 |
| ATOM | 836 | HA | SER | 52 | −3.766 | −2.101 | −10.603 | 1.00 | 0.00 |
| ATOM | 837 | CB | SER | 52 | −1.820 | −1.980 | −9.715 | 1.00 | 0.00 |
| ATOM | 838 | HB1 | SER | 52 | −1.690 | −3.005 | −10.027 | 1.00 | 0.00 |
| ATOM | 839 | HB2 | SER | 52 | −1.447 | −1.860 | −8.708 | 1.00 | 0.00 |

TABLE 5-continued

Atomic Structure Coordinates of the
Free Form of the P/CAF Bromodomain

| ATOM | 840 | OG | SER | 52 | −1.072 | −1.143 | −10.580 | 1.00 | 0.00 |
|------|-----|------|-----|----|--------|--------|---------|------|------|
| ATOM | 841 | HG | SER | 52 | −0.287 | −1.608 | −10.877 | 1.00 | 0.00 |
| ATOM | 842 | C | SER | 52 | −3.993 | −2.128 | −8.488 | 1.00 | 0.00 |
| ATOM | 843 | O | SER | 52 | −3.353 | −2.308 | −7.452 | 1.00 | 0.00 |
| ATOM | 844 | N | PRO | 53 | −3.310 | −2.378 | −8.565 | 1.00 | 0.00 |
| ATOM | 845 | CA | PRO | 53 | −6.087 | −2.882 | −7.435 | 1.00 | 0.00 |
| ATOM | 846 | HA | PRO | 53 | −6.390 | −2.083 | −6.773 | 1.00 | 0.00 |
| ATOM | 847 | CB | PRO | 53 | −7.313 | −3.484 | −8.111 | 1.00 | 0.00 |
| ATOM | 848 | HB1 | PRO | 53 | −8.160 | −3.615 | −7.450 | 1.00 | 0.00 |
| ATOM | 849 | HB2 | PRO | 53 | −7.122 | −4.519 | −8.355 | 1.00 | 0.00 |
| ATOM | 850 | CG | PRO | 53 | −7.512 | −2.661 | −9.337 | 1.00 | 0.00 |
| ATOM | 851 | HG1 | PRO | 53 | −7.963 | −3.263 | −10.110 | 1.00 | 0.00 |
| ATOM | 852 | HG2 | PRO | 53 | −8.139 | −1.812 | −9.109 | 1.00 | 0.00 |
| ATOM | 853 | CD | PRO | 53 | −6.145 | −2.197 | −9.770 | 1.00 | 0.00 |
| ATOM | 854 | HD1 | PRO | 53 | −5.780 | −2.805 | −10.584 | 1.00 | 0.00 |
| ATOM | 855 | HD2 | PRO | 53 | −6.176 | −1.257 | −10.060 | 1.00 | 0.00 |
| ATOM | 856 | C | PRO | 53 | −5.340 | −3.947 | −6.639 | 1.00 | 0.00 |
| ATOM | 857 | O | PRO | 53 | −5.425 | −5.137 | −6.943 | 1.00 | 0.00 |
| ATOM | 858 | N | MET | 54 | −4.609 | −3.512 | −5.619 | 1.00 | 0.00 |
| ATOM | 859 | HN | MET | 54 | −4.581 | −2.552 | −5.426 | 1.00 | 0.00 |
| ATOM | 860 | CA | MET | 54 | −3.850 | −4.428 | −4.777 | 1.00 | 0.00 |
| ATOM | 861 | HA | MET | 54 | −4.303 | −5.405 | −4.859 | 1.00 | 0.00 |
| ATOM | 862 | CB | MET | 54 | −2.398 | −4.508 | −5.253 | 1.00 | 0.00 |
| ATOM | 863 | HB1 | MET | 54 | −2.390 | −4.624 | −6.327 | 1.00 | 0.00 |
| ATOM | 864 | HB2 | MET | 54 | −1.897 | −3.587 | −4.995 | 1.00 | 0.00 |
| ATOM | 865 | CG | MET | 54 | −1.615 | −5.660 | −4.644 | 1.00 | 0.00 |
| ATOM | 866 | HG1 | MET | 54 | −1.472 | −5.464 | −3.592 | 1.00 | 0.00 |
| ATOM | 867 | HG2 | MET | 54 | −0.653 | −5.720 | −5.132 | 1.00 | 0.00 |
| ATOM | 868 | SD | MET | 54 | −2.452 | −7.247 | −4.826 | 1.00 | 0.00 |
| ATOM | 869 | CE | MET | 54 | −3.383 | −7.311 | −3.298 | 1.00 | 0.00 |
| ATOM | 870 | HE1 | MET | 54 | −2.905 | −7.997 | −2.612 | 1.00 | 0.00 |
| ATOM | 871 | HE2 | MET | 54 | −4.388 | −7.650 | −3.501 | 1.00 | 0.00 |
| ATOM | 872 | HE3 | MET | 54 | −3.418 | −6.327 | −2.857 | 1.00 | 0.00 |
| ATOM | 873 | C | MET | 54 | −3.897 | −3.984 | −3.320 | 1.00 | 0.00 |
| ATOM | 874 | O | MET | 54 | −2.937 | −3.415 | −2.802 | 1.00 | 0.00 |
| ATOM | 875 | N | ASP | 55 | −5.026 | −4.240 | −2.667 | 1.00 | 0.00 |
| ATOM | 876 | HN | ASP | 55 | −5.755 | −4.699 | −3.134 | 1.00 | 0.00 |
| ATOM | 877 | CA | ASP | 55 | −5.201 | −3.870 | −1.269 | 1.00 | 0.00 |
| ATOM | 878 | HA | ASP | 55 | −4.803 | −2.874 | −1.139 | 1.00 | 0.00 |
| ATOM | 879 | CB | ASP | 55 | −6.690 | −3.863 | −0.906 | 1.00 | 0.00 |
| ATOM | 880 | HB1 | ASP | 55 | −6.811 | −3.495 | 0.102 | 1.00 | 0.00 |
| ATOM | 881 | HB2 | ASP | 55 | −7.075 | −3.860 | −0.964 | 1.00 | 0.00 |
| ATOM | 882 | CG | ASP | 55 | −7.506 | −2.985 | −1.835 | 1.00 | 0.00 |
| ATOM | 883 | OD1 | ASP | 55 | −7.575 | −3.302 | −2.041 | 1.00 | 0.00 |
| ATOM | 884 | OD2 | ASP | 55 | −8.074 | −1.981 | −1.357 | 1.00 | 0.00 |
| ATOM | 885 | C | ASP | 55 | −4.435 | −4.826 | −0.360 | 1.00 | 0.00 |
| ATOM | 886 | O | ASP | 55 | −3.570 | −5.580 | −0.819 | 1.00 | 0.00 |
| ATOM | 887 | N | LEU | 56 | −4.739 | −4.786 | 0.931 | 1.00 | 0.00 |
| ATOM | 888 | HN | LEU | 56 | −5.426 | −4.263 | 1.242 | 1.00 | 0.00 |
| ATOM | 889 | CA | LEU | 56 | −4.069 | −5.644 | 1.898 | 1.00 | 0.00 |
| ATOM | 890 | HA | LEU | 56 | −3.012 | −5.620 | 1.683 | 1.00 | 0.00 |
| ATOM | 891 | CB | LEU | 56 | −4.305 | −5.115 | 3.318 | 1.00 | 0.00 |
| ATOM | 892 | HB1 | LEU | 56 | −4.223 | −5.919 | 4.008 | 1.00 | 0.00 |
| ATOM | 893 | HB2 | LEU | 56 | −5.306 | −4.729 | 3.371 | 1.00 | 0.00 |
| ATOM | 894 | CG | LEU | 56 | −3.343 | −4.015 | 3.770 | 1.00 | 0.00 |
| ATOM | 895 | HG | LEU | 56 | −3.605 | −3.702 | 4.770 | 1.00 | 0.00 |
| ATOM | 896 | CD1 | LEU | 56 | −3.425 | −2.802 | 2.859 | 1.00 | 0.00 |
| ATOM | 897 | HD11 | LEU | 56 | −3.644 | −1.924 | 3.449 | 1.00 | 0.00 |
| ATOM | 898 | HD12 | LEU | 56 | −4.204 | 2.950 | 2.132 | 1.00 | 0.00 |
| ATOM | 899 | HD13 | LEU | 56 | −2.481 | −2.668 | 2.352 | 1.00 | 0.00 |
| ATOM | 900 | CD2 | LEU | 56 | −1.929 | −4.544 | 3.801 | 1.00 | 0.00 |
| ATOM | 901 | HD21 | LEU | 56 | −1.279 | −3.850 | 3.291 | 1.00 | 0.00 |
| ATOM | 902 | HD22 | LEU | 56 | −1.898 | −5.500 | 3.303 | 1.00 | 0.00 |
| ATOM | 903 | HD23 | LEU | 56 | −1.611 | −4.656 | 4.824 | 1.00 | 0.00 |
| ATOM | 904 | C | LEU | 56 | −4.568 | −7.081 | 1.773 | 1.00 | 0.00 |
| ATOM | 905 | O | LEU | 56 | −5.294 | −7.404 | 0.815 | 1.00 | 0.00 |
| ATOM | 906 | N | LYS | 57 | −4.152 | −7.939 | 2.706 | 1.00 | 0.00 |
| ATOM | 907 | HN | LYS | 57 | −3.564 | −7.617 | 3.417 | 1.00 | 0.00 |
| ATOM | 908 | CA | LYS | 57 | −4.555 | −9.347 | 2.715 | 1.00 | 0.00 |
| ATOM | 909 | HA | LYS | 57 | −4.259 | −9.758 | 3.669 | 1.00 | 0.00 |
| ATOM | 910 | CB | LYS | 57 | −6.075 | −9.490 | 2.576 | 1.00 | 0.00 |
| ATOM | 911 | HB1 | LYS | 57 | −6.549 | −9.007 | 3.418 | 1.00 | 0.00 |
| ATOM | 912 | HB2 | LYS | 57 | −6.396 | −9.008 | 1.668 | 1.00 | 0.00 |
| ATOM | 913 | CG | LYS | 57 | −6.542 | −10.935 | 2.530 | 1.00 | 0.00 |
| ATOM | 914 | NG1 | LYS | 57 | −4.160 | −11.395 | 1.629 | 1.00 | 0.00 |
| ATOM | 915 | NG2 | LYS | 57 | −7.622 | −10.954 | 2.517 | 1.00 | 0.00 |

TABLE 5-continued

Atomic Structure Coordinates of the
Free Form of the P/CAF Bromodomain

| ATOM | 916 | CD | LYS | 57 | −6.049 | −11.720 | 3.735 | 1.00 | 0.00 |
|---|---|---|---|---|---|---|---|---|---|
| ATOM | 917 | ND1 | LYS | 57 | −5.944 | −11.047 | 4.573 | 1.00 | 0.00 |
| ATOM | 918 | ND2 | LYS | 57 | −5.090 | −12.157 | 3.498 | 1.00 | 0.00 |
| ATOM | 919 | CE | LYS | 57 | −7.017 | −12.831 | 4.112 | 1.00 | 0.00 |
| ATOM | 920 | HE1 | LYS | 57 | −7.967 | −12.640 | 3.635 | 1.00 | 0.00 |
| ATOM | 921 | HE2 | LYS | 57 | −6.621 | −13.771 | 3.759 | 1.00 | 0.00 |
| ATOM | 922 | NZ | LYS | 57 | −7.223 | −12.915 | 5.585 | 1.00 | 0.00 |
| ATOM | 923 | NZ1 | LYS | 57 | −6.363 | −12.609 | 6.084 | 1.00 | 0.00 |
| ATOM | 924 | NZ2 | LYS | 57 | −7.441 | −13.894 | 5.860 | 1.00 | 0.00 |
| ATOM | 925 | NZ3 | LYS | 57 | −8.017 | −12.302 | 6.871 | 1.00 | 0.00 |
| ATOM | 926 | C | LYS | 57 | −3.855 | −10.144 | 1.617 | 1.00 | 0.00 |
| ATOM | 927 | O | LYS | 57 | −3.197 | −11.144 | −1.895 | 1.00 | 0.00 |
| ATOM | 928 | N | THR | 58 | −4.014 | −9.714 | 0.370 | 1.00 | 0.00 |
| ATOM | 929 | HN | THR | 58 | −4.551 | −8.913 | 0.201 | 1.00 | 0.00 |
| ATOM | 930 | CA | THR | 58 | −3.403 | −10.411 | −0.755 | 1.00 | 0.00 |
| ATOM | 931 | HA | THR | 58 | −3.409 | −11.465 | −0.527 | 1.00 | 0.00 |
| ATOM | 932 | CB | THR | 58 | −4.223 | −10.177 | −2.031 | 1.00 | 0.00 |
| ATOM | 933 | KB | THR | 58 | −4.448 | −9.126 | −2.112 | 1.00 | 0.00 |
| ATOM | 934 | OG1 | THR | 58 | −5.448 | −10.897 | −1.970 | 1.00 | 0.00 |
| ATOM | 935 | HG1 | THR | 58 | −5.974 | −10.557 | −1.238 | 1.00 | 0.00 |
| ATOM | 936 | CG2 | THR | 58 | −3.515 | −10.598 | −3.304 | 1.00 | 0.00 |
| ATOM | 937 | HG21 | THR | 58 | −4.236 | −11.003 | −2.998 | 1.00 | 0.00 |
| ATOM | 938 | HG22 | THR | 58 | −2.775 | −11.349 | −3.073 | 1.00 | 0.00 |
| ATOM | 939 | HG23 | THR | 58 | −3.031 | −9.740 | −3.747 | 1.00 | 0.00 |
| ATOM | 940 | C | THR | 58 | −1.956 | −9.961 | −0.952 | 1.00 | 0.00 |
| ATOM | 941 | O | THR | 58 | −1.093 | −10.759 | −1.318 | 1.00 | 0.00 |
| ATOM | 942 | N | MET | 59 | −1.697 | −8.682 | −0.701 | 1.00 | 0.00 |
| ATOM | 943 | HN | MET | 59 | −2.426 | −8.092 | −0.413 | 1.00 | 0.00 |
| ATOM | 944 | CA | MET | 59 | −0.355 | −8.132 | −0.851 | 1.00 | 0.00 |
| ATOM | 945 | HA | MET | 59 | 0.020 | −8.431 | −1.819 | 1.00 | 0.00 |
| ATOM | 946 | CB | MET | 59 | −0.404 | −6.605 | −0.783 | 1.00 | 0.00 |
| ATOM | 947 | HB1 | MET | 59 | 0.536 | −6.209 | −1.138 | 1.00 | 0.00 |
| ATOM | 948 | HB2 | MET | 59 | −1.200 | −6.252 | −1.423 | 1.00 | 0.00 |
| ATOM | 949 | CG | MET | 59 | −0.650 | −6.072 | 0.617 | 1.00 | 0.00 |
| ATOM | 950 | HG1 | MET | 59 | −1.503 | −6.585 | 1.032 | 1.00 | 0.00 |
| ATOM | 951 | HG2 | MET | 59 | 0.218 | −6.279 | 1.223 | 1.00 | 0.00 |
| ATOM | 952 | SD | MET | 59 | −0.969 | −4.297 | 0.643 | 1.00 | 0.00 |
| ATOM | 953 | CE | MET | 59 | 0.230 | −3.715 | −0.554 | 1.00 | 0.00 |
| ATOM | 954 | HE1 | MET | 59 | 0.178 | −4.324 | −1.443 | 1.00 | 0.00 |
| ATOM | 955 | HE2 | MET | 59 | 2.221 | −3.779 | −0.131 | 1.00 | 0.00 |
| ATOM | 956 | HE3 | MET | 59 | 0.016 | −2.688 | −0.808 | 1.00 | 0.00 |
| ATOM | 957 | C | MET | 59 | 0.582 | −8.669 | 0.228 | 1.00 | 0.00 |
| ATOM | 958 | O | MET | 59 | 1.701 | −9.092 | −0.061 | 1.00 | 0.00 |
| ATOM | 959 | N | SER | 60 | 0.126 | −8.621 | 1.476 | 1.00 | 0.00 |
| ATOM | 960 | HN | SER | 60 | −0.772 | −8.270 | 1.644 | 1.00 | 0.00 |
| ATOM | 961 | CA | SER | 60 | 0.925 | −9.088 | 2.601 | 1.00 | 0.00 |
| ATOM | 962 | HA | SER | 60 | 1.789 | −8.445 | 2.682 | 1.00 | 0.00 |
| ATOM | 963 | CB | SER | 60 | 0.113 | −9.004 | 3.898 | 1.00 | 0.00 |
| ATOM | 964 | HB1 | SER | 60 | 0.214 | −8.013 | 4.315 | 1.00 | 0.00 |
| ATOM | 965 | HB2 | SER | 60 | −0.922 | −9.205 | 3.686 | 1.00 | 0.00 |
| ATOM | 966 | OG | SER | 60 | 0.579 | −9.946 | 4.052 | 1.00 | 0.00 |
| ATOM | 967 | HG | SER | 60 | 1.273 | −9.548 | 5.383 | 1.00 | 0.00 |
| ATOM | 968 | C | SER | 60 | 1.401 | −10.517 | 2.372 | 1.00 | 0.00 |
| ATOM | 969 | O | SER | 60 | 2.417 | −10.939 | 2.923 | 1.00 | 0.00 |
| ATOM | 970 | N | GLU | 61 | 0.665 | −11.258 | 1.551 | 1.00 | 0.00 |
| ATOM | 971 | HN | GLU | 61 | −0.134 | −10.867 | 1.137 | 1.00 | 0.00 |
| ATOM | 972 | CA | GLU | 61 | 1.022 | −12.636 | 1.249 | 1.00 | 0.00 |
| ATOM | 973 | HA | GLU | 61 | 1.138 | −13.156 | 2.186 | 1.00 | 0.00 |
| ATOM | 974 | CB | GLU | 61 | −0.084 | −13.309 | 0.435 | 1.00 | 0.00 |
| ATOM | 975 | HB1 | GLU | 61 | 0.025 | −14.380 | 0.516 | 1.00 | 0.00 |
| ATOM | 976 | HB2 | GLU | 61 | 0.021 | −13.022 | −0.601 | 1.00 | 0.00 |
| ATOM | 977 | CG | GLU | 61 | −1.484 | −12.937 | 0.891 | 1.00 | 0.00 |
| ATOM | 978 | HG1 | GLU | 61 | −1.460 | −12.730 | 1.951 | 1.00 | 0.00 |
| ATOM | 979 | HG2 | GLU | 61 | −1.797 | −12.051 | 0.360 | 1.00 | 0.00 |
| ATOM | 980 | CD | GLU | 61 | −2.493 | −14.039 | 0.636 | 1.00 | 0.00 |
| ATOM | 981 | OE1 | GLU | 61 | −2.755 | −14.830 | 1.567 | 1.00 | 0.00 |
| ATOM | 982 | OE2 | GLU | 61 | −3.020 | −14.112 | −0.494 | 1.00 | 0.00 |
| ATOM | 983 | C | GLU | 61 | 2.338 | −12.695 | 0.485 | 1.00 | 0.00 |
| ATOM | 984 | O | GLU | 61 | 3.295 | −13.334 | 0.922 | 1.00 | 0.00 |
| ATOM | 985 | N | ARG | 62 | 2.387 | −12.013 | −0.654 | 1.00 | 0.00 |
| ATOM | 986 | HN | ARG | 62 | 1.588 | −11.524 | −0.949 | 1.00 | 0.00 |
| ATOM | 987 | CA | ARG | 62 | 3.578 | −11.980 | −1.479 | 1.00 | 0.00 |
| ATOM | 988 | HA | ARG | 62 | 3.752 | −12.979 | −1.846 | 1.00 | 0.00 |
| ATOM | 989 | CB | ARG | 62 | 3.368 | −11.045 | −2.672 | 1.00 | 0.00 |
| ATOM | 990 | HB1 | ARG | 62 | 4.330 | −10.804 | −3.101 | 1.00 | 0.00 |
| ATOM | 991 | HB2 | ARG | 62 | 2.898 | −10.136 | −2.326 | 1.00 | 0.00 |

TABLE 5-continued

Atomic Structure Coordinates of the
Free Form of the P/CAF Bromodomain

| ATOM | 992 | CG | ARG | 62 | 2.496 | −11.652 | −3.761 | 1.00 | 0.00 |
|------|-----|------|-----|----|-------|---------|--------|------|------|
| ATOM | 993 | HG1 | ARG | 62 | 1.895 | −12.438 | −3.328 | 1.00 | 0.00 |
| ATOM | 994 | HG2 | ARG | 62 | 3.131 | −12.065 | −4.528 | 1.00 | 0.00 |
| ATOM | 995 | CG | ARG | 62 | 1.576 | −10.619 | −4.389 | 1.00 | 0.00 |
| ATOM | 996 | HD1 | ARG | 62 | 2.043 | −9.647 | −4.320 | 1.00 | 0.00 |
| ATOM | 997 | HD2 | ARG | 62 | 0.645 | −10.609 | −3.845 | 1.00 | 0.00 |
| ATOM | 998 | NE | ARG | 62 | 1.259 | −10.916 | −5.792 | 1.00 | 0.00 |
| ATOM | 999 | HE | ARG | 62 | 1.697 | −10.330 | −6.467 | 1.00 | 0.00 |
| ATOM | 1000 | CZ | ARG | 62 | 0.541 | −11.931 | −6.194 | 1.00 | 0.00 |
| ATOM | 1001 | NH1 | ARG | 62 | 0.336 | −12.136 | −7.488 | 1.00 | 0.00 |
| ATOM | 1002 | HN11 | ARG | 62 | 0.753 | −11.527 | −8.163 | 1.00 | 0.00 |
| ATOM | 1003 | HN12 | ARG | 62 | −0.235 | −12.900 | −7.789 | 1.00 | 0.00 |
| ATOM | 1004 | NH2 | ARG | 62 | −0.014 | −12.742 | −5.303 | 1.00 | 0.00 |
| ATOM | 1005 | HH21 | ARG | 62 | 0.139 | −12.590 | −4.326 | 1.00 | 0.00 |
| ATOM | 1006 | HH22 | ARG | 62 | −0.583 | −13.505 | −5.608 | 1.00 | 0.00 |
| ATOM | 1007 | C | ARG | 62 | 4.790 | −11.542 | −0.664 | 1.00 | 0.00 |
| ATOM | 1008 | O | ARG | 62 | 5.781 | −12.266 | −0.576 | 1.00 | 0.00 |
| ATOM | 1009 | N | LEU | 63 | 4.700 | −10.366 | −0.052 | 1.00 | 0.00 |
| ATOM | 1010 | HN | LEU | 63 | 3.882 | −9.815 | −0.149 | 1.00 | 0.00 |
| ATOM | 1011 | CA | LEU | 63 | 5.792 | −9.853 | 0.768 | 1.00 | 0.00 |
| ATOM | 1012 | HA | LEU | 63 | 6.634 | −9.663 | 0.117 | 1.00 | 0.00 |
| ATOM | 1013 | CB | LEU | 63 | 5.384 | −8.546 | 1.450 | 1.00 | 0.00 |
| ATOM | 1014 | HB1 | LEU | 63 | 5.208 | −7.805 | 0.603 | 1.00 | 0.00 |
| ATOM | 1015 | HB2 | LEU | 63 | 4.460 | −8.716 | 1.982 | 1.00 | 0.00 |
| ATOM | 1016 | CG | LEU | 63 | 6.413 | −7.984 | 2.636 | 1.00 | 0.00 |
| ATOM | 1017 | HG | LEU | 63 | 7.141 | −8.747 | 2.663 | 1.00 | 0.00 |
| ATOM | 1018 | CD1 | LEU | 63 | 7.148 | −6.804 | 1.825 | 1.00 | 0.00 |
| ATOM | 1019 | HD11 | LEU | 63 | 6.457 | −5.991 | 1.672 | 1.00 | 0.00 |
| ATOM | 1020 | HD12 | LEU | 63 | 7.575 | −7.097 | 0.877 | 1.00 | 0.00 |
| ATOM | 1021 | HD13 | LEU | 63 | 7.937 | −6.487 | 2.492 | 1.00 | 0.00 |
| ATOM | 1022 | CD2 | LEU | 63 | 5.741 | −7.580 | 3.738 | 1.00 | 0.00 |
| ATOM | 1023 | HD21 | LEU | 63 | 4.709 | −7.899 | 3.726 | 1.00 | 0.00 |
| ATOM | 1024 | HD22 | LEU | 63 | 5.785 | −6.507 | 3.848 | 1.00 | 0.00 |
| ATOM | 1025 | HD23 | LEU | 63 | 5.252 | −8.049 | 4.565 | 1.00 | 0.00 |
| ATOM | 1026 | C | LEU | 63 | 6.204 | −10.880 | 1.817 | 1.00 | 0.00 |
| ATOM | 1027 | O | LEU | 63 | 7.391 | −11.134 | 2.019 | 1.00 | 0.00 |
| ATOM | 1028 | N | LYS | 64 | 5.212 | −11.475 | 2.475 | 1.00 | 0.00 |
| ATOM | 1029 | HN | LYS | 64 | 4.287 | −11.235 | 2.262 | 1.00 | 0.00 |
| ATOM | 1030 | CA | LYS | 64 | 5.469 | −12.487 | 3.492 | 1.00 | 0.00 |
| ATOM | 1031 | HA | LYS | 64 | 5.962 | −12.002 | 4.333 | 1.00 | 0.00 |
| ATOM | 1032 | CB | LYS | 64 | 4.155 | −11.122 | 3.953 | 1.00 | 0.00 |
| ATOM | 1033 | HB1 | LYS | 64 | 3.506 | −13.240 | 3.098 | 1.00 | 0.00 |
| ATOM | 1034 | HB2 | LYS | 64 | 4.365 | −14.094 | 4.372 | 1.00 | 0.00 |
| ATOM | 1035 | CG | LYS | 64 | 3.416 | −12.301 | 5.000 | 1.00 | 0.00 |
| ATOM | 1036 | HG1 | LYS | 64 | 3.615 | −11.254 | 4.828 | 1.00 | 0.00 |
| ATOM | 1037 | HG2 | LYS | 64 | 2.356 | −12.488 | 4.907 | 1.00 | 0.00 |
| ATOM | 1038 | CD | LYS | 64 | 3.859 | −12.653 | 5.408 | 1.00 | 0.00 |
| ATOM | 1039 | HD1 | LYS | 64 | 3.007 | −13.038 | 6.957 | 1.00 | 0.00 |
| ATOM | 1040 | HD2 | LYS | 64 | 4.618 | −13.428 | 6.351 | 1.00 | 0.00 |
| ATOM | 1041 | CE | LYS | 64 | 4.626 | −11.459 | 7.141 | 1.00 | 0.00 |
| ATOM | 1042 | HE1 | LYS | 64 | 4.711 | −10.712 | 6.414 | 1.00 | 0.00 |
| ATOM | 1043 | HE2 | LYS | 64 | 3.663 | −11.054 | 7.790 | 1.00 | 0.00 |
| ATOM | 1044 | NZ | LYS | 64 | 5.619 | −11.817 | 7.959 | 1.00 | 0.00 |
| ATOM | 1045 | H21 | LYS | 64 | 6.085 | −12.655 | 7.560 | 1.00 | 0.00 |
| ATOM | 1046 | H22 | LYS | 64 | 5.332 | −12.025 | 8.936 | 1.00 | 0.00 |
| ATOM | 1047 | H23 | LYS | 64 | 6.295 | −11.028 | 7.968 | 1.00 | 0.00 |
| ATOM | 1048 | C | LYS | 64 | 6.407 | −13.562 | 2.953 | 1.00 | 0.00 |
| ATOM | 1049 | O | LYS | 64 | 7.255 | −14.082 | 3.677 | 1.00 | 0.00 |
| ATOM | 1050 | N | ASN | 65 | 6.256 | −13.879 | 1.671 | 1.00 | 0.00 |
| ATOM | 1051 | HN | ASN | 65 | 5.569 | −13.420 | 1.143 | 1.00 | 0.00 |
| ATOM | 1052 | CA | ASN | 65 | 7.103 | −14.872 | 1.023 | 1.00 | 0.00 |
| ATOM | 1053 | HA | ASN | 65 | 7.632 | −15.410 | 1.795 | 1.00 | 0.00 |
| ATOM | 1054 | CB | ASN | 65 | 6.254 | −15.855 | 0.214 | 1.00 | 0.00 |
| ATOM | 1055 | HB1 | ASN | 65 | 6.762 | −16.082 | −0.712 | 1.00 | 0.00 |
| ATOM | 1056 | HB2 | ASN | 65 | 3.299 | −15.400 | −0.006 | 1.00 | 0.00 |
| ATOM | 1057 | CG | ASN | 65 | 6.006 | −17.155 | 0.954 | 1.00 | 0.00 |
| ATOM | 1058 | OD1 | ASN | 65 | 6.266 | −18.239 | 0.433 | 1.00 | 0.00 |
| ATOM | 1059 | ND2 | ASN | 65 | 5.501 | −17.052 | 2.178 | 1.00 | 0.00 |
| ATOM | 1060 | HD21 | ASN | 65 | 5.318 | −16.156 | 2.538 | 1.00 | 0.00 |
| ATOM | 1061 | HD22 | ASN | 65 | 5.331 | −17.877 | 2.678 | 1.00 | 0.00 |
| ATOM | 1062 | C | ASN | 65 | 8.122 | −14.195 | 8.119 | 1.00 | 0.00 |
| ATOM | 1063 | O | ASN | 65 | 8.532 | −14.749 | −0.901 | 1.00 | 0.00 |
| ATOM | 1064 | N | ARG | 66 | 8.515 | −12.995 | 0.510 | 1.00 | 0.00 |
| ATOM | 1065 | HN | ARG | 66 | 8.174 | −12.614 | 1.338 | 1.00 | 0.00 |
| ATOM | 1066 | CA | ARG | 66 | 9.524 | −12.235 | −0.247 | 1.00 | 0.00 |
| ATOM | 1067 | HA | ARG | 66 | 9.535 | −11.232 | 0.148 | 1.00 | 0.00 |

TABLE 5-continued

Atomic Structure Coordinates of the
Free Form of the P/CAF Bromodomain

| ATOM | 1068 | CB | ARG | 66 | 10.919 | −12.948 | −0.092 | 1.00 | 0.00 |
|------|------|------|------|----|--------|---------|--------|------|------|
| ATOM | 1069 | HB1 | ARG | 66 | 11.122 | −13.471 | −0.950 | 1.00 | 0.00 |
| ATOM | 1070 | HB2 | ARG | 66 | 11.643 | −12.051 | −0.063 | 1.00 | 0.00 |
| ATOM | 1071 | CG | ARG | 66 | 11.100 | −13.692 | 1.161 | 1.00 | 0.00 |
| ATOM | 1072 | HG1 | ARG | 66 | 11.963 | −14.321 | 1.031 | 1.00 | 0.00 |
| ATOM | 1073 | HG2 | ARG | 66 | 10.225 | −14.307 | 1.303 | 1.00 | 0.00 |
| ATOM | 1074 | CD | ARG | 66 | 11.298 | −12.825 | 2.392 | 1.00 | 0.00 |
| ATOM | 1075 | HD1 | ARG | 66 | 11.969 | −12.017 | 2.143 | 1.00 | 0.00 |
| ATOM | 1076 | HD2 | ARG | 66 | 10.342 | −12.420 | 2.689 | 1.00 | 0.00 |
| ATOM | 1077 | NE | ARG | 66 | 11.860 | −13.580 | 3.509 | 1.00 | 0.00 |
| ATOM | 1078 | HE | ARG | 66 | 12.876 | −13.512 | 3.663 | 1.00 | 0.00 |
| ATOM | 1079 | CZ | ARG | 66 | 11.136 | −14.344 | 4.319 | 1.00 | 0.00 |
| ATOM | 1080 | NH1 | ARG | 66 | 11.719 | −14.998 | 5.314 | 1.00 | 0.00 |
| ATOM | 1081 | NH11 | ARG | 66 | 12.706 | −14.917 | 5.455 | 1.00 | 0.00 |
| ATOM | 1082 | NH12 | ARG | 66 | 11.173 | −15.573 | 5.923 | 1.00 | 0.00 |
| ATOM | 1083 | NH2 | ARG | 66 | 9.827 | −14.454 | 4.136 | 1.00 | 0.00 |
| ATOM | 1084 | HH21 | ARG | 66 | 9.384 | −13.963 | 3.387 | 1.00 | 0.00 |
| ATOM | 1085 | HH22 | ARG | 66 | 9.284 | −15.038 | 4.747 | 1.00 | 0.00 |
| ATOM | 1086 | C | ARG | 66 | 9.153 | −12.177 | −1.725 | 1.00 | 0.00 |
| ATOM | 1087 | O | ARG | 66 | 10.018 | −12.041 | −2.590 | 1.00 | 0.00 |
| ATOM | 1088 | N | TYR | 67 | 7.862 | −12.286 | −2.002 | 1.00 | 0.00 |
| ATOM | 1089 | HN | TYR | 67 | 7.230 | −12.408 | −1.266 | 1.00 | 0.00 |
| ATOM | 1090 | CA | TYR | 67 | 7.364 | −12.275 | −3.374 | 1.00 | 0.00 |
| ATOM | 1091 | HA | TYR | 67 | 8.125 | −12.708 | −4.008 | 1.00 | 0.00 |
| ATOM | 1092 | CB | TYR | 67 | 6.091 | −13.117 | −3.475 | 1.00 | 0.00 |
| ATOM | 1093 | HB1 | TYR | 67 | 6.193 | −13.995 | −2.856 | 1.00 | 0.00 |
| ATOM | 1094 | HB2 | TYR | 67 | 5.259 | −12.530 | −1.121 | 1.00 | 0.00 |
| ATOM | 1095 | CG | TYR | 67 | 5.767 | −13.566 | −4.881 | 1.00 | 0.00 |
| ATOM | 1096 | CD1 | TYR | 67 | 6.113 | −14.835 | −5.326 | 1.00 | 0.00 |
| ATOM | 1097 | HD1 | TYR | 67 | 6.628 | −15.506 | −4.654 | 1.00 | 0.00 |
| ATOM | 1098 | CD2 | TYR | 67 | 5.107 | −12.720 | −5.761 | 1.00 | 0.00 |
| ATOM | 1099 | HD2 | TYR | 67 | 4.827 | −11.731 | −5.427 | 1.00 | 0.00 |
| ATOM | 1100 | CE1 | TYR | 67 | 5.811 | −15.247 | −6.611 | 1.00 | 0.00 |
| ATOM | 1101 | HE1 | TYR | 67 | 6.089 | −16.237 | −6.940 | 1.00 | 0.00 |
| ATOM | 1102 | CE2 | TYR | 67 | 4.798 | −13.123 | −7.044 | 1.00 | 0.00 |
| ATOM | 1103 | HE2 | TYR | 67 | 4.281 | −12.449 | −7.711 | 1.00 | 0.00 |
| ATOM | 1104 | CZ | TYR | 67 | 5.153 | −14.387 | −7.466 | 1.00 | 0.00 |
| ATOM | 1105 | OH | TYR | 67 | 4.850 | −14.793 | −8.745 | 1.00 | 0.00 |
| ATOM | 1106 | HH | TYR | 67 | 4.026 | −15.286 | −8.737 | 1.00 | 0.00 |
| ATOM | 1107 | C | TYR | 67 | 7.066 | −10.860 | −3.859 | 1.00 | 0.00 |
| ATOM | 1108 | O | TYR | 67 | 6.990 | −10.616 | −5.063 | 1.00 | 0.00 |
| ATOM | 1109 | N | TYR | 68 | 6.859 | −9.937 | −2.935 | 1.00 | 0.00 |
| ATOM | 1110 | HN | TYR | 68 | 6.909 | −10.187 | −1.978 | 1.00 | 0.00 |
| ATOM | 1111 | CA | TYR | 68 | 6.515 | −8.568 | −3.280 | 1.00 | 0.00 |
| ATOM | 1112 | HA | TYR | 68 | 6.570 | −8.478 | −4.355 | 1.00 | 0.00 |
| ATOM | 1113 | CB | TYR | 68 | 5.089 | −8.263 | −2.821 | 1.00 | 0.00 |
| ATOM | 1114 | HB1 | TYR | 68 | 4.746 | −9.065 | −2.146 | 1.00 | 0.00 |
| ATOM | 1115 | HB2 | TYR | 68 | 5.096 | −7.348 | −2.256 | 1.00 | 0.00 |
| ATOM | 1116 | CG | TYR | 68 | 4.089 | −8.103 | −3.946 | 1.00 | 0.00 |
| ATOM | 1117 | CD1 | TYR | 68 | 4.278 | −8.729 | −5.174 | 1.00 | 0.00 |
| ATOM | 1118 | HD1 | TYR | 68 | 5.157 | −9.336 | −5.327 | 1.00 | 0.00 |
| ATOM | 1119 | CD2 | TYR | 68 | 2.946 | −7.334 | −3.772 | 1.00 | 0.00 |
| ATOM | 1120 | HD2 | TYR | 68 | 2.783 | −6.844 | −2.823 | 1.00 | 0.00 |
| ATOM | 1121 | CE1 | TYR | 68 | 3.359 | −8.582 | −6.194 | 1.00 | 0.00 |
| ATOM | 1122 | HE1 | TYR | 68 | 3.523 | −9.075 | −7.143 | 1.00 | 0.00 |
| ATOM | 1123 | CE2 | TYR | 68 | 2.022 | −7.185 | −4.789 | 1.00 | 0.00 |
| ATOM | 1124 | HE2 | TYR | 68 | 1.141 | −6.581 | −4.633 | 1.00 | 0.00 |
| ATOM | 1125 | CZ | TYR | 68 | 2.233 | −7.811 | −5.998 | 1.00 | 0.00 |
| ATOM | 1126 | OH | TYR | 68 | 1.315 | −7.665 | −7.012 | 1.00 | 0.00 |
| ATOM | 1127 | HH | TYR | 68 | 0.444 | −7.518 | −6.637 | 1.00 | 0.00 |
| ATOM | 1128 | C | TYR | 68 | 7.484 | −7.570 | −2.656 | 1.00 | 0.00 |
| ATOM | 1129 | O | TYR | 68 | 7.095 | −5.457 | −2.303 | 1.00 | 0.00 |
| ATOM | 1130 | N | TYR | 68 | 8.744 | −7.967 | −2.529 | 1.00 | 0.00 |
| ATOM | 1131 | HN | VAL | 69 | 9.000 | −8.862 | −2.835 | 1.00 | 0.00 |
| ATOM | 1132 | CA | VAL | 69 | 9.761 | −7.086 | −1.962 | 1.00 | 0.00 |
| ATOM | 1133 | HA | VAL | 69 | 9.284 | −6.461 | −1.221 | 1.00 | 0.00 |
| ATOM | 1134 | CB | VAL | 69 | 10.902 | −7.854 | −1.276 | 1.00 | 0.00 |
| ATOM | 1135 | HB | VAL | 69 | 11.715 | −7.964 | −1.194 | 1.00 | 0.00 |
| ATOM | 1136 | CG1 | VAL | 69 | 10.465 | −9.242 | −0.846 | 1.00 | 0.00 |
| ATOM | 1137 | HG11 | VAL | 69 | 9.487 | −9.183 | −0.393 | 1.00 | 0.00 |
| ATOM | 1138 | HG12 | VAL | 69 | 11.171 | −9.640 | −0.133 | 1.00 | 0.00 |
| ATOM | 1139 | HG13 | VAL | 69 | 10.423 | −9.887 | −1.712 | 1.00 | 0.00 |
| ATOM | 1140 | CG2 | VAL | 69 | 11.422 | −7.059 | −0.090 | 1.00 | 0.00 |
| ATOM | 1141 | HG21 | VAL | 69 | 12.197 | −7.619 | 0.411 | 1.00 | 0.00 |
| ATOM | 1142 | HG22 | VAL | 69 | 10.608 | −6.872 | 0.597 | 1.00 | 0.00 |
| ATOM | 1143 | HG23 | VAL | 69 | 11.822 | −6.118 | −0.438 | 1.00 | 0.00 |

TABLE 5-continued

Atomic Structure Coordinates of the
Free Form of the P/CAF Bromodomain

| ATOM | 1144 | C | VAL | 69 | 10.352 | −6.199 | −3.043 | 1.00 | 0.00 |
|---|---|---|---|---|---|---|---|---|---|
| ATOM | 1145 | O | VAL | 69 | 11.543 | −6.272 | −3.345 | 1.00 | 0.00 |
| ATOM | 1146 | N | SER | 70 | 9.507 | −5.372 | −3.634 | 1.00 | 0.00 |
| ATOM | 1147 | HN | SER | 70 | 8.566 | −5.371 | −3.359 | 1.00 | 0.00 |
| ATOM | 1148 | CA | SER | 70 | 9.934 | −4.491 | −4.703 | 1.00 | 0.00 |
| ATOM | 1149 | HA | SER | 70 | 10.985 | −4.285 | −4.564 | 1.00 | 0.00 |
| ATOM | 1150 | CB | SER | 70 | 9.734 | −5.190 | −6.045 | 1.00 | 0.00 |
| ATOM | 1151 | HB1 | SER | 70 | 10.626 | −5.749 | −6.289 | 1.00 | 0.00 |
| ATOM | 1152 | HB2 | SER | 70 | 8.898 | −5.868 | −5.966 | 1.00 | 0.00 |
| ATOM | 1153 | OG | SER | 70 | 9.476 | −4.258 | −7.081 | 1.00 | 0.00 |
| ATOM | 1154 | HG | SER | 70 | 10.175 | −3.600 | −7.102 | 1.00 | 0.00 |
| ATOM | 1155 | C | SER | 70 | 9.164 | −3.179 | −4.457 | 1.00 | 0.00 |
| ATOM | 1156 | O | SER | 70 | 7.969 | −3.158 | −4.359 | 1.00 | 0.00 |
| ATOM | 1157 | N | LYS | 71 | 9.861 | −2.083 | −4.924 | 1.00 | 0.00 |
| ATOM | 1158 | HN | LYS | 71 | 10.816 | −2.163 | −5.131 | 1.00 | 0.00 |
| ATOM | 1159 | CA | LYS | 71 | 9.258 | −0.761 | −4.863 | 1.00 | 0.00 |
| ATOM | 1160 | HA | LYS | 71 | 8.988 | −0.583 | −3.832 | 1.00 | 0.00 |
| ATOM | 1161 | CB | LYS | 71 | 10.271 | 0.305 | −5.297 | 1.00 | 0.00 |
| ATOM | 1162 | HB1 | LYS | 71 | 11.076 | 0.332 | −4.577 | 1.00 | 0.00 |
| ATOM | 1163 | HB2 | LYS | 71 | 10.673 | 0.029 | −6.261 | 1.00 | 0.00 |
| ATOM | 1164 | CG | LYS | 71 | 9.687 | 1.706 | −5.409 | 1.00 | 0.00 |
| ATOM | 1165 | HG1 | LYS | 71 | 9.954 | 2.267 | −4.528 | 1.00 | 0.00 |
| ATOM | 1166 | HG2 | LYS | 71 | 8.613 | 1.638 | −5.482 | 1.00 | 0.00 |
| ATOM | 1167 | CD | LYS | 71 | 10.218 | 2.433 | −6.634 | 1.00 | 0.00 |
| ATOM | 1168 | HD1 | LYS | 71 | 11.033 | 1.863 | −7.054 | 1.00 | 0.00 |
| ATOM | 1169 | HD2 | LYS | 71 | 9.424 | 2.521 | −7.360 | 1.00 | 0.00 |
| ATOM | 1170 | CE | LYS | 71 | 10.721 | 3.824 | −6.282 | 1.00 | 0.00 |
| ATOM | 1171 | HE1 | LYS | 71 | 11.466 | 3.737 | −5.506 | 1.00 | 0.00 |
| ATOM | 1172 | HE2 | LYS | 71 | 9.892 | 4.412 | −9.919 | 1.00 | 0.00 |
| ATOM | 1173 | NZ | LYS | 71 | 11.323 | 4.511 | −7.657 | 1.00 | 0.00 |
| ATOM | 1174 | HZ1 | LYS | 71 | 10.580 | 4.970 | −8.023 | 1.00 | 0.00 |
| ATOM | 1175 | HZ2 | LYS | 71 | 11.823 | 3.823 | −8.056 | 1.00 | 0.00 |
| ATOM | 1176 | HZ3 | LYS | 71 | 12.000 | 5.234 | −7.141 | 1.00 | 0.00 |
| ATOM | 1177 | C | LYS | 71 | 7.984 | −0.678 | −5.707 | 1.00 | 0.00 |
| ATOM | 1178 | O | LYS | 71 | 6.898 | −1.000 | −5.224 | 1.00 | 0.00 |
| ATOM | 1179 | N | LYS | 72 | 8.116 | −0.244 | −6.964 | 1.00 | 0.00 |
| ATOM | 1180 | HN | LYS | 72 | 9.002 | 0.015 | −7.290 | 1.00 | 0.00 |
| ATOM | 1181 | CA | LYS | 72 | 6.963 | −0.053 | −7.846 | 1.00 | 0.00 |
| ATOM | 1182 | HA | LYS | 72 | 6.511 | 0.892 | −7.580 | 1.00 | 0.00 |
| ATOM | 1183 | CB | LYS | 72 | 7.419 | 0.008 | −9.306 | 1.00 | 0.00 |
| ATOM | 1184 | HB1 | LYS | 72 | 8.261 | 0.680 | −9.379 | 1.00 | 0.00 |
| ATOM | 1185 | HB2 | LYS | 72 | 7.728 | −0.979 | −9.615 | 1.00 | 0.00 |
| ATOM | 1186 | CG | LYS | 72 | 6.339 | 0.491 | −10.258 | 1.00 | 0.00 |
| ATOM | 1187 | HG1 | LYS | 72 | 6.588 | 0.174 | −11.260 | 1.00 | 0.00 |
| ATOM | 1188 | HG2 | LYS | 72 | 5.394 | 0.057 | −9.965 | 1.00 | 0.00 |
| ATOM | 1189 | CD | LYS | 72 | 6.214 | 2.005 | −10.238 | 1.00 | 0.00 |
| ATOM | 1190 | HD1 | LYS | 72 | 5.264 | 2.284 | −10.669 | 1.00 | 0.00 |
| ATOM | 1191 | HD2 | LYS | 72 | 6.261 | 2.347 | −9.214 | 1.00 | 0.00 |
| ATOM | 1192 | CE | LYS | 72 | 7.329 | 2.668 | −11.031 | 1.00 | 0.00 |
| ATOM | 1193 | HE1 | LYS | 72 | 7.643 | 3.559 | −10.508 | 1.00 | 0.00 |
| ATOM | 1194 | HE2 | LYS | 72 | 8.160 | 1.981 | −11.102 | 1.00 | 0.00 |
| ATOM | 1195 | NZ | LYS | 72 | 6.889 | 3.041 | −12.403 | 1.00 | 0.00 |
| ATOM | 1196 | HZ1 | LYS | 72 | 7.488 | 3.805 | −12.775 | 1.00 | 0.00 |
| ATOM | 1197 | HZ2 | LYS | 72 | 5.902 | 3.366 | −12.386 | 1.00 | 0.00 |
| ATOM | 1198 | HZ3 | LYS | 72 | 6.961 | 2.219 | −13.037 | 1.00 | 0.00 |
| ATOM | 1199 | C | LYS | 72 | 5.915 | −1.152 | −7.680 | 1.00 | 0.00 |
| ATOM | 1200 | O | LYS | 72 | 4.723 | −0.913 | −7.869 | 1.00 | 0.00 |
| ATOM | 1201 | N | LEU | 73 | 6.357 | −2.345 | −7.305 | 1.00 | 0.00 |
| ATOM | 1202 | HN | LEU | 73 | 7.318 | −2.480 | −7.168 | 1.00 | 0.00 |
| ATOM | 1203 | CA | LEU | 73 | 5.446 | −3.462 | −7.101 | 1.00 | 0.00 |
| ATOM | 1204 | HA | LEU | 73 | 4.802 | −3.527 | −7.966 | 1.00 | 0.00 |
| ATOM | 1205 | CB | LEU | 73 | 6.231 | −4.764 | −6.964 | 1.00 | 0.00 |
| ATOM | 1206 | HB1 | LEU | 73 | 6.470 | −4.910 | −5.922 | 1.00 | 0.00 |
| ATOM | 1207 | HB2 | LEU | 73 | 7.152 | −4.656 | −7.512 | 1.00 | 0.00 |
| ATOM | 1208 | CG | LEU | 73 | 5.508 | −6.014 | −7.466 | 1.00 | 0.00 |
| ATOM | 1209 | HG | LEU | 73 | 4.553 | −6.094 | −6.966 | 1.00 | 0.00 |
| ATOM | 1210 | CD1 | LEU | 73 | 6.315 | −7.262 | −7.145 | 1.00 | 0.00 |
| ATOM | 1211 | HD11 | LEU | 73 | 6.321 | −7.421 | −6.078 | 1.00 | 0.00 |
| ATOM | 1212 | HD12 | LEU | 73 | 7.328 | −7.136 | −7.496 | 1.00 | 0.00 |
| ATOM | 1213 | HD13 | LEU | 73 | 5.868 | −8.115 | −7.633 | 1.00 | 0.00 |
| ATOM | 1214 | CD2 | LEU | 73 | 5.247 | −5.915 | −8.961 | 1.00 | 0.00 |
| ATOM | 1215 | HD21 | LEU | 73 | 4.982 | −6.889 | −9.345 | 1.00 | 0.00 |
| ATOM | 1216 | HD22 | LEU | 73 | 6.138 | −5.562 | −9.459 | 1.00 | 0.00 |
| ATOM | 1217 | HD23 | LEU | 73 | 4.437 | −5.224 | −9.140 | 1.00 | 0.00 |
| ATOM | 1218 | C | LEU | 73 | 4.587 | −3.287 | −5.861 | 1.00 | 0.00 |
| ATOM | 1219 | O | LEU | 73 | 3.375 | −3.053 | −5.958 | 1.00 | 0.00 |

TABLE 5-continued

Atomic Structure Coordinates of the
Free Form of the P/CAF Bromodomain

| ATOM | 1220 | N | PHE | 74 | 5.218 | −3.316 | −4.693 | 1.00 | 0.00 |
|---|---|---|---|---|---|---|---|---|---|
| ATOM | 1221 | HN | PHE | 74 | 6.184 | −3.474 | −4.678 | 1.00 | 0.00 |
| ATOM | 1222 | CA | PHE | 74 | 4.513 | −3.144 | −3.434 | 1.00 | 0.00 |
| ATOM | 1223 | HA | PHE | 74 | 3.549 | −3.622 | −3.526 | 1.00 | 0.00 |
| ATOM | 1224 | CB | PHE | 74 | 5.290 | −3.809 | −2.305 | 1.00 | 0.00 |
| ATOM | 1225 | HB1 | PHE | 74 | 6.174 | −3.224 | −2.095 | 1.00 | 0.00 |
| ATOM | 1226 | HB2 | PHE | 74 | 5.587 | −4.799 | −2.614 | 1.00 | 0.00 |
| ATOM | 1227 | CG | PHE | 74 | 4.504 | −3.929 | −1.033 | 1.00 | 0.00 |
| ATOM | 1228 | CD1 | PHE | 74 | 4.062 | −5.163 | −0.385 | 1.00 | 0.00 |
| ATOM | 1229 | HD1 | PHE | 74 | 4.271 | −6.043 | −1.166 | 1.00 | 0.00 |
| ATOM | 1230 | CD2 | PHE | 74 | 4.223 | −2.807 | −0.277 | 1.00 | 0.00 |
| ATOM | 1231 | HD2 | PHE | 74 | 4.578 | −1.842 | −0.610 | 1.00 | 0.00 |
| ATOM | 1232 | CE1 | PHE | 74 | 3.350 | −5.272 | 0.593 | 1.00 | 0.00 |
| ATOM | 1233 | HE1 | PHE | 74 | 3.006 | −6.238 | 0.930 | 1.00 | 0.00 |
| ATOM | 1234 | CE2 | PHE | 74 | 3.518 | −2.911 | 0.903 | 1.00 | 0.00 |
| ATOM | 1235 | HE2 | PHE | 74 | 3.316 | −0.029 | 1.489 | 1.00 | 0.00 |
| ATOM | 1236 | CZ | PHE | 74 | 3.087 | −4.144 | 1.342 | 1.00 | 0.00 |
| ATOM | 1237 | HZ | PHE | 74 | 2.524 | −4.223 | 2.257 | 1.00 | 0.00 |
| ATOM | 1238 | C | PHE | 74 | 4.300 | −1.670 | −3.113 | 1.00 | 0.00 |
| ATOM | 1239 | O | PHE | 74 | 3.172 | −1.236 | −2.879 | 1.00 | 0.00 |
| ATOM | 1240 | N | MET | 75 | 5.392 | −0.902 | −1.095 | 1.00 | 0.00 |
| ATOM | 1241 | HN | MET | 75 | 6.262 | −1.309 | −3.281 | 1.00 | 0.00 |
| ATOM | 1242 | CA | MET | 75 | 5.324 | 0.529 | −2.788 | 1.00 | 0.00 |
| ATOM | 1243 | HA | MET | 75 | 5.190 | 0.628 | −1.721 | 1.00 | 0.00 |
| ATOM | 1244 | CB | MET | 75 | 6.617 | 1.240 | −3.192 | 1.00 | 0.00 |
| ATOM | 1245 | HB1 | MET | 75 | 6.403 | 2.289 | −3.330 | 1.00 | 0.00 |
| ATOM | 1246 | HB2 | MET | 75 | 6.964 | 0.834 | −4.124 | 1.00 | 0.00 |
| ATOM | 1247 | CG | MET | 75 | 7.738 | 1.120 | −2.171 | 1.00 | 0.00 |
| ATOM | 1248 | HG1 | MET | 75 | 8.668 | 1.379 | −2.652 | 1.00 | 0.00 |
| ATOM | 1249 | HG2 | MET | 75 | 7.546 | 1.818 | −1.373 | 1.00 | 0.00 |
| ATOM | 1250 | SD | MET | 75 | 7.907 | −0.529 | −1.461 | 1.00 | 0.00 |
| ATOM | 1251 | CE | MET | 75 | 7.869 | −0.153 | 0.288 | 1.00 | 0.00 |
| ATOM | 1252 | HE1 | MET | 75 | 8.136 | −1.036 | 0.851 | 1.00 | 0.00 |
| ATOM | 1253 | HE2 | MET | 75 | 6.875 | 0.161 | 0.564 | 1.00 | 0.00 |
| ATOM | 1254 | HE3 | MET | 75 | 8.569 | 0.638 | 0.506 | 1.00 | 0.00 |
| ATOM | 1255 | C | MET | 75 | 4.136 | 1.176 | −3.488 | 1.00 | 0.00 |
| ATOM | 1256 | O | MET | 75 | 3.495 | 2.073 | −2.942 | 1.00 | 0.00 |
| ATOM | 1257 | N | ALA | 76 | 3.826 | 0.692 | −4.687 | 1.00 | 0.00 |
| ATOM | 1258 | HN | ALA | 76 | 4.346 | −0.055 | −5.060 | 1.00 | 0.00 |
| ATOM | 1259 | CA | ALA | 76 | 2.659 | 1.177 | −5.404 | 1.00 | 0.00 |
| ATOM | 1260 | HA | ALA | 76 | 2.666 | 2.259 | −5.381 | 1.00 | 0.00 |
| ATOM | 1261 | CB | ALA | 76 | 2.669 | 0.723 | −6.853 | 1.00 | 0.00 |
| ATOM | 1262 | HB1 | ALA | 76 | 1.441 | 1.251 | −7.393 | 1.00 | 0.00 |
| ATOM | 1263 | HB2 | ALA | 76 | 1.706 | 0.935 | −7.300 | 1.00 | 0.00 |
| ATOM | 1264 | HB3 | ALA | 76 | 2.858 | −0.338 | −6.895 | 1.00 | 0.00 |
| ATOM | 1265 | C | ALA | 76 | 1.409 | 0.682 | −8.714 | 1.00 | 0.00 |
| ATOM | 1266 | O | ALA | 76 | 0.613 | 1.472 | −8.236 | 1.00 | 0.00 |
| ATOM | 1267 | N | ASP | 77 | 1.286 | −0.640 | −8.600 | 1.00 | 0.00 |
| ATOM | 1268 | HN | ASP | 77 | 1.977 | −1.214 | −4.989 | 1.00 | 0.00 |
| ATOM | 1269 | CA | ASP | 77 | 0.136 | −1.260 | −3.941 | 1.00 | 0.00 |
| ATOM | 1270 | HA | ASP | 77 | −0.692 | −1.239 | −4.637 | 1.00 | 0.00 |
| ATOM | 1271 | CB | ASP | 77 | 0.454 | −2.714 | −3.586 | 1.00 | 0.00 |
| ATOM | 1272 | HB1 | ASP | 77 | 1.280 | −2.736 | −2.891 | 1.00 | 0.00 |
| ATOM | 1273 | HB2 | ASP | 77 | −0.413 | −3.164 | −3.124 | 1.00 | 0.00 |
| ATOM | 1274 | CG | ASP | 77 | 0.831 | −3.537 | −4.802 | 1.00 | 0.00 |
| ATOM | 1275 | OD1 | ASP | 77 | 0.295 | −3.261 | −5.896 | 1.00 | 0.00 |
| ATOM | 1276 | OD2 | ASP | 77 | 1.666 | −4.455 | −4.661 | 1.00 | 0.00 |
| ATOM | 1277 | C | ASP | 77 | −0.266 | −0.491 | −2.685 | 1.00 | 0.00 |
| ATOM | 1278 | O | ASP | 77 | −1.436 | −0.169 | −2.498 | 1.00 | 0.00 |
| ATOM | 1279 | N | LEU | 78 | 0.718 | −0.155 | −1.857 | 1.00 | 0.00 |
| ATOM | 1280 | HN | LEU | 78 | 1.639 | −0.417 | −2.071 | 1.00 | 0.00 |
| ATOM | 1281 | CA | LEU | 78 | 0.464 | 0.617 | −0.649 | 1.00 | 0.00 |
| ATOM | 1282 | HA | LEU | 78 | −0.294 | 0.104 | −0.077 | 1.00 | 0.00 |
| ATOM | 1283 | CB | LEU | 78 | 1.744 | 0.724 | 0.185 | 1.00 | 0.00 |
| ATOM | 1284 | HB1 | LEU | 78 | 1.931 | 1.768 | 0.378 | 1.00 | 0.00 |
| ATOM | 1285 | HB2 | LEU | 78 | 2.582 | 0.336 | −0.402 | 1.00 | 0.00 |
| ATOM | 1286 | CG | LEU | 78 | 1.726 | −0.016 | 1.529 | 1.00 | 0.00 |
| ATOM | 1287 | HG | LEU | 78 | 2.742 | −0.221 | 1.827 | 1.00 | 0.00 |
| ATOM | 1288 | CD1 | LEU | 78 | 0.998 | −1.347 | 1.413 | 1.00 | 0.00 |
| ATOM | 1289 | HD11 | LEU | 78 | −0.066 | −1.174 | 1.360 | 1.00 | 0.00 |
| ATOM | 1290 | HD12 | LEU | 78 | 1.222 | −1.955 | 2.277 | 1.00 | 0.00 |
| ATOM | 1291 | HD13 | LEU | 78 | 1.327 | −1.855 | 0.521 | 1.00 | 0.00 |
| ATOM | 1292 | CD2 | LEU | 78 | 1.094 | 0.844 | 2.606 | 1.00 | 0.00 |
| ATOM | 1293 | HD21 | LEU | 78 | 1.126 | 1.880 | 2.303 | 1.00 | 0.00 |
| ATOM | 1294 | HD22 | LEU | 78 | 1.641 | 0.721 | 3.529 | 1.00 | 0.00 |
| ATOM | 1295 | HD23 | LEU | 78 | 0.068 | 0.541 | 2.752 | 1.00 | 0.00 |

TABLE 5-continued

Atomic Structure Coordinates of the
Free Form of the P/CAF Bromodomain

| ATOM | 1296 | C | LEU | 78 | −0.045 | 2.009 | −1.009 | 1.00 | 0.00 |
|---|---|---|---|---|---|---|---|---|---|
| ATOM | 1297 | O | LEU | 78 | −1.164 | 2.385 | −0.657 | 1.00 | 0.00 |
| ATOM | 1298 | N | GLN | 79 | 0.780 | 2.760 | −1.731 | 1.00 | 0.00 |
| ATOM | 1299 | HN | GLN | 79 | 1.649 | 2.393 | −1.995 | 1.00 | 0.00 |
| ATOM | 1300 | CA | GLN | 79 | 0.410 | 4.097 | −2.184 | 1.00 | 0.00 |
| ATOM | 1301 | HA | GLN | 79 | 0.157 | 4.744 | −1.321 | 1.00 | 0.00 |
| ATOM | 1302 | CB | GLN | 79 | 1.478 | 4.621 | −3.154 | 1.00 | 0.00 |
| ATOM | 1303 | HB1 | GLN | 79 | 1.727 | 3.833 | −3.850 | 1.00 | 0.00 |
| ATOM | 1304 | HB2 | GLN | 79 | 2.367 | 4.879 | −2.591 | 1.00 | 0.00 |
| ATOM | 1305 | CG | GLN | 79 | 1.052 | 5.840 | −3.958 | 1.00 | 0.00 |
| ATOM | 1306 | HG1 | GLN | 79 | 0.674 | 5.507 | −4.913 | 1.00 | 0.00 |
| ATOM | 1307 | HG2 | GLN | 79 | 0.270 | 4.356 | −3.421 | 1.00 | 0.00 |
| ATOM | 1308 | CD | GLN | 79 | 2.194 | 6.807 | −4.202 | 1.00 | 0.00 |
| ATOM | 1309 | OE1 | GLN | 79 | 2.596 | 1.551 | −3.307 | 1.00 | 0.00 |
| ATOM | 1310 | NE2 | GLN | 79 | 2.722 | 6.801 | −5.420 | 1.00 | 0.00 |
| ATOM | 1311 | HE21 | GLN | 79 | 3.462 | 7.416 | −5.607 | 1.00 | 0.00 |
| ATOM | 1312 | HE22 | GLN | 79 | 2.350 | 6.282 | −6.083 | 1.00 | 0.00 |
| ATOM | 1313 | C | GLN | 79 | −0.953 | 4.061 | −2.870 | 1.00 | 0.00 |
| ATOM | 1314 | O | GLN | 79 | −1.745 | 4.997 | −2.768 | 1.00 | 0.00 |
| ATOM | 1315 | N | ARG | 80 | −1.205 | 2.961 | −3.563 | 1.00 | 0.00 |
| ATOM | 1316 | HN | ARG | 80 | −0.522 | 1.263 | −3.602 | 1.00 | 0.00 |
| ATOM | 1317 | CA | ARG | 80 | −2.439 | 2.755 | −6.287 | 1.00 | 0.00 |
| ATOM | 1318 | HA | ARG | 80 | −2.705 | 3.686 | −4.766 | 1.00 | 0.00 |
| ATOM | 1319 | CB | ARG | 80 | −2.211 | 1.682 | −5.363 | 1.00 | 0.00 |
| ATOM | 1320 | HB1 | ARG | 80 | −1.153 | 1.505 | −5.449 | 1.00 | 0.00 |
| ATOM | 1321 | HB2 | ARG | 80 | −2.686 | 0.767 | −5.059 | 1.00 | 0.00 |
| ATOM | 1322 | CG | ARG | 80 | −2.725 | 2.06 | −6.740 | 1.00 | 0.00 |
| ATOM | 1323 | HG1 | ARG | 80 | −2.057 | 2.795 | −7.171 | 1.00 | 0.00 |
| ATOM | 1324 | HG2 | ARG | 80 | −2.742 | 1.180 | −7.363 | 1.00 | 0.00 |
| ATOM | 1325 | CD | ARG | 80 | −4.122 | 2.649 | −6.682 | 1.00 | 0.00 |
| ATOM | 1326 | HD1 | ARG | 80 | −4.422 | 2.735 | −5.653 | 1.00 | 0.00 |
| ATOM | 1327 | HD2 | ARG | 80 | −4.792 | 1.982 | −7.193 | 1.00 | 0.00 |
| ATOM | 1328 | NE | ARG | 80 | −4.196 | 1.966 | −7.310 | 1.00 | 0.00 |
| ATOM | 1329 | HZ | ARG | 80 | −3.338 | 4.603 | −7.534 | 1.00 | 0.00 |
| ATOM | 1330 | CZ | ARG | 80 | −5.322 | 4.595 | −7.594 | 1.00 | 0.00 |
| ATOM | 1331 | NH1 | ARG | 80 | −6.486 | 6.030 | −7.305 | 1.00 | 0.00 |
| ATOM | 1332 | HH11 | ARG | 80 | −7.339 | 4.505 | −7.519 | 1.00 | 0.00 |
| ATOM | 1333 | HH12 | ARG | 80 | −6.509 | 3.129 | −6.872 | 1.00 | 0.00 |
| ATOM | 1334 | NH2 | ARG | 80 | −5.294 | 5.790 | −8.168 | 1.00 | 0.00 |
| ATOM | 1335 | HH21 | ARG | 80 | −4.418 | 6.239 | −8.386 | 1.00 | 0.00 |
| ATOM | 1336 | HH22 | ARG | 80 | −4.149 | 6.263 | −8.380 | 1.00 | 0.00 |
| ATOM | 1337 | C | ARG | 80 | −1.562 | 2.353 | −3.329 | 1.00 | 0.00 |
| ATOM | 1338 | O | ARG | 80 | −4.715 | 2.740 | −3.523 | 1.00 | 0.00 |
| ATOM | 1339 | N | VAL | 81 | −3.210 | 1.620 | −2.273 | 1.00 | 0.00 |
| ATOM | 1340 | HN | VAL | 81 | −2.271 | 1.367 | −2.155 | 1.00 | 0.00 |
| ATOM | 1341 | CA | VAL | 81 | −4.189 | 1.231 | −1.261 | 1.00 | 0.00 |
| ATOM | 1342 | HA | VAL | 81 | −4.947 | 0.630 | −1.742 | 1.00 | 0.00 |
| ATOM | 1343 | CB | VAL | 81 | −3.543 | 0.387 | −0.129 | 1.00 | 0.00 |
| ATOM | 1344 | HB | VAL | 81 | −2.648 | 0.893 | 0.201 | 1.00 | 0.00 |
| ATOM | 1345 | CG1 | VAL | 81 | −3.147 | −0.988 | −0.645 | 1.00 | 0.00 |
| ATOM | 1346 | HG11 | VAL | 81 | −2.073 | −1.089 | −0.614 | 1.00 | 0.00 |
| ATOM | 1347 | HG12 | VAL | 81 | −3.491 | −1.105 | −1.661 | 1.00 | 0.00 |
| ATOM | 1348 | HG13 | VAL | 81 | −3.597 | −1.750 | −0.023 | 1.00 | 0.00 |
| ATOM | 1349 | CG2 | VAL | 81 | −4.476 | 0.247 | 1.070 | 1.00 | 0.00 |
| ATOM | 1350 | HG21 | VAL | 81 | −5.364 | −0.291 | 0.774 | 1.00 | 0.00 |
| ATOM | 1351 | HG22 | VAL | 81 | −4.752 | 1.228 | 1.429 | 1.00 | 0.00 |
| ATOM | 1352 | HG23 | VAL | 81 | −3.972 | −0.295 | 1.857 | 1.00 | 0.00 |
| ATOM | 1353 | C | VAL | 81 | −4.844 | 2.481 | −0.674 | 1.00 | 0.00 |
| ATOM | 1354 | O | VAL | 81 | −6.050 | 3.507 | −0.427 | 1.00 | 0.00 |
| ATOM | 1355 | N | PHE | 82 | −4.037 | 3.515 | −0.459 | 1.00 | 0.00 |
| ATOM | 1356 | HN | PHE | 82 | −3.086 | 3.436 | −0.684 | 1.00 | 0.00 |
| ATOM | 1357 | CA | PHE | 82 | −4.533 | 4.774 | 0.080 | 1.00 | 0.00 |
| ATOM | 1358 | HA | PHE | 82 | −5.269 | 4.545 | 0.837 | 1.00 | 0.00 |
| ATOM | 1359 | CB | PHE | 82 | −3.390 | 3.572 | 0.717 | 1.00 | 0.00 |
| ATOM | 1360 | HB1 | PHE | 82 | −2.807 | 6.034 | −0.065 | 1.00 | 0.00 |
| ATOM | 1361 | HB2 | PHE | 82 | −3.820 | 6.342 | 1.348 | 1.00 | 0.00 |
| ATOM | 1362 | CG | PHE | 82 | −2.455 | 4.746 | 1.561 | 1.00 | 0.00 |
| ATOM | 1363 | CD1 | PHE | 82 | −2.850 | 3.520 | 2.077 | 1.00 | 0.00 |
| ATOM | 1364 | HD1 | PHE | 82 | −3.841 | 3.149 | 1.861 | 1.00 | 0.00 |
| ATOM | 1365 | CD2 | PHE | 82 | −1.180 | 5.209 | 1.850 | 1.00 | 0.00 |
| ATOM | 1366 | HD2 | PHE | 82 | −0.862 | 6.163 | 1.457 | 1.00 | 0.00 |
| ATOM | 1367 | CE1 | PHE | 82 | −1.988 | 2.768 | 2.853 | 1.00 | 0.00 |
| ATOM | 1368 | HE1 | PHE | 82 | −2.307 | 1.815 | 3.248 | 1.00 | 0.00 |
| ATOM | 1369 | CE2 | PHE | 82 | −0.316 | 4.462 | 2.627 | 1.00 | 0.00 |
| ATOM | 1370 | HE2 | PHE | 82 | 0.675 | 4.834 | 2.842 | 1.00 | 0.00 |
| ATOM | 1371 | CZ | PHE | 82 | −0.721 | 3.242 | 3.131 | 1.00 | 0.00 |

TABLE 5-continued

Atomic Structure Coordinates of the
Free Form of the P/CAF Bromodomain

| ATOM | 1372 | HZ | PHE | 82 | −0.047 | 2.659 | 3.741 | 1.00 | 0.00 |
|---|---|---|---|---|---|---|---|---|---|
| ATOM | 1373 | C | PHE | 82 | −5.194 | 5.601 | −1.014 | 1.00 | 0.00 |
| ATOM | 1374 | O | PHE | 82 | −6.353 | 5.997 | −0.895 | 1.00 | 0.00 |
| ATOM | 1375 | N | THR | 83 | −4.450 | 5.849 | −2.089 | 1.00 | 0.00 |
| ATOM | 1376 | HN | THR | 83 | −3.536 | 5.499 | −2.129 | 1.00 | 0.00 |
| ATOM | 1377 | CA | THR | 83 | −4.968 | 6.616 | −3.215 | 1.00 | 0.00 |
| ATOM | 1378 | HA | THR | 83 | −5.151 | 7.624 | −2.875 | 1.00 | 0.00 |
| ATOM | 1379 | CB | THR | 83 | −3.941 | 6.649 | −6.350 | 1.00 | 0.00 |
| ATOM | 1380 | HB | THR | 83 | −3.649 | 5.637 | −6.580 | 1.00 | 0.00 |
| ATOM | 1381 | OG1 | THR | 83 | −2.784 | 7.365 | −3.955 | 1.00 | 0.00 |
| ATOM | 1382 | HG1 | THR | 83 | −2.246 | 6.813 | −3.382 | 1.00 | 0.00 |
| ATOM | 1383 | CG2 | THR | 83 | −4.464 | 7.286 | −5.619 | 1.00 | 0.00 |
| ATOM | 1384 | HG21 | THR | 83 | −3.654 | 7.404 | −6.323 | 1.00 | 0.00 |
| ATOM | 1385 | HG22 | THR | 83 | −4.884 | 8.255 | −5.389 | 1.00 | 0.00 |
| ATOM | 1386 | HG23 | THR | 83 | −5.228 | 6.656 | −6.049 | 1.00 | 0.00 |
| ATOM | 1387 | C | THR | 83 | −6.278 | 6.017 | −3.711 | 1.00 | 0.00 |
| ATOM | 1388 | O | THR | 83 | −7.221 | 6.740 | −4.033 | 1.00 | 0.00 |
| ATOM | 1389 | N | ASN | 84 | −6.333 | 4.690 | −3.756 | 1.00 | 0.00 |
| ATOM | 1390 | HN | ASN | 84 | −5.550 | 4.170 | −3.476 | 1.00 | 0.00 |
| ATOM | 1391 | CA | ASN | 84 | −7.533 | 3.987 | −4.190 | 1.00 | 0.00 |
| ATOM | 1392 | HA | ASN | 84 | −7.822 | 4.381 | −5.153 | 1.00 | 0.00 |
| ATOM | 1393 | CB | ASN | 84 | −7.250 | 2.491 | −4.321 | 1.00 | 0.00 |
| ATOM | 1394 | HB1 | ASN | 84 | −6.457 | 2.342 | −5.039 | 1.00 | 0.00 |
| ATOM | 1395 | HB2 | ASN | 84 | −6.939 | 2.107 | −3.362 | 1.00 | 0.00 |
| ATOM | 1396 | CG | ASN | 84 | −8.464 | 1.707 | −4.778 | 1.00 | 0.00 |
| ATOM | 1397 | OD1 | ASN | 84 | −9.459 | 2.282 | −5.228 | 1.00 | 0.00 |
| ATOM | 1398 | ND2 | ASN | 84 | −8.388 | 0.385 | −4.672 | 1.00 | 0.00 |
| ATOM | 1399 | HD21 | ASN | 84 | −7.564 | −0.004 | −4.312 | 1.00 | 0.00 |
| ATOM | 1400 | HD22 | ASN | 84 | −9.158 | −0.147 | −4.960 | 1.00 | 0.00 |
| ATOM | 1401 | C | ASN | 84 | −8.670 | 4.212 | −3.201 | 1.00 | 0.00 |
| ATOM | 1402 | O | ASN | 84 | −9.656 | 4.879 | −3.514 | 1.00 | 0.00 |
| ATOM | 1403 | N | CYS | 85 | −8.520 | 3.657 | −2.003 | 1.00 | 0.00 |
| ATOM | 1404 | HN | CYS | 85 | −7.708 | 3.142 | −1.812 | 1.00 | 0.00 |
| ATOM | 1405 | CA | CYS | 85 | −9.526 | 3.808 | −0.961 | 1.00 | 0.00 |
| ATOM | 1406 | HA | CYS | 85 | −10.414 | 3.280 | −1.276 | 1.00 | 0.00 |
| ATOM | 1407 | CB | CYS | 85 | −9.028 | 3.205 | 0.354 | 1.00 | 0.00 |
| ATOM | 1408 | HB1 | CYS | 85 | −9.789 | 3.329 | 1.109 | 1.00 | 0.00 |
| ATOM | 1409 | HB2 | CYS | 85 | −8.132 | 3.724 | 0.665 | 1.00 | 0.00 |
| ATOM | 1410 | SG | CYS | 85 | −8.635 | 1.443 | 0.257 | 1.00 | 0.00 |
| ATOM | 1411 | HG | CYS | 85 | −9.362 | 0.955 | 0.652 | 1.00 | 0.00 |
| ATOM | 1412 | C | CYS | 85 | −9.873 | 5.278 | −0.759 | 1.00 | 0.00 |
| ATOM | 1413 | O | CYS | 85 | −10.996 | 5.613 | −0.398 | 1.00 | 0.00 |
| ATOM | 1414 | N | LYS | 86 | −8.898 | 6.150 | −0.993 | 1.00 | 0.00 |
| ATOM | 1415 | HN | LYS | 86 | −8.021 | 5.820 | −1.281 | 1.00 | 0.00 |
| ATOM | 1416 | CA | LYS | 86 | −9.102 | 7.586 | −0.840 | 1.00 | 0.00 |
| ATOM | 1417 | HA | LYS | 86 | −9.725 | 7.741 | 0.029 | 1.00 | 0.00 |
| ATOM | 1418 | CB | LYS | 86 | −7.758 | 8.290 | −0.623 | 1.00 | 0.00 |
| ATOM | 1419 | HB1 | LYS | 86 | −7.355 | 7.984 | 0.330 | 1.00 | 0.00 |
| ATOM | 1420 | HB2 | LYS | 86 | −7.078 | 7.990 | −1.405 | 1.00 | 0.00 |
| ATOM | 1421 | CG | LYS | 86 | −7.853 | 9.807 | −0.632 | 1.00 | 0.00 |
| ATOM | 1422 | HG1 | LYS | 86 | −8.358 | 10.091 | −0.901 | 1.00 | 0.00 |
| ATOM | 1423 | HG2 | LYS | 86 | −7.625 | 10.178 | 0.356 | 1.00 | 0.00 |
| ATOM | 1424 | CD | LYS | 86 | −6.882 | 10.424 | −1.626 | 1.00 | 0.00 |
| ATOM | 1425 | HD1 | LYS | 86 | −7.437 | 11.020 | −2.334 | 1.00 | 0.00 |
| ATOM | 1426 | HD2 | LYS | 86 | −6.363 | 9.633 | −2.147 | 1.00 | 0.00 |
| ATOM | 1427 | CE | LYS | 86 | −5.850 | 11.308 | −0.930 | 1.00 | 0.00 |
| ATOM | 1428 | HE1 | LYS | 86 | −5.744 | 10.970 | 0.090 | 1.00 | 0.00 |
| ATOM | 1429 | HE2 | LYS | 86 | −4.915 | 11.221 | −1.447 | 1.00 | 0.00 |
| ATOM | 1430 | NZ | LYS | 86 | −6.276 | 12.738 | −0.922 | 1.00 | 0.00 |
| ATOM | 1431 | HZ1 | LYS | 86 | −6.207 | 13.125 | 0.041 | 1.00 | 0.00 |
| ATOM | 1432 | HZ2 | LYS | 86 | −7.260 | 12.825 | −1.249 | 1.00 | 0.00 |
| ATOM | 1433 | HZ3 | LYS | 86 | −5.663 | 13.292 | −1.552 | 1.00 | 0.00 |
| ATOM | 1434 | C | LYS | 86 | −9.805 | 8.175 | −2.060 | 1.00 | 0.00 |
| ATOM | 1435 | O | LYS | 86 | −10.579 | 9.126 | −1.943 | 1.00 | 0.00 |
| ATOM | 1436 | N | GLU | 87 | −9.518 | 7.615 | −3.230 | 1.00 | 0.00 |
| ATOM | 1437 | HN | GLU | 87 | −8.883 | 6.869 | −3.259 | 1.00 | 0.00 |
| ATOM | 1438 | CA | GLU | 87 | −10.101 | 8.103 | −6.474 | 1.00 | 0.00 |
| ATOM | 1439 | HA | GLU | 87 | −10.301 | 9.183 | −4.435 | 1.00 | 0.00 |
| ATOM | 1440 | CB | GLU | 87 | −9.256 | 7.649 | −5.665 | 1.00 | 0.00 |
| ATOM | 1441 | HB1 | GLU | 87 | −9.884 | 7.607 | −6.542 | 1.00 | 0.00 |
| ATOM | 1442 | HB2 | GLU | 87 | −8.869 | 6.662 | −5.462 | 1.00 | 0.00 |
| ATOM | 1443 | CG | GLU | 87 | −8.084 | 8.570 | −5.963 | 1.00 | 0.00 |
| ATOM | 1444 | HG1 | GLU | 87 | −7.726 | 8.989 | −5.033 | 1.00 | 0.00 |
| ATOM | 1445 | HG2 | GLU | 87 | −7.296 | 7.993 | −6.424 | 1.00 | 0.00 |
| ATOM | 1446 | CD | GLU | 87 | −8.460 | 9.707 | −6.893 | 1.00 | 0.00 |
| ATOM | 1447 | OE1 | GLU | 87 | −9.484 | 9.583 | −7.597 | 1.00 | 0.00 |

TABLE 5-continued

Atomic Structure Coordinates of the
Free Form of the P/CAF Bromodomain

| ATOM | 1448 | OE2  | GLU | 87 | −7.732  | 10.721 | −6.916 | 1.00 | 0.00 |
|------|------|------|-----|----|---------|--------|--------|------|------|
| ATOM | 1449 | C    | GLU | 87 | −11.539 | 7.621  | −4.645 | 1.00 | 0.00 |
| ATOM | 1450 | O    | GLU | 87 | −12.423 | 8.397  | −5.010 | 1.00 | 0.00 |
| ATOM | 1451 | N    | TYR | 88 | −11.769 | 6.338  | −4.387 | 1.00 | 0.00 |
| ATOM | 1452 | HN   | TYR | 88 | −11.023 | 5.763  | −6.109 | 1.00 | 0.00 |
| ATOM | 1453 | CA   | TYR | 88 | −13.100 | 5.757  | −4.536 | 1.00 | 0.00 |
| ATOM | 1454 | HA   | TYR | 88 | −13.528 | 6.144  | −5.449 | 1.00 | 0.00 |
| ATOM | 1455 | CB   | TYR | 88 | −13.000 | 4.234  | −4.639 | 1.00 | 0.00 |
| ATOM | 1456 | HB1  | TYR | 88 | −12.032 | 3.971  | −5.040 | 1.00 | 0.00 |
| ATOM | 1457 | HB2  | TYR | 88 | −13.104 | 3.806  | −3.653 | 1.00 | 0.00 |
| ATOM | 1458 | CG   | TYR | 88 | −14.054 | 3.612  | −5.527 | 1.00 | 0.00 |
| ATOM | 1459 | CD1  | TYR | 88 | −15.165 | 2.982  | −4.982 | 1.00 | 0.00 |
| ATOM | 1460 | HD1  | TYR | 88 | −15.273 | 2.942  | −3.908 | 1.00 | 0.00 |
| ATOM | 1461 | CD2  | TYR | 88 | −13.935 | 3.651  | −6.911 | 1.00 | 0.00 |
| ATOM | 1462 | HD2  | TYR | 88 | −13.076 | 4.136  | −7.350 | 1.00 | 0.00 |
| ATOM | 1463 | CE1  | TYR | 88 | −16.130 | 2.410  | −5.790 | 1.00 | 0.00 |
| ATOM | 1464 | HE1  | TYR | 88 | −16.987 | 1.925  | −5.347 | 1.00 | 0.00 |
| ATOM | 1465 | CE2  | TYR | 88 | −14.894 | 3.081  | −7.726 | 1.00 | 0.00 |
| ATOM | 1466 | HE2  | TYR | 88 | −14.785 | 3.122  | −8.800 | 1.00 | 0.00 |
| ATOM | 1467 | CZ   | TYR | 88 | −15.990 | 2.463  | −7.161 | 1.00 | 0.00 |
| ATOM | 1468 | OH   | TYR | 88 | −16.947 | 1.893  | −7.969 | 1.00 | 0.00 |
| ATOM | 1469 | HH   | TYR | 88 | −17.473 | 2.584  | −8.378 | 1.00 | 0.00 |
| ATOM | 1470 | C    | TYR | 88 | −14.010 | 6.137  | 3.368  | 1.00 | 0.00 |
| ATOM | 1471 | O    | TYR | 88 | −14.555 | 5.265  | −2.691 | 1.00 | 0.00 |
| ATOM | 1472 | N    | ASN | 89 | −14.187 | 7.439  | −3.150 | 1.00 | 0.00 |
| ATOM | 1473 | HN   | ASN | 89 | −13.737 | 8.087  | −3.727 | 1.00 | 0.00 |
| ATOM | 1474 | CA   | ASN | 89 | −15.038 | 7.925  | −2.070 | 1.00 | 0.00 |
| ATOM | 1475 | HA   | ASN | 89 | −15.652 | 7.102  | −1.736 | 1.00 | 0.00 |
| ATOM | 1476 | CB   | ASN | 89 | −14.185 | 8.416  | −0.899 | 1.00 | 0.00 |
| ATOM | 1477 | HB1  | ASN | 89 | −14.820 | 8.581  | −0.042 | 1.00 | 0.00 |
| ATOM | 1478 | HB2  | ASN | 89 | −13.706 | 9.344  | −1.173 | 1.00 | 0.00 |
| ATOM | 1479 | CG   | ASN | 89 | −13.113 | 7.419  | −0.517 | 1.00 | 0.00 |
| ATOM | 1480 | OD1  | ASN | 89 | −12.001 | 7.796  | −0.149 | 1.00 | 0.00 |
| ATOM | 1481 | ND2  | ASN | 89 | −13.444 | 6.136  | −0.609 | 1.00 | 0.00 |
| ATOM | 1482 | HD21 | ASN | 89 | −12.769 | 5.467  | −0.377 | 1.00 | 0.00 |
| ATOM | 1483 | HD22 | ASN | 89 | −14.348 | 5.910  | −0.912 | 1.00 | 0.00 |
| ATOM | 1484 | C    | ASN | 89 | −15.944 | 9.048  | −2.552 | 1.00 | 0.00 |
| ATOM | 1485 | O    | ASN | 89 | −15.701 | 10.222 | −2.272 | 1.00 | 0.00 |
| ATOM | 1486 | N    | ALA | 90 | −16.997 | 8.680  | −3.372 | 1.00 | 0.00 |
| ATOM | 1487 | HN   | ALA | 90 | −17.141 | 7.728  | −3.456 | 1.00 | 0.00 |
| ATOM | 1488 | CA   | ALA | 90 | −17.954 | 9.655  | −3.783 | 1.00 | 0.00 |
| ATOM | 1489 | HA   | ALA | 90 | −17.486 | 10.184 | −4.599 | 1.00 | 0.00 |
| ATOM | 1490 | CB   | ALA | 90 | −19.185 | 8.946  | −4.326 | 1.00 | 0.00 |
| ATOM | 1491 | HB1  | ALA | 90 | −19.230 | 7.944  | −3.926 | 1.00 | 0.00 |
| ATOM | 1492 | HB2  | ALA | 90 | −19.128 | 8.901  | −5.404 | 1.00 | 0.00 |
| ATOM | 1493 | HB3  | ALA | 90 | −20.072 | 9.490  | −4.035 | 1.00 | 0.00 |
| ATOM | 1494 | C    | ALA | 90 | −18.356 | 10.662 | −2.705 | 1.00 | 0.00 |
| ATOM | 1495 | O    | ALA | 90 | −18.383 | 11.868 | −2.952 | 1.00 | 0.00 |
| ATOM | 1496 | N    | PRO | 91 | −18.657 | 10.179 | −1.487 | 1.00 | 0.00 |
| ATOM | 1497 | CA   | PRO | 91 | −19.087 | 11.013 | −0.381 | 1.00 | 0.00 |
| ATOM | 1498 | HA   | PRO | 91 | −19.505 | 11.951 | −0.717 | 1.00 | 0.00 |
| ATOM | 1499 | CB   | PRO | 91 | −20.176 | 10.160 | 0.237  | 1.00 | 0.00 |
| ATOM | 1500 | HB1  | PRO | 91 | −20.271 | 10.369 | 1.289  | 1.00 | 0.00 |
| ATOM | 1501 | HB2  | PRO | 91 | −21.115 | 10.323 | −0.263 | 1.00 | 0.00 |
| ATOM | 1502 | CG   | PRO | 91 | −19.704 | 8.730  | 0.022  | 1.00 | 0.00 |
| ATOM | 1503 | HG1  | PRO | 91 | −20.537 | 8.104  | −0.258 | 1.00 | 0.00 |
| ATOM | 1504 | HG2  | PRO | 91 | −19.249 | 8.358  | 0.929  | 1.00 | 0.00 |
| ATOM | 1505 | CD   | PRO | 91 | −18.679 | 8.764  | −1.094 | 1.00 | 0.00 |
| ATOM | 1506 | HD1  | PRO | 91 | −17.713 | 8.452  | −0.724 | 1.00 | 0.00 |
| ATOM | 1507 | HD2  | PRO | 91 | −18.988 | 8.139  | −1.919 | 1.00 | 0.00 |
| ATOM | 1508 | C    | PRO | 91 | −17.976 | 11.268 | 0.633  | 1.00 | 0.00 |
| ATOM | 1509 | O    | PRO | 91 | −18.242 | 11.671 | 1.766  | 1.00 | 0.00 |
| ATOM | 1510 | N    | GLU | 92 | −16.736 | 11.007 | 0.234  | 1.00 | 0.00 |
| ATOM | 1511 | HN   | GLU | 92 | −16.582 | 10.671 | −0.674 | 1.00 | 0.00 |
| ATOM | 1512 | CA   | GLU | 92 | −15.596 | 11.174 | 1.132  | 1.00 | 0.00 |
| ATOM | 1513 | HA   | GLU | 92 | −14.728 | 10.745 | 0.654  | 1.00 | 0.00 |
| ATOM | 1514 | CB   | GLU | 92 | −15.340 | 12.658 | 1.408  | 1.00 | 0.00 |
| ATOM | 1515 | HB1  | GLU | 92 | −14.454 | 12.750 | 2.020  | 1.00 | 0.00 |
| ATOM | 1516 | HB2  | GLU | 92 | −16.183 | 13.062 | 1.949  | 1.00 | 0.00 |
| ATOM | 1517 | CG   | GLU | 92 | −15.139 | 13.487 | 0.150  | 1.00 | 0.00 |
| ATOM | 1518 | HG1  | GLU | 92 | −15.062 | 12.821 | −0.696 | 1.00 | 0.00 |
| ATOM | 1519 | HG2  | GLU | 92 | −15.993 | 14.135 | 0.021  | 1.00 | 0.00 |
| ATOM | 1520 | CD   | GLU | 92 | −13.888 | 14.343 | 0.208  | 1.00 | 0.00 |
| ATOM | 1521 | OE1  | GLU | 92 | −13.118 | 14.335 | −0.775 | 1.00 | 0.00 |
| ATOM | 1522 | OE2  | GLU | 92 | −13.679 | 15.021 | 1.236  | 1.00 | 0.00 |
| ATOM | 1523 | C    | GLU | 92 | −15.843 | 10.432 | 2.436  | 1.00 | 0.00 |

TABLE 5-continued

Atomic Structure Coordinates of the
Free Form of the P/CAF Bromodomain

| ATOM | 1524 | O | GLU | 92 | −15.529 | 10.925 | 3.519 | 1.00 | 0.00 |
|---|---|---|---|---|---|---|---|---|---|
| ATOM | 1525 | N | SER | 93 | −16.427 | 9.248 | 2.313 | 1.00 | 0.00 |
| ATOM | 1526 | HN | SER | 93 | −16.649 | 8.919 | 1.417 | 1.00 | 0.00 |
| ATOM | 1527 | CA | SER | 93 | −16.725 | 8.412 | 3.463 | 1.00 | 0.00 |
| ATOM | 1528 | HA | SER | 93 | −17.495 | 8.899 | 4.042 | 1.00 | 0.00 |
| ATOM | 1529 | CB | SER | 93 | −17.234 | 7.048 | 2.986 | 1.00 | 0.00 |
| ATOM | 1530 | HB1 | SER | 93 | −17.222 | 6.350 | 3.809 | 1.00 | 0.00 |
| ATOM | 1531 | HB2 | SER | 93 | −18.243 | 7.152 | 2.615 | 1.00 | 0.00 |
| ATOM | 1532 | OG | SER | 93 | −16.418 | 6.536 | 1.947 | 1.00 | 0.00 |
| ATOM | 1533 | HG | SER | 93 | −16.849 | 6.678 | 1.101 | 1.00 | 0.00 |
| ATOM | 1534 | C | SER | 93 | −15.490 | 8.232 | 4.335 | 1.00 | 0.00 |
| ATOM | 1535 | O | SER | 93 | −14.447 | 8.833 | 4.082 | 1.00 | 0.00 |
| ATOM | 1536 | N | GLU | 94 | −15.601 | 7.370 | 5.338 | 1.00 | 0.00 |
| ATOM | 1537 | HN | GLU | 94 | −16.455 | 6.913 | 5.485 | 1.00 | 0.00 |
| ATOM | 1538 | CA | GLU | 94 | −14.485 | 7.092 | 6.230 | 1.00 | 0.00 |
| ATOM | 1539 | HA | GLU | 94 | −14.213 | 8.017 | 6.717 | 1.00 | 0.00 |
| ATOM | 1540 | CB | GLU | 94 | −14.901 | 6.073 | 7.292 | 1.00 | 0.00 |
| ATOM | 1541 | HB1 | GLU | 94 | −14.489 | 9.109 | 7.031 | 1.00 | 0.00 |
| ATOM | 1542 | HB2 | GLU | 94 | −15.979 | 6.003 | 7.305 | 1.00 | 0.00 |
| ATOM | 1543 | CG | GLU | 94 | −14.430 | 6.427 | 8.693 | 1.00 | 0.00 |
| ATOM | 1544 | HG1 | GLU | 94 | −13.574 | 7.082 | 8.616 | 1.00 | 0.00 |
| ATOM | 1545 | HG2 | GLU | 94 | −15.229 | 6.939 | 9.209 | 1.00 | 0.00 |
| ATOM | 1546 | CD | GLU | 94 | −14.035 | 5.207 | 9.502 | 1.00 | 0.00 |
| ATOM | 1547 | OE1 | GLU | 94 | −13.155 | 5.336 | 10.379 | 1.00 | 0.00 |
| ATOM | 1548 | OE2 | GLU | 94 | −14.604 | 5.123 | 9.257 | 1.00 | 0.00 |
| ATOM | 1549 | C | GLU | 94 | −13.274 | 6.569 | 5.457 | 1.00 | 0.00 |
| ATOM | 1550 | O | GLU | 94 | −12.160 | 6.551 | 5.979 | 1.00 | 0.00 |
| ATOM | 1551 | N | TYR | 95 | −13.493 | 6.137 | 4.214 | 1.00 | 0.00 |
| ATOM | 1552 | HN | TYR | 95 | −14.397 | 6.158 | 3.841 | 1.00 | 0.00 |
| ATOM | 1553 | CA | TYR | 95 | −12.412 | 5.611 | 3.393 | 1.00 | 0.00 |
| ATOM | 1554 | HA | TYR | 95 | −11.977 | 4.775 | 3.916 | 1.00 | 0.00 |
| ATOM | 1555 | CB | TYR | 95 | −12.947 | 5.131 | 2.045 | 1.00 | 0.00 |
| ATOM | 1556 | HB1 | TYR | 95 | −13.630 | 5.870 | 1.653 | 1.00 | 0.00 |
| ATOM | 1557 | HB2 | TYR | 95 | −12.119 | 5.016 | 1.365 | 1.00 | 0.00 |
| ATOM | 1558 | CG | TYR | 95 | −13.678 | 3.807 | 2.104 | 1.00 | 0.00 |
| ATOM | 1559 | CD1 | TYR | 95 | −13.724 | 2.972 | 0.996 | 1.00 | 0.00 |
| ATOM | 1560 | ND1 | TYR | 95 | −13.227 | 3.279 | 0.087 | 1.00 | 0.00 |
| ATOM | 1561 | CD2 | TYR | 95 | −14.325 | 3.394 | 3.263 | 1.00 | 0.00 |
| ATOM | 1562 | HD2 | TYR | 95 | −14.303 | 4.030 | 4.132 | 1.00 | 0.00 |
| ATOM | 1563 | CE1 | TYR | 95 | −14.390 | 1.762 | 1.040 | 1.00 | 0.00 |
| ATOM | 1564 | HE1 | TYR | 95 | −14.413 | 1.126 | 0.167 | 1.00 | 0.00 |
| ATOM | 1565 | CE2 | TYR | 95 | −14.994 | 2.187 | 3.314 | 1.00 | 0.00 |
| ATOM | 1566 | HE2 | TYR | 95 | −15.487 | 1.884 | 4.227 | 1.00 | 0.00 |
| ATOM | 1567 | CZ | TYR | 95 | −15.022 | 1.374 | 2.202 | 1.00 | 0.00 |
| ATOM | 1568 | OH | TYR | 95 | −15.687 | 0.170 | 2.250 | 1.00 | 0.00 |
| ATOM | 1569 | HH | TYR | 95 | −15.095 | −0.534 | 1.974 | 1.00 | 0.00 |
| ATOM | 1570 | C | TYR | 95 | −11.338 | 6.671 | 3.177 | 1.00 | 0.00 |
| ATOM | 1571 | O | TYR | 95 | −10.170 | 6.352 | 2.951 | 1.00 | 0.00 |
| ATOM | 1572 | N | TYR | 96 | −11.743 | 7.934 | 3.243 | 1.00 | 0.00 |
| ATOM | 1573 | HN | TYR | 96 | −12.684 | 8.125 | 3.432 | 1.00 | 0.00 |
| ATOM | 1574 | CA | TYR | 96 | −10.816 | 9.045 | 3.073 | 1.00 | 0.00 |
| ATOM | 1575 | HA | TYR | 96 | −10.140 | 8.795 | 2.268 | 1.00 | 0.00 |
| ATOM | 1576 | CB | TYR | 96 | −11.579 | 10.321 | 2.712 | 1.00 | 0.00 |
| ATOM | 1577 | HB1 | TYR | 96 | −12.376 | 10.073 | 2.027 | 1.00 | 0.00 |
| ATOM | 1578 | HB2 | TYR | 96 | −12.001 | 10.745 | 3.611 | 1.00 | 0.00 |
| ATOM | 1579 | CG | TYR | 96 | −10.717 | 11.378 | 2.060 | 1.00 | 0.00 |
| ATOM | 1580 | CD1 | TYR | 96 | −10.257 | 11.219 | 0.759 | 1.00 | 0.00 |
| ATOM | 1581 | HD1 | TYR | 96 | −10.524 | 10.326 | 0.213 | 1.00 | 0.00 |
| ATOM | 1582 | CD2 | TYR | 96 | −10.364 | 12.533 | 2.745 | 1.00 | 0.00 |
| ATOM | 1583 | HD2 | TYR | 96 | −10.714 | 12.672 | 3.758 | 1.00 | 0.00 |
| ATOM | 1584 | CE1 | TYR | 96 | −9.471 | 12.183 | 0.159 | 1.00 | 0.00 |
| ATOM | 1585 | HE1 | TYR | 96 | −9.120 | 12.039 | −0.952 | 1.00 | 0.00 |
| ATOM | 1586 | CE2 | TYR | 96 | −9.576 | 13.501 | 2.152 | 1.00 | 0.00 |
| ATOM | 1587 | HE2 | TYR | 96 | −9.312 | 14.393 | 2.701 | 1.00 | 0.00 |
| ATOM | 1588 | CZ | TYR | 96 | −9.131 | 13.320 | 0.859 | 1.00 | 0.00 |
| ATOM | 1589 | OH | TYR | 96 | −8.347 | 14.782 | 0.265 | 1.00 | 0.00 |
| ATOM | 1590 | HH | TYR | 96 | −8.832 | 14.690 | −0.456 | 1.00 | 0.00 |
| ATOM | 1591 | C | TYR | 96 | −10.009 | 9.267 | 4.346 | 1.00 | 0.00 |
| ATOM | 1592 | O | TYR | 96 | −8.884 | 9.764 | 4.303 | 1.00 | 0.00 |
| ATOM | 1593 | N | LYS | 97 | −10.593 | 8.888 | 5.478 | 1.00 | 0.00 |
| ATOM | 1594 | HN | LYS | 97 | −11.496 | 8.503 | 5.445 | 1.00 | 0.00 |
| ATOM | 1595 | CA | LYS | 97 | −9.937 | 9.050 | 6.771 | 1.00 | 0.00 |
| ATOM | 1596 | HA | LYS | 97 | −9.515 | 10.043 | 6.806 | 1.00 | 0.00 |
| ATOM | 1597 | CB | LYS | 97 | −10.960 | 8.901 | 7.898 | 1.00 | 0.00 |
| ATOM | 1598 | HB1 | LYS | 97 | −11.380 | 7.906 | 7.859 | 1.00 | 0.00 |
| ATOM | 1599 | HB2 | LYS | 97 | −10.457 | 9.033 | 8.845 | 1.00 | 0.00 |

TABLE 5-continued

Atomic Structure Coordinates of the
Free Form of the P/CAF Bromodomain

| ATOM | 1600 | CG | LYS | 97 | −12.100 | 9.903 | 7.820 | 1.00 | 0.00 |
|------|------|------|------|-----|---------|--------|--------|------|------|
| ATOM | 1601 | HG1 | LYS | 97 | −12.840 | 9.537 | 7.124 | 1.00 | 0.00 |
| ATOM | 1602 | HG2 | LYS | 97 | −11.711 | 10.849 | 7.473 | 1.00 | 0.00 |
| ATOM | 1603 | CD | LYS | 97 | −12.756 | 10.107 | 9.176 | 1.00 | 0.00 |
| ATOM | 1604 | HD1 | LYS | 97 | −13.665 | 10.674 | 9.042 | 1.00 | 0.00 |
| ATOM | 1605 | HD2 | LYS | 97 | −12.990 | 9.142 | 9.601 | 1.00 | 0.00 |
| ATOM | 1606 | CE | LYS | 97 | −11.842 | 10.857 | 10.131 | 1.00 | 0.00 |
| ATOM | 1607 | HE1 | LYS | 97 | −10.927 | 11.105 | 9.614 | 1.00 | 0.00 |
| ATOM | 1608 | HE2 | LYS | 97 | −11.618 | 10.218 | 10.972 | 1.00 | 0.00 |
| ATOM | 1609 | NZ | LYS | 97 | −12.471 | 12.111 | 10.629 | 1.00 | 0.00 |
| ATOM | 1610 | HZ1 | LYS | 97 | −11.831 | 12.917 | 10.676 | 1.00 | 0.00 |
| ATOM | 1611 | HZ2 | LYS | 97 | −12.672 | 12.031 | 11.646 | 1.00 | 0.00 |
| ATOM | 1612 | HZ3 | LYS | 97 | −13.362 | 12.289 | 10.123 | 1.00 | 0.00 |
| ATOM | 1613 | C | LYS | 97 | −8.816 | 9.031 | 6.955 | 1.00 | 0.00 |
| ATOM | 1614 | O | LYS | 97 | −7.664 | 8.395 | 7.189 | 1.00 | 0.00 |
| ATOM | 1615 | N | CYS | 98 | −9.167 | 6.753 | 6.861 | 1.00 | 0.00 |
| ATOM | 1616 | HN | CYS | 98 | −10.105 | 6.529 | 6.684 | 1.00 | 0.00 |
| ATOM | 1617 | CA | CYS | 98 | −8.203 | 5.671 | 7.039 | 1.00 | 0.00 |
| ATOM | 1618 | HA | CYS | 98 | −7.970 | 5.609 | 8.092 | 1.00 | 0.00 |
| ATOM | 1619 | CB | CYS | 98 | −8.816 | 4.348 | 6.588 | 1.00 | 0.00 |
| ATOM | 1620 | HB1 | CYS | 98 | −8.039 | 3.600 | 6.511 | 1.00 | 0.00 |
| ATOM | 1621 | HB2 | CYS | 98 | −9.554 | 4.040 | 7.311 | 1.00 | 0.00 |
| ATOM | 1622 | SG | CYS | 98 | −9.627 | 4.426 | 4.976 | 1.00 | 0.00 |
| ATOM | 1623 | HG | CYS | 98 | −10.366 | 5.034 | 5.045 | 1.00 | 0.00 |
| ATOM | 1624 | C | CYS | 98 | −6.914 | 5.931 | 6.268 | 1.00 | 0.00 |
| ATOM | 1625 | O | CYS | 98 | −5.817 | 5.796 | 6.814 | 1.00 | 0.00 |
| ATOM | 1626 | N | ALA | 99 | −7.045 | 6.278 | 4.991 | 1.00 | 0.00 |
| ATOM | 1627 | HN | ALA | 99 | −7.939 | 6.375 | 4.607 | 1.00 | 0.00 |
| ATOM | 1628 | CA | ALA | 99 | −5.885 | 6.551 | 4.158 | 1.00 | 0.00 |
| ATOM | 1629 | HA | ALA | 99 | −5.339 | 5.629 | 4.029 | 1.00 | 0.00 |
| ATOM | 1630 | CB | ALA | 99 | −6.319 | 7.042 | 2.785 | 1.00 | 0.00 |
| ATOM | 1631 | HB1 | ALA | 99 | −6.855 | 6.255 | 2.275 | 1.00 | 0.00 |
| ATOM | 1632 | HB2 | ALA | 99 | −5.448 | 7.317 | 2.209 | 1.00 | 0.00 |
| ATOM | 1633 | HB3 | ALA | 99 | −6.963 | 7.902 | 2.897 | 1.00 | 0.00 |
| ATOM | 1634 | C | ALA | 99 | −4.977 | 7.570 | 4.828 | 1.00 | 0.00 |
| ATOM | 1635 | O | ALA | 99 | −3.764 | 7.398 | 4.871 | 1.00 | 0.00 |
| ATOM | 1636 | N | ASN | 100 | −5.581 | 8.613 | 5.379 | 1.00 | 0.00 |
| ATOM | 1637 | HN | ASN | 100 | −6.555 | 8.685 | 5.321 | 1.00 | 0.00 |
| ATOM | 1638 | CA | ASN | 100 | −4.826 | 9.660 | 6.054 | 1.00 | 0.00 |
| ATOM | 1639 | HA | ASN | 100 | −4.202 | 10.142 | 5.316 | 1.00 | 0.00 |
| ATOM | 1640 | CB | ASN | 100 | −5.778 | 10.695 | 6.658 | 1.00 | 0.00 |
| ATOM | 1641 | HB1 | ASN | 100 | −6.720 | 10.660 | 6.130 | 1.00 | 0.00 |
| ATOM | 1642 | HB2 | ASN | 100 | −5.943 | 10.459 | 7.699 | 1.00 | 0.00 |
| ATOM | 1643 | CG | ASN | 100 | −5.230 | 12.106 | 6.568 | 1.00 | 0.00 |
| ATOM | 1644 | OD1 | ASN | 100 | −5.097 | 12.798 | 7.577 | 1.00 | 0.00 |
| ATOM | 1645 | ND2 | ASN | 100 | −4.910 | 12.541 | 5.354 | 1.00 | 0.00 |
| ATOM | 1646 | ND21 | ASN | 100 | −4.553 | 13.449 | 5.267 | 1.00 | 0.00 |
| ATOM | 1647 | ND22 | ASN | 100 | −5.042 | 11.934 | 4.595 | 1.00 | 0.00 |
| ATOM | 1648 | C | ASN | 100 | −3.935 | 9.073 | 7.144 | 1.00 | 0.00 |
| ATOM | 1649 | O | ASN | 100 | −2.862 | 9.602 | 7.434 | 1.00 | 0.00 |
| ATOM | 1650 | N | ILE | 101 | −4.386 | 7.975 | 7.743 | 1.00 | 0.00 |
| ATOM | 1651 | HN | ILE | 101 | −5.248 | 7.599 | 7.467 | 1.00 | 0.00 |
| ATOM | 1652 | CA | ILE | 101 | −3.630 | 7.318 | 8.803 | 1.00 | 0.00 |
| ATOM | 1653 | HA | ILE | 101 | −3.193 | 8.088 | 9.422 | 1.00 | 0.00 |
| ATOM | 1654 | CB | ILE | 101 | −4.541 | 6.453 | 9.691 | 1.00 | 0.00 |
| ATOM | 1655 | HB | ILE | 101 | −4.890 | 5.616 | 9.105 | 1.00 | 0.00 |
| ATOM | 1656 | CG1 | ILE | 101 | −5.743 | 7.374 | 10.166 | 1.00 | 0.00 |
| ATOM | 1657 | HG11 | ILE | 101 | −6.325 | 7.575 | 9.308 | 1.00 | 0.00 |
| ATOM | 1658 | HG12 | ILE | 101 | −5.387 | 8.153 | 10.682 | 1.00 | 0.00 |
| ATOM | 1659 | CG2 | ILE | 101 | −3.761 | 5.909 | 10.879 | 1.00 | 0.00 |
| ATOM | 1660 | HG21 | ILE | 101 | −4.431 | 5.373 | 11.534 | 1.00 | 0.00 |
| ATOM | 1661 | HG22 | ILE | 101 | −3.308 | 6.727 | 11.418 | 1.00 | 0.00 |
| ATOM | 1662 | HG23 | ILE | 101 | −2.990 | 5.240 | 10.526 | 1.00 | 0.00 |
| ATOM | 1663 | CD1 | ILE | 101 | −6.658 | 6.523 | 11.107 | 1.00 | 0.00 |
| ATOM | 1664 | HD11 | ILE | 101 | −7.168 | 7.226 | 11.749 | 1.00 | 0.00 |
| ATOM | 1665 | HD12 | ILE | 101 | −6.075 | 5.842 | 11.709 | 1.00 | 0.00 |
| ATOM | 1666 | HD13 | ILE | 101 | −7.384 | 5.966 | 10.534 | 1.00 | 0.00 |
| ATOM | 1667 | C | ILE | 101 | −2.511 | 6.457 | 8.226 | 1.00 | 0.00 |
| ATOM | 1668 | O | ILE | 101 | −1.335 | 6.807 | 8.332 | 1.00 | 0.00 |
| ATOM | 1669 | N | LEU | 102 | −2.876 | 5.343 | 7.590 | 1.00 | 0.00 |
| ATOM | 1670 | HN | LEU | 102 | −3.829 | 5.117 | 7.527 | 1.00 | 0.00 |
| ATOM | 1671 | CA | LEU | 102 | −1.886 | 4.457 | 6.972 | 1.00 | 0.00 |
| ATOM | 1672 | HA | LEU | 102 | −1.350 | 3.953 | 7.763 | 1.00 | 0.00 |
| ATOM | 1673 | CB | LEU | 102 | −2.569 | 3.416 | 6.082 | 1.00 | 0.00 |
| ATOM | 1674 | HB1 | LEU | 102 | −3.630 | 3.443 | 6.283 | 1.00 | 0.00 |
| ATOM | 1675 | HB2 | LEU | 102 | −2.408 | 3.700 | 5.053 | 1.00 | 0.00 |

TABLE 5-continued

Atomic Structure Coordinates of the
Free Form of the P/CAF Bromodomain

| ATOM | 1676 | CG | LEU | 102 | −2.083 | 1.971 | 6.260 | 1.00 | 0.00 |
|---|---|---|---|---|---|---|---|---|---|
| ATOM | 1677 | HG | LEU | 102 | −2.423 | 1.382 | 5.420 | 1.00 | 0.00 |
| ATOM | 1678 | CD1 | LEU | 102 | −2.676 | 1.364 | 7.523 | 1.00 | 0.00 |
| ATOM | 1679 | HD11 | LEU | 102 | −1.943 | 1.195 | 8.316 | 1.00 | 0.00 |
| ATOM | 1680 | HD12 | LEU | 102 | −2.958 | 0.338 | 7.332 | 1.00 | 0.00 |
| ATOM | 1681 | HD13 | LEU | 102 | −3.549 | 1.928 | 7.818 | 1.00 | 0.00 |
| ATOM | 1682 | CD2 | LEU | 102 | −0.559 | 1.903 | 6.250 | 1.00 | 0.00 |
| ATOM | 1683 | HD21 | LEU | 102 | −0.147 | 2.788 | 5.827 | 1.00 | 0.00 |
| ATOM | 1684 | HD22 | LEU | 102 | −0.224 | 1.027 | 5.749 | 1.00 | 0.00 |
| ATOM | 1685 | HD23 | LEU | 102 | −0.220 | 1.841 | 7.313 | 1.00 | 0.00 |
| ATOM | 1686 | C | LEU | 102 | −0.897 | 5.265 | 6.139 | 1.00 | 0.00 |
| ATOM | 1687 | O | LEU | 102 | 0.301 | 4.991 | 6.137 | 1.00 | 0.00 |
| ATOM | 1688 | N | GLU | 103 | −1.414 | 6.266 | 5.433 | 1.00 | 0.00 |
| ATOM | 1689 | HN | GLU | 103 | −2.377 | 6.439 | 5.484 | 1.00 | 0.00 |
| ATOM | 1690 | CA | GLU | 103 | −0.581 | 7.132 | 4.612 | 1.00 | 0.00 |
| ATOM | 1691 | HA | GLU | 103 | −0.056 | 6.514 | 3.900 | 1.00 | 0.00 |
| ATOM | 1692 | CB | GLU | 103 | −1.446 | 8.146 | 3.857 | 1.00 | 0.00 |
| ATOM | 1693 | HB1 | GLU | 103 | −1.912 | 8.808 | 4.572 | 1.00 | 0.00 |
| ATOM | 1694 | HB2 | GLU | 103 | −2.220 | 7.612 | 3.320 | 1.00 | 0.00 |
| ATOM | 1695 | CG | GLU | 103 | −0.670 | 8.991 | 2.860 | 1.00 | 0.00 |
| ATOM | 1696 | HG1 | GLU | 103 | −1.083 | 8.832 | 1.874 | 1.00 | 0.00 |
| ATOM | 1697 | HG2 | GLU | 103 | 0.364 | 8.680 | 2.871 | 1.00 | 0.00 |
| ATOM | 1698 | CD | GLU | 103 | −0.734 | 10.472 | 3.178 | 1.00 | 0.00 |
| ATOM | 1699 | OE1 | GLU | 103 | −1.856 | 10.996 | 3.342 | 1.00 | 0.00 |
| ATOM | 1700 | OE2 | GLU | 103 | 0.337 | 11.108 | 3.264 | 1.00 | 0.00 |
| ATOM | 1701 | C | GLU | 103 | 0.439 | 7.258 | 5.478 | 1.00 | 0.00 |
| ATOM | 1702 | O | GLU | 103 | 1.644 | 7.658 | 5.336 | 1.00 | 0.00 |
| ATOM | 1703 | N | LYS | 104 | −0.052 | 8.675 | 6.405 | 1.00 | 0.00 |
| ATOM | 1704 | HN | LYS | 104 | −1.024 | 8.786 | 6.480 | 1.00 | 0.00 |
| ATOM | 1705 | CA | LYS | 104 | 0.821 | 9.417 | 7.306 | 1.00 | 0.00 |
| ATOM | 1706 | HA | LYS | 104 | 1.329 | 10.172 | 4.725 | 1.00 | 0.00 |
| ATOM | 1707 | CB | LYS | 104 | −0.003 | 10.100 | 8.399 | 1.00 | 0.00 |
| ATOM | 1708 | HB1 | LYS | 104 | −0.949 | 9.589 | 8.492 | 1.00 | 0.00 |
| ATOM | 1709 | HB2 | LYS | 104 | 0.530 | 10.024 | 9.335 | 1.00 | 0.00 |
| ATOM | 1710 | CG | LYS | 104 | −0.278 | 11.569 | 6.125 | 1.00 | 0.00 |
| ATOM | 1711 | HG1 | LYS | 104 | 0.635 | 12.128 | 8.261 | 1.00 | 0.00 |
| ATOM | 1712 | HG2 | LYS | 104 | −1.026 | 11.920 | 8.820 | 1.00 | 0.00 |
| ATOM | 1713 | CD | LYS | 104 | −0.782 | 11.786 | 6.708 | 1.00 | 0.00 |
| ATOM | 1714 | HD1 | LYS | 104 | −0.960 | 10.824 | 6.248 | 1.00 | 0.00 |
| ATOM | 1715 | HD2 | LYS | 104 | −0.031 | 12.322 | 6.147 | 1.00 | 0.00 |
| ATOM | 1716 | CE | LYS | 104 | −2.073 | 12.589 | 6.695 | 1.00 | 0.00 |
| ATOM | 1717 | HE1 | LYS | 104 | −2.601 | 12.384 | 5.775 | 1.00 | 0.00 |
| ATOM | 1718 | HE2 | LYS | 104 | −2.680 | 12.283 | 7.534 | 1.00 | 0.00 |
| ATOM | 1719 | NZ | LYS | 104 | −1.817 | 14.053 | 6.791 | 1.00 | 0.00 |
| ATOM | 1720 | HZ1 | LYS | 104 | −2.239 | 14.433 | 7.661 | 1.00 | 0.00 |
| ATOM | 1721 | HZ2 | LYS | 104 | −2.213 | 14.543 | 5.973 | 1.00 | 0.00 |
| ATOM | 1722 | HZ3 | LYS | 104 | −0.793 | 14.236 | 6.806 | 1.00 | 0.00 |
| ATOM | 1723 | C | LYS | 104 | 1.860 | 8.497 | 7.941 | 1.00 | 0.00 |
| ATOM | 1724 | O | LYS | 104 | 2.995 | 8.903 | 8.104 | 1.00 | 0.00 |
| ATOM | 1725 | N | PHE | 105 | 1.460 | 7.259 | 8.213 | 1.00 | 0.00 |
| ATOM | 1726 | HN | PHE | 105 | 0.540 | 6.997 | 7.997 | 1.00 | 0.00 |
| ATOM | 1727 | CA | PHE | 105 | 2.351 | 6.279 | 8.824 | 1.00 | 0.00 |
| ATOM | 1728 | HA | PHE | 105 | 2.951 | 6.790 | 9.562 | 1.00 | 0.00 |
| ATOM | 1729 | CB | PHE | 105 | 1.536 | 5.184 | 9.515 | 1.00 | 0.00 |
| ATOM | 1730 | HB1 | PHE | 105 | 2.007 | 4.228 | 9.138 | 1.00 | 0.00 |
| ATOM | 1731 | HB2 | PHE | 105 | 0.540 | 5.171 | 9.097 | 1.00 | 0.00 |
| ATOM | 1732 | CG | PHE | 105 | 1.411 | 5.369 | 11.001 | 1.00 | 0.00 |
| ATOM | 1733 | CD1 | PHE | 105 | 0.521 | 6.294 | 11.524 | 1.00 | 0.00 |
| ATOM | 1734 | HD1 | PHE | 105 | −0.083 | 6.887 | 10.853 | 1.00 | 0.00 |
| ATOM | 1735 | CD2 | PHE | 105 | 2.177 | 4.614 | 11.874 | 1.00 | 0.00 |
| ATOM | 1736 | HD2 | PHE | 105 | 2.872 | 3.889 | 11.478 | 1.00 | 0.00 |
| ATOM | 1737 | CE1 | PHE | 105 | 0.400 | 6.465 | 12.890 | 1.00 | 0.00 |
| ATOM | 1738 | HE1 | PHE | 105 | −0.296 | 7.190 | 13.285 | 1.00 | 0.00 |
| ATOM | 1739 | CE2 | PHE | 105 | 2.061 | 4.780 | 13.241 | 1.00 | 0.00 |
| ATOM | 1740 | HE2 | PHE | 105 | 2.665 | 4.186 | 13.911 | 1.00 | 0.00 |
| ATOM | 1741 | CZ | PHE | 105 | 1.172 | 5.707 | 13.750 | 1.00 | 0.00 |
| ATOM | 1742 | HZ | PHE | 105 | 1.079 | 5.838 | 14.818 | 1.00 | 0.00 |
| ATOM | 1743 | C | PHE | 105 | 3.279 | 5.655 | 7.785 | 1.00 | 0.00 |
| ATOM | 1744 | O | PHE | 105 | 4.491 | 5.871 | 7.808 | 1.00 | 0.00 |
| ATOM | 1745 | N | PHE | 106 | 2.702 | 4.870 | 6.882 | 1.00 | 0.00 |
| ATOM | 1746 | HN | PHE | 106 | 1.732 | 4.732 | 6.922 | 1.00 | 0.00 |
| ATOM | 1747 | CA | PHE | 106 | 3.670 | 4.199 | 5.841 | 1.00 | 0.00 |
| ATOM | 1748 | HA | PHE | 106 | 4.078 | 3.441 | 6.316 | 1.00 | 0.00 |
| ATOM | 1749 | CB | PHE | 106 | 2.532 | 3.526 | 4.839 | 1.00 | 0.00 |
| ATOM | 1750 | HB1 | PHE | 106 | 1.891 | 2.844 | 5.366 | 1.00 | 0.00 |
| ATOM | 1751 | HB2 | PHE | 106 | 1.937 | 4.281 | 4.351 | 1.00 | 0.00 |

TABLE 5-continued

Atomic Structure Coordinates of the
Free Form of the P/CAF Bromodomain

| ATOM | 1752 | CG   | PHE | 106 | 3.254 | 2.755  | 3.777  | 1.00 | 0.00 |
|------|------|------|-----|-----|-------|--------|--------|------|------|
| ATOM | 1753 | CD1  | PHE | 106 | 3.931 | 1.590  | 4.091  | 1.00 | 0.00 |
| ATOM | 1754 | HD1  | PHE | 106 | 3.928 | 1.235  | 5.109  | 1.00 | 0.00 |
| ATOM | 1755 | CD2  | PHE | 106 | 3.267 | 3.202  | 2.469  | 1.00 | 0.00 |
| ATOM | 1756 | HD2  | PHE | 106 | 2.743 | 4.111  | 2.214  | 1.00 | 0.00 |
| ATOM | 1757 | CE1  | PHE | 106 | 4.601 | 0.879  | 3.318  | 1.00 | 0.00 |
| ATOM | 1758 | HE1  | PHE | 106 | 5.122 | −0.029 | 3.376  | 1.00 | 0.00 |
| ATOM | 1759 | CE2  | PHE | 106 | 3.941 | 2.500  | 1.491  | 1.00 | 0.00 |
| ATOM | 1760 | HE2  | PHE | 106 | 3.935 | 2.853  | 0.471  | 1.00 | 0.00 |
| ATOM | 1761 | CZ   | PHE | 106 | 4.605 | 1.334  | 1.814  | 1.00 | 0.00 |
| ATOM | 1762 | HZ   | PHE | 106 | 5.125 | 0.780  | 1.050  | 1.00 | 0.00 |
| ATOM | 1763 | C    | PHE | 106 | 4.388 | 5.173  | 5.110  | 1.00 | 0.00 |
| ATOM | 1764 | O    | PHE | 106 | 5.610 | 5.033  | 5.148  | 1.00 | 0.00 |
| ATOM | 1765 | N    | PHE | 107 | 3.795 | 6.155  | 4.434  | 1.00 | 0.00 |
| ATOM | 1766 | HN   | PHE | 107 | 2.814 | 6.212  | 4.432  | 1.00 | 0.00 |
| ATOM | 1767 | CA   | PHE | 107 | 4.575 | 7.140  | 3.686  | 1.00 | 0.00 |
| ATOM | 1768 | HA   | PHE | 107 | 5.076 | 6.616  | 2.885  | 1.00 | 0.00 |
| ATOM | 1769 | CB   | PHE | 107 | 3.662 | 8.212  | 3.077  | 1.00 | 0.00 |
| ATOM | 1770 | HB1  | PHE | 107 | 2.932 | 8.150  | 3.811  | 1.00 | 0.00 |
| ATOM | 1771 | HB2  | PHE | 107 | 4.263 | 9.070  | 2.810  | 1.00 | 0.00 |
| ATOM | 1772 | CG   | PHE | 107 | 2.918 | 7.770  | 1.838  | 1.00 | 0.00 |
| ATOM | 1773 | CD1  | PHE | 107 | 3.038 | 6.475  | 1.348  | 1.00 | 0.00 |
| ATOM | 1774 | HD1  | PHE | 107 | 3.674 | 5.771  | 1.863  | 1.00 | 0.00 |
| ATOM | 1775 | CD2  | PHE | 107 | 2.098 | 8.660  | 1.160  | 1.00 | 0.00 |
| ATOM | 1776 | HD2  | PHE | 107 | 1.995 | 9.670  | 1.528  | 1.00 | 0.00 |
| ATOM | 1777 | CE1  | PHE | 107 | 2.356 | 6.080  | 0.214  | 1.00 | 0.00 |
| ATOM | 1778 | HE1  | PHE | 107 | 2.460 | 5.069  | −0.154 | 1.00 | 0.00 |
| ATOM | 1779 | CE2  | PHE | 107 | 1.413 | 8.268  | 0.025  | 1.00 | 0.00 |
| ATOM | 1780 | HE2  | PHE | 107 | 0.777 | 8.972  | −0.492 | 1.00 | 0.00 |
| ATOM | 1781 | CZ   | PHE | 107 | 1.542 | 6.977  | −0.449 | 1.00 | 0.00 |
| ATOM | 1782 | HZ   | PHE | 107 | 1.007 | 6.669  | −1.336 | 1.00 | 0.00 |
| ATOM | 1783 | C    | PHE | 107 | 5.436 | 7.787  | 4.571  | 1.00 | 0.00 |
| ATOM | 1784 | O    | PHE | 107 | 6.638 | 8.301  | 4.075  | 1.00 | 0.00 |
| ATOM | 1785 | N    | SER | 108 | 5.411 | 7.766  | 5.883  | 1.00 | 0.00 |
| ATOM | 1786 | HN   | SER | 108 | 4.619 | 7.305  | 6.227  | 1.00 | 0.00 |
| ATOM | 1787 | CA   | SER | 108 | 6.391 | 8.287  | 6.826  | 1.00 | 0.00 |
| ATOM | 1788 | HA   | SER | 108 | 6.835 | 9.173  | 6.400  | 1.00 | 0.00 |
| ATOM | 1789 | CB   | SER | 108 | 5.730 | 8.643  | 8.157  | 1.00 | 0.00 |
| ATOM | 1790 | HB1  | SER | 108 | 6.468 | 8.597  | 8.942  | 1.00 | 0.00 |
| ATOM | 1791 | HB2  | SER | 108 | 4.940 | 7.938  | 8.364  | 1.00 | 0.00 |
| ATOM | 1792 | OG   | SER | 108 | 5.181 | 9.949  | 8.121  | 1.00 | 0.00 |
| ATOM | 1793 | HG   | SER | 108 | 4.501 | 9.993  | 7.445  | 1.00 | 0.00 |
| ATOM | 1794 | C    | SER | 108 | 7.471 | 7.243  | 7.042  | 1.00 | 0.00 |
| ATOM | 1795 | O    | SER | 108 | 8.647 | 7.561  | 7.216  | 1.00 | 0.00 |
| ATOM | 1796 | N    | LYS | 109 | 7.049 | 5.986  | 6.994  | 1.00 | 0.00 |
| ATOM | 1797 | HN   | LYS | 109 | 6.100 | 5.811  | 6.828  | 1.00 | 0.00 |
| ATOM | 1798 | CA   | LYS | 109 | 7.953 | 4.860  | 7.124  | 1.00 | 0.00 |
| ATOM | 1799 | HA   | LYS | 109 | 8.629 | 5.053  | 7.951  | 1.00 | 0.00 |
| ATOM | 1800 | CB   | LYS | 109 | 7.149 | 3.591  | 7.401  | 1.00 | 0.00 |
| ATOM | 1801 | HB1  | LYS | 109 | 6.255 | 3.607  | 6.795  | 1.00 | 0.00 |
| ATOM | 1802 | HB2  | LYS | 109 | 7.741 | 2.737  | 7.126  | 1.00 | 0.00 |
| ATOM | 1803 | CG   | LYS | 109 | 6.734 | 3.440  | 8.856  | 1.00 | 0.00 |
| ATOM | 1804 | HG1  | LYS | 109 | 5.820 | 2.866  | 8.902  | 1.00 | 0.00 |
| ATOM | 1805 | HG2  | LYS | 109 | 6.566 | 4.421  | 9.276  | 1.00 | 0.00 |
| ATOM | 1806 | CD   | LYS | 109 | 7.802 | 2.732  | 9.670  | 1.00 | 0.00 |
| ATOM | 1807 | HD1  | LYS | 109 | 8.751 | 3.219  | 9.500  | 1.00 | 0.00 |
| ATOM | 1808 | HD2  | LYS | 109 | 7.544 | 2.794  | 10.717 | 1.00 | 0.00 |
| ATOM | 1809 | CE   | LYS | 109 | 7.919 | 1.269  | 9.276  | 1.00 | 0.00 |
| ATOM | 1810 | HE1  | LYS | 109 | 6.930 | 0.835  | 9.254  | 1.00 | 0.00 |
| ATOM | 1811 | HE2  | LYS | 109 | 8.359 | 1.209  | 8.292  | 1.00 | 0.00 |
| ATOM | 1812 | NZ   | LYS | 109 | 8.763 | 0.502  | 10.233 | 1.00 | 0.00 |
| ATOM | 1813 | HZ1  | LYS | 109 | 8.800 | −0.499 | 9.955  | 1.00 | 0.00 |
| ATOM | 1814 | HZ2  | LYS | 109 | 8.368 | 0.570  | 11.192 | 1.00 | 0.00 |
| ATOM | 1815 | HZ3  | LYS | 109 | 9.731 | 0.883  | 10.241 | 1.00 | 0.00 |
| ATOM | 1816 | C    | LYS | 109 | 8.769 | 4.700  | 5.846  | 1.00 | 0.00 |
| ATOM | 1817 | O    | LYS | 109 | 9.948 | 4.348  | 5.982  | 1.00 | 0.00 |
| ATOM | 1818 | N    | ILE | 110 | 8.127 | 4.989  | 4.717  | 1.00 | 0.00 |
| ATOM | 1819 | HN   | ILE | 110 | 7.193 | 5.283  | 4.765  | 1.00 | 0.00 |
| ATOM | 1820 | CA   | ILE | 110 | 8.780 | 4.928  | 3.416  | 1.00 | 0.00 |
| ATOM | 1821 | HA   | ILE | 110 | 8.993 | 3.891  | 3.187  | 1.00 | 0.00 |
| ATOM | 1822 | CE   | ILE | 110 | 7.850 | 5.488  | 2.313  | 1.00 | 0.00 |
| ATOM | 1823 | HB   | ILE | 110 | 7.508 | 6.464  | 2.626  | 1.00 | 0.00 |
| ATOM | 1824 | CG1  | ILE | 110 | 6.640 | 4.570  | 2.129  | 1.00 | 0.00 |
| ATOM | 1825 | HG11 | ILE | 110 | 5.898 | 5.077  | 1.532  | 1.00 | 0.00 |
| ATOM | 1826 | HG12 | ILE | 110 | 6.221 | 4.342  | 3.093  | 1.00 | 0.00 |
| ATOM | 1827 | CG2  | ILE | 110 | 8.593 | 5.651  | 0.996  | 1.00 | 0.00 |

TABLE 5-continued

Atomic Structure Coordinates of the
Free Form of the P/CAF Bromodomain

| ATOM | 1828 | HG21 | ILE | 110 | 8.729 | 6.702 | 0.786 | 1.00 | 0.00 |
|---|---|---|---|---|---|---|---|---|---|
| ATOM | 1829 | HG22 | ILE | 110 | 8.022 | 5.196 | 0.201 | 1.00 | 0.00 |
| ATOM | 1830 | HG23 | ILE | 110 | 9.556 | 5.169 | 1.070 | 1.00 | 0.00 |
| ATOM | 1831 | CD1 | ILE | 110 | 6.973 | 3.260 | 1.449 | 1.00 | 0.00 |
| ATOM | 1832 | HD11 | ILE | 110 | 6.748 | 2.442 | 2.117 | 1.00 | 0.00 |
| ATOM | 1833 | HD12 | ILE | 110 | 8.023 | 3.242 | 1.201 | 1.00 | 0.00 |
| ATOM | 1834 | HD13 | ILE | 110 | 6.288 | 3.162 | 0.548 | 1.00 | 0.00 |
| ATOM | 1835 | C | ILE | 110 | 10.088 | 5.717 | 3.438 | 1.00 | 0.00 |
| ATOM | 1836 | O | ILE | 110 | 11.129 | 5.225 | 3.008 | 1.00 | 0.00 |
| ATOM | 1837 | N | LYS | 111 | 10.018 | 6.946 | 3.946 | 1.00 | 0.00 |
| ATOM | 1838 | HN | LYS | 111 | 9.153 | 7.278 | 4.263 | 1.00 | 0.00 |
| ATOM | 1839 | CA | LYS | 111 | 11.184 | 7.828 | 4.017 | 1.00 | 0.00 |
| ATOM | 1840 | HA | LYS | 111 | 11.336 | 8.250 | 3.035 | 1.00 | 0.00 |
| ATOM | 1841 | CB | LYS | 111 | 10.921 | 8.963 | 5.009 | 1.00 | 0.00 |
| ATOM | 1842 | HB1 | LYS | 111 | 11.572 | 8.840 | 5.861 | 1.00 | 0.00 |
| ATOM | 1843 | HB2 | LYS | 111 | 9.894 | 8.907 | 5.340 | 1.00 | 0.00 |
| ATOM | 1844 | CG | LYS | 111 | 11.156 | 10.346 | 4.425 | 1.00 | 0.00 |
| ATOM | 1845 | HG1 | LYS | 111 | 11.692 | 10.245 | 3.493 | 1.00 | 0.00 |
| ATOM | 1846 | HG2 | LYS | 111 | 11.746 | 10.925 | 5.121 | 1.00 | 0.00 |
| ATOM | 1847 | CD | LYS | 111 | 9.847 | 11.073 | 4.164 | 1.00 | 0.00 |
| ATOM | 1848 | HD1 | LYS | 111 | 10.065 | 12.076 | 3.827 | 1.00 | 0.00 |
| ATOM | 1849 | HD2 | LYS | 111 | 9.280 | 11.114 | 5.083 | 1.00 | 0.00 |
| ATOM | 1850 | CE | LYS | 111 | 9.018 | 10.367 | 3.104 | 1.00 | 0.00 |
| ATOM | 1851 | HE1 | LYS | 111 | 8.683 | 9.419 | 3.498 | 1.00 | 0.00 |
| ATOM | 1852 | HE2 | LYS | 111 | 9.636 | 10.195 | 2.235 | 1.00 | 0.00 |
| ATOM | 1853 | NZ | LYS | 111 | 7.830 | 11.169 | 2.702 | 1.00 | 0.00 |
| ATOM | 1854 | HZ1 | LYS | 111 | 7.360 | 11.540 | 3.543 | 1.00 | 0.00 |
| ATOM | 1855 | HZ2 | LYS | 111 | 7.151 | 10.571 | 2.187 | 1.00 | 0.00 |
| ATOM | 1856 | HZ3 | LYS | 111 | 8.121 | 11.954 | 2.084 | 1.00 | 0.00 |
| ATOM | 1857 | C | LYS | 111 | 12.448 | 7.070 | 4.425 | 1.00 | 0.00 |
| ATOM | 1858 | O | LYS | 111 | 13.491 | 7.199 | 3.785 | 1.00 | 0.00 |
| ATOM | 1859 | N | GLU | 112 | 12.347 | 6.285 | 5.491 | 1.00 | 0.00 |
| ATOM | 1860 | HN | GLU | 112 | 11.489 | 6.225 | 5.962 | 1.00 | 0.00 |
| ATOM | 1861 | CA | GLU | 112 | 13.485 | 5.516 | 5.983 | 1.00 | 0.00 |
| ATOM | 1862 | HA | GLU | 112 | 14.297 | 6.205 | 6.161 | 1.00 | 0.00 |
| ATOM | 1863 | CB | GLU | 112 | 13.126 | 4.819 | 7.296 | 1.00 | 0.00 |
| ATOM | 1864 | HB1 | GLU | 112 | 12.159 | 4.250 | 7.189 | 1.00 | 0.00 |
| ATOM | 1865 | HB2 | GLU | 112 | 13.864 | 4.058 | 7.500 | 1.00 | 0.00 |
| ATOM | 1866 | CG | GLU | 112 | 13.070 | 5.760 | 8.489 | 1.00 | 0.00 |
| ATOM | 1867 | HG1 | GLU | 112 | 12.440 | 5.320 | 9.249 | 1.00 | 0.00 |
| ATOM | 1868 | HG2 | GLU | 112 | 12.644 | 6.700 | 8.169 | 1.00 | 0.00 |
| ATOM | 1869 | CD | GLU | 112 | 14.437 | 6.026 | 9.087 | 1.00 | 0.00 |
| ATOM | 1870 | OE1 | GLU | 112 | 14.842 | 5.277 | 10.001 | 1.00 | 0.00 |
| ATOM | 1871 | OE2 | GLU | 112 | 15.203 | 6.984 | 8.641 | 1.00 | 0.00 |
| ATOM | 1872 | C | GLU | 112 | 13.934 | 4.484 | 4.954 | 1.00 | 0.00 |
| ATOM | 1873 | O | GLU | 112 | 15.128 | 4.228 | 4.798 | 1.00 | 0.00 |
| ATOM | 1874 | N | ALA | 113 | 12.970 | 3.892 | 4.257 | 1.00 | 0.00 |
| ATOM | 1875 | HN | ALA | 113 | 12.037 | 4.130 | 4.430 | 1.00 | 0.00 |
| ATOM | 1876 | CA | ALA | 113 | 13.263 | 2.883 | 3.245 | 1.00 | 0.00 |
| ATOM | 1877 | HA | ALA | 113 | 14.151 | 2.356 | 3.550 | 1.00 | 0.00 |
| ATOM | 1878 | CB | ALA | 113 | 12.120 | 1.872 | 3.167 | 1.00 | 0.00 |
| ATOM | 1879 | HB1 | ALA | 113 | 11.209 | 2.380 | 2.915 | 1.00 | 0.00 |
| ATOM | 1880 | HB2 | ALA | 113 | 12.018 | 1.381 | 4.123 | 1.00 | 0.00 |
| ATOM | 1881 | HB3 | ALA | 113 | 12.353 | 1.136 | 2.409 | 1.00 | 0.00 |
| ATOM | 1882 | C | ALA | 113 | 13.513 | 3.512 | 1.873 | 1.00 | 0.00 |
| ATOM | 1883 | O | ALA | 113 | 13.917 | 2.823 | 0.936 | 1.00 | 0.00 |
| ATOM | 1884 | N | GLY | 114 | 13.276 | 4.818 | 1.753 | 1.00 | 0.00 |
| ATOM | 1885 | HN | GLY | 114 | 12.946 | 5.324 | 2.523 | 1.00 | 0.00 |
| ATOM | 1886 | CA | GLY | 114 | 13.468 | 5.488 | 0.480 | 1.00 | 0.00 |
| ATOM | 1887 | HA1 | GLY | 114 | 14.518 | 5.464 | 0.226 | 1.00 | 0.00 |
| ATOM | 1888 | HA2 | GLY | 114 | 13.152 | 6.516 | 0.573 | 1.00 | 0.00 |
| ATOM | 1889 | C | GLY | 114 | 12.679 | 4.830 | −0.634 | 1.00 | 0.00 |
| ATOM | 1890 | O | GLY | 114 | 13.227 | 4.056 | −1.417 | 1.00 | 0.00 |
| ATOM | 1891 | N | LEU | 115 | 11.383 | 5.123 | −0.690 | 1.00 | 0.00 |
| ATOM | 1892 | HN | LEU | 115 | 11.006 | 5.743 | −0.033 | 1.00 | 0.00 |
| ATOM | 1893 | CA | LEU | 115 | 10.508 | 4.534 | −1.697 | 1.00 | 0.00 |
| ATOM | 1894 | HA | LEU | 115 | 11.123 | 4.100 | −2.150 | 1.00 | 0.00 |
| ATOM | 1895 | CB | LEU | 115 | 9.724 | 3.363 | −1.104 | 1.00 | 0.00 |
| ATOM | 1896 | HB1 | LEU | 115 | 9.340 | 3.668 | −0.144 | 1.00 | 0.00 |
| ATOM | 1897 | HB2 | LEU | 115 | 8.890 | 3.167 | −1.754 | 1.00 | 0.00 |
| ATOM | 1898 | CG | LEU | 115 | 10.497 | 2.058 | −0.907 | 1.00 | 0.00 |
| ATOM | 1899 | HG | LEU | 115 | 9.793 | 1.246 | −0.833 | 1.00 | 0.00 |
| ATOM | 1900 | CD1 | LEU | 115 | 11.280 | 2.102 | 0.391 | 1.00 | 0.00 |
| ATOM | 1901 | HD11 | LEU | 115 | 10.719 | 1.597 | 1.166 | 1.00 | 0.00 |
| ATOM | 1902 | HD12 | LEU | 115 | 11.440 | 3.130 | 0.676 | 1.00 | 0.00 |
| ATOM | 1903 | HD13 | LEU | 115 | 12.231 | 1.611 | 0.255 | 1.00 | 0.00 |

TABLE 5-continued

Atomic Structure Coordinates of the
Free Form of the P/CAF Bromodomain

| ATOM | 1904 | CD2 | LEU | 115 | 11.414 | 1.774 | −2.087 | 1.00 | 0.00 |
|---|---|---|---|---|---|---|---|---|---|
| ATOM | 1905 | HD21 | LEU | 115 | 11.066 | 2.313 | −2.953 | 1.00 | 0.00 |
| ATOM | 1906 | HD22 | LEU | 115 | 11.409 | 0.715 | −2.298 | 1.00 | 0.00 |
| ATOM | 1907 | HD23 | LEU | 115 | 12.418 | 2.086 | −1.846 | 1.00 | 0.00 |
| ATOM | 1908 | C | LEU | 115 | 9.509 | 5.550 | −2.237 | 1.00 | 0.00 |
| ATOM | 1909 | O | LEU | 115 | 9.388 | 6.653 | −1.709 | 1.00 | 0.00 |
| ATOM | 1910 | N | ILE | 116 | 8.752 | 5.124 | −3.252 | 1.00 | 0.00 |
| ATOM | 1911 | HN | ILE | 116 | 8.896 | 4.217 | −3.594 | 1.00 | 0.00 |
| ATOM | 1912 | CA | ILE | 116 | 7.707 | 5.945 | −3.865 | 1.00 | 0.00 |
| ATOM | 1913 | HA | ILE | 116 | 7.395 | 5.441 | −4.768 | 1.00 | 0.00 |
| ATOM | 1914 | CB | ILE | 116 | 6.469 | 6.061 | −2.949 | 1.00 | 0.00 |
| ATOM | 1915 | HB | ILE | 116 | 6.730 | 6.669 | −2.097 | 1.00 | 0.00 |
| ATOM | 1916 | CG1 | ILE | 116 | 6.037 | 4.676 | −2.458 | 1.00 | 0.00 |
| ATOM | 1917 | HG11 | ILE | 116 | 5.298 | 4.265 | −3.135 | 1.00 | 0.00 |
| ATOM | 1918 | HG12 | ILE | 116 | 6.898 | 4.026 | −2.435 | 1.00 | 0.00 |
| ATOM | 1919 | CG2 | ILE | 116 | 5.326 | 6.743 | −3.681 | 1.00 | 0.00 |
| ATOM | 1920 | HG21 | ILE | 116 | 5.006 | 7.609 | −3.121 | 1.00 | 0.00 |
| ATOM | 1921 | HG22 | ILE | 116 | 4.502 | 6.052 | −3.779 | 1.00 | 0.00 |
| ATOM | 1922 | HG23 | ILE | 116 | 5.659 | 7.058 | −4.661 | 1.00 | 0.00 |
| ATOM | 1923 | CD1 | ILE | 116 | 5.433 | 4.694 | −1.073 | 1.00 | 0.00 |
| ATOM | 1924 | HD11 | ILE | 116 | 6.172 | 5.032 | −0.363 | 1.00 | 0.00 |
| ATOM | 1925 | HD12 | ILE | 116 | 5.110 | 3.691 | −0.809 | 1.00 | 0.00 |
| ATOM | 1926 | HD13 | ILE | 116 | 4.586 | 5.363 | −1.057 | 1.00 | 0.00 |
| ATOM | 1927 | C | ILE | 116 | 8.213 | 7.340 | −4.246 | 1.00 | 0.00 |
| ATOM | 1928 | O | ILE | 116 | 8.498 | 7.601 | −5.415 | 1.00 | 0.00 |
| ATOM | 1929 | N | ASP | 117 | 8.305 | 8.240 | −3.268 | 1.00 | 0.00 |
| ATOM | 1930 | HN | ASP | 117 | 8.072 | 7.979 | −2.355 | 1.00 | 0.00 |
| ATOM | 1931 | CA | ASP | 117 | 8.776 | 9.600 | −3.515 | 1.00 | 0.00 |
| ATOM | 1932 | HA | ASP | 117 | 8.982 | 10.054 | −2.558 | 1.00 | 0.00 |
| ATOM | 1933 | CB | ASP | 117 | 10.063 | 9.583 | −4.345 | 1.00 | 0.00 |
| ATOM | 1934 | HB1 | ASP | 117 | 9.902 | 10.133 | −5.260 | 1.00 | 0.00 |
| ATOM | 1935 | HB2 | ASP | 117 | 10.317 | 8.560 | −4.583 | 1.00 | 0.00 |
| ATOM | 1936 | CG | ASP | 117 | 11.233 | 10.204 | −3.610 | 1.00 | 0.00 |
| ATOM | 1937 | OD1 | ASP | 117 | 11.577 | 11.368 | −3.920 | 1.00 | 0.00 |
| ATOM | 1938 | OD2 | ASP | 117 | 11.804 | 9.538 | −2.724 | 1.00 | 0.00 |
| ATOM | 1939 | C | ASP | 117 | 7.708 | 10.424 | −4.224 | 1.00 | 0.00 |
| ATOM | 1940 | O | ASP | 117 | 8.020 | 11.293 | −5.041 | 1.00 | 0.00 |
| ATOM | 1941 | N | LYS | 118 | 6.446 | 10.150 | −3.906 | 1.00 | 0.00 |
| ATOM | 1942 | HN | LYS | 118 | 6.264 | 9.447 | −3.247 | 1.00 | 0.00 |
| ATOM | 1943 | CA | LYS | 118 | 5.132 | 10.869 | −4.508 | 1.00 | 0.00 |
| ATOM | 1944 | HA | LYS | 118 | 5.635 | 11.184 | −5.496 | 1.00 | 0.00 |
| ATOM | 1945 | CB | LYS | 118 | 4.114 | 9.952 | −4.628 | 1.00 | 0.00 |
| ATOM | 1946 | HB1 | LYS | 118 | 3.696 | 9.798 | −3.644 | 1.00 | 0.00 |
| ATOM | 1947 | HB2 | LYS | 118 | 4.432 | 9.001 | −5.028 | 1.00 | 0.00 |
| ATOM | 1948 | CG | LYS | 118 | 3.021 | 10.506 | −5.527 | 1.00 | 0.00 |
| ATOM | 1949 | HG1 | LYS | 118 | 3.175 | 10.140 | −5.531 | 1.00 | 0.00 |
| ATOM | 1950 | HG2 | LYS | 118 | 3.077 | 11.505 | −5.522 | 1.00 | 0.00 |
| ATOM | 1951 | CD | LYS | 118 | 1.642 | 10.081 | −5.053 | 1.00 | 0.00 |
| ATOM | 1952 | HD1 | LYS | 118 | 1.422 | 9.100 | −5.449 | 1.00 | 0.00 |
| ATOM | 1953 | HD2 | LYS | 118 | 1.637 | 10.044 | −3.974 | 1.00 | 0.00 |
| ATOM | 1954 | CE | LYS | 118 | 0.569 | 11.052 | −5.518 | 1.00 | 0.00 |
| ATOM | 1955 | HE1 | LYS | 118 | −0.025 | 11.347 | −4.666 | 1.00 | 0.00 |
| ATOM | 1956 | HE2 | LYS | 118 | 1.048 | 11.922 | −5.942 | 1.00 | 0.00 |
| ATOM | 1957 | NZ | LYS | 118 | −0.324 | 10.443 | −6.543 | 1.00 | 0.00 |
| ATOM | 1958 | HZ1 | LYS | 118 | −0.734 | 9.558 | −6.180 | 1.00 | 0.00 |
| ATOM | 1959 | HZ2 | LYS | 118 | 0.214 | 10.234 | −7.409 | 1.00 | 0.00 |
| ATOM | 1960 | HZ3 | LYS | 118 | −1.097 | 11.099 | −6.778 | 1.00 | 0.00 |
| ATOM | 1961 | C | LYS | 118 | 4.974 | 12.103 | −3.687 | 1.00 | 0.00 |
| ATOM | 1962 | OT1 | LYS | 118 | 4.769 | 13.177 | −4.291 | 1.00 | 0.00 |
| ATOM | 1963 | OT2 | LYS | 118 | 4.901 | 11.986 | −2.445 | 1.00 | 0.00 |
| END | | | | | | | | | |

TABLE 6

Atomic Structure Coordinates of the
P/CAF Bromodomain/Acetyl-Histamine Complex

REMARK
FILENAME*'/bloch2/chris/COMPLEX__XPLOR__ARIA7/structures/it0/complex_03.'REMARK
initial random number seed: 5.960359E+10REMARK
*****************************************************************REMARK
overall, bonds, angles, improper, vdw, noe, cd1hREMARK energies: 154.107, 9.85626,
72.1621, 0, 22.2303, 36.0151, 0.204524REMARK

TABLE 6-continued

Atomic Structure Coordinates of the P/CAF Bromodomain/Acetyl-Histamine Complex

```
******************************************************************REMARK
bonds, angles, impropers, noe, cd1hREMARK rms-dev.: 2.214961E-03,
0.361077, 52.7899, 1.40651E-02, 0.249335REMARK
******************************************************************REMARK
noe, cd1hREMARK violations.: 2, 0REMARK
******************************************************************REMARK DATE:05-
```

| | | | | | | | | | | |
|---|---|---|---|---|---|---|---|---|---|---|
| Dec-98 15:11:47 | | created by user: | | | ATOM | 1 | CA | ACE | 200 | −14.038 |
| 2.661 | −4.705 | 1.00 | 0.00 | AcH | ATOM | 2 | HA1 | ACE | 200 | −14.803 |
| 1.912 | −4.558 | 1.00 | 0.00 | AcH | ATOM | 3 | HA2 | ACE | 200 | −13.320 |
| 2.304 | −5.428 | 1.00 | 0.00 | AcH | ATOM | 4 | HA3 | ACE | 200 | −14.491 |
| 3.572 | −5.067 | 1.00 | 0.00 | AcH | ATOM | 5 | C | ACE | 200 | −13.332 |
| 2.936 | −3.376 | 1.00 | 0.00 | AcH | ATOM | 6 | O | ACE | 200 | −12.385 |
| 2.238 | −3.012 | 1.00 | 0.00 | AcH | ATOM | 7 | N | HIM | 201 | −13.773 |
| 3.967 | −2.663 | 1.00 | 0.00 | AcH | ATOM | 8 | HN | HIM | 201 | −13.586 |
| 4.875 | −2.982 | 1.00 | 0.00 | AcH | ATOM | 9 | CA | HIM | 201 | −14.521 |
| 3.827 | −1.417 | 1.00 | 0.00 | AcH | ATOM | 10 | HA1 | HIM | 201 | −13.833 |
| 3.589 | −0.620 | 1.00 | 0.00 | AcH | ATOM | 11 | HA2 | HIM | 201 | −15.236 |
| 3.025 | −1.526 | 1.00 | 0.00 | AcH | ATOM | 12 | CB | HIM | 201 | −15.268 |
| 5.100 | −1.055 | 1.00 | 0.00 | AcH | ATOM | 13 | HB1 | HIM | 201 | −14.591 |
| 5.940 | −1.107 | 1.00 | 0.00 | AcH | ATOM | 14 | HB2 | HIM | 201 | −15.669 |
| 5.009 | −0.056 | 1.00 | 0.00 | AcH | ATOM | 15 | CG | HIM | 201 | −16.397 |
| 5.329 | −2.010 | 1.00 | 0.00 | AcH | ATOM | 16 | ND1 | HIM | 201 | −17.392 |
| 6.259 | −1.793 | 1.00 | 0.00 | AcH | ATOM | 17 | HD1 | HIM | 201 | −17.421 |
| 6.906 | −1.057 | 1.00 | 0.00 | AcH | ATOM | 18 | CD2 | HIM | 201 | −16.680 |
| 4.756 | −3.204 | 1.00 | 0.00 | AcH | ATOM | 19 | HD2 | HIM | 201 | −16.026 |
| 4.116 | −3.779 | 1.00 | 0.00 | AcH | ATOM | 20 | CE1 | HIM | 201 | −18.316 |
| 6.135 | −2.729 | 1.00 | 0.00 | AcH | ATOM | 21 | HE1 | HIM | 201 | −19.220 |
| 6.722 | −2.806 | 1.00 | 0.00 | AcH | ATOM | 22 | NE2 | HIM | 201 | −17.912 |
| 5.221 | −3.592 | 1.00 | 0.00 | AcH | ATOM | 23 | CA | GLY | 1 | 27.272 |
| 16.667 | −0.366 | 1.00 | 0.00 | BrD | ATOM | 24 | HA1 | GLY | 1 | 28.103 |
| 16.198 | −0.871 | 1.00 | 0.00 | BrD | ATOM | 25 | HA2 | GLY | 1 | 26.478 |
| 15.945 | −0.255 | 1.00 | 0.00 | BrD | ATOM | 26 | C | GLY | 1 | 27.724 |
| 17.114 | 1.011 | 1.00 | 0.00 | BrD | ATOM | 27 | O | GLY | 1 | 28.713 |
| 17.834 | 1.144 | 1.00 | 0.00 | BrD | ATOM | 28 | N | GLY | 1 | 26.780 |
| 17.800 | −1.198 | 1.00 | 0.00 | BrD | ATOM | 29 | HT1 | GLY | 1 | 25.769 |
| 17.963 | −1.018 | 1.00 | 0.00 | BrD | ATOM | 30 | HT2 | GLY | 1 | 26.911 |
| 17.584 | −7.207 | 1.00 | 0.00 | BrD | ATOM | 31 | HT3 | GLY | 1 | 27.307 |
| 18.667 | −0.970 | 1.00 | 0.00 | BrD | ATOM | 32 | N | SER | 2 | 26.999 |
| 16.682 | 2.037 | 1.00 | 0.00 | BrD | ATOM | 33 | HN | SER | 2 | 26.222 |
| 16.110 | 1.866 | 1.00 | 0.00 | BrD | ATOM | 34 | CA | SER | 2 | 27.328 |
| 17.063 | 3.411 | 1.00 | 0.00 | BrD | ATOM | 35 | HA | SER | 2 | 28.283 |
| 17.546 | 3.401 | 1.00 | 0.00 | BrD | ATOM | 36 | CB | SER | 2 | 26.269 |
| 17.992 | 3.975 | 1.00 | 0.00 | BrD | ATOM | 37 | HB1 | SER | 2 | 26.705 |
| 18.588 | 4.762 | 1.00 | 0.00 | BrD | ATOM | 38 | HB2 | SER | 2 | 25.448 |
| 17.414 | 4.374 | 1.00 | 0.00 | BrD | ATOM | 39 | CG | SER | 2 | 25.771 |
| 18.857 | 2.969 | 1.00 | 0.00 | BrD | ATOM | 40 | NG | SER | 2 | 26.478 |
| 19.429 | 2.660 | 1.00 | 0.00 | BrD | ATOM | 41 | C | SER | 2 | 27.435 |
| 15.801 | 4.290 | 1.00 | 0.00 | BrD | ATOM | 42 | O | SER | 2 | 26.900 |
| 14.744 | 3.956 | 1.00 | 0.00 | BrD | ATOM | 43 | N | HIS | 3 | 28.131 |
| 15.936 | 5.415 | 1.00 | 0.00 | BrD | ATOM | 44 | HN | HIS | 3 | 28.534 |
| 16.803 | 5.627 | 1.00 | 0.00 | BrD | ATOM | 45 | CA | HIS | 3 | 28.308 |
| 14.824 | 6.342 | 1.00 | 0.00 | BrD | ATOM | 46 | HA | HIS | 3 | 28.652 |
| 13.977 | 5.775 | 1.00 | 0.00 | BrD | ATOM | 47 | CB | HIS | 3 | 29.356 |
| 15.176 | 7.399 | 1.00 | 0.00 | BrD | ATOM | 48 | HB1 | HIS | 3 | 29.337 |
| 14.428 | 8.178 | 1.00 | 0.00 | BrD | ATOM | 49 | HB2 | HIS | 3 | 30.333 |
| 15.184 | 6.939 | 1.00 | 0.00 | BrD | ATOM | 50 | CG | HIS | 3 | 29.137 |
| 16.512 | 8.039 | 1.00 | 0.00 | BrD | ATOM | 51 | ND1 | HIS | 3 | 28.235 |
| 16.718 | 9.062 | 1.00 | 0.00 | BrD | ATOM | 52 | HD1 | HIS | 3 | 27.659 |
| 16.035 | 9.465 | 1.00 | 0.00 | BrD | ATOM | 53 | CD2 | HIS | 3 | 29.710 |
| 17.715 | 7.796 | 1.00 | 0.00 | BrD | ATOM | 54 | HD2 | HIS | 3 | 30.468 |
| 17.927 | 7.055 | 1.00 | 0.00 | BrD | ATOM | 55 | CE1 | HIS | 3 | 28.262 |
| 17.991 | 9.420 | 1.00 | 0.00 | BrD | ATOM | 56 | HE1 | HIS | 3 | 27.661 |
| 18.442 | 10.196 | 1.00 | 0.00 | BrD | ATOM | 57 | NE2 | HIS | 3 | 29.148 |
| 18.615 | 5.668 | 1.00 | 0.00 | BrD | ATOM | 58 | HE2 | HIS | 3 | 29.368 |
| 19.568 | 8.725 | 1.00 | 0.00 | BrD | ATOM | 59 | C | HIS | 3 | 26.991 |
| 14.463 | 7.020 | 1.00 | 0.00 | BrD | ATOM | 60 | O | HIS | 3 | 26.660 |
| 14.998 | 8.078 | 1.00 | 0.00 | BrD | ATOM | 61 | N | MET | 4 | 26.245 |
| 13.551 | 6.405 | 1.00 | 0.00 | BrD | ATOM | 62 | HN | MET | 4 | 26.563 |
| 13.161 | 5.565 | 1.00 | 0.00 | BrD | ATOM | 63 | CA | MET | 4 | 24.964 |
| 13.119 | 6.951 | 1.00 | 0.00 | BrD | ATOM | 64 | HA | MET | 4 | 25.136 |
| 12.767 | 7.958 | 1.00 | 0.00 | BrD | ATOM | 65 | CB | MET | 4 | 23.985 |
| 14.294 | 6.994 | 1.00 | 0.00 | BrD | ATOM | 66 | HB1 | MET | 4 | 24.445 |
| 15.111 | 7.531 | 1.00 | 0.00 | BrD | ATOM | 67 | HB2 | MET | 4 | 23.776 |
| 14.612 | 5.984 | 1.00 | 0.00 | BrD | ATOM | 68 | CG | MET | 4 | 22.665 |
| 13.962 | 7.672 | 1.00 | 0.00 | BrD | ATOM | 69 | HG1 | MET | 4 | 22.754 |
| 14.176 | 8.727 | 1.00 | 0.00 | BrD | ATOM | 70 | HG2 | MET | 4 | 22.461 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 12.911 | 7.535 | 1.00 | 0.00 | BrD | ATOM | 71 | SD | MET | 4 | 21.283 |
| 14.909 | 7.006 | 1.00 | 0.00 | BrD | ATOM | 72 | CE | MET | 4 | 22.027 |
| 16.531 | 6.842 | 1.00 | 0.00 | BrD | ATOM | 73 | HE1 | MET | 4 | 22.811 |
| 16.643 | 7.576 | 1.00 | 0.00 | BrD | ATOM | 74 | HE2 | MET | 4 | 21.274 |
| 17.289 | 7.000 | 1.00 | 0.00 | BrD | ATOM | 75 | HE3 | MET | 4 | 22.443 |
| 16.638 | 5.851 | 1.00 | 0.00 | BrD | ATOM | 76 | C | MET | 4 | 24.376 |
| 11.977 | 6.126 | 1.00 | 0.00 | BrD | ATOM | 77 | O | MET | 4 | 24.580 |
| 11.906 | 4.914 | 1.00 | 0.00 | BrD | ATOM | 78 | N | SER | 5 | 23.650 |
| 11.084 | 6.792 | 1.00 | 0.00 | BrD | ATOM | 79 | HN | SER | 5 | 23.528 |
| 11.194 | 7.758 | 1.00 | 0.00 | BrD | ATOM | 80 | CA | SER | 5 | 23.040 |
| 9.939 | 6.125 | 1.00 | 0.00 | BrD | ATOM | 81 | HA | SER | 5 | 23.836 |
| 9.303 | 5.767 | 1.00 | 0.00 | BrD | ATOM | 82 | CB | SER | 5 | 22.177 |
| 9.148 | 7.111 | 1.00 | 0.00 | BrD | ATOM | 83 | HB1 | SER | 5 | 21.179 |
| 9.560 | 7.123 | 1.00 | 0.00 | BrD | ATOM | 84 | HB2 | SER | 5 | 22.136 |
| 8.114 | 6.801 | 1.00 | 0.00 | BrD | ATOM | 85 | CG | SER | 5 | 22.712 |
| 9.210 | 8.421 | 1.00 | 0.00 | BrD | ATOM | 86 | HG | SER | 5 | 23.243 |
| 8.429 | 8.589 | 1.00 | 0.00 | BrD | ATOM | 87 | C | SER | 5 | 22.194 |
| 10.380 | 4.934 | 1.00 | 0.00 | BrD | ATOM | 88 | O | SER | 5 | 21.748 |
| 11.525 | 4.867 | 1.00 | 0.00 | BrD | ATOM | 89 | N | LYS | 6 | 21.973 |
| 9.460 | 3.999 | 1.00 | 0.00 | BrD | ATOM | 90 | HN | LYS | 6 | 22.355 |
| 8.565 | 4.110 | 1.00 | 0.00 | BrD | ATOM | 91 | CA | LYS | 6 | 21.180 |
| 9.751 | 2.811 | 1.00 | 0.00 | BrD | ATOM | 92 | HA | LYS | 6 | 20.720 |
| 10.720 | 2.950 | 1.00 | 0.00 | BrD | ATOM | 93 | CB | LYS | 6 | 22.078 |
| 9.801 | 1.572 | 1.00 | 0.00 | BrD | ATOM | 94 | HB1 | LYS | 6 | 21.474 |
| 10.056 | 0.716 | 1.00 | 0.00 | BrD | ATOM | 95 | HB2 | LYS | 6 | 22.512 |
| 8.824 | 1.418 | 1.00 | 0.00 | BrD | ATOM | 96 | CG | LYS | 6 | 23.208 |
| 10.813 | 1.677 | 1.00 | 0.00 | BrD | ATOM | 97 | HG1 | LYS | 6 | 23.164 |
| 11.290 | 2.645 | 1.00 | 0.00 | BrD | ATOM | 98 | HG2 | LYS | 6 | 24.151 |
| 10.299 | 1.568 | 1.00 | 0.00 | BrD | ATOM | 99 | CD | LYS | 6 | 23.100 |
| 11.879 | 0.598 | 1.00 | 0.00 | BrD | ATOM | 100 | HD1 | LYS | 6 | 22.401 |
| 11.546 | −0.155 | 1.00 | 0.00 | BrD | ATOM | 101 | HD2 | LYS | 6 | 24.072 |
| 12.024 | 0.150 | 1.00 | 0.00 | BrD | ATOM | 102 | CE | LYS | 6 | 22.618 |
| 13.203 | 1.168 | 1.00 | 0.00 | BrD | ATOM | 103 | HE1 | LYS | 6 | 21.595 |
| 13.088 | 1.494 | 1.00 | 0.00 | BrD | ATOM | 104 | HE2 | LYS | 6 | 22.666 |
| 13.953 | 0.393 | 1.00 | 0.00 | BrD | ATOM | 105 | NZ | LYS | 6 | 23.448 |
| 13.645 | 2.322 | 1.00 | 0.00 | BrD | ATOM | 106 | HZ1 | LYS | 6 | 24.293 |
| 13.065 | 2.406 | 1.00 | 0.00 | BrD | ATOM | 107 | HZ2 | LYS | 6 | 22.900 |
| 13.578 | 3.204 | 1.00 | 0.00 | BrD | ATOM | 108 | HZ3 | LYS | 6 | 23.749 |
| 14.532 | 2.189 | 1.00 | 0.00 | BrD | ATOM | 109 | C | LYS | 6 | 20.085 |
| 8.710 | 2.613 | 1.00 | 0.00 | BrD | ATOM | 110 | O | LYS | 6 | 18.897 |
| 9.022 | 2.693 | 1.00 | 0.00 | BrD | ATOM | 111 | N | GLU | 7 | 20.495 |
| 7.474 | 2.334 | 1.00 | 0.00 | BrD | ATOM | 112 | HN | GLU | 7 | 21.457 |
| 7.295 | 2.280 | 1.00 | 0.00 | BrD | ATOM | 113 | CA | GLU | 7 | 19.558 |
| 6.370 | 2.115 | 1.00 | 0.00 | BrD | ATOM | 114 | HA | GLU | 7 | 20.083 |
| 5.603 | 1.565 | 1.00 | 0.00 | BrD | ATOM | 115 | CB | GLU | 7 | 19.091 |
| 5.783 | 3.451 | 1.00 | 0.00 | BrD | ATOM | 116 | HB1 | GLU | 7 | 18.110 |
| 5.354 | 3.317 | 1.00 | 0.00 | BrD | ATOM | 117 | HB2 | GLU | 7 | 19.777 |
| 5.003 | 3.745 | 1.00 | 0.00 | BrD | ATOM | 118 | CG | GLU | 7 | 19.014 |
| 6.799 | 4.579 | 1.00 | 0.00 | BrD | ATOM | 119 | HG1 | GLU | 7 | 18.377 |
| 7.614 | 4.271 | 1.00 | 0.00 | BrD | ATOM | 120 | HG2 | GLU | 7 | 20.007 |
| 7.173 | 4.780 | 1.00 | 0.00 | BrD | ATOM | 121 | CD | GLU | 7 | 18.452 |
| 6.206 | 5.857 | 1.00 | 0.00 | BrD | ATOM | 122 | OE1 | GLU | 7 | 17.289 |
| 6.511 | 6.192 | 1.00 | 0.00 | BrD | ATOM | 123 | OE2 | GLU | 7 | 19.176 |
| 5.434 | 6.521 | 1.00 | 0.00 | BrD | ATOM | 124 | C | GLU | 7 | 18.347 |
| 6.812 | 1.290 | 1.00 | 0.00 | BrD | ATOM | 125 | O | GLU | 7 | 17.342 |
| 7.261 | 1.840 | 1.00 | 0.00 | BrD | ATOM | 126 | N | PRO | 8 | 18.430 |
| 6.681 | −0.045 | 1.00 | 0.00 | BrD | ATOM | 127 | CA | PRO | 8 | 17.346 |
| 7.054 | −0.951 | 1.00 | 0.00 | BrD | ATOM | 128 | HA | PRO | 8 | 16.908 |
| 8.003 | −0.677 | 1.00 | 0.00 | BrD | ATOM | 129 | CB | PRO | 8 | 18.034 |
| 7.176 | −2.321 | 1.00 | 0.00 | BrD | ATOM | 130 | HB1 | PRO | 8 | 17.603 |
| 6.458 | −3.004 | 1.00 | 0.00 | BrD | ATOM | 131 | HB2 | PRO | 8 | 17.887 |
| 8.174 | −2.708 | 1.00 | 0.00 | BrD | ATOM | 132 | CG | PRO | 8 | 19.488 |
| 6.895 | −2.087 | 1.00 | 0.00 | BrD | ATOM | 133 | HG1 | PRO | 8 | 19.876 |
| 6.286 | −2.890 | 1.00 | 0.00 | BrD | ATOM | 134 | HG2 | PRO | 8 | 20.034 |
| 7.825 | −2.026 | 1.00 | 0.00 | BrD | ATOM | 135 | CD | PRO | 8 | 19.578 |
| 6.155 | −0.784 | 1.00 | 0.00 | BrD | ATOM | 136 | HD1 | PRO | 8 | 20.504 |
| 6.384 | −0.278 | 1.00 | 0.00 | BrD | ATOM | 137 | HD2 | PRO | 8 | 19.481 |
| 5.090 | −0.943 | 1.00 | 0.00 | BrD | ATOM | 138 | C | PRO | 8 | 16.259 |
| 5.987 | −1.000 | 1.00 | 0.00 | BrD | ATOM | 139 | O | PRO | 8 | 15.071 |
| 6.286 | −0.874 | 1.00 | 0.00 | BrD | ATOM | 140 | N | ARG | 9 | 16.680 |
| 4.740 | −1.177 | 1.00 | 0.00 | BrD | ATOM | 141 | HN | ARG | 9 | 17.640 |
| 4.570 | −1.269 | 1.00 | 0.00 | BrD | ATOM | 142 | CA | ARG | 9 | 15.754 |
| 3.617 | −1.241 | 1.00 | 0.00 | BrD | ATOM | 143 | HA | ARG | 9 | 15.272 |
| 3.529 | −0.279 | 1.00 | 0.00 | BrD | ATOM | 144 | CB | ARG | 9 | 14.692 |
| 3.854 | −2.314 | 1.00 | 0.00 | BrD | ATOM | 145 | HB1 | ARG | 9 | 14.073 |
| 2.982 | −2.402 | 1.00 | 0.00 | BrD | ATOM | 146 | HB2 | ARG | 9 | 14.076 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 4.696 | −2.010 | 1.00 | 0.00 | BrD | ATOM | 147 | CG | ARG | 9 | 15.272
| 4.176 | −3.684 | 1.00 | 0.00 | BrD | ATOM | 148 | HG1 | ARG | 9 | 16.153
| 3.571 | −3.837 | 1.00 | 0.00 | BrD | ATOM | 149 | HG2 | ARG | 9 | 15.539
| 5.221 | −3.721 | 1.00 | 0.00 | BrD | ATOM | 150 | CD | ARG | 9 | 14.274
| 3.882 | −4.793 | 1.00 | 0.00 | BrD | ATOM | 151 | HD1 | ARG | 9 | 13.277
| 4.055 | −4.417 | 1.00 | 0.00 | BrD | ATOM | 152 | HD2 | ARG | 9 | 14.375
| 2.848 | −5.085 | 1.00 | 0.00 | BrD | ATOM | 153 | NE | ARG | 9 | 14.493
| 4.728 | −5.963 | 1.00 | 0.00 | BrD | ATOM | 154 | HE | ARG | 9 | 14.761
| 4.289 | −6.797 | 1.00 | 0.00 | BrD | ATOM | 155 | CZ | ARG | 9 | 14.350
| 6.049 | −5.955 | 1.00 | 0.00 | BrD | ATOM | 156 | NH1 | ARG | 9 | 13.988
| 6.672 | −4.842 | 1.00 | 0.00 | BrD | ATOM | 157 | NH11 | ARG | 9 | 13.823
| 6.147 | −4.006 | 1.00 | 0.00 | BrD | ATOM | 158 | NH12 | ARG | 9 | 13.880
| 7.666 | −4.837 | 1.00 | 0.00 | BrD | ATOM | 159 | NH2 | ARG | 9 | 14.567
| 6.749 | −7.059 | 1.00 | 0.00 | BrD | ATOM | 160 | HH21 | ARG | 9 | 14.458
| 7.744 | −7.051 | 1.00 | 0.00 | BrD | ATOM | 161 | HH22 | ARG | 9 | 14.840
| 6.284 | −7.901 | 1.00 | 0.00 | BrD | ATOM | 162 | C | ARG | 9 | 16.500
| 2.320 | −1.538 | 1.00 | 0.00 | BrD | ATOM | 163 | O | ARG | 9 | 17.367
| 2.278 | −2.410 | 1.00 | 0.00 | BrD | ATOM | 164 | N | ASP | 10 | 16.159
| 1.267 | −0.803 | 1.00 | 0.00 | BrD | ATOM | 165 | HN | ASP | 10 | 15.462
| −1.367 | −0.123 | 1.00 | 0.00 | BrD | ATOM | 166 | CA | ASP | 10 | 16.788
| 0.038 | −0.988 | 1.00 | 0.00 | BrD | ATOM | 167 | HA | ASP | 10 | 17.625
| −0.088 | −1.658 | 1.00 | 0.00 | BrD | ATOM | 168 | CB | ASP | 10 | 17.296
| 0.576 | 0.350 | 1.00 | 0.00 | BrD | ATOM | 169 | HB1 | ASP | 10 | 18.082
| −0.067 | 0.715 | 1.00 | 0.00 | BrD | ATOM | 170 | HB2 | ASP | 10 | 17.688
| −1.572 | 0.204 | 1.00 | 0.00 | BrD | ATOM | 171 | CG | ASP | 10 | 16.203
| −0.641 | 1.399 | 1.00 | 0.00 | BrD | ATOM | 172 | OD1 | ASP | 10 | 16.210
| 1.595 | 2.205 | 1.00 | 0.00 | BrD | ATOM | 173 | OD2 | ASP | 10 | 15.340
| −0.262 | 1.413 | 1.00 | 0.00 | BrD | ATOM | 174 | C | ASP | 10 | 15.803
| −1.028 | −1.606 | 1.00 | 0.00 | BrD | ATOM | 175 | O | ASP | 10 | 14.986
| −1.622 | −0.903 | 1.00 | 0.00 | BrD | ATOM | 176 | N | PRO | 11 | 15.866
| −1.218 | −2.936 | 1.00 | 0.00 | BrD | ATOM | 177 | CA | PRO | 11 | 14.974
| −2.118 | −3.657 | 1.00 | 0.00 | BrD | ATOM | 178 | HA | PRO | 11 | 13.975
| −2.098 | −3.267 | 1.00 | 0.00 | BrD | ATOM | 179 | CB | PRO | 11 | 14.958
| −1.540 | −5.084 | 1.00 | 0.00 | BrD | ATOM | 180 | HB1 | PRO | 11 | 13.973
| −1.156 | −5.302 | 1.00 | 0.00 | BrD | ATOM | 181 | HB2 | PRO | 11 | 15.203
| −2.321 | −5.789 | 1.00 | 0.00 | BrD | ATOM | 182 | CG | PRO | 11 | 15.982
| 0.403 | −5.113 | 1.00 | 0.00 | BrD | ATOM | 183 | HG1 | PRO | 11 | 15.487
| −0.516 | −5.149 | 1.00 | 0.00 | BrD | ATOM | 184 | HG2 | PRO | 11 | 16.620
| −0.564 | −5.976 | 1.00 | 0.00 | BrD | ATOM | 185 | CD | PRO | 11 | 16.792
| 0.558 | −3.852 | 1.00 | 0.00 | BrD | ATOM | 186 | HD1 | PRO | 11 | 17.066
| −0.418 | −3.487 | 1.00 | 0.00 | BrD | ATOM | 187 | HD2 | PRO | 11 | 17.671
| −1.163 | −4.018 | 1.00 | 0.00 | BrD | ATOM | 188 | C | PRO | 11 | 15.488
| −3.554 | −3.670 | 1.00 | 0.00 | BrD | ATOM | 189 | O | PRO | 11 | 15.551
| −4.191 | −4.721 | 1.00 | 0.00 | BrD | ATOM | 190 | N | ASP | 12 | 15.849
| −4.061 | −2.496 | 1.00 | 0.00 | BrD | ATOM | 191 | HN | ASP | 12 | 15.780
| −3.506 | −1.691 | 1.00 | 0.00 | BrD | ATOM | 192 | CA | ASP | 12 | 16.361
| −5.421 | −2.384 | 1.00 | 0.00 | BrD | ATOM | 193 | HA | ASP | 12 | 16.155
| −5.927 | −3.315 | 1.00 | 0.00 | BrD | ATOM | 194 | CB | ASP | 12 | 17.873
| −5.399 | −2.151 | 1.00 | 0.00 | BrD | ATOM | 195 | HB1 | ASP | 12 | 18.123
| −6.112 | −1.380 | 1.00 | 0.00 | BrD | ATOM | 196 | HB2 | ASP | 12 | 18.167
| −4.410 | −1.830 | 1.00 | 0.00 | BrD | ATOM | 197 | CG | ASP | 12 | 18.657
| −5.749 | −3.400 | 1.00 | 0.00 | BrD | ATOM | 198 | OD1 | ASP | 12 | 18.450
| −5.084 | −4.437 | 1.00 | 0.00 | BrD | ATOM | 199 | OD2 | ASP | 12 | 19.478
| −6.687 | −3.342 | 1.00 | 0.00 | BrD | ATOM | 200 | C | ASP | 12 | 15.676
| −6.179 | −1.253 | 1.00 | 0.00 | BrD | ATOM | 201 | O | ASP | 12 | 15.106
| −7.250 | −1.468 | 1.00 | 0.00 | BrD | ATOM | 202 | N | GLN | 13 | 15.740
| −5.626 | −0.047 | 1.00 | 0.00 | BrD | ATOM | 203 | HN | GLN | 13 | 16.206
| −4.770 | 0.063 | 1.00 | 0.00 | BrD | ATOM | 204 | CA | GLN | 13 | 15.122
| −6.258 | 1.113 | 1.00 | 0.00 | BrD | ATOM | 205 | HA | GLN | 13 | 15.336
| −7.316 | 1.069 | 1.00 | 0.00 | BrD | ATOM | 206 | CB | GLN | 13 | 15.701
| −5.684 | 2.405 | 1.00 | 0.00 | BrD | ATOM | 207 | HB1 | GLN | 13 | 16.666
| −5.251 | 2.193 | 1.00 | 0.00 | BrD | ATOM | 208 | HB2 | GLN | 13 | 15.041
| −4.910 | 2.768 | 1.00 | 0.00 | BrD | ATOM | 209 | CG | GLN | 13 | 15.870
| −6.719 | 3.505 | 1.00 | 0.00 | BrD | ATOM | 210 | HG1 | GLN | 13 | 15.520
| −6.297 | 4.436 | 1.00 | 0.00 | BrD | ATOM | 211 | HG2 | GLN | 13 | 15.277
| −7.587 | 3.258 | 1.00 | 0.00 | BrD | ATOM | 212 | CD | GLN | 13 | 17.313
| −7.150 | 3.683 | 1.00 | 0.00 | BrD | ATOM | 213 | OH1 | GLN | 13 | 18.036
| −6.611 | 4.520 | 1.00 | 0.00 | BrD | ATOM | 214 | NH2 | GLN | 13 | 17.739
| −8.128 | 2.892 | 1.00 | 0.00 | BrD | ATOM | 215 | HE21 | GLN | 13 | 18.668
| −8.427 | 2.985 | 1.00 | 0.00 | BrD | ATOM | 216 | HE22 | GLN | 13 | 17.108
| −8.512 | 2.248 | 1.00 | 0.00 | BrD | ATOM | 217 | C | GLN | 13 | 13.615
| −6.060 | 1.097 | 1.00 | 0.00 | BrD | ATOM | 218 | O | GLN | 13 | 12.855
| −6.950 | 1.478 | 1.00 | 0.00 | BrD | ATOM | 219 | N | LEU | 14 | 13.291
| −4.880 | 0.662 | 1.00 | 0.00 | BrD | ATOM | 220 | HN | LEU | 14 | 13.848
| −4.214 | 0.371 | 1.00 | 0.00 | BrD | ATOM | 221 | CA | LEU | 14 | 11.774
| −4.558 | 0.595 | 1.00 | 0.00 | BrD | ATOM | 222 | HA | LEU | 14 | 11.303

TABLE 6-continued

Atomic Structure Coordinates of the
P/CAF Bromodomain/Acetyl-Histamine Complex

| | | | | | | | | | |
|---|---|---|---|---|---|---|---|---|---|
| −4.943 | 1.487 | 1.00 | 0.00 | BrD | ATOM | 223 | CB | LEU | 14 | 11.581 |
| −3.042 | 0.541 | 1.00 | 0.00 | BrD | ATOM | 224 | HB1 | LEU | 14 | 12.212 |
| −2.592 | 1.292 | 1.00 | 0.00 | BrD | ATOM | 225 | HB2 | LEU | 14 | 10.552 |
| −2.823 | 0.781 | 1.00 | 0.00 | BrD | ATOM | 226 | CG | LEU | 14 | 11.905 |
| −2.399 | −0.808 | 1.00 | 0.00 | BrD | ATOM | 227 | HG | LEU | 14 | 12.685 |
| −2.967 | −1.292 | 1.00 | 0.00 | BrD | ATOM | 228 | CD1 | LEU | 14 | 12.609 |
| −0.978 | −0.615 | 1.00 | 0.00 | BrD | ATOM | 229 | HD11 | LEU | 14 | 11.569 |
| −0.311 | −0.497 | 1.00 | 0.00 | BrD | ATOM | 230 | HD12 | LEU | 14 | 12.986 |
| −0.682 | −1.479 | 1.00 | 0.00 | BrD | ATOM | 231 | HD13 | LEU | 14 | 13.032 |
| −0.934 | 0.266 | 1.00 | 0.00 | BrD | ATOM | 232 | CD2 | LEU | 14 | 10.682 |
| −2.418 | −1.709 | 1.00 | 0.00 | BrD | ATOM | 233 | HD21 | LEU | 14 | 10.185 |
| −1.461 | −1.660 | 1.00 | 0.00 | BrD | ATOM | 234 | HD22 | LEU | 14 | 10.005 |
| −3.192 | −1.383 | 1.00 | 0.00 | BrD | ATOM | 235 | HD23 | LEU | 14 | 10.989 |
| −2.612 | −2.727 | 1.00 | 0.00 | BrD | ATOM | 236 | C | LEU | 14 | 11.130 |
| −5.209 | −0.623 | 1.00 | 0.00 | BrD | ATOM | 237 | O | LEU | 14 | 9.989 |
| −5.666 | −0.564 | 1.00 | 0.00 | BrD | ATOM | 238 | N | TYR | 15 | 11.866 |
| −5.241 | −1.729 | 1.00 | 0.00 | BrD | ATOM | 239 | HN | TYR | 15 | 12.772 |
| −4.865 | −1.714 | 1.00 | 0.00 | BrD | ATOM | 240 | CA | TYR | 15 | 11.364 |
| −5.841 | −2.959 | 1.00 | 0.00 | BrD | ATOM | 241 | HA | TYR | 15 | 10.539 |
| −5.237 | −3.312 | 1.00 | 0.00 | BrD | ATOM | 242 | CB | TYR | 15 | 12.460 |
| −5.865 | −4.029 | 1.00 | 0.00 | BrD | ATOM | 243 | HB1 | TYR | 15 | 13.317 |
| −6.397 | −3.642 | 1.00 | 0.00 | BrD | ATOM | 244 | HB2 | TYR | 15 | 12.748 |
| −4.850 | −4.259 | 1.00 | 0.00 | BrD | ATOM | 245 | CG | TYR | 15 | 12.083 |
| −6.533 | −5.323 | 1.00 | 0.00 | BrD | ATOM | 246 | CD1 | TYR | 15 | 12.993 |
| −7.047 | −6.197 | 1.00 | 0.00 | BrD | ATOM | 247 | HD1 | TYR | 15 | 14.040 |
| −6.968 | −5.940 | 1.00 | 0.00 | BrD | ATOM | 248 | CD2 | TYR | 15 | 10.702 |
| −6.642 | −5.675 | 1.00 | 0.00 | BrD | ATOM | 249 | HD2 | TYR | 15 | 9.950 |
| −6.248 | −5.008 | 1.00 | 0.00 | BrD | ATOM | 250 | CE1 | TYR | 15 | 12.620 |
| −7.654 | −7.381 | 1.00 | 0.00 | BrD | ATOM | 251 | HE1 | TYR | 15 | 13.374 |
| −8.049 | −8.046 | 1.00 | 0.00 | BrD | ATOM | 252 | CE2 | TYR | 15 | 10.322 |
| −7.249 | −6.857 | 1.00 | 0.00 | BrD | ATOM | 253 | HR2 | TYR | 15 | 9.275 |
| −7.326 | −7.111 | 1.00 | 0.00 | BrD | ATOM | 254 | CZ | TYR | 15 | 11.284 |
| −7.752 | −7.706 | 1.00 | 0.00 | BrD | ATOM | 255 | OH | TYR | 15 | 10.908 |
| −8.358 | −8.883 | 1.00 | 0.00 | BrD | ATOM | 256 | HH | TYR | 15 | 10.572 |
| −9.238 | −8.697 | 1.00 | 0.00 | BrD | ATOM | 257 | C | TYR | 15 | 10.859 |
| −7.253 | −2.696 | 1.00 | 0.00 | BrD | ATOM | 258 | O | TYR | 15 | 9.778 |
| −7.630 | −3.146 | 1.00 | 0.00 | BrD | ATOM | 259 | N | SER | 16 | 11.641 |
| −8.026 | −1.950 | 1.00 | 0.00 | BrD | ATOM | 260 | HN | SER | 16 | 12.485 |
| −7.666 | −1.605 | 1.00 | 0.00 | BrD | ATOM | 261 | CA | SER | 16 | 11.249 |
| −9.384 | −1.602 | 1.00 | 0.00 | BrD | ATOM | 262 | HA | SER | 16 | 11.148 |
| −9.946 | −2.518 | 1.00 | 0.00 | BrD | ATOM | 263 | CB | SER | 16 | 12.315 |
| −10.040 | −0.722 | 1.00 | 0.00 | BrD | ATOM | 264 | HB1 | SER | 16 | 12.503 |
| −9.416 | 0.139 | 1.00 | 0.00 | BrD | ATOM | 265 | HB2 | SER | 16 | 13.227 |
| −10.155 | −1.289 | 1.00 | 0.00 | BrD | ATOM | 266 | CG | SER | 16 | 11.892 |
| −11.317 | −0.276 | 1.00 | 0.00 | BrD | ATOM | 267 | HG | SER | 16 | 12.601 |
| −11.952 | −0.405 | 1.00 | 0.00 | BrD | ATOM | 268 | C | SER | 16 | 9.909 |
| −9.370 | −0.879 | 1.00 | 0.00 | BrD | ATOM | 269 | O | SER | 16 | 9.028 |
| −10.182 | −1.161 | 1.00 | 0.00 | BrD | ATOM | 270 | N | THR | 17 | 9.756 |
| −8.420 | 0.038 | 1.00 | 0.00 | BrD | ATOM | 271 | HN | THR | 17 | 10.493 |
| −7.796 | 0.207 | 1.00 | 0.00 | BrD | ATOM | 272 | CA | THR | 17 | 8.514 |
| −8.269 | 0.785 | 1.00 | 0.00 | BrD | ATOM | 273 | HA | THR | 17 | 8.318 |
| −9.200 | 1.296 | 1.00 | 0.00 | BrD | ATOM | 274 | CB | THR | 17 | 8.656 |
| −7.146 | 1.820 | 1.00 | 0.00 | BrD | ATOM | 275 | HB | THR | 17 | 9.069 |
| −6.275 | 1.333 | 1.00 | 0.00 | BrD | ATOM | 276 | OG1 | THR | 17 | 9.539 |
| −7.535 | 2.857 | 1.00 | 0.00 | BrD | ATOM | 277 | HG1 | THR | 17 | 10.426 |
| −7.633 | 2.502 | 1.00 | 0.00 | BrD | ATOM | 278 | CG2 | THR | 17 | 7.346 |
| −6.733 | 2.463 | 1.00 | 0.00 | BrD | ATOM | 279 | HG21 | THR | 17 | 6.714 |
| −7.600 | 2.589 | 1.00 | 0.00 | BrD | ATOM | 280 | HG22 | THR | 17 | 6.845 |
| −6.012 | 1.832 | 1.00 | 0.00 | BrD | ATOM | 281 | HG23 | THR | 17 | 7.545 |
| −6.289 | 3.427 | 1.00 | 0.00 | BrD | ATOM | 282 | C | THR | 17 | 7.356 |
| −7.971 | −0.161 | 1.00 | 0.00 | BrD | ATOM | 283 | O | THR | 17 | 6.420 |
| −8.757 | −0.277 | 1.00 | 0.00 | BrD | ATOM | 284 | N | LEU | 18 | 7.438 |
| −6.832 | −0.843 | 1.00 | 0.00 | BrD | ATOM | 285 | HN | LEU | 18 | 8.212 |
| −6.247 | −0.702 | 1.00 | 0.00 | BrD | ATOM | 286 | CA | LEU | 18 | 6.396 |
| −6.414 | −1.776 | 1.00 | 0.00 | BrD | ATOM | 287 | HA | LEU | 18 | 5.534 |
| −6.122 | −1.197 | 1.00 | 0.00 | BrD | ATOM | 288 | CB | LEU | 18 | 6.871 |
| −5.218 | −2.591 | 1.00 | 0.00 | BrD | ATOM | 289 | HB1 | LEU | 18 | 7.669 |
| −5.542 | −3.243 | 1.00 | 0.00 | BrD | ATOM | 290 | HB2 | LEU | 18 | 6.049 |
| −4.869 | −3.198 | 1.00 | 0.00 | BrD | ATOM | 291 | CG | LEU | 18 | 7.377 |
| −4.056 | −1.750 | 1.00 | 0.00 | BrD | ATOM | 292 | HG | LEU | 18 | 8.301 |
| −4.350 | −1.275 | 1.00 | 0.00 | BrD | ATOM | 293 | CD1 | LEU | 18 | 7.653 |
| −2.840 | −2.622 | 1.00 | 0.00 | BrD | ATOM | 294 | HD11 | LEU | 18 | 6.966 |
| −2.832 | −3.455 | 1.00 | 0.00 | BrD | ATOM | 295 | HD12 | LEU | 18 | 8.667 |
| −2.885 | −2.994 | 1.00 | 0.00 | BrD | ATOM | 296 | HD13 | LEU | 18 | 7.532 |
| −1.941 | −2.039 | 1.00 | 0.00 | BrD | ATOM | 297 | CD2 | LEU | 18 | 6.369 |
| −3.727 | −0.658 | 1.00 | 0.00 | BrD | ATOM | 298 | HD21 | LEU | 18 | 5.417 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −4.180 | −0.897 | 1.00 | 0.00 | BrD | ATOM | 299 | HD22 | LEU | 18 | 6.252 |
| −2.657 | −0.584 | 1.00 | 0.00 | BrD | ATOM | 300 | HD23 | LEU | 18 | 6.722 |
| −4.117 | 0.284 | 1.00 | 0.00 | BrD | ATOM | 301 | C | LEU | 18 | 5.998 |
| −7.542 | −2.707 | 1.00 | 0.00 | BrD | ATOM | 302 | O | LEU | 18 | 4.869 |
| −8.022 | −2.667 | 1.00 | 0.00 | BrD | ATOM | 303 | N | LYS | 19 | 6.926 |
| −7.967 | −3.552 | 1.00 | 0.00 | BrD | ATOM | 304 | HN | LYS | 19 | 7.813 |
| −7.550 | −3.543 | 1.00 | 0.00 | BrD | ATOM | 305 | CA | LYS | 19 | 6.648 |
| −9.050 | −4.487 | 1.00 | 0.00 | BrD | ATOM | 306 | HA | LYS | 19 | 5.959 |
| −8.673 | −5.228 | 1.00 | 0.00 | BrD | ATOM | 307 | CB | LYS | 19 | 7.935 |
| −9.498 | −5.193 | 1.00 | 0.00 | BrD | ATOM | 308 | HB1 | LYS | 19 | 7.671 |
| −9.974 | −6.126 | 1.00 | 0.00 | BrD | ATOM | 309 | HB2 | LYS | 19 | 8.535 |
| −8.625 | −5.404 | 1.00 | 0.00 | BrD | ATOM | 310 | CG | LYS | 19 | 8.785 |
| −10.472 | −4.390 | 1.00 | 0.00 | BrD | ATOM | 311 | HG1 | LYS | 19 | 9.296 |
| −11.438 | −4.386 | 1.00 | 0.00 | BrD | ATOM | 312 | HG2 | LYS | 19 | 8.878 |
| −10.106 | −3.378 | 1.00 | 0.00 | BrD | ATOM | 313 | CD | LYS | 19 | 10.172 |
| −10.621 | −4.992 | 1.00 | 0.00 | BrD | ATOM | 314 | HD1 | LYS | 19 | 10.575 |
| −9.638 | −5.190 | 1.00 | 0.00 | BrD | ATOM | 315 | HD2 | LYS | 19 | 10.807 |
| −11.137 | −4.287 | 1.00 | 0.00 | BrD | ATOM | 316 | CE | LYS | 19 | 10.113 |
| −11.409 | −6.290 | 1.00 | 0.00 | BrD | ATOM | 317 | HE1 | LYS | 19 | 9.337 |
| −11.019 | −6.908 | 1.00 | 0.00 | BrD | ATOM | 318 | HE2 | LYS | 19 | 11.077 |
| −11.288 | −6.800 | 1.00 | 0.00 | BrD | ATOM | 319 | NZ | LYS | 19 | 9.893 |
| −12.858 | −6.050 | 1.00 | 0.00 | BrD | ATOM | 320 | HZ1 | LYS | 19 | 9.982 |
| −13.072 | −5.036 | 1.00 | 0.00 | BrD | ATOM | 321 | HZ2 | LYS | 19 | 10.587 |
| −13.427 | −6.576 | 1.00 | 0.00 | BrD | ATOM | 322 | HZ3 | LYS | 19 | 8.937 |
| −13.119 | −6.368 | 1.00 | 0.00 | BrD | ATOM | 323 | C | LYS | 19 | 5.988 |
| −10.223 | −3.761 | 1.00 | 0.00 | BrD | ATOM | 324 | O | LYS | 19 | 5.193 |
| −10.960 | −4.341 | 1.00 | 0.00 | BrD | ATOM | 325 | N | SER | 20 | 6.299 |
| −10.359 | −2.478 | 1.00 | 0.00 | BrD | ATOM | 326 | HN | SER | 20 | 6.925 |
| −9.721 | −2.061 | 1.00 | 0.00 | BrD | ATOM | 327 | CA | SER | 20 | 5.722 |
| −11.425 | −1.661 | 1.00 | 0.00 | BrD | ATOM | 328 | HA | SER | 20 | 5.660 |
| −12.306 | −2.277 | 1.00 | 0.00 | BrD | ATOM | 329 | CB | SER | 20 | 6.608 |
| −11.725 | −0.449 | 1.00 | 0.00 | BrD | ATOM | 330 | HB1 | SER | 20 | 7.086 |
| −10.815 | −0.120 | 1.00 | 0.00 | BrD | ATOM | 331 | HB2 | SER | 20 | 5.999 |
| −12.121 | 0.350 | 1.00 | 0.00 | BrD | ATOM | 332 | CG | SER | 20 | 7.610 |
| −12.674 | −0.772 | 1.00 | 0.00 | BrD | ATOM | 333 | HG | SER | 20 | 7.218 |
| −13.396 | −1.269 | 1.00 | 0.00 | BrD | ATOM | 334 | C | SER | 20 | 4.316 |
| −11.056 | −1.207 | 1.00 | 0.00 | BrD | ATOM | 335 | O | SER | 20 | 3.334 |
| −11.659 | −1.642 | 1.00 | 0.00 | BrD | ATOM | 336 | N | ILE | 21 | 4.218 |
| −10.045 | −0.349 | 1.00 | 0.00 | BrD | ATOM | 337 | HN | ILE | 21 | 5.031 |
| −9.592 | −0.044 | 1.00 | 0.00 | BrD | ATOM | 338 | CA | ILE | 21 | 2.919 |
| −9.583 | 0.129 | 1.00 | 0.00 | BrD | ATOM | 339 | HA | ILE | 21 | 2.508 |
| −10.348 | 0.771 | 1.00 | 0.00 | BrD | ATOM | 340 | CB | ILE | 21 | 3.036 |
| −8.280 | 0.945 | 1.00 | 0.00 | BrD | ATOM | 341 | HB | ILE | 21 | 2.050 |
| −7.850 | 1.036 | 1.00 | 0.00 | BrD | ATOM | 342 | CG1 | ILE | 21 | 3.956 |
| −7.280 | 0.240 | 1.00 | 0.00 | BrD | ATOM | 343 | HG11 | ILE | 21 | 4.639 |
| −6.858 | 0.962 | 1.00 | 0.00 | BrD | ATOM | 344 | HG12 | ILE | 21 | 4.519 |
| −7.792 | −0.521 | 1.00 | 0.00 | BrD | ATOM | 345 | CG2 | ILE | 21 | 3.549 |
| −8.579 | 2.346 | 1.00 | 0.00 | BrD | ATOM | 346 | HG21 | ILE | 21 | 4.618 |
| −8.431 | 2.377 | 1.00 | 0.00 | BrD | ATOM | 347 | HG22 | ILE | 21 | 3.319 |
| −9.603 | 2.603 | 1.00 | 0.00 | BrD | ATOM | 348 | HG23 | ILE | 21 | 3.073 |
| −7.915 | 3.053 | 1.00 | 0.00 | BrD | ATOM | 349 | CD1 | ILE | 21 | 3.222 |
| −6.140 | −0.427 | 1.00 | 0.00 | BrD | ATOM | 350 | HD11 | ILE | 21 | 3.805 |
| −5.235 | −0.338 | 1.00 | 0.00 | BrD | ATOM | 351 | HD12 | ILE | 21 | 2.264 |
| −4.000 | 0.051 | 1.00 | 0.00 | BrD | ATOM | 352 | HD13 | ILE | 21 | 3.075 |
| −6.371 | −1.472 | 1.00 | 0.00 | BrD | ATOM | 353 | C | ILE | 21 | 1.969 |
| −9.361 | −1.044 | 1.00 | 0.00 | BrD | ATOM | 354 | O | ILE | 21 | 0.869 |
| −9.901 | −1.074 | 1.00 | 0.00 | BrD | ATOM | 355 | N | LEU | 22 | 2.433 |
| −8.608 | −2.034 | 1.00 | 0.00 | BrD | ATOM | 356 | HN | LEU | 22 | 3.325 |
| −8.224 | −1.957 | 1.00 | 0.00 | BrD | ATOM | 357 | CA | LEU | 22 | 1.648 |
| −8.337 | −3.229 | 1.00 | 0.00 | BrD | ATOM | 358 | HA | LEU | 22 | 0.757 |
| −7.807 | −2.929 | 1.00 | 0.00 | BrD | ATOM | 359 | CB | LEU | 22 | 2.451 |
| −7.465 | −4.197 | 1.00 | 0.00 | BrD | ATOM | 360 | HB1 | LEU | 22 | 3.352 |
| −7.996 | −4.462 | 1.00 | 0.00 | BrD | ATOM | 361 | HB2 | LEU | 22 | 2.728 |
| −6.556 | −3.683 | 1.00 | 0.00 | BrD | ATOM | 362 | CG | LEU | 22 | 1.722 |
| −7.084 | −5.486 | 1.00 | 0.00 | BrD | ATOM | 363 | HG | LEU | 22 | 1.378 |
| −7.982 | −5.977 | 1.00 | 0.00 | BrD | ATOM | 364 | CD1 | LEU | 22 | 2.665 |
| −6.362 | −6.437 | 1.00 | 0.00 | BrD | ATOM | 365 | HD11 | LEU | 22 | 2.220 |
| −6.324 | −7.419 | 1.00 | 0.00 | BrD | ATOM | 366 | HD12 | LEU | 22 | 3.601 |
| −6.898 | −6.492 | 1.00 | 0.00 | BrD | ATOM | 367 | HD13 | LEU | 22 | 2.845 |
| −5.361 | −6.074 | 1.00 | 0.00 | BrD | ATOM | 368 | CD2 | LEU | 22 | 0.507 |
| −6.222 | −5.178 | 1.00 | 0.00 | BrD | ATOM | 369 | HD21 | LEU | 22 | 0.127 |
| −6.472 | −4.199 | 1.00 | 0.00 | BrD | ATOM | 370 | HD22 | LEU | 22 | −0.259 |
| −6.401 | −5.918 | 1.00 | 0.00 | BrD | ATOM | 371 | HD23 | LEU | 22 | 0.790 |
| −5.180 | −5.199 | 1.00 | 0.00 | BrD | ATOM | 372 | C | LEU | 22 | 1.243 |
| −9.636 | −3.915 | 1.00 | 0.00 | BrD | ATOM | 373 | O | LEU | 22 | 0.086 |
| −9.813 | −4.295 | 1.00 | 0.00 | BrD | ATOM | 374 | N | GLN | 23 | 2.201 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −10.552 | −4.058 | 1.00 | 0.00 | BrD | ATOM | 375 | HN | GLN | 23 | 3.107 |
| −10.354 | −3.735 | 1.00 | 0.00 | BrD | ATOM | 376 | CA | GLN | 23 | 1.941 |
| −11.841 | −4.695 | 1.00 | 0.00 | BrD | ATOM | 377 | HA | GLN | 23 | 1.828 |
| −11.670 | −5.754 | 1.00 | 0.00 | BrD | ATOM | 378 | CB | GLN | 23 | 3.118 |
| −12.793 | −4.464 | 1.00 | 0.00 | BrD | ATOM | 379 | HB1 | GLN | 23 | 3.720 |
| −12.412 | −3.653 | 1.00 | 0.00 | BrD | ATOM | 380 | HB2 | GLN | 23 | 2.731 |
| −13.763 | −4.186 | 1.00 | 0.00 | BrD | ATOM | 381 | CG | GLN | 23 | 4.012 |
| −12.969 | −5.682 | 1.00 | 0.00 | BrD | ATOM | 382 | HG1 | GLN | 23 | 4.318 |
| −11.995 | −6.035 | 1.00 | 0.00 | BrD | ATOM | 383 | HG2 | GLN | 23 | 4.986 |
| −13.535 | −5.393 | 1.00 | 0.00 | BrD | ATOM | 384 | CD | GLN | 23 | 3.316 |
| −13.697 | −6.815 | 1.00 | 0.00 | BrD | ATOM | 385 | OE1 | GLN | 23 | 2.624 |
| −14.692 | −6.597 | 1.00 | 0.00 | BrD | ATOM | 386 | NE2 | GLN | 23 | 3.494 |
| −13.203 | −8.034 | 1.00 | 0.00 | BrD | ATOM | 387 | HE21 | GLN | 23 | 4.058 |
| −12.808 | −8.134 | 1.00 | 0.00 | BrD | ATOM | 388 | HE22 | GLN | 23 | 3.055 |
| −13.654 | −8.786 | 1.00 | 0.00 | BrD | ATOM | 389 | C | GLN | 23 | 0.655 |
| −12.867 | −4.157 | 1.00 | 0.00 | BrD | ATOM | 390 | O | GLN | 23 | −0.207 |
| −12.892 | −4.925 | 1.00 | 0.00 | BrD | ATOM | 391 | N | GLN | 24 | 0.530 |
| −12.519 | −2.833 | 1.00 | 0.00 | BrD | ATOM | 392 | HN | GLN | 24 | 1.252 |
| −12.167 | −2.269 | 1.00 | 0.00 | BrD | ATOM | 393 | CA | GLN | 24 | −0.654 |
| −13.096 | −2.203 | 1.00 | 0.00 | BrD | ATOM | 394 | HA | GLN | 24 | −0.951 |
| −13.947 | −2.797 | 1.00 | 0.00 | BrD | ATOM | 395 | CB | GLN | 24 | −0.325 |
| −13.584 | −0.783 | 1.00 | 0.00 | BrD | ATOM | 396 | HB1 | GLN | 24 | 0.666 |
| −14.012 | −0.785 | 1.00 | 0.00 | BrD | ATOM | 397 | HB2 | GLN | 24 | −1.035 |
| −14.351 | −0.509 | 1.00 | 0.00 | BrD | ATOM | 398 | CG | GLN | 24 | −0.369 |
| −12.698 | 0.284 | 1.00 | 0.00 | BrD | ATOM | 399 | HG1 | GLN | 24 | −1.331 |
| −12.531 | 0.774 | 1.00 | 0.00 | BrD | ATOM | 400 | HG2 | GLN | 24 | −0.243 |
| −11.539 | −0.192 | 1.00 | 0.00 | BrD | ATOM | 401 | CD | GLN | 24 | 0.714 |
| −12.663 | 1.333 | 1.00 | 0.00 | BrD | ATOM | 402 | OE1 | GLN | 24 | 0.426 |
| −12.791 | 2.524 | 1.00 | 0.00 | BrD | ATOM | 403 | NE2 | GLN | 24 | 1.967 |
| −12.659 | 0.897 | 1.00 | 0.00 | BrD | ATOM | 404 | HE21 | GLN | 24 | 2.122 |
| −12.552 | −0.065 | 1.00 | 0.00 | BrD | ATOM | 405 | HE22 | GLN | 24 | 2.687 |
| −12.763 | 1.554 | 1.00 | 0.00 | BrD | ATOM | 406 | C | GLN | 24 | −1.816 |
| −12.099 | −2.179 | 1.00 | 0.00 | BrD | ATOM | 407 | O | GLN | 24 | −2.974 |
| −12.485 | −2.332 | 1.00 | 0.00 | BrD | ATOM | 408 | N | VAL | 25 | −1.501 |
| −10.821 | −1.974 | 1.00 | 0.00 | BrD | ATOM | 409 | HN | VAL | 25 | −0.561 |
| −10.575 | −1.859 | 1.00 | 0.00 | BrD | ATOM | 410 | CA | VAL | 25 | −2.523 |
| −9.776 | −1.922 | 1.00 | 0.00 | BrD | ATOM | 411 | HA | VAL | 25 | −3.122 |
| −9.941 | −1.036 | 1.00 | 0.00 | BrD | ATOM | 412 | CB | VAL | 25 | −1.890 |
| −8.369 | −1.813 | 1.00 | 0.00 | BrD | ATOM | 413 | HB | VAL | 25 | −1.198 |
| −8.243 | −2.632 | 1.00 | 0.00 | BrD | ATOM | 414 | CG1 | VAL | 25 | −1.116 |
| −8.236 | −0.510 | 1.00 | 0.00 | BrD | ATOM | 415 | HG11 | VAL | 25 | −1.590 |
| −7.494 | 0.116 | 1.00 | 0.00 | BrD | ATOM | 416 | HG12 | VAL | 25 | −0.102 |
| −7.932 | −0.722 | 1.00 | 0.00 | BrD | ATOM | 417 | HG13 | VAL | 25 | −1.108 |
| −9.186 | 0.003 | 1.00 | 0.00 | BrD | ATOM | 418 | CG2 | VAL | 25 | −2.945 |
| −7.277 | −1.908 | 1.00 | 0.00 | BrD | ATOM | 419 | HG21 | VAL | 25 | −3.437 |
| −7.331 | −2.868 | 1.00 | 0.00 | BrD | ATOM | 420 | HG22 | VAL | 25 | −2.472 |
| −6.313 | −1.799 | 1.00 | 0.00 | BrD | ATOM | 421 | HG23 | VAL | 25 | −3.672 |
| −7.410 | −1.121 | 1.00 | 0.00 | BrD | ATOM | 422 | C | VAL | 25 | −3.440 |
| −9.846 | −3.141 | 1.00 | 0.00 | BrD | ATOM | 423 | O | LYS | 26 | −4.659 |
| −9.930 | −3.000 | 1.00 | 0.00 | BrD | ATOM | 424 | N | LYS | 26 | −2.858 |
| −9.858 | −4.336 | 1.00 | 0.00 | BrD | ATOM | 425 | HN | LYS | 26 | −1.863 |
| −9.798 | −4.396 | 1.00 | 0.00 | BrD | ATOM | 426 | CA | LYS | 26 | −3.648 |
| −9.943 | −5.562 | 1.00 | 0.00 | BrD | ATOM | 427 | HA | LYS | 26 | −4.174 |
| −9.008 | −5.678 | 1.00 | 0.00 | BrD | ATOM | 428 | CB | LYS | 26 | −2.737 |
| −10.161 | −6.771 | 1.00 | 0.00 | BrD | ATOM | 429 | HB1 | LYS | 26 | −3.314 |
| −10.018 | −7.673 | 1.00 | 0.00 | BrD | ATOM | 430 | HB2 | LYS | 26 | −1.942 |
| −9.430 | −7.744 | 1.00 | 0.00 | BrD | ATOM | 431 | CG | LYS | 26 | −2.111 |
| −11.545 | −6.820 | 1.00 | 0.00 | BrD | ATOM | 432 | HG1 | LYS | 26 | −2.070 |
| −11.947 | −5.818 | 1.00 | 0.00 | BrD | ATOM | 433 | HG2 | LYS | 26 | −2.721 |
| −12.183 | −7.442 | 1.00 | 0.00 | BrD | ATOM | 434 | CD | LYS | 26 | −0.702 |
| −11.500 | −7.391 | 1.00 | 0.00 | BrD | ATOM | 435 | HD1 | LYS | 26 | −0.214 |
| −10.600 | −7.048 | 1.00 | 0.00 | BrD | ATOM | 436 | HD2 | LYS | 26 | −0.156 |
| −12.364 | −7.043 | 1.00 | 0.00 | BrD | ATOM | 437 | CE | LYS | 26 | −0.736 |
| −11.505 | −8.910 | 1.00 | 0.00 | BrD | ATOM | 438 | HE1 | LYS | 26 | 0.003 |
| −10.782 | −9.266 | 1.00 | 0.00 | BrD | ATOM | 439 | HE2 | LYS | 26 | −1.703 |
| −11.228 | −9.249 | 1.00 | 0.00 | BrD | ATOM | 440 | NZ | LYS | 26 | −0.371 |
| −12.844 | −9.465 | 1.00 | 0.00 | BrD | ATOM | 441 | HZ1 | LYS | 26 | −1.215 |
| −13.285 | −9.884 | 1.00 | 0.00 | BrD | ATOM | 442 | HZ2 | LYS | 26 | −0.010 |
| −13.461 | −8.710 | 1.00 | 0.00 | BrD | ATOM | 443 | HZ3 | LYS | 26 | 0.358 |
| −12.789 | −10.199 | 1.00 | 0.00 | BrD | ATOM | 444 | C | LYS | 26 | −4.673 |
| −11.073 | −5.468 | 1.00 | 0.00 | BrD | ATOM | 445 | O | LYS | 26 | −5.762 |
| −10.991 | −6.036 | 1.00 | 0.00 | BrD | ATOM | 446 | N | SER | 27 | −4.315 |
| −12.118 | −4.732 | 1.00 | 0.00 | BrD | ATOM | 447 | HN | SER | 27 | −3.439 |
| −12.109 | −4.293 | 1.00 | 0.00 | BrD | ATOM | 448 | CA | SER | 27 | −5.204 |
| −13.257 | −4.516 | 1.00 | 0.00 | BrD | ATOM | 449 | HA | SER | 27 | −6.104 |
| −13.100 | −5.091 | 1.00 | 0.00 | BrD | ATOM | 450 | CB | SER | 27 | −4.532 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −14.553 | −4.976 | 1.00 | 0.00 | BrD | ATOM | 451 | HB1 | SER | 27 | −3.629 |
| −14.710 | −4.404 | 1.00 | 0.00 | BrD | ATOM | 452 | HB2 | SER | 27 | −5.207 |
| −15.381 | −4.818 | 1.00 | 0.00 | BrD | ATOM | 453 | CG | SER | 27 | −4.197 |
| −16.492 | −6.351 | 1.00 | 0.00 | BrD | ATOM | 454 | HG | SER | 27 | −3.746 |
| −15.300 | −6.606 | 1.00 | 0.00 | BrD | ATOM | 455 | C | SER | 27 | −5.591 |
| −13.361 | −3.050 | 1.00 | 0.00 | BrD | ATOM | 456 | O | SER | 27 | −5.962 |
| −14.431 | −2.567 | 1.00 | 0.00 | BrD | ATOM | 457 | N | HIS | 28 | −5.477 |
| −12.246 | −2.339 | 1.00 | 0.00 | BrD | ATOM | 458 | HN | HIS | 28 | −5.215 |
| −11.418 | −2.785 | 1.00 | 0.00 | BrD | ATOM | 459 | CA | HIS | 28 | −5.863 |
| −12.197 | −0.946 | 1.00 | 0.00 | BrD | ATOM | 460 | HA | HIS | 28 | −5.597 |
| −13.142 | −0.497 | 1.00 | 0.00 | BrD | ATOM | 461 | CB | HIS | 28 | −5.125 |
| −11.076 | −0.217 | 1.00 | 0.00 | BrD | ATOM | 462 | HB1 | HIS | 28 | −4.073 |
| −11.308 | −0.210 | 1.00 | 0.00 | BrD | ATOM | 463 | HB2 | HIS | 28 | −5.283 |
| −10.146 | −0.742 | 1.00 | 0.00 | BrD | ATOM | 464 | CG | HIS | 28 | −5.549 |
| −10.864 | 1.205 | 1.00 | 0.00 | BrD | ATOM | 465 | ND1 | HIS | 28 | −5.742 |
| −11.931 | 2.081 | 1.00 | 0.00 | BrD | ATOM | 466 | HD1 | HIS | 28 | −5.645 |
| −12.883 | 1.866 | 1.00 | 0.00 | BrD | ATOM | 467 | CD2 | HIS | 28 | −5.780 |
| −9.754 | 1.926 | 1.00 | 0.00 | BrD | ATOM | 468 | HD2 | HIS | 28 | −5.717 |
| −8.739 | 1.549 | 1.00 | 0.00 | BrD | ATOM | 469 | CE1 | HIS | 28 | −6.092 |
| −11.456 | 3.262 | 1.00 | 0.00 | BrD | ATOM | 470 | HE1 | HIS | 28 | −6.314 |
| −12.044 | 4.141 | 1.00 | 0.00 | BrD | ATOM | 471 | NH2 | HIS | 28 | −6.119 |
| −10.139 | 3.189 | 1.00 | 0.00 | BrD | ATOM | 472 | HE2 | HIS | 28 | −6.350 |
| −9.536 | 3.925 | 1.00 | 0.00 | BrD | ATOM | 473 | C | HIS | 28 | −7.364 |
| −12.017 | −0.850 | 1.00 | 0.00 | BrD | ATOM | 474 | O | HIS | 28 | −7.979 |
| −11.356 | −1.686 | 1.00 | 0.00 | BrD | ATOM | 475 | N | GLN | 29 | −7.954 |
| −12.666 | 0.128 | 1.00 | 0.00 | BrD | ATOM | 476 | HN | GLN | 29 | −7.404 |
| −13.189 | 0.747 | 1.00 | 0.00 | BrD | ATOM | 477 | CA | GLN | 29 | −9.397 |
| −12.630 | 0.298 | 1.00 | 0.00 | BrD | ATOM | 478 | HA | GLN | 29 | −9.836 |
| −12.688 | −0.687 | 1.00 | 0.00 | BrD | ATOM | 479 | CB | GLN | 29 | −9.840 |
| −13.850 | 1.090 | 1.00 | 0.00 | BrD | ATOM | 480 | HB1 | GLN | 29 | −9.485 |
| −13.761 | 2.106 | 1.00 | 0.00 | BrD | ATOM | 481 | HB2 | GLN | 29 | −10.918 |
| −13.901 | 1.092 | 1.00 | 0.00 | BrD | ATOM | 482 | CG | GLN | 29 | −9.294 |
| −15.138 | 0.496 | 1.00 | 0.00 | BrD | ATOM | 483 | HG1 | GLN | 29 | −8.707 |
| −14.887 | −0.386 | 1.00 | 0.00 | BrD | ATOM | 484 | HG2 | GLN | 29 | −8.660 |
| −15.618 | 1.227 | 1.00 | 0.00 | BrD | ATOM | 485 | CD | GLN | 29 | −10.390 |
| −16.105 | 0.093 | 1.00 | 0.00 | BrD | ATOM | 486 | OE1 | GLN | 29 | −10.358 |
| −16.679 | −0.996 | 1.00 | 0.00 | BrD | ATOM | 487 | NE2 | GLN | 29 | −11.368 |
| −16.290 | 0.971 | 1.00 | 0.00 | BrD | ATOM | 488 | HE21 | GLN | 29 | −12.090 |
| −16.910 | 0.737 | 1.00 | 0.00 | BrD | ATOM | 489 | HE22 | GLN | 29 | −11.329 |
| −15.800 | 1.819 | 1.00 | 0.00 | BrD | ATOM | 490 | C | GLN | 29 | −9.866 |
| −11.332 | 0.951 | 1.00 | 0.00 | BrD | ATOM | 491 | O | GLN | 29 | −11.065 |
| −11.122 | 1.116 | 1.00 | 0.00 | BrD | ATOM | 492 | N | SER | 30 | −8.921 |
| −10.450 | 1.262 | 1.00 | 0.00 | BrD | ATOM | 493 | HN | SER | 30 | −7.985 |
| −10.661 | 1.074 | 1.00 | 0.00 | BrD | ATOM | 494 | CA | SER | 30 | −9.246 |
| −9.143 | 1.805 | 1.00 | 0.00 | BrD | ATOM | 495 | HA | SER | 30 | −10.329 |
| −9.036 | 1.787 | 1.00 | 0.00 | BrD | ATOM | 496 | CB | SER | 30 | −8.759 |
| −9.026 | 3.250 | 1.00 | 0.00 | BrD | ATOM | 497 | HB1 | SER | 30 | −7.829 |
| −8.479 | 3.271 | 1.00 | 0.00 | BrD | ATOM | 498 | HB2 | SER | 30 | −9.499 |
| −8.500 | 3.835 | 1.00 | 0.00 | BrD | ATOM | 499 | CG | SER | 30 | −8.552 |
| −10.307 | 3.823 | 1.00 | 0.00 | BrD | ATOM | 500 | HG | SER | 30 | −9.322 |
| −10.857 | 3.664 | 1.00 | 0.00 | BrD | ATOM | 501 | C | SER | 30 | −8.627 |
| −8.036 | 0.945 | 1.00 | 0.00 | BrD | ATOM | 502 | O | SER | 30 | −8.726 |
| −6.855 | 1.276 | 1.00 | 0.00 | BrD | ATOM | 503 | N | ALA | 31 | −7.977 |
| −8.625 | −0.157 | 1.00 | 0.00 | BrD | ATOM | 504 | HN | ALA | 31 | −7.935 |
| −9.377 | −0.385 | 1.00 | 0.00 | BrD | ATOM | 505 | CA | ALA | 31 | −7.365 |
| −7.662 | −1.066 | 1.00 | 0.00 | BrD | ATOM | 506 | HA | ALA | 31 | −6.927 |
| −6.675 | −0.470 | 1.00 | 0.00 | BrD | ATOM | 507 | CB | ALA | 31 | −6.251 |
| −8.123 | −1.861 | 1.00 | 0.00 | BrD | ATOM | 508 | HB1 | ALA | 31 | −5.395 |
| −8.274 | −1.223 | 1.00 | 0.00 | BrD | ATOM | 509 | HB2 | ALA | 31 | −5.974 |
| −7.489 | −2.691 | 1.00 | 0.00 | BrD | ATOM | 510 | HB3 | ALA | 31 | −6.593 |
| −9.078 | −2.236 | 1.00 | 0.00 | BrD | ATOM | 511 | C | ALA | 31 | −8.397 |
| −6.851 | −2.024 | 1.00 | 0.00 | BrD | ATOM | 512 | O | ALA | 31 | −8.097 |
| −5.900 | −2.736 | 1.00 | 0.00 | BrD | ATOM | 513 | N | TRP | 32 | −9.614 |
| −7.396 | −2.010 | 1.00 | 0.00 | BrD | ATOM | 514 | HN | TRP | 32 | −9.795 |
| −8.160 | −1.427 | 1.00 | 0.00 | BrD | ATOM | 515 | CA | TRP | 32 | −10.669 |
| −6.906 | −2.893 | 1.00 | 0.00 | BrD | ATOM | 516 | HA | TRP | 32 | −10.362 |
| −7.135 | −3.902 | 1.00 | 0.00 | BrD | ATOM | 517 | CB | TRP | 32 | −12.002 |
| −7.630 | −2.628 | 1.00 | 0.00 | BrD | ATOM | 518 | HB1 | TRP | 32 | −12.700 |
| −7.192 | −3.249 | 1.00 | 0.00 | BrD | ATOM | 519 | HB2 | TRP | 32 | −11.894 |
| −8.671 | −2.881 | 1.00 | 0.00 | BrD | ATOM | 520 | CG | TRP | 32 | −12.454 |
| −7.544 | −1.209 | 1.00 | 0.00 | BrD | ATOM | 521 | CD1 | TRP | 32 | −12.415 |
| −8.532 | −0.267 | 1.00 | 0.00 | BrD | ATOM | 522 | HD1 | TRP | 32 | −12.058 |
| −9.535 | −0.450 | 1.00 | 0.00 | BrD | ATOM | 523 | CD2 | TRP | 32 | −12.993 |
| −6.393 | −0.565 | 1.00 | 0.00 | BrD | ATOM | 524 | NE1 | TRP | 32 | −12.895 |
| −8.057 | 0.929 | 1.00 | 0.00 | BrD | ATOM | 525 | HE1 | TRP | 32 | −12.970 |
| −8.574 | 1.758 | 1.00 | 0.00 | BrD | ATOM | 526 | CH2 | TRP | 32 | −13.253 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −6.743 | 0.770 | 1.00 | 0.00 | BrD | ATOM | 527 | CH3 | TRP | 32 | −13.270 |
| −5.095 | −0.991 | 1.00 | 0.00 | BrD | ATOM | 528 | HE3 | TRP | 32 | −13.068 |
| −4.788 | −2.006 | 1.00 | 0.00 | BrD | ATOM | 529 | CZ2 | TRP | 32 | −13.784 |
| −5.839 | 1.681 | 1.00 | 0.00 | BrD | ATOM | 530 | HZ2 | TRP | 32 | −13.983 |
| −6.109 | 2.708 | 1.00 | 0.00 | BrD | ATOM | 531 | CZ3 | TRP | 32 | −13.786 |
| −4.196 | −0.086 | 1.00 | 0.00 | BrD | ATOM | 532 | HZ3 | TRP | 32 | −14.003 |
| −3.185 | −0.395 | 1.00 | 0.00 | BrD | ATOM | 533 | CH2 | TRP | 32 | −14.055 |
| −4.577 | 1.230 | 1.00 | 0.00 | BrD | ATOM | 534 | HH2 | TRP | 32 | −14.420 |
| −3.838 | 1.903 | 1.00 | 0.00 | BrD | ATOM | 535 | C | TRP | 32 | −10.855 |
| −5.382 | −2.797 | 1.00 | 0.00 | BrD | ATOM | 536 | O | TRP | 32 | −11.199 |
| −4.752 | −3.797 | 1.00 | 0.00 | BrD | ATOM | 537 | N | PRO | 33 | −10.636 |
| −4.741 | −1.618 | 1.00 | 0.00 | BrD | ATOM | 538 | CA | PRO | 33 | −10.800 |
| −3.297 | −1.493 | 1.00 | 0.00 | BrD | ATOM | 539 | HA | PRO | 33 | −11.693 |
| −2.959 | −1.999 | 1.00 | 0.00 | BrD | ATOM | 540 | CB | PRO | 33 | −10.947 |
| −3.057 | 0.017 | 1.00 | 0.00 | BrD | ATOM | 541 | HB1 | PRO | 33 | −10.191 |
| −2.357 | 0.341 | 1.00 | 0.00 | BrD | ATOM | 542 | HB2 | PRO | 33 | −11.926 |
| −2.646 | 0.219 | 1.00 | 0.00 | BrD | ATOM | 543 | CG | PRO | 33 | −10.771 |
| −4.386 | 0.685 | 1.00 | 0.00 | BrD | ATOM | 544 | HG1 | PRO | 33 | −11.713 |
| −4.744 | 1.048 | 1.00 | 0.00 | BrD | ATOM | 545 | HG2 | PRO | 33 | −10.075 |
| −4.288 | 1.505 | 1.00 | 0.00 | BrD | ATOM | 546 | CD | PRO | 33 | −10.223 |
| −5.333 | −0.337 | 1.00 | 0.00 | BrD | ATOM | 547 | HD1 | PRO | 33 | −10.632 |
| −6.319 | −0.205 | 1.00 | 0.00 | BrD | ATOM | 548 | HD2 | PRO | 33 | −9.165 |
| −5.358 | −0.254 | 1.00 | 0.00 | BrD | ATOM | 549 | C | PRO | 33 | −9.596 |
| −2.535 | −2.040 | 1.00 | 0.00 | BrD | ATOM | 550 | O | PRO | 33 | −9.687 |
| −1.343 | −2.332 | 1.00 | 0.00 | BrD | ATOM | 551 | N | PHE | 34 | −8.472 |
| −1.233 | −2.187 | 1.00 | 0.00 | BrD | ATOM | 552 | HN | PHE | 34 | −8.458 |
| −4.180 | −1.936 | 1.00 | 0.00 | BrD | ATOM | 553 | CA | PHE | 34 | −7.256 |
| −2.619 | −2.703 | 1.00 | 0.00 | BrD | ATOM | 554 | HA | PHE | 34 | −7.295 |
| −1.564 | −2.475 | 1.00 | 0.00 | BrD | ATOM | 555 | CB | PHE | 34 | −6.026 |
| −3.228 | −2.030 | 1.00 | 0.00 | BrD | ATOM | 556 | HB1 | PHE | 34 | −5.773 |
| −4.150 | −2.531 | 1.00 | 0.00 | BrD | ATOM | 557 | HB2 | PHE | 34 | −5.198 |
| −2.540 | −2.118 | 1.00 | 0.00 | BrD | ATOM | 558 | CG | PHE | 34 | −6.228 |
| −3.531 | −0.573 | 1.00 | 0.00 | BrD | ATOM | 559 | CD1 | PHE | 34 | −6.985 |
| −2.689 | 0.226 | 1.00 | 0.00 | BrD | ATOM | 560 | HD1 | PHE | 34 | −7.430 |
| −1.805 | −0.208 | 1.00 | 0.00 | BrD | ATOM | 561 | CD2 | PHE | 34 | −5.663 |
| −4.659 | −0.003 | 1.00 | 0.00 | BrD | ATOM | 562 | HD2 | PHE | 34 | −5.074 |
| −5.324 | −0.617 | 1.00 | 0.00 | BrD | ATOM | 563 | CE1 | PHE | 34 | −7.175 |
| −2.968 | 1.566 | 1.00 | 0.00 | BrD | ATOM | 564 | HE1 | PHE | 34 | −7.767 |
| −2.303 | 2.179 | 1.00 | 0.00 | BrD | ATOM | 565 | CE2 | PHE | 34 | −5.852 |
| −4.944 | 1.335 | 1.00 | 0.00 | BrD | ATOM | 566 | HE2 | PHE | 34 | −5.409 |
| −5.829 | 1.765 | 1.00 | 0.00 | BrD | ATOM | 567 | CZ | PHE | 34 | −6.607 |
| −4.098 | 2.122 | 1.00 | 0.00 | BrD | ATOM | 568 | HZ | PHE | 34 | −6.753 |
| −4.319 | 3.168 | 1.00 | 0.00 | BrD | ATOM | 569 | C | PHE | 34 | −7.150 |
| −2.790 | −4.213 | 1.00 | 0.00 | BrD | ATOM | 570 | O | PHE | 34 | −6.653 |
| −1.909 | −4.907 | 1.00 | 0.00 | BrD | ATOM | 571 | N | MET | 35 | −7.624 |
| −3.923 | −4.721 | 1.00 | 0.00 | BrD | ATOM | 572 | HN | MET | 35 | −8.000 |
| −4.598 | −4.119 | 1.00 | 0.00 | BrD | ATOM | 573 | CA | MET | 35 | −7.545 |
| −4.205 | −6.131 | 1.00 | 0.00 | BrD | ATOM | 574 | HA | MET | 35 | −6.600 |
| −3.825 | −6.507 | 1.00 | 0.00 | BrD | ATOM | 575 | CB | MET | 35 | −7.593 |
| −5.706 | −6.393 | 1.00 | 0.00 | BrD | ATOM | 576 | HB1 | MET | 35 | −7.670 |
| −5.889 | −7.454 | 1.00 | 0.00 | BrD | ATOM | 577 | HB2 | MET | 35 | −8.463 |
| −6.114 | −5.999 | 1.00 | 0.00 | BrD | ATOM | 578 | CG | MET | 35 | −6.367 |
| −6.423 | −5.871 | 1.00 | 0.00 | BrD | ATOM | 579 | HG1 | MET | 35 | −6.673 |
| −7.114 | −5.107 | 1.00 | 0.00 | BrD | ATOM | 580 | HG2 | MET | 35 | −5.696 |
| −5.692 | −5.444 | 1.00 | 0.00 | BrD | ATOM | 581 | SD | MET | 35 | −5.490 |
| −7.322 | −7.161 | 1.00 | 0.00 | BrD | ATOM | 582 | CE | MET | 35 | −4.032 |
| −6.298 | −7.337 | 1.00 | 0.00 | BrD | ATOM | 583 | HE1 | MET | 35 | −3.281 |
| −6.831 | −7.905 | 1.00 | 0.00 | BrD | ATOM | 584 | HE2 | MET | 35 | −3.639 |
| −6.062 | −6.358 | 1.00 | 0.00 | BrD | ATOM | 585 | HE3 | MET | 35 | −4.294 |
| −5.384 | −7.850 | 1.00 | 0.00 | BrD | ATOM | 586 | C | MET | 35 | −8.661 |
| −3.519 | −6.924 | 1.00 | 0.00 | BrD | ATOM | 587 | O | MET | 35 | −9.396 |
| −4.160 | −7.675 | 1.00 | 0.00 | BrD | ATOM | 588 | N | GLU | 36 | −8.749 |
| −2.208 | −6.762 | 1.00 | 0.00 | BrD | ATOM | 589 | HN | GLU | 36 | −8.116 |
| −1.765 | −6.164 | 1.00 | 0.00 | BrD | ATOM | 590 | CA | GLU | 36 | −9.751 |
| −1.407 | −7.457 | 1.00 | 0.00 | BrD | ATOM | 591 | HA | GLU | 36 | −9.531 |
| −1.453 | −8.515 | 1.00 | 0.00 | BrD | ATOM | 592 | CB | GLU | 36 | −11.156 |
| −1.964 | −7.207 | 1.00 | 0.00 | BrD | ATOM | 593 | HB1 | GLU | 36 | −11.084 |
| −3.018 | −6.987 | 1.00 | 0.00 | BrD | ATOM | 594 | HB2 | GLU | 36 | −11.581 |
| −1.458 | −6.354 | 1.00 | 0.00 | BrD | ATOM | 595 | CG | GLU | 36 | −12.099 |
| −1.787 | −8.385 | 1.00 | 0.00 | BrD | ATOM | 596 | HG1 | GLU | 36 | −11.527 |
| −1.466 | −9.243 | 1.00 | 0.00 | BrD | ATOM | 597 | HG2 | GLU | 36 | −12.569 |
| −2.735 | −8.600 | 1.00 | 0.00 | BrD | ATOM | 598 | CD | GLU | 36 | −13.182 |
| 0.761 | −8.114 | 1.00 | 0.00 | BrD | ATOM | 599 | OE1 | GLU | 36 | −12.865 |
| −0.447 | −8.098 | 1.00 | 0.00 | BrD | ATOM | 600 | OE2 | GLU | 36 | −14.368 |
| 1.165 | −7.919 | 1.00 | 0.00 | BrD | ATOM | 601 | C | GLU | 36 | −9.692 |
| 0.050 | −7.001 | 1.00 | 0.00 | BrD | ATOM | 602 | O | GLU | 36 | −10.470 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 0.471 | −6.145 | 1.00 | 0.00 | BrD | ATOM | 603 | N | PRO | 37 | −8.764 |
| 0.842 | −7.565 | 1.00 | 0.00 | BrD | ATOM | 604 | CA | PRO | 37 | −8.604 |
| 2.255 | −7.202 | 1.00 | 0.00 | BrD | ATOM | 605 | HA | PRO | 37 | −8.407 |
| 2.369 | −6.146 | 1.00 | 0.00 | BrD | ATOM | 606 | CB | PRO | 37 | −7.376 |
| 2.709 | −8.004 | 1.00 | 0.00 | BrD | ATOM | 607 | HB1 | PRO | 37 | −7.696 |
| 3.306 | −8.846 | 1.00 | 0.00 | BrD | ATOM | 608 | HB2 | PRO | 37 | −6.728 |
| 3.295 | −7.370 | 1.00 | 0.00 | BrD | ATOM | 609 | CG | PRO | 37 | −6.706 |
| 1.453 | −8.451 | 1.00 | 0.00 | BrD | ATOM | 610 | HG1 | PRO | 37 | −6.222 |
| 1.614 | −9.403 | 1.00 | 0.00 | BrD | ATOM | 611 | HG2 | PRO | 37 | −5.984 |
| 1.139 | −7.711 | 1.00 | 0.00 | BrD | ATOM | 612 | CD | PRO | 37 | −7.793 |
| 0.426 | −8.587 | 1.00 | 0.00 | BrD | ATOM | 613 | HD1 | PRO | 37 | −8.229 |
| −0.465 | −9.574 | 1.00 | 0.00 | BrD | ATOM | 614 | HD2 | PRO | 37 | −7.410 |
| 0.561 | −8.378 | 1.00 | 0.00 | BrD | ATOM | 615 | C | PRO | 37 | −9.822 |
| 3.093 | −7.576 | 1.00 | 0.00 | BrD | ATOM | 616 | O | PRO | 37 | −10.678 |
| 2.655 | −8.344 | 1.00 | 0.00 | BrD | ATOM | 617 | N | VAL | 38 | −9.892 |
| 4.301 | −7.025 | 1.00 | 0.00 | BrD | ATOM | 618 | HN | VAL | 38 | −9.179 |
| 4.594 | −6.422 | 1.00 | 0.00 | BrD | ATOM | 619 | CA | VAL | 38 | −11.006 |
| 5.206 | −7.300 | 1.00 | 0.00 | BrD | ATOM | 620 | HA | VAL | 38 | −11.709 |
| 4.683 | −7.931 | 1.00 | 0.00 | BrD | ATOM | 621 | CB | VAL | 38 | −11.750 |
| 5.646 | −6.012 | 1.00 | 0.00 | BrD | ATOM | 622 | HB | VAL | 38 | −11.449 |
| 6.657 | −5.781 | 1.00 | 0.00 | BrD | ATOM | 623 | CG1 | VAL | 38 | −11.395 |
| 4.767 | −4.819 | 1.00 | 0.00 | BrD | ATOM | 624 | HG11 | VAL | 38 | −11.888 |
| 5.145 | −3.935 | 1.00 | 0.00 | BrD | ATOM | 625 | HG12 | VAL | 38 | −10.326 |
| 4.779 | −4.667 | 1.00 | 0.00 | BrD | ATOM | 626 | HG13 | VAL | 38 | −11.721 |
| 3.755 | −5.008 | 1.00 | 0.00 | BrD | ATOM | 627 | CG2 | VAL | 38 | −13.253 |
| 5.646 | −6.246 | 1.00 | 0.00 | BrD | ATOM | 628 | HG21 | VAL | 38 | −13.760 |
| 5.374 | −5.333 | 1.00 | 0.00 | BrD | ATOM | 629 | HG22 | VAL | 38 | −13.497 |
| 4.934 | −7.020 | 1.00 | 0.00 | BrD | ATOM | 630 | HG23 | VAL | 38 | −13.570 |
| 6.629 | −6.553 | 1.00 | 0.00 | BrD | ATOM | 631 | C | VAL | 38 | −10.518 |
| 6.451 | −8.035 | 1.00 | 0.00 | BrD | ATOM | 632 | O | VAL | 38 | −9.410 |
| 6.473 | −8.571 | 1.00 | 0.00 | BrD | ATOM | 633 | N | LYS | 39 | −11.349 |
| 7.488 | −8.051 | 1.00 | 0.00 | BrD | ATOM | 634 | HN | LYS | 39 | −12.215 |
| 7.412 | −7.609 | 1.00 | 0.00 | BrD | ATOM | 635 | CA | LYS | 39 | −11.005 |
| 8.737 | −8.715 | 1.00 | 0.00 | BrD | ATOM | 636 | HA | LYS | 39 | −9.947 |
| 8.906 | −8.574 | 1.00 | 0.00 | BrD | ATOM | 637 | CB | LYS | 39 | −11.299 |
| 8.646 | −10.216 | 1.00 | 0.00 | BrD | ATOM | 638 | HB1 | LYS | 39 | −10.419 |
| 8.285 | −10.714 | 1.00 | 0.00 | BrD | ATOM | 639 | HB2 | LYS | 39 | −11.531 |
| 9.633 | −10.587 | 1.00 | 0.00 | BrD | ATOM | 640 | CG | LYS | 39 | −12.452 |
| 7.722 | −10.569 | 1.00 | 0.00 | BrD | ATOM | 641 | HG1 | LYS | 39 | −12.970 |
| 7.450 | −9.661 | 1.00 | 0.00 | BrD | ATOM | 642 | HG2 | LYS | 39 | −13.127 |
| 8.741 | −11.232 | 1.00 | 0.00 | BrD | ATOM | 643 | CD | LYS | 39 | −11.962 |
| 6.458 | −11.256 | 1.00 | 0.00 | BrD | ATOM | 644 | HD1 | LYS | 39 | −12.413 |
| 5.601 | −10.777 | 1.00 | 0.00 | BrD | ATOM | 645 | HD2 | LYS | 39 | −10.888 |
| 6.402 | −11.160 | 1.00 | 0.00 | BrD | ATOM | 646 | CE | LYS | 39 | −12.326 |
| 6.447 | −12.732 | 1.00 | 0.00 | BrD | ATOM | 647 | HE1 | LYS | 39 | −11.779 |
| 5.653 | −13.219 | 1.00 | 0.00 | BrD | ATOM | 648 | HE2 | LYS | 39 | −12.044 |
| 7.395 | −13.166 | 1.00 | 0.00 | BrD | ATOM | 649 | NZ | LYS | 39 | −13.784 |
| 6.232 | −12.965 | 1.00 | 0.00 | BrD | ATOM | 650 | HZ1 | LYS | 39 | −13.963 |
| 5.950 | −13.930 | 1.00 | 0.00 | BrD | ATOM | 651 | HZ2 | LYS | 39 | −14.307 |
| 7.108 | −12.783 | 1.00 | 0.00 | BrD | ATOM | 652 | HZ3 | LYS | 39 | −14.130 |
| 5.492 | −12.313 | 1.00 | 0.00 | BrD | ATOM | 653 | C | LYS | 39 | −11.772 |
| 9.903 | −8.105 | 1.00 | 0.00 | BrD | ATOM | 654 | O | LYS | 39 | −12.687 |
| 9.739 | −7.116 | 1.00 | 0.00 | BrD | ATOM | 655 | N | ARG | 40 | −11.626 |
| 11.078 | −8.706 | 1.00 | 0.00 | BrD | ATOM | 656 | HN | ARG | 40 | −11.040 |
| 11.146 | −9.888 | 1.00 | 0.00 | BrD | ATOM | 657 | CA | ARG | 40 | −12.304 |
| 12.273 | −8.223 | 1.00 | 0.00 | BrD | ATOM | 658 | HA | ARG | 40 | −12.018 |
| 12.419 | −7.191 | 1.00 | 0.00 | BrD | ATOM | 659 | CB | ARG | 40 | −11.856 |
| 13.492 | −9.037 | 1.00 | 0.00 | BrD | ATOM | 660 | HB1 | ARG | 40 | −12.313 |
| 13.435 | −10.019 | 1.00 | 0.00 | BrD | ATOM | 661 | HB2 | ARG | 40 | −10.792 |
| 13.476 | −9.139 | 1.00 | 0.00 | BrD | ATOM | 662 | CG | ARG | 40 | −12.265 |
| 14.819 | −8.410 | 1.00 | 0.00 | BrD | ATOM | 663 | HG1 | ARG | 40 | −12.664 |
| 14.634 | −7.424 | 1.00 | 0.00 | BrD | ATOM | 664 | HG2 | ARG | 40 | −13.020 |
| 15.285 | −9.025 | 1.00 | 0.00 | BrD | ATOM | 665 | CD | ARG | 40 | −11.075 |
| 15.759 | −8.292 | 1.00 | 0.00 | BrD | ATOM | 666 | HD1 | ARG | 40 | −10.715 |
| 15.988 | −9.284 | 1.00 | 0.00 | BrD | ATOM | 667 | HD2 | ARG | 40 | −10.296 |
| 15.263 | −7.732 | 1.00 | 0.00 | BrD | ATOM | 668 | NE | ARG | 40 | −11.426 |
| 17.004 | −7.616 | 1.00 | 0.00 | BrD | ATOM | 669 | HE | ARG | 40 | −11.554 |
| 17.802 | −8.171 | 1.00 | 0.00 | BrD | ATOM | 670 | CZ | ARG | 40 | −11.577 |
| 17.109 | −6.300 | 1.00 | 0.00 | BrD | ATOM | 671 | NH1 | ARG | 40 | −11.409 |
| 16.047 | −5.525 | 1.00 | 0.00 | BrD | ATOM | 672 | HH11 | ARG | 40 | −11.168 |
| 15.165 | −5.930 | 1.00 | 0.00 | BrD | ATOM | 673 | HH12 | ARG | 40 | −11.523 |
| 16.127 | −4.535 | 1.00 | 0.00 | BrD | ATOM | 674 | NH2 | ARG | 40 | −11.897 |
| 18.276 | −5.758 | 1.00 | 0.00 | BrD | ATOM | 675 | HH21 | ARG | 40 | −12.011 |
| 18.353 | −4.767 | 1.00 | 0.00 | BrD | ATOM | 676 | HH22 | ARG | 40 | −12.025 |
| 19.079 | −6.339 | 1.00 | 0.00 | BrD | ATOM | 677 | C | ARG | 40 | −13.824 |
| 12.123 | −8.293 | 1.00 | 0.00 | BrD | ATOM | 678 | O | ARG | 40 | −14.556 |

TABLE 6-continued

Atomic Structure Coordinates of the
P/CAF Bromodomain/Acetyl-Histamine Complex

| | | | | | | | | | | |
|---|---|---|---|---|---|---|---|---|---|---|
| 12.915 | −7.700 | 1.00 | 0.00 | BrD | ATOM | 679 | N | THR | 41 | −14.301 |
| 11.109 | −9.017 | 1.00 | 0.00 | BrD | ATOM | 680 | HN | THR | 41 | −13.680 |
| 10.511 | −9.481 | 1.00 | 0.00 | BrD | ATOM | 681 | CA | THR | 41 | −15.737 |
| 10.898 | −9.159 | 1.00 | 0.00 | BrD | ATOM | 682 | HA | THR | 41 | −16.228 |
| 11.725 | −8.681 | 1.00 | 0.00 | BrD | ATOM | 683 | CB | THR | 41 | −16.133 |
| 10.870 | −10.637 | 1.00 | 0.00 | BrD | ATOM | 684 | HB | THR | 41 | −15.862 |
| 11.812 | −11.090 | 1.00 | 0.00 | BrD | ATOM | 685 | OG1 | THR | 41 | −17.533 |
| 10.696 | −10.775 | 1.00 | 0.00 | BrD | ATOM | 686 | HG1 | THR | 41 | −17.988 |
| 11.239 | −10.127 | 1.00 | 0.00 | BrD | ATOM | 687 | CG2 | THR | 41 | −15.453 |
| 9.771 | −11.421 | 1.00 | 0.00 | BrD | ATOM | 688 | HG21 | THR | 41 | −14.431 |
| 9.669 | −11.083 | 1.00 | 0.00 | BrD | ATOM | 689 | HG22 | THR | 41 | −15.462 |
| 10.020 | −12.472 | 1.00 | 0.00 | BrD | ATOM | 690 | HG23 | THR | 41 | −15.979 |
| 8.841 | −11.267 | 1.00 | 0.00 | BrD | ATOM | 691 | C | THR | 41 | −16.197 |
| 9.623 | −8.467 | 1.00 | 0.00 | BrD | ATOM | 692 | O | THR | 41 | −17.123 |
| 9.656 | −7.658 | 1.00 | 0.00 | BrD | ATOM | 693 | N | GLU | 42 | −15.573 |
| 8.498 | −8.792 | 1.00 | 0.00 | BrD | ATOM | 694 | HN | GLU | 42 | −14.835 |
| 8.521 | −9.435 | 1.00 | 0.00 | BrD | ATOM | 695 | CA | GLU | 42 | −15.940 |
| 7.236 | −8.163 | 1.00 | 0.00 | BrD | ATOM | 696 | HA | GLU | 42 | −16.954 |
| 7.002 | −8.454 | 1.00 | 0.00 | BrD | ATOM | 697 | CB | GLU | 42 | −15.013 |
| 6.109 | −8.623 | 1.00 | 0.00 | BrD | ATOM | 698 | HB1 | GLU | 42 | −15.239 |
| 5.220 | −8.053 | 1.00 | 0.00 | BrD | ATOM | 699 | HB2 | GLU | 42 | −13.993 |
| 6.398 | −8.431 | 1.00 | 0.00 | BrD | ATOM | 700 | CG | GLU | 42 | −15.142 |
| 5.774 | −10.098 | 1.00 | 0.00 | BrD | ATOM | 701 | HG1 | GLU | 42 | −14.286 |
| 5.191 | −10.396 | 1.00 | 0.00 | BrD | ATOM | 702 | HG2 | GLU | 42 | −15.166 |
| 6.694 | −10.663 | 1.00 | 0.00 | BrD | ATOM | 703 | CD | GLU | 42 | −16.397 |
| 4.982 | −10.409 | 1.00 | 0.00 | BrD | ATOM | 704 | OE1 | GLU | 42 | −17.489 |
| 5.589 | −10.443 | 1.00 | 0.00 | BrD | ATOM | 705 | OE2 | GLU | 42 | −16.289 |
| 3.756 | −10.620 | 1.00 | 0.00 | BrD | ATOM | 706 | C | GLU | 42 | −15.881 |
| 7.374 | −6.647 | 1.00 | 0.00 | BrD | ATOM | 707 | O | GLU | 42 | −16.614 |
| 6.703 | −5.920 | 1.00 | 0.00 | BrD | ATOM | 708 | N | ALA | 43 | −15.028 |
| 8.279 | −6.181 | 1.00 | 0.00 | BrD | ATOM | 709 | HN | ALA | 43 | −14.457 |
| 8.774 | −6.817 | 1.00 | 0.00 | BrD | ATOM | 710 | CA | ALA | 43 | −14.861 |
| 8.509 | −4.752 | 1.00 | 0.00 | BrD | ATOM | 711 | HA | ALA | 43 | −15.712 |
| 8.080 | −4.245 | 1.00 | 0.00 | BrD | ATOM | 712 | CB | ALA | 43 | −13.609 |
| 7.810 | −4.245 | 1.00 | 0.00 | BrD | ATOM | 713 | HB1 | ALA | 43 | −12.893 |
| 7.731 | −5.049 | 1.00 | 0.00 | BrD | ATOM | 714 | HB2 | ALA | 43 | −13.866 |
| 6.822 | −3.893 | 1.00 | 0.00 | BrD | ATOM | 715 | HB3 | ALA | 43 | −13.180 |
| 8.381 | −3.435 | 1.00 | 0.00 | BrD | ATOM | 716 | C | ALA | 43 | −14.799 |
| 10.002 | −4.440 | 1.00 | 0.00 | BrD | ATOM | 717 | O | ALA | 43 | −13.721 |
| 10.555 | −4.222 | 1.00 | 0.00 | BrD | ATOM | 718 | N | PRO | 44 | −15.962 |
| 10.676 | −4.414 | 1.00 | 0.00 | BrD | ATOM | 719 | CA | PRO | 44 | −16.038 |
| 12.114 | −4.129 | 1.00 | 0.00 | BrD | ATOM | 720 | HA | PRO | 44 | −15.511 |
| 12.692 | −4.874 | 1.00 | 0.00 | BrD | ATOM | 721 | CB | PRO | 44 | −17.539 |
| 12.422 | −4.207 | 1.00 | 0.00 | BrD | ATOM | 722 | HB1 | PRO | 44 | −17.688 |
| 3.369 | −4.704 | 1.00 | 0.00 | BrD | ATOM | 723 | HB2 | PRO | 44 | −17.951 |
| 12.465 | −3.210 | 1.00 | 0.00 | BrD | ATOM | 724 | CG | PRO | 44 | −18.125 |
| 11.298 | −4.991 | 1.00 | 0.00 | BrD | ATOM | 725 | HG1 | PRO | 44 | −18.071 |
| 11.518 | −6.047 | 1.00 | 0.00 | BrD | ATOM | 726 | HG2 | PRO | 44 | −19.150 |
| 11.137 | −4.692 | 1.00 | 0.00 | BrD | ATOM | 727 | CD | PRO | 44 | −17.291 |
| 10.095 | −4.665 | 1.00 | 0.00 | BrD | ATOM | 728 | HD1 | PRO | 44 | −17.264 |
| 9.413 | −5.500 | 1.00 | 0.00 | BrD | ATOM | 729 | HD2 | PRO | 44 | −17.668 |
| 9.601 | −3.783 | 1.00 | 0.00 | BrD | ATOM | 730 | C | PRO | 44 | −15.498 |
| 12.458 | −2.746 | 1.00 | 0.00 | BrD | ATOM | 731 | O | PRO | 44 | −16.262 |
| 12.635 | −1.797 | 1.00 | 0.00 | BrD | ATOM | 732 | N | GLY | 45 | −14.177 |
| 12.551 | −2.637 | 1.00 | 0.00 | BrD | ATOM | 733 | HN | GLY | 45 | −13.617 |
| 12.400 | −3.427 | 1.00 | 0.00 | BrD | ATOM | 734 | CA | GLY | 45 | −13.560 |
| 12.875 | −1.365 | 1.00 | 0.00 | BrD | ATOM | 735 | HA1 | GLY | 45 | −13.586 |
| 13.946 | −1.228 | 1.00 | 0.00 | BrD | ATOM | 736 | HA2 | GLY | 45 | −14.128 |
| 12.409 | −0.573 | 1.00 | 0.00 | BrD | ATOM | 737 | C | GLY | 45 | −12.121 |
| 12.405 | −1.278 | 1.00 | 0.00 | BrD | ATOM | 738 | O | GLY | 45 | −11.333 |
| 12.942 | −0.499 | 1.00 | 0.00 | BrD | ATOM | 739 | N | TYR | 46 | −11.777 |
| 11.403 | −2.081 | 1.00 | 0.00 | BrD | ATOM | 740 | HN | TYR | 46 | −12.450 |
| 11.015 | −2.678 | 1.00 | 0.00 | BrD | ATOM | 741 | CA | TYR | 46 | −10.423 |
| 10.861 | −2.089 | 1.00 | 0.00 | BrD | ATOM | 742 | HA | TYR | 46 | −10.271 |
| 10.337 | −1.158 | 1.00 | 0.00 | BrD | ATOM | 743 | CB | TYR | 46 | −10.255 |
| 9.878 | −3.249 | 1.00 | 0.00 | BrD | ATOM | 744 | HB1 | TYR | 46 | −11.073 |
| 10.006 | −3.942 | 1.00 | 0.00 | BrD | ATOM | 745 | HB2 | TYR | 46 | −9.324 |
| 10.084 | −3.755 | 1.00 | 0.00 | BrD | ATOM | 746 | CG | TYR | 46 | −10.237 |
| 8.431 | −2.814 | 1.00 | 0.00 | BrD | ATOM | 747 | CD1 | TYR | 46 | −9.262 |
| 7.558 | −3.279 | 1.00 | 0.00 | BrD | ATOM | 748 | HD1 | TYR | 46 | −8.511 |
| 7.926 | −3.962 | 1.00 | 0.00 | BrD | ATOM | 749 | CD2 | TYR | 46 | −11.194 |
| 7.938 | −1.935 | 1.00 | 0.00 | BrD | ATOM | 750 | HD2 | TYR | 46 | −11.958 |
| 8.605 | −1.564 | 1.00 | 0.00 | BrD | ATOM | 751 | CE1 | TYR | 46 | −9.242 |
| 6.235 | −2.884 | 1.00 | 0.00 | BrD | ATOM | 752 | HE1 | TYR | 46 | −8.474 |
| 5.572 | −3.254 | 1.00 | 0.00 | BrD | ATOM | 753 | CE2 | TYR | 46 | −11.180 |
| 6.617 | −1.534 | 1.00 | 0.00 | BrD | ATOM | 754 | HE2 | TYR | 46 | −11.933 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 6.253 | −0.850 | 1.00 | 0.00 | BrD | ATOM | 755 | CZ | TYR | 46 | −10.203 |
| 5.769 | −2.010 | 1.00 | 0.00 | BrD | ATOM | 756 | OH | TYR | 46 | −10.186 |
| 4.452 | −1.612 | 1.00 | 0.00 | BrD | ATOM | 757 | HH | TYR | 46 | −9.895 |
| 4.397 | −0.699 | 1.00 | 0.00 | BrD | ATOM | 758 | C | TYR | 46 | −9.386 |
| 11.975 | −2.200 | 1.00 | 0.00 | BrD | ATOM | 759 | O | TYR | 46 | −9.727 |
| 13.132 | −2.446 | 1.00 | 0.00 | BrD | ATOM | 760 | N | TYR | 47 | −8.120 |
| 11.618 | −2.014 | 1.00 | 0.00 | BrD | ATOM | 761 | HN | TYR | 47 | −7.911 |
| 10.680 | −1.823 | 1.00 | 0.00 | BrD | ATOM | 762 | CA | TYR | 47 | −7.033 |
| 12.587 | −2.097 | 1.00 | 0.00 | BrD | ATOM | 763 | HA | TYR | 47 | −6.102 |
| 12.042 | −2.050 | 1.00 | 0.00 | BrD | ATOM | 764 | CB | TYR | 47 | −7.099 |
| 13.345 | −3.424 | 1.00 | 0.00 | BrD | ATOM | 765 | HB1 | TYR | 47 | −7.889 |
| 14.080 | −3.370 | 1.00 | 0.00 | BrD | ATOM | 766 | HB2 | TYR | 47 | −6.158 |
| 13.848 | −3.590 | 1.00 | 0.00 | BrD | ATOM | 767 | CG | TYR | 47 | −7.370 |
| 12.459 | −4.619 | 1.00 | 0.00 | BrD | ATOM | 768 | CD1 | TYR | 47 | −8.056 |
| 12.946 | −5.725 | 1.00 | 0.00 | BrD | ATOM | 769 | HD1 | TYR | 47 | −8.397 |
| 13.971 | −5.722 | 1.00 | 0.00 | BrD | ATOM | 770 | CD2 | TYR | 47 | −6.940 |
| 11.137 | −4.644 | 1.00 | 0.00 | BrD | ATOM | 771 | HD2 | TYR | 47 | −6.405 |
| 10.742 | −3.792 | 1.00 | 0.00 | BrD | ATOM | 772 | CE1 | TYR | 47 | −8.306 |
| 12.143 | −6.821 | 1.00 | 0.00 | BrD | ATOM | 773 | HE1 | TYR | 47 | −8.841 |
| 12.540 | −7.671 | 1.00 | 0.00 | BrD | ATOM | 774 | CH2 | TYR | 47 | −7.186 |
| 10.328 | −5.738 | 1.00 | 0.00 | BrD | ATOM | 775 | HE2 | TYR | 47 | −6.845 |
| 9.303 | −5.739 | 1.00 | 0.00 | BrD | ATOM | 776 | CZ | TYR | 47 | −7.870 |
| 10.835 | −6.823 | 1.00 | 0.00 | BrD | ATOM | 777 | OH | TYR | 47 | −8.117 |
| 10.032 | −7.912 | 1.00 | 0.00 | BrD | ATOM | 778 | HH | TYR | 47 | −7.572 |
| 10.317 | −8.650 | 1.00 | 0.00 | BrD | ATOM | 779 | C | TYR | 47 | −7.085 |
| 13.572 | −0.933 | 1.00 | 0.00 | BrD | ATOM | 780 | O | TYR | 47 | −6.183 |
| 13.605 | −0.095 | 1.00 | 0.00 | BrD | ATOM | 781 | N | GLU | 48 | −8.144 |
| 14.376 | −0.887 | 1.00 | 0.00 | BrD | ATOM | 782 | HN | GLU | 48 | −8.830 |
| 14.304 | −1.584 | 1.00 | 0.00 | BrD | ATOM | 783 | CA | GLU | 48 | −8.309 |
| 15.365 | 0.174 | 1.00 | 0.00 | BrD | ATOM | 784 | HA | GLU | 48 | −7.569 |
| 16.138 | 0.024 | 1.00 | 0.00 | BrD | ATOM | 785 | CB | GLU | 48 | −9.704 |
| 15.991 | 0.104 | 1.00 | 0.00 | BrD | ATOM | 786 | HB1 | GLU | 48 | −9.746 |
| 16.827 | 0.786 | 1.00 | 0.00 | BrD | ATOM | 787 | HB2 | GLU | 48 | −10.432 |
| 15.254 | 0.408 | 1.00 | 0.00 | BrD | ATOM | 788 | CG | GLU | 48 | −10.079 |
| 16.488 | −1.283 | 1.00 | 0.00 | BrD | ATOM | 789 | HG1 | GLU | 48 | −9.268 |
| 17.086 | −1.669 | 1.00 | 0.00 | BrD | ATOM | 790 | HG2 | GLU | 48 | −10.235 |
| 15.635 | −1.927 | 1.00 | 0.00 | BrD | ATOM | 791 | CG | GLU | 48 | −11.341 |
| 17.328 | −1.282 | 1.00 | 0.00 | BrD | ATOM | 792 | OE1 | GLU | 48 | −12.059 |
| 17.320 | −1.260 | 1.00 | 0.00 | BrD | ATOM | 793 | OE2 | GLU | 48 | −11.612 |
| 17.994 | −2.304 | 1.00 | 0.00 | BrD | ATOM | 794 | C | GLU | 48 | −8.091 |
| 14.736 | 1.547 | 1.00 | 0.00 | BrD | ATOM | 795 | O | GLU | 48 | −7.683 |
| 15.410 | 2.493 | 1.00 | 0.00 | BrD | ATOM | 796 | N | VAL | 49 | −8.360 |
| 13.439 | 1.645 | 1.00 | 0.00 | BrD | ATOM | 797 | HN | VAL | 49 | −8.682 |
| 12.958 | 0.854 | 1.00 | 0.00 | BrD | ATOM | 798 | CA | VAL | 49 | −8.192 |
| 12.712 | 2.899 | 1.00 | 0.00 | BrD | ATOM | 799 | HA | VAL | 49 | −7.919 |
| 13.423 | 3.665 | 1.00 | 0.00 | BrD | ATOM | 800 | CB | VAL | 49 | −9.495 |
| 12.010 | 3.332 | 1.00 | 0.00 | BrD | ATOM | 801 | HB | VAL | 49 | −9.555 |
| 11.964 | 2.815 | 1.00 | 0.00 | BrD | ATOM | 802 | CG1 | VAL | 49 | −10.713 |
| 12.834 | 2.949 | 1.00 | 0.00 | BrD | ATOM | 803 | HG11 | VAL | 49 | −11.006 |
| 12.591 | 1.937 | 1.00 | 0.00 | BrD | ATOM | 804 | HG12 | VAL | 49 | −10.472 |
| 13.984 | 3.011 | 1.00 | 0.00 | BrD | ATOM | 805 | HG13 | VAL | 49 | −11.526 |
| 12.609 | 3.622 | 1.00 | 0.00 | BrD | ATOM | 806 | CG2 | VAL | 49 | −9.475 |
| 11.729 | 4.827 | 1.00 | 0.00 | BrD | ATOM | 807 | HG21 | VAL | 49 | −9.393 |
| 12.661 | 5.367 | 1.00 | 0.00 | BrD | ATOM | 808 | HG22 | VAL | 49 | −8.628 |
| 11.101 | 5.062 | 1.00 | 0.00 | BrD | ATOM | 809 | HG23 | VAL | 49 | −10.387 |
| 11.226 | 5.111 | 1.00 | 0.00 | BrD | ATOM | 810 | C | VAL | 49 | −7.100 |
| 11.656 | 2.787 | 1.00 | 0.00 | BrD | ATOM | 811 | O | VAL | 49 | −6.592 |
| 11.167 | 3.797 | 1.00 | 0.00 | BrD | ATOM | 812 | N | ILE | 50 | −6.763 |
| 11.281 | 1.558 | 1.00 | 0.00 | BrD | ATOM | 813 | HN | ILE | 50 | −7.214 |
| 11.686 | 0.792 | 1.00 | 0.00 | BrD | ATOM | 814 | CA | ILE | 50 | −5.769 |
| 10.245 | 1.324 | 1.00 | 0.00 | BrD | ATOM | 815 | HA | ILE | 50 | −5.542 |
| 9.783 | 2.274 | 1.00 | 0.00 | BrD | ATOM | 816 | CB | ILE | 50 | −6.291 |
| 9.152 | 0.366 | 1.00 | 0.00 | BrD | ATOM | 817 | HB | ILE | 50 | −6.001 |
| 9.428 | −0.635 | 1.00 | 0.00 | BrD | ATOM | 818 | CG1 | ILE | 50 | −7.818 |
| 9.035 | 0.436 | 1.00 | 0.00 | BrD | ATOM | 819 | HG11 | ILE | 50 | −8.256 |
| 10.011 | 0.288 | 1.00 | 0.00 | BrD | ATOM | 820 | HG12 | ILE | 50 | −8.358 |
| 8.371 | −0.344 | 1.00 | 0.00 | BrD | ATOM | 821 | CG2 | ILE | 50 | −5.644 |
| 7.815 | 0.684 | 1.00 | 0.00 | BrD | ATOM | 822 | HG21 | ILE | 50 | −5.450 |
| 7.264 | −0.233 | 1.00 | 0.00 | BrD | ATOM | 823 | HG22 | ILE | 50 | −6.289 |
| 7.250 | 1.339 | 1.00 | 0.00 | BrD | ATOM | 824 | HG23 | ILE | 50 | −4.694 |
| 7.981 | 1.169 | 1.00 | 0.00 | BrD | ATOM | 825 | CD1 | ILE | 50 | −8.324 |
| 8.499 | 1.757 | 1.00 | 0.00 | BrD | ATOM | 826 | HD11 | ILE | 50 | −8.330 |
| 9.293 | 2.489 | 1.00 | 0.00 | BrD | ATOM | 827 | HD12 | ILE | 50 | −7.674 |
| 7.704 | 2.094 | 1.00 | 0.00 | BrD | ATOM | 828 | HD13 | ILE | 50 | −9.326 |
| 8.116 | 1.631 | 1.00 | 0.00 | BrD | ATOM | 829 | C | ILE | 50 | −4.490 |
| 10.827 | 0.738 | 1.00 | 0.00 | BrD | ATOM | 830 | O | ILE | 50 | −4.450 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 11.444 | −0.327 | 1.00 | 0.00 | BrD | ATOM | 831 | N | ARG | 51 | −3.384 |
| 10.597 | 1.428 | 1.00 | 0.00 | BrD | ATOM | 832 | HN | ARG | 51 | −3.443 |
| 10.086 | 2.260 | 1.00 | 0.00 | BrD | ATOM | 833 | CA | ARG | 51 | −2.082 |
| 11.061 | 0.969 | 1.00 | 0.00 | BrD | ATOM | 834 | HA | ARG | 51 | −2.068 |
| 12.139 | 1.024 | 1.00 | 0.00 | BrD | ATOM | 835 | CB | ARG | 51 | −0.988 |
| 10.491 | 1.870 | 1.00 | 0.00 | BrD | ATOM | 836 | HB1 | ARG | 51 | −1.452 |
| 10.081 | 2.754 | 1.00 | 0.00 | BrD | ATOM | 837 | HB2 | ARG | 51 | −0.478 |
| 9.698 | 1.341 | 1.00 | 0.00 | BrD | ATOM | 838 | CG | ARG | 51 | 0.048 |
| 11.516 | 2.301 | 1.00 | 0.00 | BrD | ATOM | 839 | HG1 | ARG | 51 | −0.399 |
| 12.185 | 3.022 | 1.00 | 0.00 | BrD | ATOM | 840 | HG2 | ARG | 51 | 0.883 |
| 11.000 | 2.753 | 1.00 | 0.00 | BrD | ATOM | 841 | CD | ARG | 51 | 0.552 |
| 12.329 | 2.120 | 1.00 | 0.00 | BrD | ATOM | 842 | HD1 | ARG | 51 | 0.514 |
| 11.713 | 0.233 | 1.00 | 0.00 | BrD | ATOM | 843 | HD2 | ARG | 51 | −0.090 |
| 13.187 | 0.989 | 1.00 | 0.00 | BrD | ATOM | 844 | NE | ARG | 51 | 1.923 |
| 12.789 | 1.318 | 1.00 | 0.00 | BrD | ATOM | 845 | HE | ARG | 51 | 2.296 |
| 12.730 | 2.222 | 1.00 | 0.00 | BrD | ATOM | 846 | CZ | ARG | 51 | 2.683 |
| 13.279 | 0.344 | 1.00 | 0.00 | BrD | ATOM | 847 | NH1 | ARG | 51 | 3.921 |
| 13.678 | 0.602 | 1.00 | 0.00 | BrD | ATOM | 848 | HH11 | ARG | 51 | 4.491 |
| 14.046 | −0.132 | 1.00 | 0.00 | BrD | ATOM | 849 | HH12 | ARG | 51 | 4.286 |
| 13.610 | 1.532 | 1.00 | 0.00 | BrD | ATOM | 850 | NH2 | ARG | 51 | 2.206 |
| 13.372 | −0.890 | 1.00 | 0.00 | BrD | ATOM | 851 | HH21 | ARG | 51 | 2.779 |
| 13.739 | −1.522 | 1.00 | 0.00 | BrD | ATOM | 852 | HH22 | ARG | 51 | 1.273 |
| 13.071 | −1.089 | 1.00 | 0.00 | BrD | ATOM | 853 | C | ARG | 51 | −1.836 |
| 10.632 | −0.471 | 1.00 | 0.00 | BrD | ATOM | 854 | O | ARG | 51 | −1.644 |
| 11.461 | −1.360 | 1.00 | 0.00 | BrD | ATOM | 855 | N | SER | 52 | −1.843 |
| 9.322 | −0.687 | 1.00 | 0.00 | BrD | ATOM | 856 | HN | SER | 52 | −2.010 |
| 8.718 | 0.067 | 1.00 | 0.00 | BrD | ATOM | 857 | CA | SER | 52 | −1.634 |
| 8.752 | −2.012 | 1.00 | 0.00 | BrD | ATOM | 858 | HA | SER | 52 | −1.991 |
| 9.462 | −2.740 | 1.00 | 0.00 | BrD | ATOM | 859 | CB | SER | 52 | −0.145 |
| 8.497 | −2.253 | 1.00 | 0.00 | BrD | ATOM | 860 | HB1 | SER | 52 | 0.426 |
| 8.900 | −1.430 | 1.00 | 0.00 | BrD | ATOM | 861 | HB2 | SER | 52 | 0.028 |
| 7.433 | −2.325 | 1.00 | 0.00 | BrD | ATOM | 862 | CG | SER | 52 | 0.290 |
| 9.112 | −3.453 | 1.00 | 0.00 | BrD | ATOM | 863 | HG | SER | 52 | −0.218 |
| 8.768 | −4.192 | 1.00 | 0.00 | BrD | ATOM | 864 | C | SER | 52 | −2.415 |
| 7.450 | −2.148 | 1.00 | 0.00 | BrD | ATOM | 865 | O | SER | 52 | −1.912 |
| 6.382 | −1.801 | 1.00 | 0.00 | BrD | ATOM | 866 | N | PRO | 53 | −3.675 |
| 7.518 | −2.619 | 1.00 | 0.00 | BrD | ATOM | 867 | CA | PRO | 53 | −4.531 |
| 6.344 | −2.745 | 1.00 | 0.00 | BrD | ATOM | 868 | HA | PRO | 53 | −4.993 |
| 6.101 | −1.800 | 1.00 | 0.00 | BrD | ATOM | 869 | CB | PRO | 53 | −5.620 |
| 6.776 | −3.738 | 1.00 | 0.00 | BrD | ATOM | 870 | HB1 | PRO | 53 | −5.555 |
| 6.173 | −4.630 | 1.00 | 0.00 | BrD | ATOM | 871 | HB2 | PRO | 53 | −6.590 |
| 6.638 | −3.284 | 1.00 | 0.00 | BrD | ATOM | 872 | CG | PRO | 53 | −5.371 |
| 8.224 | −4.043 | 1.00 | 0.00 | BrD | ATOM | 873 | HG1 | PRO | 53 | −6.296 |
| 8.775 | −3.959 | 1.00 | 0.00 | BrD | ATOM | 874 | HG2 | PRO | 53 | −4.969 |
| 8.321 | −5.041 | 1.00 | 0.00 | BrD | ATOM | 875 | CD | PRO | 53 | −4.377 |
| 8.735 | −3.034 | 1.00 | 0.00 | BrD | ATOM | 876 | HD1 | PRO | 53 | −4.886 |
| 9.191 | −2.200 | 1.00 | 0.00 | BrD | ATOM | 877 | HD2 | PRO | 53 | −3.704 |
| 9.437 | −3.398 | 1.00 | 0.00 | BrD | ATOM | 878 | C | PRO | 53 | −3.770 |
| 5.120 | −3.252 | 1.00 | 0.00 | BrD | ATOM | 879 | O | PRO | 53 | −3.456 |
| 4.218 | −2.475 | 1.00 | 0.00 | BrD | ATOM | 880 | N | MET | 54 | −3.471 |
| 5.089 | −4.553 | 1.00 | 0.00 | BrD | ATOM | 881 | HN | MET | 54 | −3.738 |
| 5.838 | −5.124 | 1.00 | 0.00 | BrD | ATOM | 882 | CA | MET | 54 | −2.734 |
| 3.970 | −5.149 | 1.00 | 0.00 | BrD | ATOM | 883 | HA | MET | 54 | −2.905 |
| 3.995 | −6.215 | 1.00 | 0.00 | BrD | ATOM | 884 | CB | MET | 54 | −1.236 |
| 4.127 | −4.877 | 1.00 | 0.00 | BrD | ATOM | 885 | HB1 | MET | 54 | −0.936 |
| 5.129 | −5.145 | 1.00 | 0.00 | BrD | ATOM | 886 | HB2 | MET | 54 | −1.057 |
| 3.978 | −3.822 | 1.00 | 0.00 | BrD | ATOM | 887 | CG | MET | 54 | −0.368 |
| 3.147 | −5.649 | 1.00 | 0.00 | BrD | ATOM | 888 | HG1 | MET | 54 | −0.510 |
| 2.160 | −5.235 | 1.00 | 0.00 | BrD | ATOM | 889 | HG2 | MET | 54 | 0.666 |
| 3.438 | −5.537 | 1.00 | 0.00 | BrD | ATOM | 890 | SD | MET | 54 | −0.767 |
| 3.101 | −7.407 | 1.00 | 0.00 | BrD | ATOM | 891 | CE | MET | 54 | −2.176 |
| 1.995 | −7.401 | 1.00 | 0.00 | BrD | ATOM | 892 | HE1 | MET | 54 | −2.086 |
| 1.294 | −8.214 | 1.00 | 0.00 | BrD | ATOM | 893 | HE2 | MET | 54 | −3.085 |
| 2.567 | −7.518 | 1.00 | 0.00 | BrD | ATOM | 894 | HE3 | MET | 54 | −2.208 |
| 1.457 | −6.665 | 1.00 | 0.00 | BrD | ATOM | 895 | C | MET | 54 | −3.229 |
| 2.630 | −4.602 | 1.00 | 0.00 | BrD | ATOM | 896 | O | MET | 54 | −2.556 |
| 1.990 | −3.795 | 1.00 | 0.00 | BrD | ATOM | 897 | N | ASP | 55 | −4.422 |
| 2.232 | −5.029 | 1.00 | 0.00 | BrD | ATOM | 898 | HN | ASP | 55 | −4.919 |
| 2.803 | −5.652 | 1.00 | 0.00 | BrD | ATOM | 899 | CA | ASP | 55 | −5.045 |
| 1.005 | −4.544 | 1.00 | 0.00 | BrD | ATOM | 900 | HA | ASP | 55 | −5.236 |
| 1.142 | −3.490 | 1.00 | 0.00 | BrD | ATOM | 901 | CB | ASP | 55 | −6.391 |
| −0.793 | −5.249 | 1.00 | 0.00 | BrD | ATOM | 902 | HB1 | ASP | 55 | −6.327 |
| 0.045 | −5.917 | 1.00 | 0.00 | BrD | ATOM | 903 | HB2 | ASP | 55 | −6.631 |
| 1.679 | −5.817 | 1.00 | 0.00 | BrD | ATOM | 904 | CG | ASP | 55 | −7.520 |
| −0.536 | −4.249 | 1.00 | 0.00 | BrD | ATOM | 905 | OD1 | ASP | 55 | −8.426 |
| 0.256 | −4.602 | 1.00 | 0.00 | BrD | ATOM | 906 | OD2 | ASP | 55 | −7.496 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −1.126 | −3.169 | 1.00 | 0.00 | BrD | ATOM | 907 | C | ASP | 55 | −4.121 |
| −0.212 | −4.704 | 1.00 | 0.00 | BrD | ATOM | 908 | O | ASP | 55 | −3.406 |
| −0.570 | −3.772 | 1.00 | 0.00 | BrD | ATOM | 909 | N | LEU | 56 | −4.142 |
| −0.856 | −5.870 | 1.00 | 0.00 | BrD | ATOM | 910 | HN | LEU | 56 | −4.715 |
| −0.533 | −6.586 | 1.00 | 0.00 | BrD | ATOM | 911 | CA | LEU | 56 | −3.306 |
| −2.030 | −6.111 | 1.00 | 0.00 | BrD | ATOM | 912 | HA | LEU | 56 | −2.301 |
| −1.790 | −5.810 | 1.00 | 0.00 | BrD | ATOM | 913 | CB | LEU | 56 | −3.804 |
| −3.224 | −5.292 | 1.00 | 0.00 | BrD | ATOM | 914 | HB1 | LEU | 56 | −3.692 |
| −4.115 | −5.892 | 1.00 | 0.00 | BrD | ATOM | 915 | HB2 | LEU | 56 | −4.852 |
| −3.082 | −5.089 | 1.00 | 0.00 | BrD | ATOM | 916 | CG | LEU | 56 | −3.088 |
| −3.651 | −3.962 | 1.00 | 0.00 | BrD | ATOM | 917 | HG | LEU | 56 | −3.356 |
| −2.661 | −3.279 | 1.00 | 0.00 | BrD | ATOM | 918 | CD1 | LEU | 56 | −3.521 |
| −4.770 | −3.344 | 1.00 | 0.00 | BrD | ATOM | 919 | HD11 | LEU | 56 | −2.809 |
| −5.539 | −3.606 | 1.00 | 0.00 | BrD | ATOM | 920 | HD12 | LEU | 56 | −4.497 |
| −5.040 | −3.719 | 1.00 | 0.00 | BrD | ATOM | 921 | HD13 | LEU | 56 | −3.562 |
| −4.668 | −2.270 | 1.00 | 0.00 | BrD | ATOM | 922 | CD2 | LEU | 56 | −1.580 |
| −3.419 | −4.253 | 1.00 | 0.00 | BrD | ATOM | 923 | HD21 | LEU | 56 | −1.352 |
| −3.388 | −5.209 | 1.00 | 0.00 | BrD | ATOM | 924 | HD22 | LEU | 56 | −1.144 |
| −4.306 | −3.716 | 1.00 | 0.00 | BrD | ATOM | 925 | HD23 | LEU | 56 | −1.175 |
| −2.542 | −3.671 | 1.00 | 0.00 | BrD | ATOM | 926 | C | LEU | 56 | −3.305 |
| −2.400 | −7.587 | 1.00 | 0.00 | BrD | ATOM | 927 | O | LEU | 56 | −2.271 |
| −2.760 | −0.150 | 1.00 | 0.00 | BrD | ATOM | 928 | N | LYS | 57 | −4.475 |
| −2.304 | −8.207 | 1.00 | 0.00 | BrD | ATOM | 929 | HN | LYS | 57 | −5.261 |
| −2.020 | −7.696 | 1.00 | 0.00 | BrD | ATOM | 930 | CA | LYS | 57 | −4.634 |
| −2.639 | −9.615 | 1.00 | 0.00 | BrD | ATOM | 931 | HA | LYS | 57 | −4.577 |
| −3.712 | −9.704 | 1.00 | 0.00 | BrD | ATOM | 932 | CB | LYS | 57 | −6.007 |
| −2.179 | −10.108 | 1.00 | 0.00 | BrD | ATOM | 933 | HB1 | LYS | 57 | −6.765 |
| −2.764 | −9.608 | 1.00 | 0.00 | BrD | ATOM | 934 | HB2 | LYS | 57 | −6.139 |
| −1.119 | −9.850 | 1.00 | 0.00 | BrD | ATOM | 935 | CG | LYS | 57 | −6.203 |
| −2.328 | −11.608 | 1.00 | 0.00 | BrD | ATOM | 936 | HG1 | LYS | 57 | −5.383 |
| −1.845 | −12.118 | 1.00 | 0.00 | BrD | ATOM | 937 | HG2 | LYS | 57 | −7.132 |
| −1.856 | −11.889 | 1.00 | 0.00 | BrD | ATOM | 938 | CD | LYS | 57 | −6.248 |
| −3.790 | −12.024 | 1.00 | 0.00 | BrD | ATOM | 939 | HD1 | LYS | 57 | −5.259 |
| −4.098 | −12.327 | 1.00 | 0.00 | BrD | ATOM | 940 | HD2 | LYS | 57 | −6.571 |
| −4.383 | −11.181 | 1.00 | 0.00 | BrD | ATOM | 941 | CE | LYS | 57 | −7.210 |
| −4.011 | −13.180 | 1.00 | 0.00 | BrD | ATOM | 942 | HE1 | LYS | 57 | −7.354 |
| −3.073 | −13.697 | 1.00 | 0.00 | BrD | ATOM | 943 | HE2 | LYS | 57 | −6.778 |
| −4.732 | −13.858 | 1.00 | 0.00 | BrD | ATOM | 944 | NZ | LYS | 57 | −8.532 |
| −4.515 | −12.715 | 1.00 | 0.00 | BrD | ATOM | 945 | HZ1 | LYS | 57 | −8.403 |
| −5.182 | −11.928 | 1.00 | 0.00 | BrD | ATOM | 946 | HZ2 | LYS | 57 | −9.022 |
| −5.003 | −13.492 | 1.00 | 0.00 | BrD | ATOM | 947 | HZ3 | LYS | 57 | −9.122 |
| −3.723 | −12.391 | 1.00 | 0.00 | BrD | ATOM | 948 | C | LYS | 57 | −3.533 |
| −2.015 | −10.473 | 1.00 | 0.00 | BrD | ATOM | 949 | O | LYS | 57 | −3.222 |
| −2.516 | −11.553 | 1.00 | 0.00 | BrD | ATOM | 950 | N | THR | 58 | −2.941 |
| −0.923 | −9.989 | 1.00 | 0.00 | BrD | ATOM | 951 | HN | THR | 58 | −3.240 |
| −0.552 | −9.135 | 1.00 | 0.00 | BrD | ATOM | 952 | CA | THR | 58 | −1.901 |
| −0.230 | −10.742 | 1.00 | 0.00 | BrD | ATOM | 953 | HA | THR | 58 | −1.819 |
| 0.717 | −11.702 | 1.00 | 0.00 | BrD | ATOM | 954 | CB | THR | 58 | −2.307 |
| 1.233 | −10.967 | 1.00 | 0.00 | BrD | ATOM | 955 | HB | THR | 58 | −2.611 |
| 1.660 | −10.024 | 1.00 | 0.00 | BrD | ATOM | 956 | OG1 | THR | 58 | −3.403 |
| 1.313 | −11.862 | 1.00 | 0.00 | BrD | ATOM | 957 | HG1 | THR | 58 | −3.101 |
| 1.133 | −12.755 | 1.00 | 0.00 | BrD | ATOM | 958 | CG2 | THR | 58 | −1.197 |
| 2.099 | −11.525 | 1.00 | 0.00 | BrD | ATOM | 959 | HG21 | THR | 58 | −0.808 |
| 2.734 | −10.743 | 1.00 | 0.00 | BrD | ATOM | 960 | HG22 | THR | 58 | −1.585 |
| 2.710 | −12.326 | 1.00 | 0.00 | BrD | ATOM | 961 | HG23 | THR | 58 | −0.405 |
| −1.469 | −11.904 | 1.00 | 0.00 | BrD | ATOM | 962 | C | THR | 58 | −0.539 |
| −0.305 | −10.045 | 1.00 | 0.00 | BrD | ATOM | 963 | O | THR | 58 | 0.499 |
| −0.220 | −10.701 | 1.00 | 0.00 | BrD | ATOM | 964 | N | MET | 59 | −0.537 |
| −0.445 | −8.721 | 1.00 | 0.00 | BrD | ATOM | 965 | HN | MET | 59 | −1.388 |
| −0.503 | −8.238 | 1.00 | 0.00 | BrD | ATOM | 966 | CA | MET | 59 | 0.718 |
| 0.505 | −7.972 | 1.00 | 0.00 | BrD | ATOM | 967 | HA | MET | 59 | 1.401 |
| −0.191 | −8.436 | 1.00 | 0.00 | BrD | ATOM | 968 | CB | MET | 59 | 0.499 |
| 0.070 | −6.513 | 1.00 | 0.00 | BrD | ATOM | 969 | HB1 | MET | 59 | 1.430 |
| 0.316 | −6.125 | 1.00 | 0.00 | BrD | ATOM | 970 | HB2 | MET | 59 | −0.238 |
| −0.717 | −6.498 | 1.00 | 0.00 | BrD | ATOM | 971 | CG | MET | 59 | 0.022 |
| −1.176 | −5.583 | 1.00 | 0.00 | BrD | ATOM | 972 | HG1 | MET | 59 | −0.822 |
| −0.811 | −5.017 | 1.00 | 0.00 | BrD | ATOM | 973 | HG2 | MET | 59 | −0.286 |
| −2.022 | −6.180 | 1.00 | 0.00 | BrD | ATOM | 974 | SD | MET | 59 | 1.300 |
| −1.715 | −4.431 | 1.00 | 0.00 | BrD | ATOM | 975 | CE | MET | 59 | 1.463 |
| −0.259 | −3.400 | 1.00 | 0.00 | BrD | ATOM | 976 | HE1 | MET | 59 | 0.629 |
| 0.205 | −2.715 | 1.00 | 0.00 | BrD | ATOM | 977 | HE2 | MET | 59 | 1.474 |
| −0.624 | −4.022 | 1.00 | 0.00 | BrD | ATOM | 978 | HE3 | MET | 59 | 2.386 |
| −0.316 | −2.841 | 1.00 | 0.00 | BrD | ATOM | 979 | C | MET | 59 | 1.345 |
| −1.901 | −8.036 | 1.00 | 0.00 | BrD | ATOM | 980 | O | MET | 59 | 2.535 |
| −2.067 | −7.767 | 1.00 | 0.00 | BrD | ATOM | 981 | N | SER | 60 | 0.542 |
| −2.898 | −8.392 | 1.00 | 0.00 | BrD | ATOM | 982 | HN | SER | 60 | −0.399 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −2.710 | −8.590 | 1.00 | 0.00 | BrD | ATOM | 983 | CA | SER | 60 | 1.205 |
| −4.271 | −8.478 | 1.00 | 0.00 | BrD | ATOM | 984 | HA | SER | 60 | 1.685 |
| −4.442 | −7.640 | 1.00 | 0.00 | BrD | ATOM | 985 | CB | SER | 60 | −0.147 |
| −5.250 | −8.396 | 1.00 | 0.00 | BrD | ATOM | 986 | HB1 | SER | 60 | −0.610 |
| −5.171 | −7.424 | 1.00 | 0.00 | BrD | ATOM | 987 | HB2 | SER | 60 | −0.871 |
| −5.006 | −9.159 | 1.00 | 0.00 | BrD | ATOM | 988 | OG | SER | 60 | 0.286 |
| −6.585 | −8.588 | 1.00 | 0.00 | BrD | ATOM | 989 | HG | SER | 60 | −0.145 |
| −6.953 | −9.363 | 1.00 | 0.00 | BrD | ATOM | 990 | C | SER | 60 | 1.803 |
| −4.503 | −9.770 | 1.00 | 0.00 | BrD | ATOM | 991 | O | SER | 60 | 2.636 |
| −5.405 | −9.850 | 1.00 | 0.00 | BrD | ATOM | 992 | N | GLU | 61 | 1.519 |
| −3.690 | −10.782 | 1.00 | 0.00 | BrD | ATOM | 993 | HN | GLU | 61 | 0.839 |
| −2.995 | −10.661 | 1.00 | 0.00 | BrD | ATOM | 994 | CA | GLU | 61 | 2.182 |
| −3.820 | −12.075 | 1.00 | 0.00 | BrD | ATOM | 995 | HA | GLU | 61 | 2.295 |
| −4.874 | −12.283 | 1.00 | 0.00 | BrD | ATOM | 996 | CB | GLU | 61 | 1.326 |
| −3.187 | −13.174 | 1.00 | 0.00 | BrD | ATOM | 997 | HB1 | GLU | 61 | 1.820 |
| −3.324 | −14.125 | 1.00 | 0.00 | BrD | ATOM | 998 | HB2 | GLU | 61 | 1.232 |
| −2.129 | −12.977 | 1.00 | 0.00 | BrD | ATOM | 999 | CG | GLU | 61 | −0.071 |
| −3.779 | −13.274 | 1.00 | 0.00 | BrD | ATOM | 1000 | HG1 | GLU | 61 | −0.494 |
| −3.836 | −12.282 | 1.00 | 0.00 | BrD | ATOM | 1001 | HG2 | GLU | 61 | −0.679 |
| −3.132 | −13.889 | 1.00 | 0.00 | BrD | ATOM | 1002 | CD | GLU | 61 | −0.073 |
| −5.167 | −13.883 | 1.00 | 0.00 | BrD | ATOM | 1003 | OE1 | GLU | 61 | −1.024 |
| −5.488 | −14.627 | 1.00 | 0.00 | BrD | ATOM | 1004 | OE2 | GLU | 61 | 0.876 |
| −5.934 | −13.617 | 1.00 | 0.00 | BrD | ATOM | 1005 | C | GLU | 61 | 3.565 |
| −3.174 | −12.060 | 1.00 | 0.00 | BrD | ATOM | 1006 | O | GLU | 61 | 4.466 |
| −3.601 | −12.782 | 1.00 | 0.00 | BrD | ATOM | 1007 | N | ARG | 62 | 3.726 |
| −2.137 | −11.244 | 1.00 | 0.00 | BrD | ATOM | 1008 | HN | ARG | 62 | 2.971 |
| −1.836 | −10.697 | 1.00 | 0.00 | BrD | ATOM | 1009 | CA | ARG | 62 | 4.999 |
| −1.420 | −11.155 | 1.00 | 0.00 | BrD | ATOM | 1010 | HA | ARG | 62 | 5.352 |
| −1.262 | −12.162 | 1.00 | 0.00 | BrD | ATOM | 1011 | CB | ARG | 62 | 4.807 |
| 0.075 | −10.468 | 1.00 | 0.00 | BrD | ATOM | 1012 | HB1 | ARG | 62 | 5.753 |
| −0.241 | −10.052 | 1.00 | 0.00 | BrD | ATOM | 1013 | HB2 | ARG | 62 | 4.091 |
| 0.187 | −9.668 | 1.00 | 0.00 | BrD | ATOM | 1014 | CG | ARG | 62 | 4.312 |
| 1.018 | −11.404 | 1.00 | 0.00 | BrD | ATOM | 1015 | HG1 | ARG | 62 | 4.852 |
| 1.928 | −11.195 | 1.00 | 0.00 | BrD | ATOM | 1016 | HG2 | ARG | 62 | 4.494 |
| 0.714 | −12.424 | 1.00 | 0.00 | BrD | ATOM | 1017 | CD | ARG | 62 | 2.826 |
| 1.278 | −11.225 | 1.00 | 0.00 | BrD | ATOM | 1018 | HD1 | ARG | 62 | 2.484 |
| 0.738 | −10.356 | 1.00 | 0.00 | BrD | ATOM | 1019 | HD2 | ARG | 62 | 2.675 |
| 2.336 | −11.072 | 1.00 | 0.00 | BrD | ATOM | 1020 | NE | ARG | 62 | 2.052 |
| −0.851 | −12.387 | 1.00 | 0.00 | BrD | ATOM | 1021 | HE | ARG | 62 | 1.621 |
| 0.028 | −12.346 | 1.00 | 0.00 | BrD | ATOM | 1022 | CZ | ARG | 62 | 1.903 |
| 1.585 | −13.485 | 1.00 | 0.00 | BrD | ATOM | 1023 | NH1 | ARG | 62 | 1.183 |
| 1.225 | −14.498 | 1.00 | 0.00 | BrD | ATOM | 1024 | HH11 | ARG | 62 | 1.072 |
| 1.678 | −15.324 | 1.00 | 0.00 | BrD | ATOM | 1025 | HH12 | ARG | 62 | 0.752 |
| 0.226 | −14.437 | 1.00 | 0.00 | BrD | ATOM | 1026 | NH2 | ARG | 62 | 2.473 |
| 2.780 | −13.571 | 1.00 | 0.00 | BrD | ATOM | 1027 | HH21 | ARG | 62 | 2.359 |
| 3.329 | −14.399 | 1.00 | 0.00 | BrD | ATOM | 1028 | HH22 | ARG | 62 | 3.018 |
| −3.130 | −12.809 | 1.00 | 0.00 | BrD | ATOM | 1029 | C | ARG | 62 | 6.040 |
| −2.255 | −10.405 | 1.00 | 0.00 | BrD | ATOM | 1030 | O | ARG | 62 | 7.101 |
| −2.569 | −10.945 | 1.00 | 0.00 | BrD | ATOM | 1031 | N | LEU | 63 | 5.734 |
| −2.606 | −9.158 | 1.00 | 0.00 | BrD | ATOM | 1032 | HN | LEU | 63 | 4.875 |
| −2.326 | −8.780 | 1.00 | 0.00 | BrD | ATOM | 1033 | CA | LEU | 63 | 6.651 |
| −3.396 | −8.339 | 1.00 | 0.00 | BrD | ATOM | 1034 | HA | LEU | 63 | 7.496 |
| −2.771 | −8.093 | 1.00 | 0.00 | BrD | ATOM | 1035 | CB | LEU | 63 | 5.962 |
| −3.840 | −7.043 | 1.00 | 0.00 | BrD | ATOM | 1036 | HB1 | LEU | 63 | 5.009 |
| −4.277 | −7.302 | 1.00 | 0.00 | BrD | ATOM | 1037 | HB2 | LEU | 63 | 5.780 |
| −2.962 | −6.442 | 1.00 | 0.00 | BrD | ATOM | 1038 | CG | LEU | 63 | 6.736 |
| −4.857 | −6.186 | 1.00 | 0.00 | BrD | ATOM | 1039 | HG | LEU | 63 | 6.629 |
| −4.754 | −5.156 | 1.00 | 0.00 | BrD | ATOM | 1040 | CD1 | LEU | 63 | 8.237 |
| −4.605 | −6.247 | 1.00 | 0.00 | BrD | ATOM | 1041 | HD11 | LEU | 63 | 8.420 |
| −3.584 | −6.547 | 1.00 | 0.00 | BrD | ATOM | 1042 | HD12 | LEU | 63 | 8.685 |
| −5.277 | −6.965 | 1.00 | 0.00 | BrD | ATOM | 1043 | HD13 | LEU | 63 | 8.671 |
| −4.779 | −5.273 | 1.00 | 0.00 | BrD | ATOM | 1044 | CD2 | LEU | 63 | 6.414 |
| −6.277 | −6.627 | 1.00 | 0.00 | BrD | ATOM | 1045 | HD21 | LEU | 63 | 7.332 |
| −6.804 | −6.842 | 1.00 | 0.00 | BrD | ATOM | 1046 | HD22 | LEU | 63 | 5.798 |
| −6.248 | −7.514 | 1.00 | 0.00 | BrD | ATOM | 1047 | HD23 | LEU | 63 | 5.883 |
| −6.787 | −5.836 | 1.00 | 0.00 | BrD | ATOM | 1048 | C | LEU | 63 | 7.150 |
| −4.618 | −9.103 | 1.00 | 0.00 | BrD | ATOM | 1049 | O | LEU | 63 | 8.354 |
| −4.853 | −9.203 | 1.00 | 0.00 | BrD | ATOM | 1050 | N | LYS | 64 | 6.224 |
| −5.390 | −9.643 | 1.00 | 0.00 | BrD | ATOM | 1051 | HN | LYS | 64 | 5.273 |
| −5.150 | −9.525 | 1.00 | 0.00 | BrD | ATOM | 1052 | CA | LYS | 64 | 6.551 |
| −6.592 | −10.397 | 1.00 | 0.00 | BrD | ATOM | 1053 | HA | LYS | 64 | 6.929 |
| −7.325 | −9.699 | 1.00 | 0.00 | BrD | ATOM | 1054 | CB | LYS | 64 | 5.303 |
| −7.152 | −11.082 | 1.00 | 0.00 | BrD | ATOM | 1055 | HB1 | LYS | 64 | 4.649 |
| −6.332 | −11.340 | 1.00 | 0.00 | BrD | ATOM | 1056 | HB2 | LYS | 64 | 5.602 |
| −7.661 | −11.987 | 1.00 | 0.00 | BrD | ATOM | 1057 | CG | LYS | 64 | 4.523 |
| −8.131 | −10.221 | 1.00 | 0.00 | BrD | ATOM | 1058 | HG1 | LYS | 64 | 3.533 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −7.734 | −10.047 | 1.00 | 0.00 | BrD | ATOM | 1059 | HG2 | LYS | 64 | 5.035 |
| −8.254 | −9.278 | 1.00 | 0.00 | BrD | ATOM | 1060 | CD | LYS | 64 | 4.198 |
| −9.488 | −10.894 | 1.00 | 0.00 | BrD | ATOM | 1061 | HD1 | LYS | 64 | 3.363 |
| −9.798 | −10.870 | 1.00 | 0.00 | BrD | ATOM | 1062 | HD2 | LYS | 64 | 4.726 |
| −9.402 | −11.920 | 1.00 | 0.00 | BrD | ATOM | 1063 | CE | LYS | 64 | 5.243 |
| −10.538 | −10.192 | 1.00 | 0.00 | BrD | ATOM | 1064 | HE1 | LYS | 64 | 5.904 |
| −10.043 | −9.496 | 1.00 | 0.00 | BrD | ATOM | 1065 | HE2 | LYS | 64 | 4.589 |
| −11.207 | −9.653 | 1.00 | 0.00 | BrD | ATOM | 1066 | NZ | LYS | 64 | 6.060 |
| −11.330 | −11.154 | 1.00 | 0.00 | BrD | ATOM | 1067 | HZ1 | LYS | 64 | 6.712 |
| −11.955 | −10.638 | 1.00 | 0.00 | BrD | ATOM | 1068 | HZ2 | LYS | 64 | 6.615 |
| −10.693 | −11.761 | 1.00 | 0.00 | BrD | ATOM | 1069 | HZ3 | LYS | 64 | 5.441 |
| −11.911 | −11.754 | 1.00 | 0.00 | BrD | ATOM | 1070 | C | LYS | 64 | 7.629 |
| −6.305 | −11.439 | 1.00 | 0.00 | BrD | ATOM | 1071 | O | LYS | 64 | 8.276 |
| −7.200 | −11.834 | 1.00 | 0.00 | BrD | ATOM | 1072 | N | ASN | 65 | 7.705 |
| −5.052 | −11.880 | 1.00 | 0.00 | BrD | ATOM | 1073 | HN | ASN | 65 | 7.080 |
| −4.383 | −11.531 | 1.00 | 0.00 | BrD | ATOM | 1074 | CA | ASN | 65 | 8.688 |
| −4.657 | −12.883 | 1.00 | 0.00 | BrD | ATOM | 1075 | HA | ASN | 65 | 9.212 |
| −5.547 | −13.198 | 1.00 | 0.00 | BrD | ATOM | 1076 | CB | ASN | 65 | 7.989 |
| −4.034 | −14.092 | 1.00 | 0.00 | BrD | ATOM | 1077 | HB1 | ASN | 65 | 8.680 |
| −3.376 | −14.600 | 1.00 | 0.00 | BrD | ATOM | 1078 | HB2 | ASN | 65 | 7.137 |
| −3.463 | −13.754 | 1.00 | 0.00 | BrD | ATOM | 1079 | CG | ASN | 65 | 7.506 |
| −5.076 | −15.081 | 1.00 | 0.00 | BrD | ATOM | 1080 | OD1 | ASN | 65 | 8.177 |
| −6.080 | −15.320 | 1.00 | 0.00 | BrD | ATOM | 1081 | ND2 | ASN | 65 | 6.334 |
| −4.844 | −15.660 | 1.00 | 0.00 | BrD | ATOM | 1082 | HD21 | ASN | 65 | 5.854 |
| −4.024 | −15.421 | 1.00 | 0.00 | BrD | ATOM | 1083 | HD22 | ASN | 65 | 5.997 |
| −5.502 | −16.303 | 1.00 | 0.00 | BrD | ATOM | 1084 | C | ASN | 65 | 9.703 |
| −3.677 | −12.308 | 1.00 | 0.00 | BrD | ATOM | 1085 | O | ASN | 65 | 10.233 |
| −2.829 | −13.023 | 1.00 | 0.00 | BrD | ATOM | 1086 | N | ARG | 66 | 9.973 |
| −3.804 | −11.014 | 1.00 | 0.00 | BrD | ATOM | 1087 | HN | ARG | 66 | 9.523 |
| −4.505 | −10.498 | 1.00 | 0.00 | BrD | ATOM | 1088 | CA | ARG | 66 | 10.942 |
| −2.943 | −10.346 | 1.00 | 0.00 | BrD | ATOM | 1089 | HA | ARG | 66 | 10.826 |
| −3.082 | −9.281 | 1.00 | 0.00 | BrD | ATOM | 1090 | CB | ARG | 66 | 12.357 |
| −3.347 | −10.739 | 1.00 | 0.00 | BrD | ATOM | 1091 | HB1 | ARG | 66 | 12.323 |
| −3.875 | −11.680 | 1.00 | 0.00 | BrD | ATOM | 1092 | HB2 | ARG | 66 | 12.959 |
| −2.458 | −10.854 | 1.00 | 0.00 | BrD | ATOM | 1093 | CG | ARG | 66 | 13.018 |
| −4.243 | −9.713 | 1.00 | 0.00 | BrD | ATOM | 1094 | HG1 | ARG | 66 | 13.744 |
| −3.664 | −9.163 | 1.00 | 0.00 | BrD | ATOM | 1095 | HG2 | ARG | 66 | 12.262 |
| −4.613 | −9.038 | 1.00 | 0.00 | BrD | ATOM | 1096 | CD | ARG | 66 | 13.710 |
| −5.423 | −10.368 | 1.00 | 0.00 | BrD | ATOM | 1097 | HD1 | ARG | 66 | 13.453 |
| −5.439 | −11.416 | 1.00 | 0.00 | BrD | ATOM | 1098 | HD2 | ARG | 66 | 13.358 |
| −6.329 | −9.898 | 1.00 | 0.00 | BrD | ATOM | 1099 | NE | ARG | 66 | 15.162 |
| −5.351 | −10.237 | 1.00 | 0.00 | BrD | ATOM | 1100 | HE | ARG | 66 | 15.688 |
| −5.255 | −11.059 | 1.00 | 0.00 | BrD | ATOM | 1101 | CZ | ARG | 66 | 15.801 |
| −5.407 | −9.074 | 1.00 | 0.00 | BrD | ATOM | 1102 | NH1 | ARG | 66 | 15.117 |
| −5.536 | −7.945 | 1.00 | 0.00 | BrD | ATOM | 1103 | HH11 | ARG | 66 | 15.599 |
| −5.578 | −7.070 | 1.00 | 0.00 | BrD | ATOM | 1104 | HH12 | ARG | 66 | 14.118 |
| −5.591 | −7.969 | 1.00 | 0.00 | BrD | ATOM | 1105 | NH2 | ARG | 66 | 17.125 |
| −5.334 | −9.037 | 1.00 | 0.00 | BrD | ATOM | 1106 | HH21 | ARG | 66 | 17.604 |
| −5.377 | −8.161 | 1.00 | 0.00 | BrD | ATOM | 1107 | HH22 | ARG | 66 | 17.643 |
| −5.237 | −9.887 | 1.00 | 0.00 | BrD | ATOM | 1108 | C | ARG | 66 | 10.708 |
| −1.474 | −10.682 | 1.00 | 0.00 | BrD | ATOM | 1109 | O | ARG | 66 | 11.654 |
| −0.705 | −10.850 | 1.00 | 0.00 | BrD | ATOM | 1110 | N | TYR | 67 | 9.441 |
| −1.097 | −10.783 | 1.00 | 0.00 | BrD | ATOM | 1111 | HN | TYR | 67 | 8.736 |
| 1.759 | −10.633 | 1.00 | 0.00 | BrD | ATOM | 1112 | CA | TYR | 67 | 9.075 |
| 0.280 | −11.094 | 1.00 | 0.00 | BrD | ATOM | 1113 | HA | TYR | 67 | 9.952 |
| 0.780 | −11.472 | 1.00 | 0.00 | BrD | ATOM | 1114 | CB | TYR | 67 | 7.982 |
| −0.309 | −12.264 | 1.00 | 0.00 | BrD | ATOM | 1115 | HB1 | TYR | 67 | 7.062 |
| −0.061 | −11.738 | 1.00 | 0.00 | BrD | ATOM | 1116 | HB2 | TYR | 67 | 8.276 |
| 0.330 | −12.984 | 1.00 | 0.00 | BrD | ATOM | 1117 | CG | TYR | 67 | 7.713 |
| 1.687 | −12.723 | 1.00 | 0.00 | BrD | ATOM | 1118 | CD1 | TYR | 67 | 7.042 |
| 2.639 | −11.970 | 1.00 | 0.00 | BrD | ATOM | 1119 | HD1 | TYR | 67 | 6.718 |
| 2.385 | −10.973 | 1.00 | 0.00 | BrD | ATOM | 1120 | CD2 | TYR | 67 | 8.123 |
| 2.032 | −14.005 | 1.00 | 0.00 | BrD | ATOM | 1121 | HD2 | TYR | 67 | 8.645 |
| 1.301 | −14.604 | 1.00 | 0.00 | BrD | ATOM | 1122 | CE1 | TYR | 67 | 6.787 |
| 3.899 | −12.475 | 1.00 | 0.00 | BrD | ATOM | 1123 | HE1 | TYR | 67 | 6.261 |
| 4.625 | −11.872 | 1.00 | 0.00 | BrD | ATOM | 1124 | CE2 | TYR | 67 | 7.872 |
| 3.291 | −14.518 | 1.00 | 0.00 | BrD | ATOM | 1125 | HE2 | TYR | 67 | 8.198 |
| 3.541 | −15.516 | 1.00 | 0.00 | BrD | ATOM | 1126 | CZ | TYR | 67 | 7.204 |
| 4.220 | −13.749 | 1.00 | 0.00 | BrD | ATOM | 1127 | OH | TYR | 67 | 6.951 |
| 5.475 | −14.256 | 1.00 | 0.00 | BrD | ATOM | 1128 | HH | TYR | 67 | 7.446 |
| 6.127 | −13.753 | 1.00 | 0.00 | BrD | ATOM | 1129 | C | TYR | 67 | 8.606 |
| 1.006 | −9.840 | 1.00 | 0.00 | BrD | ATOM | 1130 | O | TYR | 67 | 8.910 |
| 2.181 | −9.639 | 1.00 | 0.00 | BrD | ATOM | 1131 | N | TYR | 68 | 7.880 |
| −0.291 | −8.990 | 1.00 | 0.00 | BrD | ATOM | 1132 | HN | TYR | 68 | 7.686 |
| 0.647 | −9.197 | 1.00 | 0.00 | BrD | ATOM | 1133 | CA | TYR | 68 | 7.401 |
| 0.855 | −7.736 | 1.00 | 0.00 | BrD | ATOM | 1134 | HA | TYR | 68 | 7.528 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 1.924 | −7.788 | 1.00 | 0.00 | BrD | ATOM | 1135 | CB | TYR | 68 | 5.918 |
| −0.531 | −7.538 | 1.00 | 0.00 | BrD | ATOM | 1136 | HB1 | TYR | 68 | 5.666 |
| 0.286 | −8.188 | 1.00 | 0.00 | BrD | ATOM | 1137 | HB2 | TYR | 68 | 5.758 |
| 0.234 | −6.512 | 1.00 | 0.00 | BrD | ATOM | 1138 | CG | TYR | 68 | 4.987 |
| 1.689 | −7.833 | 1.00 | 0.00 | BrD | ATOM | 1139 | CD1 | TYR | 68 | 5.378 |
| 2.734 | −8.664 | 1.00 | 0.00 | BrD | ATOM | 1140 | HD1 | TYR | 68 | 6.364 |
| 2.717 | −9.101 | 1.00 | 0.00 | BrD | ATOM | 1141 | CD2 | TYR | 68 | 3.712 |
| 1.732 | −7.283 | 1.00 | 0.00 | BrD | ATOM | 1142 | HD2 | TYR | 68 | 3.392 |
| 0.927 | −6.638 | 1.00 | 0.00 | BrD | ATOM | 1143 | CE1 | TYR | 68 | 4.526 |
| 3.788 | −8.933 | 1.00 | 0.00 | BrD | ATOM | 1144 | HE1 | TYR | 68 | 4.849 |
| 4.591 | −9.579 | 1.00 | 0.00 | BrD | ATOM | 1145 | CE2 | TYR | 68 | 2.855 |
| 2.782 | −7.549 | 1.00 | 0.00 | BrD | ATOM | 1146 | HE2 | TYR | 68 | 1.868 |
| 2.797 | −7.110 | 1.00 | 0.00 | BrD | ATOM | 1147 | CZ | TYR | 68 | 3.267 |
| 3.807 | −8.374 | 1.00 | 0.00 | BrD | ATOM | 1148 | OH | TYR | 68 | 2.416 |
| 4.855 | −8.639 | 1.00 | 0.00 | BrD | ATOM | 1149 | HH | TYR | 68 | 2.457 |
| 5.490 | −7.920 | 1.00 | 0.00 | BrD | ATOM | 1150 | C | TYR | 68 | 8.206 |
| 0.327 | −6.548 | 1.00 | 0.00 | BrD | ATOM | 1151 | O | TYR | 68 | 8.001 |
| −0.759 | −5.416 | 1.00 | 0.00 | BrD | ATOM | 1152 | N | VAL | 69 | 9.149 |
| −0.579 | −6.816 | 1.00 | 0.00 | BrD | ATOM | 1153 | HN | VAL | 69 | 9.267 |
| −0.888 | −7.735 | 1.00 | 0.00 | BrD | ATOM | 1154 | CA | VAL | 69 | 9.977 |
| −1.170 | −5.769 | 1.00 | 0.00 | BrD | ATOM | 1155 | HA | VAL | 69 | 9.397 |
| −1.541 | −5.285 | 1.00 | 0.00 | BrD | ATOM | 1156 | CB | VAL | 69 | 11.232 |
| −1.825 | −6.366 | 1.00 | 0.00 | BrD | ATOM | 1157 | HB | VAL | 69 | 10.922 |
| −2.537 | −7.117 | 1.00 | 0.00 | BrD | ATOM | 1158 | CG1 | VAL | 69 | 12.107 |
| −0.778 | −7.032 | 1.00 | 0.00 | BrD | ATOM | 1159 | HG11 | VAL | 69 | 11.701 |
| −0.536 | −8.003 | 1.00 | 0.00 | BrD | ATOM | 1160 | HG12 | VAL | 69 | 13.108 |
| 1.165 | −7.146 | 1.00 | 0.00 | BrD | ATOM | 1161 | HG13 | VAL | 69 | 12.131 |
| −0.111 | −6.420 | 1.00 | 0.00 | BrD | ATOM | 1162 | CG2 | VAL | 69 | 12.001 |
| −2.572 | −5.291 | 1.00 | 0.00 | BrD | ATOM | 1163 | HG21 | VAL | 69 | 11.389 |
| −3.370 | −4.899 | 1.00 | 0.00 | BrD | ATOM | 1164 | HG22 | VAL | 69 | 12.256 |
| −1.889 | −4.494 | 1.00 | 0.00 | BrD | ATOM | 1165 | HG23 | VAL | 69 | 12.904 |
| −2.985 | −5.716 | 1.00 | 0.00 | BrD | ATOM | 1166 | C | VAL | 69 | 10.409 |
| −0.149 | −4.717 | 1.00 | 0.00 | BrD | ATOM | 1167 | O | VAL | 69 | 10.642 |
| 0.506 | −3.565 | 1.00 | 0.00 | BrD | ATOM | 1168 | N | SER | 70 | 10.508 |
| 1.123 | −5.110 | 1.00 | 0.00 | BrD | ATOM | 1169 | HN | SER | 70 | 10.321 |
| 1.350 | −6.044 | 1.00 | 0.00 | BrD | ATOM | 1170 | CA | SER | 70 | 10.909 |
| 2.190 | −4.189 | 1.00 | 0.00 | BrD | ATOM | 1171 | HA | SER | 70 | 12.983 |
| 2.145 | −4.081 | 1.00 | 0.00 | BrD | ATOM | 1172 | CB | SER | 70 | 10.525 |
| 3.552 | −4.767 | 1.00 | 0.00 | BrD | ATOM | 1173 | HB1 | SER | 70 | 11.246 |
| 3.838 | −5.518 | 1.00 | 0.00 | BrD | ATOM | 1174 | HB2 | SER | 70 | 9.546 |
| 3.483 | −5.216 | 1.00 | 0.00 | BrD | ATOM | 1175 | OG | SER | 70 | 10.498 |
| 4.547 | −3.758 | 1.00 | 0.00 | BrD | ATOM | 1176 | HG | SER | 70 | 10.908 |
| 5.349 | −4.088 | 1.00 | 0.00 | BrD | ATOM | 1177 | C | SER | 70 | 10.268 |
| 2.011 | −2.810 | 1.00 | 0.00 | BrD | ATOM | 1178 | O | SER | 70 | 9.252 |
| 1.330 | −2.674 | 1.00 | 0.00 | BrD | ATOM | 1179 | N | LYS | 71 | 10.881 |
| 2.605 | −1.791 | 1.00 | 0.00 | BrD | ATOM | 1180 | HN | LYS | 71 | 11.700 |
| 3.118 | −1.958 | 1.00 | 0.00 | BrD | ATOM | 1181 | CA | LYS | 71 | 10.393 |
| 2.470 | −0.422 | 1.00 | 0.00 | BrD | ATOM | 1182 | HA | LYS | 71 | 10.268 |
| 1.415 | −0.226 | 1.00 | 0.00 | BrD | ATOM | 1183 | CB | LYS | 71 | 11.419 |
| 2.026 | 0.564 | 1.00 | 0.00 | BrD | ATOM | 1184 | HB1 | LYS | 71 | 10.915 |
| 3.287 | 1.485 | 1.00 | 0.00 | BrD | ATOM | 1185 | HB2 | LYS | 71 | 11.848 |
| 3.933 | 0.142 | 1.00 | 0.00 | BrD | ATOM | 1186 | CG | LYS | 71 | 12.550 |
| 2.074 | 0.888 | 1.00 | 0.00 | BrD | ATOM | 1187 | HG1 | LYS | 71 | 13.159 |
| 2.237 | 0.191 | 1.00 | 0.00 | BrD | ATOM | 1188 | HG2 | LYS | 71 | 12.188 |
| 1.061 | 0.791 | 1.00 | 0.00 | BrD | ATOM | 1189 | CD | LYS | 71 | 13.069 |
| 2.279 | 2.302 | 1.00 | 0.00 | BrD | ATOM | 1190 | HD1 | LYS | 71 | 12.295 |
| 2.001 | 3.002 | 1.00 | 0.00 | BrD | ATOM | 1191 | HD2 | LYS | 71 | 13.936 |
| 1.652 | 2.452 | 1.00 | 0.00 | BrD | ATOM | 1192 | CE | LYS | 71 | 13.460 |
| 3.727 | 2.548 | 1.00 | 0.00 | BrD | ATOM | 1193 | HE1 | LYS | 71 | 14.024 |
| 4.084 | 1.699 | 1.00 | 0.00 | BrD | ATOM | 1194 | HE2 | LYS | 71 | 12.561 |
| 4.316 | 2.655 | 1.00 | 0.00 | BrD | ATOM | 1195 | NZ | LYS | 71 | 14.287 |
| 3.879 | 3.777 | 1.00 | 0.00 | BrD | ATOM | 1196 | HZ1 | LYS | 71 | 13.870 |
| 3.334 | 4.558 | 1.00 | 0.00 | BrD | ATOM | 1197 | HZ2 | LYS | 71 | 14.334 |
| 4.880 | 4.055 | 1.00 | 0.00 | BrD | ATOM | 1198 | HZ3 | LYS | 71 | 15.252 |
| 3.533 | 3.604 | 1.00 | 0.00 | BrD | ATOM | 1199 | C | LYS | 71 | 9.041 |
| 3.160 | −0.231 | 1.00 | 0.00 | BrD | ATOM | 1200 | O | LYS | 71 | 7.992 |
| 2.529 | −0.362 | 1.00 | 0.00 | BrD | ATOM | 1201 | N | LYS | 72 | 9.070 |
| 4.447 | 0.109 | 1.00 | 0.00 | BrD | ATOM | 1202 | HN | LYS | 72 | 9.933 |
| 4.898 | 0.211 | 1.00 | 0.00 | BrD | ATOM | 1203 | CA | LYS | 72 | 7.844 |
| 5.201 | 0.351 | 1.00 | 0.00 | BrD | ATOM | 1204 | HA | LYS | 72 | 7.396 |
| 4.818 | 1.255 | 1.00 | 0.00 | BrD | ATOM | 1205 | CB | LYS | 72 | 8.167 |
| 6.684 | 0.547 | 1.00 | 0.00 | BrD | ATOM | 1206 | HB1 | LYS | 72 | 7.249 |
| 7.216 | 0.752 | 1.00 | 0.00 | BrD | ATOM | 1207 | HB2 | LYS | 72 | 8.601 |
| 7.707 | −0.364 | 1.00 | 0.00 | BrD | ATOM | 1208 | CG | LYS | 72 | 9.136 |
| 6.950 | 1.687 | 1.00 | 0.00 | BrD | ATOM | 1209 | HG1 | LYS | 72 | 9.870 |
| 6.158 | 1.715 | 1.00 | 0.00 | BrD | ATOM | 1210 | HG2 | LYS | 72 | 9.629 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 7.895 | 1.515 | 1.00 | 0.00 | BrD | ATOM | 1211 | CD | LYS | 72 | 8.419
| 7.004 | 3.027 | 1.00 | 0.00 | BrD | ATOM | 1212 | HD1 | LYS | 72 | 7.833
| 6.104 | 3.147 | 1.00 | 0.00 | BrD | ATOM | 1213 | HD2 | LYS | 72 | 9.155
| 7.065 | 3.816 | 1.00 | 0.00 | BrD | ATOM | 1214 | CE | LYS | 72 | 7.497
| 8.208 | 3.117 | 1.00 | 0.00 | BrD | ATOM | 1215 | HE1 | LYS | 72 | 7.708
| 8.869 | 2.288 | 1.00 | 0.00 | BrD | ATOM | 1216 | HE2 | LYS | 72 | 6.474
| 7.868 | 3.054 | 1.00 | 0.00 | BrD | ATOM | 1217 | NZ | LYS | 72 | 7.681
| 8.956 | 4.391 | 1.00 | 0.00 | BrD | ATOM | 1218 | HZ1 | LYS | 72 | 8.150
| 8.352 | 5.096 | 1.00 | 0.00 | BrD | ATOM | 1219 | HZ2 | LYS | 72 | 6.750
| 9.256 | 4.766 | 1.00 | 0.00 | BrD | ATOM | 1220 | HZ3 | LYS | 72 | 8.267
| 9.800 | 4.229 | 1.00 | 0.00 | BrD | ATOM | 1221 | C | LYS | 72 | 6.852
| 5.034 | −0.794 | 1.00 | 0.00 | BrD | ATOM | 1222 | O | LYS | 72 | 5.641
| 5.001 | −0.578 | 1.00 | 0.00 | BrD | ATOM | 1223 | N | LEU | 73 | 7.370
| 4.933 | −2.011 | 1.00 | 0.00 | BrD | ATOM | 1224 | HN | LEU | 73 | 8.343
| 4.972 | −2.221 | 1.00 | 0.00 | BrD | ATOM | 1225 | CA | LEU | 73 | 6.528
| 4.786 | −3.191 | 1.00 | 0.00 | BrD | ATOM | 1226 | HA | LEU | 73 | 5.982
| 5.708 | −3.323 | 1.00 | 0.00 | BrD | ATOM | 1227 | CB | LEU | 73 | 7.394
| 4.539 | −4.427 | 1.00 | 0.00 | BrD | ATOM | 1228 | HB1 | LEU | 73 | 7.447
| 3.474 | −4.596 | 1.00 | 0.00 | BrD | ATOM | 1229 | HB2 | LEU | 73 | 8.389
| 4.903 | −4.219 | 1.00 | 0.00 | BrD | ATOM | 1230 | CG | LEU | 73 | 6.896
| 5.206 | −5.711 | 1.00 | 0.00 | BrD | ATOM | 1231 | HG | LEU | 73 | 5.937
| 4.787 | −5.978 | 1.00 | 0.00 | BrD | ATOM | 1232 | CD1 | LEU | 73 | 7.860
| 4.943 | −6.857 | 1.00 | 0.00 | BrD | ATOM | 1233 | HD11 | LEU | 73 | 8.166
| 3.907 | −6.840 | 1.00 | 0.00 | BrD | ATOM | 1234 | HD12 | LEU | 73 | 8.729
| 5.576 | −6.750 | 1.00 | 0.00 | BrD | ATOM | 1235 | HD13 | LEU | 73 | 7.372
| 5.158 | −7.796 | 1.00 | 0.00 | BrD | ATOM | 1236 | CD2 | LEU | 73 | 6.710
| 6.701 | −5.498 | 1.00 | 0.00 | BrD | ATOM | 1237 | HD21 | LEU | 73 | 7.104
| 6.979 | −4.531 | 1.00 | 0.00 | BrD | ATOM | 1238 | HD22 | LEU | 73 | 5.659
| 6.943 | −5.541 | 1.00 | 0.00 | BrD | ATOM | 1239 | HD23 | LEU | 73 | 7.237
| 7.243 | −6.270 | 1.00 | 0.00 | BrD | ATOM | 1240 | C | LEU | 73 | 5.528
| 3.645 | −3.025 | 1.00 | 0.00 | BrD | ATOM | 1241 | O | LEU | 73 | 4.318
| 3.860 | −3.061 | 1.00 | 0.00 | BrD | ATOM | 1242 | N | PHE | 74 | 6.041
| 2.432 | −2.860 | 1.00 | 0.00 | BrD | ATOM | 1243 | HN | PHE | 74 | 7.041
| 2.322 | −2.855 | 1.00 | 0.00 | BrD | ATOM | 1244 | CA | PHE | 74 | 5.192
| 1.253 | −2.721 | 1.00 | 0.00 | BrD | ATOM | 1245 | HA | PHE | 74 | 4.364
| −1.359 | −3.406 | 1.00 | 0.00 | BrD | ATOM | 1246 | CB | PHE | 74 | 5.984
| −0.003 | −3.084 | 1.00 | 0.00 | BrD | ATOM | 1247 | HB1 | PHE | 74 | 6.730
| 0.181 | −2.324 | 1.00 | 0.00 | BrD | ATOM | 1248 | HB2 | PHE | 74 | 6.473
| −0.154 | −4.030 | 1.00 | 0.00 | BrD | ATOM | 1249 | CG | PHE | 74 | 5.141
| −1.240 | −3.202 | 1.00 | 0.00 | BrD | ATOM | 1250 | CD1 | PHE | 74 | 4.952
| −1.851 | −4.431 | 1.00 | 0.00 | BrD | ATOM | 1251 | HD1 | PHE | 74 | 5.412
| −1.425 | −5.311 | 1.00 | 0.00 | BrD | ATOM | 1252 | CD2 | PHE | 74 | 4.546
| −1.797 | −2.082 | 1.00 | 0.00 | BrD | ATOM | 1253 | HD2 | PHE | 74 | 4.692
| −1.332 | −1.118 | 1.00 | 0.00 | BrD | ATOM | 1254 | CE3 | PHE | 74 | 4.181
| −2.993 | −4.542 | 1.00 | 0.00 | BrD | ATOM | 1255 | HE1 | PHE | 74 | 4.039
| −3.458 | −5.506 | 1.00 | 0.00 | BrD | ATOM | 1256 | CE2 | PHE | 74 | 3.780
| −2.942 | −2.186 | 1.00 | 0.00 | BrD | ATOM | 1257 | HE2 | PHE | 74 | 3.315
| −3.362 | −1.304 | 1.00 | 0.00 | BrD | ATOM | 1258 | CZ | PHE | 74 | 3.593
| −3.538 | −3.418 | 1.00 | 0.00 | BrD | ATOM | 1259 | HZ | PHE | 74 | 2.989
| 4.430 | −3.502 | 1.00 | 0.00 | BrD | ATOM | 1260 | C | PHE | 74 | 4.643
| 1.116 | −2.305 | 1.00 | 0.00 | BrD | ATOM | 1261 | O | PHE | 74 | 3.503
| 0.694 | −1.111 | 1.00 | 0.00 | BrD | ATOM | 1262 | N | MET | 75 | 5.466
| 1.447 | −0.318 | 1.00 | 0.00 | BrD | ATOM | 1263 | HN | MET | 75 | 6.372
| 1.755 | −0.532 | 1.00 | 0.00 | BrD | ATOM | 1264 | CA | MET | 75 | 5.072
| 1.308 | 1.078 | 1.00 | 0.00 | BrD | ATOM | 1265 | HA | MET | 75 | 4.603
| 0.339 | 1.187 | 1.00 | 0.00 | BrD | ATOM | 1266 | CB | MET | 75 | 6.300
| 1.365 | 1.984 | 1.00 | 0.00 | BrD | ATOM | 1267 | HB1 | MET | 75 | 6.001
| 1.734 | 2.954 | 1.00 | 0.00 | BrD | ATOM | 1268 | HB2 | MET | 75 | 7.021
| 2.043 | 1.554 | 1.00 | 0.00 | BrD | ATOM | 1269 | CG | MET | 75 | 6.966
| 0.014 | 2.171 | 1.00 | 0.00 | BrD | ATOM | 1270 | HG1 | MET | 75 | 7.524
| −0.029 | 3.092 | 1.00 | 0.00 | BrD | ATOM | 1271 | HG2 | MET | 75 | 6.200
| −0.744 | 2.231 | 1.00 | 0.00 | BrD | ATOM | 1272 | SD | MET | 75 | 8.086
| −0.403 | 0.822 | 1.00 | 0.00 | BrD | ATOM | 1273 | CE | MET | 75 | 8.173
| −2.182 | 1.002 | 1.00 | 0.00 | BrD | ATOM | 1274 | HE1 | MET | 75 | 7.211
| −2.557 | 1.319 | 1.00 | 0.00 | BrD | ATOM | 1275 | HE2 | MET | 75 | 8.917
| −2.435 | 1.741 | 1.00 | 0.00 | BrD | ATOM | 1276 | HE3 | MET | 75 | 8.438
| 2.630 | 0.054 | 1.00 | 0.00 | BrD | ATOM | 1277 | C | MET | 75 | 4.067
| 2.374 | 1.496 | 1.00 | 0.00 | BrD | ATOM | 1278 | O | MET | 75 | 2.939
| 2.052 | 1.866 | 1.00 | 0.00 | BrD | ATOM | 1279 | N | ALA | 76 | 4.472
| 3.642 | 1.462 | 1.00 | 0.00 | BrD | ATOM | 1280 | HN | ALA | 76 | 5.380
| 3.854 | 1.163 | 1.00 | 0.00 | BrD | ATOM | 1281 | CA | ALA | 76 | 3.573
| 4.722 | 1.861 | 1.00 | 0.00 | BrD | ATOM | 1282 | HA | ALA | 76 | 3.409
| 4.538 | 2.922 | 1.00 | 0.00 | BrD | ATOM | 1283 | CB | ALA | 76 | 4.182
| 6.083 | 1.595 | 1.00 | 0.00 | BrD | ATOM | 1284 | HB1 | ALA | 76 | 4.234
| 6.252 | 0.531 | 1.00 | 0.00 | BrD | ATOM | 1285 | HB2 | ALA | 76 | 5.172
| 6.125 | 2.021 | 1.00 | 0.00 | BrD | ATOM | 1286 | HB3 | ALA | 76 | 3.558

TABLE 6-continued

Atomic Structure Coordinates of the
P/CAF Bromodomain/Acetyl-Histamine Complex

| | | | | | | | | | |
|---|---|---|---|---|---|---|---|---|---|
| 6.842 | 2.049 | 1.00 | 0.00 | BrD | ATOM | 1287 | C | ALA | 76 | 2.240 |
| 4.601 | 1.147 | 1.00 | 0.00 | BrD | ATOM | 1288 | O | ALA | 76 | 1.211 |
| 5.026 | 1.666 | 1.00 | 0.00 | BrD | ATOM | 1289 | N | ASP | 77 | 2.270 |
| 4.014 | −0.044 | 1.00 | 0.00 | BrD | ATOM | 1290 | HN | ASP | 77 | 3.124 |
| 3.685 | −0.394 | 1.00 | 0.00 | BrD | ATOM | 1291 | CA | ASP | 77 | 1.058 |
| 3.804 | −0.918 | 1.00 | 0.00 | BrD | ATOM | 1292 | HA | ASP | 77 | 0.460 |
| 4.701 | −0.750 | 1.00 | 0.00 | BrD | ATOM | 1293 | CB | ASP | 77 | 1.392 |
| 2.534 | −2.283 | 1.00 | 0.00 | BrD | ATOM | 1294 | HB1 | ASP | 77 | 2.196 |
| 2.817 | −2.334 | 1.00 | 0.00 | BrD | ATOM | 1295 | HB2 | ASP | 77 | 0.521 |
| 3.128 | −2.776 | 1.00 | 0.00 | BrD | ATOM | 1296 | CG | ASP | 77 | 1.817 |
| 4.790 | −3.018 | 1.00 | 0.00 | BrD | ATOM | 1297 | OD1 | ASP | 77 | 1.353 |
| 4.995 | −4.159 | 1.00 | 0.00 | BrD | ATOM | 1298 | OD2 | ASP | 77 | 2.613 |
| 5.569 | −2.453 | 1.00 | 0.00 | BrD | ATOM | 1299 | C | ASP | 77 | 0.268 |
| 2.641 | −0.243 | 1.00 | 0.00 | BrD | ATOM | 1300 | O | ASP | 77 | −0.958 |
| 2.717 | −0.113 | 1.00 | 0.00 | BrD | ATOM | 1301 | N | LEU | 78 | 0.970 |
| 1.569 | 0.119 | 1.00 | 0.00 | BrD | ATOM | 1302 | HN | LEU | 78 | 1.944 |
| 1.570 | 0.006 | 1.00 | 0.00 | BrD | ATOM | 1303 | CA | LEU | 78 | 0.319 |
| 0.411 | 0.711 | 1.00 | 0.00 | BrD | ATOM | 1304 | HA | LEU | 78 | −0.493 |
| −0.122 | 0.060 | 1.00 | 0.00 | BrD | ATOM | 1305 | CB | LEU | 78 | 1.280 |
| −0.761 | 0.849 | 1.00 | 0.00 | BrD | ATOM | 1306 | HB1 | LEU | 78 | 2.212 |
| −0.516 | 0.358 | 1.00 | 0.00 | BrD | ATOM | 1307 | HB2 | LEU | 78 | 1.480 |
| −0.922 | 1.900 | 1.00 | 0.00 | BrD | ATOM | 1308 | CG | LEU | 78 | 0.736 |
| −2.052 | 0.259 | 1.00 | 0.00 | BrD | ATOM | 1309 | HG | LEU | 78 | −0.338 |
| −2.023 | 0.293 | 1.00 | 0.00 | BrD | ATOM | 1310 | CD1 | LEU | 78 | 1.143 |
| −2.189 | −1.193 | 1.00 | 0.00 | BrD | ATOM | 1311 | HD11 | LEU | 78 | 1.413 |
| −3.213 | −1.398 | 1.00 | 0.00 | BrD | ATOM | 1312 | HD12 | LEU | 78 | 1.985 |
| −2.543 | −1.388 | 1.00 | 0.00 | BrD | ATOM | 1313 | HD13 | LEU | 78 | 0.317 |
| −1.901 | −1.825 | 1.00 | 0.00 | BrD | ATOM | 1314 | CD2 | LEU | 78 | 1.189 |
| −3.236 | 1.078 | 1.00 | 0.00 | BrD | ATOM | 1315 | HD21 | LEU | 78 | 2.264 |
| −3.266 | 1.099 | 1.00 | 0.00 | BrD | ATOM | 1316 | HD22 | LEU | 78 | 0.808 |
| −4.145 | 0.640 | 1.00 | 0.00 | BrD | ATOM | 1317 | HD23 | LEU | 78 | 0.809 |
| 3.130 | 2.084 | 1.00 | 0.00 | BrD | ATOM | 1318 | C | LEU | 78 | −0.253 |
| −0.769 | 2.066 | 1.00 | 0.00 | BrD | ATOM | 1319 | O | LEU | 78 | −1.459 |
| 0.663 | 2.292 | 1.00 | 0.00 | BrD | ATOM | 1320 | N | GLN | 79 | 0.611 |
| 1.252 | 2.952 | 1.00 | 0.00 | BrD | ATOM | 1321 | HN | GLN | 79 | 1.551 |
| 1.353 | 2.700 | 1.00 | 0.00 | BrD | ATOM | 1322 | CA | GLN | 79 | 0.171 |
| 1.723 | 4.254 | 1.00 | 0.00 | BrD | ATOM | 1323 | HA | GLN | 79 | −0.198 |
| 0.873 | 4.807 | 1.00 | 0.00 | BrD | ATOM | 1324 | CB | GLN | 79 | 1.338 |
| 2.361 | 5.015 | 1.00 | 0.00 | BrD | ATOM | 1325 | HB1 | GLN | 79 | 1.045 |
| 2.520 | 6.038 | 1.00 | 0.00 | BrD | ATOM | 1326 | HB2 | GLN | 79 | 2.180 |
| 1.686 | 4.991 | 1.00 | 0.00 | BrD | ATOM | 1327 | CG | GLN | 79 | 1.781 |
| 3.694 | 4.448 | 1.00 | 0.00 | BrD | ATOM | 1328 | HG1 | GLN | 79 | 1.501 |
| 3.740 | 3.407 | 1.00 | 0.00 | BrD | ATOM | 1329 | HG2 | GLN | 79 | 2.855 |
| 3.766 | 4.538 | 1.00 | 0.00 | BrD | ATOM | 1330 | CD | GLN | 79 | 1.150 |
| 4.871 | 5.172 | 1.00 | 0.00 | BrD | ATOM | 1331 | OE1 | GLN | 79 | 0.409 |
| 5.651 | 4.585 | 1.00 | 0.00 | BrD | ATOM | 1332 | NH2 | GLN | 79 | 1.467 |
| 5.005 | 6.457 | 1.00 | 0.00 | BrD | ATOM | 1333 | HE21 | GLN | 79 | 1.079 |
| 5.757 | 6.950 | 1.00 | 0.00 | BrD | ATOM | 1334 | HE22 | GLN | 79 | 2.070 |
| 4.346 | 6.859 | 1.00 | 0.00 | BrD | ATOM | 1335 | C | GLN | 79 | −0.968 |
| 2.732 | 4.074 | 1.00 | 0.00 | BrD | ATOM | 1336 | O | GLN | 79 | −1.787 |
| 2.924 | 4.964 | 1.00 | 0.00 | BrD | ATOM | 1337 | N | ARG | 80 | −0.997 |
| 3.356 | 2.895 | 1.00 | 0.00 | BrD | ATOM | 1338 | HN | ARG | 80 | −0.321 |
| 3.140 | 2.216 | 1.00 | 0.00 | BrD | ATOM | 1339 | CA | ARG | 80 | −2.048 |
| 4.306 | 2.560 | 1.00 | 0.00 | BrD | ATOM | 1340 | HA | ARG | 80 | −2.275 |
| 4.880 | 3.447 | 1.00 | 0.00 | BrD | ATOM | 1341 | CB | ARG | 80 | −1.579 |
| 5.253 | 1.451 | 1.00 | 0.00 | BrD | ATOM | 1342 | HB1 | ARG | 80 | −2.401 |
| 5.429 | 0.773 | 1.00 | 0.00 | BrD | ATOM | 1343 | HB2 | ARG | 80 | −0.770 |
| 4.785 | 0.908 | 1.00 | 0.00 | BrD | ATOM | 1344 | CG | ARG | 80 | −1.092 |
| 6.598 | 1.964 | 1.00 | 0.00 | BrD | ATOM | 1345 | HG1 | ARG | 80 | −0.290 |
| 6.434 | 2.669 | 1.00 | 0.00 | BrD | ATOM | 1346 | HG2 | ARG | 80 | −0.728 |
| 7.180 | 1.131 | 1.00 | 0.00 | BrD | ATOM | 1347 | CD | ARG | 80 | −2.206 |
| 7.367 | 2.654 | 1.00 | 0.00 | BrD | ATOM | 1348 | HD1 | ARG | 80 | −3.054 |
| 6.711 | 2.780 | 1.00 | 0.00 | BrD | ATOM | 1349 | HD2 | ARG | 80 | −2.486 |
| 8.203 | 2.031 | 1.00 | 0.00 | BrD | ATOM | 1350 | NE | ARG | 80 | −1.796 |
| 7.867 | 3.962 | 1.00 | 0.00 | BrD | ATOM | 1351 | HE | ARG | 80 | −0.837 |
| 7.874 | 4.166 | 1.00 | 0.00 | BrD | ATOM | 1352 | CZ | ARG | 80 | −2.688 |
| 8.310 | 4.881 | 1.00 | 0.00 | BrD | ATOM | 1353 | NH1 | ARG | 80 | −2.198 |
| 8.750 | 6.047 | 1.00 | 0.00 | BrD | ATOM | 1354 | HH11 | ARG | 80 | −1.216 |
| 8.749 | 6.237 | 1.00 | 0.00 | BrD | ATOM | 1355 | HH12 | ARG | 80 | −2.840 |
| 9.083 | 6.738 | 1.00 | 0.00 | BrD | ATOM | 1356 | NH2 | ARG | 80 | −3.950 |
| 8.314 | 4.633 | 1.00 | 0.00 | BrD | ATOM | 1357 | HH21 | ARG | 80 | −4.590 |
| 8.647 | 5.326 | 1.00 | 0.00 | BrD | ATOM | 1358 | HH22 | ARG | 80 | −4.293 |
| 7.983 | 3.754 | 1.00 | 0.00 | BrD | ATOM | 1359 | C | ARG | 80 | −3.305 |
| 3.568 | 2.114 | 1.00 | 0.00 | BrD | ATOM | 1360 | O | ARG | 80 | −4.417 |
| 3.922 | 2.502 | 1.00 | 0.00 | BrD | ATOM | 1361 | N | VAL | 81 | −3.116 |
| 2.536 | 1.293 | 1.00 | 0.00 | BrD | ATOM | 1362 | HN | VAL | 81 | −2.203 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 2.301 | 1.024 | 1.00 | 0.00 | BrD | ATOM | 1363 | CA | VAL | 81 | −4.231 |
| 1.738 | 0.799 | 1.00 | 0.00 | BrD | ATOM | 1364 | HA | VAL | 81 | −4.849 |
| 2.374 | 0.182 | 1.00 | 0.00 | BrD | ATOM | 1365 | CB | VAL | 81 | −3.742 |
| −0.556 | −0.063 | 1.00 | 0.00 | BrD | ATOM | 1366 | HB | VAL | 81 | −3.104 |
| 0.068 | 0.546 | 1.00 | 0.00 | BrD | ATOM | 1367 | CG1 | VAL | 81 | −2.926 |
| 1.057 | −1.244 | 1.00 | 0.00 | BrD | ATOM | 1368 | HG11 | VAL | 81 | −3.467 |
| 0.861 | −2.159 | 1.00 | 0.00 | BrD | ATOM | 1369 | HG12 | VAL | 81 | −1.973 |
| 0.545 | −1.268 | 1.00 | 0.00 | BrD | ATOM | 1370 | HG13 | VAL | 81 | −2.763 |
| −2.119 | −1.146 | 1.00 | 0.00 | BrD | ATOM | 1371 | CG2 | VAL | 81 | −4.916 |
| −0.287 | −0.539 | 1.00 | 0.00 | BrD | ATOM | 1372 | HG21 | VAL | 81 | −4.851 |
| 0.425 | −1.608 | 1.00 | 0.00 | BrD | ATOM | 1373 | HG22 | VAL | 81 | −5.841 |
| −0.215 | −0.297 | 1.00 | 0.00 | BrD | ATOM | 1374 | HG23 | VAL | 81 | −4.890 |
| 1.250 | −0.050 | 1.00 | 0.00 | BrD | ATOM | 1375 | C | VAL | 81 | −5.069 |
| 1.206 | 1.957 | 1.00 | 0.00 | BrD | ATOM | 1376 | O | VAL | 81 | −6.293 |
| 1.339 | 1.964 | 1.00 | 0.00 | BrD | ATOM | 1377 | N | PHE | 82 | −4.400 |
| 0.610 | 2.937 | 1.00 | 0.00 | BrD | ATOM | 1378 | HN | PHE | 82 | −3.424 |
| 0.540 | 2.876 | 1.00 | 0.00 | BrD | ATOM | 1379 | CA | PHE | 82 | −5.079 |
| −0.070 | 4.108 | 1.00 | 0.00 | BrD | ATOM | 1380 | HA | PHE | 82 | −5.919 |
| −0.514 | 3.764 | 1.00 | 0.00 | BrD | ATOM | 1381 | CB | PHE | 82 | −4.131 |
| −0.833 | 4.899 | 1.00 | 0.00 | BrD | ATOM | 1382 | HB1 | PHE | 82 | −3.486 |
| −0.220 | 5.511 | 1.00 | 0.00 | BrD | ATOM | 1383 | HB2 | PHE | 82 | −4.712 |
| −1.484 | 5.536 | 1.00 | 0.00 | BrD | ATOM | 1384 | CG | PHE | 82 | −3.261 |
| −1.695 | 4.028 | 1.00 | 0.00 | BrD | ATOM | 1385 | CD1 | PHE | 82 | −1.979 |
| −2.035 | 4.428 | 1.00 | 0.00 | BrD | ATOM | 1386 | HD1 | PHE | 82 | −1.606 |
| −1.677 | 5.376 | 1.00 | 0.00 | BrD | ATOM | 1387 | CD2 | PHE | 82 | −3.725 |
| −2.162 | 2.809 | 1.00 | 0.00 | BrD | ATOM | 1388 | HD2 | PHE | 82 | −4.723 |
| −1.901 | 2.487 | 1.00 | 0.00 | BrD | ATOM | 1389 | CE1 | PHE | 82 | −1.177 |
| −2.827 | 3.628 | 1.00 | 0.00 | BrD | ATOM | 1390 | HE1 | PHE | 82 | −0.179 |
| −3.085 | 3.951 | 1.00 | 0.00 | BrD | ATOM | 1391 | CE2 | PHE | 82 | −2.928 |
| −2.952 | 2.004 | 1.00 | 0.00 | BrD | ATOM | 1392 | HE2 | PHE | 82 | −3.302 |
| −3.311 | 1.057 | 1.00 | 0.00 | BrD | ATOM | 1393 | CZ | PHE | 82 | −1.651 |
| −3.284 | 2.413 | 1.00 | 0.00 | BrD | ATOM | 1394 | HZ | PHE | 82 | −1.029 |
| 3.906 | 1.789 | 1.00 | 0.00 | BrD | ATOM | 1395 | C | PHE | 82 | −5.594 |
| 1.197 | 4.996 | 1.00 | 0.00 | BrD | ATOM | 1396 | O | PHE | 82 | −6.745 |
| 1.180 | 5.431 | 1.00 | 0.00 | BrD | ATOM | 1397 | N | THR | 83 | −4.740 |
| 2.185 | 5.241 | 1.00 | 0.00 | BrD | ATOM | 1398 | HN | THR | 83 | −3.841 |
| 2.149 | 4.852 | 1.00 | 0.00 | BrD | ATOM | 1399 | CA | THR | 83 | −5.119 |
| 3.337 | 6.048 | 1.00 | 0.00 | BrD | ATOM | 1400 | HA | THR | 83 | −5.427 |
| 2.977 | 7.019 | 1.00 | 0.00 | BrD | ATOM | 1401 | CB | THR | 83 | −3.927 |
| 4.282 | 6.216 | 1.00 | 0.00 | BrD | ATOM | 1402 | HB | THR | 83 | −3.525 |
| 4.516 | 5.240 | 1.00 | 0.00 | BrD | ATOM | 1403 | OG1 | THR | 83 | −2.905 |
| 3.666 | 6.982 | 1.00 | 0.00 | BrD | ATOM | 1404 | HG1 | THR | 83 | −3.138 |
| 3.699 | 7.913 | 1.00 | 0.00 | BrD | ATOM | 1405 | CG2 | THR | 83 | −4.283 |
| 5.589 | 6.892 | 1.00 | 0.00 | BrD | ATOM | 1406 | HG21 | THR | 83 | −4.813 |
| 4.222 | 6.196 | 1.00 | 0.00 | BrD | ATOM | 1407 | HG22 | THR | 83 | −3.379 |
| 6.085 | 7.214 | 1.00 | 0.00 | BrD | ATOM | 1408 | HG23 | THR | 83 | −4.910 |
| 5.391 | 7.749 | 1.00 | 0.00 | BrD | ATOM | 1409 | C | THR | 83 | −6.286 |
| 4.077 | 5.402 | 1.00 | 0.00 | BrD | ATOM | 1410 | O | THR | 83 | −7.073 |
| 4.735 | 6.082 | 1.00 | 0.00 | BrD | ATOM | 1411 | N | ASN | 84 | −6.391 |
| 3.956 | 4.082 | 1.00 | 0.00 | BrD | ATOM | 1412 | HN | ASN | 84 | −5.732 |
| 3.418 | 3.597 | 1.00 | 0.00 | BrD | ATOM | 1413 | CA | ASN | 84 | −7.458 |
| 4.609 | 3.334 | 1.00 | 0.00 | BrD | ATOM | 1414 | HA | ASN | 84 | −7.546 |
| 5.622 | 3.698 | 1.00 | 0.00 | BrD | ATOM | 1415 | CB | ASN | 84 | −7.113 |
| 4.640 | 1.844 | 1.00 | 0.00 | BrD | ATOM | 1416 | HB1 | ASN | 84 | −7.095 |
| 3.629 | 1.464 | 1.00 | 0.00 | BrD | ATOM | 1417 | HB2 | ASN | 84 | −6.138 |
| 5.086 | 1.716 | 1.00 | 0.00 | BrD | ATOM | 1418 | CG | ASN | 84 | −8.115 |
| 5.438 | 1.035 | 1.00 | 0.00 | BrD | ATOM | 1419 | OD1 | ASN | 84 | −9.269 |
| 5.596 | 1.433 | 1.00 | 0.00 | BrD | ATOM | 1420 | ND2 | ASN | 84 | −7.677 |
| 5.965 | −0.111 | 1.00 | 0.00 | BrD | ATOM | 1421 | HD21 | ASN | 84 | −6.745 |
| 5.778 | −0.365 | 1.00 | 0.00 | BrD | ATOM | 1422 | HD22 | ASN | 84 | −8.302 |
| 6.465 | −0.655 | 1.00 | 0.00 | BrD | ATOM | 1423 | C | ASN | 84 | −8.788 |
| 3.893 | 3.544 | 1.00 | 0.00 | BrD | ATOM | 1424 | O | ASN | 84 | −9.745 |
| 4.477 | 4.051 | 1.00 | 0.00 | BrD | ATOM | 1425 | N | CYS | 85 | −8.842 |
| 2.623 | 3.150 | 1.00 | 0.00 | BrD | ATOM | 1426 | HN | CYS | 85 | −8.046 |
| 2.213 | 2.751 | 1.00 | 0.00 | BrD | ATOM | 1427 | CA | CYS | 85 | −10.058 |
| 1.827 | 3.291 | 1.00 | 0.00 | BrD | ATOM | 1428 | HA | CYS | 85 | −10.778 |
| 2.193 | 2.575 | 1.00 | 0.00 | BrD | ATOM | 1429 | CB | CYS | 85 | −9.765 |
| 0.354 | 2.995 | 1.00 | 0.00 | BrD | ATOM | 1430 | HB1 | CYS | 85 | −8.806 |
| −0.277 | 2.504 | 1.00 | 0.00 | BrD | ATOM | 1431 | HB2 | CYS | 85 | −9.712 |
| −0.193 | 3.926 | 1.00 | 0.00 | BrD | ATOM | 1432 | SG | CYS | 85 | −10.992 |
| −0.444 | 1.933 | 1.00 | 0.00 | BrD | ATOM | 1433 | HG | CYS | 85 | −10.844 |
| 0.144 | 1.033 | 1.00 | 0.00 | BrD | ATOM | 1434 | C | CYS | 85 | −10.645 |
| 1.365 | 4.693 | 1.00 | 0.00 | BrD | ATOM | 1435 | O | CYS | 85 | −11.842 |
| 2.203 | 6.854 | 1.00 | 0.00 | BrD | ATOM | 1436 | N | LYS | 86 | −9.794 |
| 1.817 | 5.701 | 1.00 | 0.00 | BrD | ATOM | 1437 | HN | LYS | 86 | −8.852 |
| 1.626 | 5.508 | 1.00 | 0.00 | BrD | ATOM | 1438 | CA | LYS | 86 | −10.228 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 1.921 | 7.089 | 1.00 | 0.00 | BrD | ATOM | 1439 | HA | LYS | 86 | −11.111 |
| 1.310 | 7.203 | 1.00 | 0.00 | BrD | ATOM | 1440 | CB | LYS | 86 | −9.137 |
| 1.395 | 8.023 | 1.00 | 0.00 | BrD | ATOM | 1441 | HB1 | LYS | 86 | −9.063 |
| 0.325 | 7.903 | 1.00 | 0.00 | BrD | ATOM | 1442 | HB2 | LYS | 86 | −9.416 |
| 1.616 | 9.043 | 1.00 | 0.00 | BrD | ATOM | 1443 | CG | LYS | 86 | −7.768 |
| 1.998 | 7.763 | 1.00 | 0.00 | BrD | ATOM | 1444 | HG1 | LYS | 86 | −7.809 |
| 2.583 | 6.857 | 1.00 | 0.00 | BrD | ATOM | 1445 | HG2 | LYS | 86 | −7.050 |
| 1.199 | 7.645 | 1.00 | 0.00 | BrD | ATOM | 1446 | CD | LYS | 86 | −7.325 |
| 2.892 | 8.910 | 1.00 | 0.00 | BrD | ATOM | 1447 | HD1 | LYS | 86 | −6.477 |
| 3.478 | 8.590 | 1.00 | 0.00 | BrD | ATOM | 1448 | HD2 | LYS | 86 | −8.140 |
| 3.548 | 9.177 | 1.00 | 0.00 | BrD | ATOM | 1449 | CE | LYS | 86 | −6.929 |
| 2.076 | 10.130 | 1.00 | 0.00 | BrD | ATOM | 1450 | HE1 | LYS | 86 | −7.418 |
| 1.114 | 10.078 | 1.00 | 0.00 | BrD | ATOM | 1451 | HE2 | LYS | 86 | −5.858 |
| 1.935 | 10.120 | 1.00 | 0.00 | BrD | ATOM | 1452 | NZ | LYS | 86 | −7.317 |
| 2.749 | 11.400 | 1.00 | 0.00 | BrD | ATOM | 1453 | HZ1 | LYS | 86 | −8.019 |
| 2.174 | 11.909 | 1.00 | 0.00 | BrD | ATOM | 1454 | HZ2 | LYS | 86 | −7.729 |
| 3.682 | 11.199 | 1.00 | 0.00 | BrD | ATOM | 1455 | HZ3 | LYS | 86 | −6.482 |
| 2.874 | 12.008 | 1.00 | 0.00 | BrD | ATOM | 1456 | C | LYS | 86 | −10.379 |
| 3.360 | 7.456 | 1.00 | 0.00 | BrD | ATOM | 1457 | O | LYS | 86 | −11.293 |
| 3.603 | 8.429 | 1.00 | 0.00 | BrD | ATOM | 1458 | N | GLU | 87 | −10.076 |
| 4.314 | 6.676 | 1.00 | 0.00 | BrD | ATOM | 1459 | HN | GLU | 87 | −9.514 |
| 4.064 | 5.914 | 1.00 | 0.00 | BrD | ATOM | 1460 | CA | GLU | 87 | −10.350 |
| 5.724 | 6.926 | 1.00 | 0.00 | BrD | ATOM | 1461 | HA | GLU | 87 | −10.510 |
| 5.848 | 7.986 | 1.00 | 0.00 | BrD | ATOM | 1462 | CB | GLU | 87 | −9.158 |
| 6.583 | 6.498 | 1.00 | 0.00 | BrD | ATOM | 1463 | HB1 | GLU | 87 | −9.513 |
| 7.572 | 6.249 | 1.00 | 0.00 | BrD | ATOM | 1464 | HB2 | GLU | 87 | −8.706 |
| 6.141 | 5.622 | 1.00 | 0.00 | BrD | ATOM | 1465 | CG | GLU | 87 | −8.088 |
| 6.716 | 7.570 | 1.00 | 0.00 | BrD | ATOM | 1466 | HG1 | GLU | 87 | −7.954 |
| 5.757 | 8.048 | 1.00 | 0.00 | BrD | ATOM | 1467 | HG2 | GLU | 87 | −7.163 |
| 7.016 | 7.101 | 1.00 | 0.00 | BrD | ATOM | 1468 | CD | GLU | 87 | −8.446 |
| 7.740 | 8.629 | 1.00 | 0.00 | BrD | ATOM | 1469 | OE1 | GLU | 87 | −9.092 |
| 8.751 | 8.283 | 1.00 | 0.00 | BrD | ATOM | 1470 | OE2 | GLU | 87 | −8.079 |
| 7.531 | 9.805 | 1.00 | 0.00 | BrD | ATOM | 1471 | C | GLU | 87 | −11.504 |
| 6.172 | 6.183 | 1.00 | 0.00 | BrD | ATOM | 1472 | O | GLU | 87 | −12.542 |
| 6.692 | 6.787 | 1.00 | 0.00 | BrD | ATOM | 1473 | N | TYR | 88 | −11.617 |
| 5.962 | 4.871 | 1.00 | 0.00 | BrD | ATOM | 1474 | HN | TYR | 88 | −10.840 |
| 5.541 | 4.446 | 1.00 | 0.00 | BrD | ATOM | 1475 | CA | TYR | 88 | −12.759 |
| 6.339 | 6.046 | 1.00 | 0.00 | BrD | ATOM | 1476 | HA | TYR | 88 | −13.070 |
| 7.330 | 4.344 | 1.00 | 0.00 | BrD | ATOM | 1477 | CB | TYR | 88 | −12.361 |
| 6.363 | 2.568 | 1.00 | 0.00 | BrD | ATOM | 1478 | HB1 | TYR | 88 | −11.320 |
| 6.602 | 2.489 | 1.00 | 0.00 | BrD | ATOM | 1479 | HB2 | TYR | 88 | −12.537 |
| 5.388 | 2.139 | 1.00 | 0.00 | BrD | ATOM | 1480 | CG | TYR | 88 | −13.128 |
| 7.276 | 1.748 | 1.00 | 0.00 | BrD | ATOM | 1481 | CD1 | TYR | 88 | −12.606 |
| 8.640 | 1.505 | 1.00 | 0.00 | BrD | ATOM | 1482 | HD1 | TYR | 88 | −11.639 |
| 8.896 | 1.914 | 1.00 | 0.00 | BrD | ATOM | 1483 | CD2 | TYR | 88 | −14.372 |
| 7.077 | 1.213 | 1.00 | 0.00 | BrD | ATOM | 1484 | HD2 | TYR | 88 | −14.792 |
| 6.087 | 1.392 | 1.00 | 0.00 | BrD | ATOM | 1485 | CE1 | TYR | 88 | −13.302 |
| 9.568 | 0.755 | 1.00 | 0.00 | BrD | ATOM | 1486 | HE1 | TYR | 88 | −12.880 |
| 10.546 | 0.578 | 1.00 | 0.00 | BrD | ATOM | 1487 | CE2 | TYR | 88 | −15.075 |
| 7.989 | 0.462 | 1.00 | 0.00 | BrD | ATOM | 1488 | HE2 | TYR | 88 | −16.042 |
| 7.730 | 0.055 | 1.00 | 0.00 | BrD | ATOM | 1489 | CZ | TYR | 88 | −14.536 |
| 9.238 | 0.236 | 1.00 | 0.00 | BrD | ATOM | 1490 | OH | TYR | 88 | −15.233 |
| 10.159 | −0.512 | 1.00 | 0.00 | BrD | ATOM | 1491 | HH | TYR | 88 | −15.995 |
| 10.465 | −0.014 | 1.00 | 0.00 | BrD | ATOM | 1492 | C | TYR | 88 | −13.923 |
| 5.372 | 4.256 | 1.00 | 0.00 | BrD | ATOM | 1493 | O | TYR | 88 | −14.369 |
| 4.711 | 3.320 | 1.00 | 0.00 | BrD | ATOM | 1494 | N | ASN | 89 | −14.408 |
| 5.298 | 5.492 | 1.00 | 0.00 | BrD | ATOM | 1495 | HN | ASN | 89 | −14.012 |
| 5.852 | 6.195 | 1.00 | 0.00 | BrD | ATOM | 1496 | CA | ASN | 89 | −15.518 |
| 4.414 | 5.827 | 1.00 | 0.00 | BrD | ATOM | 1497 | HA | ASN | 89 | −16.155 |
| 4.336 | 4.958 | 1.00 | 0.00 | BrD | ATOM | 1498 | CB | ASN | 89 | −14.996 |
| 3.023 | 6.192 | 1.00 | 0.00 | BrD | ATOM | 1499 | HB1 | ASN | 89 | −15.816 |
| 2.421 | 6.557 | 1.00 | 0.00 | BrD | ATOM | 1500 | HB2 | ASN | 89 | −14.578 |
| 2.559 | 5.311 | 1.00 | 0.00 | BrD | ATOM | 1501 | CG | ASN | 89 | −13.925 |
| 3.072 | 7.263 | 1.00 | 0.00 | BrD | ATOM | 1502 | OD1 | ASN | 89 | −13.552 |
| 4.147 | 7.734 | 1.00 | 0.00 | BrD | ATOM | 1503 | ND2 | ASN | 89 | −13.424 |
| 1.906 | 7.655 | 1.00 | 0.00 | BrD | ATOM | 1504 | HD21 | ASN | 89 | −13.770 |
| 1.090 | 7.236 | 1.00 | 0.00 | BrD | ATOM | 1505 | HD22 | ASN | 89 | −12.731 |
| 1.909 | 8.347 | 1.00 | 0.00 | BrD | ATOM | 1506 | C | ASN | 89 | −16.332 |
| 4.982 | 6.985 | 1.00 | 0.00 | BrD | ATOM | 1507 | O | ASN | 89 | −16.088 |
| 4.658 | 8.147 | 1.00 | 0.00 | BrD | ATOM | 1508 | N | ALA | 90 | −17.296 |
| 5.836 | 6.659 | 1.00 | 0.00 | BrD | ATOM | 1509 | HN | ALA | 90 | −17.438 |
| 6.058 | 5.715 | 1.00 | 0.00 | BrD | ATOM | 1510 | CA | ALA | 90 | −18.142 |
| 6.458 | 7.670 | 1.00 | 0.00 | BrD | ATOM | 1511 | HA | ALA | 90 | −17.525 |
| 7.122 | 8.258 | 1.00 | 0.00 | BrD | ATOM | 1512 | CB | ALA | 90 | −19.228 |
| 7.291 | 7.006 | 1.00 | 0.00 | BrD | ATOM | 1513 | HB1 | ALA | 90 | −19.280 |
| 7.045 | 5.956 | 1.00 | 0.00 | BrD | ATOM | 1514 | HB2 | ALA | 90 | −18.997 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 8.340 | 7.119 | 1.00 | 0.00 | BrD | ATOM | 1515 | HB3 | ALA | 90 | −20.179 |
| 7.081 | 7.473 | 1.00 | 0.00 | BrD | ATOM | 1516 | C | ALA | 90 | −18.764 |
| 5.414 | 8.394 | 1.00 | 0.00 | BrD | ATOM | 1517 | O | ALA | 90 | −18.728 |
| 5.557 | 9.817 | 1.00 | 0.00 | BrD | ATOM | 1518 | N | PRO | 91 | −19.346 |
| 4.347 | 8.021 | 1.00 | 0.00 | BrD | ATOM | 1519 | CA | PRO | 91 | −20.000 |
| 3.290 | 8.783 | 1.00 | 0.00 | BrD | ATOM | 1520 | HA | PRO | 91 | −20.495 |
| 3.681 | 9.659 | 1.00 | 0.00 | BrD | ATOM | 1521 | CB | PRO | 91 | −21.048 |
| 2.740 | 7.800 | 1.00 | 0.00 | BrD | ATOM | 1522 | HB1 | PRO | 91 | −20.932 |
| 1.670 | 7.715 | 1.00 | 0.00 | BrD | ATOM | 1523 | HB2 | PRO | 91 | −22.038 |
| 2.966 | 8.169 | 1.00 | 0.00 | BrD | ATOM | 1524 | CG | PRO | 91 | −20.794 |
| 3.419 | 6.483 | 1.00 | 0.00 | BrD | ATOM | 1525 | HG1 | PRO | 91 | −20.778 |
| 2.684 | 5.692 | 1.00 | 0.00 | BrD | ATOM | 1526 | HG2 | PRO | 91 | −21.566 |
| 4.151 | 6.296 | 1.00 | 0.00 | BrD | ATOM | 1527 | CD | PRO | 91 | −19.456 |
| 4.095 | 6.587 | 1.00 | 0.00 | BrD | ATOM | 1528 | HD1 | PRO | 91 | −18.670 |
| 3.436 | 6.247 | 1.00 | 0.00 | BrD | ATOM | 1529 | HD2 | PRO | 91 | −19.450 |
| 5.018 | 6.027 | 1.00 | 0.00 | BrD | ATOM | 1530 | C | PRO | 91 | −19.035 |
| 2.183 | 9.196 | 1.00 | 0.00 | BrD | ATOM | 1531 | O | PRO | 91 | −19.458 |
| 1.079 | 9.540 | 1.00 | 0.00 | BrD | ATOM | 1532 | N | GLU | 92 | −17.736 |
| 2.481 | 9.160 | 1.00 | 0.00 | BrD | ATOM | 1533 | HN | GLU | 92 | −17.462 |
| 3.377 | 8.873 | 1.00 | 0.00 | BrD | ATOM | 1534 | CA | GLU | 92 | −16.703 |
| 1.506 | 9.521 | 1.00 | 0.00 | BrD | ATOM | 1535 | HA | GLU | 92 | −15.779 |
| 1.838 | 9.083 | 1.00 | 0.00 | BrD | ATOM | 1536 | CB | GLU | 92 | −16.529 |
| 1.439 | 11.039 | 1.00 | 0.00 | BrD | ATOM | 1537 | HB1 | GLU | 92 | −15.786 |
| 0.690 | 11.272 | 1.00 | 0.00 | BrD | ATOM | 1538 | HB2 | GLU | 92 | −16.182 |
| 2.399 | 11.393 | 1.00 | 0.00 | BrD | ATOM | 1539 | CG | GLU | 92 | −17.805 |
| 1.092 | 11.778 | 1.00 | 0.00 | BrD | ATOM | 1540 | HG1 | GLU | 92 | −18.550 |
| 1.831 | 11.537 | 1.00 | 0.00 | BrD | ATOM | 1541 | HG2 | GLU | 92 | −18.143 |
| 0.119 | 11.452 | 1.00 | 0.00 | BrD | ATOM | 1542 | CD | GLU | 92 | −17.622 |
| 1.062 | 13.283 | 1.00 | 0.00 | BrD | ATOM | 1543 | OE1 | GLU | 92 | −18.536 |
| 1.517 | 14.001 | 1.00 | 0.00 | BrD | ATOM | 1544 | OE2 | GLU | 92 | −16.564 |
| 0.581 | 13.743 | 1.00 | 0.00 | BrD | ATOM | 1545 | C | GLU | 92 | −17.029 |
| −0.119 | 8.974 | 1.00 | 0.00 | BrD | ATOM | 1546 | O | GLU | 92 | −16.862 |
| 0.887 | 9.663 | 1.00 | 0.00 | BrD | ATOM | 1547 | N | SER | 93 | −17.508 |
| 0.081 | 7.736 | 1.00 | 0.00 | BrD | ATOM | 1548 | HN | SER | 93 | −17.620 |
| −0.919 | 7.240 | 1.00 | 0.00 | BrD | ATOM | 1549 | CA | SER | 93 | −17.863 |
| −1.176 | 7.092 | 1.00 | 0.00 | BrD | ATOM | 1550 | HA | SER | 93 | −18.677 |
| −1.616 | 7.649 | 1.00 | 0.00 | BrD | ATOM | 1551 | CB | SER | 93 | −18.317 |
| −0.925 | 5.653 | 1.00 | 0.00 | BrD | ATOM | 1552 | HB1 | SER | 93 | −17.475 |
| 1.052 | 4.986 | 1.00 | 0.00 | BrD | ATOM | 1553 | HB2 | SER | 93 | −18.695 |
| −0.084 | 5.568 | 1.00 | 0.00 | BrD | ATOM | 1554 | OG | SER | 93 | −19.339 |
| −1.830 | 5.274 | 1.00 | 0.00 | BrD | ATOM | 1555 | HG | SER | 93 | −19.610 |
| −1.648 | 4.371 | 1.00 | 0.00 | BrD | ATOM | 1556 | C | SER | 93 | −16.686 |
| −2.241 | 7.099 | 1.00 | 0.00 | BrD | ATOM | 1557 | O | SER | 93 | −15.700 |
| −1.932 | 7.807 | 1.00 | 0.00 | BrD | ATOM | 1558 | N | GLU | 94 | −16.790 |
| −3.194 | 6.298 | 1.00 | 0.00 | BrD | ATOM | 1559 | HN | GLU | 94 | −17.598 |
| −3.303 | 5.754 | 1.00 | 0.00 | BrD | ATOM | 1560 | CA | GLU | 94 | −15.729 |
| −4.186 | 6.204 | 1.00 | 0.00 | BrD | ATOM | 1561 | HA | GLU | 94 | −15.574 |
| −4.596 | 7.191 | 1.00 | 0.00 | BrD | ATOM | 1562 | CB | GLU | 94 | −16.144 |
| −5.314 | 5.258 | 1.00 | 0.00 | BrD | ATOM | 1563 | HB1 | GLU | 94 | −16.411 |
| −4.887 | 4.302 | 1.00 | 0.00 | BrD | ATOM | 1564 | HB2 | GLU | 94 | −17.005 |
| −5.817 | 5.671 | 1.00 | 0.00 | BrD | ATOM | 1565 | CG | GLU | 94 | −15.054 |
| −6.346 | 5.031 | 1.00 | 0.00 | BrD | ATOM | 1566 | HG1 | GLU | 94 | −14.187 |
| −5.849 | 4.622 | 1.00 | 0.00 | BrD | ATOM | 1567 | HG2 | GLU | 94 | −14.797 |
| −6.793 | 5.981 | 1.00 | 0.00 | BrD | ATOM | 1568 | CD | GLU | 94 | −15.479 |
| −7.446 | 4.078 | 1.00 | 0.00 | BrD | ATOM | 1569 | OE1 | GLU | 94 | −16.617 |
| −7.382 | 3.568 | 1.00 | 0.00 | BrD | ATOM | 1570 | OE2 | GLU | 94 | −14.673 |
| −8.370 | 3.840 | 1.00 | 0.00 | BrD | ATOM | 1571 | C | GLU | 94 | −14.422 |
| −3.556 | 5.725 | 1.00 | 0.00 | BrD | ATOM | 1572 | O | GLU | 94 | −13.351 |
| −4.163 | 5.876 | 1.00 | 0.00 | BrD | ATOM | 1573 | N | TYR | 95 | −14.510 |
| −2.357 | 5.150 | 1.00 | 0.00 | BrD | ATOM | 1574 | HN | TYR | 95 | −15.387 |
| −1.930 | 5.057 | 1.00 | 0.00 | BrD | ATOM | 1575 | CA | TYR | 95 | −13.327 |
| −1.658 | 4.663 | 1.00 | 0.00 | BrD | ATOM | 1576 | HA | TYR | 95 | −12.919 |
| −2.227 | 3.841 | 1.00 | 0.00 | BrD | ATOM | 1577 | CB | TYR | 95 | −13.704 |
| 0.260 | 4.166 | 1.00 | 0.00 | BrD | ATOM | 1578 | HB1 | TYR | 95 | −14.444 |
| 0.160 | 4.827 | 1.00 | 0.00 | BrD | ATOM | 1579 | HB2 | TYR | 95 | −12.825 |
| −0.367 | 4.176 | 1.00 | 0.00 | BrD | ATOM | 1580 | CG | TYR | 95 | −14.270 |
| −0.244 | 2.762 | 1.00 | 0.00 | BrD | ATOM | 1581 | CD1 | TYR | 95 | −14.933 |
| −1.350 | 2.245 | 1.00 | 0.00 | BrD | ATOM | 1582 | HD1 | TYR | 95 | −15.041 |
| 2.232 | 2.859 | 1.00 | 0.00 | BrD | ATOM | 1583 | CD2 | TYR | 95 | −14.141 |
| 0.880 | 1.956 | 1.00 | 0.00 | BrD | ATOM | 1584 | HD2 | TYR | 95 | −13.630 |
| −1.749 | 2.343 | 1.00 | 0.00 | BrD | ATOM | 1585 | CE1 | TYR | 95 | −15.450 |
| −1.337 | 0.963 | 1.00 | 0.00 | BrD | ATOM | 1586 | HE1 | TYR | 95 | −15.961 |
| 2.208 | 0.579 | 1.00 | 0.00 | BrD | ATOM | 1587 | CE2 | TYR | 95 | −14.656 |
| 0.901 | 0.673 | 1.00 | 0.00 | BrD | ATOM | 1588 | HE2 | TYR | 95 | −14.546 |
| −1.785 | 0.062 | 1.00 | 0.00 | BrD | ATOM | 1589 | CZ | TYR | 95 | −15.310 |
| −0.210 | 0.182 | 1.00 | 0.00 | BrD | ATOM | 1590 | OH | TYR | 95 | −15.823 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −0.193 | −1.095 | 1.00 | 0.00 | BrD | ATOM | 1591 | HH | TYR | 95 | −16.730 |
| −0.508 | −1.079 | 1.00 | 0.00 | BrD | ATOM | 1592 | C | TYR | 95 | −12.274 |
| −1.552 | 5.761 | 1.00 | 0.00 | BrD | ATOM | 1593 | O | TYR | 95 | −11.076 |
| −1.511 | 5.485 | 1.00 | 0.00 | BrD | ATOM | 1594 | N | TYR | 96 | −12.733 |
| −1.513 | 7.007 | 1.00 | 0.00 | BrD | ATOM | 1595 | HN | TYR | 96 | −13.700 |
| −1.553 | 7.161 | 1.00 | 0.00 | BrD | ATOM | 1596 | CA | TYR | 96 | −13.835 |
| −1.421 | 8.152 | 1.00 | 0.00 | BrD | ATOM | 1597 | HA | TYR | 96 | −11.033 |
| −0.746 | 7.889 | 1.00 | 0.00 | BrD | ATOM | 1598 | CB | TYR | 96 | −12.581 |
| −0.860 | 9.365 | 1.00 | 0.00 | BrD | ATOM | 1599 | HB1 | TYR | 96 | −13.397 |
| 1.522 | 9.615 | 1.00 | 0.00 | BrD | ATOM | 1600 | HB2 | TYR | 96 | −12.977 |
| −0.114 | 9.116 | 1.00 | 0.00 | BrD | ATOM | 1601 | CG | TYR | 96 | −11.712 |
| −0.708 | 10.594 | 1.00 | 0.00 | BrD | ATOM | 1602 | CD1 | TYR | 96 | −10.351 |
| −0.458 | 10.477 | 1.00 | 0.00 | BrD | ATOM | 1603 | HD1 | TYR | 96 | −9.918 |
| −0.375 | 9.493 | 1.00 | 0.00 | BrD | ATOM | 1604 | CD2 | TYR | 96 | −12.252 |
| −0.815 | 11.870 | 1.00 | 0.00 | BrD | ATOM | 1605 | HD2 | TYR | 96 | −13.308 |
| −1.009 | 11.979 | 1.00 | 0.00 | BrD | ATOM | 1606 | CE1 | TYR | 96 | −9.551 |
| −0.319 | 11.594 | 1.00 | 0.00 | BrD | ATOM | 1607 | HE1 | TYR | 96 | −8.495 |
| −0.125 | 11.480 | 1.00 | 0.00 | BrD | ATOM | 1608 | CE2 | TYR | 96 | −11.458 |
| −0.677 | 12.993 | 1.00 | 0.00 | BrD | ATOM | 1609 | HE2 | TYR | 96 | −11.895 |
| −0.763 | 13.977 | 1.00 | 0.00 | BrD | ATOM | 1610 | CZ | TYR | 96 | −10.109 |
| −0.429 | 12.849 | 1.00 | 0.00 | BrD | ATOM | 1611 | OH | TYR | 96 | −9.315 |
| −0.291 | 13.964 | 1.00 | 0.00 | BrD | ATOM | 1612 | HH | TYR | 96 | −8.479 |
| −0.742 | 13.821 | 1.00 | 0.00 | BrD | ATOM | 1613 | C | TYR | 96 | −11.238 |
| −2.783 | 8.497 | 1.00 | 0.00 | BrD | ATOM | 1614 | O | TYR | 96 | −10.238 |
| −2.868 | 9.211 | 1.00 | 0.00 | BrD | ATOM | 1615 | N | LYS | 97 | −11.057 |
| −3.849 | 7.995 | 1.00 | 0.00 | BrD | ATOM | 1616 | HN | LYS | 97 | −12.650 |
| −3.728 | 7.435 | 1.00 | 0.00 | BrD | ATOM | 1617 | CA | LYS | 97 | −11.390 |
| −5.200 | 8.256 | 1.00 | 0.00 | BrD | ATOM | 1618 | HA | LYS | 97 | −11.067 |
| −5.248 | 9.285 | 1.00 | 0.00 | BrD | ATOM | 1619 | CB | LYS | 97 | −12.547 |
| −6.183 | 8.044 | 1.00 | 0.00 | BrD | ATOM | 1620 | HB1 | LYS | 97 | −13.075 |
| −5.901 | 7.145 | 1.00 | 0.00 | BrD | ATOM | 1621 | HB2 | LYS | 97 | −13.223 |
| −6.110 | 8.884 | 1.00 | 0.00 | BrD | ATOM | 1622 | CG | LYS | 97 | −12.120 |
| −7.632 | 7.902 | 1.00 | 0.00 | BrD | ATOM | 1623 | HG1 | LYS | 97 | −11.914 |
| −7.826 | 6.862 | 1.00 | 0.00 | BrD | ATOM | 1624 | HG2 | LYS | 97 | −11.227 |
| −7.795 | 8.487 | 1.00 | 0.00 | BrD | ATOM | 1625 | CD | LYS | 97 | −13.205 |
| −8.584 | 8.379 | 1.00 | 0.00 | BrD | ATOM | 1626 | HD1 | LYS | 97 | −14.156 |
| −8.255 | 7.989 | 1.00 | 0.00 | BrD | ATOM | 1627 | HD2 | LYS | 97 | −12.986 |
| −9.576 | 8.013 | 1.00 | 0.00 | BrD | ATOM | 1628 | CE | LYS | 97 | −13.282 |
| −8.625 | 9.897 | 1.00 | 0.00 | BrD | ATOM | 1629 | HE1 | LYS | 97 | −13.091 |
| −7.633 | 10.281 | 1.00 | 0.00 | BrD | ATOM | 1630 | HE2 | LYS | 97 | −12.527 |
| −9.304 | 10.265 | 1.00 | 0.00 | BrD | ATOM | 1631 | NZ | LYS | 97 | −14.617 |
| −9.080 | 10.374 | 1.00 | 0.00 | BrD | ATOM | 1632 | HZ1 | LYS | 97 | −14.760 |
| −10.082 | 10.135 | 1.00 | 0.00 | BrD | ATOM | 1633 | HZ2 | LYS | 97 | −15.368 |
| −8.517 | 9.926 | 1.00 | 0.00 | BrD | ATOM | 1634 | HZ3 | LYS | 97 | −14.685 |
| −8.968 | 11.406 | 1.00 | 0.00 | BrD | ATOM | 1635 | C | LYS | 97 | −10.212 |
| −5.550 | 7.349 | 1.00 | 0.00 | BrD | ATOM | 1636 | O | LYS | 97 | −9.123 |
| −5.870 | 7.824 | 1.00 | 0.00 | BrD | ATOM | 1637 | N | CYS | 98 | −10.443 |
| −5.490 | 6.040 | 1.00 | 0.00 | BrD | ATOM | 1638 | HN | CYS | 98 | −11.334 |
| −5.233 | 5.724 | 1.00 | 0.00 | BrD | ATOM | 1639 | CA | CYS | 98 | −9.408 |
| −5.811 | 5.062 | 1.00 | 0.00 | BrD | ATOM | 1640 | HA | CYS | 98 | −9.253 |
| −6.879 | 5.086 | 1.00 | 0.00 | BrD | ATOM | 1641 | CB | CYS | 98 | −9.862 |
| −5.408 | 3.660 | 1.00 | 0.00 | BrD | ATOM | 1642 | HB1 | CYS | 98 | −9.000 |
| −5.351 | 3.012 | 1.00 | 0.00 | BrD | ATOM | 1643 | HB2 | CYS | 98 | −10.337 |
| −4.440 | 3.707 | 1.00 | 0.00 | BrD | ATOM | 1644 | SG | CYS | 98 | −11.036 |
| −6.562 | 2.916 | 1.00 | 0.00 | BrD | ATOM | 1645 | HG | CYS | 98 | −11.755 |
| −6.695 | 3.538 | 1.00 | 0.00 | BrD | ATOM | 1646 | C | CYS | 98 | −8.093 |
| −5.121 | 5.405 | 1.00 | 0.00 | BrD | ATOM | 1647 | O | CYS | 98 | −7.080 |
| −5.757 | 5.442 | 1.00 | 0.00 | BrD | ATOM | 1648 | N | ALA | 99 | −8.159 |
| −3.820 | 5.668 | 1.00 | 0.00 | BrD | ATOM | 1649 | HN | ALA | 99 | −9.028 |
| −3.368 | 5.644 | 1.00 | 0.00 | BrD | ATOM | 1650 | CA | ALA | 99 | −6.975 |
| −3.066 | 6.046 | 1.00 | 0.00 | BrD | ATOM | 1651 | HA | ALA | 99 | −6.290 |
| −3.066 | 5.214 | 1.00 | 0.00 | BrD | ATOM | 1652 | CB | ALA | 99 | −7.339 |
| −1.623 | 6.363 | 1.00 | 0.00 | BrD | ATOM | 1653 | HB1 | ALA | 99 | −8.281 |
| −1.597 | 6.890 | 1.00 | 0.00 | BrD | ATOM | 1654 | HB2 | ALA | 99 | −7.425 |
| −1.063 | 5.443 | 1.00 | 0.00 | BrD | ATOM | 1655 | HB3 | ALA | 99 | −4.560 |
| −1.185 | 6.980 | 1.00 | 0.00 | BrD | ATOM | 1656 | C | ALA | 99 | −6.293 |
| −3.721 | 7.232 | 1.00 | 0.00 | BrD | ATOM | 1657 | O | ALA | 99 | −5.091 |
| −3.963 | 7.207 | 1.00 | 0.00 | BrD | ATOM | 1658 | N | ASN | 100 | −7.080 |
| −4.054 | 8.247 | 1.00 | 0.00 | BrD | ATOM | 1659 | HN | ASN | 100 | −8.039 |
| −3.848 | 8.199 | 1.00 | 0.00 | BrD | ATOM | 1660 | CA | ASN | 100 | −6.550 |
| −4.702 | 9.438 | 1.00 | 0.00 | BrD | ATOM | 1661 | HA | ASN | 100 | −5.922 |
| −3.988 | 9.949 | 1.00 | 0.00 | BrD | ATOM | 1662 | CB | ASN | 100 | −7.697 |
| −5.116 | 10.363 | 1.00 | 0.00 | BrD | ATOM | 1663 | HB1 | ASN | 100 | −8.587 |
| −4.570 | 10.089 | 1.00 | 0.00 | BrD | ATOM | 1664 | HB2 | ASN | 100 | −7.879 |
| −5.174 | 10.247 | 1.00 | 0.00 | BrD | ATOM | 1665 | CG | ASN | 100 | −7.395 |
| −4.838 | 11.822 | 1.00 | 0.00 | BrD | ATOM | 1666 | OD1 | ASN | 100 | −7.283 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −3.684 | 12.236 | 1.00 | 0.00 | BrD | ATOM | 1667 | ND2 | ASN | 100 | −7.266 |
| −5.898 | 12.611 | 1.00 | 0.00 | BrD | ATOM | 1668 | HD21 | ASN | 100 | −7.370 |
| −6.787 | 12.212 | 1.00 | 0.00 | BrD | ATOM | 1669 | HD22 | ASN | 100 | −7.072 |
| −5.748 | 13.560 | 1.00 | 0.00 | BrD | ATOM | 1670 | C | ASN | 100 | −5.711 |
| −5.922 | 9.069 | 1.00 | 0.00 | BrD | ATOM | 1671 | O | ASN | 100 | −4.740 |
| −6.251 | 9.753 | 1.00 | 0.00 | BrD | ATOM | 1672 | N | ILE | 101 | −6.088 |
| −6.587 | 7.981 | 1.00 | 0.00 | BrD | ATOM | 1673 | HN | ILE | 101 | −6.870 |
| −6.277 | 7.481 | 1.00 | 0.00 | BrD | ATOM | 1674 | CA | ILE | 101 | −5.377 |
| −7.777 | 7.524 | 1.00 | 0.00 | BrD | ATOM | 1675 | HA | ILE | 101 | −5.132 |
| −8.370 | 8.394 | 1.00 | 0.00 | BrD | ATOM | 1676 | CB | ILE | 101 | −6.254 |
| −8.636 | 6.594 | 1.00 | 0.00 | BrD | ATOM | 1677 | HB | ILE | 101 | −6.469 |
| −8.061 | 5.705 | 1.00 | 0.00 | BrD | ATOM | 1678 | CG1 | ILE | 101 | −7.569 |
| −8.996 | 7.290 | 1.00 | 0.00 | BrD | ATOM | 1679 | HG11 | ILE | 101 | −8.112 |
| −8.090 | 7.513 | 1.00 | 0.00 | BrD | ATOM | 1680 | HG12 | ILE | 101 | −7.350 |
| −9.516 | 8.212 | 1.00 | 0.00 | BrD | ATOM | 1681 | CG2 | ILE | 101 | −5.509 |
| −9.894 | 6.177 | 1.00 | 0.00 | BrD | ATOM | 1682 | HG21 | ILE | 101 | −6.221 |
| −10.659 | 5.902 | 1.00 | 0.00 | BrD | ATOM | 1683 | HG22 | ILE | 101 | −4.905 |
| −10.244 | 7.001 | 1.00 | 0.00 | BrD | ATOM | 1684 | HG23 | ILE | 101 | −4.874 |
| −9.673 | 5.333 | 1.00 | 0.00 | BrD | ATOM | 1685 | CD1 | ILE | 101 | −8.470 |
| −9.885 | 6.461 | 1.00 | 0.00 | BrD | ATOM | 1686 | HD11 | ILE | 101 | −9.158 |
| −10.406 | 7.109 | 1.00 | 0.00 | BrD | ATOM | 1687 | HD12 | ILE | 101 | −7.869 |
| −10.604 | 5.922 | 1.00 | 0.00 | BrD | ATOM | 1688 | HD13 | ILE | 101 | −9.024 |
| −9.281 | 5.758 | 1.00 | 0.00 | BrD | ATOM | 1689 | C | ILE | 101 | −4.084 |
| −7.408 | 6.802 | 1.00 | 0.00 | BrD | ATOM | 1690 | O | ILE | 101 | −2.993 |
| −7.580 | 7.345 | 1.00 | 0.00 | BrD | ATOM | 1691 | N | LEU | 102 | −4.206 |
| −6.890 | 5.579 | 1.00 | 0.00 | BrD | ATOM | 1692 | HN | LEU | 102 | −5.100 |
| −6.770 | 5.196 | 1.00 | 0.00 | BrD | ATOM | 1693 | CA | LEU | 102 | −3.033 |
| −6.488 | 4.800 | 1.00 | 0.00 | BrD | ATOM | 1694 | HA | LEU | 102 | −2.519 |
| −7.384 | 4.485 | 1.00 | 0.00 | BrD | ATOM | 1695 | CB | LEU | 102 | −3.454 |
| −5.690 | 3.365 | 1.00 | 0.00 | BrD | ATOM | 1696 | HB1 | LEU | 102 | −4.530 |
| −5.734 | 3.485 | 1.00 | 0.00 | BrD | ATOM | 1697 | HB2 | LEU | 102 | −3.164 |
| −4.661 | 3.717 | 1.00 | 0.00 | BrD | ATOM | 1698 | CG | LEU | 102 | −2.852 |
| −6.166 | 2.236 | 1.00 | 0.00 | BrD | ATOM | 1699 | HG | LEU | 102 | −2.990 |
| −5.394 | 1.493 | 1.00 | 0.00 | BrD | ATOM | 1700 | CD1 | LEU | 102 | −3.570 |
| −7.417 | 1.745 | 1.00 | 0.00 | BrD | ATOM | 1701 | HD11 | LEU | 102 | −4.201 |
| −7.803 | 2.533 | 1.00 | 0.00 | BrD | ATOM | 1702 | HD12 | LEU | 102 | −2.843 |
| −8.165 | 1.468 | 1.00 | 0.00 | BrD | ATOM | 1703 | HD13 | LEU | 102 | −4.180 |
| −7.170 | 0.887 | 1.00 | 0.00 | BrD | ATOM | 1704 | CD2 | LEU | 102 | −1.353 |
| −6.418 | 2.376 | 1.00 | 0.00 | BrD | ATOM | 1705 | HD21 | LEU | 102 | −1.167 |
| −7.481 | 2.412 | 1.00 | 0.00 | BrD | ATOM | 1706 | HD22 | LEU | 102 | −0.992 |
| −5.959 | 3.285 | 1.00 | 0.00 | BrD | ATOM | 1707 | HD23 | LEU | 102 | −0.833 |
| −5.992 | 1.529 | 1.00 | 0.00 | BrD | ATOM | 1708 | C | LEU | 102 | −2.087 |
| −5.649 | 5.649 | 1.00 | 0.00 | BrD | ATOM | 1709 | O | LEU | 102 | −0.868 |
| −5.770 | 5.546 | 1.00 | 0.00 | BrD | ATOM | 1710 | N | GLU | 103 | −2.662 |
| −4.792 | 6.486 | 1.00 | 0.00 | BrD | ATOM | 1711 | HN | GLU | 103 | −3.619 |
| −4.747 | 6.528 | 1.00 | 0.00 | BrD | ATOM | 1712 | CA | GLU | 103 | −2.872 |
| −3.948 | 7.369 | 1.00 | 0.00 | BrD | ATOM | 1713 | HA | GLU | 103 | −1.199 |
| −3.364 | 6.758 | 1.00 | 0.00 | BrD | ATOM | 1714 | CB | GLU | 103 | −2.781 |
| −3.002 | 8.159 | 1.00 | 0.00 | BrD | ATOM | 1715 | HB1 | GLU | 103 | −3.230 |
| −2.297 | 7.475 | 1.00 | 0.00 | BrD | ATOM | 1716 | HB2 | GLU | 103 | −3.559 |
| −3.579 | 8.627 | 1.00 | 0.00 | BrD | ATOM | 1717 | CG | GLU | 103 | −2.060 |
| −2.222 | 9.242 | 1.00 | 0.00 | BrD | ATOM | 1718 | HG1 | GLU | 103 | −2.356 |
| −2.611 | 10.205 | 1.00 | 0.00 | BrD | ATOM | 1719 | HG2 | GLU | 103 | −0.999 |
| −2.356 | 9.112 | 1.00 | 0.00 | BrD | ATOM | 1720 | CD | GLU | 103 | −2.373 |
| −0.740 | 9.200 | 1.00 | 0.00 | BrD | ATOM | 1721 | OE1 | GLU | 103 | −2.248 |
| −0.077 | 10.251 | 1.00 | 0.00 | BrD | ATOM | 1722 | OE2 | GLU | 103 | −2.745 |
| −0.242 | 8.117 | 1.00 | 0.00 | BrD | ATOM | 1723 | C | GLU | 103 | −1.052 |
| −4.808 | 8.322 | 1.00 | 0.00 | BrD | ATOM | 1724 | O | GLU | 103 | 0.175 |
| −4.759 | 8.317 | 1.00 | 0.00 | BrD | ATOM | 1725 | N | LYS | 104 | −1.740 |
| −5.627 | 9.114 | 1.00 | 0.00 | BrD | ATOM | 1726 | HN | LYS | 104 | −2.720 |
| −5.629 | 9.066 | 1.00 | 0.00 | BrD | ATOM | 1727 | CA | LYS | 104 | −1.072 |
| −6.511 | 10.062 | 1.00 | 0.00 | BrD | ATOM | 1728 | HA | LYS | 104 | −0.569 |
| −5.894 | 10.792 | 1.00 | 0.00 | BrD | ATOM | 1729 | CB | LYS | 104 | −2.097 |
| −7.395 | 10.777 | 1.00 | 0.00 | BrD | ATOM | 1730 | HB1 | LYS | 104 | −2.976 |
| −7.479 | 10.157 | 1.00 | 0.00 | BrD | ATOM | 1731 | HB2 | LYS | 104 | −1.670 |
| −8.377 | 10.917 | 1.00 | 0.00 | BrD | ATOM | 1732 | CG | LYS | 104 | −2.520 |
| −6.861 | 12.136 | 1.00 | 0.00 | BrD | ATOM | 1733 | HG1 | LYS | 104 | −3.354 |
| −7.445 | 12.497 | 1.00 | 0.00 | BrD | ATOM | 1734 | HG2 | LYS | 104 | −1.691 |
| −6.951 | 12.822 | 1.00 | 0.00 | BrD | ATOM | 1735 | CD | LYS | 104 | −2.938 |
| −5.401 | 12.056 | 1.00 | 0.00 | BrD | ATOM | 1736 | HD1 | LYS | 104 | −2.917 |
| −5.059 | 11.039 | 1.00 | 0.00 | BrD | ATOM | 1737 | HD2 | LYS | 104 | −2.306 |
| −4.819 | 12.712 | 1.00 | 0.00 | BrD | ATOM | 1738 | CE | LYS | 104 | −4.387 |
| −5.210 | 12.469 | 1.00 | 0.00 | BrD | ATOM | 1739 | HE1 | LYS | 104 | −4.975 |
| −5.002 | 11.587 | 1.00 | 0.00 | BrD | ATOM | 1740 | HE2 | LYS | 104 | −4.741 |
| −6.120 | 12.930 | 1.00 | 0.00 | BrD | ATOM | 1741 | NZ | LYS | 104 | −4.547 |
| −4.085 | 13.432 | 1.00 | 0.00 | BrD | ATOM | 1742 | HZ1 | LYS | 104 | −5.135 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −4.384 | 14.236 | 1.00 | 0.00 | BrD | ATOM | 1743 | HZ2 | LYS | 104 | −5.004 |
| −3.277 | 12.964 | 1.00 | 0.00 | BrD | ATOM | 1744 | HZ3 | LYS | 104 | −3.618 |
| −3.785 | 13.788 | 1.00 | 0.00 | BrD | ATOM | 1745 | C | LYS | 104 | −0.039 |
| −7.383 | 9.357 | 1.00 | 0.00 | BrD | ATOM | 1746 | O | LYS | 104 | 1.021 |
| −7.678 | 9.910 | 1.00 | 0.00 | BrD | ATOM | 1747 | N | PHE | 105 | −0.357 |
| −7.796 | 8.135 | 1.00 | 0.00 | BrD | ATOM | 1748 | HN | PHE | 105 | −1.217 |
| −7.528 | 7.749 | 1.00 | 0.00 | BrD | ATOM | 1749 | CA | PHE | 105 | 0.541 |
| −8.636 | 7.352 | 1.00 | 0.00 | BrD | ATOM | 1750 | HA | PHE | 105 | 0.954 |
| −9.385 | 8.011 | 1.00 | 0.00 | BrD | ATOM | 1751 | CB | PHE | 105 | −0.229 |
| −9.331 | 6.228 | 1.00 | 0.00 | BrD | ATOM | 1752 | HB1 | PHE | 105 | 0.455 |
| −9.569 | 5.426 | 1.00 | 0.00 | BrD | ATOM | 1753 | HB2 | PHE | 105 | −0.992 |
| −8.662 | 5.857 | 1.00 | 0.00 | BrD | ATOM | 1754 | CG | PHE | 105 | −0.899 |
| −10.604 | 6.658 | 1.00 | 0.00 | BrD | ATOM | 1755 | CD1 | PHE | 105 | −0.202 |
| −11.559 | 7.381 | 1.00 | 0.00 | BrD | ATOM | 1756 | HD1 | PHE | 105 | 0.833 |
| −11.381 | 7.633 | 1.00 | 0.00 | BrD | ATOM | 1757 | CD2 | PHE | 105 | −2.226 |
| −10.844 | 6.342 | 1.00 | 0.00 | BrD | ATOM | 1758 | HD2 | PHE | 105 | −2.779 |
| −10.106 | 5.780 | 1.00 | 0.00 | BrD | ATOM | 1759 | CE1 | PHE | 105 | −0.816 |
| −12.730 | 7.780 | 1.00 | 0.00 | BrD | ATOM | 1760 | HE1 | PHE | 105 | −0.262 |
| −13.467 | 8.342 | 1.00 | 0.00 | BrD | ATOM | 1761 | CE2 | PHE | 105 | −2.846 |
| −12.013 | 6.738 | 1.00 | 0.00 | BrD | ATOM | 1762 | HE2 | PHE | 105 | −3.891 |
| −12.188 | 6.485 | 1.00 | 0.00 | BrD | ATOM | 1763 | CZ | PHE | 105 | −2.140 |
| −12.958 | 7.458 | 1.00 | 0.00 | BrD | ATOM | 1764 | HZ | PHE | 105 | −2.623 |
| −13.873 | 7.768 | 1.00 | 0.00 | BrD | ATOM | 1765 | C | PHE | 105 | 1.684 |
| −7.817 | 6.766 | 1.00 | 0.00 | BrD | ATOM | 1766 | O | PHE | 105 | 2.845 |
| −7.998 | 7.133 | 1.00 | 0.00 | BrD | ATOM | 1767 | N | PHE | 106 | 1.347 |
| −6.917 | 5.849 | 1.00 | 0.00 | BrD | ATOM | 1768 | HN | PHE | 106 | 0.405 |
| −6.824 | 5.595 | 1.00 | 0.00 | BrD | ATOM | 1769 | CA | PHE | 106 | 2.344 |
| −6.075 | 5.202 | 1.00 | 0.00 | BrD | ATOM | 1770 | HA | PHE | 106 | 2.956 |
| −6.711 | 4.579 | 1.00 | 0.00 | BrD | ATOM | 1771 | CB | PHE | 106 | 1.665 |
| −5.021 | 4.325 | 1.00 | 0.00 | BrD | ATOM | 1772 | HB1 | PHE | 106 | 0.985 |
| −5.512 | 3.644 | 1.00 | 0.00 | BrD | ATOM | 1773 | HB2 | PHE | 106 | 1.110 |
| −4.341 | 4.954 | 1.00 | 0.00 | BrD | ATOM | 1774 | CG | PHE | 106 | 2.633 |
| −4.213 | 3.510 | 1.00 | 0.00 | BrD | ATOM | 1775 | CD1 | PHE | 106 | 3.519 |
| −4.836 | 2.649 | 1.00 | 0.00 | BrD | ATOM | 1776 | HD1 | PHE | 106 | 3.508 |
| −5.913 | 2.565 | 1.00 | 0.00 | BrD | ATOM | 1777 | CD2 | PHE | 106 | 2.662 |
| −2.831 | 3.612 | 1.00 | 0.00 | BrD | ATOM | 1778 | HD2 | PHE | 106 | 1.974 |
| −2.333 | 4.279 | 1.00 | 0.00 | BrD | ATOM | 1779 | CE1 | PHE | 106 | 4.413 |
| −4.098 | 1.898 | 1.00 | 0.00 | BrD | ATOM | 1780 | HE1 | PHE | 106 | 5.098 |
| −4.598 | 1.229 | 1.00 | 0.00 | BrD | ATOM | 1781 | CE2 | PHE | 106 | 3.548 |
| −2.086 | 2.857 | 1.00 | 0.00 | BrD | ATOM | 1782 | HE2 | PHE | 106 | 3.562 |
| −1.010 | 2.946 | 1.00 | 0.00 | BrD | ATOM | 1783 | CZ | PHE | 106 | 4.432 |
| −2.721 | 2.005 | 1.00 | 0.00 | BrD | ATOM | 1784 | HZ | PHE | 106 | 5.127 |
| −2.142 | 1.417 | 1.00 | 0.00 | BrD | ATOM | 1785 | C | PHE | 106 | 3.236 |
| −5.388 | 6.230 | 1.00 | 0.00 | BrD | ATOM | 1786 | O | PHE | 106 | 4.439 |
| −5.637 | 6.282 | 1.00 | 0.00 | BrD | ATOM | 1787 | N | PHE | 107 | 2.643 |
| −4.516 | 7.043 | 1.00 | 0.00 | BrD | ATOM | 1788 | HN | PHE | 107 | 1.679 |
| −4.349 | 6.948 | 1.00 | 0.00 | BrD | ATOM | 1789 | CA | PHE | 107 | 3.401 |
| −3.784 | 8.058 | 1.00 | 0.00 | BrD | ATOM | 1790 | HA | PHE | 107 | 4.035 |
| −3.076 | 7.543 | 1.00 | 0.00 | BrD | ATOM | 1791 | CB | PHE | 107 | 2.462 |
| −3.014 | 8.995 | 1.00 | 0.00 | BrD | ATOM | 1792 | HB1 | PHE | 107 | 1.719 |
| −3.692 | 9.384 | 1.00 | 0.00 | BrD | ATOM | 1793 | HB2 | PHE | 107 | 3.040 |
| −2.618 | 9.817 | 1.00 | 0.00 | BrD | ATOM | 1794 | CG | PHE | 107 | 1.741 |
| −1.858 | 8.345 | 1.00 | 0.00 | BrD | ATOM | 1795 | CD1 | PHE | 107 | 1.007 |
| −0.971 | 9.117 | 1.00 | 0.00 | BrD | ATOM | 1796 | HD1 | PHE | 107 | 0.954 |
| −1.118 | 10.186 | 1.00 | 0.00 | BrD | ATOM | 1797 | CD2 | PHE | 107 | 1.798 |
| −1.652 | 6.972 | 1.00 | 0.00 | BrD | ATOM | 1798 | HD2 | PHE | 107 | 2.368 |
| 2.334 | 6.357 | 1.00 | 0.00 | BrD | ATOM | 1799 | CE1 | PHE | 107 | 0.345 |
| 0.095 | 8.537 | 1.00 | 0.00 | BrD | ATOM | 1800 | HE1 | PHE | 107 | −0.224 |
| −0.776 | 9.151 | 1.00 | 0.00 | BrD | ATOM | 1801 | CE2 | PHE | 107 | 1.137 |
| −0.588 | 6.387 | 1.00 | 0.00 | BrD | ATOM | 1802 | HE2 | PHE | 107 | 1.192 |
| 0.439 | 5.318 | 1.00 | 0.00 | BrD | ATOM | 1803 | CZ | PHE | 107 | 0.410 |
| 0.286 | 7.171 | 1.00 | 0.00 | BrD | ATOM | 1804 | HZ | PHE | 107 | −0.108 |
| −1.118 | 6.718 | 1.00 | 0.00 | BrD | ATOM | 1805 | C | PHE | 107 | 4.287 |
| −4.727 | 8.867 | 1.00 | 0.00 | BrD | ATOM | 1806 | O | PHE | 107 | 5.369 |
| −4.345 | 9.312 | 1.00 | 0.00 | BrD | ATOM | 1807 | N | SER | 108 | 3.825 |
| −5.960 | 9.054 | 1.00 | 0.00 | BrD | ATOM | 1808 | HN | SER | 108 | 2.968 |
| −6.218 | 8.654 | 1.00 | 0.00 | BrD | ATOM | 1809 | CA | SER | 108 | 4.607 |
| −6.959 | 9.773 | 1.00 | 0.00 | BrD | ATOM | 1810 | HA | SER | 108 | 4.981 |
| −6.503 | 10.678 | 1.00 | 0.00 | BrD | ATOM | 1811 | CB | SER | 108 | 3.740 |
| −8.166 | 10.136 | 1.00 | 0.00 | BrD | ATOM | 1812 | HB1 | SER | 108 | 2.987 |
| −7.864 | 10.848 | 1.00 | 0.00 | BrD | ATOM | 1813 | HB2 | SER | 108 | 3.262 |
| −8.546 | 9.245 | 1.00 | 0.00 | BrD | ATOM | 1814 | OG | SER | 108 | 4.521 |
| −9.200 | 10.711 | 1.00 | 0.00 | BrD | ATOM | 1815 | HG | SER | 108 | 4.902 |
| −9.739 | 10.014 | 1.00 | 0.00 | BrD | ATOM | 1816 | C | SER | 108 | 5.784 |
| −7.395 | 8.915 | 1.00 | 0.00 | BrD | ATOM | 1817 | O | SER | 108 | 6.887 |
| −7.618 | 9.413 | 1.00 | 0.00 | BrD | ATOM | 1818 | N | LYS | 109 | 5.540 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −7.475 | 7.613 | 1.00 | 0.00 | BrD | ATOM | 1819 HN | LYS | 109 | 4.643 |
| −7.256 | 7.283 | 1.00 | 0.00 | BrD | ATOM | 1820 CA | LYS | 109 | 6.578 |
| −7.819 | 6.654 | 1.00 | 0.00 | BrD | ATOM | 1821 HA | LYS | 109 | 7.113 |
| −8.679 | 7.032 | 1.00 | 0.00 | BrD | ATOM | 1822 CB | LYS | 109 | 5.950 |
| −8.163 | 5.306 | 1.00 | 0.00 | BrD | ATOM | 1823 HB1 | LYS | 109 | 4.898 |
| −7.992 | 5.340 | 1.00 | 0.00 | BrD | ATOM | 1824 HB2 | LYS | 109 | 6.421 |
| −7.566 | 4.542 | 1.00 | 0.00 | BrD | ATOM | 1825 CG | LYS | 109 | 6.090 |
| −9.626 | 4.926 | 1.00 | 0.00 | BrD | ATOM | 1826 HG1 | LYS | 109 | 5.522 |
| −9.811 | 4.026 | 1.00 | 0.00 | BrD | ATOM | 1827 HG2 | LYS | 109 | 7.133 |
| −9.864 | 4.748 | 1.00 | 0.00 | BrD | ATOM | 1828 CD | LYS | 109 | 5.577 |
| −10.535 | 6.029 | 1.00 | 0.00 | BrD | ATOM | 1829 HD1 | LYS | 109 | 6.413 |
| −10.864 | 6.629 | 1.00 | 0.00 | BrD | ATOM | 1830 HD2 | LYS | 109 | 4.885 |
| −9.981 | 6.646 | 1.00 | 0.00 | BrD | ATOM | 1831 CE | LYS | 109 | 4.866 |
| −11.751 | 5.462 | 1.00 | 0.00 | BrD | ATOM | 1832 HE1 | LYS | 109 | 5.179 |
| −11.889 | 4.438 | 1.00 | 0.00 | BrD | ATOM | 1833 HE2 | LYS | 109 | 3.801 |
| −11.575 | 5.491 | 1.00 | 0.00 | BrD | ATOM | 1834 NZ | LYS | 109 | 5.175 |
| −12.986 | 6.235 | 1.00 | 0.00 | BrD | ATOM | 1835 HZ1 | LYS | 109 | 6.202 |
| −13.148 | 6.254 | 1.00 | 0.00 | BrD | ATOM | 1836 HZ2 | LYS | 109 | 4.715 |
| −13.808 | 5.795 | 1.00 | 0.00 | BrD | ATOM | 1837 HZ3 | LYS | 109 | 4.831 |
| −12.892 | 7.212 | 1.00 | 0.00 | BrD | ATOM | 1838 C | LYS | 109 | 7.547 |
| −6.653 | 6.504 | 1.00 | 0.00 | BrD | ATOM | 1839 O | LYS | 109 | 8.761 |
| −6.842 | 6.428 | 1.00 | 0.00 | BrD | ATOM | 1840 N | ILE | 110 | 6.994 |
| −5.441 | 6.492 | 1.00 | 0.00 | BrD | ATOM | 1841 HN | ILE | 110 | 6.022 |
| −5.363 | 6.581 | 1.00 | 0.00 | BrD | ATOM | 1842 CA | ILE | 110 | 7.796 |
| −4.223 | 6.407 | 1.00 | 0.00 | BrD | ATOM | 1843 HA | ILE | 110 | 8.198 |
| −4.138 | 5.605 | 1.00 | 0.00 | BrD | ATOM | 1844 CB | ILE | 110 | 6.935 |
| −2.973 | 6.692 | 1.00 | 0.00 | BrD | ATOM | 1845 HB | ILE | 110 | 6.495 |
| −3.087 | 7.673 | 1.00 | 0.00 | BrD | ATOM | 1846 CG1 | ILE | 110 | 5.811 |
| −2.844 | 5.654 | 1.00 | 0.00 | BrD | ATOM | 1847 HG11 | ILE | 110 | 5.353 |
| −3.811 | 5.511 | 1.00 | 0.00 | BrD | ATOM | 1848 HG12 | ILE | 110 | 5.068 |
| −2.153 | 6.026 | 1.00 | 0.00 | BrD | ATOM | 1849 CG2 | ILE | 110 | 7.798 |
| −1.722 | 6.712 | 1.00 | 0.00 | BrD | ATOM | 1850 HG21 | ILE | 110 | 8.756 |
| −1.945 | 6.264 | 1.00 | 0.00 | BrD | ATOM | 1851 HG22 | ILE | 110 | 7.944 |
| −1.401 | 7.732 | 1.00 | 0.00 | BrD | ATOM | 1852 HG23 | ILE | 110 | 7.311 |
| −0.938 | 6.152 | 1.00 | 0.00 | BrD | ATOM | 1853 CD3 | ILE | 110 | 6.269 |
| −2.345 | 4.297 | 1.00 | 0.00 | BrD | ATOM | 1854 HD11 | ILE | 110 | 6.222 |
| −3.153 | 3.583 | 1.00 | 0.00 | BrD | ATOM | 1855 HD12 | ILE | 110 | 7.283 |
| −1.985 | 4.366 | 1.00 | 0.00 | BrD | ATOM | 1856 HD13 | ILE | 110 | 5.623 |
| −1.540 | 3.971 | 1.00 | 0.00 | BrD | ATOM | 1857 C | ILE | 110 | 8.948 |
| −4.274 | 7.411 | 1.00 | 0.00 | BrD | ATOM | 1858 O | ILE | 110 | 10.104 |
| −4.065 | 7.060 | 1.00 | 0.00 | BrD | ATOM | 1859 N | LYS | 111 | 8.615 |
| −4.582 | 8.662 | 1.00 | 0.00 | BrD | ATOM | 1860 HN | LYS | 111 | 7.676 |
| −4.752 | 8.875 | 1.00 | 0.00 | BrD | ATOM | 1861 CA | LYS | 111 | 9.608 |
| −4.664 | 9.730 | 1.00 | 0.00 | BrD | ATOM | 1862 HA | LYS | 111 | 9.919 |
| −3.660 | 9.972 | 1.00 | 0.00 | BrD | ATOM | 1863 CB | LYS | 111 | 8.989 |
| −5.308 | 10.972 | 1.00 | 0.00 | BrD | ATOM | 1864 HB1 | LYS | 111 | 9.742 |
| −5.373 | 11.743 | 1.00 | 0.00 | BrD | ATOM | 1865 HB2 | LYS | 111 | 8.661 |
| −6.304 | 10.718 | 1.00 | 0.00 | BrD | ATOM | 1866 CG | LYS | 111 | 7.801 |
| −4.562 | 11.528 | 1.00 | 0.00 | BrD | ATOM | 1867 HG1 | LYS | 111 | 7.127 |
| −4.304 | 10.718 | 1.00 | 0.00 | BrD | ATOM | 1868 HG2 | LYS | 111 | 7.293 |
| −5.162 | 12.252 | 1.00 | 0.00 | BrD | ATOM | 1869 CD | LYS | 111 | 8.237 |
| −3.252 | 12.203 | 1.00 | 0.00 | BrD | ATOM | 1870 HD1 | LYS | 111 | 8.872 |
| −2.701 | 11.525 | 1.00 | 0.00 | BrD | ATOM | 1871 HD2 | LYS | 111 | 7.361 |
| −2.666 | 12.437 | 1.00 | 0.00 | BrD | ATOM | 1872 CE | LYS | 111 | 9.006 |
| −3.527 | 13.485 | 1.00 | 0.00 | BrD | ATOM | 1873 HE1 | LYS | 111 | 10.044 |
| −3.698 | 13.239 | 1.00 | 0.00 | BrD | ATOM | 1874 HE2 | LYS | 111 | 8.597 |
| −4.411 | 13.952 | 1.00 | 0.00 | BrD | ATOM | 1875 NZ | LYS | 111 | 8.916 |
| −2.389 | 14.442 | 1.00 | 0.00 | BrD | ATOM | 1876 HZ1 | LYS | 111 | 9.335 |
| −2.656 | 15.356 | 1.00 | 0.00 | BrD | ATOM | 1877 HZ2 | LYS | 111 | 7.921 |
| −2.127 | 14.593 | 1.00 | 0.00 | BrD | ATOM | 1878 HZ3 | LYS | 111 | 9.428 |
| −1.565 | 14.066 | 1.00 | 0.00 | BrD | ATOM | 1879 C | LYS | 111 | 10.828 |
| −5.465 | 9.289 | 1.00 | 0.00 | BrD | ATOM | 1880 O | LYS | 111 | 11.964 |
| −5.112 | 9.607 | 1.00 | 0.00 | BrD | ATOM | 1881 N | GLU | 112 | 10.585 |
| −6.549 | 8.561 | 1.00 | 0.00 | BrD | ATOM | 1882 HN | GLU | 112 | 9.658 |
| −6.780 | 8.344 | 1.00 | 0.00 | BrD | ATOM | 1883 CA | GLU | 112 | 11.662 |
| −7.407 | 8.085 | 1.00 | 0.00 | BrD | ATOM | 1884 HA | GLU | 112 | 12.130 |
| −7.588 | 8.914 | 1.00 | 0.00 | BrD | ATOM | 1885 CB | GLU | 112 | 11.098 |
| −8.745 | 7.600 | 1.00 | 0.00 | BrD | ATOM | 1886 HB1 | GLU | 112 | 10.689 |
| −8.589 | 6.661 | 1.00 | 0.00 | BrD | ATOM | 1887 HB2 | GLU | 112 | 11.917 |
| −9.432 | 7.445 | 1.00 | 0.00 | BrD | ATOM | 1888 CG | GLU | 112 | 10.120 |
| −9.383 | 8.573 | 1.00 | 0.00 | BrD | ATOM | 1889 HG1 | GLU | 112 | 10.678 |
| −9.856 | 9.367 | 1.00 | 0.00 | BrD | ATOM | 1890 HG2 | GLU | 112 | 9.489 |
| −8.611 | 8.987 | 1.00 | 0.00 | BrD | ATOM | 1891 CD | GLU | 112 | 9.240 |
| −10.425 | 7.912 | 1.00 | 0.00 | BrD | ATOM | 1892 OE1 | GLU | 112 | 9.625 |
| −10.932 | 6.837 | 1.00 | 0.00 | BrD | ATOM | 1893 OE2 | GLU | 112 | 8.165 |
| −10.734 | 8.468 | 1.00 | 0.00 | BrD | ATOM | 1894 C | GLU | 112 | 12.447 |

TABLE 6-continued

Atomic Structure Coordinates of the
P/CAF Bromodomain/Acetyl-Histamine Complex

| | | | | | | | | | |
|---|---|---|---|---|---|---|---|---|---|
| −6.739 | 6.960 | 1.00 | 0.00 | BrD | ATOM | 1895 | O | GLU | 112 | 13.583 |
| −7.120 | 6.677 | 1.00 | 0.00 | BrD | ATOM | 1896 | N | ALA | 113 | 11.840 |
| −5.744 | 6.318 | 1.00 | 0.00 | BrD | ATOM | 1897 | HN | ALA | 113 | 10.932 |
| −5.486 | 6.579 | 1.00 | 0.00 | BrD | ATOM | 1898 | CA | ALA | 113 | 12.492 |
| −5.046 | 5.216 | 1.00 | 0.00 | BrD | ATOM | 1899 | HA | ALA | 113 | 13.355 |
| −5.620 | 4.936 | 1.00 | 0.00 | BrD | ATOM | 1900 | CB | ALA | 113 | 11.573 |
| −4.989 | 4.008 | 1.00 | 0.00 | BrD | ATOM | 1901 | HB1 | ALA | 113 | 11.649 |
| −5.914 | 3.455 | 1.00 | 0.00 | BrD | ATOM | 1902 | HB2 | ALA | 113 | 11.865 |
| −4.166 | 3.373 | 1.00 | 0.00 | BrD | ATOM | 1903 | HB3 | ALA | 113 | 10.554 |
| −4.848 | 4.336 | 1.00 | 0.00 | BrD | ATOM | 1904 | C | ALA | 113 | 12.953 |
| −3.645 | 5.624 | 1.00 | 0.00 | BrD | ATOM | 1905 | O | ALA | 113 | 13.778 |
| −3.035 | 4.943 | 1.00 | 0.00 | BrD | ATOM | 1906 | N | GLY | 114 | 12.435 |
| −3.146 | 6.743 | 1.00 | 0.00 | BrD | ATOM | 1907 | HN | GLY | 114 | 11.790 |
| −3.678 | 7.255 | 1.00 | 0.00 | BrD | ATOM | 1908 | CA | GLY | 114 | 12.833 |
| −1.836 | 7.229 | 1.00 | 0.00 | BrD | ATOM | 1909 | HA1 | GLY | 114 | 12.506 |
| −1.732 | 8.253 | 1.00 | 0.00 | BrD | ATOM | 1910 | HA2 | GLY | 114 | 13.911 |
| −1.769 | 7.200 | 1.00 | 0.00 | BrD | ATOM | 1911 | C | GLY | 114 | 12.252 |
| 0.695 | 6.414 | 1.00 | 0.00 | BrD | ATOM | 1912 | O | GLY | 114 | 12.991 |
| −0.085 | 5.813 | 1.00 | 0.00 | BrD | ATOM | 1913 | N | LEU | 115 | 10.927 |
| −0.590 | 6.405 | 1.00 | 0.00 | BrD | ATOM | 1914 | HN | LEU | 115 | 10.398 |
| 1.231 | 6.921 | 1.00 | 0.00 | BrD | ATOM | 1915 | CA | LEU | 115 | 10.244 |
| 0.482 | 5.683 | 1.00 | 0.00 | BrD | ATOM | 1916 | HA | LEU | 115 | 10.991 |
| −1.195 | 5.369 | 1.00 | 0.00 | BrD | ATOM | 1917 | CB | LEU | 115 | 9.523 |
| −0.066 | 4.442 | 1.00 | 0.00 | BrD | ATOM | 1918 | HB1 | LEU | 115 | 8.622 |
| 0.563 | 4.768 | 1.00 | 0.00 | BrD | ATOM | 1919 | HB2 | LEU | 115 | 9.240 |
| −0.773 | 3.824 | 1.00 | 0.00 | BrD | ATOM | 1920 | CG | LEU | 115 | 10.322 |
| −1.047 | 3.570 | 1.00 | 0.00 | BrD | ATOM | 1921 | HG | LEU | 115 | 9.929 |
| −1.000 | 2.565 | 1.00 | 0.00 | BrD | ATOM | 1922 | CD1 | LEU | 115 | 10.120 |
| −2.469 | 4.061 | 1.00 | 0.00 | BrD | ATOM | 1923 | HD11 | LEU | 115 | 10.216 |
| −3.149 | 3.228 | 1.00 | 0.00 | BrD | ATOM | 1924 | HD12 | LEU | 115 | 9.137 |
| −2.571 | 4.493 | 1.00 | 0.00 | BrD | ATOM | 1925 | HD13 | LEU | 115 | 10.868 |
| −2.699 | 4.804 | 1.00 | 0.00 | BrD | ATOM | 1926 | CD2 | LEU | 115 | 11.790 |
| −0.683 | 3.517 | 1.00 | 0.00 | BrD | ATOM | 1927 | HD21 | LEU | 115 | 12.358 |
| 1.397 | 4.094 | 1.00 | 0.00 | BrD | ATOM | 1928 | HD22 | LEU | 115 | 12.932 |
| −0.306 | 3.924 | 1.00 | 0.00 | BrD | ATOM | 1929 | HD23 | LEU | 115 | 12.127 |
| 0.701 | 2.491 | 1.00 | 0.00 | BrD | ATOM | 1930 | C | LEU | 115 | 9.246 |
| 1.193 | 6.603 | 1.00 | 0.00 | BrD | ATOM | 1931 | O | LEU | 115 | 9.407 |
| 1.183 | 7.823 | 1.00 | 0.00 | BrD | ATOM | 1932 | N | ILE | 116 | 8.209 |
| 1.801 | 6.018 | 1.00 | 0.00 | BrD | ATOM | 1933 | HN | ILE | 116 | 8.131 |
| 1.787 | 5.043 | 1.00 | 0.00 | BrD | ATOM | 1934 | CA | ILE | 116 | 7.196 |
| 2.518 | 6.794 | 1.00 | 0.00 | BrD | ATOM | 1935 | HA | ILE | 116 | 7.614 |
| 3.470 | 7.083 | 1.00 | 0.00 | BrD | ATOM | 1936 | CB | ILE | 116 | 5.930 |
| 2.786 | 5.956 | 1.00 | 0.00 | BrD | ATOM | 1937 | HB | ILE | 116 | 5.183 |
| 3.218 | 6.605 | 1.00 | 0.00 | BrD | ATOM | 1938 | CG1 | ILE | 116 | 5.388 |
| 1.480 | 5.367 | 1.00 | 0.00 | BrD | ATOM | 1939 | HG11 | ILE | 116 | 4.697 |
| 1.713 | 4.570 | 1.00 | 0.00 | BrD | ATOM | 1940 | HG12 | ILE | 116 | 6.209 |
| 0.904 | 4.968 | 1.00 | 0.00 | BrD | ATOM | 1941 | CG2 | ILE | 116 | 6.228 |
| 3.786 | 4.850 | 1.00 | 0.00 | BrD | ATOM | 1942 | HG21 | ILE | 116 | 5.309 |
| 4.261 | 4.538 | 1.00 | 0.00 | BrD | ATOM | 1943 | HG22 | ILE | 116 | 6.671 |
| 3.271 | 4.010 | 1.00 | 0.00 | BrD | ATOM | 1944 | HG23 | ILE | 116 | 6.914 |
| 4.534 | 5.217 | 1.00 | 0.00 | BrD | ATOM | 1945 | CD1 | ILE | 116 | 4.662 |
| 0.615 | 6.373 | 1.00 | 0.00 | BrD | ATOM | 1946 | HD11 | ILE | 116 | 3.870 |
| 0.073 | 5.875 | 1.00 | 0.00 | BrD | ATOM | 1947 | HD12 | ILE | 116 | 4.240 |
| −1.238 | 7.147 | 1.00 | 0.00 | BrD | ATOM | 1948 | HD13 | ILE | 116 | 5.356 |
| 0.086 | 6.812 | 1.00 | 0.00 | BrD | ATOM | 1949 | C | ILE | 116 | 6.802 |
| 1.751 | 8.053 | 1.00 | 0.00 | BrD | ATOM | 1950 | O | ILE | 116 | 7.024 |
| 0.544 | 8.154 | 1.00 | 0.00 | BrD | ATOM | 1951 | N | ASP | 117 | 6.222 |
| 2.465 | 9.014 | 1.00 | 0.00 | BrD | ATOM | 1952 | HN | ASP | 117 | 6.079 |
| 3.424 | 8.874 | 1.00 | 0.00 | BrD | ATOM | 1953 | CA | ASP | 117 | 5.805 |
| 1.862 | 10.275 | 1.00 | 0.00 | BrD | ATOM | 1954 | HA | ASP | 117 | 5.197 |
| 2.585 | 10.798 | 1.00 | 0.00 | BrD | ATOM | 1955 | CB | ASP | 117 | 4.967 |
| −0.609 | 10.013 | 1.00 | 0.00 | BrD | ATOM | 1956 | HB1 | ASP | 117 | 5.564 |
| 0.267 | 10.220 | 1.00 | 0.00 | BrD | ATOM | 1957 | HB2 | ASP | 117 | 4.664 |
| 0.596 | 8.976 | 1.00 | 0.00 | BrD | ATOM | 1958 | CG | ASP | 117 | 3.722 |
| 0.555 | 10.876 | 1.00 | 0.00 | BrD | ATOM | 1959 | OD1 | ASP | 117 | 2.897 |
| −1.488 | 10.787 | 1.00 | 0.00 | BrD | ATOM | 1960 | OD2 | ASP | 117 | 3.572 |
| 0.421 | 11.641 | 1.00 | 0.00 | BrD | ATOM | 1961 | C | ASP | 117 | 7.006 |
| 1.506 | 11.154 | 1.00 | 0.00 | BrD | ATOM | 1962 | O | ASP | 117 | 6.846 |
| 0.892 | 12.209 | 1.00 | 0.00 | BrD | ATOM | 1963 | N | LYS | 118 | 8.206 |
| 1.897 | 10.725 | 1.00 | 0.00 | BrD | ATOM | 1964 | HN | LYS | 118 | 8.282 |
| 2.384 | 9.879 | 1.00 | 0.00 | BrD | ATOM | 1965 | CA | LYS | 118 | 9.416 |
| 1.613 | 11.488 | 1.00 | 0.00 | BrD | ATOM | 1966 | HA | LYS | 118 | 10.248 |
| 2.063 | 10.968 | 1.00 | 0.00 | BrD | ATOM | 1967 | CB | LYS | 118 | 9.315 |
| 2.220 | 12.889 | 1.00 | 0.00 | BrD | ATOM | 1968 | HB1 | LYS | 118 | 8.636 |
| 1.624 | 13.480 | 1.00 | 0.00 | BrD | ATOM | 1969 | HB2 | LYS | 118 | 10.292 |
| 2.199 | 13.349 | 1.00 | 0.00 | BrD | ATOM | 1970 | CG | LYS | 118 | 8.818 |

TABLE 6-continued

Atomic Structure Coordinates of the
P/CAF Bromodomain/Acetyl-Histamine Complex

| | | | | | | | | | |
|---|---|---|---|---|---|---|---|---|---|
| 3.656 | 12.895 | 1.00 | 0.00 | BrD | ATOM | 1971 | HG1 | LYS | 118 | 7.921 |
| 3.719 | 12.296 | 1.00 | 0.00 | BrD | ATOM | 1972 | HG2 | LYS | 118 | 8.595 |
| 3.946 | 13.911 | 1.00 | 0.00 | BrD | ATOM | 1973 | CD | LYS | 118 | 9.857 |
| 4.608 | 12.327 | 1.00 | 0.00 | BrD | ATOM | 1974 | HD1 | LYS | 118 | 10.477 |
| 4.972 | 13.133 | 1.00 | 0.00 | BrD | ATOM | 1975 | HD2 | LYS | 118 | 10.469 |
| 4.075 | 11.613 | 1.00 | 0.00 | BrD | ATOM | 1976 | CE | LYS | 118 | 9.208 |
| 5.794 | 11.631 | 1.00 | 0.00 | BrD | ATOM | 1977 | HE1 | LYS | 118 | 8.502 |
| 5.425 | 10.902 | 1.00 | 0.00 | BrD | ATOM | 1978 | HE2 | LYS | 118 | 8.607 |
| 6.386 | 12.369 | 1.00 | 0.00 | BrD | ATOM | 1979 | NZ | LYS | 118 | 10.212 |
| 6.652 | 10.943 | 1.00 | 0.00 | BrD | ATOM | 1980 | HZ1 | LYS | 118 | 11.163 |
| 6.458 | 11.316 | 1.00 | 0.00 | BrD | ATOM | 1981 | HZ2 | LYS | 118 | 9.989 |
| 7.656 | 11.096 | 1.00 | 0.00 | BrD | ATOM | 1982 | HZ3 | LYS | 118 | 10.206 |
| 6.459 | 9.921 | 1.00 | 0.00 | BrD | ATOM | 1983 | C | LYS | 118 | 9.657 |
| −0.110 | 11.591 | 1.00 | 0.00 | BrD | ATOM | 1984 | OT1 | LYS | 118 | 9.047 |
| −0.641 | 10.802 | 1.00 | 0.00 | BrD | ATOM | 1985 | OT2 | LYS | 118 | 10.454 |
| 0.302 | 12.459 | 1.00 | 0.00 | BrD | END | | | | | |

TABLE 10

Atomic Structure Coordinates of the P/CAF Bromadomain and HIV-1 Tat Peptide Complex REMARK   FILENAME=*/scratch/yan/brdt_structure/aria/006_aria/structure/it8/com$^2$
REMARK   initial random number seed: 7.181155E+08
REMARK   ==========================================================
REMARK         overall,bonds,angles,improper,vdw,noe,cdih
REMARK   energies: 357.846, 19.6767, 221.828, 0, 46.7405, 53.2937, 0.322397
REMARK   ==========================================================
REMARK         bonds,angles,impropers,noe,cdih
REMARK   rms-dev.: 2.981175E−03,0.603415,49.7283,1.944833E−02,0.313045
REMARK   ==========================================================
REMARK         noe, cdih
REMARK   violations.: 0, 0
REMARK   ==========================================================
REMARK   DATE:22-Jun-00 03:41:18    created by user: yan

| | | | | | | | | | |
|---|---|---|---|---|---|---|---|---|---|
| ATOM | 1 | CA | SBR | 201 | −17.505 | −2.996 | −13.433 | 1.00 | 0.00 | PEPT |
| ATOM | 2 | HA | SBR | 201 | −17.429 | −4.006 | −13.060 | 1.00 | 0.00 | PEPT |
| ATOM | 3 | CB | SBR | 201 | −17.337 | −2.976 | −14.954 | 1.00 | 0.00 | PEPT |
| ATOM | 4 | HB1 | SBR | 201 | −18.136 | −2.400 | −15.398 | 1.00 | 0.00 | PEPT |
| ATOM | 5 | HB2 | SBR | 201 | −16.387 | −2.527 | −15.206 | 1.00 | 0.00 | PEPT |
| ATOM | 6 | OG | SBR | 201 | −17.378 | −4.305 | −15.453 | 1.00 | 0.00 | PEPT |
| ATOM | 7 | HG | SBR | 201 | −16.763 | −4.365 | −16.188 | 1.00 | 0.00 | PEPT |
| ATOM | 8 | C | SBR | 201 | −16.455 | −2.101 | −12.771 | 1.00 | 0.00 | PEPT |
| ATOM | 9 | O | SBR | 201 | −15.403 | −1.847 | −13.325 | 1.00 | 0.00 | PEPT |
| ATOM | 10 | N | SBR | 201 | −18.872 | −2.455 | −13.192 | 1.00 | 0.00 | PEPT |
| ATOM | 11 | HT1 | SBR | 201 | −18.899 | −1.449 | −13.457 | 1.00 | 0.00 | PEPT |
| ATOM | 12 | HT2 | SBR | 201 | −19.112 | −2.555 | −12.185 | 1.00 | 0.00 | PEPT |
| ATOM | 13 | HT3 | SBR | 201 | −18.560 | −2.983 | −13.766 | 1.00 | 0.00 | PEPT |
| ATOM | 14 | N | TYR | 202 | −16.732 | −1.618 | −11.591 | 1.00 | 0.00 | PEPT |
| ATOM | 15 | HN | TYR | 202 | −17.585 | −1.834 | −11.161 | 1.00 | 0.00 | PEPT |
| ATOM | 16 | CA | TYR | 202 | −15.749 | −0.740 | −10.896 | 1.00 | 0.00 | PEPT |
| ATOM | 17 | HA | TYR | 202 | −14.933 | −0.492 | −11.559 | 1.00 | 0.00 | PEPT |
| ATOM | 18 | CB | TYR | 2902 | −16.539 | 0.519 | −10.531 | 1.00 | 0.00 | PEPT |
| ATOM | 19 | HB1 | TYR | 202 | −17.594 | 0.333 | −10.666 | 1.00 | 0.00 | PEPT |
| ATOM | 20 | HB2 | TYR | 202 | −16.437 | 0.778 | −9.500 | 1.00 | 0.00 | PEPT |
| ATOM | 21 | CG | TYR | 202 | −16.111 | 1.659 | −11.425 | 1.00 | 0.00 | PEPT |
| ATOM | 22 | CD1 | TYR | 202 | −14.755 | 1.990 | −11.538 | 1.00 | 0.00 | PEPT |
| ATOM | 23 | HD1 | TYR | 202 | −14.015 | 1.429 | −10.988 | 1.00 | 0.00 | PEPT |
| ATOM | 24 | CD2 | TYR | 202 | −17.071 | 2.387 | −12.138 | 1.00 | 0.00 | PEPT |
| ATOM | 25 | HD2 | TYR | 202 | −18.117 | 2.132 | −12.050 | 1.00 | 0.00 | PEPT |
| ATOM | 26 | CE1 | TYR | 202 | −14.360 | 3.048 | −12.365 | 1.00 | 0.00 | PEPT |
| ATOM | 27 | HE1 | TYR | 202 | −13.314 | 3.303 | −12.454 | 1.00 | 0.00 | PEPT |
| ATOM | 28 | CE2 | TYR | 202 | −16.676 | 3.445 | −12.965 | 1.00 | 0.00 | PEPT |
| ATOM | 29 | HE2 | TYR | 202 | −17.417 | 4.006 | −13.515 | 1.00 | 0.00 | PEPT |
| ATOM | 30 | CZ | TYR | 202 | −15.321 | 3.776 | −13.078 | 1.00 | 0.00 | PEPT |
| ATOM | 31 | OH | TYR | 202 | −14.931 | 4.818 | −13.894 | 1.00 | 0.00 | PEPT |
| ATOM | 32 | NH | TYR | 202 | −14.871 | 4.485 | −14.793 | 1.00 | 0.00 | PEPT |
| ATOM | 33 | C | TYR | 202 | −15.221 | −1.425 | −9.613 | 1.00 | 0.00 | PEPT |
| ATOM | 34 | O | TYR | 202 | −15.566 | −2.551 | −9.336 | 1.00 | 0.00 | PEPT |
| ATOM | 35 | N | GLY | 203 | −14.384 | −0.755 | −8.889 | 1.00 | 0.00 | PEPT |
| ATOM | 36 | HN | GLY | 203 | −14.115 | 0.151 | −9.148 | 1.00 | 0.00 | PEPT |
| ATOM | 37 | CA | GLY | 203 | −13.828 | −1.370 | −7.651 | 1.00 | 0.00 | PEPT |
| ATOM | 38 | HA1 | GLY | 203 | −13.045 | −0.738 | −7.254 | 1.00 | 0.00 | PEPT |
| ATOM | 39 | HA2 | GLY | 203 | −13.422 | −2.343 | −7.884 | 1.00 | 0.00 | PEPT |

TABLE 10-continued

Atomic Structure Coordinates of the P/CAF Bromadomain and HIV-1 Tat Peptide Complex

| ATOM | 40 | C | GLY | 203 | −14.940 | −1.519 | −6.610 | 1.00 | 0.00 | PEPT |
|---|---|---|---|---|---|---|---|---|---|---|
| ATOM | 41 | O | GLY | 203 | −16.084 | −1.193 | −6.858 | 1.00 | 0.00 | PEPT |
| ATOM | 42 | N | ARG | 204 | −14.612 | −2.005 | −5.445 | 1.00 | 0.00 | PEPT |
| ATOM | 43 | HN | ARG | 204 | −13.682 | −2.258 | −5.264 | 1.00 | 0.00 | PEPT |
| ATOM | 44 | CA | ARG | 204 | −15.646 | −2.167 | −4.385 | 1.00 | 0.00 | PEPT |
| ATOM | 45 | HA | ARG | 204 | −16.369 | −1.366 | −4.441 | 1.00 | 0.00 | PEPT |
| ATOM | 46 | CB | ARG | 204 | −16.316 | −3.509 | −4.687 | 1.00 | 0.00 | PEPT |
| ATOM | 47 | HB1 | ARG | 204 | −15.760 | −4.023 | −5.458 | 1.00 | 0.00 | PEPT |
| ATOM | 48 | HB2 | ARG | 204 | −16.333 | −4.113 | −3.792 | 1.00 | 0.00 | PEPT |
| ATOM | 49 | CG | ARG | 204 | −17.748 | −3.267 | −5.167 | 1.00 | 0.00 | PEPT |
| ATOM | 50 | HG1 | ARG | 204 | −18.183 | −4.200 | −5.492 | 1.00 | 0.00 | PEPT |
| ATOM | 51 | HG2 | ARG | 204 | −17.739 | −2.588 | −5.990 | 1.00 | 0.00 | PEPT |
| ATOM | 52 | CD | ARG | 204 | −18.579 | −2.690 | −4.019 | 1.00 | 0.00 | PEPT |
| ATOM | 53 | HD1 | ARG | 204 | −17.933 | −2.323 | −3.235 | 1.00 | 0.00 | PEPT |
| ATOM | 54 | HD2 | ARG | 204 | −19.254 | −3.439 | −3.631 | 1.00 | 0.00 | PEPT |
| ATOM | 55 | NE | ARG | 204 | −19.347 | −1.565 | −4.631 | 1.00 | 0.00 | PEPT |
| ATOM | 56 | HE | ARG | 204 | −19.456 | −1.527 | −5.604 | 1.00 | 0.00 | PEPT |
| ATOM | 57 | CE | ARG | 204 | −19.876 | −0.625 | −3.882 | 1.00 | 0.00 | PEPT |
| ATOM | 58 | NH1 | ARG | 204 | −20.540 | 0.346 | −4.446 | 1.00 | 0.00 | PEPT |
| ATOM | 59 | HH11 | ARG | 204 | −20.643 | 0.370 | −5.441 | 1.00 | 0.00 | PEPT |
| ATOM | 60 | HH12 | ARG | 204 | −20.948 | 1.066 | −3.884 | 1.00 | 0.00 | PEPT |
| ATOM | 61 | NH2 | ARG | 204 | −19.747 | −0.647 | −2.578 | 1.00 | 0.00 | PEPT |
| ATOM | 62 | HH21 | ARG | 204 | −19.242 | −1.385 | −2.132 | 1.00 | 0.00 | PEPT |
| ATOM | 63 | HH22 | ARG | 204 | −20.159 | 0.078 | −2.026 | 1.00 | 0.00 | PEPT |
| ATOM | 64 | C | ARG | 204 | −14.989 | −2.196 | −3.004 | 1.00 | 0.00 | PEPT |
| ATOM | 65 | O | ARG | 204 | −14.176 | −3.050 | −2.711 | 1.00 | 0.00 | PEPT |
| ATOM | 66 | N | ACK | 205 | −15.330 | −1.265 | −2.157 | 1.00 | 0.00 | PEPT |
| ATOM | 67 | HN | ACK | 205 | −15.987 | −0.585 | −2.414 | 1.00 | 0.00 | PEPT |
| ATOM | 68 | CA | ACK | 205 | −14.721 | −1.234 | −0.798 | 1.00 | 0.00 | PEPT |
| ATOM | 69 | HA | ACK | 205 | −13.812 | −1.818 | −0.780 | 1.00 | 0.00 | PEPT |
| ATOM | 70 | CB | ACK | 205 | −14.409 | 0.242 | −0.543 | 1.00 | 0.00 | PEPT |
| ATOM | 71 | HB1 | ACK | 205 | −13.927 | 0.348 | 0.417 | 1.00 | 0.00 | PEPT |
| ATOM | 72 | HB2 | ACK | 205 | −15.327 | 0.811 | −0.550 | 1.00 | 0.00 | PEPT |
| ATOM | 73 | CG | ACK | 205 | −13.478 | 0.763 | −1.641 | 1.00 | 0.00 | PEPT |
| ATOM | 74 | HG1 | ACK | 205 | −13.504 | 1.842 | −1.654 | 1.00 | 0.00 | PEPT |
| ATOM | 75 | HG2 | ACK | 205 | −13.803 | 0.383 | −2.598 | 1.00 | 0.00 | PEPT |
| ATOM | 76 | CD | ACK | 205 | −12.050 | 0.290 | −1.364 | 1.00 | 0.00 | PEPT |
| ATOM | 77 | HD1 | ACK | 205 | −11.951 | 0.036 | −0.318 | 1.00 | 0.00 | PEPT |
| ATOM | 78 | HD2 | ACK | 205 | −11.355 | 1.079 | −1.610 | 1.00 | 0.00 | PEPT |
| ATOM | 79 | CE | ACK | 205 | −11.746 | −0.942 | −2.218 | 1.00 | 0.00 | PEPT |
| ATOM | 80 | HE1 | ACK | 205 | −11.397 | −0.645 | −3.196 | 1.00 | 0.00 | PEPT |
| ATOM | 81 | HH2 | ACK | 205 | −12.623 | −1.566 | −2.304 | 1.00 | 0.00 | PEPT |
| ATOM | 82 | HZ | ACK | 205 | −10.670 | −1.661 | −1.480 | 1.00 | 0.00 | PEPT |
| ATOM | 83 | HZ | ACK | 205 | −10.904 | −2.343 | −0.816 | 1.00 | 0.00 | PEPT |
| ATOM | 84 | CH | ACK | 205 | −8.427 | −1.745 | −0.561 | 1.00 | 0.00 | PEPT |
| ATOM | 85 | HH1 | ACK | 205 | −8.427 | −2.823 | −0.493 | 1.00 | 0.00 | PEPT |
| ATOM | 86 | HH2 | ACK | 205 | −8.712 | −1.324 | 0.392 | 1.00 | 0.00 | PEPT |
| ATOM | 87 | HH3 | ACK | 205 | −7.438 | −1.401 | −0.825 | 1.00 | 0.00 | PEPT |
| ATOM | 88 | C | ACK | 205 | −15.713 | −1.760 | 0.241 | 1.00 | 0.00 | PEPT |
| ATOM | 89 | O | ACK | 205 | −16.629 | −2.490 | −0.078 | 1.00 | 0.00 | PEPT |
| ATOM | 90 | C1 | ACK | 205 | −9.425 | −1.302 | −1.632 | 1.00 | 0.00 | PEPT |
| ATOM | 91 | O1 | ACK | 205 | −9.083 | −0.591 | −2.556 | 1.00 | 0.00 | PEPT |
| ATOM | 92 | N | LYS | 206 | −15.537 | −1.398 | 1.483 | 1.00 | 0.00 | PEPT |
| ATOM | 93 | HN | LYS | 206 | −14.788 | −0.812 | 1.722 | 1.00 | 0.00 | PEPT |
| ATOM | 94 | CA | LYS | 206 | −16.647 | −1.889 | 2.537 | 1.00 | 0.00 | PEPT |
| ATOM | 95 | HA | LYS | 206 | −16.350 | −2.954 | 2.666 | 1.00 | 0.00 | PEPT |
| ATOM | 96 | CB | LYS | 206 | −16.042 | −1.154 | 3.812 | 1.00 | 0.00 | PEPT |
| ATOM | 97 | HB1 | LYS | 206 | 15.494 | −0.262 | 3.548 | 1.00 | 0.00 | PEPT |
| ATOM | 98 | HB2 | LYS | 206 | −16.920 | −0.882 | 4.379 | 1.00 | 0.00 | PEPT |
| ATOM | 99 | CG | LYS | 206 | −15.152 | −2.068 | 4.657 | 1.00 | 0.00 | PEPT |
| ATOM | 100 | HG1 | LYS | 206 | −14.830 | −2.909 | 24.060 | 1.00 | 0.00 | PEPT |
| ATOM | 101 | HG2 | LYS | 206 | −14.289 | −1.516 | 4.996 | 1.00 | 0.00 | PEPT |
| ATOM | 102 | CD | LYS | 206 | −15.942 | −2.573 | 5.866 | 1.00 | 0.00 | PEPT |
| ATOM | 103 | HD1 | LYS | 206 | −16.711 | −3.255 | 5.535 | 1.00 | 0.00 | PEPT |
| ATOM | 104 | HD2 | LYS | 206 | −16.397 | −1.736 | 6.374 | 1.00 | 0.00 | PEPT |
| ATOM | 105 | CE | LYS | 206 | −14.997 | −3.299 | 6.825 | 1.00 | 0.00 | PEPT |
| ATOM | 106 | HE1 | LYS | 206 | −14.494 | −2.590 | 7.466 | 1.00 | 0.00 | PEPT |
| ATOM | 107 | HE2 | LYS | 206 | −14.276 | −3.884 | 6.272 | 1.00 | 0.00 | PEPT |
| ATOM | 108 | NZ | LYS | 206 | −15.880 | −4.190 | 7.629 | 1.00 | 0.00 | PEPT |
| ATOM | 109 | HE1 | LYS | 206 | −15.300 | −4.761 | 8.276 | 1.00 | 0.00 | PEPT |
| ATOM | 110 | HE2 | LYS | 206 | −16.410 | −4.818 | 6.992 | 1.00 | 0.00 | PEPT |
| ATOM | 111 | NZ3 | LYS | 206 | −16.546 | −3.612 | 8.179 | 1.00 | 0.00 | PEPT |
| ATOM | 112 | C | LYS | 206 | −17.918 | −1.557 | 2.166 | 1.00 | 0.00 | PEPT |
| ATOM | 113 | O | LYS | 206 | −18.595 | −2.344 | 1.535 | 1.00 | 0.00 | PEPT |
| ATOM | 114 | N | ARG | 207 | −18.408 | −0.404 | 2.554 | 1.00 | 0.00 | PEPT |
| ATOM | 115 | HN | ARG | 207 | −17.849 | 0.223 | 3.056 | 1.00 | 0.00 | PEPT |
| ATOM | 116 | CA | ARG | 287 | −19.815 | −0.032 | 2.217 | 1.00 | 0.00 | PEPT |

TABLE 10-continued

Atomic Structure Coordinates of the P/CAF Bromadomain and HIV-1 Tat Peptide Complex

| ATOM | 117 | HA | ARG | 207 | −20.105 | 0.058 | 2.755 | 1.00 | 0.00 | PEPT |
|---|---|---|---|---|---|---|---|---|---|---|
| ATOM | 118 | CB | ARG | 207 | −19.799 | 0.240 | 0.712 | 1.00 | 0.009 | PEPT |
| ATOM | 119 | HE1 | ARG | 207 | −18.778 | 0.299 | 0.367 | 1.00 | 0.00 | PEPT |
| ATOM | 120 | HB2 | ARG | 207 | −20.308 | −0.560 | 0.195 | 1.00 | 0.00 | PEPT |
| ATOM | 121 | CG | ARG | 207 | −20.511 | 1.565 | 0.428 | 1.00 | 0.00 | PEPT |
| ATOM | 122 | HG1 | ARG | 207 | −20.749 | 1.627 | −0.624 | 1.00 | 0.00 | PEPT |
| ATOM | 123 | HG2 | ARG | 207 | −21.422 | 1.615 | 1.006 | 1.00 | 0.00 | PEPT |
| ATOM | 124 | CD | ARG | 207 | −19.595 | 2.729 | 0.813 | 1.00 | 0.00 | PEPT |
| ATOM | 125 | HD1 | ARG | 207 | −18.731 | 2.365 | 1.350 | 1.00 | 0.00 | PEPT |
| ATOM | 126 | HD2 | ARG | 207 | −19.289 | 3.274 | −0.067 | 1.00 | 0.00 | PEPT |
| ATOM | 127 | NE | ARG | 207 | −20.428 | 3.597 | 1.698 | 1.00 | 0.00 | PEPT |
| ATOM | 128 | HE | ARG | 207 | −21.363 | 3.357 | 1.869 | 1.00 | 0.00 | PEPT |
| ATOM | 129 | CZ | ARG | 207 | −19.925 | 4.678 | 2.248 | 1.00 | 0.00 | PEPT |
| ATOM | 130 | NH1 | ARG | 207 | −20.678 | 5.417 | 3.016 | 1.00 | 0.00 | PEPT |
| ATOM | 131 | HH11 | ARG | 207 | −20.304 | 6.242 | 3.440 | 1.00 | 0.00 | PEPT |
| ATOM | 132 | HH12 | ARG | 207 | −21.630 | 5.158 | 3.181 | 1.00 | 0.00 | PEPT |
| ATOM | 133 | NH2 | ARG | 207 | −18.679 | 5.027 | 2.039 | 1.00 | 0.00 | PEPT |
| ATOM | 134 | HH21 | ARG | 207 | −18.316 | 5.854 | 2.468 | 1.00 | 0.00 | PEPT |
| ATOM | 135 | HH22 | ARG | 207 | −18.090 | 4.472 | 1.453 | 1.00 | 0.00 | PEPT |
| ATOM | 136 | C | ARG | 207 | −20.773 | −1.184 | 2.540 | 1.00 | 0.00 | PEPT |
| ATOM | 137 | O | ARG | 207 | −21.447 | −1.705 | 1.673 | 1.00 | 0.00 | PEPT |
| ATOM | 138 | N | ARG | 208 | −20.833 | −1.590 | 3.779 | 1.00 | 0.00 | PEPT |
| ATOM | 139 | HN | ARG | 208 | −20.279 | −1.159 | 4.463 | 1.00 | 0.00 | PEPT |
| ATOM | 140 | CA | ARG | 208 | −21.740 | −2.713 | 4.155 | 1.00 | 0.00 | PEPT |
| ATOM | 141 | HA | ARG | 208 | −21.360 | −3.647 | 3.766 | 1.00 | 0.00 | PEPT |
| ATOM | 142 | CB | ARG | 208 | −21.730 | −2.732 | 5.685 | 1.00 | 0.00 | PEPT |
| ATOM | 143 | HB1 | ARG | 208 | −22.428 | −3.476 | 6.041 | 1.00 | 0.00 | PEPT |
| ATOM | 144 | HB2 | ARG | 208 | −20.737 | −2.975 | 6.035 | 1.00 | 0.00 | PEPT |
| ATOM | 145 | CG | ARG | 208 | −22.135 | −1.356 | 6.218 | 1.00 | 0.00 | PEPT |
| ATOM | 146 | HG1 | ARG | 208 | −22.919 | −1.471 | 6.952 | 1.00 | 0.00 | PEPT |
| ATOM | 147 | HG2 | ARG | 208 | −22.493 | −0.745 | 5.402 | 1.00 | 0.00 | PEPT |
| ATOM | 148 | CD | ARG | 208 | −20.923 | −0.684 | 6.866 | 1.00 | 0.00 | PEPT |
| ATOM | 149 | HD1 | ARG | 208 | −20.219 | −1.428 | 7.209 | 1.00 | 0.00 | PEPT |
| ATOM | 150 | HD2 | ARG | 208 | −20.448 | −0.010 | 6.167 | 1.00 | 0.00 | PEPT |
| ATOM | 151 | NE | ARG | 208 | −21.480 | 0.077 | 8.024 | 1.00 | 0.00 | PEPT |
| ATOM | 152 | HE | ARG | 208 | −22.448 | 0.220 | 8.088 | 1.00 | 0.00 | PEPT |
| ATOM | 153 | CZ | ARG | 208 | −20.691 | 0.558 | 8.957 | 1.00 | 0.00 | PEPT |
| ATOM | 154 | NH1 | ARG | 208 | −21.207 | 1.219 | 9.957 | 1.00 | 0.00 | PEPT |
| ATOM | 155 | HH11 | ARG | 208 | −22.197 | 1.356 | 10.008 | 1.00 | 0.00 | PEPT |
| ATOM | 156 | HH12 | ARG | 208 | −20.614 | 1.588 | 10.672 | 1.00 | 0.00 | PEPT |
| ATOM | 157 | NH2 | ARG | 208 | −19.393 | 0.384 | 8.900 | 1.00 | 0.00 | PEPT |
| ATOM | 158 | HH21 | ARG | 208 | −18.810 | 0.758 | 9.621 | 1.00 | 0.00 | PEPT |
| ATOM | 159 | HH22 | ARG | 208 | −18.983 | −0.119 | 8.141 | 1.00 | 0.00 | PEPT |
| ATOM | 160 | C | ARG | 208 | −23.156 | −2.457 | 3.633 | 1.00 | 0.00 | PEPT |
| ATOM | 161 | O | ARG | 208 | −23.538 | −1.334 | 3.371 | 1.00 | 0.00 | PEPT |
| ATOM | 162 | N | GLN | 209 | −23.934 | −3.492 | 3.472 | 1.00 | 0.00 | PEPT |
| ATOM | 163 | HN | GLN | 209 | −23.605 | −4.391 | 3.685 | 1.00 | 0.00 | PEPT |
| ATOM | 164 | CA | GLN | 209 | −25.320 | −3.309 | 2.958 | 1.00 | 0.00 | PEPT |
| ATOM | 165 | HA | GLN | 209 | −25.592 | −2.264 | 2.972 | 1.00 | 0.00 | PEPT |
| ATOM | 166 | CB | GLN | 209 | −25.272 | −3.828 | 1.520 | 1.00 | 0.00 | PEPT |
| ATOM | 167 | HB1 | GLN | 209 | −24.571 | −3.239 | 0.947 | 1.00 | 0.00 | PEPT |
| ATOM | 168 | HB2 | GLN | 209 | −26.253 | −3.752 | 1.076 | 1.00 | 0.00 | PEPT |
| ATOM | 169 | CG | GLN | 209 | −24.826 | −5.291 | 1.523 | 1.00 | 0.00 | PEPT |
| ATOM | 170 | HG1 | GLN | 209 | −23.853 | −5.370 | 1.987 | 1.00 | 0.00 | PEPT |
| ATOM | 171 | HG2 | GLN | 209 | −25.538 | −5.884 | 2.078 | 1.00 | 0.00 | PEPT |
| ATOM | 172 | CD | GLN | 209 | −24.747 | −5.803 | 0.084 | 1.00 | 0.00 | PEPT |
| ATOM | 173 | OE1 | GLN | 209 | −25.655 | −5.600 | −0.697 | 1.00 | 0.00 | PEPT |
| ATOM | 174 | NE2 | GLN | 209 | −23.690 | −6.464 | −0.304 | 1.00 | 0.00 | PEPT |
| ATOM | 175 | HE21 | GLN | 209 | −22.957 | −6.628 | 0.326 | 1.00 | 0.00 | PEPT |
| ATOM | 176 | HE22 | GLN | 209 | −23.630 | −6.796 | −1.224 | 1.00 | 0.00 | PEPT |
| ATOM | 177 | C | GLN | 209 | −26.310 | −4.131 | 3.786 | 1.00 | 0.00 | PEPT |
| ATOM | 178 | O | GLN | 209 | −27.150 | −4.828 | 3.253 | 1.00 | 0.00 | PEPT |
| ATOM | 179 | N | ARG | 210 | −26.219 | −4.056 | 5.085 | 1.00 | 0.00 | PEPT |
| ATOM | 180 | HN | ARG | 210 | −25.534 | −3.488 | 5.496 | 1.00 | 0.00 | PEPT |
| ATOM | 181 | CA | ARG | 210 | −27.156 | −4.833 | 5.942 | 1.00 | 0.00 | PEPT |
| ATOM | 182 | HA | ARG | 210 | −27.759 | −5.494 | 5.337 | 1.00 | 0.00 | PEPT |
| ATOM | 183 | CB | ARG | 210 | −26.255 | −5.642 | 6.876 | 1.00 | 0.00 | PEPT |
| ATOM | 184 | HB1 | ARG | 210 | −25.239 | −5.612 | 6.511 | 1.00 | 0.00 | PEPT |
| ATOM | 185 | HB2 | ARG | 210 | −26.292 | −5.220 | 7.869 | 1.00 | 0.00 | PEPT |
| ATOM | 186 | CG | ARG | 210 | −26.739 | −7.093 | 6.920 | 1.00 | 0.00 | PEPT |
| ATOM | 187 | HG1 | ARG | 210 | −27.268 | −7.268 | 7.844 | 1.00 | 0.00 | PEPT |
| ATOM | 188 | HG2 | ARG | 210 | −27.400 | −7.277 | 6.085 | 1.00 | 0.00 | PEPT |
| ATOM | 189 | CD | ARG | 210 | −25.536 | −8.034 | 6.834 | 1.00 | 0.00 | PEPT |
| ATOM | 190 | HD1 | ARG | 210 | −24.755 | −7.593 | 6.233 | 1.00 | 0.00 | PEPT |
| ATOM | 191 | HD2 | ARG | 210 | −25.833 | −8.988 | 6.424 | 1.00 | 0.00 | PEPT |
| ATOM | 192 | NE | ARG | 210 | −25.076 | −8.196 | 8.245 | 1.00 | 0.00 | PEPT |
| ATOM | 193 | HE | ARG | 210 | −25.548 | −7.726 | 8.964 | 1.00 | 0.00 | PEPT |

TABLE 10-continued

Atomic Structure Coordinates of the P/CAF Bromadomain and HIV-1 Tat Peptide Complex

| ATOM | 194 | CZ | ARG | 210 | −24.048 | −8.959 | 8.536 | 1.00 | 0.00 | PEPT |
|------|-----|------|-----|-----|---------|---------|---------|------|------|------|
| ATOM | 195 | NH1 | ARG | 210 | −23.396 | −9.600 | 7.598 | 1.00 | 0.00 | PEPT |
| ATOM | 196 | HH11 | ARG | 210 | −23.673 | −9.517 | 6.642 | 1.00 | 0.00 | PEPT |
| ATOM | 197 | HH12 | ARG | 210 | −22.615 | −10.177 | 7.840 | 1.00 | 0.00 | PEPT |
| ATOM | 198 | NH2 | ARG | 210 | −23.670 | −9.081 | 9.780 | 1.00 | 0.00 | PEPT |
| ATOM | 199 | HH21 | ARG | 210 | −24.163 | −8.595 | 10.502 | 1.00 | 0.00 | PEPT |
| ATOM | 200 | HH22 | ARG | 210 | −22.889 | −9.660 | 10.010 | 1.00 | 0.00 | PEPT |
| ATOM | 201 | C | ARG | 210 | −28.049 | −3.887 | 6.748 | 1.00 | 0.00 | PEPT |
| ATOM | 202 | O | ARG | 210 | −27.996 | −3.849 | 7.961 | 1.00 | 0.00 | PEPT |
| ATOM | 203 | N | CYS | 211 | −28.871 | −3.123 | 6.081 | 1.00 | 0.00 | PEPT |
| ATOM | 204 | HN | CYS | 211 | −28.899 | −3.170 | 5.103 | 1.00 | 0.00 | PEPT |
| ATOM | 205 | CA | CYS | 211 | −29.768 | −2.181 | 6.808 | 1.00 | 0.00 | PEPT |
| ATOM | 206 | HA | CYS | 211 | −29.218 | −1.650 | 7.571 | 1.00 | 0.00 | PEPT |
| ATOM | 207 | CB | CYS | 211 | −30.265 | −1.210 | 5.735 | 1.00 | 0.00 | PEPT |
| ATOM | 208 | HB1 | CYS | 211 | −31.316 | −1.016 | 5.885 | 1.00 | 0.00 | PEPT |
| ATOM | 209 | HB2 | CYS | 211 | −30.115 | −1.645 | 4.758 | 1.00 | 0.00 | PEPT |
| ATOM | 210 | SG | CYS | 211 | −29.342 | 0.343 | 5.852 | 1.00 | 0.00 | PEPT |
| ATOM | 211 | HG | CYS | 211 | −29.855 | 1.026 | 5.412 | 1.00 | 0.00 | PEPT |
| ATOM | 212 | C | CYS | 211 | −30.945 | −2.938 | 7.426 | 1.00 | 0.00 | PEPT |
| ATOM | 213 | OT1 | CYS | 211 | −31.469 | −2.467 | 8.422 | 1.00 | 0.00 | PEPT |
| ATOM | 214 | OT2 | CYS | 211 | −31.335 | −3.948 | 6.863 | 1.00 | 0.00 | PEPT |
| ATOM | 215 | CA | GLY | 1 | 17.925 | −0.524 | −16.383 | 1.00 | 0.00 | PROT |
| ATOM | 216 | HA1 | GLY | 1 | 18.902 | −0.984 | −16.371 | 1.00 | 0.00 | PROT |
| ATOM | 217 | HA2 | GLY | 1 | 17.350 | −0.921 | −17.207 | 1.00 | 0.00 | PROT |
| ATOM | 218 | C | GLY | 1 | 17.204 | −0.822 | −15.067 | 1.00 | 0.00 | PROT |
| ATOM | 219 | O | GLY | 1 | 16.580 | 0.040 | −14.481 | 1.00 | 0.00 | PROT |
| ATOM | 220 | N | GLY | 1 | 18.073 | 0.950 | −16.545 | 1.00 | 0.00 | PROT |
| ATOM | 221 | HT1 | GLY | 1 | 18.494 | 1.157 | −17.473 | 1.00 | 0.00 | PROT |
| ATOM | 222 | HT2 | GLY | 1 | 18.690 | 1.321 | −15.794 | 1.00 | 0.00 | PROT |
| ATOM | 223 | HT3 | GLY | 1 | 17.138 | 1.401 | −16.479 | 1.00 | 0.00 | PROT |
| ATOM | 224 | N | SER | 2 | 17.286 | −2.037 | −14.598 | 1.00 | 0.00 | PROT |
| ATOM | 225 | HN | SER | 2 | 17.795 | −2.718 | −15.085 | 1.00 | 0.00 | PROT |
| ATOM | 226 | CA | SER | 2 | 16.606 | −2.390 | −13.319 | 1.00 | 0.00 | PROT |
| ATOM | 227 | HA | SER | 2 | 16.408 | −1.500 | −12.741 | 1.00 | 0.00 | PROT |
| ATOM | 228 | CB | SER | 2 | 15.294 | −3.053 | −13.743 | 1.00 | 0.00 | PROT |
| ATOM | 229 | HB1 | SER | 2 | 14.650 | −3.159 | −12.883 | 1.00 | 0.00 | PROT |
| ATOM | 230 | HB2 | SER | 2 | 14.804 | −2.440 | −14.486 | 1.00 | 0.00 | PROT |
| ATOM | 231 | OG | SER | 2 | 15.567 | −4.334 | −14.292 | 1.00 | 0.00 | PROT |
| ATOM | 232 | HG | SER | 2 | 14.944 | −4.957 | −13.912 | 1.00 | 0.00 | PROT |
| ATOM | 233 | C | SER | 2 | 17.462 | −3.369 | −12.514 | 1.00 | 0.00 | PROT |
| ATOM | 234 | O | SER | 2 | 16.955 | −4.243 | −11.839 | 1.00 | 0.00 | PROT |
| ATOM | 235 | N | HIS | 3 | 18.758 | −3.231 | −12.579 | 1.00 | 0.00 | PROT |
| ATOM | 236 | HN | HIS | 3 | 19.148 | −2.520 | −13.129 | 1.00 | 0.00 | PROT |
| ATOM | 237 | CA | HIS | 3 | 19.645 | −4.154 | −11.817 | 1.00 | 0.00 | PROT |
| ATOM | 238 | HA | HIS | 3 | 19.067 | −4.738 | −11.117 | 1.00 | 0.00 | PROT |
| ATOM | 239 | CB | HIS | 3 | 20.270 | −5.060 | −12.879 | 1.00 | 0.00 | PROT |
| ATOM | 240 | HB1 | HIS | 3 | 21.308 | −5.234 | −12.637 | 1.00 | 0.00 | PROT |
| ATOM | 241 | HB2 | HIS | 3 | 20.201 | −4.582 | −13.845 | 1.00 | 0.00 | PROT |
| ATOM | 242 | CG | HIS | 3 | 19.537 | −6.372 | −12.914 | 1.00 | 0.00 | PROT |
| ATOM | 243 | ND1 | HIS | 3 | 20.188 | −7.586 | −12.767 | 1.00 | 0.00 | PROT |
| ATOM | 244 | HD1 | HIS | 3 | 21.150 | −7.714 | −12.630 | 1.00 | 0.00 | PROT |
| ATOM | 245 | CD2 | HIS | 3 | 18.208 | −6.677 | −13.082 | 1.00 | 0.00 | PROT |
| ATOM | 246 | HD2 | HIS | 3 | 17.417 | −5.955 | −13.224 | 1.00 | 0.00 | PROT |
| ATOM | 247 | CE1 | HIS | 3 | 19.260 | −8.556 | −12.847 | 1.00 | 0.00 | PROT |
| ATOM | 248 | HE1 | HIS | 3 | 19.478 | −9.611 | −12.767 | 1.00 | 0.00 | PROT |
| ATOM | 249 | NE2 | HIS | 3 | 18.036 | −8.057 | −13.039 | 1.00 | 0.00 | PROT |
| ATOM | 250 | C | HIS | 3 | 20.732 | −3.364 | −11.084 | 1.00 | 0.00 | PROT |
| ATOM | 251 | O | HIS | 3 | 21.067 | −3.654 | −9.953 | 1.00 | 0.00 | PROT |
| ATOM | 252 | N | MET | 4 | 21.285 | −2.366 | −11.720 | 1.00 | 0.00 | PROT |
| ATOM | 253 | HN | MET | 4 | 21.000 | −2.148 | −12.632 | 1.00 | 0.00 | PROT |
| ATOM | 254 | CA | MET | 4 | 22.348 | −1.558 | −11.058 | 1.00 | 0.00 | PROT |
| ATOM | 255 | HA | MET | 4 | 22.732 | −2.079 | −10.193 | 1.00 | 0.00 | PROT |
| ATOM | 256 | CB | MET | 4 | 23.443 | −1.406 | −12.116 | 1.00 | 0.00 | PROT |
| ATOM | 257 | HB1 | MET | 4 | 23.093 | −0.757 | −12.905 | 1.00 | 0.00 | PROT |
| ATOM | 258 | HB2 | MET | 4 | 23.684 | −2.375 | −12.527 | 1.00 | 0.00 | PROT |
| ATOM | 259 | CG | MET | 4 | 24.692 | −0.800 | −11.473 | 1.00 | 0.00 | PROT |
| ATOM | 260 | HG1 | MET | 4 | 24.729 | −1.072 | −10.429 | 1.00 | 0.00 | PROT |
| ATOM | 261 | HG2 | MET | 4 | 24.658 | 0.276 | −11.563 | 1.00 | 0.00 | PROT |
| ATOM | 262 | SD | MET | 4 | 26.168 | −1.427 | −12.313 | 1.00 | 0.00 | PROT |
| ATOM | 263 | CE | MET | 4 | 26.561 | −2.741 | −11.131 | 1.00 | 0.00 | PROT |
| ATOM | 264 | HE1 | MET | 4 | 26.796 | −2.304 | −10.172 | 1.00 | 0.00 | PROT |
| ATOM | 265 | HE2 | MET | 4 | 27.412 | −3.303 | −11.489 | 1.00 | 0.00 | PROT |
| ATOM | 266 | HE3 | MET | 4 | 25.712 | −3.400 | −11.029 | 1.00 | 0.00 | PROT |
| ATOM | 267 | C | MET | 4 | 21.803 | −0.186 | −10.656 | 1.00 | 0.00 | PROT |
| ATOM | 268 | O | MET | 4 | 22.538 | 0.774 | −10.534 | 1.00 | 0.00 | PROT |
| ATOM | 269 | N | SER | 5 | 20.519 | −0.085 | −10.450 | 1.00 | 0.00 | PROT |
| ATOM | 270 | HN | SER | 5 | 19.943 | −0.871 | −10.553 | 1.00 | 0.00 | PROT |

TABLE 10-continued

Atomic Structure Coordinates of the P/CAF Bromadomain and HIV-1 Tat Peptide Complex

| ATOM | 271 | CA  | SER | 5 | 19.928 | 1.225  | −10.055 | 1.00 | 0.00 | PROT |
|------|-----|-----|-----|---|--------|--------|---------|------|------|------|
| ATOM | 272 | HA  | SER | 5 | 20.603 | 1.761  | −9.405  | 1.00 | 0.00 | PROT |
| ATOM | 273 | CB  | SER | 5 | 19.740 | 1.984  | −11.370 | 1.00 | 0.00 | PROT |
| ATOM | 274 | HB1 | SER | 5 | 18.706 | 1.924  | −11.676 | 1.00 | 0.00 | PROT |
| ATOM | 275 | HB2 | SER | 5 | 20.366 | 1.544  | −12.132 | 1.00 | 0.00 | PROT |
| ATOM | 276 | OG  | SER | 5 | 20.102 | 3.344  | −11.186 | 1.00 | 0.00 | PROT |
| ATOM | 277 | HG  | SER | 5 | 20.950 | 3.368  | −10.737 | 1.00 | 0.00 | PROT |
| ATOM | 278 | C   | SER | 5 | 18.580 | 1.010  | −9.365  | 1.00 | 0.00 | PROT |
| ATOM | 279 | O   | SER | 5 | 17.934 | −0.004 | −9.546  | 1.00 | 0.00 | PROT |
| ATOM | 280 | N   | LYS | 6 | 18.150 | 1.953  | −8.571  | 1.00 | 0.00 | PROT |
| ATOM | 281 | HN  | LYS | 6 | 18.686 | 2.762  | −8.437  | 1.00 | 0.00 | PROT |
| ATOM | 282 | CA  | LYS | 6 | 16.844 | 1.799  | −7.868  | 1.00 | 0.00 | PROT |
| ATOM | 283 | HA  | LYS | 6 | 16.679 | 2.628  | −7.196  | 1.00 | 0.00 | PROT |
| ATOM | 284 | CB  | LYS | 6 | 15.795 | 1.801  | −8.985  | 1.00 | 0.00 | PROT |
| ATOM | 285 | HB1 | LYS | 6 | 15.515 | 0.784  | −9.217  | 1.00 | 0.00 | PROT |
| ATOM | 286 | HB2 | LYS | 6 | 16.208 | 2.270  | −9.866  | 1.00 | 0.00 | PROT |
| ATOM | 287 | CG  | LYS | 6 | 14.559 | 2.577  | −8.526  | 1.00 | 0.00 | PROT |
| ATOM | 288 | HG1 | LYS | 6 | 13.676 | 1.977  | −8.689  | 1.00 | 0.00 | PROT |
| ATOM | 289 | HG2 | LYS | 6 | 14.648 | 2.807  | −7.474  | 1.00 | 0.00 | PROT |
| ATOM | 290 | CD  | LYS | 6 | 14.445 | 3.878  | −9.325  | 1.00 | 0.00 | PROT |
| ATOM | 291 | HD1 | LYS | 6 | 14.762 | 4.707  | −8.710  | 1.00 | 0.00 | PROT |
| ATOM | 292 | HD2 | LYS | 6 | 15.074 | 3.818  | −10.201 | 1.00 | 0.00 | PROT |
| ATOM | 293 | CE  | LYS | 6 | 12.991 | 4.087  | −9.754  | 1.00 | 0.00 | PROT |
| ATOM | 294 | HE1 | LYS | 6 | 12.328 | 3.952  | −8.912  | 1.00 | 0.00 | PROT |
| ATOM | 295 | HE2 | LYS | 6 | 12.733 | 3.405  | −10.551 | 1.00 | 0.00 | PROT |
| ATOM | 296 | NZ  | LYS | 6 | 12.935 | 5.495  | −10.238 | 1.00 | 0.00 | PROT |
| ATOM | 297 | HZ1 | LYS | 6 | 12.993 | 6.143  | −9.426  | 1.00 | 0.00 | PROT |
| ATOM | 298 | HZ2 | LYS | 6 | 12.040 | 5.652  | −10.743 | 1.00 | 0.00 | PROT |
| ATOM | 299 | HZ3 | LYS | 6 | 13.733 | 5.672  | −10.881 | 1.00 | 0.00 | PROT |
| ATOM | 300 | C   | LYS | 6 | 16.806 | 0.474  | −7.103  | 1.00 | 0.00 | PROT |
| ATOM | 301 | O   | LYS | 6 | 16.081 | −0.436 | −7.454  | 1.00 | 0.00 | PROT |
| ATOM | 302 | N   | GLU | 7 | 17.584 | 0.355  | −6.061  | 1.00 | 0.00 | PROT |
| ATOM | 303 | HN  | GLU | 7 | 18.165 | 1.099  | −5.796  | 1.00 | 0.00 | PROT |
| ATOM | 304 | CA  | GLU | 7 | 17.598 | −0.916 | −5.282  | 1.00 | 0.00 | PROT |
| ATOM | 305 | HA  | GLU | 7 | 16.681 | −1.464 | −5.442  | 1.00 | 0.00 | PROT |
| ATOM | 306 | CB  | GLU | 7 | 18.790 | −1.699 | −5.837  | 1.00 | 0.00 | PROT |
| ATOM | 307 | HB1 | GLU | 7 | 19.185 | −2.347 | −5.070  | 1.00 | 0.00 | PROT |
| ATOM | 308 | HB2 | GLU | 7 | 19.558 | −1.008 | −6.154  | 1.00 | 0.00 | PROT |
| ATOM | 309 | CG  | GLU | 7 | 18.338 | −2.540 | −7.032  | 1.00 | 0.00 | PROT |
| ATOM | 310 | HG1 | GLU | 7 | 19.195 | −2.797 | −7.636  | 1.00 | 0.00 | PROT |
| ATOM | 311 | HG2 | GLU | 7 | 17.635 | −1.974 | −7.626  | 1.00 | 0.00 | PROT |
| ATOM | 312 | CD  | GLU | 7 | 17.667 | −3.820 | −6.529  | 1.00 | 0.00 | PROT |
| ATOM | 313 | OE1 | GLU | 7 | 18.338 | −4.600 | −5.874  | 1.00 | 0.00 | PROT |
| ATOM | 314 | OE2 | GLU | 7 | 16.493 | −3.998 | −6.809  | 1.00 | 0.00 | PROT |
| ATOM | 315 | C   | GLU | 7 | 17.798 | −0.631 | −3.787  | 1.00 | 0.00 | PROT |
| ATOM | 316 | O   | GLU | 7 | 18.086 | 0.486  | −3.407  | 1.00 | 0.00 | PROT |
| ATOM | 317 | N   | PRO | 8 | 17.670 | −1.663 | −2.985  | 1.00 | 0.00 | PROT |
| ATOM | 318 | CA  | PRO | 8 | 17.831 | −1.510 | −1.520  | 1.00 | 0.00 | PROT |
| ATOM | 319 | HA  | PRO | 8 | 17.380 | −0.589 | −1.179  | 1.00 | 0.00 | PROT |
| ATOM | 320 | CB  | PRO | 8 | 17.082 | −2.716 | −0.960  | 1.00 | 0.00 | PROT |
| ATOM | 321 | HB1 | PRO | 8 | 17.568 | −3.072 | −0.064  | 1.00 | 0.00 | PROT |
| ATOM | 322 | HB2 | PRO | 8 | 16.050 | −2.458 | −0.747  | 1.00 | 0.00 | PROT |
| ATOM | 323 | CG  | PRO | 8 | 17.156 | −3.756 | −2.035  | 1.00 | 0.00 | PROT |
| ATOM | 324 | HG1 | PRO | 8 | 18.008 | −4.396 | −1.864  | 1.00 | 0.00 | PROT |
| ATOM | 325 | HG2 | PRO | 8 | 16.252 | −4.346 | −2.040  | 1.00 | 0.00 | PROT |
| ATOM | 326 | CD  | PRO | 8 | 17.310 | −3.041 | −3.355  | 1.00 | 0.00 | PROT |
| ATOM | 327 | HD2 | PRO | 8 | 16.380 | −3.054 | −3.902  | 1.00 | 0.00 | PROT |
| ATOM | 328 | HD1 | PRO | 8 | 18.098 | −3.493 | −3.937  | 1.00 | 0.00 | PROT |
| ATOM | 329 | C   | PRO | 8 | 19.308 | −1.575 | −1.113  | 1.00 | 0.00 | PROT |
| ATOM | 330 | O   | PRO | 8 | 19.625 | −1.690 | 0.054   | 1.00 | 0.00 | PROT |
| ATOM | 331 | N   | ARG | 9 | 20.212 | −1.513 | −2.059  | 1.00 | 0.00 | PROT |
| ATOM | 332 | HN  | ARG | 9 | 19.936 | −1.431 | −2.994  | 1.00 | 0.00 | PROT |
| ATOM | 333 | CA  | ARG | 9 | 21.665 | −1.591 | −1.720  | 1.00 | 0.00 | PROT |
| ATOM | 334 | HA  | ARG | 9 | 22.256 | −1.586 | −2.624  | 1.00 | 0.00 | PROT |
| ATOM | 335 | CB  | ARG | 9 | 21.957 | −0.333 | −0.896  | 1.00 | 0.00 | PROT |
| ATOM | 336 | HB1 | ARG | 9 | 21.186 | −0.198 | −0.153  | 1.00 | 0.00 | PROT |
| ATOM | 337 | HB2 | ARG | 9 | 22.914 | −0.438 | −0.405  | 1.00 | 0.00 | PROT |
| ATOM | 338 | CG  | ARG | 9 | 21.991 | 0.886  | −1.820  | 1.00 | 0.00 | PROT |
| ATOM | 339 | HG1 | ARG | 9 | 22.503 | 1.699  | −1.325  | 1.00 | 0.00 | PROT |
| ATOM | 340 | HG2 | ARG | 9 | 22.513 | 0.633  | −2.731  | 1.00 | 0.00 | PROT |
| ATOM | 341 | CD  | ARG | 9 | 20.560 | 1.312  | −2.153  | 1.00 | 0.00 | PROT |
| ATOM | 342 | HD1 | ARG | 9 | 20.215 | 0.803  | −3.041  | 1.00 | 0.00 | PROT |
| ATOM | 343 | HD2 | ARG | 9 | 19.903 | 1.106  | −1.321  | 1.00 | 0.00 | PROT |
| ATOM | 344 | NE  | ARG | 9 | 20.647 | 2.782  | −2.397  | 1.00 | 0.00 | PROT |
| ATOM | 345 | HE  | ARG | 9 | 20.296 | 3.405  | −1.727  | 1.00 | 0.00 | PROT |
| ATOM | 346 | CZ  | ARG | 9 | 21.187 | 3.252  | −3.497  | 1.00 | 0.00 | PROT |
| ATOM | 347 | NH1 | ARG | 9 | 21.250 | 4.542  | −3.682  | 1.00 | 0.00 | PROT |

TABLE 10-continued

Atomic Structure Coordinates of the P/CAF Bromadomain and HIV-1 Tat Peptide Complex

| ATOM | 348 | HH11 | ARG | 9 | 20.887 | 5.165 | −2.988 | 1.00 | 0.00 | PROT |
|---|---|---|---|---|---|---|---|---|---|---|
| ATOM | 349 | HH12 | ARG | 9 | 21.659 | 4.909 | −4.517 | 1.00 | 0.00 | PROT |
| ATOM | 350 | NH2 | ARG | 9 | 21.666 | 2.446 | −4.413 | 1.00 | 0.00 | PROT |
| ATOM | 351 | HH21 | ARG | 9 | 21.625 | 1.456 | −4.286 | 1.00 | 0.00 | PROT |
| ATOM | 352 | HH22 | ARG | 9 | 22.073 | 2.823 | −5.244 | 1.00 | 0.00 | PROT |
| ATOM | 353 | C | ARG | 9 | 21.953 | −2.861 | −0.910 | 1.00 | 0.00 | PROT |
| ATOM | 354 | O | ARG | 9 | 22.263 | −3.898 | −1.463 | 1.00 | 0.00 | PROT |
| ATOM | 355 | N | ASP | 10 | 21.852 | −2.798 | 0.392 | 1.00 | 0.00 | PROT |
| ATOM | 356 | HN | ASP | 10 | 21.586 | −1.963 | 0.827 | 1.00 | 0.00 | PROT |
| ATOM | 357 | CA | ASP | 10 | 22.098 | −4.015 | 1.213 | 1.00 | 0.00 | PROT |
| ATOM | 358 | HA | ASP | 10 | 22.660 | −4.742 | 0.647 | 1.00 | 0.00 | PROT |
| ATOM | 359 | CB | ASP | 10 | 22.913 | −3.524 | 2.410 | 1.00 | 0.00 | PROT |
| ATOM | 360 | HB1 | ASP | 10 | 23.100 | −2.466 | 2.308 | 1.00 | 0.00 | PROT |
| ATOM | 361 | HB2 | ASP | 10 | 22.362 | −3.707 | 3.321 | 1.00 | 0.00 | PROT |
| ATOM | 362 | CG | ASP | 10 | 24.246 | −4.274 | 2.461 | 1.00 | 0.00 | PROT |
| ATOM | 363 | OD1 | ASP | 10 | 24.263 | −5.378 | 2.980 | 1.00 | 0.00 | PROT |
| ATOM | 364 | OD2 | ASP | 10 | 25.227 | −3.731 | 1.980 | 1.00 | 0.00 | PROT |
| ATOM | 365 | C | ASP | 10 | 20.761 | −4.606 | 1.679 | 1.00 | 0.00 | PROT |
| ATOM | 366 | O | ASP | 10 | 19.868 | −3.874 | 2.058 | 1.00 | 0.00 | PROT |
| ATOM | 367 | N | PRO | 11 | 20.653 | −5.911 | 1.623 | 1.00 | 0.00 | PROT |
| ATOM | 368 | CA | PRO | 11 | 19.396 | −6.574 | 2.044 | 1.00 | 0.00 | PROT |
| ATOM | 369 | HA | PRO | 11 | 18.593 | −6.327 | 1.364 | 1.00 | 0.00 | PROT |
| ATOM | 370 | CB | PRO | 11 | 19.721 | −8.067 | 1.970 | 1.00 | 0.00 | PROT |
| ATOM | 371 | HB1 | PRO | 11 | 19.963 | −8.446 | 2.952 | 1.00 | 0.00 | PROT |
| ATOM | 372 | HB2 | PRO | 11 | 18.887 | −8.611 | 1.554 | 1.00 | 0.00 | PROT |
| ATOM | 373 | CG | PRO | 11 | 20.910 | −8.172 | 1.068 | 1.00 | 0.00 | PROT |
| ATOM | 374 | HG1 | PRO | 11 | 20.586 | −8.321 | 0.048 | 1.00 | 0.00 | PROT |
| ATOM | 375 | HG2 | PRO | 11 | 21.537 | −8.994 | 1.379 | 1.00 | 0.00 | PROT |
| ATOM | 376 | CD | PRO | 11 | 21.668 | −6.877 | 1.180 | 1.00 | 0.00 | PROT |
| ATOM | 377 | HD2 | PRO | 11 | 22.071 | −6.589 | 0.221 | 1.00 | 0.00 | PROT |
| ATOM | 378 | HD1 | PRO | 11 | 22.455 | −6.961 | 1.914 | 1.00 | 0.00 | PROT |
| ATOM | 379 | C | PRO | 11 | 19.031 | −6.172 | 3.474 | 1.00 | 0.00 | PROT |
| ATOM | 380 | O | PRO | 11 | 17.872 | −6.048 | 3.816 | 1.00 | 0.00 | PROT |
| ATOM | 381 | N | ASP | 12 | 20.010 | −5.958 | 4.309 | 1.00 | 0.00 | PROT |
| ATOM | 382 | HN | ASP | 12 | 20.939 | −6.062 | 4.012 | 1.00 | 0.00 | PROT |
| ATOM | 383 | CA | ASP | 12 | 19.717 | −5.560 | 5.714 | 1.00 | 0.00 | PROT |
| ATOM | 384 | HA | ASP | 12 | 18.879 | −6.124 | 6.097 | 1.00 | 0.00 | PROT |
| ATOM | 385 | CB | ASP | 12 | 20.989 | −5.900 | 6.492 | 1.00 | 0.00 | PROT |
| ATOM | 386 | HB1 | ASP | 12 | 21.742 | −5.151 | 6.296 | 1.00 | 0.00 | PROT |
| ATOM | 387 | HB2 | ASP | 12 | 21.355 | −6.867 | 6.180 | 1.00 | 0.00 | PROT |
| ATOM | 388 | CG | ASP | 12 | 20.679 | −5.931 | 7.990 | 1.00 | 0.00 | PROT |
| ATOM | 389 | OD1 | ASP | 12 | 20.111 | −6.914 | 8.436 | 1.00 | 0.00 | PROT |
| ATOM | 390 | OD2 | ASP | 12 | 21.014 | −4.972 | 8.664 | 1.00 | 0.00 | PROT |
| ATOM | 391 | C | ASP | 12 | 19.430 | −4.058 | 5.793 | 1.00 | 0.00 | PROT |
| ATOM | 392 | O | ASP | 12 | 18.729 | −3.596 | 6.671 | 1.00 | 0.00 | PROT |
| ATOM | 393 | N | GLN | 13 | 19.969 | −3.293 | 4.883 | 1.00 | 0.00 | PROT |
| ATOM | 394 | HN | GLN | 13 | 20.532 | −3.685 | 4.184 | 1.00 | 0.00 | PROT |
| ATOM | 395 | CA | GLN | 13 | 19.730 | −1.821 | 4.909 | 1.00 | 0.00 | PROT |
| ATOM | 396 | HA | GLN | 13 | 20.041 | −1.407 | 5.857 | 1.00 | 0.00 | PROT |
| ATOM | 397 | CB | GLN | 13 | 20.592 | −1.261 | 3.775 | 1.00 | 0.00 | PROT |
| ATOM | 398 | HB1 | GLN | 13 | 20.701 | −2.008 | 3.002 | 1.00 | 0.00 | PROT |
| ATOM | 399 | HB2 | GLN | 13 | 20.116 | −0.384 | 3.362 | 1.00 | 0.00 | PROT |
| ATOM | 400 | CG | GLN | 13 | 21.971 | −0.882 | 4.319 | 1.00 | 0.00 | PROT |
| ATOM | 401 | HG1 | GLN | 13 | 22.210 | −1.510 | 5.164 | 1.00 | 0.00 | PROT |
| ATOM | 402 | HG2 | GLN | 13 | 22.713 | −1.018 | 3.547 | 1.00 | 0.00 | PROT |
| ATOM | 403 | CD | GLN | 13 | 21.958 | 0.583 | 4.760 | 1.00 | 0.00 | PROT |
| ATOM | 404 | OE1 | GLN | 13 | 21.906 | 0.875 | 5.939 | 1.00 | 0.00 | PROT |
| ATOM | 405 | NE2 | GLN | 13 | 22.002 | 1.525 | 3.857 | 1.00 | 0.00 | PROT |
| ATOM | 406 | HE21 | GLN | 13 | 22.044 | 1.290 | 2.906 | 1.00 | 0.00 | PROT |
| ATOM | 407 | HE22 | GLN | 13 | 21.994 | 2.466 | 4.130 | 1.00 | 0.00 | PROT |
| ATOM | 408 | C | GLN | 13 | 18.254 | −1.514 | 4.651 | 1.00 | 0.00 | PROT |
| ATOM | 409 | O | GLN | 13 | 17.550 | −1.029 | 5.514 | 1.00 | 0.00 | PROT |
| ATOM | 410 | N | LEU | 14 | 17.783 | −1.786 | 3.465 | 1.00 | 0.00 | PROT |
| ATOM | 411 | HN | LEU | 14 | 18.371 | −2.172 | 2.783 | 1.00 | 0.00 | PROT |
| ATOM | 412 | CA | LEU | 14 | 16.357 | −1.500 | 3.143 | 1.00 | 0.00 | PROT |
| ATOM | 413 | HA | LEU | 14 | 16.161 | −0.442 | 3.221 | 1.00 | 0.00 | PROT |
| ATOM | 414 | CB | LEU | 14 | 16.188 | −1.963 | 1.696 | 1.00 | 0.00 | PROT |
| ATOM | 415 | HB1 | LEU | 14 | 16.405 | −3.017 | 1.628 | 1.00 | 0.00 | PROT |
| ATOM | 416 | HB2 | LEU | 14 | 16.869 | −1.413 | 1.064 | 1.00 | 0.00 | PROT |
| ATOM | 417 | CG | LEU | 14 | 14.751 | −1.714 | 1.235 | 1.00 | 0.00 | PROT |
| ATOM | 418 | HG | LEU | 14 | 14.164 | −1.382 | 2.068 | 1.00 | 0.00 | PROT |
| ATOM | 419 | CD1 | LEU | 14 | 14.158 | −3.011 | 0.684 | 1.00 | 0.00 | PROT |
| ATOM | 420 | HD11 | LEU | 14 | 13.501 | −2.782 | −0.142 | 1.00 | 0.00 | PROT |
| ATOM | 421 | HD12 | LEU | 14 | 13.598 | −3.508 | 1.462 | 1.00 | 0.00 | PROT |
| ATOM | 422 | HD13 | LEU | 14 | 14.954 | −3.656 | 0.344 | 1.00 | 0.00 | PROT |
| ATOM | 423 | CD2 | LEU | 14 | 14.731 | −0.644 | 0.144 | 1.00 | 0.00 | PROT |
| ATOM | 424 | HD21 | LEU | 14 | 15.677 | −0.123 | 0.133 | 1.00 | 0.00 | PROT |

TABLE 10-continued

Atomic Structure Coordinates of the P/CAF Bromadomain and HIV-1 Tat Peptide Complex

| ATOM | 425 | HD22 | LEU | 14 | 13.936 | 0.057 | 0.345 | 1.00 | 0.00 | PROT |
|------|-----|------|-----|----|--------|-------|-------|------|------|------|
| ATOM | 426 | HD23 | LEU | 14 | 14.565 | −1.112 | −0.815 | 1.00 | 0.00 | PROT |
| ATOM | 427 | C | LEU | 14 | 15.427 | −2.284 | 4.071 | 1.00 | 0.00 | PROT |
| ATOM | 428 | O | LEU | 14 | 14.312 | −1.881 | 4.325 | 1.00 | 0.00 | PROT |
| ATOM | 429 | N | TYR | 15 | 15.879 | −3.392 | 4.597 | 1.00 | 0.00 | PROT |
| ATOM | 430 | HN | TYR | 15 | 16.785 | −3.700 | 4.386 | 1.00 | 0.00 | PROT |
| ATOM | 431 | CA | TYR | 15 | 15.012 | −4.192 | 5.513 | 1.00 | 0.00 | PROT |
| ATOM | 432 | HA | TYR | 15 | 14.237 | −4.696 | 4.953 | 1.00 | 0.00 | PROT |
| ATOM | 433 | CB | TYR | 15 | 15.954 | −5.213 | 6.154 | 1.00 | 0.00 | PROT |
| ATOM | 434 | HB1 | TYR | 15 | 16.750 | −4.695 | 6.667 | 1.00 | 0.00 | PROT |
| ATOM | 435 | HB2 | TYR | 15 | 16.372 | −5.847 | 5.387 | 1.00 | 0.00 | PROT |
| ATOM | 436 | CG | TYR | 15 | 15.186 | −6.059 | 7.140 | 1.00 | 0.00 | PROT |
| ATOM | 437 | CD1 | TYR | 15 | 14.223 | −6.967 | 6.683 | 1.00 | 0.00 | PROT |
| ATOM | 438 | HD1 | TYR | 15 | 14.029 | −7.060 | 5.625 | 1.00 | 0.00 | PROT |
| ATOM | 439 | CD2 | TYR | 15 | 15.438 | −5.938 | 8.512 | 1.00 | 0.00 | PROT |
| ATOM | 440 | HD2 | TYR | 15 | 16.181 | −5.238 | 8.865 | 1.00 | 0.00 | PROT |
| ATOM | 441 | CE1 | TYR | 15 | 13.511 | −7.752 | 7.598 | 1.00 | 0.00 | PROT |
| ATOM | 442 | HE1 | TYR | 15 | 12.768 | −8.452 | 7.245 | 1.00 | 0.00 | PROT |
| ATOM | 443 | CE2 | TYR | 15 | 14.726 | −6.723 | 9.427 | 1.00 | 0.00 | PROT |
| ATOM | 444 | HE2 | TYR | 15 | 14.920 | −6.629 | 10.485 | 1.00 | 0.00 | PROT |
| ATOM | 445 | CZ | TYR | 15 | 13.763 | −7.631 | 8.970 | 1.00 | 0.00 | PROT |
| ATOM | 446 | OH | TYR | 15 | 13.061 | −8.405 | 9.871 | 1.00 | 0.00 | PROT |
| ATOM | 447 | HH | TYR | 15 | 12.159 | −8.487 | 9.553 | 1.00 | 0.00 | PROT |
| ATOM | 448 | C | TYR | 15 | 14.393 | −3.290 | 6.584 | 1.00 | 0.00 | PROT |
| ATOM | 449 | O | TYR | 15 | 13.187 | −3.156 | 6.678 | 1.00 | 0.00 | PROT |
| ATOM | 450 | N | SER | 16 | 15.206 | −2.642 | 7.370 | 1.00 | 0.00 | PROT |
| ATOM | 451 | HN | SER | 16 | 16.176 | −2.746 | 7.269 | 1.00 | 0.00 | PROT |
| ATOM | 452 | CA | SER | 16 | 14.655 | −1.726 | 8.403 | 1.00 | 0.00 | PROT |
| ATOM | 453 | HA | SER | 16 | 13.931 | −2.247 | 9.012 | 1.00 | 0.00 | PROT |
| ATOM | 454 | CB | SER | 16 | 15.864 | −1.313 | 9.257 | 1.00 | 0.00 | PROT |
| ATOM | 455 | HB1 | SER | 16 | 16.704 | −1.949 | 9.017 | 1.00 | 0.00 | PROT |
| ATOM | 456 | HB2 | SER | 16 | 15.614 | −1.430 | 10.301 | 1.00 | 0.00 | PROT |
| ATOM | 457 | OG | SER | 16 | 16.214 | 0.042 | 9.005 | 1.00 | 0.00 | PROT |
| ATOM | 458 | HG | SER | 16 | 16.542 | 0.420 | 9.825 | 1.00 | 0.00 | PROT |
| ATOM | 459 | C | SER | 16 | 14.002 | −0.521 | 7.720 | 1.00 | 0.00 | PROT |
| ATOM | 460 | O | SER | 16 | 13.078 | 0.073 | 8.239 | 1.00 | 0.00 | PROT |
| ATOM | 461 | N | THR | 17 | 14.458 | −0.170 | 6.546 | 1.00 | 0.00 | PROT |
| ATOM | 462 | HN | THR | 17 | 15.192 | −0.671 | 6.132 | 1.00 | 0.00 | PROT |
| ATOM | 463 | CA | THR | 17 | 13.830 | 0.970 | 5.826 | 1.00 | 0.00 | PROT |
| ATOM | 464 | HA | THR | 17 | 13.940 | 1.880 | 6.396 | 1.00 | 0.00 | PROT |
| ATOM | 465 | CB | THR | 17 | 14.579 | 1.082 | 4.499 | 1.00 | 0.00 | PROT |
| ATOM | 466 | HB | THR | 17 | 14.332 | 0.240 | 3.870 | 1.00 | 0.00 | PROT |
| ATOM | 467 | OG1 | THR | 17 | 15.977 | 1.098 | 4.746 | 1.00 | 0.00 | PROT |
| ATOM | 468 | HG1 | THR | 17 | 16.418 | 1.371 | 3.938 | 1.00 | 0.00 | PROT |
| ATOM | 469 | CG2 | THR | 17 | 14.171 | 2.378 | 3.798 | 1.00 | 0.00 | PROT |
| ATOM | 470 | HG21 | THR | 17 | 15.055 | 2.919 | 3.497 | 1.00 | 0.00 | PROT |
| ATOM | 471 | HG22 | THR | 17 | 13.592 | 2.986 | 4.477 | 1.00 | 0.00 | PROT |
| ATOM | 472 | HG23 | THR | 17 | 13.576 | 2.145 | 2.927 | 1.00 | 0.00 | PROT |
| ATOM | 473 | C | THR | 17 | 12.352 | 0.664 | 5.591 | 1.00 | 0.00 | PROT |
| ATOM | 474 | O | THR | 17 | 11.486 | 1.380 | 6.053 | 1.00 | 0.00 | PROT |
| ATOM | 475 | N | LEU | 18 | 12.048 | −0.423 | 4.924 | 1.00 | 0.00 | PROT |
| ATOM | 476 | HN | LEU | 18 | 12.757 | −1.009 | 4.587 | 1.00 | 0.00 | PROT |
| ATOM | 477 | CA | LEU | 18 | 10.614 | −0.789 | 4.732 | 1.00 | 0.00 | PROT |
| ATOM | 478 | HA | LEU | 18 | 10.119 | −0.070 | 4.100 | 1.00 | 0.00 | PROT |
| ATOM | 479 | CB | LEU | 18 | 10.611 | −2.174 | 4.066 | 1.00 | 0.00 | PROT |
| ATOM | 480 | HB1 | LEU | 18 | 10.953 | −2.908 | 4.780 | 1.00 | 0.00 | PROT |
| ATOM | 481 | HB2 | LEU | 18 | 9.603 | −2.418 | 3.764 | 1.00 | 0.00 | PROT |
| ATOM | 482 | CG | LEU | 18 | 11.531 | −2.205 | 2.830 | 1.00 | 0.00 | PROT |
| ATOM | 483 | HG | LEU | 18 | 12.555 | −2.290 | 3.149 | 1.00 | 0.00 | PROT |
| ATOM | 484 | CD1 | LEU | 18 | 11.171 | −3.421 | 1.976 | 1.00 | 0.00 | PROT |
| ATOM | 485 | HD11 | LEU | 18 | 10.097 | −3.479 | 1.864 | 1.00 | 0.00 | PROT |
| ATOM | 486 | HD12 | LEU | 18 | 11.530 | −4.319 | 2.456 | 1.00 | 0.00 | PROT |
| ATOM | 487 | HD13 | LEU | 18 | 11.628 | −3.325 | 1.002 | 1.00 | 0.00 | PROT |
| ATOM | 488 | CD2 | LEU | 18 | 11.366 | −0.937 | 1.982 | 1.00 | 0.00 | PROT |
| ATOM | 489 | HD21 | LEU | 18 | 10.333 | −0.622 | 2.000 | 1.00 | 0.00 | PROT |
| ATOM | 490 | HD22 | LEU | 18 | 11.662 | −1.146 | 0.964 | 1.00 | 0.00 | PROT |
| ATOM | 491 | HD23 | LEU | 18 | 11.990 | −0.153 | 2.384 | 1.00 | 0.00 | PROT |
| ATOM | 492 | C | LEU | 18 | 9.938 | −0.854 | 6.100 | 1.00 | 0.00 | PROT |
| ATOM | 493 | O | LEU | 18 | 8.806 | −0.446 | 6.270 | 1.00 | 0.00 | PROT |
| ATOM | 494 | N | LYS | 19 | 10.655 | −1.316 | 7.088 | 1.00 | 0.00 | PROT |
| ATOM | 495 | HN | LYS | 19 | 11.577 | −1.613 | 6.930 | 1.00 | 0.00 | PROT |
| ATOM | 496 | CA | LYS | 19 | 10.091 | −1.348 | 8.462 | 1.00 | 0.00 | PROT |
| ATOM | 497 | HA | LYS | 19 | 9.216 | −1.978 | 8.502 | 1.00 | 0.00 | PROT |
| ATOM | 498 | CB | LYS | 19 | 11.213 | −1.922 | 9.333 | 1.00 | 0.00 | PROT |
| ATOM | 499 | HB1 | LYS | 19 | 11.757 | −2.670 | 8.776 | 1.00 | 0.00 | PROT |
| ATOM | 500 | HB2 | LYS | 19 | 11.886 | −1.128 | 9.621 | 1.00 | 0.00 | PROT |
| ATOM | 501 | CG | LYS | 19 | 10.612 | −2.557 | 10.589 | 1.00 | 0.00 | PROT |

TABLE 10-continued

Atomic Structure Coordinates of the P/CAF Bromadomain and HIV-1 Tat Peptide Complex

| ATOM | 502 | HG1 | LYS | 19 | 10.753 | −1.893 | 11.429 | 1.00 | 0.00 | PROT |
|------|-----|------|-----|----|--------|--------|--------|------|------|------|
| ATOM | 503 | HG2 | LYS | 19 | 9.557 | −2.727 | 10.437 | 1.00 | 0.00 | PROT |
| ATOM | 504 | CD | LYS | 19 | 11.310 | −3.889 | 10.870 | 1.00 | 0.00 | PROT |
| ATOM | 505 | HD1 | LYS | 19 | 11.239 | −4.523 | 9.999 | 1.00 | 0.00 | PROT |
| ATOM | 506 | HD2 | LYS | 19 | 10.834 | −4.375 | 11.709 | 1.00 | 0.00 | PROT |
| ATOM | 507 | CE | LYS | 19 | 12.782 | −3.633 | 11.198 | 1.00 | 0.00 | PROT |
| ATOM | 508 | HE1 | LYS | 19 | 13.388 | −3.736 | 10.310 | 1.00 | 0.00 | PROT |
| ATOM | 509 | HE2 | LYS | 19 | 12.906 | −2.649 | 11.627 | 1.00 | 0.00 | PROT |
| ATOM | 510 | NZ | LYS | 19 | 13.139 | −4.681 | 12.195 | 1.00 | 0.00 | PROT |
| ATOM | 511 | HZ1 | LYS | 19 | 12.968 | −5.622 | 11.785 | 1.00 | 0.00 | PROT |
| ATOM | 512 | HZ2 | LYS | 19 | 12.555 | −4.563 | 13.047 | 1.00 | 0.00 | PROT |
| ATOM | 513 | HZ3 | LYS | 19 | 14.144 | −4.591 | 12.448 | 1.00 | 0.00 | PROT |
| ATOM | 514 | C | LYS | 19 | 9.754 | 0.077 | 8.900 | 1.00 | 0.00 | PROT |
| ATOM | 515 | O | LYS | 19 | 8.767 | 0.319 | 9.563 | 1.00 | 0.00 | PROT |
| ATOM | 516 | N | SER | 20 | 10.562 | 1.027 | 8.509 | 1.00 | 0.00 | PROT |
| ATOM | 517 | HN | SER | 20 | 11.350 | 0.806 | 7.969 | 1.00 | 0.00 | PROT |
| ATOM | 518 | CA | SER | 20 | 10.297 | 2.443 | 8.889 | 1.00 | 0.00 | PROT |
| ATOM | 519 | HA | SER | 20 | 10.110 | 2.518 | 9.950 | 1.00 | 0.00 | PROT |
| ATOM | 520 | CB | SER | 20 | 11.579 | 3.192 | 8.521 | 1.00 | 0.00 | PROT |
| ATOM | 521 | HB1 | SER | 20 | 12.433 | 2.559 | 8.710 | 1.00 | 0.00 | PROT |
| ATOM | 522 | HB2 | SER | 20 | 11.552 | 3.458 | 7.475 | 1.00 | 0.00 | PROT |
| ATOM | 523 | OG | SBR | 20 | 11.681 | 4.371 | 9.306 | 1.00 | 0.00 | PROT |
| ATOM | 524 | HG | SER | 20 | 11.878 | 4.111 | 10.209 | 1.00 | 0.00 | PROT |
| ATOM | 525 | C | SER | 20 | 9.110 | 2.996 | 8.098 | 1.00 | 0.00 | PROT |
| ATOM | 526 | O | SER | 20 | 8.119 | 3.413 | 8.663 | 1.00 | 0.00 | PROT |
| ATOM | 527 | N | ILE | 21 | 9.196 | 2.999 | 6.791 | 1.00 | 0.00 | PROT |
| ATOM | 528 | HN | ILE | 21 | 10.002 | 2.654 | 6.353 | 1.00 | 0.00 | PROT |
| ATOM | 529 | CA | ILE | 21 | 8.063 | 3.519 | 5.967 | 1.00 | 0.00 | PROT |
| ATOM | 530 | HA | ILE | 21 | 8.013 | 4.596 | 6.032 | 1.00 | 0.00 | PROT |
| ATOM | 531 | CB | ILE | 21 | 8.387 | 3.085 | 4.531 | 1.00 | 0.00 | PROT |
| ATOM | 532 | HB | ILE | 21 | 8.538 | 2.016 | 4.506 | 1.00 | 0.00 | PROT |
| ATOM | 533 | CG1 | ILE | 21 | 9.660 | 3.792 | 4.046 | 1.00 | 0.00 | PROT |
| ATOM | 534 | HG11 | ILE | 21 | 9.460 | 4.309 | 3.117 | 1.00 | 0.00 | PROT |
| ATOM | 535 | HG12 | ILE | 21 | 9.986 | 4.501 | 4.792 | 1.00 | 0.00 | PROT |
| ATOM | 536 | CG2 | ILE | 21 | 7.225 | 3.453 | 3.608 | 1.00 | 0.00 | PROT |
| ATOM | 537 | H521 | ILE | 21 | 7.601 | 3.616 | 2.609 | 1.00 | 0.00 | PROT |
| ATOM | 538 | HG22 | ILE | 21 | 6.752 | 4.355 | 3.967 | 1.00 | 0.00 | PROT |
| ATOM | 539 | HG23 | ILE | 21 | 6.506 | 2.648 | 3.597 | 1.00 | 0.00 | PROT |
| ATOM | 540 | CD1 | ILE | 21 | 10.757 | 2.758 | 3.810 | 1.00 | 0.00 | PROT |
| ATOM | 541 | HD11 | ILE | 21 | 11.659 | 3.070 | 4.313 | 1.00 | 0.00 | PROT |
| ATOM | 542 | HD12 | ILE | 21 | 10.945 | 2.671 | 2.751 | 1.00 | 0.00 | PROT |
| ATOM | 543 | HD13 | ILE | 21 | 10.438 | 1.806 | 4.198 | 1.00 | 0.00 | PROT |
| ATOM | 544 | C | ILE | 21 | 6.741 | 2.892 | 6.432 | 1.00 | 0.00 | PROT |
| ATOM | 545 | O | ILE | 21 | 5.750 | 3.570 | 6.625 | 1.00 | 0.00 | PROT |
| ATOM | 546 | N | LEU | 22 | 6.733 | 1.604 | 6.645 | 1.00 | 0.00 | PROT |
| ATOM | 547 | HN | LEU | 22 | 7.547 | 1.080 | 6.492 | 1.00 | 0.00 | PROT |
| ATOM | 548 | CA | LEU | 22 | 5.491 | 0.926 | 7.114 | 1.00 | 0.00 | PROT |
| ATOM | 549 | HA | LEU | 22 | 4.666 | 1.150 | 6.456 | 1.00 | 0.00 | PROT |
| ATOM | 550 | CB | LEU | 22 | 5.825 | −0.563 | 7.057 | 1.00 | 0.00 | PROT |
| ATOM | 551 | HB1 | LEU | 22 | 6.531 | −0.737 | 6.263 | 1.00 | 0.00 | PROT |
| ATOM | 552 | HB2 | LEU | 22 | 6.259 | −0.868 | 7.998 | 1.00 | 0.00 | PROT |
| ATOM | 553 | CG | LEU | 22 | 4.547 | −1.368 | 6.800 | 1.00 | 0.00 | PROT |
| ATOM | 554 | HG | LEU | 22 | 3.685 | −0.745 | 6.989 | 1.00 | 0.00 | PROT |
| ATOM | 555 | CD1 | LEU | 22 | 4.513 | −2.582 | 7.731 | 1.00 | 0.00 | PROT |
| ATOM | 556 | HD11 | LEU | 22 | 3.588 | −2.581 | 8.289 | 1.00 | 0.00 | PROT |
| ATOM | 557 | HD12 | LEU | 22 | 5.346 | −2.534 | 8.416 | 1.00 | 0.00 | PROT |
| ATOM | 558 | HD13 | LEU | 22 | 4.580 | −3.486 | 7.145 | 1.00 | 0.00 | PROT |
| ATOM | 559 | CD2 | LEU | 22 | 4.523 | −1.842 | 5.345 | 1.00 | 0.00 | PROT |
| ATOM | 560 | HD21 | LEU | 22 | 4.490 | −0.986 | 4.687 | 1.00 | 0.00 | PROT |
| ATOM | 561 | HD22 | LEU | 22 | 3.649 | −2.457 | 5.180 | 1.00 | 0.00 | PROT |
| ATOM | 562 | HD23 | LEU | 22 | 5.412 | −2.420 | 5.139 | 1.00 | 0.00 | PROT |
| ATOM | 563 | C | LEU | 22 | 5.168 | 1.333 | 8.553 | 1.00 | 0.00 | PROT |
| ATOM | 564 | O | LEU | 22 | 4.035 | 1.607 | 8.897 | 1.00 | 0.00 | PROT |
| ATOM | 565 | N | GLN | 23 | 6.161 | 1.350 | 9.398 | 1.00 | 0.00 | PROT |
| ATOM | 566 | HN | GLN | 23 | 7.058 | 1.116 | 9.092 | 1.00 | 0.00 | PROT |
| ATOM | 567 | CA | GLN | 23 | 5.936 | 1.713 | 10.826 | 1.00 | 0.00 | PROT |
| ATOM | 568 | HA | GLN | 23 | 5.392 | 0.927 | 11.330 | 1.00 | 0.00 | PROT |
| ATOM | 569 | CB | GLN | 23 | 7.344 | 1.846 | 11.416 | 1.00 | 0.00 | PROT |
| ATOM | 570 | HB1 | GLN | 23 | 7.819 | 0.877 | 11.432 | 1.00 | 0.00 | PROT |
| ATOM | 571 | HB2 | GLN | 23 | 7.927 | 2.522 | 10.808 | 1.00 | 0.00 | PROT |
| ATOM | 572 | CG | GLN | 23 | 7.263 | 2.388 | 12.845 | 1.00 | 0.00 | PROT |
| ATOM | 573 | HG1 | GLN | 23 | 6.810 | 3.369 | 12.833 | 1.00 | 0.00 | PROT |
| ATOM | 574 | HG2 | GLN | 23 | 8.257 | 2.455 | 13.258 | 1.00 | 0.00 | PROT |
| ATOM | 575 | CD | GLN | 23 | 6.417 | 1.444 | 13.702 | 1.00 | 0.00 | PROT |
| ATOM | 576 | OE1 | GLN | 23 | 5.329 | 1.793 | 14.116 | 1.00 | 0.00 | PROT |
| ATOM | 577 | NE2 | GLN | 23 | 6.873 | 0.255 | 13.986 | 1.00 | 0.00 | PROT |
| ATOM | 578 | HE21 | GLN | 23 | 6.338 | −0.356 | 14.534 | 1.00 | 0.00 | PROT |

TABLE 10-continued

Atomic Structure Coordinates of the P/CAF Bromadomain and HIV-1 Tat Peptide Complex

| ATOM | 579 | HE22 | GLN | 23 | 7.750 | −0.026 | 13.651 | 1.00 | 0.00 | PROT |
| --- | --- | --- | --- | --- | --- | --- | --- | --- | --- | --- |
| ATOM | 580 | C | GLN | 23 | 5.178 | 3.036 | 10.931 | 1.00 | 0.00 | PROT |
| ATOM | 581 | O | GLN | 23 | 4.301 | 3.191 | 11.759 | 1.00 | 0.00 | PROT |
| ATOM | 582 | N | GLN | 24 | 5.525 | 4.003 | 10.129 | 1.00 | 0.00 | PROT |
| ATOM | 583 | HN | GLN | 24 | 6.221 | 3.856 | 9.449 | 1.00 | 0.00 | PROT |
| ATOM | 584 | CA | GLN | 24 | 4.792 | 5.300 | 10.191 | 1.00 | 0.00 | PROT |
| ATOM | 585 | HA | GLN | 24 | 4.598 | 5.570 | 11.217 | 1.00 | 0.00 | PROT |
| ATOM | 586 | CB | GLN | 24 | 5.719 | 6.328 | 9.539 | 1.00 | 0.00 | PROT |
| ATOM | 587 | HB1 | GLN | 24 | 5.218 | 7.283 | 9.491 | 1.00 | 0.00 | PROT |
| ATOM | 588 | HB2 | GLN | 24 | 6.619 | 6.424 | 10.129 | 1.00 | 0.00 | PROT |
| ATOM | 589 | CG | GLN | 24 | 6.083 | 5.875 | 8.128 | 1.00 | 0.00 | PROT |
| ATOM | 590 | HG1 | GLN | 24 | 6.867 | 5.135 | 8.176 | 1.00 | 0.00 | PROT |
| ATOM | 591 | HG2 | GLN | 24 | 5.215 | 5.451 | 7.649 | 1.00 | 0.00 | PROT |
| ATOM | 592 | CD | GLN | 24 | 6.572 | 7.073 | 7.325 | 1.00 | 0.00 | PROT |
| ATOM | 593 | OE1 | GLN | 24 | 7.084 | 8.025 | 7.880 | 1.00 | 0.00 | PROT |
| ATOM | 594 | NE2 | GLN | 24 | 6.437 | 7.069 | 6.033 | 1.00 | 0.00 | PROT |
| ATOM | 595 | HE21 | GLN | 24 | 6.029 | 6.299 | 5.583 | 1.00 | 0.00 | PROT |
| ATOM | 596 | HE22 | GLN | 24 | 6.754 | 7.828 | 5.512 | 1.00 | 0.00 | PROT |
| ATOM | 597 | C | GLN | 24 | 3.480 | 5.174 | 9.420 | 1.00 | 0.00 | PROT |
| ATOM | 598 | O | GLN | 24 | 2.503 | 5.835 | 9.713 | 1.00 | 0.00 | PROT |
| ATOM | 599 | N | VAL | 25 | 3.443 | 4.288 | 8.465 | 1.00 | 0.00 | PROT |
| ATOM | 600 | HN | VAL | 25 | 4.242 | 3.756 | 8.264 | 1.00 | 0.00 | PROT |
| ATOM | 601 | CA | VAL | 25 | 2.194 | 4.061 | 7.693 | 1.00 | 0.00 | PROT |
| ATOM | 602 | HA | VAL | 25 | 1.782 | 4.996 | 7.354 | 1.00 | 0.00 | PROT |
| ATOM | 603 | CB | VAL | 25 | 2.660 | 3.206 | 6.502 | 1.00 | 0.00 | PROT |
| ATOM | 604 | HB | VAL | 25 | 3.410 | 2.515 | 6.845 | 1.00 | 0.00 | PROT |
| ATOM | 605 | CG1 | VAL | 25 | 3.269 | 4.118 | 5.434 | 1.00 | 0.00 | PROT |
| ATOM | 606 | HG11 | VAL | 25 | 2.533 | 4.320 | 4.671 | 1.00 | 0.00 | PROT |
| ATOM | 607 | HG12 | VAL | 25 | 4.123 | 3.629 | 4.989 | 1.00 | 0.00 | PROT |
| ATOM | 608 | HG13 | VAL | 25 | 3.581 | 5.046 | 5.888 | 1.00 | 0.00 | PROT |
| ATOM | 609 | CG2 | VAL | 25 | 1.497 | 2.420 | 5.892 | 1.00 | 0.00 | PROT |
| ATOM | 610 | HG21 | VAL | 25 | 0.575 | 2.960 | 6.044 | 1.00 | 0.00 | PROT |
| ATOM | 611 | HG22 | VAL | 25 | 1.433 | 1.454 | 6.371 | 1.00 | 0.00 | PROT |
| ATOM | 612 | HG23 | VAL | 25 | 1.669 | 2.286 | 4.834 | 1.00 | 0.00 | PROT |
| ATOM | 613 | C | VAL | 25 | 1.186 | 3.314 | 8.576 | 1.00 | 0.00 | PROT |
| ATOM | 614 | O | VAL | 25 | −0.010 | 3.485 | 8.456 | 1.00 | 0.00 | PROT |
| ATOM | 615 | N | LYS | 26 | 1.671 | 2.491 | 9.462 | 1.00 | 0.00 | PROT |
| ATOM | 616 | HN | LYS | 26 | 2.640 | 2.373 | 9.541 | 1.00 | 0.00 | PROT |
| ATOM | 617 | CA | LYS | 26 | 0.756 | 1.736 | 10.361 | 1.00 | 0.00 | PROT |
| ATOM | 618 | HA | LYS | 26 | −0.017 | 1.246 | 9.788 | 1.00 | 0.00 | PROT |
| ATOM | 619 | CB | LYS | 26 | 1.655 | 0.705 | 11.040 | 1.00 | 0.00 | PROT |
| ATOM | 620 | HB1 | LYS | 26 | 2.377 | 0.337 | 10.326 | 1.00 | 0.00 | PROT |
| ATOM | 621 | HB2 | LYS | 26 | 2.171 | 1.167 | 11.868 | 1.00 | 0.00 | PROT |
| ATOM | 622 | CG | LYS | 26 | 0.804 | −0.457 | 11.555 | 1.00 | 0.00 | PROT |
| ATOM | 623 | HG1 | LYS | 26 | −0.139 | −0.474 | 11.029 | 1.00 | 0.00 | PROT |
| ATOM | 624 | HG2 | LYS | 26 | 1.326 | −1.388 | 11.388 | 1.00 | 0.00 | PROT |
| ATOM | 625 | CD | LYS | 26 | 0.549 | −0.277 | 13.052 | 1.00 | 0.00 | PROT |
| ATOM | 626 | HD1 | LYS | 26 | 0.242 | 0.740 | 13.245 | 1.00 | 0.00 | PROT |
| ATOM | 627 | HD2 | LYS | 26 | 1.456 | −0.488 | 13.600 | 1.00 | 0.00 | PROT |
| ATOM | 628 | CE | LYS | 26 | −0.553 | −1.237 | 13.501 | 1.00 | 0.00 | PROT |
| ATOM | 629 | HE1 | LYS | 26 | −0.614 | −2.080 | 12.828 | 1.00 | 0.00 | PROT |
| ATOM | 630 | HE2 | LYS | 26 | −1.502 | −0.724 | 13.549 | 1.00 | 0.00 | PROT |
| ATOM | 631 | NZ | LYS | 26 | −0.137 | −1.687 | 14.859 | 1.00 | 0.00 | PROT |
| ATOM | 632 | HZ1 | LYS | 26 | 0.022 | −0.858 | 15.466 | 1.00 | 0.00 | PROT |
| ATOM | 633 | HZ2 | LYS | 26 | 0.742 | −2.238 | 14.787 | 1.00 | 0.00 | PROT |
| ATOM | 634 | HZ3 | LYS | 26 | −0.885 | −2.280 | 15.272 | 1.00 | 0.00 | PROT |
| ATOM | 635 | C | LYS | 26 | 0.143 | 2.676 | 11.398 | 1.00 | 0.00 | PROT |
| ATOM | 636 | O | LYS | 26 | −0.940 | 2.446 | 11.898 | 1.00 | 0.00 | PROT |
| ATOM | 637 | N | SER | 27 | 0.830 | 3.736 | 11.724 | 1.00 | 0.00 | PROT |
| ATOM | 638 | HN | SER | 27 | 1.697 | 3.907 | 11.301 | 1.00 | 0.00 | PROT |
| ATOM | 639 | CA | SER | 27 | 0.283 | 4.701 | 12.717 | 1.00 | 0.00 | PROT |
| ATOM | 640 | HA | SER | 27 | −0.464 | 4.223 | 13.332 | 1.00 | 0.00 | PROT |
| ATOM | 641 | CB | SER | 27 | 1.489 | 5.110 | 13.566 | 1.00 | 0.00 | PROT |
| ATOM | 642 | HB1 | SER | 27 | 1.963 | 4.226 | 13.966 | 1.00 | 0.00 | PROT |
| ATOM | 643 | HB2 | SER | 27 | 1.160 | 5.741 | 14.378 | 1.00 | 0.00 | PROT |
| ATOM | 644 | OG | SER | 27 | 2.417 | 5.821 | 12.760 | 1.00 | 0.00 | PROT |
| ATOM | 645 | HG | SER | 27 | 2.946 | 5.180 | 12.280 | 1.00 | 0.00 | PROT |
| ATOM | 646 | C | SER | 27 | −0.311 | 5.923 | 12.007 | 1.00 | 0.00 | PROT |
| ATOM | 647 | O | SER | 27 | −0.670 | 6.900 | 12.634 | 1.00 | 0.00 | PROT |
| ATOM | 648 | N | HIS | 28 | −0.424 | 5.878 | 10.704 | 1.00 | 0.00 | PROT |
| ATOM | 649 | HN | HIS | 28 | −0.133 | 5.083 | 10.211 | 1.00 | 0.00 | PROT |
| ATOM | 650 | CA | HIS | 28 | −1.000 | 7.037 | 9.966 | 1.00 | 0.00 | PROT |
| ATOM | 651 | HA | HIS | 28 | −0.455 | 7.939 | 10.199 | 1.00 | 0.00 | PROT |
| ATOM | 652 | CB | HIS | 28 | −0.834 | 6.681 | 8.487 | 1.00 | 0.00 | PROT |
| ATOM | 653 | HB1 | HIS | 28 | −1.806 | 6.617 | 8.022 | 1.00 | 0.00 | PROT |
| ATOM | 654 | HB2 | HIS | 28 | −0.331 | 5.730 | 8.398 | 1.00 | 0.00 | PROT |
| ATOM | 655 | CG | HIS | 28 | −0.019 | 7.744 | 7.804 | 1.00 | 0.00 | PROT |

TABLE 10-continued

Atomic Structure Coordinates of the P/CAF Bromadomain and HIV-1 Tat Peptide Complex

| ATOM | 656 | ND1 | HIS | 28 | −0.567 | 8.954 | 7.408 | 1.00 | 0.00 | PROT |
|---|---|---|---|---|---|---|---|---|---|---|
| ATOM | 657 | HD1 | HIS | 28 | −1.499 | 9.233 | 7.523 | 1.00 | 0.00 | PROT |
| ATOM | 658 | CD2 | HIS | 28 | 1.304 | 7.795 | 7.443 | 1.00 | 0.00 | PROT |
| ATOM | 659 | HD2 | HIS | 28 | 2.025 | 7.008 | 7.608 | 1.00 | 0.00 | PROT |
| ATOM | 660 | CE1 | HIS | 28 | 0.415 | 9.675 | 6.836 | 1.00 | 0.00 | PROT |
| ATOM | 661 | HE1 | HIS | 28 | 0.280 | 10.666 | 6.430 | 1.00 | 0.00 | PROT |
| ATOM | 662 | NE2 | HIS | 28 | 1.576 | 9.015 | 6.831 | 1.00 | 0.00 | PROT |
| ATOM | 663 | C | HIS | 28 | −2.481 | 7.202 | 10.310 | 1.00 | 0.00 | PROT |
| ATOM | 664 | O | HIS | 28 | −3.165 | 6.249 | 10.625 | 1.00 | 0.00 | PROT |
| ATOM | 665 | N | GLN | 29 | −2.981 | 8.407 | 10.260 | 1.00 | 0.00 | PROT |
| ATOM | 666 | HN | GLN | 29 | −2.412 | 9.162 | 10.004 | 1.00 | 0.00 | PROT |
| ATOM | 667 | CA | GLN | 29 | −4.418 | 8.632 | 10.585 | 1.00 | 0.00 | PROT |
| ATOM | 668 | HA | GLN | 29 | −4.700 | 8.058 | 11.444 | 1.00 | 0.00 | PROT |
| ATOM | 669 | CB | GLN | 29 | −4.516 | 10.116 | 10.905 | 1.00 | 0.00 | PROT |
| ATOM | 670 | HB1 | GLN | 29 | −4.258 | 10.678 | 10.031 | 1.00 | 0.00 | PROT |
| ATOM | 671 | HB2 | GLN | 29 | −3.835 | 10.360 | 11.707 | 1.00 | 0.00 | PROT |
| ATOM | 672 | CG | GLN | 29 | −5.947 | 10.453 | 11.328 | 1.00 | 0.00 | PROT |
| ATOM | 673 | HG1 | GLN | 29 | −6.597 | 10.408 | 10.466 | 1.00 | 0.00 | PROT |
| ATOM | 674 | HG2 | GLN | 29 | −6.281 | 9.741 | 12.068 | 1.00 | 0.00 | PROT |
| ATOM | 675 | CD | GLN | 29 | −5.985 | 11.862 | 11.922 | 1.00 | 0.00 | PROT |
| ATOM | 676 | OE1 | GLN | 29 | −5.747 | 12.044 | 13.099 | 1.00 | 0.00 | PROT |
| ATOM | 677 | NE2 | GLN | 29 | −6.276 | 12.874 | 11.151 | 1.00 | 0.00 | PROT |
| ATOM | 678 | HE21 | GLN | 29 | −6.303 | 13.780 | 11.521 | 1.00 | 0.00 | PROT |
| ATOM | 679 | HE22 | GLN | 29 | −6.468 | 12.726 | 10.201 | 1.00 | 0.00 | PROT |
| ATOM | 680 | C | GLN | 29 | −5.316 | 8.283 | 9.391 | 1.00 | 0.00 | PROT |
| ATOM | 681 | O | GLN | 29 | −6.525 | 8.377 | 9.471 | 1.00 | 0.00 | PROT |
| ATOM | 682 | N | SER | 30 | −4.744 | 7.887 | 8.283 | 1.00 | 0.00 | PROT |
| ATOM | 683 | HN | SER | 30 | −3.769 | 7.818 | 8.229 | 1.00 | 0.00 | PROT |
| ATOM | 684 | CA | SER | 30 | −5.582 | 7.546 | 7.098 | 1.00 | 0.00 | PROT |
| ATOM | 685 | HA | SER | 30 | −6.629 | 7.642 | 7.341 | 1.00 | 0.00 | PROT |
| ATOM | 686 | CB | SER | 30 | −5.189 | 8.573 | 6.034 | 1.00 | 0.00 | PROT |
| ATOM | 687 | HB1 | SER | 30 | −4.403 | 9.206 | 6.415 | 1.00 | 0.00 | PROT |
| ATOM | 688 | HB2 | SER | 30 | −4.839 | 8.058 | 5.150 | 1.00 | 0.00 | PROT |
| ATOM | 689 | OG | SER | 30 | −6.318 | 9.367 | 5.703 | 1.00 | 0.00 | PROT |
| ATOM | 690 | HG | SER | 30 | −6.360 | 10.096 | 6.327 | 1.00 | 0.00 | PROT |
| ATOM | 691 | C | SER | 30 | −5.278 | 6.129 | 6.597 | 1.00 | 0.00 | PROT |
| ATOM | 692 | O | SER | 30 | −5.795 | 5.704 | 5.587 | 1.00 | 0.00 | PROT |
| ATOM | 693 | N | ALA | 31 | −4.419 | 5.409 | 7.268 | 1.00 | 0.00 | PROT |
| ATOM | 694 | HN | ALA | 31 | −4.003 | 5.767 | 8.078 | 1.00 | 0.00 | PROT |
| ATOM | 695 | CA | ALA | 31 | −4.086 | 4.026 | 6.813 | 1.00 | 0.00 | PROT |
| ATOM | 696 | HA | ALA | 31 | −3.997 | 4.001 | 5.738 | 1.00 | 0.00 | PROT |
| ATOM | 697 | CB | ALA | 31 | −2.732 | 3.731 | 7.461 | 1.00 | 0.00 | PROT |
| ATOM | 698 | HB1 | ALA | 31 | −2.845 | 3.702 | 8.534 | 1.00 | 0.00 | PROT |
| ATOM | 699 | HB2 | ALA | 31 | −2.031 | 4.508 | 7.191 | 1.00 | 0.00 | PROT |
| ATOM | 700 | HB3 | ALA | 31 | −2.366 | 2.778 | 7.110 | 1.00 | 0.00 | PROT |
| ATOM | 701 | C | ALA | 31 | −5.139 | 3.010 | 7.282 | 1.00 | 0.00 | PROT |
| ATOM | 702 | O | ALA | 31 | −4.954 | 1.816 | 7.157 | 1.00 | 0.00 | PROT |
| ATOM | 703 | M | TRP | 32 | −6.237 | 3.467 | 7.823 | 1.00 | 0.00 | PROT |
| ATOM | 704 | HN | TRP | 32 | −6.367 | 4.430 | 7.927 | 1.00 | 0.00 | PROT |
| ATOM | 705 | CA | TRP | 32 | −7.281 | 2.522 | 8.315 | 1.00 | 0.00 | PROT |
| ATOM | 706 | HA | TRP | 32 | −6.883 | 1.906 | 9.106 | 1.00 | 0.00 | PROT |
| ATOM | 707 | CB | TRP | 32 | −8.393 | 3.414 | 8.864 | 1.00 | 0.00 | PROT |
| ATOM | 708 | HB1 | TRP | 32 | −8.727 | 4.078 | 8.086 | 1.00 | 0.00 | PROT |
| ATOM | 709 | HB2 | TRP | 32 | −9.220 | 2.795 | 9.180 | 1.00 | 0.00 | PROT |
| ATOM | 710 | CG | TRP | 32 | −7.912 | 4.226 | 10.032 | 1.00 | 0.00 | PROT |
| ATOM | 711 | CD1 | TRP | 32 | −8.668 | 5.149 | 10.671 | 1.00 | 0.00 | PROT |
| ATOM | 712 | HD1 | TRP | 32 | −9.687 | 5.406 | 10.420 | 1.00 | 0.00 | PROT |
| ATOM | 713 | CD2 | TRP | 32 | −6.614 | 4.221 | 10.716 | 1.00 | 0.00 | PROT |
| ATOM | 714 | NE1 | TRP | 32 | −7.930 | 5.710 | 11.694 | 1.00 | 0.00 | PROT |
| ATOM | 715 | HE1 | TRP | 32 | −8.250 | 6.405 | 12.306 | 1.00 | 0.00 | PROT |
| ATOM | 716 | CE2 | TRP | 32 | −6.661 | 5.175 | 11.765 | 1.00 | 0.00 | PROT |
| ATOM | 717 | CE3 | TRP | 32 | −5.413 | 3.499 | 10.541 | 1.00 | 0.00 | PROT |
| ATOM | 718 | HE3 | TRP | 32 | −5.332 | 2.764 | 9.759 | 1.00 | 0.00 | PROT |
| ATOM | 719 | CZ2 | TRP | 32 | −5.568 | 5.403 | 12.601 | 1.00 | 0.00 | PROT |
| ATOM | 720 | HE2 | TRP | 32 | −5.633 | 6.136 | 13.392 | 1.00 | 0.00 | PROT |
| ATOM | 721 | CZ3 | TRP | 32 | −4.313 | 3.730 | 11.384 | 1.00 | 0.00 | PROT |
| ATOM | 722 | HZ3 | TRP | 32 | −3.400 | 3.171 | 11.240 | 1.00 | 0.00 | PROT |
| ATOM | 723 | CH2 | TRP | 32 | −4.391 | 4.679 | 12.411 | 1.00 | 0.00 | PROT |
| ATOM | 724 | HH2 | TRP | 32 | −3.541 | 4.850 | 13.055 | 1.00 | 0.00 | PROT |
| ATOM | 725 | C | TRP | 32 | −7.842 | 1.626 | 7.192 | 1.00 | 0.00 | PROT |
| ATOM | 726 | O | TRP | 32 | −8.016 | 0.443 | 7.402 | 1.00 | 0.00 | PROT |
| ATOM | 727 | N | PRO | 33 | −8.174 | 2.206 | 6.054 | 1.00 | 0.00 | PROT |
| ATOM | 728 | CA | PRO | 33 | −8.773 | 1.397 | 4.960 | 1.00 | 0.00 | PROT |
| ATOM | 729 | HA | PRO | 33 | −9.657 | 0.885 | 5.310 | 1.00 | 0.00 | PROT |
| ATOM | 730 | CB | PRO | 33 | −9.143 | 2.430 | 3.895 | 1.00 | 0.00 | PROT |
| ATOM | 731 | HB1 | PRO | 33 | −8.932 | 2.044 | 2.909 | 1.00 | 0.00 | PROT |
| ATOM | 732 | HB2 | PRO | 33 | −10.186 | 2.700 | 3.979 | 1.00 | 0.00 | PROT |

TABLE 10-continued

Atomic Structure Coordinates of the P/CAF Bromadomain and HIV-1 Tat Peptide Complex

| ATOM | 733 | CG  | PRO | 33 | −8.277  | 3.611  | 4.185  | 1.00 | 0.00 | PROT |
|------|-----|-----|-----|----|---------|--------|--------|------|------|------|
| ATOM | 734 | HG1 | PRO | 33 | −7.336  | 3.510  | 3.665  | 1.00 | 0.00 | PROT |
| ATOM | 735 | HG2 | PRO | 33 | −8.772  | 4.520  | 3.876  | 1.00 | 0.00 | PROT |
| ATOM | 736 | CD  | PRO | 33 | −8.041  | 3.622  | 5.672  | 1.00 | 0.00 | PROT |
| ATOM | 737 | HD2 | PRO | 33 | −7.054  | 3.984  | 5.879  | 1.00 | 0.00 | PROT |
| ATOM | 738 | HD1 | PRO | 33 | −8.785  | 4.225  | 6.169  | 1.00 | 0.00 | PROT |
| ATOM | 739 | C   | PRO | 33 | −7.765  | 0.399  | 4.396  | 1.00 | 0.00 | PROT |
| ATOM | 740 | O   | PRO | 33 | −8.130  | −0.579 | 3.773  | 1.00 | 0.00 | PROT |
| ATOM | 741 | N   | PHE | 34 | −6.500  | 0.636  | 4.593  | 1.00 | 0.00 | PROT |
| ATOM | 742 | HN  | PHE | 34 | −6.219  | 1.436  | 5.087  | 1.00 | 0.00 | PROT |
| ATOM | 743 | CA  | PHE | 34 | −5.482  | −0.297 | 4.035  | 1.00 | 0.00 | PROT |
| ATOM | 744 | HA  | PHE | 34 | −5.881  | −0.806 | 3.173  | 1.00 | 0.00 | PROT |
| ATOM | 745 | CB  | PHE | 34 | −4.299  | 0.590  | 3.620  | 1.00 | 0.00 | PROT |
| ATOM | 746 | HB1 | PHE | 34 | −3.605  | 0.003  | 3.038  | 1.00 | 0.00 | PROT |
| ATOM | 747 | HB2 | PHE | 34 | −3.800  | 0.950  | 4.508  | 1.00 | 0.00 | PROT |
| ATOM | 748 | CG  | PHE | 34 | −4.762  | 1.780  | 2.792  | 1.00 | 0.00 | PROT |
| ATOM | 749 | CD1 | PHE | 34 | −3.932  | 2.898  | 2.691  | 1.00 | 0.00 | PROT |
| ATOM | 750 | HD1 | PHE | 34 | −2.979  | 2.902  | 3.193  | 1.00 | 0.00 | PROT |
| ATOM | 751 | CD2 | PHE | 34 | −5.997  | 1.767  | 2.122  | 1.00 | 0.00 | PROT |
| ATOM | 752 | HD2 | PHE | 34 | −6.645  | 0.908  | 2.202  | 1.00 | 0.00 | PROT |
| ATOM | 753 | CE1 | PHE | 34 | −4.330  | 4.006  | 1.935  | 1.00 | 0.00 | PROT |
| ATOM | 754 | HE1 | PHE | 34 | −3.684  | 4.869  | 1.860  | 1.00 | 0.00 | PROT |
| ATOM | 755 | CE2 | PHE | 34 | −6.400  | 2.879  | 1.373  | 1.00 | 0.00 | PROT |
| ATOM | 756 | HE2 | PHE | 34 | −7.352  | 2.872  | 0.865  | 1.00 | 0.00 | PROT |
| ATOM | 757 | CZ  | PHE | 34 | −5.564  | 3.997  | 1.277  | 1.00 | 0.00 | PROT |
| ATOM | 758 | HZ  | PHE | 34 | −5.871  | 4.852  | 0.695  | 1.00 | 0.00 | PROT |
| ATOM | 759 | C   | PHE | 34 | −5.034  | −1.314 | 5.090  | 1.00 | 0.00 | PROT |
| ATOM | 760 | O   | PHE | 34 | −4.145  | −2.105 | 4.855  | 1.00 | 0.00 | PROT |
| ATOM | 761 | N   | MET | 35 | −5.639  | −1.309 | 6.247  | 1.00 | 0.00 | PROT |
| ATOM | 762 | HN  | MET | 35 | −6.354  | −0.665 | 6.429  | 1.00 | 0.00 | PROT |
| ATOM | 763 | CA  | MET | 35 | −5.227  | −2.279 | 7.296  | 1.00 | 0.00 | PROT |
| ATOM | 764 | HA  | MET | 35 | −4.192  | −2.555 | 7.165  | 1.00 | 0.00 | PROT |
| ATOM | 765 | CB  | MET | 35 | −5.411  | −1.530 | 8.614  | 1.00 | 0.00 | PROT |
| ATOM | 766 | HB1 | MET | 35 | −5.537  | −2.243 | 9.413  | 1.00 | 0.00 | PROT |
| ATOM | 767 | HB2 | MET | 35 | −6.285  | −0.894 | 8.552  | 1.00 | 0.00 | PROT |
| ATOM | 768 | CG  | MET | 35 | −4.174  | −0.672 | 8.886  | 1.00 | 0.00 | PROT |
| ATOM | 769 | HG1 | MET | 35 | −4.409  | 0.366  | 8.703  | 1.00 | 0.00 | PROT |
| ATOM | 770 | HG2 | MET | 35 | −3.372  | −0.980 | 8.231  | 1.00 | 0.00 | PROT |
| ATOM | 771 | SD  | MET | 35 | −3.659  | −0.879 | 10.608 | 1.00 | 0.00 | PROT |
| ATOM | 772 | CE  | MET | 35 | −3.019  | 0.795  | 10.851 | 1.00 | 0.00 | PROT |
| ATOM | 773 | HE1 | MET | 35 | −1.991  | 0.838  | 10.523 | 1.00 | 0.00 | PROT |
| ATOM | 774 | HE2 | MET | 35 | −3.075  | 1.054  | 11.898 | 1.00 | 0.00 | PROT |
| ATOM | 775 | HE3 | MET | 35 | −3.610  | 1.492  | 10.275 | 1.00 | 0.00 | PROT |
| ATOM | 776 | C   | MET | 35 | −6.115  | −3.525 | 7.256  | 1.00 | 0.00 | PROT |
| ATOM | 777 | O   | MET | 35 | −6.232  | −4.248 | 8.224  | 1.00 | 0.00 | PROT |
| ATOM | 778 | N   | GLU | 36 | −6.730  | −3.787 | 6.136  | 1.00 | 0.00 | PROT |
| ATOM | 779 | HN  | GLU | 36 | −6.614  | −3.195 | 5.364  | 1.00 | 0.00 | PROT |
| ATOM | 780 | CA  | GLU | 36 | −7.593  | −4.997 | 6.021  | 1.00 | 0.00 | PROT |
| ATOM | 781 | HA  | GLU | 36 | −7.233  | −5.781 | 6.670  | 1.00 | 0.00 | PROT |
| ATOM | 782 | CB  | GLU | 36 | −8.982  | −4.532 | 6.464  | 1.00 | 0.00 | PROT |
| ATOM | 783 | HB1 | GLU | 36 | −9.735  | −5.135 | 5.977  | 1.00 | 0.00 | PROT |
| ATOM | 784 | HB2 | GLU | 36 | −9.119  | −3.497 | 6.190  | 1.00 | 0.00 | PROT |
| ATOM | 785 | CG  | GLU | 36 | −9.113  | −4.680 | 7.981  | 1.00 | 0.00 | PROT |
| ATOM | 786 | HG1 | GLU | 36 | −8.466  | −3.966 | 8.470  | 1.00 | 0.00 | PROT |
| ATOM | 787 | HG2 | GLU | 36 | −8.830  | −5.681 | 8.272  | 1.00 | 0.00 | PROT |
| ATOM | 788 | CD  | GLU | 36 | −10.564 | −4.419 | 8.395  | 1.00 | 0.00 | PROT |
| ATOM | 789 | OE1 | GLU | 36 | −11.272 | −3.785 | 7.630  | 1.00 | 0.00 | PROT |
| ATOM | 790 | OE2 | GLU | 36 | −10.942 | −4.859 | 9.468  | 1.00 | 0.00 | PROT |
| ATOM | 791 | C   | GLU | 36 | −7.629  | −5.475 | 4.566  | 1.00 | 0.00 | PROT |
| ATOM | 792 | O   | GLU | 36 | −7.127  | −4.802 | 3.688  | 1.00 | 0.00 | PROT |
| ATOM | 793 | N   | PRO | 37 | −8.213  | −6.628 | 4.349  | 1.00 | 0.00 | PROT |
| ATOM | 794 | CA  | PRO | 37 | −8.314  | −7.163 | 2.972  | 1.00 | 0.00 | PROT |
| ATOM | 795 | HA  | PRO | 37 | −7.336  | −7.428 | 2.595  | 1.00 | 0.00 | PROT |
| ATOM | 796 | CB  | PRO | 37 | −9.191  | −8.406 | 3.119  | 1.00 | 0.00 | PROT |
| ATOM | 797 | HB1 | PRO | 37 | −10.200 | −8.185 | 2.833  | 1.00 | 0.00 | PROT |
| ATOM | 798 | HB2 | PRO | 37 | −8.800  | −9.214 | 2.519  | 1.00 | 0.00 | PROT |
| ATOM | 799 | CG  | PRO | 37 | −9.144  | −8.766 | 4.566  | 1.00 | 0.00 | PROT |
| ATOM | 800 | HG1 | PRO | 37 | −10.095 | −9.175 | 4.874  | 1.00 | 0.00 | PROT |
| ATOM | 801 | HG2 | PRO | 37 | −8.365  | −9.486 | 4.732  | 1.00 | 0.00 | PROT |
| ATOM | 802 | CD  | PRO | 37 | −8.855  | −7.505 | 5.336  | 1.00 | 0.00 | PROT |
| ATOM | 803 | HD2 | PRO | 37 | −9.773  | −7.063 | 5.695  | 1.00 | 0.00 | PROT |
| ATOM | 804 | HD1 | PRO | 37 | −8.184  | −7.706 | 6.157  | 1.00 | 0.00 | PROT |
| ATOM | 805 | C   | PRO | 37 | −8.984  | −6.131 | 2.062  | 1.00 | 0.00 | PROT |
| ATOM | 806 | O   | PRO | 37 | −9.281  | −5.030 | 2.483  | 1.00 | 0.00 | PROT |
| ATOM | 807 | N   | VAL | 38 | −9.233  | −6.467 | 0.825  | 1.00 | 0.00 | PROT |
| ATOM | 808 | HN  | VAL | 38 | −8.979  | −7.353 | 0.493  | 1.00 | 0.00 | PROT |
| ATOM | 809 | CA  | VAL | 38 | −9.871  | −5.470 | −0.087 | 1.00 | 0.00 | PROT |

TABLE 10-continued

Atomic Structure Coordinates of the P/CAF Bromadomain and HIV-1 Tat Peptide Complex

| ATOM | 810 | HA | VAL | 38 | −9.183 | −4.656 | −0.263 | 1.00 | 0.00 | PROT |
|---|---|---|---|---|---|---|---|---|---|---|
| ATOM | 811 | CB | VAL | 38 | −10.158 | −6.192 | −1.422 | 1.00 | 0.00 | PROT |
| ATOM | 812 | HB | VAL | 38 | −10.891 | −5.625 | −1.977 | 1.00 | 0.00 | PROT |
| ATOM | 813 | CG1 | VAL | 38 | −8.866 | −6.273 | −2.237 | 1.00 | 0.00 | PROT |
| ATOM | 814 | HG11 | VAL | 38 | −8.966 | −7.036 | −2.995 | 1.00 | 0.00 | PROT |
| ATOM | 815 | HG12 | VAL | 38 | −8.043 | −6.520 | −1.583 | 1.00 | 0.00 | PROT |
| ATOM | 816 | HG13 | VAL | 38 | −8.678 | −5.319 | −2.708 | 1.00 | 0.00 | PROT |
| ATOM | 817 | CG2 | VAL | 38 | −10.695 | −7.609 | −1.190 | 1.00 | 0.00 | PROT |
| ATOM | 818 | HG21 | VAL | 38 | −10.845 | −7.770 | −0.134 | 1.00 | 0.00 | PROT |
| ATOM | 819 | HG22 | VAL | 38 | −9.985 | −8.330 | −1.566 | 1.00 | 0.00 | PROT |
| ATOM | 820 | HG23 | VAL | 38 | −11.639 | −7.726 | −1.710 | 1.00 | 0.00 | PROT |
| ATOM | 821 | C | VAL | 38 | −11.162 | −4.918 | 0.535 | 1.00 | 0.00 | PROT |
| ATOM | 822 | O | VAL | 38 | −11.590 | −3.828 | 0.210 | 1.00 | 0.00 | PROT |
| ATOM | 823 | N | LYS | 39 | −11.757 | −5.619 | 1.469 | 1.00 | 0.00 | PROT |
| ATOM | 824 | HN | LYS | 39 | −11.411 | −6.498 | 1.724 | 1.00 | 0.00 | PROT |
| ATOM | 825 | CA | LYS | 39 | −13.000 | −5.090 | 2.103 | 1.00 | 0.00 | PROT |
| ATOM | 826 | HA | LYS | 39 | −12.863 | −4.057 | 2.369 | 1.00 | 0.00 | PROT |
| ATOM | 827 | CB | LYS | 39 | −14.075 | −5.196 | 1.016 | 1.00 | 0.00 | PROT |
| ATOM | 828 | HB1 | LYS | 39 | −14.955 | −4.655 | 1.332 | 1.00 | 0.00 | PROT |
| ATOM | 829 | HB2 | LYS | 39 | −13.700 | −4.763 | 0.101 | 1.00 | 0.00 | PROT |
| ATOM | 830 | CG | LYS | 39 | −14.447 | −6.659 | 0.766 | 1.00 | 0.00 | PROT |
| ATOM | 831 | HG1 | LYS | 39 | −14.628 | −7.151 | 1.697 | 1.00 | 0.00 | PROT |
| ATOM | 832 | HG2 | LYS | 39 | −15.335 | −6.693 | 0.179 | 1.00 | 0.00 | PROT |
| ATOM | 833 | CD | LYS | 39 | −13.310 | −7.365 | 0.025 | 1.00 | 0.00 | PROT |
| ATOM | 834 | HD1 | LYS | 39 | −12.552 | −7.659 | 0.726 | 1.00 | 0.00 | PROT |
| ATOM | 835 | HD2 | LYS | 39 | −12.882 | −6.684 | −0.693 | 1.00 | 0.00 | PROT |
| ATOM | 836 | CE | LYS | 39 | −13.828 | −8.613 | −0.695 | 1.00 | 0.00 | PROT |
| ATOM | 837 | HE1 | LYS | 39 | −14.523 | −8.339 | −1.469 | 1.00 | 0.00 | PROT |
| ATOM | 838 | HE2 | LYS | 39 | −13.003 | −9.169 | −1.115 | 1.00 | 0.00 | PROT |
| ATOM | 839 | NZ | LYS | 39 | −14.507 | −9.419 | 0.361 | 1.00 | 0.00 | PROT |
| ATOM | 840 | HZ1 | LYS | 39 | −13.849 | −9.581 | 1.149 | 1.00 | 0.00 | PROT |
| ATOM | 841 | HZ2 | LYS | 39 | −14.800 | −10.334 | −0.038 | 1.00 | 0.00 | PROT |
| ATOM | 842 | HZ3 | LYS | 39 | −15.344 | −8.909 | 0.707 | 1.00 | 0.00 | PROT |
| ATOM | 843 | C | LYS | 39 | −13.390 | −5.900 | 3.351 | 1.00 | 0.00 | PROT |
| ATOM | 844 | O | LYS | 39 | −13.908 | −5.363 | 4.310 | 1.00 | 0.00 | PROT |
| ATOM | 845 | N | ARG | 40 | −13.151 | −7.185 | 3.347 | 1.00 | 0.00 | PROT |
| ATOM | 846 | HN | ARG | 40 | −12.772 | −7.606 | 2.556 | 1.00 | 0.00 | PROT |
| ATOM | 847 | CA | ARG | 40 | −13.565 | −8.028 | 4.500 | 1.00 | 0.00 | PROT |
| ATOM | 848 | HA | ARG | 40 | −13.332 | −9.066 | 4.312 | 1.00 | 0.00 | PROT |
| ATOM | 849 | CB | ARG | 40 | −12.758 | −7.508 | 5.693 | 1.00 | 0.00 | PROT |
| ATOM | 850 | HB1 | ARG | 40 | −13.260 | −6.653 | 6.122 | 1.00 | 0.00 | PROT |
| ATOM | 851 | HB2 | ARG | 40 | −11.772 | −7.217 | 5.361 | 1.00 | 0.00 | PROT |
| ATOM | 852 | CG | ARG | 40 | −12.637 | −8.611 | 6.747 | 1.00 | 0.00 | PROT |
| ATOM | 853 | HG1 | ARG | 40 | −13.019 | −9.537 | 6.343 | 1.00 | 0.00 | PROT |
| ATOM | 854 | HG2 | ARG | 40 | −11.600 | −8.737 | 7.018 | 1.00 | 0.00 | PROT |
| ATOM | 855 | CD | ARG | 40 | −13.445 | −8.223 | 7.986 | 1.00 | 0.00 | PROT |
| ATOM | 856 | HD1 | ARG | 40 | −14.028 | −9.063 | 8.333 | 1.00 | 0.00 | PROT |
| ATOM | 857 | HD2 | ARG | 40 | −14.088 | −7.382 | 7.769 | 1.00 | 0.00 | PROT |
| ATOM | 858 | NE | ARG | 40 | −12.422 | −7.845 | 9.006 | 1.00 | 0.00 | PROT |
| ATOM | 859 | HE | ARG | 40 | −11.471 | −7.888 | 8.775 | 1.00 | 0.00 | PROT |
| ATOM | 860 | CZ | ARG | 40 | −12.780 | −7.455 | 10.208 | 1.00 | 0.00 | PROT |
| ATOM | 861 | NH1 | ARG | 40 | −14.044 | −7.386 | 10.547 | 1.00 | 0.00 | PROT |
| ATOM | 862 | HH11 | ARG | 40 | −14.758 | −7.631 | 9.893 | 1.00 | 0.00 | PROT |
| ATOM | 863 | HH12 | ARG | 40 | −14.296 | −7.087 | 11.468 | 1.00 | 0.00 | PROT |
| ATOM | 864 | NH2 | ARG | 40 | −11.863 | −7.131 | 11.077 | 1.00 | 0.00 | PROT |
| ATOM | 865 | HH21 | ARG | 40 | −12.127 | −6.833 | 11.994 | 1.00 | 0.00 | PROT |
| ATOM | 866 | HH22 | ARG | 40 | −10.896 | −7.180 | 10.826 | 1.00 | 0.00 | PROT |
| ATOM | 867 | C | ARG | 40 | −15.063 | −7.853 | 4.746 | 1.00 | 0.00 | PROT |
| ATOM | 868 | O | ARG | 40 | −15.485 | −7.529 | 5.838 | 1.00 | 0.00 | PROT |
| ATOM | 869 | N | THR | 41 | −15.871 | −8.020 | 3.725 | 1.00 | 0.00 | PROT |
| ATOM | 870 | HN | THR | 41 | −15.517 | −8.295 | 2.859 | 1.00 | 0.00 | PROT |
| ATOM | 871 | CA | THR | 41 | −17.340 | −7.853 | 3.910 | 1.00 | 0.00 | PROT |
| ATOM | 872 | HA | THR | 41 | −17.677 | −8.507 | 4.691 | 1.00 | 0.00 | PROT |
| ATOM | 873 | CB | THR | 41 | −17.546 | −6.389 | 4.330 | 1.00 | 0.00 | PROT |
| ATOM | 874 | HB | THR | 41 | −17.144 | −6.238 | 5.319 | 1.00 | 0.00 | PROT |
| ATOM | 875 | OG1 | THR | 41 | −18.937 | −6.098 | 4.341 | 1.00 | 0.00 | PROT |
| ATOM | 876 | HG1 | THR | 41 | −19.232 | −6.094 | 5.254 | 1.00 | 0.00 | PROT |
| ATOM | 877 | CG2 | THR | 41 | −16.843 | −5.449 | 3.346 | 1.00 | 0.00 | PROT |
| ATOM | 878 | HG21 | THR | 41 | −15.874 | −5.849 | 3.089 | 1.00 | 0.00 | PROT |
| ATOM | 879 | HG22 | THR | 41 | −16.720 | −4.479 | 3.803 | 1.00 | 0.00 | PROT |
| ATOM | 880 | HG23 | THR | 41 | −17.440 | −5.352 | 2.452 | 1.00 | 0.00 | PROT |
| ATOM | 881 | C | THR | 41 | −18.125 | −8.152 | 2.628 | 1.00 | 0.00 | PROT |
| ATOM | 882 | O | THR | 41 | −19.098 | −8.879 | 2.668 | 1.00 | 0.00 | PROT |
| ATOM | 883 | N | GLU | 42 | −17.776 | −7.565 | 1.504 | 1.00 | 0.00 | PROT |
| ATOM | 884 | HN | GLU | 42 | −16.992 | −6.973 | 1.470 | 1.00 | 0.00 | PROT |
| ATOM | 885 | CA | GLU | 42 | −18.593 | −7.827 | 0.273 | 1.00 | 0.00 | PROT |
| ATOM | 886 | HA | GLU | 42 | −18.698 | −8.890 | 0.117 | 1.00 | 0.00 | PROT |

TABLE 10-continued

Atomic Structure Coordinates of the P/CAF Bromadomain and HIV-1 Tat Peptide Complex

| ATOM | 887 | CB  | GLU | 42 | −19.956 | −7.203  | 0.577   | 1.00 | 0.00 | PROT |
| ATOM | 888 | HB1 | GLU | 42 | −20.408 | −7.715  | 1.407   | 1.00 | 0.00 | PROT |
| ATOM | 889 | HB2 | GLU | 42 | −20.594 | −7.291  | −0.291  | 1.00 | 0.00 | PROT |
| ATOM | 890 | CG  | GLU | 42 | −19.773 | −5.726  | 0.928   | 1.00 | 0.00 | PROT |
| ATOM | 891 | HG1 | GLU | 42 | −20.130 | −5.547  | 1.931   | 1.00 | 0.00 | PROT |
| ATOM | 892 | HG2 | GLU | 42 | −18.725 | −5.469  | 0.868   | 1.00 | 0.00 | PROT |
| ATOM | 893 | CD  | GLU | 42 | −20.566 | −4.865  | −0.057  | 1.00 | 0.00 | PROT |
| ATOM | 894 | OE1 | GLU | 42 | −19.983 | −4.433  | −1.038  | 1.00 | 0.00 | PROT |
| ATOM | 895 | OE2 | GLU | 42 | −21.743 | −4.656  | 0.185   | 1.00 | 0.00 | PROT |
| ATOM | 896 | C   | GLU | 42 | −18.019 | −7.165  | −0.981  | 1.00 | 0.00 | PROT |
| ATOM | 897 | O   | GLU | 42 | −18.713 | −6.448  | −1.675  | 1.00 | 0.00 | PROT |
| ATOM | 898 | N   | ALA | 43 | −16.802 | −7.457  | −1.334  | 1.00 | 0.00 | PROT |
| ATOM | 899 | HN  | ALA | 43 | −16.253 | −8.049  | −0.770  | 1.00 | 0.00 | PROT |
| ATOM | 900 | CA  | ALA | 43 | −16.248 | −6.865  | −2.595  | 1.00 | 0.00 | PROT |
| ATOM | 901 | HA  | ALA | 43 | −17.007 | −6.293  | −3.095  | 1.00 | 0.00 | PROT |
| ATOM | 902 | CB  | ALA | 43 | −15.111 | −5.942  | −2.167  | 1.00 | 0.00 | PROT |
| ATOM | 903 | HB1 | ALA | 43 | −14.957 | −5.190  | −2.927  | 1.00 | 0.00 | PROT |
| ATOM | 904 | HB2 | ALA | 43 | −14.209 | −6.516  | −2.047  | 1.00 | 0.00 | PROT |
| ATOM | 905 | HB3 | ALA | 43 | −15.368 | −5.461  | −1.236  | 1.00 | 0.00 | PROT |
| ATOM | 906 | C   | ALA | 43 | −15.731 | −7.967  | −3.528  | 1.00 | 0.00 | PROT |
| ATOM | 907 | O   | ALA | 43 | −14.563 | −7.992  | −3.861  | 1.00 | 0.00 | PROT |
| ATOM | 908 | N   | PRO | 44 | −16.625 | −8.837  | −3.937  | 1.00 | 0.00 | PROT |
| ATOM | 909 | CA  | PRO | 44 | −16.242 | −9.942  | −4.849  | 1.00 | 0.00 | PROT |
| ATOM | 910 | HA  | PRO | 44 | −15.384 | −10.473 | −4.463  | 1.00 | 0.00 | PROT |
| ATOM | 911 | CB  | PRO | 44 | −17.473 | −10.848 | −4.860  | 1.00 | 0.00 | PROT |
| ATOM | 912 | HB1 | PRO | 44 | −17.358 | −11.646 | −4.141  | 1.00 | 0.00 | PROT |
| ATOM | 913 | HB2 | PRO | 44 | −17.632 | −11.253 | −5.848  | 1.00 | 0.00 | PROT |
| ATOM | 914 | CG  | PRO | 44 | −18.614 | −9.961  | −4.473  | 1.00 | 0.00 | PROT |
| ATOM | 915 | HG1 | PRO | 44 | −19.357 | −10.531 | −3.934  | 1.00 | 0.00 | PROT |
| ATOM | 916 | HG2 | PRO | 44 | −19.055 | −9.523  | −5.356  | 1.00 | 0.00 | PROT |
| ATOM | 917 | CD  | PRO | 44 | −18.054 | −8.879  | −3.588  | 1.00 | 0.00 | PROT |
| ATOM | 918 | HD2 | PRO | 44 | −18.182 | −9.138  | −2.547  | 1.00 | 0.00 | PROT |
| ATOM | 919 | HD1 | PRO | 44 | −18.525 | −7.932  | −3.804  | 1.00 | 0.00 | PROT |
| ATOM | 920 | C   | PRO | 44 | −15.960 | −9.408  | −6.257  | 1.00 | 0.00 | PROT |
| ATOM | 921 | O   | PRO | 44 | −15.338 | −10.067 | −7.067  | 1.00 | 0.00 | PROT |
| ATOM | 922 | N   | GLY | 45 | −16.407 | −8.217  | −6.555  | 1.00 | 0.00 | PROT |
| ATOM | 923 | HN  | GLY | 45 | −16.910 | −7.702  | −5.891  | 1.00 | 0.00 | PROT |
| ATOM | 924 | CA  | GLY | 45 | −16.168 | −7.648  | −7.912  | 1.00 | 0.00 | PROT |
| ATOM | 925 | HA1 | GLY | 45 | −16.251 | −8.434  | −8.649  | 1.00 | 0.00 | PROT |
| ATOM | 926 | HA2 | GLY | 45 | −16.909 | −6.889  | −8.116  | 1.00 | 0.00 | PROT |
| ATOM | 927 | C   | GLY | 45 | −14.768 | −7.023  | −7.992  | 1.00 | 0.00 | PROT |
| ATOM | 928 | O   | GLY | 45 | −14.424 | −6.391  | −8.971  | 1.00 | 0.00 | PROT |
| ATOM | 929 | N   | TYR | 46 | −13.955 | −7.195  | −6.982  | 1.00 | 0.00 | PROT |
| ATOM | 930 | HN  | TYR | 46 | −14.247 | −7.697  | −6.197  | 1.00 | 0.00 | PROT |
| ATOM | 931 | CA  | TYR | 46 | −12.586 | −6.605  | −7.017  | 1.00 | 0.00 | PROT |
| ATOM | 932 | HA  | TYR | 46 | −12.650 | −5.529  | −7.087  | 1.00 | 0.00 | PROT |
| ATOM | 933 | CB  | TYR | 46 | −11.950 | −7.012  | −5.671  | 1.00 | 0.00 | PROT |
| ATOM | 934 | HB1 | TYR | 46 | −11.084 | −6.396  | −5.487  | 1.00 | 0.00 | PROT |
| ATOM | 935 | HB2 | TYR | 46 | −12.668 | −6.857  | −4.879  | 1.00 | 0.00 | PROT |
| ATOM | 936 | CG  | TYR | 46 | −11.532 | −8.472  | −5.683  | 1.00 | 0.00 | PROT |
| ATOM | 937 | CD1 | TYR | 46 | −10.188 | −8.810  | −5.889  | 1.00 | 0.00 | PROT |
| ATOM | 938 | HD1 | TYR | 46 | −9.453  | −8.033  | −6.039  | 1.00 | 0.00 | PROT |
| ATOM | 939 | CD2 | TYR | 46 | −12.482 | −9.483  | −5.483  | 1.00 | 0.00 | PROT |
| ATOM | 940 | HD2 | TYR | 46 | −13.517 | −9.229  | −5.321  | 1.00 | 0.00 | PROT |
| ATOM | 941 | CE1 | TYR | 46 | −9.795  | −10.153 | −5.899  | 1.00 | 0.00 | PROT |
| ATOM | 942 | HE1 | TYR | 46 | −8.759  | −10.411 | −6.060  | 1.00 | 0.00 | PROT |
| ATOM | 943 | CE2 | TYR | 46 | −12.088 | −10.827 | −5.493  | 1.00 | 0.00 | PROT |
| ATOM | 944 | HE2 | TYR | 46 | −12.821 | −11.605 | −5.341  | 1.00 | 0.00 | PROT |
| ATOM | 945 | CZ  | TYR | 46 | −10.745 | −11.161 | −5.701  | 1.00 | 0.00 | PROT |
| ATOM | 946 | OH  | TYR | 46 | −10.357 | −12.486 | −5.712  | 1.00 | 0.00 | PROT |
| ATOM | 947 | HH  | TYR | 46 | −10.517 | −12.835 | −6.592  | 1.00 | 0.00 | PROT |
| ATOM | 948 | C   | TYR | 46 | −11.795 | −7.162  | −8.211  | 1.00 | 0.00 | PROT |
| ATOM | 949 | O   | TYR | 46 | −12.363 | −7.637  | −9.174  | 1.00 | 0.00 | PROT |
| ATOM | 950 | N   | TYR | 47 | −10.484 | −7.135  | −8.140  | 1.00 | 0.00 | PROT |
| ATOM | 951 | HN  | TYR | 47 | −10.050 | −6.750  | −7.351  | 1.00 | 0.00 | PROT |
| ATOM | 952 | CA  | TYR | 47 | −9.640  | −7.665  | −9.264  | 1.00 | 0.00 | PROT |
| ATOM | 953 | HA  | TYR | 47 | −8.604  | −7.700  | −8.959  | 1.00 | 0.00 | PROT |
| ATOM | 954 | CB  | TYR | 47 | −10.150 | −9.086  | −9.542  | 1.00 | 0.00 | PROT |
| ATOM | 955 | HB1 | TYR | 47 | −10.768 | −9.079  | −10.428 | 1.00 | 0.00 | PROT |
| ATOM | 956 | HB2 | TYR | 47 | −10.733 | −9.428  | −8.700  | 1.00 | 0.00 | PROT |
| ATOM | 957 | CG  | TYR | 47 | −8.979  | −10.015 | −9.753  | 1.00 | 0.00 | PROT |
| ATOM | 958 | CD1 | TYR | 47 | −8.901  | −11.215 | −9.038  | 1.00 | 0.00 | PROT |
| ATOM | 959 | HD1 | TYR | 47 | −9.677  | −11.475 | −8.333  | 1.00 | 0.00 | PROT |
| ATOM | 960 | CD2 | TYR | 47 | −7.974  | −9.679  | −10.668 | 1.00 | 0.00 | PROT |
| ATOM | 961 | HD2 | TYR | 47 | −8.035  | −8.753  | −11.221 | 1.00 | 0.00 | PROT |
| ATOM | 962 | CE1 | TYR | 47 | −7.817  | −12.079 | −9.234  | 1.00 | 0.00 | PROT |
| ATOM | 963 | HE1 | TYR | 47 | −7.756  | −13.005 | −8.681  | 1.00 | 0.00 | PROT |

TABLE 10-continued

Atomic Structure Coordinates of the P/CAF Bromadomain and HIV-1 Tat Peptide Complex

| ATOM | 964 | CE2 | TYR | 47 | −6.890 | −10.542 | −10.865 | 1.00 | 0.00 | PROT |
|---|---|---|---|---|---|---|---|---|---|---|
| ATOM | 965 | HE2 | TYR | 47 | −6.114 | −10.283 | −11.570 | 1.00 | 0.00 | PROT |
| ATOM | 966 | CZ | TYR | 47 | −6.811 | −11.742 | −10.148 | 1.00 | 0.00 | PROT |
| ATOM | 967 | OH | TYR | 47 | −5.742 | −12.593 | −10.343 | 1.00 | 0.00 | PROT |
| ATOM | 968 | HH | TYR | 47 | −5.617 | −13.100 | −9.538 | 1.00 | 0.00 | PROT |
| ATOM | 969 | C | TYR | 47 | −9.786 | −6.791 | −10.515 | 1.00 | 0.00 | PROT |
| ATOM | 970 | O | TYR | 47 | −8.825 | −6.231 | −11.004 | 1.00 | 0.00 | PROT |
| ATOM | 971 | N | GLU | 48 | −10.978 | −6.671 | −11.040 | 1.00 | 0.00 | PROT |
| ATOM | 972 | HN | GLU | 48 | −11.739 | −7.137 | −10.636 | 1.00 | 0.00 | PROT |
| ATOM | 973 | CA | GLU | 48 | −11.182 | −5.842 | −12.266 | 1.00 | 0.00 | PROT |
| ATOM | 974 | HA | GLU | 48 | −10.802 | −6.360 | −13.132 | 1.00 | 0.00 | PROT |
| ATOM | 975 | CB | GLU | 48 | −12.698 | −5.668 | −12.373 | 1.00 | 0.00 | PROT |
| ATOM | 976 | HB1 | GLU | 48 | −12.934 | −5.101 | −13.261 | 1.00 | 0.00 | PROT |
| ATOM | 977 | HB2 | GLU | 48 | −13.061 | −5.141 | −11.503 | 1.00 | 0.00 | PROT |
| ATOM | 978 | CG | GLU | 48 | −13.367 | −7.041 | −12.453 | 1.00 | 0.00 | PROT |
| ATOM | 979 | HG1 | GLU | 48 | −13.726 | −7.325 | −11.475 | 1.00 | 0.00 | PROT |
| ATOM | 980 | HG2 | GLU | 48 | −12.651 | −7.771 | −12.800 | 1.00 | 0.00 | PROT |
| ATOM | 981 | CD | GLU | 48 | −14.544 | −6.977 | −13.429 | 1.00 | 0.00 | PROT |
| ATOM | 982 | OE1 | GLU | 48 | −15.052 | −5.889 | −13.641 | 1.00 | 0.00 | PROT |
| ATOM | 983 | OE2 | GLU | 48 | −14.915 | −8.017 | −13.948 | 1.00 | 0.00 | PROT |
| ATOM | 984 | C | GLU | 48 | −10.501 | −4.479 | −12.124 | 1.00 | 0.00 | PROT |
| ATOM | 985 | O | GLU | 48 | −9.786 | −4.037 | −13.001 | 1.00 | 0.00 | PROT |
| ATOM | 986 | N | VAL | 49 | −10.722 | −3.808 | −11.030 | 1.00 | 0.00 | PROT |
| ATOM | 987 | HN | VAL | 49 | −11.289 | −4.188 | −10.328 | 1.00 | 0.00 | PROT |
| ATOM | 988 | CA | VAL | 49 | −10.067 | −2.484 | −10.824 | 1.00 | 0.00 | PROT |
| ATOM | 989 | HA | VAL | 49 | −9.838 | −2.021 | −11.773 | 1.00 | 0.00 | PROT |
| ATOM | 990 | CB | VAL | 49 | −11.076 | −1.637 | −10.037 | 1.00 | 0.00 | PROT |
| ATOM | 991 | HB | VAL | 49 | −11.117 | −1.990 | −9.016 | 1.00 | 0.00 | PROT |
| ATOM | 992 | CG1 | VAL | 49 | −12.466 | −1.741 | −10.674 | 1.00 | 0.00 | PROT |
| ATOM | 993 | HG11 | VAL | 49 | −12.370 | −2.078 | −11.695 | 1.00 | 0.00 | PROT |
| ATOM | 994 | HG12 | VAL | 49 | −12.943 | −0.772 | −10.658 | 1.00 | 0.00 | PROT |
| ATOM | 995 | HG13 | VAL | 49 | −13.065 | −2.448 | −10.116 | 1.00 | 0.00 | PROT |
| ATOM | 996 | CG2 | VAL | 49 | −10.626 | −0.176 | −10.048 | 1.00 | 0.00 | PROT |
| ATOM | 997 | HG21 | VAL | 49 | −9.941 | −0.005 | −9.231 | 1.00 | 0.00 | PROT |
| ATOM | 998 | HG22 | VAL | 49 | −11.486 | 0.467 | −9.937 | 1.00 | 0.00 | PROT |
| ATOM | 999 | HG23 | VAL | 49 | −10.132 | 0.042 | −10.983 | 1.00 | 0.00 | PROT |
| ATOM | 1000 | C | VAL | 49 | −8.800 | −2.680 | −10.001 | 1.00 | 0.00 | PROT |
| ATOM | 1001 | O | VAL | 49 | −7.806 | −2.007 | −10.186 | 1.00 | 0.00 | PROT |
| ATOM | 1002 | N | ILE | 50 | −8.838 | −3.611 | −9.091 | 1.00 | 0.00 | PROT |
| ATOM | 1003 | HN | ILE | 50 | −9.652 | −4.142 | −8.975 | 1.00 | 0.00 | PROT |
| ATOM | 1004 | CA | ILE | 50 | −7.643 | −3.889 | −8.246 | 1.00 | 0.00 | PROT |
| ATOM | 1005 | HA | ILE | 50 | −7.029 | −3.005 | −8.154 | 1.00 | 0.00 | PROT |
| ATOM | 1006 | CB | ILE | 50 | −8.185 | −4.319 | −6.867 | 1.00 | 0.00 | PROT |
| ATOM | 1007 | HB | ILE | 50 | −8.482 | −5.356 | −6.912 | 1.00 | 0.00 | PROT |
| ATOM | 1008 | CG1 | ILE | 50 | −9.398 | −3.467 | −6.453 | 1.00 | 0.00 | PROT |
| ATOM | 1009 | HG11 | ILE | 50 | −9.688 | −3.724 | −5.445 | 1.00 | 0.00 | PROT |
| ATOM | 1010 | HG12 | ILE | 50 | −10.220 | −3.666 | −7.125 | 1.00 | 0.00 | PROT |
| ATOM | 1011 | CG2 | ILE | 50 | −7.082 | −4.160 | −5.818 | 1.00 | 0.00 | PROT |
| ATOM | 1012 | HG21 | ILE | 50 | −7.302 | −4.788 | −4.967 | 1.00 | 0.00 | PROT |
| ATOM | 1013 | HG22 | ILE | 50 | −7.032 | −3.129 | −5.501 | 1.00 | 0.00 | PROT |
| ATOM | 1014 | HG23 | ILE | 50 | −6.134 | −4.452 | −6.245 | 1.00 | 0.00 | PROT |
| ATOM | 1015 | CD1 | ILE | 50 | −9.040 | −1.981 | −6.515 | 1.00 | 0.00 | PROT |
| ATOM | 1016 | HD11 | ILE | 50 | −7.998 | −1.871 | −6.772 | 1.00 | 0.00 | PROT |
| ATOM | 1017 | HD12 | ILE | 50 | −9.224 | −1.526 | −5.552 | 1.00 | 0.00 | PROT |
| ATOM | 1018 | HD13 | ILE | 50 | −9.649 | −1.495 | −7.263 | 1.00 | 0.00 | PROT |
| ATOM | 1019 | C | ILE | 50 | −6.844 | −5.036 | −8.870 | 1.00 | 0.00 | PROT |
| ATOM | 1020 | O | ILE | 50 | −7.069 | −6.190 | −8.566 | 1.00 | 0.00 | PROT |
| ATOM | 1021 | N | ARG | 51 | −5.934 | −4.732 | −9.763 | 1.00 | 0.00 | PROT |
| ATOM | 1022 | HN | ARG | 51 | −5.785 | −3.795 | −10.006 | 1.00 | 0.00 | PROT |
| ATOM | 1023 | CA | ARG | 51 | −5.137 | −5.811 | −10.431 | 1.00 | 0.00 | PROT |
| ATOM | 1024 | HA | ARG | 51 | −5.728 | −6.294 | −11.193 | 1.00 | 0.00 | PROT |
| ATOM | 1025 | CB | ARG | 51 | −3.946 | −5.091 | −11.066 | 1.00 | 0.00 | PROT |
| ATOM | 1026 | HB1 | ARG | 51 | −3.256 | −5.820 | −11.460 | 1.00 | 0.00 | PROT |
| ATOM | 1027 | HB2 | ARG | 51 | −3.449 | −4.491 | −10.322 | 1.00 | 0.00 | PROT |
| ATOM | 1028 | CG | ARG | 51 | −4.434 | −4.195 | −12.200 | 1.00 | 0.00 | PROT |
| ATOM | 1029 | HG1 | ARG | 51 | −3.972 | −4.505 | −13.124 | 1.00 | 0.00 | PROT |
| ATOM | 1030 | HG2 | ARG | 51 | −5.505 | −4.276 | −12.288 | 1.00 | 0.00 | PROT |
| ATOM | 1031 | CD | ARG | 51 | −4.050 | −2.746 | −11.900 | 1.00 | 0.00 | PROT |
| ATOM | 1032 | HD1 | ARG | 51 | −3.823 | −2.630 | −10.851 | 1.00 | 0.00 | PROT |
| ATOM | 1033 | HD2 | ARG | 51 | −4.847 | −2.077 | −12.190 | 1.00 | 0.00 | PROT |
| ATOM | 1034 | HE | ARG | 51 | −2.832 | −2.495 | −12.728 | 1.00 | 0.00 | PROT |
| ATOM | 1035 | HE | ARG | 51 | −2.328 | −3.255 | −13.088 | 1.00 | 0.00 | PROT |
| ATOM | 1036 | CZ | ARG | 51 | −2.429 | −1.272 | −12.982 | 1.00 | 0.00 | PROT |
| ATOM | 1037 | NH1 | ARG | 51 | −3.081 | −0.235 | −12.517 | 1.00 | 0.00 | PROT |
| ATOM | 1038 | HH11 | ARG | 51 | −2.757 | 0.689 | −12.721 | 1.00 | 0.00 | PROT |
| ATOM | 1039 | HH12 | ARG | 51 | −3.900 | −0.362 | −11.958 | 1.00 | 0.00 | PROT |
| ATOM | 1040 | NH2 | ARG | 51 | −1.362 | −1.085 | −13.710 | 1.00 | 0.00 | PROT |

TABLE 10-continued

Atomic Structure Coordinates of the P/CAF Bromadomain and HIV-1 Tat Peptide Complex

| ATOM | 1041 | HH21 | ARG | 51 | −0.858 | −1.871 | −14.069 | 1.00 | 0.00 | PROT |
|---|---|---|---|---|---|---|---|---|---|---|
| ATOM | 1042 | HH22 | ARG | 51 | −1.048 | −0.157 | −13.908 | 1.00 | 0.00 | PROT |
| ATOM | 1043 | C | ARG | 51 | −4.640 | −6.837 | −9.409 | 1.00 | 0.00 | PROT |
| ATOM | 1044 | O | ARG | 51 | −4.971 | −8.004 | −9.473 | 1.00 | 0.00 | PROT |
| ATOM | 1045 | N | PHE | 52 | −3.859 | −6.404 | −8.462 | 1.00 | 0.00 | PROT |
| ATOM | 1046 | HN | PHE | 52 | −3.612 | −5.457 | −8.427 | 1.00 | 0.00 | PROT |
| ATOM | 1047 | CA | PHE | 52 | −3.354 | −7.343 | −7.425 | 1.00 | 0.00 | PROT |
| ATOM | 1048 | HA | PHE | 52 | −3.751 | −8.332 | −7.584 | 1.00 | 0.00 | PROT |
| ATOM | 1049 | CB | PHE | 52 | −1.834 | −7.343 | −7.606 | 1.00 | 0.00 | PROT |
| ATOM | 1050 | HB1 | PHE | 52 | −1.357 | −7.417 | −6.640 | 1.00 | 0.00 | PROT |
| ATOM | 1051 | HB2 | PHE | 52 | −1.529 | −6.426 | −8.088 | 1.00 | 0.00 | PROT |
| ATOM | 1052 | CG | PHE | 52 | −1.426 | −8.520 | −8.459 | 1.00 | 0.00 | PROT |
| ATOM | 1053 | CD1 | PHE | 52 | −1.408 | −9.809 | −7.912 | 1.00 | 0.00 | PROT |
| ATOM | 1054 | HD1 | PHE | 52 | −1.691 | −9.961 | −6.881 | 1.00 | 0.00 | PROT |
| ATOM | 1055 | CD2 | PHE | 52 | −1.059 | −8.321 | −9.795 | 1.00 | 0.00 | PROT |
| ATOM | 1056 | HD2 | PHE | 52 | −1.071 | −7.327 | −10.217 | 1.00 | 0.00 | PROT |
| ATOM | 1057 | CE1 | PHE | 52 | −1.027 | −10.899 | −8.703 | 1.00 | 0.00 | PROT |
| ATOM | 1058 | HE1 | PHE | 52 | −1.014 | −11.893 | −8.281 | 1.00 | 0.00 | PROT |
| ATOM | 1059 | CE2 | PHE | 52 | −0.676 | −9.412 | −10.586 | 1.00 | 0.00 | PROT |
| ATOM | 1060 | HE2 | PHE | 52 | −0.394 | −9.259 | −11.617 | 1.00 | 0.00 | PROT |
| ATOM | 1061 | CZ | PHE | 52 | −0.661 | −10.701 | −10.039 | 1.00 | 0.00 | PROT |
| ATOM | 1062 | HZ | PHE | 52 | −0.366 | −11.542 | −10.649 | 1.00 | 0.00 | PROT |
| ATOM | 1063 | C | PHE | 52 | −3.721 | −6.825 | −6.030 | 1.00 | 0.00 | PROT |
| ATOM | 1064 | O | PHE | 52 | −3.039 | −5.971 | −5.500 | 1.00 | 0.00 | PROT |
| ATOM | 1065 | N | PRO | 53 | −4.787 | −7.356 | −5.467 | 1.00 | 0.00 | PROT |
| ATOM | 1066 | CA | PRO | 53 | −5.235 | −6.916 | −4.123 | 1.00 | 0.00 | PROT |
| ATOM | 1067 | HA | PRO | 53 | −5.764 | −5.977 | −4.195 | 1.00 | 0.00 | PROT |
| ATOM | 1068 | CB | PRO | 53 | −6.184 | −8.024 | −3.656 | 1.00 | 0.00 | PROT |
| ATOM | 1069 | HB1 | PRO | 53 | −7.143 | −7.602 | −3.393 | 1.00 | 0.00 | PROT |
| ATOM | 1070 | HB2 | PRO | 53 | −5.761 | −8.538 | −2.806 | 1.00 | 0.00 | PROT |
| ATOM | 1071 | CG | PRO | 53 | −6.341 | −8.978 | −4.809 | 1.00 | 0.00 | PROT |
| ATOM | 1072 | HG1 | PRO | 53 | −5.870 | −9.920 | −4.568 | 1.00 | 0.00 | PROT |
| ATOM | 1073 | HG2 | PRO | 53 | −7.390 | −9.137 | −5.009 | 1.00 | 0.00 | PROT |
| ATOM | 1074 | CD | PRO | 53 | −5.679 | −8.376 | −6.021 | 1.00 | 0.00 | PROT |
| ATOM | 1075 | HD2 | PRO | 53 | −6.416 | −7.922 | −6.668 | 1.00 | 0.00 | PROT |
| ATOM | 1076 | HD1 | PRO | 53 | −5.120 | −9.128 | −6.553 | 1.00 | 0.00 | PROT |
| ATOM | 1077 | C | PRO | 53 | −4.046 | −6.784 | −3.168 | 1.00 | 0.00 | PROT |
| ATOM | 1078 | O | PRO | 53 | −3.066 | −7.494 | −3.282 | 1.00 | 0.00 | PROT |
| ATOM | 1079 | N | MET | 54 | −4.102 | −5.853 | −2.259 | 1.00 | 0.00 | PROT |
| ATOM | 1080 | HN | MET | 54 | −4.894 | −5.281 | −2.185 | 1.00 | 0.00 | PROT |
| ATOM | 1081 | CA | MET | 54 | −2.960 | −5.657 | −1.332 | 1.00 | 0.00 | PROT |
| ATOM | 1082 | HA | MET | 54 | −2.666 | −6.596 | −0.887 | 1.00 | 0.00 | PROT |
| ATOM | 1083 | CB | MET | 54 | −1.840 | −5.106 | −2.213 | 1.00 | 0.00 | PROT |
| ATOM | 1084 | HB1 | MET | 54 | −2.012 | −4.056 | −2.398 | 1.00 | 0.00 | PROT |
| ATOM | 1085 | HB2 | MET | 54 | −1.826 | −5.639 | −3.153 | 1.00 | 0.00 | PROT |
| ATOM | 1086 | CG | MET | 54 | −0.498 | −5.284 | −1.506 | 1.00 | 0.00 | PROT |
| ATOM | 1087 | HG1 | MET | 54 | −0.666 | −5.464 | −0.454 | 1.00 | 0.00 | PROT |
| ATOM | 1088 | HG2 | MET | 54 | 0.093 | −4.389 | −1.628 | 1.00 | 0.00 | PROT |
| ATOM | 1089 | SD | MET | 54 | 0.381 | −6.694 | −2.226 | 1.00 | 0.00 | PROT |
| ATOM | 1090 | CE | MET | 54 | 1.146 | −7.290 | −0.698 | 1.00 | 0.00 | PROT |
| ATOM | 1091 | HE1 | MET | 54 | 1.495 | −8.302 | −0.841 | 1.00 | 0.00 | PROT |
| ATOM | 1092 | HE2 | MET | 54 | 0.419 | −7.269 | 0.101 | 1.00 | 0.00 | PROT |
| ATOM | 1093 | HE3 | MET | 54 | 1.981 | −6.654 | −0.442 | 1.00 | 0.00 | PROT |
| ATOM | 1094 | C | MET | 54 | −3.336 | −4.646 | −0.254 | 1.00 | 0.00 | PROT |
| ATOM | 1095 | O | MET | 54 | −4.117 | −3.743 | −0.480 | 1.00 | 0.00 | PROT |
| ATOM | 1096 | N | ASP | 55 | −2.796 | −4.794 | 0.921 | 1.00 | 0.00 | PROT |
| ATOM | 1097 | HN | ASP | 55 | −2.177 | −5.535 | 1.086 | 1.00 | 0.00 | PROT |
| ATOM | 1098 | CA | ASP | 55 | −3.138 | −3.852 | 2.019 | 1.00 | 0.00 | PROT |
| ATOM | 1099 | HA | ASP | 55 | −2.995 | −2.831 | 1.698 | 1.00 | 0.00 | PROT |
| ATOM | 1100 | CB | ASP | 55 | −4.618 | −4.125 | 2.305 | 1.00 | 0.00 | PROT |
| ATOM | 1101 | HB1 | ASP | 55 | −4.743 | −4.383 | 3.342 | 1.00 | 0.00 | PROT |
| ATOM | 1102 | HB2 | ASP | 55 | −4.955 | −4.946 | 1.690 | 1.00 | 0.00 | PROT |
| ATOM | 1103 | CG | ASP | 55 | −5.446 | −2.878 | 1.983 | 1.00 | 0.00 | PROT |
| ATOM | 1104 | OD1 | ASP | 55 | −4.968 | −2.051 | 1.224 | 1.00 | 0.00 | PROT |
| ATOM | 1105 | OD2 | ASP | 55 | −6.547 | −2.773 | 2.497 | 1.00 | 0.00 | PROT |
| ATOM | 1106 | C | ASP | 55 | −2.278 | −4.153 | 3.247 | 1.00 | 0.00 | PROT |
| ATOM | 1107 | O | ASP | 55 | −1.845 | −5.270 | 3.445 | 1.00 | 0.00 | PROT |
| ATOM | 1108 | N | LEU | 56 | −2.002 | −3.155 | 4.055 | 1.00 | 0.00 | PROT |
| ATOM | 1109 | HN | LEU | 56 | −2.359 | −2.265 | 3.860 | 1.00 | 0.00 | PROT |
| ATOM | 1110 | CA | LEU | 56 | −1.141 | −3.362 | 5.267 | 1.00 | 0.00 | PROT |
| ATOM | 1111 | HA | LEU | 56 | −0.100 | −3.386 | 4.985 | 1.00 | 0.00 | PROT |
| ATOM | 1112 | CB | LEU | 56 | −1.417 | −2.150 | 6.168 | 1.00 | 0.00 | PROT |
| ATOM | 1113 | HB1 | LEU | 56 | −2.471 | −2.107 | 6.394 | 1.00 | 0.00 | PROT |
| ATOM | 1114 | HB2 | LEU | 56 | −0.859 | −2.255 | 7.087 | 1.00 | 0.00 | PROT |
| ATOM | 1115 | CG | LEU | 56 | −0.997 | −0.849 | 5.466 | 1.00 | 0.00 | PROT |
| ATOM | 1116 | HG | LEU | 56 | −1.648 | −0.666 | 4.625 | 1.00 | 0.00 | PROT |
| ATOM | 1117 | CD1 | LEU | 56 | −1.110 | 0.314 | 6.452 | 1.00 | 0.00 | PROT |

TABLE 10-continued

Atomic Structure Coordinates of the P/CAF Bromadomain and HIV-1 Tat Peptide Complex

| ATOM | 1118 | HD11 | LEU | 56 | -0.157 | 0.470 | 6.936 | 1.00 | 0.00 | PROT |
|------|------|------|-----|----|--------|-------|-------|------|------|------|
| ATOM | 1119 | HD12 | LEU | 56 | -1.858 | 0.084 | 7.196 | 1.00 | 0.00 | PROT |
| ATOM | 1120 | HD13 | LEU | 56 | -1.394 | 1.210 | 5.921 | 1.00 | 0.00 | PROT |
| ATOM | 1121 | CD2 | LEU | 56 | 0.450 | -0.955 | 4.975 | 1.00 | 0.00 | PROT |
| ATOM | 1122 | HD21 | LEU | 56 | 0.927 | -1.810 | 5.432 | 1.00 | 0.00 | PROT |
| ATOM | 1123 | HD22 | LEU | 56 | 0.988 | -0.058 | 5.242 | 1.00 | 0.00 | PROT |
| ATOM | 1124 | HD23 | LEU | 56 | 0.457 | -1.071 | 3.901 | 1.00 | 0.00 | PROT |
| ATOM | 1125 | C | LEU | 56 | -1.522 | -4.655 | 5.995 | 1.00 | 0.00 | PROT |
| ATOM | 1126 | O | LEU | 56 | -0.674 | -5.444 | 6.363 | 1.00 | 0.00 | PROT |
| ATOM | 1127 | N | LYS | 57 | -2.794 | -4.896 | 6.160 | 1.00 | 0.00 | PROT |
| ATOM | 1128 | HN | LYS | 57 | -3.457 | -4.239 | 5.856 | 1.00 | 0.00 | PROT |
| ATOM | 1129 | CA | LYS | 57 | -3.246 | -6.145 | 6.842 | 1.00 | 0.00 | PROT |
| ATOM | 1130 | HA | LYS | 57 | -3.052 | -6.072 | 7.901 | 1.00 | 0.00 | PROT |
| ATOM | 1131 | CB | LYS | 57 | -4.783 | -6.170 | 6.594 | 1.00 | 0.00 | PROT |
| ATOM | 1132 | HB1 | LYS | 57 | -5.290 | -6.101 | 7.545 | 1.00 | 0.00 | PROT |
| ATOM | 1133 | HB2 | LYS | 57 | -5.050 | -5.316 | 5.995 | 1.00 | 0.00 | PROT |
| ATOM | 1134 | CG | LYS | 57 | -5.257 | -7.441 | 5.869 | 1.00 | 0.00 | PROT |
| ATOM | 1135 | HG1 | LYS | 57 | -6.283 | -7.315 | 5.549 | 1.00 | 0.00 | PROT |
| ATOM | 1136 | HG2 | LYS | 57 | -4.632 | -7.617 | 5.006 | 1.00 | 0.00 | PROT |
| ATOM | 1137 | CD | LYS | 57 | -5.163 | -8.635 | 6.818 | 1.00 | 0.00 | PROT |
| ATOM | 1138 | HD1 | LYS | 57 | -4.607 | -8.352 | 7.699 | 1.00 | 0.00 | PROT |
| ATOM | 1139 | HD2 | LYS | 57 | -6.155 | -8.951 | 7.102 | 1.00 | 0.00 | PROT |
| ATOM | 1140 | CE | LYS | 57 | -4.445 | -9.782 | 6.108 | 1.00 | 0.00 | PROT |
| ATOM | 1141 | HE1 | LYS | 57 | -5.137 | -10.334 | 5.490 | 1.00 | 0.00 | PROT |
| ATOM | 1142 | HE2 | LYS | 57 | -3.631 | -9.397 | 5.513 | 1.00 | 0.00 | PROT |
| ATOM | 1143 | NZ | LYS | 57 | -3.925 | -10.645 | 7.205 | 1.00 | 0.00 | PROT |
| ATOM | 1144 | HZ1 | LYS | 57 | -3.468 | -11.486 | 6.798 | 1.00 | 0.00 | PROT |
| ATOM | 1145 | HZ2 | LYS | 57 | -4.712 | -10.941 | 7.817 | 1.00 | 0.00 | PROT |
| ATOM | 1146 | HZ3 | LYS | 57 | -3.231 | -10.112 | 7.767 | 1.00 | 0.00 | PROT |
| ATOM | 1147 | C | LYS | 57 | -2.512 | -7.373 | 6.265 | 1.00 | 0.00 | PROT |
| ATOM | 1148 | O | LYS | 57 | -2.337 | -8.369 | 6.939 | 1.00 | 0.00 | PROT |
| ATOM | 1149 | N | THR | 58 | -2.067 | -7.306 | 5.037 | 1.00 | 0.00 | PROT |
| ATOM | 1150 | HN | THR | 58 | -2.232 | -6.506 | 4.496 | 1.00 | 0.00 | PROT |
| ATOM | 1151 | CA | THR | 58 | -1.392 | -8.494 | 4.435 | 1.00 | 0.00 | PROT |
| ATOM | 1152 | HA | THR | 58 | -1.379 | -9.305 | 5.148 | 1.00 | 0.00 | PROT |
| ATOM | 1153 | CB | THR | 58 | -2.264 | -8.875 | 3.233 | 1.00 | 0.00 | PROT |
| ATOM | 1154 | HB | THR | 58 | -3.227 | -9.217 | 3.583 | 1.00 | 0.00 | PROT |
| ATOM | 1155 | OG1 | THR | 58 | -1.631 | -9.916 | 2.504 | 1.00 | 0.00 | PROT |
| ATOM | 1156 | HG1 | THR | 58 | -2.183 | -10.125 | 1.746 | 1.00 | 0.00 | PROT |
| ATOM | 1157 | CG2 | THR | 58 | -2.457 | -7.660 | 2.321 | 1.00 | 0.00 | PROT |
| ATOM | 1158 | HG21 | THR | 58 | -2.908 | -7.975 | 1.393 | 1.00 | 0.00 | PROT |
| ATOM | 1159 | HG22 | THR | 58 | -1.499 | -7.205 | 2.119 | 1.00 | 0.00 | PROT |
| ATOM | 1160 | HG23 | THR | 58 | -3.101 | -6.943 | 2.809 | 1.00 | 0.00 | PROT |
| ATOM | 1161 | C | THR | 58 | 0.040 | -8.183 | 3.975 | 1.00 | 0.00 | PROT |
| ATOM | 1162 | O | THR | 58 | 0.902 | -9.038 | 4.025 | 1.00 | 0.00 | PROT |
| ATOM | 1163 | N | MET | 59 | 0.309 | -6.992 | 3.499 | 1.00 | 0.00 | PROT |
| ATOM | 1164 | HM | MET | 59 | -0.392 | -6.310 | 3.443 | 1.00 | 0.00 | PROT |
| ATOM | 1165 | CA | MET | 59 | 1.693 | -6.701 | 3.010 | 1.00 | 0.00 | PROT |
| ATOM | 1166 | HA | MET | 59 | 2.041 | -7.515 | 2.393 | 1.00 | 0.00 | PROT |
| ATOM | 1167 | CB | MET | 59 | 1.591 | -5.424 | 2.172 | 1.00 | 0.00 | PROT |
| ATOM | 1168 | HB1 | MET | 59 | 0.874 | -5.569 | 1.378 | 1.00 | 0.00 | PROT |
| ATOM | 1169 | HB2 | MET | 59 | 2.560 | -5.204 | 1.749 | 1.00 | 0.00 | PROT |
| ATOM | 1170 | CG | MET | 59 | 1.157 | -4.249 | 3.044 | 1.00 | 0.00 | PROT |
| ATOM | 1171 | HG1 | MET | 59 | 1.785 | -4.196 | 3.920 | 1.00 | 0.00 | PROT |
| ATOM | 1172 | HG2 | MET | 59 | 0.131 | -4.381 | 3.343 | 1.00 | 0.00 | PROT |
| ATOM | 1173 | SD | MET | 59 | 1.320 | -2.718 | 2.092 | 1.00 | 0.00 | PROT |
| ATOM | 1174 | CE | MET | 59 | 3.122 | -2.585 | 2.192 | 1.00 | 0.00 | PROT |
| ATOM | 1175 | HE1 | MET | 59 | 3.556 | -3.573 | 2.217 | 1.00 | 0.00 | PROT |
| ATOM | 1176 | HE2 | MET | 59 | 3.395 | -2.050 | 3.089 | 1.00 | 0.00 | PROT |
| ATOM | 1177 | HE3 | MET | 59 | 3.492 | -2.051 | 1.329 | 1.00 | 0.00 | PROT |
| ATOM | 1178 | C | MET | 59 | 2.657 | -6.487 | 4.176 | 1.00 | 0.00 | PROT |
| ATOM | 1179 | O | MET | 59 | 3.835 | -6.766 | 4.069 | 1.00 | 0.00 | PROT |
| ATOM | 1180 | N | SER | 60 | 2.184 | -5.978 | 5.278 | 1.00 | 0.00 | PROT |
| ATOM | 1181 | HN | SER | 60 | 1.232 | -5.761 | 5.356 | 1.00 | 0.00 | PROT |
| ATOM | 1182 | CA | SER | 60 | 3.100 | -5.756 | 6.426 | 1.00 | 0.00 | PROT |
| ATOM | 1183 | HA | SER | 60 | 3.967 | -5.197 | 6.105 | 1.00 | 0.00 | PROT |
| ATOM | 1184 | CB | SER | 60 | 2.289 | -4.952 | 7.442 | 1.00 | 0.00 | PROT |
| ATOM | 1185 | HB1 | SER | 60 | 2.962 | -4.470 | 8.135 | 1.00 | 0.00 | PROT |
| ATOM | 1186 | HB2 | SER | 60 | 1.629 | -5.615 | 7.982 | 1.00 | 0.00 | PROT |
| ATOM | 1187 | OG | SER | 60 | 1.522 | -3.968 | 6.763 | 1.00 | 0.00 | PROT |
| ATOM | 1188 | HG | SER | 60 | 1.083 | -3.427 | 7.423 | 1.00 | 0.00 | PROT |
| ATOM | 1189 | C | SER | 60 | 3.518 | -7.100 | 7.016 | 1.00 | 0.00 | PROT |
| ATOM | 1190 | O | SER | 60 | 4.567 | -7.231 | 7.616 | 1.00 | 0.00 | PROT |
| ATOM | 1191 | N | GLU | 61 | 2.708 | -8.105 | 6.835 | 1.00 | 0.00 | PROT |
| ATOM | 1192 | HN | GLU | 61 | 1.872 | -7.977 | 6.341 | 1.00 | 0.00 | PROT |
| ATOM | 1193 | CA | GLU | 61 | 3.058 | -9.449 | 7.364 | 1.00 | 0.00 | PROT |
| ATOM | 1194 | HA | GLU | 61 | 3.246 | -9.397 | 8.424 | 1.00 | 0.00 | PROT |

TABLE 10-continued

Atomic Structure Coordinates of the P/CAF Bromadomain and HIV-1 Tat Peptide Complex

| ATOM | 1195 | CB   | GLU | 61 | 1.822  | −10.300 | 7.097  | 1.00 | 0.00 | PROT |
|------|------|------|-----|----|--------|---------|--------|------|------|------|
| ATOM | 1196 | HB1  | GLU | 61 | 2.106  | −11.336 | 6.980  | 1.00 | 0.00 | PROT |
| ATOM | 1197 | HB2  | GLU | 61 | 1.336  | −9.954  | 6.212  | 1.00 | 0.00 | PROT |
| ATOM | 1198 | CG   | GLU | 61 | 0.869  | −10.154 | 8.265  | 1.00 | 0.00 | PROT |
| ATOM | 1199 | HG1  | GLU | 61 | 1.419  | −9.817  | 9.115  | 1.00 | 0.00 | PROT |
| ATOM | 1200 | HG2  | GLU | 61 | 0.117  | −9.426  | 8.019  | 1.00 | 0.00 | PROT |
| ATOM | 1201 | CD   | GLU | 61 | 0.209  | −11.500 | 8.571  | 1.00 | 0.00 | PROT |
| ATOM | 1202 | OE1  | GLU | 61 | 0.933  | −12.466 | 8.749  | 1.00 | 0.00 | PROT |
| ATOM | 1203 | OE2  | GLU | 61 | −1.009 | −11.541 | 8.623  | 1.00 | 0.00 | PROT |
| ATOM | 1204 | C    | GLU | 61 | 4.271  | −10.009 | 6.619  | 1.00 | 0.00 | PROT |
| ATOM | 1205 | O    | GLU | 61 | 4.970  | −10.875 | 7.107  | 1.00 | 0.00 | PROT |
| ATOM | 1206 | N    | ARG | 62 | 4.528  | −9.515  | 5.437  | 1.00 | 0.00 | PROT |
| ATOM | 1207 | HN   | ARG | 62 | 3.950  | −8.817  | 5.063  | 1.00 | 0.00 | PROT |
| ATOM | 1208 | CA   | ARG | 62 | 5.694  | −10.009 | 4.653  | 1.00 | 0.00 | PROT |
| ATOM | 1209 | HA   | ARG | 62 | 5.663  | −11.085 | 4.573  | 1.00 | 0.00 | PROT |
| ATOM | 1210 | CB   | ARG | 62 | 5.534  | −9.368  | 3.275  | 1.00 | 0.00 | PROT |
| ATOM | 1211 | HB1  | ARG | 62 | 5.464  | −8.295  | 3.382  | 1.00 | 0.00 | PROT |
| ATOM | 1212 | HB2  | ARG | 62 | 6.387  | −9.615  | 2.660  | 1.00 | 0.00 | PROT |
| ATOM | 1213 | CG   | ARG | 62 | 4.260  | −9.900  | 2.622  | 1.00 | 0.00 | PROT |
| ATOM | 1214 | HG1  | ARG | 62 | 3.403  | −9.389  | 3.036  | 1.00 | 0.00 | PROT |
| ATOM | 1215 | HG2  | ARG | 62 | 4.177  | −10.959 | 2.816  | 1.00 | 0.00 | PROT |
| ATOM | 1216 | CD   | ARG | 62 | 4.319  | −9.656  | 1.114  | 1.00 | 0.00 | PROT |
| ATOM | 1217 | HD1  | ARG | 62 | 5.316  | −9.841  | 0.744  | 1.00 | 0.00 | PROT |
| ATOM | 1218 | HD2  | ARG | 62 | 4.012  | −8.647  | 0.884  | 1.00 | 0.00 | PROT |
| ATOM | 1219 | NE   | ARG | 62 | 3.358  | −10.637 | 0.530  | 1.00 | 0.00 | PROT |
| ATOM | 1220 | HE   | ARG | 62 | 2.494  | −10.324 | 0.191  | 1.00 | 0.00 | PROT |
| ATOM | 1221 | CZ   | ARG | 62 | 3.656  | −11.915 | 0.465  | 1.00 | 0.00 | PROT |
| ATOM | 1222 | NH1  | ARG | 62 | 2.795  | −12.748 | −0.052 | 1.00 | 0.00 | PROT |
| ATOM | 1223 | HH11 | ARG | 62 | 3.013  | −13.723 | −0.105 | 1.00 | 0.00 | PROT |
| ATOM | 1224 | HH12 | ARG | 62 | 1.917  | −12.413 | −0.394 | 1.00 | 0.00 | PROT |
| ATOM | 1225 | NH2  | ARG | 62 | 4.803  | −12.365 | 0.910  | 1.00 | 0.00 | PROT |
| ATOM | 1226 | HH21 | ARG | 62 | 5.472  | −11.738 | 1.308  | 1.00 | 0.00 | PROT |
| ATOM | 1227 | HH22 | ARG | 62 | 5.010  | −13.341 | 0.851  | 1.00 | 0.00 | PROT |
| ATOM | 1228 | C    | ARG | 62 | 7.001  | −9.559  | 5.303  | 1.00 | 0.00 | PROT |
| ATOM | 1229 | O    | ARG | 62 | 7.903  | −10.346 | 5.508  | 1.00 | 0.00 | PROT |
| ATOM | 1230 | N    | LEU | 63 | 7.112  | −8.301  | 5.640  | 1.00 | 0.00 | PROT |
| ATOM | 1231 | HN   | LEU | 63 | 6.372  | −7.680  | 5.474  | 1.00 | 0.00 | PROT |
| ATOM | 1232 | CA   | LEU | 63 | 8.362  | −7.818  | 6.291  | 1.00 | 0.00 | PROT |
| ATOM | 1233 | HA   | LEU | 63 | 9.182  | −7.836  | 5.588  | 1.00 | 0.00 | PROT |
| ATOM | 1234 | CB   | LEU | 63 | 8.064  | −6.383  | 6.724  | 1.00 | 0.00 | PROT |
| ATOM | 1235 | HB1  | LEU | 63 | 7.309  | −5.959  | 6.077  | 1.00 | 0.00 | PROT |
| ATOM | 1236 | HB2  | LEU | 63 | 7.708  | −6.381  | 7.744  | 1.00 | 0.00 | PROT |
| ATOM | 1237 | CG   | LEU | 63 | 9.348  | −5.556  | 6.630  | 1.00 | 0.00 | PROT |
| ATOM | 1238 | HG   | LEU | 63 | 10.100 | −6.121  | 6.099  | 1.00 | 0.00 | PROT |
| ATOM | 1239 | CD1  | LEU | 63 | 9.853  | −5.236  | 8.038  | 1.00 | 0.00 | PROT |
| ATOM | 1240 | HD11 | LEU | 63 | 10.400 | −6.084  | 8.425  | 1.00 | 0.00 | PROT |
| ATOM | 1241 | HD12 | LEU | 63 | 9.013  | −5.024  | 8.682  | 1.00 | 0.00 | PROT |
| ATOM | 1242 | HD13 | LEU | 63 | 10.504 | −4.375  | 7.999  | 1.00 | 0.00 | PROT |
| ATOM | 1243 | CD2  | LEU | 63 | 9.067  | −4.254  | 5.878  | 1.00 | 0.00 | PROT |
| ATOM | 1244 | HD21 | LEU | 63 | 9.631  | −3.451  | 6.328  | 1.00 | 0.00 | PROT |
| ATOM | 1245 | HD22 | LEU | 63 | 8.012  | −4.028  | 5.931  | 1.00 | 0.00 | PROT |
| ATOM | 1246 | HD23 | LEU | 63 | 9.360  | −4.366  | 4.844  | 1.00 | 0.00 | PROT |
| ATOM | 1247 | C    | LEU | 63 | 8.683  | −8.689  | 7.506  | 1.00 | 0.00 | PROT |
| ATOM | 1248 | O    | LEU | 63 | 9.828  | −8.979  | 7.791  | 1.00 | 0.00 | PROT |
| ATOM | 1249 | N    | LYS | 64 | 7.676  | −9.128  | 8.209  | 1.00 | 0.00 | PROT |
| ATOM | 1250 | HN   | LYS | 64 | 6.758  | −8.901  | 7.948  | 1.00 | 0.00 | PROT |
| ATOM | 1251 | CA   | LYS | 64 | 7.920  | −10.021 | 9.373  | 1.00 | 0.00 | PROT |
| ATOM | 1252 | HA   | LYS | 64 | 8.527  | −9.522  | 10.114 | 1.00 | 0.00 | PROT |
| ATOM | 1253 | CB   | LYS | 64 | 6.530  | −10.328 | 9.932  | 1.00 | 0.00 | PROT |
| ATOM | 1254 | HB1  | LYS | 64 | 6.032  | −11.040 | 9.291  | 1.00 | 0.00 | PROT |
| ATOM | 1255 | HB2  | LYS | 64 | 5.950  | −9.418  | 9.976  | 1.00 | 0.00 | PROT |
| ATOM | 1256 | CG   | LYS | 64 | 6.663  | −10.915 | 11.339 | 1.00 | 0.00 | PROT |
| ATOM | 1257 | HG1  | LYS | 64 | 7.354  | −10.317 | 11.914 | 1.00 | 0.00 | PROT |
| ATOM | 1258 | HG2  | LYS | 64 | 7.031  | −11.928 | 11.273 | 1.00 | 0.00 | PROT |
| ATOM | 1259 | CD   | LYS | 64 | 5.294  | −10.913 | 12.023 | 1.00 | 0.00 | PROT |
| ATOM | 1260 | HD1  | LYS | 64 | 4.702  | −10.094 | 11.641 | 1.00 | 0.00 | PROT |
| ATOM | 1261 | HD2  | LYS | 64 | 5.425  | −10.796 | 13.089 | 1.00 | 0.00 | PROT |
| ATOM | 1262 | CE   | LYS | 64 | 4.577  | −12.235 | 11.739 | 1.00 | 0.00 | PROT |
| ATOM | 1263 | HE1  | LYS | 64 | 4.821  | −12.590 | 10.749 | 1.00 | 0.00 | PROT |
| ATOM | 1264 | HE2  | LYS | 64 | 4.844  | −12.974 | 12.481 | 1.00 | 0.00 | PROT |
| ATOM | 1265 | NZ   | LYS | 64 | 3.126  | −11.909 | 11.831 | 1.00 | 0.00 | PROT |
| ATOM | 1266 | HZ1  | LYS | 64 | 2.956  | −11.319 | 12.670 | 1.00 | 0.00 | PROT |
| ATOM | 1267 | HZ2  | LYS | 64 | 2.577  | −12.789 | 11.909 | 1.00 | 0.00 | PROT |
| ATOM | 1268 | HZ3  | LYS | 64 | 2.833  | −11.392 | 10.978 | 1.00 | 0.00 | PROT |
| ATOM | 1269 | C    | LYS | 64 | 8.599  | −11.300 | 8.888  | 1.00 | 0.00 | PROT |
| ATOM | 1270 | O    | LYS | 64 | 9.399  | −11.896 | 9.582  | 1.00 | 0.00 | PROT |
| ATOM | 1271 | N    | ASN | 65 | 8.300  | −11.708 | 7.684  | 1.00 | 0.00 | PROT |

TABLE 10-continued

Atomic Structure Coordinates of the P/CAF Bromadomain and HIV-1 Tat Peptide Complex

| ATOM | 1272 | HN | ASN | 65 | 7.658 | −11.203 | 7.140 | 1.00 | 0.00 | PROT |
|---|---|---|---|---|---|---|---|---|---|---|
| ATOM | 1273 | CA | ASN | 65 | 8.940 | −12.929 | 7.127 | 1.00 | 0.00 | PROT |
| ATOM | 1274 | HA | ASN | 65 | 9.238 | −13.597 | 7.922 | 1.00 | 0.00 | PROT |
| ATOM | 1275 | CB | ASN | 65 | 7.851 | −13.573 | 6.268 | 1.00 | 0.00 | PROT |
| ATOM | 1276 | HB1 | ASN | 65 | 6.880 | −13.312 | 6.664 | 1.00 | 0.00 | PROT |
| ATOM | 1277 | HB2 | ASN | 65 | 7.934 | −13.213 | 5.252 | 1.00 | 0.00 | PROT |
| ATOM | 1278 | CG | ASN | 65 | 8.017 | −15.092 | 6.289 | 1.00 | 0.00 | PROT |
| ATOM | 1279 | OD1 | ASN | 65 | 8.240 | −15.705 | 5.264 | 1.00 | 0.00 | PROT |
| ATOM | 1280 | ND2 | ASN | 65 | 7.918 | −15.730 | 7.422 | 1.00 | 0.00 | PROT |
| ATOM | 1281 | HD21 | ASN | 65 | 7.739 | −15.236 | 8.249 | 1.00 | 0.00 | PROT |
| ATOM | 1282 | HD22 | ASN | 65 | 8.023 | −16.703 | 7.447 | 1.00 | 0.00 | PROT |
| ATOM | 1283 | C | ASN | 65 | 10.146 | −12.557 | 6.256 | 1.00 | 0.00 | PROT |
| ATOM | 1284 | O | ASN | 65 | 10.759 | −13.407 | 5.640 | 1.00 | 0.00 | PROT |
| ATOM | 1285 | N | ARG | 66 | 10.487 | −11.295 | 6.184 | 1.00 | 0.00 | PROT |
| ATOM | 1286 | HN | ARG | 66 | 9.982 | −10.618 | 6.678 | 1.00 | 0.00 | PROT |
| ATOM | 1287 | CA | ARG | 66 | 11.641 | −10.883 | 5.335 | 1.00 | 0.00 | PROT |
| ATOM | 1288 | HA | ARG | 66 | 11.731 | −9.807 | 5.322 | 1.00 | 0.00 | PROT |
| ATOM | 1289 | CB | ARG | 66 | 12.866 | −11.510 | 6.002 | 1.00 | 0.00 | PROT |
| ATOM | 1290 | HB1 | ARG | 66 | 12.850 | −12.579 | 5.852 | 1.00 | 0.00 | PROT |
| ATOM | 1291 | HB2 | ARG | 66 | 12.848 | −11.293 | 7.060 | 1.00 | 0.00 | PROT |
| ATOM | 1292 | CG | ARG | 66 | 14.138 | −10.925 | 5.383 | 1.00 | 0.00 | PROT |
| ATOM | 1293 | HG1 | ARG | 66 | 13.895 | −10.017 | 4.852 | 1.00 | 0.00 | PROT |
| ATOM | 1294 | HG2 | ARG | 66 | 14.850 | −10.705 | 6.164 | 1.00 | 0.00 | PROT |
| ATOM | 1295 | CD | ARG | 66 | 14.744 | −11.938 | 4.409 | 1.00 | 0.00 | PROT |
| ATOM | 1296 | HD1 | ARG | 66 | 14.133 | −12.827 | 4.363 | 1.00 | 0.00 | PROT |
| ATOM | 1297 | HD2 | ARG | 66 | 14.846 | −11.500 | 3.427 | 1.00 | 0.00 | PROT |
| ATOM | 1298 | NE | ARG | 66 | 16.087 | −12.260 | 4.977 | 1.00 | 0.00 | PROT |
| ATOM | 1299 | HE | ARG | 66 | 16.322 | −11.943 | 5.874 | 1.00 | 0.00 | PROT |
| ATOM | 1300 | CZ | ARG | 66 | 16.958 | −12.964 | 4.290 | 1.00 | 0.00 | PROT |
| ATOM | 1301 | NH1 | ARG | 66 | 16.675 | −13.403 | 3.089 | 1.00 | 0.00 | PROT |
| ATOM | 1302 | HH11 | ARG | 66 | 15.787 | −13.208 | 2.675 | 1.00 | 0.00 | PROT |
| ATOM | 1303 | HH12 | ARG | 66 | 17.352 | −13.938 | 2.582 | 1.00 | 0.00 | PROT |
| ATOM | 1304 | NH2 | ARG | 66 | 18.124 | −13.230 | 4.813 | 1.00 | 0.00 | PROT |
| ATOM | 1305 | HH21 | ARG | 66 | 18.348 | −12.899 | 5.730 | 1.00 | 0.00 | PROT |
| ATOM | 1306 | HH22 | ARG | 66 | 18.793 | −13.766 | 4.297 | 1.00 | 0.00 | PROT |
| ATOM | 1307 | C | ARG | 66 | 11.465 | −11.420 | 3.915 | 1.00 | 0.00 | PROT |
| ATOM | 1308 | O | ARG | 66 | 12.036 | −12.427 | 3.544 | 1.00 | 0.00 | PROT |
| ATOM | 1309 | N | TYR | 67 | 10.662 | −10.765 | 3.123 | 1.00 | 0.00 | PROT |
| ATOM | 1310 | HN | TYR | 67 | 10.210 | −9.957 | 3.445 | 1.00 | 0.00 | PROT |
| ATOM | 1311 | CA | TYR | 67 | 10.435 | −11.239 | 1.730 | 1.00 | 0.00 | PROT |
| ATOM | 1312 | HA | TYR | 67 | 11.182 | −11.968 | 1.454 | 1.00 | 0.00 | PROT |
| ATOM | 1313 | CB | TYR | 67 | 9.047 | −11.881 | 1.757 | 1.00 | 0.00 | PROT |
| ATOM | 1314 | HB1 | TYR | 67 | 8.815 | −12.194 | 2.765 | 1.00 | 0.00 | PROT |
| ATOM | 1315 | HB2 | TYR | 67 | 8.311 | −11.164 | 1.425 | 1.00 | 0.00 | PROT |
| ATOM | 1316 | CG | TYR | 67 | 9.029 | −13.082 | 0.842 | 1.00 | 0.00 | PROT |
| ATOM | 1317 | CD1 | TYR | 67 | 9.800 | −14.209 | 1.151 | 1.00 | 0.00 | PROT |
| ATOM | 1318 | HD1 | TYR | 67 | 10.408 | −14.219 | 2.043 | 1.00 | 0.00 | PROT |
| ATOM | 1319 | CD2 | TYR | 67 | 8.241 | −13.068 | −0.315 | 1.00 | 0.00 | PROT |
| ATOM | 1320 | HD2 | TYR | 67 | 7.646 | −12.199 | −0.553 | 1.00 | 0.00 | PROT |
| ATOM | 1321 | CE1 | TYR | 67 | 9.784 | −15.322 | 0.302 | 1.00 | 0.00 | PROT |
| ATOM | 1322 | HE1 | TYR | 67 | 10.379 | −16.191 | 0.540 | 1.00 | 0.00 | PROT |
| ATOM | 1323 | CE2 | TYR | 67 | 8.225 | −14.181 | −1.164 | 1.00 | 0.00 | PROT |
| ATOM | 1324 | HE2 | TYR | 67 | 7.617 | −14.171 | −2.057 | 1.00 | 0.00 | PROT |
| ATOM | 1325 | CZ | TYR | 67 | 8.996 | −15.308 | −0.856 | 1.00 | 0.00 | PROT |
| ATOM | 1326 | OH | TYR | 67 | 8.980 | −16.406 | −1.692 | 1.00 | 0.00 | PROT |
| ATOM | 1327 | HH | TYR | 67 | 9.451 | −16.174 | −2.495 | 1.00 | 0.00 | PROT |
| ATOM | 1328 | C | TYR | 67 | 10.457 | −10.057 | 0.761 | 1.00 | 0.00 | PROT |
| ATOM | 1329 | O | TYR | 67 | 11.132 | −10.084 | −0.249 | 1.00 | 0.00 | PROT |
| ATOM | 1330 | N | TYR | 68 | 9.730 | −9.016 | 1.061 | 1.00 | 0.00 | PROT |
| ATOM | 1331 | HN | TYR | 68 | 9.196 | −9.010 | 1.885 | 1.00 | 0.00 | PROT |
| ATOM | 1332 | CA | TYR | 68 | 9.725 | −7.832 | 0.156 | 1.00 | 0.00 | PROT |
| ATOM | 1333 | HA | TYR | 68 | 9.823 | −8.144 | −0.870 | 1.00 | 0.00 | PROT |
| ATOM | 1334 | CB | TYR | 68 | 8.375 | −7.148 | 0.391 | 1.00 | 0.00 | PROT |
| ATOM | 1335 | HB1 | TYR | 68 | 8.464 | −6.097 | 0.157 | 1.00 | 0.00 | PROT |
| ATOM | 1336 | HB2 | TYR | 68 | 8.091 | −7.260 | 1.426 | 1.00 | 0.00 | PROT |
| ATOM | 1337 | CG | TYR | 68 | 7.320 | −7.769 | −0.497 | 1.00 | 0.00 | PROT |
| ATOM | 1338 | CD1 | TYR | 68 | 6.395 | −6.949 | −1.156 | 1.00 | 0.00 | PROT |
| ATOM | 1339 | HD1 | TYR | 68 | 6.439 | −5.877 | −1.030 | 1.00 | 0.00 | PROT |
| ATOM | 1340 | CD2 | TYR | 68 | 7.259 | −9.160 | −0.658 | 1.00 | 0.00 | PROT |
| ATOM | 1341 | HD2 | TYR | 68 | 7.970 | −9.795 | −0.152 | 1.00 | 0.00 | PROT |
| ATOM | 1342 | CE1 | TYR | 68 | 5.415 | −7.518 | −1.978 | 1.00 | 0.00 | PROT |
| ATOM | 1343 | HE1 | TYR | 68 | 4.703 | −6.884 | −2.487 | 1.00 | 0.00 | PROT |
| ATOM | 1344 | CE2 | TYR | 68 | 6.280 | −9.727 | −1.483 | 1.00 | 0.00 | PROT |
| ATOM | 1345 | HE2 | TYR | 68 | 6.234 | −10.799 | −1.607 | 1.00 | 0.00 | PROT |
| ATOM | 1346 | CZ | TYR | 68 | 5.357 | −8.906 | −2.141 | 1.00 | 0.00 | PROT |
| ATOM | 1347 | OH | TYR | 68 | 4.391 | −9.467 | −2.952 | 1.00 | 0.00 | PROT |
| ATOM | 1348 | HH | TYR | 68 | 3.556 | −9.444 | −2.478 | 1.00 | 0.00 | PROT |

TABLE 10-continued

Atomic Structure Coordinates of the P/CAF Bromadomain and HIV-1 Tat Peptide Complex

| ATOM | 1349 | C | TYR | 68 | 10.862 | −6.893 | 0.523 | 1.00 | 0.00 | PROT |
|---|---|---|---|---|---|---|---|---|---|---|
| ATOM | 1350 | O | TYR | 68 | 10.669 | −5.713 | 0.724 | 1.00 | 0.00 | PROT |
| ATOM | 1351 | N | VAL | 69 | 12.051 | −7.409 | 0.594 | 1.00 | 0.00 | PROT |
| ATOM | 1352 | HN | VAL | 69 | 12.179 | −8.366 | 0.434 | 1.00 | 0.00 | PROT |
| ATOM | 1353 | CA | VAL | 69 | 13.209 | −6.562 | 0.956 | 1.00 | 0.00 | PROT |
| ATOM | 1354 | HA | VAL | 69 | 12.929 | −5.841 | 1.710 | 1.00 | 0.00 | PROT |
| ATOM | 1355 | CB | VAL | 69 | 14.225 | −7.551 | 1.517 | 1.00 | 0.00 | PROT |
| ATOM | 1356 | HB | VAL | 69 | 13.798 | −8.067 | 2.365 | 1.00 | 0.00 | PROT |
| ATOM | 1357 | CG1 | VAL | 69 | 15.462 | −6.788 | 1.956 | 1.00 | 0.00 | PROT |
| ATOM | 1358 | HG11 | VAL | 69 | 16.224 | −6.878 | 1.199 | 1.00 | 0.00 | PROT |
| ATOM | 1359 | HG12 | VAL | 69 | 15.823 | −7.195 | 2.887 | 1.00 | 0.00 | PROT |
| ATOM | 1360 | HG13 | VAL | 69 | 15.205 | −5.748 | 2.091 | 1.00 | 0.00 | PROT |
| ATOM | 1361 | CG2 | VAL | 69 | 14.608 | −8.568 | 0.439 | 1.00 | 0.00 | PROT |
| ATOM | 1362 | HG21 | VAL | 69 | 14.248 | −8.229 | −0.521 | 1.00 | 0.00 | PROT |
| ATOM | 1363 | HG22 | VAL | 69 | 14.164 | −9.524 | 0.672 | 1.00 | 0.00 | PROT |
| ATOM | 1364 | HG23 | VAL | 69 | 15.683 | −8.670 | 0.405 | 1.00 | 0.00 | PROT |
| ATOM | 1365 | C | VAL | 69 | 13.771 | −5.856 | −0.280 | 1.00 | 0.00 | PROT |
| ATOM | 1366 | O | VAL | 69 | 14.890 | −6.098 | −0.689 | 1.00 | 0.00 | PROT |
| ATOM | 1367 | N | SER | 70 | 13.005 | −4.985 | −0.883 | 1.00 | 0.00 | PROT |
| ATOM | 1368 | HN | SER | 70 | 12.109 | −4.797 | −0.533 | 1.00 | 0.00 | PROT |
| ATOM | 1369 | CA | SER | 70 | 13.502 | −4.257 | −2.086 | 1.00 | 0.00 | PROT |
| ATOM | 1370 | HA | SER | 70 | 14.432 | −3.758 | −1.863 | 1.00 | 0.00 | PROT |
| ATOM | 1371 | CB | SER | 70 | 13.719 | −5.340 | −3.147 | 1.00 | 0.00 | PROT |
| ATOM | 1372 | HB1 | SER | 70 | 14.694 | −5.786 | −3.012 | 1.00 | 0.00 | PROT |
| ATOM | 1373 | HB2 | SER | 70 | 12.958 | −6.100 | −3.048 | 1.00 | 0.00 | PROT |
| ATOM | 1374 | OG | SER | 70 | 13.642 | −4.758 | −4.440 | 1.00 | 0.00 | PROT |
| ATOM | 1375 | HG | SER | 70 | 14.287 | −4.049 | −4.486 | 1.00 | 0.00 | PROT |
| ATOM | 1376 | C | SER | 70 | 12.462 | −3.246 | −2.568 | 1.00 | 0.00 | PROT |
| ATOM | 1377 | O | SER | 70 | 11.283 | −3.378 | −2.302 | 1.00 | 0.00 | PROT |
| ATOM | 1378 | N | LYS | 71 | 12.889 | −2.236 | −3.276 | 1.00 | 0.00 | PROT |
| ATOM | 1379 | HN | LYS | 71 | 13.844 | −2.149 | −3.479 | 1.00 | 0.00 | PROT |
| ATOM | 1380 | CA | LYS | 71 | 11.926 | −1.217 | −3.776 | 1.00 | 0.00 | PROT |
| ATOM | 1381 | HA | LYS | 71 | 11.512 | −0.659 | −2.950 | 1.00 | 0.00 | PROT |
| ATOM | 1382 | CB | LYS | 71 | 12.759 | −0.300 | −4.678 | 1.00 | 0.00 | PROT |
| ATOM | 1383 | HB1 | LYS | 71 | 13.491 | 0.222 | −4.079 | 1.00 | 0.00 | PROT |
| ATOM | 1384 | HB2 | LYS | 71 | 13.264 | −0.893 | −5.425 | 1.00 | 0.00 | PROT |
| ATOM | 1385 | CG | LYS | 71 | 11.848 | 0.721 | −5.369 | 1.00 | 0.00 | PROT |
| ATOM | 1386 | HG1 | LYS | 71 | 11.962 | 1.684 | −4.895 | 1.00 | 0.00 | PROT |
| ATOM | 1387 | HG2 | LYS | 71 | 10.820 | 0.404 | −5.293 | 1.00 | 0.00 | PROT |
| ATOM | 1388 | CD | LYS | 71 | 12.235 | 0.831 | −6.845 | 1.00 | 0.00 | PROT |
| ATOM | 1389 | HD1 | LYS | 71 | 12.274 | −0.156 | −7.281 | 1.00 | 0.00 | PROT |
| ATOM | 1390 | HD2 | LYS | 71 | 13.204 | 1.300 | −6.928 | 1.00 | 0.00 | PROT |
| ATOM | 1391 | CE | LYS | 71 | 11.193 | 1.674 | −7.583 | 1.00 | 0.00 | PROT |
| ATOM | 1392 | HE1 | LYS | 71 | 11.524 | 2.700 | −7.656 | 1.00 | 0.00 | PROT |
| ATOM | 1393 | HE2 | LYS | 71 | 10.240 | 1.620 | −7.079 | 1.00 | 0.00 | PROT |
| ATOM | 1394 | NZ | LYS | 71 | 11.098 | 1.063 | −8.939 | 1.00 | 0.00 | PROT |
| ATOM | 1395 | HZ1 | LYS | 71 | 11.935 | 1.326 | −9.497 | 1.00 | 0.00 | PROT |
| ATOM | 1396 | HZ2 | LYS | 71 | 10.240 | 1.408 | −9.415 | 1.00 | 0.00 | PROT |
| ATOM | 1397 | HZ3 | LYS | 71 | 11.052 | 0.028 | −8.850 | 1.00 | 0.00 | PROT |
| ATOM | 1398 | C | LYS | 71 | 10.812 | −1.895 | −4.576 | 1.00 | 0.00 | PROT |
| ATOM | 1399 | O | LYS | 71 | 9.696 | −2.022 | −4.115 | 1.00 | 0.00 | PROT |
| ATOM | 1400 | N | LYS | 72 | 11.118 | −2.345 | −5.767 | 1.00 | 0.00 | PROT |
| ATOM | 1401 | HN | LYS | 72 | 12.023 | −2.219 | −6.113 | 1.00 | 0.00 | PROT |
| ATOM | 1402 | CA | LYS | 72 | 10.089 | −3.016 | −6.621 | 1.00 | 0.00 | PROT |
| ATOM | 1403 | HA | LYS | 72 | 9.444 | −2.280 | −7.076 | 1.00 | 0.00 | PROT |
| ATOM | 1404 | CB | LYS | 72 | 10.893 | −3.752 | −7.695 | 1.00 | 0.00 | PROT |
| ATOM | 1405 | HB1 | LYS | 72 | 11.924 | −3.831 | −7.382 | 1.00 | 0.00 | PROT |
| ATOM | 1406 | HB2 | LYS | 72 | 10.483 | −4.741 | −7.838 | 1.00 | 0.00 | PROT |
| ATOM | 1407 | CG | LYS | 72 | 10.817 | −2.973 | −9.010 | 1.00 | 0.00 | PROT |
| ATOM | 1408 | HG1 | LYS | 72 | 11.745 | −3.088 | −9.551 | 1.00 | 0.00 | PROT |
| ATOM | 1409 | HG2 | LYS | 72 | 10.650 | −1.927 | −8.800 | 1.00 | 0.00 | PROT |
| ATOM | 1410 | CD | LYS | 72 | 9.663 | −3.514 | −9.857 | 1.00 | 0.00 | PROT |
| ATOM | 1411 | HD1 | LYS | 72 | 9.691 | −4.593 | −9.857 | 1.00 | 0.00 | PROT |
| ATOM | 1412 | HD2 | LYS | 72 | 8.725 | −3.178 | −9.442 | 1.00 | 0.00 | PROT |
| ATOM | 1413 | CE | LYS | 72 | 9.798 | −3.000 | −11.292 | 1.00 | 0.00 | PROT |
| ATOM | 1414 | HE1 | LYS | 72 | 10.838 | −2.838 | −11.537 | 1.00 | 0.00 | PROT |
| ATOM | 1415 | HE2 | LYS | 72 | 9.234 | −2.089 | −11.420 | 1.00 | 0.00 | PROT |
| ATOM | 1416 | NZ | LYS | 72 | 9.230 | −4.085 | −12.140 | 1.00 | 0.00 | PROT |
| ATOM | 1417 | HZ1 | LYS | 72 | 9.455 | −3.899 | −13.139 | 1.00 | 0.00 | PROT |
| ATOM | 1418 | HZ2 | LYS | 72 | 8.197 | −4.116 | −12.018 | 1.00 | 0.00 | PROT |
| ATOM | 1419 | HZ3 | LYS | 72 | 9.639 | −4.998 | −11.857 | 1.00 | 0.00 | PROT |
| ATOM | 1420 | C | LYS | 72 | 9.261 | −4.014 | −5.805 | 1.00 | 0.00 | PROT |
| ATOM | 1421 | O | LYS | 72 | 8.121 | −4.284 | −6.116 | 1.00 | 0.00 | PROT |
| ATOM | 1422 | N | LEU | 73 | 9.823 | −4.558 | −4.762 | 1.00 | 0.00 | PROT |
| ATOM | 1423 | HN | LEU | 73 | 10.742 | −4.321 | −4.519 | 1.00 | 0.00 | PROT |
| ATOM | 1424 | CA | LEU | 73 | 9.050 | −5.507 | −3.915 | 1.00 | 0.00 | PROT |
| ATOM | 1425 | HA | LEU | 73 | 8.459 | −6.166 | −4.534 | 1.00 | 0.00 | PROT |

TABLE 10-continued

Atomic Structure Coordinates of the P/CAF Bromadomain and HIV-1 Tat Peptide Complex

| ATOM | 1426 | CB | LEU | 73 | 10.104 | −6.304 | −3.147 | 1.00 | 0.00 | PROT |
|---|---|---|---|---|---|---|---|---|---|---|
| ATOM | 1427 | HB1 | LEU | 73 | 11.040 | −5.765 | −3.151 | 1.00 | 0.00 | PROT |
| ATOM | 1428 | HB2 | LEU | 73 | 9.776 | −6.449 | −2.128 | 1.00 | 0.00 | PROT |
| ATOM | 1429 | CG | LEU | 73 | 10.296 | −7.664 | −3.820 | 1.00 | 0.00 | PROT |
| ATOM | 1430 | HG | LEU | 73 | 10.522 | −7.519 | −4.866 | 1.00 | 0.00 | PROT |
| ATOM | 1431 | CD1 | LEU | 73 | 11.450 | −8.410 | −3.149 | 1.00 | 0.00 | PROT |
| ATOM | 1432 | HD11 | LEU | 73 | 11.254 | −9.471 | −3.171 | 1.00 | 0.00 | PROT |
| ATOM | 1433 | HD12 | LEU | 73 | 11.543 | −8.081 | −2.124 | 1.00 | 0.00 | PROT |
| ATOM | 1434 | HD13 | LEU | 73 | 12.368 | −8.202 | −3.678 | 1.00 | 0.00 | PROT |
| ATOM | 1435 | CD2 | LEU | 73 | 9.010 | −8.484 | −3.687 | 1.00 | 0.00 | PROT |
| ATOM | 1436 | HD21 | LEU | 73 | 9.254 | −9.489 | −3.375 | 1.00 | 0.00 | PROT |
| ATOM | 1437 | HD22 | LEU | 73 | 8.503 | −8.516 | −4.640 | 1.00 | 0.00 | PROT |
| ATOM | 1438 | HD23 | LEU | 73 | 8.366 | −8.026 | −2.951 | 1.00 | 0.00 | PROT |
| ATOM | 1439 | C | LEU | 73 | 8.147 | −4.731 | −2.951 | 1.00 | 0.00 | PROT |
| ATOM | 1440 | O | LEU | 73 | 6.948 | −4.916 | −2.927 | 1.00 | 0.00 | PROT |
| ATOM | 1441 | N | PHE | 74 | 8.715 | −3.847 | −2.171 | 1.00 | 0.00 | PROT |
| ATOM | 1442 | HN | PHE | 74 | 9.684 | −3.710 | −2.214 | 1.00 | 0.00 | PROT |
| ATOM | 1443 | CA | PHE | 74 | 7.892 | −3.045 | −1.217 | 1.00 | 0.00 | PROT |
| ATOM | 1444 | HA | PHE | 74 | 7.206 | −3.682 | −0.677 | 1.00 | 0.00 | PROT |
| ATOM | 1445 | CB | PHE | 74 | 8.906 | −2.414 | −0.262 | 1.00 | 0.00 | PROT |
| ATOM | 1446 | HB1 | PHE | 74 | 9.366 | −1.561 | −0.742 | 1.00 | 0.00 | PROT |
| ATOM | 1447 | HB2 | PHE | 74 | 9.665 | −3.140 | −0.008 | 1.00 | 0.00 | PROT |
| ATOM | 1448 | CG | PHE | 74 | 8.202 | −1.959 | 0.994 | 1.00 | 0.00 | PROT |
| ATOM | 1449 | CD1 | PHE | 74 | 8.019 | −0.592 | 1.234 | 1.00 | 0.00 | PROT |
| ATOM | 1450 | HD1 | PHE | 74 | 8.379 | 0.134 | 0.520 | 1.00 | 0.00 | PROT |
| ATOM | 1451 | CD2 | PHE | 74 | 7.735 | −2.901 | 1.918 | 1.00 | 0.00 | PROT |
| ATOM | 1452 | HD2 | PHE | 74 | 7.877 | −3.956 | 1.732 | 1.00 | 0.00 | PROT |
| ATOM | 1453 | CE1 | PHE | 74 | 7.369 | −0.167 | 2.398 | 1.00 | 0.00 | PROT |
| ATOM | 1454 | HE1 | PHE | 74 | 7.227 | 0.887 | 2.583 | 1.00 | 0.00 | PROT |
| ATOM | 1455 | CE2 | PHE | 74 | 7.085 | −2.476 | 3.082 | 1.00 | 0.00 | PROT |
| ATOM | 1456 | HE2 | PHE | 74 | 6.724 | −3.203 | 3.795 | 1.00 | 0.00 | PROT |
| ATOM | 1457 | CZ | PHE | 74 | 6.901 | −1.109 | 3.322 | 1.00 | 0.00 | PROT |
| ATOM | 1458 | HZ | PHE | 74 | 6.401 | −0.781 | 4.220 | 1.00 | 0.00 | PROT |
| ATOM | 1459 | C | PHE | 74 | 7.138 | −1.943 | −1.958 | 1.00 | 0.00 | PROT |
| ATOM | 1460 | O | PHE | 74 | 5.930 | −1.839 | −1.885 | 1.00 | 0.00 | PROT |
| ATOM | 1461 | N | MET | 75 | 7.852 | −1.106 | −2.654 | 1.00 | 0.00 | PROT |
| ATOM | 1462 | HN | MET | 75 | 8.826 | −1.209 | −2.689 | 1.00 | 0.00 | PROT |
| ATOM | 1463 | CA | MET | 75 | 7.200 | 0.006 | −3.397 | 1.00 | 0.00 | PROT |
| ATOM | 1464 | HA | MET | 75 | 6.821 | 0.746 | −2.708 | 1.00 | 0.00 | PROT |
| ATOM | 1465 | CB | MET | 75 | 8.324 | 0.604 | 4.242 | 1.00 | 0.00 | PROT |
| ATOM | 1466 | HB1 | MET | 75 | 7.921 | 1.351 | −4.906 | 1.00 | 0.00 | PROT |
| ATOM | 1467 | HB2 | MET | 75 | 8.792 | −0.169 | −4.821 | 1.00 | 0.00 | PROT |
| ATOM | 1468 | CG | MET | 75 | 9.365 | 1.235 | −3.316 | 1.00 | 0.00 | PROT |
| ATOM | 1469 | HG1 | MET | 75 | 9.058 | 1.110 | −2.289 | 1.00 | 0.00 | PROT |
| ATOM | 1470 | HG2 | MET | 75 | 10.319 | 0.757 | −3.466 | 1.00 | 0.00 | PROT |
| ATOM | 1471 | SD | MET | 75 | 9.512 | 2.993 | −3.689 | 1.00 | 0.00 | PROT |
| ATOM | 1472 | CE | MET | 75 | 7.867 | 3.463 | −3.126 | 1.00 | 0.00 | PROT |
| ATOM | 1473 | HE1 | MET | 75 | 7.927 | 3.799 | −2.102 | 1.00 | 0.00 | PROT |
| ATOM | 1474 | HE2 | MET | 75 | 7.209 | 2.609 | −3.189 | 1.00 | 0.00 | PROT |
| ATOM | 1475 | HE3 | MET | 75 | 7.490 | 4.261 | −3.751 | 1.00 | 0.00 | PROT |
| ATOM | 1476 | C | MET | 75 | 6.068 | −0.524 | −4.282 | 1.00 | 0.00 | PROT |
| ATOM | 1477 | O | MET | 75 | 5.160 | 0.199 | −4.639 | 1.00 | 0.00 | PROT |
| ATOM | 1478 | N | ALA | 76 | 6.097 | −1.786 | −4.617 | 1.00 | 0.00 | PROT |
| ATOM | 1479 | HN | ALA | 76 | 6.838 | −2.356 | −4.324 | 1.00 | 0.00 | PROT |
| ATOM | 1480 | CA | ALA | 76 | 5.017 | −2.351 | −5.474 | 1.00 | 0.00 | PROT |
| ATOM | 1481 | HA | ALA | 76 | 4.859 | −1.724 | −6.339 | 1.00 | 0.00 | PROT |
| ATOM | 1482 | CE | ALA | 76 | 5.533 | −3.725 | −5.903 | 1.00 | 0.00 | PROT |
| ATOM | 1483 | HB1 | ALA | 76 | 4.696 | −4.387 | −6.072 | 1.00 | 0.00 | PROT |
| ATOM | 1484 | HB2 | ALA | 76 | 6.162 | −4.133 | −5.125 | 1.00 | 0.00 | PROT |
| ATOM | 1485 | HB3 | ALA | 76 | 6.104 | −3.627 | −6.814 | 1.00 | 0.00 | PROT |
| ATOM | 1486 | C | ALA | 76 | 3.715 | −2.502 | −4.682 | 1.00 | 0.00 | PROT |
| ATOM | 1487 | O | ALA | 76 | 2.753 | −1.798 | −4.915 | 1.00 | 0.00 | PROT |
| ATOM | 1488 | N | ASP | 77 | 3.668 | −3.429 | −3.760 | 1.00 | 0.00 | PROT |
| ATOM | 1489 | HN | ASP | 77 | 4.449 | −3.996 | −3.597 | 1.00 | 0.00 | PROT |
| ATOM | 1490 | CA | ASP | 77 | 2.412 | −3.647 | −2.984 | 1.00 | 0.00 | PROT |
| ATOM | 1491 | HA | ASP | 77 | 1.640 | −4.028 | −3.636 | 1.00 | 0.00 | PROT |
| ATOM | 1492 | CB | ASP | 77 | 2.766 | −4.697 | −1.923 | 1.00 | 0.00 | PROT |
| ATOM | 1493 | HB1 | ASP | 77 | 1.930 | −4.828 | −1.255 | 1.00 | 0.00 | PROT |
| ATOM | 1494 | HB2 | ASP | 77 | 2.986 | −5.636 | −2.409 | 1.00 | 0.00 | PROT |
| ATOM | 1495 | CG | ASP | 77 | 3.986 | −4.245 | −1.121 | 1.00 | 0.00 | PROT |
| ATOM | 1496 | OD1 | ASP | 77 | 3.851 | −4.078 | 0.080 | 1.00 | 0.00 | PROT |
| ATOM | 1497 | OD2 | ASP | 77 | 5.034 | −4.080 | −1.718 | 1.00 | 0.00 | PROT |
| ATOM | 1498 | C | ASP | 77 | 1.944 | −2.345 | −2.327 | 1.00 | 0.00 | PROT |
| ATOM | 1499 | O | ASP | 77 | 0.781 | −1.993 | −2.389 | 1.00 | 0.00 | PROT |
| ATOM | 1500 | N | LEU | 78 | 2.830 | −1.621 | −1.700 | 1.00 | 0.00 | PROT |
| ATOM | 1501 | HN | LEU | 78 | 3.766 | −1.906 | −1.667 | 1.00 | 0.00 | PROT |
| ATOM | 1502 | CA | LEU | 78 | 2.415 | −0.345 | −1.057 | 1.00 | 0.00 | PROT |

TABLE 10-continued

Atomic Structure Coordinates of the P/CAF Bromadomain and HIV-1 Tat Peptide Complex

| ATOM | 1503 | HA | LEU | 78 | 1.688 | −0.536 | −0.282 | 1.00 | 0.00 | PROT |
| ATOM | 1504 | CB | LEU | 78 | 3.705 | 0.226 | −0.455 | 1.00 | 0.00 | PROT |
| ATOM | 1505 | HB1 | LEU | 78 | 4.265 | −0.572 | 0.010 | 1.00 | 0.00 | PROT |
| ATOM | 1506 | HB2 | LEU | 78 | 4.299 | 0.671 | −1.239 | 1.00 | 0.00 | PROT |
| ATOM | 1507 | CG | LEU | 78 | 3.370 | 1.291 | 0.596 | 1.00 | 0.00 | PROT |
| ATOM | 1508 | HG | LEU | 78 | 2.897 | 2.134 | 0.116 | 1.00 | 0.00 | PROT |
| ATOM | 1509 | CD1 | LEU | 78 | 4.661 | 1.751 | 1.277 | 1.00 | 0.00 | PROT |
| ATOM | 1510 | HD11 | LEU | 78 | 5.445 | 1.842 | 0.541 | 1.00 | 0.00 | PROT |
| ATOM | 1511 | HD12 | LEU | 78 | 4.951 | 1.027 | 2.025 | 1.00 | 0.00 | PROT |
| ATOM | 1512 | HD13 | LEU | 78 | 4.497 | 2.709 | 1.749 | 1.00 | 0.00 | PROT |
| ATOM | 1513 | CD2 | LEU | 78 | 2.427 | 0.708 | 1.653 | 1.00 | 0.00 | PROT |
| ATOM | 1514 | HD21 | LEU | 78 | 2.801 | 0.942 | 2.638 | 1.00 | 0.00 | PROT |
| ATOM | 1515 | HD22 | LEU | 78 | 2.373 | −0.364 | 1.534 | 1.00 | 0.00 | PROT |
| ATOM | 1516 | HD23 | LEU | 78 | 1.442 | 1.134 | 1.530 | 1.00 | 0.00 | PROT |
| ATOM | 1517 | C | LEU | 78 | 1.834 | 0.598 | −2.112 | 1.00 | 0.00 | PROT |
| ATOM | 1518 | O | LEU | 78 | 0.727 | 1.090 | −1.981 | 1.00 | 0.00 | PROT |
| ATOM | 1519 | N | GLN | 79 | 2.550 | 0.823 | −3.180 | 1.00 | 0.00 | PROT |
| ATOM | 1520 | HN | GLN | 79 | 3.427 | 0.397 | −3.285 | 1.00 | 0.00 | PROT |
| ATOM | 1521 | CA | GLN | 79 | 2.003 | 1.691 | −4.256 | 1.00 | 0.00 | PROT |
| ATOM | 1522 | HA | GLN | 79 | 1.775 | 2.673 | −3.870 | 1.00 | 0.00 | PROT |
| ATOM | 1523 | CB | GLN | 79 | 3.106 | 1.772 | −5.312 | 1.00 | 0.00 | PROT |
| ATOM | 1524 | HB1 | GLN | 79 | 4.000 | 2.185 | −4.869 | 1.00 | 0.00 | PROT |
| ATOM | 1525 | HB2 | GLN | 79 | 3.316 | 0.783 | −5.691 | 1.00 | 0.00 | PROT |
| ATOM | 1526 | CG | GLN | 79 | 2.642 | 2.670 | −6.461 | 1.00 | 0.00 | PROT |
| ATOM | 1527 | HG1 | GLN | 79 | 3.421 | 2.734 | −7.206 | 1.00 | 0.00 | PROT |
| ATOM | 1528 | HG2 | GLN | 79 | 1.751 | 2.252 | −6.907 | 1.00 | 0.00 | PROT |
| ATOM | 1529 | CD | GLN | 79 | 2.334 | 4.070 | −5.923 | 1.00 | 0.00 | PROT |
| ATOM | 1530 | OE1 | GLN | 79 | 3.200 | 4.920 | −5.878 | 1.00 | 0.00 | PROT |
| ATOM | 1531 | NE2 | GLN | 79 | 1.126 | 4.346 | −5.510 | 1.00 | 0.00 | PROT |
| ATOM | 1532 | HE21 | GLN | 79 | 0.427 | 3.660 | −5.546 | 1.00 | 0.00 | PROT |
| ATOM | 1533 | HE22 | GLN | 79 | 0.919 | 5.239 | −5.164 | 1.00 | 0.00 | PROT |
| ATOM | 1534 | C | GLN | 79 | 0.751 | 1.040 | −4.840 | 1.00 | 0.00 | PROT |
| ATOM | 1535 | O | GLN | 79 | −0.188 | 1.707 | −5.223 | 1.00 | 0.00 | PROT |
| ATOM | 1536 | N | ARG | 80 | 0.722 | −0.266 | −4.886 | 1.00 | 0.00 | PROT |
| ATOM | 1537 | HN | ARG | 80 | 1.485 | −0.785 | −4.559 | 1.00 | 0.00 | PROT |
| ATOM | 1538 | CA | ARG | 80 | −0.480 | −0.962 | −5.420 | 1.00 | 0.00 | PROT |
| ATOM | 1539 | HA | ARG | 80 | −0.746 | −0.558 | −6.383 | 1.00 | 0.00 | PROT |
| ATOM | 1540 | CB | ARG | 80 | −0.074 | −2.432 | −5.547 | 1.00 | 0.00 | PROT |
| ATOM | 1541 | HB1 | ARG | 80 | 0.739 | −2.639 | −4.868 | 1.00 | 0.00 | PROT |
| ATOM | 1542 | HB2 | ARG | 80 | −0.918 | −3.059 | −5.296 | 1.00 | 0.00 | PROT |
| ATOM | 1543 | CG | ARG | 80 | 0.373 | −2.731 | −6.984 | 1.00 | 0.00 | PROT |
| ATOM | 1544 | HG1 | ARG | 80 | 0.694 | −3.759 | −7.049 | 1.00 | 0.00 | PROT |
| ATOM | 1545 | HG2 | ARG | 80 | 1.197 | −2.083 | −7.244 | 1.00 | 0.00 | PROT |
| ATOM | 1546 | CD | ARG | 80 | −0.785 | −2.498 | −7.968 | 1.00 | 0.00 | PROT |
| ATOM | 1547 | HD1 | ARG | 80 | −0.534 | −2.896 | −8.940 | 1.00 | 0.00 | PROT |
| ATOM | 1548 | HD2 | ARG | 80 | −1.008 | −1.446 | −8.043 | 1.00 | 0.00 | PROT |
| ATOM | 1549 | NE | ARG | 80 | −1.951 | −3.240 | −7.395 | 1.00 | 0.00 | PROT |
| ATOM | 1550 | HE | ARG | 80 | −1.794 | −3.974 | −6.765 | 1.00 | 0.00 | PROT |
| ATOM | 1551 | CZ | ARG | 80 | −3.181 | −2.927 | −7.732 | 1.00 | 0.00 | PROT |
| ATOM | 1552 | NH1 | ARG | 80 | −3.427 | −1.954 | −8.574 | 1.00 | 0.00 | PROT |
| ATOM | 1553 | HH11 | ARG | 80 | −4.372 | −1.732 | −8.814 | 1.00 | 0.00 | PROT |
| ATOM | 1554 | HH12 | ARG | 80 | −2.678 | −1.433 | −8.980 | 1.00 | 0.00 | PROT |
| ATOM | 1555 | NH2 | ARG | 80 | −4.179 | −3.592 | −7.218 | 1.00 | 0.00 | PROT |
| ATOM | 1556 | HH21 | ARG | 80 | −5.117 | −3.357 | −7.470 | 1.00 | 0.00 | PROT |
| ATOM | 1557 | HH22 | ARG | 80 | −4.004 | −4.337 | −6.574 | 1.00 | 0.00 | PROT |
| ATOM | 1558 | C | ARG | 80 | −1.649 | −0.820 | −4.445 | 1.00 | 0.00 | PROT |
| ATOM | 1559 | O | ARG | 80 | −2.784 | −1.067 | −4.792 | 1.00 | 0.00 | PROT |
| ATOM | 1560 | N | VAL | 81 | −1.381 | −0.472 | −3.213 | 1.00 | 0.00 | PROT |
| ATOM | 1561 | HN | VAL | 81 | −0.468 | −0.226 | −2.958 | 1.00 | 0.00 | PROT |
| ATOM | 1562 | CA | VAL | 81 | −2.497 | −0.266 | −2.253 | 1.00 | 0.00 | PROT |
| ATOM | 1563 | HA | VAL | 81 | −3.256 | −1.024 | −2.380 | 1.00 | 0.00 | PROT |
| ATOM | 1564 | CB | VAL | 81 | −1.866 | −0.359 | −0.857 | 1.00 | 0.00 | PROT |
| ATOM | 1565 | HB | VAL | 81 | −0.983 | 0.264 | −0.817 | 1.00 | 0.00 | PROT |
| ATOM | 1566 | CG1 | VAL | 81 | −1.480 | −1.810 | −0.570 | 1.00 | 0.00 | PROT |
| ATOM | 1567 | HG11 | VAL | 81 | −1.187 | −2.293 | −1.490 | 1.00 | 0.00 | PROT |
| ATOM | 1568 | HG12 | VAL | 81 | −2.326 | −2.329 | −0.144 | 1.00 | 0.00 | PROT |
| ATOM | 1569 | HG13 | VAL | 81 | −0.655 | −1.832 | 0.129 | 1.00 | 0.00 | PROT |
| ATOM | 1570 | CG2 | VAL | 81 | −2.872 | 0.112 | 0.201 | 1.00 | 0.00 | PROT |
| ATOM | 1571 | HG21 | VAL | 81 | −3.713 | −0.565 | 0.223 | 1.00 | 0.00 | PROT |
| ATOM | 1572 | HG22 | VAL | 81 | −3.217 | 1.106 | −0.046 | 1.00 | 0.00 | PROT |
| ATOM | 1573 | HG23 | VAL | 81 | −2.396 | 0.126 | 1.170 | 1.00 | 0.00 | PROT |
| ATOM | 1574 | C | VAL | 81 | −3.071 | 1.119 | −2.498 | 1.00 | 0.00 | PROT |
| ATOM | 1575 | O | VAL | 81 | −4.262 | 1.338 | −2.448 | 1.00 | 0.00 | PROT |
| ATOM | 1576 | N | PHE | 82 | −2.211 | 2.052 | −2.777 | 1.00 | 0.00 | PROT |
| ATOM | 1577 | HN | PHE | 82 | −1.256 | 1.830 | −2.832 | 1.00 | 0.00 | PROT |
| ATOM | 1578 | CA | PHE | 82 | −2.670 | 3.430 | −3.074 | 1.00 | 0.00 | PROT |
| ATOM | 1579 | HA | PHE | 82 | −3.460 | 3.724 | −2.398 | 1.00 | 0.00 | PROT |

TABLE 10-continued

Atomic Structure Coordinates of the P/CAF Bromadomain and HIV-1 Tat Peptide Complex

| ATOM | 1580 | CB | PHE | 82 | −1.430 | 4.302 | −2.869 | 1.00 | 0.00 | PROT |
|---|---|---|---|---|---|---|---|---|---|---|
| ATOM | 1581 | HB1 | PHE | 82 | −0.691 | 4.048 | −3.609 | 1.00 | 0.00 | PROT |
| ATOM | 1582 | HB2 | PHE | 82 | −1.702 | 5.331 | −2.983 | 1.00 | 0.00 | PROT |
| ATOM | 1583 | CG | PHE | 82 | −0.850 | 4.088 | −1.486 | 1.00 | 0.00 | PROT |
| ATOM | 1584 | CD1 | PHE | 82 | 0.538 | 4.105 | −1.307 | 1.00 | 0.00 | PROT |
| ATOM | 1585 | HD1 | PHE | 82 | 1.190 | 4.259 | −2.154 | 1.00 | 0.00 | PROT |
| ATOM | 1586 | CD2 | PHE | 82 | −1.695 | 3.896 | −0.384 | 1.00 | 0.00 | PROT |
| ATOM | 1587 | HD2 | PHE | 82 | −2.766 | 3.886 | −0.520 | 1.00 | 0.00 | PROT |
| ATOM | 1588 | CE1 | PHE | 82 | 1.083 | 3.916 | −0.032 | 1.00 | 0.00 | PROT |
| ATOM | 1589 | HE1 | PHE | 82 | 2.154 | 3.925 | 0.105 | 1.00 | 0.00 | PROT |
| ATOM | 1590 | CE2 | PHE | 82 | −1.148 | 3.705 | 0.891 | 1.00 | 0.00 | PROT |
| ATOM | 1591 | HE2 | PHE | 82 | −1.797 | 3.551 | 1.739 | 1.00 | 0.00 | PROT |
| ATOM | 1592 | CZ | PHE | 82 | 0.240 | 3.716 | 1.067 | 1.00 | 0.00 | PROT |
| ATOM | 1593 | HZ | PHE | 82 | 0.661 | 3.569 | 2.051 | 1.00 | 0.00 | PROT |
| ATOM | 1594 | C | PHE | 82 | −3.139 | 3.510 | −4.526 | 1.00 | 0.00 | PROT |
| ATOM | 1595 | O | PHE | 82 | −4.149 | 4.111 | −4.835 | 1.00 | 0.00 | PROT |
| ATOM | 1596 | N | THR | 83 | −2.407 | 2.900 | −5.419 | 1.00 | 0.00 | PROT |
| ATOM | 1597 | HN | THR | 83 | −1.599 | 2.420 | −5.141 | 1.00 | 0.00 | PROT |
| ATOM | 1598 | CA | THR | 83 | −2.798 | 2.923 | −6.855 | 1.00 | 0.00 | PROT |
| ATOM | 1599 | HA | THR | 83 | −2.812 | 3.938 | −7.224 | 1.00 | 0.00 | PROT |
| ATOM | 1600 | CB | THR | 83 | −1.711 | 2.111 | −7.564 | 1.00 | 0.00 | PROT |
| ATOM | 1601 | HB | THR | 83 | −1.671 | 1.118 | −7.142 | 1.00 | 0.00 | PROT |
| ATOM | 1602 | OG1 | THR | 83 | −0.455 | 2.751 | −7.391 | 1.00 | 0.00 | PROT |
| ATOM | 1603 | HG1 | THR | 83 | −0.446 | 3.541 | −7.936 | 1.00 | 0.00 | PROT |
| ATOM | 1604 | CG2 | THR | 83 | −2.029 | 2.019 | −9.057 | 1.00 | 0.00 | PROT |
| ATOM | 1605 | HG21 | THR | 83 | −1.107 | 1.973 | −9.618 | 1.00 | 0.00 | PROT |
| ATOM | 1606 | HG22 | THR | 83 | −2.592 | 2.889 | −9.359 | 1.00 | 0.00 | PROT |
| ATOM | 1607 | HG23 | THR | 83 | −2.661 | 1.129 | −9.246 | 1.00 | 0.00 | PROT |
| ATOM | 1608 | C | THR | 83 | −4.166 | 2.267 | −7.040 | 1.00 | 0.00 | PROT |
| ATOM | 1609 | O | THR | 83 | −5.064 | 2.842 | −7.623 | 1.00 | 0.00 | PROT |
| ATOM | 1610 | N | ASN | 84 | −4.341 | 1.070 | −6.545 | 1.00 | 0.00 | PROT |
| ATOM | 1611 | HN | ASN | 84 | −3.612 | 0.620 | −6.070 | 1.00 | 0.00 | PROT |
| ATOM | 1612 | CA | ASN | 84 | −5.666 | 0.405 | −6.690 | 1.00 | 0.00 | PROT |
| ATOM | 1613 | HA | ASN | 84 | −5.929 | 0.343 | −7.735 | 1.00 | 0.00 | PROT |
| ATOM | 1614 | CB | ASN | 84 | −5.475 | −1.020 | −6.114 | 1.00 | 0.00 | PROT |
| ATOM | 1615 | HB1 | ASN | 84 | −6.068 | −1.713 | −6.697 | 1.00 | 0.00 | PROT |
| ATOM | 1616 | HB2 | ASN | 84 | −4.432 | −1.291 | −6.193 | 1.00 | 0.00 | PROT |
| ATOM | 1617 | CG | ASN | 84 | −5.902 | −1.115 | −4.636 | 1.00 | 0.00 | PROT |
| ATOM | 1618 | OD1 | ASN | 84 | −7.044 | −0.865 | −4.304 | 1.00 | 0.00 | PROT |
| ATOM | 1619 | ND2 | ASN | 84 | −5.032 | −1.484 | −3.739 | 1.00 | 0.00 | PROT |
| ATOM | 1620 | HD21 | ASN | 84 | −5.296 | −1.548 | −2.797 | 1.00 | 0.00 | PROT |
| ATOM | 1621 | HD22 | ASN | 84 | −4.111 | −1.689 | −4.004 | 1.00 | 0.00 | PROT |
| ATOM | 1622 | C | ASN | 84 | −6.725 | 1.219 | −5.938 | 1.00 | 0.00 | PROT |
| ATOM | 1623 | O | ASN | 84 | −7.789 | 1.500 | −6.452 | 1.00 | 0.00 | PROT |
| ATOM | 1624 | N | CYS | 85 | −6.429 | 1.616 | −4.727 | 1.00 | 0.00 | PROT |
| ATOM | 1625 | HN | CYS | 85 | −5.558 | 1.390 | −4.333 | 1.00 | 0.00 | PROT |
| ATOM | 1626 | CA | CYS | 85 | −7.407 | 2.437 | −3.960 | 1.00 | 0.00 | PROT |
| ATOM | 1627 | HA | CYS | 85 | −8.278 | 1.850 | −3.710 | 1.00 | 0.00 | PROT |
| ATOM | 1628 | CB | CYS | 85 | −6.667 | 2.863 | −2.690 | 1.00 | 0.00 | PROT |
| ATOM | 1629 | HB1 | CYS | 85 | −7.062 | 3.805 | −2.342 | 1.00 | 0.00 | PROT |
| ATOM | 1630 | HB2 | CYS | 85 | −5.615 | 2.973 | −2.906 | 1.00 | 0.00 | PROT |
| ATOM | 1631 | SG | CYS | 85 | −6.897 | 1.605 | −1.409 | 1.00 | 0.00 | PROT |
| ATOM | 1632 | HG | CYS | 85 | −6.090 | 1.088 | −1.353 | 1.00 | 0.00 | PROT |
| ATOM | 1633 | C | CYS | 85 | −7.804 | 3.659 | −4.787 | 1.00 | 0.00 | PROT |
| ATOM | 1634 | O | CYS | 85 | −8.959 | 3.871 | −5.072 | 1.00 | 0.00 | PROT |
| ATOM | 1635 | N | LYS | 86 | −6.847 | 4.433 | −5.219 | 1.00 | 0.00 | PROT |
| ATOM | 1636 | HN | LYS | 86 | −5.915 | 4.232 | −4.996 | 1.00 | 0.00 | PROT |
| ATOM | 1637 | CA | LYS | 86 | −7.174 | 5.616 | −6.064 | 1.00 | 0.00 | PROT |
| ATOM | 1638 | HA | LYS | 86 | −7.808 | 6.303 | −5.524 | 1.00 | 0.00 | PROT |
| ATOM | 1639 | CB | LYS | 86 | −5.823 | 6.263 | −6.367 | 1.00 | 0.00 | PROT |
| ATOM | 1640 | HB1 | LYS | 86 | −5.174 | 5.538 | −6.837 | 1.00 | 0.00 | PROT |
| ATOM | 1641 | HB2 | LYS | 86 | −5.966 | 7.102 | −7.031 | 1.00 | 0.00 | PROT |
| ATOM | 1642 | CG | LYS | 86 | −5.189 | 6.745 | −5.062 | 1.00 | 0.00 | PROT |
| ATOM | 1643 | HG1 | LYS | 86 | −5.557 | 6.147 | −4.241 | 1.00 | 0.00 | PROT |
| ATOM | 1644 | HG2 | LYS | 86 | −4.115 | 6.647 | −5.125 | 1.00 | 0.00 | PROT |
| ATOM | 1645 | CD | LYS | 86 | −5.557 | 8.212 | −4.829 | 1.00 | 0.00 | PROT |
| ATOM | 1646 | HD1 | LYS | 86 | −6.383 | 8.270 | −4.136 | 1.00 | 0.00 | PROT |
| ATOM | 1647 | HD2 | LYS | 86 | −5.841 | 8.665 | −5.767 | 1.00 | 0.00 | PROT |
| ATOM | 1648 | CE | LYS | 86 | −4.351 | 8.953 | −4.250 | 1.00 | 0.00 | PROT |
| ATOM | 1649 | HE1 | LYS | 86 | −3.545 | 8.261 | −4.050 | 1.00 | 0.00 | PROT |
| ATOM | 1650 | HE2 | LYS | 86 | −4.630 | 9.477 | −3.347 | 1.00 | 0.00 | PROT |
| ATOM | 1651 | NZ | LYS | 86 | −3.952 | 9.921 | −5.310 | 1.00 | 0.00 | PROT |
| ATOM | 1652 | HZ1 | LYS | 86 | −3.914 | 9.433 | −6.228 | 1.00 | 0.00 | PROT |
| ATOM | 1653 | HZ2 | LYS | 86 | −3.015 | 10.313 | −5.087 | 1.00 | 0.00 | PROT |
| ATOM | 1654 | HZ3 | LYS | 86 | −4.649 | 10.692 | −5.355 | 1.00 | 0.00 | PROT |
| ATOM | 1655 | C | LYS | 86 | −7.855 | 5.163 | −7.360 | 1.00 | 0.00 | PROT |
| ATOM | 1656 | O | LYS | 86 | −8.543 | 5.924 | −8.012 | 1.00 | 0.00 | PROT |

TABLE 10-continued

Atomic Structure Coordinates of the P/CAF Bromadomain and HIV-1 Tat Peptide Complex

| ATOM | 1657 | N | GLU | 87 | −7.671 | 3.924 | −7.734 | 1.00 | 0.00 | PROT |
|---|---|---|---|---|---|---|---|---|---|---|
| ATOM | 1658 | HN | GLU | 87 | −7.112 | 3.329 | −7.192 | 1.00 | 0.00 | PROT |
| ATOM | 1659 | CA | GLU | 87 | −8.305 | 3.412 | −8.981 | 1.00 | 0.00 | PROT |
| ATOM | 1660 | HA | GLU | 87 | −7.975 | 3.985 | −9.836 | 1.00 | 0.00 | PROT |
| ATOM | 1661 | CB | GLU | 87 | −7.819 | 1.964 | −9.088 | 1.00 | 0.00 | PROT |
| ATOM | 1662 | HB1 | GLU | 87 | −6.936 | 1.836 | −8.480 | 1.00 | 0.00 | PROT |
| ATOM | 1663 | HB2 | GLU | 87 | −8.594 | 1.295 | −8.740 | 1.00 | 0.00 | PROT |
| ATOM | 1664 | CG | GLU | 87 | −7.485 | 1.638 | −10.544 | 1.00 | 0.00 | PROT |
| ATOM | 1665 | HG1 | GLU | 87 | −7.780 | 2.463 | −11.176 | 1.00 | 0.00 | PROT |
| ATOM | 1666 | HG2 | GLU | 87 | −8.016 | 0.747 | −10.843 | 1.00 | 0.00 | PROT |
| ATOM | 1667 | CD | GLU | 87 | −5.980 | 1.403 | −10.680 | 1.00 | 0.00 | PROT |
| ATOM | 1668 | OE1 | GLU | 87 | −5.228 | 2.317 | −10.382 | 1.00 | 0.00 | PROT |
| ATOM | 1669 | OE2 | GLU | 87 | −5.604 | 0.312 | −11.074 | 1.00 | 0.00 | PROT |
| ATOM | 1670 | C | GLU | 87 | −9.831 | 3.452 | −8.864 | 1.00 | 0.00 | PROT |
| ATOM | 1671 | O | GLU | 87 | −10.529 | 3.767 | −9.807 | 1.00 | 0.00 | PROT |
| ATOM | 1672 | N | TYR | 88 | −10.352 | 3.133 | −7.711 | 1.00 | 0.00 | PROT |
| ATOM | 1673 | HN | TYR | 88 | −9.768 | 2.870 | −6.970 | 1.00 | 0.00 | PROT |
| ATOM | 1674 | CA | TYR | 88 | −11.833 | 3.129 | −7.530 | 1.00 | 0.00 | PROT |
| ATOM | 1675 | HA | TYR | 88 | −12.324 | 3.399 | −8.453 | 1.00 | 0.00 | PROT |
| ATOM | 1676 | CB | TYR | 88 | −12.153 | 1.671 | −7.162 | 1.00 | 0.00 | PROT |
| ATOM | 1677 | HB1 | TYR | 88 | −12.049 | 1.052 | −8.041 | 1.00 | 0.00 | PROT |
| ATOM | 1678 | HB2 | TYR | 88 | −11.460 | 1.335 | −6.405 | 1.00 | 0.00 | PROT |
| ATOM | 1679 | CG | TYR | 88 | −13.564 | 1.553 | −6.634 | 1.00 | 0.00 | PROT |
| ATOM | 1680 | CD1 | TYR | 88 | −14.640 | 2.046 | −7.380 | 1.00 | 0.00 | PROT |
| ATOM | 1681 | HD1 | TYR | 88 | −14.465 | 2.512 | −8.339 | 1.00 | 0.00 | PROT |
| ATOM | 1682 | CD2 | TYR | 88 | −13.790 | 0.950 | −5.392 | 1.00 | 0.00 | PROT |
| ATOM | 1683 | HD2 | TYR | 88 | −12.958 | 0.571 | −4.817 | 1.00 | 0.00 | PROT |
| ATOM | 1684 | CE1 | TYR | 88 | −15.944 | 1.934 | −6.883 | 1.00 | 0.00 | PROT |
| ATOM | 1685 | HE1 | TYR | 88 | −16.775 | 2.313 | −7.459 | 1.00 | 0.00 | PROT |
| ATOM | 1686 | CE2 | TYR | 88 | −15.091 | 0.840 | −4.895 | 1.00 | 0.00 | PROT |
| ATOM | 1687 | HE2 | TYR | 88 | −15.262 | 0.372 | −3.939 | 1.00 | 0.00 | PROT |
| ATOM | 1688 | CZ | TYR | 88 | −16.170 | 1.330 | −5.640 | 1.00 | 0.00 | PROT |
| ATOM | 1689 | OH | TYR | 88 | −17.455 | 1.219 | −5.149 | 1.00 | 0.00 | PROT |
| ATOM | 1690 | HH | TYR | 88 | −18.049 | 1.106 | −5.895 | 1.00 | 0.00 | PROT |
| ATOM | 1691 | C | TYR | 88 | −12.244 | 4.092 | −6.402 | 1.00 | 0.00 | PROT |
| ATOM | 1692 | O | TYR | 88 | −13.395 | 4.460 | −6.280 | 1.00 | 0.00 | PROT |
| ATOM | 1693 | N | ASN | 89 | −11.311 | 4.498 | −5.582 | 1.00 | 0.00 | PROT |
| ATOM | 1694 | HN | ASN | 89 | −10.393 | 4.178 | −5.695 | 1.00 | 0.00 | PROT |
| ATOM | 1695 | CA | ASN | 89 | −11.633 | 5.425 | −4.454 | 1.00 | 0.00 | PROT |
| ATOM | 1696 | HA | ASN | 89 | −12.102 | 4.887 | −3.643 | 1.00 | 0.00 | PROT |
| ATOM | 1697 | CB | ASN | 89 | −10.276 | 5.982 | −4.013 | 1.00 | 0.00 | PROT |
| ATOM | 1698 | HB1 | ASN | 89 | −9.588 | 5.946 | −4.843 | 1.00 | 0.00 | PROT |
| ATOM | 1699 | HB2 | ASN | 89 | −10.397 | 7.007 | −3.695 | 1.00 | 0.00 | PROT |
| ATOM | 1700 | CG | ASN | 89 | −9.715 | 5.156 | −2.852 | 1.00 | 0.00 | PROT |
| ATOM | 1701 | OD1 | ASN | 89 | −8.962 | 5.662 | −2.045 | 1.00 | 0.00 | PROT |
| ATOM | 1702 | ND2 | ASN | 89 | −10.032 | 3.896 | −2.740 | 1.00 | 0.00 | PROT |
| ATOM | 1703 | HD21 | ASN | 89 | −9.667 | 3.366 | −2.001 | 1.00 | 0.00 | PROT |
| ATOM | 1704 | HD22 | ASN | 89 | −10.635 | 3.481 | −3.391 | 1.00 | 0.00 | PROT |
| ATOM | 1705 | C | ASN | 89 | −12.527 | 6.579 | −4.921 | 1.00 | 0.00 | PROT |
| ATOM | 1706 | O | ASN | 89 | −12.553 | 6.904 | −6.091 | 1.00 | 0.00 | PROT |
| ATOM | 1707 | N | PRO | 90 | −13.220 | 7.179 | −3.983 | 1.00 | 0.00 | PROT |
| ATOM | 1708 | CA | PRO | 90 | −14.089 | 8.334 | −4.311 | 1.00 | 0.00 | PROT |
| ATOM | 1709 | HA | PRO | 90 | −14.903 | 8.033 | −4.943 | 1.00 | 0.00 | PROT |
| ATOM | 1710 | CB | PRO | 90 | −14.615 | 8.801 | −2.954 | 1.00 | 0.00 | PROT |
| ATOM | 1711 | HB1 | PRO | 90 | −14.055 | 9.655 | −2.612 | 1.00 | 0.00 | PROT |
| ATOM | 1712 | HB2 | PRO | 90 | −15.664 | 9.044 | −3.023 | 1.00 | 0.00 | PROT |
| ATOM | 1713 | CG | PRO | 90 | −14.411 | 7.644 | −2.028 | 1.00 | 0.00 | PROT |
| ATOM | 1714 | HG1 | PRO | 90 | −14.206 | 8.003 | −1.031 | 1.00 | 0.00 | PROT |
| ATOM | 1715 | HG2 | PRO | 90 | −15.291 | 7.018 | −2.022 | 1.00 | 0.00 | PROT |
| ATOM | 1716 | CD | PRO | 90 | −13.233 | 6.870 | −2.547 | 1.00 | 0.00 | PROT |
| ATOM | 1717 | HD2 | PRO | 90 | −13.375 | 5.811 | −2.388 | 1.00 | 0.00 | PROT |
| ATOM | 1718 | HD1 | PRO | 90 | −12.320 | 7.207 | −2.078 | 1.00 | 0.00 | PROT |
| ATOM | 1719 | C | PRO | 90 | −13.255 | 9.435 | −4.976 | 1.00 | 0.00 | PROT |
| ATOM | 1720 | O | PRO | 90 | −12.044 | 9.364 | −4.985 | 1.00 | 0.00 | PROT |
| ATOM | 1721 | N | PRO | 91 | −13.920 | 10.415 | −5.529 | 1.00 | 0.00 | PROT |
| ATOM | 1722 | CA | PRO | 91 | −13.192 | 11.542 | −6.157 | 1.00 | 0.00 | PROT |
| ATOM | 1723 | HA | PRO | 91 | −12.548 | 11.189 | −6.949 | 1.00 | 0.00 | PROT |
| ATOM | 1724 | CB | PRO | 91 | −14.298 | 12.444 | −6.713 | 1.00 | 0.00 | PROT |
| ATOM | 1725 | HB1 | PRO | 91 | −14.390 | 13.335 | −6.110 | 1.00 | 0.00 | PROT |
| ATOM | 1726 | HB2 | PRO | 91 | −14.083 | 12.709 | −7.738 | 1.00 | 0.00 | PROT |
| ATOM | 1727 | CG | PRO | 91 | −15.561 | 11.638 | −6.642 | 1.00 | 0.00 | PROT |
| ATOM | 1728 | HG1 | PRO | 91 | −15.740 | 11.151 | −7.589 | 1.00 | 0.00 | PROT |
| ATOM | 1729 | HG2 | PRO | 91 | −16.394 | 12.279 | −6.394 | 1.00 | 0.00 | PROT |
| ATOM | 1730 | CD | PRO | 91 | −15.372 | 10.606 | −5.565 | 1.00 | 0.00 | PROT |
| ATOM | 1731 | HD2 | PRO | 91 | −15.870 | 9.685 | −5.829 | 1.00 | 0.00 | PROT |
| ATOM | 1732 | HD1 | PRO | 91 | −15.731 | 10.976 | −4.616 | 1.00 | 0.00 | PROT |
| ATOM | 1733 | C | PRO | 91 | −12.386 | 12.274 | −5.083 | 1.00 | 0.00 | PROT |

TABLE 10-continued

Atomic Structure Coordinates of the P/CAF Bromadomain and HIV-1 Tat Peptide Complex

| ATOM | 1734 | O   | PRO | 91 | −11.242 | 12.636 | −5.276 | 1.00 | 0.00 | PROT |
|------|------|-----|-----|----|---------|--------|--------|------|------|------|
| ATOM | 1735 | N   | GLU | 92 | −12.984 | 12.463 | −3.940 | 1.00 | 0.00 | PROT |
| ATOM | 1736 | HN  | GLU | 92 | −13.902 | 12.142 | −3.819 | 1.00 | 0.00 | PROT |
| ATOM | 1737 | CA  | GLU | 92 | −12.291 | 13.137 | −2.805 | 1.00 | 0.00 | PROT |
| ATOM | 1738 | HA  | GLU | 92 | −11.390 | 12.603 | −2.540 | 1.00 | 0.00 | PROT |
| ATOM | 1739 | CB  | GLU | 92 | −11.956 | 14.546 | −3.302 | 1.00 | 0.00 | PROT |
| ATOM | 1740 | HB1 | GLU | 92 | −12.754 | 15.222 | −3.303 | 1.00 | 0.00 | PROT |
| ATOM | 1741 | HB2 | GLU | 92 | −11.841 | 14.534 | −4.375 | 1.00 | 0.00 | PROT |
| ATOM | 1742 | CG  | GLU | 92 | −10.650 | 15.014 | −2.653 | 1.00 | 0.00 | PROT |
| ATOM | 1743 | HG1 | GLU | 92 | −9.920  | 15.220 | −3.442 | 1.00 | 0.00 | PROT |
| ATOM | 1744 | HG2 | GLU | 92 | −10.274 | 14.240 | −1.998 | 1.00 | 0.00 | PROT |
| ATOM | 1745 | CD  | GLU | 92 | −10.910 | 16.285 | −1.843 | 1.00 | 0.00 | PROT |
| ATOM | 1746 | OE1 | GLU | 92 | −10.924 | 17.350 | −2.437 | 1.00 | 0.00 | PROT |
| ATOM | 1747 | OE2 | GLU | 92 | −11.089 | 16.172 | −0.641 | 1.00 | 0.00 | PROT |
| ATOM | 1748 | C   | GLU | 92 | −13.247 | 13.203 | −1.615 | 1.00 | 0.00 | PROT |
| ATOM | 1749 | O   | GLU | 92 | −13.531 | 14.259 | −1.087 | 1.00 | 0.00 | PROT |
| ATOM | 1750 | N   | SER | 93 | −13.786 | 12.079 | −1.225 | 1.00 | 0.00 | PROT |
| ATOM | 1751 | HN  | SER | 93 | −13.554 | 11.245 | −1.680 | 1.00 | 0.00 | PROT |
| ATOM | 1752 | CA  | SER | 93 | −14.767 | 12.067 | −0.106 | 1.00 | 0.00 | PROT |
| ATOM | 1753 | HA  | SER | 93 | −15.148 | 13.059 | 0.067  | 1.00 | 0.00 | PROT |
| ATOM | 1754 | CB  | SER | 93 | −15.893 | 11.146 | −0.584 | 1.00 | 0.00 | PROT |
| ATOM | 1755 | HB1 | SER | 93 | −15.602 | 10.116 | −0.438 | 1.00 | 0.00 | PROT |
| ATOM | 1756 | HB2 | SER | 93 | −16.081 | 11.322 | −1.632 | 1.00 | 0.00 | PROT |
| ATOM | 1757 | OG  | SER | 93 | −17.072 | 11.414 | 0.161  | 1.00 | 0.00 | PROT |
| ATOM | 1758 | HG  | SER | 93 | −17.698 | 10.707 | −0.011 | 1.00 | 0.00 | PROT |
| ATOM | 1759 | C   | SER | 93 | −14.138 | 11.515 | 1.170  | 1.00 | 0.00 | PROT |
| ATOM | 1760 | O   | SER | 93 | −14.011 | 12.212 | 2.157  | 1.00 | 0.00 | PROT |
| ATOM | 1761 | N   | GLU | 94 | −13.765 | 10.264 | 1.176  | 1.00 | 0.00 | PROT |
| ATOM | 1762 | HN  | GLU | 94 | −13.882 | 9.706  | 0.370  | 1.00 | 0.00 | PROT |
| ATOM | 1763 | CA  | GLU | 94 | −13.170 | 9.689  | 2.417  | 1.00 | 0.00 | PROT |
| ATOM | 1764 | HA  | GLU | 94 | −12.742 | 10.472 | 3.022  | 1.00 | 0.00 | PROT |
| ATOM | 1765 | CB  | GLU | 94 | −14.346 | 9.044  | 3.150  | 1.00 | 0.00 | PROT |
| ATOM | 1766 | HB1 | GLU | 94 | −15.248 | 9.192  | 2.577  | 1.00 | 0.00 | PROT |
| ATOM | 1767 | HB2 | GLU | 94 | −14.163 | 7.986  | 3.268  | 1.00 | 0.00 | PROT |
| ATOM | 1768 | CG  | GLU | 94 | −14.506 | 9.692  | 4.527  | 1.00 | 0.00 | PROT |
| ATOM | 1769 | HG1 | GLU | 94 | −14.319 | 10.753 | 4.449  | 1.00 | 0.00 | PROT |
| ATOM | 1770 | HG2 | GLU | 94 | −15.511 | 9.529  | 4.888  | 1.00 | 0.00 | PROT |
| ATOM | 1771 | CD  | GLU | 94 | −13.506 | 9.070  | 5.505  | 1.00 | 0.00 | PROT |
| ATOM | 1772 | OE1 | GLU | 94 | −13.835 | 8.052  | 6.091  | 1.00 | 0.00 | PROT |
| ATOM | 1773 | OE2 | GLU | 94 | −12.429 | 9.624  | 5.652  | 1.00 | 0.00 | PROT |
| ATOM | 1774 | C   | GLU | 94 | −12.114 | 8.639  | 2.083  | 1.00 | 0.00 | PROT |
| ATOM | 1775 | O   | GLU | 94 | −11.068 | 8.579  | 2.697  | 1.00 | 0.00 | PROT |
| ATOM | 1776 | N   | TYR | 95 | −12.387 | 7.795  | 1.131  | 1.00 | 0.00 | PROT |
| ATOM | 1777 | HN  | TYR | 95 | −13.236 | 7.862  | 0.646  | 1.00 | 0.00 | PROT |
| ATOM | 1778 | CA  | TYR | 95 | −11.394 | 6.747  | 0.768  | 1.00 | 0.00 | PROT |
| ATOM | 1779 | HA  | TYR | 95 | −11.000 | 6.278  | 1.657  | 1.00 | 0.00 | PROT |
| ATOM | 1780 | CB  | TYR | 95 | −12.180 | 5.731  | −0.064 | 1.00 | 0.00 | PROT |
| ATOM | 1781 | HB1 | TYR | 95 | −11.681 | 5.577  | −1.010 | 1.00 | 0.00 | PROT |
| ATOM | 1782 | HB2 | TYR | 95 | −13.178 | 6.104  | −0.239 | 1.00 | 0.00 | PROT |
| ATOM | 1783 | CG  | TYR | 95 | −12.255 | 4.421  | 0.683  | 1.00 | 0.00 | PROT |
| ATOM | 1784 | CD1 | TYR | 95 | −13.277 | 4.205  | 1.617  | 1.00 | 0.00 | PROT |
| ATOM | 1785 | HD1 | TYR | 95 | −14.011 | 4.975  | 1.801  | 1.00 | 0.00 | PROT |
| ATOM | 1786 | CD2 | TYR | 95 | −11.303 | 3.422  | 0.445  | 1.00 | 0.00 | PROT |
| ATOM | 1787 | HD2 | TYR | 95 | −10.516 | 3.589  | −0.273 | 1.00 | 0.00 | PROT |
| ATOM | 1788 | CE1 | TYR | 95 | −13.346 | 2.991  | 2.310  | 1.00 | 0.00 | PROT |
| ATOM | 1789 | HE1 | TYR | 95 | −14.134 | 2.824  | 3.030  | 1.00 | 0.00 | PROT |
| ATOM | 1790 | CE2 | TYR | 95 | −11.373 | 2.208  | 1.139  | 1.00 | 0.00 | PROT |
| ATOM | 1791 | HE2 | TYR | 95 | −10.638 | 1.438  | 0.954  | 1.00 | 0.00 | PROT |
| ATOM | 1792 | CZ  | TYR | 95 | −12.394 | 1.992  | 2.071  | 1.00 | 0.00 | PROT |
| ATOM | 1793 | OH  | TYR | 95 | −12.461 | 0.796  | 2.755  | 1.00 | 0.00 | PROT |
| ATOM | 1794 | HH  | TYR | 95 | −11.566 | 0.536  | 2.985  | 1.00 | 0.00 | PROT |
| ATOM | 1795 | C   | TYR | 95 | −10.263 | 7.359  | −0.058 | 1.00 | 0.00 | PROT |
| ATOM | 1796 | O   | TYR | 95 | −9.128  | 6.931  | 0.009  | 1.00 | 0.00 | PROT |
| ATOM | 1797 | N   | TYR | 96 | −10.562 | 8.375  | −0.818 | 1.00 | 0.00 | PROT |
| ATOM | 1798 | HN  | TYR | 96 | −11.485 | 8.704  | −0.854 | 1.00 | 0.00 | PROT |
| ATOM | 1799 | CA  | TYR | 96 | −9.511  | 9.020  | −1.652 | 1.00 | 0.00 | PROT |
| ATOM | 1800 | HA  | TYR | 96 | −8.931  | 8.273  | −2.171 | 1.00 | 0.00 | PROT |
| ATOM | 1801 | CB  | TYR | 96 | −10.287 | 9.877  | −2.650 | 1.00 | 0.00 | PROT |
| ATOM | 1802 | HB1 | TYR | 96 | −10.677 | 10.750 | −2.148 | 1.00 | 0.00 | PROT |
| ATOM | 1803 | HB2 | TYR | 96 | −11.103 | 9.301  | −3.054 | 1.00 | 0.00 | PROT |
| ATOM | 1804 | CG  | TYR | 96 | −9.365  | 10.308 | −3.766 | 1.00 | 0.00 | PROT |
| ATOM | 1805 | CD1 | TYR | 96 | −8.796  | 11.587 | −3.747 | 1.00 | 0.00 | PROT |
| ATOM | 1806 | HD1 | TYR | 96 | −9.018  | 12.265 | −2.937 | 1.00 | 0.00 | PROT |
| ATOM | 1807 | CD2 | TYR | 96 | −9.077  | 9.428  | −4.816 | 1.00 | 0.00 | PROT |
| ATOM | 1808 | HD2 | TYR | 96 | −9.515  | 8.441  | −4.830 | 1.00 | 0.00 | PROT |
| ATOM | 1809 | CE1 | TYR | 96 | −7.940  | 11.987 | −4.780 | 1.00 | 0.00 | PROT |
| ATOM | 1810 | HE1 | TYR | 96 | −7.502  | 12.974 | −4.766 | 1.00 | 0.00 | PROT |

TABLE 10-continued

Atomic Structure Coordinates of the P/CAF Bromadomain and HIV-1 Tat Peptide Complex

| ATOM | 1811 | CE2 | TYR | 96 | −8.221 | 9.829 | −5.849 | 1.00 | 0.00 | PROT |
|---|---|---|---|---|---|---|---|---|---|---|
| ATOM | 1812 | HE2 | TYR | 96 | −7.999 | 9.151 | −6.660 | 1.00 | 0.00 | PROT |
| ATOM | 1813 | CZ | TYR | 96 | −7.652 | 11.108 | −5.831 | 1.00 | 0.00 | PROT |
| ATOM | 1814 | OH | TYR | 96 | −6.808 | 11.503 | −6.850 | 1.00 | 0.00 | PROT |
| ATOM | 1815 | HH | TYR | 96 | −6.254 | 12.213 | −6.519 | 1.00 | 0.00 | PROT |
| ATOM | 1816 | C | TYR | 96 | −8.603 | 9.905 | −0.798 | 1.00 | 0.00 | PROT |
| ATOM | 1817 | O | TYR | 96 | −7.535 | 10.294 | −1.220 | 1.00 | 0.00 | PROT |
| ATOM | 1818 | N | LYS | 97 | −9.023 | 10.241 | 0.390 | 1.00 | 0.00 | PROT |
| ATOM | 1819 | HN | LYS | 97 | −9.895 | 9.929 | 0.709 | 1.00 | 0.00 | PROT |
| ATOM | 1820 | CA | LYS | 97 | −8.186 | 11.122 | 1.253 | 1.00 | 0.00 | PROT |
| ATOM | 1821 | HA | LYS | 97 | −7.766 | 11.928 | 0.669 | 1.00 | 0.00 | PROT |
| ATOM | 1822 | CB | LYS | 97 | −9.156 | 11.675 | 2.300 | 1.00 | 0.00 | PROT |
| ATOM | 1823 | HB1 | LYS | 97 | −9.527 | 10.864 | 2.910 | 1.00 | 0.00 | PROT |
| ATOM | 1824 | HB2 | LYS | 97 | −8.641 | 12.388 | 2.926 | 1.00 | 0.00 | PROT |
| ATOM | 1825 | CG | LYS | 97 | −10.330 | 12.364 | 1.599 | 1.00 | 0.00 | PROT |
| ATOM | 1826 | HG1 | LYS | 97 | −11.167 | 11.683 | 1.545 | 1.00 | 0.00 | PROT |
| ATOM | 1827 | HG2 | LYS | 97 | −10.034 | 12.652 | 0.602 | 1.00 | 0.00 | PROT |
| ATOM | 1828 | CD | LYS | 97 | −10.735 | 13.609 | 2.391 | 1.00 | 0.00 | PROT |
| ATOM | 1829 | HD1 | LYS | 97 | −11.605 | 14.058 | 1.936 | 1.00 | 0.00 | PROT |
| ATOM | 1830 | HD2 | LYS | 97 | −10.965 | 13.329 | 3.408 | 1.00 | 0.00 | PROT |
| ATOM | 1831 | CE | LYS | 97 | −9.581 | 14.613 | 2.387 | 1.00 | 0.00 | PROT |
| ATOM | 1832 | HE1 | LYS | 97 | −8.897 | 14.402 | 3.195 | 1.00 | 0.00 | PROT |
| ATOM | 1833 | HE2 | LYS | 97 | −9.064 | 14.588 | 1.439 | 1.00 | 0.00 | PROT |
| ATOM | 1834 | NZ | LYS | 97 | −10.229 | 15.939 | 2.589 | 1.00 | 0.00 | PROT |
| ATOM | 1835 | HZ1 | LYS | 97 | −10.831 | 16.159 | 1.769 | 1.00 | 0.00 | PROT |
| ATOM | 1836 | HZ2 | LYS | 97 | −9.498 | 16.671 | 2.688 | 1.00 | 0.00 | PROT |
| ATOM | 1837 | HZ3 | LYS | 97 | −10.813 | 15.913 | 3.450 | 1.00 | 0.00 | PROT |
| ATOM | 1838 | C | LYS | 97 | −7.075 | 10.316 | 1.934 | 1.00 | 0.00 | PROT |
| ATOM | 1839 | O | LYS | 97 | −6.083 | 10.862 | 2.376 | 1.00 | 0.00 | PROT |
| ATOM | 1840 | N | CYS | 98 | −7.235 | 9.024 | 2.029 | 1.00 | 0.00 | PROT |
| ATOM | 1841 | HN | CYS | 98 | −8.045 | 8.604 | 1.675 | 1.00 | 0.00 | PROT |
| ATOM | 1842 | CA | CYS | 98 | −6.196 | 8.189 | 2.699 | 1.00 | 0.00 | PROT |
| ATOM | 1843 | HA | CYS | 98 | −5.857 | 8.667 | 3.606 | 1.00 | 0.00 | PROT |
| ATOM | 1844 | CB | CYS | 98 | −6.901 | 6.874 | 3.024 | 1.00 | 0.00 | PROT |
| ATOM | 1845 | HB1 | CYS | 98 | −6.210 | 6.209 | 3.518 | 1.00 | 0.00 | PROT |
| ATOM | 1846 | HB2 | CYS | 98 | −7.244 | 6.419 | 2.109 | 1.00 | 0.00 | PROT |
| ATOM | 1847 | SG | CYS | 98 | −8.314 | 7.196 | 4.110 | 1.00 | 0.00 | PROT |
| ATOM | 1848 | HG | CYS | 98 | −9.117 | 7.036 | 3.608 | 1.00 | 0.00 | PROT |
| ATOM | 1849 | C | CYS | 98 | −5.018 | 7.927 | 1.762 | 1.00 | 0.00 | PROT |
| ATOM | 1850 | O | CYS | 98 | −3.923 | 8.407 | 1.980 | 1.00 | 0.00 | PROT |
| ATOM | 1851 | N | ALA | 99 | −5.225 | 7.160 | 0.721 | 1.00 | 0.00 | PROT |
| ATOM | 1852 | HN | ALA | 99 | −6.115 | 6.776 | 0.561 | 1.00 | 0.00 | PROT |
| ATOM | 1853 | CA | ALA | 99 | −4.104 | 6.863 | −0.219 | 1.00 | 0.00 | PROT |
| ATOM | 1854 | HA | ALA | 99 | −3.401 | 6.186 | 0.243 | 1.00 | 0.00 | PROT |
| ATOM | 1855 | CB | ALA | 99 | −4.764 | 6.193 | −1.425 | 1.00 | 0.00 | PROT |
| ATOM | 1856 | HB1 | ALA | 99 | −5.133 | 6.951 | −2.100 | 1.00 | 0.00 | PROT |
| ATOM | 1857 | HB2 | ALA | 99 | −5.587 | 5.578 | −1.087 | 1.00 | 0.00 | PROT |
| ATOM | 1858 | HB3 | ALA | 99 | −4.037 | 5.576 | −1.936 | 1.00 | 0.00 | PROT |
| ATOM | 1859 | C | ALA | 99 | −3.399 | 8.157 | −0.633 | 1.00 | 0.00 | PROT |
| ATOM | 1860 | O | ALA | 99 | −2.235 | 8.157 | −0.977 | 1.00 | 0.00 | PROT |
| ATOM | 1861 | N | ASN | 100 | −4.084 | 9.266 | −0.565 | 1.00 | 0.00 | PROT |
| ATOM | 1862 | HN | ASN | 100 | −5.017 | 9.249 | −0.268 | 1.00 | 0.00 | PROT |
| ATOM | 1863 | CA | ASN | 100 | −3.437 | 10.562 | −0.910 | 1.00 | 0.00 | PROT |
| ATOM | 1864 | HA | ASN | 100 | −2.916 | 10.487 | −1.852 | 1.00 | 0.00 | PROT |
| ATOM | 1865 | CB | ASN | 100 | −4.588 | 11.563 | −1.010 | 1.00 | 0.00 | PROT |
| ATOM | 1866 | HB1 | ASN | 100 | −4.519 | 12.272 | −0.198 | 1.00 | 0.00 | PROT |
| ATOM | 1867 | HB2 | ASN | 100 | −5.526 | 11.037 | −0.947 | 1.00 | 0.00 | PROT |
| ATOM | 1868 | CG | ASN | 100 | −4.506 | 12.305 | −2.344 | 1.00 | 0.00 | PROT |
| ATOM | 1869 | OD1 | ASN | 100 | −5.292 | 12.061 | −3.237 | 1.00 | 0.00 | PROT |
| ATOM | 1870 | ND2 | ASN | 100 | −3.581 | 13.208 | −2.516 | 1.00 | 0.00 | PROT |
| ATOM | 1871 | HD21 | ASN | 100 | −3.519 | 13.691 | −3.367 | 1.00 | 0.00 | PROT |
| ATOM | 1872 | HD22 | ASN | 100 | −2.947 | 13.405 | −1.794 | 1.00 | 0.00 | PROT |
| ATOM | 1873 | C | ASN | 100 | −2.478 | 10.971 | 0.208 | 1.00 | 0.00 | PROT |
| ATOM | 1874 | O | ASN | 100 | −1.321 | 11.258 | −0.024 | 1.00 | 0.00 | PROT |
| ATOM | 1875 | N | ILE | 101 | −2.954 | 10.991 | 1.424 | 1.00 | 0.00 | PROT |
| ATOM | 1876 | HN | ILE | 101 | −3.889 | 10.748 | 1.588 | 1.00 | 0.00 | PROT |
| ATOM | 1877 | CA | ILE | 101 | −2.072 | 11.364 | 2.564 | 1.00 | 0.00 | PROT |
| ATOM | 1878 | HA | ILE | 101 | −1.648 | 12.345 | 2.407 | 1.00 | 0.00 | PROT |
| ATOM | 1879 | CB | ILE | 101 | −2.994 | 11.369 | 3.786 | 1.00 | 0.00 | PROT |
| ATOM | 1880 | HB | ILE | 101 | −3.503 | 10.419 | 3.857 | 1.00 | 0.00 | PROT |
| ATOM | 1881 | CG1 | ILE | 101 | −4.025 | 12.490 | 3.639 | 1.00 | 0.00 | PROT |
| ATOM | 1882 | HG11 | ILE | 101 | −3.553 | 13.442 | 3.836 | 1.00 | 0.00 | PROT |
| ATOM | 1883 | HG12 | ILE | 101 | −4.420 | 12.486 | 2.634 | 1.00 | 0.00 | PROT |
| ATOM | 1884 | CG2 | ILE | 101 | −2.169 | 11.603 | 5.054 | 1.00 | 0.00 | PROT |
| ATOM | 1885 | HG21 | ILE | 101 | −2.822 | 11.606 | 5.914 | 1.00 | 0.00 | PROT |
| ATOM | 1886 | HG22 | ILE | 101 | −1.662 | 12.553 | 4.984 | 1.00 | 0.00 | PROT |
| ATOM | 1887 | HG23 | ILE | 101 | −1.439 | 10.813 | 5.160 | 1.00 | 0.00 | PROT |

TABLE 10-continued

Atomic Structure Coordinates of the P/CAF Bromadomain and HIV-1 Tat Peptide Complex

| ATOM | 1888 | CD1 | ILE | 101 | −5.164 | 12.270 | 4.635 | 1.00 | 0.00 | PROT |
|---|---|---|---|---|---|---|---|---|---|---|
| ATOM | 1889 | HD11 | ILE | 101 | −5.483 | 11.239 | 4.596 | 1.00 | 0.00 | PROT |
| ATOM | 1890 | HD12 | ILE | 101 | −5.994 | 12.913 | 4.382 | 1.00 | 0.00 | PROT |
| ATOM | 1891 | HD13 | ILE | 101 | −4.820 | 12.502 | 5.632 | 1.00 | 0.00 | PROT |
| ATOM | 1892 | C | ILE | 101 | −0.964 | 10.323 | 2.728 | 1.00 | 0.00 | PROT |
| ATOM | 1893 | O | ILE | 101 | −0.207 | 10.645 | 2.711 | 1.00 | 0.00 | PROT |
| ATOM | 1894 | N | LEU | 102 | −1.319 | 9.072 | 2.865 | 1.00 | 0.00 | PROT |
| ATOM | 1895 | HN | LEU | 102 | −2.271 | 8.824 | 2.873 | 1.00 | 0.00 | PROT |
| ATOM | 1896 | CA | LEU | 102 | −0.274 | 8.021 | 3.011 | 1.00 | 0.00 | PROT |
| ATOM | 1897 | HA | LEU | 102 | −0.219 | 8.110 | 3.967 | 1.00 | 0.00 | PROT |
| ATOM | 1898 | CB | LEU | 102 | −1.037 | 6.700 | 2.926 | 1.00 | 0.00 | PROT |
| ATOM | 1899 | HB1 | LEU | 102 | −2.068 | 6.894 | 2.670 | 1.00 | 0.00 | PROT |
| ATOM | 1900 | HB2 | LEU | 102 | −0.588 | 6.073 | 2.170 | 1.00 | 0.00 | PROT |
| ATOM | 1901 | CG | LEU | 102 | −0.972 | 5.993 | 4.279 | 1.00 | 0.00 | PROT |
| ATOM | 1902 | HG | LEU | 102 | −1.350 | 6.650 | 5.048 | 1.00 | 0.00 | PROT |
| ATOM | 1903 | CD1 | LEU | 102 | −1.820 | 4.724 | 4.229 | 1.00 | 0.00 | PROT |
| ATOM | 1904 | HD11 | LEU | 102 | −2.052 | 4.406 | 5.233 | 1.00 | 0.00 | PROT |
| ATOM | 1905 | HD12 | LEU | 102 | −1.272 | 3.944 | 3.721 | 1.00 | 0.00 | PROT |
| ATOM | 1906 | HD13 | LEU | 102 | −2.738 | 4.925 | 3.694 | 1.00 | 0.00 | PROT |
| ATOM | 1907 | CD2 | LEU | 102 | 0.480 | 5.624 | 4.589 | 1.00 | 0.00 | PROT |
| ATOM | 1908 | HD21 | LEU | 102 | 0.500 | 4.808 | 5.295 | 1.00 | 0.00 | PROT |
| ATOM | 1909 | HD22 | LEU | 102 | 0.986 | 6.479 | 5.012 | 1.00 | 0.00 | PROT |
| ATOM | 1910 | HD23 | LEU | 102 | 0.978 | 5.325 | 3.678 | 1.00 | 0.00 | PROT |
| ATOM | 1911 | C | LEU | 102 | 0.743 | 8.123 | 1.872 | 1.00 | 0.00 | PROT |
| ATOM | 1912 | O | LEU | 102 | 1.936 | 8.165 | 2.094 | 1.00 | 0.00 | PROT |
| ATOM | 1913 | N | GLU | 103 | 0.276 | 8.181 | 0.654 | 1.00 | 0.00 | PROT |
| ATOM | 1914 | HN | GLU | 103 | 0.691 | 8.152 | 0.499 | 1.00 | 0.00 | PROT |
| ATOM | 1915 | CA | GLU | 103 | 1.210 | 8.293 | −0.503 | 1.00 | 0.00 | PROT |
| ATOM | 1916 | HA | GLU | 103 | 1.759 | 7.373 | −0.634 | 1.00 | 0.00 | PROT |
| ATOM | 1917 | CB | GLU | 103 | 0.299 | 8.550 | −1.710 | 1.00 | 0.00 | PROT |
| ATOM | 1918 | HB1 | GLU | 103 | −0.341 | 9.394 | −1.500 | 1.00 | 0.00 | PROT |
| ATOM | 1919 | HB2 | GLU | 103 | −0.308 | 7.676 | −1.891 | 1.00 | 0.00 | PROT |
| ATOM | 1920 | CG | GLU | 103 | 1.141 | 8.849 | −2.956 | 1.00 | 0.00 | PROT |
| ATOM | 1921 | HG1 | GLU | 103 | 0.519 | 9.318 | −3.704 | 1.00 | 0.00 | PROT |
| ATOM | 1922 | HG2 | GLU | 103 | 1.953 | 9.513 | −2.698 | 1.00 | 0.00 | PROT |
| ATOM | 1923 | CD | GLU | 103 | −1.706 | 7.542 | −3.515 | 1.00 | 0.00 | PROT |
| ATOM | 1924 | OE1 | GLU | 103 | 2.718 | 7.600 | −4.195 | 1.00 | 0.00 | PROT |
| ATOM | 1925 | OE2 | GLU | 103 | 1.120 | 6.506 | −3.252 | 1.00 | 0.00 | PROT |
| ATOM | 1926 | C | GLU | 103 | 2.169 | 9.467 | −0.297 | 1.00 | 0.00 | PROT |
| ATOM | 1927 | O | GLU | 103 | 3.361 | 9.349 | −0.491 | 1.00 | 0.00 | PROT |
| ATOM | 1928 | N | LYS | 104 | 1.653 | 10.603 | 0.079 | 1.00 | 0.00 | PROT |
| ATOM | 1929 | HN | LYS | 104 | 0.686 | 10.682 | 0.213 | 1.00 | 0.00 | PROT |
| ATOM | 1930 | CA | LYS | 104 | 2.524 | 11.793 | 0.271 | 1.00 | 0.00 | PROT |
| ATOM | 1931 | HA | LYS | 104 | 3.076 | 12.000 | −0.632 | 1.00 | 0.00 | PROT |
| ATOM | 1932 | CB | LYS | 104 | 1.549 | 12.929 | 0.565 | 1.00 | 0.00 | PROT |
| ATOM | 1933 | HB1 | LYS | 104 | 2.101 | 13.808 | 0.863 | 1.00 | 0.00 | PROT |
| ATOM | 1934 | HB2 | LYS | 104 | 0.881 | 12.635 | 1.360 | 1.00 | 0.00 | PROT |
| ATOM | 1935 | CG | LYS | 104 | 0.741 | 13.235 | −0.695 | 1.00 | 0.00 | PROT |
| ATOM | 1936 | HG1 | LYS | 104 | 0.739 | 12.372 | −1.343 | 1.00 | 0.00 | PROT |
| ATOM | 1937 | HG2 | LYS | 104 | −0.271 | 13.480 | −0.420 | 1.00 | 0.00 | PROT |
| ATOM | 1938 | CD | LYS | 104 | 1.373 | 14.417 | −1.423 | 1.00 | 0.00 | PROT |
| ATOM | 1939 | HD1 | LYS | 104 | 2.032 | 14.936 | −0.747 | 1.00 | 0.00 | PROT |
| ATOM | 1940 | HD2 | LYS | 104 | 1.934 | 14.061 | −2.274 | 1.00 | 0.00 | PROT |
| ATOM | 1941 | CE | LYS | 104 | 0.276 | 15.368 | −1.892 | 1.00 | 0.00 | PROT |
| ATOM | 1942 | HE1 | LYS | 104 | −0.562 | 15.327 | −1.216 | 1.00 | 0.00 | PROT |
| ATOM | 1943 | HE2 | LYS | 104 | −0.035 | 15.120 | −2.896 | 1.00 | 0.00 | PROT |
| ATOM | 1944 | NZ | LYS | 104 | 0.902 | 16.720 | −1.860 | 1.00 | 0.00 | PROT |
| ATOM | 1945 | HZ1 | LYS | 104 | 0.941 | 17.061 | −0.879 | 1.00 | 0.00 | PROT |
| ATOM | 1946 | HZ2 | LYS | 104 | 0.336 | 17.378 | −2.434 | 1.00 | 0.00 | PROT |
| ATOM | 1947 | HZ3 | LYS | 104 | 1.866 | 16.665 | −2.247 | 1.00 | 0.00 | PROT |
| ATOM | 1948 | C | LYS | 104 | 3.475 | 11.596 | 1.454 | 1.00 | 0.00 | PROT |
| ATOM | 1949 | O | LYS | 104 | 4.632 | 11.963 | 1.399 | 1.00 | 0.00 | PROT |
| ATOM | 1950 | N | PHE | 105 | 2.990 | 11.042 | 2.531 | 1.00 | 0.00 | PROT |
| ATOM | 1951 | HN | PHE | 105 | 2.049 | 10.771 | 2.561 | 1.00 | 0.00 | PROT |
| ATOM | 1952 | CA | PHE | 105 | 3.856 | 10.863 | 3.731 | 1.00 | 0.00 | PROT |
| ATOM | 1953 | HA | PHE | 105 | 4.327 | 11.799 | 3.992 | 1.00 | 0.00 | PROT |
| ATOM | 1954 | CB | PHE | 105 | 2.897 | 10.429 | 4.841 | 1.00 | 0.00 | PROT |
| ATOM | 1955 | HB1 | PHE | 105 | 3.366 | 9.666 | 5.445 | 1.00 | 0.00 | PROT |
| ATOM | 1956 | HB2 | PHE | 105 | 1.992 | 10.035 | 4.402 | 1.00 | 0.00 | PROT |
| ATOM | 1957 | CG | PHE | 105 | 2.560 | 11.620 | 5.706 | 1.00 | 0.00 | PROT |
| ATOM | 1958 | CD1 | PHE | 105 | 1.521 | 12.482 | 5.336 | 1.00 | 0.00 | PROT |
| ATOM | 1959 | HD1 | PHE | 105 | 0.960 | 12.295 | 4.433 | 1.00 | 0.00 | PROT |
| ATOM | 1960 | CD2 | PHE | 105 | 3.288 | 11.863 | 6.877 | 1.00 | 0.00 | PROT |
| ATOM | 1961 | HD2 | PHE | 105 | 4.090 | 11.198 | 7.162 | 1.00 | 0.00 | PROT |
| ATOM | 1962 | CE1 | PHE | 105 | 1.210 | 13.587 | 6.137 | 1.00 | 0.00 | PROT |
| ATOM | 1963 | HE1 | PHE | 105 | 0.408 | 14.252 | 5.851 | 1.00 | 0.00 | PROT |
| ATOM | 1964 | CE2 | PHE | 105 | 2.977 | 12.969 | 7.678 | 1.00 | 0.00 | PROT |

TABLE 10-continued

Atomic Structure Coordinates of the P/CAF Bromadomain and HIV-1 Tat Peptide Complex

| ATOM | 1965 | HE2 | PHE | 105 | 3.538 | 13.156 | 8.581 | 1.00 | 0.00 | PROT |
|---|---|---|---|---|---|---|---|---|---|---|
| ATOM | 1966 | CZ | PHE | 105 | 1.938 | 13.830 | 7.308 | 1.00 | 0.00 | PROT |
| ATOM | 1967 | HZ | PHE | 105 | 1.697 | 14.683 | 7.926 | 1.00 | 0.00 | PROT |
| ATOM | 1968 | C | PHE | 105 | 4.918 | 9.785 | 3.494 | 1.00 | 0.00 | PROT |
| ATOM | 1969 | O | PHE | 105 | 6.093 | 10.006 | 3.711 | 1.00 | 0.00 | PROT |
| ATOM | 1970 | N | PHE | 106 | 4.521 | 8.614 | 3.075 | 1.00 | 0.00 | PROT |
| ATOM | 1971 | HN | PHE | 106 | 3.568 | 8.444 | 2.918 | 1.00 | 0.00 | PROT |
| ATOM | 1972 | CA | PHE | 106 | 5.521 | 7.527 | 2.866 | 1.00 | 0.00 | PROT |
| ATOM | 1973 | HA | PHE | 106 | 6.096 | 7.393 | 3.768 | 1.00 | 0.00 | PROT |
| ATOM | 1974 | CB | PHE | 106 | 4.675 | 6.251 | 2.606 | 1.00 | 0.00 | PROT |
| ATOM | 1975 | HB1 | PHE | 106 | 3.663 | 6.429 | 2.936 | 1.00 | 0.00 | PROT |
| ATOM | 1976 | HB2 | PHE | 106 | 5.091 | 5.435 | 3.179 | 1.00 | 0.00 | PROT |
| ATOM | 1977 | CG | PHE | 106 | 4.650 | 5.857 | 1.140 | 1.00 | 0.00 | PROT |
| ATOM | 1978 | CD1 | PHE | 106 | 3.890 | 6.595 | 0.228 | 1.00 | 0.00 | PROT |
| ATOM | 1979 | HD1 | PHE | 106 | 3.318 | 7.444 | 0.567 | 1.00 | 0.00 | PROT |
| ATOM | 1980 | CD2 | PHE | 106 | 5.391 | 4.752 | 0.701 | 1.00 | 0.00 | PROT |
| ATOM | 1981 | HD2 | PHE | 106 | 5.979 | 4.182 | 1.406 | 1.00 | 0.00 | PROT |
| ATOM | 1982 | CE1 | PHE | 106 | 3.868 | 6.230 | −1.123 | 1.00 | 0.00 | PROT |
| ATOM | 1983 | HE1 | PHE | 106 | 3.282 | 6.800 | −1.826 | 1.00 | 0.00 | PROT |
| ATOM | 1984 | CE2 | PHE | 106 | 5.370 | 4.387 | −0.650 | 1.00 | 0.00 | PROT |
| ATOM | 1985 | HE2 | PHE | 106 | 5.942 | 3.536 | −0.988 | 1.00 | 0.00 | PROT |
| ATOM | 1986 | CZ | PHE | 106 | 4.609 | 5.126 | −1.562 | 1.00 | 0.00 | PROT |
| ATOM | 1987 | HZ | PHE | 106 | 4.593 | 4.845 | −2.605 | 1.00 | 0.00 | PROT |
| ATOM | 1988 | C | PHE | 106 | 6.470 | 7.884 | 1.708 | 1.00 | 0.00 | PROT |
| ATOM | 1989 | O | PHE | 106 | 7.540 | 7.326 | 1.584 | 1.00 | 0.00 | PROT |
| ATOM | 1990 | N | PHE | 107 | 6.088 | 8.813 | 0.872 | 1.00 | 0.00 | PROT |
| ATOM | 1991 | HN | PHE | 107 | 5.223 | 9.256 | 0.994 | 1.00 | 0.00 | PROT |
| ATOM | 1992 | CA | PHE | 107 | 6.970 | 9.200 | −0.269 | 1.00 | 0.00 | PROT |
| ATOM | 1993 | HA | PHE | 107 | 7.128 | 8.358 | −0.930 | 1.00 | 0.00 | PROT |
| ATOM | 1994 | CB | PHE | 107 | 6.212 | 10.316 | −0.993 | 1.00 | 0.00 | PROT |
| ATOM | 1995 | HB1 | PHE | 107 | 5.237 | 10.437 | −0.549 | 1.00 | 0.00 | PROT |
| ATOM | 1996 | HB2 | PHE | 107 | 6.763 | 11.241 | −0.903 | 1.00 | 0.00 | PROT |
| ATOM | 1997 | CG | PHE | 107 | 6.061 | 9.964 | −2.454 | 1.00 | 0.00 | PROT |
| ATOM | 1998 | CD1 | PHE | 107 | 5.537 | 8.721 | −2.826 | 1.00 | 0.00 | PROT |
| ATOM | 1999 | HD1 | PHE | 107 | 5.244 | 8.010 | −2.068 | 1.00 | 0.00 | PROT |
| ATOM | 2000 | CD2 | PHE | 107 | 6.442 | 10.886 | −3.437 | 1.00 | 0.00 | PROT |
| ATOM | 2001 | HD2 | PHE | 107 | 6.845 | 11.846 | −3.149 | 1.00 | 0.00 | PROT |
| ATOM | 2002 | CE1 | PHE | 107 | 5.399 | 8.397 | −4.181 | 1.00 | 0.00 | PROT |
| ATOM | 2003 | HE1 | PHE | 107 | 4.996 | 7.437 | −4.469 | 1.00 | 0.00 | PROT |
| ATOM | 2004 | CE2 | PHE | 107 | 6.302 | 10.563 | −4.791 | 1.00 | 0.00 | PROT |
| ATOM | 2005 | HE2 | PHE | 107 | 6.597 | 11.274 | −5.549 | 1.00 | 0.00 | PROT |
| ATOM | 2006 | CZ | PHE | 107 | 5.780 | 9.319 | −5.164 | 1.00 | 0.00 | PROT |
| ATOM | 2007 | HZ | PHE | 107 | 5.672 | 9.070 | −6.209 | 1.00 | 0.00 | PROT |
| ATOM | 2008 | C | PHE | 107 | 8.308 | 9.732 | 0.247 | 1.00 | 0.00 | PROT |
| ATOM | 2009 | O | PHE | 107 | 9.360 | 9.217 | −0.078 | 1.00 | 0.00 | PROT |
| ATOM | 2010 | N | SER | 108 | 8.276 | 10.768 | 1.042 | 1.00 | 0.00 | PROT |
| ATOM | 2011 | HN | SER | 108 | 7.416 | 11.172 | 1.284 | 1.00 | 0.00 | PROT |
| ATOM | 2012 | CA | SER | 108 | 9.544 | 11.350 | 1.569 | 1.00 | 0.00 | PROT |
| ATOM | 2013 | HA | SER | 108 | 10.066 | 11.879 | 0.787 | 1.00 | 0.00 | PROT |
| ATOM | 2014 | CB | SER | 108 | 9.102 | 12.323 | 2.665 | 1.00 | 0.00 | PROT |
| ATOM | 2015 | HB1 | SER | 108 | 8.031 | 12.456 | 2.619 | 1.00 | 0.00 | PROT |
| ATOM | 2016 | HB2 | SER | 108 | 9.374 | 11.925 | 3.632 | 1.00 | 0.00 | PROT |
| ATOM | 2017 | OG | SER | 108 | 9.743 | 13.575 | 2.471 | 1.00 | 0.00 | PROT |
| ATOM | 2018 | HG | SER | 108 | 9.794 | 14.017 | 3.321 | 1.00 | 0.00 | PROT |
| ATOM | 2019 | C | SER | 108 | 10.438 | 10.257 | 2.159 | 1.00 | 0.00 | PROT |
| ATOM | 2020 | O | SER | 108 | 11.645 | 10.379 | 2.188 | 1.00 | 0.00 | PROT |
| ATOM | 2021 | N | LYS | 109 | 9.857 | 9.193 | 2.639 | 1.00 | 0.00 | PROT |
| ATOM | 2022 | HN | LYS | 109 | 8.884 | 9.107 | 2.602 | 1.00 | 0.00 | PROT |
| ATOM | 2023 | CA | LYS | 109 | 10.683 | 8.099 | 3.219 | 1.00 | 0.00 | PROT |
| ATOM | 2024 | HA | LYS | 109 | 11.483 | 8.510 | 3.814 | 1.00 | 0.00 | PROT |
| ATOM | 2025 | CB | LYS | 109 | 9.727 | 7.293 | 4.099 | 1.00 | 0.00 | PROT |
| ATOM | 2026 | HB1 | LYS | 109 | 10.239 | 6.416 | 4.471 | 1.00 | 0.00 | PROT |
| ATOM | 2027 | HB2 | LYS | 109 | 8.874 | 6.987 | 3.512 | 1.00 | 0.00 | PROT |
| ATOM | 2028 | CG | LYS | 109 | 9.252 | 8.150 | 5.282 | 1.00 | 0.00 | PROT |
| ATOM | 2029 | HG1 | LYS | 109 | 8.653 | 8.969 | 4.911 | 1.00 | 0.00 | PROT |
| ATOM | 2030 | HG2 | LYS | 109 | 8.655 | 7.542 | 5.944 | 1.00 | 0.00 | PROT |
| ATOM | 2031 | CD | LYS | 109 | 10.452 | 8.709 | 6.058 | 1.00 | 0.00 | PROT |
| ATOM | 2032 | HD1 | LYS | 109 | 10.991 | 9.407 | 5.436 | 1.00 | 0.00 | PROT |
| ATOM | 2033 | HD2 | LYS | 109 | 10.099 | 9.219 | 6.942 | 1.00 | 0.00 | PROT |
| ATOM | 2034 | CE | LYS | 109 | 11.383 | 7.566 | 6.472 | 1.00 | 0.00 | PROT |
| ATOM | 2035 | HE1 | LYS | 109 | 12.320 | 7.632 | 5.938 | 1.00 | 0.00 | PROT |
| ATOM | 2036 | HE2 | LYS | 109 | 10.911 | 6.612 | 6.290 | 1.00 | 0.00 | PROT |
| ATOM | 2037 | NZ | LYS | 109 | 11.604 | 7.766 | 7.932 | 1.00 | 0.00 | PROT |
| ATOM | 2038 | HZ1 | LYS | 109 | 10.739 | 7.514 | 8.451 | 1.00 | 0.00 | PROT |
| ATOM | 2039 | HZ2 | LYS | 109 | 11.838 | 8.763 | 8.114 | 1.00 | 0.00 | PROT |
| ATOM | 2040 | HZ3 | LYS | 109 | 12.389 | 7.162 | 8.250 | 1.00 | 0.00 | PROT |
| ATOM | 2041 | C | LYS | 109 | 11.253 | 7.218 | 2.112 | 1.00 | 0.00 | PROT |

TABLE 10-continued

Atomic Structure Coordinates of the P/CAF Bromadomain and HIV-1 Tat Peptide Complex

| ATOM | 2042 | O    | LYS | 109 | 12.438 | 6.985  | 2.052  | 1.00 | 0.00 | PROT |
|------|------|------|-----|-----|--------|--------|--------|------|------|------|
| ATOM | 2043 | N    | ILE | 110 | 10.424 | 6.721  | 1.234  | 1.00 | 0.00 | PROT |
| ATOM | 2044 | HN   | ILE | 110 | 9.467  | 6.904  | 1.303  | 1.00 | 0.00 | PROT |
| ATOM | 2045 | CA   | ILE | 110 | 10.947 | 5.844  | 0.148  | 1.00 | 0.00 | PROT |
| ATOM | 2046 | HA   | ILE | 110 | 11.404 | 4.968  | 0.576  | 1.00 | 0.00 | PROT |
| ATOM | 2047 | CB   | ILE | 110 | 9.733  | 5.444  | −0.695 | 1.00 | 0.00 | PROT |
| ATOM | 2048 | HB   | ILE | 110 | 10.965 | 4.890  | −1.556 | 1.00 | 0.00 | PROT |
| ATOM | 2049 | CG1  | ILE | 110 | 8.981  | 6.688  | −1.169 | 1.00 | 0.00 | PROT |
| ATOM | 2050 | HG11 | ILE | 110 | 8.552  | 7.178  | −0.330 | 1.00 | 0.00 | PROT |
| ATOM | 2051 | HG12 | ILE | 110 | 9.667  | 7.365  | −1.652 | 1.00 | 0.00 | PROT |
| ATOM | 2052 | CG2  | ILE | 110 | 8.804  | 4.565  | 0.139  | 1.00 | 0.00 | PROT |
| ATOM | 2053 | HG21 | ILE | 110 | 7.778  | 4.836  | −0.058 | 1.00 | 0.00 | PROT |
| ATOM | 2054 | HG22 | ILE | 110 | 9.020  | 4.706  | 1.187  | 1.00 | 0.00 | PROT |
| ATOM | 2055 | HG23 | ILE | 110 | 8.961  | 3.529  | −0.124 | 1.00 | 0.00 | PROT |
| ATOM | 2056 | CD1  | ILE | 110 | 7.905  | 6.265  | −2.166 | 1.00 | 0.00 | PROT |
| ATOM | 2057 | HD11 | ILE | 110 | 8.373  | 5.809  | −3.022 | 1.00 | 0.00 | PROT |
| ATOM | 2058 | HD12 | ILE | 110 | 7.345  | 7.132  | −2.480 | 1.00 | 0.00 | PROT |
| ATOM | 2059 | HD13 | ILE | 110 | 7.239  | 5.555  | −1.698 | 1.00 | 0.00 | PROT |
| ATOM | 2060 | C    | ILE | 110 | 11.963 | 6.600  | −0.707 | 1.00 | 0.00 | PROT |
| ATOM | 2061 | O    | ILE | 110 | 12.936 | 6.040  | −1.171 | 1.00 | 0.00 | PROT |
| ATOM | 2062 | N    | LYS | 111 | 11.748 | 7.867  | −0.920 | 1.00 | 0.00 | PROT |
| ATOM | 2063 | HN   | LYS | 111 | 10.958 | 8.303  | −0.537 | 1.00 | 0.00 | PROT |
| ATOM | 2064 | CA   | LYS | 111 | 12.707 | 8.650  | −1.741 | 1.00 | 0.00 | PROT |
| ATOM | 2065 | HA   | LYS | 111 | 12.912 | 8.139  | −2.670 | 1.00 | 0.00 | PROT |
| ATOM | 2066 | CB   | LYS | 111 | 12.005 | 9.976  | −2.008 | 1.00 | 0.00 | PROT |
| ATOM | 2067 | HB1  | LYS | 111 | 12.370 | 10.725 | −1.322 | 1.00 | 0.00 | PROT |
| ATOM | 2068 | HB2  | LYS | 111 | 10.941 | 9.851  | −1.876 | 1.00 | 0.00 | PROT |
| ATOM | 2069 | CG   | LYS | 111 | 12.298 | 10.409 | −3.443 | 1.00 | 0.00 | PROT |
| ATOM | 2070 | HG1  | LYS | 111 | 13.346 | 10.638 | −3.538 | 1.00 | 0.00 | PROT |
| ATOM | 2071 | HG2  | LYS | 111 | 12.045 | 9.606  | −4.115 | 1.00 | 0.00 | PROT |
| ATOM | 2072 | CD   | LYS | 111 | 11.481 | 11.652 | −3.791 | 1.00 | 0.00 | PROT |
| ATOM | 2073 | HD1  | LYS | 111 | 11.705 | 12.430 | −3.081 | 1.00 | 0.00 | PROT |
| ATOM | 2074 | HD2  | LYS | 111 | 11.744 | 11.987 | −4.784 | 1.00 | 0.00 | PROT |
| ATOM | 2075 | CE   | LYS | 111 | 9.986  | 11.326 | −3.743 | 1.00 | 0.00 | PROT |
| ATOM | 2076 | HE1  | LYS | 111 | 9.698  | 11.020 | −2.749 | 1.00 | 0.00 | PROT |
| ATOM | 2077 | HE2  | LYS | 111 | 9.746  | 10.555 | −4.460 | 1.00 | 0.00 | PROT |
| ATOM | 2078 | NZ   | LYS | 111 | 9.308  | 12.602 | −4.108 | 1.00 | 0.00 | PROT |
| ATOM | 2079 | HZ1  | LYS | 111 | 9.300  | 13.239 | −3.285 | 1.00 | 0.00 | PROT |
| ATOM | 2080 | HZ2  | LYS | 111 | 8.330  | 12.404 | −4.401 | 1.00 | 0.00 | PROT |
| ATOM | 2081 | HZ3  | LYS | 111 | 9.819  | 13.056 | −4.892 | 1.00 | 0.00 | PROT |
| ATOM | 2082 | C    | LYS | 111 | 13.995 | 8.874  | −0.959 | 1.00 | 0.00 | PROT |
| ATOM | 2083 | O    | LYS | 111 | 15.083 | 8.650  | −1.453 | 1.00 | 0.00 | PROT |
| ATOM | 2084 | N    | GLU | 112 | 13.883 | 9.307  | 0.264  | 1.00 | 0.00 | PROT |
| ATOM | 2085 | HN   | GLU | 112 | 12.993 | 9.458  | 0.652  | 1.00 | 0.00 | PROT |
| ATOM | 2086 | CA   | GLU | 112 | 15.102 | 9.501  | 1.090  | 1.00 | 0.00 | PROT |
| ATOM | 2087 | HA   | GLU | 112 | 15.831 | 10.088 | 0.555  | 1.00 | 0.00 | PROT |
| ATOM | 2088 | CB   | GLU | 112 | 14.621 | 10.253 | 2.329  | 1.00 | 0.00 | PROT |
| ATOM | 2089 | HB1  | GLU | 112 | 13.881 | 9.660  | 2.843  | 1.00 | 0.00 | PROT |
| ATOM | 2090 | HB2  | GLU | 112 | 15.457 | 10.439 | 2.987  | 1.00 | 0.00 | PROT |
| ATOM | 2091 | CG   | GLU | 112 | 14.002 | 11.585 | 1.896  | 1.00 | 0.00 | PROT |
| ATOM | 2092 | HG1  | GLU | 112 | 13.216 | 11.857 | 2.585  | 1.00 | 0.00 | PROT |
| ATOM | 2093 | HG2  | GLU | 112 | 13.590 | 11.484 | 0.899  | 1.00 | 0.00 | PROT |
| ATOM | 2094 | CD   | GLU | 112 | 15.079 | 12.672 | 1.896  | 1.00 | 0.00 | PROT |
| ATOM | 2095 | OE1  | GLU | 112 | 16.109 | 12.458 | 1.277  | 1.00 | 0.00 | PROT |
| ATOM | 2096 | OE2  | GLU | 112 | 14.855 | 13.700 | 2.513  | 1.00 | 0.00 | PROT |
| ATOM | 2097 | C    | GLU | 112 | 15.680 | 8.135  | 1.460  | 1.00 | 0.00 | PROT |
| ATOM | 2098 | O    | GLU | 112 | 16.865 | 7.989  | 1.688  | 1.00 | 0.00 | PROT |
| ATOM | 2099 | N    | ALA | 113 | 14.852 | 7.125  | 1.476  | 1.00 | 0.00 | PROT |
| ATOM | 2100 | HN   | ALA | 113 | 13.905 | 7.263  | 1.257  | 1.00 | 0.00 | PROT |
| ATOM | 2101 | CA   | ALA | 113 | 15.349 | 5.753  | 1.761  | 1.00 | 0.00 | PROT |
| ATOM | 2102 | HA   | ALA | 113 | 15.938 | 5.737  | 2.666  | 1.00 | 0.00 | PROT |
| ATOM | 2103 | CB   | ALA | 113 | 14.089 | 4.895  | 1.912  | 1.00 | 0.00 | PROT |
| ATOM | 2104 | HB1  | ALA | 113 | 13.403 | 5.114  | 1.105  | 1.00 | 0.00 | PROT |
| ATOM | 2105 | HB2  | ALA | 113 | 13.614 | 5.112  | 2.857  | 1.00 | 0.00 | PROT |
| ATOM | 2106 | HB3  | ALA | 113 | 14.359 | 3.849  | 1.877  | 1.00 | 0.00 | PROT |
| ATOM | 2107 | C    | ALA | 113 | 16.166 | 5.268  | 0.571  | 1.00 | 0.00 | PROT |
| ATOM | 2108 | O    | ALA | 113 | 17.078 | 4.476  | 0.702  | 1.00 | 0.00 | PROT |
| ATOM | 2109 | N    | GLY | 114 | 15.835 | 5.747  | −0.595 | 1.00 | 0.00 | PROT |
| ATOM | 2110 | HN   | GLY | 114 | 15.093 | 6.382  | −0.670 | 1.00 | 0.00 | PROT |
| ATOM | 2111 | CA   | GLY | 114 | 16.572 | 5.328  | −1.810 | 1.00 | 0.00 | PROT |
| ATOM | 2112 | HA1  | GLY | 114 | 17.497 | 4.849  | −1.524 | 1.00 | 0.00 | PROT |
| ATOM | 2113 | HA2  | GLY | 114 | 16.788 | 6.194  | −2.418 | 1.00 | 0.00 | PROT |
| ATOM | 2114 | C    | GLY | 114 | 15.716 | 4.347  | −2.607 | 1.00 | 0.00 | PROT |
| ATOM | 2115 | O    | GLY | 114 | 16.226 | 3.572  | −3.393 | 1.00 | 0.00 | PROT |
| ATOM | 2116 | N    | LEU | 115 | 14.418 | 4.357  | −2.415 | 1.00 | 0.00 | PROT |
| ATOM | 2117 | HN   | LEU | 115 | 14.008 | 4.992  | −1.787 | 1.00 | 0.00 | PROT |
| ATOM | 2118 | CA   | LEU | 115 | 13.570 | 3.416  | −3.196 | 1.00 | 0.00 | PROT |

TABLE 10-continued

Atomic Structure Coordinates of the P/CAF Bromadomain and HIV-1 Tat Peptide Complex

| ATOM | 2119 | HA   | LEU | 115 | 14.123 | 2.522  | −3.437  | 1.00 | 0.00 | PROT |
|------|------|------|-----|-----|--------|--------|---------|------|------|------|
| ATOM | 2120 | CB   | LEU | 115 | 12.308 | 3.073  | −2.367  | 1.00 | 0.00 | PROT |
| ATOM | 2121 | HB1  | LEU | 115 | 11.817 | 2.247  | −2.855  | 1.00 | 0.00 | PROT |
| ATOM | 2122 | HB2  | LEU | 115 | 11.647 | 3.926  | −2.391  | 1.00 | 0.00 | PROT |
| ATOM | 2123 | CG   | LEU | 115 | 12.544 | 2.674  | −0.880  | 1.00 | 0.00 | PROT |
| ATOM | 2124 | HG   | LEU | 115 | 12.053 | 3.395  | −0.251  | 1.00 | 0.00 | PROT |
| ATOM | 2125 | CD1  | LEU | 115 | 11.907 | 1.303  | −0.634  | 1.00 | 0.00 | PROT |
| ATOM | 2126 | HD11 | LEU | 115 | 11.704 | 1.184  | 0.420   | 1.00 | 0.00 | PROT |
| ATOM | 2127 | HD12 | LEU | 115 | 12.582 | 0.527  | −0.962  | 1.00 | 0.00 | PROT |
| ATOM | 2128 | HD13 | LEU | 115 | 10.982 | 1.234  | −1.188  | 1.00 | 0.00 | PROT |
| ATOM | 2129 | CD2  | LEU | 115 | 14.014 | 2.603  | −0.477  | 1.00 | 0.00 | PROT |
| ATOM | 2130 | HD21 | LEU | 115 | 14.591 | 2.179  | −1.283  | 1.00 | 0.00 | PROT |
| ATOM | 2131 | HD22 | LEU | 115 | 14.111 | 1.989  | 0.405   | 1.00 | 0.00 | PROT |
| ATOM | 2132 | HD23 | LEU | 115 | 14.367 | 3.600  | −0.259  | 1.00 | 0.00 | PROT |
| ATOM | 2133 | C    | LEU | 115 | 13.128 | 4.117  | −4.473  | 1.00 | 0.00 | PROT |
| ATOM | 2134 | O    | LEU | 115 | 12.989 | 3.509  | −5.516  | 1.00 | 0.00 | PROT |
| ATOM | 2135 | N    | ILE | 116 | 12.855 | 5.389  | −4.384  | 1.00 | 0.00 | PROT |
| ATOM | 2136 | HN   | ILE | 116 | 13.005 | 5.871  | −3.548  | 1.00 | 0.00 | PROT |
| ATOM | 2137 | CA   | ILE | 116 | 12.450 | 6.140  | −5.581  | 1.00 | 0.00 | PROT |
| ATOM | 2138 | HA   | ILE | 116 | 12.135 | 5.473  | −6.369  | 1.00 | 0.00 | PROT |
| ATOM | 2139 | CB   | ILE | 116 | 11.311 | 7.028  | −5.134  | 1.00 | 0.00 | PROT |
| ATOM | 2140 | HB   | ILE | 116 | 11.653 | 7.686  | −4.349  | 1.00 | 0.00 | PROT |
| ATOM | 2141 | CG1  | ILE | 116 | 10.184 | 6.165  | −4.615  | 1.00 | 0.00 | PROT |
| ATOM | 2142 | HG11 | ILE | 116 | 10.537 | 5.556  | −3.796  | 1.00 | 0.00 | PROT |
| ATOM | 2143 | HG12 | ILE | 116 | 9.414  | 6.811  | −4.277  | 1.00 | 0.00 | PROT |
| ATOM | 2144 | CG2  | ILE | 116 | 10.807 | 7.860  | −6.315  | 1.00 | 0.00 | PROT |
| ATOM | 2145 | HG21 | ILE | 116 | 10.921 | 8.910  | −6.091  | 1.00 | 0.00 | PROT |
| ATOM | 2146 | HG22 | ILE | 116 | 9.761  | 7.639  | −6.486  | 1.00 | 0.00 | PROT |
| ATOM | 2147 | HG23 | ILE | 116 | 11.376 | 7.614  | −7.197  | 1.00 | 0.00 | PROT |
| ATOM | 2148 | CD1  | ILE | 116 | 9.648  | 5.268  | −5.739  | 1.00 | 0.00 | PROT |
| ATOM | 2149 | HD11 | ILE | 116 | 9.450  | 5.866  | −6.616  | 1.00 | 0.00 | PROT |
| ATOM | 2150 | HD12 | ILE | 116 | 8.734  | 4.792  | −5.413  | 1.00 | 0.00 | PROT |
| ATOM | 2151 | HD13 | ILE | 116 | 10.382 | 4.512  | −5.976  | 1.00 | 0.00 | PROT |
| ATOM | 2152 | C    | ILE | 116 | 13.600 | 6.991  | −6.022  | 1.00 | 0.00 | PROT |
| ATOM | 2153 | O    | ILE | 116 | 13.688 | 8.158  | −5.697  | 1.00 | 0.00 | PROT |
| ATOM | 2154 | N    | ASP | 117 | 14.486 | 6.420  | −6.746  | 1.00 | 0.00 | PROT |
| ATOM | 2155 | HN   | ASP | 117 | 14.377 | 5.475  | −6.969  | 1.00 | 0.00 | PROT |
| ATOM | 2156 | CA   | ASP | 117 | 15.654 | 7.200  | −7.239  | 1.00 | 0.00 | PROT |
| ATOM | 2157 | HA   | ASP | 117 | 16.149 | 7.694  | −6.416  | 1.00 | 0.00 | PROT |
| ATOM | 2158 | CB   | ASP | 117 | 16.583 | 6.163  | −7.873  | 1.00 | 0.00 | PROT |
| ATOM | 2159 | HB1  | ASP | 117 | 16.314 | 6.023  | −8.909  | 1.00 | 0.00 | PROT |
| ATOM | 2160 | HB2  | ASP | 117 | 16.488 | 5.225  | −7.346  | 1.00 | 0.00 | PROT |
| ATOM | 2161 | CG   | ASP | 117 | 18.030 | 6.653  | −7.783  | 1.00 | 0.00 | PROT |
| ATOM | 2162 | OD1  | ASP | 117 | 18.708 | 6.627  | −8.797  | 1.00 | 0.00 | PROT |
| ATOM | 2163 | OD2  | ASP | 117 | 18.434 | 7.048  | −6.702  | 1.00 | 0.00 | PROT |
| ATOM | 2164 | C    | ASP | 117 | 15.201 | 8.227  | −8.285  | 1.00 | 0.00 | PROT |
| ATOM | 2165 | O    | ASP | 117 | 15.724 | 8.278  | −9.380  | 1.00 | 0.00 | PROT |
| ATOM | 2166 | N    | LYS | 118 | 14.228 | 9.047  | −7.962  | 1.00 | 0.00 | PROT |
| ATOM | 2167 | HN   | LYS | 118 | 13.808 | 8.998  | −7.069  | 1.00 | 0.00 | PROT |
| ATOM | 2168 | CA   | LYS | 118 | 13.755 | 10.060 | −8.948  | 1.00 | 0.00 | PROT |
| ATOM | 2169 | HA   | LYS | 118 | 13.247 | 9.576  | −9.769  | 1.00 | 0.00 | PROT |
| ATOM | 2170 | CB   | LYS | 118 | 12.782 | 10.944 | −8.167  | 1.00 | 0.00 | PROT |
| ATOM | 2171 | HB1  | LYS | 118 | 12.394 | 11.715 | −8.817  | 1.00 | 0.00 | PROT |
| ATOM | 2172 | HB2  | LYS | 118 | 11.965 | 10.342 | −7.797  | 1.00 | 0.00 | PROT |
| ATOM | 2173 | CG   | LYS | 118 | 13.512 | 11.591 | −6.989  | 1.00 | 0.00 | PROT |
| ATOM | 2174 | HG1  | LYS | 118 | 13.044 | 11.288 | −6.064  | 1.00 | 0.00 | PROT |
| ATOM | 2175 | HG2  | LYS | 118 | 14.546 | 11.277 | −6.990  | 1.00 | 0.00 | PROT |
| ATOM | 2176 | CD   | LYS | 118 | 13.443 | 13.115 | −7.119  | 1.00 | 0.00 | PROT |
| ATOM | 2177 | HD1  | LYS | 118 | 13.925 | 13.420 | −8.036  | 1.00 | 0.00 | PROT |
| ATOM | 2178 | HD2  | LYS | 118 | 13.946 | 13.571 | −6.279  | 1.00 | 0.00 | PROT |
| ATOM | 2179 | CE   | LYS | 118 | 11.978 | 13.560 | −7.141  | 1.00 | 0.00 | PROT |
| ATOM | 2180 | HE1  | LYS | 118 | 11.327 | 12.716 | −6.966  | 1.00 | 0.00 | PROT |
| ATOM | 2181 | HE2  | LYS | 118 | 11.742 | 14.028 | −8.085  | 1.00 | 0.00 | PROT |
| ATOM | 2182 | NZ   | LYS | 118 | 11.861 | 14.546 | −6.030  | 1.00 | 0.00 | PROT |
| ATOM | 2183 | HZ1  | LYS | 118 | 11.876 | 14.045 | −5.119  | 1.00 | 0.00 | PROT |
| ATOM | 2184 | HZ2  | LYS | 118 | 10.967 | 15.068 | −6.123  | 1.00 | 0.00 | PROT |
| ATOM | 2185 | HZ3  | LYS | 118 | 12.658 | 15.212 | −6.072  | 1.00 | 0.00 | PROT |
| ATOM | 2186 | C    | LYS | 118 | 14.933 | 10.889 | −9.464  | 1.00 | 0.00 | PROT |
| ATOM | 2187 | OT1  | LYS | 118 | 14.725 | 11.675 | −10.374 | 1.00 | 0.00 | PROT |
| ATOM | 2188 | OT2  | LYS | 118 | 16.023 | 10.723 | −8.942  | 1.00 | 0.00 | PROT |
| END  |      |      |     |     |        |        |         |      |      |      |

TABLE 11

Chemical Shifts vector do (rmsd = 4.611) (resid 202 and name HA)
vector do (rmsd = 3.117) (resid 202 and name HB1)
vector do (rmsd = 2.895) (resid 202 and name HB2)
vector do (rmsd = 7.126) (resid 202 and name HD1)
vector do (rmsd = 7.126) (resid 202 and name HD2)
vector do (rmsd = 6.846) (resid 202 and name HE1)
vector do (rmsd = 6.846) (resid 202 and name HE2)
vector do (rmsd = 3.921) (resid 203 and name HA1)
vector do (rmsd = 3.921) (resid 203 and name HA2)
vector do (rmsd = 4.418) (resid 204 and name HA)
vector do (rmsd = 1.862) (resid 204 and name HB1)
vector do (rmsd = 1.775) (resid 204 and name HB2)
vector do (rmsd = 1.644) (resid 204 and name HG1)
vector do (rmsd = 3.190) (resid 204 and name HD1)
vector do (rmsd = 4.289) (resid 205 and name HA)
vector do (rmsd = 1.765) (resid 205 and name HB1)
vector do (rmsd = 1.295) (resid 205 and name HG1)
vector do (rmsd = 1.145) (resid 205 and name HG2)
vector do (rmsd = 1.415) (resid 205 and name HD1)
vector do (rmsd = 3.072) (resid 205 and name HE1)
vector do (rmsd = 7.881) (resid 205 and name HZ)
vector do (rmsd = 1.872) (resid 205 and name HH#)
vector do (rmsd = 4.312) (resid 206 and name HA)
vector do (rmsd = 1.440) (resid 206 and name HG1)
vector do (rmsd = 3.156) (resid 206 and name HE1)
vector do (rmsd = 4.296) (resid 207 and name HA)
vector do (rmsd = 1.805) (resid 207 and name HB1)
vector do (rmsd = 1.660) (resid 207 and name HG1)
vector do (rmsd = 3.202) (resid 207 and name HD1)
vector do (rmsd = 4.310) (resid 208 and name HA)
vector do (rmsd = 1.776) (resid 208 and name HB1)
vector do (rmsd = 1.613) (resid 208 and name HG1)
vector do (rmsd = 3.149) (resid 208 and name HD1)
vector do (rmsd = 4.314) (resid 209 and name HA)
vector do (rmsd = 2.073) (resid 209 and name HB1)
vector do (rmsd = 1.977) (resid 209 and name HB2)
vector do (rmsd = 2.356) (resid 209 and name HG1)
vector do (rmsd = 7.328) (resid 209 and name HE21)
vector do (rmsd = 6.862) (resid 209 and name HE22)
vector do (rmsd = 4.315) (resid 210 and name HA)
vector do (rmsd = 1.795) (resid 210 and name HB1)
vector do (rmsd = 1.626) (resid 210 and name HG1)
vector do (rmsd = 3.149) (resid 210 and name HD1)
vector do (rmsd = 4.465) (resid 211 and name HA)
vector do (rmsd = 2.910) (resid 211 and name HB1)
vector do (rmsd = 58.274) (resid 5 and name CA)
vector do (rmsd = 4.465) (resid 5 and name HA)
vector do (rmsd = 63.709) (resid 5 and name CB)
vector do (rmsd = 3.905) (resid 5 and name HB2)
vector do (rmsd = 56.036) (resid 6 and name CA)
vector do (rmsd = 4.375) (resid 6 and name HA)
vector do (rmsd = 32.965) (resid 6 and name CB)
vector do (rmsd = 1.885) (resid 6 and name HB1)
vector do (rmsd = 1.790) (resid 6 and name HB2)
vector do (rmsd = 24.718) (resid 6 and name CG)
vector do (rmsd = 1.447) (resid 6 and name HG1)
vector do (rmsd = 1.432) (resid 6 and name HG2)
vector do (rmsd = 28.968) (resid 6 and name CD)
vector do (rmsd = 1.680) (resid 6 and name HD1)
vector do (rmsd = 41.812) (resid 6 and name CE)
vector do (rmsd = 3.008) (resid 6 and name HE1)
vector do (rmsd = 54.337) (resid 7 and name CA)
vector do (rmsd = 4.584) (resid 7 and name HA)
vector do (rmsd = 29.653) (resid 7 and name CB)
vector do (rmsd = 2.078) (resid 7 and name HB1)
vector do (rmsd = 1.943) (resid 7 and name HB2)
vector do (rmsd = 35.919) (resid 7 and name CG)
vector do (rmsd = 2.302) (resid 7 and name HG1)
vector do (rmsd = 63.005) (resid 8 and name CA)
vector do (rmsd = 4.457) (resid 8 and name HA)
vector do (rmsd = 31.877) (resid 8 and name CB)
vector do (rmsd = 2.299) (resid 8 and name HB1)
vector do (rmsd = 1.913) (resid 8 and name HB2)
vector do (rmsd = 27.421) (resid 8 and name CG)
vector do (rmsd = 2.058) (resid 8 and name HG1)
vector do (rmsd = 50.560) (resid 8 and name CD)
vector do (rmsd = 3.724) (resid 8 and name HD2)
vector do (rmsd = 3.869) (resid 8 and name HD1)
vector do (rmsd = 55.787) (resid 9 and name CA)
vector do (rmsd = 4.357) (resid 9 and name HA)
vector do (rmsd = 30.898) (resid 9 and name CB)
vector do (rmsd = 1.873) (resid 9 and name HB1)
vector do (rmsd = 1.831) (resid 9 and name HB2)
vector do (rmsd = 27.211) (resid 9 and name CG)
vector do (rmsd = 1.689) (resid 9 and name HG1)
vector do (rmsd = 43.342) (resid 9 and name CD)
vector do (rmsd = 3.221) (resid 9 and name HD1)
vector do (rmsd = 53.302) (resid 10 and name CA)
vector do (rmsd = 4.913) (resid 10 and name HA)
vector do (rmsd = 41.450) (resid 10 and name CB)
vector do (rmsd = 2.800) (resid 10 and name HB1)
vector do (rmsd = 2.734) (resid 10 and name HB2)
vector do (rmsd = 64.747) (resid 11 and name CA)
vector do (rmsd = 4.375) (resid 11 and name HA)
vector do (rmsd = 32.391) (resid 11 and name CB)
vector do (rmsd = 2.356) (resid 11 and name HB1)
vector do (rmsd = 2.086) (resid 11 and name HB2)
vector do (rmsd = 27.470) (resid 11 and name CG)
vector do (rmsd = 2.098) (resid 11 and name HG1)
vector do (rmsd = 50.809) (resid 11 and name CD)
vector do (rmsd = 3.907) (resid 11 and name HD1)
vector do (rmsd = 55.837) (resid 12 and name CA)
vector do (rmsd = 4.717) (resid 12 and name HA)
vector do (rmsd = 40.853) (resid 12 and name CB)
vector do (rmsd = 2.848) (resid 12 and name HB1)
vector do (rmsd = 2.794) (resid 12 and name HB2)
vector do (rmsd = 58.276) (resid 13 and name CA)
vector do (rmsd = 4.217) (resid 13 and name HA)
vector do (rmsd = 28.906) (resid 13 and name CB)
vector do (rmsd = 2.188) (resid 13 and name HB1)
vector do (rmsd = 33.852) (resid 13 and name CG)
vector do (rmsd = 2.530) (resid 13 and name HG1)
vector do (rmsd = 2.421) (resid 13 and name HG2)
vector do (rmsd = 58.276) (resid 14 and name CA)
vector do (rmsd = 4.098) (resid 14 and name HA)
vector do (rmsd = 41.102) (resid 14 and name CB)
vector do (rmsd = 1.874) (resid 14 and name HB1)
vector do (rmsd = 1.595) (resid 14 and name HB2)
vector do (rmsd = 26.915) (resid 14 and name CG)
vector do (rmsd = 1.424) (resid 14 and name HG)
vector do (rmsd = 25.671) (resid 14 and name CD1)
vector do (rmsd = 0.855) (resid 14 and name HD1#)
vector do (rmsd = 23.182) (resid 14 and name CD2)
vector do (rmsd = 0.833) (resid 14 and name HD2#)
vector do (rmsd = 62.071) (resid 15 and name CA)
vector do (rmsd = 4.055) (resid 15 and name HA)
vector do (rmsd = 38.561) (resid 15 and name CB)
vector do (rmsd = 3.346) (resid 15 and name HB1)
vector do (rmsd = 3.084) (resid 15 and name HB2)
vector do (rmsd = 132.705) (resid 15 and name CD1)
vector do (rmsd = 7.126) (resid 15 and name HD1)
vector do (rmsd = 118.507) (resid 15 and name CE1)
vector do (rmsd = 6.925) (resid 15 and name HE1)
vector do (rmsd = 57.529) (resid 16 and name CA)
vector do (rmsd = 4.188) (resid 16 and name HA)
vector do (rmsd = 62.009) (resid 16 and name CB)
vector do (rmsd = 4.023) (resid 16 and name HB1)
vector do (rmsd = 3.940) (resid 16 and name HB2)
vector do (rmsd = 66.738) (resid 17 and name CA)
vector do (rmsd = 3.975) (resid 17 and name HA)
vector do (rmsd = 68.481) (resid 17 and name CB)
vector do (rmsd = 4.267) (resid 17 and name HB)
vector do (rmsd = 21.440) (resid 17 and name CG2)
vector do (rmsd = 1.177) (resid 17 and name HG2#)
vector do (rmsd = 57.778) (resid 18 and name CA)
vector do (rmsd = 3.303) (resid 18 and name HA)
vector do (rmsd = 39.609) (resid 18 and name CB)
vector do (rmsd = 1.556) (resid 18 and name HB1)
vector do (rmsd = 0.346) (resid 18 and name HB2)
vector do (rmsd = 24.675) (resid 18 and name CG)
vector do (rmsd = 1.698) (resid 18 and name HG)
vector do (rmsd = 25.422) (resid 18 and name CD1)
vector do (rmsd = 0.514) (resid 18 and name HD1#)
vector do (rmsd = 19.983) (resid 18 and name CD2)

TABLE 11-continued

Chemical Shifts vector do (rmsd = −0.159) (resid 18 and name HD2#)
vector do (rmsd = 59.898) (resid 19 and name CA)
vector do (rmsd = 3.720) (resid 19 and name HA)
vector do (rmsd = 32.391) (resid 19 and name CB)
vector do (rmsd = 1.737) (resid 19 and name HB1)
vector do (rmsd = 1.410) (resid 19 and name HB2)
vector do (rmsd = 24.702) (resid 19 and name CG)
vector do (rmsd = 1.307) (resid 19 and name HG1)
vector do (rmsd = 29.721) (resid 19 and name CD)
vector do (rmsd = 1.647) (resid 19 and name HD1)
vector do (rmsd = 41.600) (resid 19 and name CE)
vector do (rmsd = 2.967) (resid 19 and name HE1)
vector do (rmsd = 61.263) (resid 20 and name CA)
vector do (rmsd = 4.324) (resid 20 and name HA)
vector do (rmsd = 62.759) (resid 20 and name CB)
vector do (rmsd = 4.099) (resid 20 and name HB1)
vector do (rmsd = 65.245) (resid 21 and name CA)
vector do (rmsd = 3.798) (resid 21 and name HA)
vector do (rmsd = 37.547) (resid 21 and name CB)
vector do (rmsd = 1.953) (resid 21 and name HB)
vector do (rmsd = 28.409) (resid 21 and name CG1)
vector do (rmsd = 1.781) (resid 21 and name HG11)
vector do (rmsd = 1.077) (resid 21 and name HG12)
vector do (rmsd = 17.208) (resid 21 and name CG2)
vector do (rmsd = 1.016) (resid 21 and name HG2#)
vector do (rmsd = 13.433) (resid 21 and name CD1)
vector do (rmsd = 0.651) (resid 21 and name HD1#)
vector do (rmsd = 58.276) (resid 22 and name CA)
vector do (rmsd = 4.147) (resid 22 and name HA)
vector do (rmsd = 41.600) (resid 22 and name CB)
vector do (rmsd = 2.126) (resid 22 and name HB1)
vector do (rmsd = 1.736) (resid 22 and name HB2)
vector do (rmsd = 27.413) (resid 22 and name CG)
vector do (rmsd = 1.799) (resid 22 and name HG)
vector do (rmsd = 26.418) (resid 22 and name CD1)
vector do (rmsd = 1.106) (resid 22 and name HD1#)
vector do (rmsd = 23.776) (resid 22 and name CD2)
vector do (rmsd = 1.049) (resid 22 and name HD2#)
vector do (rmsd = 59.520) (resid 23 and name CA)
vector do (rmsd = 4.078) (resid 23 and name HA)
vector do (rmsd = 28.160) (resid 23 and name CB)
vector do (rmsd = 2.359) (resid 23 and name HB1)
vector do (rmsd = 2.247) (resid 23 and name HB2)
vector do (rmsd = 33.884) (resid 23 and name CG)
vector do (rmsd = 2.591) (resid 23 and name HG1)
vector do (rmsd = 2.484) (resid 23 and name HG2)
vector do (rmsd = 59.520) (resid 24 and name CA)
vector do (rmsd = 4.227) (resid 24 and name HA)
vector do (rmsd = 29.653) (resid 24 and name CB)
vector do (rmsd = 2.519) (resid 24 and name HB1)
vector do (rmsd = 2.418) (resid 24 and name HB2)
vector do (rmsd = 35.353) (resid 24 and name CG)
vector do (rmsd = 2.890) (resid 24 and name HG1)
vector do (rmsd = 2.502) (resid 24 and name HG2)
vector do (rmsd = 180.060) (resid 24 and name CD)
vector do (rmsd = 67.236) (resid 25 and name CA)
vector do (rmsd = 3.864) (resid 25 and name HA)
vector do (rmsd = 31.644) (resid 25 and name CB)
vector do (rmsd = 2.437) (resid 25 and name HB)
vector do (rmsd = 22.933) (resid 25 and name CG1)
vector do (rmsd = 1.244) (resid 25 and name HG1#)
vector do (rmsd = 22.186) (resid 25 and name CG2)
vector do (rmsd = 1.076) (resid 25 and name HG2#)
vector do (rmsd = 59.520) (resid 26 and name CA)
vector do (rmsd = 3.926) (resid 26 and name HA)
vector do (rmsd = 32.640) (resid 26 and name CB)
vector do (rmsd = 1.896) (resid 26 and name HB1)
vector do (rmsd = 26.666) (resid 26 and name CG)
vector do (rmsd = 1.532) (resid 26 and name HG1)
vector do (rmsd = 31.147) (resid 26 and name CD)
vector do (rmsd = 1.839) (resid 26 and name HD1)
vector do (rmsd = 41.102) (resid 26 and name CE)
vector do (rmsd = 2.820) (resid 26 and name HE1)
vector do (rmsd = 58.713) (resid 27 and name CA)
vector do (rmsd = 4.486) (resid 27 and name HA)
vector do (rmsd = 63.955) (resid 27 and name CB)
vector do (rmsd = 4.051) (resid 27 and name HB1)
vector do (rmsd = 58.276) (resid 28 and name CA)
vector do (rmsd = 4.019) (resid 28 and name HA)
vector do (rmsd = 32.251) (resid 28 and name CB)
vector do (rmsd = 3.023) (resid 28 and name HB1)
vector do (rmsd = 2.821) (resid 28 and name HB2)
vector do (rmsd = 5.024) (resid 28 and name HD2)
vector do (rmsd = 59.023) (resid 29 and name CA)
vector do (rmsd = 4.225) (resid 29 and name HA)
vector do (rmsd = 28.160) (resid 29 and name CB)
vector do (rmsd = 2.139) (resid 29 and name HB1)
vector do (rmsd = 33.635) (resid 29 and name CG)
vector do (rmsd = 2.492) (resid 29 and name HG1)
vector do (rmsd = 2.428) (resid 29 and name HG2)
vector do (rmsd = 60.018) (resid 30 and name CA)
vector do (rmsd = 4.846) (resid 30 and name HA)
vector do (rmsd = 63.503) (resid 30 and name CB)
vector do (rmsd = 4.350) (resid 30 and name HB1)
vector do (rmsd = 3.980) (resid 30 and name HB2)
vector do (rmsd = 53.233) (resid 31 and name CA)
vector do (rmsd = 4.440) (resid 31 and name HA)
vector do (rmsd = 20.014) (resid 31 and name CB)
vector do (rmsd = 1.762) (resid 31 and name HB#)
vector do (rmsd = 60.570) (resid 32 and name CA)
vector do (rmsd = 4.423) (resid 32 and name HA)
vector do (rmsd = 27.911) (resid 32 and name CB)
vector do (rmsd = 3.637) (resid 32 and name HB1)
vector do (rmsd = 3.408) (resid 32 and name HB2)
vector do (rmsd = 127.381) (resid 32 and name CD1)
vector do (rmsd = 7.889) (resid 32 and name HD1)
vector do (rmsd = 10.403) (resid 32 and name HE1)
vector do (rmsd = 7.359) (resid 32 and name HE3)
vector do (rmsd = 7.190) (resid 32 and name HH2)
vector do (rmsd = 64.498) (resid 33 and name CA)
vector do (rmsd = 3.990) (resid 33 and name HA)
vector do (rmsd = 30.151) (resid 33 and name CB)
vector do (rmsd = 1.078) (resid 33 and name HB1)
vector do (rmsd = −0.432) (resid 33 and name HB2)
vector do (rmsd = 25.671) (resid 33 and name CG)
vector do (rmsd = 0.271) (resid 33 and name HG1)
vector do (rmsd = −0.875) (resid 33 and name HG2)
vector do (rmsd = 50.062) (resid 33 and name CD)
vector do (rmsd = 1.570) (resid 33 and name HD2)
vector do (rmsd = 2.268) (resid 33 and name HD1)
vector do (rmsd = 55.777) (resid 34 and name CA)
vector do (rmsd = 5.005) (resid 34 and name HA)
vector do (rmsd = 39.111) (resid 34 and name CB)
vector do (rmsd = 3.516) (resid 34 and name HB1)
vector do (rmsd = 2.613) (resid 34 and name HB2)
vector do (rmsd = 7.180) (resid 34 and name HD1)
vector do (rmsd = 7.199) (resid 34 and name HE1)
vector do (rmsd = 7.278) (resid 34 and name HZ)
vector do (rmsd = 57.031) (resid 35 and name CA)
vector do (rmsd = 4.325) (resid 35 and name HA)
vector do (rmsd = 32.391) (resid 35 and name CB)
vector do (rmsd = 2.314) (resid 35 and name HB1)
vector do (rmsd = 2.224) (resid 35 and name HB2)
vector do (rmsd = 33.138) (resid 35 and name CG)
vector do (rmsd = 2.902) (resid 35 and name HG1)
vector do (rmsd = 16.753) (resid 35 and name CE)
vector do (rmsd = 2.217) (resid 35 and name HE#)
vector do (rmsd = 53.298) (resid 36 and name CA)
vector do (rmsd = 4.867) (resid 36 and name HA)
vector do (rmsd = 31.395) (resid 36 and name CB)
vector do (rmsd = 2.149) (resid 36 and name HB1)
vector do (rmsd = 1.800) (resid 36 and name HB2)
vector do (rmsd = 35.905) (resid 36 and name CG)
vector do (rmsd = 2.205) (resid 36 and name HG1)
vector do (rmsd = 63.005) (resid 37 and name CA)
vector do (rmsd = 4.271) (resid 37 and name HA)
vector do (rmsd = 31.921) (resid 37 and name CB)
vector do (rmsd = 2.381) (resid 37 and name HB1)
vector do (rmsd = 1.703) (resid 37 and name HB2)
vector do (rmsd = 27.164) (resid 37 and name CG)
vector do (rmsd = 2.182) (resid 37 and name HG1)
vector do (rmsd = 2.040) (resid 37 and name HG2)
vector do (rmsd = 50.560) (resid 37 and name CD)
vector do (rmsd = 3.706) (resid 37 and name HD1)

TABLE 11-continued

Chemical Shifts vector do (rmsd = 63.752) (resid 38 and name CA)
vector do (rmsd = 3.492) (resid 38 and name HA)
vector do (rmsd = 32.139) (resid 38 and name CB)
vector do (rmsd = 1.071) (resid 38 and name HB)
vector do (rmsd = 22.188) (resid 38 and name CG1)
vector do (rmsd = 0.498) (resid 38 and name HG1#)
vector do (rmsd = 21.440) (resid 38 and name CG2)
vector do (rmsd = −0.008) (resid 38 and name HG2#)
vector do (rmsd = 56.815) (resid 39 and name CA)
vector do (rmsd = 4.441) (resid 39 and name HA)
vector do (rmsd = 32.142) (resid 39 and name CB)
vector do (rmsd = 2.033) (resid 39 and name HB1)
vector do (rmsd = 1.924) (resid 39 and name HB2)
vector do (rmsd = 25.671) (resid 39 and name CG)
vector do (rmsd = 1.644) (resid 39 and name HG1)
vector do (rmsd = 1.463) (resid 39 and name HG2)
vector do (rmsd = 28.906) (resid 39 and name CD)
vector do (rmsd = 1.715) (resid 39 and name HD1)
vector do (rmsd = 1.644) (resid 39 and name HD2)
vector do (rmsd = 40.356) (resid 39 and name CE)
vector do (rmsd = 3.186) (resid 39 and name HE1)
vector do (rmsd = 2.950) (resid 39 and name HE2)
vector do (rmsd = 3.679) (resid 40 and name HA)
vector do (rmsd = 62.756) (resid 41 and name CA)
vector do (rmsd = 4.097) (resid 41 and name HA)
vector do (rmsd = 68.441) (resid 41 and name CB)
vector do (rmsd = 4.343) (resid 41 and name HB)
vector do (rmsd = 22.435) (resid 41 and name CG2)
vector do (rmsd = 1.320) (resid 41 and name HG2#)
vector do (rmsd = 56.145) (resid 42 and name CA)
vector do (rmsd = 4.501) (resid 42 and name HA)
vector do (rmsd = 30.874) (resid 42 and name CB)
vector do (rmsd = 2.217) (resid 42 and name HB1)
vector do (rmsd = 2.075) (resid 42 and name HB2)
vector do (rmsd = 36.637) (resid 42 and name CG)
vector do (rmsd = 2.362) (resid 42 and name HG1)
vector do (rmsd = 2.268) (resid 42 and name HG2)
vector do (rmsd = 49.565) (resid 43 and name CA)
vector do (rmsd = 5.000) (resid 43 and name HA)
vector do (rmsd = 20.427) (resid 43 and name CB)
vector do (rmsd = 0.969) (resid 43 and name HB#)
vector do (rmsd = 64.249) (resid 44 and name CA)
vector do (rmsd = 4.549) (resid 44 and name HA)
vector do (rmsd = 31.644) (resid 44 and name CB)
vector do (rmsd = 2.415) (resid 44 and name HB1)
vector do (rmsd = 2.053) (resid 44 and name HB2)
vector do (rmsd = 27.662) (resid 44 and name CG)
vector do (rmsd = 2.209) (resid 44 and name HG1)
vector do (rmsd = 2.079) (resid 44 and name HG2)
vector do (rmsd = 50.311) (resid 44 and name CD)
vector do (rmsd = 3.564) (resid 44 and name HD2)
vector do (rmsd = 3.838) (resid 44 and name HD1)
vector do (rmsd = 43.342) (resid 45 and name CA)
vector do (rmsd = 3.912) (resid 45 and name HA1)
vector do (rmsd = 62.697) (resid 46 and name CA)
vector do (rmsd = 3.506) (resid 46 and name HA)
vector do (rmsd = 39.609) (resid 46 and name CB)
vector do (rmsd = 2.784) (resid 46 and name HB1)
vector do (rmsd = 2.400) (resid 46 and name HB2)
vector do (rmsd = 5.998) (resid 46 and name HE1)
vector do (rmsd = 60.516) (resid 47 and name CA)
vector do (rmsd = 4.148) (resid 47 and name HA)
vector do (rmsd = 36.871) (resid 47 and name CB)
vector do (rmsd = 3.236) (resid 47 and name HB1)
vector do (rmsd = 2.861) (resid 47 and name HB2)
vector do (rmsd = 133.149) (resid 47 and name CD1)
vector do (rmsd = 7.409) (resid 47 and name HD1)
vector do (rmsd = 117.620) (resid 47 and name CE1)
vector do (rmsd = 6.675) (resid 47 and name HE1)
vector do (rmsd = 57.529) (resid 48 and name CA)
vector do (rmsd = 4.097) (resid 48 and name HA)
vector do (rmsd = 30.898) (resid 48 and name CB)
vector do (rmsd = 2.127) (resid 48 and name HB1)
vector do (rmsd = 2.104) (resid 48 and name HB2)
vector do (rmsd = 37.120) (resid 48 and name CG)
vector do (rmsd = 2.352) (resid 48 and name HG1)
vector do (rmsd = 2.247) (resid 48 and name HG2)
vector do (rmsd = 63.005) (resid 49 and name CA)
vector do (rmsd = 4.110) (resid 49 and name HA)
vector do (rmsd = 33.635) (resid 49 and name CB)
vector do (rmsd = 1.926) (resid 49 and name HB)
vector do (rmsd = 20.195) (resid 49 and name CG1)
vector do (rmsd = 0.990) (resid 49 and name HG1#)
vector do (rmsd = 20.957) (resid 49 and name CG2)
vector do (rmsd = 0.917) (resid 49 and name HG2#)
vector do (rmsd = 57.280) (resid 50 and name CA)
vector do (rmsd = 3.948) (resid 50 and name HA)
vector do (rmsd = 34.133) (resid 50 and name CB)
vector do (rmsd = 1.256) (resid 50 and name HB)
vector do (rmsd = 24.426) (resid 50 and name CG1)
vector do (rmsd = 0.826) (resid 50 and name HG11)
vector do (rmsd = 0.190) (resid 50 and name HG12)
vector do (rmsd = 16.175) (resid 50 and name CG2)
vector do (rmsd = 0.420) (resid 50 and name HG2#)
vector do (rmsd = 9.173) (resid 50 and name HD1)
vector do (rmsd = 0.582) (resid 50 and name HD1#)
vector do (rmsd = 57.031) (resid 51 and name CA)
vector do (rmsd = 3.876) (resid 51 and name HA)
vector do (rmsd = 30.400) (resid 51 and name CB)
vector do (rmsd = 1.396) (resid 51 and name HB1)
vector do (rmsd = 1.214) (resid 51 and name HB2)
vector do (rmsd = 26.915) (resid 51 and name CG)
vector do (rmsd = 1.350) (resid 51 and name HG1)
vector do (rmsd = 1.196) (resid 51 and name HG2)
vector do (rmsd = 42.638) (resid 51 and name CD)
vector do (rmsd = 3.025) (resid 51 and name HD1)
vector do (rmsd = 54.294) (resid 52 and name CA)
vector do (rmsd = 5.037) (resid 52 and name HA)
vector do (rmsd = 38.566) (resid 52 and name CB)
vector do (rmsd = 3.088) (resid 52 and name HB1)
vector do (rmsd = 2.955) (resid 52 and name HB2)
vector do (rmsd = 132.262) (resid 52 and name CD1)
vector do (rmsd = 7.281) (resid 52 and name HD1)
vector do (rmsd = 63.005) (resid 53 and name CA)
vector do (rmsd = 4.112) (resid 53 and name HA)
vector do (rmsd = 32.391) (resid 53 and name CB)
vector do (rmsd = 2.249) (resid 53 and name HB1)
vector do (rmsd = 27.911) (resid 53 and name CG)
vector do (rmsd = 2.275) (resid 53 and name HG1)
vector do (rmsd = 1.941) (resid 53 and name HG2)
vector do (rmsd = 50.311) (resid 53 and name CD)
vector do (rmsd = 3.446) (resid 53 and name HD2)
vector do (rmsd = 3.649) (resid 53 and name HD1)
vector do (rmsd = 53.547) (resid 54 and name CA)
vector do (rmsd = 4.987) (resid 54 and name HA)
vector do (rmsd = 31.147) (resid 54 and name CB)
vector do (rmsd = 2.057) (resid 54 and name HB1)
vector do (rmsd = 1.386) (resid 54 and name HB2)
vector do (rmsd = 30.649) (resid 54 and name CG)
vector do (rmsd = 2.737) (resid 54 and name HG1)
vector do (rmsd = 1.898) (resid 54 and name HG2)
vector do (rmsd = 14.027) (resid 54 and name CE)
vector do (rmsd = 2.002) (resid 54 and name HE#)
vector do (rmsd = 53.298) (resid 55 and name CA)
vector do (rmsd = 4.779) (resid 55 and name HA)
vector do (rmsd = 44.089) (resid 55 and name CB)
vector do (rmsd = 2.409) (resid 55 and name HB1)
vector do (rmsd = 57.529) (resid 56 and name CA)
vector do (rmsd = 4.075) (resid 56 and name HA)
vector do (rmsd = 41.102) (resid 56 and name CB)
vector do (rmsd = 2.115) (resid 56 and name HB1)
vector do (rmsd = 1.442) (resid 56 and name HB2)
vector do (rmsd = 27.150) (resid 56 and name CG)
vector do (rmsd = 1.768) (resid 56 and name HG)
vector do (rmsd = 26.930) (resid 56 and name CD1)
vector do (rmsd = 0.980) (resid 56 and name HD1#)
vector do (rmsd = 22.535) (resid 56 and name CD2)
vector do (rmsd = 0.678) (resid 56 and name HD2#)
vector do (rmsd = 60.267) (resid 57 and name CA)
vector do (rmsd = 3.910) (resid 57 and name HA)
vector do (rmsd = 30.400) (resid 57 and name CB)
vector do (rmsd = 1.144) (resid 57 and name HB1)
vector do (rmsd = 1.149) (resid 57 and name HB2)
vector do (rmsd = 24.924) (resid 57 and name CG)

TABLE 11-continued

Chemical Shifts vector do (rmsd = 1.531) (resid 57 and name HG1)
vector do (rmsd = 29.385) (resid 57 and name CD)
vector do (rmsd = 1.752) (resid 57 and name HD1)
vector do (rmsd = 0.919) (resid 57 and name HD2)
vector do (rmsd = 43.813) (resid 57 and name CE)
vector do (rmsd = 2.614) (resid 57 and name HE1)
vector do (rmsd = 2.109) (resid 57 and name HE2)
vector do (rmsd = 66.738) (resid 58 and name CA)
vector do (rmsd = 3.880) (resid 58 and name HA)
vector do (rmsd = 67.236) (resid 58 and name CB)
vector do (rmsd = 4.119) (resid 58 and name HB)
vector do (rmsd = 21.900) (resid 58 and name CG2)
vector do (rmsd = 1.090) (resid 58 and name HG2#)
vector do (rmsd = 60.784) (resid 59 and name CA)
vector do (rmsd = 4.357) (resid 59 and name HA)
vector do (rmsd = 33.038) (resid 59 and name CB)
vector do (rmsd = 2.145) (resid 59 and name HB1)
vector do (rmsd = 1.936) (resid 59 and name HB2)
vector do (rmsd = 32.889) (resid 59 and name CG)
vector do (rmsd = 2.651) (resid 59 and name HG1)
vector do (rmsd = 2.558) (resid 59 and name HG2)
vector do (rmsd = 16.164) (resid 59 and name CE)
vector do (rmsd = 1.310) (resid 59 and name HE#)
vector do (rmsd = 62.615) (resid 60 and name CA)
vector do (rmsd = 4.445) (resid 60 and name HA)
vector do (rmsd = 62.650) (resid 60 and name CB)
vector do (rmsd = 4.248) (resid 60 and name HB1)
vector do (rmsd = 4.065) (resid 60 and name HB2)
vector do (rmsd = 59.321) (resid 61 and name CA)
vector do (rmsd = 4.102) (resid 61 and name HA)
vector do (rmsd = 28.906) (resid 61 and name CB)
vector do (rmsd = 2.248) (resid 61 and name HB1)
vector do (rmsd = 2.112) (resid 61 and name HB2)
vector do (rmsd = 36.111) (resid 61 and name CG)
vector do (rmsd = 2.409) (resid 61 and name HG1)
vector do (rmsd = 2.277) (resid 61 and name HG2)
vector do (rmsd = 60.237) (resid 62 and name CA)
vector do (rmsd = 3.919) (resid 62 and name HA)
vector do (rmsd = 32.652) (resid 62 and name CB)
vector do (rmsd = 2.069) (resid 62 and name HB1)
vector do (rmsd = 1.077) (resid 62 and name HB2)
vector do (rmsd = 1.733) (resid 62 and name HG1)
vector do (rmsd = 0.839) (resid 62 and name HG2)
vector do (rmsd = 42.587) (resid 62 and name CD)
vector do (rmsd = 2.581) (resid 62 and name HD1)
vector do (rmsd = 58.247) (resid 63 and name CA)
vector do (rmsd = 4.717) (resid 63 and name HA)
vector do (rmsd = 42.098) (resid 63 and name CB)
vector do (rmsd = 2.354) (resid 63 and name HB1)
vector do (rmsd = 1.978) (resid 63 and name HB2)
vector do (rmsd = 27.164) (resid 63 and name CG)
vector do (rmsd = 1.849) (resid 63 and name HG)
vector do (rmsd = 26.915) (resid 63 and name CD1)
vector do (rmsd = 0.918) (resid 63 and name HD1#)
vector do (rmsd = 25.422) (resid 63 and name CD2)
vector do (rmsd = 1.082) (resid 63 and name HD2#)
vector do (rmsd = 59.093) (resid 64 and name CA)
vector do (rmsd = 4.376) (resid 64 and name HA)
vector do (rmsd = 32.391) (resid 64 and name CB)
vector do (rmsd = 2.061) (resid 64 and name HB1)
vector do (rmsd = 24.819) (resid 64 and name CG)
vector do (rmsd = 1.650) (resid 64 and name HG1)
vector do (rmsd = 29.493) (resid 64 and name CD)
vector do (rmsd = 1.788) (resid 64 and name HD1)
vector do (rmsd = 42.098) (resid 64 and name CE)
vector do (rmsd = 3.024) (resid 64 and name HE1)
vector do (rmsd = 53.298) (resid 65 and name CA)
vector do (rmsd = 4.805) (resid 65 and name HA)
vector do (rmsd = 41.102) (resid 65 and name CB)
vector do (rmsd = 3.024) (resid 65 and name HB1)
vector do (rmsd = 2.777) (resid 65 and name HB2)
vector do (rmsd = 56.534) (resid 66 and name CA)
vector do (rmsd = 4.449) (resid 66 and name HA)
vector do (rmsd = 25.422) (resid 66 and name CB)
vector do (rmsd = 2.124) (resid 66 and name HB1)
vector do (rmsd = 2.051) (resid 66 and name HB2)
vector do (rmsd = 27.662) (resid 66 and name CG)
vector do (rmsd = 1.614) (resid 66 and name HG1)
vector do (rmsd = 1.564) (resid 66 and name HG2)
vector do (rmsd = 42.596) (resid 66 and name CD)
vector do (rmsd = 3.103) (resid 66 and name HD1)
vector do (rmsd = 3.061) (resid 66 and name HD2)
vector do (rmsd = 60.018) (resid 67 and name CA)
vector do (rmsd = 4.108) (resid 67 and name HA)
vector do (rmsd = 40.604) (resid 67 and name CB)
vector do (rmsd = 3.003) (resid 67 and name HB1)
vector do (rmsd = 2.093) (resid 67 and name HB2)
vector do (rmsd = 133.149) (resid 67 and name CD1)
vector do (rmsd = 6.323) (resid 67 and name HD1)
vector do (rmsd = 117.620) (resid 67 and name CE1)
vector do (rmsd = 6.737) (resid 67 and name HE1)
vector do (rmsd = 57.778) (resid 68 and name CA)
vector do (rmsd = 4.561) (resid 68 and name HA)
vector do (rmsd = 36.077) (resid 68 and name CB)
vector do (rmsd = 3.093) (resid 68 and name HB1)
vector do (rmsd = 2.958) (resid 68 and name HB2)
vector do (rmsd = 131.818) (resid 68 and name CD1)
vector do (rmsd = 7.211) (resid 68 and name HD1)
vector do (rmsd = 118.951) (resid 68 and name CE1)
vector do (rmsd = 7.315) (resid 68 and name HE1)
vector do (rmsd = 62.009) (resid 69 and name CA)
vector do (rmsd = 4.122) (resid 69 and name HA)
vector do (rmsd = 31.411) (resid 69 and name CB)
vector do (rmsd = 2.350) (resid 69 and name HB)
vector do (rmsd = 21.520) (resid 69 and name CG1)
vector do (rmsd = 0.990) (resid 69 and name HG1#)
vector do (rmsd = 18.702) (resid 69 and name CG2)
vector do (rmsd = 0.859) (resid 69 and name HG2#)
vector do (rmsd = 55.464) (resid 70 and name CA)
vector do (rmsd = 4.804) (resid 70 and name HA)
vector do (rmsd = 65.992) (resid 70 and name CB)
vector do (rmsd = 4.226) (resid 70 and name HB1)
vector do (rmsd = 3.783) (resid 70 and name HB2)
vector do (rmsd = 59.520) (resid 72 and name CA)
vector do (rmsd = 4.085) (resid 72 and name HA)
vector do (rmsd = 31.644) (resid 72 and name CB)
vector do (rmsd = 1.925) (resid 72 and name HB1)
vector do (rmsd = 1.850) (resid 72 and name HB2)
vector do (rmsd = 24.675) (resid 72 and name CG)
vector do (rmsd = 1.539) (resid 72 and name HG1)
vector do (rmsd = 28.409) (resid 72 and name CD)
vector do (rmsd = 1.673) (resid 72 and name HD1)
vector do (rmsd = 41.351) (resid 72 and name CE)
vector do (rmsd = 3.237) (resid 72 and name HE1)
vector do (rmsd = 57.778) (resid 73 and name CA)
vector do (rmsd = 4.260) (resid 73 and name HA)
vector do (rmsd = 43.591) (resid 73 and name CB)
vector do (rmsd = 2.034) (resid 73 and name HB1)
vector do (rmsd = 1.919) (resid 73 and name HB2)
vector do (rmsd = 27.392) (resid 73 and name CG)
vector do (rmsd = 1.808) (resid 73 and name HG)
vector do (rmsd = 25.755) (resid 73 and name CD1)
vector do (rmsd = 0.976) (resid 73 and name HD1#)
vector do (rmsd = 23.347) (resid 73 and name CD2)
vector do (rmsd = 0.928) (resid 73 and name HD2#)
vector do (rmsd = 60.765) (resid 74 and name CA)
vector do (rmsd = 3.801) (resid 74 and name HA)
vector do (rmsd = 39.609) (resid 74 and name CB)
vector do (rmsd = 3.004) (resid 74 and name HB1)
vector do (rmsd = 2.425) (resid 74 and name HB2)
vector do (rmsd = 132.262) (resid 74 and name CD1)
vector do (rmsd = 6.425) (resid 74 and name HD1)
vector do (rmsd = 6.976) (resid 74 and name HE1)
vector do (rmsd = 59.520) (resid 75 and name CA)
vector do (rmsd = 4.101) (resid 75 and name HA)
vector do (rmsd = 33.138) (resid 75 and name CB)
vector do (rmsd = 2.959) (resid 75 and name HB1)
vector do (rmsd = 2.656) (resid 75 and name HB2)
vector do (rmsd = 32.292) (resid 75 and name CG)
vector do (rmsd = 2.362) (resid 75 and name HG1)
vector do (rmsd = 2.242) (resid 75 and name HG2)
vector do (rmsd = 16.960) (resid 75 and name CE)
vector do (rmsd = 2.096) (resid 75 and name HE#)
vector do (rmsd = 55.040) (resid 76 and name CA)

TABLE 11-continued

Chemical Shifts vector do (rmsd = 4.113) (resid 76 and name HA)
vector do (rmsd = 18.204) (resid 76 and name CB)
vector do (rmsd = 1.531) (resid 76 and name HB#)
vector do (rmsd = 57.485) (resid 77 and name CA)
vector do (rmsd = 4.393) (resid 77 and name HA)
vector do (rmsd = 38.862) (resid 77 and name CB)
vector do (rmsd = 2.749) (resid 77 and name HB1)
vector do (rmsd = 57.778) (resid 78 and name CA)
vector do (rmsd = 3.414) (resid 78 and name HA)
vector do (rmsd = 40.107) (resid 78 and name CB)
vector do (rmsd = 0.740) (resid 78 and name HB1)
vector do (rmsd = 0.471) (resid 78 and name HB2)
vector do (rmsd = 27.413) (resid 78 and name CG)
vector do (rmsd = 0.692) (resid 78 and name HG)
vector do (rmsd = 25.920) (resid 78 and name CD1)
vector do (rmsd = 0.091) (resid 78 and name HD1#)
vector do (rmsd = 24.177) (resid 78 and name CD2)
vector do (rmsd = 0.196) (resid 78 and name HD2#)
vector do (rmsd = 58.889) (resid 79 and name CA)
vector do (rmsd = 3.856) (resid 79 and name HA)
vector do (rmsd = 28.918) (resid 79 and name CB)
vector do (rmsd = 2.222) (resid 79 and name HB1)
vector do (rmsd = 2.112) (resid 79 and name HB2)
vector do (rmsd = 35.331) (resid 79 and name CG)
vector do (rmsd = 2.481) (resid 79 and name HG1)
vector do (rmsd = 180.113) (resid 79 and name CD)
vector do (rmsd = 58.027) (resid 80 and name CA)
vector do (rmsd = 4.098) (resid 80 and name HA)
vector do (rmsd = 29.404) (resid 80 and name CB)
vector do (rmsd = 2.020) (resid 80 and name HB1)
vector do (rmsd = 1.958) (resid 80 and name HB2)
vector do (rmsd = 26.915) (resid 80 and name CG)
vector do (rmsd = 1.783) (resid 80 and name HG1)
vector do (rmsd = 43.182) (resid 80 and name CD)
vector do (rmsd = 3.404) (resid 80 and name HD1)
vector do (rmsd = 3.325) (resid 80 and name HD2)
vector do (rmsd = 66.493) (resid 81 and name CA)
vector do (rmsd = 3.127) (resid 81 and name HA)
vector do (rmsd = 30.649) (resid 81 and name CB)
vector do (rmsd = 1.465) (resid 81 and name HB)
vector do (rmsd = 22.186) (resid 81 and name CG1)
vector do (rmsd = 0.510) (resid 81 and name HG1#)
vector do (rmsd = 21.720) (resid 81 and name CG2)
vector do (rmsd = 0.156) (resid 81 and name HG2#)
vector do (rmsd = 58.500) (resid 82 and name CA)
vector do (rmsd = 4.222) (resid 82 and name HA)
vector do (rmsd = 37.867) (resid 82 and name CB)
vector do (rmsd = 3.134) (resid 82 and name HB1)
vector do (rmsd = 3.031) (resid 82 and name HB2)
vector do (rmsd = 130.935) (resid 82 and name CD1)
vector do (rmsd = 6.680) (resid 82 and name HD1)
vector do (rmsd = 6.487) (resid 82 and name HE1)
vector do (rmsd = 66.573) (resid 83 and name CA)
vector do (rmsd = 3.898) (resid 83 and name HA)
vector do (rmsd = 68.232) (resid 83 and name CB)
vector do (rmsd = 4.236) (resid 83 and name HB)
vector do (rmsd = 22.216) (resid 83 and name CG2)
vector do (rmsd = 1.340) (resid 83 and name HG2#)
vector do (rmsd = 55.289) (resid 84 and name CA)
vector do (rmsd = 4.343) (resid 84 and name HA)
vector do (rmsd = 37.658) (resid 84 and name CB)
vector do (rmsd = 3.022) (resid 84 and name HB1)
vector do (rmsd = 2.718) (resid 84 and name HB2)
vector do (rmsd = 61.746) (resid 85 and name CA)
vector do (rmsd = 4.513) (resid 85 and name HA)
vector do (rmsd = 26.666) (resid 85 and name CB)
vector do (rmsd = 3.418) (resid 85 and name HB1)
vector do (rmsd = 3.104) (resid 85 and name HB2)
vector do (rmsd = 58.249) (resid 86 and name CA)
vector do (rmsd = 4.265) (resid 86 and name HA)
vector do (rmsd = 32.391) (resid 86 and name CB)
vector do (rmsd = 1.779) (resid 86 and name HB1)
vector do (rmsd = 25.422) (resid 86 and name CG)
vector do (rmsd = 1.333) (resid 86 and name HG1)
vector do (rmsd = 0.160) (resid 86 and name HG2)
vector do (rmsd = 29.902) (resid 86 and name CD)
vector do (rmsd = 1.341) (resid 86 and name HD1)

TABLE 11-continued

Chemical Shifts vector do (rmsd = 41.000) (resid 86 and name CE)
vector do (rmsd = 2.487) (resid 86 and name HE1)
vector do (rmsd = 2.465) (resid 86 and name HE2)
vector do (rmsd = 57.951) (resid 87 and name CA)
vector do (rmsd = 4.327) (resid 87 and name HA)
vector do (rmsd = 30.151) (resid 87 and name CB)
vector do (rmsd = 2.230) (resid 87 and name HB1)
vector do (rmsd = 2.075) (resid 87 and name HB2)
vector do (rmsd = 36.390) (resid 87 and name CG)
vector do (rmsd = 2.440) (resid 87 and name HG1)
vector do (rmsd = 2.238) (resid 87 and name HG2)
vector do (rmsd = 61.263) (resid 88 and name CA)
vector do (rmsd = 4.320) (resid 88 and name HA)
vector do (rmsd = 40.895) (resid 88 and name CB)
vector do (rmsd = 2.958) (resid 88 and name HB1)
vector do (rmsd = 2.915) (resid 88 and name HB2)
vector do (rmsd = 133.149) (resid 88 and name CD1)
vector do (rmsd = 6.968) (resid 88 and name HD1)
vector do (rmsd = 6.968) (resid 88 and name HD2)
vector do (rmsd = 118.064) (resid 88 and name CE1)
vector do (rmsd = 6.672) (resid 88 and name HE1)
vector do (rmsd = 51.817) (resid 89 and name CA)
vector do (rmsd = 5.091) (resid 89 and name HA)
vector do (rmsd = 40.604) (resid 89 and name CB)
vector do (rmsd = 3.100) (resid 89 and name HB1)
vector do (rmsd = 2.903) (resid 89 and name HB2)
vector do (rmsd = 61.263) (resid 90 and name CA)
vector do (rmsd = 4.659) (resid 90 and name HA)
vector do (rmsd = 31.147) (resid 90 and name CB)
vector do (rmsd = 2.349) (resid 90 and name HB1)
vector do (rmsd = 2.175) (resid 90 and name HB2)
vector do (rmsd = 50.191) (resid 90 and name CD)
vector do (rmsd = 3.945) (resid 90 and name HD2)
vector do (rmsd = 4.116) (resid 90 and name HD1)
vector do (rmsd = 63.752) (resid 91 and name CA)
vector do (rmsd = 2.586) (resid 91 and name HA)
vector do (rmsd = 31.644) (resid 91 and name CB)
vector do (rmsd = 1.625) (resid 91 and name HB1)
vector do (rmsd = 27.413) (resid 91 and name CG)
vector do (rmsd = 1.994) (resid 91 and name HG1)
vector do (rmsd = 1.708) (resid 91 and name HG2)
vector do (rmsd = 57.018) (resid 92 and name CA)
vector do (rmsd = 4.252) (resid 92 and name HA)
vector do (rmsd = 28.160) (resid 92 and name CB)
vector do (rmsd = 2.105) (resid 92 and name HB1)
vector do (rmsd = 2.023) (resid 92 and name HB2)
vector do (rmsd = 37.120) (resid 92 and name CG)
vector do (rmsd = 2.387) (resid 92 and name HG1)
vector do (rmsd = 2.263) (resid 92 and name HG2)
vector do (rmsd = 64.000) (resid 93 and name CA)
vector do (rmsd = 4.527) (resid 93 and name HA)
vector do (rmsd = 67.236) (resid 93 and name CB)
vector do (rmsd = 3.873) (resid 93 and name HB1)
vector do (rmsd = 59.082) (resid 94 and name CA)
vector do (rmsd = 4.244) (resid 94 and name HA)
vector do (rmsd = 28.658) (resid 94 and name CB)
vector do (rmsd = 2.144) (resid 94 and name HB1)
vector do (rmsd = 2.035) (resid 94 and name HB2)
vector do (rmsd = 36.079) (resid 94 and name CG)
vector do (rmsd = 2.257) (resid 94 and name HG1)
vector do (rmsd = 61.125) (resid 95 and name CA)
vector do (rmsd = 3.651) (resid 95 and name HA)
vector do (rmsd = 38.613) (resid 95 and name CB)
vector do (rmsd = 2.953) (resid 95 and name HB1)
vector do (rmsd = 2.634) (resid 95 and name HB2)
vector do (rmsd = 6.869) (resid 95 and name HD1)
vector do (rmsd = 6.862) (resid 95 and name HD2)
vector do (rmsd = 61.597) (resid 96 and name CA)
vector do (rmsd = 3.828) (resid 96 and name HA)
vector do (rmsd = 40.107) (resid 96 and name CB)
vector do (rmsd = 3.429) (resid 96 and name HB1)
vector do (rmsd = 2.580) (resid 96 and name HB2)
vector do (rmsd = 134.924) (resid 96 and name CD1)
vector do (rmsd = 7.122) (resid 96 and name HD1)
vector do (rmsd = 118.064) (resid 96 and name CE1)
vector do (rmsd = 7.054) (resid 96 and name HE1)
vector do (rmsd = 60.266) (resid 97 and name CA)

TABLE 11-continued

Chemical Shifts vector do (rmsd = 4.236) (resid 97 and name HA)
vector do (rmsd = 32.241) (resid 97 and name CB)
vector do (rmsd = 2.112) (resid 97 and name HB1)
vector do (rmsd = 25.714) (resid 97 and name CG)
vector do (rmsd = 1.827) (resid 97 and name HG1)
vector do (rmsd = 1.617) (resid 97 and name HG2)
vector do (rmsd = 29.653) (resid 97 and name CD)
vector do (rmsd = 1.840) (resid 97 and name HD1)
vector do (rmsd = 41.801) (resid 97 and name CE)
vector do (rmsd = 3.009) (resid 97 and name HE1)
vector do (rmsd = 64.996) (resid 98 and name CA)
vector do (rmsd = 4.220) (resid 98 and name HA)
vector do (rmsd = 26.655) (resid 98 and name CB)
vector do (rmsd = 3.402) (resid 98 and name HB1)
vector do (rmsd = 3.078) (resid 98 and name HB2)
vector do (rmsd = 55.289) (resid 99 and name CA)
vector do (rmsd = 3.909) (resid 99 and name HA)
vector do (rmsd = 18.323) (resid 99 and name CB)
vector do (rmsd = 1.660) (resid 99 and name HB#)
vector do (rmsd = 55.753) (resid 100 and name CA)
vector do (rmsd = 4.362) (resid 100 and name HA)
vector do (rmsd = 38.726) (resid 100 and name CB)
vector do (rmsd = 2.916) (resid 100 and name HB1)
vector do (rmsd = 2.851) (resid 100 and name HB2)
vector do (rmsd = 64.747) (resid 101 and name CA)
vector do (rmsd = 3.693) (resid 101 and name HA)
vector do (rmsd = 38.862) (resid 101 and name CB)
vector do (rmsd = 1.947) (resid 101 and name HB)
vector do (rmsd = 29.404) (resid 101 and name CG1)
vector do (rmsd = 1.885) (resid 101 and name HG11)
vector do (rmsd = 1.241) (resid 101 and name HG12)
vector do (rmsd = 17.706) (resid 101 and name CG2)
vector do (rmsd = 1.032) (resid 101 and name HG2#)
vector do (rmsd = 13.475) (resid 101 and name CD1)
vector do (rmsd = 0.993) (resid 101 and name HD1#)
vector do (rmsd = 56.534) (resid 102 and name CA)
vector do (rmsd = 3.722) (resid 102 and name HA)
vector do (rmsd = 41.600) (resid 102 and name CB)
vector do (rmsd = 1.484) (resid 102 and name HB1)
vector do (rmsd = 1.266) (resid 102 and name HB2)
vector do (rmsd = 26.666) (resid 102 and name CG)
vector do (rmsd = 1.591) (resid 102 and name HG)
vector do (rmsd = 25.173) (resid 102 and name CD1)
vector do (rmsd = 0.763) (resid 102 and name HD1#)
vector do (rmsd = 24.190) (resid 102 and name CD2)
vector do (rmsd = 0.766) (resid 102 and name HD2#)
vector do (rmsd = 59.520) (resid 103 and name CA)
vector do (rmsd = 3.222) (resid 103 and name HA)
vector do (rmsd = 29.816) (resid 103 and name CB)
vector do (rmsd = 1.801) (resid 103 and name HB1)
vector do (rmsd = 1.333) (resid 103 and name HB2)
vector do (rmsd = 37.065) (resid 103 and name CG)
vector do (rmsd = 2.043) (resid 103 and name HG1)
vector do (rmsd = 1.957) (resid 103 and name HG2)
vector do (rmsd = 59.520) (resid 104 and name CA)
vector do (rmsd = 4.112) (resid 104 and name HA)
vector do (rmsd = 32.185) (resid 104 and name CB)
vector do (rmsd = 1.960) (resid 104 and name HB1)
vector do (rmsd = 25.246) (resid 104 and name CG)
vector do (rmsd = 1.557) (resid 104 and name HG1)
vector do (rmsd = 1.464) (resid 104 and name HG2)
vector do (rmsd = 29.053) (resid 104 and name CD)
vector do (rmsd = 1.706) (resid 104 and name HD1)
vector do (rmsd = 41.855) (resid 104 and name CE)
vector do (rmsd = 3.036) (resid 104 and name HE1)
vector do (rmsd = 61.431) (resid 105 and name CA)
vector do (rmsd = 4.352) (resid 105 and name HA)
vector do (rmsd = 39.111) (resid 105 and name CB)
vector do (rmsd = 3.138) (resid 105 and name HB1)
vector do (rmsd = 3.101) (resid 105 and name HB2)
vector do (rmsd = 131.818) (resid 105 and name CD1)
vector do (rmsd = 7.242) (resid 105 and name HD1)
vector do (rmsd = 60.516) (resid 106 and name CA)
vector do (rmsd = 3.997) (resid 106 and name HA)
vector do (rmsd = 38.592) (resid 106 and name CB)
vector do (rmsd = 3.356) (resid 106 and name HB1)
vector do (rmsd = 3.134) (resid 106 and name HB2)
vector do (rmsd = 132.262) (resid 106 and name CD1)
vector do (rmsd = 6.956) (resid 106 and name HD1)
vector do (rmsd = 61.512) (resid 107 and name CA)
vector do (rmsd = 3.857) (resid 107 and name HA)
vector do (rmsd = 37.867) (resid 107 and name CB)
vector do (rmsd = 3.098) (resid 107 and name HB1)
vector do (rmsd = 131.374) (resid 107 and name CD1)
vector do (rmsd = 7.239) (resid 107 and name HD1)
vector do (rmsd = 61.512) (resid 108 and name CA)
vector do (rmsd = 4.236) (resid 108 and name HA)
vector do (rmsd = 62.591) (resid 108 and name CB)
vector do (rmsd = 4.022) (resid 108 and name HB1)
vector do (rmsd = 56.783) (resid 109 and name CA)
vector do (rmsd = 4.074) (resid 109 and name HA)
vector do (rmsd = 31.644) (resid 109 and name CB)
vector do (rmsd = 1.770) (resid 109 and name HB1)
vector do (rmsd = 1.587) (resid 109 and name HB2)
vector do (rmsd = 23.020) (resid 109 and name CG)
vector do (rmsd = 0.852) (resid 109 and name HG1)
vector do (rmsd = 27.005) (resid 109 and name CD)
vector do (rmsd = 1.417) (resid 109 and name HD1)
vector do (rmsd = 42.098) (resid 109 and name CE)
vector do (rmsd = 2.618) (resid 109 and name HE1)
vector do (rmsd = 2.483) (resid 109 and name HE2)
vector do (rmsd = 64.249) (resid 110 and name CA)
vector do (rmsd = 3.854) (resid 110 and name HA)
vector do (rmsd = 37.120) (resid 110 and name CB)
vector do (rmsd = 1.796) (resid 110 and name HB)
vector do (rmsd = 26.418) (resid 110 and name CG1)
vector do (rmsd = 1.162) (resid 110 and name HG11)
vector do (rmsd = 1.090) (resid 110 and name HG12)
vector do (rmsd = 18.619) (resid 110 and name CG2)
vector do (rmsd = 0.693) (resid 110 and name HG2#)
vector do (rmsd = 13.226) (resid 110 and name CD1)
vector do (rmsd = 0.571) (resid 110 and name HD1#)
vector do (rmsd = 59.520) (resid 111 and name CA)
vector do (rmsd = 4.094) (resid 111 and name HA)
vector do (rmsd = 32.858) (resid 111 and name CB)
vector do (rmsd = 1.930) (resid 111 and name HB1)
vector do (rmsd = 1.793) (resid 111 and name HB2)
vector do (rmsd = 25.195) (resid 111 and name CG)
vector do (rmsd = 1.453) (resid 111 and name HG1)
vector do (rmsd = 1.350) (resid 111 and name HG2)
vector do (rmsd = 29.409) (resid 111 and name CD)
vector do (rmsd = 1.664) (resid 111 and name HD1)
vector do (rmsd = 41.351) (resid 111 and name CE)
vector do (rmsd = 2.942) (resid 111 and name HE1)
vector do (rmsd = 58.525) (resid 112 and name CA)
vector do (rmsd = 4.025) (resid 112 and name HA)
vector do (rmsd = 30.077) (resid 112 and name CB)
vector do (rmsd = 2.097) (resid 112 and name HB1)
vector do (rmsd = 36.227) (resid 112 and name CG)
vector do (rmsd = 2.394) (resid 112 and name HG1)
vector do (rmsd = 2.252) (resid 112 and name HG2)
vector do (rmsd = 52.302) (resid 113 and name CA)
vector do (rmsd = 4.354) (resid 113 and name HA)
vector do (rmsd = 19.449) (resid 113 and name CB)
vector do (rmsd = 1.405) (resid 113 and name HB#)
vector do (rmsd = 46.021) (resid 114 and name CA)
vector do (rmsd = 4.265) (resid 114 and name HA1)
vector do (rmsd = 4.070) (resid 114 and name HA2)
vector do (rmsd = 55.538) (resid 115 and name CA)
vector do (rmsd = 4.251) (resid 115 and name HA)
vector do (rmsd = 42.845) (resid 115 and name CB)
vector do (rmsd = 1.613) (resid 115 and name HB2)
vector do (rmsd = 27.077) (resid 115 and name CG)
vector do (rmsd = 1.571) (resid 115 and name HG)
vector do (rmsd = 25.485) (resid 115 and name CD1)
vector do (rmsd = 0.750) (resid 115 and name HD1#)
vector do (rmsd = 23.302) (resid 115 and name CD2)
vector do (rmsd = 0.783) (resid 115 and name HD2#)
vector do (rmsd = 60.018) (resid 116 and name CA)
vector do (rmsd = 4.275) (resid 116 and name HA)
vector do (rmsd = 39.609) (resid 116 and name CB)
vector do (rmsd = 1.851) (resid 116 and name HB)
vector do (rmsd = 26.903) (resid 116 and name CG1)
vector do (rmsd = 1.346) (resid 116 and name HG11)

TABLE 11-continued

Chemical Shifts vector do (rmsd = 0.964) (resid 116 and name HG12)
vector do (rmsd = 17.706) (resid 116 and name CG2)
vector do (rmsd = 0.854) (resid 116 and name HG2#)
vector do (rmsd = 13.193) (resid 116 and name CD1)
vector do (rmsd = 0.825) (resid 116 and name HD1#)
vector do (rmsd = 54.543) (resid 117 and name CA)
vector do (rmsd = 4.602) (resid 117 and name HA)
vector do (rmsd = 41.387) (resid 117 and name CB)
vector do (rmsd = 2.732) (resid 117 and name HB1)
vector do (rmsd = 2.582) (resid 117 and name HB2)
vector do (rmsd = 57.883) (resid 118 and name CA)
vector do (rmsd = 4.076) (resid 118 and name HA)
vector do (rmsd = 33.670) (resid 118 and name CB)
vector do (rmsd = 1.799) (resid 118 and name HB1)
vector do (rmsd = 1.693) (resid 118 and name HB2)
vector do (rmsd = 24.639) (resid 118 and name CG)
vector do (rmsd = 1.373) (resid 118 and name HG1)
vector do (rmsd = 29.653) (resid 118 and name CD)
vector do (rmsd = 1.672) (resid 118 and name HD1)
vector do (rmsd = 40.506) (resid 118 and name CE)
vector do (rmsd = 2.997) (resid 118 and name HE1)

TABLE 12

Hydrogen Bond Distance Restraints

!Helix Z

| | | | |
|---|---|---|---|
| assign (residue 19 and name HN) (residue 15 and name O) | 1.80 | 0.0 | 0.40 |
| assign (residue 19 and name N) (residue 15 and name O) | 2.80 | 0.30 | 0.40 |
| assign (residue 22 and name HN) (residue 18 and name O) | 1.80 | 0.0 | 0.40 |
| assign (residue 22 and name N) (residue 18 and name O) | 2.80 | 0.30 | 0.40 |
| assign (residue 23 and name HN) (residue 19 and name O) | 1.80 | 0.0 | 0.40 |
| assign (residue 23 and name N) (residue 19 and name O) | 2.80 | 0.30 | 0.40 |
| assign (residue 24 and name HN) (residue 20 and name O) | 1.80 | 0.0 | 0.40 |
| assign (residue 24 and name N) (residue 20 and name O) | 2.80 | 0.30 | 0.40 |
| assign (residue 25 and name HN) (residue 21 and name O) | 1.80 | 0.0 | 0.40 |
| assign (residue 25 and name N) (residue 21 and name O) | 2.80 | 0.30 | 0.40 |

!Helix B

| | | | |
|---|---|---|---|
| assign (residue 75 and name HN) (residue 71 and name O) | 1.80 | 0.0 | 0.40 |
| assign (residue 75 and name N) (residue 71 and name O) | 2.80 | 0.30 | 0.40 |
| !assign (residue 77 and name HN) (residue 73 and name O) | 1.80 | 0.0 | 0.40 |
| !assign (residue 77 and name N) (residue 73 and name O) | 2.80 | 0.30 | 0.40 |
| assign (residue 78 and name HN) (residue 74 and name O) | 1.80 | 0.0 | 0.40 |
| assign (residue 78 and name N) (residue 74 and name O) | 2.80 | 0.30 | 0.40 |
| assign (residue 79 and name HN) (residue 75 and name O) | 1.80 | 0.0 | 0.40 |
| assign (residue 79 and name N) (residue 75 and name O) | 2.80 | 0.30 | 0.40 |
| !assign (residue 80 and name HN) (residue 76 and name O) | 1.80 | 0.0 | 0.40 |
| !assign (residue 80 and name N) (residue 76 and name O) | 2.80 | 0.30 | 0.40 |
| assign (residue 81 and name HN) (residue 77 and name O) | 1.80 | 0.0 | 0.40 |
| assign (residue 81 and name N) (residue 77 and name O) | 2.80 | 0.30 | 0.40 |
| assign (residue 82 and name HN) (residue 78 and name O) | 1.80 | 0.0 | 0.40 |
| assign (residue 82 and name N) (residue 78 and name O) | 2.80 | 0.30 | 0.40 |

!Helix C

| | | | |
|---|---|---|---|
| assign (residue 102 and name HN) (residue 98 and name O) | 1.80 | 0.0 | 0.40 |
| assign (residue 102 and name N) (residue 98 and name O) | 2.80 | 0.30 | 0.40 |
| assign (residue 103 and name HN) (residue 99 and name O) | 1.80 | 0.0 | 0.40 |
| assign (residue 103 and name N) (residue 99 and name O) | 2.80 | 0.30 | 0.40 |
| assign (residue 104 and name HN) (residue 100 and name O) | 1.80 | 0.0 | 0.40 |
| assign (residue 104 and name N) (residue 100 and name O) | 2.80 | 0.30 | 0.40 |
| assign (residue 105 and name HN) (residue 101 and name O) | 1.80 | 0.0 | 0.40 |
| assign (residue 105 and name N) (residue 101 and name O) | 2.80 | 0.30 | 0.40 |

TABLE 13

Unambiguous NOE Distance Restraints

ASSI {1}
((segid "PROT" and resid 29 and name HN))
((segid "PROT" and resid 28 and name HN))
  3.300  2.700  2.200 peak     1 weight  0.10000E+01 volume  0.18248E+01 ppm1  8.583 ppm2  7.565
ASSI {11}
((segid "PROT" and resid 29 and name HN))
((segid "PROT" and resid 29 and name HA))
  2.700  1.800  1.800 peak    11 weight  0.10000E+01 volume  0.64796E+01 ppm1  8.584 ppm2  4.224
ASSI {21}
((segid "PROT" and resid 29 and name HN))
((segid "PROT" and resid 28 and name HA))
  2.400  1.400  1.400 peak    21 weight  0.10000E+01 volume  0.14203E+02 ppm1  8.583 ppm2  3.997
ASSI {31}
((segid "PROT" and resid 29 and name HN))
((segid "PROT" and resid 28 and name HB1))
  3.500  3.100  2.000 peak    31 weight  0.10000E+01 volume  0.14751E+01 ppm1  8.583 ppm2  3.019

TABLE 13-continued

| Unambiguous NOE Distance Restraints |
|---|

ASSI {41}
((segid "PROT" and resid 29 and name HN))
((segid "PROT" and resid 29 and name HG2))
  3.000  2.200  2.200 peak        41 weight  0.10000E+01 volume  0.37768E+01 ppm1     8.583  ppm2  2.419
ASSI {51}
((segid "PROT" and resid 29 and name HN))
((segid "PROT" and resid 29 and name HB1))
  2.400  1.400  1.400 peak        51 weight  0.10000E+01 volume  0.13363E+02 ppm1     8.583  ppm2  2.125
ASSI {71}
((segid "PROT" and resid 29 and name HN))
((segid "PROT" and resid 28 and name HB2))
  3.400  2.900  2.100 peak        71 weight  0.10000E+01 volume  0.15259E+01 ppm1     8.598  ppm2  2.776
ASSI {81}
((segid "PROT" and resid 57 and name HN))
((segid "PROT" and resid 57 and name HG1))
  3.300  2.700  2.200 peak        81 weight  0.10000E+01 volume  0.19711E+01 ppm1     8.807  ppm2  1.511
ASSI {91}
((segid "PROT" and resid 57 and name HN))
((segid "PROT" and resid 58 and name HN))
  2.600  1.700  1.700 peak        91 weight  0.10000E+01 volume  0.89521E+01 ppm1     8.801  ppm2  9.439
ASSI {101}
((segid "PROT" and resid 57 and name HN))
((segid "PROT" and resid 56 and name HN))
  2.800  2.000  2.000 peak      101 weight  0.10000E+01 volume  0.49351E+01 ppm1     8.803  ppm2  9.125
ASSI {111}
((segid "PROT" and resid 57 and name HN))
((segid "PROT" and resid 59 and name HN))
  3.400  2.900  2.100 peak      111 weight  0.10000E+01 volume  0.16857E+01 ppm1     8.801  ppm2  7.884
ASSI {121}
((segid "PROT" and resid 57 and name HN))
((segid "PROT" and resid 36 and name HA))
  3.100  2.400  2.400 peak      121 weight  0.10000E+01 volume  0.30255E+01 ppm1     8.802  ppm2  4.847
ASSI {131}
((segid "PROT" and resid 57 and name HN))
((segid "PROT" and resid 55 and name HA))
  2.900  2.100  2.100 peak      131 weight  0.10000E+01 volume  0.41647E+01 ppm1     8.802  ppm2  4.741
ASSI {151}
((segid "PROT" and resid 57 and name HN))
((segid "PROT" and resid 56 and name HA))
  3.300  2.700  2.200 peak      151 weight  0.10000E+01 volume  0.19189E+01 ppm1     8.798  ppm2  4.063
ASSI {171}
((segid "PROT" and resid 57 and name HN))
((segid "PROT" and resid 55 and name HB1))
  2.500  1.600  1.600 peak      171 weight  0.10000E+01 volume  0.95863E+01 ppm1     8.801  ppm2  2.371
ASSI {181}
((segid "PROT" and resid 57 and name HN))
((segid "PROT" and resid 35 and name HB1))
  2.600  2.600  1.900 peak      181 weight  0.10000E+01 volume  0.84398E+01 ppm1     8.801  ppm2  2.269
ASSI {191}
((segid "PROT" and resid 57 and name HN))
((segid "PROT" and resid 56 and name HB1))
  3.200  2.600  2.300 peak      191 weight  0.10000E+01 volume  0.24962E+01 ppm1     8.803  ppm2  2.090
ASSI {201}
((segid "PROT" and resid 57 and name HN))
((segid "PROT" and resid 57 and name HD1))
  3.200  2.600  2.300 peak      201 weight  0.10000E+01 volume  0.24126E+01 ppm1     8.800  ppm2  1.724
ASSI {211}
((segid "PROT" and resid 57 and name HN))
((segid "PROT" and resid 56 and name HB2))
  3.100  2.400  2.400 peak      211 weight  0.10000E+01 volume  0.27264E+01 ppm1     8.800  ppm2  1.424
ASSI {261}
((segid "PROT" and resid 118 and name HN))
((segid "PROT" and resid 117 and name HA))
  2.200  1.200  1.200 peak      261 weight  0.10000E+01 volume  0.21965E+02 ppm1     7.777  ppm2  4.583
ASSI {271}
((segid "PROT" and resid 118 and name HN))
((segid "PROT" and resid 118 and name HA))
  2.300  1.300  1.300 peak      271 weight  0.10000E+01 volume  0.15108E+02 ppm1     7.774  ppm2  4.076
ASSI {281}
((segid "PROT" and resid 118 and name HN))
((segid "PROT" and resid 117 and name HB1))
  2.900  2.100  2.100 peak      281 weight  0.10000E+01 volume  0.45666E+01 ppm1     7.775  ppm2  2.710
ASSI {291}
((segid "PROT" and resid 118 and name HN))
((segid "PROT" and resid 117 and name HB2))
  3.200  2.600  2.300 peak      291 weight  0.10000E+01 volume  0.21751E+01 ppm1     7.775  ppm2  2.569

TABLE 13-continued

Unambiguous NOE Distance Restraints

ASSI {301}
((segid "PROT" and resid 118 and name HN))
((segid "PROT" and resid 118 and name HB1))
 2.800  2.000  2.000 peak     301 weight  0.10000E+01 volume  0.47059E+01 ppm1   7.776 ppm2  1.799
ASSI {311}
((segid "PROT" and resid 118 and name HN))
((segid "PROT" and resid 118 and name HB2))
 2.600  1.700  1.700 peak     311 weight  0.10000E+01 volume  0.80279E+01 ppm1   7.776 ppm2  1.693
ASSI {321}
((segid "PROT" and resid 118 and name HN))
(segid "PROT" and resid 116 and name HD1%)
 3.000  2.200  2.200 peak     321 weight  0.10000E+01 volume  0.36749E+01 ppm1   7.773 ppm2  0.824
ASSI {331}
((segid "PROT" and resid 118 and name HN))
((segid "PROT" and resid 116 and name HN))
 2.700  1.800  1.800 peak     331 weight  0.10000E+01 volume  0.67264E+01 ppm1   7.768 ppm2  7.476
ASSI {341}
((segid "PROT" and resid 51 and name HN))
((segid "PROT" and resid 49 and name HN))
 3.200  2.600  2.300 peak     341 weight  0.10000E+01 volume  0.22818E+01 ppm1   7.768 ppm2  7.100
ASSI {351}
((segid "PROT" and resid 118 and name HN))
((segid "PROT" and resid 116 and name HA))
 2.800  2.000  2.000 peak     351 weight  0.10000E+01 volume  0.48649E+01 ppm1   7.770 ppm2  4.308
ASSI {361}
((segid "PROT" and resid 118 and name HN))
((segid "PROT" and resid 116 and name HG12))
 3.500  3.100  2.000 peak     361 weight  0.10000E+01 volume  0.14512E+01 ppm1   7.771 ppm2  0.923
ASSI {411}
((segid "PROT" and resid 28 and name HN))
((segid "PROT" and resid 28 and name HA))
 2.600  1.700  1.700 peak     411 weight  0.10000E+01 volume  0.75737E+01 ppm1   7.561 ppm2  4.010
ASSI {421}
((segid "PROT" and resid 28 and name HN))
((segid "PROT" and resid 25 and name HA))
 3.100  2.400  2.400 peak     421 weight  0.10000E+01 volume  0.30883E+01 ppm1   7.564 ppm2  3.858
ASSI {431}
((segid "PROT" and resid 28 and name HN))
((segid "PROT" and resid 28 and name HB1))
 2.600  1.700  1.700 peak     431 weight  0.10000E+01 volume  0.85703E+01 ppm1   7.562 ppm2  2.994
ASSI {441}
((segid "PROT" and resid 28 and name HN))
((segid "PROT" and resid 26 and name HD1))
 3.500  3.100  2.000 peak     441 weight  0.10000E+01 volume  0.13903E+01 ppm1   7.562 ppm2  1.839
ASSI {451}
((segid "PROT" and resid 28 and name HN))
(segid "PROT" and resid 31 and name HB%)
 2.800  2.000  2.000 peak     451 weight  0.10000E+01 volume  0.53325E+01 ppm1   7.561 ppm2  1.734
ASSI {461}
((segid "PROT" and resid 28 and name HN))
(segid "PROT" and resid 102 and name HD1%)
 3.000  2.200  2.200 peak     461 weight  0.10000E+01 volume  0.32864E+01 ppm1   7.561 ppm2  0.733
ASSI {471}
((segid "PROT" and resid 28 and name HN))
((segid "PROT" and resid 27 and name HA))
 3.100  2.400  2.400 peak     471 weight  0.10000E+01 volume  0.28492E+01 ppm1   7.559 ppm2  4.462
ASSI {481}
((segid "PROT" and resid 28 and name HN))
((segid "PROT" and resid 28 and name HB2))
 2.500  1.600  1.600 peak     481 weight  0.10000E+01 volume  0.92253E+01 ppm1   7.558 ppm2  2.796
ASSI {491}
((segid "PROT" and resid 51 and name HN))
((segid "PROT" and resid 51 and name HD1))
 3.300  2.700  2.200 peak     491 weight  0.10000E+01 volume  0.18829E+01 ppm1   7.766 ppm2  3.005
ASSI {501}
((segid "PROT" and resid 118 and name HN))
((segid "PROT" and resid 118 and name HG1))
 2.300  1.300  1.300 peak     501 weight  0.10000E+01 volume  0.16392E+02 ppm1   7.764 ppm2  1.373
ASSI {511}
((segid "PROT" and resid 51 and name HN))
((segid "PROT" and resid 52 and name HN))
 2.500  1.600  1.600 peak     511 weight  0.10000E+01 volume  0.10570E+02 ppm1   7.756 ppm2  8.424
ASSI {521}
((segid "PROT" and resid 51 and name HN))
((segid "PROT" and resid 50 and name HA))
 2.100  1.100  1.100 peak     521 weight  0.10000E+01 volume  0.28178E+02 ppm1   7.762 ppm2  3.931

TABLE 13-continued

Unambiguous NOE Distance Restraints

ASSI {531}
((segid "PROT" and resid 51 and name HN))
((segid "PROT" and resid 51 and name HB2))
  2.500  1.600  1.600 peak        531 weight  0.10000E+01 volume  0.10172E+02 ppm1    7.757 ppm2    1.182
ASSI {541}
((segid "PROT" and resid 51 and name HN))
((segid "PROT" and resid 50 and name HD1%))
  2.900  2.100  2.100 peak        541 weight  0.10000E+01 volume  0.41637E+01 ppm1    7.756 ppm2    0.553
ASSI {551}
((segid "PROT" and resid 51 and name HN))
(segid "PROT" and resid 50 and name HG2%)
  2.900  2.100  2.100 peak        551 weight  0.10000E+01 volume  0.43238E+01 ppm1    7.755 ppm2    0.397
ASSI {561}
((segid "PROT" and resid 51 and name HN))
((segid "PROT" and resid 50 and name HN))
  3.200  2.600  2.300 peak        561 weight  0.10000E+01 volume  0.22364E+01 ppm1    7.752 ppm2    7.979
ASSI {571}
((segid "PROT" and resid 38 and name HN))
((segid "PROT" and resid 37 and name HA))
  2.600  1.700  1.700 peak        571 weight  0.10000E+01 volume  0.79316E+01 ppm1    8.336 ppm2    4.242
ASSI {581}
((segid "PROT" and resid 38 and name HN))
((segid "PROT" and resid 38 and name HA))
  3.200  2.600  2.300 peak        581 weight  0.10000E+01 volume  0.24318E+01 ppm1    8.334 ppm2    3.475
ASSI {591}
((segid "PROT" and resid 38 and name HN))
((segid "PROT" and resid 37 and name HB1))
  3.100  2.400  2.400 peak        591 weight  0.10000E+01 volume  0.26287E+01 ppm1    8.336 ppm2    2.361
ASSI {601}
((segid "PROT" and resid 38 and name HN))
((segid "PROT" and resid 38 and name HB))
  2.800  2.000  2.000 peak        601 weight  0.10000E+01 volume  0.49359E+01 ppm1    8.339 ppm2    1.058
ASSI {611}
((segid "PROT" and resid 38 and name HN))
(segid "PROT" and resid 38 and name HG1%)
  2.700  1.800  1.800 peak        611 weight  0.10000E+01 volume  0.67420E+01 ppm1    8.336 ppm2    0.469
ASSI {621}
((segid "PROT" and resid 38 and name HN))
((segid "PROT" and resid 37 and name HB2))
  3.500  3.100  2.000 peak        621 weight  0.10000E+01 volume  0.14362E+01 ppm1    8.331 ppm2    1.685
ASSI {631}
((segid "PROT" and resid 38 and name HN))
(segid "PROT" and resid 38 and name HG2%)
  3.300  2.700  2.200 peak        631 weight  0.10000E+01 volume  0.17918E+01 ppm1    8.328 ppm2   −0.027
ASSI {651}
((segid "PROT" and resid 61 and name HN))
((segid "PROT" and resid 60 and name HB1))
  3.100  2.400  2.400 peak        651 weight  0.10000E+01 volume  0.30032E+01 ppm1    8.163 ppm2    4.212
ASSI {661}
((segid "PROT" and resid 61 and name HN))
((segid "PROT" and resid 61 and name HA))
  2.600  1.700  1.700 peak        661 weight  0.10000E+01 volume  0.77544E+01 ppm1    8.162 ppm2    4.060
ASSI {671}
((segid "PROT" and resid 61 and name HN))
((segid "PROT" and resid 58 and name HA))
  3.300  2.700  2.200 peak        671 weight  0.10000E+01 volume  0.19907E+01 ppm1    8.162 ppm2    3.866
ASSI {681}
((segid "PROT" and resid 61 and name HN))
((segid "PROT" and resid 61 and name HG2))
  2.500  1.600  1.600 peak        681 weight  0.10000E+01 volume  0.10559E+02 ppm1    8.163 ppm2    2.245
ASSI {691}
((segid "PROT" and resid 61 and name HN))
((segid "PROT" and resid 61 and name HB2))
  2.700  1.800  1.800 peak        691 weight  0.10000E+01 volume  0.70727E+01 ppm1    8.163 ppm2    2.089
ASSI {701}
((segid "PROT" and resid 61 and name HN))
(segid "PROT" and resid 58 and name HG2%)
  3.400  2.900  2.100 peak        701 weight  0.10000E+01 volume  0.17011E+01 ppm1    8.164 ppm2    1.075
ASSI {711}
((segid "PROT" and resid 61 and name HN))
((segid "PROT" and resid 62 and name HN))
  2.700  1.800  1.800 peak        711 weight  0.10000E+01 volume  0.60705E+01 ppm1    8.161 ppm2    8.378
ASSI {721}
((segid "PROT" and resid 61 and name HN))
((segid "PROT" and resid 60 and name HA))
  3.100  2.400  2.400 peak        721 weight  0.10000E+01 volume  0.27541E+01 ppm1    8.158 ppm2    4.417

TABLE 13-continued

Unambiguous NOE Distance Restraints

```
ASSI {731}
((segid "PROT" and resid 61 and name HN))
((segid "PROT" and resid 61 and name HG1))
  2.700  1.800  1.800 peak       731 weight  0.10000E+01 volume  0.60769E+01 ppm1    8.160 ppm2  2.388
ASSI {741}
((segid "PROT" and resid 117 and name HN))
((segid "PROT" and resid 118 and name HN))
  3.000  2.200  2.200 peak       741 weight  0.10000E+01 volume  0.33860E+01 ppm1    8.278 ppm2  7.777
ASSI {751}
((segid "PROT" and resid 117 and name HN))
((segid "PROT" and resid 116 and name HN))
  3.100  2.400  2.400 peak       751 weight  0.10000E+01 volume  0.30296E+01 ppm1    8.276 ppm2  7.477
ASSI {761}
((segid "PROT" and resid 117 and name HN))
((segid "PROT" and resid 117 and name HA))
  2.800  2.000  2.000 peak       761 weight  0.10000E+01 volume  0.56966E+01 ppm1    8.279 ppm2  4.584
ASSI {771}
((segid "PROT" and resid 117 and name HN))
((segid "PROT" and resid 115 and name HA))
  2.400  2.400  2.100 peak       771 weight  0.10000E+01 volume  0.11755E+02 ppm1    8.279 ppm2  4.253
ASSI {791}
((segid "PROT" and resid 117 and name HN))
((segid "PROT" and resid 117 and name HB1))
  3.100  2.400  2.400 peak       791 weight  0.10000E+01 volume  0.30574E+01 ppm1    8.279 ppm2  2.708
ASSI {801}
((segid "PROT" and resid 117 and name HN))
((segid "PROT" and resid 117 and name HB2))
  2.800  2.000  2.000 peak       801 weight  0.10000E+01 volume  0.52392E+01 ppm1    8.276 ppm2  2.564
ASSI {811}
((segid "PROT" and resid 117 and name HN))
((segid "PROT" and resid 116 and name HB))
  2.800  2.000  2.000 peak       811 weight  0.10000E+01 volume  0.47120E+01 ppm1    8.279 ppm2  1.829
ASSI {821}
((segid "PROT" and resid 117 and name HN))
((segid "PROT" and resid 111 and name HG2))
  3.500  3.100  2.000 peak       821 weight  0.10000E+01 volume  0.13421E+01 ppm1    8.279 ppm2  1.309
ASSI {831}
((segid "PROT" and resid 117 and name HN))
(segid "PROT" and resid 116 and name HD1%)
  3.100  2.400  2.400 peak       831 weight  0.10000E+01 volume  0.30974E+01 ppm1    8.279 ppm2  0.827
ASSI {841}
((segid "PROT" and resid 6 and name HN))
((segid "PROT" and resid 6 and name HB2))
  3.500  3.100  2.000 peak       841 weight  0.10000E+01 volume  0.12891E+01 ppm1    8.404 ppm2  1.751
ASSI {851}
((segid "PROT" and resid 6 and name HN))
((segid "PROT" and resid 5 and name HA))
  3.100  2.400  2.400 peak       851 weight  0.10000E+01 volume  0.28648E+01 ppm1    8.391 ppm2  4.447
ASSI {871}
((segid "PROT" and resid 50 and name HN))
((segid "PROT" and resid 49 and name HN))
  2.300  1.300  1.300 peak       871 weight  0.10000E+01 volume  0.15808E+02 ppm1    7.961 ppm2  7.117
ASSI {881}
((segid "PROT" and resid 50 and name HN))
((segid "PROT" and resid 48 and name HA))
  2.800  2.000  2.000 peak       881 weight  0.10000E+01 volume  0.48582E+01 ppm1    7.960 ppm2  4.097
ASSI {891}
((segid "PROT" and resid 50 and name HN))
((segid "PROT" and resid 50 and name HA))
  2.900  2.100  2.100 peak       891 weight  0.10000E+01 volume  0.39149E+01 ppm1    7.959 ppm2  3.931
ASSI {901}
((segid "PROT" and resid 50 and name HN))
((segid "PROT" and resid 49 and name HB))
  2.800  2.000  2.000 peak       901 weight  0.10000E+01 volume  0.50087E+01 ppm1    7.960 ppm2  1.908
ASSI {911}
((segid "PROT" and resid 50 and name HN))
((segid "PROT" and resid 50 and name HB))
  2.600  1.700  1.700 peak       911 weight  0.10000E+01 volume  0.88755E+01 ppm1    7.961 ppm2  1.220
ASSI {921}
((segid "PROT" and resid 50 and name HN))
(segid "PROT" and resid 49 and name HG2%)
  2.800  2.000  2.000 peak       921 weight  0.10000E+01 volume  0.51983E+01 ppm1    7.961 ppm2  0.935
ASSI {931}
((segid "PROT" and resid 50 and name HN))
((segid "PROT" and resid 50 and name HG11))
  2.900  2.100  2.100 peak       931 weight  0.10000E+01 volume  0.42899E+01 ppm1    7.959 ppm2  0.807
```

TABLE 13-continued

| Unambiguous NOE Distance Restraints |
| --- |

ASSI {941}
((segid "PROT" and resid 50 and name HN))
(segid "PROT" and resid 50 and name HD1%)
  2.900  2.100  2.100 peak      941 weight  0.10000E+01 volume  0.39098E+01 ppm1      7.963 ppm2  0.549
ASSI {951}
((segid "PROT" and resid 50 and name HN))
(segid "PROT" and resid 50 and name HG2%)
  2.900  2.100  2.100 peak      951 weight  0.10000E+01 volume  0.39287E+01 ppm1      7.961 ppm2  0.395
ASSI {961}
((segid "PROT" and resid 50 and name HN))
((segid "PROT" and resid 50 and name HG12))
  3.200  2.600  2.300 peak      961 weight  0.10000E+01 volume  0.21710E+01 ppm1      7.961 ppm2  0.162
ASSI {971}
((segid "PROT" and resid 50 and name HN))
((segid "PROT" and resid 46 and name HA))
  3.500  3.100  2.000 peak      971 weight  0.10000E+01 volume  0.12530E+01 ppm1      7.957 ppm2  3.478
ASSI {981}
((segid "PROT" and resid 7 and name HN))
((segid "PROT" and resid 7 and name HB1))
  2.900  2.100  2.100 peak      981 weight  0.10000E+01 volume  0.42394E+01 ppm1      8.324 ppm2  2.043
ASSI {991}
((segid "PROT" and resid 7 and name HN))
((segid "PROT" and resid 7 and name HA))
  2.800  2.000  2.000 peak      991 weight  0.10000E+01 volume  0.53094E+01 ppm1      8.324 ppm2  4.561
ASSI {1001}
((segid "PROT" and resid 7 and name HN))
((segid "PROT" and resid 6 and name HA))
  2.400  1.400  1.400 peak     1001 weight  0.10000E+01 volume  0.13634E+02 ppm1      8.324 ppm2  4.372
ASSI {1011}
((segid "PROT" and resid 7 and name HN))
((segid "PROT" and resid 8 and name HD2))
  3.600  3.200  1.900 peak     1011 weight  0.10000E+01 volume  0.12154E+01 ppm1      8.322 ppm2  3.707
ASSI {1021}
((segid "PROT" and resid 7 and name HN))
((segid "PROT" and resid 7 and name HG1))
  2.900  2.100  2.100 peak     1021 weight  0.10000E+01 volume  0.40289E+01 ppm1      8.321 ppm2  2.294
ASSI {1031}
((segid "PROT" and resid 7 and name HN))
((segid "PROT" and resid 7 and name HB2))
  2.600  1.700  1.700 peak     1031 weight  0.10000E+01 volume  0.80771E+01 ppm1      8.323 ppm2  1.912
ASSI {1041}
((segid "PROT" and resid 102 and name HN))
((segid "PROT" and resid 101 and name HN))
  2.600  1.700  1.700 peak     1041 weight  0.10000E+01 volume  0.88803E+01 ppm1      8.518 ppm2  8.030
ASSI {1051}
((segid "PROT" and resid 102 and name HN))
((segid "PROT" and resid 105 and name HN))
  3.400  2.900  2.100 peak     1051 weight  0.10000E+01 volume  0.16580E+01 ppm1      8.517 ppm2  7.932
ASSI {1061}
((segid "PROT" and resid 102 and name HN))
((segid "PROT" and resid 98 and name HA))
  3.500  3.100  2.000 peak     1061 weight  0.10000E+01 volume  0.13507E+01 ppm1      8.515 ppm2  4.197
ASSI {1071}
((segid "PROT" and resid 102 and name HN))
((segid "PROT" and resid 99 and name HA))
  3.300  2.700  2.200 peak     1071 weight  0.10000E+01 volume  0.17668E+01 ppm1      8.518 ppm2  3.874
ASSI {1081}
((segid "PROT" and resid 102 and name HN))
((segid "PROT" and resid 102 and name HA))
  2.800  2.000  2.000 peak     1081 weight  0.10000E+01 volume  0.49359E+01 ppm1      8.516 ppm2  3.686
ASSI {1111}
((segid "PROT" and resid 102 and name HN))
((segid "PROT" and resid 102 and name HG))
  3.100  2.400  2.400 peak     1111 weight  0.10000E+01 volume  0.25668E+01 ppm1      8.517 ppm2  1.554
ASSI {1121}
((segid "PROT" and resid 102 and name HN))
((segid "PROT" and resid 102 and name HB1))
  2.800  2.000  2.000 peak     1121 weight  0.10000E+01 volume  0.54544E+01 ppm1      8.516 ppm2  1.434
ASSI {1131}
((segid "PROT" and resid 102 and name HN))
((segid "PROT" and resid 102 and name HB2))
  2.600  1.700  1.700 peak     1131 weight  0.10000E+01 volume  0.74477E+01 ppm1      8.516 ppm2  1.232
ASSI {1141}
((segid "PROT" and resid 102 and name HN))
(segid "PROT" and resid 101 and name HG2%)
  2.900  2.100  2.100 peak     1141 weight  0.10000E+01 volume  0.42361E+01 ppm1      8.517 ppm2  1.002

TABLE 13-continued

Unambiguous NOE Distance Restraints

ASSI {1151}
((segid "PROT" and resid 102 and name HN))
((segid "PROT" and resid 102 and name HD1%))
  2.900  2.100  2.100 peak      1151 weight  0.10000E+01 volume    0.42645E+01 ppm1      8.517  ppm2  0.732
ASSI {1161}
((segid "PROT" and resid 102 and name HN))
((segid "PROT" and resid 104 and name HN))
  3.400  2.900  2.100 peak      1161 weight  0.10000E+01 volume    0.15534E+01 ppm1      8.511  ppm2  7.182
ASSI {1171}
((segid "PROT" and resid 103 and name HN))
((segid "PROT" and resid 102 and name HN))
  2.900  2.100  2.100 peak      1171 weight  0.10000E+01 volume    0.42887E+01 ppm1      8.040  ppm2  8.466
ASSI {1191}
((segid "PROT" and resid 46 and name HN))
((segid "PROT" and resid 43 and name HA))
  3.400  2.900  2.100 peak      1191 weight  0.10000E+01 volume    0.15537E+01 ppm1      8.047  ppm2  4.931
ASSI {1201}
((segid "PROT" and resid 46 and name HN))
((segid "PROT" and resid 44 and name HA))
  3.400  2.900  2.100 peak      1201 weight  0.10000E+01 volume    0.15220E+01 ppm1      8.041  ppm2  4.522
ASSI {1221}
((segid "PROT" and resid 46 and name HN))
((segid "PROT" and resid 46 and name HA))
  2.800  2.000  2.000 peak      1221 weight  0.10000E+01 volume    0.52605E+01 ppm1      8.039  ppm2  3.484
ASSI {1231}
((segid "PROT" and resid 103 and name HN))
((segid "PROT" and resid 103 and name HA))
  3.600  3.200  1.900 peak      1231 weight  0.10000E+01 volume    0.11229E+01 ppm1      8.043  ppm2  3.216
ASSI {1241}
((segid "PROT" and resid 46 and name HN))
((segid "PROT" and resid 46 and name HB1))
  2.600  1.700  1.700 peak      1241 weight  0.10000E+01 volume    0.84467E+01 ppm1      8.040  ppm2  2.731
ASSI {1251}
((segid "PROT" and resid 46 and name HN))
((segid "PROT" and resid 46 and name HB2))
  2.600  1.700  1.700 peak      1251 weight  0.10000E+01 volume    0.81520E+01 ppm1      8.039  ppm2  2.395
ASSI {1261}
((segid "PROT" and resid 46 and name HN))
(segid "PROT" and resid 43 and name HB%)
  2.900  2.100  2.100 peak      1261 weight  0.10000E+01 volume    0.42142E+01 ppm1      8.040  ppm2  0.962
ASSI {1271}
((segid "PROT" and resid 46 and name HN))
((segid "PROT" and resid 48 and name HN))
  3.400  2.900  2.100 peak      1271 weight  0.10000E+01 volume    0.16926E+01 ppm1      8.036  ppm2  7.723
ASSI {1321}
((segid "PROT" and resid 58 and name HN))
((segid "PROT" and resid 59 and name HN))
  2.900  2.100  2.100 peak      1321 weight  0.10000E+01 volume    0.38254E+01 ppm1      9.442  ppm2  7.886
ASSI {1331}
((segid "PROT" and resid 58 and name HN))
((segid "PROT" and resid 58 and name HB))
  3.000  2.200  2.200 peak      1331 weight  0.10000E+01 volume    0.32050E+01 ppm1      9.442  ppm2  4.084
ASSI {1341}
((segid "PROT" and resid 58 and name HN))
(segid "PROT" and resid 58 and name HG2%)
  3.200  2.600  2.300 peak      1341 weight  0.10000E+01 volume    0.25336E+01 ppm1      9.442  ppm2  1.074
ASSI {1351}
((segid "PROT" and resid 58 and name HN))
((segid "PROT" and resid 37 and name HA))
  3.400  2.900  2.100 peak      1351 weight  0.10000E+01 volume    0.16753E+01 ppm1      9.442  ppm2  4.206
ASSI {1361}
((segid "PROT" and resid 102 and name HN))
((segid "PROT" and resid 98 and name HB2))
  3.600  3.200  1.900 peak      1361 weight  0.10000E+01 volume    0.11010E+01 ppm1      8.501  ppm2  3.051
ASSI {1371}
((segid "PROT" and resid 111 and name HN))
((segid "PROT" and resid 112 and name HN))
  2.500  1.600  1.600 peak      1371 weight  0.10000E+01 volume    0.10907E+02 ppm1      7.568  ppm2  8.068
ASSI {1391}
((segid "PROT" and resid 111 and name HN))
((segid "PROT" and resid 111 and name HA))
  2.600  1.700  1.700 peak      1391 weight  0.10000E+01 volume    0.76380E+01 ppm1      7.569  ppm2  4.066
ASSI {1401}
((segid "PROT" and resid 111 and name HN))
((segid "PROT" and resid 107 and name HA))
  3.000  2.200  2.200 peak      1401 weight  0.10000E+01 volume    0.36812E+01 ppm1      7.567  ppm2  3.835

TABLE 13-continued

Unambiguous NOE Distance Restraints

ASSI {1411}
((segid "PROT" and resid 111 and name HN))
((segid "PROT" and resid 112 and name HB1))
  3.300  2.700  2.200 peak    1411 weight  0.10000E+01 volume  0.18701E+01 ppm1    7.568  ppm2  2.073
ASSI {1421}
((segid "PROT" and resid 111 and name HN))
((segid "PROT" and resid 111 and name HB1))
  2.600  1.700  1.700 peak    1421 weight  0.10000E+01 volume  0.90750E+01 ppm1    7.568  ppm2  1.875
ASSI {1431}
((segid "PROT" and resid 111 and name HN))
((segid "PROT" and resid 111 and name HD1))
  3.100  2.400  2.400 peak    1431 weight  0.10000E+01 volume  0.27225E+01 ppm1    7.569  ppm2  1.650
ASSI {1441}
((segid "PROT" and resid 111 and name HN))
((segid "PROT" and resid 111 and name HG1))
  3.000  2.200  2.200 peak    1441 weight  0.10000E+01 volume  0.32606E+01 ppm1    7.568  ppm2  1.416
ASSI {1451}
((segid "PROT" and resid 111 and name HN))
((segid "PROT" and resid 111 and name HG2))
  3.100  2.400  2.400 peak    1451 weight  0.10000E+01 volume  0.27421E+01 ppm1    7.568  ppm2  1.322
ASSI {1471}
((segid "PROT" and resid 111 and name HN))
(segid "PROT" and resid 110 and name HD1%)
  3.300  2.700  2.200 peak    1471 weight  0.10000E+01 volume  0.17681E+01 ppm1    7.568  ppm2  0.543
ASSI {1481}
((segid "PROT" and resid 111 and name HN))
((segid "PROT" and resid 108 and name HA))
  3.200  2.600  2.300 peak    1481 weight  0.10000E+01 volume  0.21677E+01 ppm1    7.565  ppm2  4.202
ASSI {1491}
((segid "PROT" and resid 111 and name HN))
((segid "PROT" and resid 112 and name HG1))
  3.500  3.100  2.000 peak    1491 weight  0.10000E+01 volume  0.12577E+01 ppm1    7.560  ppm2  2.363
ASSI {1501}
((segid "PROT" and resid 111 and name HN))
((segid "PROT" and resid 111 and name HB2))
  2.400  1.400  1.400 peak    1501 weight  0 10000E+01 volume  0.13622E+02 ppm1    7.567  ppm2  1.761
ASSI {1511}
((segid "PROT" and resid 111 and name HN))
((segid "PROT" and resid 110 and name HG12))
  3.000  2.200  2.200 peak    1511 weight  0.10000E+01 volume  0.37474E+01 ppm1    7.567  ppm2  1.074
ASSI {1521}
((segid "PROT" and resid 111 and name HN))
(segid "PROT" and resid 110 and name HG2%)
  3.000  2.200  2.200 peak    1521 weight  0.10000E+01 volume  0.32871E+01 ppm1    7.566  ppm2  0.665
ASSI {1531}
((segid "PROT" and resid 58 and name HN))
((segid "PROT" and resid 56 and name HB2))
  3.400  2.900  2.100 peak    1531 weight  0.10000E+01 volume  0.16528E+01 ppm1    9.448  ppm2  1.432
ASSI {1551}
((segid "PROT" and resid 58 and name HN
((segid "PROT" and resid 58 and name HA))
  3.000  2.200  2.200 peak    1551 weight  0.10000E+01 volume  0.32345E+01 ppm1    9.443  ppm2  3.856
ASSI {1571}
((segid "PROT" and resid 58 and name HN))
((segid "PROT" and resid 55 and name HB1))
  3.000  2.200  2.200 peak    1571 weight  0.10000E+01 volume  0.37144E+01 ppm1    9.443  ppm2  2.375
ASSI {1581}
((segid "PROT" and resid 58 and name HN))
((segid "PROT" and resid 59 and name HB1))
  3.400  2.900  2.100 peak    1581 weight  0.10000E+01 volume  0.16873E+01 ppm1    9.445  ppm2  2.167
ASSI {1621}
((segid "PROT" and resid 10 and name HN))
((segid "PROT" and resid 9 and name HG1))
  3.600  3.200  1.900 peak    1621 weight  0.10000E+01 volume  0.11241E+01 ppm1    8.310  ppm2  1.649
ASSI {1631}
((segid "PROT" and resid 10 and name HN))
((segid "PROT" and resid 10 and name HA))
  3.000  2.200  2.200 peak    1631 weight  0.10000E+01 volume  0.35515E+01 ppm1    8.304  ppm2  4.893
ASSI {1641}
((segid "PROT" and resid 10 and name HN))
((segid "PROT" and resid 8 and name HA))
  3.400  2.900  2.100 peak    1641 weight  0.10000E+01 volume  0.17142E+01 ppm1    8.301  ppm2  4.437
ASSI {1651}
((segid "PROT" and resid 10 and name HN))
((segid "PROT" and resid 9 and name HA))
  2.500  1.600  1.600 peak    1651 weight  0.10000E+01 volume  0.10059E+02 ppm1    8.305  ppm2  4.337

TABLE 13-continued

Unambiguous NOE Distance Restraints

ASSI {1671}
((segid "PROT" and resid 10 and name HN))
((segid "PROT" and resid 11 and name HD1))
 3.500  3.100  2.000 peak     1671 weight 0.10000E+01 volume 0.13217E+01 ppm1  8.303 ppm2  3.874
ASSI {1681}
((segid "PROT" and resid 10 and name HN))
((segid "PROT" and resid 10 and name HB1))
 2.900  2.100  2.100 peak     1681 weight 0.10000E+01 volume 0.41755E+01 ppm1  8.305 ppm2  2.768
ASSI {1691}
((segid "PROT" and resid 10 and name HN))
((segid "PROT" and resid 10 and name HB2))
 2.800  2.000  2.000 peak     1691 weight 0.10000E+01 volume 0.49103E+01 ppm1  8.306 ppm2  2.707
ASSI {1701}
((segid "PROT" and resid 10 and name HN))
((segid "PROT" and resid 13 and name HB1))
 3.400  2.900  2.100 peak     1701 weight 0.10000E+01 volume 0.15663E+01 ppm1  8.307 ppm2  2.166
ASSI {1711}
((segid "PROT" and resid 10 and name HN))
((segid "PROT" and resid 9 and name HB1))
 3.400  2.900  2.100 peak     1711 weight 0.10000E+01 volume 0.17647E+01 ppm1  8.308 ppm2  1.864
ASSI {1731}
((segid "PROT" and resid 43 and name HN))
((segid "PROT" and resid 44 and name HD1))
 3.500  3.100  2.000 peak     1731 weight 0.10000E+01 volume 0.12797E+01 ppm1  7.180 ppm2  3.801
ASSI {1741}
((segid "PROT" and resid 43 and name HN))
((segid "PROT" and resid 39 and name HB2))
 3.500  3.100  2.000 peak     1741 weight 0.10000E+01 volume 0.13282E+01 ppm1  7.188 ppm2  1.905
ASSI {1751}
((segid "PROT" and resid 43 and name HN))
((segid "PROT" and resid 43 and name HA))
 3.100  2.400  2.400 peak     1751 weight 0.10000E+01 volume 0.26725E+01 ppm1  7.178 ppm2  4.963
ASSI {1761}
((segid "PROT" and resid 43 and name HN))
((segid "PROT" and resid 42 and name HA))
 3.200  2.600  2.300 peak     1761 weight 0.10000E+01 volume 0.23728E+01 ppm1  7.181 ppm2  4.472
ASSI {1771}
((segid "PROT" and resid 43 and name HN))
((segid "PROT" and resid 41 and name HA))
 3.300  2.700  2.200 peak     1771 weight 0.10000E+01 volume 0.19062E+01 ppm1  7.179 ppm2  4.078
ASSI {1781}
((segid "PROT" and resid 43 and name HN))
((segid "PROT" and resid 44 and name HD2))
 3.300  2.700  2.200 peak     1781 weight 0.10000E+01 volume 0.17857E+01 ppm1  7.180 ppm2  3.546
ASSI {1791}
((segid "PROT" and resid 43 and name HN))
((segid "PROT" and resid 42 and name HB1))
 3.300  2.700  2.200 peak     1791 weight 0.10000E+01 volume 0.18305E+01 ppm1  7.180 ppm2  2.196
ASSI {1801}
((segid "PROT" and resid 43 and name HN))
(segid "PROT" and resid 43 and name HB%)
 2.700  1.800  1.800 peak     1801 weight 0.10000E+01 volume 0.58026E+01 ppm1  7.180 ppm2  0.964
ASSI {1811}
((segid "PROT" and resid 43 and name HN))
(segid "PROT" and resid 38 and name HG2%)
 3.500  3.100  2.000 peak     1811 weight 0.10000E+01 volume 0.13977E+01 ppm1  7.183 ppm2  −0.019
ASSI {1821}
((segid "PROT" and resid 43 and name HN))
((segid "PROT" and resid 42 and name HB2))
 3.400  2.900  2.100 peak     1821 weight 0.10000E+01 volume 0.17166E+01 ppm1  7.179 ppm2  2.055
ASSI {1831}
((segid "PROT" and resid 14 and name HN))
((segid "PROT" and resid 14 and name HB1))
 2.600  1.700  1.700 peak     1831 weight 0.10000E+01 volume 0.81036E+01 ppm1  8.204 ppm2  1.862
ASSI {1841}
((segid "PROT" and resid 14 and name HN))
((segid "PROT" and resid 14 and name HB2))
 2.700  1.800  1.800 peak     1841 weight 0.10000E+01 volume 0.69081E+01 ppm1  8.204 ppm2  1.572
ASSI {1851}
((segid "PROT" and resid 14 and name HN))
((segid "PROT" and resid 14 and name HG))
 3.000  2.200  2.200 peak     1851 weight 0.10000E+01 volume 0.31980E+01 ppm1  8.205 ppm2  1.470
ASSI {1861}
((segid "PROT" and resid 14 and name HN))
(segid "PROT" and resid 14 and name HD1%)
 2.800  2.000  2.000 peak     1861 weight 0.10000E+01 volume 0.47954E+01 ppm1  8.206 ppm2  0.812

TABLE 13-continued

Unambiguous NOE Distance Restraints

```
ASSI {1881}
((segid "PROT" and resid 14 and name HN))
((segid "PROT" and resid 11 and name HA))
 3.200  2.600   2.300 peak      1881 weight  0.10000E+01 volume  0.22640E+01 ppm1   8.195 ppm2  4.351
ASSI {1891}
((segid "PROT" and resid 14 and name HN))
((segid "PROT" and resid 14 and name HA))
 2.700  1.800   1.800 peak      1891 weight  0.10000E+01 volume  0.59973E+01 ppm1   8.201 ppm2  4.064
ASSI {1901}
((segid "PROT" and resid 13 and name HN))
((segid "PROT" and resid 13 and name HG1))
 3.000  2.200   2.200 peak      1901 weight  0.10000E+01 volume  0.37757E+01 ppm1   8.187 ppm2  2.507
ASSI {1911}
((segid "PROT" and resid 13 and name HN))
((segid "PROT" and resid 12 and name HB2))
 2.800  2.000   2.000 peak      1911 weight  0.10000E+01 volume  0.49834E+01 ppm1   8.184 ppm2  2.773
ASSI {1921}
((segid "PROT" and resid 13 and name HN))
((segid "PROT" and resid 12 and name HA))
 2.000  2.000   2.500 peak      1921 weight  0.10000E+01 volume  0.40529E+02 ppm1   8.191 ppm2  4.738
ASSI {1931}
((segid "PROT" and resid 13 and name HN))
((segid "PROT" and resid 13 and name HA))
 2.600  1.700   1.700 peak      1931 weight  0.10000E+01 volume  0.72316E+01 ppm1   8.189 ppm2  4.186
ASSI {1941}
((segid "PROT" and resid 13 and name HN))
((segid "PROT" and resid 15 and name HB2))
 3.500  3.100   2.000 peak      1941 weight  0.10000E+01 volume  0.14798E+01 ppm1   8.188 ppm2  3.060
ASSI {1951}
((segid "PROT" and resid 13 and name HN))
((segid "PROT" and resid 13 and name HB1))
 2.300  1.300   1.300 peak      1951 weight  0 10000E+01 volume  0.17203E+02 ppm1   8.188 ppm2  2.169
ASSI {1971}
((segid "PROT" and resid 13 and name HN))
((segid "PROT" and resid 13 and name HG2))
 2.900  2.100   2.100 peak      1971 weight  0.10000E+01 volume  0.42736E+01 ppm1   8.183 ppm2  2.406
ASSI {1981}
((segid "PROT" and resid 9 and name HN))
((segid "PROT" and resid 10 and name HN))
 3.000  2.200   2.200 peak      1981 weight  0.10000E+01 volume  0.31853E+01 ppm1   8.448 ppm2  8.320
ASSI {1991}
((segid "PROT" and resid 9 and name HN))
((segid "PROT" and resid 7 and name HA))
 3.200  2.600   2.300 peak      1991 weight  0.10000E+01 volume  0.21603E+01 ppm1   8.450 ppm2  4.562
ASSI {2001}
((segid "PROT" and resid 9 and name HN))
((segid "PROT" and resid 8 and name HA))
 2.300  1.300   1.300 peak      2001 weight  0.10000E+01 volume  0.19003E+02 ppm1   8.447 ppm2  4.440
ASSI {2011}
((segid "PROT" and resid 9 and name HN))
((segid "PROT" and resid 9 and name HA))
 2.700  1.800   1.800 peak      2011 weight  0.10000E+01 volume  0.60317E+01 ppm1   8.447 ppm2  4.335
ASSI {2021}
((segid "PROT" and resid 9 and name HN))
((segid "PROT" and resid 8 and name HB1))
 3.100  2.400   2.400 peak      2021 weight  0.10000E+01 volume  0.27796E+01 ppm1   8.445 ppm2  2.277
ASSI {2031}
((segid "PROT" and resid 9 and name HN))
(( segid "PROT" and resid 8 and name HG1))
 3.400  2.900   2.100 peak      2031 weight  0.10000E+01 volume  0.16094E+01 ppm1   8.444 ppm2  2.032
ASSI {2051}
((segid "PROT" and resid 9 and name HN))
((segid "PROT" and resid 9 and name HG1))
 3.000  2.200   2.200 peak      2051 weight  0.10000E+01 volume  0.32889E+01 ppm1   8.445 ppm2  1.685
ASSI {2061}
((segid "PROT" and resid 112 and name HN))
((segid "PROT" and resid 108 and name HA))
 3.200  2.600   2.300 peak      2061 weight  0.10000E+01 volume  0.22954E+01 ppm1   8.062 ppm2  4.205
ASSI {2071}
((segid "PROT" and resid 112 and name HN))
((segid "PROT" and resid 114 and name HN))
 3.100  2.400   2.400 peak      2071 weight  0.10000E+01 volume  0.29684E+01 ppm1   8.062 ppm2  7.777
ASSI {2081}
((segid "PROT" and resid 112 and name HN))
((segid "PROT" and resid 113 and name HN))
 2.400  1.400   1.400 peak      2081 weight  0.10000E+01 volume  0.12819E+02 ppm1   8.062 ppm2  7.594
```

TABLE 13-continued

Unambiguous NOE Distance Restraints

ASSI {2091}
((segid "PROT" and resid 112 and name HN))
((segid "PROT" and resid 113 and name HA))
 3.300  2.700  2.200 peak      2091 weight  0.10000E+01 volume  0.18076E+01 ppm1    8.062 ppm2  4.319
ASSI {2101}
((segid "PROT" and resid 112 and name HN))
((segid "PROT" and resid 112 and name HA))
 2.400  1.400  1.400 peak      2101 weight  0.10000E+01 volume  0.12528E+02 ppm1    8.062 ppm2  4.004
ASSI {2111}
((segid "PROT" and resid 112 and name HN))
((segid "PROT" and resid 112 and name HG1))
 2.800  2.000  2.000 peak      2111 weight  0.10000E+01 volume  0.53710E+01 ppm1    8.063 ppm2  2.367
ASSI {2121}
((segid "PROT" and resid 112 and name HN))
((segid "PROT" and resid 112 and name HG2))
 2.900  2.100  2.100 peak      2121 weight  0.10000E+01 volume  0.39999E+01 ppm1    8.061 ppm2  2.229
ASSI {2131}
((segid "PROT" and resid 112 and name HN))
((segid "PROT" and resid 112 and name HB1))
 2.200  1.200  1.200 peak      2131 weight  0.10000E+01 volume  0.19429E+02 ppm1    8.063 ppm2  2.082
ASSI {2141}
((segid "PROT" and resid 112 and name HN))
((segid "PROT" and resid 111 and name HB1))
 2.600  1.700  1.700 peak      2141 weight  0.10000E+01 volume  0.76296E+01 ppm1    8.063 ppm2  1.878
ASSI {2151}
((segid "PROT" and resid 112 and name HN))
((segid "PROT" and resid 111 and name HG1))
 2.900  2.100  2.100 peak      2151 weight  0.10000E+01 volume  0.39254E+01 ppm1    8.062 ppm2  1.400
ASSI {2171}
((segid "PROT" and resid 105 and name HN))
((segid "PROT" and resid 106 and name HN)
 2.700  1.800  1.800 peak      2171 weight  0.10000E+01 volume  0.64918E+01 ppm1    7.895 ppm2  9.143
ASSI {2181}
((segid "PROT" and resid 105 and name HN))
((segid "PROT" and resid 105 and name HB2))
 2.600  1.700  1.700 peak      2181 weight  0.10000E+01 volume  0.82226E+01 ppm1    7.897 ppm2  3.069
ASSI {2191}
((segid "PROT" and resid 109 and name HN))
((segid "PROT" and resid 112 and name HN))
 2.400  2.400  2.100 peak      2191 weight  0.10000E+01 volume  0.13989E+02 ppm1    7.966 ppm2  8.061
ASSI {2201}
((segid "PROT" and resid 105 and name HN))
((segid "PROT" and resid 107 and name HN))
 3.500  3.100  2.000 peak      2201 weight  0.10000E+01 volume  0.13375E+01 ppm1    7.906 ppm2  8.386
ASSI {2221}
((segid "PROT" and resid 105 and name HN))
((segid "PROT" and resid 104 and name HN))
 2.500  1.600  1.600 peak      2221 weight  0.10000E+01 volume  0.98549E+01 ppm1    7.898 ppm2  7.183
ASSI {2231}
((segid "PROT" and resid 105 and name HN))
((segid "PROT" and resid 105 and name HN))
 2.800  2.000  2.000 peak      2231 weight  0.10000E+01 volume  0.54794E+01 ppm1    7.898 ppm2  4.341
ASSI {2241}
((segid "PROT" and resid 105 and name HN))
((segid "PROT" and resid 101 and name HA))
 2.900  2.100  2.100 peak      2241 weight  0.10000E+01 volume  0.40771E+01 ppm1    7.899 ppm2  3.693
ASSI {2251}
((segid "PROT" and resid 105 and name HN))
((segid "PROT" and resid 105 and name HB1))
 2.600  1.700  1.700 peak      2251 weight  0.10000E+01 volume  0.78556E+01 ppm1    7.897 ppm2  3.149
ASSI {2261}
((segid "PROT" and resid 105 and name HN))
((segid "PROT" and resid 104 and name HB1))
 2.600  1.700  1.700 peak      2261 weight  0.10000E+01 volume  0.79995E+01 ppm1    7.897 ppm2  1.951
ASSI {2271}
((segid "PROT" and resid 105 and name HN))
((segid "PROT" and resid 104 and name HG1))
 3.400  2.900  2.100 peak      2271 weight  0.10000E+01 volume  0.16588E+01 ppm1    7.894 ppm2  1.538
ASSI {2281}
((segid "PROT" and resid 105 and name HN))
(segid "PROT" and resid 102 and name HD2%)
 3.200  2.600  2.300 peak      2281 weight  0.10000E+01 volume  0.22009E+01 ppm1    7.898 ppm2  0.737
ASSI {2301}
((segid "PROT" and resid 109 and name HN))
((segid "PROT" and resid 108 and name HA))
 3.100  2.400  2.400 peak      2301 weight  0.10000E+01 volume  0.25704E+01 ppm1    7.966 ppm2  4.207

TABLE 13-continued

| Unambiguous NOE Distance Restraints |
|---|

ASSI {2311}
((segid "PROT" and resid 109 and name HN))
((segid "PROT" and resid 109 and name HE2))
  3.400  2.900  2.100 peak    2311  weight  0.10000E+01 volume  0.15036E+01 ppm1    7.969  ppm2  2.462
ASSI {2321}
((segid "PROT" and resid 109 and name HN))
((segid "PROT" and resid 109 and name HG1))
  2.600  1.700  1.700 peak    2321  weight  0.10000E+01 volume  0.78656E+01 ppm1    7.966  ppm2  0.828
ASSI {2331}
((segid "PROT" and resid 109 and name HN))
((segid "PROT" and resid 111 and name HN))
  3.100  2.400  2.400 peak    2331  weight  0.10000E+01 volume  0.27030E+01 ppm1    7.959  ppm2  7.567
ASSI {2341}
((segid "PROT" and resid 109 and name HN))
((segid "PROT" and resid 105 and name HA))
  3.400  2.900  2.100 peak    2341  weight  0.10000E+01 volume  0.15976E+01 ppm1    7.964  ppm2  4.340
ASSI {2351}
((segid "PROT" and resid 109 and name HN))
((segid "PROT" and resid 108 and name HB1))
  2.500  1.600  1.600 peak    2351  weight  0.10000E+01 volume  0.95438E+01 ppm1    7.965  ppm2  4.004
ASSI {2361}
((segid "PROT" and resid 109 and name HN))
((segid "PROT" and resid 107 and name HA))
  3.200  2.600  2.300 peak    2361  weight  0.10000E+01 volume  0.23540E+01 ppm1    7.963  ppm2  3.853
ASSI {2371}
((segid "PROT" and resid 109 and name HN))
((segid "PROT" and resid 109 and name HB1))
  2.600  1.700  1.700 peak    2371  weight  0.10000E+01 volume  0.85245E+01 ppm1    7.965  ppm2  1.736
ASSI {2381}
((segid "PROT" and resid 109 and name HN))
((segid "PROT" and resid 109 and name HB2))
  2.800  2.000  2.000 peak    2381  weight  0.10000E+01 volume  0.48841E+01 ppm1    7.964  ppm2  1.564
ASSI {2391}
((segid "PROT" and resid 109 and name HN))
((segid "PROT" and resid 109 and name HD1))
  2.900  2.100  2.100 peak    2391  weight  0.10000E+01 volume  0.42717E+01 ppm1    7.961  ppm2  1.394
ASSI {2401}
((segid "PROT" and resid 109 and name HN))
((segid "PROT" and resid 110 and name HG11))
  3.400  2.900  2.100 peak    2401  weight  0.10000E+01 volume  0.15305E+01 ppm1    7.962  ppm2  1.140
ASSI {2411}
((segid "PROT" and resid 109 and name HN))
((segid "PROT" and resid 107 and name HN))
  3.600  3.200  1.900 peak    2411  weight  0.10000E+01 volume  0.11700E+01 ppm1    7.954  ppm2  8.397
ASSI {2421}
((segid "PROT" and resid 106 and name HN))
((segid "PROT" and resid 102 and name HA))
  3.400  2.900  2.100 peak    2421  weight  0.10000E+01 volume  0.16616E+01 ppm1    9.157  ppm2  3.700
ASSI {2431}
((segid "PROT" and resid 106 and name HN))
((segid "PROT" and resid 107 and name HN))
  2.800  2.000  2.000 peak    2431  weight  0.10000E+01 volume  0.54826E+01 ppm1    9.149  ppm2  8.399
ASSI {2451}
((segid "PROT" and resid 106 and name HN))
((segid "PROT" and resid 24 and name HE21))
  3.300  2.700  2.200 peak    2451  weight  0.10000E+01 volume  0.17819E+01 ppm1    9.147  ppm2  7.060
ASSI {2461}
((segid "PROT" and resid 106 and name HN))
(segid "PROT" and resid 106 and name HD%))
  3.500  3.100  2.000 peak    2461  weight  0.10000E+01 volume  0.13574E+01 ppm1    9.153  ppm2  6.913
ASSI {2471}
((segid "PROT" and resid 106 and name HN))
((segid "PROT" and resid 106 and name HA))
  2.900  2.100  2.100 peak    2471  weight  0.10000E+01 volume  0.45571E+01 ppm1    9.146  ppm2  3.977
ASSI {2481}
((segid "PROT" and resid 106 and name HN))
((segid "PROT" and resid 106 and name HB1))
  2.700  1.800  1.800 peak    2481  weight  0.10000E+01 volume  0.65451E+01 ppm1    9.149  ppm2  3.314
ASSI {2491}
((segid "PROT" and resid 106 and name HN))
((segid "PROT" and resid 106 and name HB2))
  2.500  1.600  1.600 peak    2491  weight  0.10000E+01 volume  0.92358E+01 ppm1    9.148  ppm2  3.100
ASSI {2511}
((segid "PROT" and resid 106 and name HN))
(segid "PROT" and resid 25 and name HG1%)
  3.500  3.100  2.000 peak    2511  weight  0.10000E+01 volume  0.14013E+01 ppm1    9.149  ppm2  1.222

TABLE 13-continued

Unambiguous NOE Distance Restraints

ASSI {2521}
((segid "PROT" and resid 106 and name HN))
((segid "PROT" and resid 104 and name HN))
 3.300  2.700  2.200 peak     2521 weight 0.10000E+01 volume 0.18869E+01 ppm1  9.146 ppm2 7.178
ASSI {2541}
((segid "PROT" and resid 106 and name HN))
((segid "PROT" and resid 105 and name HA))
 3.500  3.100  2.000 peak     2541 weight 0.10000E+01 volume 0.14398E+01 ppm1  9.142 ppm2 4.338
ASSI {2551}
((segid "PROT" and resid 106 and name HN))
((segid "PROT" and resid 104 and name HA))
 3.400  2.900  2.100 peak     2551 weight 0.10000E+01 volume 0.15238E+01 ppm1  9.143 ppm2 4.087
ASSI {2561}
((segid "PROT" and resid 106 and name HN))
(segid "PROT" and resid 102 and name HD2%)
 3.400  2.900  2.100 peak     2561 weight 0.10000E+01 volume 0.15872E+01 ppm1  9.146 ppm2 0.732
ASSI {2571}
((segid "PROT" and resid 84 and name HN))
((segid "PROT" and resid 83 and name HA))
 3.300  2.700  2.200 peak     2571 weight 0.10000E+01 volume 0.17659E+01 ppm1  8.875 ppm2 3.865
ASSI {2581}
((segid "PROT" and resid 84 and name HN))
((segid "PROT" and resid 83 and name HN))
 2.600  1.700  1.700 peak     2581 weight 0.10000E+01 volume 0.75945E+01 ppm1  8.874 ppm2 9.085
ASSI {2601}
((segid "PROT" and resid 84 and name HN))
((segid "PROT" and resid 80 and name HN))
 3.200  2.600  2.300 peak     2601 weight 0.10000E+01 volume 0.21504E+01 ppm1  8.870 ppm2 7.410
ASSI {2611}
((segid "PROT" and resid 84 and name HN))
((segid "PROT" and resid 85 and name HN))
 2.800  2.000  2.000 peak     2611 weight 0.10000E+01 volume 0.55696E+01 ppm1  8.872 ppm2 6.913
ASSI {2621}
((segid "PROT" and resid 84 and name HN))
((segid "PROT" and resid 82 and name HN))
 3.500  3.100  2.000 peak     2621 weight 0.10000E+01 volume 0.13351E+01 ppm1  8.872 ppm2 6.408
ASSI {2631}
((segid "PROT" and resid 84 and name HN))
((segid "PROT" and resid 84 and name HA))
 2.700  1.800  1.800 peak     2631 weight 0.10000E+01 volume 0.67391E+01 ppm1  8.874 ppm2 4.314
ASSI {2641}
((segid "PROT" and resid 84 and name HN))
((segid "PROT" and resid 83 and name HB))
 2.800  2.000  2.000 peak     2641 weight 0.10000E+01 volume 0.51222E+01 ppm1  8.874 ppm2 4.216
ASSI {2651}
((segid "PROT" and resid 84 and name HN))
((segid "PROT" and resid 80 and name HA))
 3.000  2.200  2.200 peak     2651 weight 0.10000E+01 volume 0.35702E+01 ppm1  8.873 ppm2 4.073
ASSI {2661}
((segid "PROT" and resid 84 and name HN))
((segid "PROT" and resid 81 and name HA))
 3.200  2.600  2.300 peak     2661 weight 0.10000E+01 volume 0.24366E+01 ppm1  8.875 ppm2 3.080
ASSI {2671}
((segid "PROT" and resid 84 and name HN))
((segid "PROT" and resid 84 and name HB1))
 2.800  2.000  2.000 peak     2671 weight 0.10000E+01 volume 0.49574E+01 ppm1  8.874 ppm2 2.988
ASSI {2681}
((segid "PROT" and resid 84 and name HN))
((segid "PROT" and resid 84 and name HB2))
 3.000  2.200  2.200 peak     2681 weight 0.10000E+01 volume 0.34031E+01 ppm1  8.873 ppm2 2.695
ASSI {2691}
((segid "PROT" and resid 84 and name HN))
(segid "PROT" and resid 83 and name HG2%)
 3.000  2.200  2.200 peak     2691 weight 0.10000E+01 volume 0.32105E+01 ppm1  8.872 ppm2 1.322
ASSI {2701}
((segid "PROT" and resid 40 and name HN))
((segid "PROT" and resid 40 and name HA))
 3.200  2.600  2.300 peak     2701 weight 0.10000E+01 volume 0.21281E+01 ppm1  8.066 ppm2 3.679
ASSI {2721}
((segid "PROT" and resid 40 and name HN))
((segid "PROT" and resid 42 and name HN))
 2.600  1.700  1.700 peak     2721 weight 0.10000E+01 volume 0.84529E+01 ppm1  8.061 ppm2 7.182
ASSI {2741}
((segid "PROT" and resid 17 and name HN))
((segid "PROT" and resid 15 and name HB2))
 3.300  2.700  2.200 peak     2741 weight 0.10000E+01 volume 0.20300E+01 ppm1  8.061 ppm2 3.089

TABLE 13-continued

| Unambiguous NOE Distance Restraints |
|---|

ASSI {2751}
((segid "PROT" and resid 40 and name HN))
((segid "PROT" and resid 39 and name HB2))
 2.800  2.000  2.000 peak     2751 weight  0.10000E+01 volume  0.54119E+01 ppm1    8.061 ppm2  1.944
ASSI {2761}
((segid "PROT" and resid 112 and name HN))
((segid "PROT" and resid 111 and name HB2))
 2.500  1.600  1.600 peak     2761 weight  0.10000E+01 volume  0.91964E+01 ppm1    8.060 ppm2  1.761
ASSI {2781}
((segid "PROT" and resid 40 and name HN))
((segid "PROT" and resid 39 and name HG2))
 2.900  2.100  2.100 peak     2781 weight  0.10000E+01 volume  0.40049E+01 ppm1    8.058 ppm2  1.420
ASSI {2791}
((segid "PROT" and resid 40 and name HN))
(segid "PROT" and resid 41 and name HG2%)
 2.600  1.700  1.700 peak     2791 weight  0.10000E+01 volume  0.90273E+01 ppm1    8.059 ppm2  1.310
ASSI {2811}
((segid "PROT" and resid 18 and name HN))
((segid "PROT" and resid 16 and name HN))
 3.300  2.700  2.200 peak     2811 weight  0.10000E+01 volume  0.18261E+01 ppm1    8.480 ppm2  8.180
ASSI {2821}
((segid "PROT" and resid 18 and name HN))
((segid "PROT" and resid 15 and name HA))
 3.200  2.600  2.300 peak     2821 weight  0.10000E+01 volume  0.23600E+01 ppm1    8.479 ppm2  4.068
ASSI {2831}
((segid "PROT" and resid 18 and name HN))
((segid "PROT" and resid 18 and name HB2))
 3.100  2.400  2.400 peak     2831 weight  0.10000E+01 volume  0.28105E+01 ppm1    8.479 ppm2  0.321
ASSI {2841}
((segid "PROT" and resid 18 and name HN))
((segid "PROT" and resid 19 and name HN))
 2.700  1.800  1.800 peak     2841 weight  0.10000E+01 volume  0.63709E+01 ppm1    8.477 ppm2  8.560
ASSI {2861}
((segid "PROT" and resid 18 and name HN))
((segid "PROT" and resid 17 and name HB))
 2.800  2.000  2.000 peak     2861 weight  0.10000E+01 volume  0.46980E+01 ppm1    8.476 ppm2  4.264
ASSI {2871}
((segid "PROT" and resid 18 and name HN))
((segid "PROT" and resid 17 and name HA))
 3.200  2.600  2.300 peak     2871 weight  0.10000E+01 volume  0.23422E+01 ppm1    8.476 ppm2  3.944
ASSI {2881}
((segid "PROT" and resid 18 and name HN))
((segid "PROT" and resid 18 and name HA))
 3.000  2.200  2.200 peak     2881 weight  0.10000E+01 volume  0.32947E+01 ppm1    8.474 ppm2  3.286
ASSI {2891}
((segid "PROT" and resid 18 and name HN))
((segid "PROT" and resid 18 and name HG))
 2.700  1.800  1.800 peak     2891 weight  0.10000E+01 volume  0.63912E+01 ppm1    8.475 ppm2  1.680
ASSI {2901}
((segid "PROT" and resid 18 and name HN))
((segid "PROT" and resid 18 and name HB1))
 2.800  2.000  2.000 peak     2901 weight  0.10000E+01 volume  0.48006E+01 ppm1    8.475 ppm2  1.523
ASSI {2911}
((segid "PROT" and resid 18 and name HN))
(segid "PROT" and resid 17 and name HG2%)
 3.000  2.200  2.200 peak     2911 weight  0.10000E+01 volume  0.31480E+01 ppm1    8.476 ppm2  1.153
ASSI {2931}
((segid "PROT" and resid 18 and name HN))
(segid "PROT" and resid 14 and name HD2%)
 3.300  2.700  2.200 peak     2931 weight  0.10000E+01 volume  0.20785E+01 ppm1    8.476 ppm2  0.807
ASSI {2941}
((segid "PROT" and resid 18 and name HN))
(segid "PROT" and resid 18 and name HD1%)
 3.000  2.200  2.200 peak     2941 weight  0.10000E+01 volume  0.31846E+01 ppm1    8.476 ppm2  0.482
ASSI {2951}
((segid "PROT" and resid 18 and name HN))
(segid "PROT" and resid 18 and name HD2%)
 2.900  2.100  2.100 peak     2951 weight  0.10000E+01 volume  0.41898E+01 ppm1    8.475 ppm2  −0.188
ASSI {2961}
((segid "PROT" and resid 21 and name HN))
((segid "PROT" and resid 19 and name HN))
 3.100  2.400  2.400 peak     2961 weight  0.10000E+01 volume  0.28005E+01 ppm1    7.926 ppm2  8.572
ASSI {2981}
((segid "PROT" and resid 21 and name HN))
((segid "PROT" and resid 20 and name HB1))
 2.600  1.700  1.700 peak     2981 weight  0.10000E+01 volume  0.74039E+01 ppm1    7.927 ppm2  4.077

TABLE 13-continued

Unambiguous NOE Distance Restraints

```
ASSI {2991}
((segid "PROT" and resid 21 and name HN))
((segid "PROT" and resid 21 and name HB))
 2.500  1.600   1.600 peak       2991 weight  0.10000E+01 volume   0.92632E+01 ppm1    7.926 ppm2   1.918
ASSI {3001}
((segid "PROT" and resid 21 and name HN))
((segid "PROT" and resid 109 and name HB1))
 2.600  1.700   1.700 peak       3001 weight  0.10000E+01 volume   0.77416E+01 ppm1    7.928 ppm2   1.766
ASSI {3011}
((segid "PROT" and resid 21 and name HN))
(segid "PROT" and resid 21 and name HG2%)
 2.700  1.800   1.800 peak       3011 weight  0.10000E+01 volume   0.61275E+01 ppm1    7.928 ppm2   1.014
ASSI {3021}
((segid "PROT" and resid 21 and name HN))
((segid "PROT" and resid 22 and name HN))
 2.600  1.700   1.700 peak       3021 weight  0.10000E+01 volume   0.72631E+01 ppm1    7.925 ppm2   8.852
ASSI {3041}
((segid "PROT" and resid 21 and name HN))
((segid "PROT" and resid 21 and name HA))
 2.900  2.100   2.100 peak       3041 weight  0.10000E+01 volume   0.45192E+01 ppm1    7.925 ppm2   3.776
ASSI {3051}
((segid "PROT" and resid 21 and name HN))
((segid "PROT" and resid 18 and name HA))
 3.300  2.700   2.200 peak       3051 weight  0.10000E+01 volume   0.20113E+01 ppm1    7.922 ppm2   3.290
ASSI {3061}
((segid "PROT" and resid 21 and name HN))
(segid "PROT" and resid 21 and name HD1%)
 2.900  2.100   2.100 peak       3061 weight  0.10000E+01 volume   0.38874E+01 ppm1    7.925 ppm2   0.629
ASSI {3071}
((segid "PROT" and resid 63 and name HN))
((segid "PROT" and resid 62 and name HN))
 2.800  2.000   2.000 peak       3071 weight  0.10000E+01 volume   0.52291E+01 ppm1    8.888 ppm2   8.376
ASSI {3081}
((segid "PROT" and resid 63 and name HN))
((segid "PROT" and resid 61 and name HN))
 3.300  2.700   2.200 peak       3081 weight  0.10000E+01 volume   0.18178E+01 ppm1    8.888 ppm2   8.161
ASSI {3091}
((segid "PROT" and resid 63 and name HN))
((segid "PROT" and resid 64 and name HN))
 2.700  1.800   1.800 peak       3091 weight  0.10000E+01 volume   0.60476E+01 ppm1    8.888 ppm2   8.016
ASSI {3121}
((segid "PROT" and resid 63 and name HN))
((segid "PROT" and resid 62 and name HA))
 3.400  2.900   2.100 peak       3121 weight  0.10000E+01 volume   0.15880E+01 ppm1    8.892 ppm2   3.879
ASSI {3131}
((segid "PROT" and resid 63 and name HN))
((segid "PROT" and resid 63 and name HB1))
 2.700  1.800   1.800 peak       3131 weight  0.10000E+01 volume   0.58695E+01 ppm1    8.888 ppm2   2.320
ASSI {3141}
((segid "PROT" and resid 63 and name HN))
((segid "PROT" and resid 62 and name HB1))
 2.800  2.000   2.000 peak       3141 weight  0.10000E+01 volume   0.46788E+01 ppm1    8.888 ppm2   2.057
ASSI {3151}
((segid "PROT" and resid 63 and name HN))
((segid "PROT" and resid 63 and name HB2))
 2.700  1.800   1.800 peak       3151 weight  0.10000E+01 volume   0.63702E+01 ppm1    8.886 ppm2   1.941
ASSI {3161}
((segid "PROT" and resid 63 and name HN))
((segid "PROT" and resid 63 and name HG))
 3.100  2.400   2.400 peak       3161 weight  0.10000E+01 volume   0.27969E+01 ppm1    8.889 ppm2   1.820
ASSI {3171}
((segid "PROT" and resid 63 and name HN))
(segid "PROT" and resid 63 and name HD2%)
 3.000  2.200   2.200 peak       3171 weight  0.10000E+01 volume   0.35417E+01 ppm1    8.888 ppm2   1.060
ASSI {3181}
((segid "PROT" and resid 17 and name HN))
((segid "PROT" and resid 18 and name HN))
 2.500  1.600   1.600 peak       3181 weight  0.10000E+01 volume   0.95309E+01 ppm1    8.069 ppm2   8.473
ASSI {3191}
((segid "PROT" and resid 17 and name HN))
((segid "PROT" and resid 16 and name HN))
 2.500  1.600   1.600 peak       3191 weight  0.10000E+01 volume   0.10057E+02 ppm1    8.071 ppm2   8.187
ASSI {3201}
((segid "PROT" and resid 17 and name HN))
((segid "PROT" and resid 20 and name HN))
 3.400  2.900   2.100 peak       3201 weight  0.10000E+01 volume   0.15862E+01 ppm1    8.066 ppm2   7.549
```

TABLE 13-continued

Unambiguous NOE Distance Restraints

ASSI {3211}
((segid "PROT" and resid 17 and name HN))
((segid "PROT" and resid 17 and name HB))
  2.500  1.600  1.600 peak      3211 weight  0.10000E+01 volume  0.10024E+02 ppm1     8.069 ppm2  4.262
ASSI {3221}
((segid "PROT" and resid 17 and name HN))
((segid "PROT" and resid 15 and name HA))
  2.600  1.700  1.700 peak      3221 weight  0.10000E+01 volume  0.85882E+01 ppm1     8.069 ppm2  4.044
ASSI {3231}
((segid "PROT" and resid 17 and name HN))
((segid "PROT" and resid 17 and name HA))
  2.500  1.600  1.600 peak      3231 weight  0.10000E+01 volume  0.93972E+01 ppm1     8.070 ppm2  3.947
ASSI {3241}
((segid "PROT" and resid 17 and name HN))
(segid "PROT" and resid 17 and name HG2%)
  2.900  2.100  2.100 peak      3241 weight  0.10000E+01 volume  0.44457E+01 ppm1     8.070 ppm2  1.153
ASSI {3271}
((segid "PROT" and resid 21 and name HN))
((segid "PROT" and resid 17 and name HA))
  3.100  2.400  2.400 peak      3271 weight  0.10000E+01 volume  0.29963E+01 ppm1     7.934 ppm2  3.946
ASSI {3291}
((segid "PROT" and resid 21 and name HN))
((segid "PROT" and resid 20 and name HA))
  3.200  2.600  2.300 peak      3291 weight  0.10000E+01 volume  0.25173E+01 ppm1     7.926 ppm2  4.300
ASSI {3321}
((segid "PROT" and resid 63 and name HN))
((segid "PROT" and resid 62 and name HG2))
  3.200  2.600  2.300 peak      3321 weight  0.10000E+01 volume  0.23209E+01 ppm1     8.888 ppm2  0.886
ASSI {3331}
((segid "PROT" and resid 62 and name HN))
((segid "PROT" and resid 60 and name HN))
  3.500  3.100  2.000 peak      3331 weight  0.10000E+01 volume  0.13912E+01 ppm1     8.384 ppm2  7.972
ASSI {3341}
((segid "PROT" and resid 62 and name HN))
((segid "PROT" and resid 62 and name HD1))
  3.500  3.100  2.000 peak      3341 weight  0.10000E+01 volume  0.13872E+01 ppm1     8.383 ppm2  2.575
ASSI {3351}
((segid "PROT" and resid 62 and name HN))
((segid "PROT" and resid 63 and name HB1))
  3.500  3.100  2.000 peak      3351 weight  0.10000E+01 volume  0.14084E+01 ppm1     8.384 ppm2  2.382
ASSI {3361}
((segid "PROT" and resid 62 and name HN))
((segid "PROT" and resid 62 and name HG1))
  3.000  2.200  2.200 peak      3361 weight  0.10000E+01 volume  0.33068E+01 ppm1     8.384 ppm2  1.733
ASSI {3371}
((segid "PROT" and resid 62 and name HN))
((segid "PROT" and resid 62 and name HG2))
  3.200  2.600  2.300 peak      3371 weight  0.10000E+01 volume  0.23585E+01 ppm1     8.382 ppm2  0.889
ASSI {3401}
((segid "PROT" and resid 62 and name HN))
((segid "PROT" and resid 59 and name HA))
  3.400  2.900  2.100 peak      3401 weight  0.10000E+01 volume  0.16609E+01 ppm1     8.380 ppm2  4.316
ASSI {3411}
((segid "PROT" and resid 62 and name HN))
((segid "PROT" and resid 60 and name HB2))
  3.400  2.900  2.100 peak      3411 weight  0.10000E+01 volume  0.15850E+01 ppm1     8.379 ppm2  4.058
ASSI {3421}
((segid "PROT" and resid 62 and name HN))
((segid "PROT" and resid 62 and name HA))
  3.000  2.200  2.200 peak      3421 weight  0.10000E+01 volume  0.37803E+01 ppm1     8.379 ppm2  3.882
ASSI {3431}
((segid "PROT" and resid 62 and name HN))
((segid "PROT" and resid 61 and name HB1))
  2.900  2.100  2.100 peak      3431 weight  0.10000E+01 volume  0.46420E+01 ppm1     8.378 ppm2  2.239
ASSI {3441}
((segid "PROT" and resid 62 and name HN))
((segid "PROT" and resid 62 and name HB1))
  2.600  1.700  1.700 peak      3441 weight  0.10000E+01 volume  0.77987E+01 ppm1     8.379 ppm2  2.071
ASSI {3451}
((segid "PROT" and resid 62 and name HN))
((segid "PROT" and resid 62 and name HB2))
  3.000  2.200  2.200 peak      3451 weight  0.10000E+01 volume  0.36613E+01 ppm1     8.380 ppm2  1.079
ASSI {3461}
((segid "PROT" and resid 64 and name HN))
((segid "PROT" and resid 64 and name HA))
  2.500  1.600  1.600 peak      3461 weight  0.10000E+01 volume  0.92573E+01 ppm1     8.027 ppm2  4.344

TABLE 13-continued

Unambiguous NOE Distance Restraints

ASSI {3471}
((segid "PROT" and resid 64 and name HN))
((segid "PROT" and resid 61 and name HA))
  2.800  2.000   2.000 peak     3471  weight  0.10000E+01 volume  0.51878E+01 ppm1     8.029  ppm2  4.057
ASSI {3491}
((segid "PROT" and resid 64 and name HN))
((segid "PROT" and resid 64 and name HD1))
  2.900  2.100   2.100 peak     3491  weight  0.10000E+01 volume  0.43075E+01 ppm1     8.029  ppm2  1.803
ASSI {3501}
((segid "PROT" and resid 64 and name HN
((segid "PROT" and resid 64 and name HG1))
  2.900  2.100   2.100 peak     3501  weight  0.10000E+01 volume  0.45945E+01 ppm1     8.024  ppm2  1.645
ASSI {3521}
((segid "PROT" and resid 64 and name HN))
((segid "PROT" and resid 62 and name HN))
  3.500  3.100   2.000 peak     3521  weight  0.10000E+01 volume  0.12743E+01 ppm1     8.021  ppm2  8.369
ASSI {3531}
((segid "PROT" and resid 64 and name HN))
((segid "PROT" and resid 63 and name HB1))
  2.800  2.000   2.000 peak     3531  weight  0.10000E+01 volume  0.56024E+01 ppm1     8.020  ppm2  2.320
ASSI {3541}
((segid "PROT" and resid 64 and name HN))
((segid "PROT" and resid 64 and name HB1))
  2.200  1.200   1.200 peak     3541  weight  0.10000E+01 volume  0.19404E+02 ppm1     8.019  ppm2  2.060
ASSI {3551}
((segid "PROT" and resid 64 and name HN))
(segid "PROT" and resid 63 and name HD2%)
  3.300  2.700   2.200 peak     3551  weight  0.10000E+01 volume  0.19248E+01 ppm1     8.021  ppm2  1.055
ASSI {3561}
((segid "PROT" and resid 64 and name HN))
((segid "PROT" and resid 63 and name HD1%)
  3.200  2.600   2.300 peak     3561  weight  0.10000E+01 volume  0.25258E+01 ppm1     8.021  ppm2  0.890
ASSI {3571}
((segid "PROT" and resid 22 and name HN))
((segid "PROT" and resid 21 and name HA))
  3.400  2.900   2.100 peak     3571  weight  0.10000E+01 volume  0.16579E+01 ppm1     8.852  ppm2  3.768
ASSI {3581}
((segid "PROT" and resid 72 and name HN))
((segid "PROT" and resid 72 and name HA))
  3.000  2.200   2.200 peak     3581  weight  0.10000E+01 volume  0.37203E+01 ppm1     8.211  ppm2  4.061
ASSI {3591}
((segid "PROT" and resid 72 and name HN))
((segid "PROT" and resid 72 and name HB1))
  2.800  2.000   2.000 peak     3591  weight  0.10000E+01 volume  0.46635E+01 ppm1     8.210  ppm2  1.925
ASSI {3601}
((segid "PROT" and resid 72 and name HN))
((segid "PROT" and resid 73 and name HN))
  3.000  2.200   2.200 peak     3601  weight  0.10000E+01 volume  0.32739E+01 ppm1     8.206  ppm2  7.441
ASSI {3611}
((segid "PROT" and resid 99 and name HN))
((segid "PROT" and resid 97 and name HA))
  3.100  2.400   2.400 peak     3611  weight  0.10000E+01 volume  0.27035E+01 ppm1     8.191  ppm2  4.210
ASSI {3621}
((segid "PROT" and resid 72 and name HN))
((segid "PROT" and resid 72 and name HB2))
  2.800  2.000   2.000 peak     3621  weight  0.10000E+01 volume  0.47097E+01 ppm1     8.208  ppm2  1.850
ASSI {3631}
((segid "PROT" and resid 72 and name HN))
((segid "PROT" and resid 72 and name HG1))
  3.100  2.400   2.400 peak     3631  weight  0.10000E+01 volume  0.30016E+01 ppm1     8.207  ppm2  1.539
ASSI {3641}
((segid "PROT" and resid 72 and name HN))
((segid "PROT" and resid 6 and name HG1))
  3.300  2.700   2.200 peak     3641  weight  0.10000E+01 volume  0.18696E+01 ppm1     8.199  ppm2  1.432
ASSI {3661}
((segid "PROT" and resid 99 and name HN))
((segid "PROT" and resid 100 and name HN))
  2.600  1.700   1.700 peak     3661  weight  0.10000E+01 volume  0.76299E+01 ppm1     8.188  ppm2  8.080
ASSI {3671}
((segid "PROT" and resid 99 and name HN))
((segid "PROT" and resid 97 and name HN))
  3.400  2.900   2.100 peak     3671  weight  0.10000E+01 volume  0.17229E+01 ppm1     8.189  ppm2  7.960
ASSI {3681}
((segid "PROT" and resid 99 and name HN))
((segid "PROT" and resid 100 and name HA))
  3.600  3.200   1.900 peak     3681  weight  0.10000E+01 volume  0.12058E+01 ppm1     8.193  ppm2  4.341

TABLE 13-continued

Unambiguous NOE Distance Restraints

ASSI {3691}
((segid "PROT" and resid 99 and name HN))
((segid "PROT" and resid 99 and name HA))
  2.900  2.100  2.100 peak     3691  weight  0.10000E+01 volume  0.45059E+01 ppm1    8.192  ppm2  3.884
ASSI {3701}
((segid "PROT" and resid 99 and name HN))
((segid "PROT" and resid 98 and name HB1))
  3.300  2.700  2.200 peak     3701  weight  0.10000E+01 volume  0.19188E+01 ppm1    8.188  ppm2  3.381
ASSI {3711}
((segid "PROT" and resid 99 and name HN))
((segid "PROT" and resid 98 and name HB2))
  3.100  2.400  2.400 peak     3711  weight  0.10000E+01 volume  0.26963E+01 ppm1    8.193  ppm2  3.033
ASSI {3721}
((segid "PROT" and resid 99 and name HN))
(segid "PROT" and resid 99 and name HB%)
  2.500  1.600  1.600 peak     3721  weight  0.10000E+01 volume  0.10441E+02 ppm1    8.191  ppm2  1.632
ASSI {3731}
((segid "PROT" and resid 64 and name HN))
((segid "PROT" and resid 64 and name HE1))
  3.400  2.900  2.100 peak     3731  weight  0.10000E+01 volume  0.15156E+01 ppm1    8.019  ppm2  3.024
ASSI {3761}
((segid "PROT" and resid 22 and name HN))
((segid "PROT" and resid 22 and name HA))
  2.800  2.000  2.000 peak     3761  weight  0.10000E+01 volume  0.47526E+01 ppm1    8.854  ppm2  4.126
ASSI {3771}
((segid "PROT" and resid 22 and name HN))
((segid "PROT" and resid 22 and name HB1))
  2.700  1.800  1.800 peak     3771  weight  0.10000E+01 volume  0.60546E+01 ppm1    8.854  ppm2  2.103
ASSI {3781}
((segid "PROT" and resid 22 and name HN))
((segid "PROT" and resid 21 and name HB))
  2.800  2.000  2.000 peak     3781  weight  0.10000E+01 volume  0.54991E+01 ppm1    8.856  ppm2  1.916
ASSI {3791}
((segid "PROT" and resid 22 and name HN))
((segid "PROT" and resid 22 and name HB2))
  2.600  1.700  1.700 peak     3791  weight  0.10000E+01 volume  0.72128E+01 ppm1    8.853  ppm2  1.710
ASSI {3801}
((segid "PROT" and resid 22 and name HN))
((segid "PROT" and resid 19 and name HA))
  3.400  2.900  2.100 peak     3801  weight  0.10000E+01 volume  0.15388E+01 ppm1    8.849  ppm2  3.708
ASSI {3821}
((segid "PROT" and resid 22 and name HN))
(segid "PROT" and resid 21 and name HG2%)
  2.800  2.000  2.000 peak     3821  weight  0.10000E+01 volume  0.57390E+01 ppm1    8.853  ppm2  1.013
ASSI {3831}
((segid "PROT" and resid 25 and name HN))
((segid "PROT" and resid 23 and name HA))
  3.300  2.700  2.200 peak     3831  weight  0.10000E+01 volume  0.17967E+01 ppm1    8.565  ppm2  4.041
ASSI {3841}
((segid "PROT" and resid 25 and name HN))
((segid "PROT" and resid 24 and name HG1))
  3.300  2.700  2.200 peak     3841  weight  0.10000E+01 volume  0.18150E+01 ppm1    8.571  ppm2  2.864
ASSI {3861}
((segid "PROT" and resid 25 and name HN))
((segid "PROT" and resid 28 and name HN))
  3.400  2.900  2.100 peak     3861  weight  0.10000E+01 volume  0.15678E+01 ppm1    8.564  ppm2  7.564
ASSI {3871}
((segid "PROT" and resid 25 and name HN))
((segid "PROT" and resid 22 and name HA))
  3.200  2.600  2.300 peak     3871  weight  0.10000E+01 volume  0.24333E+01 ppm1    8.563  ppm2  4.150
ASSI {3881}
((segid "PROT" and resid 25 and name HN))
((segid "PROT" and resid 25 and name HA))
  2.900  2.100  2.100 peak     3881  weight  0.10000E+01 volume  0.44045E+01 ppm1    8.563  ppm2  3.836
ASSI {3891}
((segid "PROT" and resid 25 and name HN))
((segid "PROT" and resid 24 and name HB2))
  2.400  2.400  2.100 peak     3891  weight  0.10000E+01 volume  0.11850E+02 ppm1    8.565  ppm2  2.408
ASSI {3901}
((segid "PROT" and resid 25 and name HN))
((segid "PROT" and resid 25 and name HB))
  2.600  1.700  1.700 peak     3901  weight  0.10000E+01 volume  0.74683E+01 ppm1    8.565  ppm2  2.458
ASSI {3911}
((segid "PROT" and resid 25 and name HN))
(segid "PROT" and resid 25 and name HG1%)
  2.500  1.600  1.600 peak     3911  weight  0.10000E+01 volume  0.10519E+02 ppm1    8.564  ppm2  1.210

TABLE 13-continued

Unambiguous NOE Distance Restraints

ASSI {3921}
((segid "PROT" and resid 25 and name HN))
((segid "PROT" and resid 21 and name HG2%)
  2.800  2.000  2.000 peak    3921  weight  0.10000E+01 volume  0.56705E+01 ppm1    8.565  ppm2  1.036
ASSI {3941}
((segid "PROT" and resid 76 and name HN))
((segid "PROT" and resid 74 and name HN))
  3.300  2.700  2.200 peak    3941  weight  0.10000E+01 volume  0.18542E+01 ppm1    8.021  ppm2  6.919
ASSI {3951}
((segid "PROT" and resid 101 and name HN))
((segid "PROT" and resid 98 and name HA))
  2.800  2.000  2.000 peak    3951  weight  0.10000E+01 volume  0.56914E+01 ppm1    8.017  ppm2  4.218
ASSI {3961}
((segid "PROT" and resid 76 and name HN))
((segid "PROT" and resid 75 and name HA))
  2.500  1.600  1.600 peak    3961  weight  0.10000E+01 volume  0.10452E+02 ppm1    8.020  ppm2  4.091
ASSI {3971}
((segid "PROT" and resid 101 and name HN))
((segid "PROT" and resid 99 and name HA))
  3.100  2.400  2.400 peak    3971  weight  0.10000E+01 volume  0.27135E+01 ppm1    8.020  ppm2  3.936
ASSI {3981}
((segid "PROT" and resid 76 and name HN))
((segid "PROT" and resid 74 and name HA))
  3.500  3.100  2.000 peak    3981  weight  0.10000E+01 volume  0.14645E+01 ppm1    8.019  ppm2  3.766
ASSI {3991}
((segid "PROT" and resid 101 and name HN))
((segid "PROT" and resid 100 and name HB1))
  2.800  2.000  2.000 peak    3991  weight  0.10000E+01 volume  0.46606E+01 ppm1    8.016  ppm2  2.920
ASSI {4001}
((segid "PROT" and resid 101 and name HN))
((segid "PROT" and resid 100 and name HA))
  3.000  2.200  2.200 peak    4001  weight  0.10000E+01 volume  0.32888E+01 ppm1    8.015  ppm2  4.334
ASSI {4011}
((segid "PROT" and resid 76 and name HN))
((segid "PROT" and resid 75 and name HG1))
  2.900  2.100  2.100 peak    4011  weight  0.10000E+01 volume  0.42412E+01 ppm1    8.020  ppm2  2.320
ASSI {4031}
((segid "PROT" and resid 101 and name HN))
((segid "PROT" and resid 101 and name HA))
  2.800  2.000  2.000 peak    4031  weight  0.10000E+01 volume  0.55917E+01 ppm1    8.014  ppm2  3.673
ASSI {4041}
((segid "PROT" and resid 101 and name HN))
((segid "PROT" and resid 100 and name HB2))
  3.000  2.200  2.200 peak    4041  weight  0.10000E+01 volume  0.35319E+01 ppm1    8.015  ppm2  2.818
ASSI {4051}
((segid "PROT" and resid 101 and name HN))
((segid "PROT" and resid 101 and name HG11))
  2.400  1.400  1.400 peak    4051  weight  0.10000E+01 volume  0.13903E+02 ppm1    8.014  ppm2  1.901
ASSI {4061}
((segid "PROT" and resid 101 and name HN))
((segid "PROT" and resid 101 and name HG12))
  2.900  2.100  2.100 peak    4061  weight  0.10000E+01 volume  0.44776E+01 ppm1    8.014  ppm2  1.223
ASSI {4071}
((segid "PROT" and resid 101 and name HN))
(segid "PROT" and resid 101 and name HD1%)
  2.600  1.700  1.700 peak    4071  weight  0.10000E+01 volume  0.77589E+01 ppm1    8.014  ppm2  0.990
ASSI {4081}
((segid "PROT" and resid 96 and name HN))
(segid "PROT" and resid 96 and name HD%)
  3.200  2.600  2.300 peak    4081  weight  0.10000E+01 volume  0.23492E+01 ppm1    7.370  ppm2  7.132
ASSI {4101}
((segid "PROT" and resid 96 and name HN))
((segid "PROT" and resid 89 and name HB2))
  3.100  2.400  2.400 peak    4101  weight  0.10000E+01 volume  0.28581E+01 ppm1    7.368  ppm2  2.926
ASSI {4111}
((segid "PROT" and resid 96 and name HN))
((segid "PROT" and resid 96 and name HB2))
  2.800  2.000  2.000 peak    4111  weight  0.10000E+01 volume  0.54335E+01 ppm1    7.367  ppm2  2.566
ASSI {4131}
((segid "PROT" and resid 96 and name HN))
((segid "PROT" and resid 96 and name HA))
  2.900  2.100  2.100 peak    4131  weight  0.10000E+01 volume  0.38508E+01 ppm1    7.361  ppm2  3.798
ASSI {4141}
((segid "PROT" and resid 12 and name HN))
((segid "PROT" and resid 12 and name HA))
  2.500  1.600  1.600 peak    4141  weight  0.10000E+01 volume  0.10299E+02 ppm1    8.423  ppm2  4.706

TABLE 13-continued

Unambiguous NOE Distance Restraints

ASSI {4151}
((segid "PROT" and resid 12 and name HN))
((segid "PROT" and resid 11 and name HD1))
 2.900  2.100  2.100 peak     4151 weight  0.10000E+01 volume  0.44553E+01 ppm1    8.423 ppm2  3.878
ASSI {4161}
((segid "PROT" and resid 12 and name HN))
((segid "PROT" and resid 15 and name HB2))
 3.600  3.200  1.900 peak     4161 weight  0.10000E+01 volume  0.12071E+01 ppm1    8.424 ppm2  3.067
ASSI {4171}
((segid "PROT" and resid 12 and name HN))
((segid "PROT" and resid 12 and name HB2))
 2.500  1.600  1.600 peak     4171 weight  0.10000E+01 volume  0.10156E+02 ppm1    8.422 ppm2  2.762
ASSI {4181}
((segid "PROT" and resid 12 and name HN))
((segid "PROT" and resid 11 and name HB1))
 3.300  2.700  2.200 peak     4181 weight  0.10000E+01 volume  0.18905E+01 ppm1    8.423 ppm2  2.358
ASSI {4191}
((segid "PROT" and resid 12 and name HN))
((segid "PROT" and resid 13 and name HB1))
 3.300  2.700  2.200 peak     4191 weight  0.10000E+01 volume  0.19426E+01 ppm1    8.422 ppm2  2.160
ASSI {4201}
((segid "PROT" and resid 12 and name HN))
((segid "PROT" and resid 11 and name HB2))
 2.900  2.100  2.100 peak     4201 weight  0.10000E+01 volume  0.38127E+01 ppm1    8.424 ppm2  2.084
ASSI {4211}
((segid "PROT" and resid 12 and name HN))
((segid "PROT" and resid 13 and name HN))
 2.600  1.700  1.700 peak     4211 weight  0.10000E+01 volume  0.86085E+01 ppm1    8.421 ppm2  8.184
ASSI {4221}
((segid "PROT" and resid 12 and name HN))
((segid "PROT" and resid 10 and name HA))
 3.600  3.200  1.900 peak     4221 weight  0.10000E+01 volume  0.11464E+01 ppm1    8.420 ppm2  4.904
ASSI {4231}
((segid "PROT" and resid 12 and name HN))
((segid "PROT" and resid 11 and name HA))
 2.800  2.000  2.000 peak     4231 weight  0.10000E+01 volume  0.54533E+01 ppm1    8.421 ppm2  4.353
ASSI {4251}
((segid "PROT" and resid 76 and name HN))
((segid "PROT" and resid 75 and name HB2))
 3.400  2.900  2.100 peak     4251 weight  0.10000E+01 volume  0.17162E+01 ppm1    8.022 ppm2  2.617
ASSI {4261}
((segid "PROT" and resid 76 and name HN))
((segid "PROT" and resid 75 and name HG2))
 2.800  2.000  2.000 peak     4261 weight  0.10000E+01 volume  0.53106E+01 ppm1    8.020 ppm2  2.216
ASSI {4271}
((segid "PROT" and resid 76 and name HN))
(segid "PROT" and resid 76 and name HB%)
 2.200  1.200  1.200 peak     4271 weight  0.10000E+01 volume  0.22283E+02 ppm1    8.021 ppm2  1.511
ASSI {4291}
((segid "PROT" and resid 78 and name HN))
((segid "PROT" and resid 77 and name HA))
 2.700  1.800  1.800 peak     4291 weight  0.10000E+01 volume  0.65577E+01 ppm1    7.380 ppm2  4.367
ASSI {4301}
((segid "PROT" and resid 78 and name HN))
((segid "PROT" and resid 75 and name HA))
 2.900  2.100  2.100 peak     4301 weight  0.10000E+01 volume  0.39670E+01 ppm1    7.381 ppm2  4.089
ASSI {4311}
((segid "PROT" and resid 78 and name HN))
((segid "PROT" and resid 78 and name HA))
 2.800  2.000  2.000 peak     4311 weight  0.10000E+01 volume  0.53868E+01 ppm1    7.380 ppm2  3.389
ASSI {4321}
((segid "PROT" and resid 78 and name HN))
((segid "PROT" and resid 80 and name HB1))
 3.300  2.700  2.200 peak     4321 weight  0.10000E+01 volume  0.21033E+01 ppm1    7.381 ppm2  1.980
ASSI {4361}
((segid "PROT" and resid 96 and name HN))
((segid "PROT" and resid 94 and name HA))
 3.200  2.600  2.300 peak     4361 weight  0.10000E+01 volume  0.24482E+01 ppm1    7.375 ppm2  4.225
ASSI {4371}
((segid "PROT" and resid 78 and name HN))
((segid "PROT" and resid 77 and name HB1))
 2.500  1.600  1.600 peak     4371 weight  0.10000E+01 volume  0.10999E+02 ppm1    7.379 ppm2  2.729
ASSI {4381}
((segid "PROT" and resid 77 and name HN))
(segid "PROT" and resid 76 and name HB%)
 2.500  1.600  1.600 peak     4381 weight  0.10000E+01 volume  0.10974E+02 ppm1    7.379 ppm2  1.510

TABLE 13-continued

Unambiguous NOE Distance Restraints

ASSI {4401}
((segid "PROT" and resid 89 and name HD22))
((segid "PROT" and resid 89 and name HD21))
  3.000  2.200  2.200 peak    4401  weight  0.10000E+01 volume  0.32494E+01 ppm1    7.821  ppm2  8.354
ASSI {4411}
((segid "PROT" and resid 78 and name HN))
((segid "PROT" and resid 79 and name HN))
  2.600  1.700  1.700 peak    4411  weight  0.10000E+01 volume  0.77884E+01 ppm1    7.385  ppm2  8.099
ASSI {4421}
((segid "PROT" and resid 78 and name HN))
((segid "PROT" and resid 79 and name HB1))
  3.300  2.700  2.200 peak    4421  weight  0.10000E+01 volume  0.19297E+01 ppm1    7.385  ppm2  2.189
ASSI {4431}
((segid "PROT" and resid 78 and name HN))
(segid "PROT" and resid 59 and name HE%)
  2.700  1.800  1.800 peak    4431  weight  0.10000E+01 volume  0.62776E+01 ppm1    7.384  ppm2  1.280
ASSI {4441}
((segid "PROT" and resid 78 and name HN))
((segid "PROT" and resid 78 and name HB1))
  2.600  1.700  1.700 peak    4441  weight  0.10000E+01 volume  0.76075E+01 ppm1    7.385  ppm2  0.719
ASSI {4451}
((segid "PROT" and resid 78 and name HN))
((segid "PROT" and resid 78 and name HB2))
  2.600  1.700  1.700 peak    4451  weight  0.10000E+01 volume  0.90536E+01 ppm1    7.384  ppm2  0.446
ASSI {4461}
((segid "PROT" and resid 78 and name HN))
(segid "PROT" and resid 78 and name HD2%)
  3.300  2.700  2.200 peak    4461  weight  0.10000E+01 volume  0.20077E+01 ppm1    7.386  ppm2  0.169
ASSI {4471}
((segid "PROT" and resid 78 and name HN))
(segid "PROT" and resid 78 and name HD1%)
  3.200  2.600  2.300 peak    4471  weight  0.10000E+01 volume  0.22843E+01 ppm1    7.387  ppm2  0.070
ASSI {4491}
((segid "PROT" and resid 54 and name HN))
((segid "PROT" and resid 55 and name HN))
  2.900  2.100  2.100 peak    4491  weight  0.10000E+01 volume  0.44496E+01 ppm1    8.520  ppm2  7.416
ASSI {4501}
((segid "PROT" and resid 54 and name HN))
((segid "PROT" and resid 54 and name HA))
  3.200  2.600  2.300 peak    4501  weight  0.10000E+01 volume  0.24899E+01 ppm1    8.520  ppm2  4.962
ASSI {4521}
((segid "PROT" and resid 54 and name HN))
((segid "PROT" and resid 53 and name HB1))
  3.000  2.200  2.200 peak    4521  weight  0.10000E+01 volume  0.31395E+01 ppm1    8.520  ppm2  2.246
ASSI {4531}
((segid "PROT" and resid 54 and name HN))
((segid "PROT" and resid 54 and name HG2))
  3.300  2.700  2.200 peak    4531  weight  0.10000E+01 volume  0.17850E+01 ppm1    8.520  ppm2  1.915
ASSI {4541}
((segid "PROT" and resid 54 and name HN))
((segid "PROT" and resid 54 and name HB2))
  3.400  2.900  2.100 peak    4541  weight  0.10000E+01 volume  0.17029E+01 ppm1    8.526  ppm2  1.348
ASSI {4551}
((segid "PROT" and resid 54 and name HN))
(segid "PROT" and resid 50 and name HG2%)
  3.300  2.700  2.200 peak    4551  weight  0.10000E+01 volume  0.17768E+01 ppm1    8.520  ppm2  0.397
ASSI {4561}
((segid "PROT" and resid 54 and name HN))
((segid "PROT" and resid 53 and name HA))
  2.600  1.700  1.700 peak    4561  weight  0.10000E+01 volume  0.77293E+01 ppm1    8.518  ppm2  4.099
ASSI {4571}
((segid "PROT" and resid 54 and name HN))
((segid "PROT" and resid 80 and name HB2))
  3.300  2.700  2.200 peak    4571  weight  0.10000E+01 volume  0.19268E+01 ppm1    8.520  ppm2  1.983
ASSI {4581}
((segid "PROT" and resid 30 and name HN))
((segid "PROT" and resid 29 and name HN))
  3.000  2.200  2.200 peak    4581  weight  0.10000E+01 volume  0.31596E+01 ppm1   11.696  ppm2  8.578
ASSI {4591}
((segid "PROT" and resid 30 and name HN))
((segid "PROT" and resid 31 and name HN))
  2.700  1.800  1.800 peak    4591  weight  0.10000E+01 volume  0.65999E+01 ppm1   11.698  ppm2  7.913
ASSI {4601}
((segid "PROT" and resid 30 and name HN))
((segid "PROT" and resid 30 and name HA))
  3.000  2.200  2.200 peak    4601  weight  0.10000E+01 volume  0.34965E+01 ppm1   11.695  ppm2  4.829

TABLE 13-continued

Unambiguous NOE Distance Restraints

ASSI {4611}
((segid "PROT" and resid 30 and name HN))
((segid "PROT" and resid 30 and name HB1))
  3.100  2.400  2.400 peak    4611 weight  0.10000E+01 volume  0.28201E+01 ppm1    11.695 ppm2  4.332
ASSI {4621}
((segid "PROT" and resid 30 and name HN))
((segid "PROT" and resid 29 and name HA))
  3.200  2.600  2.300 peak    4621 weight  0.10000E+01 volume  0.22951E+01 ppm1    11.698 ppm2  4.226
ASSI {4631}
((segid "PROT" and resid 30 and name HN))
((segid "PROT" and resid 30 and name HB2))
  2.900  2.100  2.100 peak    4631 weight  0.10000E+01 volume  0.40640E+01 ppm1    11.695 ppm2  3.957
ASSI {4641}
((segid "PROT" and resid 30 and name HN))
((segid "PROT" and resid 29 and name HB1))
  3.100  2.400  2.400 peak    4641 weight  0.10000E+01 volume  0.30464E+01 ppm1    11.694 ppm2  2.126
ASSI {4651}
((segid "PROT" and resid 30 and name HN))
((segid "PROT" and resid 31 and name HB%))
  3.500  3.100  2.000 peak    4651 weight  0.10000E+01 volume  0.12947E+01 ppm1    11.693 ppm2  1.735
ASSI {4661}
((segid "PROT" and resid 30 and name HN))
(segid "PROT" and resid 101 and name HG2%)
  3.600  3.200  1.900 peak    4661 weight  0.10000E+01 volume  0.11385E+01 ppm1    11.694 ppm2  1.011
ASSI {4681}
((segid "PROT" and resid 30 and name HN))
((segid "PROT" and resid 28 and name HN))
  3.400  2.900  2.100 peak    4681 weight  0.10000E+01 volume  0.16627E+01 ppm1    11.691 ppm2  7.563
ASSI {4701}
((segid "PROT" and resid 15 and name HN))
((segid "PROT" and resid 14 and name HN))
  2.400  1.400  1.400 peak    4701 weight  0.10000E+01 volume  0.11587E+02 ppm1    7.994 ppm2  8.197
ASSI {4711}
((segid "PROT" and resid 15 and name HN))
(segid "PROT" and resid 15 and name HD%)
  3.400  2.900  2.100 peak    4711 weight  0.10000E+01 volume  0.16091E+01 ppm1    7.996 ppm2  7.070
ASSI {4721}
((segid "PROT" and resid 15 and name HN))
((segid "PROT" and resid 15 and name HA))
  2.600  1.700  1.700 peak    4721 weight  0.10000E+01 volume  0.74337E+01 ppm1    7.995 ppm2  4.026
ASSI {4741}
((segid "PROT" and resid 15 and name HN))
((segid "PROT" and resid 15 and name HB1))
  2.600  1.700  1.700 peak    4741 weight  0.10000E+01 volume  0.86825E+01 ppm1    7.994 ppm2  3.218
ASSI {4751}
((segid "PROT" and resid 15 and name HN))
((segid "PROT" and resid 15 and name HB2))
  2.600  1.700  1.700 peak    4751 weight  0.10000E+01 volume  0.82436E+01 ppm1    7.993 ppm2  3.047
ASSI {4761}
((segid "PROT" and resid 15 and name HN))
((segid "PROT" and resid 14 and name HB1))
  2.900  2.100  2.100 peak    4761 weight  0.10000E+01 volume  0.43406E+01 ppm1    7.994 ppm2  1.858
ASSI {4771}
((segid "PROT" and resid 15 and name HN))
((segid "PROT" and resid 14 and name HB2))
  3.000  2.200  2.200 peak    4771 weight  0.10000E+01 volume  0.36582E+01 ppm1    7.997 ppm2  1.572
ASSI {4781}
((segid "PROT" and resid 15 and name HN))
((segid "PROT" and resid 14 and name HG))
  3.300  2.700  2.200 peak    4781 weight  0.10000E+01 volume  0.20741E+01 ppm1    7.996 ppm2  1.467
ASSI {4791}
((segid "PROT" and resid 15 and name HN))
(segid "PROT" and resid 14 and name HD2%)
  3.100  2.400  2.400 peak    4791 weight  0.10000E+01 volume  0.29619E+01 ppm1    7.992 ppm2  0.817
ASSI {4801}
((segid "PROT" and resid 15 and name HN))
((segid "PROT" and resid 12 and name HA))
  3.000  2.200  2.200 peak    4801 weight  0.10000E+01 volume  0.37120E+01 ppm1    7.990 ppm2  4.731
ASSI {4821}
((segid "PROT" and resid 55 and name HN))
((segid "PROT" and resid 54 and name HA))
  2.500  1.600  1.600 peak    4821 weight  0.10000E+01 volume  0.10125E+02 ppm1    7.380 ppm2  4.956
ASSI {4831}
((segid "PROT" and resid 55 and name HN))
((segid "PROT" and resid 55 and name HA))
  2.600  1.700  1.700 peak    4831 weight  0.10000E+01 volume  0.84076E+01 ppm1    7.383 ppm2  4.742

TABLE 13-continued

| Unambiguous NOE Distance Restraints |
| --- |

ASSI {4841}
((segid "PROT" and resid 55 and name HN))
((segid "PROT" and resid 54 and name HG1))
  3.100  2.400  2.400 peak    4841  weight  0.10000E+01 volume  0.27028E+01 ppm1    7.382  ppm2  2.706
ASSI {4851}
((segid "PROT" and resid 55 and name HN))
((segid "PROT" and resid 59 and name HG2))
  3.600  3.200  1.900 peak    4851  weight  0.10000E+01 volume  0.12119E+01 ppm1    7.386  ppm2  2.546
ASSI {4861}
((segid "PROT" and resid 55 and name HN))
((segid "PROT" and resid 54 and name HB2))
  3.500  3.100  2.000 peak    4861  weight  0.10000E+01 volume  0.14758E+01 ppm1    7.385  ppm2  1.352
ASSI {4871}
((segid "PROT" and resid 55 and name HN))
(segid "PROT" and resid 58 and name HG2%)
  3.200  2.600  2.300 peak    4871  weight  0.10000E+01 volume  0.24734E+01 ppm1    7.381  ppm2  1.072
ASSI {4881}
((segid "PROT" and resid 55 and name HN))
(segid "PROT" and resid 81 and name HG1%)
  3.100  2.400  2.400 peak    4881  weight  0.10000E+01 volume  0.28394E+01 ppm1    7.383  ppm2  0.476
ASSI {4891}
((segid "PROT" and resid 55 and name HN))
((segid "PROT" and resid 55 and name HB1))
  3.200  2.600  2.300 peak    4891  weight  0.10000E+01 volume  0.22382E+01 ppm1    7.378  ppm2  2.376
ASSI {4901}
((segid "PROT" and resid 24 and name HN))
((segid "PROT" and resid 27 and name HN))
  3.500  3.100  2.000 peak    4901  weight  0.10000E+01 volume  0.12574E+01 ppm1    8.045  ppm2  7.569
ASSI {4921}
((segid "PROT" and resid 74 and name HN))
(segid "PROT" and resid 18 and name HD2%)
  3.500  3.100  2.000 peak    4921  weight  0.10000E+01 volume  0.12668E+01 ppm1    6.927  ppm2  −0.183
ASSI {4931}
((segid "PROT" and resid 74 and name HN))
(segid "PROT" and resid 73 and name HD2%)
  3.500  3.100  2.000 peak    4931  weight  0.10000E+01 volume  0.14113E+01 ppm1    6.917  ppm2  0.943
ASSI {4941}
((segid "PROT" and resid 19 and name HN))
(segid "PROT" and resid 18 and name HD2%)
  3.500  3.100  2.000 peak    4941  weight  0.10000E+01 volume  0.12909E+01 ppm1    8.569  ppm2  −0.181
ASSI {4951}
((segid "PROT" and resid 24 and name HN))
(segid "PROT" and resid 25 and name HG1%)
  3.500  3.100  2.000 peak    4951  weight  0.10000E+01 volume  0.14575E+01 ppm1    8.048  ppm2  1.208
ASSI {4961}
((segid "PROT" and resid 24 and name HN))
((segid "PROT" and resid 25 and name HN))
  2.300  1.300  1.300 peak    4961  weight  0.10000E+01 volume  0.15441E+02 ppm1    8.046  ppm2  8.568
ASSI {4971}
((segid "PROT" and resid 24 and name HN))
((segid "PROT" and resid 24 and name HE21))
  3.600  3.200  1.900 peak    4971  weight  0.10000E+01 volume  0.12268E+01 ppm1    8.044  ppm2  7.031
ASSI {4981}
((segid "PROT" and resid 24 and name HN))
((segid "PROT" and resid 24 and name HA))
  2.800  2.000  2.000 peak    4981  weight  0.10000E+01 volume  0.51016E+01 ppm1    8.045  ppm2  4.194
ASSI {5001}
((segid "PROT" and resid 24 and name HN))
((segid "PROT" and resid 21 and name HA))
  3.200  2.600  2.300 peak    5001  weight  0.10000E+01 volume  0.23114E+01 ppm1    8.046  ppm2  3.782
ASSI {5011}
((segid "PROT" and resid 24 and name HN))
((segid "PROT" and resid 24 and name HG1))
  2.600  1.700  1.700 peak    5011  weight  0.10000E+01 volume  0.77445E+01 ppm1    8.045  ppm2  2.866
ASSI {5021}
((segid "PROT" and resid 24 and name HN))
((segid "PROT" and resid 24 and name HB1))
  2.400  1.400  1.400 peak    5021  weight  0.10000E+01 volume  0.13011E+02 ppm1    8.045  ppm2  2.480
ASSI {5031}
((segid "PROT" and resid 24 and name HN))
((segid "PROT" and resid 24 and name HB2))
  2.600  1.700  1.700 peak    5031  weight  0.10000E+01 volume  0.77725E+01 ppm1    8.045  ppm2  2.386
ASSI {5041}
((segid "PROT" and resid 24 and name HN))
((segid "PROT" and resid 23 and name HB2))
  2.900  2.100  2.100 peak    5041  weight  0.10000E+01 volume  0.45542E+01 ppm1    8.045  ppm2  2.241

TABLE 13-continued

Unambiguous NOE Distance Restraints

ASSI {5051}
((segid "PROT" and resid 24 and name HN))
((segid "PROT" and resid 22 and name HB1))
  3.500  3.100   2.000 peak      5051  weight  0.10000E+01 volume  0.12517E+01 ppm1     8.044  ppm2  2.103
ASSI {5061}
((segid "PROT" and resid 24 and name HN))
(segid "PROT" and resid 25 and name HG2%)
  3.500  3.100   2.000 peak      5061  weight  0.10000E+01 volume  0.14572E+01 ppm1     8.043  ppm2  1.018
ASSI {5081}
((segid "PROT" and resid 73 and name HN))
((segid "PROT" and resid 75 and name HN))
  3.500  3.100   2.000 peak      5081  weight  0.10000E+01 volume  0.12647E+01 ppm1     7.444  ppm2  8.505
ASSI {5101}
((segid "PROT" and resid 73 and name HN))
((segid "PROT" and resid 74 and name HN))
  2.600  1.700   1.700 peak      5101  weight  0.10000E+01 volume  0.80031E+01 ppm1     7.442  ppm2  6.928
ASSI {5111}
((segid "PROT" and resid 73 and name HN))
((segid "PROT" and resid 70 and name HB1))
  2.700  1.800   1.800 peak      5111  weight  0.10000E+01 volume  0.70510E+01 ppm1     7.440  ppm2  4.231
ASSI {5121}
((segid "PROT" and resid 73 and name HN))
(segid "PROT" and resid 73 and name HD2%)
  3.000  2.200   2.200 peak      5121  weight  0.10000E+01 volume  0.34221E+01 ppm1     7.444  ppm2  0.928
ASSI {5131}
((segid "PROT" and resid 73 and name HN))
((segid "PROT" and resid 73 and name HG))
  2.500  1.600   1.600 peak      5131  weight  0.10000E+01 volume  0.99511E+01 ppm1     7.434  ppm2  1.777
ASSI {5141}
((segid "PROT" and resid 80 and name HN))
((segid "PROT" and resid 80 and name HB2))
  2.400  1.400   1.400 peak      5141  weight  0.10000E+01 volume  0.14158E+02 ppm1     7.422  ppm2  1.988
ASSI {5161}
((segid "PROT" and resid 80 and name HN))
(segid "PROT" and resid 76 and name HB%)
  3.200  2.600   2.300 peak      5161  weight  0.10000E+01 volume  0.21895E+01 ppm1     7.427  ppm2  1.508
ASSI {5181}
((segid "PROT" and resid 80 and name HN))
((segid "PROT" and resid 81 and name HN))
  2.600  1.700   1.700 peak      5181  weight  0.10000E+01 volume  0.75351E+01 ppm1     7.416  ppm2  7.031
ASSI {5191}
((segid "PROT" and resid 80 and name HN))
((segid "PROT" and resid 80 and name HA))
  2.600  1.700   1.700 peak      5191  weight  0.10000E+01 volume  0.74789E+01 ppm1     7.417  ppm2  4.072
ASSI {5201}
((segid "PROT" and resid 80 and name HN))
((segid "PROT" and resid 79 and name HA))
  3.200  2.600   2.300 peak      5201  weight  0.10000E+01 volume  0.22928E+01 ppm1     7.419  ppm2  3.815
ASSI {5211}
((segid "PROT" and resid 80 and name HN))
((segid "PROT" and resid 78 and name HA))
  3.500  3.100   2.000 peak      5211  weight  0.10000E+01 volume  0.12621E+01 ppm1     7.416  ppm2  3.386
ASSI {5221}
((segid "PROT" and resid 80 and name HN))
((segid "PROT" and resid 79 and name HB1))
  2.900  2.100   2.100 peak      5221  weight  0.10000E+01 volume  0.39082E+01 ppm1     7.416  ppm2  2.187
ASSI {5231}
((segid "PROT" and resid 80 and name HN))
((segid "PROT" and resid 79 and name HG1))
  3.300  2.700   2.200 peak      5231  weight  0.10000E+01 volume  0.18927E+01 ppm1     7.413  ppm2  2.441
ASSI {5251}
((segid "PROT" and resid 74 and name HN))
((segid "PROT" and resid 70 and name HB1))
  3.300  2.700   2.200 peak      5251  weight  0.10000E+01 volume  0.20701E+01 ppm1     6.926  ppm2  4.229
ASSI {5261}
((segid "PROT" and resid 74 and name HN))
((segid "PROT" and resid 75 and name HN))
  2.700  1.800   1.800 peak      5261  weight  0.10000E+01 volume  0.70119E+01 ppm1     6.922  ppm2  8.499
ASSI {5281}
((segid "PROT" and resid 24 and name HE22))
((segid "PROT" and resid 109 and name HA))
  3.100  2.400   2.400 peak      5281  weight  0.10000E+01 volume  0.27313E+01 ppm1     6.921  ppm2  4.037
ASSI {5291}
((segid "PROT" and resid 74 and name HN))
((segid "PROT" and resid 74 and name HA))
  3.000  2.200   2.200 peak      5291  weight  0.10000E+01 volume  0.37588E+01 ppm1     6.920  ppm2  3.782

TABLE 13-continued

| Unambiguous NOE Distance Restraints |
|---|

ASSI {5301}
((segid "PROT" and resid 74 and name HN))
((segid "PROT" and resid 74 and name HB1))
  2.700  1.800  1.800 peak     5301 weight  0.10000E+01 volume  0.68724E+01 ppm1  6.922 ppm2  2.958
ASSI {5311}
((segid "PROT" and resid 74 and name HN))
((segid "PROT" and resid 74 and name HB2))
  2.800  2.000  2.000 peak     5311 weight  0.10000E+01 volume  0.49112E+01 ppm1  6.923 ppm2  2.394
ASSI {5321}
((segid "PROT" and resid 74 and name HN))
((segid "PROT" and resid 73 and name HB1))
  3.100  2.400  2.400 peak     5321 weight  0.10000E+01 volume  0.30104E+01 ppm1  6.924 ppm2  1.999
ASSI {5331}
((segid "PROT" and resid 74 and name HN))
((segid "PROT" and resid 73 and name HB2))
  3.000  2.200  2.200 peak     5331 weight  0.10000E+01 volume  0.34844E+01 ppm1  6.921 ppm2  1.893
ASSI {5341}
((segid "PROT" and resid 74 and name HN))
((segid "PROT" and resid 73 and name HG))
  3.400  2.900  2.100 peak     5341 weight  0.10000E+01 volume  0.17239E+01 ppm1  6.921 ppm2  1.778
ASSI {5351}
((segid "PROT" and resid 74 and name HN))
(segid "PROT" and resid 18 and name HD1%)
  3.500  3.100  2.000 peak     5351 weight  0.10000E+01 volume  0.12974E+01 ppm1  6.921 ppm2  0.480
ASSI {5361}
((segid "PROT" and resid 24 and name HE22))
((segid "PROT" and resid 24 and name HN))
  3.600  3.200  1.900 peak     5361 weight  0.10000E+01 volume  0.11576E+01 ppm1  6.910 ppm2  8.026
ASSI {5381}
((segid "PROT" and resid 19 and name HN))
(segid "PROT" and resid 17 and name HG2%)
  3.400  2.900  2.100 peak     5381 weight  0.10000E+01 volume  0.15290E+01 ppm1  8.578 ppm2  1.151
ASSI {5391}
((segid "PROT" and resid 19 and name HN))
(segid "PROT" and resid 18 and name HD1%)
  3.500  3.100  2.000 peak     5391 weight  0.10000E+01 volume  0.14602E+01 ppm1  8.576 ppm2  0.482
ASSI {5421}
((segid "PROT" and resid 19 and name HN))
((segid "PROT" and resid 15 and name HA))
  3.200  2.600  2.300 peak     5421 weight  0.10000E+01 volume  0.24616E+01 ppm1  8.574 ppm2  4.029
ASSI {5431}
((segid "PROT" and resid 19 and name HN))
((segid "PROT" and resid 17 and name HA))
  3.000  2.200  2.200 peak     5431 weight  0.10000E+01 volume  0.32388E+01 ppm1  8.573 ppm2  3.928
ASSI {5441}
((segid "PROT" and resid 19 and name HN))
((segid "PROT" and resid 19 and name HA))
  2.800  2.000  2.000 peak     5441 weight  0.10000E+01 volume  0.54958E+01 ppm1  8.574 ppm2  3.693
ASSI {5451}
((segid "PROT" and resid 19 and name HN))
((segid "PROT" and resid 18 and name HA))
  3.300  2.700  2.200 peak     5451 weight  0.10000E+01 volume  0.18487E+01 ppm1  8.571 ppm2  3.290
ASSI {5461}
((segid "PROT" and resid 19 and name HN))
((segid "PROT" and resid 19 and name HB1))
  2.600  1.700  1.700 peak     5461 weight  0.10000E+01 volume  0.87577E+01 ppm1  8.574 ppm2  1.703
ASSI {5471}
((segid "PROT" and resid 19 and name HN))
((segid "PROT" and resid 18 and name HB1))
  2.900  2.100  2.100 peak     5471 weight  0.10000E+01 volume  0.39883E+01 ppm1  8.575 ppm2  1.531
ASSI {5481}
((segid "PROT" and resid 19 and name HN))
((segid "PROT" and resid 19 and name HB2))
  2.600  1.700  1.700 peak     5481 weight  0.10000E+01 volume  0.78056E+01 ppm1  8.574 ppm2  1.378
ASSI {5491}
((segid "PROT" and resid 19 and name HN))
((segid "PROT" and resid 19 and name HG1))
  2.800  2.000  2.000 peak     5491 weight  0.10000E+01 volume  0.49710E+01 ppm1  8.575 ppm2  1.282
ASSI {5501}
((segid "PROT" and resid 19 and name HN))
(segid "PROT" and resid 63 and name HD2%)
  3.100  2.400  2.400 peak     5501 weight  0.10000E+01 volume  0.27977E+01 ppm1  8.573 ppm2  1.044
ASSI {5511}
((segid "PROT" and resid 19 and name HN))
(segid "PROT" and resid 63 and name HD1%)
  3.000  2.200  2.200 peak     5511 weight  0.10000E+01 volume  0.32125E+01 ppm1  8.573 ppm2  0.891

TABLE 13-continued

| Unambiguous NOE Distance Restraints |
|---|

ASSI {5521}
((segid "PROT" and resid 19 and name HN))
((segid "PROT" and resid 18 and name HB2))
  3.200  2.600  2.300 peak     5521 weight  0.10000E+01 volume  0.25168E+01 ppm1        8.574 ppm2    0.321
ASSI {5531}
((segid "PROT" and resid 19 and name HN))
((segid "PROT" and resid 17 and name HB))
  3.400  2.900  2.100 peak     5531 weight  0.10000E+01 volume  0.15384E+01 ppm1        8.566 ppm2    4.264
ASSI {5541}
((segid "PROT" and resid 80 and name HN))
((segid "PROT" and resid 77 and name HA))
  3.300  2.700  2.200 peak     5541 weight  0.10000E+01 volume  0.19122E+01 ppm1        7.416 ppm2    4.370
ASSI {5551}
((segid "PROT" and resid 42 and name HN))
((segid "PROT" and resid 39 and name HB2))
  3.000  2.200  2.200 peak     5551 weight  0.10000E+01 volume  0.31705E+01 ppm1        7.210 ppm2    1.919
ASSI {5561}
((segid "PROT" and resid 42 and name HN))
((segid "PROT" and resid 42 and name HA))
  2.800  2.000  2.000 peak     5561 weight  0.10000E+01 volume  0.47858E+01 ppm1        7.204 ppm2    4.477
ASSI {5571}
((segid "PROT" and resid 42 and name HN))
((segid "PROT" and resid 41 and name HB))
  3.400  2.900  2.100 peak     5571 weight  0.10000E+01 volume  0.16358E+01 ppm1        7.202 ppm2    4.338
ASSI {5581}
((segid "PROT" and resid 42 and name HN))
((segid "PROT" and resid 41 and name HA))
  3.100  2.400  2.400 peak     5581 weight  0.10000E+01 volume  0.25691E+01 ppm1        7.204 ppm2    4.074
ASSI {5591}
((segid "PROT" and resid 42 and name HN))
((segid "PROT" and resid 42 and name HG2))
  3.000  2.200  2.200 peak     5591 weight  0.10000E+01 volume  0.35712E+01 ppm1        7.204 ppm2    2.268
ASSI {5601}
((segid "PROT" and resid 42 and name HN))
((segid "PROT" and resid 42 and name HB1))
  2.900  2.100  2.100 peak     5601 weight  0.10000E+01 volume  0.42597E+01 ppm1        7.207 ppm2    2.194
ASSI {5611}
((segid "PROT" and resid 42 and name HN))
((segid "PROT" and resid 42 and name HB2))
  2.800  2.000  2.000 peak     5611 weight  0.10000E+01 volume  0.53742E+01 ppm1        7.207 ppm2    2.046
ASSI {5621}
((segid "PROT" and resid 42 and name HN))
((segid "PROT" and resid 42 and name HG1))
  3.200  2.600  2.300 peak     5621 weight  0.10000E+01 volume  0.24540E+01 ppm1        7.206 ppm2    2.334
ASSI {5631}
((segid "PROT" and resid 42 and name HN))
((segid "PROT" and resid 39 and name HD2))
  3.100  2.400  2.400 peak     5631 weight  0.10000E+01 volume  0.30124E+01 ppm1        7.204 ppm2    1.650
ASSI {5641}
((segid "PROT" and resid 42 and name HN))
((segid "PROT" and resid 39 and name HG2))
  3.500  3.100  2.000 peak     5641 weight  0.10000E+01 volume  0.12606E+01 ppm1        7.205 ppm2    1.455
ASSI {5651}
((segid "PROT" and resid 42 and name HN))
(segid "PROT" and resid 38 and name HG2%)
  3.600  3.200  1.900 peak     5651 weight  0.10000E+01 volume  0.11209E+01 ppm1        7.202 ppm2  −0.032
ASSI {5661}
((segid "PROT" and resid 42 and name HN))
(segid "PROT" and resid 43 and name HB%)
  3.500  3.100  2.000 peak     5661 weight  0.10000E+01 volume  0.14702E+01 ppm1        7.203 ppm2    0.963
ASSI {5671}
((segid "PROT" and resid 107 and name HN))
(segid "PROT" and resid 107 and name HD%)
  3.400  2.900  2.100 peak     5671 weight  0.10000E+01 volume  0.17606E+01 ppm1        8.406 ppm2    7.197
ASSI {5691}
((segid "PROT" and resid 107 and name HN))
((segid "PROT" and resid 110 and name HN))
  3.500  3.100  2.000 peak     5691 weight  0.10000E+01 volume  0.13382E+01 ppm1        8.401 ppm2    8.129
ASSI {5731}
((segid "PROT" and resid 107 and name HN))
(segid "PROT" and resid 106 and name HD%)
  3.500  3.100  2.000 peak     5731 weight  0.10000E+01 volume  0.14164E+01 ppm1        8.405 ppm2    6.913
ASSI {5741}
((segid "PROT" and resid 107 and name HN))
((segid "PROT" and resid 106 and name HA))
  3.000  2.200  2.200 peak     5741 weight  0.10000E+01 volume  0.33201E+01 ppm1        8.401 ppm2    3.973

TABLE 13-continued

Unambiguous NOE Distance Restraints

ASSI {5751}
((segid "PROT" and resid 107 and name HN))
((segid "PROT" and resid 107 and name HA))
  2.700  1.800  1.800 peak    5751 weight  0.10000E+01 volume  0.58816E+01 ppm1    8.402 ppm2  3.841
ASSI {5761}
((segid "PROT" and resid 107 and name HN))
((segid "PROT" and resid 106 and name HB1))
  2.900  2.100  2.100 peak    5761 weight  0.10000E+01 volume  0.42118E+01 ppm1    8.403 ppm2  3.311
ASSI {5771}
((segid "PROT" and resid 107 and name HN))
((segid "PROT" and resid 107 and name HB1))
  2.300  1.300  1.300 peak    5771 weight  0.10000E+01 volume  0.18413E+02 ppm1    8.402 ppm2  3.073
ASSI {5781}
((segid "PROT" and resid 87 and name HN))
(segid "PROT" and resid 50 and name HD1%)
  3.400  2.900  2.100 peak    5781 weight  0.10000E+01 volume  0.15742E+01 ppm1    7.951 ppm2  0.557
ASSI {5791}
((segid "PROT" and resid 87 and name HN))
((segid "PROT" and resid 86 and name HG1))
  3.300  2.700  2.200 peak    5791 weight  0.10000E+01 volume  0.18417E+01 ppm1    7.948 ppm2  1.313
ASSI {5801}
((segid "PROT" and resid 107 and name HN))
((segid "PROT" and resid 104 and name HA))
  3.100  2.400  2.400 peak    5801 weight  0.10000E+01 volume  0.30498E+01 ppm1    8.404 ppm2  4.086
ASSI {5811}
((segid "PROT" and resid 107 and name HN))
((segid "PROT" and resid 104 and name HB1))
  3.500  3.100  2.000 peak    5811 weight  0.10000E+01 volume  0.12855E+01 ppm1    8.404 ppm2  1.940
ASSI {5821}
((segid "PROT" and resid 107 and name HN))
((segid "PROT" and resid 110 and name HG11))
  3.600  3.200  1.900 peak    5821 weight  0.10000E+01 volume  0.11312E+01 ppm1    8.402 ppm2  1.128
ASSI {5831}
((segid "PROT" and resid 87 and name HN))
((segid "PROT" and resid 89 and name HN))
  3.300  2.700  2.200 peak    5831 weight  0.10000E+01 volume  0.20634E+01 ppm1    7.950 ppm2  8.119
ASSI {5841}
((segid "PROT" and resid 87 and name HN))
((segid "PROT" and resid 85 and name HN))
  3.600  3.200  1.900 peak    5841 weight  0.10000E+01 volume  0.11971E+01 ppm1    7.950 ppm2  6.901
ASSI {5851}
((segid "PROT" and resid 87 and name HN))
((segid "PROT" and resid 84 and name HB1))
  3.300  2.700  2.200 peak    5851 weight  0.10000E+01 volume  0.19660E+01 ppm1    7.955 ppm2  3.000
ASSI {5861}
((segid "PROT" and resid 87 and name HN))
((segid "PROT" and resid 87 and name HG1))
  2.800  2.000  2.000 peak    5861 weight  0.10000E+01 volume  0.48232E+01 ppm1    7.950 ppm2  2.414
ASSI {5871}
((segid "PROT" and resid 87 and name HN))
((segid "PROT" and resid 87 and name HB1))
  2.400  1.400  1.400 peak    5871 weight  0.10000E+01 volume  0.11647E+02 ppm1    7.951 ppm2  2.203
ASSI {5881}
((segid "PROT" and resid 87 and name HN))
((segid "PROT" and resid 86 and name HN))
  2.500  1.600  1.600 peak    5881 weight  0.10000E+01 volume  0.98805E+01 ppm1    7.949 ppm2  7.840
ASSI {5891}
((segid "PROT" and resid 87 and name HN))
((segid "PROT" and resid 87 and name HA))
  2.500  1.600  1.600 peak    5891 weight  0.10000E+01 volume  0.97274E+01 ppm1    7.949 ppm2  4.312
ASSI {5901}
((segid "PROT" and resid 87 and name HN))
((segid "PROT" and resid 88 and name HB2))
  3.400  2.900  2.100 peak    5901 weight  0.10000E+01 volume  0.15195E+01 ppm1    7.948 ppm2  2.915
ASSI {5911}
((segid "PROT" and resid 115 and name HN))
((segid "PROT" and resid 114 and name HA1))
  2.400  1.400  1.400 peak    5911 weight  0.10000E+01 volume  0.11986E+02 ppm1    7.733 ppm2  4.230
ASSI {5921}
((segid "PROT" and resid 48 and name HN))
((segid "PROT" and resid 48 and name HA))
  2.700  1.800  1.800 peak    5921 weight  0.10000E+01 volume  0.62082E+01 ppm1    7.731 ppm2  4.097
ASSI {5931}
((segid "PROT" and resid 48 and name HN))
((segid "PROT" and resid 47 and name HN))
  2.700  1.800  1.800 peak    5931 weight  0.10000E+01 volume  0.67305E+01 ppm1    7.724 ppm2  8.464

TABLE 13-continued

Unambiguous NOE Distance Restraints

ASSI {5951}
((segid "PROT" and resid 48 and name HN))
((segid "PROT" and resid 50 and name HN))
  2.800  2.000    2.000 peak      5951  weight  0.10000E+01 volume  0.54418E+01 ppm1      7.729  ppm2  7.953
ASSI {5961}
((segid "PROT" and resid 48 and name HN))
((segid "PROT" and resid 49 and name HN))
  2.300  1.300    1.300 peak      5961  weight  0.10000E+01 volume  0.15564E+02 ppm1      7.724  ppm2  7.117
ASSI {5971}
((segid "PROT" and resid 48 and name HN))
((segid "PROT" and resid 47 and name HB2))
  3.300  2.700    2.200 peak      5971  weight  0.10000E+01 volume  0.18444E+01 ppm1      7.723  ppm2  2.802
ASSI {5981}
((segid "PROT" and resid 48 and name HN))
((segid "PROT" and resid 48 and name HG1))
  2.900  2.100    2.100 peak      5981  weight  0.10000E+01 volume  0.41807E+01 ppm1      7.725  ppm2  2.352
ASSI {5991}
((segid "PROT" and resid 48 and name HN))
((segid "PROT" and resid 48 and name HG2))
  2.700  1.800    1.800 peak      5991  weight  0.10000E+01 volume  0.59443E+01 ppm1      7.724  ppm2  2.247
ASSI {6001}
((segid "PROT" and resid 48 and name HN))
((segid "PROT" and resid 48 and name HB2))
  2.500  1.600    1.600 peak      6001  weight  0.10000E+01 volume  0.10445E+02 ppm1      7.726  ppm2  2.112
ASSI {6011}
((segid "PROT" and resid 48 and name HN))
((segid "PROT" and resid 49 and name HB))
  3.300  2.700    2.200 peak      6011  weight  0.10000E+01 volume  0.19824E+01 ppm1      7.728  ppm2  1.928
ASSI {6021}
((segid "PROT" and resid 115 and name HN))
((segid "PROT" and resid 116 and name HG12))
  3.100  2.400    2.400 peak      6021  weight  0.10000E+01 volume  0.27995E+01 ppm1      7.728  ppm2  0.938
ASSI {6031}
((segid "PROT" and resid 48 and name HN))
((segid "PROT" and resid 47 and name HB1))
  3.600  3.200    1.900 peak      6031  weight  0.10000E+01 volume  0.11030E+01 ppm1      7.722  ppm2  3.212
ASSI {6041}
((segid "PROT" and resid 97 and name HN))
((segid "PROT" and resid 98 and name HN))
  2.800  2.000    2.000 peak      6041  weight  0.10000E+01 volume  0.49406E+01 ppm1      7.962  ppm2  8.467
ASSI {6051}
((segid "PROT" and resid 97 and name HN))
((segid "PROT" and resid 96 and name HN))
  2.800  2.000    2.000 peak      6051  weight  0.10000E+01 volume  0.50772E+01 ppm1      7.963  ppm2  7.365
ASSI {6061}
((segid "PROT" and resid 97 and name HN))
((segid "PROT" and resid 97 and name HA))
  2.600  1.700    1.700 peak      6061  weight  0.10000E+01 volume  0.83858E+01 ppm1      7.961  ppm2  4.212
ASSI {6071}
((segid "PROT" and resid 97 and name HN))
((segid "PROT" and resid 96 and name HA))
  3.400  2.900    2.100 peak      6071  weight  0.10000E+01 volume  0.16577E+01 ppm1      7.963  ppm2  3.810
ASSI {6081}
((segid "PROT" and resid 97 and name HN))
((segid "PROT" and resid 96 and name HB1))
  3.000  2.200    2.200 peak      6081  weight  0.10000E+01 volume  0.33617E+01 ppm1      7.962  ppm2  3.393
ASSI {6091}
((segid "PROT" and resid 97 and name HN))
((segid "PROT" and resid 96 and name HB2))
  3.100  2.400    2.400 peak      6091  weight  0.10000E+01 volume  0.27139E+01 ppm1      7.965  ppm2  2.563
ASSI {6101}
((segid "PROT" and resid 97 and name HN))
((segid "PROT" and resid 97 and name HB1))
  2.400  1.400    1.400 peak      6101  weight  0.10000E+01 volume  0.11569E+02 ppm1      7.962  ppm2  2.090
ASSI {6111}
((segid "PROT" and resid 97 and name HN))
((segid "PROT" and resid 97 and name HG1))
  2.600  1.700    1.700 peak      6111  weight  0.10000E+01 volume  0.78350E+01 ppm1      7.962  ppm2  1.819
ASSI {6121}
((segid "PROT" and resid 97 and name HN))
((segid "PROT" and resid 97 and name HG2))
  3.000  2.200    2.200 peak      6121  weight  0.10000E+01 volume  0.33860E+01 ppm1      7.962  ppm2  1.602
ASSI {6151}
((segid "PROT" and resid 59 and name HN))
((segid "PROT" and resid 55 and name HN))
  3.300  2.700    2.200 peak      6151  weight  0.10000E+01 volume  0.20861E+01 ppm1      7.884  ppm2  7.380

TABLE 13-continued

Unambiguous NOE Distance Restraints

ASSI {6161}
((segid "PROT" and resid 59 and name HN))
((segid "PROT" and resid 55 and name HA))
 2.800  2.000  2.000 peak      6161 weight 0.10000E+01 volume 0.54472E+01 ppm1  7.888 ppm2 4.740
ASSI {6171}
((segid "PROT" and resid 59 and name HN))
((segid "PROT" and resid 59 and name HA))
 2.900  2.100  2.100 peak      6171 weight 0.10000E+01 volume 0.43029E+01 ppm1  7.888 ppm2 4.300
ASSI {6181}
((segid "PROT" and resid 59 and name HN))
((segid "PROT" and resid 58 and name HA))
 3.300  2.700  2.200 peak      6181 weight 0.10000E+01 volume 0.20113E+01 ppm1  7.887 ppm2 3.855
ASSI {6191}
((segid "PROT" and resid 59 and name HN))
((segid "PROT" and resid 59 and name HG1))
 3.000  2.200  2.200 peak      6191 weight 0.10000E+01 volume 0.31885E+01 ppm1  7.887 ppm2 2.640
ASSI {6201}
((segid "PROT" and resid 59 and name HN))
((segid "PROT" and resid 59 and name HG2))
 2.900  2.100  2.100 peak      6201 weight 0.10000E+01 volume 0.41094E+01 ppm1  7.887 ppm2 2.523
ASSI {6211}
((segid "PROT" and resid 59 and name HN))
((segid "PROT" and resid 55 and name HB1))
 3.300  2.700  2.200 peak      6211 weight 0.10000E+01 volume 0.21032E+01 ppm1  7.887 ppm2 2.409
ASSI {6221}
((segid "PROT" and resid 59 and name HN))
((segid "PROT" and resid 59 and name HB1))
 2.800  2.000  2.000 peak      6221 weight 0.10000E+01 volume 0.46693E+01 ppm1  7.887 ppm2 2.117
ASSI {6231}
((segid "PROT" and resid 59 and name HN))
((segid "PROT" and resid 59 and name HB2))
 2.900  2.100  2.100 peak      6231 weight 0.10000E+01 volume 0.43295E+01 ppm1  7.887 ppm2 1.894
ASSI {6241}
((segid "PROT" and resid 59 and name HN))
(segid "PROT" and resid 59 and name HE%)
 3.200  2.600  2.300 peak      6241 weight 0.10000E+01 volume 0.21931E+01 ppm1  7.890 ppm2 1.281
ASSI {6251}
((segid "PROT" and resid 59 and name HN))
(segid "PROT" and resid 58 and name HG2%)
 2.900  2.100  2.100 peak      6251 weight 0.10000E+01 volume 0.39266E+01 ppm1  7.886 ppm2 1.073
ASSI {6261}
((segid "PROT" and resid 59 and name HN))
(segid "PROT" and resid 56 and name HD2%)
 3.500  3.100  2.000 peak      6261 weight 0.10000E+01 volume 0.13248E+01 ppm1  7.891 ppm2 0.647
ASSI {6281}
((segid "PROT" and resid 59 and name HN))
((segid "PROT" and resid 56 and name HA))
 2.900  2.100  2.100 peak      6281 weight 0.10000E+01 volume 0.46129E+01 ppm1  7.887 ppm2 4.067
ASSI {6311}
((segid "PROT" and resid 115 and name HN))
((segid "PROT" and resid 110 and name HB))
 3.100  2.400  2.400 peak      6311 weight 0.10000E+01 volume 0.26218E+01 ppm1  7.753 ppm2 1.767
ASSI {6321}
((segid "PROT" and resid 115 and name HN))
((segid "PROT" and resid 115 and name HG))
 2.300  1.300  1.300 peak      6321 weight 0.10000E+01 volume 0.16690E+02 ppm1  7.747 ppm2 1.572
ASSI {6331}
((segid "PROT" and resid 115 and name HN))
(segid "PROT" and resid 113 and name HB%)
 2.900  2.100  2.100 peak      6331 weight 0.10000E+01 volume 0.44807E+01 ppm1  7.747 ppm2 1.387
ASSI {6341}
((segid "PROT" and resid 115 and name HN))
((segid "PROT" and resid 116 and name HN))
 2.400  1.400  1.400 peak      6341 weight 0.10000E+01 volume 0.12116E+02 ppm1  7.746 ppm2 7.473
ASSI {6351}
((segid "PROT" and resid 115 and name HN))
((segid "PROT" and resid 110 and name HA))
 3.200  2.600  2.300 peak      6351 weight 0.10000E+01 volume 0.23760E+01 ppm1  7.744 ppm2 3.835
ASSI {6361}
((segid "PROT" and resid 115 and name HN))
(segid "PROT" and resid 110 and name HG2%)
 2.800  2.000  2.000 peak      6361 weight 0.10000E+01 volume 0.49594E+01 ppm1  7.750 ppm2 0.733
ASSI {6371}
((segid "PROT" and resid 113 and name HN))
((segid "PROT" and resid 114 and name HN))
 2.300  1.300  1.300 peak      6371 weight 0.10000E+01 volume 0.18295E+02 ppm1  7.628 ppm2 7.752

TABLE 13-continued

Unambiguous NOE Distance Restraints

ASSI {6381}
((segid "PROT" and resid 113 and name HN))
((segid "PROT" and resid 114 and name HA1))
 3.200 2.600 2.300 peak     6381 weight 0.10000E+01 volume 0.22373E+01 ppm1 7.626 ppm2 4.224
ASSI {6391}
((segid "PROT" and resid 113 and name HN))
((segid "PROT" and resid 110 and name HA))
 3.000 2.200 2.200 peak     6391 weight 0.10000E+01 volume 0.31767E+01 ppm1 7.627 ppm2 3.841
ASSI {6401}
((segid "PROT" and resid 113 and name HN))
((segid "PROT" and resid 112 and name HG2))
 3.300 2.700 2.200 peak     6401 weight 0.10000E+01 volume 0.19652E+01 ppm1 7.629 ppm2 2.228
ASSI {6411}
((segid "PROT" and resid 113 and name HN))
((segid "PROT" and resid 109 and name HB1))
 3.400 2.900 2.100 peak     6411 weight 0.10000E+01 volume 0.16895E+01 ppm1 7.627 ppm2 1.755
ASSI {6421}
((segid "PROT" and resid 113 and name HN))
((segid "PROT" and resid 109 and name HB2))
 3.100 2.400 2.400 peak     6421 weight 0.10000E+01 volume 0.29609E+01 ppm1 7.630 ppm2 1.554
ASSI {6441}
((segid "PROT" and resid 113 and name HN))
(segid "PROT" and resid 110 and name HG2%)
 3.600 3.200 1.900 peak     6441 weight 0.10000E+01 volume 0.12178E+01 ppm1 7.626 ppm2 0.742
ASSI {6451}
((segid "PROT" and resid 113 and name HN))
(segid "PROT" and resid 21 and name HD1%)
 3.400 2.900 2.100 peak     6451 weight 0.10000E+01 volume 0.16502E+01 ppm1 7.627 ppm2 0.640
ASSI {6471}
((segid "PROT" and resid 113 and name HN))
((segid "PROT" and resid 113 and name HA))
 2.600 1.700 1.700 peak     6471 weight 0.10000E+01 volume 0.87618E+01 ppm1 7.624 ppm2 4.315
ASSI {6481}
((segid "PROT" and resid 113 and name HN))
((segid "PROT" and resid 112 and name HA))
 2.800 2.000 2.000 peak     6481 weight 0.10000E+01 volume 0.55195E+01 ppm1 7.624 ppm2 3.999
ASSI {6491}
((segid "PROT" and resid 113 and name HN))
((segid "PROT" and resid 112 and name HG1))
 3.400 2.900 2.100 peak     6491 weight 0.10000E+01 volume 0.16104E+01 ppm1 7.622 ppm2 2.363
ASSI {6501}
((segid "PROT" and resid 113 and name HN))
((segid "PROT" and resid 112 and name HB1))
 2.500 1.600 1.600 peak     6501 weight 0.10000E+01 volume 0.92492E+01 ppm1 7.623 ppm2 2.082
ASSI {6511}
((segid "PROT" and resid 113 and name HN))
((segid "PROT" and resid 111 and name HB1))
 3.500 3.100 2.000 peak     6511 weight 0.10000E+01 volume 0.13800E+01 ppm1 7.621 ppm2 1.871
ASSI {6521}
((segid "PROT" and resid 113 and name HN))
(segid "PROT" and resid 113 and name HB%)
 2.200 1.200 1.200 peak     6521 weight 0.10000E+01 volume 0.21421E+02 ppm1 7.624 ppm2 1.386
ASSI {6541}
((segid "PROT" and resid 81 and name HN))
((segid "PROT" and resid 77 and name HA))
 3.600 3.200 1.900 peak     6541 weight 0.10000E+01 volume 0.11964E+01 ppm1 7.019 ppm2 4.358
ASSI {6561}
((segid "PROT" and resid 104 and name HN))
((segid "PROT" and resid 103 and name HN))
 2.700 1.800 1.800 peak     6561 weight 0.10000E+01 volume 0.71341E+01 ppm1 7.178 ppm2 8.061
ASSI {6581}
((segid "PROT" and resid 104 and name HN))
((segid "PROT" and resid 104 and name HA))
 2.600 1.700 1.700 peak     6581 weight 0.10000E+01 volume 0.74430E+01 ppm1 7.180 ppm2 4.089
ASSI {6591}
((segid "PROT" and resid 104 and name HN))
((segid "PROT" and resid 101 and name HA))
 3.200 2.600 2.300 peak     6591 weight 0.10000E+01 volume 0.22040E+01 ppm1 7.180 ppm2 3.679
ASSI {6601}
((segid "PROT" and resid 104 and name HN))
((segid "PROT" and resid 103 and name HA))
 3.200 2.600 2.300 peak     6601 weight 0.10000E+01 volume 0.25243E+01 ppm1 7.178 ppm2 3.191
ASSI {6611}
((segid "PROT" and resid 104 and name HN))
((segid "PROT" and resid 105 and name HB2))
 3.300 2.700 2.200 peak     6611 weight 0.10000E+01 volume 0.18405E+01 ppm1 7.178 ppm2 3.075

TABLE 13-continued

Unambiguous NOE Distance Restraints

ASSI {6621}
((segid "PROT" and resid 104 and name HN))
((segid "PROT" and resid 104 and name HB1))
 2.300  1.300   1.300 peak       6621  weight  0.10000E+01 volume  0.17956E+02 ppm1    7.180  ppm2  1.952
ASSI {6631}
((segid "PROT" and resid 104 and name HN))
((segid "PROT" and resid 104 and name HD1))
 2.600  2.600   1.900 peak       6631  weight  0.10000E+01 volume  0.72669E+01 ppm1    7.181  ppm2  1.714
ASSI {6641}
((segid "PROT" and resid 104 and name HN))
((segid "PROT" and resid 103 and name HB2))
 3.200  2.600   2.300 peak       6641  weight  0.10000E+01 volume  0.25289E+01 ppm1    7.178  ppm2  1.307
ASSI {6661}
((segid "PROT" and resid 104 and name HN))
((segid "PROT" and resid 104 and name HG1))
 3.100  2.400   2.400 peak       6661  weight  0.10000E+01 volume  0.29965E+01 ppm1    7.176  ppm2  1.534
ASSI {6671}
((segid "PROT" and resid 35 and name HN))
((segid "PROT" and resid 34 and name HA))
 3.300  2.700   2.200 peak       6671  weight  0.10000E+01 volume  0.19137E+01 ppm1    7.152  ppm2  4.989
ASSI {6681}
((segid "PROT" and resid 35 and name HN))
((segid "PROT" and resid 36 and name HN))
 2.500  1.600   1.600 peak       6681  weight  0.10000E+01 volume  0.92061E+01 ppm1    7.150  ppm2  7.689
ASSI {6701}
((segid "PROT" and resid 35 and name HN))
((segid "PROT" and resid 35 and name HA))
 2.800  2.000   2.000 peak       6701  weight  0.10000E+01 volume  0.55220E+01 ppm1    7.152  ppm2  4.315
ASSI {6711}
((segid "PROT" and resid 35 and name HN))
((segid "PROT" and resid 35 and name HG1))
 2.500  1.600   1.600 peak       6711  weight  0.10000E+01 volume  0.10122E+02 ppm1    7.152  ppm2  2.867
ASSI {6721}
((segid "PROT" and resid 35 and name HN))
((segid "PROT" and resid 35 and name HB2))
 2.500  1.600   1.600 peak       6721  weight  0.10000E+01 volume  0.10214E+02 ppm1    7.152  ppm2  2.210
ASSI {6741}
((segid "PROT" and resid 81 and name HN))
((segid "PROT" and resid 83 and name HN))
 3.600  3.200   1.900 peak       6741  weight  0.10000E+01 volume  0.11953E+01 ppm1    7.033  ppm2  9.095
ASSI {6751}
((segid "PROT" and resid 81 and name HN))
((segid "PROT" and resid 82 and name HN))
 2.700  1.800   1.800 peak       6751  weight  0.10000E+01 volume  0.62507E+01 ppm1    7.031  ppm2  6.404
ASSI {6761}
((segid "PROT" and resid 81 and name HN))
((segid "PROT" and resid 81 and name HA))
 2.900  2.100   2.100 peak       6761  weight  0.10000E+01 volume  0.43231E+01 ppm1    7.032  ppm2  3.104
ASSI {6771}
((segid "PROT" and resid 81 and name HN))
((segid "PROT" and resid 82 and name HB2))
 3.500  3.100   2.000 peak       6771  weight  0.10000E+01 volume  0.12809E+01 ppm1    7.033  ppm2  3.003
ASSI {6791}
((segid "PROT" and resid 81 and name HN))
((segid "PROT" and resid 79 and name HB1))
 3.300  2.700   2.200 peak       6791  weight  0.10000E+01 volume  0.18620E+01 ppm1    7.035  ppm2  2.189
ASSI {6801}
((segid "PROT" and resid 81 and name HN))
((segid "PROT" and resid 80 and name HB2))
 2.900  2.100   2.100 peak       6801  weight  0.10000E+01 volume  0.45127E+01 ppm1    7.035  ppm2  1.944
ASSI {6811}
((segid "PROT" and resid 81 and name HN))
((segid "PROT" and resid 80 and name HG1))
 3.200  2.600   2.300 peak       6811  weight  0.10000E+01 volume  0.22692E+01 ppm1    7.034  ppm2  1.764
ASSI {6831}
((segid "PROT" and resid 81 and name HN))
(segid "PROT" and resid 81 and name HG2%)
 3.000  2.200   2.200 peak       6831  weight  0.10000E+01 volume  0.37030E+01 ppm1    7.031  ppm2  0.139
ASSI {6851}
((segid "PROT" and resid 81 and name HN))
((segid "PROT" and resid 80 and name HA))
 3.200  2.600   2.300 peak       6851  weight  0.10000E+01 volume  0.23560E+01 ppm1    7.029  ppm2  4.088
ASSI {6861}
((segid "PROT" and resid 81 and name HN))
((segid "PROT" and resid 78 and name HA))
 3.200  2.600   2.300 peak       6861  weight  0.10000E+01 volume  0.23796E+01 ppm1    7.029  ppm2  3.387

TABLE 13-continued

Unambiguous NOE Distance Restraints

ASSI {6871}
((segid "PROT" and resid 81 and name HN))
((segid "PROT" and resid 81 and name HB))
  2.600  1.700    1.700 peak      6871  weight  0.10000E+01 volume  0.77216E+01 ppm1      7.029  ppm2  1.435
ASSI {6881}
((segid "PROT" and resid 81 and name HN))
(segid "PROT" and resid 81 and name HG1%)
  2.500  1.600    1.600 peak      6881  weight  0.10000E+01 volume  0.10928E+02 ppm1      7.029  ppm2  0.480
ASSI {6891}
((segid "PROT" and resid 85 and name HN))
(segid "PROT" and resid 82 and name HN))
  3.600  3.200    1.900 peak      6891  weight  0.10000E+01 volume  0.12246E+01 ppm1      6.918  ppm2  6.392
ASSI {6911}
((segid "PROT" and resid 85 and name HN))
(segid "PROT" and resid 81 and name HG1%)
  3.300  2.700    2.200 peak      6911  weight  0.10000E+01 volume  0.20441E+01 ppm1      6.915  ppm2  0.485
ASSI {6931}
((segid "PROT" and resid 31 and name HN))
((segid "PROT" and resid 102 and name HG))
  3.100  2.400    2.400 peak      6931  weight  0.10000E+01 volume  0.26707E+01 ppm1      7.914  ppm2  1.638
ASSI {6941}
((segid "PROT" and resid 31 and name HN))
((segid "PROT" and resid 28 and name HN))
  3.400  2.900    2.100 peak      6941  weight  0.10000E+01 volume  0.17063E+01 ppm1      7.913  ppm2  7.563
ASSI {6951}
((segid "PROT" and resid 31 and name HN))
((segid "PROT" and resid 32 and name HN))
  2.500  1.600    1.600 peak      6951  weight  0.10000E+01 volume  0.96419E+01 ppm1      7.913  ppm2  7.103
ASSI {6961}
((segid "PROT" and resid 31 and name HN))
((segid "PROT" and resid 30 and name HA))
  3.100  2.400    2.400 peak      6961  weight  0.10000E+01 volume  0.29200E+01 ppm1      7.913  ppm2  4.830
ASSI {6981}
((segid "PROT" and resid 31 and name HN))
((segid "PROT" and resid 28 and name HB1))
  3.200  2.600    2.300 peak      6981  weight  0.10000E+01 volume  0.25210E+01 ppm1      7.913  ppm2  2.999
ASSI {6991}
((segid "PROT" and resid 31 and name HN))
((segid "PROT" and resid 28 and name HB2))
  3.500  3.100    2.000 peak      6991  weight  0.10000E+01 volume  0.12877E+01 ppm1      7.913  ppm2  2.801
ASSI {7001}
((segid "PROT" and resid 31 and name HN))
(segid "PROT" and resid 31 and name HB%)
  2.200  1.200    1.200 peak      7001  weight  0.10000E+01 volume  0.19840E+02 ppm1      7.913  ppm2  1.734
ASSI {7011}
((segid "PROT" and resid 31 and name HN))
(segid "PROT" and resid 102 and name HD1%)
  2.900  2.100    2.100 peak      7011  weight  0.10000E+01 volume  0.43175E+01 ppm1      7.912  ppm2  0.733
ASSI {7041}
((segid "PROT" and resid 85 and name HN))
((segid "PROT" and resid 88 and name HN))
  3.600  3.200    1.900 peak      7041  weight  0.10000E+01 volume  0.11543E+01 ppm1      6.911  ppm2  7.948
ASSI {7051}
((segid "PROT" and resid 85 and name HN))
((segid "PROT" and resid 85 and name HA))
  3.100  2.400    2.400 peak      7051  weight  0.10000E+01 volume  0.29023E+01 ppm1      6.912  ppm2  4.476
ASSI {7061}
((segid "PROT" and resid 85 and name HN))
((segid "PROT" and resid 82 and name HA))
  3.200  2.600    2.300 peak      7061  weight  0.10000E+01 volume  0.23120E+01 ppm1      6.909  ppm2  4.198
ASSI {7071}
((segid "PROT" and resid 85 and name HN))
((segid "PROT" and resid 85 and name HB1))
  2.900  2.100    2.100 peak      7071  weight  0.10000E+01 volume  0.44281E+01 ppm1      6.909  ppm2  3.391
ASSI {7081}
((segid "PROT" and resid 85 and name HN))
((segid "PROT" and resid 85 and name HB2))
  2.700  1.800    1.800 peak      7081  weight  0.10000E+01 volume  0.60371E+01 ppm1      6.909  ppm2  3.075
ASSI {7101}
((segid "PROT" and resid 85 and name HN))
((segid "PROT" and resid 86 and name HN))
  2.800  2.000    2.000 peak      7101  weight  0.10000E+01 volume  0.52021E+01 ppm1      6.907  ppm2  7.827
ASSI {7111}
((segid "PROT" and resid 85 and name HN))
((segid "PROT" and resid 84 and name HA))
  3.300  2.700    2.200 peak      7111  weight  0.10000E+01 volume  0.20680E+01 ppm1      6.905  ppm2  4.314

TABLE 13-continued

Unambiguous NOE Distance Restraints

ASSI {7121}
((segid "PROT" and resid 85 and name HN))
((segid "PROT" and resid 84 and name HB2))
  3.400  2.900  2.100 peak       7121 weight  0.10000E+01 volume    0.15050E+01 ppm1      6.907  ppm2  2.701
ASSI {7141}
((segid "PROT" and resid 23 and name HN))
((segid "PROT" and resid 22 and name HN))
  2.600  1.700  1.700 peak       7141 weight  0.10000E+01 volume    0.76228E+01 ppm1      8.580  ppm2  8.853
ASSI {7151}
((segid "PROT" and resid 23 and name HN))
((segid "PROT" and resid 24 and name HN))
  2.600  1.700  1.700 peak       7151 weight  0.10000E+01 volume    0.82564E+01 ppm1      8.582  ppm2  8.045
ASSI {7161}
((segid "PROT" and resid 23 and name HN))
((segid "PROT" and resid 20 and name HN))
  3.500  3.100  2.000 peak       7161 weight  0.10000E+01 volume    0.13939E+1 ppm1       8.582  ppm2  7.547
ASSI {7171}
((segid "PROT" and resid 23 and name HN))
((segid "PROT" and resid 20 and name HA))
  3.100  2.400  2.400 peak       7171 weight  0.10000E+01 volume    0.28370E+01 ppm1      8.582  ppm2  4.304
ASSI {7181}
((segid "PROT" and resid 23 and name HN))
((segid "PROT" and resid 23 and name HA))
  2.600  1.700  1.700 peak       7181 weight  0.10000E+01 volume    0.82765E+01 ppm1      8.580  ppm2  4.040
ASSI {7201}
((segid "PROT" and resid 23 and name HN))
((segid "PROT" and resid 19 and name HA))
  3.400  2.900  2.100 peak       7201 weight  0.10000E+01 volume    0.15541E+01 ppm1      8.583  ppm2  3.698
ASSI {7211}
((segid "PROT" and resid 23 and name HN))
((segid "PROT" and resid 24 and name HG1))
  3.500  3.100  2.000 peak       7211 weight  0.10000E+01 volume    0.13521E+01 ppm1      8.578  ppm2  2.858
ASSI {7221}
((segid "PROT" and resid 23 and name HN))
((segid "PROT" and resid 23 and name HG1))
  2.800  2.000  2.000 peak       7221 weight  0.10000E+01 volume    0.52073E+01 ppm1      8.578  ppm2  2.576
ASSI {7231}
((segid "PROT" and resid 23 and name HN))
((segid "PROT" and resid 23 and name HG2))
  2.700  1.800  1.800 peak       7231 weight  0.10000E+01 volume    0.61263E+01 ppm1      8.580  ppm2  2.460
ASSI {7241}
((segid "PROT" and resid 23 and name HN))
((segid "PROT" and resid 23 and name HB1))
  2.400  1.400  1.400 peak       7241 weight  0.10000E+01 volume    0.12017E+02 ppm1      8.581  ppm2  2.344
ASSI {7251}
((segid "PROT" and resid 23 and name HN))
((segid "PROT" and resid 23 and name HB2))
  2.500  1.600  1.600 peak       7251 weight  0.10000E+01 volume    0.97676E+01 ppm1      8.580  ppm2  2.235
ASSI {7261}
((segid "PROT" and resid 23 and name HN))
((segid "PROT" and resid 22 and name HB1))
  2.800  2.000  2.000 peak       7261 weight  0.10000E+01 volume    0.52458E+01 ppm1      8.580  ppm2  2.102
ASSI {7271}
((segid "PROT" and resid 23 and name HN))
((segid "PROT" and resid 22 and name HB2))
  3.000  2.200  2.200 peak       7271 weight  0.10000E+01 volume    0.34592E+01 ppm1      8.579  ppm2  1.709
ASSI {7281}
((segid "PROT" and resid 23 and name HN))
(segid "PROT" and resid 25 and name HG2%)
  3.300  2.700  2.200 peak       7281 weight  0.10000E+01 volume    0.20526E+01 ppm1      8.581  ppm2  1.028
ASSI {7291}
((segid "PROT" and resid 23 and name HN))
((segid "PROT" and resid 21 and name HN))
  3.400  2.900  2.100 peak       7291 weight  0.10000E+01 volume    0.17095E+01 ppm1      8.575  ppm2  7.927
ASSI {7301}
((segid "PROT" and resid 23 and name HN))
((segid "PROT" and resid 21 and name HB))
  3.300  2.700  2.200 peak       7301 weight  0.10000E+01 volume    0.18595E+01 ppm1      8.576  ppm2  1.934
ASSI {7311}
((segid "PROT" and resid 110 and name HN))
((segid "PROT" and resid 109 and name HN))
  2.600  1.700  1.700 peak       7311 weight  0.10000E+01 volume    0.81388E+01 ppm1      8.123  ppm2  7.965
ASSI {7321}
((segid "PROT" and resid 110 and name HN))
((segid "PROT" and resid 111 and name HN))
  2.600  1.700  1.700 peak       7321 weight  0.10000E+01 volume    0.90365E+01 ppm1      8.124  ppm2  7.568

TABLE 13-continued

| Unambiguous NOE Distance Restraints |
|---|

ASSI {7331}
((segid "PROT" and resid 110 and name HN))
((segid "PROT" and resid 109 and name HA))
  3.100  2.400  2.400 peak      7331 weight  0.10000E+01 volume  0.27003E+01 ppm1      8.123  ppm2  4.051
ASSI {7341}
((segid "PROT" and resid 110 and name HN))
((segid "PROT" and resid 107 and name HA))
  2.600  1.700  1.700 peak      7341 weight  0.10000E+01 volume  0.82467E+01 ppm1      8.123  ppm2  3.835
ASSI {7351}
((segid "PROT" and resid 110 and name HN))
((segid "PROT" and resid 109 and name HB1))
  2.600  1.700  1.700 peak      7351 weight  0.10000E+01 volume  0.83498E+01 ppm1      8.124  ppm2  1.760
ASSI {7361}
((segid "PROT" and resid 110 and name HN))
((segid "PROT" and resid 109 and name HB2))
  3.100  2.400  2.400 peak      7361 weight  0.10000E+01 volume  0.30691E+01 ppm1      8.123  ppm2  1.556
ASSI {7371}
((segid "PROT" and resid 110 and name HN))
((segid "PROT" and resid 110 and name HG12))
  2.600  1.700  1.700 peak      7371 weight  0.10000E+01 volume  0.78805E+01 ppm1      8.124  ppm2  1.117
ASSI {7381}
((segid "PROT" and resid 110 and name HN))
(segid "PROT" and resid 115 and name HD2%)
  3.200  2.600  2.300 peak      7381 weight  0.10000E+01 volume  0.22974E+01 ppm1      8.124  ppm2  0.800
ASSI {7391}
((segid "PROT" and resid 110 and name HN))
(segid "PROT" and resid 110 and name HG2%)
  2.600  1.700  1.700 peak      7391 weight  0.10000E+01 volume  0.85494E+01 ppm1      8.123  ppm2  0.665
ASSI {7401}
((segid "PROT" and resid 110 and name HN))
(segid "PROT" and resid 110 and name HD1%)
  3.000  2.200  2.200 peak      7401 weight  0.10000E+01 volume  0.37184E+01 ppm1      8.124  ppm2  0.546
ASSI {7411}
((segid "PROT" and resid 110 and name HN))
((segid "PROT" and resid 106 and name HA))
  3.200  2.600  2.300 peak      7411 weight  0.10000E+01 volume  0.24296E+01 ppm1      8.123  ppm2  3.977
ASSI {7421}
((segid "PROT" and resid 110 and name HN))
((segid "PROT" and resid 109 and name HD1))
  3.200  2.600  2.300 peak      7421 weight  0.10000E+01 volume  0.21558E+01 ppm1      8.119  ppm2  1.390
ASSI {7461}
((segid "PROT" and resid 86 and name HN))
((segid "PROT" and resid 86 and name HA))
  2.900  2.100  2.100 peak      7461 weight  0.10000E+01 volume  0.39371E+01 ppm1      7.829  ppm2  4.228
ASSI {7471}
((segid "PROT" and resid 86 and name HN))
((segid "PROT" and resid 83 and name HA))
  3.100  2.400  2.400 peak      7471 weight  0.10000E+01 volume  0.26907E+01 ppm1      7.830  ppm2  3.863
ASSI {7481}
((segid "PROT" and resid 86 and name HN))
((segid "PROT" and resid 85 and name HB2))
  3.100  2.400  2.400 peak      7481 weight  0.10000E+01 volume  0.28548E+01 ppm1      7.831  ppm2  3.076
ASSI {7491}
((segid "PROT" and resid 86 and name HN))
((segid "PROT" and resid 86 and name HG1))
  2.700  1.800  1.800 peak      7491 weight  0.10000E+01 volume  0.63400E+01 ppm1      7.828  ppm2  1.315
ASSI {7501}
((segid "PROT" and resid 86 and name HN))
((segid "PROT" and resid 86 and name HG2))
  3.100  2.400  2.400 peak      7501 weight  0.10000E+01 volume  0.29455E+01 ppm1      7.832  ppm2  0.144
ASSI {7511}
((segid "PROT" and resid 86 and name HN))
((segid "PROT" and resid 85 and name HB1))
  3.400  2.900  2.100 peak      7511 weight  0.10000E+01 volume  0.16551E+01 ppm1      7.827  ppm2  3.392
ASSI {7521}
((segid "PROT" and resid 86 and name HN))
((segid "PROT" and resid 86 and name HB1))
  2.800  2.000  2.000 peak      7521 weight  0.10000E+01 volume  0.57275E+01 ppm1      7.827  ppm2  1.752
ASSI {7531}
((segid "PROT" and resid 86 and name HN))
(segid "PROT" and resid 99 and name HB%)
  3.100  2.400  2.400 peak      7531 weight  0.10000E+01 volume  0.29669E+01 ppm1      7.826  ppm2  1.647
ASSI {7541}
((segid "PROT" and resid 82 and name HN))
((segid "PROT" and resid 80 and name HN))
  3.400  2.900  2.100 peak      7541 weight  0.10000E+01 volume  0.15786E+01 ppm1      6.404  ppm2  7.412

TABLE 13-continued

Unambiguous NOE Distance Restraints

ASSI {7551}
((segid "PROT" and resid 82 and name HN))
((segid "PROT" and resid 82 and name HB2))
  2.900  2.100  2.100 peak      7551  weight  0.10000E+01 volume  0.41049E+01 ppm1    6.399  ppm2  2.982
ASSI {7571}
((segid "PROT" and resid 82 and name HN))
(segid "PROT" and resid 99 and name HB%)
  3.600  3.200  1.900 peak      7571  weight  0.10000E+01 volume  0.11485E+01 ppm1    6.394  ppm2  1.629
ASSI {7581}
((segid "PROT" and resid 82 and name HN))
((segid "PROT" and resid 79 and name HA))
  3.100  2.400  2.400 peak      7581  weight  0.10000E+01 volume  0.26091E+01 ppm1    6.405  ppm2  3.834
ASSI {7591}
((segid "PROT" and resid 82 and name HN))
((segid "PROT" and resid 83 and name HN))
  2.700  1.800  1.800 peak      7591  weight  0.10000E+01 volume  0.67167E+01 ppm1    6.398  ppm2  9.087
ASSI {7611}
((segid "PROT" and resid 82 and name HN))
((segid "PROT" and resid 82 and name HA))
  3.000  2.200  2.200 peak      7611  weight  0.10000E+01 volume  0.35557E+01 ppm1    6.402  ppm2  4.182
ASSI {7621}
((segid "PROT" and resid 82 and name HN))
((segid "PROT" and resid 81 and name HA))
  2.900  2.100  2.100 peak      7621  weight  0.10000E+01 volume  0.42652E+01 ppm1    6.401  ppm2  3.098
ASSI {7661}
((segid "PROT" and resid 82 and name HN))
((segid "PROT" and resid 81 and name HB))
  2.700  1.800  1.800 peak      7661  weight  0.10000E+01 volume  0.65677E+01 ppm1    6.398  ppm2  1.437
ASSI {7681}
((segid "PROT" and resid 82 and name HN))
(segid "PROT" and resid 81 and name HG1%)
  3.100  2.400  2.400 peak      7681  weight  0.10000E+01 volume  0.28381E+01 ppm1    6.396  ppm2  0.485
ASSI {7691}
((segid "PROT" and resid 82 and name HN))
(segid "PROT" and resid 81 and name HG2%)
  3.000  2.200  2.200 peak      7691  weight  0.10000E+01 volume  0.35300E+01 ppm1    6.401  ppm2  0.132
ASSI {7701}
((segid "PROT" and resid 67 and name HN))
((segid "PROT" and resid 62 and name HA))
  3.600  3.200  1.900 peak      7701  weight  0.10000E+01 volume  0.10882E+01 ppm1    8.249  ppm2  3.932
ASSI {7711}
((segid "PROT" and resid 67 and name HN))
((segid "PROT" and resid 68 and name HN))
  2.600  1.700  1.700 peak      7711  weight  0.10000E+01 volume  0.79629E+01 ppm1    8.244  ppm2  8.011
ASSI {7721}
((segid "PROT" and resid 67 and name HN))
((segid "PROT" and resid 63 and name HA))
  3.100  2.400  2.400 peak      7721  weight  0.10000E+01 volume  0.28926E+01 ppm1    8.243  ppm2  4.736
ASSI {7731}
((segid "PROT" and resid 67 and name HN))
((segid "PROT" and resid 66 and name HA))
  2.900  2.100  2.100 peak      7731  weight  0.10000E+01 volume  0.40872E+01 ppm1    8.243  ppm2  4.413
ASSI {7741}
((segid "PROT" and resid 67 and name HN))
((segid "PROT" and resid 67 and name HA))
  2.800  2.000  2.000 peak      7741  weight  0.10000E+01 volume  0.48819E+01 ppm1    8.243  ppm2  4.080
ASSI {7751}
((segid "PROT" and resid 67 and name HN))
((segid "PROT" and resid 67 and name HB1))
  2.600  1.700  1.700 peak      7751  weight  0.10000E+01 volume  0.73162E+01 ppm1    8.244  ppm2  2.976
ASSI {7761}
((segid "PROT" and resid 67 and name HN))
((segid "PROT" and resid 65 and name HB2))
  3.300  2.700  2.200 peak      7761  weight  0.10000E+01 volume  0.19397E+01 ppm1    8.244  ppm2  2.777
ASSI {7771}
((segid "PROT" and resid 67 and name HN))
((segid "PROT" and resid 67 and name HB2))
  2.600  1.700  1.700 peak      7771  weight  0.10000E+01 volume  0.79008E+01 ppm1    8.244  ppm2  2.065
ASSI {7781}
((segid "PROT" and resid 67 and name HN))
((segid "PROT" and resid 62 and name HB2))
  3.400  2.900  2.100 peak      7781  weight  0.10000E+01 volume  0.17159E+01 ppm1    8.245  ppm2  1.104
ASSI {7791}
((segid "PROT" and resid 67 and name HN))
(segid "PROT" and resid 69 and name HG1%)
  3.600  3.200  1.900 peak      7791  weight  0.10000E+01 volume  0.11159E+01 ppm1    8.245  ppm2  0.985

TABLE 13-continued

Unambiguous NOE Distance Restraints

ASSI {7831}
((segid "PROT" and resid 98 and name HN))
((segid "PROT" and resid 99 and name HN))
 2.700  1.800  1.800 peak      7831 weight  0.10000E+01 volume  0.67297E+01 ppm1    8.468 ppm2  8.193
ASSI {7861}
((segid "PROT" and resid 98 and name HN))
((segid "PROT" and resid 98 and name HA))
 2.700  1.800  1.800 peak      7861 weight  0.10000E+01 volume  0.70923E+01 ppm1    8.469 ppm2  4.203
ASSI {7871}
((segid "PROT" and resid 98 and name HN))
((segid "PROT" and resid 98 and name HB1))
 2.900  2.100  2.100 peak      7871 weight  0.10000E+01 volume  0.40399E+01 ppm1    8.463 ppm2  3.387
ASSI {7881}
((segid "PROT" and resid 98 and name HN))
((segid "PROT" and resid 98 and name HB2))
 2.700  1.800  1.800 peak      7881 weight  0.10000E+01 volume  0.60660E+01 ppm1    8.465 ppm2  3.031
ASSI {7891}
((segid "PROT" and resid 98 and name HN))
((segid "PROT" and resid 97 and name HG2))
 3.200  2.600  2.300 peak      7891 weight  0.10000E+01 volume  0.22366E+01 ppm1    8.469 ppm2  1.629
ASSI {7911}
((segid "PROT" and resid 98 and name HN))
((segid "PROT" and resid 96 and name HN))
 3.200  2.600  2.300 peak      7911 weight  0.10000E+01 volume  0.25397E+01 ppm1    8.436 ppm2  7.377
ASSI {7921}
((segid "PROT" and resid 52 and name HN))
((segid "PROT" and resid 50 and name HA))
 3.000  2.200  2.200 peak      7921 weight  0.10000E+01 volume  0.36881E+01 ppm1    8.430 ppm2  3.923
ASSI {7931}
((segid "PROT" and resid 52 and name HN))
((segid "PROT" and resid 53 and name HD1))
 3.200  2.600  2.300 peak      7931 weight  0.10000E+01 volume  0.21891E+01 ppm1    8.437 ppm2  3.634
ASSI {7941}
((segid "PROT" and resid 52 and name HN))
((segid "PROT" and resid 52 and name HB2))
 2.700  1.800  1.800 peak      7941 weight  0.10000E+01 volume  0.71866E+01 ppm1    8.431 ppm2  2.936
ASSI {7961}
((segid "PROT" and resid 52 and name HN))
(segid "PROT" and resid 52 and name HD%)
 3.300  2.700  2.200 peak      7961 weight  0.10000E+01 volume  0.20400E+01 ppm1    8.426 ppm2  7.245
ASSI {7971}
((segid "PROT" and resid 52 and name HN))
((segid "PROT" and resid 52 and name HA))
 2.800  2.000  2.000 peak      7971 weight  0.10000E+01 volume  0.47172E+01 ppm1    8.427 ppm2  5.013
ASSI {7981}
((segid "PROT" and resid 52 and name HN))
((segid "PROT" and resid 51 and name HA))
 2.900  2.100  2.100 peak      7981 weight  0.10000E+01 volume  0.44512E+01 ppm1    8.430 ppm2  3.854
ASSI {7991}
((segid "PROT" and resid 52 and name HN))
((segid "PROT" and resid 51 and name HG1))
 2.900  2.100  2.100 peak      7991 weight  0.10000E+01 volume  0.40272E+01 ppm1    8.428 ppm2  1.365
ASSI {8001}
((segid "PROT" and resid 52 and name HN))
((segid "PROT" and resid 51 and name HG2))
 2.800  2.000  2.000 peak      8001 weight  0.10000E+01 volume  0.48060E+01 ppm1    8.429 ppm2  1.183
ASSI {8011}
((segid "PROT" and resid 52 and name HN))
(segid "PROT" and resid 50 and name HG2%)
 2.700  1.800  1.800 peak      8011 weight  0.10000E+01 volume  0.57798E+01 ppm1    8.430 ppm2  0.391
ASSI {8031}
((segid "PROT" and resid 32 and name HN))
((segid "PROT" and resid 29 and name HA))
 3.500  3.100  2.000 peak      8031 weight  0.10000E+01 volume  0.14468E+01 ppm1    7.101 ppm2  4.239
ASSI {8041}
((segid "PROT" and resid 32 and name HN))
(segid "PROT" and resid 102 and name HD1%)
 3.500  3.100  2.000 peak      8041 weight  0.10000E+01 volume  0.14091E+01 ppm1    7.098 ppm2  0.734
ASSI {8051}
((segid "PROT" and resid 75 and name HN))
(segid "PROT" and resid 74 and name HD%)
 3.400  2.900  2.100 peak      8051 weight  0.10000E+01 volume  0.15423E+01 ppm1    8.509 ppm2  6.405
ASSI {8061}
((segid "PROT" and resid 75 and name HN))
((segid "PROT" and resid 72 and name HA))
 3.000  2.200  2.200 peak      8061 weight  0.10000E+01 volume  0.36517E+01 ppm1    8.502 ppm2  4.063

TABLE 13-continued

Unambiguous NOE Distance Restraints

ASSI {8071}
((segid "PROT" and resid 75 and name HN))
((segid "PROT" and resid 74 and name HA))
  3.200  2.600  2.300 peak    8071 weight  0.10000E+01 volume  0.23481E+01 ppm1    8.494 ppm2  3.791
ASSI {8081}
((segid "PROT" and resid 75 and name HN))
((segid "PROT" and resid 73 and name HB2))
  3.400  2.900  2.100 peak    8081 weight  0.10000E+01 volume  0.16840E+01 ppm1    8.486 ppm2  1.891
ASSI {8091}
((segid "PROT" and resid 98 and name HN))
((segid "PROT" and resid 97 and name HB1))
  2.600  1.700  1.700 peak    8091 weight  0.10000E+01 volume  0.73028E+01 ppm1    8.473 ppm2  2.090
ASSI {8101}
((segid "PROT" and resid 98 and name HN))
((segid "PROT" and resid 97 and name HG1))
  3.200  2.600  2.300 peak    8101 weight  0.10000E+01 volume  0.22962E+01 ppm1    8.471 ppm2  1.827
ASSI {8111}
((segid "PROT" and resid 95 and name HN))
((segid "PROT" and resid 96 and name HN))
  3.600  3.200  1.900 peak    8111 weight  0.10000E+01 volume  0.11106E+01 ppm1    7.966 ppm2  7.391
ASSI {8121}
((segid "PROT" and resid 60 and name HN))
((segid "PROT" and resid 60 and name HA))
  2.700  1.800  1.800 peak    8121 weight  0.10000E+01 volume  0.60698E+01 ppm1    7.963 ppm2  4.414
ASSI {8131}
((segid "PROT" and resid 95 and name HN))
((segid "PROT" and resid 94 and name HA))
  2.600  1.700  1.700 peak    8131 weight  0.10000E+01 volume  0.76180E+01 ppm1    7.963 ppm2  4.222
ASSI {8141}
((segid "PROT" and resid 60 and name HN))
((segid "PROT" and resid 61 and name HG1))
  3.200  2.600  2.300 peak    8141 weight  0.10000E+01 volume  0.23031E+01 ppm1    7.959 ppm2  2.382
ASSI {8151}
((segid "PROT" and resid 65 and name HN))
((segid "PROT" and resid 63 and name HB2))
  3.000  2.200  2.200 peak    8151 weight  0.10000E+01 volume  0.34813E+01 ppm1    7.961 ppm2  1.915
ASSI {8161}
((segid "PROT" and resid 65 and name HN))
((segid "PROT" and resid 62 and name HB2))
  2.900  2.100  2.100 peak    8161 weight  0.10000E+01 volume  0.42507E+01 ppm1    7.963 ppm2  1.076
ASSI {8171}
((segid "PROT" and resid 65 and name HN))
((segid "PROT" and resid 62 and name HG2))
  3.600  3.200  1.900 peak    8171 weight  0.10000E+01 volume  0.11342E+01 ppm1    7.965 ppm2  0.891
ASSI {8191}
((segid "PROT" and resid 88 and name HN))
((segid "PROT" and resid 88 and name HA))
  2.600  1.700  1.700 peak    8191 weight  0.10000E+01 volume  0.74064E+01 ppm1    7.940 ppm2  4.309
ASSI {8201}
((segid "PROT" and resid 88 and name HN))
((segid "PROT" and resid 88 and name HB1))
  2.800  2.000  2.000 peak    8201 weight  0.10000E+01 volume  0.50457E+01 ppm1    7.943 ppm2  2.936
ASSI {8211}
((segid "PROT" and resid 88 and name HN))
((segid "PROT" and resid 87 and name HB1))
  2.900  2.100  2.100 peak    8211 weight  0.10000E+01 volume  0.46367E+01 ppm1    7.948 ppm2  2.198
ASSI {8221}
((segid "PROT" and resid 88 and name HN))
(segid "PROT" and resid 50 and name HD1%)
  3.200  2.600  2.300 peak    8221 weight  0.10000E+01 volume  0.21507E+01 ppm1    7.940 ppm2  0.559
ASSI {8241}
((segid "PROT" and resid 32 and name HN))
((segid "PROT" and resid 32 and name HE1))
  3.400  2.900  2.100 peak    8241 weight  0.10000E+01 volume  0.15718E+01 ppm1    7.101 ppm2  10.403
ASSI {8271}
((segid "PROT" and resid 32 and name HN))
((segid "PROT" and resid 30 and name HA))
  3.500  3.100  2.000 peak    8271 weight  0.10000E+01 volume  0.12594E+01 ppm1    7.102 ppm2  4.829
ASSI {8281}
((segid "PROT" and resid 32 and name HN))
((segid "PROT" and resid 32 and name HA))
  2.700  1.800  1.800 peak    8281 weight  0.10000E+01 volume  0.68837E+01 ppm1    7.101 ppm2  4.399
ASSI {8291}
((segid "PROT" and resid 32 and name HN))
((segid "PROT" and resid 32 and name HB1))
  2.900  2.100  2.100 peak    8291 weight  0.10000E+01 volume  0.43852E+01 ppm1    7.100 ppm2  3.614

TABLE 13-continued

| Unambiguous NOE Distance Restraints |
|---|

ASSI {8301}
((segid "PROT" and resid 32 and name HN))
((segid "PROT" and resid 32 and name HB2))
  2.700  1.800    1.800 peak        8301  weight  0.10000E+01 volume  0.59584E+01 ppm1      7.099  ppm2  3.384
ASSI {8311}
((segid "PROT" and resid 32 and name HN))
((segid "PROT" and resid 35 and name HB2))
  3.300  2.700    2.200 peak        8311  weight  0.10000E+01 volume  0.21134E+01 ppm1      7.100  ppm2  2.216
ASSI {8321}
((segid "PROT" and resid 32 and name HN))
(segid "PROT" and resid 31 and name HB%)
  2.800  2.000    2.000 peak        8321  weight  0.10000E+01 volume  0.49211E+01 ppm1      7.100  ppm2  1.734
ASSI {8331}
((segid "PROT" and resid 32 and name HN))
((segid "PROT" and resid 33 and name HD2))
  3.000  2.200    2.200 peak        8331  weight  0.10000E+01 volume  0.36037E+01 ppm1      7.101  ppm2  1.553
ASSI {8341}
((segid "PROT" and resid 32 and name HN))
((segid "PROT" and resid 34 and name HN))
  3.500  3.100    2.000 peak        8341  weight  0.10000E+01 volume  0.13342E+01 ppm1      7.093  ppm2  7.630
ASSI {8351}
((segid "PROT" and resid 56 and name HN))
((segid "PROT" and resid 56 and name HB2))
  3.200  2.600    2.300 peak        8351  weight  0.10000E+01 volume  0.22617E+01 ppm1      9.137  ppm2  1.417
ASSI {8361}
((segid "PROT" and resid 56 and name HN))
(segid "PROT" and resid 56 and name HD1%)
  3.200  2.600    2.300 peak        8361  weight  0.10000E+01 volume  0.21571E+01 ppm1      9.136  ppm2  0.952
ASSI {8371}
((segid "PROT" and resid 75 and name HN))
((segid "PROT" and resid 76 and name HN))
  2.600  1.700    1.700 peak        8371  weight  0.10000E+01 volume  0.76502E+01 ppm1      8.504  ppm2  8.021
ASSI {8421}
((segid "PROT" and resid 75 and name HN))
((segid "PROT" and resid 75 and name HB1))
  2.600  1.700    1.700 peak        8421  weight  0.10000E+01 volume  0.88439E+01 ppm1      8.504  ppm2  2.947
ASSI {8431}
((segid "PROT" and resid 75 and name HN))
((segid "PROT" and resid 75 and name HB2))
  2.900  2.100    2.100 peak        8431  weight  0.10000E+01 volume  0.41666E+01 ppm1      8.504  ppm2  2.619
ASSI {8441}
((segid "PROT" and resid 75 and name HN))
((segid "PROT" and resid 75 and name HG1))
  2.800  2.000    2.000 peak        8441  weight  0.10000E+01 volume  0.47167E+01 ppm1      8.506  ppm2  2.322
ASSI {8451}
((segid "PROT" and resid 75 and name HN))
((segid "PROT" and resid 75 and name HG2))
  2.700  1.800    1.800 peak        8451  weight  0.10000E+01 volume  0.59655E+01 ppm1      8.507  ppm2  2.221
ASSI {8471}
((segid "PROT" and resid 60 and name HN))
((segid "PROT" and resid 63 and name HN))
  3.300  2.700    2.200 peak        8471  weight  0.10000E+01 volume  0.18372E+01 ppm1      7.966  ppm2  8.884
ASSI {8481}
((segid "PROT" and resid 65 and name HN))
((segid "PROT" and resid 62 and name HN))
  3.600  3.200    1.900 peak        8481  weight  0.10000E+01 volume  0.12461E+01 ppm1      7.958  ppm2  8.376
ASSI {8491}
((segid "PROT" and resid 60 and name HN))
((segid "PROT" and resid 61 and name HN))
  2.300  1.300    1.300 peak        8491  weight  0.10000E+01 volume  0.16597E+02 ppm1      7.963  ppm2  8.166
ASSI {8501}
((segid "PROT" and resid 65 and name HN))
((segid "PROT" and resid 65 and name HD21))
  3.100  2.400    2.400 peak        8501  weight  0.10000E+01 volume  0.29272E+01 ppm1      7.960  ppm2  7.603
ASSI {8511}
((segid "PROT" and resid 65 and name HN))
((segid "PROT" and resid 65 and name HD22))
  3.300  2.700    2.200 peak        8511  weight  0.10000E+01 volume  0.20934E+01 ppm1      7.960  ppm2  6.977
ASSI {8521}
((segid "PROT" and resid 65 and name HN))
((segid "PROT" and resid 65 and name HA))
  2.700  1.800    1.800 peak        8521  weight  0.10000E+01 volume  0.69853E+01 ppm1      7.962  ppm2  4.805
ASSI {8531}
((segid "PROT" and resid 95 and name HN))
((segid "PROT" and resid 93 and name HA))
  3.400  2.900    2.100 peak        8531  weight  0.10000E+01 volume  0.17105E+01 ppm1      7.962  ppm2  4.527

TABLE 13-continued

Unambiguous NOE Distance Restraints

ASSI {8541}
((segid "PROT" and resid 60 and name HN))
((segid "PROT" and resid 60 and name HB2))
  2.700  1.800  1.800 peak      8541  weight  0.10000E+01 volume  0.68005E+01 ppm1       7.963  ppm2  4.059
ASSI {8551}
((segid "PROT" and resid 65 and name HN))
((segid "PROT" and resid 62 and name HA))
  3.100  2.400  2.400 peak      8551  weight  0.10000E+01 volume  0.28044E+01 ppm1       7.963  ppm2  3.886
ASSI {8571}
((segid "PROT" and resid 65 and name HN))
((segid "PROT" and resid 65 and name HB2))
  2.500  1.600  1.600 peak      8571  weight  0.10000E+01 volume  0.98965E+01 ppm1       7.961  ppm2  2.786
ASSI {8581}
((segid "PROT" and resid 65 and name HN))
((segid "PROT" and resid 64 and name HB1))
  2.500  1.600  1.600 peak      8581  weight  0.10000E+01 volume  0.10932E+02 ppm1       7.960  ppm2  2.061
ASSI {8611}
((segid "PROT" and resid 65 and name HN))
((segid "PROT" and resid 65 and name HB1))
  2.600  1.700  1.700 peak      8611  weight  0.10000E+01 volume  0.86756E+01 ppm1       7.958  ppm2  3.027
ASSI {8621}
((segid "PROT" and resid 56 and name HN))
((segid "PROT" and resid 34 and name HB1))
  3.500  3.100  2.000 peak      8621  weight  0.10000E+01 volume  0.13755E+01 ppm1       9.138  ppm2  3.495
ASSI {8631}
((segid "PROT" and resid 56 and name HN))
((segid "PROT" and resid 56 and name HB1))
  3.100  2.400  2.400 peak      8631  weight  0.10000E+01 volume  0.27193E+01 ppm1       9.139  ppm2  2.074
ASSI {8651}
((segid "PROT" and resid 56 and name HN))
((segid "PROT" and resid 55 and name HA))
  2.800  2.000  2.000 peak      8651  weight  0.10000E+01 volume  0.49101E+01 ppm1       9.133  ppm2  4.746
ASSI {8661}
((segid "PROT" and resid 56 and name HN))
((segid "PROT" and resid 35 and name HA))
  3.500  3.100  2.000 peak      8661  weight  0.10000E+01 volume  0.12922E+01 ppm1       9.134  ppm2  4.311
ASSI {8671}
((segid "PROT" and resid 56 and name HN))
((segid "PROT" and resid 56 and name HA))
  3.300  2.700  2.200 peak      8671  weight  0.10000E+01 volume  0.20678E+01 ppm1       9.134  ppm2  4.038
ASSI {8681}
((segid "PROT" and resid 56 and name HN))
((segid "PROT" and resid 55 and name HB1))
  2.800  2.000  2.000 peak      8681  weight  0.10000E+01 volume  0.49656E+01 ppm1       9.136  ppm2  2.380
ASSI {8691}
((segid "PROT" and resid 56 and name HN))
((segid "PROT" and resid 56 and name HG))
  2.800  2.000  2.000 peak      8691  weight  0.10000E+01 volume  0.48001E+01 ppm1       9.133  ppm2  1.733
ASSI {8711}
((segid "PROT" and resid 56 and name HN))
(segid "PROT" and resid 56 and name HD2%)
  3.100  2.400  2.400 peak      8711  weight  0.10000E+01 volume  0.28913E+01 ppm1       9.137  ppm2  0.647
ASSI {8721}
((segid "PROT" and resid 56 and name HN))
(segid "PROT" and resid 81 and name HG1%)
  3.600  3.200  1.900 peak      8721  weight  0.10000E+01 volume  0.11502E+01 ppm1       9.131  ppm2  0.486
ASSI {8751}
((segid "PROT" and resid 69 and name HN))
((segid "PROT" and resid 68 and name HA))
  2.600  1.700  1.700 peak      8751  weight  0.10000E+01 volume  0.87535E+01 ppm1       7.703  ppm2  4.550
ASSI {8761}
((segid "PROT" and resid 69 and name HN))
((segid "PROT" and resid 69 and name HA))
  2.800  2.000  2.000 peak      8761  weight  0.10000E+01 volume  0.55954E+01 ppm1       7.703  ppm2  4.099
ASSI {8771}
((segid "PROT" and resid 69 and name HN))
((segid "PROT" and resid 69 and name HB))
  3.100  2.400  2.400 peak      8771  weight  0.10000E+01 volume  0.25963E+01 ppm1       7.705  ppm2  2.334
ASSI {8781}
((segid "PROT" and resid 69 and name HN))
(segid "PROT" and resid 69 and name HG1%)
  2.300  1.300  1.300 peak      8781  weight  0.10000E+01 volume  0.15076E+02 ppm1       7.703  ppm2  0.960
ASSI {8791}
((segid "PROT" and resid 69 and name HN))
(segid "PROT" and resid 69 and name HG2%)
  2.400  1.400  1.400 peak      8791  weight  0.10000E+01 volume  0.14135E+02 ppm1       7.703  ppm2  0.840

TABLE 13-continued

Unambiguous NOE Distance Restraints

ASSI {8801}
((segid "PROT" and resid 69 and name HN))
((segid "PROT" and resid 68 and name HB2))
  3.500  3.100   2.000 peak       8801  weight  0.10000E+01 volume   0.13700E+01 ppm1     7.697  ppm2  2.922
ASSI {8811}
((segid "PROT" and resid 93 and name HN))
((segid "PROT" and resid 90 and name HD1))
  3.400  2.900   2.100 peak       8811  weight  0.10000E+01 volume   0.14810E+01 ppm1     8.123  ppm2  4.101
ASSI {8821}
((segid "PROT" and resid 93 and name HN))
((segid "PROT" and resid 92 and name HG2))
  3.100  2.400   2.400 peak       8821  weight  0.10000E+01 volume   0.27236E+01 ppm1     8.117  ppm2  2.231
ASSI {8831}
((segid "PROT" and resid 93 and name HN))
((segid "PROT" and resid 94 and name HN))
  2.600  1.700   1.700 peak       8831  weight  0.10000E+01 volume   0.72426E+01 ppm1     8.122  ppm2  8.399
ASSI {8841}
((segid "PROT" and resid 93 and name HN))
((segid "PROT" and resid 90 and name HA))
  3.400  2.900   2.100 peak       8841  weight  0.10000E+01 volume   0.15414E+01 ppm1     8.126  ppm2  4.634
ASSI {8851}
((segid "PROT" and resid 93 and name HN))
((segid "PROT" and resid 93 and name HA))
  2.800  2.000   2.000 peak       8851  weight  0.10000E+01 volume   0.47169E+01 ppm1     8.123  ppm2  4.498
ASSI {8861}
((segid "PROT" and resid 93 and name HN))
((segid "PROT" and resid 96 and name HA))
  3.600  3.200   1.900 peak       8861  weight  0.10000E+01 volume   0.12225E+01 ppm1     8.131  ppm2  3.813
ASSI {8871}
((segid "PROT" and resid 93 and name HN))
((segid "PROT" and resid 96 and name HB1))
  3.200  2.600   2.300 peak       8871  weight  0.10000E+01 volume   0.22127E+01 ppm1     8.121  ppm2  3.389
ASSI {8881}
((segid "PROT" and resid 93 and name HN))
((segid "PROT" and resid 96 and name HB2))
  3.200  2.600   2.300 peak       8881  weight  0.10000E+01 volume   0.22961E+01 ppm1     8.122  ppm2  2.561
ASSI {8891}
((segid "PROT" and resid 93 and name HN))
((segid "PROT" and resid 96 and name HN))
  3.500  3.100   2.000 peak       8891  weight  0.10000E+01 volume   0.13954E+01 ppm1     8.120  ppm2  7.358
ASSI {8901}
((segid "PROT" and resid 93 and name HN))
((segid "PROT" and resid 92 and name HA))
  2.700  1.800   1.800 peak       8901  weight  0.10000E+01 volume   0.59769E+01 ppm1     8.118  ppm2  4.240
ASSI {8911}
((segid "PROT" and resid 93 and name HN))
((segid "PROT" and resid 92 and name HB1))
  2.900  2.100   2.100 peak       8911  weight  0.10000E+01 volume   0.38660E+01 ppm1     8.118  ppm2  2.079
ASSI {8921}
((segid "PROT" and resid 100 and name HN))
((segid "PROT" and resid 98 and name HN))
  3.400  2.900   2.100 peak       8921  weight  0.10000E+01 volume   0.15387E+01 ppm1     8.078  ppm2  8.500
ASSI {8941}
((segid "PROT" and resid 100 and name HN))
((segid "PROT" and resid 97 and name HA))
  2.800  2.000   2.000 peak       8941  weight  0.10000E+01 volume   0.50553E+01 ppm1     8.076  ppm2  4.216
ASSI {8951}
((segid "PROT" and resid 100 and name HN))
((segid "PROT" and resid 99 and name HA))
  3.200  2.600   2.300 peak       8951  weight  0.10000E+01 volume   0.21329E+01 ppm1     8.075  ppm2  3.886
ASSI {8961}
((segid "PROT" and resid 100 and name HN))
((segid "PROT" and resid 96 and name HA))
  3.500  3.100   2.000 peak       8961  weight  0.10000E+01 volume   0.13805E+01 ppm1     8.072  ppm2  3.815
ASSI {8971}
((segid "PROT" and resid 100 and name HN))
((segid "PROT" and resid 100 and name HB2))
  2.500  1.600   1.600 peak       8971  weight  0.10000E+01 volume   0.11200E+02 ppm1     8.073  ppm2  2.819
ASSI {8981}
((segid "PROT" and resid 100 and name HN))
((segid "PROT" and resid 101 and name HB))
  3.400  2.900   2.100 peak       8981  weight  0.10000E+01 volume   0.16226E+01 ppm1     8.072  ppm2  1.924
ASSI {8991}
((segid "PROT" and resid 100 and name HN))
((segid "PROT" and resid 103 and name HB1))
  3.400  2.900   2.100 peak       8991  weight  0.10000E+01 volume   0.16128E+01 ppm1     8.074  ppm2  1.798

TABLE 13-continued

| Unambiguous NOE Distance Restraints |
| --- |

ASSI {9001}
((segid "PROT" and resid 100 and name HN))
((segid "PROT" and resid 100 and name HA))
  2.600  1.700   1.700 peak       9001  weight  0.10000E+01 volume  0.77227E+01 ppm1     8.070 ppm2  4.336
ASSI {9011}
((segid "PROT" and resid 100 and name HN))
((segid "PROT" and resid 100 and name HB1))
  2.600  1.700   1.700 peak       9011  weight  0.10000E+01 volume  0.85998E+01 ppm1     8.070 ppm2  2.902
ASSI {9021}
((segid "PROT" and resid 100 and name HN))
(segid "PROT" and resid 99 and name HB%)
  2.600  1.700   1.700 peak       9021  weight  0.10000E+01 volume  0.72646E+01 ppm1     8.070 ppm2  1.633
ASSI {9031}
((segid "PROT" and resid 83 and name HN))
((segid "PROT" and resid 81 and name HA))
  3.100  2.400   2.400 peak       9031  weight  0.10000E+01 volume  0.27010E+01 ppm1     9.097 ppm2  3.099
ASSI {9051}
((segid "PROT" and resid 83 and name HN))
((segid "PROT" and resid 79 and name HE21))
  3.500  3.100   2.000 peak       9051  weight  0.10000E+01 volume  0.12887E+01 ppm1     9.097 ppm2  7.316
ASSI {9081}
((segid "PROT" and resid 83 and name HN))
((segid "PROT" and resid 83 and name HB))
  2.800  2.000   2.000 peak       9081  weight  0.10000E+01 volume  0.50910E+01 ppm1     9.095 ppm2  4.211
ASSI {9091}
((segid "PROT" and resid 83 and name HN))
((segid "PROT" and resid 80 and name HA))
  3.000  2.200   2.200 peak       9091  weight  0.10000E+01 volume  0.37309E+01 ppm1     9.094 ppm2  4.081
ASSI {9101}
((segid "PROT" and resid 83 and name HN))
((segid "PROT" and resid 83 and name HA))
  2.800  2.000   2.000 peak       9101  weight  0.10000E+01 volume  0.47850E+01 ppm1     9.095 ppm2  3.886
ASSI {9111}
((segid "PROT" and resid 83 and name HN))
((segid "PROT" and resid 82 and name HB2))
  3.000  2.200   2.200 peak       9111  weight  0.10000E+01 volume  0.35514E+01 ppm1     9.096 ppm2  2.980
ASSI {9121}
((segid "PROT" and resid 83 and name HN))
(segid "PROT" and resid 83 and name HG2%)
  2.600  1.700   1.700 peak       9121  weight  0.10000E+01 volume  0.77238E+01 ppm1     9.096 ppm2  1.319
ASSI {9171}
((segid "PROT" and resid 116 and name HN))
((segid "PROT" and resid 115 and name HA))
  2.500  1.600   1.600 peak       9171  weight  0.10000E+01 volume  0.10961E+02 ppm1     7.472 ppm2  4.243
ASSI {9181}
((segid "PROT" and resid 116 and name HN))
((segid "PROT" and resid 111 and name HA))
  2.900  2.100   2.100 peak       9181  weight  0.10000E+01 volume  0.41946E+01 ppm1     7.472 ppm2  4.067
ASSI {9191}
((segid "PROT" and resid 116 and name HN))
((segid "PROT" and resid 116 and name HB))
  2.600  1.700   1.700 peak       9191  weight  0.10000E+01 volume  0.82844E+01 ppm1     7.473 ppm2  1.827
ASSI {9201}
((segid "PROT" and resid 116 and name HN))
((segid "PROT" and resid 115 and name HG))
  2.800  2.000   2.000 peak       9201  weight  0.10000E+01 volume  0.52666E+01 ppm1     7.472 ppm2  1.582
ASSI {9211}
((segid "PROT" and resid 116 and name HN))
((segid "PROT" and resid 116 and name HG11))
  2.800  2.000   2.000 peak       9211  weight  0.10000E+01 volume  0.51800E+01 ppm1     7.472 ppm2  1.326
ASSI {9221}
((segid "PROT" and resid 116 and name HN))
((segid "PROT" and resid 116 and name HG12))
  2.700  1.800   1.800 peak       9221  weight  0.10000E+01 volume  0.61501E+01 ppm1     7.472 ppm2  0.937
ASSI {9231}
((segid "PROT" and resid 116 and name HN))
(segid "PROT" and resid 116 and name HD1%)
  2.800  2.000   2.000 peak       9231  weight  0.10000E+01 volume  0.56999E+01 ppm1     7.472 ppm2  0.822
ASSI {9241}
((segid "PROT" and resid 116 and name HN))
(segid "PROT" and resid 110 and name HG2%)
  3.400  2.900   2.100 peak       9241  weight  0.10000E+01 volume  0.16152E+01 ppm1     7.474 ppm2  0.683
ASSI {9261}
((segid "PROT" and resid 89 and name HN))
((segid "PROT" and resid 89 and name HD21))
  3.000  2.200   2.200 peak       9261  weight  0.10000E+01 volume  0.33062E+01 ppm1     8.116 ppm2  8.355

TABLE 13-continued

Unambiguous NOE Distance Restraints

ASSI {9271}
((segid "PROT" and resid 89 and name HN))
((segid "PROT" and resid 88 and name HN))
  2.600  1.700  1.700 peak     9271 weight  0.10000E+01 volume  0.81545E+01 ppm1    8.115  ppm2  7.938
ASSI {9281}
((segid "PROT" and resid 89 and name HN))
((segid "PROT" and resid 86 and name HN))
  3.100  2.400  2.400 peak     9281 weight  0.10000E+01 volume  0.30920E+01 ppm1    8.119  ppm2  7.822
ASSI {9291}
((segid "PROT" and resid 89 and name HN))
((segid "PROT" and resid 86 and name HA))
  3.400  2.900  2.100 peak     9291 weight  0.10000E+01 volume  0.15463E+01 ppm1    8.113  ppm2  4.229
ASSI {9301}
((segid "PROT" and resid 89 and name HN))
((segid "PROT" and resid 89 and name HB1))
  2.900  2.100  2.100 peak     9301 weight  0.10000E+01 volume  0.37959E+01 ppm1    8.117  ppm2  3.068
ASSI {9311}
((segid "PROT" and resid 89 and name HN))
((segid "PROT" and resid 89 and name HA))
  3.100  2.400  2.400 peak     9311 weight  0.10000E+01 volume  0.27926E+01 ppm1    8.111  ppm2  5.063
ASSI {9321}
((segid "PROT" and resid 89 and name HN))
((segid "PROT" and resid 87 and name HA))
  3.300  2.700  2.200 peak     9321 weight  0.10000E+01 volume  0.20761E+01 ppm1    8.111  ppm2  4.307
ASSI {9331}
((segid "PROT" and resid 89 and name HN))
((segid "PROT" and resid 89 and name HB2))
  2.800  2.000  2.000 peak     9331 weight  0.10000E+01 volume  0.50152E+01 ppm1    8.112  ppm2  2.891
ASSI {9341}
((segid "PROT" and resid 108 and name HN))
((segid "PROT" and resid 110 and name HN))
  2.900  2.100  2.100 peak     9341 weight  0.10000E+01 volume  0.40916E+01 ppm1    7.945  ppm2  8.119
ASSI {9351}
((segid "PROT" and resid 108 and name HN))
((segid "PROT" and resid 107 and name HN))
  2.500  1.600  1.600 peak     9351 weight  0.10000E+01 volume  0.95030E+01 ppm1    7.934  ppm2  8.399
ASSI {9361}
((segid "PROT" and resid 108 and name HN))
((segid "PROT" and resid 105 and name HA))
  3.100  2.400  2.400 peak     9361 weight  0.10000E+01 volume  0.29117E+01 ppm1    7.935  ppm2  4.336
ASSI {9371}
((segid "PROT" and resid 108 and name HN))
((segid "PROT" and resid 104 and name HA))
  2.900  2.100  2.100 peak     9371 weight  0.10000E+01 volume  0.44614E+01 ppm1    7.935  ppm2  4.086
ASSI {9381}
((segid "PROT" and resid 108 and name HN))
((segid "PROT" and resid 107 and name HB1))
  2.600  1.700  1.700 peak     9381 weight  0.10000E+01 volume  0.86992E+01 ppm1    7.934  ppm2  3.071
ASSI {9391}
((segid "PROT" and resid 108 and name HN))
((segid "PROT" and resid 108 and name HA))
  2.700  1.800  1.800 peak     9391 weight  0.10000E+01 volume  0.69670E+01 ppm1    7.933  ppm2  4.207
ASSI {9401}
((segid "PROT" and resid 108 and name HN))
((segid "PROT" and resid 108 and name HB1))
  2.300  1.300  1.300 peak     9401 weight  0.10000E+01 volume  0.15144E+02 ppm1    7.933  ppm2  3.994
ASSI {9411}
((segid "PROT" and resid 108 and name HN))
((segid "PROT" and resid 107 and name HA))
  3.000  2.200  2.200 peak     9411 weight  0.10000E+01 volume  0.36835E+01 ppm1    7.931  ppm2  3.856
ASSI {9431}
((segid "PROT" and resid 108 and name HN))
((segid "PROT" and resid 109 and name HG1))
  3.500  3.100  2.000 peak     9431 weight  0.10000E+01 volume  0.14551E+01 ppm1    7.928  ppm2  0.819
ASSI {9441}
((segid "PROT" and resid 49 and name HN))
((segid "PROT" and resid 50 and name HB))
  3.500  3.100  2.000 peak     9441 weight  0.10000E+01 volume  0.14054E+01 ppm1    7.116  ppm2  1.212
ASSI {9471}
((segid "PROT" and resid 49 and name HN))
((segid "PROT" and resid 48 and name HA))
  2.800  2.000  2.000 peak     9471 weight  0.10000E+01 volume  0.50132E+01 ppm1    7.114  ppm2  4.092
ASSI {9481}
((segid "PROT" and resid 49 and name HN))
((segid "PROT" and resid 48 and name HB2))
  3.000  2.200  2.200 peak     9481 weight  0.10000E+01 volume  0.32610E+01 ppm1    7.114  ppm2  2.104

TABLE 13-continued

Unambiguous NOE Distance Restraints

ASSI {9491}
((segid "PROT" and resid 49 and name HN))
((segid "PROT" and resid 49 and name HB))
  2.900  2.100   2.100 peak      9491 weight  0.10000E+01 volume  0.39099E+01 ppm1      7.113  ppm2  1.909
ASSI {9501}
((segid "PROT" and resid 49 and name HN))
(segid "PROT" and resid 49 and name HG1%)
  2.600  1.700   1.700 peak      9501 weight  0.10000E+01 volume  0.78825E+01 ppm1      7.115  ppm2  0.938
ASSI {9531}
((segid "PROT" and resid 68 and name HN))
((segid "PROT" and resid 69 and name HN))
  3.300  2.700   2.200 peak      9531 weight  0.10000E+01 volume  0.19914E+01 ppm1      8.008  ppm2  7.709
ASSI {9561}
((segid "PROT" and resid 68 and name HN))
((segid "PROT" and resid 63 and name HA))
  2.800  2.000   2.000 peak      9561 weight  0.10000E+01 volume  0.51283E+01 ppm1      8.010  ppm2  4.736
ASSI {9571}
((segid "PROT" and resid 68 and name HN))
((segid "PROT" and resid 68 and name HA))
  3.000  2.200   2.200 peak      9571 weight  0.10000E+01 volume  0.33992E+01 ppm1      8.012  ppm2  4.545
ASSI {9581}
((segid "PROT" and resid 68 and name HN))
((segid "PROT" and resid 66 and name HA))
  3.200  2.600   2.300 peak      9581 weight  0.10000E+01 volume  0.25061E+01 ppm1      8.007  ppm2  4.406
ASSI {9591}
((segid "PROT" and resid 68 and name HN))
((segid "PROT" and resid 67 and name HA))
  3.200  2.600   2.300 peak      9591 weight  0.10000E+01 volume  0.22241E+01 ppm1      8.008  ppm2  4.080
ASSI {9601}
((segid "PROT" and resid 68 and name HN))
((segid "PROT" and resid 68 and name HB1))
  2.700  1.800   1.800 peak      9601 weight  0.10000E+01 volume  0.64844E+01 ppm1      8.010  ppm2  3.066
ASSI {9611}
((segid "PROT" and resid 68 and name HN))
((segid "PROT" and resid 68 and name HB2))
  2.800  2.000   2.000 peak      9611 weight  0.10000E+01 volume  0.52689E+01 ppm1      8.013  ppm2  2.942
ASSI {9621}
((segid "PROT" and resid 68 and name HN))
((segid "PROT" and resid 62 and name HB1))
  3.000  2.200   2.200 peak      9621 weight  0.10000E+01 volume  0.34737E+01 ppm1      8.012  ppm2  2.069
ASSI {9631}
((segid "PROT" and resid 68 and name HN))
((segid "PROT" and resid 62 and name HB2))
  3.300  2.700   2.200 peak      9631 weight  0.10000E+01 volume  0.20544E+01 ppm1      8.009  ppm2  1.048
ASSI {9641}
((segid "PROT" and resid 68 and name HN))
((segid "PROT" and resid 62 and name HD2))
  3.500  3.100   2.000 peak      9641 weight  0.10000E+01 volume  0.13121E+01 ppm1      8.009  ppm2  0.839
ASSI {9661}
((segid "PROT" and resid 68 and name HN))
(segid "PROT" and resid 73 and name HD1%)
  3.300  2.700   2.200 peak      9661 weight  0.10000E+01 volume  0.18934E+01 ppm1      8.006  ppm2  0.968
ASSI {9671}
((segid "PROT" and resid 49 and name HN))
((segid "PROT" and resid 46 and name HA))
  3.600  3.200   1.900 peak      9671 weight  0.10000E+01 volume  0.11481E+01 ppm1      7.104  ppm2  3.480
ASSI {9681}
((segid "PROT" and resid 26 and name HN))
((segid "PROT" and resid 24 and name HN))
  3.600  3.200   1.900 peak      9681 weight  0.10000E+01 volume  0.11188E+01 ppm1      8.577  ppm2  8.046
ASSI {9691}
((segid "PROT" and resid 26 and name HN))
((segid "PROT" and resid 28 and name HN))
  2.700  1.800   1.800 peak      9691 weight  0.10000E+01 volume  0.58413E+01 ppm1      8.577  ppm2  7.555
ASSI {9701}
((segid "PROT" and resid 26 and name HN))
((segid "PROT" and resid 25 and name HB))
  2.800  2.000   2.000 peak      9701 weight  0.10000E+01 volume  0.48076E+01 ppm1      8.580  ppm2  2.409
ASSI {9711}
((segid "PROT" and resid 26 and name HN))
((segid "PROT" and resid 26 and name HB1))
  2.500  1.600   1.600 peak      9711 weight  0.10000E+01 volume  0.10862E+02 ppm1      8.577  ppm2  1.885
ASSI {9721}
((segid "PROT" and resid 26 and name HN))
((segid "PROT" and resid 26 and name HG1))
  3.200  2.600   2.300 peak      9721 weight  0.10000E+01 volume  0.25005E+01 ppm1      8.578  ppm2  1.503

TABLE 13-continued

| Unambiguous NOE Distance Restraints |
|---|

ASSI {9731}
((segid "PROT" and resid 26 and name HN))
(segid "PROT" and resid 25 and name HG2%)
  2.900  2.100   2.100 peak      9731  weight  0.10000E+01  volume  0.41014E+01  ppm1    8.577  ppm2  1.032
ASSI {9741}
((segid "PROT" and resid 26 and name HN))
((segid "PROT" and resid 23 and name HA))
  3.000  2.200   2.200 peak      9741  weight  0.10000E+01  volume  0.36360E+01  ppm1    8.575  ppm2  4.040
ASSI {9751}
((segid "PROT" and resid 26 and name HN))
((segid "PROT" and resid 26 and name HA))
  2.800  2.000   2.000 peak      9751  weight  0.10000E+01  volume  0.51742E+01  ppm1    8.575  ppm2  3.899
ASSI {9761}
((segid "PROT" and resid 26 and name HN))
((segid "PROT" and resid 28 and name HB2))
  3.300  2.700   2.200 peak      9761  weight  0.10000E+01  volume  0.17856E+01  ppm1    8.571  ppm2  2.822
ASSI {9771}
((segid "PROT" and resid 26 and name HN))
((segid "PROT" and resid 22 and name HB2))
  3.200  2.600   2.300 peak      9771  weight  0.10000E+01  volume  0.24703E+01  ppm1    8.574  ppm2  1.720
ASSI {9781}
((segid "PROT" and resid 26 and name HN))
(segid "PROT" and resid 25 and name HG1%)
  3.200  2.600   2.300 peak      9781  weight  0.10000E+01  volume  0.21814E+01  ppm1    8.575  ppm2  1.204
ASSI {9791}
((segid "PROT" and resid 68 and name HN))
(segid "PROT" and resid 68 and name HD %)
  3.400  2.900   2.100 peak      9791  weight  0.10000E+01  volume  0.17151E+01  ppm1    8.012  ppm2  7.177
ASSI {9811}
((segid "PROT" and resid 66 and name HN))
((segid "PROT" and resid 66 and name HB2))
  2.900  2.100   2.100 peak      9811  weight  0.10000E+01  volume  0.45427E+01  ppm1    8.165  ppm2  2.064
ASSI {9821}
((segid "PROT" and resid 66 and name HN))
((segid "PROT" and resid 65 and name HN))
  2.500  1.600   1.600 peak      9821  weight  0.10000E+01  volume  0.94679E+01  ppm1    8.167  ppm2  7.964
ASSI {9831}
((segid "PROT" and resid 66 and name HN))
((segid "PROT" and resid 65 and name HA))
  3.100  2.400   2.400 peak      9831  weight  0.10000E+01  volume  0.29187E+01  ppm1    8.168  ppm2  4.805
ASSI {9841}
((segid "PROT" and resid 66 and name HN))
((segid "PROT" and resid 63 and name HA))
  2.900  2.100   2.100 peak      9841  weight  0.10000E+01  volume  0.39314E+01  ppm1    8.166  ppm2  4.740
ASSI {9851}
((segid "PROT" and resid 66 and name HN))
((segid "PROT" and resid 66 and name HA))
  2.400  1.400   1.400 peak      9851  weight  0.10000E+01  volume  0.12932E+02  ppm1    8.168  ppm2  4.413
ASSI {9881}
((segid "PROT" and resid 66 and name HN))
((segid "PROT" and resid 66 and name HG2))
  2.900  2.100   2.100 peak      9881  weight  0.10000E+01  volume  0.40718E+01  ppm1    8.168  ppm2  1.558
ASSI {9891}
((segid "PROT" and resid 66 and name HN))
((segid "PROT" and resid 65 and name HB2))
  3.400  2.900   2.100 peak      9891  weight  0.10000E+01  volume  0.16398E+01  ppm1    8.160  ppm2  2.783
ASSI {9901}
((segid "PROT" and resid 79 and name HN))
((segid "PROT" and resid 80 and name HN))
  2.300  1.300   1.300 peak      9901  weight  0.10000E+01  volume  0.14943E+02  ppm1    8.099  ppm2  7.402
ASSI {9911}
((segid "PROT" and resid 79 and name HN))
((segid "PROT" and resid 81 and name HN))
  3.300  2.700   2.200 peak      9911  weight  0.10000E+01  volume  0.18162E+01  ppm1    8.097  ppm2  7.043
ASSI {9921}
((segid "PROT" and resid 79 and name HN))
((segid "PROT" and resid 75 and name HA))
  3.100  2.400   2.400 peak      9921  weight  0.10000E+01  volume  0.26898E+01  ppm1    8.100  ppm2  4.089
ASSI {9941}
((segid "PROT" and resid 79 and name HN))
((segid "PROT" and resid 79 and name HA))
  2.700  1.800   1.800 peak      9941  weight  0.10000E+01  volume  0.59060E+01  ppm1    8.098  ppm2  3.824
ASSI {9951}
((segid "PROT" and resid 79 and name HN))
((segid "PROT" and resid 78 and name HA))
  3.400  2.900   2.100 peak      9951  weight  0.10000E+01  volume  0.17317E+01  ppm1    8.102  ppm2  3.388

TABLE 13-continued

Unambiguous NOE Distance Restraints

ASSI {9961}
((segid "PROT" and resid 79 and name HN))
((segid "PROT" and resid 79 and name HG1))
 2.800  2.000  2.000 peak      9961 weight  0.10000E+01 volume  0.52811E+01 ppm1    8.100  ppm2  2.455
ASSI {9971}
((segid "PROT" and resid 79 and name HN))
((segid "PROT" and resid 79 and name HB1))
 2.500  1.600  1.600 peak      9971 weight  0.10000E+01 volume  0.10887E+02 ppm1    8.099  ppm2  2.184
ASSI {9981}
((segid "PROT" and resid 79 and name HN))
((segid "PROT" and resid 79 and name HB2))
 2.500  1.600  1.600 peak      9981 weight  0.10000E+01 volume  0.95335E+01 ppm1    8.101  ppm2  2.088
ASSI {9991}
((segid "PROT" and resid 79 and name HN))
((segid "PROT" and resid 78 and name HB1))
 2.900  2.100  2.100 peak      9991 weight  0.10000E+01 volume  0.38537E+01 ppm1    8.096  ppm2  0.720
ASSI {10001}
((segid "PROT" and resid 79 and name HN))
((segid "PROT" and resid 78 and name HB2))
 3.100  2.400  2.400 peak     10001 weight  0.10000E+01 volume  0.25858E+01 ppm1    8.098  ppm2  0.451
ASSI {10011}
((segid "PROT" and resid 79 and name HN))
(segid "PROT" and resid 78 and name HD1%)
 3.500  3.100  2.000 peak     10011 weight  0.10000E+01 volume  0.13409E+01 ppm1    8.094  ppm2  0.067
ASSI {10021}
((segid "PROT" and resid 36 and name HN))
((segid "PROT" and resid 56 and name HN))
 3.500  3.100  2.000 peak     10021 weight  0.10000E+01 volume  0.12688E+01 ppm1    7.690  ppm2  9.127
ASSI {10041}
((segid "PROT" and resid 36 and name HN))
((segid "PROT" and resid 34 and name HA))
 3.500  3.100  2.000 peak     10041 weight  0.10000E+01 volume  0.13356E+01 ppm1    7.691  ppm2  4.975
ASSI {10051}
((segid "PROT" and resid 36 and name HN))
((segid "PROT" and resid 36 and name HA))
 2.700  1.800  1.800 peak     10051 weight  0.10000E+01 volume  0.61193E+01 ppm1    7.691  ppm2  4.846
ASSI {10061}
((segid "PROT" and resid 36 and name HN))
((segid "PROT" and resid 55 and name HA))
 3.000  2.200  2.200 peak     10061 weight  0.10000E+01 volume  0.33550E+01 ppm1    7.693  ppm2  4.744
ASSI {10071}
((segid "PROT" and resid 36 and name HN))
((segid "PROT" and resid 35 and name HA))
 3.000  2.200  2.200 peak     10071 weight  0.10000E+01 volume  0.33318E+01 ppm1    7.692  ppm2  4.310
ASSI {10081}
((segid "PROT" and resid 36 and name HN))
((segid "PROT" and resid 36 and name HG1))
 2.400  1.400  1.400 peak     10081 weight  0.10000E+01 volume  0.12415E+02 ppm1    7.692  ppm2  2.186
ASSI {10091}
((segid "PROT" and resid 36 and name HN))
((segid "PROT" and resid 36 and name HB2))
 2.600  1.700  1.700 peak     10091 weight  0.10000E+01 volume  0.75637E+01 ppm1    7.691  ppm2  1.775
ASSI {10101}
((segid "PROT" and resid 36 and name HN))
((segid "PROT" and resid 57 and name HN))
 3.600  3.200  1.900 peak     10101 weight  0.10000E+01 volume  0.11945E+01 ppm1    7.686  ppm2  8.787
ASSI {10111}
((segid "PROT" and resid 36 and name HN))
((segid "PROT" and resid 37 and name HD1))
 3.300  2.700  2.200 peak     10111 weight  0.10000E+01 volume  0.19817E+01 ppm1    7.685  ppm2  3.675
ASSI {10121}
((segid "PROT" and resid 36 and name HN))
((segid "PROT" and resid 35 and name HG1))
 3.400  2.900  2.100 peak     10121 weight  0.10000E+01 volume  0.16945E+01 ppm1    7.688  ppm2  2.874
ASSI {10131}
((segid "PROT" and resid 47 and name HN))
((segid "PROT" and resid 53 and name HD1))
 3.200  2.600  2.300 peak     10131 weight  0.10000E+01 volume  0.23466E+01 ppm1    8.421  ppm2  3.609
ASSI {10151}
((segid "PROT" and resid 94 and name HN))
((segid "PROT" and resid 94 and name HA))
 2.600  1.700  1.700 peak     10151 weight  0.10000E+01 volume  0.75591E+01 ppm1    8.402  ppm2  4.230
ASSI {10161}
((segid "PROT" and resid 94 and name HN))
((segid "PROT" and resid 96 and name HB2))
 3.000  2.200  2.200 peak     10161 weight  0.10000E+01 volume  0.31379E+01 ppm1    8.397  ppm2  2.566

TABLE 13-continued

| Unambiguous NOE Distance Restraints |
|---|

ASSI {10171}
((segid "PROT" and resid 94 and name HN))
((segid "PROT" and resid 90 and name HB1))
  3.200  2.600  2.300 peak    10171 weight  0.10000E+01 volume  0.22427E+01 ppm1    8.405 ppm2  2.336
ASSI {10181}
((segid "PROT" and resid 94 and name HN))
((segid "PROT" and resid 94 and name HG1))
  2.600  1.700  1.700 peak    10181 weight  0.10000E+01 volume  0.83426E+01 ppm1    8.401 ppm2  2.236
ASSI {10201}
((segid "PROT" and resid 94 and name HN))
((segid "PROT" and resid 94 and name HB2))
  2.500  1.600  1.600 peak    10201 weight  0.10000E+01 volume  0.92976E+01 ppm1    8.402 ppm2  1.989
ASSI {10211}
((segid "PROT" and resid 94 and name HN))
((segid "PROT" and resid 97 and name HG1))
  3.600  3.200  1.900 peak    10211 weight  0.10000E+01 volume  0.12042E+01 ppm1    8.403 ppm2  1.853
ASSI {10231}
((segid "PROT" and resid 20 and name HN))
((segid "PROT" and resid 22 and name HN))
  3.300  2.700  2.200 peak    10231 weight  0.10000E+01 volume  0.19933E+01 ppm1    7.546 ppm2  8.853
ASSI {10241}
((segid "PROT" and resid 20 and name HN))
((segid "PROT" and resid 19 and name HN))
  2.500  1.600  1.600 peak    10241 weight  0.10000E+01 volume  0.93544E+01 ppm1    7.545 ppm2  8.569
ASSI {10251}
((segid "PROT" and resid 20 and name HN))
((segid "PROT" and resid 21 and name HN))
  2.500  1.600  1.600 peak    10251 weight  0.10000E+01 volume  0.94546E+01 ppm1    7.546 ppm2  7.924
ASSI {10261}
((segid "PROT" and resid 20 and name HN))
((segid "PROT" and resid 18 and name HN))
  3.300  2.700  2.200 peak    10261 weight  0.10000E+01 volume  0.18399E+01 ppm1    7.547 ppm2  8.489
ASSI {10281}
((segid "PROT" and resid 20 and name HN))
((segid "PROT" and resid 20 and name HA))
  2.600  1.700  1.700 peak    10281 weight  0.10000E+01 volume  0.89922E+01 ppm1    7.547 ppm2  4.302
ASSI {10291}
((segid "PROT" and resid 20 and name HN))
((segid "PROT" and resid 16 and name HA))
  2.900  2.100  2.100 peak    10291 weight  0.10000E+01 volume  0.38903E+01 ppm1    7.547 ppm2  4.188
ASSI {10301}
((segid "PROT" and resid 20 and name HN))
((segid "PROT" and resid 20 and name HB1))
  2.200  1.200  1.200 peak    10301 weight  0.10000E+01 volume  0.20909E+02 ppm1    7.546 ppm2  4.077
ASSI {10311}
((segid "PROT" and resid 20 and name HN))
((segid "PROT" and resid 17 and name HA))
  2.700  1.800  1.800 peak    10311 weight  0.10000E+01 volume  0.67614E+01 ppm1    7.547 ppm2  3.948
ASSI {10321}
((segid "PROT" and resid 20 and name HN))
((segid "PROT" and resid 21 and name HA))
  3.400  2.900  2.100 peak    10321 weight  0.10000E+01 volume  0.17488E+01 ppm1    7.547 ppm2  3.788
ASSI {10331}
((segid "PROT" and resid 20 and name HN))
((segid "PROT" and resid 21 and name HB))
  3.400  2.900  2.100 peak    10331 weight  0.10000E+01 volume  0.16067E+01 ppm1    7.546 ppm2  1.925
ASSI {10341}
((segid "PROT" and resid 20 and name HN))
((segid "PROT" and resid 19 and name HB1))
  2.600  1.700  1.700 peak    10341 weight  0.10000E+01 volume  0.76773E+01 ppm1    7.545 ppm2  1.708
ASSI {10351}
((segid "PROT" and resid 20 and name HN))
((segid "PROT" and resid 19 and name HB2))
  2.900  2.100  2.100 peak    10351 weight  0.10000E+01 volume  0.42261E+01 ppm1    7.546 ppm2  1.379
ASSI {10361}
((segid "PROT" and resid 20 and name HN))
((segid "PROT" and resid 19 and name HG1))
  2.900  2.100  2.100 peak    10361 weight  0.10000E+01 volume  0.44504E+01 ppm1    7.547 ppm2  1.283
ASSI {10371}
((segid "PROT" and resid 20 and name HN))
(segid "PROT" and resid 17 and name HG2%)
  3.400  2.900  2.100 peak    10371 weight  0.10000E+01 volume  0.15554E+01 ppm1    7.549 ppm2  1.166
ASSI {10391}
((segid "PROT" and resid 20 and name HN))
((segid "PROT" and resid 19 and name HA))
  3.000  2.200  2.200 peak    10391 weight  0.10000E+01 volume  0.34252E+01 ppm1    7.543 ppm2  3.696

TABLE 13-continued

Unambiguous NOE Distance Restraints

ASSI {10401}
((segid "PROT" and resid 20 and name HN))
((segid "PROT" and resid 21 and name HG12))
 3.300  2.700  2.200 peak     10401 weight  0.10000E+01 volume  0.17938E+01 ppm1    7.542  ppm2   1.039
ASSI {10411}
((segid "PROT" and resid 34 and name HN))
((segid "PROT" and resid 35 and name HN))
 2.300  1.300  1.300 peak     10411 weight  0.10000E+01 volume  0.15055E+02 ppm1    7.612  ppm2   7.150
ASSI {10421}
((segid "PROT" and resid 34 and name HN))
((segid "PROT" and resid 34 and name HA))
 3.000  2.200  2.200 peak     10421 weight  0.10000E+01 volume  0.34973E+01 ppm1    7.614  ppm2   4.977
ASSI {10431}
((segid "PROT" and resid 34 and name HN))
((segid "PROT" and resid 32 and name HA))
 3.200  2.600  2.300 peak     10431 weight  0.10000E+01 volume  0.22167E+01 ppm1    7.615  ppm2   4.402
ASSI {10441}
((segid "PROT" and resid 34 and name HN))
((segid "PROT" and resid 34 and name HB1))
 3.000  2.200  2.200 peak     10441 weight  0.10000E+01 volume  0.31345E+01 ppm1    7.614  ppm2   3.488
ASSI {10451}
((segid "PROT" and resid 34 and name HN))
((segid "PROT" and resid 35 and name HG1))
 3.100  2.400  2.400 peak     10451 weight  0.10000E+01 volume  0.30809E+01 ppm1    7.612  ppm2   2.867
ASSI {10461}
((segid "PROT" and resid 34 and name HN))
((segid "PROT" and resid 34 and name HB2))
 2.800  2.000  2.000 peak     10461 weight  0.10000E+01 volume  0.48777E+01 ppm1    7.612  ppm2   2.596
ASSI {10471}
((segid "PROT" and resid 34 and name HN))
((segid "PROT" and resid 33 and name HD1))
 2.900  2.100  2.100 peak     10471 weight  0.10000E+01 volume  0.40744E+01 ppm1    7.614  ppm2   2.227
ASSI {10481}
((segid "PROT" and resid 34 and name HN))
((segid "PROT" and resid 56 and name HG))
 3.200  2.600  2.300 peak     10481 weight  0.10000E+01 volume  0.22953E+01 ppm1    7.611  ppm2   1.734
ASSI {10491}
((segid "PROT" and resid 34 and name HN))
((segid "PROT" and resid 33 and name HD2))
 3.400  2.900  2.100 peak     10491 weight  0.10000E+01 volume  0.17403E+01 ppm1    7.613  ppm2   1.555
ASSI {10501}
((segid "PROT" and resid 34 and name HN))
((segid "PROT" and resid 33 and name HB1))
 3.400  2.900  2.100 peak     10501 weight  0.10000E+01 volume  0.15736E+01 ppm1    7.611  ppm2   1.022
ASSI {10521}
((segid "PROT" and resid 34 and name HN))
(segid "PROT" and resid 81 and name HG2%)
 3.500  3.100  2.000 peak     10521 weight  0.10000E+01 volume  0.13578E+01 ppm1    7.614  ppm2   0.128
ASSI {10531}
((segid "PROT" and resid 34 and name HN))
((segid "PROT" and resid 33 and name HB2))
 3.500  3.100  2.000 peak     10531 weight  0.10000E+01 volume  0.13341E+01 ppm1    7.613  ppm2  −0.480
ASSI {10541}
((segid "PROT" and resid 92 and name HN))
((segid "PROT" and resid 92 and name HA))
 3.500  3.100  2.000 peak     10541 weight  0.10000E+01 volume  0.12495E+01 ppm1    8.471  ppm2   4.224
ASSI {10551}
((segid "PROT" and resid 92 and name HN))
((segid "PROT" and resid 90 and name HD1))
 3.100  2.400  2.400 peak     10551 weight  0.10000E+01 volume  0.27898E+01 ppm1    8.475  ppm2   4.115
ASSI {10561}
((segid "PROT" and resid 47 and name HN))
((segid "PROT" and resid 47 and name HB1))
 3.200  2.600  2.300 peak     10561 weight  0.10000E+01 volume  0.23977E+01 ppm1    8.473  ppm2   3.212
ASSI {10571}
((segid "PROT" and resid 92 and name HN))
((segid "PROT" and resid 92 and name HG1))
 3.200  2.600  2.300 peak     10571 weight  0.10000E+01 volume  0.22443E+01 ppm1    8.476  ppm2   2.389
ASSI {10581}
((segid "PROT" and resid 47 and name HN))
((segid "PROT" and resid 46 and name HN))
 3.100  2.400  2.400 peak     10581 weight  0.10000E+01 volume  0.29705E+01 ppm1    8.469  ppm2   8.038
ASSI {10601}
((segid "PROT" and resid 92 and name HN))
((segid "PROT" and resid 96 and name HN))
 3.400  2.900  2.100 peak     10601 weight  0.10000E+01 volume  0.16185E+01 ppm1    8.470  ppm2   7.383

TABLE 13-continued

Unambiguous NOE Distance Restraints

ASSI {10621}
((segid "PROT" and resid 47 and name HN))
((segid "PROT" and resid 47 and name HB2))
  3.000  2.200  2.200 peak    10621  weight  0.10000E+01 volume  0.34111E+01 ppm1    8.468  ppm2  2.819
ASSI {10631}
((segid "PROT" and resid 34 and name HN))
((segid "PROT" and resid 33 and name HA))
  3.300  2.700  2.200 peak    10631  weight  0.10000E+01 volume  0.18895E+01 ppm1    7.619  ppm2  3.944
ASSI {10641}
((segid "PROT" and resid 65 and name HD21))
((segid "PROT" and resid 65 and name HB2))
  3.200  2.600  2.300 peak    10641  weight  0.10000E+01 volume  0.22232E+01 ppm1    7.608  ppm2  2.798
ASSI {10651}
((segid "PROT" and resid 34 and name HN))
((segid "PROT" and resid 56 and name HB1))
  3.400  2.900  2.100 peak    10651  weight  0.10000E+01 volume  0.16335E+01 ppm1    7.613  ppm2  2.105
ASSI {10661}
((segid "PROT" and resid 65 and name HD21))
((segid "PROT" and resid 65 and name HD22))
  2.200  1.200  1.200 peak    10661  weight  0.10000E+01 volume  0.19920E+02 ppm1    7.602  ppm2  6.975
ASSI {10671}
((segid "PROT" and resid 65 and name HD21))
((segid "PROT" and resid 65 and name HB1))
  3.400  2.900  2.100 peak    10671  weight  0.10000E+01 volume  0.16947E+01 ppm1    7.608  ppm2  3.037
ASSI {10691}
((segid "PROT" and resid 65 and name HD22))
((segid "PROT" and resid 65 and name HB1))
  3.500  3.100  2.000 peak    10691  weight  0.10000E+01 volume  0.13236E+01 ppm1    6.963  ppm2  3.024
ASSI {10701}
((segid "PROT" and resid 32 and name HE1))
((segid "PROT" and resid 32 and name HD1))
  2.600  1.700  1.700 peak    10701  weight  0.10000E+01 volume  0.72566E+01 ppm1   10.416  ppm2  7.865
ASSI {10731}
((segid "PROT" and resid 32 and name HE1))
((segid "PROT" and resid 30 and name HA))
  3.200  2.600  2.300 peak    10731  weight  0.10000E+01 volume  0.23935E+01 ppm1   10.418  ppm2  4.831
ASSI {10741}
((segid "PROT" and resid 32 and name HE1))
((segid "PROT" and resid 32 and name HB2))
  3.500  3.100  2.000 peak    10741  weight  0.10000E+01 volume  0.12701E+01 ppm1   10.417  ppm2  3.361
ASSI {10771}
((segid "PROT" and resid 32 and name HE1))
((segid "PROT" and resid 32 and name HE3))
  3.100  2.400  2.400 peak    10771  weight  0.10000E+01 volume  0.27416E+01 ppm1   10.414  ppm2  7.340
ASSI {10791}
((segid "PROT" and resid 32 and name HE1))
((segid "PROT" and resid 29 and name HG2))
  3.400  2.900  2.100 peak    10791  weight  0.10000E+01 volume  0.16873E+01 ppm1   10.419  ppm2  2.423
ASSI {10801}
((segid "PROT" and resid 16 and name HN))
(segid "PROT" and resid 15 and name HD%)
  3.200  2.600  2.300 peak    10801  weight  0.10000E+01 volume  0.22526E+01 ppm1    8.194  ppm2  7.068
ASSI {10821}
((segid "PROT" and resid 16 and name HN))
((segid "PROT" and resid 15 and name HN))
  2.600  1.700  1.700 peak    10821  weight  0.10000E+01 volume  0.86346E+01 ppm1    8.190  ppm2  7.998
ASSI {10851}
((segid "PROT" and resid 16 and name HN))
((segid "PROT" and resid 12 and name HA))
  2.700  1.800  1.800 peak    10851  weight  0.10000E+01 volume  0.66059E+01 ppm1    8.188  ppm2  4.738
ASSI {10861}
((segid "PROT" and resid 16 and name HN))
((segid "PROT" and resid 16 and name HA))
  2.900  2.100  2.100 peak    10861  weight  0.10000E+01 volume  0.42394E+01 ppm1    8.186  ppm2  4.176
ASSI {10871}
((segid "PROT" and resid 16 and name HN))
((segid "PROT" and resid 16 and name HB1))
  2.300  1.300  1.300 peak    10871  weight  0.10000E+01 volume  0.15224E+02 ppm1    8.189  ppm2  4.023
ASSI {10881}
((segid "PROT" and resid 16 and name HN))
((segid "PROT" and resid 16 and name HB2))
  2.500  1.600  1.600 peak    10881  weight  0.10000E+01 volume  0.91687E+01 ppm1    8.190  ppm2  3.935
ASSI {10891}
((segid "PROT" and resid 16 and name HN))
((segid "PROT" and resid 15 and name HB1))
  2.900  2.100  2.100 peak    10891  weight  0.10000E+01 volume  0.40710E+01 ppm1    8.189  ppm2  3.220

TABLE 13-continued

Unambiguous NOE Distance Restraints

ASSI {10901}
((segid "PROT" and resid 16 and name HN))
((segid "PROT" and resid 15 and name HB2))
  2.700  1.800  1.800 peak    10901 weight  0.10000E+01 volume  0.61026E+01 ppm1    8.190 ppm2  3.051
ASSI {10911}
((segid "PROT" and resid 16 and name HN))
((segid "PROT" and resid 18 and name HG))
  3.600  3.200  1.900 peak    10911 weight  0.10000E+01 volume  0.12027E+01 ppm1    8.188 ppm2  1.683
ASSI {10931}
((segid "PROT" and resid 16 and name HN))
((segid "PROT" and resid 17 and name HB))
  3.400  2.900  2.100 peak    10931 weight  0.10000E+01 volume  0.16655E+01 ppm1    8.186 ppm2  4.263
ASSI {10951}
((segid "PROT" and resid 29 and name HE21))
((segid "PROT" and resid 29 and name HE22))
  2.000  1.000  1.000 peak    10951 weight  0.10000E+01 volume  0.39167E+02 ppm1    7.574 ppm2  6.873
ASSI {11041}
((segid "PROT" and resid 70 and name HN))
((segid "PROT" and resid 69 and name HN))
  2.500  1.600  1.600 peak    11041 weight  0.10000E+01 volume  0.10515E+02 ppm1    7.446 ppm2  7.703
ASSI {11051}
((segid "PROT" and resid 70 and name HN))
(segid "PROT" and resid 68 and name HD%)
  3.400  2.900  2.100 peak    11051 weight  0.10000E+01 volume  0.15733E+01 ppm1    7.448 ppm2  7.174
ASSI {11061}
((segid "PROT" and resid 70 and name HN))
((segid "PROT" and resid 74 and name HN))
  3.500  3.100  2.000 peak    11061 weight  0.10000E+01 volume  0.14404E+01 ppm1    7.452 ppm2  6.918
ASSI {11071}
((segid "PROT" and resid 70 and name HN))
((segid "PROT" and resid 68 and name HA))
  2.900  2.100  2.100 peak    11071 weight  0.10000E+01 volume  0.37994E+01 ppm1    7.449 ppm2  4.548
ASSI {11081}
((segid "PROT" and resid 70 and name HN))
((segid "PROT" and resid 70 and name HB1))
  3.000  2.200  2.200 peak    11081 weight  0.10000E+01 volume  0.32723E+01 ppm1    7.445 ppm2  4.226
ASSI {11091}
((segid "PROT" and resid 70 and name HN))
((segid "PROT" and resid 70 and name HB2))
  3.000  2.200  2.200 peak    11091 weight  0.10000E+01 volume  0.35063E+01 ppm1    7.446 ppm2  3.774
ASSI {11101}
((segid "PROT" and resid 70 and name HN))
((segid "PROT" and resid 68 and name HB2))
  3.400  2.900  2.100 peak    11101 weight  0.10000E+01 volume  0.16583E+01 ppm1    7.446 ppm2  2.935
ASSI {11111}
((segid "PROT" and resid 70 and name HN))
((segid "PROT" and resid 73 and name HB1))
  3.100  2.400  2.400 peak    11111 weight  0.10000E+01 volume  0.29172E+01 ppm1    7.446 ppm2  2.000
ASSI {11121}
((segid "PROT" and resid 70 and name HN))
((segid "PROT" and resid 73 and name HB2))
  3.100  2.400  2.400 peak    11121 weight  0.10000E+01 volume  0.26620E+01 ppm1    7.447 ppm2  1.894
ASSI {11131}
((segid "PROT" and resid 70 and name HN))
(segid "PROT" and resid 14 and name HD2%)
  2.500  1.600  1.600 peak    11131 weight  0.10000E+01 volume  0.11170E+02 ppm1    7.446 ppm2  0.836
ASSI {11141}
((segid "PROT" and resid 70 and name HN))
((segid "PROT" and resid 69 and name HA))
  2.900  2.100  2.100 peak    11141 weight  0.10000E+01 volume  0.44901E+01 ppm1    7.445 ppm2  4.097
ASSI {11151}
((segid "PROT" and resid 70 and name HN))
((segid "PROT" and resid 69 and name HB))
  3.200  2.600  2.300 peak    11151 weight  0.10000E+01 volume  0.25399E+01 ppm1    7.445 ppm2  2.326
ASSI {11161}
((segid "PROT" and resid 70 and name HN))
((segid "PROT" and resid 73 and name HG))
  3.400  2.900  2.100 peak    11161 weight  0.10000E+01 volume  0.15757E+01 ppm1    7.443 ppm2  1.769
ASSI {11171}
((segid "PROT" and resid 70 and name HN))
(segid "PROT" and resid 73 and name HD1%)
  2.500  1.600  1.600 peak    11171 weight  0.10000E+01 volume  0.10896E+02 ppm1    7.445 ppm2  0.952
ASSI {11181}
((segid "PROT" and resid 79 and name HE21))
((segid "PROT" and resid 79 and name HE22))
  2.100  1.100  1.100 peak    11181 weight  0.10000E+01 volume  0.30858E+02 ppm1    7.315 ppm2  7.232

TABLE 13-continued

Unambiguous NOE Distance Restraints

ASSI {11191}
((segid "PROT" and resid 79 and name HE21))
((segid "PROT" and resid 79 and name HG1))
  3.000  2.200  2.200 peak    11191  weight  0.10000E+01 volume  0.31916E+01 ppm1    7.310 ppm2  2.457
ASSI {11221}
((segid "PROT" and resid 79 and name HE22))
((segid "PROT" and resid 79 and name HG1))
  3.500  3.100  2.000 peak    11221  weight  0.10000E+01 volume  0.13222E+01 ppm1    7.232 ppm2  2.458
ASSI {11231}
((segid "PROT" and resid 27 and name HN))
((segid "PROT" and resid 26 and name HN))
  2.600  1.700  1.700 peak    11231  weight  0.10000E+01 volume  0.89340E+01 ppm1    7.552 ppm2  8.572
ASSI {11241}
((segid "PROT" and resid 27 and name HN))
((segid "PROT" and resid 27 and name HA))
  2.700  1.800  1.800 peak    11241  weight  0.10000E+01 volume  0.63843E+01 ppm1    7.552 ppm2  4.465
ASSI {11251}
((segid "PROT" and resid 27 and name HN))
((segid "PROT" and resid 24 and name HA))
  3.000  2.200  2.200 peak    11251  weight  0.10000E+01 volume  0.31959E+01 ppm1    7.551 ppm2  4.188
ASSI {11261}
((segid "PROT" and resid 27 and name HN))
((segid "PROT" and resid 28 and name HB1))
  3.500  3.100  2.000 peak    11261  weight  0.10000E+01 volume  0.14785E+01 ppm1    7.552 ppm2  2.997
ASSI {11271}
((segid "PROT" and resid 27 and name HN))
((segid "PROT" and resid 28 and name HB2))
  3.500  3.100  2.000 peak    11271  weight  0.10000E+01 volume  0.13992E+01 ppm1    7.554 ppm2  2.778
ASSI {11291}
((segid "PROT" and resid 27 and name HN))
(segid "PROT" and resid 31 and name HB%)
  3.400  2.900  2.100 peak    11291  weight  0.10000E+01 volume  0.14984E+01 ppm1    7.553 ppm2  1.733
ASSI {11301}
((segid "PROT" and resid 27 and name HN))
((segid "PROT" and resid 27 and name HB1))
  2.400  1.400  1.400 peak    11301  weight  0.10000E+01 volume  0.12213E+02 ppm1    7.551 ppm2  4.034
ASSI {11311}
((segid "PROT" and resid 27 and name HN))
((segid "PROT" and resid 26 and name HA))
  2.900  2.100  2.100 peak    11311  weight  0.10000E+01 volume  0.39762E+01 ppm1    7.550 ppm2  3.908
ASSI {11321}
((segid "PROT" and resid 27 and name HN))
((segid "PROT" and resid 26 and name HB1))
  2.800  2.000  2.000 peak    11321  weight  0.10000E+01 volume  0.48756E+01 ppm1    7.551 ppm2  1.892
ASSI {11331}
((segid "PROT" and resid 24 and name HE21))
((segid "PROT" and resid 24 and name HE22))
  2.100  1.100  1.100 peak    11331  weight  0.10000E+01 volume  0.25925E+02 ppm1    7.026 ppm2  6.911
ASSI {11341}
((segid "PROT" and resid 24 and name HE21))
((segid "PROT" and resid 24 and name HG1))
  3.200  2.600  2.300 peak    11341  weight  0.10000E+01 volume  0.24518E+01 ppm1    7.025 ppm2  2.863
ASSI {11351}
((segid "PROT" and resid 24 and name HE21))
((segid "PROT" and resid 24 and name HG2))
  3.400  2.900  2.100 peak    11351  weight  0.10000E+01 volume  0.16618E+01 ppm1    7.026 ppm2  2.481
ASSI {11371}
((segid "PROT" and resid 24 and name HE22))
((segid "PROT" and resid 24 and name HG1))
  3.600  3.200  1.900 peak    11371  weight  0.10000E+01 volume  0.11102E+01 ppm1    6.903 ppm2  2.863
ASSI {11381}
((segid "PROT" and resid 39 and name HN))
((segid "PROT" and resid 39 and name HG2))
  3.000  2.200  2.200 peak    11381  weight  0.10000E+01 volume  0.31902E+01 ppm1    9.090 ppm2  1.449
ASSI {11391}
((segid "PROT" and resid 39 and name HN))
((segid "PROT" and resid 38 and name HN))
  3.600  3.200  1.900 peak    11391  weight  0.10000E+01 volume  0.11942E+01 ppm1    9.087 ppm2  8.338
ASSI {11401}
((segid "PROT" and resid 39 and name HN))
((segid "PROT" and resid 39 and name HA))
  3.100  2.400  2.400 peak    11401  weight  0.10000E+01 volume  0.26384E+01 ppm1    9.083 ppm2  4.436
ASSI {11411}
((segid "PROT" and resid 39 and name HN))
((segid "PROT" and resid 38 and name HA))
  2.300  1.300  1.300 peak    11411  weight  0.10000E+01 volume  0.15682E+02 ppm1    9.086 ppm2  3.475

TABLE 13-continued

Unambiguous NOE Distance Restraints

ASSI {11431}
((segid "PROT" and resid 39 and name HN))
((segid "PROT" and resid 39 and name HB1))
  3.300  2.700  2.200 peak    11431 weight  0.10000E+01 volume  0.18750E+01 ppm1    9.085  ppm2    2.033
ASSI {11441}
((segid "PROT" and resid 39 and name HN))
((segid "PROT" and resid 39 and name HB2))
  3.000  2.200  2.200 peak    11441 weight  0.10000E+01 volume  0.37080E+01 ppm1    9.083  ppm2    1.911
ASSI {11451}
((segid "PROT" and resid 39 and name HN))
((segid "PROT" and resid 39 and name HD2))
  2.500  1.600  1.600 peak    11451 weight  0.10000E+01 volume  0.93310E+01 ppm1    9.086  ppm2    1.639
ASSI {11461}
((segid "PROT" and resid 39 and name HN))
((segid "PROT" and resid 38 and name HB))
  3.500  3.100  2.000 peak    11461 weight  0.10000E+01 volume  0.12532E+01 ppm1    9.086  ppm2    1.057
ASSI {11471}
((segid "PROT" and resid 39 and name HN))
(segid "PROT" and resid 38 and name HG1%)
  3.100  2.400  2.400 peak    11471 weight  0.10000E+01 volume  0.26696E+01 ppm1    9.082  ppm2    0.470
ASSI {11481}
((segid "PROT" and resid 39 and name HN))
(segid "PROT" and resid 38 and name HG2%)
  2.800  2.000  2.000 peak    11481 weight  0.10000E+01 volume  0.55974E+01 ppm1    9.085  ppm2   −0.027
ASSI {11491}
((segid "PROT" and resid 76 and name HN))
((segid "PROT" and resid 78 and name HN))
  2.600  1.700  1.700 peak    11491 weight  0.10000E+01 volume  0.88670E+01 ppm1    8.020  ppm2    7.383
ASSI {11511}
((segid "PROT" and resid 110 and name HN))
((segid "PROT" and resid 111 and name HB1))
  3.400  2.900  2.100 peak    11511 weight  0.10000E+01 volume  0.16849E+01 ppm1    8.123  ppm2    1.889
ASSI {11531}
((segid "PROT" and resid 31 and name HN))
((segid "PROT" and resid 29 and name HA))
  3.100  2.400  2.400 peak    11531 weight  0.10000E+01 volume  0.30332E+01 ppm1    7.915  ppm2    4.219
ASSI {11541}
((segid "PROT" and resid 31 and name HN))
((segid "PROT" and resid 98 and name HB1))
  3.500  3.100  2.000 peak    11541 weight  0.10000E+01 volume  0.14720E+01 ppm1    7.918  ppm2    3.384
ASSI {11551}
((segid "PROT" and resid 31 and name HN))
((segid "PROT" and resid 30 and name HB2))
  3.300  2.700  2.200 peak    11551 weight  0.10000E+01 volume  0.20522E+01 ppm1    7.914  ppm2    3.975
ASSI {11561}
((segid "PROT" and resid 87 and name HN))
((segid "PROT" and resid 87 and name HB2))
  2.600  1.700  1.700 peak    11561 weight  0.10000E+01 volume  0.79508E+01 ppm1    7.951  ppm2    2.048
ASSI {11571}
((segid "PROT" and resid 75 and name HN))
((segid "PROT" and resid 77 and name HN))
  3.400  2.900  2.100 peak    11571 weight  0.10000E+01 volume  0.16867E+01 ppm1    8.505  ppm2    7.389
ASSI {11581}
((segid "PROT" and resid 12 and name HN))
((segid "PROT" and resid 15 and name HB1))
  3.600  3.200  1.900 peak    11581 weight  0.10000E+01 volume  0.10787E+01 ppm1    8.421  ppm2    3.231
ASSI {11591}
((segid "PROT" and resid 112 and name HN))
((segid "PROT" and resid 110 and name HA))
  3.400  2.900  2.100 peak    11591 weight  0.10000E+01 volume  0.17506E+01 ppm1    8.062  ppm2    3.881
ASSI {11611}
((segid "PROT" and resid 9 and name HN))
((segid "PROT" and resid 9 and name HB2))
  2.900  2.100  2.100 peak    11611 weight  0.10000E+01 volume  0.44369E+01 ppm1    8.447  ppm2    1.837
ASSI {11621}
((segid "PROT" and resid 63 and name HN))
((segid "PROT" and resid 63 and name HA))
  3.000  2.200  2.200 peak    11621 weight  0.10000E+01 volume  0.36776E+01 ppm1    8.888  ppm2    4.695
ASSI {11631}
((segid "PROT" and resid 55 and name HN))
((segid "PROT" and resid 56 and name HA))
  3.000  2.200  2.200 peak    11631 weight  0.10000E+01 volume  0.35373E+01 ppm1    7.381  ppm2    4.088
ASSI {11641}
((segid "PROT" and resid 55 and name HN))
(segid "PROT" and resid 54 and name HE%)
  2.800  2.000  2.000 peak    11641 weight  0.10000E+01 volume  0.49789E+01 ppm1    7.384  ppm2    1.984

TABLE 13-continued

Unambiguous NOE Distance Restraints

```
ASSI {11651}
((segid "PROT" and resid 55 and name HN))
((segid "PROT" and resid 59 and name HB2))
  2.900  2.100   2.100 peak     11651 weight  0.10000E+01 volume  0.46532E+01 ppm1   7.383 ppm2   1.876
ASSI {11661}
((segid "PROT" and resid 27 and name HN))
(segid "PROT" and resid 25 and name HG2%)
  3.600  3.200   1.900 peak     11661 weight  0.10000E+01 volume  0.11987E+01 ppm1   7.554 ppm2   1.036
ASSI {11681}
((segid "PROT" and resid 94 and name HN))
((segid "PROT" and resid 97 and name HG2))
  2.900  2.100   2.100 peak     11681 weight  0.10000E+01 volume  0.38242E+01 ppm1   8.402 ppm2   1.585
ASSI {11691}
((segid "PROT" and resid 24 and name HN))
((segid "PROT" and resid 23 and name HA))
  3.000  2.200   2.200 peak     11691 weight  0.10000E+01 volume  0.35931E+01 ppm1   8.042 ppm2   4.044
ASSI {11701}
((segid "PROT" and resid 15 and name HN))
((segid "PROT" and resid 13 and name HA))
  3.200  2.600   2.300 peak     11701 weight  0.10000E+01 volume  0.21533E+01 ppm1   7.997 ppm2   4.181
ASSI {11711}
((segid "PROT" and resid 29 and name HN))
((segid "PROT" and resid 31 and name HN))
  3.700  3.400   1.800 peak     11711 weight  0.10000E+01 volume  0.91890E+00 ppm1   8.580 ppm2   7.899
ASSI {11731}
((segid "PROT" and resid 82 and name HN))
((segid "PROT" and resid 80 and name HA))
  3.700  3.400   1.800 peak     11731 weight  0.10000E+01 volume  0.10073E+01 ppm1   6.398 ppm2   4.050
ASSI {11741}
((segid "PROT" and resid 82 and name HN))
((segid "PROT" and resid 78 and name HA))
  3.600  3.200   1.900 peak     11741 weight  0.10000E+01 volume  0.10688E+01 ppm1   6.397 ppm2   3.388
ASSI {11761}
((segid "PROT" and resid 70 and name HN))
((segid "PROT" and resid 68 and name HB1))
  3.700  3.400   1.800 peak     11761 weight  0.10000E+01 volume  0.91320E+00 ppm1   7.444 ppm2   3.074
ASSI {11781}
((segid "PROT" and resid 32 and name HE1))
((segid "PROT" and resid 32 and name HB1))
  3.700  3.400   1.800 peak     11781 weight  0.10000E+01 volume  0.93370E+00 ppm1  10.419 ppm2   3.640
ASSI {11791}
((segid "PROT" and resid 34 and name HN))
((segid "PROT" and resid 33 and name HG1))
  3.700  3.400   1.800 peak     11791 weight  0.10000E+01 volume  0.92660E+00 ppm1   7.615 ppm2   0.252
ASSI {11801}
((segid "PROT" and resid 34 and name HN))
(segid "PROT" and resid 102 and name HD1%)
  3.700  3.400   1.800 peak     11801 weight  0.10000E+01 volume  0.92480E+00 ppm1   7.614 ppm2   0.725
ASSI {11811}
((segid "PROT" and resid 39 and name HN))
((segid "PROT" and resid 43 and name HN))
  3.700  3.400   1.800 peak     11811 weight  0.10000E+01 volume  0.96060E+00 ppm1   9.087 ppm2   7.184
ASSI {11851}
((segid "PROT" and resid 27 and name HN))
((segid "PROT" and resid 25 and name HA))
  3.200  2.600   2.300 peak     11851 weight  0.10000E+01 volume  0.21545E+01 ppm1   7.551 ppm2   3.858
ASSI {11941}
((segid "PROT" and resid 34 and name HN))
((segid "PROT" and resid 33 and name HG2))
  3.800  3.600   1.700 peak     11941 weight  0.10000E+01 volume  0.80610E+00 ppm1   7.613 ppm2  -0.888
ASSI {11981}
((segid "PROT" and resid 94 and name HN))
((segid "PROT" and resid 93 and name HA))
  3.700  3.400   1.800 peak     11981 weight  0.10000E+01 volume  0.93310E+00 ppm1   8.401 ppm2   4.504
ASSI {12011}
((segid "PROT" and resid 94 and name HN))
((segid "PROT" and resid 95 and name HA))
  3.300  2.700   2.200 peak     12011 weight  0.10000E+01 volume  0.19064E+01 ppm1   8.402 ppm2   3.667
ASSI {12081}
((segid "PROT" and resid 26 and name HN))
((segid "PROT" and resid 22 and name HA))
  3.400  2.900   2.100 peak     12081 weight  0.10000E+01 volume  0.15330E+01 ppm1   8.575 ppm2   4.116
ASSI {12101}
((segid "PROT" and resid 68 and name HN))
((segid "PROT" and resid 63 and name HB1))
  3.800  3.600   1.700 peak     12101 weight  0.10000E+01 volume  0.88970E+00 ppm1   8.010 ppm2   2.329
```

TABLE 13-continued

Unambiguous NOE Distance Restraints

ASSI {12161}
((segid "PROT" and resid 89 and name HN))
((segid "PROT" and resid 85 and name HA))
  3.600  3.200   1.900 peak     12161 weight  0.10000E+01 volume  0.10598E+01 ppm1     8.123 ppm2  4.469
ASSI {12201}
((segid "PROT" and resid 108 and name HN))
((segid "PROT" and resid 110 and name HG11))
  3.800  3.600   1.700 peak     12201 weight  0.10000E+01 volume  0.82640E+00 ppm1     7.931 ppm2  1.128
ASSI {12221}
((segid "PROT" and resid 49 and name HN))
((segid "PROT" and resid 47 and name HB2))
  3.700  3.400   1.800 peak     12221 weight  0.10000E+01 volume  0.10274E+01 ppm1     7.119 ppm2  2.796
ASSI {12231}
((segid "PROT" and resid 49 and name HN))
((segid "PROT" and resid 48 and name HG1))
  3.500  3.100   2.000 peak     12231 weight  0.10000E+01 volume  0.12697E+01 ppm1     7.117 ppm2  2.362
ASSI {12241}
((segid "PROT" and resid 49 and name HN))
((segid "PROT" and resid 48 and name HG2))
  3.600  3.200   1.900 peak     12241 weight  0.10000E+01 volume  0.11663E+01 ppm1     7.115 ppm2  2.243
ASSI {12251}
((segid "PROT" and resid 49 and name HN))
(segid "PROT" and resid 50 and name HG2%))
  3.900  3.800   1.600 peak     12251 weight  0.10000E+01 volume  0.74400E+00 ppm1     7.114 ppm2  0.391
ASSI {12271}
((segid "PROT" and resid 49 and name HN))
((segid "PROT" and resid 47 and name HN))
  3.700  3.400   1.800 peak     12271 weight  0.10000E+01 volume  0.10061E+01 ppm1     7.113 ppm2  8.447
ASSI {12281}
((segid "PROT" and resid 83 and name HN))
((segid "PROT" and resid 85 and name HN))
  3.700  3.400   1.800 peak     12281 weight  0.10000E+01 volume  0.92080E+00 ppm1     9.095 ppm2  6.900
ASSI {12311}
((segid "PROT" and resid 116 and name HN))
(segid "PROT" and resid 110 and name HD1%))
  3.600  3.200   1.900 peak     12311 weight  0.10000E+01 volume  0.11475E+01 ppm1     7.473 ppm2  0.537
ASSI {12421}
((segid "PROT" and resid 75 and name HN))
((segid "PROT" and resid 78 and name HB2))
  3.700  3.400   1.800 peak     12421 weight  0.10000E+01 volume  0.10440E+01 ppm1     8.512 ppm2  0.470
ASSI {12431}
((segid "PROT" and resid 60 and name HN))
((segid "PROT" and resid 57 and name HN))
  3.800  3.600   1.700 peak     12431 weight  0.10000E+01 volume  0.87300E+00 ppm1     7.958 ppm2  8.813
ASSI {12461}
((segid "PROT" and resid 60 and name HN))
(segid "PROT" and resid 59 and name HE%))
  3.700  3.400   1.800 peak     12461 weight  0.10000E+01 volume  0.95910E+00 ppm1     7.969 ppm2  1.273
ASSI {12501}
((segid "PROT" and resid 82 and name HN))
((segid "PROT" and resid 79 and name HN))
  3.800  3.600   1.700 peak     12501 weight  0.10000E+01 volume  0.79110E+00 ppm1     6.397 ppm2  8.086
ASSI {12541}
((segid "PROT" and resid 86 and name HN))
((segid "PROT" and resid 85 and name HA))
  3.700  3.400   1.800 peak     12541 weight  0.10000E+01 volume  0.10186E+01 ppm1     7.830 ppm2  4.477
ASSI {12551}
((segid "PROT" and resid 86 and name HN))
((segid "PROT" and resid 84 and name HA))
  3.400  2.900   2.100 peak     12551 weight  0.10000E+01 volume  0.15928E+01 ppm1     7.829 ppm2  4.336
ASSI {12561}
((segid "PROT" and resid 86 and name HN))
((segid "PROT" and resid 87 and name HB1))
  3.700  3.400   1.800 peak     12561 weight  0.10000E+01 volume  0.10415E+01 ppm1     7.830 ppm2  2.209
ASSI {12621}
((segid "PROT" and resid 85 and name HN))
((segid "PROT" and resid 83 and name HA))
  3.700  3.400   1.800 peak     12621 weight  0.10000E+01 volume  0.92730E+00 ppm1     6.910 ppm2  3.853
ASSI {12651}
((segid "PROT" and resid 85 and name HN))
((segid "PROT" and resid 86 and name HG1))
  3.800  3.600   1.700 peak     12651 weight  0.10000E+01 volume  0.89670E+00 ppm1     6.907 ppm2  1.311
ASSI {12661}
((segid "PROT" and resid 85 and name HN))
((segid "PROT" and resid 86 and name HG2))
  3.900  3.800   1.600 peak     12661 weight  0.10000E+01 volume  0.74160E+00 ppm1     6.911 ppm2  0.141

TABLE 13-continued

Unambiguous NOE Distance Restraints

ASSI {12691}
((segid "PROT" and resid 35 and name HN))
((segid "PROT" and resid 34 and name HB1))
  3.500  3.100  2.000 peak    12691 weight  0.10000E+01 volume  0.12493E+01 ppm1    7.159 ppm2  3.483
ASSI {12711}
((segid "PROT" and resid 97 and name HN))
((segid "PROT" and resid 93 and name HN))
  3.500  3.100  2.000 peak    12711 weight  0.10000E+01 volume  0.13450E+01 ppm1    7.960 ppm2  8.132
ASSI {12871}
((segid "PROT" and resid 55 and name HN))
((segid "PROT" and resid 56 and name HN))
  3.700  3.400  1.800 peak    12871 weight  0.10000E+01 volume  0.94890E+00 ppm1    7.380 ppm2  9.125
ASSI {12891}
((segid "PROT" and resid 54 and name HN))
((segid "PROT" and resid 55 and name HB1))
  3.900  3.800  1.600 peak    12891 weight  0.10000E+01 volume  0.74390E+00 ppm1    8.519 ppm2  2.386
ASSI {12901}
((segid "PROT" and resid 54 and name HN))
(segid "PROT" and resid 81 and name HG1%)
  3.600  3.200  1.900 peak    12901 weight  0.10000E+01 volume  0.10879E+01 ppm1    8.520 ppm2  0.484
ASSI {12911}
((segid "PROT" and resid 89 and name HD21))
((segid "PROT" and resid 89 and name HB1))
  3.700  3.400  1.800 peak    12911 weight  0.10000E+01 volume  0.97110E+00 ppm1    8.352 ppm2  3.097
ASSI {12921}
((segid "PROT" and resid 89 and name HD22))
(segid "PROT" and resid 85 and name HB2))
  3.700  3.400  1.800 peak    12921 weight  0.10000E+01 volume  0.98340E+00 ppm1    7.822 ppm2  3.091
ASSI {12981}
((segid "PROT" and resid 77 and name HN))
((segid "PROT" and resid 79 and name HN))
  2.700  1.800  1.800 peak    12981 weight  0.10000E+01 volume  0.67122E+01 ppm1    7.380 ppm2  8.096
ASSI {13001}
((segid "PROT" and resid 25 and name HN))
((segid "PROT" and resid 26 and name HB1))
  3.600  3.200  1.900 peak    13001 weight  0.10000E+01 volume  0.11043E+01 ppm1    8.566 ppm2  1.896
ASSI {13071}
((segid "PROT" and resid 22 and name HN))
((segid "PROT" and resid 20 and name HA))
  3.700  3.400  1.800 peak    13071 weight  0.10000E+01 volume  0.96300E+00 ppm1    8.853 ppm2  4.287
ASSI {13091}
((segid "PROT" and resid 22 and name HN))
((segid "PROT" and resid 18 and name HA))
  3.700  3.400  1.800 peak    13091 weight  0.10000E+01 volume  0.91100E+00 ppm1    8.855 ppm2  3.287
ASSI {13111}
((segid "PROT" and resid 22 and name HN))
((segid "PROT" and resid 18 and name HB1))
  3.700  3.400  1.800 peak    13111 weight  0.10000E+01 volume  0.99160E+00 ppm1    8.855 ppm2  1.541
ASSI {13121}
((segid "PROT" and resid 63 and name HN))
(segid "PROT" and resid 63 and name HD1%)
  3.500  3.100  2.000 peak    13121 weight  0.10000E+01 volume  0.13848E+01 ppm1    8.853 ppm2  0.893
ASSI {13131}
((segid "PROT" and resid 22 and name HN))
(segid "PROT" and resid 21 and name HD1%)
  3.600  3.200  1.900 peak    13131 weight  0.10000E+01 volume  0.10970E+01 ppm1    8.855 ppm2  0.632
ASSI {13141}
((segid "PROT" and resid 99 and name HN))
((segid "PROT" and resid 89 and name HD21))
  3.700  3.400  1.800 peak    13141 weight  0.10000E+01 volume  0.98450E+00 ppm1    8.205 ppm2  8.372
ASSI {13161}
((segid "PROT" and resid 99 and name HN))
((segid "PROT" and resid 96 and name HA))
  3.200  2.600  2.300 peak    13161 weight  0.10000E+01 volume  0.21348E+01 ppm1    8.192 ppm2  3.802
ASSI {13201}
((segid "PROT" and resid 62 and name HN))
((segid "PROT" and resid 60 and name HB1))
  3.700  3.400  1.800 peak    13201 weight  0.10000E+01 volume  0.10256E+01 ppm1    8.378 ppm2  4.220
ASSI {13221}
((segid "PROT" and resid 64 and name HN))
((segid "PROT" and resid 63 and name HB2))
  2.800  2.000  2.000 peak    13221 weight  0.10000E+01 volume  0.54381E+01 ppm1    8.023 ppm2  1.952
ASSI {13231}
((segid "PROT" and resid 84 and name HN))
((segid "PROT" and resid 81 and name HN))
  3.800  3.600  1.700 peak    13231 weight  0.10000E+01 volume  0.82060E+00 ppm1    8.891 ppm2  7.048

TABLE 13-continued

Unambiguous NOE Distance Restraints

ASSI {13241}
((segid "PROT" and resid 17 and name HN))
((segid "PROT" and resid 19 and name HN))
  3.200  2.600  2.300 peak      13241 weight  0.10000E+01 volume  0.23334E+01 ppm1     8.069  ppm2    8.547
ASSI {13321}
((segid "PROT" and resid 84 and name HN))
((segid "PROT" and resid 87 and name HN))
  3.600  3.200  1.900 peak      13321 weight  0.10000E+01 volume  0.11311E+01 ppm1     8.875  ppm2    7.947
ASSI {13331}
((segid "PROT" and resid 84 and name HN))
((segid "PROT" and resid 86 and name HN))
  3.600  3.200  1.900 peak      13331 weight  0.10000E+01 volume  0.10625E+01 ppm1     8.875  ppm2    7.838
ASSI {13341}
((segid "PROT" and resid 63 and name HN))
((segid "PROT" and resid 60 and name HA))
  3.600  3.200  1.900 peak      13341 weight  0.10000E+01 volume  0.12154E+01 ppm1     8.874  ppm2    4.429
ASSI {13351}
((segid "PROT" and resid 106 and name HN))
((segid "PROT" and resid 107 and name HA))
  3.800  3.600  1.700 peak      13351 weight  0.10000E+01 volume  0.83500E+00 ppm1     9.148  ppm2    3.844
ASSI {13361}
((segid "PROT" and resid 84 and name HN))
((segid "PROT" and resid 80 and name HD2))
  3.800  3.600  1.700 peak      13361 weight  0.10000E+01 volume  0.82650E+00 ppm1     8.876  ppm2    3.295
ASSI {13421}
((segid "PROT" and resid 9 and name HN))
((segid "PROT" and resid 9 and name HD1))
  3.700  3.400  1.800 peak      13421 weight  0.10000E+01 volume  0.90930E+00 ppm1     8.449  ppm2    3.211
ASSI {13431}
((segid "PROT" and resid 112 and name HN))
((segid "PROT" and resid 111 and name HG2))
  3.200  2.600  2.300 peak      13431 weight  0.10000E+01 volume  0.24687E+01 ppm1     8.062  ppm2    1.315
ASSI {13471}
((segid "PROT" and resid 43 and name HN))
((segid "PROT" and resid 42 and name HG1))
  3.700  3.400  1.800 peak      13471 weight  0.10000E+01 volume  0.10242E+01 ppm1     7.179  ppm2    2.353
ASSI {13481}
((segid "PROT" and resid 58 and name HN))
((segid "PROT" and resid 56 and name HN))
  3.700  3.400  1.800 peak      13481 weight  0.10000E+01 volume  0.91120E+00 ppm1     9.443  ppm2    9.140
ASSI {13521}
((segid "PROT" and resid 10 and name HN))
((segid "PROT" and resid 13 and name HG1))
  3.900  3.800  1.600 peak      13521 weight  0.10000E+01 volume  0.74580E+00 ppm1     8.303  ppm2    2.503
ASSI {13531}
((segid "PROT" and resid 111 and name HN))
((segid "PROT" and resid 115 and name HN))
  3.700  3.400  1.800 peak      13531 weight  0.10000E+01 volume  0.93850E+00 ppm1     7.571  ppm2    7.746
ASSI {13561}
((segid "PROT" and resid 102 and name HN))
((segid "PROT" and resid 99 and name HN))
  3.900  3.800  1.600 peak      13561 weight  0.10000E+01 volume  0.72150E+00 ppm1     8.518  ppm2    8.184
ASSI {13571}
((segid "PROT" and resid 46 and name HN))
(segid "PROT" and resid 38 and name HG2%)
  3.700  3.400  1.800 peak      13571 weight  0.10000E+01 volume  0.94700E+00 ppm1     8.040  ppm2  −0.024
ASSI {13591}
((segid "PROT" and resid 50 and name HN))
((segid "PROT" and resid 51 and name HA))
  3.500  3.100  2.000 peak      13591 weight  0.10000E+01 volume  0.12928E+01 ppm1     7.959  ppm2    3.841
ASSI {13611}
((segid "PROT" and resid 117 and name HN))
((segid "PROT" and resid 115 and name HB2))
  3.900  3.800  1.600 peak      13611 weight  0.10000E+01 volume  0.70970E+00 ppm1     8.278  ppm2    1.577
ASSI {13621}
((segid "PROT" and resid 117 and name HN))
((segid "PROT" and resid 116 and name HG12))
  3.800  3.600  1.700 peak      13621 weight  0.10000E+01 volume  0.85950E+00 ppm1     8.280  ppm2    0.920
ASSI {13641}
((segid "PROT" and resid 61 and name HN))
((segid "PROT" and resid 59 and name HN))
  3.300  2.700  2.200 peak      13641 weight  0.10000E+01 volume  0.20489E+01 ppm1     8.162  ppm2    7.895
ASSI {13681}
((segid "PROT" and resid 28 and name HN))
((segid "PROT" and resid 25 and name HB))
  3.700  3.400  1.800 peak      13681 weight  0.10000E+01 volume  0.10506E+01 ppm1     7.558  ppm2    2.429

TABLE 13-continued

Unambiguous NOE Distance Restraints

ASSI {13691}
((segid "PROT" and resid 32 and name HN))
((segid "PROT" and resid 35 and name HG1))
  3.800  3.600  1.700 peak      13691 weight  0.10000E+01 volume  0.85360E+00 ppm1     7.100  ppm2  2.876
ASSI {13711}
((segid "PROT" and resid 31 and name HN))
((segid "PROT" and resid 29 and name HB1))
  3.200  2.600  2.300 peak      13711 weight  0.10000E+01 volume  0.22241E+01 ppm1     7.910  ppm2  2.114
ASSI {13741}
((segid "PROT" and resid 28 and name HN))
(segid "PROT" and resid 25 and name HG2%)
  3.700  3.400  1.800 peak      13741 weight  0.10000E+01 volume  0.90760E+00 ppm1     7.559  ppm2  1.032
ASSI {13761}
((segid "PROT" and resid 88 and name HN))
(segid "PROT" and resid 88 and name HD%)
  3.400  2.900  2.100 peak      13761 weight  0.10000E+01 volume  0.15402E+01 ppm1     7.948  ppm2  6.929
ASSI {13781}
((segid "PROT" and resid 57 and name HN))
((segid "PROT" and resid 34 and name HA))
  3.700  3.400  1.800 peak      13781 weight  0.10000E+01 volume  0.96800E+00 ppm1     8.797  ppm2  4.985
ASSI {13821}
((segid "PROT" and resid 21 and name HN))
((segid "PROT" and resid 19 and name HA))
  3.500  3.100  2.000 peak      13821 weight  0.10000E+01 volume  0.12899E+01 ppm1     7.922  ppm2  3.666
ASSI {13831}
((segid "PROT" and resid 72 and name HN))
((segid "PROT" and resid 75 and name HB1))
  3.400  2.900  2.100 peak      13831 weight  0.10000E+01 volume  0.15591E+01 ppm1     8.194  ppm2  2.939
ASSI {13841}
((segid "PROT" and resid 12 and name HN))
((segid "PROT" and resid 13 and name HA))
  3.600  3.200  1.900 peak      13841 weight  0.10000E+01 volume  0.10753E+01 ppm1     8.426  ppm2  4.193
ASSI {13871}
((segid "PROT" and resid 77 and name HN))
((segid "PROT" and resid 80 and name HB1))
  3.400  2.900  2.100 peak      13871 weight  0.10000E+01 volume  0.15887E+01 ppm1     7.383  ppm2  1.979
ASSI {13891}
((segid "PROT" and resid 73 and name HN))
((segid "PROT" and resid 76 and name HN))
  3.400  2.900  2.100 peak      13891 weight  0.10000E+01 volume  0.17531E+01 ppm1     7.440  ppm2  8.021
ASSI {13921}
((segid "PROT" and resid 59 and name HN))
((segid "PROT" and resid 56 and name HB2))
  3.800  3.600  1.700 peak      13921 weight  0.10000E+01 volume  0.89130E+00 ppm1     7.889  ppm2  1.399
ASSI {13951}
((segid "PROT" and resid 35 and name HN))
((segid "PROT" and resid 36 and name HA))
  3.900  3.800  1.600 peak      13951 weight  0.10000E+01 volume  0.71570E+00 ppm1     7.154  ppm2  4.859
ASSI {14001}
((segid "PROT" and resid 67 and name HN))
(segid "PROT" and resid 67 and name HD%)
  3.700  3.400  1.800 peak      14001 weight  0.10000E+01 volume  0.10122E+01 ppm1     8.239  ppm2  6.300
ASSI {14021}
((segid "PROT" and resid 92 and name HN))
((segid "PROT" and resid 92 and name HG2))
  3.700  3.400  1.800 peak      14021 weight  0.10000E+01 volume  0.10336E+01 ppm1     8.477  ppm2  2.297
ASSI {2211}
((segid "PROT" and resid 105 and name HN))
(segid "PROT" and resid 101 and name HG2%)
  3.400  2.900  2.100 peak       2211 weight  0.10000E+01 volume  0.15190E+01 ppm1     7.908  ppm2  1.015
ASSI {2921}
((segid "PROT" and resid 18 and name HN))
(segid "PROT" and resid 63 and name HD2%)
  3.400  2.900  2.100 peak       2921 weight  0.10000E+01 volume  0.17279E+01 ppm1     8.475  ppm2  1.048
ASSI {3251}
((segid "PROT" and resid 17 and name HN))
(segid "PROT" and resid 14 and name HD2%)
  3.400  2.900  2.100 peak       3251 weight  0.10000E+01 volume  0.16389E+01 ppm1     8.071  ppm2  0.805
OR {3251}
((segid "PROT" and resid 17 and name HN))
(segid "PROT" and resid 14 and name HD1%)
ASSI {3281}
((segid "PROT" and resid 21 and name HN))
((segid "PROT" and resid 24 and name HE21))
  3.500  3.100  2.000 peak       3281 weight  0.10000E+01 volume  0.14220E+01 ppm1     7.929  ppm2  7.046

TABLE 13-continued

Unambiguous NOE Distance Restraints

ASSI {3311}
((segid "PROT" and resid 21 and name HN))
(segid "PROT" and resid 17 and name HG2%)
  3.200  2.600    2.300 peak      3311 weight  0.10000E+01 volume  0.21566E+01 ppm1      7.925  ppm2  1.144
ASSI {3481}
((segid "PROT" and resid 64 and name HN))
((segid "PROT" and resid 61 and name HB1))
  3.100  2.400    2.400 peak      3481 weight  0.10000E+01 volume  0.25719E+01 ppm1      8.025  ppm2  2.212
OR {3481}
((segid "PROT" and resid 64 and name HN))
((segid "PROT" and resid 61 and name HG2))
ASSI {4021}
((segid "PROT" and resid 101 and name HN))
(segid "PROT" and resid 99 and name HB%)
  3.000  2.200    2.200 peak      4021 weight  0.10000E+01 volume  0.33742E+01 ppm1      8.016  ppm2  1.608
ASSI {4281}
((segid "PROT" and resid 101 and name HN))
((segid "PROT" and resid 102 and name HB1))
  3.100  2.400    2.400 peak      4281 weight  0.10000E+01 volume  0.30641E+01 ppm1      8.020  ppm2  1.423
ASSI {4481}
((segid "PROT" and resid 96 and name HN))
((segid "PROT" and resid 90 and name HD2))
  3.100  2.400    2.400 peak      4481 weight  0.10000E+01 volume  0.28902E+01 ppm1      7.380  ppm2  3.918
ASSI {4671}
((segid "PROT" and resid 30 and name HN))
(segid "PROT" and resid 102 and name HD1%)
  3.400  2.900    2.100 peak      4671 weight  0.10000E+01 volume  0.15055E+01 ppm1    11.693  ppm2  0.737
OR {4671}
((segid "PROT" and resid 30 and name HN))
(segid "PROT" and resid 102 and name HD2%)
ASSI {5721}
((segid "PROT" and resid 107 and name HN))
((segid "PROT" and resid 24 and name HE21))
  3.200  2.600    2.300 peak      5721 weight  0.10000E+01 volume  0.22871E+01 ppm1      8.402  ppm2  7.065
ASSI {6921}
((segid "PROT" and resid 85 and name HN))
((segid "PROT" and resid 86 and name HB1))
  3.500  3.100    2.000 peak      6921 weight  0.10000E+01 volume  0.12926E+01 ppm1      6.894  ppm2  1.777
ASSI {7091}
((segid "PROT" and resid 85 and name HN))
(segid "PROT" and resid 99 and name HB%)
  3.400  2.900    2.100 peak      7091 weight  0.10000E+01 volume  0.15606E+01 ppm1      6.912  ppm2  1.640
ASSI {7131}
((segid "PROT" and resid 23 and name HN))
(segid "PROT" and resid 25 and name HG1%)
  3.600  3.200    1.900 peak      7131 weight  0.10000E+01 volume  0.11801E+01 ppm1      8.589  ppm2  1.237
ASSI {7561}
((segid "PROT" and resid 82 and name HN))
((segid "PROT" and resid 80 and name HB2))
  3.600  3.200    1.900 peak      7561 weight  0.10000E+01 volume  0.12116E+01 ppm1      6.400  ppm2  1.912
ASSI {7821}
((segid "PROT" and resid 98 and name HN))
((segid "PROT" and resid 34 and name HZ))
  3.500  3.100    2.000 peak      7821 weight  0.10000E+01 volume  0.13298E+01 ppm1      8.471  ppm2  7.275
ASSI {8461}
((segid "PROT" and resid 75 and name HN))
(segid "PROT" and resid 76 and name HB%)
  3.200  2.600    2.300 peak      8461 weight  0.10000E+01 volume  0.21341E+01 ppm1      8.505  ppm2  1.518
ASSI {9801}
((segid "PROT" and resid 68 and name HN))
((segid "PROT" and resid 65 and name HB2))
  3.400  2.900    2.100 peak      9801 weight  0.10000E+01 volume  0.17553E+01 ppm1      7.992  ppm2  2.790
ASSI {10381}
((segid "PROT" and resid 20 and name HN))
(segid "PROT" and resid 63 and name HD1%)
  3.400  2.900    2.100 peak     10381 weight  0.10000E+01 volume  0.17105E+01 ppm1      7.544  ppm2  0.890
ASSI {10511}
((segid "PROT" and resid 34 and name HN))
(segid "PROT" and resid 56 and name HD1%)
  3.100  2.400    2.400 peak     10511 weight  0.10000E+01 volume  0.26440E+01 ppm1      7.610  ppm2  0.954
ASSI {11201}
((segid "PROT" and resid 79 and name HE21))
((segid "PROT" and resid 79 and name HB2))
  3.500  3.100    2.000 peak     11201 weight  0.10000E+01 volume  0.12542E+01 ppm1      7.314  ppm2  2.072

TABLE 13-continued

Unambiguous NOE Distance Restraints

ASSI {11281}
((segid "PROT" and resid 27 and name HN))
((segid "PROT" and resid 24 and name HB1))
  3.600  3.200  1.900 peak    11281 weight  0.10000E+01 volume  0.11570E+01 ppm1    7.551 ppm2  2.509
OR {11281}
((segid "PROT" and resid 27 and name HN))
((segid "PROT" and resid 24 and name HG2))
ASSI {11521}
((segid "PROT" and resid 31 and name HN))
((segid "PROT" and resid 31 and name HA))
  3.400  2.900  2.100 peak    11521 weight  0.10000E+01 volume  0.15623E+01 ppm1    7.904 ppm2  4.412
ASSI {11891}
((segid "PROT" and resid 70 and name HN))
(segid "PROT" and resid 18 and name HD1%)
  3.400  2.900  2.100 peak    11891 weight  0.10000E+01 volume  0.16604E+01 ppm1    7.447 ppm2  0.738
ASSI {11961}
((segid "PROT" and resid 20 and name HN))
((segid "PROT" and resid 22 and name HB1))
  3.800  3.600  1.700 peak    11961 weight  0.10000E+01 volume  0.79920E+00 ppm1    7.546 ppm2  2.090
ASSI {11971}
((segid "PROT" and resid 94 and name HN))
((segid "PROT" and resid 90 and name HA))
  3.700  3.400  1.800 peak    11971 weight  0.10000E+01 volume  0.96270E+00 ppm1    8.401 ppm2  4.644
ASSI {12001}
((segid "PROT" and resid 94 and name HN))
((segid "PROT" and resid 90 and name HD1))
  3.600  3.200  1.900 peak    12001 weight  0.10000E+01 volume  0.11885E+01 ppm1    8.401 ppm2  4.108
ASSI {12051}
((segid "PROT" and resid 79 and name HN))
((segid "PROT" and resid 75 and name HB1))
  3.700  3.400  1.800 peak    12051 weight  0.10000E+01 volume  0.92950E+00 ppm1    8.100 ppm2  2.912
ASSI {12061}
((segid "PROT" and resid 79 and name HN))
(segid "PROT" and resid 78 and name HD2%)
  3.700  3.400  1.800 peak    12061 weight  0.10000E+01 volume  0.93350E+00 ppm1    8.101 ppm2  0.165
ASSI {12141}
((segid "PROT" and resid 89 and name HN))
(segid "PROT" and resid 96 and name HD%)
  3.700  3.400  1.800 peak    12141 weight  0.10000E+01 volume  0.10188E+01 ppm1    8.115 ppm2  7.097
ASSI {12151}
((segid "PROT" and resid 89 and name HN))
(segid "PROT" and resid 95 and name HD%)
  3.800  3.600  1.700 peak    12151 weight  0.10000E+01 volume  0.83030E+00 ppm1    8.117 ppm2  6.849
ASSI {12181}
((segid "PROT" and resid 89 and name HN))
((segid "PROT" and resid 90 and name HD1))
  3.800  3.600  1.700 peak    12181 weight  0.10000E+01 volume  0.78650E+00 ppm1    8.115 ppm2  4.076
ASSI {12301}
((segid "PROT" and resid 116 and name HN))
((segid "PROT" and resid 112 and name HN))
  3.700  3.400  1.800 peak    12301 weight  0.10000E+01 volume  0.10505E+01 ppm1    7.480 ppm2  8.064
ASSI {12341}
((segid "PROT" and resid 69 and name HN))
(segid "PROT" and resid 68 and name HD%)
  3.700  3.400  1.800 peak    12341 weight  0.10000E+01 volume  0.10495E+01 ppm1    7.708 ppm2  7.143
ASSI {12391}
((segid "PROT" and resid 56 and name HN))
((segid "PROT" and resid 34 and name HB2))
  3.700  3.400  1.800 peak    12391 weight  0.10000E+01 volume  0.10296E+01 ppm1    9.134 ppm2  2.567
ASSI {12471}
((segid "PROT" and resid 32 and name HN))
((segid "PROT" and resid 32 and name HE3))
  3.700  3.400  1.800 peak    12471 weight  0.10000E+01 volume  0.94240E+00 ppm1    7.098 ppm2  7.314
ASSI {12481}
((segid "PROT" and resid 32 and name HN))
((segid "PROT" and resid 34 and name HB2))
  3.700  3.400  1.800 peak    12481 weight  0.10000E+01 volume  0.97880E+00 ppm1    7.103 ppm2  2.572
ASSI {12511}
((segid "PROT" and resid 82 and name HN))
((segid "PROT" and resid 84 and name HB2))
  3.900  3.800  1.600 peak    12511 weight  0.10000E+01 volume  0.71250E+00 ppm1    6.400 ppm2  2.689
ASSI {12581}
((segid "PROT" and resid 86 and name HN))
((segid "PROT" and resid 87 and name HB2))
  3.700  3.400  1.800 peak    12581 weight  0.10000E+01 volume  0.93270E+00 ppm1    7.832 ppm2  2.045

TABLE 13-continued

Unambiguous NOE Distance Restraints

ASSI {12601}
((segid "PROT" and resid 23 and name HN))
((segid "PROT" and resid 19 and name HB2))
  3.700  3.400  1.800 peak     12601 weight  0.10000E+01 volume  0.90500E+00 ppm1     8.583  ppm2    1.394
ASSI {12631}
((segid "PROT" and resid 85 and name HN))
((segid "PROT" and resid 87 and name HB1))
  3.700  3.400  1.800 peak     12631 weight  0.10000E+01 volume  0.90190E+00 ppm1     6.908  ppm2    2.174
ASSI {12681}
((segid "PROT" and resid 81 and name HN))
((segid "PROT" and resid 85 and name HN))
  3.500  3.100  2.000 peak     12681 weight  0.10000E+01 volume  0.13641E+01 ppm1     7.032  ppm2    6.863
ASSI {12721}
((segid "PROT" and resid 97 and name HN))
(segid "PROT" and resid 96 and name HD%)
  3.600  3.200  1.900 peak     12721 weight  0.10000E+01 volume  0.11781E+01 ppm1     7.964  ppm2    7.096
ASSI {12751}
((segid "PROT" and resid 107 and name HN))
((segid "PROT" and resid 108 and name HA))
  3.700  3.400  1.800 peak     12751 weight  0.10000E+01 volume  0.93010E+00 ppm1     8.399  ppm2    4.217
ASSI {12801}
((segid "PROT" and resid 74 and name HN))
((segid "PROT" and resid 75 and name HG2))
  3.600  3.200  1.900 peak     12801 weight  0.10000E+01 volume  0.10996E+01 ppm1     6.922  ppm2    2.202
ASSI {12811}
((segid "PROT" and resid 74 and name HN))
(segid "PROT" and resid 76 and name HB%)
  3.700  3.400  1.800 peak     12811 weight  0.10000E+01 volume  0.93300E+00 ppm1     6.922  ppm2    1.505
ASSI {12831}
((segid "PROT" and resid 30 and name HN))
((segid "PROT" and resid 32 and name HE3))
  3.800  3.600  1.700 peak     12831 weight  0.10000E+01 volume  0.82040E+00 ppm1    11.693  ppm2    7.371
ASSI {12841}
((segid "PROT" and resid 30 and name HN))
((segid "PROT" and resid 101 and name HB))
  3.800  3.600  1.700 peak     12841 weight  0.10000E+01 volume  0.82760E+00 ppm1    11.697  ppm2    1.892
ASSI {12991}
((segid "PROT" and resid 96 and name HN))
((segid "PROT" and resid 89 and name HA))
  3.900  3.800  1.600 peak     12991 weight  0.10000E+01 volume  0.74480E+00 ppm1     7.378  ppm2    5.068
ASSI {13051}
((segid "PROT" and resid 22 and name HN))
((segid "PROT" and resid 24 and name HE21))
  3.400  2.900  2.100 peak     13051 weight  0.10000E+01 volume  0.17366E+01 ppm1     8.852  ppm2    7.062
ASSI {13261}
((segid "PROT" and resid 17 and name HN))
(segid "PROT" and resid 18 and name HD2%)
  3.800  3.600  1.700 peak     13261 weight  0.10000E+01 volume  0.84610E+00 ppm1     8.070  ppm2   −0.192
ASSI {13301}
((segid "PROT" and resid 21 and name HN))
((segid "PROT" and resid 22 and name HB1))
  3.200  2.600  2.300 peak     13301 weight  0.10000E+01 volume  0.21404E+01 ppm1     7.927  ppm2    2.069
ASSI {13401}
((segid "PROT" and resid 21 and name HN))
((segid "PROT" and resid 24 and name HG1))
  3.800  3.600  1.700 peak     13401 weight  0.10000E+01 volume  0.89640E+00 ppm1     7.957  ppm2    2.829
ASSI {13511}
((segid "PROT" and resid 58 and name HN))
((segid "PROT" and resid 61 and name HG2))
  2.900  2.100  2.100 peak     13511 weight  0.10000E+01 volume  0.44447E+01 ppm1     9.443  ppm2    2.259
OR {13511}
((segid "PROT" and resid 58 and name HN))
((segid "PROT" and resid 61 and name HB1))
ASSI {13791}
((segid "PROT" and resid 50 and name HN))
((segid "PROT" and resid 87 and name HB2))
  3.800  3.600  1.700 peak     13791 weight  0.10000E+01 volume  0.77760E+00 ppm1     7.960  ppm2    2.038
ASSI {13931}
((segid "PROT" and resid 115 and name HN))
((segid "PROT" and resid 111 and name HG2))
  3.500  3.100  2.000 peak     13931 weight  0.10000E+01 volume  0.12820E+01 ppm1     7.749  ppm2    1.285
ASSI {14011}
((segid "PROT" and resid 52 and name HN))
(segid "PROT" and resid 50 and name HD1%)
  3.600  3.200  1.900 peak     14011 weight  0.10000E+01 volume  0.12035E+01 ppm1     8.422  ppm2    0.549

TABLE 13-continued

| Unambiguous NOE Distance Restraints |
|---|

ASSI {14041}
((segid "PROT" and resid 99 and name HN))
(segid "PROT" and resid 34 and name HE%)
 3.500  3.100  2.000 peak     14041 weight  0.10000E+01 volume  0.14222E+01 ppm1    8.189 ppm2  7.221
ASSI {12}
((segid "PROT" and resid 17 and name HA))
((segid "PROT" and resid 17 and name HB))
 2.300  1.300  1.300 peak        12 weight  0.10000E+01 volume  0.64338E+01 ppm1    3.970 ppm2  4.285
ASSI {42}
(segid "PROT" and resid 14 and name HD2%)
((segid "PROT" and resid 17 and name HB))
 2.800  2.000  2.000 peak        42 weight  0.10000E+01 volume  0.23074E+01 ppm1    0.832 ppm2  4.289
ASSI {72}
((segid "PROT" and resid 58 and name HA))
((segid "PROT" and resid 58 and name HB))
 2.300  1.300  1.300 peak        72 weight  0.10000E+01 volume  0.68641E+01 ppm1    3.881 ppm2  4.117
ASSI {92}
((segid "PROT" and resid 25 and name HB))
((segid "PROT" and resid 25 and name HA))
 2.700  1.800  1.800 peak        92 weight  0.10000E+01 volume  0.23933E+01 ppm1    2.440 ppm2  3.873
ASSI {102}
(segid "PROT" and resid 58 and name HG2%)
((segid "PROT" and resid 58 and name HA))
 2.200  1.200  1.200 peak       102 weight  0.10000E+01 volume  0.90603E+01 ppm1    1.092 ppm2  3.879
ASSI {122}
((segid "PROT" and resid 20 and name HB1))
((segid "PROT" and resid 17 and name HA))
 2.400  1.400  1.400 peak       122 weight  0.10000E+01 volume  0.59096E+01 ppm1    4.103 ppm2  3.964
ASSI {132}
((segid "PROT" and resid 61 and name HG2))
((segid "PROT" and resid 58 and name HA))
 2.800  2.000  2.000 peak       132 weight  0.10000E+01 volume  0.23380E+01 ppm1    2.261 ppm2  3.883
ASSI {142}
(segid "PROT" and resid 17 and name HG2%)
((segid "PROT" and resid 17 and name HA))
 2.100  1.100  1.100 peak       142 weight  0.10000E+01 volume  0.10421E+02 ppm1    1.179 ppm2  3.970
ASSI {172}
((segid "PROT" and resid 83 and name HB))
((segid "PROT" and resid 83 and name HA))
 2.200  1.200  1.200 peak       172 weight  0.10000E+01 volume  0.96793E+01 ppm1    4.238 ppm2  3.876
ASSI {182}
((segid "PROT" and resid 86 and name HB1))
((segid "PROT" and resid 83 and name HA))
 2.800  2.000  2.000 peak       182 weight  0.10000E+01 volume  0.23242E+01 ppm1    1.777 ppm2  3.898
ASSI {232}
((segid "PROT" and resid 70 and name HA))
((segid "PROT" and resid 70 and name HB1))
 2.300  1.300  1.300 peak       232 weight  0.10000E+01 volume  0.74409E+01 ppm1    4.807 ppm2  4.232
ASSI {242}
((segid "PROT" and resid 70 and name HA))
((segid "PROT" and resid 70 and name HB2))
 2.400  1.400  1.400 peak       242 weight  0.10000E+01 volume  0.57670E+01 ppm1    4.803 ppm2  3.793
ASSI {252}
((segid "PROT" and resid 70 and name HB1))
((segid "PROT" and resid 70 and name HB2))
 1.800  0.800  0.800 peak       252 weight  0.10000E+01 volume  0.26334E+02 ppm1    4.233 ppm2  3.789
ASSI {272}
(segid "PROT" and resid 69 and name HG2%)
((segid "PROT" and resid 70 and name HB2))
 2.700  1.800  1.800 peak       272 weight  0.10000E+01 volume  0.27129E+01 ppm1    0.861 ppm2  3.787
ASSI {292}
((segid "PROT" and resid 30 and name HB1))
((segid "PROT" and resid 98 and name HA))
 2.800  2.000  2.000 peak       292 weight  0.10000E+01 volume  0.21823E+01 ppm1    4.352 ppm2  4.223
ASSI {302}
((segid "PROT" and resid 98 and name HB1))
((segid "PROT" and resid 98 and name HA))
 2.700  1.800  1.800 peak       302 weight  0.10000E+01 volume  0.24715E+01 ppm1    3.396 ppm2  4.223
ASSI {342}
((segid "PROT" and resid 11 and name HB1))
((segid "PROT" and resid 11 and name HA))
 2.200  1.200  1.200 peak       342 weight  0.10000E+01 volume  0.86937E+01 ppm1    2.382 ppm2  4.376
ASSI {362}
((segid "PROT" and resid 101 and name HB))
((segid "PROT" and resid 101 and name HA))
 2.400  1.400  1.400 peak       362 weight  0.10000E+01 volume  0.53397E+01 ppm1    1.953 ppm2  3.694

TABLE 13-continued

| Unambiguous NOE Distance Restraints |
|---|

ASSI {372}
((segid "PROT" and resid 101 and name HG11))
((segid "PROT" and resid 101 and name HA))
  2.400  1.400  1.400 peak      372 weight  0.10000E+01 volume  0.50966E+01 ppm1    1.902 ppm2  3.693
ASSI {382}
((segid "PROT" and resid 14 and name HB1))
((segid "PROT" and resid 11 and name HA))
  2.800  2.000  2.000 peak      382 weight  0.10000E+01 volume  0.20827E+01 ppm1    1.895 ppm2  4.377
ASSI {392}
((segid "PROT" and resid 101 and name HG12))
((segid "PROT" and resid 101 and name HA))
  2.400  1.400  1.400 peak      392 weight  0.10000E+01 volume  0.47337E+01 ppm1    1.240 ppm2  3.693
ASSI {402}
(segid "PROT" and resid 101 and name HG2%)
((segid "PROT" and resid 101 and name HA))
  2.200  1.200  1.200 peak      402 weight  0.10000E+01 volume  0.91301E+01 ppm1    1.026 ppm2  3.696
ASSI {422}
((segid "PROT" and resid 33 and name HB2))
((segid "PROT" and resid 33 and name HA))
  2.900  2.100  2.100 peak      422 weight  0.10000E+01 volume  0.17116E+01 ppm1  −0.429 ppm2  3.992
ASSI {432}
((segid "PROT" and resid 44 and name HB2))
((segid "PROT" and resid 44 and name HA))
  2.600  1.700  1.700 peak      432 weight  0.10000E+01 volume  0.33766E+01 ppm1    2.059 ppm2  4.551
ASSI {442}
((segid "PROT" and resid 110 and name HB))
((segid "PROT" and resid 110 and name HA))
  2.300  1.300  1.300 peak      442 weight  0.10000E+01 volume  0.67160E+01 ppm1    1.794 ppm2  3.855
ASSI {452}
((segid "PROT" and resid 115 and name HB2))
((segid "PROT" and resid 110 and name HA))
  2.700  1.800  1.800 peak      452 weight  0.10000E+01 volume  0.27910E+01 ppm1    1.609 ppm2  3.856
ASSI {462}
(segid "PROT" and resid 113 and name HB%)
((segid "PROT" and resid 110 and name HA))
  2.300  1.300  1.300 peak      462 weight  0.10000E+01 volume  0.65923E+01 ppm1    1.410 ppm2  3.857
ASSI {472}
(segid "PROT" and resid 17 and name HG2%)
((segid "PROT" and resid 110 and name HA))
  2.900  2.100  2.100 peak      472 weight  0.10000E+01 volume  0.18150E+01 ppm1    1.168 ppm2  3.856
ASSI {492}
(segid "PROT" and resid 110 and name HD1%)
((segid "PROT" and resid 110 and name HA))
  2.500  1.600  1.600 peak      492 weight  0.10000E+01 volume  0.43046E+01 ppm1    0.568 ppm2  3.857
ASSI {502}
((segid "PROT" and resid 27 and name HA))
((segid "PROT" and resid 27 and name HB1))
  2.100  1.100  1.100 peak      502 weight  0.10000E+01 volume  0.13211E+02 ppm1    4.487 ppm2  4.051
ASSI {522}
((segid "PROT" and resid 5 and name HA))
((segid "PROT" and resid 5 and name HB2))
  2.200  1.200  1.200 peak      522 weight  0.10000E+01 volume  0.86878E+01 ppm1    4.471 ppm2  3.905
ASSI {542}
((segid "PROT" and resid 38 and name HB))
((segid "PROT" and resid 38 and name HA))
  2.700  1.800  1.800 peak      542 weight  0.10000E+01 volume  0.26095E+01 ppm1    1.072 ppm2  3.492
ASSI {552}
(segid "PROT" and resid 38 and name HG1%)
((segid "PROT" and resid 38 and name HA))
  2.100  1.100  1.100 peak      552 weight  0.10000E+01 volume  0.10687E+02 ppm1    0.496 ppm2  3.493
ASSI {572}
((segid "PROT" and resid 30 and name HA))
((segid "PROT" and resid 30 and name HB2))
  2.900  2.100  2.100 peak      572 weight  0.10000E+01 volume  0.17806E+01 ppm1    4.854 ppm2  3.992
ASSI {582}
((segid "PROT" and resid 30 and name HB2))
((segid "PROT" and resid 30 and name HB1))
  2.300  1.300  1.300 peak      582 weight  0.10000E+01 volume  0.65273E+01 ppm1    3.978 ppm2  4.346
ASSI {632}
((segid "PROT" and resid 37 and name HB1))
((segid "PROT" and resid 37 and name HA))
  2.200  1.200  1.200 peak      632 weight  0.10000E+01 volume  0.90616E+01 ppm1    2.379 ppm2  4.272
ASSI {642}
((segid "PROT" and resid 8 and name HB1))
((segid "PROT" and resid 8 and name HA))
  2.300  1.300  1.300 peak      642 weight  0.10000E+01 volume  0.70364E+01 ppm1    2.293 ppm2  4.460

TABLE 13-continued

| Unambiguous NOE Distance Restraints |
|---|

ASSI {662}
((segid "PROT" and resid 37 and name HG1))
((segid "PROT" and resid 37 and name HA))
  2.800  2.000  2.000 peak      662 weight  0.10000E+01 volume  0.21062E+01 ppm1    2.184 ppm2  4.272
ASSI {682}
((segid "PROT" and resid 49 and name HB))
((segid "PROT" and resid 49 and name HA))
  2.300  1.300  1.300 peak      682 weight  0.10000E+01 volume  0.72941E+01 ppm1    1.931 ppm2  4.111
ASSI {702}
((segid "PROT" and resid 37 and name HB2))
((segid "PROT" and resid 37 and name HA))
  2.600  1.700  1.700 peak      702 weight  0.10000E+01 volume  0.31708E+01 ppm1    1.702 ppm2  4.271
ASSI {712}
(segid "PROT" and resid 49 and name HG2%)
((segid "PROT" and resid 49 and name HA))
  2.300  1.300  1.300 peak      712 weight  0.10000E+01 volume  0.71135E+01 ppm1    0.908 ppm2  4.109
ASSI {742}
((segid "PROT" and resid 60 and name HA))
((segid "PROT" and resid 60 and name HB1))
  2.500  1.600  1.600 peak      742 weight  0.10000E+01 volume  0.38154E+01 ppm1    4.444 ppm2  4.248
ASSI {752}
((segid "PROT" and resid 60 and name HA))
((segid "PROT" and resid 60 and name HB2))
  2.100  1.100  1.100 peak      752 weight  0.10000E+01 volume  0.11798E+02 ppm1    4.442 ppm2  4.065
ASSI {762}
((segid "PROT" and resid 41 and name HB))
((segid "PROT" and resid 41 and name HA))
  1.800  0.800  0.800 peak      762 weight  0.10000E+01 volume  0.34478E+02 ppm1    4.331 ppm2  4.095
ASSI {772}
((segid "PROT" and resid 46 and name HB1))
((segid "PROT" and resid 46 and name HA))
  2.700  1.800  1.800 peak      772 weight  0.10000E+01 volume  0.24573E+01 ppm1    2.762 ppm2  3.505
ASSI {782}
((segid "PROT" and resid 46 and name HB2))
((segid "PROT" and resid 46 and name HA))
  2.900  2.100  2.100 peak      782 weight  0.10000E+01 volume  0.16661E+01 ppm1    2.431 ppm2  3.504
ASSI {842}
(segid "PROT" and resid 15 and name HD%)
((segid "PROT" and resid 15 and name HA))
  2.800  2.000  2.000 peak      842 weight  0.10000E+01 volume  0.20619E+01 ppm1    7.104 ppm2  4.049
ASSI {852}
((segid "PROT" and resid 15 and name HB1))
((segid "PROT" and resid 15 and name HA))
  2.500  1.600  1.600 peak      852 weight  0.10000E+01 volume  0.46305E+01 ppm1    3.250 ppm2  4.046
ASSI {862}
((segid "PROT" and resid 15 and name HB2))
((segid "PROT" and resid 15 and name HA))
  2.600  1.700  1.700 peak      862 weight  0.10000E+01 volume  0.35482E+01 ppm1    3.085 ppm2  4.045
ASSI {912}
(segid "PROT" and resid 69 and name HG2%)
((segid "PROT" and resid 69 and name HA))
  2.300  1.300  1.300 peak      912 weight  0.10000E+01 volume  0.63782E+01 ppm1    0.861 ppm2  4.123
ASSI {932}
((segid "PROT" and resid 85 and name HB2))
((segid "PROT" and resid 85 and name HA))
  2.800  2.000  2.000 peak      932 weight  0.10000E+01 volume  0.20935E+01 ppm1    3.093 ppm2  4.513
ASSI {942}
(segid "PROT" and resid 107 and name HD%)
((segid "PROT" and resid 107 and name HA))
  2.700  1.800  1.800 peak      942 weight  0.10000E+01 volume  0.28373E+01 ppm1    7.242 ppm2  3.855
ASSI {952}
((segid "PROT" and resid 108 and name HB1))
((segid "PROT" and resid 105 and name HA))
  2.500  1.600  1.600 peak      952 weight  0.10000E+01 volume  0.41582E+01 ppm1    4.018 ppm2  4.352
ASSI {962}
((segid "PROT" and resid 108 and name HB1))
((segid "PROT" and resid 108 and name HA))
  2.000  1.000  1.000 peak      962 weight  0.10000E+01 volume  0.16845E+02 ppm1    4.017 ppm2  4.236
ASSI {972}
((segid "PROT" and resid 96 and name HB1))
((segid "PROT" and resid 96 and name HA))
  2.700  1.800  1.800 peak      972 weight  0.10000E+01 volume  0.28585E+01 ppm1    3.420 ppm2  3.825
ASSI {982}
((segid "PROT" and resid 107 and name HB1))
((segid "PROT" and resid 107 and name HA))
  2.200  1.200  1.200 peak      982 weight  0.10000E+01 volume  0.83628E+01 ppm1    3.093 ppm2  3.855

TABLE 13-continued

| Unambiguous NOE Distance Restraints |
| --- |

ASSI {992}
((segid "PROT" and resid 96 and name HB2))
((segid "PROT" and resid 96 and name HA))
 2.600  1.700  1.700 peak      992 weight  0.10000E+01 volume  0.34567E+01 ppm1    2.583 ppm2  3.825
ASSI {1002}
((segid "PROT" and resid 111 and name HB1))
((segid "PROT" and resid 108 and name HA))
 2.800  2.000  2.000 peak     1002 weight  0.10000E+01 volume  0.21206E+01 ppm1    1.909 ppm2  4.234
ASSI {1012}
((segid "PROT" and resid 110 and name HB))
((segid "PROT" and resid 107 and name HA))
 2.700  1.800  1.800 peak     1012 weight  0.10000E+01 volume  0.26266E+01 ppm1    1.801 ppm2  3.854
ASSI {1022}
((segid "PROT" and resid 111 and name HB2))
((segid "PROT" and resid 108 and name HA))
 2.900  2.100  2.100 peak     1022 weight  0.10000E+01 volume  0.18539E+01 ppm1    1.786 ppm2  4.236
ASSI {1042}
((segid "PROT" and resid 110 and name HG11))
((segid "PROT" and resid 107 and name HA))
 2.400  1.400  1.400 peak     1042 weight  0.10000E+01 volume  0.50798E+01 ppm1    1.154 ppm2  3.857
ASSI {1052}
(segid "PROT" and resid 110 and name HG2%)
((segid "PROT" and resid 107 and name HA))
 2.800  2.000  2.000 peak     1052 weight  0.10000E+01 volume  0.22040E+01 ppm1    0.695 ppm2  3.855
ASSI {1062}
(segid "PROT" and resid 110 and name HD1%)
((segid "PROT" and resid 107 and name HA))
 2.600  1.700  1.700 peak     1062 weight  0.10000E+01 volume  0.35344E+01 ppm1    0.569 ppm2  3.856
ASSI {1072}
(segid "PROT" and resid 105 and name HD%)
((segid "PROT" and resid 105 and name HA))
 2.600  1.700  1.700 peak     1072 weight  0.10000E+01 volume  0.30484E+01 ppm1    7.234 ppm2  4.364
ASSI {1092}
(segid "PROT" and resid 88 and name HD%)
((segid "PROT" and resid 88 and name HA))
 2.800  2.000  2.000 peak     1092 weight  0.10000E+01 volume  0.19898E+01 ppm1    6.977 ppm2  4.331
ASSI {1102}
((segid "PROT" and resid 105 and name HB1))
((segid "PROT" and resid 105 and name HA))
 2.500  1.600  1.600 peak     1102 weight  0.10000E+01 volume  0.44197E+01 ppm1    3.172 ppm2  4.362
ASSI {1112}
((segid "PROT" and resid 105 and name HB2))
((segid "PROT" and resid 105 and name HA))
 2.600  1.700  1.700 peak     1112 weight  0.10000E+01 volume  0.34973E+01 ppm1    3.103 ppm2  4.362
ASSI {1132}
(segid "PROT" and resid 95 and name HD%)
((segid "PROT" and resid 95 and name HA))
 2.900  2.100  2.100 peak     1132 weight  0.10000E+01 volume  0.16794E+01 ppm1    6.869 ppm2  3.647
ASSI {1142}
((segid "PROT" and resid 20 and name HB1))
((segid "PROT" and resid 20 and name HA))
 1.900  0.900  0.900 peak     1142 weight  0.10000E+01 volume  0.20468E+02 ppm1    4.099 ppm2  4.330
ASSI {1152}
((segid "PROT" and resid 98 and name HB2))
((segid "PROT" and resid 95 and name HA))
 2.900  2.100  2.100 peak     1152 weight  0.10000E+01 volume  0.15905E+01 ppm1    3.054 ppm2  3.651
ASSI {1162}
((segid "PROT" and resid 95 and name HB1))
((segid "PROT" and resid 95 and name HA))
 2.800  2.000  2.000 peak     1162 weight  0.10000E+01 volume  0.21842E+01 ppm1    2.947 ppm2  3.649
ASSI {1192}
(segid "PROT" and resid 74 and name HD%)
((segid "PROT" and resid 74 and name HA))
 2.900  2.100  2.100 peak     1192 weight  0.10000E+01 volume  0.17594E+01 ppm1    6.440 ppm2  3.805
ASSI {1202}
((segid "PROT" and resid 74 and name HB1))
((segid "PROT" and resid 74 and name HA))
 2.700  1.800  1.800 peak     1202 weight  0.10000E+01 volume  0.25521E+01 ppm1    3.000 ppm2  3.810
ASSI {1212}
((segid "PROT" and resid 62 and name HD1))
((segid "PROT" and resid 59 and name HA))
 2.800  2.000  2.000 peak     1212 weight  0.10000E+01 volume  0.20013E+01 ppm1    2.581 ppm2  4.327
ASSI {1222}
((segid "PROT" and resid 74 and name HB2))
((segid "PROT" and resid 74 and name HA))
 2.700  1.800  1.800 peak     1222 weight  0.10000E+01 volume  0.25019E+01 ppm1    2.428 ppm2  3.801

TABLE 13-continued

Unambiguous NOE Distance Restraints

ASSI {1232}
(segid "PROT" and resid 47 and name HD%)
((segid "PROT" and resid 47 and name HA))
  2.800  2.000  2.000 peak      1232 weight  0.10000E+01 volume  0.19922E+01 ppm1     7.410  ppm2  4.152
ASSI {1242}
(segid "PROT" and resid 106 and name HD%)
((segid "PROT" and resid 106 and name HA))
  2.700  1.800  1.800 peak      1242 weight  0.10000E+01 volume  0.28829E+01 ppm1     6.951  ppm2  4.002
ASSI {1252}
((segid "PROT" and resid 32 and name HB1))
((segid "PROT" and resid 32 and name HA))
  2.500  1.600  1.600 peak      1252 weight  0.10000E+01 volume  0.43254E+01 ppm1     3.639  ppm2  4.422
ASSI {1262}
((segid "PROT" and resid 32 and name HB2))
((segid "PROT" and resid 32 and name HA))
  2.500  1.600  1.600 peak      1262 weight  0.10000E+01 volume  0.45345E+01 ppm1     3.408  ppm2  4.424
ASSI {1272}
((segid "PROT" and resid 106 and name HB1))
((segid "PROT" and resid 106 and name HA))
  2.600  1.700  1.700 peak      1272 weight  0.10000E+01 volume  0.30595E+01 ppm1     3.360  ppm2  3.998
ASSI {1282}
((segid "PROT" and resid 47 and name HB1))
((segid "PROT" and resid 47 and name HA))
  2.600  1.700  1.700 peak      1282 weight  0.10000E+01 volume  0.34928E+01 ppm1     3.244  ppm2  4.144
ASSI {1292}
((segid "PROT" and resid 106 and name HB2))
((segid "PROT" and resid 106 and name HA))
  2.400  1.400  1.400 peak      1292 weight  0.10000E+01 volume  0.47428E+01 ppm1     3.136  ppm2  4.000
ASSI {1302}
((segid "PROT" and resid 35 and name HG1))
((segid "PROT" and resid 32 and name HA))
  2.500  1.600  1.600 peak      1302 weight  0.10000E+01 volume  0.37666E+01 ppm1     2.896  ppm2  4.423
ASSI {1312}
((segid "PROT" and resid 47 and name HB2))
((segid "PROT" and resid 47 and name HA))
  2.700  1.800  1.800 peak      1312 weight  0.10000E+01 volume  0.27409E+01 ppm1     2.846  ppm2  4.145
ASSI {1322}
((segid "PROT" and resid 59 and name HG1))
((segid "PROT" and resid 59 and name HA))
  2.800  2.000  2.000 peak      1322 weight  0.10000E+01 volume  0.20732E+01 ppm1     2.663  ppm2  4.338
ASSI {1342}
((segid "PROT" and resid 59 and name HB2))
((segid "PROT" and resid 59 and name HA))
  2.900  2.100  2.100 peak      1342 weight  0.10000E+01 volume  0.16833E+01 ppm1     1.928  ppm2  4.332
ASSI {1362}
((segid "PROT" and resid 58 and name HG2%)
((segid "PROT" and resid 59 and name HA))
  2.900  2.100  2.100 peak      1362 weight  0.10000E+01 volume  0.17814E+01 ppm1     1.110  ppm2  4.338
ASSI {1402}
((segid "PROT" and resid 57 and name HE2))
((segid "PROT" and resid 57 and name HA))
  2.500  1.600  1.600 peak      1402 weight  0.10000E+01 volume  0.37335E+01 ppm1     2.082  ppm2  3.909
ASSI {1422}
((segid "PROT" and resid 115 and name HB2))
((segid "PROT" and resid 116 and name HA))
  2.500  2.500  2.000 peak      1422 weight  0.10000E+01 volume  0.40056E+01 ppm1     1.620  ppm2  4.238
ASSI {1452}
((segid "PROT" and resid 57 and name HB2))
((segid "PROT" and resid 57 and name HA))
  2.800  2.000  2.000 peak      1452 weight  0.10000E+01 volume  0.21470E+01 ppm1     1.117  ppm2  3.907
ASSI {1462}
((segid "PROT" and resid 57 and name HD2))
((segid "PROT" and resid 57 and name HA))
  2.600  1.700  1.700 peak      1462 weight  0.10000E+01 volume  0.31356E+01 ppm1     0.915  ppm2  3.902
ASSI {1472}
((segid "PROT" and resid 67 and name HD%)
((segid "PROT" and resid 67 and name HA))
  2.800  2.000  2.000 peak      1472 weight  0.10000E+01 volume  0.21386E+01 ppm1     6.321  ppm2  4.108
ASSI {1482}
((segid "PROT" and resid 67 and name HB1))
((segid "PROT" and resid 67 and name HA))
  2.300  1.300  1.300 peak      1482 weight  0.10000E+01 volume  0.60720E+01 ppm1     3.005  ppm2  4.099
ASSI {1492}
((segid "PROT" and resid 116 and name HB))
((segid "PROT" and resid 116 and name HA))
  2.100  1.100  1.100 peak      1492 weight  0.10000E+01 volume  0.10649E+02 ppm1     1.851  ppm2  4.267

TABLE 13-continued

| Unambiguous NOE Distance Restraints |
| --- |

ASSI {1512}
((segid "PROT" and resid 19 and name HG1))
((segid "PROT" and resid 19 and name HA))
  2.400  1.400   1.400 peak       1512 weight  0.10000E+01 volume   0.53544E+01 ppm1     1.309 ppm2  3.719
ASSI {1522}
((segid "PROT" and resid 63 and name HD2%))
((segid "PROT" and resid 19 and name HA))
  2.700  1.800   1.800 peak       1522 weight  0.10000E+01 volume   0.24664E+01 ppm1     1.088 ppm2  3.720
ASSI {1542}
((segid "PROT" and resid 63 and name HD1%))
((segid "PROT" and resid 19 and name HA))
  2.200  1.200   1.200 peak       1542 weight  0.10000E+01 volume   0.78864E+01 ppm1     0.917 ppm2  3.720
ASSI {1552}
((segid "PROT" and resid 116 and name HG2%))
((segid "PROT" and resid 116 and name HA))
  2.200  1.200   1.200 peak       1552 weight  0.10000E+01 volume   0.85343E+01 ppm1     0.860 ppm2  4.275
ASSI {1582}
((segid "PROT" and resid 107 and name HB1))
((segid "PROT" and resid 104 and name HA))
  2.400  1.400   1.400 peak       1582 weight  0.10000E+01 volume   0.52143E+01 ppm1     3.089 ppm2  4.111
ASSI {1602}
((segid "PROT" and resid 103 and name HG1))
((segid "PROT" and resid 103 and name HA))
  2.700  1.800   1.800 peak       1602 weight  0.10000E+01 volume   0.23739E+01 ppm1     2.039 ppm2  3.221
ASSI {1612}
((segid "PROT" and resid 104 and name HB1))
((segid "PROT" and resid 104 and name HA))
  1.900  0.900   0.900 peak       1612 weight  0.10000E+01 volume   0.22561E+02 ppm1     1.962 ppm2  4.102
ASSI {1632}
((segid "PROT" and resid 103 and name HB1))
((segid "PROT" and resid 103 and name HA))
  2.700  1.800   1.800 peak       1632 weight  0.10000E+01 volume   0.24604E+01 ppm1     1.783 ppm2  3.225
ASSI {1682}
((segid "PROT" and resid 103 and name HB2))
((segid "PROT" and resid 103 and name HA))
  2.600  1.700   1.700 peak       1682 weight  0.10000E+01 volume   0.35179E+01 ppm1     1.332 ppm2  3.221
ASSI {1702}
((segid "PROT" and resid 116 and name HG12))
((segid "PROT" and resid 111 and name HA))
  2.800  2.000   2.000 peak       1702 weight  0.10000E+01 volume   0.20569E+01 ppm1     0.976 ppm2  4.097
ASSI {1742}
((segid "PROT" and resid 61 and name HG2))
((segid "PROT" and resid 61 and name HA))
  2.000  1.000   1.000 peak       1742 weight  0.10000E+01 volume   0.14343E+02 ppm1     2.268 ppm2  4.079
ASSI {1752}
((segid "PROT" and resid 111 and name HB1))
((segid "PROT" and resid 111 and name HA))
  1.900  1.900   2.600 peak       1752 weight  0.10000E+01 volume   0.22665E+02 ppm1     1.915 ppm2  4.078
ASSI {1792}
((segid "PROT" and resid 29 and name HG2))
((segid "PROT" and resid 29 and name HA))
  2.200  1.200   1.200 peak       1792 weight  0.10000E+01 volume   0.81264E+01 ppm1     2.431 ppm2  4.224
ASSI {1812}
((segid "PROT" and resid 29 and name HB1))
((segid "PROT" and resid 29 and name HA))
  1.900  0.900   0.900 peak       1812 weight  0.10000E+01 volume   0.21970E+02 ppm1     2.139 ppm2  4.238
ASSI {1922}
((segid "PROT" and resid 82 and name HD%))
((segid "PROT" and resid 82 and name HA))
  2.500  1.600   1.600 peak       1922 weight  0.10000E+01 volume   0.42297E+01 ppm1     6.693 ppm2  4.214
ASSI {1932}
((segid "PROT" and resid 82 and name HB1))
((segid "PROT" and resid 82 and name HA))
  2.500  1.600   1.600 peak       1932 weight  0.10000E+01 volume   0.37394E+01 ppm1     3.128 ppm2  4.216
ASSI {1952}
((segid "PROT" and resid 86 and name HG1))
((segid "PROT" and resid 86 and name HA))
  2.700  1.800   1.800 peak       1952 weight  0.10000E+01 volume   0.28775E+01 ppm1     1.344 ppm2  4.264
ASSI {1962}
((segid "PROT" and resid 86 and name HG2))
((segid "PROT" and resid 86 and name HA))
  2.700  1.800   1.800 peak       1962 weight  0.10000E+01 volume   0.29223E+01 ppm1     0.165 ppm2  4.263
ASSI {2022}
((segid "PROT" and resid 28 and name HB2))
((segid "PROT" and resid 28 and name HA))
  2.600  1.700   1.700 peak       2022 weight  0.10000E+01 volume   0.30612E+01 ppm1     2.817 ppm2  4.021

TABLE 13-continued

Unambiguous NOE Distance Restraints

ASSI {2032}
((segid "PROT" and resid 13 and name HB1))
((segid "PROT" and resid 13 and name HA))
 2.000  1.000  1.000 peak     2032 weight  0.10000E+01 volume  0.14730E+02 ppm1   2.191 ppm2  4.217
ASSI {2042}
((segid "PROT" and resid 86 and name HB1))
((segid "PROT" and resid 86 and name HA))
 2.500  1.600  1.600 peak     2042 weight  0.10000E+01 volume  0.45267E+01 ppm1   1.810 ppm2  4.265
ASSI {2052}
((segid "PROT" and resid 14 and name HG))
((segid "PROT" and resid 14 and name HA))
 2.800  2.000  2.000 peak     2052 weight  0.10000E+01 volume  0.19350E+01 ppm1   1.426 ppm2  4.090
ASSI {2112}
((segid "PROT" and resid 87 and name HG2))
((segid "PROT" and resid 87 and name HA))
 2.200  1.200  1.200 peak     2112 weight  0.10000E+01 volume  0.95163E+01 ppm1   2.235 ppm2  4.334
ASSI {2132}
((segid "PROT" and resid 80 and name HB1))
((segid "PROT" and resid 80 and name HA))
 2.400  1.400  1.400 peak     2132 weight  0.10000E+01 volume  0.55458E+01 ppm1   2.013 ppm2  4.098
ASSI {2142}
((segid "PROT" and resid 68 and name HD%))
((segid "PROT" and resid 68 and name HA))
 2.900  2.100  2.100 peak     2142 weight  0.10000E+01 volume  0.18798E+01 ppm1   7.208 ppm2  4.583
ASSI {2152}
((segid "PROT" and resid 21 and name HB))
((segid "PROT" and resid 18 and name HA))
 2.700  1.800  1.800 peak     2152 weight  0.10000E+01 volume  0.26066E+01 ppm1   1.954 ppm2  3.312
ASSI {2162}
((segid "PROT" and resid 73 and name HB2))
((segid "PROT" and resid 73 and name HA))
 2.400  1.400  1.400 peak     2162 weight  0.10000E+01 volume  0.47318E+01 ppm1   1.919 ppm2  4.261
ASSI {2172}
((segid "PROT" and resid 18 and name HG))
((segid "PROT" and resid 18 and name HA))
 3.000  2.200  2.200 peak     2172 weight  0.10000E+01 volume  0.15478E+01 ppm1   1.708 ppm2  3.315
ASSI {2182}
((segid "PROT" and resid 81 and name HB))
((segid "PROT" and resid 78 and name HA))
 2.900  2.100  2.100 peak     2182 weight  0.10000E+01 volume  0.16328E+01 ppm1   1.471 ppm2  3.416
ASSI {2192}
((segid "PROT" and resid 59 and name HE%))
((segid "PROT" and resid 78 and name HA))
 2.800  2.000  2.000 peak     2192 weight  0.10000E+01 volume  0.19929E+01 ppm1   1.311 ppm2  3.422
ASSI {2212}
((segid "PROT" and resid 78 and name HB1))
((segid "PROT" and resid 78 and name HA))
 2.600  1.700  1.700 peak     2212 weight  0.10000E+01 volume  0.36430E+01 ppm1   0.739 ppm2  3.417
ASSI {2242}
((segid "PROT" and resid 18 and name HD1%))
((segid "PROT" and resid 18 and name HA))
 2.700  1.800  1.800 peak     2242 weight  0.10000E+01 volume  0.24789E+01 ppm1   0.511 ppm2  3.318
ASSI {2282}
((segid "PROT" and resid 77 and name HB1))
((segid "PROT" and resid 77 and name HA))
 2.500  1.600  1.600 peak     2282 weight  0.10000E+01 volume  0.45855E+01 ppm1   2.749 ppm2  4.395
ASSI {2292}
((segid "PROT" and resid 80 and name HB2))
((segid "PROT" and resid 77 and name HA))
 2.700  1.800  1.800 peak     2292 weight  0.10000E+01 volume  0.25994E+01 ppm1   1.942 ppm2  4.393
ASSI {2302}
((segid "PROT" and resid 50 and name HG11))
((segid "PROT" and resid 50 and name HA))
 2.900  2.100  2.100 peak     2302 weight  0.10000E+01 volume  0.16293E+01 ppm1   0.837 ppm2  3.951
ASSI {2312}
((segid "PROT" and resid 50 and name HD1%))
((segid "PROT" and resid 50 and name HA))
 2.100  1.100  1.100 peak     2312 weight  0.10000E+01 volume  0.10702E+02 ppm1   0.582 ppm2  3.952
ASSI {2342}
((segid "PROT" and resid 92 and name HG2))
((segid "PROT" and resid 92 and name HA))
 2.300  1.300  1.300 peak     2342 weight  0.10000E+01 volume  0.72564E+01 ppm1   2.257 ppm2  4.253
ASSI {2352}
((segid "PROT" and resid 92 and name HB1))
((segid "PROT" and resid 92 and name HA))
 2.200  1.200  1.200 peak     2352 weight  0.10000E+01 volume  0.82085E+01 ppm1   2.103 ppm2  4.253

TABLE 13-continued

Unambiguous NOE Distance Restraints

ASSI {2362}
((segid "PROT" and resid 92 and name HB2))
((segid "PROT" and resid 92 and name HA))
 2.300  1.300  1.300 peak     2362 weight  0.10000E+01 volume  0.76333E+01 ppm1   2.023 ppm2  4.252
ASSI {2372}
((segid "PROT" and resid 51 and name HB2))
((segid "PROT" and resid 51 and name HA))
 2.200  1.200  1.200 peak     2372 weight  0.10000E+01 volume  0.93999E+01 ppm1   1.212 ppm2  3.878
ASSI {2402}
((segid "PROT" and resid 109 and name HB2))
((segid "PROT" and resid 109 and name HA))
 2.500  1.600  1.600 peak     2402 weight  0.10000E+01 volume  0.37867E+01 ppm1   1.586 ppm2  4.072
ASSI {2412}
((segid "PROT" and resid 109 and name HD1))
((segid "PROT" and resid 109 and name HA))
 2.200  1.200  1.200 peak     2412 weight  0.10000E+01 volume  0.98857E+01 ppm1   1.421 ppm2  4.069
ASSI {2422}
((segid "PROT" and resid 109 and name HG1))
((segid "PROT" and resid 109 and name HA))
 2.700  1.800  1.800 peak     2422 weight  0.10000E+01 volume  0.29134E+01 ppm1   0.852 ppm2  4.074
ASSI {2432}
((segid "PROT" and resid 105 and name HB1))
((segid "PROT" and resid 102 and name HA))
 2.600  1.700  1.700 peak     2432 weight  0.10000E+01 volume  0.31410E+01 ppm1   3.172 ppm2  3.721
ASSI {2442}
((segid "PROT" and resid 105 and name HB2))
((segid "PROT" and resid 102 and name HA))
 2.600  1.700  1.700 peak     2442 weight  0.10000E+01 volume  0.34157E+01 ppm1   3.110 ppm2  3.725
ASSI {2452}
((segid "PROT" and resid 66 and name HD1))
((segid "PROT" and resid 66 and name HA))
 2.600  1.700  1.700 peak     2452 weight  0.10000E+01 volume  0.34111E+01 ppm1   3.102 ppm2  4.444
ASSI {2462}
((segid "PROT" and resid 66 and name HB1))
((segid "PROT" and resid 66 and name HA))
 2.500  1.600  1.600 peak     2462 weight  0.10000E+01 volume  0.45998E+01 ppm1   2.125 ppm2  4.442
ASSI {2472}
((segid "PROT" and resid 102 and name HG))
((segid "PROT" and resid 102 and name HA))
 2.900  2.100  2.100 peak     2472 weight  0.10000E+01 volume  0.15660E+01 ppm1   1.598 ppm2  3.722
ASSI {2492}
((segid "PROT" and resid 102 and name HB2))
((segid "PROT" and resid 102 and name HA))
 2.600  1.700  1.700 peak     2492 weight  0.10000E+01 volume  0.29926E+01 ppm1   1.266 ppm2  3.725
ASSI {2502}
(segid "PROT" and resid 101 and name HG2%)
((segid "PROT" and resid 102 and name HA))
 2.900  2.100  2.100 peak     2502 weight  0.10000E+01 volume  0.16802E+01 ppm1   1.035 ppm2  3.725
ASSI {2512}
(segid "PROT" and resid 102 and name HD2%)
((segid "PROT" and resid 102 and name HA))
 2.200  1.200  1.200 peak     2512 weight  0.10000E+01 volume  0.92912E+01 ppm1   0.765 ppm2  3.722
ASSI {2522}
((segid "PROT" and resid 42 and name HB1))
((segid "PROT" and resid 42 and name HA))
 2.500  1.600  1.600 peak     2522 weight  0.10000E+01 volume  0.43700E+01 ppm1   2.218 ppm2  4.498
ASSI {2582}
((segid "PROT" and resid 6 and name HB1))
((segid "PROT" and resid 6 and name HA))
 2.300  1.300  1.300 peak     2582 weight  0.10000E+01 volume  0.76268E+01 ppm1   1.885 ppm2  4.371
ASSI {2592}
((segid "PROT" and resid 6 and name HB2))
((segid "PROT" and resid 6 and name HA))
 2.300  1.300  1.300 peak     2592 weight  0.10000E+01 volume  0.76524E+01 ppm1   1.790 ppm2  4.373
ASSI {2622}
(segid "PROT" and resid 34 and name HD%)
((segid "PROT" and resid 34 and name HA))
 2.700  1.800  1.800 peak     2622 weight  0.10000E+01 volume  0.27444E+01 ppm1   7.182 ppm2  5.002
ASSI {2632}
((segid "PROT" and resid 34 and name HB1))
((segid "PROT" and resid 34 and name HA))
 2.700  1.800  1.800 peak     2632 weight  0.10000E+01 volume  0.28879E+01 ppm1   3.515 ppm2  5.002
ASSI {2642}
((segid "PROT" and resid 15 and name HB1))
((segid "PROT" and resid 12 and name HA))
 2.600  1.700  1.700 peak     2642 weight  0.10000E+01 volume  0.32274E+01 ppm1   3.248 ppm2  4.707

TABLE 13-continued

Unambiguous NOE Distance Restraints

ASSI {2662}
((segid "PROT" and resid 15 and name HB2))
((segid "PROT" and resid 12 and name HA))
 2.900  2.100  2.100 peak    2662 weight  0.10000E+01 volume  0.16345E+01 ppm1   3.089 ppm2  4.717
ASSI {2702}
((segid "PROT" and resid 103 and name HB2))
((segid "PROT" and resid 100 and name HA))
 2.900  2.100  2.100 peak    2702 weight  0.10000E+01 volume  0.16134E+01 ppm1   1.345 ppm2  4.362
ASSI {2712}
((segid "PROT" and resid 34 and name HZ))
((segid "PROT" and resid 99 and name HA))
 2.800  2.000  2.000 peak    2712 weight  0.10000E+01 volume  0.22850E+01 ppm1   7.294 ppm2  3.915
ASSI {2742}
((segid "PROT" and resid 115 and name HB2))
((segid "PROT" and resid 115 and name HA))
 2.200  1.200  1.200 peak    2742 weight  0.10000E+01 volume  0.98559E+01 ppm1   1.608 ppm2  4.256
ASSI {2772}
(segid "PROT" and resid 82 and name HD%)
((segid "PROT" and resid 99 and name HA))
 2.900  2.100  2.100 peak    2772 weight  0.10000E+01 volume  0.16551E+01 ppm1   6.698 ppm2  3.908
ASSI {2782}
((segid "PROT" and resid 84 and name HB1))
((segid "PROT" and resid 84 and name HA))
 2.600  1.700  1.700 peak    2782 weight  0.10000E+01 volume  0.32197E+01 ppm1   3.027 ppm2  4.340
ASSI {2792}
((segid "PROT" and resid 84 and name HB2))
((segid "PROT" and resid 84 and name HA))
 2.700  1.800  1.800 peak    2792 weight  0.10000E+01 volume  0.29245E+01 ppm1   2.710 ppm2  4.343
ASSI {2802}
((segid "PROT" and resid 87 and name HB1))
((segid "PROT" and resid 84 and name HA))
 2.800  2.000  2.000 peak    2802 weight  0.10000E+01 volume  0.21085E+01 ppm1   2.231 ppm2  4.341
ASSI {2832}
((segid "PROT" and resid 79 and name HB2))
((segid "PROT" and resid 76 and name HA))
 2.800  2.000  2.000 peak    2832 weight  0.10000E+01 volume  0.23028E+01 ppm1   2.109 ppm2  4.118
ASSI {2862}
(segid "PROT" and resid 52 and name HD%)
((segid "PROT" and resid 52 and name HA))
 2.800  2.000  2.000 peak    2862 weight  0.10000E+01 volume  0.23174E+01 ppm1   7.277 ppm2  5.037
ASSI {2892}
((segid "PROT" and resid 53 and name HD1))
((segid "PROT" and resid 52 and name HA))
 2.400  1.400  1.400 peak    2892 weight  0.10000E+01 volume  0.55449E+01 ppm1   3.654 ppm2  5.038
ASSI {2902}
((segid "PROT" and resid 53 and name HD2))
((segid "PROT" and resid 52 and name HA))
 2.400  1.400  1.400 peak    2902 weight  0.10000E+01 volume  0.48228E+01 ppm1   3.442 ppm2  5.036
ASSI {2912}
((segid "PROT" and resid 52 and name HB1))
((segid "PROT" and resid 52 and name HA))
 2.600  1.700  1.700 peak    2912 weight  0.10000E+01 volume  0.33008E+01 ppm1   3.088 ppm2  5.040
ASSI {2922}
((segid "PROT" and resid 52 and name HB2))
((segid "PROT" and resid 52 and name HA))
 2.700  1.800  1.800 peak    2922 weight  0.10000E+01 volume  0.25314E+01 ppm1   2.964 ppm2  5.037
ASSI {2952}
(segid "PROT" and resid 34 and name HD%)
((segid "PROT" and resid 31 and name HA))
 2.600  1.700  1.700 peak    2952 weight  0.10000E+01 volume  0.33249E+01 ppm1   7.187 ppm2  4.441
ASSI {2962}
((segid "PROT" and resid 55 and name HB1))
((segid "PROT" and resid 55 and name HA))
 2.400  1.400  1.400 peak    2962 weight  0.10000E+01 volume  0.52960E+01 ppm1   2.405 ppm2  4.780
ASSI {2992}
(segid "PROT" and resid 102 and name HD1%)
((segid "PROT" and resid 31 and name HA))
 2.300  1.300  1.300 peak    2992 weight  0.10000E+01 volume  0.69041E+01 ppm1   0.763 ppm2  4.440
ASSI {3012}
((segid "PROT" and resid 11 and name HD1))
((segid "PROT" and resid 10 and name HA))
 2.100  1.100  1.100 peak    3012 weight  0.10000E+01 volume  0.11211E+02 ppm1   3.909 ppm2  4.917
ASSI {3052}
((segid "PROT" and resid 90 and name HD1))
((segid "PROT" and resid 89 and name HA))
 2.500  1.600  1.600 peak    3052 weight  0.10000E+01 volume  0.37580E+01 ppm1   4.115 ppm2  5.088

TABLE 13-continued

| Unambiguous NOE Distance Restraints |
|---|

ASSI {3062}
((segid "PROT" and resid 90 and name HD2))
((segid "PROT" and resid 89 and name HA))
  2.600  1.700  1.700 peak    3062 weight  0.10000E+01 volume  0.34612E+01 ppm1    3.940  ppm2  5.091
ASSI {3072}
((segid "PROT" and resid 89 and name HB1))
((segid "PROT" and resid 89 and name HA))
  2.800  2.000  2.000 peak    3072 weight  0.10000E+01 volume  0.19657E+01 ppm1    3.111  ppm2  5.078
ASSI {3082}
((segid "PROT" and resid 89 and name HB2))
((segid "PROT" and resid 89 and name HA))
  2.900  2.100  2.100 peak    3082 weight  0.10000E+01 volume  0.16124E+01 ppm1    2.904  ppm2  5.088
ASSI {3092}
((segid "PROT" and resid 11 and name HA))
((segid "PROT" and resid 11 and name HD1))
  2.800  2.000  2.000 peak    3092 weight  0.10000E+01 volume  0.19160E+01 ppm1    4.370  ppm2  3.904
ASSI {3102}
((segid "PROT" and resid 8 and name HG1))
((segid "PROT" and resid 8 and name HD1))
  2.100  1.100  1.100 peak    3102 weight  0.10000E+01 volume  0.11827E+02 ppm1    2.074  ppm2  3.882
ASSI {3112}
((segid "PROT" and resid 36 and name HA))
((segid "PROT" and resid 37 and name HD1))
  2.700  1.800  1.800 peak    3112 weight  0.10000E+01 volume  0.28261E+01 ppm1    4.872  ppm2  3.704
ASSI {3122}
((segid "PROT" and resid 7 and name HA))
((segid "PROT" and resid 8 and name HD1))
  2.300  1.300  1.300 peak    3122 weight  0.10000E+01 volume  0.76265E+01 ppm1    4.585  ppm2  3.865
ASSI {3132}
((segid "PROT" and resid 7 and name HA))
((segid "PROT" and resid 8 and name HD2))
  2.300  1.300  1.300 peak    3132 weight  0.10000E+01 volume  0.66114E+01 ppm1    4.587  ppm2  3.716
ASSI {3142}
((segid "PROT" and resid 8 and name HD2))
((segid "PROT" and resid 8 and name HD1))
  1.800  0.800  0.800 peak    3142 weight  0.10000E+01 volume  0.26186E+02 ppm1    3.720  ppm2  3.860
ASSI {3152}
((segid "PROT" and resid 37 and name HB1))
((segid "PROT" and resid 37 and name HD1))
  2.700  1.800  1.800 peak    3152 weight  0.10000E+01 volume  0.28240E+01 ppm1    2.371  ppm2  3.695
ASSI {3162}
((segid "PROT" and resid 8 and name HB1))
((segid "PROT" and resid 8 and name HD1))
  2.900  2.100  2.100 peak    3162 weight  0.10000E+01 volume  0.17476E+01 ppm1    2.298  ppm2  3.866
ASSI {3172}
((segid "PROT" and resid 53 and name HG1))
((segid "PROT" and resid 53 and name HD1))
  2.400  1.400  1.400 peak    3172 weight  0.10000E+01 volume  0.53813E+01 ppm1    2.286  ppm2  3.674
ASSI {3182}
((segid "PROT" and resid 37 and name HG1))
((segid "PROT" and resid 37 and name HD1))
  2.300  1.300  1.300 peak    3182 weight  0.10000E+01 volume  0.67841E+01 ppm1    2.181  ppm2  3.700
ASSI {3192}
((segid "PROT" and resid 8 and name HG1))
((segid "PROT" and resid 8 and name HD2))
  2.200  1.200  1.200 peak    3192 weight  0.10000E+01 volume  0.10002E+02 ppm1    2.053  ppm2  3.717
ASSI {3212}
((segid "PROT" and resid 37 and name HB2))
((segid "PROT" and resid 37 and name HD1))
  2.500  1.600  1.600 peak    3212 weight  0.10000E+01 volume  0.40424E+01 ppm1    1.710  ppm2  3.686
ASSI {3262}
((segid "PROT" and resid 43 and name HA))
((segid "PROT" and resid 44 and name HD2))
  2.400  1.400  1.400 peak    3262 weight  0.10000E+01 volume  0.56600E+01 ppm1    4.992  ppm2  3.570
ASSI {3282}
((segid "PROT" and resid 90 and name HD2))
((segid "PROT" and resid 90 and name HD1))
  2.500  1.600  1.600 peak    3282 weight  0.10000E+01 volume  0.38203E+01 ppm1    3.937  ppm2  4.103
ASSI {3292}
((segid "PROT" and resid 44 and name HD1))
((segid "PROT" and resid 44 and name HD2))
  2.100  1.100  1.100 peak    3292 weight  0.10000E+01 volume  0.11588E+02 ppm1    3.826  ppm2  3.570
ASSI {3302}
((segid "PROT" and resid 53 and name HD1))
((segid "PROT" and resid 53 and name HD2))
  2.100  1.100  1.100 peak    3302 weight  0.10000E+01 volume  0.11080E+02 ppm1    3.654  ppm2  3.447

TABLE 13-continued

Unambiguous NOE Distance Restraints

ASSI {3332}
((segid "PROT" and resid 53 and name HG1))
((segid "PROT" and resid 53 and name HD2))
 2.600  1.700  1.700 peak     3332 weight  0.10000E+01 volume  0.34260E+01 ppm1    2.280 ppm2  3.443
ASSI {3342}
((segid "PROT" and resid 44 and name HG1))
((segid "PROT" and resid 44 and name HD1))
 2.500  1.600  1.600 peak     3342 weight  0.10000E+01 volume  0.38679E+01 ppm1    2.211 ppm2  3.827
ASSI {3352}
((segid "PROT" and resid 44 and name HG1))
((segid "PROT" and resid 44 and name HD2))
 2.500  1.600  1.600 peak     3352 weight  0.10000E+01 volume  0.38481E+01 ppm1    2.209 ppm2  3.573
ASSI {3362}
((segid "PROT" and resid 90 and name HB2))
((segid "PROT" and resid 90 and name HD1))
 2.800  2.000  2.000 peak     3362 weight  0.10000E+01 volume  0.20486E+01 ppm1    2.199 ppm2  4.116
ASSI {3372}
((segid "PROT" and resid 90 and name HB2))
((segid "PROT" and resid 90 and name HD2))
 2.700  1.800  1.800 peak     3372 weight  0.10000E+01 volume  0.25162E+01 ppm1    2.199 ppm2  3.945
ASSI {3382}
((segid "PROT" and resid 44 and name HB2))
((segid "PROT" and resid 44 and name HD2))
 2.500  1.600  1.600 peak     3382 weight  0.10000E+01 volume  0.45799E+01 ppm1    2.077 ppm2  3.574
ASSI {3392}
((segid "PROT" and resid 53 and name HG2))
((segid "PROT" and resid 53 and name HD2))
 2.700  1.800  1.800 peak     3392 weight  0.10000E+01 volume  0.26881E+01 ppm1    1.943 ppm2  3.442
ASSI {3412}
((segid "PROT" and resid 33 and name HD1))
((segid "PROT" and resid 33 and name HD2))
 2.500  1.600  1.600 peak     3412 weight  0.10000E+01 volume  0.46632E+01 ppm1    2.268 ppm2  1.576
ASSI {3432}
((segid "PROT" and resid 44 and name HD1))
((segid "PROT" and resid 43 and name HA))
 2.400  1.400  1.400 peak     3432 weight  0.10000E+01 volume  0.53974E+01 ppm1    3.826 ppm2  4.987
ASSI {3462}
((segid "PROT" and resid 114 and name HA1))
((segid "PROT" and resid 114 and name HA2))
 2.100  1.100  1.100 peak     3462 weight  0.10000E+01 volume  0.10591E+02 ppm1    4.258 ppm2  4.070
ASSI {3492}
((segid "PROT" and resid 37 and name HA))
((segid "PROT" and resid 55 and name HB1))
 2.900  2.100  2.100 peak     3492 weight  0.10000E+01 volume  0.16441E+01 ppm1    4.278 ppm2  2.404
ASSI {3512}
((segid "PROT" and resid 57 and name HE2))
((segid "PROT" and resid 57 and name HE1))
 2.300  1.300  1.300 peak     3512 weight  0.10000E+01 volume  0.74338E+01 ppm1    2.077 ppm2  2.615
ASSI {3522}
((segid "PROT" and resid 57 and name HD1))
((segid "PROT" and resid 57 and name HE1))
 2.800  2.000  2.000 peak     3522 weight  0.10000E+01 volume  0.20286E+01 ppm1    1.759 ppm2  2.624
ASSI {3552}
((segid "PROT" and resid 57 and name HD2))
((segid "PROT" and resid 57 and name HE1))
 2.900  2.100  2.100 peak     3552 weight  0.10000E+01 volume  0.16708E+01 ppm1    0.917 ppm2  2.626
ASSI {3572}
(segid "PROT" and resid 68 and name HD%)
((segid "PROT" and resid 73 and name HB2))
 2.900  2.100  2.100 peak     3572 weight  0.10000E+01 volume  0.16761E+01 ppm1    7.210 ppm2  1.912
ASSI {3582}
(segid "PROT" and resid 68 and name HD%)
((segid "PROT" and resid 73 and name HB1))
 2.800  2.000  2.000 peak     3582 weight  0.10000E+01 volume  0.21142E+01 ppm1    7.199 ppm2  2.025
ASSI {3612}
((segid "PROT" and resid 73 and name HA))
((segid "PROT" and resid 73 and name HB1))
 2.600  1.700  1.700 peak     3612 weight  0.10000E+01 volume  0.31935E+01 ppm1    4.261 ppm2  2.026
ASSI {3632}
((segid "PROT" and resid 73 and name HB1))
((segid "PROT" and resid 73 and name HB2))
 2.200  1.200  1.200 peak     3632 weight  0.10000E+01 volume  0.94680E+01 ppm1    2.031 ppm2  1.912
ASSI {3652}
((segid "PROT" and resid 73 and name HG))
((segid "PROT" and resid 73 and name HB1))
 2.400  1.400  1.400 peak     3652 weight  0.10000E+01 volume  0.56300E+01 ppm1    1.804 ppm2  2.035

TABLE 13-continued

| Unambiguous NOE Distance Restraints |
| --- |

ASSI {3662}
((segid "PROT" and resid 73 and name HG))
((segid "PROT" and resid 73 and name HB2))
  2.500  1.600  1.600 peak      3662 weight  0.10000E+01 volume  0.38407E+01 ppm1    1.805 ppm2  1.924
ASSI {3702}
((segid "PROT" and resid 9 and name HA))
((segid "PROT" and resid 9 and name HD1))
  2.600  1.700  1.700 peak      3702 weight  0.10000E+01 volume  0.35675E+01 ppm1    4.368 ppm2  3.223
ASSI {3752}
((segid "PROT" and resid 80 and name HA))
((segid "PROT" and resid 80 and name HD2))
  2.400  1.400  1.400 peak      3752 weight  0.10000E+01 volume  0.48838E+01 ppm1    4.096 ppm2  3.319
ASSI {3762}
((segid "PROT" and resid 80 and name HA))
((segid "PROT" and resid 80 and name HD1))
  2.800  2.000  2.000 peak      3762 weight  0.10000E+01 volume  0.20750E+01 ppm1    4.096 ppm2  3.401
ASSI {3772}
((segid "PROT" and resid 80 and name HB1))
((segid "PROT" and resid 80 and name HD1))
  2.700  1.800  1.800 peak      3772 weight  0.10000E+01 volume  0.25765E+01 ppm1    2.006 ppm2  3.398
ASSI {3782}
((segid "PROT" and resid 80 and name HB1))
((segid "PROT" and resid 80 and name HD2))
  2.700  1.800  1.800 peak      3782 weight  0.10000E+01 volume  0.27643E+01 ppm1    2.008 ppm2  3.325
ASSI {3792}
((segid "PROT" and resid 80 and name HG1))
((segid "PROT" and resid 80 and name HD1))
  2.300  1.300  1.300 peak      3792 weight  0.10000E+01 volume  0.65114E+01 ppm1    1.786 ppm2  3.404
ASSI {3802}
((segid "PROT" and resid 80 and name HG1))
((segid "PROT" and resid 80 and name HD2))
  2.400  1.400  1.400 peak      3802 weight  0.10000E+01 volume  0.57598E+01 ppm1    1.784 ppm2  3.325
ASSI {3822}
((segid "PROT" and resid 110 and name HB))
((segid "PROT" and resid 115 and name HB2))
  2.400  1.400  1.400 peak      3822 weight  0.10000E+01 volume  0.52191E+01 ppm1    1.784 ppm2  1.605
ASSI {3842}
(segid "PROT" and resid 115 and name HD1%)
((segid "PROT" and resid 115 and name HB2))
  2.100  1.100  1.100 peak      3842 weight  0.10000E+01 volume  0.10686E+02 ppm1    0.759 ppm2  1.614
ASSI {3902}
((segid "PROT" and resid 51 and name HA))
((segid "PROT" and resid 51 and name HD1))
  2.500  1.600  1.600 peak      3902 weight  0.10000E+01 volume  0.38455E+01 ppm1    3.878 ppm2  3.021
ASSI {3912}
((segid "PROT" and resid 51 and name HG1))
((segid "PROT" and resid 51 and name HD1))
  2.200  1.200  1.200 peak      3912 weight  0.10000E+01 volume  0.82005E+01 ppm1    1.353 ppm2  3.022
ASSI {3922}
((segid "PROT" and resid 51 and name HG2))
((segid "PROT" and resid 51 and name HD1))
  2.200  1.200  1.200 peak      3922 weight  0.10000E+01 volume  0.97970E+01 ppm1    1.200 ppm2  3.022
ASSI {3972}
((segid "PROT" and resid 109 and name HA))
((segid "PROT" and resid 109 and name HE2))
  2.800  2.000  2.000 peak      3972 weight  0.10000E+01 volume  0.19750E+01 ppm1    4.072 ppm2  2.476
ASSI {3982}
((segid "PROT" and resid 109 and name HE1))
((segid "PROT" and resid 109 and name HE2))
  1.900  0.900  0.900 peak      3982 weight  0.10000E+01 volume  0.18921E+02 ppm1    2.617 ppm2  2.486
ASSI {4002}
((segid "PROT" and resid 63 and name HB2))
((segid "PROT" and resid 63 and name HB1))
  2.400  1.400  1.400 peak      4002 weight  0.10000E+01 volume  0.52005E+01 ppm1    1.969 ppm2  2.354
ASSI {4012}
((segid "PROT" and resid 63 and name HG))
((segid "PROT" and resid 63 and name HB1))
  2.700  1.800  1.800 peak      4012 weight  0.10000E+01 volume  0.29071E+01 ppm1    1.854 ppm2  2.356
ASSI {4022}
((segid "PROT" and resid 63 and name HG))
((segid "PROT" and resid 63 and name HB2))
  2.900  2.100  2.100 peak      4022 weight  0.10000E+01 volume  0.17630E+01 ppm1    1.851 ppm2  1.979
ASSI {4032}
((segid "PROT" and resid 109 and name HD1))
((segid "PROT" and resid 109 and name HE1))
  2.500  1.600  1.600 peak      4032 weight  0.10000E+01 volume  0.45997E+01 ppm1    1.422 ppm2  2.620

TABLE 13-continued

Unambiguous NOE Distance Restraints

ASSI {4042}
((segid "PROT" and resid 109 and name HD1))
((segid "PROT" and resid 109 and name HE2))
  2.400  1.400  1.400 peak     4042 weight  0.10000E+01 volume  0.47654E+01 ppm1    1.422 ppm2  2.475
ASSI {4092}
((segid "PROT" and resid 109 and name HG1))
((segid "PROT" and resid 109 and name HE2))
  2.700  1.800  1.800 peak     4092 weight  0.10000E+01 volume  0.27075E+01 ppm1    0.852 ppm2  2.483
ASSI {4102}
((segid "PROT" and resid 109 and name HG1))
((segid "PROT" and resid 109 and name HE1))
  2.600  1.700  1.700 peak     4102 weight  0.10000E+01 volume  0.31579E+01 ppm1    0.846 ppm2  2.624
ASSI {4202}
((segid "PROT" and resid 104 and name HG2))
((segid "PROT" and resid 104 and name HE1))
  2.100  1.100  1.100 peak     4202 weight  0.10000E+01 volume  0.12880E+02 ppm1    1.452 ppm2  3.036
ASSI {4312}
(segid "PROT" and resid 82 and name HE%)
((segid "PROT" and resid 102 and name HB1))
  2.900  2.100  2.100 peak     4312 weight  0.10000E+01 volume  0.16565E+01 ppm1    6.485 ppm2  1.468
ASSI {4322}
((segid "PROT" and resid 22 and name HA))
((segid "PROT" and resid 22 and name HB2))
  2.700  1.800  1.800 peak     4322 weight  0.10000E+01 volume  0.27856E+01 ppm1    4.153 ppm2  1.731
ASSI {4342}
((segid "PROT" and resid 102 and name HA))
((segid "PROT" and resid 102 and name HB1))
  2.700  1.800  1.800 peak     4342 weight  0.10000E+01 volume  0.24930E+01 ppm1    3.720 ppm2  1.476
ASSI {4352}
((segid "PROT" and resid 22 and name HB1))
((segid "PROT" and resid 22 and name HB2))
  2.300  1.300  1.300 peak     4352 weight  0.10000E+01 volume  0.66173E+01 ppm1    2.133 ppm2  1.733
ASSI {4372}
((segid "PROT" and resid 102 and name HG))
((segid "PROT" and resid 102 and name HB2))
  2.700  1.800  1.800 peak     4372 weight  0.10000E+01 volume  0.24653E+01 ppm1    1.593 ppm2  1.264
ASSI {4382}
((segid "PROT" and resid 102 and name HB1))
((segid "PROT" and resid 102 and name HB2))
  2.300  1.300  1.300 peak     4382 weight  0.10000E+01 volume  0.76368E+01 ppm1    1.471 ppm2  1.265
ASSI {4432}
(segid "PROT" and resid 102 and name HD2%)
((segid "PROT" and resid 102 and name HB1))
  2.300  1.300  1.300 peak     4432 weight  0.10000E+01 volume  0.60665E+01 ppm1    0.763 ppm2  1.471
ASSI {4452}
((segid "PROT" and resid 10 and name HA))
((segid "PROT" and resid 10 and name HB1))
  2.500  1.600  1.600 peak     4452 weight  0.10000E+01 volume  0.40905E+01 ppm1    4.918 ppm2  2.800
ASSI {4462}
((segid "PROT" and resid 117 and name HA))
((segid "PROT" and resid 117 and name HB1))
  2.600  1.700  1.700 peak     4462 weight  0.10000E+01 volume  0.33594E+01 ppm1    4.604 ppm2  2.737
ASSI {4472}
((segid "PROT" and resid 117 and name HA))
((segid "PROT" and resid 117 and name HB2))
  2.900  2.100  2.100 peak     4472 weight  0.10000E+01 volume  0.17695E+01 ppm1    4.604 ppm2  2.577
ASSI {4482}
((segid "PROT" and resid 11 and name HD1))
((segid "PROT" and resid 10 and name HB2))
  2.600  1.700  1.700 peak     4482 weight  0.10000E+01 volume  0.35230E+01 ppm1    3.901 ppm2  2.734
ASSI {4492}
((segid "PROT" and resid 117 and name HB1))
((segid "PROT" and resid 117 and name HB2))
  1.800  0.800  0.800 peak     4492 weight  0.10000E+01 volume  0.26744E+02 ppm1    2.728 ppm2  2.582
ASSI {4512}
((segid "PROT" and resid 111 and name HB1))
((segid "PROT" and resid 111 and name HE1))
  2.500  1.600  1.600 peak     4512 weight  0.10000E+01 volume  0.44685E+01 ppm1    1.914 ppm2  2.943
ASSI {4532}
((segid "PROT" and resid 35 and name HA))
((segid "PROT" and resid 56 and name HB1))
  2.800  2.000  2.000 peak     4532 weight  0.10000E+01 volume  0.23547E+01 ppm1    4.338 ppm2  2.108
ASSI {4542}
((segid "PROT" and resid 35 and name HA))
((segid "PROT" and resid 56 and name HB2))
  2.800  2.000  2.000 peak     4542 weight  0.10000E+01 volume  0.20197E+01 ppm1    4.339 ppm2  1.457

TABLE 13-continued

Unambiguous NOE Distance Restraints

ASSI {4592}
((segid "PROT" and resid 56 and name HB1))
((segid "PROT" and resid 56 and name HB2))
  2.600  1.700  1.700 peak      4592 weight  0.10000E+01 volume  0.36040E+01 ppm1    2.107 ppm2  1.443
ASSI {4602}
((segid "PROT" and resid 14 and name HB1))
((segid "PROT" and resid 14 and name HB2))
  2.200  1.200  1.200 peak      4602 weight  0.10000E+01 volume  0.84236E+01 ppm1    1.892 ppm2  1.594
ASSI {4702}
(segid "PROT" and resid 14 and name HD1%)
((segid "PROT" and resid 14 and name HB1))
  2.200  1.200  1.200 peak      4702 weight  0.10000E+01 volume  0.81373E+01 ppm1    0.844 ppm2  1.888
ASSI {4712}
(segid "PROT" and resid 14 and name HD2%)
((segid "PROT" and resid 14 and name HB2))
  2.200  1.200  1.200 peak      4712 weight  0.10000E+01 volume  0.84093E+01 ppm1    0.842 ppm2  1.595
ASSI {4752}
(segid "PROT" and resid 88 and name HD%)
((segid "PROT" and resid 88 and name HB1))
  2.800  2.000  2.000 peak      4752 weight  0.10000E+01 volume  0.23178E+01 ppm1    6.968 ppm2  2.964
ASSI {4762}
((segid "PROT" and resid 12 and name HA))
((segid "PROT" and resid 12 and name HB1))
  2.400  1.400  1.400 peak      4762 weight  0.10000E+01 volume  0.54235E+01 ppm1    4.724 ppm2  2.848
ASSI {4772}
((segid "PROT" and resid 88 and name HA))
((segid "PROT" and resid 88 and name HB1))
  2.600  1.700  1.700 peak      4772 weight  0.10000E+01 volume  0.29527E+01 ppm1    4.328 ppm2  2.958
ASSI {4782}
(segid "PROT" and resid 67 and name HD%)
((segid "PROT" and resid 67 and name HB1))
  2.800  2.000  2.000 peak      4782 weight  0.10000E+01 volume  0.21224E+01 ppm1    6.328 ppm2  3.002
ASSI {4792}
(segid "PROT" and resid 67 and name HD%)
((segid "PROT" and resid 67 and name HB2))
  2.900  2.100  2.100 peak      4792 weight  0.10000E+01 volume  0.16139E+01 ppm1    6.323 ppm2  2.095
ASSI {4812}
((segid "PROT" and resid 67 and name HA))
((segid "PROT" and resid 67 and name HB2))
  2.700  1.800  1.800 peak      4812 weight  0.10000E+01 volume  0.23919E+01 ppm1    4.100 ppm2  2.095
ASSI {4832}
((segid "PROT" and resid 67 and name HB2))
((segid "PROT" and resid 67 and name HB1))
  2.400  1.400  1.400 peak      4832 weight  0.10000E+01 volume  0.59989E+01 ppm1    2.093 ppm2  3.004
ASSI {4842}
(segid "PROT" and resid 96 and name HD%)
((segid "PROT" and resid 96 and name HB2))
  3.000  2.200  2.200 peak      4842 weight  0.10000E+01 volume  0.13526E+01 ppm1    7.152 ppm2  2.580
ASSI {4882}
((segid "PROT" and resid 96 and name HB1))
((segid "PROT" and resid 96 and name HB2))
  2.400  1.400  1.400 peak      4882 weight  0.10000E+01 volume  0.48230E+01 ppm1    3.422 ppm2  2.580
ASSI {4922}
(segid "PROT" and resid 59 and name HE%)
((segid "PROT" and resid 78 and name HB1))
  2.800  2.000  2.000 peak      4922 weight  0.10000E+01 volume  0.22267E+01 ppm1    1.310 ppm2  0.747
ASSI {4942}
((segid "PROT" and resid 78 and name HB1))
((segid "PROT" and resid 78 and name HB2))
  2.100  1.100  1.100 peak      4942 weight  0.10000E+01 volume  0.11151E+02 ppm1    0.741 ppm2  0.466
ASSI {5002}
(segid "PROT" and resid 74 and name HD%)
((segid "PROT" and resid 74 and name HB1))
  2.800  2.000  2.000 peak      5002 weight  0.10000E+01 volume  0.21667E+01 ppm1    6.439 ppm2  3.002
ASSI {5012}
(segid "PROT" and resid 74 and name HD%)
((segid "PROT" and resid 74 and name HB2))
  2.800  2.000  2.000 peak      5012 weight  0.10000E+01 volume  0.19346E+01 ppm1    6.429 ppm2  2.428
ASSI {5092}
((segid "PROT" and resid 74 and name HB1))
((segid "PROT" and resid 74 and name HB2))
  2.400  1.400  1.400 peak      5092 weight  0.10000E+01 volume  0.52357E+01 ppm1    2.997 ppm2  2.425
ASSI {5102}
((segid "PROT" and resid 46 and name HB1))
((segid "PROT" and resid 46 and name HB2))
  2.500  1.600  1.600 peak      5102 weight  0.10000E+01 volume  0.39310E+01 ppm1    2.759 ppm2  2.426

TABLE 13-continued

Unambiguous NOE Distance Restraints

ASSI {5132}
((segid "PROT" and resid 18 and name HB1))
((segid "PROT" and resid 18 and name HB2))
  2.500  1.600  1.600 peak      5132 weight  0.10000E+01 volume  0.40166E+01 ppm1      1.562 ppm2  0.344
ASSI {5172}
((segid "PROT" and resid 116 and name HG12))
((segid "PROT" and resid 116 and name HB))
  2.800  2.000  2.000 peak      5172 weight  0.10000E+01 volume  0.21986E+01 ppm1      0.966 ppm2  1.847
ASSI {5182}
(segid "PROT" and resid 116 and name HG2%)
((segid "PROT" and resid 116 and name HB))
  2.100  1.100  1.100 peak      5182 weight  0.10000E+01 volume  0.12445E+02 ppm1      0.861 ppm2  1.847
ASSI {5192}
(segid "PROT" and resid 18 and name HD1%)
((segid "PROT" and resid 74 and name HB1))
  3.000  2.200  2.200 peak      5192 weight  0.10000E+01 volume  0.15029E+01 ppm1      0.513 ppm2  3.005
ASSI {5262}
(segid "PROT" and resid 34 and name HD%)
((segid "PROT" and resid 34 and name HB1))
  2.900  2.100  2.100 peak      5262 weight  0.10000E+01 volume  0.18411E+01 ppm1      7.188 ppm2  3.521
ASSI {5272}
(segid "PROT" and resid 34 and name HD%)
((segid "PROT" and resid 34 and name HB2))
  2.800  2.000  2.000 peak      5272 weight  0.10000E+01 volume  0.19384E+01 ppm1      7.190 ppm2  2.628
ASSI {5292}
((segid "PROT" and resid 34 and name HA))
((segid "PROT" and resid 34 and name HB2))
  2.800  2.000  2.000 peak      5292 weight  0.10000E+01 volume  0.19990E+01 ppm1      4.999 ppm2  2.642
ASSI {5312}
((segid "PROT" and resid 34 and name HB1))
((segid "PROT" and resid 34 and name HB2))
  2.500  1.600  1.600 peak      5312 weight  0.10000E+01 volume  0.39383E+01 ppm1      3.516 ppm2  2.634
ASSI {5332}
(segid "PROT" and resid 56 and name HD1%)
((segid "PROT" and resid 34 and name HB1))
  2.900  2.100  2.100 peak      5332 weight  0.10000E+01 volume  0.16847E+01 ppm1      0.978 ppm2  3.522
ASSI {5352}
(segid "PROT" and resid 102 and name HD2%)
((segid "PROT" and resid 105 and name HB1))
  2.800  2.000  2.000 peak      5352 weight  0.10000E+01 volume  0.21496E+01 ppm1      0.768 ppm2  3.140
ASSI {5372}
((segid "PROT" and resid 98 and name HA))
((segid "PROT" and resid 101 and name HB))
  2.600  1.700  1.700 peak      5372 weight  0.10000E+01 volume  0.34216E+01 ppm1      4.223 ppm2  1.942
ASSI {5412}
(segid "PROT" and resid 106 and name HD%)
((segid "PROT" and resid 106 and name HB1))
  2.800  2.000  2.000 peak      5412 weight  0.10000E+01 volume  0.23568E+01 ppm1      6.952 ppm2  3.355
ASSI {5422}
(segid "PROT" and resid 106 and name HD%)
((segid "PROT" and resid 106 and name HB2))
  2.700  1.800  1.800 peak      5422 weight  0.10000E+01 volume  0.27113E+01 ppm1      6.948 ppm2  3.135
ASSI {5432}
((segid "PROT" and resid 100 and name HA))
((segid "PROT" and resid 100 and name HB2))
  2.300  1.300  1.300 peak      5432 weight  0.10000E+01 volume  0.75634E+01 ppm1      4.370 ppm2  2.851
ASSI {5442}
((segid "PROT" and resid 100 and name HA))
((segid "PROT" and resid 100 and name HB1))
  2.300  1.300  1.300 peak      5442 weight  0.10000E+01 volume  0.77384E+01 ppm1      4.368 ppm2  2.916
ASSI {5452}
((segid "PROT" and resid 97 and name HA))
((segid "PROT" and resid 100 and name HB1))
  2.600  1.700  1.700 peak      5452 weight  0.10000E+01 volume  0.33747E+01 ppm1      4.235 ppm2  2.901
ASSI {5462}
((segid "PROT" and resid 97 and name HA))
((segid "PROT" and resid 100 and name HB2))
  2.500  1.600  1.600 peak      5462 weight  0.10000E+01 volume  0.37542E+01 ppm1      4.236 ppm2  2.848
ASSI {5502}
((segid "PROT" and resid 80 and name HD1))
((segid "PROT" and resid 52 and name HB2))
  2.900  2.100  2.100 peak      5502 weight  0.10000E+01 volume  0.18956E+01 ppm1      3.411 ppm2  2.955
ASSI {5512}
((segid "PROT" and resid 106 and name HB1))
((segid "PROT" and resid 106 and name HB2))
  2.300  1.300  1.300 peak      5512 weight  0.10000E+01 volume  0.76377E+01 ppm1      3.354 ppm2  3.134

TABLE 13-continued

| Unambiguous NOE Distance Restraints |
|---|

ASSI {5522}
((segid "PROT" and resid 80 and name HD2))
((segid "PROT" and resid 52 and name HB2))
  3.000  2.200  2.200 peak     5522  weight  0.10000E+01 volume  0.15004E+01 ppm1    3.331  ppm2  2.955
ASSI {5542}
((segid "PROT" and resid 95 and name HB2))
((segid "PROT" and resid 95 and name HB1))
  2.400  1.400  1.400 peak     5542  weight  0.10000E+01 volume  0.54751E+01 ppm1    2.639  ppm2  2.953
ASSI {5572}
(segid "PROT" and resid 52 and name HD%)
((segid "PROT" and resid 52 and name HB2))
  2.700  1.800  1.800 peak     5572  weight  0.10000E+01 volume  0.25372E+01 ppm1    7.280  ppm2  2.968
ASSI {5582}
(segid "PROT" and resid 52 and name HD%)
((segid "PROT" and resid 52 and name HB1))
  2.500  1.600  1.600 peak     5582  weight  0.10000E+01 volume  0.40623E+01 ppm1    7.278  ppm2  3.094
ASSI {5592}
(segid "PROT" and resid 15 and name HD%)
((segid "PROT" and resid 15 and name HB2))
  2.800  2.000  2.000 peak     5592  weight  0.10000E+01 volume  0.22258E+01 ppm1    7.107  ppm2  3.091
ASSI {5602}
(segid "PROT" and resid 15 and name HD%)
((segid "PROT" and resid 15 and name HB1))
  2.800  2.000  2.000 peak     5602  weight  0.10000E+01 volume  0.20171E+01 ppm1    7.104  ppm2  3.242
ASSI {5662}
((segid "PROT" and resid 15 and name HB1))
((segid "PROT" and resid 15 and name HB2))
  2.200  1.200  1.200 peak     5662  weight  0.10000E+01 volume  0.10177E+02 ppm1    3.237  ppm2  3.094
ASSI {5722}
(segid "PROT" and resid 82 and name HD%)
((segid "PROT" and resid 82 and name HB1))
  2.700  1.800  1.800 peak     5722  weight  0.10000E+01 volume  0.25453E+01 ppm1    6.693  ppm2  3.141
ASSI {5732}
(segid "PROT" and resid 82 and name HD%)
((segid "PROT" and resid 82 and name HB2))
  2.800  2.000  2.000 peak     5732  weight  0.10000E+01 volume  0.21571E+01 ppm1    6.691  ppm2  3.009
ASSI {5772}
((segid "PROT" and resid 84 and name HB2))
((segid "PROT" and resid 84 and name HB1))
  2.300  1.300  1.300 peak     5772  weight  0.10000E+01 volume  0.65685E+01 ppm1    2.715  ppm2  3.014
ASSI {5852}
((segid "PROT" and resid 92 and name HA))
((segid "PROT" and resid 92 and name HG1))
  2.400  1.400  1.400 peak     5852  weight  0.10000E+01 volume  0.57224E+01 ppm1    4.255  ppm2  2.387
ASSI {5882}
((segid "PROT" and resid 103 and name HA))
((segid "PROT" and resid 103 and name HG2))
  2.700  1.800  1.800 peak     5882  weight  0.10000E+01 volume  0.24953E+01 ppm1    3.225  ppm2  1.964
ASSI {5922}
((segid "PROT" and resid 110 and name HG11))
((segid "PROT" and resid 110 and name HB))
  2.600  1.700  1.700 peak     5922  weight  0.10000E+01 volume  0.29669E+01 ppm1    1.151  ppm2  1.796
ASSI {5932}
((segid "PROT" and resid 110 and name HG12))
((segid "PROT" and resid 110 and name HB))
  2.700  1.800  1.800 peak     5932  weight  0.10000E+01 volume  0.28889E+01 ppm1    1.092  ppm2  1.795
ASSI {5992}
((segid "PROT" and resid 47 and name HB2))
((segid "PROT" and resid 47 and name HB1))
  2.300  1.300  1.300 peak     5992  weight  0.10000E+01 volume  0.69282E+01 ppm1    2.844  ppm2  3.243
ASSI {6002}
((segid "PROT" and resid 42 and name HA))
((segid "PROT" and resid 42 and name HG1))
  2.500  1.600  1.600 peak     6002  weight  0.10000E+01 volume  0.40649E+01 ppm1    4.505  ppm2  2.362
ASSI {6022}
((segid "PROT" and resid 87 and name HA))
((segid "PROT" and resid 87 and name HG1))
  2.600  1.700  1.700 peak     6022  weight  0.10000E+01 volume  0.35044E+01 ppm1    4.342  ppm2  2.440
ASSI {6052}
(segid "PROT" and resid 83 and name HG2%)
((segid "PROT" and resid 87 and name HG1))
  2.900  2.100  2.100 peak     6052  weight  0.10000E+01 volume  0.17805E+01 ppm1    1.341  ppm2  2.456
ASSI {6072}
((segid "PROT" and resid 68 and name HA))
((segid "PROT" and resid 68 and name HB2))
  2.900  2.100  2.100 peak     6072  weight  0.10000E+01 volume  0.17045E+01 ppm1    4.576  ppm2  2.958

TABLE 13-continued

Unambiguous NOE Distance Restraints

ASSI {6082}
((segid "PROT" and resid 94 and name HA))
((segid "PROT" and resid 94 and name HG1))
  2.200  1.200  1.200 peak      6082  weight  0.10000E+01 volume  0.84120E+01 ppm1    4.252  ppm2  2.257
ASSI {6092}
((segid "PROT" and resid 61 and name HA))
((segid "PROT" and resid 61 and name HG1))
  2.500  1.600  1.600 peak      6092  weight  0.10000E+01 volume  0.40902E+01 ppm1    4.086  ppm2  2.414
ASSI {6112}
((segid "PROT" and resid 112 and name HA))
((segid "PROT" and resid 112 and name HG1))
  2.600  1.700  1.700 peak      6112  weight  0.10000E+01 volume  0.34812E+01 ppm1    4.024  ppm2  2.394
ASSI {6122}
((segid "PROT" and resid 112 and name HA))
((segid "PROT" and resid 112 and name HG2))
  2.600  1.700  1.700 peak      6122  weight  0.10000E+01 volume  0.35539E+01 ppm1    4.024  ppm2  2.252
ASSI {6132}
((segid "PROT" and resid 68 and name HB1))
((segid "PROT" and resid 68 and name HB2))
  2.400  1.400  1.400 peak      6132  weight  0.10000E+01 volume  0.51026E+01 ppm1    3.099  ppm2  2.959
ASSI {6152}
((segid "PROT" and resid 74 and name HB2))
((sesid "PROT" and resid 68 and name HB1))
  2.800  2.000  2.000 peak      6152  weight  0.10000E+01 volume  0.19665E+01 ppm1    2.416  ppm2  3.093
ASSI {6162}
((segid "PROT" and resid 61 and name HB2))
((segid "PROT" and resid 61 and name HG1))
  1.800  0.800  0.800 peak      6162  weight  0.10000E+01 volume  0.28485E+02 ppm1    2.116  ppm2  2.409
ASSI {6212}
((segid "PROT" and resid 36 and name HA))
((segid "PROT" and resid 36 and name HG1))
  2.800  2.000  2.000 peak      6212  weight  0.10000E+01 volume  0.23202E+01 ppm1    4.870  ppm2  2.207
ASSI {6222}
((segid "PROT" and resid 7 and name HA))
((sepid "PROT" and resid 7 and name HG1))
  2.800  2.000  2.000 peak      6222  weight  0.10000E+01 volume  0.19256E+01 ppm1    4.584  ppm2  2.309
ASSI {6232}
((segid "PROT" and resid 108 and name HA))
((segid "PROT" and resid 112 and name HG1))
  2.400  1.400  1.400 peak      6232  weight  0.10000E+01 volume  0.59666E+01 ppm1    4.231  ppm2  2.438
ASSI {6242}
((segid "PROT" and resid 8 and name HD2))
((segid "PROT" and resid 7 and name HG1))
  2.900  2.100  2.100 peak      6242  weight  0.10000E+01 volume  0.17750E+01 ppm1    3.735  ppm2  2.302
ASSI {6252}
((segid "PROT" and resid 37 and name HD1))
((segid "PROT" and resid 36 and name HG1))
  2.700  1.800  1.800 peak      6252  weight  0.10000E+01 volume  0.27081E+01 ppm1    3.706  ppm2  2.205
ASSI {6262}
((segid "PROT" and resid 7 and name HB2))
((segid "PROT" and resid 7 and name HG1))
  2.200  1.200  1.200 peak      6262  weight  0.10000E+01 volume  0.10332E+02 ppm1    1.946  ppm2  2.303
ASSI {6272}
((segid "PROT" and resid 36 and name HB1))
((segid "PROT" and resid 36 and name HG1))
  2.100  1.100  1.100 peak      6272  weight  0.10000E+01 volume  0.12608E+02 ppm1    1.808  ppm2  2.210
ASSI {6282}
((segid "PROT" and resid 24 and name HA))
((segid "PROT" and resid 24 and name HG1))
  2.500  1.600  1.600 peak      6282  weight  0.10000E+01 volume  0.40773E+01 ppm1    4.220  ppm2  2.889
ASSI {6292}
((segid "PROT" and resid 24 and name HA))
((segid "PROT" and resid 24 and name HG2))
  2.300  1.300  1.300 peak      6292  weight  0.10000E+01 volume  0.62451E+01 ppm1    4.222  ppm2  2.498
ASSI {6302}
((segid "PROT" and resid 79 and name HA))
((segid "PROT" and resid 79 and name HG1))
  2.400  1.400  1.400 peak      6302  weight  0.10000E+01 volume  0.53286E+01 ppm1    3.858  ppm2  2.467
ASSI {6322}
((segid "PROT" and resid 24 and name HG2))
((segid "PROT" and resid 24 and name HG1))
  1.900  0.900  0.900 peak      6322  weight  0.10000E+01 volume  0.19215E+02 ppm1    2.505  ppm2  2.890
ASSI {6332}
(segid "PROT" and resid 83 and name HG2%)
((segid "PROT" and resid 79 and name HG1))
  2.800  2.000  2.000 peak      6332  weight  0.10000E+01 volume  0.22432E+01 ppm1    1.343  ppm2  2.481

TABLE 13-continued

Unambiguous NOE Distance Restraints

ASSI {6372}
((segid "PROT" and resid 13 and name HA))
((segid "PROT" and resid 13 and name HG1))
 2.500  1.600  1.600 peak   6372 weight  0.10000E+01 volume  0.38637E+01 ppm1     4.222 ppm2  2.535
ASSI {6392}
((segid "PROT" and resid 23 and name HA))
((segid "PROT" and resid 23 and name HG1))
 2.500  1.600  1.600 peak   6392 weight  0.10000E+01 volume  0.39163E+01 ppm1     4.065 ppm2  2.594
ASSI {6402}
((segid "PROT" and resid 23 and name HA))
((segid "PROT" and resid 23 and name HG2))
 2.500  1.600  1.600 peak   6402 weight  0.10000E+01 volume  0.41947E+01 ppm1     4.065 ppm2  2.484
ASSI {6412}
((segid "PROT" and resid 10 and name HB1))
((segid "PROT" and resid 13 and name HG1))
 3.000  2.200  2.200 peak   6412 weight  0.10000E+01 volume  0.15094E+01 ppm1     2.806 ppm2  2.528
ASSI {6422}
((segid "PROT" and resid 10 and name HB1))
((segid "PROT" and resid 13 and name HG2))
 2.800  2.000  2.000 peak   6422 weight  0.10000E+01 volume  0.20457E+01 ppm1     2.797 ppm2  2.417
ASSI {6432}
((segid "PROT" and resid 23 and name HB1))
((segid "PROT" and resid 23 and name HG1))
 2.100  1.100  1.100 peak   6432 weight  0.10000E+01 volume  0.10562E+02 ppm1     2.372 ppm2  2.598
ASSI {6442}
((segid "PROT" and resid 23 and name HB2))
((segid "PROT" and resid 23 and name HG1))
 2.300  1.300  1.300 peak   6442 weight  0.10000E+01 volume  0.70727E+01 ppm1     2.270 ppm2  2.591
ASSI {6472}
(segid "PROT" and resid 49 and name HG1%)
((segid "PROT" and resid 49 and name HB))
 2.300  1.300  1.300 peak   6472 weight  0.10000E+01 volume  0.67655E+01 ppm1     0.964 ppm2  1.928
ASSI {6492}
((segid "PROT" and resid 60 and name HA))
((segid "PROT" and resid 59 and name HB2))
 2.400  2.400  2.100 peak   6492 weight  0.10000E+01 volume  0.56526E+01 ppm1     4.451 ppm2  1.936
ASSI {6582}
((segid "PROT" and resid 75 and name HB1))
((segid "PROT" and resid 75 and name HB2))
 2.100  1.100  1.100 peak   6582 weight  0.10000E+01 volume  0.12724E+02 ppm1     2.964 ppm2  2.649
ASSI {6602}
((segid "PROT" and resid 112 and name HG2))
((segid "PROT" and resid 111 and name HB1))
 2.400  1.400  1.400 peak   6602 weight  0.10000E+01 volume  0.55476E+01 ppm1     2.218 ppm2  1.930
ASSI {6622}
(segid "PROT" and resid 75 and name HE%)
((segid "PROT" and resid 75 and name HB2))
 2.600  1.700  1.700 peak   6622 weight  0.10000E+01 volume  0.29895E+01 ppm1     2.095 ppm2  2.645
ASSI {6702}
((segid "PROT" and resid 53 and name HA))
((segid "PROT" and resid 53 and name HB1))
 2.200  1.200  1.200 peak   6702 weight  0.10000E+01 volume  0.84112E+01 ppm1     4.123 ppm2  2.249
ASSI {6722}
((segid "PROT" and resid 16 and name HB2))
((segid "PROT" and resid 19 and name HB1))
 2.600  1.700  1.700 peak   6722 weight  0.10000E+01 volume  0.32944E+01 ppm1     3.944 ppm2  1.738
ASSI {6732}
((segid "PROT" and resid 16 and name HB2))
((segid "PROT" and resid 19 and name HB2))
 2.800  2.000  2.000 peak   6732 weight  0.10000E+01 volume  0.19396E+01 ppm1     3.944 ppm2  1.404
ASSI {6742}
((segid "PROT" and resid 11 and name HD1))
((segid "PROT" and resid 11 and name HB1))
 2.500  1.600  1.600 peak   6742 weight  0.10000E+01 volume  0.38499E+01 ppm1     3.937 ppm2  2.367
ASSI {6802}
((segid "PROT" and resid 19 and name HD1))
((segid "PROT" and resid 19 and name HB2))
 2.700  1.800  1.800 peak   6802 weight  0.10000E+01 volume  0.24759E+01 ppm1     1.636 ppm2  1.405
ASSI {6822}
((segid "PROT" and resid 104 and name HG1))
((segid "PROT" and resid 104 and name HB1))
 2.100  1.100  1.100 peak   6822 weight  0.10000E+01 volume  0.11956E+02 ppm1     1.557 ppm2  1.957
ASSI {6832}
((segid "PROT" and resid 14 and name HG))
((segid "PROT" and resid 8 and name HB2))
 2.200  1.200  1.200 peak   6832 weight  0.10000E+01 volume  0.10296E+02 ppm1     1.456 ppm2  1.895

TABLE 13-continued

Unambiguous NOE Distance Restraints

```
ASSI {6842}
((segid "PROT" and resid 19 and name HB2))
((segid "PROT" and resid 19 and name HB1))
  2.100  1.100   1.100 peak      6842 weight  0.10000E+01 volume  0.10486E+02 ppm1    1.412 ppm2  1.745
ASSI {6852}
((segid "PROT" and resid 111 and name HG2))
((segid "PROT" and resid 111 and name HB1))
  2.400  1.400   1.400 peak      6852 weight  0.10000E+01 volume  0.49775E+01 ppm1    1.346 ppm2  1.886
ASSI {6862}
((segid "PROT" and resid 19 and name HG1))
((segid "PROT" and resid 19 and name HB1))
  2.200  1.200   1.200 peak      6862 weight  0.10000E+01 volume  0.90954E+01 ppm1    1.337 ppm2  1.761
ASSI {6872}
(segid "PROT" and resid 63 and name HD1%)
((segid "PROT" and resid 19 and name HB2))
  2.600  1.700   1.700 peak      6872 weight  0.10000E+01 volume  0.32948E+01 ppm1    0.920 ppm2  1.410
ASSI {6902}
((segid "PROT" and resid 11 and name HA))
((segid "PROT" and resid 11 and name HB2))
  2.000  1.000   1.000 peak      6902 weight  0.10000E+01 volume  0.13888E+02 ppm1    4.376 ppm2  2.086
ASSI {6912}
((segid "PROT" and resid 70 and name HB1))
((segid "PROT" and resid 8 and name HB2))
  2.400  2.400   2.100 peak      6912 weight  0.10000E+01 volume  0.52516E+01 ppm1    4.239 ppm2  1.913
ASSI {6952}
((segid "PROT" and resid 8 and name HD2))
((segid "PROT" and resid 8 and name HB1))
  2.600  1.700   1.700 peak      6952 weight  0.10000E+01 volume  0.29567E+01 ppm1    3.713 ppm2  2.281
ASSI {6962}
((segid "PROT" and resid 19 and name HA))
((segid "PROT" and resid 19 and name HB1))
  2.500  1.600   1.600 peak      6962 weight  0.10000E+01 volume  0.38082E+01 ppm1    3.713 ppm2  1.728
ASSI {6972}
((segid "PROT" and resid 101 and name HA))
((segid "PROT" and resid 104 and name HB1))
  2.600  1.700   1.700 peak      6972 weight  0.10000E+01 volume  0.30264E+01 ppm1    3.697 ppm2  1.968
ASSI {6992}
((segid "PROT" and resid 107 and name HB1))
((segid "PROT" and resid 104 and name HB1))
  3.000  2.200   2.200 peak      6992 weight  0.10000E+01 volume  0.15093E+01 ppm1    3.092 ppm2  1.960
ASSI {7002}
((segid "PROT" and resid 104 and name HE1))
((segid "PROT" and resid 104 and name HB1))
  2.600  1.700   1.700 peak      7002 weight  0.10000E+01 volume  0.33778E+01 ppm1    3.034 ppm2  1.925
ASSI {7012}
((segid "PROT" and resid 28 and name HB2))
((segid "PROT" and resid 28 and name HB1))
  2.400  1.400   1.400 peak      7012 weight  0.10000E+01 volume  0.48156E+01 ppm1    2.819 ppm2  3.020
ASSI {7042}
((segid "PROT" and resid 19 and name HG1))
((segid "PROT" and resid 19 and name HB2))
  2.300  1.300   1.300 peak      7042 weight  0.10000E+01 volume  0.66324E+01 ppm1    1.309 ppm2  1.420
ASSI {7052}
(segid "PROT" and resid 63 and name HD1%)
((segid "PROT" and resid 19 and name HB1))
  2.800  2.000   2.000 peak      7052 weight  0.10000E+01 volume  0.21494E+01 ppm1    0.915 ppm2  1.742
ASSI {7062}
(segid "PROT" and resid 14 and name HD1%)
((segid "PROT" and resid 8 and name HB2))
  2.400  1.400   1.400 peak      7062 weight  0.10000E+01 volume  0.52317E+01 ppm1    0.836 ppm2  1.906
ASSI {7152}
((segid "PROT" and resid 37 and name HB1))
((segid "PROT" and resid 37 and name HB2))
  2.100  1.100   1.100 peak      7152 weight  0.10000E+01 volume  0.11186E+02 ppm1    2.376 ppm2  1.703
ASSI {7162}
((segid "PROT" and resid 8 and name HB1))
((segid "PROT" and resid 8 and name HB2))
  1.900  0.900   0.900 peak      7162 weight  0.10000E+01 volume  0.19399E+02 ppm1    2.291 ppm2  1.917
ASSI {7202}
((segid "PROT" and resid 57 and name HG1))
((segid "PROT" and resid 37 and name HB1))
  2.800  2.000   2.000 peak      7202 weight  0.10000E+01 volume  0.23225E+01 ppm1    1.533 ppm2  2.381
ASSI {7212}
((segid "PROT" and resid 14 and name HG))
((segid "PROT" and resid 8 and name HB1))
  2.800  2.000   2.000 peak      7212 weight  0.10000E+01 volume  0.21068E+01 ppm1    1.460 ppm2  2.341
```

TABLE 13-continued

| Unambiguous NOE Distance Restraints |
| --- |

ASSI {7232}
((segid "PROT" and resid 44 and name HA))
((segid "PROT" and resid 44 and name HB1))
  2.300  1.300  1.300 peak      7232 weight  0.10000E+01 volume  0.61173E+01 ppm1    4.550 ppm2  2.417
ASSI {7252}
((segid "PROT" and resid 44 and name HD1))
((segid "PROT" and resid 44 and name HB2))
  3.000  2.200  2.200 peak      7252 weight  0.10000E+01 volume  0.15117E+01 ppm1    3.843 ppm2  2.051
ASSI {7262}
((segid "PROT" and resid 91 and name HG1))
((segid "PROT" and resid 91 and name HB1))
  2.400  1.400  1.400 peak      7262 weight  0.10000E+01 volume  0.59619E+01 ppm1    1.990 ppm2  1.628
ASSI {7302}
((segid "PROT" and resid 109 and name HG1))
((segid "PROT" and resid 109 and name HB2))
  2.600  1.700  1.700 peak      7302 weight  0.10000E+01 volume  0.36664E+01 ppm1    0.853 ppm2  1.586
ASSI {7312}
((segid "PROT" and resid 36 and name HA))
((segid "PROT" and resid 36 and name HB1))
  2.900  2.100  2.100 peak      7312 weight  0.10000E+01 volume  0.17361E+01 ppm1    4.873 ppm2  2.145
ASSI {7322}
((segid "PROT" and resid 36 and name HA))
((segid "PROT" and resid 36 and name HB2))
  2.900  2.100  2.100 peak      7322 weight  0.10000E+01 volume  0.18767E+01 ppm1    4.866 ppm2  1.802
ASSI {7332}
((segid "PROT" and resid 69 and name HA))
((segid "PROT" and resid 69 and name HB))
  2.100  1.100  1.100 peak      7332 weight  0.10000E+01 volume  0.11082E+02 ppm1    4.121 ppm2  2.350
ASSI {7342}
((segid "PROT" and resid 36 and name HG1))
((segid "PROT" and resid 36 and name HB2))
  2.000  1.000  1.000 peak      7342 weight  0.10000E+01 volume  0.14522E+02 ppm1    2.193 ppm2  1.800
ASSI {7352}
((segid "PROT" and resid 36 and name HB2))
((segid "PROT" and resid 36 and name HB1))
  2.000  1.000  1.000 peak      7352 weight  0.10000E+01 volume  0.13927E+02 ppm1    1.804 ppm2  2.149
ASSI {7392}
((segid "PROT" and resid 54 and name HG1))
((segid "PROT" and resid 54 and name HB2))
  2.900  2.100  2.100 peak      7392 weight  0.10000E+01 volume  0.16439E+01 ppm1    2.747 ppm2  1.390
ASSI {7402}
((segid "PROT" and resid 54 and name HG1))
((segid "PROT" and resid 54 and name HB1))
  2.900  2.100  2.100 peak      7402 weight  0.10000E+01 volume  0.16583E+01 ppm1    2.739 ppm2  2.035
ASSI {7412}
((segid "PROT" and resid 90 and name HB1))
((segid "PROT" and resid 90 and name HB2))
  2.100  1.100  1.100 peak      7412 weight  0.10000E+01 volume  0.12123E+02 ppm1    2.347 ppm2  2.182
ASSI {7422}
((segid "PROT" and resid 54 and name HB1))
((segid "PROT" and resid 54 and name HB2))
  2.600  1.700  1.700 peak      7422 weight  0.10000E+01 volume  0.35394E+01 ppm1    2.028 ppm2  1.380
ASSI {7452}
((segid "PROT" and resid 42 and name HA))
((segid "PROT" and resid 42 and name HB2))
  2.600  1.700  1.700 peak      7452 weight  0.10000E+01 volume  0.33452E+01 ppm1    4.508 ppm2  2.075
ASSI {7462}
((segid "PROT" and resid 9 and name HA))
((segid "PROT" and resid 9 and name HB1))
  2.300  1.300  1.300 peak      7462 weight  0.10000E+01 volume  0.64998E+01 ppm1    4.364 ppm2  1.873
ASSI {7492}
((segid "PROT" and resid 81 and name HA))
((segid "PROT" and resid 81 and name HB))
  2.700  1.800  1.800 peak      7492 weight  0.10000E+01 volume  0.25831E+01 ppm1    3.126 ppm2  1.465
ASSI {7502}
((segid "PROT" and resid 54 and name HG1))
((segid "PROT" and resid 54 and name HG2))
  2.600  1.700  1.700 peak      7502 weight  0.10000E+01 volume  0.36087E+01 ppm1    2.746 ppm2  1.897
ASSI {7532}
(segid "PROT" and resid 81 and name HG1%)
((segid "PROT" and resid 54 and name HG2))
  2.800  2.000  2.000 peak      7532 weight  0.10000E+01 volume  0.21318E+01 ppm1    0.508 ppm2  1.898
ASSI {7602}
((segid "PROT" and resid 51 and name HD1))
((segid "PROT" and resid 51 and name HB2))
  2.700  1.800  1.800 peak      7602 weight  0.10000E+01 volume  0.27404E+01 ppm1    3.022 ppm2  1.212

TABLE 13-continued

| Unambiguous NOE Distance Restraints |
|---|

ASSI {7612}
((segid "PROT" and resid 57 and name HE2))
((segid "PROT" and resid 57 and name HB2))
 2.600  1.700   1.700 peak      7612 weight  0.10000E+01 volume  0.31496E+01 ppm1    2.081 ppm2  1.144
ASSI {7632}
((segid "PROT" and resid 51 and name HB2))
((segid "PROT" and resid 51 and name HB1))
 1.900  0.900   0.900 peak      7632 weight  0.10000E+01 volume  0.23953E+02 ppm1    1.213 ppm2  1.384
ASSI {7652}
((segid "PROT" and resid 87 and name HA))
((segid "PROT" and resid 87 and name HB1))
 2.200  1.200   1.200 peak      7652 weight  0.10000E+01 volume  0.80014E+01 ppm1    4.343 ppm2  2.226
ASSI {7662}
((segid "PROT" and resid 87 and name HA))
((segid "PROT" and resid 87 and name HB2))
 2.200  1.200   1.200 peak      7662 weight  0.10000E+01 volume  0.87899E+01 ppm1    4.341 ppm2  2.060
ASSI {7682}
((segid "PROT" and resid 87 and name HG2))
((segid "PROT" and resid 87 and name HB2))
 1.700  0.700   0.700 peak      7682 weight  0.10000E+01 volume  0.37037E+02 ppm1    2.240 ppm2  2.075
ASSI {7692}
(segid "PROT" and resid 113 and name HB%)
((segid "PROT" and resid 112 and name HB1))
 2.500  1.600   1.600 peak      7692 weight  0.10000E+01 volume  0.37285E+01 ppm1    1.414 ppm2  2.097
ASSI {7702}
((segid "PROT" and resid 33 and name HB1))
((segid "PROT" and resid 33 and name HB2))
 3.000  2.200   2.200 peak      7702 weight  0.10000E+01 volume  0.15063E+01 ppm1    1.078 ppm2  −0.431
ASSI {7712}
(segid "PROT" and resid 49 and name HG2%)
((segid "PROT" and resid 87 and name HB2))
 2.900  2.100   2.100 peak      7712 weight  0.10000E+01 volume  0.15587E+01 ppm1    0.905 ppm2  2.080
ASSI {7762}
((segid "PROT" and resid 104 and name HA))
((segid "PROT" and resid 103 and name HG2))
 2.200  1.200   1.200 peak      7762 weight  0.10000E+01 volume  0.86935E+01 ppm1    4.098 ppm2  1.957
ASSI {7772}
((segid "PROT" and resid 112 and name HA))
((segid "PROT" and resid 112 and name HB1))
 2.000  1.000   1.000 peak      7772 weight  0.10000E+01 volume  0.14908E+02 ppm1    4.024 ppm2  2.107
ASSI {7832}
((segid "PROT" and resid 103 and name HG2))
((segid "PROT" and resid 103 and name HB2))
 2.500  1.600   1.600 peak      7832 weight  0.10000E+01 volume  0.43617E+01 ppm1    1.952 ppm2  1.324
ASSI {7842}
((segid "PROT" and resid 103 and name HB1))
((segid "PROT" and resid 103 and name HB2))
 2.100  1.100   1.100 peak      7842 weight  0.10000E+01 volume  0.10363E+02 ppm1    1.792 ppm2  1.333
ASSI {7902}
((segid "PROT" and resid 7 and name HA))
((segid "PROT" and resid 7 and name HB1))
 2.700  1.800   1.800 peak      7902 weight  0.10000E+01 volume  0.24043E+01 ppm1    4.586 ppm2  2.070
ASSI {7912}
((segid "PROT" and resid 7 and name HA))
((segid "PROT" and resid 7 and name HB2))
 2.800  2.000   2.000 peak      7912 weight  0.10000E+01 volume  0.21766E+01 ppm1    4.585 ppm2  1.943
ASSI {7942}
((segid "PROT" and resid 24 and name HA))
((segid "PROT" and resid 24 and name HB1))
 2.600  1.700   1.700 peak      7942 weight  0.10000E+01 volume  0.31104E+01 ppm1    4.221 ppm2  2.495
ASSI {7972}
((segid "PROT" and resid 8 and name HD2))
((segid "PROT" and resid 7 and name HB1))
 2.900  2.100   2.100 peak      7972 weight  0.10000E+01 volume  0.17393E+01 ppm1    3.717 ppm2  2.078
ASSI {7992}
((segid "PROT" and resid 111 and name HE1))
((segid "PROT" and resid 111 and name HD1))
 2.100  1.100   1.100 peak      7992 weight  0.10000E+01 volume  0.13020E+02 ppm1    2.959 ppm2  1.646
ASSI {8002}
((segid "PROT" and resid 24 and name HG1))
((segid "PROT" and resid 24 and name HB1))
 2.500  1.600   1.600 peak      8002 weight  0.10000E+01 volume  0.39707E+01 ppm1    2.890 ppm2  2.505
ASSI {8022}
((segid "PROT" and resid 24 and name HG2))
((segid "PROT" and resid 24 and name HB2))
 2.200  1.200   1.200 peak      8022 weight  0.10000E+01 volume  0.10130E+02 ppm1    2.510 ppm2  2.415

TABLE 13-continued

| Unambiguous NOE Distance Restraints |
|---|

ASSI {8042}
((segid "PROT" and resid 24 and name HB2))
((segid "PROT" and resid 24 and name HB1))
  2.400  1.400   1.400 peak      8042  weight  0.10000E+01  volume  0.59198E+01  ppm1      2.416  ppm2  2.519
ASSI {8052}
((segid "PROT" and resid 112 and name HG1))
((segid "PROT" and resid 112 and name HB1))
  1.800  0.800   0.800 peak      8052  weight  0.10000E+01  volume  0.25596E+02  ppm1      2.396  ppm2  2.120
ASSI {8082}
((segid "PROT" and resid 111 and name HG2))
((segid "PROT" and resid 111 and name HD1))
  2.000  1.000   1.000 peak      8082  weight  0.10000E+01  volume  0.17175E+02  ppm1      1.323  ppm2  1.639
ASSI {8092}
(segid "PROT" and resid 63 and name HD1%)
((segid "PROT" and resid 19 and name HD1))
  2.700  1.800   1.800 peak      8092  weight  0.10000E+01  volume  0.28800E+01  ppm1      0.916  ppm2  1.647
ASSI {8112}
((segid "PROT" and resid 64 and name HA))
((segid "PROT" and resid 64 and name HD1))
  2.600  1.700   1.700 peak      8112  weight  0.10000E+01  volume  0.36099E+01  ppm1      4.372  ppm2  1.788
ASSI {8142}
((segid "PROT" and resid 80 and name HD1))
((segid "PROT" and resid 80 and name HB2))
  2.900  2.100   2.100 peak      8142  weight  0.10000E+01  volume  0.16213E+01  ppm1      3.407  ppm2  1.957
ASSI {8172}
((segid "PROT" and resid 61 and name HG2))
((segid "PROT" and resid 57 and name HE2))
  1.700  1.700   2.800 peak      8172  weight  0.10000E+01  volume  0.41822E+02  ppm1      2.258  ppm2  2.109
ASSI {8192}
((segid "PROT" and resid 101 and name HG11))
((segid "PROT" and resid 101 and name HG12))
  2.100  1.100   1.100 peak      8192  weight  0.10000E+01  volume  0.11529E+02  ppm1      1.893  ppm2  1.242
ASSI {8252}
((segid "PROT" and resid 104 and name HA))
((segid "PROT" and resid 104 and name HD1))
  2.300  1.300   1.300 peak      8252  weight  0.10000E+01  volume  0.66354E+01  ppm1      4.101  ppm2  1.755
ASSI {8272}
((segid "PROT" and resid 104 and name HE1))
((segid "PROT" and resid 104 and name HD1))
  1.800  0.800   0.800 peak      8272  weight  0.10000E+01  volume  0.33570E+02  ppm1      3.023  ppm2  1.747
ASSI {8282}
((segid "PROT" and resid 57 and name HE2))
((segid "PROT" and resid 57 and name HD2))
  2.800  2.000   2.000 peak      8282  weight  0.10000E+01  volume  0.22756E+01  ppm1      2.085  ppm2  0.913
ASSI {8292}
((segid "PROT" and resid 104 and name HB1))
((segid "PROT" and resid 104 and name HD1))
  2.000  1.000   1.000 peak      8292  weight  0.10000E+01  volume  0.18472E+02  ppm1      1.961  ppm2  1.747
ASSI {8312}
((segid "PROT" and resid 104 and name HG1))
((segid "PROT" and resid 104 and name HD1))
  1.700  1.700   2.800 peak      8312  weight  0.10000E+01  volume  0.40675E+02  ppm1      1.554  ppm2  1.741
ASSI {8322}
((segid "PROT" and resid 104 and name HG2))
((segid "PROT" and resid 104 and name HD1))
  1.600  1.600   2.900 peak      8322  weight  0.10000E+01  volume  0.59831E+02  ppm1      1.468  ppm2  1.706
ASSI {8332}
((segid "PROT" and resid 57 and name HD2))
((segid "PROT" and resid 57 and name HD1))
  2.600  1.700   1.700 peak      8332  weight  0.10000E+01  volume  0.35657E+01  ppm1      0.915  ppm2  1.760
ASSI {8342}
((segid "PROT" and resid 61 and name HA))
((segid "PROT" and resid 61 and name HB1))
  2.300  1.300   1.300 peak      8342  weight  0.10000E+01  volume  0.77843E+01  ppm1      4.093  ppm2  2.248
ASSI {8352}
((segid "PROT" and resid 79 and name HA))
((segid "PROT" and resid 79 and name HB1))
  2.300  1.300   1.300 peak      8352  weight  0.10000E+01  volume  0.66007E+01  ppm1      3.864  ppm2  2.222
ASSI {8362}
((segid "PROT" and resid 79 and name HA))
((segid "PROT" and resid 79 and name HB2))
  2.300  1.300   1.300 peak      8362  weight  0.10000E+01  volume  0.61698E+01  ppm1      3.862  ppm2  2.112
ASSI {8372}
((segid "PROT" and resid 94 and name HA))
((segid "PROT" and resid 94 and name HB1))
  1.900  0.900   0.900 peak      8372  weight  0.10000E+01  volume  0.24388E+02  ppm1      4.244  ppm2  2.144

TABLE 13-continued

Unambiguous NOE Distance Restraints

ASSI {8382}
((segid "PROT" and resid 10 and name HB1))
((segid "PROT" and resid 13 and name HB1))
  2.600  1.700  1.700 peak     8382 weight  0.10000E+01 volume  0.29895E+01 ppm1   2.798 ppm2  2.191
ASSI {8392}
((segid "PROT" and resid 13 and name HG1))
((segid "PROT" and resid 13 and name HB1))
  2.000  1.000  1.000 peak     8392 weight  0.10000E+01 volume  0.13858E+02 ppm1   2.536 ppm2  2.194
ASSI {8402}
((segid "PROT" and resid 13 and name HG2))
((segid "PROT" and resid 13 and name HB1))
  1.800  0.800  0.800 peak     8402 weight  0.10000E+01 volume  0.32827E+02 ppm1   2.431 ppm2  2.183
ASSI {8472}
((segid "PROT" and resid 106 and name HB2))
((segid "PROT" and resid 21 and name HG11))
  2.400  2.400  2.100 peak     8472 weight  0.10000E+01 volume  0.49094E+01 ppm1   3.161 ppm2  1.823
ASSI {8482}
((segid "PROT" and resid 21 and name HB))
((segid "PROT" and resid 21 and name HG11))
  2.000  1.000  1.000 peak     8482 weight  0.10000E+01 volume  0.13836E+02 ppm1   1.954 ppm2  1.787
ASSI {8512}
((segid "PROT" and resid 21 and name HG12))
((segid "PROT" and resid 21 and name HG11))
  2.100  1.100  1.100 peak     8512 weight  0.10000E+01 volume  0.11436E+02 ppm1   1.070 ppm2  1.790
ASSI {8542}
((segid "PROT" and resid 20 and name HA))
((segid "PROT" and resid 23 and name HB1))
  2.600  1.700  1.700 peak     8542 weight  0.10000E+01 volume  0.33979E+01 ppm1   4.328 ppm2  2.370
ASSI {8552}
((segid "PROT" and resid 20 and name HA))
((segid "PROT" and resid 23 and name HB2))
  2.600  1.700  1.700 peak     8552 weight  0.10000E+01 volume  0.34588E+01 ppm1   4.325 ppm2  2.260
ASSI {8562}
((segid "PROT" and resid 23 and name HA))
((segid "PROT" and resid 23 and name HB1))
  2.300  1.300  1.300 peak     8562 weight  0.10000E+01 volume  0.72048E+01 ppm1   4.066 ppm2  2.368
ASSI {8592}
((segid "PROT" and resid 23 and name HG2))
((segid "PROT" and resid 23 and name HB1))
  2.300  1.300  1.300 peak     8592 weight  0.10000E+01 volume  0.65153E+01 ppm1   2.490 ppm2  2.359
ASSI {8602}
((segid "PROT" and resid 23 and name HB1))
((segid "PROT" and resid 23 and name HB2))
  1.900  0.900  0.900 peak     8602 weight  0.10000E+01 volume  0.20845E+02 ppm1   2.371 ppm2  2.263
ASSI {8652}
((segid "PROT" and resid 53 and name HA))
((segid "PROT" and resid 53 and name HG2))
  2.800  2.000  2.000 peak     8652 weight  0.10000E+01 volume  0.23066E+01 ppm1   4.123 ppm2  1.937
ASSI {8682}
((segid "PROT" and resid 32 and name HB1))
((segid "PROT" and resid 32 and name HB2))
  2.400  1.400  1.400 peak     8682 weight  0.10000E+01 volume  0.48514E+01 ppm1   3.640 ppm2  3.407
ASSI {8712}
((segid "PROT" and resid 53 and name HG1))
((segid "PROT" and resid 53 and name HG2))
  2.000  1.000  1.000 peak     8712 weight  0.10000E+01 volume  0.17544E+02 ppm1   2.274 ppm2  1.953
ASSI {8752}
((segid "PROT" and resid 44 and name HA))
((segid "PROT" and resid 44 and name HG2))
  2.600  1.700  1.700 peak     8752 weight  0.10000E+01 volume  0.31327E+01 ppm1   4.552 ppm2  2.078
ASSI {8762}
((segid "PROT" and resid 44 and name HA))
((segid "PROT" and resid 44 and name HG1))
  2.900  2.100  2.100 peak     8762 weight  0.10000E+01 volume  0.18869E+01 ppm1   4.546 ppm2  2.204
ASSI {8772}
((segid "PROT" and resid 66 and name HA))
((segid "PROT" and resid 66 and name HG1))
  2.600  1.700  1.700 peak     8772 weight  0.10000E+01 volume  0.35462E+01 ppm1   4.442 ppm2  1.614
ASSI {8792}
((segid "PROT" and resid 44 and name HD2))
((segid "PROT" and resid 44 and name HG2))
  2.600  1.700  1.700 peak     8792 weight  0.10000E+01 volume  0.37158E+01 ppm1   3.569 ppm2  2.086
ASSI {8812}
((segid "PROT" and resid 66 and name HD1))
((segid "PROT" and resid 66 and name HG1))
  2.500  1.600  1.600 peak     8812 weight  0.10000E+01 volume  0.43300E+01 ppm1   3.103 ppm2  1.614

TABLE 13-continued

Unambiguous NOE Distance Restraints

```
ASSI {8822}
((segid "PROT" and resid 66 and name HB1))
((segid "PROT" and resid 66 and name HG2))
 2.300  1.300  1.300 peak      8822 weight  0.10000E+01 volume  0.67305E+01 ppm1   2.133 ppm2  1.573
ASSI {8832}
((segid "PROT" and resid 66 and name HB2))
((segid "PROT" and resid 66 and name HG2))
 2.400  1.400  1.400 peak      8832 weight  0.10000E+01 volume  0.56248E+01 ppm1   2.050 ppm2  1.575
ASSI {8862}
((segid "PROT" and resid 78 and name HB2))
((segid "PROT" and resid 78 and name HG))
 2.400  1.400  1.400 peak      8862 weight  0.10000E+01 volume  0.56132E+01 ppm1   0.474 ppm2  0.694
ASSI {8892}
((segid "PROT" and resid 10 and name HA))
((segid "PROT" and resid 11 and name HG1))
 2.900  2.100  2.100 peak      8892 weight  0.10000E+01 volume  0.15699E+01 ppm1   4.919 ppm2  2.106
ASSI {8902}
((segid "PROT" and resid 8 and name HA))
((segid "PROT" and resid 8 and name HG1))
 2.500  1.600  1.600 peak      8902 weight  0.10000E+01 volume  0.38281E+01 ppm1   4.463 ppm2  2.061
ASSI {8912}
((segid "PROT" and resid 11 and name HA))
((segid "PROT" and resid 11 and name HG1))
 2.500  1.600  1.600 peak      8912 weight  0.10000E+01 volume  0.41483E+01 ppm1   4.376 ppm2  2.096
ASSI {8932}
((segid "PROT" and resid 11 and name HD1))
((segid "PROT" and resid 11 and name HG1))
 2.000  1.000  1.000 peak      8932 weight  0.10000E+01 volume  0.15330E+02 ppm1   3.902 ppm2  2.097
ASSI {8962}
((segid "PROT" and resid 91 and name HA))
((segid "PROT" and resid 91 and name HG2))
 2.800  2.000  2.000 peak      8962 weight  0.10000E+01 volume  0.19450E+01 ppm1   2.589 ppm2  1.708
ASSI {8972}
((segid "PROT" and resid 11 and name HB1))
((segid "PROT" and resid 11 and name HG1))
 2.000  1.000  1.000 peak      8972 weight  0.10000E+01 volume  0.17135E+02 ppm1   2.382 ppm2  2.098
ASSI {8982}
((segid "PROT" and resid 8 and name HB1))
((segid "PROT" and resid 8 and name HG1))
 1.800  0.800  0.800 peak      8982 weight  0.10000E+01 volume  0.27927E+02 ppm1   2.290 ppm2  2.056
ASSI {8992}
((segid "PROT" and resid 8 and name HB2))
((segid "PROT" and resid 8 and name HG1))
 2.100  1.100  1.100 peak      8992 weight  0.10000E+01 volume  0.11694E+02 ppm1   1.923 ppm2  2.056
ASSI {9002}
((segid "PROT" and resid 91 and name HG2))
((segid "PROT" and resid 91 and name HG1))
 2.000  1.000  1.000 peak      9002 weight  0.10000E+01 volume  0.16829E+02 ppm1   1.710 ppm2  1.994
ASSI {9022}
(segid "PROT" and resid 73 and name HD1%)
((segid "PROT" and resid 73 and name HG))
 2.100  1.100  1.100 peak      9022 weight  0.10000E+01 volume  0.10664E+02 ppm1   0.971 ppm2  1.797
ASSI {9032}
(segid "PROT" and resid 73 and name HD2%)
((segid "PROT" and resid 73 and name HG))
 2.100  1.100  1.100 peak      9032 weight  0.10000E+01 volume  0.10796E+02 ppm1   0.932 ppm2  1.808
ASSI {9042}
(segid "PROT" and resid 14 and name HD2%)
((segid "PROT" and resid 8 and name HG1))
 2.800  2.000  2.000 peak      9042 weight  0.10000E+01 volume  0.20174E+01 ppm1   0.832 ppm2  2.058
ASSI {9062}
((segid "PROT" and resid 9 and name HA))
((segid "PROT" and resid 9 and name HG1))
 2.500  1.600  1.600 peak      9062 weight  0.10000E+01 volume  0.42875E+01 ppm1   4.362 ppm2  1.682
ASSI {9072}
((segid "PROT" and resid 115 and name HA))
((segid "PROT" and resid 115 and name HG))
 2.700  1.800  1.800 peak      9072 weight  0.10000E+01 volume  0.26718E+01 ppm1   4.257 ppm2  1.567
ASSI {9092}
((segid "PROT" and resid 9 and name HD1))
((segid "PROT" and resid 9 and name HG1))
 2.300  1.300  1.300 peak      9092 weight  0.10000E+01 volume  0.71572E+01 ppm1   3.224 ppm2  1.693
ASSI {9122}
((segid "PROT" and resid 22 and name HB1))
((segid "PROT" and resid 22 and name HG))
 2.300  1.300  1.300 peak      9122 weight  0.10000E+01 volume  0.64668E+01 ppm1   2.122 ppm2  1.784
```

TABLE 13-continued

Unambiguous NOE Distance Restraints

ASSI {9132}
((segid "PROT" and resid 80 and name HB1))
((segid "PROT" and resid 80 and name HG1))
 1.900  0.900  0.900 peak       9132 weight  0.10000E+01 volume  0.21048E+02 ppm1   2.009 ppm2  1.780
ASSI {9142}
((segid "PROT" and resid 9 and name HB1))
((segid "PROT" and resid 9 and name HG1))
 1.900  0.900  0.900 peak       9142 weight  0.10000E+01 volume  0.23404E+02 ppm1   1.864 ppm2  1.689
ASSI {9152}
((segid "PROT" and resid 37 and name HB2))
((segid "PROT" and resid 37 and name HG1))
 2.500  1.600  1.600 peak       9152 weight  0.10000E+01 volume  0.37817E+01 ppm1   1.704 ppm2  2.175
ASSI {9172}
(segid "PROT" and resid 115 and name HD1%)
((segid "PROT" and resid 115 and name HG))
 2.000  1.000  1.000 peak       9172 weight  0.10000E+01 volume  0.15406E+02 ppm1   0.766 ppm2  1.571
ASSI {9192}
(segid "PROT" and resid 110 and name HG2%)
((segid "PROT" and resid 115 and name HG))
 2.900  2.100  2.100 peak       9192 weight  0.10000E+01 volume  0.16502E+01 ppm1   0.684 ppm2  1.556
ASSI {9202}
(segid "PROT" and resid 15 and name HE%)
(segid "PROT" and resid 63 and name HD1%)
 2.600  1.700  1.700 peak       9202 weight  0.10000E+01 volume  0.29945E+01 ppm1   6.925 ppm2  0.919
ASSI {9212}
((segid "PROT" and resid 35 and name HA))
(segid "PROT" and resid 56 and name HD1%)
 2.700  1.800  1.800 peak       9212 weight  0.10000E+01 volume  0.25843E+01 ppm1   4.340 ppm2  0.976
ASSI {9222}
((segid "PROT" and resid 116 and name HA))
((segid "PROT" and resid 116 and name HG11))
 2.800  2.000  2.000 peak       9222 weight  0.10000E+01 volume  0.19299E+01 ppm1   4.274 ppm2  1.350
ASSI {9232}
((segid "PROT" and resid 116 and name HA))
((segid "PROT" and resid 116 and name HG12))
 2.700  1.800  1.800 peak       9232 weight  0.10000E+01 volume  0.25639E+01 ppm1   4.273 ppm2  0.964
ASSI {9242}
((segid "PROT" and resid 56 and name HA))
(segid "PROT" and resid 56 and name HD1%)
 2.600  1.700  1.700 peak       9242 weight  0.10000E+01 volume  0.30591E+01 ppm1   4.078 ppm2  0.966
ASSI {9272}
((segid "PROT" and resid 26 and name HA))
(segid "PROT" and resid 56 and name HD1%)
 2.500  1.600  1.600 peak       9272 weight  0.10000E+01 volume  0.37902E+01 ppm1   3.935 ppm2  0.976
ASSI {9352}
((segid "PROT" and resid 34 and name HB2))
(segid "PROT" and resid 56 and name HD1%)
 2.700  1.800  1.800 peak       9352 weight  0.10000E+01 volume  0.23627E+01 ppm1   2.636 ppm2  0.979
ASSI {9382}
(segid "PROT" and resid 35 and name HE%)
(segid "PROT" and resid 56 and name HD1%)
 2.700  1.800  1.800 peak       9382 weight  0.10000E+01 volume  0.24784E+01 ppm1   2.218 ppm2  0.976
ASSI {9392}
((segid "PROT" and resid 112 and name HB1))
((segid "PROT" and resid 109 and name HD1))
 2.700  1.800  1.800 peak       9392 weight  0.10000E+01 volume  0.25178E+01 ppm1   2.113 ppm2  1.417
ASSI {9402}
((segid "PROT" and resid 56 and name HB1))
(segid "PROT" and resid 56 and name HD1%)
 2.500  1.600  1.600 peak       9402 weight  0.10000E+01 volume  0.42717E+01 ppm1   2.108 ppm2  0.974
ASSI {9422}
((segid "PROT" and resid 116 and name HB))
((segid "PROT" and resid 116 and name HG11))
 2.400  1.400  1.400 peak       9422 weight  0.10000E+01 volume  0.48995E+01 ppm1   1.853 ppm2  1.353
ASSI {9442}
((segid "PROT" and resid 56 and name HG))
(segid "PROT" and resid 56 and name HD1%)
 2.100  1.100  1.100 peak       9442 weight  0.10000E+01 volume  0.12057E+02 ppm1   1.763 ppm2  0.967
ASSI {9462}
((segid "PROT" and resid 56 and name HB2))
(segid "PROT" and resid 56 and name HD1%)
 2.500  1.600  1.600 peak       9462 weight  0.10000E+01 volume  0.42508E+01 ppm1   1.450 ppm2  0.967
ASSI {9482}
((segid "PROT" and resid 116 and name HG11))
((segid "PROT" and resid 116 and name HG12))
 1.900  0.900  0.900 peak       9482 weight  0.10000E+01 volume  0.19352E+02 ppm1   1.347 ppm2  0.964

TABLE 13-continued

| Unambiguous NOE Distance Restraints |
|---|

ASSI {9492}
((segid "PROT" and resid 51 and name HB2))
((segid "PROT" and resid 51 and name HG1))
  1.900  0.900  0.900 peak     9492  weight  0.10000E+01 volume  0.20832E+02 ppm1    1.212  ppm2  1.350
ASSI {9512}
(segid "PROT" and resid 63 and name HD2%)
(segid "PROT" and resid 63 and name HD1%)
  1.900  0.900  0.900 peak     9512  weight  0.10000E+01 volume  0.20111E+02 ppm1    1.080  ppm2  0.919
ASSI {9542}
(segid "PROT" and resid 14 and name HD1%)
((segid "PROT" and resid 14 and name HG))
  2.000  1.000  1.000 peak     9542  weight  0.10000E+01 volume  0.14691E+02 ppm1    0.846  ppm2  1.439
ASSI {9582}
((segid "PROT" and resid 34 and name HZ))
((segid "PROT" and resid 85 and name HB1))
  2.700  1.800  1.800 peak     9582  weight  0.10000E+01 volume  0.27166E+01 ppm1    7.291  ppm2  3.407
ASSI {9592}
((segid "PROT" and resid 34 and name HZ))
((segid "PROT" and resid 85 and name HB2))
  2.900  2.100  2.100 peak     9592  weight  0.10000E+01 volume  0.18097E+01 ppm1    7.295  ppm2  3.062
ASSI {9602}
(segid "PROT" and resid 82 and name HE%)
((segid "PROT" and resid 102 and name HG))
  2.800  2.000  2.000 peak     9602  weight  0.10000E+01 volume  0.23143E+01 ppm1    6.462  ppm2  1.600
ASSI {9612}
((segid "PROT" and resid 85 and name HA))
((segid "PROT" and resid 85 and name HB1))
  2.700  1.800  1.800 peak     9612  weight  0.10000E+01 volume  0.25087E+01 ppm1    4.515  ppm2  3.415
ASSI {9642}
((segid "PROT" and resid 98 and name HA))
((segid "PROT" and resid 98 and name HB2))
  2.700  1.800  1.800 peak     9642  weight  0.10000E+01 volume  0.24656E+01 ppm1    4.220  ppm2  3.078
ASSI {9652}
((segid "PROT" and resid 85 and name HB1))
((segid "PROT" and resid 85 and name HB2))
  2.200  1.200  1.200 peak     9652  weight  0.10000E+01 volume  0.83966E+01 ppm1    3.413  ppm2  3.084
ASSI {9692}
(segid "PROT" and resid 25 and name HG2%)
((segid "PROT" and resid 102 and name HG))
  2.700  1.800  1.800 peak     9692  weight  0.10000E+01 volume  0.26216E+01 ppm1    1.068  ppm2  1.577
ASSI {9712}
((segid "PROT" and resid 60 and name HB1))
(segid "PROT" and resid 22 and name HD1%)
  2.300  1.300  1.300 peak     9712  weight  0.10000E+01 volume  0.75192E+01 ppm1    4.243  ppm2  1.108
ASSI {9732}
((segid "PROT" and resid 60 and name HB2))
(segid "PROT" and resid 22 and name HD1%)
  2.600  1.700  1.700 peak     9732  weight  0.10000E+01 volume  0.32675E+01 ppm1    4.068  ppm2  1.106
ASSI {9742}
((segid "PROT" and resid 110 and name HA))
((segid "PROT" and resid 110 and name HG11))
  2.300  2.300  2.200 peak     9742  weight  0.10000E+01 volume  0.76467E+01 ppm1    3.864  ppm2  1.164
ASSI {9752}
((segid "PROT" and resid 22 and name HB1))
(segid "PROT" and resid 22 and name HD1%)
  2.300  1.300  1.300 peak     9752  weight  0.10000E+01 volume  0.68112E+01 ppm1    2.133  ppm2  1.110
ASSI {9762}
((segid "PROT" and resid 22 and name HG))
(segid "PROT" and resid 22 and name HD1%)
  2.100  1.100  1.100 peak     9762  weight  0.10000E+01 volume  0.12147E+02 ppm1    1.796  ppm2  1.106
ASSI {9832}
((segid "PROT" and resid 78 and name HA))
(segid "PROT" and resid 78 and name HD1%)
  2.500  1.600  1.600 peak     9832  weight  0.10000E+01 volume  0.38272E+01 ppm1    3.413  ppm2  0.094
ASSI {9842}
(segid "PROT" and resid 25 and name HG1%)
(segid "PROT" and resid 78 and name HD1%)
  2.400  1.400  1.400 peak     9842  weight  0.10000E+01 volume  0.54518E+01 ppm1    1.247  ppm2  0.094
ASSI {9852}
(segid "PROT" and resid 25 and name HG2%)
(segid "PROT" and resid 78 and name HD1%)
  2.300  1.300  1.300 peak     9852  weight  0.10000E+01 volume  0.77910E+01 ppm1    1.063  ppm2  0.094
ASSI {9862}
((segid "PROT" and resid 78 and name HG))
(segid "PROT" and resid 78 and name HD1%)
  2.100  1.100  1.100 peak     9862  weight  0.10000E+01 volume  0.12211E+02 ppm1    0.695  ppm2  0.096

TABLE 13-continued

Unambiguous NOE Distance Restraints

ASSI {9872}
((segid "PROT" and resid 78 and name HB1))
(segid "PROT" and resid 78 and name HD1%)
  2.300  1.300  1.300 peak      9872 weight  0.10000E+01 volume  0.76579E+01 ppm1    0.746 ppm2   0.098
ASSI {9882}
(segid "PROT" and resid 78 and name HD2%)
(segid "PROT" and resid 78 and name HD1%)
  1.900  0.900  0.900 peak      9882 weight  0.10000E+01 volume  0.23626E+02 ppm1    0.198 ppm2   0.092
ASSI {9892}
(segid "PROT" and resid 68 and name HD%)
(segid "PROT" and resid 73 and name HD1%)
  3.000  2.200  2.200 peak      9892 weight  0.10000E+01 volume  0.15029E+01 ppm1    7.197 ppm2   0.975
ASSI {9922}
((segid "PROT" and resid 68 and name HA))
(segid "PROT" and resid 73 and name HD1%)
  2.700  1.800  1.800 peak      9922 weight  0.10000E+01 volume  0.24042E+01 ppm1    4.579 ppm2   0.973
ASSI {9932}
((segid "PROT" and resid 11 and name HA))
(segid "PROT" and resid 14 and name HD1%)
  2.900  2.100  2.100 peak      9932 weight  0.10000E+01 volume  0.17985E+01 ppm1    4.374 ppm2   0.853
ASSI {9942}
((segid "PROT" and resid 73 and name HA))
(segid "PROT" and resid 73 and name HD1%)
  2.600  1.700  1.700 peak      9942 weight  0.10000E+01 volume  0.35846E+01 ppm1    4.253 ppm2   0.976
ASSI {9962}
((segid "PROT" and resid 14 and name HA))
(segid "PROT" and resid 14 and name HD1%)
  2.400  1.400  1.400 peak      9962 weight  0.10000E+01 volume  0.48248E+01 ppm1    4.104 ppm2   0.849
ASSI {9972}
((segid "PROT" and resid 70 and name HB2))
(segid "PROT" and resid 73 and name HD1%)
  2.800  2.000  2.000 peak      9972 weight  0.10000E+01 volume  0.22200E+01 ppm1    3.786 ppm2   0.978
ASSI {9992}
((segid "PROT" and resid 73 and name HB1))
(segid "PROT" and resid 73 and name HD1%)
  2.300  1.300  1.300 peak      9992 weight  0.10000E+01 volume  0.72852E+01 ppm1    2.029 ppm2   0.973
ASSI {10002}
((segid "PROT" and resid 73 and name HB2))
(segid "PROT" and resid 73 and name HD1%)
  2.300  1.300  1.300 peak     10002 weight  0.10000E+01 volume  0.72588E+01 ppm1    1.916 ppm2   0.972
ASSI {10052}
((segid "PROT" and resid 14 and name HB2))
(segid "PROT" and resid 14 and name HD1%)
  2.200  1.200  1.200 peak     10052 weight  0.10000E+01 volume  0.93159E+01 ppm1    1.590 ppm2   0.845
ASSI {10062}
((segid "PROT" and resid 33 and name HD2))
((segid "PROT" and resid 33 and name HG1))
  2.900  2.100  2.100 peak     10062 weight  0.10000E+01 volume  0.15987E+01 ppm1    1.574 ppm2   0.274
ASSI {10072}
((segid "PROT" and resid 33 and name HD2))
((segid "PROT" and resid 33 and name HG2))
  2.900  2.100  2.100 peak     10072 weight  0.10000E+01 volume  0.15869E+01 ppm1    1.572 ppm2  −0.867
ASSI {10132}
((segid "PROT" and resid 33 and name HG2))
((segid "PROT" and resid 33 and name HG1))
  2.500  1.600  1.600 peak     10132 weight  0.10000E+01 volume  0.43453E+01 ppm1   −0.869 ppm2   0.275
ASSI {10182}
(segid "PROT" and resid 74 and name HD%)
(segid "PROT" and resid 18 and name HD1%)
  2.800  2.000  2.000 peak     10182 weight  0.10000E+01 volume  0.23158E+01 ppm1    6.436 ppm2   0.515
ASSI {10192}
((segid "PROT" and resid 63 and name HA))
(segid "PROT" and resid 63 and name HD2%)
  2.300  1.300  1.300 peak     10192 weight  0.10000E+01 volume  0.61524E+01 ppm1    4.722 ppm2   1.076
ASSI {10252}
((segid "PROT" and resid 15 and name HA))
(segid "PROT" and resid 18 and name HD1%)
  2.500  1.600  1.600 peak     10252 weight  0.10000E+01 volume  0.38191E+01 ppm1    4.060 ppm2   0.514
ASSI {10262}
((segid "PROT" and resid 110 and name HA))
(segid "PROT" and resid 115 and name HD1%)
  2.500  1.600  1.600 peak     10262 weight  0.10000E+01 volume  0.43512E+01 ppm1    3.859 ppm2   0.753
ASSI {10292}
((segid "PROT" and resid 68 and name HB1))
(segid "PROT" and resid 18 and name HD1%)
  2.600  1.700  1.700 peak     10292 weight  0.10000E+01 volume  0.32587E+01 ppm1    3.105 ppm2   0.509

TABLE 13-continued

Unambiguous NOE Distance Restraints

ASSI {10302}
((segid "PROT" and resid 66 and name HD2))
((segid "PROT" and resid 66 and name HB2))
 3.000  2.200  2.200 peak    10302 weight  0.10000E+01 volume  0.15198E+01 ppm1   3.068 ppm2  2.051
ASSI {10312}
((segid "PROT" and resid 68 and name HB2))
(segid "PROT" and resid 18 and name HD1%)
 2.400  1.400  1.400 peak    10312 weight  0.10000E+01 volume  0.47243E+01 ppm1   2.967 ppm2  0.515
ASSI {10322}
((segid "PROT" and resid 74 and name HB2))
(segid "PROT" and resid 18 and name HD1%)
 2.700  1.800  1.800 peak    10322 weight  0.10000E+01 volume  0.25991E+01 ppm1   2.427 ppm2  0.515
ASSI {10332}
((segid "PROT" and resid 63 and name HB1))
(segid "PROT" and resid 63 and name HD2%)
 2.600  1.700  1.700 peak    10332 weight  0.10000E+01 volume  0.35188E+01 ppm1   2.354 ppm2  1.078
ASSI {10342}
((segid "PROT" and resid 66 and name HB1))
((segid "PROT" and resid 66 and name HB2))
 2.200  1.200  1.200 peak    10342 weight  0.10000E+01 volume  0.86683E+01 ppm1   2.141 ppm2  2.046
ASSI {10382}
((segid "PROT" and resid 8 and name HB2))
(segid "PROT" and resid 115 and name HD1%)
 2.600  1.700  1.700 peak    10382 weight  0.10000E+01 volume  0.34114E+01 ppm1   1.908 ppm2  0.758
ASSI {10392}
((segid "PROT" and resid 14 and name HB1))
(segid "PROT" and resid 18 and name HD1%)
 2.900  2.100  2.100 peak    10392 weight  0.10000E+01 volume  0.18010E+01 ppm1   1.884 ppm2  0.515
ASSI {10402}
((segid "PROT" and resid 63 and name HG))
(segid "PROT" and resid 63 and name HD2%)
 2.200  1.200  1.200 peak    10402 weight  0.10000E+01 volume  0.88532E+01 ppm1   1.852 ppm2  1.078
ASSI {10412}
((segid "PROT" and resid 56 and name HG))
(segid "PROT" and resid 102 and name HD1%)
 2.100  2.100  2.400 peak    10412 weight  0.10000E+01 volume  0.10879E+02 ppm1   1.766 ppm2  0.757
ASSI {10422}
((segid "PROT" and resid 18 and name HG))
(segid "PROT" and resid 18 and name HD1%)
 2.400  1.400  1.400 peak    10422 weight  0.10000E+01 volume  0.59544E+01 ppm1   1.702 ppm2  0.514
ASSI {10432}
((segid "PROT" and resid 66 and name HG1))
((segid "PROT" and resid 66 and name HB2))
 2.500  1.600  1.600 peak    10432 weight  0.10000E+01 volume  0.41346E+01 ppm1   1.600 ppm2  2.049
ASSI {10442}
((segid "PROT" and resid 66 and name HG1))
((segid "PROT" and resid 66 and name HB1))
 2.500  1.600  1.600 peak    10442 weight  0.10000E+01 volume  0.41383E+01 ppm1   1.601 ppm2  2.130
ASSI {10452}
((segid "PROT" and resid 18 and name HB1))
(segid "PROT" and resid 63 and name HD2%)
 2.500  1.600  1.600 peak    10452 weight  0.10000E+01 volume  0.43181E+01 ppm1   1.557 ppm2  1.078
ASSI {10462}
((segid "PROT" and resid 18 and name HB1))
(segid "PROT" and resid 18 and name HD1%)
 2.400  1.400  1.400 peak    10462 weight  0.10000E+01 volume  0.55398E+01 ppm1   1.554 ppm2  0.514
ASSI {10482}
((segid "PROT" and resid 86 and name HG1))
((segid "PROT" and resid 86 and name HG2))
 2.300  1.300  1.300 peak    10482 weight  0.10000E+01 volume  0.61301E+01 ppm1   1.341 ppm2  0.166
ASSI {10492}
(segid "PROT" and resid 17 and name HG2%)
(segid "PROT" and resid 115 and name HD1%)
 2.200  1.200  1.200 peak    10492 weight  0.10000E+01 volume  0.99350E+01 ppm1   1.178 ppm2  0.748
ASSI {10522}
(segid "PROT" and resid 14 and name HD2%)
(segid "PROT" and resid 18 and name HD1%)
 2.200  1.200  1.200 peak    10522 weight  0.10000E+01 volume  0.78947E+01 ppm1   0.826 ppm2  0.513
ASSI {10532}
(segid "PROT" and resid 110 and name HD1%)
(segid "PROT" and resid 115 and name HD1%)
 2.600  2.600  1.900 peak    10532 weight  0.10000E+01 volume  0.34067E+01 ppm1   0.568 ppm2  0.761
ASSI {10542}
(segid "PROT" and resid 18 and name HD1%)
(segid "PROT" and resid 63 and name HD2%)
 2.400  1.400  1.400 peak    10542 weight  0.10000E+01 volume  0.48392E+01 ppm1   0.516 ppm2  1.079

TABLE 13-continued

Unambiguous NOE Distance Restraints

ASSI {10552}
((segid "PROT" and resid 18 and name HB2))
(segid "PROT" and resid 63 and name HD2%)
  2.700  1.800   1.800 peak      10552 weight  0.10000E+01 volume  0.25611E+01 ppm1    0.343  ppm2  1.079
ASSI {10562}
((segid "PROT" and resid 18 and name HB2))
(segid "PROT" and resid 18 and name HD1%)
  2.500  1.600   1.600 peak      10562 weight  0.10000E+01 volume  0.41021E+01 ppm1    0.346  ppm2  0.517
ASSI {10592}
(segid "PROT" and resid 18 and name HD2%)
(segid "PROT" and resid 115 and name HD1%)
  2.300  1.300   1.300 peak      10592 weight  0.10000E+01 volume  0.64278E+01 ppm1  −0.160  ppm2  0.749
ASSI {10632}
(segid "PROT" and resid 82 and name HE%)
(segid "PROT" and resid 102 and name HD1%)
  2.400  1.400   1.400 peak      10632 weight  0.10000E+01 volume  0.49504E+01 ppm1    6.476  ppm2  0.761
ASSI {10662}
((segid "PROT" and resid 104 and name HA))
((segid "PROT" and resid 104 and name HG1))
  2.300  1.300   1.300 peak      10662 weight  0.10000E+01 volume  0.62943E+01 ppm1    4.103  ppm2  1.550
ASSI {10672}
((segid "PROT" and resid 104 and name HA))
((segid "PROT" and resid 104 and name HG2))
  2.300  1.300   1.300 peak      10672 weight  0.10000E+01 volume  0.73311E+01 ppm1    4.097  ppm2  1.453
ASSI {10682}
((segid "PROT" and resid 104 and name HE1))
((segid "PROT" and resid 104 and name HG1))
  2.100  1.100   1.100 peak      10682 weight  0.10000E+01 volume  0.11157E+02 ppm1    3.028  ppm2  1.569
ASSI {10702}
((segid "PROT" and resid 111 and name HE1))
((segid "PROT" and resid 111 and name HG1))
  2.600  1.700   1.700 peak      10702 weight  0.10000E+01 volume  0.33124E+01 ppm1    2.934  ppm2  1.450
ASSI {10762}
((segid "PROT" and resid 102 and name HB1))
(segid "PROT" and resid 102 and name HD1%)
  2.300  1.300   1.300 peak      10762 weight  0.10000E+01 volume  0.66432E+01 ppm1    1.468  ppm2  0.764
ASSI {10772}
((segid "PROT" and resid 102 and name HB2))
(segid "PROT" and resid 102 and name HD1%)
  2.300  1.300   1.300 peak      10772 weight  0.10000E+01 volume  0.71507E+01 ppm1    1.261  ppm2  0.761
ASSI {10782}
(segid "PROT" and resid 25 and name HG2%)
(segid "PROT" and resid 102 and name HD1%)
  2.100  1.100   1.100 peak      10782 weight  0.10000E+01 volume  0.10874E+02 ppm1    1.072  ppm2  0.760
ASSI {10792}
(segid "PROT" and resid 116 and name HG2%)
((segid "PROT" and resid 111 and name HG1))
  2.700  1.800   1.800 peak      10792 weight  0.10000E+01 volume  0.28695E+01 ppm1    0.835  ppm2  1.453
ASSI {10802}
((segid "PROT" and resid 64 and name HA))
((segid "PROT" and resid 64 and name HG1))
  2.500  1.600   1.600 peak      10802 weight  0.10000E+01 volume  0.42177E+01 ppm1    4.377  ppm2  1.650
ASSI {10862}
((segid "PROT" and resid 16 and name HB2))
((segid "PROT" and resid 19 and name HG1))
  2.900  2.100   2.100 peak      10862 weight  0.10000E+01 volume  0.17444E+01 ppm1    3.940  ppm2  1.316
ASSI {10902}
(segid "PROT" and resid 14 and name HD2%)
(segid "PROT" and resid 18 and name HG)
  2.700  1.800   1.800 peak      10902 weight  0.10000E+01 volume  0.24419E+01 ppm1    0.833  ppm2  1.690
ASSI {10932}
((segid "PROT" and resid 81 and name HB))
(segid "PROT" and resid 78 and name HD2%)
  2.600  1.700   1.700 peak      10932 weight  0.10000E+01 volume  0.30227E+01 ppm1    1.467  ppm2  0.196
ASSI {10942}
(segid "PROT" and resid 59 and name HE%)
(segid "PROT" and resid 78 and name HD2%)
  2.400  1.400   1.400 peak      10942 weight  0.10000E+01 volume  0.59847E+01 ppm1    1.310  ppm2  0.194
ASSI {10952}
((segid "PROT" and resid 50 and name HB))
((segid "PROT" and resid 50 and name HG12))
  2.400  1.400   1.400 peak      10952 weight  0.10000E+01 volume  0.59613E+01 ppm1    1.249  ppm2  0.193
ASSI {10992}
((segid "PROT" and resid 50 and name HG12))
((segid "PROT" and resid 50 and name HG11))
  2.500  1.600   1.600 peak      10992 weight  0.10000E+01 volume  0.39414E+01 ppm1    0.185  ppm2  0.827

TABLE 13-continued

Unambiguous NOE Distance Restraints

ASSI {11052}
((segid "PROT" and resid 25 and name HA))
(segid "PROT" and resid 102 and name HD2%)
  2.500  1.600  1.600 peak     11052  weight  0.10000E+01 volume  0.41975E+01 ppm1     3.869  ppm2  0.766
ASSI {11072}
((segid "PROT" and resid 78 and name HA))
(segid "PROT" and resid 78 and name HD2%)
  2.200  1.200  1.200 peak     11072  weight  0.10000E+01 volume  0.82572E+01 ppm1     3.416  ppm2  0.198
ASSI {11082}
((segid "PROT" and resid 105 and name HB2))
(segid "PROT" and resid 102 and name HD2%)
  2.500  1.600  1.600 peak     11082  weight  0.10000E+01 volume  0.41341E+01 ppm1     3.101  ppm2  0.766
ASSI {11092}
((segid "PROT" and resid 28 and name HB1))
(segid "PROT" and resid 102 and name HD2%)
  2.400  1.400  1.400 peak     11092  weight  0.10000E+01 volume  0.49393E+01 ppm1     3.023  ppm2  0.767
ASSI {11102}
((segid "PROT" and resid 28 and name HB2))
(segid "PROT" and resid 102 and name HD2%)
  2.600  1.700  1.700 peak     11102  weight  0.10000E+01 volume  0.32553E+01 ppm1     2.819  ppm2  0.763
ASSI {11112}
((segid "PROT" and resid 102 and name HB2))
(segid "PROT" and resid 102 and name HD2%)
  2.200  1.200  1.200 peak     11112  weight  0.10000E+01 volume  0.80020E+01 ppm1     1.257  ppm2  0.766
ASSI {11132}
(segid "PROT" and resid 25 and name HG2%)
(segid "PROT" and resid 78 and name HD2%)
  2.200  1.200  1.200 peak     11132  weight  0.10000E+01 volume  0.84055E+01 ppm1     1.062  ppm2  0.196
ASSI {11142}
((segid "PROT" and resid 78 and name HG))
(segid "PROT" and resid 78 and name HD2%)
  2.000  1.000  1.000 peak     11142  weight  0.10000E+01 volume  0.17074E+02 ppm1     0.691  ppm2  0.194
ASSI {11152}
((segid "PROT" and resid 78 and name HB2))
(segid "PROT" and resid 78 and name HD2%)
  2.300  1.300  1.300 peak     11152  weight  0.10000E+01 volume  0.74312E+01 ppm1     0.500  ppm2  0.195
ASSI {11182}
((segid "PROT" and resid 22 and name HA))
(segid "PROT" and resid 22 and name HD2%)
  2.100  1.100  1.100 peak     11182  weight  0.10000E+01 volume  0.11230E+02 ppm1     4.153  ppm2  1.051
ASSI {11192}
((segid "PROT" and resid 56 and name HA))
(segid "PROT" and resid 22 and name HD2%)
  2.600  1.700  1.700 peak     11192  weight  0.10000E+01 volume  0.30625E+01 ppm1     4.068  ppm2  1.051
ASSI {11202}
((segid "PROT" and resid 25 and name HB))
(segid "PROT" and resid 22 and name HD2%)
  2.700  1.800  1.800 peak     11202  weight  0.10000E+01 volume  0.24545E+01 ppm1     2.446  ppm2  1.047
ASSI {11212}
((segid "PROT" and resid 22 and name HB1))
(segid "PROT" and resid 22 and name HD2%)
  2.400  1.400  1.400 peak     11212  weight  0.10000E+01 volume  0.56798E+01 ppm1     2.136  ppm2  1.050
ASSI {11222}
((segid "PROT" and resid 59 and name HB2))
(segid "PROT" and resid 22 and name HD2%)
  2.500  1.600  1.600 peak     11222  weight  0.10000E+01 volume  0.41435E+01 ppm1     1.915  ppm2  1.051
ASSI {11232}
((segid "PROT" and resid 22 and name HG))
(segid "PROT" and resid 22 and name HD2%)
  2.200  1.200  1.200 peak     11232  weight  0.10000E+01 volume  0.99228E+01 ppm1     1.793  ppm2  1.049
ASSI {11242}
(segid "PROT" and resid 59 and name HE%)
(segid "PROT" and resid 22 and name HD2%)
  2.300  1.300  1.300 peak     11242  weight  0.10000E+01 volume  0.61801E+01 ppm1     1.309  ppm2  1.049
ASSI {11272}
(segid "PROT" and resid 78 and name HD2%)
(segid "PROT" and resid 22 and name HD2%)
  2.700  1.800  1.800 peak     11272  weight  0.10000E+01 volume  0.28974E+01 ppm1     0.196  ppm2  1.049
ASSI {11282}
(segid "PROT" and resid 78 and name HD1%)
(segid "PROT" and resid 22 and name HD2%)
  2.900  2.100  2.100 peak     11282  weight  0.10000E+01 volume  0.18093E+01 ppm1     0.095  ppm2  1.049
ASSI {11302}
((segid "PROT" and resid 73 and name HA))
(segid "PROT" and resid 73 and name HD2%)
  2.000  1.000  1.000 peak     11302  weight  0.10000E+01 volume  0.13997E+02 ppm1     4.260  ppm2  0.928

TABLE 13-continued

Unambiguous NOE Distance Restraints

ASSI {11312}
((segid "PROT" and resid 73 and name HB1))
(segid "PROT" and resid 73 and name HD2%)
  2.400  1.400   1.400 peak      11312  weight  0.10000E+01 volume  0.52914E+01 ppm1     2.029  ppm2  0.928
ASSI {11322}
((segid "PROT" and resid 73 and name HB2))
(segid "PROT" and resid 73 and name HD2%)
  2.300  1.300   1.300 peak      11322  weight  0.10000E+01 volume  0.73295E+01 ppm1     1.916  ppm2  0.924
ASSI {11342}
(segid "PROT" and resid 17 and name HG2%)
(segid "PROT" and resid 115 and name HD2%)
  2.300  1.300   1.300 peak      11342  weight  0.10000E+01 volume  0.73274E+01 ppm1     1.178  ppm2  0.784
ASSI {11352}
((segid "PROT" and resid 115 and name HA))
(segid "PROT" and resid 115 and name HD2%)
  2.000  1.000   1.000 peak      11352  weight  0.10000E+01 volume  0.13990E+02 ppm1     4.258  ppm2  0.783
ASSI {11362}
((segid "PROT" and resid 14 and name HA))
(segid "PROT" and resid 14 and name HD2%)
  2.000  1.000   1.000 peak      11362  weight  0.10000E+01 volume  0.17448E+02 ppm1     4.086  ppm2  0.830
ASSI {11382}
((segid "PROT" and resid 14 and name HB1))
(segid "PROT" and resid 14 and name HD2%)
  2.100  1.100   1.100 peak      11382  weight  0.10000E+01 volume  0.10938E+02 ppm1     1.899  ppm2  0.824
ASSI {11412}
((segid "PROT" and resid 14 and name HG))
(segid "PROT" and resid 14 and name HD2%)
  2.200  1.200   1.200 peak      11412  weight  0.10000E+01 volume  0.93323E+01 ppm1     1.426  ppm2  0.838
ASSI {11432}
(segid "PROT" and resid 18 and name HD2%)
(segid "PROT" and resid 14 and name HD2%)
  2.200  1.200   1.200 peak      11432  weight  0.10000E+01 volume  0.99743E+01 ppm1   −0.160  ppm2  0.822
ASSI {11462}
(segid "PROT" and resid 106 and name HD%)
(segid "PROT" and resid 25 and name HG1%)
  2.600  1.700   1.700 peak      11462  weight  0.10000E+01 volume  0.32864E+01 ppm1     6.951  ppm2  1.244
ASSI {11472}
((segid "PROT" and resid 22 and name HA))
(segid "PROT" and resid 25 and name HG1%)
  2.600  1.700   1.700 peak      11472  weight  0.10000E+01 volume  0.33649E+01 ppm1     4.154  ppm2  1.248
ASSI {11482}
((segid "PROT" and resid 106 and name HA))
(segid "PROT" and resid 25 and name HG1%)
  2.600  1.700   1.700 peak      11482  weight  0.10000E+01 volume  0.30836E+01 ppm1     4.000  ppm2  1.243
ASSI {11492}
((segid "PROT" and resid 25 and name HA))
(segid "PROT" and resid 25 and name HG1%)
  2.200  1.200   1.200 peak      11492  weight  0.10000E+01 volume  0.89668E+01 ppm1     3.867  ppm2  1.246
ASSI {11502}
((segid "PROT" and resid 106 and name HB2))
(segid "PROT" and resid 25 and name HG1%)
  2.800  2.000   2.000 peak      11502  weight  0.10000E+01 volume  0.20827E+01 ppm1     3.136  ppm2  1.245
ASSI {11532}
((segid "PROT" and resid 25 and name HB))
(segid "PROT" and resid 25 and name HG1%)
  2.100  1.100   1.100 peak      11532  weight  0.10000E+01 volume  0.10379E+02 ppm1     2.445  ppm2  1.245
ASSI {11552}
((segid "PROT" and resid 102 and name HG))
(segid "PROT" and resid 25 and name HG1%)
  2.900  2.100   2.100 peak      11552  weight  0.10000E+01 volume  0.15965E+01 ppm1     1.595  ppm2  1.239
ASSI {11562}
(segid "PROT" and resid 25 and name HG2%)
(segid "PROT" and resid 25 and name HG1%)
  1.900  0.900   0.900 peak      11562  weight  0.10000E+01 volume  0.22735E+02 ppm1     1.069  ppm2  1.243
ASSI {11572}
(segid "PROT" and resid 102 and name HD2%)
(segid "PROT" and resid 25 and name HG1%)
  2.400  1.400   1.400 peak      11572  weight  0.10000E+01 volume  0.56418E+01 ppm1     0.764  ppm2  1.242
ASSI {11592}
(segid "PROT" and resid 78 and name HD2%)
(segid "PROT" and resid 25 and name HG1%)
  2.600  1.700   1.700 peak      11592  weight  0.10000E+01 volume  0.31395E+01 ppm1     0.196  ppm2  1.242
ASSI {11612}
((segid "PROT" and resid 41 and name HB))
(segid "PROT" and resid 41 and name HG2%)
  1.900  0.900   0.900 peak      11612  weight  0.10000E+01 volume  0.22674E+02 ppm1     4.345  ppm2  1.320

TABLE 13-continued

Unambiguous NOE Distance Restraints

ASSI {11632}
((segid "PROT" and resid 39 and name HB2))
(segid "PROT" and resid 41 and name HG2%)
 2.800  2.000  2.000 peak    11632 weight  0.10000E+01 volume  0.20175E+01 ppm1    1.958 ppm2  1.319
ASSI {11642}
((segid "PROT" and resid 59 and name HB2))
(segid "PROT" and resid 56 and name HD2%)
 2.700  1.800  1.800 peak    11642 weight  0.10000E+01 volume  0.27107E+01 ppm1    1.922 ppm2  0.680
ASSI {11662}
((segid "PROT" and resid 56 and name HG))
(segid "PROT" and resid 56 and name HD2%)
 2.200  1.200  1.200 peak    11662 weight  0.10000E+01 volume  0.99064E+01 ppm1    1.764 ppm2  0.678
ASSI {11672}
((segid "PROT" and resid 39 and name HD2))
(segid "PROT" and resid 41 and name HG2%)
 2.900  2.100  2.100 peak    11672 weight  0.10000E+01 volume  0.17126E+01 ppm1    1.680 ppm2  1.313
ASSI {11682}
((segid "PROT" and resid 56 and name HB2))
(segid "PROT" and resid 56 and name HD2%)
 2.500  1.600  1.600 peak    11682 weight  0.10000E+01 volume  0.46505E+01 ppm1    1.451 ppm2  0.678
ASSI {11692}
(segid "PROT" and resid 78 and name HD2%)
(segid "PROT" and resid 56 and name HD2%)
 2.300  1.300  1.300 peak    11692 weight  0.10000E+01 volume  0.78069E+01 ppm1    0.194 ppm2  0.677
ASSI {11702}
(segid "PROT" and resid 78 and name HD1%)
(segid "PROT" and resid 56 and name HD2%)
 2.500  1.600  1.600 peak    11702 weight  0.10000E+01 volume  0.38946E+01 ppm1    0.097 ppm2  0.678
ASSI {11722}
((segid "PROT" and resid 54 and name HA))
(segid "PROT" and resid 81 and name HG1%)
 2.800  2.000  2.000 peak    11722 weight  0.10000E+01 volume  0.19593E+01 ppm1    4.986 ppm2  0.503
ASSI {11732}
((segid "PROT" and resid 55 and name HA))
(segid "PROT" and resid 81 and name HG1%)
 2.500  1.600  1.600 peak    11732 weight  0.10000E+01 volume  0.38747E+01 ppm1    4.778 ppm2  0.507
ASSI {11742}
((segid "PROT" and resid 83 and name HB))
(segid "PROT" and resid 83 and name HG2%)
 1.900  0.900  0.900 peak    11742 weight  0.10000E+01 volume  0.21486E+02 ppm1    4.240 ppm2  1.343
ASSI {11752}
((segid "PROT" and resid 83 and name HA))
(segid "PROT" and resid 83 and name HG2%)
 2.000  1.000  1.000 peak    11752 weight  0.10000E+01 volume  0.15158E+02 ppm1    3.894 ppm2  1.343
ASSI {11772}
((segid "PROT" and resid 78 and name HA))
(segid "PROT" and resid 81 and name HG1%)
 2.300  1.300  1.300 peak    11772 weight  0.10000E+01 volume  0.69671E+01 ppm1    3.419 ppm2  0.509
ASSI {11782}
((segid "PROT" and resid 81 and name HA))
(segid "PROT" and resid 81 and name HG1%)
 2.100  1.100  1.100 peak    11782 weight  0.10000E+01 volume  0.10502E+02 ppm1    3.127 ppm2  0.508
ASSI {11792}
((segid "PROT" and resid 54 and name HG1))
(segid "PROT" and resid 81 and name HG1%)
 2.500  1.600  1.600 peak    11792 weight  0.10000E+01 volume  0.42195E+01 ppm1    2.741 ppm2  0.511
ASSI {11812}
((segid "PROT" and resid 25 and name HB))
(segid "PROT" and resid 25 and name HG2%)
 2.100  1.100  1.100 peak    11812 weight  0.10000E+01 volume  0.10819E+02 ppm1    2.445 ppm2  1.073
ASSI {11832}
((segid "PROT" and resid 53 and name HG2))
(segid "PROT" and resid 38 and name HG1%)
 2.000  2.000  2.500 peak    11832 weight  0.10000E+01 volume  0.15230E+02 ppm1    1.938 ppm2  0.498
ASSI {11852}
((segid "PROT" and resid 81 and name HB))
(segid "PROT" and resid 81 and name HG1%)
 2.100  1.100  1.100 peak    11852 weight  0.10000E+01 volume  0.10363E+02 ppm1    1.466 ppm2  0.509
ASSI {11862}
((segid "PROT" and resid 38 and name HB))
(segid "PROT" and resid 38 and name HG1%)
 2.100  1.100  1.100 peak    11862 weight  0.10000E+01 volume  0.12690E+02 ppm1    1.072 ppm2  0.496
ASSI {11872}
(segid "PROT" and resid 43 and name HB%)
(segid "PROT" and resid 38 and name HG1%)
 2.600  1.700  1.700 peak    11872 weight  0.10000E+01 volume  0.32089E+01 ppm1    0.992 ppm2  0.499

TABLE 13-continued

Unambiguous NOE Distance Restraints

ASSI {11882}
(segid "PROT" and resid 56 and name HD2%)
(segid "PROT" and resid 25 and name HG2%)
  2.300  1.300   1.300 peak    11882 weight  0.10000E+01 volume   0.66325E+01 ppm1    0.678 ppm2   1.074
ASSI {11892}
(segid "PROT" and resid 56 and name HD2%)
(segid "PROT" and resid 81 and name HG1%)
  2.300  1.300   1.300 peak    11892 weight  0.10000E+01 volume   0.73060E+01 ppm1    0.678 ppm2   0.508
ASSI {11912}
(segid "PROT" and resid 81 and name HG2%)
(segid "PROT" and resid 81 and name HG1%)
  2.000  1.000   1.000 peak    11912 weight  0.10000E+01 volume   0.18518E+02 ppm1    0.157 ppm2   0.510
ASSI {11932}
(segid "PROT" and resid 38 and name HG2%)
(segid "PROT" and resid 38 and name HG1%)
  2.000  1.000   1.000 peak    11932 weight  0.10000E+01 volume   0.17706E+02 ppm1   −0.011 ppm2   0.496
ASSI {11942}
(segid "PROT" and resid 82 and name HD%)
(segid "PROT" and resid 81 and name HG2%)
  2.800  2.000   2.000 peak    11942 weight  0.10000E+01 volume   0.19816E+01 ppm1    6.692 ppm2   0.156
ASSI {11952}
(segid "PROT" and resid 82 and name HE%)
(segid "PROT" and resid 81 and name HG2%)
  2.900  2.100   2.100 peak    11952 weight  0.10000E+01 volume   0.16984E+01 ppm1    6.489 ppm2   0.157
ASSI {11962}
((segid "PROT" and resid 54 and name HA))
(segid "PROT" and resid 58 and name HG2%)
  2.900  2.100   2.100 peak    11962 weight  0.10000E+01 volume   0.16768E+01 ppm1    4.987 ppm2   1.099
ASSI {11972}
((segid "PROT" and resid 55 and name HA))
(segid "PROT" and resid 81 and name HG2%)
  2.800  2.000   2.000 peak    11972 weight  0.10000E+01 volume   0.22875E+01 ppm1    4.780 ppm2   0.156
ASSI {11982}
((segid "PROT" and resid 58 and name HB))
(segid "PROT" and resid 58 and name HG2%)
  1.900  0.900   0.900 peak    11982 weight  0.10000E+01 volume   0.18798E+02 ppm1    4.121 ppm2   1.097
ASSI {12002}
(segid "PROT" and resid 34 and name HD%)
(segid "PROT" and resid 81 and name HG2%)
  2.500  1.600   1.600 peak    12002 weight  0.10000E+01 volume   0.41738E+01 ppm1    7.185 ppm2   0.155
ASSI {12012}
((segid "PROT" and resid 34 and name HB1))
(segid "PROT" and resid 81 and name HG2%)
  2.500  1.600   1.600 peak    12012 weight  0.10000E+01 volume   0.44360E+01 ppm1    3.515 ppm2   0.155
ASSI {12022}
((segid "PROT" and resid 85 and name HB1))
(segid "PROT" and resid 81 and name HG2%)
  2.800  2.000   2.000 peak    12022 weight  0.10000E+01 volume   0.20402E+01 ppm1    3.415 ppm2   0.152
ASSI {12032}
((segid "PROT" and resid 81 and name HA))
(segid "PROT" and resid 81 and name HG2%)
  2.200  1.200   1.200 peak    12032 weight  0.10000E+01 volume   0.80317E+01 ppm1    3.128 ppm2   0.155
ASSI {12042}
((segid "PROT" and resid 34 and name HB2))
(segid "PROT" and resid 81 and name HG2%)
  2.700  1.800   1.800 peak    12042 weight  0.10000E+01 volume   0.28427E+01 ppm1    2.638 ppm2   0.156
ASSI {12052}
((segid "PROT" and resid 57 and name HE1))
(segid "PROT" and resid 58 and name HG2%)
  2.600  1.700   1.700 peak    12052 weight  0.10000E+01 volume   0.34800E+01 ppm1    2.612 ppm2   1.098
ASSI {12072}
((segid "PROT" and resid 81 and name HB))
(segid "PROT" and resid 81 and name HG2%)
  2.100  1.100   1.100 peak    12072 weight  0.10000E+01 volume   0.10373E+02 ppm1    1.469 ppm2   0.156
ASSI {12082}
(segid "PROT" and resid 102 and name HD1%)
(segid "PROT" and resid 81 and name HG2%)
  2.900  2.100   2.100 peak    12082 weight  0.10000E+01 volume   0.15611E+01 ppm1    0.755 ppm2   0.156
ASSI {12092}
(segid "PROT" and resid 56 and name HD2%)
(segid "PROT" and resid 81 and name HG2%)
  2.700  1.800   1.800 peak    12092 weight  0.10000E+01 volume   0.28031E+01 ppm1    0.680 ppm2   0.154
ASSI {12122}
((segid "PROT" and resid 69 and name HA))
(segid "PROT" and resid 69 and name HG1%)
  2.000  1.000   1.000 peak    12122 weight  0.10000E+01 volume   0.17855E+02 ppm1    4.119 ppm2   0.988

TABLE 13-continued

Unambiguous NOE Distance Restraints

```
ASSI {12132}
((segid "PROT" and resid 38 and name HA))
(segid "PROT" and resid 38 and name HG2%)
 2.300  1.300   1.300 peak      12132  weight  0.10000E+01 volume  0.66566E+01 ppm1      3.494 ppm2  −0.010
ASSI {12142}
((segid "PROT" and resid 69 and name HB))
(segid "PROT" and resid 69 and name HG1%)
 2.000  1.000   1.000 peak      12142  weight  0.10000E+01 volume  0.18250E+02 ppm1      2.352 ppm2   0.990
ASSI {12172}
(segid "PROT" and resid 113 and name HB%)
(segid "PROT" and resid 17 and name HG2%)
 2.100  1.100   1.100 peak      12172  weight  0.10000E+01 volume  0.10423E+02 ppm1      1.411 ppm2   1.175
ASSI {12182}
((segid "PROT" and resid 38 and name HB))
(segid "PROT" and resid 38 and name HG2%)
 2.200  1.200   1.200 peak      12182  weight  0.10000E+01 volume  0.92232E+01 ppm1      1.072 ppm2  −0.010
ASSI {12192}
(segid "PROT" and resid 43 and name HB%)
(segid "PROT" and resid 38 and name HG2%)
 2.100  1.100   1.100 peak      12192  weight  0.10000E+01 volume  0.10645E+02 ppm1      0.988 ppm2  −0.010
ASSI {12202}
(segid "PROT" and resid 21 and name HD1%)
(segid "PROT" and resid 17 and name HG2%)
 2.100  1.100   1.100 peak      12202  weight  0.10000E+01 volume  0.11281E+02 ppm1      0.654 ppm2   1.179
ASSI {12222}
(segid "PROT" and resid 18 and name HD2%)
(segid "PROT" and resid 17 and name HG2%)
 2.500  1.600   1.600 peak      12222  weight  0.10000E+01 volume  0.45180E+01 ppm1     −0.160 ppm2   1.179
ASSI {12232}
((segid "PROT" and resid 88 and name HA))
(segid "PROT" and resid 49 and name HG2%)
 2.800  2.000   2.000 peak      12232  weight  0.10000E+01 volume  0.19275E+01 ppm1      4.335 ppm2   0.917
ASSI {12252}
((segid "PROT" and resid 49 and name HB))
(segid "PROT" and resid 49 and name HG2%)
 2.100  1.100   1.100 peak      12252  weight  0.10000E+01 volume  0.11893E+02 ppm1      1.928 ppm2   0.910
ASSI {12262}
(segid "PROT" and resid 50 and name HD1%)
(segid "PROT" and resid 49 and name HG2%)
 2.300  1.300   1.300 peak      12262  weight  0.10000E+01 volume  0.67910E+01 ppm1      0.581 ppm2   0.912
ASSI {12302}
((segid "PROT" and resid 43 and name HA))
(segid "PROT" and resid 43 and name HB%)
 2.200  1.200   1.200 peak      12302  weight  0.10000E+01 volume  0.99216E+01 ppm1      4.988 ppm2   0.987
ASSI {12312}
((segid "PROT" and resid 44 and name HD1))
(segid "PROT" and resid 43 and name HB%)
 2.900  2.100   2.100 peak      12312  weight  0.10000E+01 volume  0.17587E+01 ppm1      3.830 ppm2   0.988
ASSI {12322}
((segid "PROT" and resid 46 and name HB1))
(segid "PROT" and resid 43 and name HB%)
 2.500  1.600   1.600 peak      12322  weight  0.10000E+01 volume  0.47081E+01 ppm1      2.762 ppm2   0.987
ASSI {12332}
((segid "PROT" and resid 46 and name HB2))
(segid "PROT" and resid 43 and name HB%)
 2.500  1.600   1.600 peak      12332  weight  0.10000E+01 volume  0.40150E+01 ppm1      2.426 ppm2   0.984
ASSI {12342}
((segid "PROT" and resid 39 and name HG2))
(segid "PROT" and resid 43 and name HB%)
 2.800  2.000   2.000 peak      12342  weight  0.10000E+01 volume  0.20520E+01 ppm1      1.443 ppm2   0.986
ASSI {12352}
(segid "PROT" and resid 41 and name HG2%)
(segid "PROT" and resid 43 and name HB%)
 2.600  1.700   1.700 peak      12352  weight  0.10000E+01 volume  0.31831E+01 ppm1      1.342 ppm2   0.985
ASSI {12382}
(segid "PROT" and resid 34 and name HD%)
(segid "PROT" and resid 31 and name HB%)
 2.800  2.000   2.000 peak      12382  weight  0.10000E+01 volume  0.21740E+01 ppm1      7.180 ppm2   1.761
ASSI {12402}
(segid "PROT" and resid 74 and name HD%)
(segid "PROT" and resid 18 and name HD2%)
 2.700  1.800   1.800 peak      12402  weight  0.10000E+01 volume  0.27909E+01 ppm1      6.432 ppm2  −0.161
ASSI {12412}
((segid "PROT" and resid 31 and name HA))
(segid "PROT" and resid 31 and name HB%)
 2.100  1.100   1.100 peak      12412  weight  0.10000E+01 volume  0.11588E+02 ppm1      4.438 ppm2   1.763
```

TABLE 13-continued

Unambiguous NOE Distance Restraints

ASSI {12422}
((segid "PROT" and resid 14 and name HA))
(segid "PROT" and resid 18 and name HD2%)
  2.500  1.600   1.600 peak     12422 weight  0.10000E+01 volume    0.46610E+01 ppm1     4.061  ppm2  −0.160
ASSI {12432}
((segid "PROT" and resid 26 and name HA))
(segid "PROT" and resid 31 and name HB%)
  2.300  1.300   1.300 peak     12432 weight  0.10000E+01 volume    0.63967E+01 ppm1     3.932  ppm2    1.762
ASSI {12442}
((segid "PROT" and resid 18 and name HA))
(segid "PROT" and resid 18 and name HD2%)
  2.100  1.100   1.100 peak     12442 weight  0.10000E+01 volume    0.11266E+02 ppm1     3.315  ppm2  −0.161
ASSI {12452}
((segid "PROT" and resid 28 and name HB1))
(segid "PROT" and resid 31 and name HB%)
  2.800  2.000   2.000 peak     12452 weight  0.10000E+01 volume    0.21964E+01 ppm1     3.014  ppm2    1.761
ASSI {12462}
((segid "PROT" and resid 74 and name HB1))
(segid "PROT" and resid 18 and name HD2%)
  2.700  1.800   1.800 peak     12462 weight  0.10000E+01 volume    0.27167E+01 ppm1     2.985  ppm2  −0.159
ASSI {12472}
((segid "PROT" and resid 35 and name HG1))
(segid "PROT" and resid 31 and name HB%)
  2.900  2.100   2.100 peak     12472 weight  0.10000E+01 volume    0.18022E+01 ppm1     2.893  ppm2    1.761
ASSI {12482}
((segid "PROT" and resid 28 and name HB2))
(segid "PROT" and resid 31 and name HB%)
  2.800  2.000   2.000 peak     12482 weight  0.10000E+01 volume    0.19169E+01 ppm1     2.827  ppm2    1.761
ASSI {12492}
((segid "PROT" and resid 74 and name HB2))
(segid "PROT" and resid 18 and name HD2%)
  2.900  2.100   2.100 peak     12492 weight  0.10000E+01 volume    0.16460E+01 ppm1     2.426  ppm2  −0.159
ASSI {12502}
(segid "PROT" and resid 35 and name HE%)
(segid "PROT" and resid 31 and name HB%)
  2.500  1.600   1.600 peak     12502 weight  0.10000E+01 volume    0.46210E+01 ppm1     2.220  ppm2    1.761
ASSI {12512}
((segid "PROT" and resid 14 and name HB1))
(segid "PROT" and resid 18 and name HD2%)
  2.700  1.800   1.800 peak     12512 weight  0.10000E+01 volume    0.24259E+01 ppm1     1.907  ppm2  −0.160
ASSI {12522}
((segid "PROT" and resid 18 and name HG))
(segid "PROT" and resid 18 and name HD2%)
  2.200  1.200   1.200 peak     12522 weight  0.10000E+01 volume    0.90471E+01 ppm1     1.706  ppm2  −0.160
ASSI {12532}
((segid "PROT" and resid 18 and name HB1))
(segid "PROT" and resid 18 and name HD2%)
  2.400  1.400   1.400 peak     12532 weight  0.10000E+01 volume    0.47694E+01 ppm1     1.563  ppm2  −0.162
ASSI {12552}
(segid "PROT" and resid 63 and name HD2%)
(segid "PROT" and resid 18 and name HD2%)
  2.900  2.100   2.100 peak     12552 weight  0.10000E+01 volume    0.18027E+01 ppm1     1.078  ppm2  −0.159
ASSI {12572}
(segid "PROT" and resid 56 and name HD1%)
(segid "PROT" and resid 31 and name HB%)
  2.300  1.300   1.300 peak     12572 weight  0.10000E+01 volume    0.76065E+01 ppm1     0.978  ppm2    1.761
ASSI {12592}
(segid "PROT" and resid 102 and name HD1%)
(segid "PROT" and resid 31 and name HB%)
  2.100  1.100   1.100 peak     12592 weight  0.10000E+01 volume    0.13169E+02 ppm1     0.763  ppm2    1.762
ASSI {12612}
(segid "PROT" and resid 21 and name HD1%)
(segid "PROT" and resid 18 and name HD2%)
  2.500  1.600   1.600 peak     12612 weight  0.10000E+01 volume    0.39733E+01 ppm1     0.654  ppm2  −0.158
ASSI {12622}
(segid "PROT" and resid 18 and name HD1%)
(segid "PROT" and resid 18 and name HD2%)
  2.000  1.000   1.000 peak     12622 weight  0.10000E+01 volume    0.15661E+02 ppm1     0.515  ppm2  −0.160
ASSI {12632}
((segid "PROT" and resid 18 and name HB2))
(segid "PROT" and resid 18 and name HD2%)
  2.600  1.700   1.700 peak     12632 weight  0.10000E+01 volume    0.35201E+01 ppm1     0.341  ppm2  −0.159
ASSI {12642}
((segid "PROT" and resid 113 and name HA))
(segid "PROT" and resid 113 and name HB%)
  1.900  0.900   0.900 peak     12642 weight  0.10000E+01 volume    0.23011E+02 ppm1     4.338  ppm2    1.411

TABLE 13-continued

Unambiguous NOE Distance Restraints

```
ASSI {12672}
((segid "PROT" and resid 115 and name HG))
(segid "PROT" and resid 113 and name HB%)
 2.300  1.300  1.300 peak    12672 weight 0.10000E+01 volume 0.77795E+01 ppm1   1.564 ppm2  1.407
ASSI {12712}
(segid "PROT" and resid 115 and name HD1%)
(segid "PROT" and resid 113 and name HB%)
 2.300  1.300  1.300 peak    12712 weight 0.10000E+01 volume 0.75629E+01 ppm1   0.752 ppm2  1.412
ASSI {12742}
(segid "PROT" and resid 74 and name HE%)
(segid "PROT" and resid 110 and name HG2%)
 2.700  1.800  1.800 peak    12742 weight 0.10000E+01 volume 0.27255E+01 ppm1   6.958 ppm2  0.694
ASSI {12762}
((segid "PROT" and resid 110 and name HA))
(segid "PROT" and resid 110 and name HG2%)
 2.100  1.100  1.100 peak    12762 weight 0.10000E+01 volume 0.13460E+02 ppm1   3.858 ppm2  0.694
ASSI {12782}
((segid "PROT" and resid 69 and name HB))
(segid "PROT" and resid 69 and name HG2%)
 2.000  1.000  1.000 peak    12782 weight 0.10000E+01 volume 0.18266E+02 ppm1   2.352 ppm2  0.864
ASSI {12802}
((segid "PROT" and resid 110 and name HB))
(segid "PROT" and resid 110 and name HG2%)
 2.100  1.100  1.100 peak    12802 weight 0.10000E+01 volume 0.12814E+02 ppm1   1.796 ppm2  0.694
ASSI {12812}
((segid "PROT" and resid 115 and name HB2))
(segid "PROT" and resid 110 and name HG2%)
 2.400  1.400  1.400 peak    12812 weight 0.10000E+01 volume 0.58675E+01 ppm1   1.609 ppm2  0.693
ASSI {12822}
((segid "PROT" and resid 110 and name HG11))
(segid "PROT" and resid 110 and name HG2%)
 2.400  1.400  1.400 peak    12822 weight 0.10000E+01 volume 0.53638E+01 ppm1   1.154 ppm2  0.692
ASSI {12832}
((segid "PROT" and resid 110 and name HG12))
(segid "PROT" and resid 110 and name HG2%)
 2.400  1.400  1.400 peak    12832 weight 0.10000E+01 volume 0.58609E+01 ppm1   1.086 ppm2  0.693
ASSI {12852}
(segid "PROT" and resid 69 and name HG1%)
(segid "PROT" and resid 69 and name HG2%)
 1.700  0.700  0.700 peak    12852 weight 0.10000E+01 volume 0.41193E+02 ppm1   0.986 ppm2  0.861
ASSI {12872}
((segid "PROT" and resid 34 and name HZ))
(segid "PROT" and resid 99 and name HB%)
 2.300  1.300  1.300 peak    12872 weight 0.10000E+01 volume 0.63690E+01 ppm1   7.303 ppm2  1.665
ASSI {12882}
(segid "PROT" and resid 82 and name HD%)
(segid "PROT" and resid 99 and name HB%)
 2.500  1.600  1.600 peak    12882 weight 0.10000E+01 volume 0.37187E+01 ppm1   6.695 ppm2  1.663
ASSI {12892}
((segid "PROT" and resid 77 and name HA))
(segid "PROT" and resid 76 and name HB%)
 2.900  2.100  2.100 peak    12892 weight 0.10000E+01 volume 0.16636E+01 ppm1   4.399 ppm2  1.531
ASSI {12902}
((segid "PROT" and resid 73 and name HA))
(segid "PROT" and resid 76 and name HB%)
 2.200  1.200  1.200 peak    12902 weight 0.10000E+01 volume 0.96069E+01 ppm1   4.260 ppm2  1.534
ASSI {12912}
((segid "PROT" and resid 82 and name HA))
(segid "PROT" and resid 99 and name HB%)
 2.400  1.400  1.400 peak    12912 weight 0.10000E+01 volume 0.52839E+01 ppm1   4.217 ppm2  1.660
ASSI {12922}
((segid "PROT" and resid 76 and name HA))
(segid "PROT" and resid 76 and name HB%)
 1.900  0.900  0.900 peak    12922 weight 0.10000E+01 volume 0.23966E+02 ppm1   4.116 ppm2  1.534
ASSI {12932}
((segid "PROT" and resid 99 and name HA))
(segid "PROT" and resid 99 and name HB%)
 2.100  1.100  1.100 peak    12932 weight 0.10000E+01 volume 0.12282E+02 ppm1   3.914 ppm2  1.662
ASSI {12942}
((segid "PROT" and resid 96 and name HA))
(segid "PROT" and resid 99 and name HB%)
 2.400  1.400  1.400 peak    12942 weight 0.10000E+01 volume 0.58392E+01 ppm1   3.832 ppm2  1.662
ASSI {12952}
((segid "PROT" and resid 85 and name HB1))
(segid "PROT" and resid 99 and name HB%)
 2.600  1.700  1.700 peak    12952 weight 0.10000E+01 volume 0.35679E+01 ppm1   3.416 ppm2  1.662
```

TABLE 13-continued

Unambiguous NOE Distance Restraints

```
ASSI {12962}
((segid "PROT" and resid 80 and name HG1))
(segid "PROT" and resid 76 and name HB%)
 2.900  2.100  2.100 peak    12962 weight  0.10000E+01 volume  0.15862E+01 ppm1   1.796 ppm2  1.527
ASSI {12972}
((segid "PROT" and resid 103 and name HB2))
(segid "PROT" and resid 99 and name HB%)
 2.500  1.600  1.600 peak    12972 weight  0.10000E+01 volume  0.42980E+01 ppm1   1.331 ppm2  1.660
ASSI {12982}
((segid "PROT" and resid 86 and name HG2))
(segid "PROT" and resid 99 and name HB%)
 2.700  1.800  1.800 peak    12982 weight  0.10000E+01 volume  0.29370E+01 ppm1   0.163 ppm2  1.664
ASSI {13002}
((segid "PROT" and resid 30 and name HB1))
(segid "PROT" and resid 101 and name HG2%)
 2.600  1.700  1.700 peak    13002 weight  0.10000E+01 volume  0.32336E+01 ppm1   4.351 ppm2  1.035
ASSI {13022}
((segid "PROT" and resid 98 and name HA))
(segid "PROT" and resid 101 and name HG2%)
 2.700  1.800  1.800 peak    13022 weight  0.10000E+01 volume  0.26908E+01 ppm1   4.222 ppm2  1.033
ASSI {13032}
((segid "PROT" and resid 30 and name HB2))
(segid "PROT" and resid 101 and name HG2%)
 2.600  1.700  1.700 peak    13032 weight  0.10000E+01 volume  0.35525E+01 ppm1   3.979 ppm2  1.031
ASSI {13072}
((segid "PROT" and resid 115 and name HB2))
(segid "PROT" and resid 116 and name HG2%)
 2.900  2.100  2.100 peak    13072 weight  0.10000E+01 volume  0.17551E+01 ppm1   1.618 ppm2  0.859
ASSI {13082}
((segid "PROT" and resid 116 and name HG11))
(segid "PROT" and resid 116 and name HG2%)
 2.500  1.600  1.600 peak    13082 weight  0.10000E+01 volume  0.41175E+01 ppm1   1.347 ppm2  0.858
ASSI {13092}
(segid "PROT" and resid 110 and name HD1%)
(segid "PROT" and resid 116 and name HG2%)
 2.500  1.600  1.600 peak    13092 weight  0.10000E+01 volume  0.46372E+01 ppm1   0.568 ppm2  0.861
ASSI {13102}
((segid "PROT" and resid 24 and name HE21))
(segid "PROT" and resid 21 and name HG2%)
 2.500  1.600  1.600 peak    13102 weight  0.10000E+01 volume  0.40731E+01 ppm1   7.061 ppm2  1.020
ASSI {13112}
(segid "PROT" and resid 106 and name HD%)
(segid "PROT" and resid 21 and name HG2%)
 2.200  1.200  1.200 peak    13112 weight  0.10000E+01 volume  0.97563E+01 ppm1   6.961 ppm2  1.020
ASSI {13122}
((segid "PROT" and resid 22 and name HA))
(segid "PROT" and resid 21 and name HG2%)
 2.900  2.100  2.100 peak    13122 weight  0.10000E+01 volume  0.17544E+01 ppm1   4.152 ppm2  1.016
ASSI {13132}
((segid "PROT" and resid 21 and name HA))
(segid "PROT" and resid 21 and name HG2%)
 2.200  1.200  1.200 peak    13132 weight  0.10000E+01 volume  0.82544E+01 ppm1   3.800 ppm2  1.019
ASSI {13142}
((segid "PROT" and resid 18 and name HA))
(segid "PROT" and resid 21 and name HG2%)
 2.900  2.100  2.100 peak    13142 weight  0.10000E+01 volume  0.16321E+01 ppm1   3.319 ppm2  1.017
ASSI {13162}
((segid "PROT" and resid 21 and name HG11))
(segid "PROT" and resid 21 and name HG2%)
 2.300  1.300  1.300 peak    13162 weight  0.10000E+01 volume  0.61393E+01 ppm1   1.785 ppm2  1.018
ASSI {13202}
(segid "PROT" and resid 78 and name HD2%)
(segid "PROT" and resid 21 and name HG2%)
 2.900  2.100  2.100 peak    13202 weight  0.10000E+01 volume  0.15853E+01 ppm1   0.196 ppm2  1.016
ASSI {13212}
(segid "PROT" and resid 78 and name HD1%)
(segid "PROT" and resid 21 and name HG2%)
 2.700  1.800  1.800 peak    13212 weight  0.10000E+01 volume  0.24623E+01 ppm1   0.093 ppm2  1.018
ASSI {13292}
((segid "PROT" and resid 75 and name HB1))
(segid "PROT" and resid 75 and name HE%)
 2.700  1.800  1.800 peak    13292 weight  0.10000E+01 volume  0.24960E+01 ppm1   2.964 ppm2  2.093
ASSI {13322}
((segid "PROT" and resid 75 and name HG1))
(segid "PROT" and resid 75 and name HE%)
 2.400  1.400  1.400 peak    13322 weight  0.10000E+01 volume  0.47718E+01 ppm1   2.353 ppm2  2.090
```

TABLE 13-continued

Unambiguous NOE Distance Restraints

ASSI {13332}
((segid "PROT" and resid 75 and name HG2))
(segid "PROT" and resid 75 and name HE%)
  2.400  1.400   1.400 peak     13332 weight  0.10000E+01 volume  0.50489E+01 ppm1    2.245  ppm2  2.089
ASSI {13342}
((segid "PROT" and resid 115 and name HB2))
(segid "PROT" and resid 75 and name HE%)
  2.700  1.800   1.800 peak     13342 weight  0.10000E+01 volume  0.25149E+01 ppm1    1.610  ppm2  2.097
ASSI {13362}
(segid "PROT" and resid 116 and name HG2%)
(segid "PROT" and resid 75 and name HE%)
  2.500  1.600   1.600 peak     13362 weight  0.10000E+01 volume  0.44297E+01 ppm1    0.848  ppm2  2.096
ASSI {13372}
(segid "PROT" and resid 115 and name HD1%)
(segid "PROT" and resid 75 and name HE%)
  2.600  1.700   1.700 peak     13372 weight  0.10000E+01 volume  0.32468E+01 ppm1    0.752  ppm2  2.096
ASSI {13382}
(segid "PROT" and resid 110 and name HG2%)
(segid "PROT" and resid 75 and name HE%)
  2.400  1.400   1.400 peak     13382 weight  0.10000E+01 volume  0.50045E+01 ppm1    0.691  ppm2  2.096
ASSI {13392}
(segid "PROT" and resid 110 and name HD1%)
(segid "PROT" and resid 75 and name HE%)
  2.400  1.400   1.400 peak     13392 weight  0.10000E+01 volume  0.54701E+01 ppm1    0.579  ppm2  2.094
ASSI {13402}
((segid "PROT" and resid 32 and name HA))
(segid "PROT" and resid 35 and name HE%)
  2.700  1.800   1.800 peak     13402 weight  0.10000E+01 volume  0.26368E+01 ppm1    4.426  ppm2  2.218
ASSI {13412}
((segid "PROT" and resid 35 and name HA))
(segid "PROT" and resid 35 and name HE%)
  2.700  1.800   1.800 peak     13412 weight  0.10000E+01 volume  0.23762E+01 ppm1    4.340  ppm2  2.215
ASSI {13422}
((segid "PROT" and resid 26 and name HA))
(segid "PROT" and resid 35 and name HE%)
  2.800  2.000   2.000 peak     13422 weight  0.10000E+01 volume  0.21502E+01 ppm1    3.936  ppm2  2.227
ASSI {13432}
((segid "PROT" and resid 35 and name HG1))
(segid "PROT" and resid 35 and name HE%)
  2.200  1.200   1.200 peak     13432 weight  0.10000E+01 volume  0.99990E+00 ppm1    2.894  ppm2  2.218
ASSI {13442}
((segid "PROT" and resid 35 and name HB1))
(segid "PROT" and resid 35 and name HE%)
  2.400  1.400   1.400 peak     13442 weight  0.10000E+01 volume  0.60108E+01 ppm1    2.319  ppm2  2.207
ASSI {13452}
((segid "PROT" and resid 26 and name HB1))
(segid "PROT" and resid 35 and name HE%)
  2.400  2.400   2.100 peak     13452 weight  0.10000E+01 volume  0.47279E+01 ppm1    1.919  ppm2  2.220
ASSI {13482}
((segid "PROT" and resid 26 and name HG1))
(segid "PROT" and resid 35 and name HE%)
  2.900  2.100   2.100 peak     13482 weight  0.10000E+01 volume  0.17649E+01 ppm1    1.532  ppm2  2.221
ASSI {13542}
((segid "PROT" and resid 84 and name HA))
(segid "PROT" and resid 50 and name HG2%)
  2.800  2.000   2.000 peak     13542 weight  0.10000E+01 volume  0.19891E+01 ppm1    4.343  ppm2  0.420
ASSI {13552}
((segid "PROT" and resid 59 and name HA))
(segid "PROT" and resid 59 and name HE%)
  2.800  2.000   2.000 peak     13552 weight  0.10000E+01 volume  0.20245E+01 ppm1    4.337  ppm2  1.307
ASSI {13562}
((segid "PROT" and resid 53 and name HA))
(segid "PROT" and resid 50 and name HG2%)
  2.200  1.200   1.200 peak     13562 weight  0.10000E+01 volume  0.82735E+01 ppm1    4.125  ppm2  0.419
ASSI {13572}
((segid "PROT" and resid 50 and name HA))
(segid "PROT" and resid 50 and name HG2%)
  2.200  1.200   1.200 peak     13572 weight  0.10000E+01 volume  0.79741E+01 ppm1    3.953  ppm2  0.421
ASSI {13582}
((segid "PROT" and resid 74 and name HA))
(segid "PROT" and resid 59 and name HE%)
  2.700  1.800   1.800 peak     13582 weight  0.10000E+01 volume  0.25189E+01 ppm1    3.803  ppm2  1.311
ASSI {13592}
((segid "PROT" and resid 53 and name HD2))
(segid "PROT" and resid 50 and name HG2%)
  2.800  2.000   2.000 peak     13592 weight  0.10000E+01 volume  0.20585E+01 ppm1    3.445  ppm2  0.420

TABLE 13-continued

| Unambiguous NOE Distance Restraints |
|---|

ASSI {13612}
((segid "PROT" and resid 84 and name HB1))
(segid "PROT" and resid 50 and name HG2%)
  2.700  1.800  1.800 peak     13612  weight  0.10000E+01 volume  0.27693E+01 ppm1    3.035 ppm2  0.417
ASSI {13622}
((segid "PROT" and resid 77 and name HB1))
(segid "PROT" and resid 59 and name HE%)
  2.300  1.300  1.300 peak     13622  weight  0.10000E+01 volume  0.75013E+01 ppm1    2.753 ppm2  1.308
ASSI {13632}
((segid "PROT" and resid 84 and name HB2))
(segid "PROT" and resid 50 and name HG2%)
  2.700  1.800  1.800 peak     13632  weight  0.10000E+01 volume  0.28676E+01 ppm1    2.712 ppm2  0.420
ASSI {13642}
((segid "PROT" and resid 59 and name HG2))
(segid "PROT" and resid 59 and name HE%)
  2.600  1.700  1.700 peak     13642  weight  0.10000E+01 volume  0.33032E+01 ppm1    2.560 ppm2  1.310
ASSI {13652}
((segid "PROT" and resid 53 and name HB1))
(segid "PROT" and resid 50 and name HG2%)
  2.600  1.700  1.700 peak     13652  weight  0.10000E+01 volume  0.34701E+01 ppm1    2.259 ppm2  0.419
ASSI {13662}
((segid "PROT" and resid 59 and name HB1))
(segid "PROT" and resid 59 and name HE%)
  2.400  1.400  1.400 peak     13662  weight  0.10000E+01 volume  0.54884E+01 ppm1    2.154 ppm2  1.309
ASSI {13672}
((segid "PROT" and resid 59 and name HB2))
(segid "PROT" and resid 59 and name HE%)
  2.500  1.600  1.600 peak     13672  weight  0.10000E+01 volume  0.41611E+01 ppm1    1.932 ppm2  1.309
ASSI {13682}
((segid "PROT" and resid 53 and name HG2))
(segid "PROT" and resid 50 and name HG2%)
  2.600  1.700  1.700 peak     13682  weight  0.10000E+01 volume  0.31884E+01 ppm1    1.934 ppm2  0.421
ASSI {13692}
((segid "PROT" and resid 50 and name HB))
(segid "PROT" and resid 50 and name HG2%)
  2.100  1.100  1.100 peak     13692  weight  0.10000E+01 volume  0.11042E+02 ppm1    1.250 ppm2  0.421
ASSI {13712}
((segid "PROT" and resid 50 and name HG11))
(segid "PROT" and resid 50 and name HG2%)
  2.500  1.600  1.600 peak     13712  weight  0.10000E+01 volume  0.37929E+01 ppm1    0.830 ppm2  0.420
ASSI {13722}
((segid "PROT" and resid 78 and name HG))
(segid "PROT" and resid 59 and name HE%)
  2.500  1.600  1.600 peak     13722  weight  0.10000E+01 volume  0.39705E+01 ppm1    0.704 ppm2  1.311
ASSI {13732}
(segid "PROT" and resid 50 and name HD1%)
(segid "PROT" and resid 50 and name HG2%)
  2.000  1.000  1.000 peak     13732  weight  0.10000E+01 volume  0.14950E+02 ppm1    0.581 ppm2  0.419
ASSI {13742}
((segid "PROT" and resid 78 and name HB2))
(segid "PROT" and resid 59 and name HE%)
  2.400  1.400  1.400 peak     13742  weight  0.10000E+01 volume  0.56802E+01 ppm1    0.475 ppm2  1.310
ASSI {13762}
((segid "PROT" and resid 50 and name HG12))
(segid "PROT" and resid 50 and name HG2%)
  2.400  1.400  1.400 peak     13762  weight  0.10000E+01 volume  0.49893E+01 ppm1    0.188 ppm2  0.422
ASSI {13782}
((segid "PROT" and resid 54 and name HA))
(segid "PROT" and resid 54 and name HE%)
  2.200  1.200  1.200 peak     13782  weight  0.10000E+01 volume  0.96092E+01 ppm1    4.986 ppm2  2.003
ASSI {13792}
((segid "PROT" and resid 77 and name HA))
(segid "PROT" and resid 54 and name HE%)
  2.900  2.100  2.100 peak     13792  weight  0.10000E+01 volume  0.17796E+01 ppm1    4.395 ppm2  2.006
ASSI {13802}
((segid "PROT" and resid 54 and name HG1))
(segid "PROT" and resid 54 and name HE%)
  2.400  1.400  1.400 peak     13802  weight  0.10000E+01 volume  0.54019E+01 ppm1    2.742 ppm2  2.001
ASSI {13812}
((segid "PROT" and resid 54 and name HB2))
(segid "PROT" and resid 54 and name HE%)
  2.500  1.600  1.600 peak     13812  weight  0.10000E+01 volume  0.37957E+01 ppm1    1.383 ppm2  2.004
ASSI {13832}
(segid "PROT" and resid 81 and name HG1%)
(segid "PROT" and resid 54 and name HE%)
  2.700  1.800  1.800 peak     13832  weight  0.10000E+01 volume  0.24284E+01 ppm1    0.510 ppm2  2.002

TABLE 13-continued

Unambiguous NOE Distance Restraints

ASSI {13852}
((segid "PROT" and resid 98 and name HA))
(segid "PROT" and resid 101 and name HD1%)
  2.400  1.400  1.400 peak     13852  weight  0.10000E+01  volume  0.57589E+01  ppm1    4.226  ppm2  0.997
ASSI {13862}
((segid "PROT" and resid 101 and name HA))
(segid "PROT" and resid 101 and name HD1%)
  2.500  1.600  1.600 peak     13862  weight  0.10000E+01  volume  0.41504E+01  ppm1    3.695  ppm2  1.001
ASSI {13872}
((segid "PROT" and resid 18 and name HA))
(segid "PROT" and resid 21 and name HD1%)
  2.600  1.700  1.700 peak     13872  weight  0.10000E+01  volume  0.31541E+01  ppm1    3.312  ppm2  0.653
ASSI {13892}
((segid "PROT" and resid 97 and name HB1))
(segid "PROT" and resid 101 and name HD1%)
  2.800  2.000  2.000 peak     13892  weight  0.10000E+01  volume  0.19889E+01  ppm1    2.112  ppm2  0.993
ASSI {13902}
((segid "PROT" and resid 21 and name HB))
(segid "PROT" and resid 21 and name HD1%)
  2.300  1.300  1.300 peak     13902  weight  0.10000E+01  volume  0.69789E+01  ppm1    1.951  ppm2  0.652
ASSI {13912}
((segid "PROT" and resid 101 and name HG11))
(segid "PROT" and resid 101 and name HD1%)
  2.000  1.000  1.000 peak     13912  weight  0.10000E+01  volume  0.16613E+02  ppm1    1.897  ppm2  0.998
ASSI {13922}
((segid "PROT" and resid 21 and name HG11))
(segid "PROT" and resid 21 and name HD1%)
  2.100  1.100  1.100 peak     13922  weight  0.10000E+01  volume  0.12244E+02  ppm1    1.786  ppm2  0.651
ASSI {13932}
((segid "PROT" and resid 109 and name HB2))
(segid "PROT" and resid 21 and name HD1%)
  2.600  1.700  1.700 peak     13932  weight  0.10000E+01  volume  0.35134E+01  ppm1    1.581  ppm2  0.646
ASSI {13942}
(segid "PROT" and resid 113 and name HB%)
(segid "PROT" and resid 21 and name HD1%)
  2.100  1.100  1.100 peak     13942  weight  0.10000E+01  volume  0.12667E+02  ppm1    1.411  ppm2  0.651
ASSI {13952}
((segid "PROT" and resid 101 and name HG12))
(segid "PROT" and resid 101 and name HD1%)
  2.000  1.000  1.000 peak     13952  weight  0.10000E+01  volume  0.17265E+02  ppm1    1.239  ppm2  0.997
ASSI {13972}
(segid "PROT" and resid 21 and name HG2%)
(segid "PROT" and resid 21 and name HD1%)
  1.900  0.900  0.900 peak     13972  weight  0.10000E+01  volume  0.21366E+02  ppm1    1.024  ppm2  0.651
ASSI {13992}
(segid "PROT" and resid 106 and name HD%)
(segid "PROT" and resid 110 and name HD1%)
  2.800  2.000  2.000 peak     13992  weight  0.10000E+01  volume  0.21957E+01  ppm1    6.962  ppm2  0.566
ASSI {14002}
((segid "PROT" and resid 116 and name HA))
(segid "PROT" and resid 116 and name HD1%)
  2.500  1.600  1.600 peak     14002  weight  0.10000E+01  volume  0.37164E+01  ppm1    4.274  ppm2  0.829
ASSI {14012}
((segid "PROT" and resid 75 and name HA))
(segid "PROT" and resid 116 and name HD1%)
  2.800  2.000  2.000 peak     14012  weight  0.10000E+01  volume  0.22585E+01  ppm1    4.096  ppm2  0.828
ASSI {14052}
(segid "PROT" and resid 75 and name HE%)
(segid "PROT" and resid 116 and name HD1%)
  2.700  1.800  1.800 peak     14052  weight  0.10000E+01  volume  0.23966E+01  ppm1    2.095  ppm2  0.826
ASSI {14082}
((segid "PROT" and resid 6 and name HD1))
(segid "PROT" and resid 116 and name HD1%)
  2.900  2.100  2.100 peak     14082  weight  0.10000E+01  volume  0.18157E+01  ppm1    1.663  ppm2  0.826
ASSI {14092}
((segid "PROT" and resid 115 and name HB2))
(segid "PROT" and resid 110 and name HD1%)
  2.600  1.700  1.700 peak     14092  weight  0.10000E+01  volume  0.33126E+01  ppm1    1.602  ppm2  0.575
ASSI {14102}
((segid "PROT" and resid 116 and name HG11))
(segid "PROT" and resid 116 and name HD1%)
  2.100  1.100  1.100 peak     14102  weight  0.10000E+01  volume  0.13147E+02  ppm1    1.345  ppm2  0.826
ASSI {14112}
((segid "PROT" and resid 110 and name HG11))
(segid "PROT" and resid 110 and name HD1%)
  2.200  1.200  1.200 peak     14112  weight  0.10000E+01  volume  0.10025E+02  ppm1    1.157  ppm2  0.578

TABLE 13-continued

| Unambiguous NOE Distance Restraints |
| --- |

ASSI {14132}
((segid "PROT" and resid 110 and name HG12))
(segid "PROT" and resid 110 and name HD1%)
  2.100  1.100  1.100 peak     14132 weight  0.10000E+01 volume  0.11467E+02 ppm1    1.088 ppm2  0.578
ASSI {14142}
((segid "PROT" and resid 116 and name HG12))
(segid "PROT" and resid 116 and name HD1%)
  2.000  1.000  1.000 peak     14142 weight  0.10000E+01 volume  0.15573E+02 ppm1    0.961 ppm2  0.825
ASSI {14152}
(segid "PROT" and resid 116 and name HD1%)
(segid "PROT" and resid 110 and name HD1%)
  2.300  1.300  1.300 peak     14152 weight  0.10000E+01 volume  0.75073E+01 ppm1    0.844 ppm2  0.569
ASSI {14212}
((segid "PROT" and resid 84 and name HA))
(segid "PROT" and resid 50 and name HD1%)
  2.200  1.200  1.200 peak     14212 weight  0.10000E+01 volume  0.81666E+01 ppm1    4.342 ppm2  0.580
ASSI {14222}
((segid "PROT" and resid 53 and name HA))
(segid "PROT" and resid 50 and name HD1%)
  2.900  2.100  2.100 peak     14222 weight  0.10000E+01 volume  0.16892E+01 ppm1    4.122 ppm2  0.584
ASSI {14242}
((segid "PROT" and resid 84 and name HB1))
(segid "PROT" and resid 50 and name HD1%)
  2.500  1.600  1.600 peak     14242 weight  0.10000E+01 volume  0.45606E+01 ppm1    3.035 ppm2  0.580
ASSI {14252}
((segid "PROT" and resid 88 and name HB1))
(segid "PROT" and resid 50 and name HD1%)
  2.600  1.700  1.700 peak     14252 weight  0.10000E+01 volume  0.34453E+01 ppm1    2.949 ppm2  0.582
ASSI {14262}
((segid "PROT" and resid 84 and name HB2))
(segid "PROT" and resid 50 and name HD1%)
  2.700  1.800  1.800 peak     14262 weight  0.10000E+01 volume  0.24442E+01 ppm1    2.714 ppm2  0.580
ASSI {14272}
((segid "PROT" and resid 87 and name HB1))
(segid "PROT" and resid 50 and name HD1%)
  2.500  1.600  1.600 peak     14272 weight  0.10000E+01 volume  0.41877E+01 ppm1    2.234 ppm2  0.583
ASSI {14282}
((segid "PROT" and resid 87 and name HB2))
(segid "PROT" and resid 50 and name HD1%)
  2.600  1.700  1.700 peak     14282 weight  0.10000E+01 volume  0.30054E+01 ppm1    2.059 ppm2  0.581
ASSI {14292}
((segid "PROT" and resid 50 and name HB))
(segid "PROT" and resid 50 and name HD1%)
  2.500  1.600  1.600 peak     14292 weight  0.10000E+01 volume  0.43255E+01 ppm1    1.249 ppm2  0.580
ASSI {14302}
(segid "PROT" and resid 49 and name HG1%)
(segid "PROT" and resid 50 and name HD1%)
  2.400  1.400  1.400 peak     14302 weight  0.10000E+01 volume  0.48009E+01 ppm1    0.954 ppm2  0.580
ASSI {14322}
((segid "PROT" and resid 50 and name HG11))
(segid "PROT" and resid 50 and name HD1%)
  2.200  1.200  1.200 peak     14322 weight  0.10000E+01 volume  0.93672E+01 ppm1    0.834 ppm2  0.582
ASSI {14342}
((segid "PROT" and resid 50 and name HG12))
(segid "PROT" and resid 50 and name HD1%)
  2.200  1.200  1.200 peak     14342 weight  0.10000E+01 volume  0.83520E+01 ppm1    0.190 ppm2  0.583
ASSI {14352}
((segid "PROT" and resid 6 and name HD1))
((segid "PROT" and resid 6 and name HA))
  2.400  1.400  1.400 peak     14352 weight  0.10000E+01 volume  0.48806E+01 ppm1    1.680 ppm2  4.375
ASSI {14382}
((segid "PROT" and resid 7 and name HG1))
((segid "PROT" and resid 7 and name HB1))
  1.800  0.800  0.800 peak     14382 weight  0.10000E+01 volume  0.31365E+02 ppm1    2.308 ppm2  2.086
ASSI {14422}
((segid "PROT" and resid 61 and name HB2))
((segid "PROT" and resid 61 and name HA))
  2.000  1.000  1.000 peak     14422 weight  0.10000E+01 volume  0.15249E+02 ppm1    2.101 ppm2  4.084
ASSI {14462}
((segid "PROT" and resid 92 and name HG2))
((segid "PROT" and resid 92 and name HG1))
  1.700  0.700  0.700 peak     14462 weight  0.10000E+01 volume  0.36116E+02 ppm1    2.266 ppm2  2.386
ASSI {14472}
((segid "PROT" and resid 94 and name HA))
((segid "PROT" and resid 94 and name HB2))
  2.300  1.300  1.300 peak     14472 weight  0.10000E+01 volume  0.67398E+01 ppm1    4.244 ppm2  2.035

TABLE 13-continued

| Unambiguous NOE Distance Restraints |
| --- |

ASSI {14542}
(segid "PROT" and resid 41 and name HG2%)
((segid "PROT" and resid 41 and name HA))
  2.200  1.200    1.200 peak     14542  weight  0.10000E+01  volume  0.86782E+01  ppm1     1.318  ppm2  4.097
ASSI {14582}
((segid "PROT" and resid 30 and name HA))
((segid "PROT" and resid 30 and name HB1))
  3.100  2.400    2.400 peak     14582  weight  0.10000E+01  volume  0.12468E+01  ppm1     4.854  ppm2  4.344
ASSI {14632}
((segid "PROT" and resid 89 and name HB2))
((segid "PROT" and resid 89 and name HB1))
  2.400  1.400    1.400 peak     14632  weight  0.10000E+01  volume  0.59384E+01  ppm1     2.904  ppm2  3.100
ASSI {14642}
((segid "PROT" and resid 10 and name HA))
((segid "PROT" and resid 10 and name HB2))
  2.500  1.600    1.600 peak     14642  weight  0.10000E+01  volume  0.42768E+01  ppm1     4.918  ppm2  2.734
ASSI {14652}
((segid "PROT" and resid 12 and name HA))
((segid "PROT" and resid 12 and name HB2))
  2.500  1.600    1.600 peak     14652  weight  0.10000E+01  volume  0.46107E+01  ppm1     4.723  ppm2  2.794
ASSI {14692}
((segid "PROT" and resid 13 and name HG2))
((segid "PROT" and resid 13 and name HA))
  2.300  1.300    1.300 peak     14692  weight  0.10000E+01  volume  0.67869E+01  ppm1     2.430  ppm2  4.217
ASSI {14722}
((segid "PROT" and resid 20 and name HA))
((segid "PROT" and resid 23 and name HG1))
  3.000  2.200    2.200 peak     14722  weight  0.10000E+01  volume  0.12728E+01  ppm1     4.319  ppm2  2.575
ASSI {14732}
((segid "PROT" and resid 20 and name HA))
((segid "PROT" and resid 23 and name HG2))
  3.100  2.400    2.400 peak     14732  weight  0.10000E+01  volume  0.10567E+01  ppm1     4.319  ppm2  2.482
ASSI {14782}
((segid "PROT" and resid 23 and name HB2))
((segid "PROT" and resid 23 and name HA))
  2.100  1.100    1.100 peak     14782  weight  0.10000E+01  volume  0.12638E+02  ppm1     2.272  ppm2  4.078
ASSI {14802}
((segid "PROT" and resid 23 and name HG2))
((segid "PROT" and resid 23 and name HB2))
  2.100  1.100    1.100 peak     14802  weight  0.10000E+01  volume  0.11531E+02  ppm1     2.492  ppm2  2.247
ASSI {14822}
((segid "PROT" and resid 24 and name HB2))
((segid "PROT" and resid 24 and name HA))
  2.300  1.300    1.300 peak     14822  weight  0.10000E+01  volume  0.73231E+01  ppm1     2.421  ppm2  4.227
ASSI {14842}
((segid "PROT" and resid 24 and name HG1))
((segid "PROT" and resid 24 and name HB2))
  2.700  1.800    1.800 peak     14842  weight  0.10000E+01  volume  0.29089E+01  ppm1     2.891  ppm2  2.418
ASSI {14852}
((segid "PROT" and resid 21 and name HA))
((segid "PROT" and resid 24 and name HG1))
  3.200  2.600    2.300 peak     14852  weight  0.10000E+01  volume  0.98750E+00  ppm1     3.800  ppm2  2.889
ASSI {14862}
((segid "PROT" and resid 29 and name HG1))
((segid "PROT" and resid 29 and name HA))
  2.300  1.300    1.300 peak     14862  weight  0.10000E+01  volume  0.65450E+01  ppm1     2.506  ppm2  4.225
ASSI {14912}
((segid "PROT" and resid 79 and name HB1))
((segid "PROT" and resid 79 and name HG1))
  2.100  1.100    1.100 peak     14912  weight  0.10000E+01  volume  0.13602E+02  ppm1     2.216  ppm2  2.463
ASSI {14922}
((segid "PROT" and resid 79 and name HB2))
((segid "PROT" and resid 79 and name HG1))
  2.100  1.100    1.100 peak     14922  weight  0.10000E+01  volume  0.11814E+02  ppm1     2.118  ppm2  2.465
ASSI {14932}
((segid "PROT" and resid 56 and name HG))
((segid "PROT" and resid 34 and name HB1))
  3.000  2.200    2.200 peak     14932  weight  0.10000E+01  volume  0.14093E+01  ppm1     1.768  ppm2  3.519
ASSI {14962}
((segid "PROT" and resid 56 and name HG))
((segid "PROT" and resid 34 and name HB2))
  3.100  2.400    2.400 peak     14962  weight  0.10000E+01  volume  0.10685E+01  ppm1     1.761  ppm2  2.631
ASSI {14982}
((segid "PROT" and resid 53 and name HG1))
((segid "PROT" and resid 52 and name HA))
  3.100  2.400    2.400 peak     14982  weight  0.10000E+01  volume  0.11187E+01  ppm1     2.273  ppm2  5.037

TABLE 13-continued

Unambiguous NOE Distance Restraints

```
ASSI {15012}
((segid "PROT" and resid 82 and name HB2))
((segid "PROT" and resid 82 and name HA))
 2.600  1.700  1.700 peak    15012 weight  0.10000E+01 volume  0.29905E+01 ppm1    3.033 ppm2   4.215
ASSI {15052}
(segid "PROT" and resid 102 and name HD2%)
((segid "PROT" and resid 106 and name HB2))
 2.900  2.100  2.100 peak    15052 weight  0.10000E+01 volume  0.16469E+01 ppm1    0.767 ppm2   3.138
ASSI {15072}
((segid "PROT" and resid 18 and name HB1))
((segid "PROT" and resid 15 and name HA))
 3.000  2.200  2.200 peak    15072 weight  0.10000E+01 volume  0.12939E+01 ppm1    1.550 ppm2   4.042
ASSI {15092}
((segid "PROT" and resid 62 and name HA))
((segid "PROT" and resid 67 and name HB2))
 3.100  2.400  2.400 peak    15092 weight  0.10000E+01 volume  0.11858E+01 ppm1    3.919 ppm2   2.090
ASSI {15102}
((segid "PROT" and resid 68 and name HB1))
((segid "PROT" and resid 68 and name HA))
 3.100  2.400  2.400 peak    15102 weight  0.10000E+01 volume  0.11603E+01 ppm1    3.114 ppm2   4.581
ASSI {15132}
((segid "PROT" and resid 62 and name HB2))
((segid "PROT" and resid 68 and name HB2))
 3.300  2.700  2.200 peak    15132 weight  0.10000E+01 volume  0.82400E+00 ppm1    1.080 ppm2   2.966
ASSI {15142}
((segid "PROT" and resid 62 and name HB2))
((segid "PROT" and resid 68 and name HB1))
 3.300  2.700  2.200 peak    15142 weight  0.10000E+01 volume  0.85460E+00 ppm1    1.077 ppm2   3.106
ASSI {15162}
((segid "PROT" and resid 57 and name HE1))
((segid "PROT" and resid 57 and name HA))
 3.300  2.700  2.200 peak    15162 weight  0.10000E+01 volume  0.86210E+00 ppm1    2.603 ppm2   3.909
ASSI {15172}
((segid "PROT" and resid 28 and name HB1))
((segid "PROT" and resid 28 and name HA))
 2.600  1.700  1.700 peak    15172 weight  0.10000E+01 volume  0.30616E+01 ppm1    3.016 ppm2   4.021
ASSI {15212}
((segid "PROT" and resid 28 and name HB2))
((segid "PROT" and resid 25 and name HA))
 3.100  2.400  2.400 peak    15212 weight  0.10000E+01 volume  0.12595E+01 ppm1    2.817 ppm2   3.868
ASSI {15242}
(segid "PROT" and resid 25 and name HG2%)
((segid "PROT" and resid 25 and name HA))
 2.300  1.300  1.300 peak    15242 weight  0.10000E+01 volume  0.70013E+01 ppm1    1.069 ppm2   3.871
ASSI {15262}
((segid "PROT" and resid 106 and name HB1))
(segid "PROT" and resid 25 and name HG1%)
 3.200  2.600  2.300 peak    15262 weight  0.10000E+01 volume  0.94350E+00 ppm1    3.357 ppm2   1.244
ASSI {15292}
((segid "PROT" and resid 37 and name HA))
(segid "PROT" and resid 38 and name HG1%)
 3.200  2.600  2.300 peak    15292 weight  0.10000E+01 volume  0.10144E+01 ppm1    4.278 ppm2   0.489
ASSI {15302}
((segid "PROT" and resid 55 and name HB1))
(segid "PROT" and resid 81 and name HG1%)
 3.000  2.200  2.200 peak    15302 weight  0.10000E+01 volume  0.14883E+01 ppm1    2.400 ppm2   0.506
ASSI {15322}
((segid "PROT" and resid 43 and name HA))
(segid "PROT" and resid 38 and name HG2%)
 3.000  2.200  2.200 peak    15322 weight  0.10000E+01 volume  0.12695E+01 ppm1    4.983 ppm2  −0.010
ASSI {15432}
((segid "PROT" and resid 82 and name HA))
(segid "PROT" and resid 81 and name HG2%)
 3.000  2.200  2.200 peak    15432 weight  0.10000E+01 volume  0.14427E+01 ppm1    4.218 ppm2   0.155
ASSI {15452}
((segid "PROT" and resid 33 and name HG2))
((segid "PROT" and resid 33 and name HA))
 3.200  2.600  2.300 peak    15452 weight  0.10000E+01 volume  0.88590E+00 ppm1   −0.871 ppm2   3.994
ASSI {15462}
((segid "PROT" and resid 33 and name HB1))
((segid "PROT" and resid 33 and name HA))
 3.000  2.200  2.200 peak    15462 weight  0.10000E+01 volume  0.12852E+01 ppm1    1.064 ppm2   3.985
ASSI {15472}
((segid "PROT" and resid 14 and name HB2))
((segid "PROT" and resid 14 and name HA))
 2.500  1.600  1.600 peak    15472 weight  0.10000E+01 volume  0.41749E+01 ppm1    1.597 ppm2   4.090
```

TABLE 13-continued

Unambiguous NOE Distance Restraints

ASSI {15482}
((segid "PROT" and resid 14 and name HB1))
((segid "PROT" and resid 14 and name HA))
 2.200  1.200  1.200 peak     15482 weight  0.10000E+01 volume  0.79299E+01 ppm1   1.913 ppm2   4.085
ASSI {15502}
(segid "PROT" and resid 17 and name HG2%)
((segid "PROT" and resid 14 and name HA))
 3.100  2.400  2.400 peak     15502 weight  0.10000E+01 volume  0.11760E+01 ppm1   1.179 ppm2   4.098
ASSI {15512}
((segid "PROT" and resid 11 and name HA))
((segid "PROT" and resid 14 and name HB2))
 3.000  2.200  2.200 peak     15512 weight  0.10000E+01 volume  0.13340E+01 ppm1   4.372 ppm2   1.592
ASSI {15522}
((segid "PROT" and resid 70 and name HN))
((segid "PROT" and resid 14 and name HG))
 3.100  2.400  2.400 peak     15522 weight  0.10000E+01 volume  0.10950E+01 ppm1   7.488 ppm2   1.424
ASSI {15542}
((segid "PROT" and resid 70 and name HA))
(segid "PROT" and resid 14 and name HD2%)
 3.100  2.400  2.400 peak     15542 weight  0.10000E+01 volume  0.11378E+01 ppm1   4.807 ppm2   0.833
ASSI {15552}
((segid "PROT" and resid 18 and name HB1))
((segid "PROT" and resid 18 and name HA))
 2.800  2.000  2.000 peak     15552 weight  0.10000E+01 volume  0.22536E+01 ppm1   1.562 ppm2   3.316
ASSI {15562}
(segid "PROT" and resid 17 and name HG2%)
((segid "PROT" and resid 18 and name HA))
 3.000  2.200  2.200 peak     15562 weight  0.10000E+01 volume  0.14142E+01 ppm1   1.178 ppm2   3.312
ASSI {15572}
((segid "PROT" and resid 21 and name HG12))
((segid "PROT" and resid 18 and name HA))
 3.000  2.200  2.200 peak     15572 weight  0.10000E+01 volume  0.14946E+01 ppm1   1.071 ppm2   3.312
ASSI {15592}
((segid "PROT" and resid 18 and name HB2))
((segid "PROT" and resid 18 and name HA))
 2.700  1.800  1.800 peak     15592 weight  0.10000E+01 volume  0.26695E+01 ppm1   0.342 ppm2   3.314
ASSI {15642}
((segid "PROT" and resid 18 and name HG))
((segid "PROT" and resid 18 and name HB2))
 3.100  2.400  2.400 peak     15642 weight  0.10000E+01 volume  0.11294E+01 ppm1   1.704 ppm2   0.342
ASSI {15662}
(segid "PROT" and resid 74 and name HE %)
(segid "PROT" and resid 18 and name HD1%)
 3.100  2.400  2.400 peak     15662 weight  0.10000E+01 volume  0.10555E+01 ppm1   6.968 ppm2   0.519
ASSI {15672}
(segid "PROT" and resid 68 and name HD %)
(segid "PROT" and resid 18 and name HD1%)
 3.000  2.200  2.200 peak     15672 weight  0.10000E+01 volume  0.13402E+01 ppm1   7.213 ppm2   0.512
ASSI {15692}
((segid "PROT" and resid 17 and name HB))
(segid "PROT" and resid 18 and name HD2%)
 3.000  2.200  2.200 peak     15692 weight  0.10000E+01 volume  0.14210E+01 ppm1   4.288 ppm2  −0.161
ASSI {15702}
((segid "PROT" and resid 22 and name HA))
((segid "PROT" and resid 22 and name HB1))
 2.800  2.000  2.000 peak     15702 weight  0.10000E+01 volume  0.21005E+01 ppm1   4.154 ppm2   2.131
ASSI {15722}
(segid "PROT" and resid 22 and name HD1%)
((segid "PROT" and resid 22 and name HA))
 2.700  1.800  1.800 peak     15722 weight  0.10000E+01 volume  0.23790E+01 ppm1   1.105 ppm2   4.152
ASSI {15762}
((segid "PROT" and resid 22 and name HA))
((segid "PROT" and resid 22 and name HG))
 2.900  2.100  2.100 peak     15762 weight  0.10000E+01 volume  0.18179E+01 ppm1   4.155 ppm2   1.788
ASSI {15772}
((segid "PROT" and resid 22 and name HB2))
(segid "PROT" and resid 22 and name HD1%)
 2.300  1.300  1.300 peak     15772 weight  0.10000E+01 volume  0.71485E+01 ppm1   1.734 ppm2   1.106
ASSI {15782}
((segid "PROT" and resid 22 and name HB2))
(segid "PROT" and resid 22 and name HD2%)
 2.300  1.300  1.300 peak     15782 weight  0.10000E+01 volume  0.69966E+01 ppm1   1.730 ppm2   1.049
ASSI {15822}
((segid "PROT" and resid 56 and name HA))
((segid "PROT" and resid 56 and name HB1))
 3.000  2.200  2.200 peak     15822 weight  0.10000E+01 volume  0.13848E+01 ppm1   4.066 ppm2   2.092

TABLE 13-continued

Unambiguous NOE Distance Restraints

ASSI {15832}
((segid "PROT" and resid 56 and name HG))
((segid "PROT" and resid 56 and name HA))
  2.500  1.600  1.600 peak      15832 weight  0.10000E+01 volume  0.45909E+01 ppm1   1.772 ppm2  4.074
ASSI {15842}
((segid "PROT" and resid 56 and name HG))
((segid "PROT" and resid 56 and name HB1))
  2.400  1.400  1.400 peak      15842 weight  0.10000E+01 volume  0.48109E+01 ppm1   1.765 ppm2  2.115
ASSI {15852}
((segid "PROT" and resid 56 and name HA))
(segid "PROT" and resid 56 and name HD2%)
  2.200  1.200  1.200 peak      15852 weight  0.10000E+01 volume  0.97607E+01 ppm1   4.064 ppm2  0.677
ASSI {15862}
((segid "PROT" and resid 56 and name HB1))
(segid "PROT" and resid 56 and name HD2%)
  2.600  1.700  1.700 peak      15862 weight  0.10000E+01 volume  0.36257E+01 ppm1   2.123 ppm2  0.678
ASSI {15872}
(segid "PROT" and resid 56 and name HD1%)
(segid "PROT" and resid 56 and name HD2%)
  2.000  1.000  1.000 peak      15872 weight  0.10000E+01 volume  0.14850E+02 ppm1   0.980 ppm2  0.676
ASSI {15882}
(segid "PROT" and resid 22 and name HD2%)
(segid "PROT" and resid 56 and name HD2%)
  2.000  1.000  1.000 peak      15882 weight  0.10000E+01 volume  0.15848E+02 ppm1   1.058 ppm2  0.676
ASSI {15902}
(segid "PROT" and resid 59 and name HE %)
(segid "PROT" and resid 56 and name HD2%)
  3.200  2.600  2.300 peak      15902 weight  0.10000E+01 volume  0.10042E+01 ppm1   1.306 ppm2  0.675
ASSI {15912}
((segid "PROT" and resid 25 and name HB))
(segid "PROT" and resid 56 and name HD2%)
  3.200  2.600  2.300 peak      15912 weight  0.10000E+01 volume  0.99240E+00 ppm1   2.443 ppm2  0.681
ASSI {15922}
((segid "PROT" and resid 59 and name HG1))
(segid "PROT" and resid 56 and name HD2%)
  3.100  2.400  2.400 peak      15922 weight  0.10000E+01 volume  0.12677E+01 ppm1   2.648 ppm2  0.680
ASSI {15932}
((segid "PROT" and resid 34 and name HB1))
(segid "PROT" and resid 56 and name HD2%)
  3.100  2.400  2.400 peak      15932 weight  0.10000E+01 volume  0.11626E+01 ppm1   3.513 ppm2  0.676
ASSI {15942}
((segid "PROT" and resid 35 and name HA))
(segid "PROT" and resid 56 and name HD2%)
  3.000  2.200  2.200 peak      15942 weight  0.10000E+01 volume  0.14845E+01 ppm1   4.342 ppm2  0.676
ASSI {15952}
(segid "PROT" and resid 78 and name HD2%)
(segid "PROT" and resid 56 and name HD1%)
  3.300  2.700  2.200 peak      15952 weight  0.10000E+01 volume  0.84570E+00 ppm1   0.179 ppm2  0.984
ASSI {15972}
((segid "PROT" and resid 31 and name HA))
(segid "PROT" and resid 56 and name HD1%)
  3.200  2.600  2.300 peak      15972 weight  0.10000E+01 volume  0.10184E+01 ppm1   4.434 ppm2  0.979
ASSI {15982}
((segid "PROT" and resid 63 and name HD1%)
((segid "PROT" and resid 63 and name HA))
  3.200  2.600  2.300 peak      15982 weight  0.10000E+01 volume  0.98600E+00 ppm1   0.919 ppm2  4.719
ASSI {15992}
((segid "PROT" and resid 63 and name HG))
((segid "PROT" and resid 63 and name HA))
  3.100  2.400  2.400 peak      15992 weight  0.10000E+01 volume  0.11802E+01 ppm1   1.865 ppm2  4.719
ASSI {16002}
((segid "PROT" and resid 63 and name HB2))
((segid "PROT" and resid 63 and name HA))
  3.000  2.200  2.200 peak      16002 weight  0.10000E+01 volume  0.14688E+01 ppm1   1.972 ppm2  4.719
ASSI {16012}
((segid "PROT" and resid 67 and name HB2))
((segid "PROT" and resid 63 and name HA))
  3.400  2.900  2.100 peak      16012 weight  0.10000E+01 volume  0.71580E+00 ppm1   2.086 ppm2  4.719
ASSI {16052}
((segid "PROT" and resid 63 and name HA))
((segid "PROT" and resid 63 and name HB1))
  3.000  2.200  2.200 peak      16052 weight  0.10000E+01 volume  0.14729E+01 ppm1   4.717 ppm2  2.352
ASSI {16092}
((segid "PROT" and resid 63 and name HG))
(segid "PROT" and resid 63 and name HD1%)
  2.200  1.200  1.200 peak      16092 weight  0.10000E+01 volume  0.90416E+01 ppm1   1.852 ppm2  0.922

TABLE 13-continued

Unambiguous NOE Distance Restraints

ASSI {16102}
((segid "PROT" and resid 63 and name HB2))
(segid "PROT" and resid 63 and name HD1%)
 2.500  1.600  1.600 peak    16102 weight  0.10000E+01 volume  0.45661E+01 ppm1   1.966 ppm2  0.923
ASSI {16112}
((segid "PROT" and resid 63 and name HB1))
(segid "PROT" and resid 63 and name HD1%)
 2.400  1.400  1.400 peak    16112 weight  0.10000E+01 volume  0.51188E+01 ppm1   2.355 ppm2  0.918
ASSI {16142}
((segid "PROT" and resid 63 and name HB2))
(segid "PROT" and resid 63 and name HD2%)
 2.400  1.400  1.400 peak    16142 weight  0.10000E+01 volume  0.52687E+01 ppm1   1.965 ppm2  1.078
ASSI {16152}
((segid "PROT" and resid 73 and name HG))
((segid "PROT" and resid 73 and name HA))
 2.500  1.600  1.600 peak    16152 weight  0.10000E+01 volume  0.40193E+01 ppm1   1.802 ppm2  4.260
ASSI {16182}
((segid "PROT" and resid 68 and name HA))
((segid "PROT" and resid 73 and name HB1))
 3.200  2.600  2.300 peak    16182 weight  0.10000E+01 volume  0.87100E+00 ppm1   4.581 ppm2  2.019
ASSI {16192}
((segid "PROT" and resid 68 and name HA))
((segid "PROT" and resid 73 and name HB2))
 3.200  2.600  2.300 peak    16192 weight  0.10000E+01 volume  0.87570E+00 ppm1   4.575 ppm2  1.929
ASSI {16202}
(segid "PROT" and resid 68 and name HE %)
((segid "PROT" and resid 73 and name HB2))
 3.000  2.200  2.200 peak    16202 weight  0.10000E+01 volume  0.13823E+01 ppm1   7.316 ppm2  1.918
ASSI {16232}
(segid "PROT" and resid 68 and name HD %)
((segid "PROT" and resid 73 and name HG))
 3.000  2.200  2.200 peak    16232 weight  0.10000E+01 volume  0.14152E+01 ppm1   7.214 ppm2  1.805
ASSI {16262}
((segid "PROT" and resid 68 and name HA))
(segid "PROT" and resid 73 and name HD2%)
 3.000  2.200  2.200 peak    16262 weight  0.10000E+01 volume  0.13485E+01 ppm1   4.573 ppm2  0.922
ASSI {16272}
(segid "PROT" and resid 68 and name HD %)
(segid "PROT" and resid 73 and name HD2%)
 3.000  2.200  2.200 peak    16272 weight  0.10000E+01 volume  0.13605E+01 ppm1   7.216 ppm2  0.927
ASSI {16282}
(segid "PROT" and resid 68 and name HE %)
(segid "PROT" and resid 73 and name HD2%)
 3.000  2.200  2.200 peak    16282 weight  0.10000E+01 volume  0.14572E+01 ppm1   7.317 ppm2  0.931
ASSI {16292}
(segid "PROT" and resid 68 and name HE %)
(segid "PROT" and resid 73 and name HD1%)
 3.100  2.400  2.400 peak    16292 weight  0.10000E+01 volume  0.12364E+01 ppm1   7.315 ppm2  0.976
ASSI {16302}
((segid "PROT" and resid 78 and name HG))
((segid "PROT" and resid 78 and name HA))
 2.600  1.700  1.700 peak    16302 weight  0.10000E+01 volume  0.36564E+01 ppm1   0.695 ppm2  3.417
ASSI {16312}
((segid "PROT" and resid 78 and name HB2))
((segid "PROT" and resid 78 and name HA))
 2.400  1.400  1.400 peak    16312 weight  0.10000E+01 volume  0.51147E+01 ppm1   0.467 ppm2  3.415
ASSI {16332}
((segid "PROT" and resid 78 and name HB1))
(segid "PROT" and resid 78 and name HD2%)
 2.300  1.300  1.300 peak    16332 weight  0.10000E+01 volume  0.63946E+01 ppm1   0.742 ppm2  0.197
ASSI {16352}
((segid "PROT" and resid 78 and name HB2))
(segid "PROT" and resid 78 and name HD1%)
 2.400  1.400  1.400 peak    16352 weight  0.10000E+01 volume  0.55770E+01 ppm1   0.476 ppm2  0.092
ASSI {16392}
((segid "PROT" and resid 81 and name HB))
(segid "PROT" and resid 78 and name HD1%)
 3.200  2.600  2.300 peak    16392 weight  0.10000E+01 volume  0.10149E+01 ppm1   1.461 ppm2  0.093
ASSI {16402}
((segid "PROT" and resid 106 and name HB2))
(segid "PROT" and resid 78 and name HD1%)
 3.000  2.200  2.200 peak    16402 weight  0.10000E+01 volume  0.14513E+01 ppm1   3.146 ppm2  0.091
ASSI {16422}
((segid "PROT" and resid 102 and name HG))
((segid "PROT" and resid 102 and name HB1))
 2.600  1.700  1.700 peak    16422 weight  0.10000E+01 volume  0.30300E+01 ppm1   1.593 ppm2  1.484

TABLE 13-continued

Unambiguous NOE Distance Restraints

ASSI {16442}
((segid "PROT" and resid 102 and name HG))
(segid "PROT" and resid 102 and name HD1%)
  1.900  0.900    0.900 peak      16442  weight  0.10000E+01  volume    0.19614E+02 ppm1      1.596  ppm2  0.756
ASSI {16462}
((segid "PROT" and resid 102 and name HA))
(segid "PROT" and resid 102 and name HD1%)
  2.700  1.800    1.800 peak      16462  weight  0.10000E+01  volume    0.28719E+01 ppm1      3.722  ppm2  0.763
ASSI {16472}
(segid "PROT" and resid 82 and name HE%)
((segid "PROT" and resid 102 and name HB2))
  3.300  2.700    2.200 peak      16472  weight  0.10000E+01  volume    0.74030E+00 ppm1      6.487  ppm2  1.270
ASSI {16492}
(segid "PROT" and resid 102 and name HD2%)
((segid "PROT" and resid 102 and name HG))
  2.100  1.100    1.100 peak      16492  weight  0.10000E+01  volume    0.12673E+02 ppm1      0.763  ppm2  1.591
ASSI {16512}
((segid "PROT" and resid 28 and name HD2))
(segid "PROT" and resid 102 and name HD2%)
  3.000  2.200    2.200 peak      16512  weight  0.10000E+01  volume    0.14555E+01 ppm1      5.006  ppm2  0.767
ASSI {16552}
(segid "PROT" and resid 115 and name HD1%)
((segid "PROT" and resid 115 and name HA))
  2.200  1.200    1.200 peak      16552  weight  0.10000E+01  volume    0.80718E+01 ppm1      0.763  ppm2  4.251
ASSI {16572}
((segid "PROT" and resid 21 and name HB))
(segid "PROT" and resid 21 and name HA))
  2.700  1.800    1.800 peak      16572  weight  0.10000E+01  volume    0.25287E+01 ppm1      1.948  ppm2  3.798
ASSI {16582}
((segid "PROT" and resid 21 and name HG11))
(segid "PROT" and resid 21 and name HA))
  2.600  1.700    1.700 peak      16582  weight  0.10000E+01  volume    0.33367E+01 ppm1      1.786  ppm2  3.802
ASSI {16602}
((segid "PROT" and resid 21 and name HG12))
(segid "PROT" and resid 21 and name HA))
  2.500  1.600    1.600 peak      16602  weight  0.10000E+01  volume    0.46692E+01 ppm1      1.074  ppm2  3.798
ASSI {16622}
((segid "PROT" and resid 24 and name HG2))
(segid "PROT" and resid 21 and name HA))
  2.700  1.800    1.800 peak      16622  weight  0.10000E+01  volume    0.26895E+01 ppm1      2.502  ppm2  3.797
ASSI {16632}
((segid "PROT" and resid 24 and name HB2))
(segid "PROT" and resid 21 and name HA))
  3.200  2.600    2.300 peak      16632  weight  0.10000E+01  volume    0.10089E+01 ppm1      2.430  ppm2  3.797
ASSI {16642}
((segid "PROT" and resid 21 and name HA))
(segid "PROT" and resid 21 and name HD1%)
  2.500  1.600    1.600 peak      16642  weight  0.10000E+01  volume    0.40517E+01 ppm1      3.800  ppm2  0.655
ASSI {16652}
((segid "PROT" and resid 21 and name HG12))
((segid "PROT" and resid 21 and name HB))
  2.600  1.700    1.700 peak      16652  weight  0.10000E+01  volume    0.33647E+01 ppm1      1.074  ppm2  1.950
ASSI {16672}
((segid "PROT" and resid 21 and name HB))
(segid "PROT" and resid 21 and name HG2%)
  2.000  1.000    1.000 peak      16672  weight  0.10000E+01  volume    0.16452E+02 ppm1      1.947  ppm2  1.019
ASSI {16682}
(segid "PROT" and resid 18 and name HD2%)
((segid "PROT" and resid 21 and name HB))
  3.300  2.700    2.200 peak      16682  weight  0.10000E+01  volume    0.83910E+00 ppm1    −0.157  ppm2  1.947
ASSI {16692}
((segid "PROT" and resid 109 and name HD1))
((segid "PROT" and resid 21 and name HG12))
  3.100  2.400    2.400 peak      16692  weight  0.10000E+01  volume    0.12669E+01 ppm1      1.416  ppm2  1.077
ASSI {16702}
(segid "PROT" and resid 106 and name HD%)
((segid "PROT" and resid 21 and name HG11))
  3.300  2.700    2.200 peak      16702  weight  0.10000E+01  volume    0.73640E+00 ppm1      6.962  ppm2  1.781
ASSI {16712}
((segid "PROT" and resid 21 and name HG12))
(segid "PROT" and resid 21 and name HD1%)
  2.100  1.100    1.100 peak      16712  weight  0.10000E+01  volume    0.12596E+02 ppm1      1.078  ppm2  0.650
ASSI {16722}
(segid "PROT" and resid 18 and name HD2%)
(segid "PROT" and resid 21 and name HG2%)
  3.000  2.200    2.200 peak      16722  weight  0.10000E+01  volume    0.13840E+01 ppm1    −0.159  ppm2  1.020

TABLE 13-continued

| Unambiguous NOE Distance Restraints |
|---|

ASSI {16742}
((segid "PROT" and resid 17 and name HA))
((segid "PROT" and resid 21 and name HD1%)
  3.100  2.400  2.400 peak    16742  weight  0.10000E+01  volume  0.11559E+01  ppm1    3.975  ppm2  0.660
ASSI {16782}
((segid "PROT" and resid 47 and name HA))
((segid "PROT" and resid 50 and name HB))
  3.200  2.600  2.300 peak    16782  weight  0.10000E+01  volume  0.98740E+00  ppm1    4.139  ppm2  1.249
ASSI {16792}
((segid "PROT" and resid 50 and name HB))
((segid "PROT" and resid 50 and name HA))
  2.600  1.700  1.700 peak    16792  weight  0.10000E+01  volume  0.33271E+01  ppm1    1.252  ppm2  3.951
ASSI {16822}
((segid "PROT" and resid 50 and name HA))
((segid "PROT" and resid 50 and name HG12))
  3.000  2.200  2.200 peak    16822  weight  0.10000E+01  volume  0.14239E+01  ppm1    3.956  ppm2  0.190
ASSI {16832}
((segid "PROT" and resid 53 and name HG2))
((segid "PROT" and resid 50 and name HB))
  3.300  2.700  2.200 peak    16832  weight  0.10000E+01  volume  0.81300E+00  ppm1    1.933  ppm2  1.256
ASSI {16842}
((segid "PROT" and resid 50 and name HB))
((segid "PROT" and resid 50 and name HG11))
  2.600  1.700  1.700 peak    16842  weight  0.10000E+01  volume  0.29784E+01  ppm1    1.250  ppm2  0.830
ASSI {16882}
((segid "PROT" and resid 49 and name HB))
((segid "PROT" and resid 50 and name HG12))
  3.300  2.700  2.200 peak    16882  weight  0.10000E+01  volume  0.76190E+00  ppm1    1.928  ppm2  0.182
ASSI {16892}
((segid "PROT" and resid 49 and name HB))
(segid "PROT" and resid 50 and name HD1%)
  3.100  2.400  2.400 peak    16892  weight  0.10000E+01  volume  0.12022E+01  ppm1    1.926  ppm2  0.586
ASSI {16902}
((segid "PROT" and resid 87 and name HG1))
(segid "PROT" and resid 50 and name HD1%)
  3.200  2.600  2.300 peak    16902  weight  0.10000E+01  volume  0.92330E+00  ppm1    2.438  ppm2  0.586
ASSI {16912}
((segid "PROT" and resid 85 and name HN))
(segid "PROT" and resid 50 and name HD1%)
  3.200  2.600  2.300 peak    16912  weight  0.10000E+01  volume  0.98650E+00  ppm1    6.889  ppm2  0.579
ASSI {16952}
((segid "PROT" and resid 53 and name HD1))
(segid "PROT" and resid 50 and name HG2%)
  3.200  2.600  2.300 peak    16952  weight  0.10000E+01  volume  0.98080E+00  ppm1    3.648  ppm2  0.420
ASSI {16982}
((segid "PROT" and resid 104 and name HD1))
((segid "PROT" and resid 101 and name HA))
  3.100  2.400  2.400 peak    16982  weight  0.10000E+01  volume  0.10838E+01  ppm1    1.729  ppm2  3.693
ASSI {16992}
((segid "PROT" and resid 101 and name HB))
((segid "PROT" and resid 101 and name HG12))
  2.400  1.400  1.400 peak    16992  weight  0.10000E+01  volume  0.51879E+01  ppm1    1.948  ppm2  1.241
ASSI {17012}
((segid "PROT" and resid 101 and name HB))
(segid "PROT" and resid 101 and name HD1%)
  2.100  1.100  1.100 peak    17012  weight  0.10000E+01  volume  0.11433E+02  ppm1    1.949  ppm2  0.993
ASSI {17022}
((segid "PROT" and resid 101 and name HB))
(segid "PROT" and resid 101 and name HG2%)
  1.900  0.900  0.900 peak    17022  weight  0.10000E+01  volume  0.20229E+02  ppm1    1.949  ppm2  1.032
ASSI {17032}
((segid "PROT" and resid 101 and name HG11))
(segid "PROT" and resid 101 and name HG2%)
  2.100  1.100  1.100 peak    17032  weight  0.10000E+01  volume  0.10554E+02  ppm1    1.899  ppm2  1.032
ASSI {17042}
((segid "PROT" and resid 30 and name HB1))
((segid "PROT" and resid 101 and name HB))
  3.200  2.600  2.300 peak    17042  weight  0.10000E+01  volume  0.89790E+00  ppm1    4.360  ppm2  1.943
ASSI {17082}
((segid "PROT" and resid 101 and name HG12))
(segid "PROT" and resid 101 and name HG2%)
  2.100  1.100  1.100 peak    17082  weight  0.10000E+01  volume  0.11790E+02  ppm1    1.241  ppm2  1.032
ASSI {17122}
((segid "PROT" and resid 30 and name HB1))
(segid "PROT" and resid 101 and name HD1%)
  3.000  2.200  2.200 peak    17122  weight  0.10000E+01  volume  0.13541E+01  ppm1    4.342  ppm2  0.990

TABLE 13-continued

Unambiguous NOE Distance Restraints

ASSI {17152}
((segid "PROT" and resid 110 and name HA))
((segid "PROT" and resid 110 and name HG12))
  2.400  1.400   1.400 peak     17152 weight  0.10000E+01 volume  0.54547E+01 ppm1     3.863  ppm2  1.098
ASSI {17162}
((segid "PROT" and resid 110 and name HB))
(segid "PROT" and resid 110 and name HD1%)
  2.300  1.300   1.300 peak     17162 weight  0.10000E+01 volume  0.78140E+01 ppm1     1.798  ppm2  0.575
ASSI {17192}
(segid "PROT" and resid 110 and name HG2%)
(segid "PROT" and resid 110 and name HD1%)
  1.900  0.900   0.900 peak     17192 weight  0.10000E+01 volume  0.19792E+02 ppm1     0.694  ppm2  0.568
ASSI {17232}
((segid "PROT" and resid 75 and name HB2))
(segid "PROT" and resid 110 and name HD1%)
  3.100  2.400   2.400 peak     17232 weight  0.10000E+01 volume  0.11996E+01 ppm1     2.651  ppm2  0.571
ASSI {17282}
(segid "PROT" and resid 116 and name HD1%)
((segid "PROT" and resid 116 and name HB))
  2.100  1.100   1.100 peak     17282 weight  0.10000E+01 volume  0.10804E+02 ppm1     0.832  ppm2  1.851
ASSI {17292}
(segid "PROT" and resid 110 and name HD1%)
((segid "PROT" and resid 116 and name HB))
  3.200  2.600   2.300 peak     17292 weight  0.10000E+01 volume  0.95100E+00 ppm1     0.564  ppm2  1.846
ASSI {17312}
((segid "PROT" and resid 9 and name HA))
((segid "PROT" and resid 9 and name HB2))
  2.400  1.400   1.400 peak     17312 weight  0.10000E+01 volume  0.58458E+01 ppm1     4.363  ppm2  1.828
ASSI {17322}
((segid "PROT" and resid 9 and name HD1))
((segid "PROT" and resid 9 and name HB2))
  2.500  1.600   1.600 peak     17322 weight  0.10000E+01 volume  0.39205E+01 ppm1     3.223  ppm2  1.831
ASSI {17332}
((segid "PROT" and resid 9 and name HB1))
((segid "PROT" and resid 9 and name HD1))
  2.300  1.300   1.300 peak     17332 weight  0.10000E+01 volume  0.77754E+01 ppm1     1.879  ppm2  3.221
ASSI {17362}
((segid "PROT" and resid 51 and name HG1))
((segid "PROT" and resid 51 and name HA))
  2.500  1.600   1.600 peak     17362 weight  0.10000E+01 volume  0.39373E+01 ppm1     1.354  ppm2  3.879
ASSI {17372}
((segid "PROT" and resid 51 and name HB1))
((segid "PROT" and resid 51 and name HA))
  2.400  1.400   1.400 peak     17372 weight  0.10000E+01 volume  0.53335E+01 ppm1     1.390  ppm2  3.877
ASSI {17382}
((segid "PROT" and resid 51 and name HB1))
((segid "PROT" and resid 51 and name HD1))
  2.300  1.300   1.300 peak     17382 weight  0.10000E+01 volume  0.65385E+01 ppm1     1.382  ppm2  3.022
ASSI {17402}
((segid "PROT" and resid 51 and name HA))
((segid "PROT" and resid 51 and name HG2))
  2.300  1.300   1.300 peak     17402 weight  0.10000E+01 volume  0.65716E+01 ppm1     3.878  ppm2  1.196
ASSI {17442}
((segid "PROT" and resid 51 and name HG2))
((segid "PROT" and resid 51 and name HB1))
  1.900  0.900   0.900 peak     17442 weight  0.10000E+01 volume  0.20102E+02 ppm1     1.197  ppm2  1.381
ASSI {17452}
((segid "PROT" and resid 51 and name HG2))
((segid "PROT" and resid 51 and name HG1))
  2.000  1.000   1.000 peak     17452 weight  0.10000E+01 volume  0.17189E+02 ppm1     1.196  ppm2  1.350
ASSI {17472}
(segid "PROT" and resid 110 and name HG2%)
((segid "PROT" and resid 116 and name HG11))
  3.000  2.200   2.200 peak     17472 weight  0.10000E+01 volume  0.13662E+01 ppm1     0.683  ppm2  1.349
ASSI {17482}
(segid "PROT" and resid 110 and name HD1%)
((segid "PROT" and resid 116 and name HG11))
  3.100  2.400   2.400 peak     17482 weight  0.10000E+01 volume  0.10860E+01 ppm1     0.568  ppm2  1.350
ASSI {17502}
((segid "PROT" and resid 66 and name HB2))
((segid "PROT" and resid 66 and name HA))
  2.300  1.300   1.300 peak     17502 weight  0.10000E+01 volume  0.62411E+01 ppm1     2.051  ppm2  4.445
ASSI {17512}
((segid "PROT" and resid 66 and name HA))
((segid "PROT" and resid 66 and name HG2))
  2.500  1.600   1.600 peak     17512 weight  0.10000E+01 volume  0.37845E+01 ppm1     4.442  ppm2  1.564

TABLE 13-continued

| Unambiguous NOE Distance Restraints |

ASSI {17532}
((segid "PROT" and resid 66 and name HA))
((segid "PROT" and resid 66 and name HD2))
 2.300  2.300  2.200 peak     17532  weight  0.10000E+01 volume  0.71490E+01 ppm1     4.443  ppm2  3.061
ASSI {17542}
((segid "PROT" and resid 66 and name HD1))
((segid "PROT" and resid 66 and name HB2))
 3.100  2.400  2.400 peak     17542  weight  0.10000E+01 volume  0.12368E+01 ppm1     3.103  ppm2  2.051
ASSI {17552}
((segid "PROT" and resid 66 and name HD2))
((segid "PROT" and resid 66 and name HB1))
 3.000  2.200  2.200 peak     17552  weight  0.10000E+01 volume  0.12950E+01 ppm1     3.068  ppm2  2.124
ASSI {17562}
((segid "PROT" and resid 66 and name HD1))
((segid "PROT" and resid 66 and name HB1))
 3.100  2.400  2.400 peak     17562  weight  0.10000E+01 volume  0.12382E+01 ppm1     3.103  ppm2  2.124
ASSI {17572}
((segid "PROT" and resid 66 and name HD1))
((segid "PROT" and resid 66 and name HG2))
 2.500  1.600  1.600 peak     17572  weight  0.10000E+01 volume  0.38907E+01 ppm1     3.103  ppm2  1.564
ASSI {17582}
((segid "PROT" and resid 66 and name HD2))
((segid "PROT" and resid 66 and name HG1))
 2.500  1.600  1.600 peak     17582  weight  0.10000E+01 volume  0.40198E+01 ppm1     3.063  ppm2  1.614
ASSI {17592}
((segid "PROT" and resid 66 and name HD2))
((segid "PROT" and resid 66 and name HG2))
 2.600  1.700  1.700 peak     17592  weight  0.10000E+01 volume  0.35354E+01 ppm1     3.065  ppm2  1.564
ASSI {17612}
((segid "PROT" and resid 80 and name HD2))
((segid "PROT" and resid 80 and name HB2))
 3.000  2.200  2.200 peak     17612  weight  0.10000E+01 volume  0.14931E+01 ppm1     3.325  ppm2  1.958
ASSI {17632}
((segid "PROT" and resid 80 and name HB2))
((segid "PROT" and resid 80 and name HA))
 2.400  1.400  1.400 peak     17632  weight  0.10000E+01 volume  0.57680E+01 ppm1     1.956  ppm2  4.098
ASSI {17652}
((segid "PROT" and resid 80 and name HG1))
((segid "PROT" and resid 80 and name HA))
 2.300  1.300  1.300 peak     17652  weight  0.10000E+01 volume  0.72244E+01 ppm1     1.783  ppm2  4.098
ASSI {17672}
((segid "PROT" and resid 19 and name HB2))
((segid "PROT" and resid 19 and name HA))
 2.500  1.600  1.600 peak     17672  weight  0.10000E+01 volume  0.39072E+01 ppm1     1.408  ppm2  3.718
ASSI {17692}
((segid "PROT" and resid 19 and name HA))
((segid "PROT" and resid 19 and name HD1))
 2.900  2.100  2.100 peak     17692  weight  0.10000E+01 volume  0.16489E+01 ppm1     3.722  ppm2  1.622
ASSI {17712}
((segid "PROT" and resid 22 and name HB1))
((segid "PROT" and resid 19 and name HA))
 2.900  2.100  2.100 peak     17712  weight  0.10000E+01 volume  0.18959E+01 ppm1     2.124  ppm2  3.718
ASSI {17752}
((segid "PROT" and resid 109 and name HE1))
((segid "PROT" and resid 109 and name HA))
 3.300  2.700  2.200 peak     17752  weight  0.10000E+01 volume  0.80270E+00 ppm1     2.619  ppm2  4.069
ASSI {17772}
((segid "PROT" and resid 109 and name HA))
((segid "PROT" and resid 109 and name HB1))
 2.400  1.400  1.400 peak     17772  weight  0.10000E+01 volume  0.47284E+01 ppm1     4.070  ppm2  1.762
ASSI {17802}
((segid "PROT" and resid 109 and name HD1))
((segid "PROT" and resid 109 and name HB1))
 2.400  1.400  1.400 peak     17802  weight  0.10000E+01 volume  0.55212E+01 ppm1     1.415  ppm2  1.770
ASSI {17812}
((segid "PROT" and resid 109 and name HD1))
((segid "PROT" and resid 109 and name HB2))
 2.700  1.800  1.800 peak     17812  weight  0.10000E+01 volume  0.25524E+01 ppm1     1.415  ppm2  1.587
ASSI {17822}
(segid "PROT" and resid 21 and name HD1%)
((segid "PROT" and resid 109 and name HB1))
 3.300  2.700  2.200 peak     17822  weight  0.10000E+01 volume  0.75320E+00 ppm1     0.658  ppm2  1.765
ASSI {17842}
(segid "PROT" and resid 21 and name HG2%)
((segid "PROT" and resid 109 and name HB1))
 3.200  2.600  2.300 peak     17842  weight  0.10000E+01 volume  0.10322E+01 ppm1     1.023  ppm2  1.765

TABLE 13-continued

| Unambiguous NOE Distance Restraints |
|---|

ASSI {17862}
((segid "PROT" and resid 109 and name HB1))
((segid "PROT" and resid 109 and name HB2))
  2.200  1.200  1.200 peak     17862 weight  0.10000E+01 volume  0.97810E+01 ppm1    1.762 ppm2  1.587
ASSI {17872}
((segid "PROT" and resid 111 and name HA))
((segid "PROT" and resid 111 and name HE1))
  2.600  1.700  1.700 peak     17872 weight  0.10000E+01 volume  0.29552E+01 ppm1    4.081 ppm2  2.942
ASSI {17882}
((segid "PROT" and resid 111 and name HG2))
((segid "PROT" and resid 111 and name HA))
  2.600  1.700  1.700 peak     17882 weight  0.10000E+01 volume  0.34200E+01 ppm1    1.348 ppm2  4.085
ASSI {17892}
((segid "PROT" and resid 111 and name HG1))
((segid "PROT" and resid 111 and name HA))
  2.500  1.600  1.600 peak     17892 weight  0.10000E+01 volume  0.42726E+01 ppm1    1.450 ppm2  4.085
ASSI {17902}
((segid "PROT" and resid 111 and name HB2))
((segid "PROT" and resid 111 and name HA))
  2.100  1.100  1.100 peak     17902 weight  0.10000E+01 volume  0.12554E+02 ppm1    1.791 ppm2  4.077
ASSI {17912}
((segid "PROT" and resid 111 and name HE1))
((segid "PROT" and resid 111 and name HB2))
  3.300  2.700  2.200 peak     17912 weight  0.10000E+01 volume  0.85920E+00 ppm1    2.954 ppm2  1.785
ASSI {17922}
((segid "PROT" and resid 111 and name HG2))
((segid "PROT" and resid 111 and name HB2))
  2.300  1.300  1.300 peak     17922 weight  0.10000E+01 volume  0.63823E+01 ppm1    1.349 ppm2  1.793
ASSI {17932}
((segid "PROT" and resid 111 and name HG1))
((segid "PROT" and resid 111 and name HB1))
  2.200  1.200  1.200 peak     17932 weight  0.10000E+01 volume  0.87727E+01 ppm1    1.451 ppm2  1.913
ASSI {17962}
((segid "PROT" and resid 111 and name HD1))
((segid "PROT" and resid 111 and name HG1))
  1.700  0.700  0.700 peak     17962 weight  0.10000E+01 volume  0.37190E+02 ppm1    1.643 ppm2  1.450
ASSI {17972}
((segid "PROT" and resid 8 and name HA))
((segid "PROT" and resid 8 and name HB2))
  2.500  1.600  1.600 peak     17972 weight  0.10000E+01 volume  0.37603E+01 ppm1    4.463 ppm2  1.917
ASSI {17992}
((segid "PROT" and resid 8 and name HA))
((segid "PROT" and resid 8 and name HD2))
  3.300  2.700  2.200 peak     17992 weight  0.10000E+01 volume  0.82050E+00 ppm1    4.463 ppm2  3.708
ASSI {18002}
((segid "PROT" and resid 8 and name HD1))
((segid "PROT" and resid 8 and name HA))
  3.000  2.200  2.200 peak     18002 weight  0.10000E+01 volume  0.14398E+01 ppm1    3.873 ppm2  4.445
ASSI {18102}
((segid "PROT" and resid 37 and name HA))
((segid "PROT" and resid 37 and name HG2))
  2.700  1.800  1.800 peak     18102 weight  0.10000E+01 volume  0.24227E+01 ppm1    4.277 ppm2  2.039
ASSI {18112}
((segid "PROT" and resid 37 and name HA))
((segid "PROT" and resid 37 and name HD1))
  3.000  2.200  2.200 peak     18112 weight  0.10000E+01 volume  0.13649E+01 ppm1    4.276 ppm2  3.706
ASSI {18122}
((segid "PROT" and resid 37 and name HG2))
((segid "PROT" and resid 37 and name HB1))
  1.900  0.900  0.900 peak     18122 weight  0.10000E+01 volume  0.24810E+02 ppm1    2.042 ppm2  2.389
ASSI {18142}
((segid "PROT" and resid 37 and name HD1))
((segid "PROT" and resid 37 and name HG2))
  2.200  1.200  1.200 peak     18142 weight  0.10000E+01 volume  0.94260E+01 ppm1    3.715 ppm2  2.040
ASSI {18192}
((segid "PROT" and resid 44 and name HB1))
((segid "PROT" and resid 44 and name HD2))
  3.000  2.200  2.200 peak     18192 weight  0.10000E+01 volume  0.14606E+01 ppm1    2.413 ppm2  3.573
ASSI {18202}
((segid "PROT" and resid 44 and name HB1))
((segid "PROT" and resid 44 and name HD1))
  3.000  2.200  2.200 peak     18202 weight  0.10000E+01 volume  0.14741E+01 ppm1    2.413 ppm2  3.838
ASSI {18222}
((segid "PROT" and resid 44 and name HB2))
((segid "PROT" and resid 44 and name HB1))
  1.900  0.900  0.900 peak     18222 weight  0.10000E+01 volume  0.21799E+02 ppm1    2.062 ppm2  2.415

TABLE 13-continued

Unambiguous NOE Distance Restraints

ASSI {18262}
((segid "PROT" and resid 44 and name HA))
((segid "PROT" and resid 44 and name HD2))
 3.200  2.600  2.300 peak    18262 weight  0.10000E+01 volume  0.98750E+00 ppm1   4.553 ppm2  3.564
ASSI {18272}
((segid "PROT" and resid 44 and name HG1))
((segid "PROT" and resid 44 and name HB2))
 2.100  1.100  1.100 peak    18272 weight  0.10000E+01 volume  0.11240E+02 ppm1   2.207 ppm2  2.053
ASSI {18312}
(segid "PROT" and resid 49 and name HG1%)
((segid "PROT" and resid 49 and name HA))
 2.300  1.300  1.300 peak    18312 weight  0.10000E+01 volume  0.68598E+01 ppm1   0.962 ppm2  4.110
ASSI {18332}
((segid "PROT" and resid 54 and name HB2))
((segid "PROT" and resid 54 and name HA))
 3.000  2.200  2.200 peak    18332 weight  0.10000E+01 volume  0.14619E+01 ppm1   1.394 ppm2  4.986
ASSI {18352}
((segid "PROT" and resid 54 and name HG1))
((segid "PROT" and resid 54 and name HA))
 3.200  2.600  2.300 peak    18352 weight  0.10000E+01 volume  0.89060E+00 ppm1   2.737 ppm2  4.985
ASSI {18362}
((segid "PROT" and resid 53 and name HA))
((segid "PROT" and resid 54 and name HA))
 3.300  2.700  2.200 peak    18362 weight  0.10000E+01 volume  0.74720E+00 ppm1   4.121 ppm2  4.989
ASSI {18372}
((segid "PROT" and resid 28 and name HD2))
((segid "PROT" and resid 28 and name HB1))
 3.400  2.900  2.100 peak    18372 weight  0.10000E+01 volume  0.70920E+00 ppm1   5.011 ppm2  3.024
ASSI {18382}
((segid "PROT" and resid 28 and name HD2))
((segid "PROT" and resid 28 and name HB2))
 3.200  2.600  2.300 peak    18382 weight  0.10000E+01 volume  0.10243E+01 ppm1   5.011 ppm2  2.811
ASSI {18422}
((segid "PROT" and resid 58 and name HB))
(segid "PROT" and resid 54 and name HE%)
 3.000  2.200  2.200 peak    18422 weight  0.10000E+01 volume  0.14720E+01 ppm1   4.119 ppm2  2.005
ASSI {18452}
((segid "PROT" and resid 54 and name HB1))
((segid "PROT" and resid 54 and name HA))
 2.600  1.700  1.700 peak    18452 weight  0.10000E+01 volume  0.32741E+01 ppm1   2.049 ppm2  4.986
ASSI {18502}
((segid "PROT" and resid 59 and name HB1))
((segid "PROT" and resid 59 and name HA))
 2.700  1.800  1.800 peak    18502 weight  0.10000E+01 volume  0.24749E+01 ppm1   2.151 ppm2  4.333
ASSI {18522}
((segid "PROT" and resid 59 and name HG2))
((segid "PROT" and resid 59 and name HA))
 2.900  2.100  2.100 peak    18522 weight  0.10000E+01 volume  0.17299E+01 ppm1   2.558 ppm2  4.341
ASSI {18552}
((segid "PROT" and resid 59 and name HG1))
(segid "PROT" and resid 59 and name HE%)
 2.500  1.600  1.600 peak    18552 weight  0.10000E+01 volume  0.43371E+01 ppm1   2.651 ppm2  1.309
ASSI {18562}
(segid "PROT" and resid 25 and name HG2%)
(segid "PROT" and resid 59 and name HE%)
 2.600  1.700  1.700 peak    18562 weight  0.10000E+01 volume  0.30262E+01 ppm1   1.109 ppm2  1.316
ASSI {18572}
((segid "PROT" and resid 72 and name HA))
((segid "PROT" and resid 75 and name HB1))
 3.100  2.400  2.400 peak    18572 weight  0.10000E+01 volume  0.11453E+01 ppm1   4.083 ppm2  2.967
ASSI {18582}
((segid "PROT" and resid 72 and name HA))
((segid "PROT" and resid 75 and name HB2))
 3.000  2.200  2.200 peak    18582 weight  0.10000E+01 volume  0.15018E+01 ppm1   4.085 ppm2  2.640
ASSI {18592}
((segid "PROT" and resid 75 and name HA))
((segid "PROT" and resid 75 and name HG1))
 2.600  1.700  1.700 peak    18592 weight  0.10000E+01 volume  0.33006E+01 ppm1   4.096 ppm2  2.362
ASSI {18602}
((segid "PROT" and resid 75 and name HA))
((segid "PROT" and resid 75 and name HG2))
 2.300  1.300  1.300 peak    18602 weight  0.10000E+01 volume  0.65760E+01 ppm1   4.096 ppm2  2.244
ASSI {18612}
(segid "PROT" and resid 75 and name HE%)
((segid "PROT" and resid 75 and name HA))
 2.000  1.000  1.000 peak    18612 weight  0.10000E+01 volume  0.14267E+02 ppm1   2.099 ppm2  4.091

TABLE 13-continued

Unambiguous NOE Distance Restraints

ASSI {18622}
((segid "PROT" and resid 116 and name HA))
(segid "PROT" and resid 75 and name HE%)
  3.200  2.600  2.300 peak    18622  weight  0.10000E+01 volume  0.10323E+01 ppm1    4.275  ppm2  2.094
ASSI {18642}
((segid "PROT" and resid 75 and name HG2))
((segid "PROT" and resid 75 and name HB1))
  2.400  1.400  1.400 peak    18642  weight  0.10000E+01 volume  0.55414E+01 ppm1    2.240  ppm2  2.959
ASSI {18652}
((segid "PROT" and resid 75 and name HG2))
((segid "PROT" and resid 75 and name HB2))
  2.600  1.700  1.700 peak    18652  weight  0.10000E+01 volume  0.34575E+01 ppm1    2.240  ppm2  2.640
ASSI {18662}
((segid "PROT" and resid 75 and name HG1))
((segid "PROT" and resid 75 and name HB2))
  2.600  1.700  1.700 peak    18662  weight  0.10000E+01 volume  0.33311E+01 ppm1    2.358  ppm2  2.640
ASSI {18672}
((segid "PROT" and resid 75 and name HG1))
((segid "PROT" and resid 75 and name HB1))
  2.600  1.700  1.700 peak    18672  weight  0.10000E+01 volume  0.33310E+01 ppm1    2.358  ppm2  2.959
ASSI {18692}
((segid "PROT" and resid 53 and name HD2))
((segid "PROT" and resid 53 and name HB1))
  3.000  2.200  2.200 peak    18692  weight  0.10000E+01 volume  0.14740E+01 ppm1    3.443  ppm2  2.248
ASSI {18722}
((segid "PROT" and resid 35 and name HB1))
((segid "PROT" and resid 35 and name HG1))
  2.400  1.400  1.400 peak    18722  weight  0.10000E+01 volume  0.47598E+01 ppm1    2.316  ppm2  2.903
ASSI {18732}
((segid "PROT" and resid 35 and name HB2))
((segid "PROT" and resid 35 and name HG1))
  2.200  1.200  1.200 peak    18732  weight  0.10000E+01 volume  0.97482E+01 ppm1    2.223  ppm2  2.902
ASSI {18742}
((segid "PROT" and resid 35 and name HG1))
((segid "PROT" and resid 35 and name HA))
  2.700  1.800  1.800 peak    18742  weight  0.10000E+01 volume  0.25097E+01 ppm1    2.900  ppm2  4.342
ASSI {18752}
((segid "PROT" and resid 35 and name HB1))
((segid "PROT" and resid 35 and name HA))
  2.800  2.000  2.000 peak    18752  weight  0.10000E+01 volume  0.23049E+01 ppm1    2.320  ppm2  4.342
ASSI {18762}
((segid "PROT" and resid 35 and name HB2))
((segid "PROT" and resid 35 and name HA))
  2.400  1.400  1.400 peak    18762  weight  0.10000E+01 volume  0.56264E+01 ppm1    2.228  ppm2  4.342
ASSI {18792}
((segid "PROT" and resid 111 and name HD1))
((segid "PROT" and resid 108 and name HA))
  3.200  2.600  2.300 peak    18792  weight  0.10000E+01 volume  0.87530E+00 ppm1    1.657  ppm2  4.236
ASSI {18802}
((segid "PROT" and resid 95 and name HB2))
((segid "PROT" and resid 95 and name HA))
  3.000  2.200  2.200 peak    18802  weight  0.10000E+01 volume  0.14977E+01 ppm1    2.643  ppm2  3.648
ASSI {18812}
((segid "PROT" and resid 33 and name HG1))
((segid "PROT" and resid 95 and name HA))
  3.300  2.700  2.200 peak    18812  weight  0.10000E+01 volume  0.73410E+00 ppm1    0.269  ppm2  3.651
ASSI {18822}
((segid "PROT" and resid 33 and name HG2))
((segid "PROT" and resid 95 and name HA))
  3.400  2.900  2.100 peak    18822  weight  0.10000E+01 volume  0.67160E+00 ppm1   −0.875  ppm2  3.643
ASSI {18832}
((segid "PROT" and resid 57 and name HD1))
((segid "PROT" and resid 57 and name HA))
  2.600  1.700  1.700 peak    18832  weight  0.10000E+01 volume  0.37031E+01 ppm1    1.759  ppm2  3.910
ASSI {18842}
((segid "PROT" and resid 106 and name HB1))
((segid "PROT" and resid 103 and name HA))
  2.600  1.700  1.700 peak    18842  weight  0.10000E+01 volume  0.29665E+01 ppm1    3.358  ppm2  3.217
ASSI {18912}
((segid "PROT" and resid 79 and name HB1))
((segid "PROT" and resid 76 and name HA))
  2.700  1.800  1.800 peak    18912  weight  0.10000E+01 volume  0.26684E+01 ppm1    2.212  ppm2  4.115
ASSI {18932}
((segid "PROT" and resid 10 and name HB1))
((segid "PROT" and resid 11 and name HD1))
  2.800  2.000  2.000 peak    18932  weight  0.10000E+01 volume  0.20083E+01 ppm1    2.788  ppm2  3.901

TABLE 13-continued

| Unambiguous NOE Distance Restraints |
|---|

ASSI {18942}
((segid "PROT" and resid 89 and name HB1))
((segid "PROT" and resid 90 and name HD2))
  3.100  2.400  2.400 peak    18942  weight  0.10000E+01 volume  0.12160E+01 ppm1    3.110  ppm2    3.947
ASSI {18952}
((segid "PROT" and resid 89 and name HB1))
((segid "PROT" and resid 90 and name HD1))
  3.300  2.700  2.200 peak    18952  weight  0.10000E+01 volume  0.77340E+00 ppm1    3.120  ppm2    4.108
ASSI {18962}
((segid "PROT" and resid 89 and name HB2))
((segid "PROT" and resid 90 and name HD2))
  3.200  2.600  2.300 peak    18962  weight  0.10000E+01 volume  0.10193E+01 ppm1    2.915  ppm2    3.947
ASSI {19002}
((segid "PROT" and resid 33 and name HB2))
((segid "PROT" and resid 33 and name HD2))
  3.400  2.900  2.100 peak    19002  weight  0.10000E+01 volume  0.69650E+00 ppm1    −0.441  ppm2    1.567
ASSI {19022}
((segid "PROT" and resid 33 and name HG1))
((segid "PROT" and resid 33 and name HD1))
  3.000  2.200  2.200 peak    19022  weight  0.10000E+01 volume  0.13980E+01 ppm1    0.280  ppm2    2.263
ASSI {19032}
((segid "PROT" and resid 33 and name HB2))
((segid "PROT" and resid 33 and name HD1))
  3.400  2.900  2.100 peak    19032  weight  0.10000E+01 volume  0.62420E+00 ppm1    −0.431  ppm2    2.263
ASSI {19152}
((segid "PROT" and resid 37 and name HD1))
((segid "PROT" and resid 36 and name HB2))
  2.600  1.700  1.700 peak    19152  weight  0.10000E+01 volume  0.34164E+01 ppm1    3.706  ppm2    1.800
ASSI {19202}
((segid "PROT" and resid 33 and name HG2))
((segid "PROT" and resid 33 and name HB2))
  3.300  2.700  2.200 peak    19202  weight  0.10000E+01 volume  0.79620E+00 ppm1    −0.870  ppm2    −0.431
ASSI {19222}
((segid "PROT" and resid 33 and name HG1))
((segid "PROT" and resid 33 and name HB2))
  3.300  2.700  2.200 peak    19222  weight  0.10000E+01 volume  0.76140E+00 ppm1    0.272  ppm2    −0.431
ASSI {19252}
((segid "PROT" and resid 57 and name HB2))
((segid "PROT" and resid 57 and name HD2))
  2.900  2.100  2.100 peak    19252  weight  0.10000E+01 volume  0.18111E+01 ppm1    1.108  ppm2    0.913
ASSI {19322}
((segid "PROT" and resid 15 and name HA))
(segid "PROT" and resid 63 and name HD2%)
  2.600  1.700  1.700 peak    19322  weight  0.10000E+01 volume  0.33620E+01 ppm1    4.057  ppm2    1.079
ASSI {19332}
((segid "PROT" and resid 68 and name HB1))
(segid "PROT" and resid 63 and name HD2%)
  2.800  2.000  2.000 peak    19332  weight  0.10000E+01 volume  0.20548E+01 ppm1    3.103  ppm2    1.080
ASSI {19342}
((segid "PROT" and resid 33 and name HD1))
((segid "PROT" and resid 33 and name HG2))
  3.000  2.200  2.200 peak    19342  weight  0.10000E+01 volume  0.12899E+01 ppm1    2.273  ppm2    −0.868
ASSI {19372}
((segid "PROT" and resid 34 and name HA))
(segid "PROT" and resid 81 and name HG2%)
  2.800  2.000  2.000 peak    19372  weight  0.10000E+01 volume  0.22956E+01 ppm1    5.007  ppm2    0.153
ASSI {19382}
((segid "PROT" and resid 46 and name HA))
(segid "PROT" and resid 49 and name HG1%)
  2.500  1.600  1.600 peak    19382  weight  0.10000E+01 volume  0.38294E+01 ppm1    3.506  ppm2    0.971
ASSI {19412}
((segid "PROT" and resid 42 and name HB2))
(segid "PROT" and resid 43 and name HB%)
  3.000  2.200  2.200 peak    19412  weight  0.10000E+01 volume  0.14358E+01 ppm1    2.081  ppm2    0.973
ASSI {19422}
((segid "PROT" and resid 82 and name HB1))
(segid "PROT" and resid 99 and name HB%)
  2.400  1.400  1.400 peak    19422  weight  0.10000E+01 volume  0.49197E+01 ppm1    3.136  ppm2    1.659
ASSI {19442}
((segid "PROT" and resid 109 and name HB2))
(segid "PROT" and resid 21 and name HG2%)
  2.800  2.000  2.000 peak    19442  weight  0.10000E+01 volume  0.19394E+01 ppm1    1.585  ppm2    1.016
ASSI {19452}
(segid "PROT" and resid 102 and name HD2%)
(segid "PROT" and resid 21 and name HG2%)
  2.500  2.500  2.000 peak    19452  weight  0.10000E+01 volume  0.38076E+01 ppm1    0.762  ppm2    1.024

TABLE 13-continued

Unambiguous NOE Distance Restraints

ASSI {19492}
((segid "PROT" and resid 33 and name HA))
((segid "PROT" and resid 33 and name HG1))
  3.400  2.900  2.100 peak     19492 weight  0.10000E+01 volume  0.66660E+00 ppm1    3.992 ppm2  0.280
ASSI {19532}
((segid "PROT" and resid 33 and name HB1))
((segid "PROT" and resid 33 and name HG1))
  3.300  2.700  2.200 peak     19532 weight  0.10000E+01 volume  0.76740E+00 ppm1    1.075 ppm2  0.269
ASSI {19552}
((segid "PROT" and resid 53 and name HG2))
((segid "PROT" and resid 53 and name HD1))
  2.500  1.600  1.600 peak     19552 weight  0.10000E+01 volume  0.38667E+01 ppm1    1.948 ppm2  3.649
ASSI {19582}
(segid "PROT" and resid 50 and name HG2%)
((segid "PROT" and resid 53 and name HG1))
  3.200  2.600  2.300 peak     19582 weight  0.10000E+01 volume  0.89220E+00 ppm1    0.421 ppm2  2.280
ASSI {19602}
((segid "PROT" and resid 53 and name HA))
((segid "PROT" and resid 53 and name HG1))
  2.500  1.600  1.600 peak     19602 weight  0.10000E+01 volume  0.43485E+01 ppm1    4.119 ppm2  2.264
ASSI {19612}
((segid "PROT" and resid 53 and name HA))
((segid "PROT" and resid 53 and name HD1))
  3.200  2.600  2.300 peak     19612 weight  0.10000E+01 volume  0.92980E+00 ppm1    4.123 ppm2  3.649
ASSI {19622}
((segid "PROT" and resid 53 and name HA))
((segid "PROT" and resid 53 and name HD2))
  3.200  2.600  2.300 peak     19622 weight  0.10000E+01 volume  0.91130E+00 ppm1    4.123 ppm2  3.446
ASSI {19652}
((segid "PROT" and resid 53 and name HG2))
((segid "PROT" and resid 53 and name HB1))
  2.000  1.000  1.000 peak     19652 weight  0.10000E+01 volume  0.15739E+02 ppm1    1.936 ppm2  2.247
ASSI {19662}
((segid "PROT" and resid 53 and name HD1))
((segid "PROT" and resid 53 and name HB1))
  2.900  2.100  2.100 peak     19662 weight  0.10000E+01 volume  0.16703E+01 ppm1    3.652 ppm2  2.249
ASSI {19692}
((segid "PROT" and resid 57 and name HE2))
((segid "PROT" and resid 57 and name HD1))
  2.100  1.100  1.100 peak     19692 weight  0.10000E+01 volume  0.11051E+02 ppm1    2.082 ppm2  1.752
ASSI {19732}
((segid "PROT" and resid 21 and name HG11))
(segid "PROT" and resid 17 and name HG2%)
  2.700  1.800  1.800 peak     19732 weight  0.10000E+01 volume  0.24805E+01 ppm1    1.783 ppm2  1.175
ASSI {19762}
((segid "PROT" and resid 17 and name HB))
(segid "PROT" and resid 17 and name HG2%)
  2.000  1.000  1.000 peak     19762 weight  0.10000E+01 volume  0.16615E+02 ppm1    4.290 ppm2  1.178
ASSI {19772}
(segid "PROT" and resid 102 and name HD2%)
(segid "PROT" and resid 25 and name HG2%)
  2.000  1.000  1.000 peak     19772 weight  0.10000E+01 volume  0.16186E+02 ppm1    0.763 ppm2  1.073
ASSI {19812}
(segid "PROT" and resid 31 and name HB%)
(segid "PROT" and resid 25 and name HG2%)
  2.400  1.400  1.400 peak     19812 weight  0.10000E+01 volume  0.53511E+01 ppm1    1.761 ppm2  1.082
ASSI {19852}
((segid "PROT" and resid 57 and name HE2))
(segid "PROT" and resid 58 and name HG2%)
  2.600  1.700  1.700 peak     19852 weight  0.10000E+01 volume  0.33672E+01 ppm1    2.081 ppm2  1.095
ASSI {19862}
(segid "PROT" and resid 54 and name HE%)
(segid "PROT" and resid 58 and name HG2%)
  2.100  1.100  1.100 peak     19862 weight  0.10000E+01 volume  0.11606E+02 ppm1    2.004 ppm2  1.097
ASSI {19912}
((segid "PROT" and resid 57 and name HE1))
((segid "PROT" and resid 57 and name HB2))
  3.400  2.900  2.100 peak     19912 weight  0.10000E+01 volume  0.69760E+00 ppm1    2.617 ppm2  1.141
ASSI {19922}
((segid "PROT" and resid 57 and name HD1))
((segid "PROT" and resid 57 and name HB2))
  3.200  2.600  2.300 peak     19922 weight  0.10000E+01 volume  0.95330E+00 ppm1    1.757 ppm2  1.144
ASSI {19952}
((segid "PROT" and resid 96 and name HB1))
((segid "PROT" and resid 91 and name HA))
  3.100  2.400  2.400 peak     19952 weight  0.10000E+01 volume  0.10916E+01 ppm1    3.416 ppm2  2.586

TABLE 13-continued

| Unambiguous NOE Distance Restraints |
| --- |

ASSI {19982}
((segid "PROT" and resid 91 and name HA))
((segid "PROT" and resid 91 and name HB1))
 2.300  1.300   1.300 peak    19982 weight  0.10000E+01 volume  0.66821E+01 ppm1    2.590  ppm2  1.625
ASSI {19992}
((segid "PROT" and resid 91 and name HA))
((segid "PROT" and resid 91 and name HG1))
 3.100  2.400   2.400 peak    19992 weight  0.10000E+01 volume  0.12229E+01 ppm1    2.589  ppm2  1.994
ASSI {20022}
((segid "PROT" and resid 8 and name HB2))
((segid "PROT" and resid 8 and name HD1))
 3.000  2.200   2.200 peak    20022 weight  0.10000E+01 volume  0.14969E+01 ppm1    1.927  ppm2  3.869
ASSI {20052}
((segid "PROT" and resid 90 and name HA))
((segid "PROT" and resid 90 and name HB2))
 3.100  2.400   2.400 peak    20052 weight  0.10000E+01 volume  0.11109E+01 ppm1    4.645  ppm2  2.168
ASSI {20062}
((segid "PROT" and resid 90 and name HA))
((segid "PROT" and resid 90 and name HB1))
 3.000  2.200   2.200 peak    20062 weight  0.10000E+01 volume  0.14418E+01 ppm1    4.643  ppm2  2.353
ASSI {20082}
((segid "PROT" and resid 90 and name HD2))
((segid "PROT" and resid 90 and name HB1))
 3.200  2.600   2.300 peak    20082 weight  0.10000E+01 volume  0.91280E+00 ppm1    3.930  ppm2  2.351
ASSI {20182}
((segid "PROT" and resid 30 and name HB2))
(segid "PROT" and resid 102 and name HD1%)
 2.800  2.000   2.000 peak    20182 weight  0.10000E+01 volume  0.21637E+01 ppm1    3.970  ppm2  0.761
ASSI {20252}
((segid "PROT" and resid 28 and name HD2))
((segid "PROT" and resid 28 and name HA))
 3.100  2.400   2.400 peak    20252 weight  0.10000E+01 volume  0.11231E+01 ppm1    5.008  ppm2  4.019
ASSI {20282}
((segid "PROT" and resid 32 and name HE3))
((segid "PROT" and resid 32 and name HB2))
 3.000  2.200   2.200 peak    20282 weight  0.10000E+01 volume  0.13378E+01 ppm1    7.355  ppm2  3.414
ASSI {20292}
((segid "PROT" and resid 32 and name HE3))
((segid "PROT" and resid 32 and name HB1))
 3.000  2.200   2.200 peak    20292 weight  0.10000E+01 volume  0.13945E+01 ppm1    7.357  ppm2  3.634
ASSI {20302}
((segid "PROT" and resid 32 and name HD1))
((segid "PROT" and resid 32 and name HB1))
 3.300  2.700   2.200 peak    20302 weight  0.10000E+01 volume  0.86510E+00 ppm1    7.888  ppm2  3.645
ASSI {20312}
((segid "PROT" and resid 32 and name HD1))
((segid "PROT" and resid 32 and name HB2))
 3.000  2.200   2.200 peak    20312 weight  0.10000E+01 volume  0.13496E+01 ppm1    7.887  ppm2  3.406
ASSI {20322}
((segid "PROT" and resid 32 and name HD1))
((segid "PROT" and resid 30 and name HA))
 3.300  2.700   2.200 peak    20322 weight  0.10000E+01 volume  0.84000E+00 ppm1    7.887  ppm2  4.846
ASSI {20332}
((segid "PROT" and resid 75 and name HA))
((segid "PROT" and resid 74 and name HB1))
 2.800  2.000   2.000 peak    20332 weight  0.10000E+01 volume  0.19988E+01 ppm1    4.058  ppm2  3.004
ASSI {20342}
(segid "PROT" and resid 82 and name HE%)
((segid "PROT" and resid 82 and name HB1))
 3.500  3.100   2.000 peak    20342 weight  0.10000E+01 volume  0.58330E+00 ppm1    6.488  ppm2  3.143
ASSI {20382}
(segid "PROT" and resid 105 and name HD%)
((segid "PROT" and resid 105 and name HB1))
 2.600  1.700   1.700 peak    20382 weight  0.10000E+01 volume  0.35159E+01 ppm1    7.235  ppm2  3.138
ASSI {20412}
(segid "PROT" and resid 107 and name HD%)
((segid "PROT" and resid 107 and name HB1))
 2.500  1.600   1.600 peak    20412 weight  0.10000E+01 volume  0.39879E+01 ppm1    7.241  ppm2  3.090
ASSI {20432}
(segid "PROT" and resid 96 and name HD%)
((segid "PROT" and resid 96 and name HA))
 3.200  2.600   2.300 peak    20432 weight  0.10000E+01 volume  0.10372E+01 ppm1    7.151  ppm2  3.826
ASSI {20462}
(segid "PROT" and resid 47 and name HD%)
((segid "PROT" and resid 47 and name HB1))
 2.900  2.100   2.100 peak    20462 weight  0.10000E+01 volume  0.18851E+01 ppm1    7.401  ppm2  3.245

TABLE 13-continued

| Unambiguous NOE Distance Restraints |
| --- |

ASSI {20472}
(segid "PROT" and resid 47 and name HD%)
((segid "PROT" and resid 47 and name HB2))
  3.000  2.200  2.200 peak    20472 weight  0.10000E+01 volume  0.13814E+01 ppm1    7.409  ppm2  2.843
ASSI {20482}
(segid "PROT" and resid 47 and name HE%)
((segid "PROT" and resid 47 and name HB1))
  3.400  2.900  2.100 peak    20482 weight  0.10000E+01 volume  0.68190E+00 ppm1    6.688  ppm2  3.236
ASSI {20492}
(segid "PROT" and resid 47 and name HE%)
((segid "PROT" and resid 47 and name HB2))
  3.500  3.100  2.000 peak    20492 weight  0.10000E+01 volume  0.54300E+00 ppm1    6.675  ppm2  2.861
ASSI {20502}
(segid "PROT" and resid 47 and name HE%)
((segid "PROT" and resid 47 and name HA))
  3.300  2.700  2.200 peak    20502 weight  0.10000E+01 volume  0.81170E+00 ppm1    6.675  ppm2  4.131
ASSI {20512}
(segid "PROT" and resid 15 and name HE%)
((segid "PROT" and resid 15 and name HA))
  3.400  2.900  2.100 peak    20512 weight  0.10000E+01 volume  0.67340E+00 ppm1    6.926  ppm2  4.050
ASSI {20522}
(segid "PROT" and resid 67 and name HE%)
((segid "PROT" and resid 67 and name HA))
  3.300  2.700  2.200 peak    20522 weight  0.10000E+01 volume  0.82160E+00 ppm1    6.735  ppm2  4.108
ASSI {20532}
(segid "PROT" and resid 67 and name HE%)
((segid "PROT" and resid 67 and name HB2))
  3.700  3.400  1.800 peak    20532 weight  0.10000E+01 volume  0.39270E+00 ppm1    6.737  ppm2  2.093
ASSI {20542}
(segid "PROT" and resid 67 and name HE%)
((segid "PROT" and resid 67 and name HB1))
  3.400  2.900  2.100 peak    20542 weight  0.10000E+01 volume  0.68200E+00 ppm1    6.737  ppm2  3.003
ASSI {20552}
(segid "PROT" and resid 68 and name HE%)
((segid "PROT" and resid 68 and name HA))
  3.200  2.600  2.300 peak    20552 weight  0.10000E+01 volume  0.96420E+00 ppm1    7.310  ppm2  4.583
ASSI {20582}
((segid "PROT" and resid 67 and name HA))
((segid "PROT" and resid 68 and name HA))
  3.000  2.200  2.200 peak    20582 weight  0.10000E+01 volume  0.13549E+01 ppm1    4.106  ppm2  4.583
ASSI {20602}
(segid "PROT" and resid 68 and name HD%)
((segid "PROT" and resid 68 and name HB2))
  3.000  2.200  2.200 peak    20602 weight  0.10000E+01 volume  0.14100E+01 ppm1    7.209  ppm2  2.960
ASSI {20612}
(segid "PROT" and resid 68 and name HD%)
((segid "PROT" and resid 68 and name HB1))
  2.900  2.100  2.100 peak    20612 weight  0.10000E+01 volume  0.15572E+01 ppm1    7.209  ppm2  3.104
ASSI {20622}
(segid "PROT" and resid 68 and name HE%)
((segid "PROT" and resid 68 and name HB2))
  3.200  2.600  2.300 peak    20622 weight  0.10000E+01 volume  0.95790E+00 ppm1    7.315  ppm2  2.958
ASSI {20632}
(segid "PROT" and resid 68 and name HE%)
((segid "PROT" and resid 68 and name HB1))
  3.300  2.700  2.200 peak    20632 weight  0.10000E+01 volume  0.77790E+00 ppm1    7.316  ppm2  3.095
ASSI {20642}
(segid "PROT" and resid 88 and name HE%)
((segid "PROT" and resid 88 and name HA))
  3.300  2.700  2.200 peak    20642 weight  0.10000E+01 volume  0.74810E+00 ppm1    6.652  ppm2  4.331
ASSI {20652}
(segid "PROT" and resid 50 and name HD1%)
((segid "PROT" and resid 88 and name HA))
  3.300  2.700  2.200 peak    20652 weight  0.10000E+01 volume  0.73730E+00 ppm1    0.582  ppm2  4.313
ASSI {20732}
(segid "PROT" and resid 96 and name HD%)
((segid "PROT" and resid 96 and name HB1))
  3.000  2.200  2.200 peak    20732 weight  0.10000E+01 volume  0.12722E+01 ppm1    7.122  ppm2  3.421
ASSI {20742}
(segid "PROT" and resid 96 and name HE%)
((segid "PROT" and resid 96 and name HB2))
  3.200  2.600  2.300 peak    20742 weight  0.10000E+01 volume  0.10176E+01 ppm1    7.054  ppm2  2.580
ASSI {20752}
(segid "PROT" and resid 96 and name HE%)
((segid "PROT" and resid 96 and name HB1))
  3.200  2.600  2.300 peak    20752 weight  0.10000E+01 volume  0.98070E+00 ppm1    7.054  ppm2  3.429

TABLE 13-continued

| Unambiguous NOE Distance Restraints |
|---|

ASSI {20762}
(segid "PROT" and resid 96 and name HE%)
((segid "PROT" and resid 96 and name HA))
  3.200  2.600  2.300 peak    20762 weight  0.10000E+01 volume  0.10206E+01 ppm1    7.054 ppm2  3.823
ASSI {20792}
(segid "PROT" and resid 99 and name HB%)
(segid "PROT" and resid 81 and name HG2%)
  3.100  2.400  2.400 peak    20792 weight  0.10000E+01 volume  0.12313E+01 ppm1    1.655 ppm2  0.157
ASSI {20812}
((segid "PROT" and resid 44 and name HG2))
((segid "PROT" and resid 43 and name HA))
  3.300  2.700  2.200 peak    20812 weight  0.10000E+01 volume  0.81200E+00 ppm1    2.075 ppm2  4.987
ASSI {20822}
(segid "PROT" and resid 46 and name HE%)
(segid "PROT" and resid 43 and name HB%)
  3.100  2.400  2.400 peak    20822 weight  0.10000E+01 volume  0.11247E+01 ppm1    5.998 ppm2  0.978
ASSI {20832}
((segid "PROT" and resid 39 and name HE2))
(segid "PROT" and resid 43 and name HB%)
  3.100  2.400  2.400 peak    20832 weight  0.10000E+01 volume  0.12227E+01 ppm1    2.950 ppm2  0.972
ASSI {20842}
((segid "PROT" and resid 61 and name HB2))
((segid "PROT" and resid 58 and name HA))
  3.100  2.400  2.400 peak    20842 weight  0.10000E+01 volume  0.12246E+01 ppm1    2.120 ppm2  3.883
ASSI {20862}
((segid "PROT" and resid 70 and name HB1))
(segid "PROT" and resid 69 and name HG2%)
  2.800  2.000  2.000 peak    20862 weight  0.10000E+01 volume  0.20271E+01 ppm1    4.227 ppm2  0.859
ASSI {20872}
((segid "PROT" and resid 110 and name HG12))
((segid "PROT" and resid 107 and name HA))
  2.600  1.700  1.700 peak    20872 weight  0.10000E+01 volume  0.36962E+01 ppm1    1.090 ppm2  3.857
ASSI {20992}
((segid "PROT" and resid 79 and name HB2))
(segid "PROT" and resid 83 and name HG2%)
  3.200  2.600  2.300 peak    20992 weight  0.10000E+01 volume  0.96340E+00 ppm1    2.102 ppm2  1.343
ASSI {21032}
((segid "PROT" and resid 68 and name HB2))
(segid "PROT" and resid 63 and name HD2%)
  3.100  2.400  2.400 peak    21032 weight  0.10000E+01 volume  0.12579E+01 ppm1    2.956 ppm2  1.082
ASSI {21062}
((segid "PROT" and resid 116 and name HA))
(segid "PROT" and resid 110 and name HD1%)
  3.300  2.700  2.200 peak    21062 weight  0.10000E+01 volume  0.75760E+00 ppm1    4.275 ppm2  0.571
ASSI {21102}
((segid "PROT" and resid 75 and name HG1))
(segid "PROT" and resid 116 and name HD1%)
  3.100  2.400  2.400 peak    21102 weight  0.10000E+01 volume  0.12677E+01 ppm1    2.317 ppm2  0.825
ASSI {21172}
((segid "PROT" and resid 97 and name HG2))
(segid "PROT" and resid 101 and name HD1%)
  3.100  2.400  2.400 peak    21172 weight  0.10000E+01 volume  0.11617E+01 ppm1    1.617 ppm2  0.997
ASSI {21222}
((segid "PROT" and resid 30 and name HB2))
(segid "PROT" and resid 101 and name HD1%)
  3.300  2.700  2.200 peak    21222 weight  0.10000E+01 volume  0.83430E+00 ppm1    3.976 ppm2  0.993
ASSI {21242}
((segid "PROT" and resid 59 and name HG1))
(segid "PROT" and resid 54 and name HE%)
  2.800  2.000  2.000 peak    21242 weight  0.10000E+01 volume  0.19137E+01 ppm1    2.624 ppm2  2.002
ASSI {21312}
((segid "PROT" and resid 56 and name HA))
(segid "PROT" and resid 59 and name HE%)
  3.300  2.700  2.200 peak    21312 weight  0.10000E+01 volume  0.81010E+00 ppm1    4.056 ppm2  1.308
ASSI {21382}
((segid "PROT" and resid 116 and name HG12))
(segid "PROT" and resid 75 and name HE%)
  3.600  3.200  1.900 peak    21382 weight  0.10000E+01 volume  0.47290E+00 ppm1    0.970 ppm2  2.096
ASSI {21432}
(segid "PROT" and resid 25 and name HG1%)
(segid "PROT" and resid 21 and name HG2%)
  2.100  1.100  1.100 peak    21432 weight  0.10000E+01 volume  0.11034E+02 ppm1    1.244 ppm2  1.023
ASSI {21442}
((segid "PROT" and resid 25 and name HB))
(segid "PROT" and resid 21 and name HG2%)
  3.200  2.600  2.300 peak    21442 weight  0.10000E+01 volume  0.97890E+00 ppm1    2.446 ppm2  1.018

TABLE 13-continued

| Unambiguous NOE Distance Restraints |
|---|

ASSI {21512}
((segid "PROT" and resid 116 and name HG12))
(segid "PROT" and resid 116 and name HG2%)
  2.300  1.300   1.300 peak    21512  weight  0.10000E+01 volume  0.68119E+01 ppm1   0.986 ppm2  0.854
ASSI {21552}
((segid "PROT" and resid 105 and name HB1))
(segid "PROT" and resid 101 and name HG2%)
  3.100  2.400   2.400 peak    21552  weight  0.10000E+01 volume  0.10529E+01 ppm1   3.188 ppm2  1.032
ASSI {21632}
(segid "PROT" and resid 73 and name HD2%)
(segid "PROT" and resid 76 and name HB%)
  2.700  1.800   1.800 peak    21632  weight  0.10000E+01 volume  0.27029E+01 ppm1   0.929 ppm2  1.533
ASSI {21662}
((segid "PROT" and resid 79 and name HB1))
(segid "PROT" and resid 76 and name HB%)
  3.100  2.400   2.400 peak    21662  weight  0.10000E+01 volume  0.11536E+01 ppm1   2.220 ppm2  1.530
ASSI {21672}
((segid "PROT" and resid 79 and name HB2))
(segid "PROT" and resid 76 and name HB%)
  3.300  2.700   2.200 peak    21672  weight  0.10000E+01 volume  0.84220E+00 ppm1   2.111 ppm2  1.529
ASSI {21682}
((segid "PROT" and resid 80 and name HB2))
(segid "PROT" and resid 76 and name HB%)
  3.100  2.400   2.400 peak    21682  weight  0.10000E+01 volume  0.12504E+01 ppm1   1.938 ppm2  1.531
ASSI {21692}
((segid "PROT" and resid 80 and name HB1))
(segid "PROT" and resid 76 and name HB%)
  3.100  2.400   2.400 peak    21692  weight  0.10000E+01 volume  0.10520E+01 ppm1   2.003 ppm2  1.531
ASSI {21732}
((segid "PROT" and resid 100 and name HA))
(segid "PROT" and resid 99 and name HB%)
  3.000  2.200   2.200 peak    21732  weight  0.10000E+01 volume  0.12872E+01 ppm1   4.363 ppm2  1.659
ASSI {21752}
(segid "PROT" and resid 82 and name HE%)
(segid "PROT" and resid 99 and name HB%)
  3.200  2.600   2.300 peak    21752  weight  0.10000E+01 volume  0.93520E+00 ppm1   6.489 ppm2  1.660
ASSI {21762}
(segid "PROT" and resid 34 and name HE%)
(segid "PROT" and resid 99 and name HB%)
  3.200  2.600   2.300 peak    21762  weight  0.10000E+01 volume  0.10406E+01 ppm1   7.173 ppm2  1.663
ASSI {21772}
(segid "PROT" and resid 68 and name HE%)
(segid "PROT" and resid 76 and name HB%)
  3.200  2.600   2.300 peak    21772  weight  0.10000E+01 volume  0.88080E+00 ppm1   7.319 ppm2  1.535
ASSI {21922}
((segid "PROT" and resid 14 and name HA))
(segid "PROT" and resid 113 and name HB%)
  3.200  2.600   2.300 peak    21922  weight  0.10000E+01 volume  0.10349E+01 ppm1   4.100 ppm2  1.406
ASSI {21952}
((segid "PROT" and resid 33 and name HG1))
(segid "PROT" and resid 31 and name HB%)
  3.500  3.100   2.000 peak    21952  weight  0.10000E+01 volume  0.53810E+00 ppm1   0.265 ppm2  1.760
ASSI {21962}
(segid "PROT" and resid 56 and name HD2%)
(segid "PROT" and resid 31 and name HB%)
  3.300  2.700   2.200 peak    21962  weight  0.10000E+01 volume  0.75920E+00 ppm1   0.678 ppm2  1.762
ASSI {21972}
((segid "PROT" and resid 34 and name HN))
(segid "PROT" and resid 31 and name HB%)
  3.700  3.400   1.800 peak    21972  weight  0.10000E+01 volume  0.42810E+00 ppm1   7.588 ppm2  1.760
ASSI {21992}
((segid "PROT" and resid 42 and name HB1))
(segid "PROT" and resid 43 and name HB%)
  3.200  2.600   2.300 peak    21992  weight  0.10000E+01 volume  0.89240E+00 ppm1   2.221 ppm2  0.984
ASSI {22022}
((segid "PROT" and resid 87 and name HG2))
(segid "PROT" and resid 49 and name HG2%)
  3.100  2.400   2.400 peak    22022  weight  0.10000E+01 volume  0.10861E+01 ppm1   2.245 ppm2  0.910
ASSI {22032}
((segid "PROT" and resid 39 and name HA))
(segid "PROT" and resid 38 and name HG2%)
  3.600  3.200   1.900 peak    22032  weight  0.10000E+01 volume  0.44230E+00 ppm1   4.441 ppm2  −0.010
ASSI {22052}
(segid "PROT" and resid 18 and name HD1%)
(segid "PROT" and resid 69 and name HG1%)
  3.500  3.100   2.000 peak    22052  weight  0.10000E+01 volume  0.55350E+00 ppm1   0.503 ppm2  0.989

TABLE 13-continued

Unambiguous NOE Distance Restraints

ASSI {22062}
((segid "PROT" and resid 68 and name HA))
(segid "PROT" and resid 69 and name HG1%)
  3.400  2.900  2.100 peak    22062 weight  0.10000E+01 volume    0.63530E+00 ppm1    4.580 ppm2    0.991
ASSI {22072}
((segid "PROT" and resid 33 and name HB1))
(segid "PROT" and resid 81 and name HG2%)
  3.500  3.100  2.000 peak    22072 weight  0.10000E+01 volume    0.57540E+00 ppm1    1.066 ppm2    0.155
ASSI {22092}
((segid "PROT" and resid 77 and name HA))
(segid "PROT" and resid 81 and name HG1%)
  3.600  3.200  1.900 peak    22092 weight  0.10000E+01 volume    0.47080E+00 ppm1    4.407 ppm2    0.510
ASSI {22152}
((segid "PROT" and resid 106 and name HB2))
(segid "PROT" and resid 25 and name HG2%)
  3.300  2.700  2.200 peak    22152 weight  0.10000E+01 volume    0.76240E+00 ppm1    3.135 ppm2    1.076
ASSI {22192}
((segid "PROT" and resid 42 and name HA))
(segid "PROT" and resid 41 and name HG2%)
  3.200  2.600  2.300 peak    22192 weight  0.10000E+01 volume    0.91170E+00 ppm1    4.500 ppm2    1.320
ASSI {22312}
((segid "PROT" and resid 56 and name HB2))
(segid "PROT" and resid 22 and name HD2%)
  3.000  2.200  2.200 peak    22312 weight  0.10000E+01 volume    0.13684E+01 ppm1    1.428 ppm2    1.049
ASSI {22342}
((segid "PROT" and resid 60 and name HA))
(segid "PROT" and resid 22 and name HD2%)
  3.500  3.100  2.000 peak    22342 weight  0.10000E+01 volume    0.54580E+00 ppm1    4.434 ppm2    1.047
ASSI {22362}
(segid "PROT" and resid 31 and name HB%)
(segid "PROT" and resid 102 and name HD2%)
  2.300  1.300  1.300 peak    22362 weight  0.10000E+01 volume    0.61478E+01 ppm1    1.763 ppm2    0.768
ASSI {22422}
((segid "PROT" and resid 106 and name HB2))
(segid "PROT" and resid 78 and name HD2%)
  3.300  2.700  2.200 peak    22422 weight  0.10000E+01 volume    0.75770E+00 ppm1    3.129 ppm2    0.196
ASSI {22432}
((segid "PROT" and resid 103 and name HA))
(segid "PROT" and resid 102 and name HD2%)
  2.700  1.800  1.800 peak    22432 weight  0.10000E+01 volume    0.25754E+01 ppm1    3.195 ppm2    0.766
ASSI {22482}
(segid "PROT" and resid 82 and name HE%)
(segid "PROT" and resid 102 and name HD2%)
  2.800  2.000  2.000 peak    22482 weight  0.10000E+01 volume    0.19487E+01 ppm1    6.468 ppm2    0.763
ASSI {22552}
(segid "PROT" and resid 56 and name HD1%)
(segid "PROT" and resid 102 and name HD1%)
  2.500  1.600  1.600 peak    22552 weight  0.10000E+01 volume    0.45008E+01 ppm1    0.986 ppm2    0.760
ASSI {22582}
((segid "PROT" and resid 34 and name HB2))
(segid "PROT" and resid 102 and name HD1%)
  3.400  2.900  2.100 peak    22582 weight  0.10000E+01 volume    0.62740E+00 ppm1    2.649 ppm2    0.760
ASSI {22612}
((segid "PROT" and resid 101 and name HA))
((segid "PROT" and resid 104 and name HG1))
  2.900  2.100  2.100 peak    22612 weight  0.10000E+01 volume    0.16583E+01 ppm1    3.706 ppm2    1.550
ASSI {22652}
(segid "PROT" and resid 63 and name HD1%)
((segid "PROT" and resid 66 and name HB2))
  3.600  3.200  1.900 peak    22652 weight  0.10000E+01 volume    0.45770E+00 ppm1    0.917 ppm2    2.048
ASSI {22712}
((segid "PROT" and resid 74 and name HA))
(segid "PROT" and resid 18 and name HD1%)
  3.200  2.600  2.300 peak    22712 weight  0.10000E+01 volume    0.97160E+00 ppm1    3.804 ppm2    0.514
ASSI {22722}
((segid "PROT" and resid 68 and name HA))
(segid "PROT" and resid 18 and name HD1%)
  3.400  2.900  2.100 peak    22722 weight  0.10000E+01 volume    0.62210E+00 ppm1    4.578 ppm2    0.514
ASSI {22752}
((segid "PROT" and resid 33 and name HB1))
((segid "PROT" and resid 33 and name HG2))
  3.500  3.100  2.000 peak    22752 weight  0.10000E+01 volume    0.57510E+00 ppm1    1.036 ppm2  −0.870
ASSI {22772}
((segid "PROT" and resid 98 and name HB1))
((segid "PROT" and resid 33 and name HG1))
  3.300  2.700  2.200 peak    22772 weight  0.10000E+01 volume    0.77490E+00 ppm1    3.392 ppm2    0.271

TABLE 13-continued

| Unambiguous NOE Distance Restraints |
|---|

ASSI {22792}
((segid "PROT" and resid 34 and name HZ))
((segid "PROT" and resid 33 and name HG1))
  3.200  2.600   2.300 peak     22792 weight  0.10000E+01 volume  0.90520E+00 ppm1    7.250  ppm2  0.266
ASSI {22802}
((segid "PROT" and resid 70 and name HA))
(segid "PROT" and resid 14 and name HD1%)
  2.600  1.700   1.700 peak     22802 weight  0.10000E+01 volume  0.33402E+01 ppm1    4.795  ppm2  0.855
ASSI {22842}
(segid "PROT" and resid 59 and name HE%)
(segid "PROT" and resid 78 and name HD1%)
  2.500  1.600   1.600 peak     22842 weight  0.10000E+01 volume  0.45695E+01 ppm1    1.310  ppm2  0.094
ASSI {22932}
((segid "PROT" and resid 60 and name HA))
(segid "PROT" and resid 22 and name HD1%)
  3.000  2.200   2.200 peak     22932 weight  0.10000E+01 volume  0.14457E+01 ppm1    4.433  ppm2  1.106
ASSI {23032}
((segid "PROT" and resid 35 and name HG1))
(segid "PROT" and resid 56 and name HD1%)
  3.200  2.600   2.300 peak     23032 weight  0.10000E+01 volume  0.96100E+00 ppm1    2.893  ppm2  0.977
ASSI {23122}
((segid "PROT" and resid 78 and name HN))
((segid "PROT" and resid 78 and name HG))
  3.600  3.200   1.900 peak     23122 weight  0.10000E+01 volume  0.50520E+00 ppm1    7.384  ppm2  0.692
ASSI {23152}
((segid "PROT" and resid 44 and name HG1))
((segid "PROT" and resid 44 and name HG2))
  1.800  0.800   0.800 peak     23152 weight  0.10000E+01 volume  0.30462E+02 ppm1    2.203  ppm2  2.079
ASSI {23202}
((segid "PROT" and resid 52 and name HA))
((segid "PROT" and resid 53 and name HG2))
  3.400  2.900   2.100 peak     23202 weight  0.10000E+01 volume  0.70630E+00 ppm1    5.047  ppm2  1.939
ASSI {23252}
((segid "PROT" and resid 35 and name HN))
((segid "PROT" and resid 32 and name HB2))
  3.500  3.100   2.000 peak     23252 weight  0.10000E+01 volume  0.53670E+00 ppm1    7.151  ppm2  3.408
ASSI {23312}
((segid "PROT" and resid 21 and name HA))
((segid "PROT" and resid 24 and name HB1))
  3.000  2.200   2.200 peak     23312 weight  0.10000E+01 volume  0.14681E+01 ppm1    3.796  ppm2  2.501
ASSI {23362}
((segid "PROT" and resid 9 and name HD1))
((segid "PROT" and resid 7 and name HB2))
  2.700  1.800   1.800 peak     23362 weight  0.10000E+01 volume  0.26162E+01 ppm1    3.211  ppm2  1.943
ASSI {23422}
((segid "PROT" and resid 52 and name HA))
((segid "PROT" and resid 51 and name HB2))
  3.500  3.100   2.000 peak     23422 weight  0.10000E+01 volume  0.55120E+00 ppm1    5.036  ppm2  1.214
ASSI {23442}
(segid "PROT" and resid 82 and name HD%)
((segid "PROT" and resid 81 and name HB))
  3.400  2.900   2.100 peak     23442 weight  0.10000E+01 volume  0.63500E+00 ppm1    6.702  ppm2  1.465
ASSI {23452}
((segid "PROT" and resid 54 and name HB2))
((segid "PROT" and resid 54 and name HG2))
  2.800  2.000   2.000 peak     23452 weight  0.10000E+01 volume  0.23115E+01 ppm1    1.379  ppm2  1.886
ASSI {23682}
((segid "PROT" and resid 10 and name HA))
((segid "PROT" and resid 11 and name HB1))
  3.300  2.700   2.200 peak     23682 weight  0.10000E+01 volume  0.74660E+00 ppm1    4.909  ppm2  2.381
ASSI {23692}
((segid "PROT" and resid 34 and name HA))
((segid "PROT" and resid 35 and name HB2))
  3.400  2.900   2.100 peak     23692 weight  0.10000E+01 volume  0.63830E+00 ppm1    5.015  ppm2  2.239
ASSI {23742}
(segid "PROT" and resid 110 and name HG2%)
((segid "PROT" and resid 75 and name HB2))
  3.300  2.700   2.200 peak     23742 weight  0.10000E+01 volume  0.81390E+00 ppm1    0.689  ppm2  2.656
ASSI {23802}
(segid "PROT" and resid 74 and name HD%)
((segid "PROT" and resid 75 and name HB1))
  3.300  2.700   2.200 peak     22802 weight  0.10000E+01 volume  0.82510E+00 ppm1    6.425  ppm2  2.966
ASSI {23822}
((segid "PROT" and resid 29 and name HE21))
((segid "PROT" and resid 29 and name HG2))
  3.300  2.700   2.200 peak     23822 weight  0.10000E+01 volume  0.78340E+00 ppm1    7.587  ppm2  2.428

TABLE 13-continued

Unambiguous NOE Distance Restraints

```
ASSI {23832}
((segid "PROT" and resid 29 and name HE21))
((segid "PROT" and resid 29 and name HG1))
  3.400  2.900  2.100 peak    23832 weight  0.10000E+01 volume  0.64100E+00 ppm1    7.588 ppm2  2.492
ASSI {23842}
((segid "PROT" and resid 50 and name HA))
((segid "PROT" and resid 49 and name HB))
  2.800  2.000  2.000 peak    23842 weight  0.10000E+01 volume  0.19918E+01 ppm1    3.934 ppm2  1.925
ASSI {23862}
((segid "PROT" and resid 88 and name HB1))
((segid "PROT" and resid 49 and name HB))
  3.300  2.700  2.200 peak    23862 weight  0.10000E+01 volume  0.73730E+00 ppm1    2.966 ppm2  1.926
ASSI {23882}
((segid "PROT" and resid 87 and name HG2))
((segid "PROT" and resid 49 and name HB))
  2.800  2.000  2.000 peak    23882 weight  0.10000E+01 volume  0.22351E+01 ppm1    2.214 ppm2  1.924
ASSI {23892}
((segid "PROT" and resid 50 and name HG11))
((segid "PROT" and resid 49 and name HB))
  3.500  3.100  2.000 peak    23892 weight  0.10000E+01 volume  0.55230E+00 ppm1    0.800 ppm2  1.928
ASSI {23932}
((segid "PROT" and resid 19 and name HG1))
((segid "PROT" and resid 23 and name HG2))
  3.500  3.100  2.000 peak    23932 weight  0.10000E+01 volume  0.58220E+00 ppm1    1.292 ppm2  2.484
ASSI {24002}
((segid "PROT" and resid 111 and name HG2))
((segid "PROT" and resid 112 and name HG2))
  3.400  2.900  2.100 peak    24002 weight  0.10000E+01 volume  0.70990E+00 ppm1    1.339 ppm2  2.254
ASSI {24032}
(segid "PROT" and resid 116 and name HD1%)
((segid "PROT" and resid 110 and name HB))
  3.200  2.600  2.300 peak    24032 weight  0.10000E+01 volume  0.89320E+00 ppm1    0.840 ppm2  1.796
ASSI {24052}
((segid "PROT" and resid 92 and name HB1))
((segid "PROT" and resid 92 and name HG2 ))
  2.000  1.000  1.000 peak    24052 weight  0.10000E+01 volume  0.15248E+02 ppm1    2.094 ppm2  2.263
ASSI {24062}
((segid "PROT" and resid 92 and name HB1))
((segid "PROT" and resid 92 and name HG1))
  2.000  1.000  1.000 peak    24062 weight  0.10000E+01 volume  0.14295E+02 ppm1    2.105 ppm2  2.387
ASSI {24132}
((segid "PROT" and resid 110 and name HG11))
((segid "PROT" and resid 107 and name HB1))
  3.500  3.100  2.000 peak    24132 weight  0.10000E+01 volume  0.52990E+00 ppm1    1.150 ppm2  3.098
ASSI {24152}
((segid "PROT" and resid 103 and name HB2))
((segid "PROT" and resid 82 and name HB1))
  3.300  2.700  2.200 peak    24152 weight  0.10000E+01 volume  0.85610E+00 ppm1    1.337 ppm2  3.134
ASSI {24172}
(segid "PROT" and resid 78 and name HD1%)
((segid "PROT" and resid 106 and name HB1))
  3.600  3.200  1.900 peak    24172 weight  0.10000E+01 volume  0.48250E+00 ppm1    0.088 ppm2  3.343
ASSI {24202}
((segid "PROT" and resid 30 and name HB2))
((segid "PROT" and resid 101 and name HB))
  3.400  2.900  2.100 peak    24202 weight  0.10000E+01 volume  0.68200E+00 ppm1    3.981 ppm2  1.942
ASSI {24212}
(segid "PROT" and resid 56 and name HD2%)
((segid "PROT" and resid 34 and name HB2))
  3.400  2.900  2.100 peak    24212 weight  0.10000E+01 volume  0.65310E+00 ppm1    0.682 ppm2  2.633
ASSI {24252}
(segid "PROT" and resid 63 and name HD1%)
((segid "PROT" and resid 18 and name HB2))
  3.500  3.100  2.000 peak    24252 weight  0.10000E+01 volume  0.55670E+00 ppm1    0.912 ppm2  0.346
ASSI {24272}
(segid "PROT" and resid 14 and name HD2%)
((segid "PROT" and resid 18 and name HB1))
  3.300  2.700  2.200 peak    24272 weight  0.10000E+01 volume  0.73750E+00 ppm1    0.844 ppm2  1.556
ASSI {24342}
(segid "PROT" and resid 18 and name HD1%)
((segid "PROT" and resid 14 and name HB2))
  3.400  2.900  2.100 peak    24342 weight  0.10000E+01 volume  0.67750E+00 ppm1    0.517 ppm2  1.595
ASSI {24372}
((segid "PROT" and resid 26 and name HA))
((segid "PROT" and resid 56 and name HB1))
  3.200  2.600  2.300 peak    24372 weight  0.10000E+01 volume  0.87170E+00 ppm1    3.925 ppm2  2.094
```

TABLE 13-continued

| Unambiguous NOE Distance Restraints |
|---|

ASSI {24382}
((segid "PROT" and resid 26 and name HA))
((segid "PROT" and resid 56 and name HB2))
  3.200  2.600  2.300 peak    24382 weight  0.10000E+01 volume  0.90000E+00 ppm1    3.926 ppm2  1.456
ASSI {24402}
(segid "PROT" and resid 82 and name HD%)
((segid "PROT" and resid 102 and name HB1))
  3.500  3.100  2.000 peak    24402 weight  0.10000E+01 volume  0.52400E+00 ppm1    6.701 ppm2  1.471
ASSI {24532}
(segid "PROT" and resid 116 and name HD1%)
((segid "PROT" and resid 115 and name HB2))
  3.100  2.400  2.400 peak    24532 weight  0.10000E+01 volume  0.12534E+01 ppm1    0.843 ppm2  1.613
ASSI {24562}
((segid "PROT" and resid 57 and name HG1))
((segid "PROT" and resid 57 and name HE2))
  3.400  2.900  2.100 peak    24562 weight  0.10000E+01 volume  0.70530E+00 ppm1    1.531 ppm2  2.065
ASSI {24592}
((segid "PROT" and resid 39 and name HG2))
((segid "PROT" and resid 43 and name HA))
  3.400  2.900  2.100 peak    24592 weight  0.10000E+01 volume  0.67070E+00 ppm1    1.463 ppm2  4.989
ASSI {24612}
((segid "PROT" and resid 44 and name HG1))
((segid "PROT" and resid 43 and name HA))
  3.200  2.600  2.300 peak    24612 weight  0.10000E+01 volume  0.99940E+00 ppm1    2.209 ppm2  4.983
ASSI {24652}
((segid "PROT" and resid 32 and name HD1))
((segid "PROT" and resid 33 and name HD1))
  3.600  3.200  1.900 peak    24652 weight  0.10000E+01 volume  0.49260E+00 ppm1    7.899 ppm2  2.263
ASSI {24662}
((segid "PROT" and resid 32 and name HD1))
((segid "PROT" and resid 33 and name HD2))
  3.500  3.100  2.000 peak    24662 weight  0.10000E+01 volume  0.59000E+00 ppm1    7.890 ppm2  1.572
ASSI {24692}
(segid "PROT" and resid 115 and name HD2%)
((segid "PROT" and resid 113 and name HA))
  3.300  2.700  2.200 peak    24692 weight  0.10000E+01 volume  0.72980E+00 ppm1    0.771 ppm2  4.336
ASSI {24722}
((segid "PROT" and resid 33 and name HD2))
((segid "PROT" and resid 31 and name HA))
  3.300  2.700  2.200 peak    24722 weight  0.10000E+01 volume  0.77360E+00 ppm1    1.580 ppm2  4.438
ASSI {24732}
((segid "PROT" and resid 33 and name HD1))
((segid "PROT" and resid 31 and name HA))
  3.200  2.600  2.300 peak    24732 weight  0.10000E+01 volume  0.88700E+00 ppm1    2.262 ppm2  4.438
ASSI {24742}
((segid "PROT" and resid 34 and name HB2))
((segid "PROT" and resid 31 and name HA))
  3.300  2.700  2.200 peak    24742 weight  0.10000E+01 volume  0.72970E+00 ppm1    2.637 ppm2  4.436
ASSI {24782}
((segid "PROT" and resid 54 and name HG2))
((segid "PROT" and resid 54 and name HA))
  3.100  2.400  2.400 peak    24782 weight  0.10000E+01 volume  0.11966E+01 ppm1    1.893 ppm2  4.985
ASSI {24792}
((segid "PROT" and resid 79 and name HG1))
((segid "PROT" and resid 76 and name HA))
  3.300  2.700  2.200 peak    24792 weight  0.10000E+01 volume  0.78020E+00 ppm1    2.452 ppm2  4.113
ASSI {24822}
(segid "PROT" and resid 102 and name HD1%)
((segid "PROT" and resid 99 and name HA))
  3.200  2.600  2.300 peak    24822 weight  0.10000E+01 volume  0.95780E+00 ppm1    0.759 ppm2  3.907
ASSI {24832}
((segid "PROT" and resid 102 and name HB2))
((segid "PROT" and resid 99 and name HA))
  3.400  2.900  2.100 peak    24832 weight  0.10000E+01 volume  0.64070E+00 ppm1    1.268 ppm2  3.911
ASSI {24842}
((segid "PROT" and resid 87 and name HB2))
((segid "PROT" and resid 84 and name HA))
  2.900  2.100  2.100 peak    24842 weight  0.10000E+01 volume  0.16758E+01 ppm1    2.059 ppm2  4.343
ASSI {24852}
(segid "PROT" and resid 82 and name HE%)
((segid "PROT" and resid 99 and name HA))
  3.400  2.900  2.100 peak    24852 weight  0.10000E+01 volume  0.69880E+00 ppm1    6.487 ppm2  3.907
ASSI {24892}
((segid "PROT" and resid 10 and name HA))
((segid "PROT" and resid 9 and name HA))
  3.200  2.600  2.300 peak    24892 weight  0.10000E+01 volume  0.99840E+00 ppm1    4.935 ppm2  4.357

TABLE 13-continued

| Unambiguous NOE Distance Restraints |
|---|

ASSI {24912}
((segid "PROT" and resid 56 and name HG))
((segid "PROT" and resid 34 and name HA))
  3.500  3.100  2.000 peak    24912 weight  0.10000E+01 volume  0.53580E+00 ppm1    1.755 ppm2  5.006
ASSI {24992}
((segid "PROT" and resid 30 and name HB1))
((segid "PROT" and resid 102 and name HA))
  3.300  2.700  2.200 peak    24992 weight  0.10000E+01 volume  0.79400E+00 ppm1    4.361 ppm2  3.721
ASSI {25022}
((segid "PROT" and resid 112 and name HG1))
((segid "PROT" and resid 109 and name HA))
  3.500  3.100  2.000 peak    25022 weight  0.10000E+01 volume  0.52490E+00 ppm1    2.382 ppm2  4.074
ASSI {25032}
((segid "PROT" and resid 52 and name HA))
((segid "PROT" and resid 51 and name HA))
  3.500  3.100  2.000 peak    25032 weight  0.10000E+01 volume  0.59780E+00 ppm1    5.048 ppm2  3.876
ASSI {25092}
((segid "PROT" and resid 56 and name HB2))
((segid "PROT" and resid 56 and name HA))
  2.400  1.400  1.400 peak    25092 weight  0.10000E+01 volume  0.47870E+01 ppm1    1.422 ppm2  4.075
ASSI {25112}
((segid "PROT" and resid 21 and name HG11))
((segid "PROT" and resid 18 and name HA))
  3.300  2.700  2.200 peak    25112 weight  0.10000E+01 volume  0.75700E+00 ppm1    1.776 ppm2  3.313
ASSI {25122}
((segid "PROT" and resid 21 and name HA))
((segid "PROT" and resid 18 and name HA))
  3.300  2.700  2.200 peak    25122 weight  0.10000E+01 volume  0.85990E+00 ppm1    3.800 ppm2  3.313
ASSI {25152}
((segid "PROT" and resid 73 and name HA))
((segid "PROT" and resid 68 and name HA))
  2.900  2.100  2.100 peak    25152 weight  0.10000E+01 volume  0.16472E+01 ppm1    4.267 ppm2  4.561
ASSI {25262}
(segid "PROT" and resid 82 and name HD%)
((segid "PROT" and resid 103 and name HA))
  3.300  2.700  2.200 peak    25262 weight  0.10000E+01 volume  0.84370E+00 ppm1    6.680 ppm2  3.223
ASSI {25272}
(segid "PROT" and resid 106 and name HD%)
((segid "PROT" and resid 103 and name HA))
  3.100  2.400  2.400 peak    25272 weight  0.10000E+01 volume  0.12238E+01 ppm1    6.956 ppm2  3.222
ASSI {25312}
((segid "PROT" and resid 18 and name HB1))
((segid "PROT" and resid 19 and name HA))
  3.500  3.100  2.000 peak    25312 weight  0.10000E+01 volume  0.56690E+00 ppm1    1.567 ppm2  3.719
ASSI {25322}
((segid "PROT" and resid 109 and name HB2))
((segid "PROT" and resid 106 and name HA))
  3.300  2.700  2.200 peak    25322 weight  0.10000E+01 volume  0.81090E+00 ppm1    1.582 ppm2  3.997
ASSI {25362}
((segid "PROT" and resid 77 and name HB1))
((segid "PROT" and resid 74 and name HA))
  3.100  2.400  2.400 peak    25362 weight  0.10000E+01 volume  0.11329E+01 ppm1    2.743 ppm2  3.801
ASSI {25452}
((segid "PROT" and resid 13 and name HB1))
((segid "PROT" and resid 8 and name HA))
  3.300  2.700  2.200 peak    25452 weight  0.10000E+01 volume  0.83930E+00 ppm1    2.205 ppm2  4.457
ASSI {25462}
((segid "PROT" and resid 38 and name HA))
((segid "PROT" and resid 37 and name HA))
  3.500  3.100  2.000 peak    25462 weight  0.10000E+01 volume  0.51900E+00 ppm1    3.494 ppm2  4.271
ASSI {25512}
(segid "PROT" and resid 102 and name HD2%)
((segid "PROT" and resid 30 and name HB1))
  3.300  2.700  2.200 peak    25512 weight  0.10000E+01 volume  0.72760E+00 ppm1    0.769 ppm2  4.350
ASSI {25552}
((segid "PROT" and resid 39 and name HD2))
((segid "PROT" and resid 38 and name HA))
  3.400  2.900  2.100 peak    25552 weight  0.10000E+01 volume  0.70210E+00 ppm1    1.644 ppm2  3.492
ASSI {25612}
((segid "PROT" and resid 33 and name HD2))
((segid "PROT" and resid 33 and name HA))
  3.400  2.900  2.100 peak    25612 weight  0.10000E+01 volume  0.67050E+00 ppm1    1.563 ppm2  3.990
ASSI {25662}
(segid "PROT" and resid 18 and name HD2%)
((segid "PROT" and resid 17 and name HA))
  3.500  3.100  2.000 peak    25662 weight  0.10000E+01 volume  0.52650E+00 ppm1    −0.159 ppm2  3.972

TABLE 13-continued

Unambiguous NOE Distance Restraints

ASSI {25742}
((segid "PROT" and resid 18 and name HA))
((segid "PROT" and resid 17 and name HB))
  3.300  2.700  2.200 peak    25742 weight  0.10000E+01 volume  0.76330E+00 ppm1    3.321 ppm2  4.267
ASSI {25772}
((segid "PROT" and resid 33 and name HD1))
(segid "PROT" and resid 31 and name HB%)
  3.100  2.400  2.400 peak    25772 weight  0.10000E+01 volume  0.10817E+01 ppm1    2.264 ppm2  1.762
ASSI {25782}
((segid "PROT" and resid 34 and name HB2))
(segid "PROT" and resid 31 and name HB%)
  3.600  3.200  1.900 peak    25782 weight  0.10000E+01 volume  0.45500E+00 ppm1    2.622 ppm2  1.754
ASSI {25792}
((segid "PROT" and resid 25 and name HA))
(segid "PROT" and resid 31 and name HB%)
  3.000  2.200  2.200 peak    25792 weight  0.10000E+01 volume  0.14541E+01 ppm1    3.874 ppm2  1.758
ASSI {25802}
((segid "PROT" and resid 28 and name HA))
(segid "PROT" and resid 31 and name HB%)
  3.000  2.200  2.200 peak    25802 weight  0.10000E+01 volume  0.13195E+01 ppm1    4.008 ppm2  1.762
ASSI {25832}
((segid "PROT" and resid 44 and name HA))
((segid "PROT" and resid 43 and name HA))
  3.600  3.200  1.900 peak    25832 weight  0.10000E+01 volume  0.43420E+00 ppm1    4.550 ppm2  4.990
ASSI {25862}
((segid "PROT" and resid 38 and name HB))
(segid "PROT" and resid 43 and name HB%)
  2.400  1.400  1.400 peak    25862 weight  0.10000E+01 volume  0.48630E+01 ppm1    1.079 ppm2  0.972
ASSI {25872}
((segid "PROT" and resid 39 and name HB2))
(segid "PROT" and resid 43 and name HB%)
  2.400  1.400  1.400 peak    25872 weight  0.10000E+01 volume  0.54502E+01 ppm1    1.924 ppm2  0.978
ASSI {25882}
((segid "PROT" and resid 44 and name HD2))
(segid "PROT" and resid 43 and name HB%)
  2.900  2.100  2.100 peak    25882 weight  0.10000E+01 volume  0.15646E+01 ppm1    3.567 ppm2  0.988
ASSI {25922}
((segid "PROT" and resid 102 and name HB1))
((segid "PROT" and resid 99 and name HA))
  3.100  2.400  2.400 peak    25922 weight  0.10000E+01 volume  0.11328E+01 ppm1    1.478 ppm2  3.919
ASSI {25932}
((segid "PROT" and resid 103 and name HB2))
((segid "PROT" and resid 99 and name HA))
  3.700  3.400  1.800 peak    25932 weight  0.10000E+01 volume  0.39400E+00 ppm1    1.319 ppm2  3.909
ASSI {25942}
((segid "PROT" and resid 102 and name HG))
((segid "PROT" and resid 99 and name HA))
  3.200  2.600  2.300 peak    25942 weight  0.10000E+01 volume  0.89150E+00 ppm1    1.606 ppm2  3.905
ASSI {25962}
((segid "PROT" and resid 82 and name HB1))
((segid "PROT" and resid 99 and name HA))
  3.700  3.400  1.800 peak    25962 weight  0.10000E+01 volume  0.38960E+00 ppm1    3.153 ppm2  3.915
ASSI {25972}
((segid "PROT" and resid 98 and name HA))
((segid "PROT" and resid 99 and name HA))
  3.400  2.900  2.100 peak    25972 weight  0.10000E+01 volume  0.65570E+00 ppm1    4.227 ppm2  3.919
ASSI {25982}
(segid "PROT" and resid 34 and name HE%)
((segid "PROT" and resid 99 and name HA))
  3.500  3.100  2.000 peak    25982 weight  0.10000E+01 volume  0.57510E+00 ppm1    7.199 ppm2  3.918
ASSI {25992}
((segid "PROT" and resid 86 and name HG1))
(segid "PROT" and resid 99 and name HB%)
  2.500  1.600  1.600 peak    25992 weight  0.10000E+01 volume  0.45856E+01 ppm1    1.349 ppm2  1.658
ASSI {26002}
((segid "PROT" and resid 86 and name HB1))
(segid "PROT" and resid 99 and name HB%)
  2.700  1.800  1.800 peak    26002 weight  0.10000E+01 volume  0.28316E+01 ppm1    1.779 ppm2  1.650
ASSI {26012}
((segid "PROT" and resid 85 and name HB2))
(segid "PROT" and resid 99 and name HB%)
  2.400  1.400  1.400 peak    26012 weight  0.10000E+01 volume  0.50444E+01 ppm1    3.088 ppm2  1.657
ASSI {26062}
(segid "PROT" and resid 17 and name HG2%)
((segid "PROT" and resid 113 and name HA))
  3.300  2.700  2.200 peak    26062 weight  0.10000E+01 volume  0.74500E+00 ppm1    1.176 ppm2  4.352

TABLE 13-continued

| Unambiguous NOE Distance Restraints |
|---|

ASSI {26072}
((segid "PROT" and resid 115 and name HG))
((segid "PROT" and resid 113 and name HA))
  3.600  3.200   1.900 peak     26072  weight  0.10000E+01 volume   0.47150E+00 ppm1    1.567 ppm2  4.354
ASSI {26092}
((segid "PROT" and resid 112 and name HA))
((segid "PROT" and resid 113 and name HA))
  3.700  3.400   1.800 peak     26092  weight  0.10000E+01 volume   0.41410E+00 ppm1    4.027 ppm2  4.359
ASSI (26102)
(segid "PROT" and resid 18 and name HD2%)
(segid "PROT" and resid 113 and name HB%)
  3.500  3.100   2.000 peak     26102  weight  0.10000E+01 volume   0.53320E+00 ppm1   −0.167 ppm2  1.415
ASSI {26112}
(segid "PROT" and resid 14 and name HD1%)
(segid "PROT" and resid 113 and name HB%)
  3.300  2.700   2.200 peak     26112  weight  0.10000E+01 volume   0.78270E+00 ppm1    0.842 ppm2  1.411
ASSI {26122}
((segid "PROT" and resid 115 and name HB2))
(segid "PROT" and resid 113 and name HB%)
  2.400  1.400   1.400 peak     26122  weight  0.10000E+01 volume   0.50600E+01 ppm1    1.609 ppm2  1.405
ASSI {26162}
((segid "PROT" and resid 28 and name HB1))
((segid "PROT" and resid 25 and name HA))
  3.200  2.600   2.300 peak     26162  weight  0.10000E+01 volume   0.96480E+00 ppm1    3.022 ppm2  3.869
ASSI {26172}
((segid "PROT" and resid 28 and name HD2))
((segid "PROT" and resid 25 and name HA))
  3.600  3.200   1.900 peak     26172  weight  0.10000E+01 volume   0.47840E+00 ppm1    5.024 ppm2  3.873
ASSI {26182}
(segid "PROT" and resid 78 and name HD1%)
((segid "PROT" and resid 25 and name HB))
  3.600  3.200   1.900 peak     26182  weight  0.10000E+01 volume   0.49810E+00 ppm1    0.104 ppm2  2.445
ASSI {26192}
(segid "PROT" and resid 102 and name HD2%)
((segid "PROT" and resid 25 and name HB))
  3.300  2.700   2.200 peak     26192  weight  0.10000E+01 volume   0.72760E+00 ppm1    0.766 ppm2  2.437
ASSI {26202}
((segid "PROT" and resid 22 and name HA))
((segid "PROT" and resid 25 and name HB))
  2.500  1.600   1.600 peak     26202  weight  0.10000E+01 volume   0.42061E+01 ppm1    4.151 ppm2  2.441
ASSI {26222}
(segid "PROT" and resid 63 and name HD1%)
(segid "PROT" and resid 18 and name HD1%)
  2.800  2.000   2.000 peak     26222  weight  0.10000E+01 volume   0.23014E+01 ppm1    0.880 ppm2  0.513
ASSI {26242}
((segid "PROT" and resid 85 and name HB1))
((segid "PROT" and resid 82 and name HA))
  3.200  2.600   2.300 peak     26242  weight  0.10000E+01 volume   0.92110E+00 ppm1    3.421 ppm2  4.230
ASSI {26292}
(segid "PROT" and resid 102 and name HD2%)
((segid "PROT" and resid 30 and name HB2))
  3.000  2.200   2.200 peak     26292  weight  0.10000E+01 volume   0.15286E+01 ppm1    0.773 ppm2  3.978
ASSI {26312}
((segid "PROT" and resid 102 and name HG))
((segid "PROT" and resid 30 and name HB2))
  3.500  3.100   2.000 peak     26312  weight  0.10000E+01 volume   0.57310E+00 ppm1    1.596 ppm2  3.980
ASSI {26332}
((segid "PROT" and resid 32 and name HE3))
((segid "PROT" and resid 32 and name HA))
  3.000  2.200   2.200 peak     26332  weight  0.10000E+01 volume   0.12697E+01 ppm1    7.359 ppm2  4.412
ASSI {26342}
((segid "PROT" and resid 32 and name HD1))
((segid "PROT" and resid 32 and name HA))
  3.400  2.900   2.100 peak     26342  weight  0.10000E+01 volume   0.67130E+00 ppm1    7.889 ppm2  4.410
ASSI {26352}
((segid "PROT" and resid 35 and name HB2))
((segid "PROT" and resid 32 and name HB1))
  3.500  3.100   2.000 peak     26352  weight  0.10000E+01 volume   0.52260E+00 ppm1    2.213 ppm2  3.637
ASSI {26392}
((segid "PROT" and resid 32 and name HB2))
((segid "PROT" and resid 33 and name HD2))
  3.400  2.900   2.100 peak     26392  weight  0.10000E+01 volume   0.60950E+00 ppm1    3.409 ppm2  1.593
ASSI {26442}
(segid "PROT" and resid 69 and name HG2%)
((segid "PROT" and resid 11 and name HB1))
  2.800  2.000   2.000 peak     26442  weight  0.10000E+01 volume   0.21371E+01 ppm1    0.863 ppm2  2.357

TABLE 13-continued

Unambiguous NOE Distance Restraints

ASSI {26452}
(segid "PROT" and resid 69 and name HG1%)
((segid "PROT" and resid 11 and name HB1))
  2.800  2.000  2.000 peak     26452 weight  0.10000E+01 volume  0.20188E+01 ppm1    0.990 ppm2  2.356
ASSI {26562}
((segid "PROT" and resid 54 and name HB2))
((segid "PROT" and resid 81 and name HA))
  3.100  2.400  2.400 peak     26562 weight  0.10000E+01 volume  0.12209E+01 ppm1    1.398 ppm2  3.123
ASSI {26572}
(segid "PROT" and resid 73 and name HD1%)
((segid "PROT" and resid 70 and name HB1))
  3.100  2.400  2.400 peak     26572 weight  0.10000E+01 volume  0.10554E+01 ppm1    0.969 ppm2  4.226
ASSI {26612}
(segid "PROT" and resid 68 and name HD%)
((segid "PROT" and resid 74 and name HA))
  2.800  2.000  2.000 peak     26612 weight  0.10000E+01 volume  0.19551E+01 ppm1    7.210 ppm2  3.815
ASSI {26622}
((segid "PROT" and resid 66 and name HD1))
((segid "PROT" and resid 67 and name HA))
  2.600  1.700  1.700 peak     26622 weight  0.10000E+01 volume  0.32309E+01 ppm1    3.088 ppm2  4.108
ASSI {26632}
(segid "PROT" and resid 116 and name HG2%)
((segid "PROT" and resid 111 and name HA))
  2.600  1.700  1.700 peak     26632 weight  0.10000E+01 volume  0.31272E+01 ppm1    0.840 ppm2  4.094
ASSI {26642}
((segid "PROT" and resid 110 and name HG12))
((segid "PROT" and resid 111 and name HA))
  3.300  2.700  2.200 peak     26642 weight  0.10000E+01 volume  0.86670E+00 ppm1    1.099 ppm2  4.092
ASSI {26692}
((segid "PROT" and resid 34 and name HZ))
(segid "PROT" and resid 81 and name HG2%)
  2.700  1.800  1.800 peak     26692 weight  0.10000E+01 volume  0.23973E+01 ppm1    7.278 ppm2  0.151
ASSI {26712}
((segid "PROT" and resid 82 and name HN))
((segid "PROT" and resid 82 and name HB1))
  3.800  3.600  1.700 peak     26712 weight  0.10000E+01 volume  0.36330E+00 ppm1    6.440 ppm2  3.146
ASSI {26792}
(segid "PROT" and resid 107 and name HD%)
((segid "PROT" and resid 104 and name HA))
  3.000  2.200  2.200 peak     26792 weight  0.10000E+01 volume  0.13833E+01 ppm1    7.239 ppm2  4.112
ASSI {352}
((segid "PROT" and resid 11 and name HA))
((segid "PROT" and resid 8 and name HG1))
  2.400  2.400  2.100 peak       352 weight  0.10000E+01 volume  0.50737E+01 ppm1    4.376 ppm2  2.024
ASSI {1382}
((segid "PROT" and resid 62 and name HA))
((segid "PROT" and resid 65 and name HB2))
  2.800  2.000  2.000 peak      1382 weight  0.10000E+01 volume  0.23053E+01 ppm1    3.907 ppm2  2.808
ASSI {1392}
((segid "PROT" and resid 97 and name HA))
((segid "PROT" and resid 92 and name HG2))
  2.600  1.700  1.700 peak      1392 weight  0.10000E+01 volume  0.37031E+01 ppm1    4.250 ppm2  2.295
ASSI {1442}
((segid "PROT" and resid 116 and name HA))
((segid "PROT" and resid 6 and name HG1))
  2.700  1.800  1.800 peak      1442 weight  0.10000E+01 volume  0.24084E+01 ppm1    4.257 ppm2  1.453
OR {1442}
((segid "PROT" and resid 116 and name HA))
((segid "PROT" and resid 6 and name HG2))
ASSI {1562}
((segid "PROT" and resid 103 and name HA ))
(segid "PROT" and resid 82 and name HE%)
  2.800  2.000  2.000 peak      1562 weight  0.10000E+01 volume  0.20471E+01 ppm1    3.221 ppm2  6.482
ASSI {1622}
((segid "PROT" and resid 26 and name HA))
((segid "PROT" and resid 26 and name HB1))
  2.300  1.300  1.300 peak      1622 weight  0.10000E+01 volume  0.67915E+01 ppm1    3.934 ppm2  1.916
ASSI {1662}
((segid "PROT" and resid 26 and name HA))
((segid "PROT" and resid 26 and name HG1))
  2.700  1.800  1.800 peak      1662 weight  0.10000E+01 volume  0.26801E+01 ppm1    3.935 ppm2  1.533
ASSI {1912}
((segid "PROT" and resid 86 and name HA))
(segid "PROT" and resid 96 and name HE%)
  2.600  1.700  1.700 peak      1912 weight  0.10000E+01 volume  0.36159E+01 ppm1    4.263 ppm2  7.051

TABLE 13-continued

Unambiguous NOE Distance Restraints

```
ASSI {3732}
((segid "PROT" and resid 9 and name HD1))
((segid "PROT" and resid 7 and name HB1))
  2.900  2.100  2.100 peak      3732 weight  0.10000E+01 volume  0.17407E+01 ppm1   3.222 ppm2  2.070
ASSI {3742}
((segid "PROT" and resid 9 and name HD1))
(segid "PROT" and resid 14 and name HD1%)
  2.900  2.100  2.100 peak      3742 weight  0.10000E+01 volume  0.15626E+01 ppm1   3.227 ppm2  0.837
OR {3742}
((segid "PROT" and resid 9 and name HD1))
(segid "PROT" and resid 14 and name HD2%)
ASSI {3962}
((segid "PROT" and resid 63 and name HB1))
((segid "PROT" and resid 60 and name HB1))
  2.900  2.100  2.100 peak      3962 weight  0.10000E+01 volume  0.19046E+01 ppm1   2.349 ppm2  4.239
ASSI {4122}
((segid "PROT" and resid 6 and name HE1))
((segid PROT" and resid 116 and name HA))
  2.100  1.100  1.100 peak      4122 weight  0.10000E+01 volume  0.11238E+02 ppm1   3.015 ppm2  4.245
ASSI {4162}
((segid "PROT" and resid 64 and name HE1))
((segid "PROT" and resid 61 and name HG1))
  2.800  2.000  2.000 peak      4162 weight  0.10000E+01 volume  0.19795E+01 ppm1   3.053 ppm2  2.392
ASSI {4182}
((segid "PROT" and resid 97 and name HE1))
((segid "PROT" and resid 97 and name HB1))
  2.300  1.300  1.300 peak      4182 weight  0.10000E+01 volume  0.75764E+01 ppm1   3.027 ppm2  2.101
ASSI {4222}
((segid "PROT" and resid 19 and name HE1))
((segid "PROT" and resid 19 and name HG1))
  2.200  1.200  1.200 peak      4222 weight  0.10000E+01 volume  0.87095E+01 ppm1   2.967 ppm2  1.310
ASSI {4252}
((segid "PROT" and resid 19 and name HE1))
(segid "PROT" and resid 63 and name HD1%)
  2.800  2.000  2.000 peak      4252 weight  0.10000E+01 volume  0.20298E+01 ppm1   2.990 ppm2  0.921
ASSI {4612}
((segid "PROT" and resid 86 and name HE1))
((segid "PROT" and resid 103 and name HB1))
  2.800  2.000  2.000 peak      4612 weight  0.10000E+01 volume  0.21144E+01 ppm1   2.508 ppm2  1.828
ASSI {4632}
((segid "PROT" and resid 86 and name HE1))
(segid "PROT" and resid 99 and name HB%)
  2.800  2.000  2.000 peak      4632 weight  0.10000E+01 volume  0.19300E+01 ppm1   2.506 ppm2  1.665
ASSI {4672}
((segid "PROT" and resid 86 and name HE1))
((segid "PROT" and resid 86 and name HD1))
  2.400  1.400  1.400 peak      4672 weight  0.10000E+01 volume  0.59325E+01 ppm1   2.506 ppm2  1.340
OR {4672}
((segid "PROT" and resid 86 and name HE1))
((segid "PROT" and resid 86 and name HG1))
ASSI {4742}
((segid "PROT" and resid 86 and name HE1))
((segid "PROT" and resid 86 and name HG2))
  2.900  2.100  2.100 peak      4742 weight  0.10000E+01 volume  0.16989E+01 ppm1   2.498 ppm2  0.168
OR {4742}
((segid "PROT" and resid 86 and name HE2))
((segid "PROT" and resid 86 and name HG2))
ASSI {6012}
((segid "PROT" and resid 42 and name HG2))
((segid "PROT" and resid 39 and name HG1))
  2.700  1.800  1.800 peak      6012 weight  0.10000E+01 volume  0.29022E+01 ppm1   2.303 ppm2  1.675
ASSI {6632}
((segid "PROT" and resid 111 and name HB1))
((segid "PROT" and resid 111 and name HD1))
  1.900  0.900  0.900 peak      6632 weight  0.10000E+01 volume  0.19710E+02 ppm1   1.940 ppm2  1.692
ASSI {6682}
((segid "PROT" and resid 86 and name HB1))
(segid "PROT" and resid 96 and name HE%)
  2.900  2.100  2.100 peak      6682 weight  0.10000E+01 volume  0.16294E+01 ppm1   1.808 ppm2  7.051
ASSI {6922}
((segid "PROT" and resid 64 and name HB1))
((segid "PROT" and resid 61 and name HA))
  2.200  1.200  1.200 peak      6922 weight  0.10000E+01 volume  0.80769E+01 ppm1   2.068 ppm2  4.094
ASSI {7882}
((segid "PROT" and resid 86 and name HD1))
(segid "PROT" and resid 96 and name HE%)
  3.000  2.200  2.200 peak      7882 weight  0.10000E+01 volume  0.15219E+01 ppm1   1.364 ppm2  7.049
```

TABLE 13-continued

| Unambiguous NOE Distance Restraints |

ASSI {7892}
((segid "PROT" and resid 19 and name HD1))
(segid "PROT" and resid 15 and name HE%)
  2.600  1.700  1.700 peak      7892 weight  0.10000E+01 volume  0.34592E+01 ppm1    1.640 ppm2  6.922
ASSI {7922}
((segid "PROT" and resid 86 and name HD1))
((segid "PROT" and resid 86 and name HA))
  2.900  2.100  2.100 peak      7922 weight  0.10000E+01 volume  0.18440E+01 ppm1    1.341 ppm2  4.265
ASSI {7952}
((segid "PROT" and resid 112 and name HB1))
((segid "PROT" and resid 109 and name HA))
  2.100  1.100  1.100 peak      7952 weight  0.10000E+01 volume  0.11736E+02 ppm1    2.106 ppm2  4.081
ASSI {7982}
((segid "PROT" and resid 57 and name HD1))
((segid "PROT" and resid 37 and name HD1))
  2.700  1.800  1.800 peak      7982 weight  0.10000E+01 volume  0.28210E+01 ppm1    1.730 ppm2  3.708
ASSI {8012}
((segid "PROT" and resid 86 and name HD1))
((segid "PROT" and resid 86 and name HE1))
  2.700  1.800  1.800 peak      8012 weight  0.10000E+01 volume  0.27789E+01 ppm1    1.336 ppm2  2.524
ASSI {8032}
((segid "PROT" and resid 86 and name HD1))
((segid "PROT" and resid 86 and name HE2))
  2.600  1.700  1.700 peak      8032 weight  0.10000E+01 volume  0.29928E+01 ppm1    1.368 ppm2  2.471
OR {8032}
((segid "PROT" and resid 86 and name HD1))
((segid "PROT" and resid 86 and name HE1))
ASSI {8072}
((segid "PROT" and resid 111 and name HD1))
((segid "PROT" and resid 112 and name HG2))
  2.400  2.400  2.100 peak      8072 weight  0.10000E+01 volume  0.48306E+01 ppm1    1.696 ppm2  2.215
ASSI {8102}
((segid "PROT" and resid 86 and name HD1))
((segid "PROT" and resid 86 and name HG2))
  2.400  1.400  1.400 peak      8102 weight  0.10000E+01 volume  0.47467E+01 ppm1    1.360 ppm2  0.169
ASSI {8182}
((segid "PROT" and resid 64 and name HD1))
((segid "PROT" and resid 64 and name HB1))
  2.000  1.000  1.000 peak      8182 weight  0.10000E+01 volume  0.14643E+02 ppm1    1.792 ppm2  2.096
ASSI {8242}
((segid "PROT" and resid 39 and name HD2))
((segid "PROT" and resid 39 and name HA))
  2.600  1.700  1.700 peak      8242 weight  0.10000E+01 volume  0.30605E+01 ppm1    1.676 ppm2  4.452
ASSI {8742}
((segid "PROT" and resid 78 and name HG))
(segid "PROT" and resid 82 and name HE%)
  3.000  2.200  2.200 peak      8742 weight  0.10000E+01 volume  0.15179E+01 ppm1    0.689 ppm2  6.468
ASSI {9112}
((segid "PROT" and resid 115 and name HG))
((segid "PROT" and resid 75 and name HG2))
  2.900  2.100  2.100 peak      9112 weight  0.10000E+01 volume  0.18866E+01 ppm1    1.545 ppm2  2.216
ASSI {9162}
((segid "PROT" and resid 56 and name HG))
((segid "PROT" and resid 56 and name HB2))
  2.800  2.000  2.000 peak      9162 weight  0.10000E+01 volume  0.19931E+01 ppm1    1.776 ppm2  1.409
ASSI {9412}
((segid "PROT" and resid 26 and name HG1))
((segid "PROT" and resid 26 and name HB1))
  2.100  1.100  1.100 peak      9412 weight  0.10000E+01 volume  0.12118E+02 ppm1    1.528 ppm2  1.896
ASSI {9452}
((segid "PROT" and resid 63 and name HG))
((segid "PROT" and resid 18 and name HB1))
  2.300  1.300  1.300 peak      9452 weight  0.10000E+01 volume  0.69171E+01 ppm1    1.875 ppm2  1.539
ASSI {9522}
((segid "PROT" and resid 26 and name HG1))
(segid "PROT" and resid 56 and name HD1%)
  2.600  1.700  1.700 peak      9522 weight  0.10000E+01 volume  0.30036E+01 ppm1    1.532 ppm2  0.976
ASSI {9982}
((segid "PROT" and resid 97 and name HG1))
((segid "PROT" and resid 97 and name HE1))
  2.600  1.700  1.700 peak      9982 weight  0.10000E+01 volume  0.35375E+01 ppm1    1.844 ppm2  3.009
ASSI {10022}
((segid "PROT" and resid 97 and name HG2))
((segid "PROT" and resid 97 and name HG1))
  2.000  1.000  1.000 peak    10022 weight  0.10000E+01 volume  0.17308E+02 ppm1    1.609 ppm2  1.842

TABLE 13-continued

Unambiguous NOE Distance Restraints

ASSI {10202}
((segid "PROT" and resid 39 and name HG1))
((segid "PROT" and resid 39 and name HA))
  2.700  1.800  1.800 peak    10202 weight  0.10000E+01 volume  0.28740E+01 ppm1    1.623 ppm2  4.451
ASSI {10212}
((segid "PROT" and resid 39 and name HG2))
((segid "PROT" and resid 39 and name HA))
  2.500  1.600  1.600 peak    10212 weight  0.10000E+01 volume  0.46613E+01 ppm1    1.470 ppm2  4.449
ASSI {10612}
(segid "PROT" and resid 102 and name HD1%)
((segid "PROT" and resid 34 and name HZ))
  2.500  1.600  1.600 peak    10612 weight  0.10000E+01 volume  0.42774E+01 ppm1    0.762 ppm2  7.257
ASSI {10622}
(segid "PROT" and resid 102 and name HD1%)
(segid "PROT" and resid 34 and name HD%)
  2.500  1.600  1.600 peak    10622 weight  0.10000E+01 volume  0.45270E+01 ppm1    0.763 ppm2  7.189
OR {10622}
(segid "PROT" and resid 102 and name HD1%)
(segid "PROT" and resid 34 and name HE%)
ASSI {10642}
((segid "PROT" and resid 57 and name HG1))
((segid "PROT" and resid 37 and name HA))
  2.400  1.400  1.400 peak    10642 weight  0.10000E+01 volume  0.51970E+01 ppm1    1.545 ppm2  4.249
ASSI {10822}
((segid "PROT" and resid 64 and name HG1))
((segid "PROT" and resid 64 and name HB1))
  2.100  1.100  1.100 peak    10822 weight  0.10000E+01 volume  0.11069E+02 ppm1    1.647 ppm2  2.091
ASSI {10832}
((segid "PROT" and resid 6 and name HG1))
((segid "PROT" and resid 6 and name HB1))
  2.000  1.000  1.000 peak    10832 weight  0.10000E+01 volume  0.14254E+02 ppm1    1.459 ppm2  1.889
OR {10832}
((segid "PROT" and resid 6 and name HG2))
((segid "PROT" and resid 6 and name HB1))
ASSI {10842}
((segid "PROT" and resid 64 and name HG1))
((segid "PROT" and resid 64 and name HD1))
  1.900  0.900  0.900 peak    10842 weight  0.10000E+01 volume  0.24855E+02 ppm1    1.623 ppm2  1.783
ASSI {10892}
((segid "PROT" and resid 19 and name HG1))
(segid "PROT" and resid 63 and name HD1%)
  2.400  1.400  1.400 peak    10892 weight  0.10000E+01 volume  0.52665E+01 ppm1    1.302 ppm2  0.919
ASSI {11172}
(segid "PROT" and resid 22 and name HD2%)
(segid "PROT" and resid 74 and name HE%)
  2.400  2.400  2.100 peak    11172 weight  0.10000E+01 volume  0.54920E+01 ppm1    1.050 ppm2  6.962
ASSI {11252}
(segid "PROT" and resid 22 and name HD2%)
(segid "PROT" and resid 25 and name HG1%)
  2.600  1.700  1.700 peak    11252 weight  0.10000E+01 volume  0.33026E+01 ppm1    1.054 ppm2  1.253
ASSI {11392}
((segid "PROT" and resid 109 and name HG1))
((segid "PROT" and resid 109 and name HB1))
  2.200  1.200  1.200 peak    11392 weight  0.10000E+01 volume  0.98792E+01 ppm1    0.815 ppm2  1.750
ASSI {11712}
(segid "PROT" and resid 38 and name HG1%)
(segid "PROT" and resid 46 and name HE%)
  2.600  1.700  1.700 peak    11712 weight  0.10000E+01 volume  0.34807E+01 ppm1    0.496 ppm2  5.996
ASSI {11822}
(segid "PROT" and resid 41 and name HG2%)
((segid PROT" and resid 42 and name HG2))
  2.800  2.000  2.000 peak    11822 weight  0.10000E+01 volume  0.20436E+01 ppm1    1.342 ppm2  2.237
OR {11822}
(segid "PROT" and resid 41 and name HG2%)
((segid "PROT" and resid 42 and name HB1))
ASSI {12062}
(segid "PROT" and resid 81 and name HG2%)
((segid "PROT" and resid 56 and name HG))
  2.800  2.000  2.000 peak    12062 weight  0.1.0000E+01 volume  0.19114E+01 ppm1    0.159 ppm2  1.772
ASSI {12272}
(segid "PROT" and resid 49 and name HG2%)
(segid "PROT" and resid 88 and name HD%)
  2.600  1.700  1.700 peak    12272 weight  0.10000E+01 volume  0.34730E+01 ppm1    0.946 ppm2  6.976
ASSI {12392}
(segid "PROT" and resid 18 and name HD2%)
(segid "PROT" and resid 74 and name HE%)
  2.700  1.800  1.800 peak    12392 weight  0.10000E+01 volume  0.28804E+01 ppm1  −0.158 ppm2  6.969

TABLE 13-continued

| Unambiguous NOE Distance Restraints |
| --- |

ASSI {12842}
(segid "PROT" and resid 110 and name HG2%)
(segid "PROT" and resid 21 and name HG2%)
 2.400  1.400   1.400 peak    12842 weight  0.10000E+01 volume   0.57140E+01 ppm1    0.693 ppm2  1.023
ASSI {13192}
(segid "PROT" and resid 21 and name HG2%)
(segid "PROT" and resid 110 and name HD1%)
 2.800  2.000   2.000 peak    13192 weight  0.10000E+01 volume   0.20914E+01 ppm1    1.018 ppm2  0.571
ASSI {13312}
(segid "PROT" and resid 75 and name HE%)
((segid "PROT" and resid 79 and name HG1))
 2.800  2.000   2.000 peak    13312 weight  0.10000E+01 volume   0.21237E+01 ppm1    2.092 ppm2  2.493
ASSI {13522}
(segid "PROT" and resid 59 and name HE%)
(segid "PROT" and resid 74 and name HE%)
 2.500  1.600   1.600 peak    13522 weight  0.10000E+01 volume   0.46777E+01 ppm1    1.309 ppm2  6.967
ASSI {13532}
(segid "PROT" and resid 59 and name HE%)
(segid "PROT" and resid 74 and name HD%)
 2.800  2.000   2.000 peak    13532 weight  0.10000E+01 volume   0.22023E+01 ppm1    1.313 ppm2  6.438
ASSI {13882}
(segid "PROT" and resid 101 and name HD1%)
((segid "PROT" and resid 97 and name HE1))
 3.000  2.200   2.200 peak    13882 weight  0.10000E+01 volume   0.15141E+01 ppm1    0.992 ppm2  3.007
ASSI {14042}
(segid "PROT" and resid 116 and name HD1%)
((segid "PROT" and resid 75 and name HB1))
 2.900  2.100   2.100 peak    14042 weight  0.10000E+01 volume   0.17704E+01 ppm1    0.827 ppm2  2.933
ASSI {14122}
(segid "PROT" and resid 116 and name HD1%)
((segid "PROT" and resid 110 and name HG12))
 2.600  1.700   1.700 peak    14122 weight  0.10000E+01 volume   0.30126E+01 ppm1    0.821 ppm2  1.083
ASSI {14172}
(segid "PROT" and resid 110 and name HD1%)
(segid "PROT" and resid 107 and name HD%)
 2.700  1.800   1.800 peak    14172 weight  0.10000E+01 volume   0.25688E+01 ppm1    0.568 ppm2  7.237
ASSI {14532}
(segid "PROT" and resid 17 and name HG2%)
(segid "PROT" and resid 18 and name HD1%)
 3.100  2.400   2.400 peak    14532 weight  0.10000E+01 volume   0.11123E+01 ppm1    1.184 ppm2  0.520
ASSI {15272}
(segid "PROT" and resid 81 and name HG1%)
(segid "PROT" and resid 34 and name HD%)
 3.200  2.600   2.300 peak    15272 weight  0.10000E+01 volume   0.91000E+00 ppm1    0.499 ppm2  7.183
OR {15272}
(segid "PROT" and resid 81 and name HG1%)
(segid "PROT" and resid 34 and name HE%)
ASSI {15312}
(segid "PROT" and resid 38 and name HG2%)
(segid "PROT" and resid 46 and name HE%)
 3.000  2.200   2.200 peak    15312 weight  0.10000E+01 volume   0.14457E+01 ppm1   −0.010 ppm2  5.996
ASSI {15362}
(segid "PROT" and resid 38 and name HG2%)
((segid "PROT" and resid 46 and name HB1))
 3.100  2.400   2.400 peak    15362 weight  0.10000E+01 volume   0.10649E+01 ppm1   −0.007 ppm2  2.757
ASSI {15892}
(segid "PROT" and resid 56 and name HD2%)
(segid "PROT" and resid 25 and name HG1%)
 3.100  2.400   2.400 peak    15892 weight  0.10000E+01 volume   0.10650E+01 ppm1    0.679 ppm2  1.248
ASSI {16042}
((segid "PROT" and resid 63 and name HB2))
((segid "PROT" and resid 60 and name HB1))
 3.200  2.600   2.300 peak    16042 weight  0.10000E+01 volume   0.96490E+00 ppm1    1.967 ppm2  4.248
ASSI {16132}
(segid "PROT" and resid 63 and name HD2%)
(segid "PROT" and resid 74 and name HD%)
 3.100  2.400   2.400 peak    16132 weight  0.10000E+01 volume   0.11722E+01 ppm1    1.080 ppm2  6.426
ASSI {16252}
(segid "PROT" and resid 73 and name HD2%)
((segid "PROT" and resid 70 and name HB2))
 3.200  2.600   2.300 peak    16252 weight  0.10000E+01 volume   0.96550E+00 ppm1    0.929 ppm2  3.790
ASSI {16922}
(segid "PROT" and resid 50 and name HD1%)
(segid "PROT" and resid 88 and name HD%)
 3.000  2.200   2.200 peak    16922 weight  0.10000E+01 volume   0.13378E+01 ppm1    0.582 ppm2  6.971

TABLE 13-continued

Unambiguous NOE Distance Restraints

ASSI {17102}
(segid "PROT" and resid 101 and name HG2%)
((segid "PROT" and resid 29 and name HB1))
  3.400  2.900  2.100 peak     17102 weight  0.10000E+01 volume  0.61290E+00 ppm1     1.029  ppm2    2.109
ASSI {17302}
((segid "PROT" and resid 116 and name HB))
(segid "PROT" and resid 110 and name HG2%)
  3.300  2.700  2.200 peak     17302 weight  0.10000E+01 volume  0.80280E+00 ppm1     1.852  ppm2    0.694
ASSI {18462}
((segid "PROT" and resid 54 and name HB1))
(segid "PROT" and resid 58 and name HG2%)
  3.400  2.900  2.100 peak     18462 weight  0.10000E+01 volume  0.64170E+00 ppm1     2.058  ppm2    1.120
ASSI {18482}
(segid "PROT" and resid 59 and name HE%)
(segid "PROT" and resid 18 and name HD2%)
  3.400  2.900  2.100 peak     18482 weight  0.10000E+01 volume  0.60840E+00 ppm1     1.306  ppm2  −0.172
ASSI {18852}
((segid "PROT" and resid 64 and name HA))
((segid "PROT" and resid 64 and name HB1))
  2.100  1.100  1.100 peak     18852 weight  0.10000E+01 volume  0.11301E+02 ppm1     4.374  ppm2    2.092
ASSI {19072}
((segid "PROT" and resid 45 and name HA1))
((segid "PROT" and resid 44 and name HA))
  3.300  2.700  2.200 peak     19072 weight  0.10000E+01 volume  0.78950E+00 ppm1     3.907  ppm2    4.526
ASSI {19292}
((segid "PROT" and resid 97 and name HG1))
((segid "PROT" and resid 97 and name HB1))
  2.200  1.200  1.200 peak     19292 weight  0.10000E+01 volume  0.81546E+01 ppm1     1.853  ppm2    2.117
ASSI {19312}
((segid "PROT" and resid 97 and name HG2))
((segid "PROT" and resid 97 and name HB1))
  2.300  1.300  1.300 peak     19312 weight  0.10000E+01 volume  0.65967E+01 ppm1     1.608  ppm2    2.109
ASSI {19392}
(segid "PROT" and resid 49 and name HG1%)
((segid "PEPT" and resid 202 and name HB1))
  2.700  1.800  1.800 peak     19392 weight  0.10000E+01 volume  0.25893E+01 ppm1     0.974  ppm2    3.133
ASSI {19542}
((segid "PROT" and resid 53 and name HD2))
((segid "PROT" and resid 51 and name HB2))
  3.500  3.100  2.000 peak     19542 weight  0.10000E+01 volume  0.55650E+00 ppm1     3.438  ppm2    1.208
OR {19542}
((segid "PROT" and resid 53 and name HD2))
((segid "PROT" and resid 51 and name HG2))
ASSI {19902}
(segid "PROT" and resid 49 and name HG2%)
(segid "PEPT" and resid 202 and name HD%)
  2.800  2.000  2.000 peak     19902 weight  0.10000E+01 volume  0.19805E+01 ppm1     0.950  ppm2    7.165
ASSI {20122}
((segid "PROT" and resid 36 and name HB1))
((segid "PROT" and resid 37 and name HD1))
  2.500  1.600  1.600 peak     20122 weight  0.10000E+01 volume  0.43249E+01 ppm1     2.155  ppm2    3.703
ASSI {20352}
((segid "PROT" and resid 82 and name HB2))
(segid "PROT" and resid 82 and name HE%)
  3.500  3.100  2.000 peak     20352 weight  0.10000E+01 volume  0.57940E+00 ppm1     3.014  ppm2    6.489
ASSI {20372}
((segid "PROT" and resid 106 and name HB1))
(segid "PROT" and resid 82 and name HE%)
  3.100  2.400  2.400 peak     20372 weight  0.10000E+01 volume  0.12466E+01 ppm1     3.360  ppm2    6.464
ASSI {20402}
((segid "PROT" and resid 106 and name HA))
(segid "PROT" and resid 110 and name HG2%)
  3.500  3.100  2.000 peak     20402 weight  0.10000E+01 volume  0.59050E+00 ppm1     4.003  ppm2    0.702
ASSI {20782}
(segid "PROT" and resid 38 and name HG2%)
((segid "PROT" and resid 39 and name HG2))
  3.300  2.700  2.200 peak     20782 weight  0.10000E+01 volume  0.72730E+00 ppm1   −0.003  ppm2    1.478
ASSI {20982}
((segid "PROT" and resid 26 and name HG1))
((segid "PROT" and resid 35 and name HG1))
  3.200  2.600  2.300 peak     20982 weight  0.10000E+01 volume  0.10083E+01 ppm1     1.534  ppm2    2.892
ASSI {21042}
(segid "PROT" and resid 50 and name HD1%)
(segid "PROT" and resid 88 and name HE%)
  3.300  2.700  2.200 peak     21042 weight  0.10000E+01 volume  0.73200E+00 ppm1     0.582  ppm2    6.661

TABLE 13-continued

Unambiguous NOE Distance Restraints

ASSI {21132}
(segid "PROT" and resid 116 and name HD1%)
(segid "PROT" and resid 107 and name HD%)
 3.000  2.200  2.200 peak      21132 weight 0.10000E+01 volume  0.14426E+01 ppm1   0.827 ppm2   7.236
ASSI {21212}
(segid "PROT" and resid 21 and name HD1%)
((segid "PROT" and resid 74 and name HB1))
 3.200  2.600  2.300 peak      21212 weight 0.10000E+01 volume  0.96830E+00 ppm1   0.656 ppm2   3.041
ASSI {21232}
(segid "PROT" and resid 21 and name HD1%)
((segid "PROT" and resid 17 and name HB))
 3.100  2.400  2.400 peak      21232 weight 0.10000E+01 volume  0.11130E+01 ppm1   0.652 ppm2   4.288
ASSI {21342}
(segid "PROT" and resid 35 and name HE%)
((segid "PROT" and resid 32 and name HH2))
 3.500  3.100  2.000 peak      21342 weight 0.10000E+01 volume  0.55660E+00 ppm1   2.216 ppm2   7.208
ASSI {21352}
(segid "PROT" and resid 75 and name HE%)
(segid "PROT" and resid 78 and name HD1%)
 3.500  3.100  2.000 peak      21352 weight 0.10000E+01 volume  0.57510E+00 ppm1   2.099 ppm2   0.091
ASSI {21362}
(segid "PROT" and resid 75 and name HE%)
(segid "PROT" and resid 21 and name HG2%)
 3.500  3.100  2.000 peak      21362 weight 0.10000E+01 volume  0.58360E+00 ppm1   2.096 ppm2   1.033
ASSI {21372}
(segid "PROT" and resid 75 and name HE%)
((segid "PROT" and resid 110 and name HG12))
 3.400  2.900  2.100 peak      21372 weight 0.10000E+01 volume  0.62060E+00 ppm1   2.096 ppm2   1.085
ASSI {21412}
(segid "PROT" and resid 75 and name HE%)
(segid "PROT" and resid 74 and name HD%)
 3.700  3.400  1.800 peak      21412 weight 0.10000E+01 volume  0.41590E+00 ppm1   2.095 ppm2   6.444
ASSI {21452}
(segid "PROT" and resid 21 and name HG2%)
(segid "PROT" and resid 74 and name HD%)
 3.400  2.900  2.100 peak      21452 weight 0.10000E+01 volume  0.69490E+00 ppm1   1.011 ppm2   6.431
ASSI {21502}
(segid "PROT" and resid 101 and name HG2%)
(segid "PROT" and resid 102 and name HD2%)
 2.500  1.600  1.600 peak      21502 weight 0.10000E+01 volume  0.44117E+01 ppm1   1.031 ppm2   0.764
OR {21502)}
(segid "PROT" and resid 101 and name HG2%)
(segid "PROT" and resid 102 and name HD1%)
ASSI {21572}
(segid "PROT" and resid 116 and name HG2%)
((segid "PROT" and resid 117 and name HA))
 3.400  2.900  2.100 peak      21572 weight 0.10000E+01 volume  0.69010E+00 ppm1   0.856 ppm2   4.600
ASSI {21612}
(segid "PROT" and resid 99 and name HB%)
((segid "PROT" and resid 33 and name HG2))
 3.700  3.400  1.800 peak      21612 weight 0.10000E+01 volume  0.42110E+00 ppm1   1.661 ppm2  −0.880
ASSI {21642}
(segid "PROT" and resid 76 and name HB%)
((segid "PROT" and resid 72 and name HD1))
 2.300  2.300  2.200 peak      21642 weight 0.10000E+01 volume  0.65500E+01 ppm1   1.523 ppm2   1.658
ASSI {21742}
(segid "PROT" and resid 99 and name HB%)
((segid "PROT" and resid 85 and name HA))
 3.400  2.900  2.100 peak      21742 weight 0.10000E+01 volume  0.65540E+00 ppm1   1.659 ppm2   4.510
ASSI {21812}
(segid "PROT" and resid 110 and name HG2%)
(segid "PROT" and resid 113 and name HB%)
 2.900  2.100  2.100 peak      21812 weight 0.10000E+01 volume  0.18327E+01 ppm1   0.692 ppm2   1.411
ASSI {21822}
(segid "PROT" and resid 69 and name HG2%)
((segid "PROT" and resid 14 and name HB1))
 3.100  2.400  2.400 peak      21822 weight 0.10000E+01 volume  0.12228E+01 ppm1   0.861 ppm2   1.850
ASSI {21832}
(segid "PROT" and resid 69 and name HG2%)
((segid "PROT" and resid 68 and name HA))
 3.400  2.900  2.100 peak      21832 weight 0.10000E+01 volume  0.62230E+00 ppm1   0.861 ppm2   4.575
ASSI {21872}
(segid "PROT" and resid 113 and name HB%)
(segid "PROT" and resid 110 and name HD1%)
 3.000  2.200  2.200 peak      21872 weight 0.10000E+01 volume  0.12843E+01 ppm1   1.412 ppm2   0.572

TABLE 13-continued

Unambiguous NOE Distance Restraints

ASSI {21902}
(segid "PROT" and resid 113 and name HB%)
((segid "PROT" and resid 17 and name HA))
 3.000  2.200  2.200 peak    21902 weight  0.10000E+01 volume  0.13747E+01 ppm1   1.409 ppm2  3.966
ASSI {22082}
(segid "PROT" and resid 81 and name HG2%)
((segid "PROT" and resid 55 and name HB1))
 3.600  3.200  1.900 peak    22082 weight  0.10000E+01 volume  0.43360E+00 ppm1   0.155 ppm2  2.405
ASSI {22182}
(segid "PROT" and resid 56 and name HD2%)
((segid "PROT" and resid 78 and name HA))
 3.400  2.900  2.100 peak    22182 weight  0.10000E+01 volume  0.66210E+00 ppm1   0.675 ppm2  3.414
ASSI {22202}
(segid "PROT" and resid 56 and name HD2%)
(segid "PROT" and resid 34 and name HD%)
 3.500  3.100  2.000 peak    22202 weight  0.10000E+01 volume  0.59280E+00 ppm1   0.675 ppm2  7.196
OR {22202}
(segid "PROT" and resid 56 and name HD2%)
(segid "PROT" and resid 34 and name HE%)
ASSI {22212}
(segid "PROT" and resid 25 and name HG1%)
(segid "PROT" and resid 82 and name HE%)
 3.200  2.600  2.300 peak    22212 weight  0.10000E+01 volume  0.89620E+00 ppm1   1.241 ppm2  6.454
ASSI {22352}
(segid "PROT" and resid 22 and name HD2%)
(segid "PROT" and resid 74 and name HD%)
 3.300  2.700  2.200 peak    22352 weight  0.10000E+01 volume  0.78330E+00 ppm1   1.052 ppm2  6.445
ASSI {22472}
(segid "PROT" and resid 102 and name HD2%)
((segid "PROT" and resid 31 and name HA))
 2.600  1.700  1.700 peak    22472 weight  0.10000E+01 volume  0.31247E+01 ppm1   0.765 ppm2  4.437
ASSI {22502}
(segid "PROT" and resid 78 and name HD2%)
(segid "PROT" and resid 82 and name HD%)
 3.300  2.700  2.200 peak    22502 weight  0.10000E+01 volume  0.80400E+00 ppm1   0.199 ppm2  6.702
ASSI {22602}
(segid "PROT" and resid 102 and name HD1%)
(segid "PROT" and resid 82 and name HD%)
 3.500  3.100  2.000 peak    22602 weight  0.10000E+01 volume  0.58490E+00 ppm1   0.762 ppm2  6.676
ASSI {22622}
((segid "PROT" and resid 57 and name HG1))
((segid "PROT" and resid 57 and name HD2))
 3.100  2.400  2.400 peak    22622 weight  0.10000E+01 volume  0.12324E+01 ppm1   1.569 ppm2  0.932
ASSI {22632}
((segid "PROT" and resid 111 and name HG1))
((segid "PROT" and resid 116 and name HG12))
 3.200  2.600  2.300 peak    22632 weight  0.10000E+01 volume  0.10190E+01 ppm1   1.464 ppm2  0.938
ASSI {22672}
(segid "PROT" and resid 115 and name HD1%)
((segid "PROT" and resid 75 and name HG2))
 3.200  2.600  2.300 peak    22672 weight  0.10000E+01 volume  0.10174E+01 ppm1   0.744 ppm2  2.225
ASSI {22782}
((segid "PROT" and resid 33 and name HG1))
(segid "PROT" and resid 95 and name HD%)
 3.400  2.900  2.100 peak    22782 weight  0.10000E+01 volume  0.69740E+00 ppm1   0.267 ppm2  6.866
ASSI {22812}
(segid "PROT" and resid 73 and name HD1%)
((segid "PROT" and resid 69 and name HB))
 3.100  2.400  2.400 peak    22812 weight  0.10000E+01 volume  0.12027E+01 ppm1   0.970 ppm2  2.351
ASSI {22872}
(segid "PROT" and resid 78 and name HD1%)
((segid "PROT" and resid 106 and name HA))
 3.100  2.400  2.400 peak    22872 weight  0.10000E+01 volume  0.10589E+01 ppm1   0.094 ppm2  3.962
ASSI {22882}
(segid "PROT" and resid 78 and name HD1%)
((segid "PROT" and resid 22 and name HA))
 3.300  2.700  2.200 peak    22882 weight  0.10000E+01 volume  0.75140E+00 ppm1   0.089 ppm2  4.153
ASSI {22922}
(segid "PROT" and resid 22 and name HD1%)
(segid "PROT" and resid 63 and name HB1))
 3.000  2.200  2.200 peak    22922 weight  0.10000E+01 volume  0.14674E+01 ppm1   1.109 ppm2  2.349
ASSI {23192}
((segid "PROT" and resid 66 and name HG2))
((segid "PROT" and resid 69 and name HB))
 3.500  3.100  2.000 peak    23192 weight  0.10000E+01 volume  0.59710E+00 ppm1   1.566 ppm2  2.327

TABLE 13-continued

Unambiguous NOE Distance Restraints

ASSI {23212}
((segid "PROT" and resid 53 and name HG1))
(segid "PROT" and resid 46 and name HE%)
 3.200  2.600  2.300 peak   23212 weight 0.10000E+01 volume 0.94430E+00 ppm1  2.282 ppm2  5.997
ASSI {23222}
((segid "PROT" and resid 53 and name HG2))
(segid "PROT" and resid 46 and name HE%)
 3.200  2.600  2.300 peak   23222 weight 0.10000E+01 volume 0.88660E+00 ppm1  1.933 ppm2  5.988
ASSI {23392}
((segid "PROT" and resid 87 and name HB1))
(segid "PROT" and resid 83 and name HG2%)
 3.400  2.900  2.100 peak   23392 weight 0.10000E+01 volume 0.68860E+00 ppm1  2.232 ppm2  1.344
ASSI {23482}
((segid "PROT" and resid 54 and name HB2))
((segid "PROT" and resid 80 and name HG1))
 3.000  2.200  2.200 peak   23482 weight 0.10000E+01 volume 0.12929E+01 ppm1  1.385 ppm2  1.761
ASSI {23502}
((segid "PROT" and resid 86 and name HB1))
((segid "PROT" and resid 86 and name HG2))
 3.000  2.200  2.200 peak   23502 weight 0.10000E+01 volume 0.14819E+01 ppm1  1.812 ppm2  0.171
ASSI {23522}
((segid "PROT" and resid 28 and name HB1))
((segid "PROT" and resid 32 and name HE3))
 3.500  3.100  2.000 peak   23522 weight 0.10000E+01 volume 0.55110E+00 ppm1  3.026 ppm2  7.342
ASSI {23582}
((segid "PROT" and resid 19 and name HB2))
((segid "PROT" and resid 19 and name HE1))
 3.300  2.700  2.200 peak   23582 weight 0.10000E+01 volume 0.79520E+00 ppm1  1.404 ppm2  2.976
ASSI {23592}
((segid "PROT" and resid 19 and name HB1))
((segid "PROT" and resid 19 and name HE1))
 3.200  2.600  2.300 peak   23592 weight 0.10000E+01 volume 0.88430E+00 ppm1  1.738 ppm2  2.961
ASSI {23652}
((segid "PROT" and resid 38 and name HB))
(segid "PROT" and resid 50 and name HG2%)
 3.400  2.900  2.100 peak   23652 weight 0.10000E+01 volume 0.65450E+00 ppm1  1.073 ppm2  0.414
ASSI {23752}
((segid "PROT" and resid 75 and name HB2))
(segid "PROT" and resid 115 and name HD1%)
 3.500  3.100  2.000 peak   23752 weight 0.10000E+01 volume 0.54290E+00 ppm1  2.655 ppm2  0.763
OR {23752}
((segid "PROT" and resid 75 and name HB2))
(segid "PROT" and resid 115 and name HD2%)
ASSI {23762}
((segid "PROT" and resid 59 and name HG1))
((segid "PROT" and resid 62 and name HG1))
 3.500  3.100  2.000 peak   23762 weight 0.10000E+01 volume 0.57320E+00 ppm1  2.654 ppm2  1.727
ASSI {23852}
((segid "PROT" and resid 49 and name HB))
((segid "PROT" and resid 46 and name HA))
 3.400  2.900  2.100 peak   23852 weight 0.10000E+01 volume 0.63410E+00 ppm1  1.926 ppm2  3.509
ASSI {23872}
((segid "PROT" and resid 49 and name HB))
((segid "PROT" and resid 84 and name HB1))
 3.400  2.900  2.100 peak   23872 weight 0.10000E+01 volume 0.68110E+00 ppm1  1.930 ppm2  3.009
ASSI {23912}
((segid "PROT" and resid 49 and name HB))
(segid "PROT" and resid 88 and name HD%)
 3.300  2.700  2.200 peak   23912 weight 0.10000E+01 volume 0.79550E+00 ppm1  1.932 ppm2  6.968
ASSI {24042}
((segid "PROT" and resid 110 and name HB))
(segid "PROT" and resid 113 and name HB%)
 3.200  2.600  2.300 peak   24042 weight 0.10000E+01 volume 0.99190E+00 ppm1  1.794 ppm2  1.406
ASSI {24092}
((segid "PROT" and resid 21 and name HB))
(segid "PROT" and resid 17 and name HG2%)
 3.400  2.900  2.100 peak   24092 weight 0.10000E+01 volume 0.66400E+00 ppm1  1.950 ppm2  1.168
ASSI {24192}
((segid "PROT" and resid 101 and name HB))
(segid "PROT" and resid 102 and name HD1%)
 3.500  3.100  2.000 peak   24192 weight 0.10000E+01 volume 0.56440E+00 ppm1  1.947 ppm2  0.778
OR {24192}
((segid "PROT" and resid 101 and name HB))
(segid "PROT" and resid 102 and name HD2%)

TABLE 13-continued

Unambiguous NOE Distance Restraints

ASSI {24262}
((segid "PROT" and resid 18 and name HB2))
(segid "PROT" and resid 74 and name HE%)
  3.400  2.900  2.100 peak    24262  weight  0.10000E+01 volume  0.67690E+00 ppm1    0.347  ppm2  6.978
ASSI {24492}
((segid "PROT" and resid 51 and name HD1))
((segid "PROT" and resid 80 and name HD1))
  2.400  1.400  1.400 peak    24492  weight  0.10000E+01 volume  0.59941E+01 ppm1    3.020  ppm2  3.406
ASSI {24622}
((segid "PROT" and resid 43 and name HA))
((segid "PROT" and resid 42 and name HA))
  3.400  2.900  2.100 peak    24622  weight  0.10000E+01 volume  0.67930E+00 ppm1    4.987  ppm2  4.480
ASSI {24632}
((segid "PROT" and resid 33 and name HD1))
((segid "PROT" and resid 32 and name HE3))
  3.300  2.700  2.200 peak    24632  weight  0.10000E+01 volume  0.73690E+00 ppm1    2.265  ppm2  7.320
ASSI {24672}
((segid "PROT" and resid 8 and name HD2))
(segid "PROT" and resid 115 and name HD1%)
  3.300  2.700  2.200 peak    24672  weight  0.10000E+01 volume  0.74890E+00 ppm1    3.713  ppm2  0.781
OR {24672}
((segid "PROT" and resid 8 and name HD2))
(segid "PROT" and resid 115 and name HD2%)
ASSI {24682}
((segid "PROT" and resid 89 and name HA))
((segid "PROT" and resid 90 and name HB2))
  3.100  2.400  2.400 peak    24682  weight  0.10000E+01 volume  0.11403E+01 ppm1    5.093  ppm2  2.202
ASSI {24902}
((segid "PROT" and resid 34 and name HA))
(segid "PROT" and resid 102 and name HD1%)
  3.400  2.900  2.100 peak    24902  weight  0.10000E+01 volume  0.62620E+00 ppm1    5.008  ppm2  0.773
ASSI {24942}
((segid "PROT" and resid 100 and name HA))
((segid "PROT" and resid 86 and name HE2))
  3.100  2.400  2.400 peak    24942  weight  0.10000E+01 volume  0.12073E+01 ppm1    4.380  ppm2  2.466
OR {24942}
((segid "PROT" and resid 100 and name HA))
((segid "PROT" and resid 86 and name HE1))
AASI {24972}
((segid "PROT" and resid 39 and name HA))
((segid "PROT" and resid 39 and name HB2))
  2.500  1.600  1.600 peak    24972  weight  0.10000E+01 volume  0.46002E+01 ppm1    4.444  ppm2  1.935
ASSI {25082}
((segid "PROT" and resid 77 and name HA))
(segid "PROT" and resid 59 and name HE%)
  3.300  2.700  2.200 peak    25082  weight  0.10000E+01 volume  0.74310E+00 ppm1    4.400  ppm2  1.310
ASSI {25282}
((segid "PROT" and resid 26 and name HA))
(segid "PROT" and resid 25 and name HG2%)
  2.900  2.100  2.100 peak    25282  weight  0.10000E+01 volume  0.18601E+01 ppm1    3.928  ppm2  1.068
ASSI {25372}
((segid "PROT" and resid 16 and name HB2))
((segid "PROT" and resid 19 and name HD1))
  3.100  2.400  2.400 peak    25372  weight  0.10000E+01 volume  0.10814E+01 ppm1    3.953  ppm2  1.636
ASSI {25382}
((segid "PROT" and resid 46 and name HA))
(segid "PROT" and resid 38 and name HG2%)
  3.600  3.200  1.900 peak    25382  weight  0.10000E+01 volume  0.49500E+00 ppm1    3.505  ppm2  −0.005
ASSI {25562}
((segid "PROT" and resid 38 and name HA))
((segid "PROT" and resid 39 and name HB2))
  3.400  2.900  2.100 peak    25562  weight  0.10000E+01 volume  0.71250E+00 ppm1    3.491  ppm2  1.940
ASSI {25622}
((segid "PROT" and resid 21 and name HA))
(segid "PROT" and resid 17 and name HG2%)
  3.400  2.900  2.100 peak    25622  weight  0.10000E+01 volume  0.65110E+00 ppm1    3.795  ppm2  1.169
ASSI {25702}
((segid "PROT" and resid 25 and name HA))
((segid "PROT" and resid 26 and name HB1))
  3.500  3.100  2.000 peak    25702  weight  0.10000E+01 volume  0.52050E+00 ppm1    3.863  ppm2  1.890
ASSI {25732}
((segid "PROT" and resid 17 and name HB))
(segid "PROT" and resid 115 and name HD2%)
  3.200  2.600  2.300 peak    25732  weight  0.10000E+01 volume  0.89690E+00 ppm1    4.292  ppm2  0.754
OR {25732}
((segid "PROT" and resid 17 and name HB))
(segid "PROT" and resid 115 and name HD1%)

TABLE 13-continued

Unambiguous NOE Distance Restraints

ASSI {25822}
((segid "PROT" and resid 43 and name HA))
((segid "PEPT" and resid 204 and name HA))
  3.400  2.900   2.100 peak     25822 weight  0.10000E+01 volume   0.68700E+00 ppm1     4.984  ppm2   4.392
ASSI {26032}
(segid "PROT" and resid 99 and name HB%)
(segid "PROT" and resid 96 and name HE%)
  3.200  2.600   2.300 peak     26032 weight  0.10000E+01 volume   0.87540E+00 ppm1     1.670  ppm2   7.060
ASSI {26052}
((segid "PROT" and resid 113 and name HA))
(segid "PROT" and resid 21 and name HD1%)
  3.500  3.100   2.000 peak     26052 weight  0.10000E+01 volume   0.52350E+00 ppm1     4.340  ppm2   0.652
ASSI {26212}
(segid "PROT" and resid 18 and name HD1%)
(segid "PROT" and resid 78 and name HD1%)
  3.600  3.200   1.900 peak     26212 weight  0.10000E+01 volume   0.49240E+00 ppm1     0.517  ppm2   0.083
ASSI {26252}
((segid "PROT" and resid 94 and name HA))
((segid "PROT" and resid 93 and name HA))
  3.100  2.400   2.400 peak     26252 weight  0.10000E+01 volume   0.11336E+01 ppm1     4.226  ppm2   4.535
ASSI {26402}
((segid "PROT" and resid 33 and name HD2))
(segid "PROT" and resid 34 and name HD%)
  3.100  2.400   2.400 peak     26402 weight  0.10000E+01 volume   0.10972E+01 ppm1     1.563  ppm2   7.197
OR {26402}
((segid "PROT" and resid 33 and name HD2))
(segid "PROT" and resid 34 and name HE%)
ASSI {26472}
(segid "PROT" and resid 35 and name HE%)
((segid "PROT" and resid 34 and name HB2))
  3.400  2.900   2.100 peak     26472 weight  0.10000E+01 volume   0.63450E+00 ppm1     2.211  ppm2   2.595
ASSI {26652}
((segid "PROT" and resid 18 and name HA))
((segid "PROT" and resid 22 and name HB1))
  3.500  3.100   2.000 peak     26652 weight  0.10000E+01 volume   0.57230E+00 ppm1     3.303  ppm2   2.087
ASSI {26672}
((segid "PROT" and resid 6 and name HA))
((segid "PROT" and resid 117 and name HB1))
  3.400  2.900   2.100 peak     26672 weight  0.10000E+01 volume   0.65680E+00 ppm1     4.374  ppm2   2.708
ASSI {26742}
((segid "PROT" and resid 80 and name HB2))
((segid "PROT" and resid 81 and name HA))
  2.800  2.000   2.000 peak     26742 weight  0.10000E+01 volume   0.21410E+01 ppm1     1.935  ppm2   3.165
ASSI {26752}
((segid "PROT" and resid 75 and name HB2))
((segid "PROT" and resid 115 and name HB2))
  3.500  3.100   2.000 peak     26752 weight  0.10000E+01 volume   0.53270E+00 ppm1     2.645  ppm2   1.628
ASSI {26782}
((segid "PROT" and resid 9 and name HD1))
((segid "PROT" and resid 8 and name HD2))
  3.100  2.400   2.400 peak     26782 weight  0.10000E+01 volume   0.11437E+01 ppm1     3.215  ppm2   3.740
ASSI {3}
((segid "PEPT" and resid 205 and name HZ))
(segid "PROT" and resid 38 and name HG1%)
  2.700  1.800   1.800 peak        3 weight  0.10000E+01 volume   0.10950E+02 ppm1     7.879  ppm2   0.468
ASSI {13}
((segid "PEPT" and resid 205 and name HZ)
(segid "PROT" and resid 38 and name HG2%)
  3.400  2.900   2.100 peak       13 weight  0.10000E+01 volume   0.28090E+01 ppm1     7.879  ppm2  −0.020
ASSI {23}
((segid "PEPT" and resid 205 and name HZ))
((segid "PROT" and resid 38 and name HB))
  3.000  2.200   2.200 peak       23 weight  0.10000E+01 volume   0.54143E+01 ppm1     7.877  ppm2   1.049
ASSI {143}
((segid "PEPT" and resid 203 and name HN))
((segid "PEPT" and resid 203 and name HA1))
  3.700  3.400   1.800 peak      143 weight  0.10000E+01 volume   0.16378E+01 ppm1     8.295  ppm2   3.918
ASSI {163}
(segid "PEPT" and resid 202 and name HE%)
(segid "PROT" and resid 49 and name HG2%)
  3.100  2.400   2.400 peak      163 weight  0.10000E+01 volume   0.48713E+01 ppm1     6.846  ppm2   0.927
ASSI {183}
((segid "PEPT" and resid 204 and name HN))
((segid "PEPT" and resid 204 and name HA))
  3.300  2.700   2.200 peak      183 weight  0.10000E+01 volume   0.33794E+01 ppm1     8.095  ppm2   4.418

TABLE 13-continued

| Unambiguous NOE Distance Restraints |
|---|

ASSI {193}
((segid "PEPT" and resid 204 and name HN))
((segid "PEPT" and resid 203 and name HA1))
  3.000  2.200  2.200 peak      193 weight  0.10000E+01 volume  0.60320E+01 ppm1    8.095  ppm2  3.921
ASSI {213}
((segid "PEPT" and resid 204 and name HN))
((segid "PEPT" and resid 204 and name HB1))
  3.200  2.600  2.300 peak      213 weight  0.10000E+01 volume  0.40313E+01 ppm1    8.095  ppm2  1.862
ASSI {223}
((segid "PEPT" and resid 204 and name HN))
((segid "PEPT" and resid 204 and name HB2))
  3.100  2.400  2.400 peak      223 weight  0.10000E+01 volume  0.46608E+01 ppm1    8.094  ppm2  1.775
ASSI {233}
((segid "PEPT" and resid 204 and name HN))
((segid "PEPT" and resid 204 and name HG1))
  3.100  2.400  2.400 peak      233 weight  0.10000E+01 volume  0.42672E+01 ppm1    8.094  ppm2  1.644
ASSI {243}
((segid "PEPT" and resid 209 and name HE21))
((segid "PEPT" and resid 209 and name HE22))
  2.000  1.000  1.000 peak      243 weight  0.10000E+01 volume  0.62472E+02 ppm1    7.537  ppm2  6.862
ASSI {253}
((segid "PEPT" and resid 205 and name HZ))
((segid "PEPT" and resid 205 and name HE1))
  2.300  1.300  1.300 peak      253 weight  0.10000E+01 volume  0.24517E+02 ppm1    7.880  ppm2  3.072
ASSI {273}
((segid "PEPT" and resid 205 and name HZ))
((segid "PEPT" and resid 205 and name HD1))
  2.700  1.800  1.800 peak      273 weight  0.10000E+01 volume  0.10758E+02 ppm1    7.878  ppm2  1.415
ASSI {283}
((segid "PEPT" and resid 208 and name HN))
((segid "PEPT" and resid 207 and name HA))
  2.700  1.800  1.800 peak      283 weight  0.10000E+01 volume  0.10151E+02 ppm1    8.545  ppm2  4.296
ASSI {293}
((segid "PEPT" and resid 208 and name HN))
((segid "PEPT" and resid 208 and name HB1))
  2.900  2.100  2.100 peak      293 weight  0.10000E+01 volume  0.75665E+01 ppm1    8.544  ppm2  1.791
ASSI {303}
((segid "PEPT" and resid 208 and name HN))
((segid "PEPT" and resid 208 and name HG1))
  3.300  2.700  2.200 peak      303 weight  0.10000E+01 volume  0.32720E+01 ppm1    8.544  ppm2  1.613
ASSI {313}
((segid "PEPT" and resid 209 and name HN))
((segid "PEPT" and resid 208 and name HA))
  2.600  1.700  1.700 peak      313 weight  0.10000E+01 volume  0.14079E+02 ppm1    8.499  ppm2  4.310
ASSI {323}
((segid "PEPT" and resid 209 and name HN))
((segid "PEPT" and resid 208 and name HB1))
  2.700  1.800  1.800 peak      323 weight  0.10000E+01 volume  0.10348E+02 ppm1    8.498  ppm2  1.776
ASSI {333}
((segid "PEPT" and resid 207 and name HN))
((segid "PEPT" and resid 207 and name HA))
  2.500  1.600  1.600 peak      333 weight  0.10000E+01 volume  0.15139E+02 ppm1    8.450  ppm2  4.330
ASSI {343}
((segid "PEPT" and resid 207 and name HN))
((segid "PEPT" and resid 207 and name HB1))
  2.600  1.700  1.700 peak      343 weight  0.10000E+01 volume  0.12386E+02 ppm1    8.450  ppm2  1.805
ASSI {353}
((segid "PEPT" and resid 207 and name HN))
((segid "PEPT" and resid 206 and name HG1))
  3.300  2.700  2.200 peak      353 weight  0.10000E+01 volume  0.29440E+01 ppm1    8.451  ppm2  1.440
ASSI {363}
((segid "PEPT" and resid 205 and name HZ))
(segid "PEPT" and resid 205 and name HH%)
  2.100  1.100  1.100 peak      363 weight  0.10000E+01 volume  0.50754E+02 ppm1    7.876  ppm2  1.872
ASSI {373}
((segid "PEPT" and resid 205 and name HZ))
((segid "PEPT" and resid 204 and name HN))
  3.200  2.600  2.300 peak      373 weight  0.10000E+01 volume  0.40017E+01 ppm1    7.881  ppm2  8.105
ASSI {144}
(sagid "PEPT" and resid 202 and name HD%)
((segid "PEPT" and resid 202 and name HB2))
  2.700  1.800  1.800 peak      144 weight  0.10000E+01 volume  0.25326E+01 ppm1    7.133  ppm2  2.913
ASSI {154}
(segid "PEPT" and resid 202 and name HD%)
((segid "PEPT" and resid 202 and name HB1))
  2.700  1.800  1.800 peak      154 weight  0.10000E+01 volume  0.25762E+01 ppm1    7.134  ppm2  3.130

TABLE 13-continued

| Unambiguous NOE Distance Restraints |
|---|

ASSI {164}
(segid "PEPT" and resid 202 and name HD%)
((segid "PEPT" and resid 202 and name HA))
 2.700  1.800  1.800 peak        164 weight  0.10000E+01 volume  0.25087E+01 ppm1     7.134 ppm2  4.622
ASSI {184}
((segid "PEPT" and resid 205 and name HZ))
((segid "PEPT" and resid 205 and name HG1))
 2.900  2.100  2.100 peak        184 weight  0.10000E+01 volume  0.14841E+01 ppm1     7.882 ppm2  1.321
ASSI {194}
(segid "PROT" and resid 88 and name HD%)
((segid "PEPT" and resid 202 and name HB2))
 3.800  3.600  1.700 peak        194 weight  0.10000E+01 volume  0.29670E+00 ppm1     7.008 ppm2  2.919
ASSI {214}
((segid "PROT" and resid 89 and name HD22))
((segid "PEPT" and resid 205 and name HE1))
 3.400  2.900  2.100 peak        214 weight  0.10000E+01 volume  0.58630E+00 ppm1     7.822 ppm2  3.090
ASSI {264}
((segid "PEPT" and resid 209 and name HN))
((segid "PEPT" and resid 209 and name HB2))
 3.500  3.100  2.000 peak        264 weight  0.10000E+01 volume  0.47310E+00 ppm1     8.499 ppm2  1.974
ASSI {5}
(segid "PEPT" and resid 202 and name HD%)
(segid "PROT" and resid 49 and name HG1%)
 2.900  2.100  2.100 peak          5 weight  0.11000E+02 volume  0.17073E+01 ppm1     7.134 ppm2  0.978
ASSI {95}
((segid "PEPT" and resid 202 and name HB2))
(segid "PROT" and resid 49 and name HG1%)
 3.300  2.700  2.200 peak         95 weight  0.11000E+02 volume  0.87280E+00 ppm1     2.894 ppm2  0.977
ASSI {125}
((segid "PEPT" and resid 206 and name HG1))
(segid "PROT" and resid 43 and name HB%)
 3.200  2.600  2.300 peak        125 weight  0.10000E+01 volume  0.10680E+01 ppm1     1.462 ppm2  1.047
ASSI {135}
((sagid "PEPT" and resid 204 and name HB2))
(segid "PROT" and resid 43 and name HB%)
 3.100  2.400  2.400 peak        135 weight  0.10000E+01 volume  0.11770E+01 ppm1     1.778 ppm2  1.036
ASSI {145}
((sagid "PEPT" and resid 205 and name HE1))
(segid "PROT" and resid 38 and name HG1%)
 3.300  2.700  2.200 peak        145 weight  0.10000E+01 volume  0.89880E+00 ppm1     3.068 ppm2  0.458
ASSI {155}
(segid "PEPT" and resid 205 and name HH%)
(segid "PROT" and resid 38 and name HG1%)
 2.200  1.200  1.200 peak        155 weight  0.10000E+01 volume  0.87158E+01 ppm1     1.893 ppm2  0.463
ASSI {165}
(segid "PEPT" and resid 205 and name HH%)
((segid "PROT" and resid 38 and name HA))
 3.200  2.600  2.300 peak        165 weight  0.10000E+01 volume  0.10856E+01 ppm1     1.890 ppm2  3.506
ASSI {195}
((segid "PEPT" and resid 208 and name HB1))
((segid "PROT" and resid 42 and name HG1))
 3.200  2.600  2.300 peak        195 weight  0.10000E+01 volume  0.96050E+00 ppm1     1.781 ppm2  2.325
ASSI {205}
((segid "PEPT" and resid 209 and name HB1))
((segid "PROT" and resid 42 and name HG1))
 3.100  2.400  2.400 peak        205 weight  0.10000E+01 volume  0.11438E+01 ppm1     2.109 ppm2  2.322
ASSI {215}
((segid "PEPT" and resid 209 and name HG1))
((segid "PROT" and resid 42 and name HG2))
 3.500  3.100  2.000 peak        215 weight  0.10000E+01 volume  0.54870E+00 ppm1     2.343 ppm2  2.245
ASSI {255}
((segid "PEPT" and resid 208 and name HA))
((segid "PROT" and resid 42 and name HG1))
 2.900  2.100  2.100 peak        255 weight  0.10000E+01 volume  0.16895E+01 ppm1     4.326 ppm2  2.322
ASSI {275}
((segid "PEPT" and resid 209 and name HE22))
((segid "PROT" and resid 42 and name HG2))
 3.500  3.100  2.000 peak        275 weight  0.10000E+01 volume  0.56640E+00 ppm1     6.869 ppm2  2.323
ASSI {375}
((segid "PEPT" and resid 208 and name HA))
((segid "PROT" and resid 42 and name HB1))
 3.100  2.400  2.400 peak        375 weight  0.10000E+01 volume  0.12561E+01 ppm1     4.319 ppm2  2.168
ASSI {405}
((segid "PEPT" and resid 208 and name HA))
((segid "PROT" and resid 42 and name HB2))
 3.200  2.600  2.300 peak        405 weight  0.10000E+01 volume  0.10728E+01 ppm1     4.319 ppm2  2.075

TABLE 13-continued

Unambiguous NOE Distance Restraints

ASSI {425}
((segid "PEPT" and resid 209 and name HE22))
((segid "PROT" and resid 42 and name HB2))
 3.200  2.600  2.300 peak     425 weight  0.10000E+01 volume  0.10307E+01 ppm1   6.870 ppm2   2.072
ASSI {445}
(segid "PEPT" and resid 205 and name HH%)
((segid "PROT" and resid 33 and name HB2))
 3.300  2.700  2.200 peak     445 weight  0.10000E+01 volume  0.84810E+00 ppm1   1.886 ppm2  −0.445
ASSI {525}
(segid "PEPT" and resid 205 and name HH%)
(segid "PROT" and resid 81 and name HG1%)
 2.300  2.300  2.200 peak     525 weight  0.10000E+01 volume  0.81157E+01 ppm1   1.885 ppm2   0.496
ASSI {535}
((segid "PEPT" and resid 203 and name HN))
(segid "PROT" and resid 50 and name HD1%)
 3.600  3.200  1.900 peak     535 weight  0.10000E+01 volume  0.45510E+00 ppm1   8.245 ppm2   0.597
ASSI {245}
((segid "PROT" and resid 42 and name HG2))
((segid "PROT" and resid 41 and name HA))
 3.200  2.600  2.300 peak     245 weight  0.10000E+01 volume  0.95560E+00 ppm1   2.323 ppm2   4.076
OR {245}
((segid "PROT" and resid 42 and name HG1))
((segid "PROT" and resid 41 and name HA))
ASSI {265}
((segid "PROT" and resid 42 and name HG2))
((segid "PROT" and resid 42 and name HA))
 3.300  2.700  2.200 peak     265 weight  0.10000E+01 volume  0.85890E+00 ppm1   2.339 ppm2   4.484
OR {265}
((segid "PROT" and resid 42 and name HG1))
((segid "PROT" and resid 42 and name HA))
ASSI {465}
((segid "PROT" and resid 33 and name HB2))
((segid "PROT" and resid 95 and name HA))
 3.500  3.100  2.000 peak     465 weight  0.10000E+01 volume  0.59690E+00 ppm1  −0.448 ppm2   3.636
ASSI {6}
((segid "PEPT" and resid 205 and name HB1))
(segid "PROT" and resid 95 and name HE%)
 2.900  2.100  2.100 peak       6 weight  0.11000E+02 volume  0.20642E+01 ppm1   1.768 ppm2   7.010
ASSI {16}
((segid "PEPT" and resid 205 and name HB1))
(segid "PROT" and resid 88 and name HE%)
 3.200  2.600  2.300 peak      16 weight  0.11000E+02 volume  0.12360E+01 ppm1   1.782 ppm2   6.634
ASSI {26}
((segid "PEPT" and resid 205 and name HD1))
(segid "PROT" and resid 88 and name HE%)
 3.000  2.200  2.200 peak      26 weight  0.11000E+02 volume  0.18014E+01 ppm1   1.431 ppm2   6.631
ASSI {36}
((segid "PEPT" and resid 205 and name HG1))
(segid "PROT" and resid 88 and name HE%)
 3.100  2.400  2.400 peak      36 weight  0.11000E+02 volume  0.15181E+01 ppm1   1.327 ppm2   6.632
ASSI {46}
((segid "PEPT" and resid 202 and name HB1))
(segid "PROT" and resid 88 and name HE%)
 3.200  2.600  2.300 peak      46 weight  0.11000E+02 volume  0.11426E+01 ppm1   3.114 ppm2   6.636
ASSI {56}
((segid "PEPT" and resid 205 and name HD1))
(segid "PROT" and resid 95 and name HE%)
 3.500  3.100  2.000 peak      56 weight  0.11000E+02 volume  0.77060E+00 ppm1   1.430 ppm2   7.010
ASSI {66}
((segid "PEPT" and resid 205 and name HG1))
(segid "PROT" and resid 95 and name HE%)
 3.600  3.200  1.900 peak      66 weight  0.11000E+02 volume  0.58800E+00 ppm1   1.320 ppm2   7.010
ASSI {76}
((segid "PEPT" and resid 205 and name HG2))
(segid "PROT" and resid 95 and name HE%)
 3.700  3.400  1.800 peak      76 weight  0.11000E+02 volume  0.50830E+00 ppm1   1.160 ppm2   7.015
ASSI {86}
(segid "PEPT" and resid 205 and name HH%)
((segid "PROT" and resid 95 and name HE%)
 3.200  2.600  2.300 peak      86 weight  0.11000E+02 volume  0.11871E+01 ppm1   1.914 ppm2   7.010
ASSI {96}
(segid "PEPT" and resid 205 and name HE1))
(segid "PROT" and resid 95 and name HE%)
 3.500  3.100  2.000 peak      96 weight  0.11000E+02 volume  0.68560E+00 ppm1   3.113 ppm2   7.019

TABLE 13-continued

| Unambiguous NOE Distance Restraints |
|---|

ASSI {106}
((segid "PEPT" and resid 205 and name HA))
(segid "PROT" and resid 95 and name HE%)
 3.400  2.900   2.100 peak       106  weight   0.11000E+02 volume    0.80400E+00 ppm1        4.325  ppm2   7.010
ASSI {116}
((segid "PEPT" and resid 202 and name HB1))
(segid "PROT" and resid 88 and name HD%)
 3.200  2.600   2.300 peak       116  weight   0.11000E+02 volume    0.12205E+01 ppm1        3.122  ppm2   6.962
ASSI {136}
((segid "PEPT" and resid 205 and name HD1))
(segid "PROT" and resid 88 and name HD%)
 3.600  3.200   1.900 peak       136  weight   0.11000E+02 volume    0.60120E+00 ppm1        1.436  ppm2   6.961
ASSI {146}
((segid "PEPT" and resid 205 and name HG1))
(segid "PROT" and resid 88 and name HD%)
 3.600  3.200   1.900 peak       146  weight   0.11000E+02 volume    0.61310E+00 ppm1        1.326  ppm2   6.959
ASSI {156}
(segid "PEPT" and resid 205 and name HH%)
(segid "PROT" and resid 95 and name HD%)
 2.900  2.100   2.100 peak       156  weight   0.11000E+02 volume    0.20765E+01 ppm1        1.930  ppm2   6.845
ASSI {126}
(segid "PROT" and resid 88 and name HD%)
((segid "PROT" and resid 88 and name HB1))
 3.600  3.200   1.900 peak       126  weight   0.10000E+01 volume    0.59050E+00 ppm1        6.959  ppm2   2.946
OR {126}
(segid "PROT" and resid 88 and name HD%)
((segid "PROT" and resid 88 and name HB2))

TABLE 14

| Ambiguous NOE Distance Restraints |
|---|

ASSI {1101}
    ((segid "PROT" and resid 102 and name HN))
    ((segid "PROT" and resid 31 and name HB %))
        3.500  3.100  2.000 peak     1101 weight    0.10000E + 01 volume   0.13797E + 01 ppm1       8.519 ppm2    1.706
OR {1101}
    ((segid "PROT" and resid 102 and name HN))
    ((segid "PROT" and resid 104 and name HD1))
ASSI {1211}
    ((segid "PROT" and resid 103 and name HN))
    ((segid "PROT" and resid 104 and name HA))
        3.200  2.600  2.300 peak     1211 weight    0.10000E + 01 volume   0.23779E + 01 ppm1       8.042 ppm2    4.062
OR {1211}
    ((segid "PROT" and resid 46 and name HN))
    ((segid "PROT" and resid 48 and name HA))
ASSI {1311}
    ((segid "PROT" and resid 103 and name HN))
    ((segid "PROT" and resid 98 and name HA))
        3.200  2.600  2.300 peak     1311 weight    0.10000E + 01 volume   0.24662E + 01 ppm1       8.037 ppm2    4.220
OR {1311}
    ((segid "PROT" and resid 103 and name HN100))
    ((segid "PROT" and resid 82 and name HA))
ASSI {2161}
    ((segid "PROT" and resid 112 and name HN))
    (segid "PROT" and resid 115 and name HD 2%)
        3.400  2.900  2.100 peak     2161 weight    0.10000E + 01 volume   0.15055E + 01 ppm1       8.097 ppm2    0.824
OR {2161}
    ((segid "PROT" and resid 112 and name HN))
    ((segid "PROT" and resid 109 and name HG1))
OR {2161}
    ((segid "PROT" and resid 112 and name HN))
    (segid "PROT" and resid 116 and name HD 2%)
OR {2161}
    ((segid "PROT" and resid 112 and name HN))
    (segid "PROT" and resid 116 and name HD 1%)
ASSI {2501}
    (segid "PROT" and resid 106 and name HN))
    ((segid "PROT" and resid 102 and name HG))
        3.600  3.200  1.900 peak     2501 weight    0.10000E + 01 volume   0.11395E + 01 ppm1       9.149 ppm2    1.562
OR {2501}
    ((segid "PROT" and resid 106 and name HN))
    ((segid "PROT" and resid 109 and name HB2))

TABLE 14-continued

| Ambiguous NOE Distance Restraints | | | | | |
|---|---|---|---|---|---|
| OR {2501} | | | | | |
| ((segid "PROT" and resid 106 and name HN)) | | | | | |
| ((segid "PROT" and resid 104 and name HG1)) | | | | | |
| ASSI {2711} | | | | | |
| ((segid "PROT" and resid 17 and name HN)) | | | | | |
| (segid "PROT" and resid 18 and name HD 1%) | | | | | |
| 3.300  2.700  2.200 peak     2711 weight | 0.10000E + 01 volume | 0.19671E + 01 ppm1 | 8.065 ppm2 | 0.730 |
| OR {2711} | | | | | |
| ((segid "PROT" and resid 17 and name HN)) | | | | | |
| (segid "PROT" and resid 115 and name HD 1%) | | | | | |
| ASSI {2731} | | | | | |
| ((segid "PROT" and resid 40 and name HN)) | | | | | |
| ((segid "PROT" and resid 39 and name HE1)) | | | | | |
| 2.700  1.800  1.800 peak     2731 weight | 0.10000E + 01 volume | 0.59635E + 01 ppm1 | 8.059 ppm2 | 3.194 |
| OR {2731} | | | | | |
| ((segid "PROT" and resid 17 and name HN)) | | | | | |
| ((segid "PROT" and rapid 15 and name HB1)) | | | | | |
| ASSI {2771} | | | | | |
| ((segid "PROT" and resid 17 and name HN)) | | | | | |
| ((segid "PROT" and resid 15 and name HB1)) | | | | | |
| 3.200  2.600  2.300 peak     2771 weight | 0.10000E + 01 volume | 0.21928E + 01 ppm1 | 8.060 ppm2 | 1.555 |
| OR {2771} | | | | | |
| ((segid "PROT" and resid 17 and name HN)) | | | | | |
| ((segid "PROT" and resid 14 and name HB2)) | | | | | |
| ASSI {4121} | | | | | |
| ((segid "PROT" and resid 76 and name HN)) | | | | | |
| ((segid "PROT" and resid 79 and name HB2)) | | | | | |
| 3.200  2.600  2.300 peak     4121 weight | 0 10000E + 01 volume | 0.21825E + 01 ppm1 | 7.368 ppm2 | 2.089 |
| OR {4121} | | | | | |
| ((segid "PROT" and resid 78 and name HN)) | | | | | |
| (segid "PROT" and resid 75 and name HE %) | | | | | |
| OR {4121} | | | | | |
| ((segid "PROT" and resid 96 and name HN)) | | | | | |
| ((segid "PROT" and resid 97 and name HB1)) | | | | | |
| OR {4121} | | | | | |
| ((segid "PROT" and resid 77 and name HN)) | | | | | |
| ((segid "PROT" and resid 79 and name HB2)) | | | | | |
| OR {4121} | | | | | |
| ((segid "PROT" and resid 78 and name HN)) | | | | | |
| ((segid "PROT" and resid 54 and name HB1)) | | | | | |
| OR {4121} | | | | | |
| ((segid "PROT" and resid 77 and name HN)) | | | | | |
| ((segid "PROT" and resid 54 and name HB1)) | | | | | |
| ASSI {4331} | | | | | |
| ((segid "PROT" and resid 79 and name HN)) | | | | | |
| ((segid "PROT" and resid 81 and name HB)) | | | | | |
| 3.300  2.700  2.200 peak     4331 weight | 0.10000E + 01 volume | 0.21033E + 01 ppm1 | 7.382 ppm2 | 1.417 |
| OR {4331} | | | | | |
| ((segid "PROT" and resid 77 and name HN)) | | | | | |
| ((segid "PROT" and resid 81 and name HB)) | | | | | |
| ASSI {4731} | | | | | |
| ((segid "PROT" and resid 15 and name HN)) | | | | | |
| ((segid "PROT" and resid 16 and name HB2)) | | | | | |
| 3.300  2.700  2.200 peak     4731 weight | 0.10000E + 01 volume | 0.19906E + 01 ppm1 | 7.992 ppm2 | 3.907 |
| OR {4731} | | | | | |
| ((segid "PROT" and resid 15 and name HN)) | | | | | |
| ((segid "PROT" and resid 17 and name HA)) | | | | | |
| OR {4731} | | | | | |
| ((segid "PROT" and resid 15 and name HN)) | | | | | |
| ((segid "PROT" and resid 11 and name HD1)) | | | | | |
| ASSI {6431} | | | | | |
| ((segid "PROT" and resid 113 and name HN)) | | | | | |
| ((segid "PROT" and resid 111 and name HG2)) | | | | | |
| 3.200  2.600  2.300 peak     6431 weight | 0.10000E + 01 volume | 0.23779E + 01 ppm1 | 7.627 ppm2 | 1.290 |
| OR {6431} | | | | | |
| ((segid "PROT" and resid 113 and name HN)) | | | | | |
| ((segid "PROT" and resid 116 and name HG11)) | | | | | |
| ASSI {6531} | | | | | |
| ((segid "PROT" and resid 104 and name HN)) | | | | | |
| ((segid "PROT" and resid 102 and name HB1)) | | | | | |
| 3.500  3.100  2.000 peak     6531 weight | 0.10000E + 01 volume | 0.12949E + 01 ppm1 | 7.168 ppm2 | 1.396 |
| OR {6531} | | | | | |
| ((segid "PROT" and resid 35 and name HN)) | | | | | |
| ((segid "PROT" and resid 56 and name HB2)) | | | | | |

TABLE 14-continued

| Ambiguous NOE Distance Restraints |
|---|

ASSI {6731}
    ((segid "PROT" and resid 35 and name HN))
    (segid "PROT" and resid 56 and name HD 1%))
        3.400  2.900  2.100 peak      6731 weight    0.10000E + 01 volume  0.15507E + 01 ppm1      7.148 ppm2    0.971
OR {6731}
    ((segid "PROT" and resid 104 and name HN))
    (segid "PROT" and resid 101 and name HG 2%)
ASSI {7671}
    ((segid "PROT" and resid 62 and name HN))
    (segid "PROT" and resid 63 and name HG 2%)
        3.200  2.600  2.300 peak      7671 weight    0.10000E + 01 volume  0.24316E + 01 ppm1      6.396 ppm2    1.323
OR {7671}
    ((segid "PROT" and resid 82 and name HN))
    ((segid "PROT" and resid 54 and name HB2))
OR {7671}
    ((segid "PROT" and resid 62 and name HN))
    ((segid "PROT" and resid 103 and name HB2))
ASSI {7851}
    ((segid "PROT" and resid 96 and name HN))
    ((segid "PROT" and resid 30 and name HB1))
        3.400  2.900  2.100 peak      7851 weight    0.10000E + 01 volume  0.15319E + 01 ppm1      8.470 ppm2    4.315
OR {7851}
    ((segid "PROT" and resid 98 and name HN))
    ((segid "PROT" and resid 100 and name HA))
ASSI {8591}
    ((segid "PROT" and resid 95 and name HN))
    ((segid "PROT" and resid 97 and name HG1))
        3.300  2.700  2.200 peak      8591 weight    0.10000E + 01 volume  0.18918E + 01 ppm1      7.964 ppm2    1.794
OR {8591}
    ((segid "PROT" and resid 65 and name HN))
    ((segid "PROT" and resid 64 and name HD1))
OR {8591}
    ((segid "PROT" and resid 60 and name HN))
    ((segid "PROT" and resid 22 and name HG))
ASSI {8701}
    ((segid "PROT" and resid 56 and name HN))
    (segid "PROT" and resid 25 and name HG 2%)
        3.400  2.900  2.100 peak      8701 weight    0.10000E + 01 volume  0.15401E + 01 ppm1      9.133 ppm2    1.035
OR {8701}
    ((segid "PROT" and resid 56 and name HN))
    (segid "PROT" and resid 22 and name HD 2%)
ASSI {11861}
    ((segid "PROT" and resid 24 and name HE22))
    ((segid "PROT" and resid 24 and name HG2))
        3.700  3.400  1.600 peak    11861 weight    0.10000E + 01 volume  0.91710E + 00 ppm1      6.901 ppm2    2.481
OR {11861}
    ((segid "PROT" and resid 24 and name HE22))
    ((segid "PROT" and resid 109 and name HE2))
ASSI {12111}
    ((segid "PROT" and resid 68 and name HN))
    ((segid "PROT" and resid 66 and name HG1))
        3.800  3.600  1.700 peak    12111 weight    0.10000E + 01 volume  0.85210E + 00 ppm1      8.011 ppm2    1.643
OR {12111}
    ((segid "PROT" and resid 68 and name HN))
    ((segid "PROT" and resid 18 and name HG))
ASSI {12191}
    ((segid "PROT" and resid 68 and name HN))
    ((segid "PEPT" and resid 203 and name HA1))
        3.700  3.400  1.800 peak    12191 weight    0.10000E + 01 volume  0 10424E + 01 ppm1      8.114 ppm2    3.902
OR {12191}
    ((segid "PROT" and resid 89 and name HN))
    ((segid "PROT" and resid 83 and name HA))
OR {12191}
    ((segid "PROT" and resid 69 and name HN))
    ((segid "PROT" and resid 50 and name HA))
ASSI {12361}
    ((segid "PROT" and resid 69 and name HN))
    ((segid "PROT" and resid 70 and name HB1))
        3.700  3.400  1.800 peak    12361 weight    0.10000E + 01 volume  0.10231E + 01 ppm1      7.707 ppm2    4.230
OR {12361}
    ((segid "PROT" and resid 69 and name HN))
    ((segid "PROT" and resid 73 and name HA))
ASSI {12371}
    ((segid "PROT" and resid 69 and name HN))
    (segid "PROT" and resid 63 and name HD 2%)
        3.500  3.100  2.000 peak    12371 weight    0.10000E + 01 volume  0.14140E + 01 ppm1      7.709 ppm2    1.055

TABLE 14-continued

Ambiguous NOE Distance Restraints

```
OR {12371}
    ((segid "PROT" and resid 69 and name HN))
    ((segid "PROT" and resid 62 and name HB2))
ASSI {12571}
    ((segid "PROT" and resid 110 and name HN))
    (segid "PROT" and resid 75 and name HE %)
        3.600  3.200  1.900 peak     12571 weight    0.10000E + 01 volume  0.12095E + 01 ppm1    8.119 ppm2    2.066
OR {12571}
    ((segid "PROT" and resid 110 and name HN))
    ((segid "PROT" and resid 112 and name HB1))
ASSI {12731}
    ((segid "PROT" and resid 107 and name HN))
    ((segid "PROT" and resid 111 and name HB2))
        3.700  3.400  1.800 peak     12731 weight    0.10000E + 01 volume  0.10305E + 01 ppm1    8.400 ppm2    1.726
OR {13731}
    ((segid "PROT" and resid 107 and name HN))
    ((segid "PROT" and resid 104 and name HD1))
OR {12731}
    ((segid "PROT" and resid 107 and name HN))
    ((segid "PROT" and resid 109 and name HB1))
ASSI {12741}
    ((segid "PROT" and resid 107 and name HN))
    ((segid "PROT" and resid 109 and name HG1))
        3.700  3.400  1.800 peak     12741 weight    0.10000E + 01 volume  0.94540E + 00 ppm1    8.398 ppm2    0.803
OR {12741}
    ((segid "PROT" and resid 107 and name HN))
    (segid "PROT" and resid 116 and name HD 1%)
ASSI {12761}
    ((segid "PROT" and resid 19 and name HN))
    ((segid "PROT" and resid 19 and name HE1))
        3.700  3.400  1.800 peak     12761 weight    0 10000E + 01 volume  0.95080E + 00 ppm1    8.574 ppm2    2.934
OR {12761}
    ((segid "PROT" and resid 19 and name HN))
    ((segid "PROT" and resid 68 and name HB2))
ASSI {12961}
    ((segid "PROT" and resid 76 and name HN))
    (segid "PROT" and resid 74 and name HD %)
        3.600  3.600  1.700 peak     12961 weight    0.10000E + 01 volume  0.65250E + 00 ppm1    7.386 ppm2    6.387
OR {12961}
    ((segid "PROT" and resid 77 and name HN))
    (segid "PROT" and resid 74 and name HD %)
ASSI {13011}
    ((segid "PROT" and resid 25 and name HN))
    (segid "PROT" and resid 31 and name HB %)
        3.600  3.200  1.900 peak     13011 weight    0.10000E + 01 volume  0.11117E + 01 ppm1    8.563 ppm2    1.722
OR {13011}
    ((segid "PROT" and resid 29 and name HN))
    ((segid "PROT" and resid 22 and name HB2))
ASSI {13031}
    ((segid "PROT" and resid 101 and name HN))
    ((segid "PROT" and resid 104 and name HN))
        3.700  3.400  1.800 peak     13031 weight    0.10000E + 01 volume  0.10135E + 01 ppm1    8.016 ppm2    7.190
OR {13031}
    ((segid "PROT" and resid 101 and name HN))
    (segid "PROT" and resid 34 and name HE %)
ASSI {13101}
    ((segid "PROT" and resid 22 and name HN))
    ((segid "PROT" and resid 23 and name HB1))
        3.800  3.600  1.700 peak     13101 weight    0.10000E + 01 volume  0.88170E + 00 ppm1    8.853 ppm2    2.327
OR {13101}
    ((segid "PROT" and resid 22 and name HN)
    ((segid "PROT" and resid 63 and name HB1))
ASSI {13211}
    ((segid "PROT" and resid 62 and name HN))
    ((segid "PROT" and resid 67 and name HB1))
        3.600  3.200  1.900 peak     13211 weight    0.10000E + 01 volume  0.10881E + 01 ppm1    8.378 ppm2    2.990
OR {13211}
    ((segid "PROT" and resid 62 and name HN))
    ((segid "PROT" and resid 65 and name HB1))
OR {13211}
    ((segid "PROT" and resid 62 and name HN))
    ((segid "PROT" and resid 64 and name HE1))
ASSI {13271}
    ((segid "PROT" and resid 18 and name HN))
    ((segid "PROT" and resid 19 and name HB2))
        3.400  2.900  2.100 peak     13271 weight    0.10000E + 01 volume  0.16318E + 01 ppm1    8.476 ppm2    1.409
```

TABLE 14-continued

| Ambiguous NOE Distance Restraints |
|---|

```
OR {13271}
    ((segid "PROT" and resid 18 and name HN))
    (segid "PROT" and resid 113 and name HB %)
ASSI {13881}
    ((segid "PROT" and resid 77 and name HN))
    ((segid "PROT" and resid 80 and name HB2))
        3.600  3.200  1.900 peak    13881 weight   0.10000E + 01 volume  0.12199E + 01 ppm1    7.383 ppm2 1.915
OR {13881}
    ((segid "PROT" and resid 78 and name HN))
    ((segid "PROT" and resid 80 and name HB2))
OR {13881}
    ((segid "PROT" and resid 77 and name HN))
    ((segid "PROT" and resid 54 and name HG2))
OR {13881}
    ((segid "PROT" and resid 77 and name HN))
    ((segid "PROT" and resid 73 and name HB2))
OR {13881}
    ((segid "PROT" and resid 78 and name HN))
    ((segid "PROT" and resid 59 and name HB2))
OR {13881}
    ((segid "PROT" and resid 78 and name HN))
    ((segid "PROT" and resid 54 and name HG2))
ASSI {13971}
    ((segid "PROT" and resid 85 and name HN))
    ((segid "PROT" and resid 80 and name HA))
        3.700  3.400  1.800 peak    13971 weight   0.10000E + 01 volume  0.93300E + 00 ppm1    6.905 ppm2 4.080
OR {13971}
    ((segid "PROT" and resid 85 and name HN))
    ((segid "PROT" and resid 53 and name HA))
ASSI {4172}
    ((segid "PROT" and resid 84 and name HE1))
    ((segid "PROT" and resid 61 and name HG2))
        2.800  2.000  2.000 peak     4172 weight   0.10000E + 01 volume  0.22580E + 01 ppm1    3.048 ppm2 2.282
OR {4172}
    ((segid "PROT" and resid 97 and name HE1))
    ((segid "PROT" and resid 94 and name HG1))
OR {4172}
    ((segid "PROT" and resid 64 and name HE1))
    ((segid "PROT" and resid 61 and name HB1))
ASSI {4232}
    ((segid "PROT" and resid 19 and name HE1))
    (segid "PROT" and resid 63 and name HD 2%)
        2.900  2.100  2.100 peak     4232 weight   0.10000E + 01 volume  0.16659E + 01 ppm1    3.002 ppm2 1.094
OR {4232}
    ((segid "PROT" and resid 19 and name HE1))
    (segid "PROT" and resid 22 and name HD 1%)
OR {4232}
    ((segid "PROT" and resid 64 and name HE1))
    (segid "PROT" and resid 22 and name HD 1%)
ASSI {4242}
    ((segid "PROT" and resid 97 and name HE1))
    (segid "PROT" and resid 101 and name HD 1%)
        2.700  1.800  1.800 peak     4242 weight   0.10000E + 01 volume  0.24492E + 01 ppm1    3.006 ppm2 0.997
OR {4242}
    ((segid "PROT" and resid 6 and name HE1))
    ((segid "PROT" and resid 116 and name HG12))
ASSI {4582}
    ((segid "PROT" and resid 66 and name HE1))
    ((segid "PROT" and resid 99 and name HA))
        2.900  2.100  2.100 peak     4582 weight   0.10000E + 01 volume  0.15734E + 01 ppm1    2.513 ppm2 3.899
OR {4582}
    ((segid "PROT" and resid 66 and name HE1))
    ((segid "PROT" and resid 83 and name HA))
ASSI {6142}
    ((segid "PROT" and resid 94 and name HG1))
    ((segid "PROT" and resid 97 and name HE1))
        2.900  2.100  2.100 peak     6142 weight   0.10000E + 01 volume  0.16943E + 01 ppm1    2.228 ppm2 3.037
OR {6142}
    ((segid "PROT" and resid 87 and name HG2))
    ((segid "PROT" and resid 94 and name HB1))
ASSI {7022}
    ((segid "PROT" and resid 64 and name HB1))
    ((segid "PROT" and resid 61 and name HG1))
        1.900  1.900  2.600 peak     7022 weight   0.10000E + 01 volume  0.22077E + 02 ppm1    2.025 ppm2 2    387
OR {7022}
    ((segid "PROT" and resid 64 and name HB1))
    ((segid "PROT" and resid 63 and name HB1))
```

TABLE 14-continued

Ambiguous NOE Distance Restraints

```
OR {7022}
    ((segid "PROT" and resid 39 and name HB1))
    ((segid "PROT" and resid 42 and name HG1))
ASSI {7822}
    ((segid "PROT" and resid 97 and name HD1))
    ((segid "PROT" and resid 94 and name HG1))
        2.600  1.700  1.700 peak      7822 weight   0.10000E + 01 volume  0.31606E + 01 ppm1    1.844 ppm2   2.284
OR {7822}
    ((segid "PROT" and resid 97 and name HD1))
    ((segid "PROT" and resid 92 and name HG2))
ASSI {8232}
    ((segid "PROT" and resid 6 and name HD1))
    (segid "PROT" and resid 116 and name HD 1%)
        2.900  2.100  2.100 peak      8232 weight   0.10000E + 01 volume  0.18699E + 01 ppm1    1.677 ppm2   0.840
OR {8232}
    ((segid "PROT" and resid 118 and name HD1))
    (segid "PROT" and resid 116 and name HG 2%)
OR {8232}
    ((segid "PROT" and resid 6 and name HD1))
    (segid "PROT" and resid 116 and name HG 2%)
OR {8232}
    ((segid "PROT" and resid 111 and name HD1))
    (segid "PROT" and resid 116 and name HG 2%)
ASSI {9772}
    ((segid "PROT" and resid 110 and name HG12))
    ((segid "PROT" and resid 115 and name HB2))
        3.000  2.200  2.200 peak      9772 weight   0.10000E + 01 volume  0.15374E + 01 ppm1    1.125 ppm2   1.618
OR {9772}
    ((segid "PROT" and resid 110 and name HG11))
    ((segid "PROT" and resid 119 and name HB2))
OR {9772}
    ((segid "PROT" and resid 110 and name HG11))
    ((segid "PROT" and resid 109 and name HB2))
ASSI {9822}
    (segid "PROT" and resid 78 and name HD 1%)
    (segid "PROT" and resid 74 and name HD %)
        2.400  1.400  1.400 peak      9822 weight   0.10000E + 01 volume  0.47381E + 01 ppm1    0.096 ppm2   6.459
OR {9822}
    (segid "PROT" and resid 78 and name HD 1%)
    (segid "PROT" and resid 82 and name HE %)
ASSI {9052}
    ((segid "PROT" and resid 97 and name HG2))
    ((segid "PROT" and resid 94 and name HA))
        2.400  1.400  1.400 peak      9952 weight   0.10000E + 01 volume  0.50570E + 01 ppm1    1.607 ppm2   4.239
OR {9952}
    ((segid "PROT" and resid 97 and name HG2))
    ((segid "PROT" and resid 97 and name HA))
ASSI {10652}
    ((segid "PROT" and resid 6 and name HG1))
    (segid "PROT" and resid 115 and name HA))
        2.400  1.400  1.400 peak     10652 weight   0.10000E + 01 volume  0.48739E + 01 ppm1    1.470 ppm2   4.248
OR {10652}
    ((segid "PROT" and resid 6 and name HG1))
    ((segid "PROT" and resid HB and name HA))
OR {10652}
    ((segid "PROT" and resid 6 and name HG2))
    ((segid "PROT" and resid 115 and name HA))
OR {10652}
    ((segid "PROT" and resid 6 and name HG2))
    ((segid "PROT" and resid 116 and name HA))
OR {10652}
    ((segid "PROT" and resid 111 and name HG1))
    ((segid "PROT" and resid 108 and name HA))
ASSI {10712}
    ((segid "PROT" and resid 57 and name HG1))
    ((segid "PROT" and resid 37 and name HB1))
        2.500  1.600  1.600 peak     10712 weight   0.10000E + 01 volume  0.40188E + 01 ppm1    1.522 ppm2   2.399
OR {10712}
    ((segid "PROT" and resid 57 and name HG1))
    ((segid "PROT" and resid 55 and name HB1))
ASSI {10852}
    ((segid "PROT" and resid 6 and name HG2))
    ((segid "PROT" and resid 6 and name HD1))
        1.600  0.600  0.600 peak     10852 weight   0.10000E + 01 volume  0.64288E + 02 ppm1    1.451 ppm2   1.709
OR {10852}
    ((segid "PROT" and resid 104 and name HG2))
    ((segid "PROT" and resid 104 and name HD1))
```

TABLE 14-continued

Ambiguous NOE Distance Restraints

```
OR {10852}
    ((segid "PROT" and resid 6 and name HG1))
    ((segid "PROT" and resid 6 and name HD1))
ASSI {11042}
    ((segid "PROT" and resid 102 and name HG 2%))
    ((segid "PROT" and resid 28 and name HA))
        2.600  1.700  1.700 peak    11042 weight   0.10000E + 01 volume   0.30164E + 01 ppm1    0.766 ppm2    3.994
OR {11042}
    (segid "PROT" and resid 102 and name HG 2%)
    ((segid "PROT" and resid 30 and name HB2))
OR {11042}
    (segid "PROT" and resid 102 and name HD 2%)
    ((segid "PROT" and resid 106 and name HA))
ASSI {11372}
    (segid "PROT" and resid 115 and name HG 2%)
    (segid "PROT" and resid 75 and name HE %)
        2.800  2.000  2.000 peak    11372 weight   0.10000E + 01 volume   0.22403E + 01 ppm1    0.792 ppm2    2.095
OR {11372}
    (segid "PROT" and resid 115 and name HD 2%)
    ((segid "PROT" and resid 8 and name HG1))
ASSI {11542}
    (segid "PROT" and resid 25 and name HG 1%)
    (segid "PROT" and resid 31 and name HB %)
        2.800  2.000  2.000 peak    11542 weight   0.10000E + 01 volume   0.19754E + 01 ppm1    1.246 ppm2    1.764
OR {11542}
    (segid "PROT" and resid 25 and name HG 1%)
    ((segid "PROT" and resid 21 and name HG11))
OR {11542}
    (segid "PROT" and resid 25 and name HG 1%)
    ((segid "PROT" and resid 22 and name HB2))
OR {11542}
    (segid "PROT" and resid 25 and name HG 1%)
    ((segid "PROT" and resid 22 and name HG))
ASSI {11582}
    (segid "PROT" and resid 25 and name HG 1%)
    (segid "PROT" and resid 56 and name HD 2%)
        2.700  1.800  1.800 peak    11582 weight   0.10000E + 01 volume   0.27149E + 01 ppm1    1.242 ppm2    0.676
OR {11582}
    (segid "PROT" and resid 25 and name HG 1%)
    ((segid "PROT" and resid 78 and name HG))
OR {11582}
    (segid "PROT" and resid 25 and name HG 1%)
    (segid "PROT" and resid 110 and name HG 2%)
ASSI {11652}
    (segid "PROT" and resid 83 and name HG 2%)
    ((segid "PROT" and resid 86 and name HB1))
        2.600  2.000  2.000 peak    11652 weight   0.10000E + 01 volume   0.20985 + 01 ppm1    1.322 ppm2    1.811
OR {11652}
    (segid "PROT" and resid 83 and name HG 2%)
    ((segid "PROT" and resid 80 and name HG1))
OR {11652}
    (segid "PROT" and resid 41 and name HG 2%)
    ((segid "PEPT" and resid 206 and name HB1))
ASSI {11842}
    (segid "PROT" and resid 81 and name HG 1%)
    ((segid "PROT" and resid 56 and name HG))
        2.000  2.100  2.100 peak    11842 weight   0.10000E + 01 volume   0.17306E + 01 ppm1    0.514 ppm2    1.778
OR {11842}
    (segid "PROT" and resid 81 and name HG 1%)
    ((segid "PROT" and resid 80 and name HG1))
OR {11642}
    (segid "PROT" and resid 38 and name HG 1%)
    ((segid "PROT" and resid 205 and name HB1))
OR {11842}
    (segid "PROT" and resid 38 and name HG 1%)
    ((segid "PROT" and resid 36 and name HB2))
ASSI {12152}
    (segid "PROT" and resid 69 and name HG 1%)
    ((segid "PROT" and resid 11 and name HB2))
        2.900  2.100  2.100 peak    12152 weight   0.10000E + 01 volume   0.15613E + 01 ppm1    0.968 ppm2    2.086
OR {12182}
    (segid "PROT" and resid 69 and name HG 1%)
    (segid "PROT" and resid 66 and name HB2))
ASSI {12162}
    (segid "PROT" and resid 17 and name HG 2%)
    ((segid "PROT" and resid 115 and name HG))
        2.700  1.800  1.800 peak    12162 weight   0.10000E + 01 volume   0.25853E + 01 ppm1    1.176 ppm2    1.577
```

TABLE 14-continued

Ambiguous NOE Distance Restraints

OR {12162}
    (segid "PROT" and resid 17 and name HG 2%)
    ((segid "PROT" and resid 109 and name HB2))
ASSI {12662}
    (segid "PROT" and resid 113 and name HB %)
    ((segid "PROT" and resid 110 and name HB))
       2.600  1.700  1.700 peak    12662 weight    0.10000E + 01 volume  0.30533E + 01 ppm1    1.409 ppm2    1.786
OR {12662}
    (segid "PROT" and resid 113 and name HB %)
    ((segid "PROT" and resid 109 and name HB1))
OR {12662}
    (segid "PROT" and resid 113 and name HB %)
    ((segid "PROT" and resid 21 and name HG11))
ASSI {12692}
    (segid "PROT" and resid 113 and name HB %)
    ((segid "PROT" and resid 21 and name HG12))
       2.900  2.100  2.100 peak    12692 weight    0.10000E + 01 volume  0.17007E + 01 ppm1    1.416 ppm2    1.073
OR {12692}
    (segid "PROT" and resid 113 and name HB %)
    ((segid "PROT" and resid 110 and name HG12))
ASSI {13152}
(segid "PROT" and resid 21 and name HG 2%)
    ((segid "PROT" and resid 24 and name HG2))
       2.900  2.100  2.100 peak    13152 weight    0.10000E + 01 volume  0.16386E + 01 ppm1    1.019 ppm2    2.511
OR {13192}
    (segid "PROT" and resid 21 and name HG 2%)
    ((segid "PROT" and resid 109 and name HE2))
ASSI {13172}
    (segid "PROT" and resid 21 and name HG 2%)
    (segid "PROT" and resid 113 and name HB %))
       2.900  2.100  2.100 peak    13172 weight    0.10000E + 01 volume  0.15888E + 01 ppm1    1.022 ppm2    1.412
OR {13172}
    (segid "PROT" and resid 21 and name HG 2%)
    ((segid PROT" and resid 109 and name HD1))
ASSI {13282}
    (segid "PROT" and resid 75 and name HE %)
    ((segid "PROT" and resid 6 and name HE1))
       2.700  1.800  1.800 peak    13282 weight    0.10000E + 01 volume  0.290483 + 01 ppm1    2.097 ppm2    3.036
OR {13282}
    (segid "PROT" and resid 75 and name HE %)
    ((segid "PROT" and resid 74 and name HB1))
OR {13282}
    (segid "PROT" and resid 75 and name HE %)
    ((segid "PROT" and resid 82 and name HB2))
ASSI {13352}
    (segid "PROT" and resid 75 and name HE %)
    (segid "PROT" and resid 113 and name HB %)
       2.900  2.100  2.100 peak    13352 weight    0.10000E + 01 volume  0.15571E + 01 ppm1    2.095 ppm2    1.436
OR {13352}
    (segid "PROT" and resid 75 and name HE %)
    ((segid "PROT" and resid 6 and name HG1))
OR {13352}
    (segid "PROT" and resid 75 and name HE %)
    ((segid "PROT" and resid 6 and name HG2))
OR {13352}
    (segid "PROT" and resid 75 and name HE %)
    ((segid "PROT" and resid 81 and name HB))
ASSI {14022}
    (segid "PROT" and resid 116 and name HD 1%)
    ((segid "PROT" and resid 107 and name HA))
       2.900  2.100  2.100 peak    14022 weight    0.10000E + 01 volume  0.16161E + 01 ppm1    0.826 ppm2    3.863
OR {14022}
    (segid "PROT" and resid 116 and name HD 1%)
    ((segid "PROT" and resid 110 and name HA))
ASSI {14402}
    ((segid "PROT" and resid 74 and name HB2))
    ((segid "PROT" and resid 75 and name HA))
       3.200  2.600  2.300 peak    14402 weight    0.10000E + 01 volume  0.10054E + 01 ppm1    2.415 ppm2    4.066
OR {14402}
    ((segid "PROT" and resid 74 and name HB2))
    ((segid "PROT" and resid 15 and name HA))
OR {14402}
    ((segid "PROT" and resid 74 and name HB2))
    ((segid "PROT" and resid 72 and name HA))

TABLE 14-continued

Ambiguous NOE Distance Restraints

```
ASSI {14792}
    ((segid "PROT" and resid 53 and name HG1))
    ((segid "PROT" and resid 52 and name HB1))
        3.300  2.700  2.200  peak    14792 weight    0.10000E + 01 volume   0.77210E + 00 ppm1    2.267 ppm2    3.049
OR {14792}
    ((segid "PROT" and resid 53 and name HG1))
    ((segid "PROT" and resid 84 and name HB1))
ASSI {15152}
    ((segid "PROT" and resid 96 and name HB1))
    (segid "PROT" and resid 99 and name HB %)
        3.200  2.600  2.300  peak    15152 weight    0.10000E + 01 volume   0.91940E + 00 ppm1    3.417 ppm2    1.640
OR {15152}
    ((segid "PROT" and resid 96 and name HB1))
    ((segid "PROT" and resid 97 and name HG2))
ASSI {15342}
    (segid "PROT" and resid 38 and name HG 2%)
    ((segid "PROT" and resid 53 and name HA))
        3.200  2.600  2.300  peak    15342 weight    0.10000E + 01 volume   0.94230E + 00 ppm1   −0.005 ppm2    4.101
OR {15342}
    (segid "PROT" and resid 38 and name HG 2%)
    ((segid "PROT" and resid 41 and name HA))
ASSI {15372}
    (segid "PROT" and resid 38 and name HG 2%)
    ((segid "PROT" and resid 46 and name HB2))
        3.000  2.200  2.200  peak    15372 weight    0.10000E + 01 volume   0.13687E + 01 ppm1   −0.009 ppm2    2.414
OR {15372}
    (segid "PROT" and resid 38 and name HG 2%)
    ((segid "PROT" and resid 37 and name HB1))
ASSI {15382}
    (segid "PROT" and resid 38 and name HG 2%)
    ((segid "PROT" and resid 39 and name HB2))
        3.000  2.200  2.200  peak    15382 weight    0.10000E + 01 volume   0.12723E + 01 ppm1   −0.012 ppm2    1.942
OR {15382}
    (segid "PROT" and resid 38 and name HG 2%)
    ((segid "PROT" and resid 53 and name HG2))
ASSI {15422}
    (segid "PROT" and resid 81 and name HG 2%)
    ((segid "PROT" and resid 80 and name HB2))
        3.200  2.600  2.300  peak    15422 weight    0.10000E + 01 volume   0.98300E + 00 ppm1    0.152 ppm2    1.938
OR {15422}
    (segid "PROT" and resid 81 and name HG 2%)
    ((segid "PROT" and resid 59 and name HB2))
ASSI {15442}
    (segid "PROT" and resid 81 and name HG 2%)
    ((segid "PROT" and resid 31 and name HA))
        3.200  2.600  2.300  peak    15442 weight    0.10000E + 01 volume   0.91520E + 00 ppm1    0.154 ppm2    4.431
OR {15442}
    (segid "PROT" and resid 81 and name HG 2%)
    ((segid "PROT" and resid 77 and name HA))
ASSI {15682}
    (segid "PROT" and resid 18 and name HD 2%)
    ((segid "PROT" and resid 74 and name HA))
        3.300  2.700  2.200  peak    15682 weight    0.10000E + 01 volume   0.81490E + 00 ppm1   −0.161 ppm2    3.801
OR {15682}
    (segid "PROT" and resid 18 and name HD 2%)
    ((segid "PROT" and resid 70 and name HB2))
ASSI {16372}
    (segid "PROT" and resid 78 and name HD 2%)
    ((segid "PROT" and resid 22 and name HA))
        3.200  2.600  2.300  peak    16272 weight    0.10000E + 01 volume   0 10279E + 01 ppm1    0.201 ppm2    4.142
OR {16372}
    ((segid "PROT" and resid 50 and name HD12))
    ((segid "PROT" and resid 53 and name HA))
OR {16372}
    ((segid "PROT" and resid 50 and name HD12))
    ((segid "PROT" and resid 47 and name HA))
ASSI {16562}
    ((segid "PROT" and resid 115 and name HB2))
    ((segid "PROT" and resid 110 and name HG11))
        3.200  2.600  2.300  peak    16562 weight    0.10000E + 01 volume   0.10189E + 01 ppm1    1.619 ppm2    1.169
OR {16562}
    ((segid "PROT" and resid 115 and name HB2))
    (segid "PROT" and resid 17 and name HG 2%)
ASSI {16752}
    (segid "PROT" and resid 21 and name HD 1%)
    ((segid "PROT" and resid 20 and name HB1))
        3.100  2.400  2.400  peak    16752 weight    0.10000E + 01 volume   0.11661E + 01 ppm1    0.657 ppm2    4.106
```

TABLE 14-continued

| Ambiguous NOE Distance Restraints | | | | | |
|---|---|---|---|---|---|
| OR {16752} | | | | | |
| (segid "PROT" and resid 21 and name HD 1%) | | | | | |
| ((segid "PROT" and resid 109 and name HA)) | | | | | |
| ASSI {16872} | | | | | |
| (segid "PROT" and resid 78 and name HD 2%) | | | | | |
| ((segid "PROT" and resid 56 and name HG)) | | | | | |
| 3.300 2.700 2.200 peak 16872 weight | 0.10000E + 01 volume | 0.83710E + 00 ppm1 | 0.182 ppm2 | 1.768 | |
| OR {16872} | | | | | |
| (segid "PROT" and resid 78 and name HD 2%) | | | | | |
| (segid "PROT" and resid 31 and name HB %) | | | | | |
| OR {16872} | | | | | |
| (segid "PROT" and resid 78 and name HD 2%) | | | | | |
| ((segid "PROT" and resid 22 and name HG)) | | | | | |
| OR {16872} | | | | | |
| (segid "PROT" and resid 78 and name HD 2%) | | | | | |
| ((segid "PROT" and resid 22 and name HB2)) | | | | | |
| ASSI {16942} | | | | | |
| (segid "PROT" and resid 50 and name HG 2%) | | | | | |
| (segid "PROT" and resid 49 and name HG 2%) | | | | | |
| 3.200 2.600 2.300 peak 16942 weight | 0.10000E + 01 volume | 0.10136E + 01 ppm1 | 0.420 ppm2 | 0.947 | |
| OR {16942} | | | | | |
| (segid "PROT" and resid 50 and name HG 2%) | | | | | |
| (segid "PROT" and resid 43 and name HB %) | | | | | |
| ASSI {17202} | | | | | |
| (segid "PROT" and resid 110 and name HG 2%) | | | | | |
| ((segid "PROT" and resid 75 and name HB2)) | | | | | |
| 3.400 2.900 2.100 peak 17202 weight | 0.10000E + 01 volume | 0.64990E + 00 ppm1 | 0.697 ppm2 | 2.651 | |
| OR {17202} | | | | | |
| (segid "PROT" and resid 110 and name HG 2%) | | | | | |
| ((segid "PROT" and resid 109 and name HE1)) | | | | | |
| ASSI {17212} | | | | | |
| (segid "PROT" and resid 110 and name HG 2%) | | | | | |
| ((segid "PROT" and resid 75 and name HA)) | | | | | |
| 3.000 2.200 2.200 peak 17212 weight | 0.10000E + 01 volume | 0.13418E + 01 ppm1 | 0.693 ppm2 | 4.096 | |
| OR {17212} | | | | | |
| (segid "PROT" and resid 110 and name HG 2%) | | | | | |
| ((segid "PROT" and resid 109 and name HA)) | | | | | |
| OR {17212} | | | | | |
| (segid "PROT" and resid 110 and name HG 2%) | | | | | |
| ((segid "PROT" and resid 111 and name HA)) | | | | | |
| ASSI {17222} | | | | | |
| (segid "PROT" and resid 110 and name HG 2%) | | | | | |
| ((segid "PROT" and resid 115 and name HA)) | | | | | |
| 3.000 2.200 2.200 peak 17222 weight | 0.10000E + 01 volume | 0.12816E + 01 ppm1 | 0.693 ppm2 | 4.268 | |
| OR {17222} | | | | | |
| (segid "PROT" and resid 110 and name HG 2%) | | | | | |
| ((segid "PROT" and resid 17 and name HB)) | | | | | |
| OR {17222} | | | | | |
| (segid "PROT" and resid 110 and name HG 2%) | | | | | |
| ((segid "PROT" and resid 116 and name HA)) | | | | | |
| OR {17222} | | | | | |
| (segid "PROT" and resid 110 and name HG 2%) | | | | | |
| ((segid "PROT" and resid 108 and name HA)) | | | | | |
| ASSI {17242} | | | | | |
| (segid "PROT" and resid 110 and name HD 1%) | | | | | |
| ((segid "PROT" and resid 75 and name HB1)) | | | | | |
| 3.200 2.600 2.300 peak 17242 weight | 0.10000E + 01 volume | 0.96060E + 00 ppm1 | 0.566 ppm2 | 2.968 | |
| OR {17242} | | | | | |
| (segid "PROT" and resid 110 and name HD 1%) | | | | | |
| ((segid "PROT" and resid 74 and name HB1)) | | | | | |
| ASSI {17732} | | | | | |
| ((segid "PROT" and resid 104 and name HB1)) | | | | | |
| ((segid "PROT" and resid 105 and name HB2)) | | | | | |
| 3.000 2.200 2.200 peak 17732 weight | 0.10000E + 01 volume | 0.13380E + 01 ppm1 | 1.956 ppm2 | 3.093 | |
| OR {17732} | | | | | |
| ((segid "PROT" and resid 104 and name HB1)) | | | | | |
| ((segid "PROT" and resid 107 and name HB1)) | | | | | |
| ASSI {18402} | | | | | |
| ((segid "PROT" and resid 54 and name HE %)) | | | | | |
| ((segid "PROT" and resid 78 and name HA)) | | | | | |
| 3.200 2.600 2.300 peak 18402 weight | 0.10000E + 01 volume | 0.91630E + 00 ppm1 | 2.004 ppm2 | 3.407 | |
| OR {18402} | | | | | |
| (segid "PROT" and resid 54 and name HE %) | | | | | |
| ((segid "PROT" and resid 53 and name HD 2)) | | | | | |
| OR {18402} | | | | | |
| (segid "PROT" and resid 54 and name HE %) | | | | | |
| ((segid "PROT" and resid 80 and name HD1)) | | | | | |

TABLE 14-continued

| Ambiguous NOE Distance Restraints |
| --- |

```
ASSI {18632}
    (segid "PROT" and resid 75 and name HE %)
    ((segid "PROT" and resid 107 and name HA))
        3.200  2.600  2.300  peak    18632 weight   0.10000E + 01 volume  0.93700E + 00 ppm1    2.094 ppm2   3.856
OR {18632}
    (segid "PROT" and resid 75 and name HE %)
    ((segid "PROT" and resid 79 and name HA))
ASSI {19102}
    ((segid "PROT" and resid 92 and name HB2))
    ((segid "PROT" and resid 80 and name HG1))
        3.300  2.700  2.200  peak    19102 weight   0.10000E + 01 volume  0.60800E + 00 ppm1    2.952 ppm2   1.789
OR {19102}
    ((segid "PROT" and resid 100 and name HB1))
    ((segid "PROT" and resid 103 and name HB1))
OR {19102}
    ((segid "PROT" and resid 100 and name HB1))
    ((segid "PROT" and resid 97 and name HG1))
ASSI {19112}
    ((segid "PROT" and resid 52 and name HB2))
    ((segid "PROT" and resid 80 and name HB2))
        3.300  2.700  2.200  peak    19112 weight   0.10000E + 01 volume  0.95230E + 00 ppm1    2.952 ppm2   1.993
OR {19112}
    ((segid "PROT" and resid 100 and name HB1))
    ((segid "PROT" and resid 101 and name HB))
ASSI {19132}
    ((segid "PROT" and resid 19 and name HB2))
    ((segid "PROT" and resid 63 and name HD 2%))
        3.100  2.400  2.400  peak    19132 weight   0.10000E + 01 volume  0.11757E + 01 ppm1    1.414 ppm2   1.074
OR {19132}
    ((segid "PROT" and resid 19 and name HB2))
    (segid "PROT" and resid 22 and name HD 1%)
ASSI {19302}
    ((segid "PROT" and resid 97 and name HG1))
    ((segid "PROT" and resid 94 and name HA))
        2.500  1.600  1.600  peak    19302 weight   0.10000E + 01 volume  0.39386E + 01 ppm1    1.850 ppm2   4.236
OR {19302}
    ((segid "PROT" and resid 97 and name HG1))
    ((segid "PROT" and resid 97 and name HA))
ASSI {19402}
    (segid "PROT" and resid 49 and name HG 1%)
    ((segid "PROT" and resid 94 and name HB1))
        2.900  2.100  2.100  peak    19402 weight   0.10000E + 01 volume  0.15644E + 01 ppm1    0.969 ppm2   3.045
OR {19402}
    (segid "PROT" and resid 43 and name HB %)
    ((segid "PEPT" and resid 205 and name HE1))
ASSI {19792}
    (segid "PROT" and resid 25 and name HG 2%)
    ((segid "PROT" and resid 56 and name HB2))
        3.000  2.200  2.200  peak    19792 weight   0.10000E + 01 volume  0.14304E + 01 ppm1    1.076 ppm2   1.466
OR {19792}
    (segid "PROT" and resid 25 and name HD 2%)
    ((segid "PROT" and resid 102 and name HB1))
ASSI {19832}
    (segid "PROT" and resid 58 and name HG 2%)
    ((segid "PROT" and resid 57 and name HE1))
        2.600  1.700  1.700  peak    19832 weight   0.10000E + 01 volume  0.33967E + 01 ppm1    1.097 ppm2   2.611
OR {19832}
    (segid "PROT" and resid 25 and name HG 2%)
    ((segid "PROT" and resid 34 and name HB2))
ASSI {19842}
    (segid "PROT" and resid 58 and name HG 2%)
    ((segid "PROT" and resid 61 and name HG2))
        3.100  2.400  2.400  peak    19842 weight   0.10000E + 01 volume  0.11239E + 01 ppm1    1.100 ppm2   2.265
OR {19842}
    (segid "PROT" and resid 58 and name HG 2%)
    ((segid "PROT" and resid 61 and name HB1))
OR {19842}
    (segid "PROT" and resid 58 and name HG 2%)
    ((segid "PROT" and resid 53 and name HB1))
ASSI {20142}
    ((segid "PROT" and resid 39 and name HB2))
    (segid "PROT" and resid 38 and name HG 1%)
        3.500  3.100  2.000  peak    20142 weight   0.10000E + 01 volume  0.60320E + 00 ppm1    1.913 ppm2   0.516
OR {20142}
    ((segid "PROT" and resid 8 and name HB2))
    (segid "PROT" and resid 18 and name HD 1%)
```

TABLE 14-continued

| Ambiguous NOE Distance Restraints |
|---|

ASSI {20192}
    (segid "PROT" and resid 102 and name HD 1%)
    ((segid "PROT" and resid 28 and name HB1))
        2.800  2.000  2.000 peak    20192 weight    0.10000E + 01 volume  0.20545E + 01 ppm1    0.754 ppm2    3.007
OR {20192}
    (segid "PROT" and resid 115 and name HD 1%)
    ((segid "PROT" and resid 74 and name HB1))
ASSI {21012}
    (segid "PROT" and resid 35 and name HE %)
    (segid "PROT" and resid 25 and name HG 2%)
        3.300  2.700  2.200 peak    21012 weight    0.10000E + 01 volume  0.73890E + 00 ppm1    2.221 ppm2    1.062
OR {21012}
    (segid "PROT" and resid 35 and name HE %)
    (segid "PROT" and resid 22 and name HD 2%)
ASSI {21052}
    (segid "PROT" and resid 50 and name HD 1%)
    (segid "PROT" and resid 83 and name HG 2%)
        3.600  3.200  1.900 peak    21052 weight    0.10000E + 01 volume  0.47270E + 00 ppm1    0.580 ppm2    1.342
OR {21052}
    (segid "PROT" and resid 50 and name HD 1%)
    ((segid "PROT" and resid 51 and name HG1))
OR {21052}
    (segid "PROT" and resid 50 and name HD 1%)
    ((segid "PROT" and resid 86 and name HG1))
ASSI {21072}
    (segid "PROT" and resid 110 and name HD 1%)
    ((segid "PROT" and resid 107 and name HB1))
        3.300  2.700  2.200 peak    21072 weight    0.10000E + 01 volume  0.77140E + 00 ppm1    0.567 ppm2    3.097
OR {21072}
    (segid "PROT" and resid 110 and name HD 1%)
    ((segid "PROT" and resid 108 and name HB2))
ASSI {21122}
    (segid "PROT" and resid 110 and name HD 1%)
    ((segid "PROT" and resid 75 and name HA))
        3.300  2.700  2.200 peak    21122 weight    0.10000E + 01 volume  0.78390E + 00 ppm1    0.564 ppm2    4.090
OR {21122}
    (segid "PROT" and resid 110 and name HD 1%)
    ((segid "PROT" and resid 111 and name HA))
ASSI {21192}
    (segid "PROT" and resid 21 and name HD 1%)
    ((segid "PROT" and resid 109 and name HE2))
        3.800  3.100  2.000 peak    21192 weight    0.10000E + 01 volume  0.57950E + 00 ppm1    0.655 ppm2    2.513
OR {21192}
    (segid "PROT" and resid 21 and name HD 1%)
    ((segid "PROT" and resid 24 and name HG2))
ASSI {21202}
    (segid "PROT" and resid 101 and name HD 1%)
    ((segid "PROT" and resid 29 and name HG1))
        3.300  2.700  2.200 peak    21202 weight    0.10000E + 01 volume  0.73140E + 00 ppm1    1.003 ppm2    2.491
OR {21202}
    (segid "PROT" and resid 101 and name HD 1%)
    ((segid "PROT" and resid 86 and name HE2))
ASSI {21252}
    (segid "PROT" and resid 54 and name HE %)
    ((segid "PROT" and resid 52 and name HB1))
        3.300  2.700  2.200 peak    21252 weight    0.10000E + 01 volume  0.73170E + 00 ppm1    2.001 ppm2    3.055
OR {21252}
    (segid "PROT" and resid 54 and name HE %)
    ((segid "PROT" and resid 68 and name HB1))
ASSI {21262}
    (segid "PROT" and resid 59 and name HE %)
    ((segid "PROT" and resid 22 and name HG))
        3.300  2.700  2.200 peak    21262 weight    0.10000E + 01 volume  0.72600E + 00 ppm1    1.304 ppm2    1.770
OR {21262}
    (segid "PROT" and resid 59 and name HE %)
    ((segid "PROT" and resid 22 and name HB2))
OR {21262}
    (segid "PROT" and resid 59 and name HE %)
    ((segid "PROT" and resid 56 and name HG))
ASSI {21272}
    (segid "PROT" and resid 59 and name HE %)
    ((segid "PROT" and resid 74 and name HB2))
        3.500  3.100  2.000 peak    21272 weight    0.10000E + 01 volume  0.59840E + 00 ppm1    1.308 ppm2    2.414
OR {21272}
    (segid "PROT" and resid 59 and name HE %)
    ((segid "PROT" and resid 25 and name HB))

TABLE 14-continued

| Ambiguous NOE Distance Restraints |
| --- |

```
ASSI {21282}
    (segid "PROT" and resid 59 and name HE %)
    ((segid "PROT" and resid 68 and name HB2))
        3.300  2.700  2.200  peak    21282 weight   0.10000E + 01 volume   0.76270E + 00 ppm1      1.307 ppm2    2.928
OR {21282}
    (segid "PROT" and resid 59 and name HE %)
    ((segid "PROT" and resid 75 and name HB1))
ASSI {21292}
    (segid "PROT" and resid 59 and name HE %)
    ((segid "PROT" and resid 74 and name HB1))
        3.100  2.400  2.400  peak    21292 weight   0.10000E + 01 volume   0.12489E + 01 ppm1      1.307 ppm2    3.001
OR {21292}
    (segid "PROT" and resid 59 and name HE %)
    ((segid "PROT" and resid 82 and name HB2))
ASSI {21302}
    (segid "PROT" and resid 50 and name HG 2%)
    ((segid PROT" and resid 81 and name HA))
        3.300  2.700  2.200  peak    21302 weight   0.10000E + 01 volume   0.74050E + 00 ppm1      0.418 ppm2    3.139
OR {21302}
    (segid "PROT" and resid 50 and name HG 2%)
    ((segid "PROT" and resid 85 and name HB2))
ASSI {21392}
(segid "PROT" and resid 75 and name HE %)
    (segid "PROT" and resid 21 and name HG11))
        2.900  2.100  2.100  peak    21392 weight   0.10000E + 01 volume   0.16056E + 01 ppm1      2.097 ppm2    1.744
OR {21392}
    (segid "PROT" and resid 75 and name HE %)
    ((segid "PROT" and resid 109 and name HB1))
ASSI {21422}
    (segid "PROT" and resid 75 and name HE %)
    (segid "PROT" and resid 106 and name HD %)
        3.400  2.900  2.100  peak    21422 weight   0.10000E + 01 volume   0.65170E + 00 ppm1      2.094 ppm2    6.965
OR {21422}
    (segid "PROT" and resid 75 and name HE %)
    (segid "PROT" and resid 74 and name HE %)
ASSI {21532}
    (segid "PROT" and resid 101 and name HG 2%)
    ((segid "PROT" and resid 29 and name HD1))
        3.100  2.400  2.400  peak    21532 weight   0.10000E + 01 volume   0.11597E + 01 ppm1      1.029 ppm2    2.512
OR {21532}
    (segid "PROT" and resid 101 and name HG 2%)
    ((segid "PROT" and resid 24 and name HB1))
ASSI {21542}
    (segid "PROT" and resid 101 and name HG 2%)
    ((segid "PROT" and resid 28 and name HB1))
        3.000  2.200  2.200  peak    21542 weight   0.10000E + 01 volume   0.12716E + 01 ppm1      1.029 ppm2    3.048
OR {21542}
    (segid "PROT" and resid 101 and name HG 2%)
    ((segid "PROT" and resid 98 and name HB2))
OR {21542}
    (segid "PROT" and resid 101 and name HG 2%)
    ((segid "PROT" and resid 104 and name HE1))
ASSI {21652}
    (segid "PROT" and resid 99 and name HB %)
    ((segid "PROT" and resid 101 and name HB))
        3.200  2.800  2.300  peak    21652 weight   0.10000E + 01 volume   0.91970E + 00 ppm1      1.661 ppm2    1.940
OR {21652}
    (segid "PROT" and resid 99 and name HB %)
    ((segid "PROT" and resid 103 and name HG2))
ASSI {21882}
    (segid "PROT" and resid 113 and name HB %)
    ((segid "PROT" and resid 112 and name HG2))
        3.600  3.200  1.900  peak    21882 weight   0.10000E + 01 volume   0.47230E + 00 ppm1      1.410 ppm2    2.255
OR {21882}
    (segid "PROT" and resid 113 and name HB %)
    ((segid "PROT" and resid 75 and name HG2))
ASSI {21912}
    (segid "PROT" and resid 113 and name HB %)
    ((segid "PROT" and resid 112 and name HA))
        3.100  2.400  2.400  peak    21912 weight   0.10000E + 01 volume   0.12419E + 01 ppm1      1.406 ppm2    4.025
OR {21912}
    (segid "PROT" and resid 113 and name HB %)
    ((segid PROT" and resid 106 and name HA))
ASSI {21932}
    (segid "PROT" and resid 18 and name HD 2%)
    (segid "PROT" and resid 21 and name HG 2%)
        3.100  2.400  2.400  peak    21932 weight   0.10000E + 01 volume   0.10470E + 01 ppm1     -0.162 ppm2    1.023
```

TABLE 14-continued

Ambiguous NOE Distance Restraints

```
OR {21932}
    (segid "PROT" and resid 18 and name HD 2%)
    (segid "PROT" and resid 22 and name HD 2%)
ASSI {21942}
    (segid "PROT" and resid 18 and name HG 2%)
    (segid "PROT" and resid 113 and name HB %)
        3.400  2.900  2.100 peak    21942 weight   0.10000E + 01 volume   0 65970E + 00 ppm1    −0.162 ppm2   1.424
OR {21942}
    (segid "PROT" and resid 18 and name HD 2%)
    ((segid "PROT" and resid 14 and name HG))
ASSI {22002}
    (segid "PROT" and resid 43 and name HB %)
    ((segid "PROT" and resid 39 and name HA))
        3.300  2.700  2.200 peak    22002 weight   0.10000E + 01 volume   0.79200E + 00 ppm1     0.988 ppm2   4.446
OR {22002}
    (segid "PROT" and resid 43 and name HB %)
    ((segid "PEPT" and resid 204 and name HA))
ASSI {22012}
    (segid "PROT" and resid 49 and name HG 2%)
    ((segid "PROT" and resid 87 and name HB2))
        3.100  2.400  2.400 peak    22012 weight   0.10000E + 01 volume   0.12017E + 01 ppm1     0.909 ppm2   2.082
OR {22012}
    (segid "PROT" and resid 49 and name HG 2%)
    ((segid "PROT" and resid 48 and name HB2))
ASSI {22162}
    (segid "PROT" and resid 25 and name HG 2%)
    ((segid "PROT" and resid 31 and name HA))
        3.300  2.700  2.200 peak    22162 weight   0.10000E + 01 volume   0.83230E + 00 ppm1     1.084 ppm2   4.438
OR {22162}
    (segid "PROT" and resid 25 and name HG 2%)
    ((segid "PROT" and resid 60 and name HA))
ASSI {22242}
  ( segid "PROT" and resid 115 and name HD 2%)
    ((segid "PROT" and resid 21 and name HG11))
        2.200  2.200  2.300 peak    22242 weight   0.10000E + 01 volume   0.90954E + 01 ppm1     0.786 ppm2   1.755
OR {22242}
    (segid "PROT" and resid 115 and name HD 2%)
    ((segid "PROT" and resid 109 and name HB1))
OR {22242}
    (segid "PROT" and resid 115 and name HD 2%)
    ((segid "PROT" and resid 111 and name HB2))
ASSI {22252}
    (segid "PROT" and resid 115 and name HD 2%)
    ((segid "PROT" and resid 75 and name HG2))
        3.200  2.600  2.300 peak    22252 weight   0.10000E + 01 volume   0.10049E + 01 ppm1     0.783 ppm2   2.265
OR {22252}
    (segid "PROT" and resid 115 and name HD 2%)
    ((segid "PROT" and resid 8 and name HB1))
ASSI {22272}
    (segid "PROT" and resid 73 and name HD 2%)
    ((segid "PROT" and resid 74 and name HB1))
        3.200  2.600  2.300 peak    22272 weight   0.10000E + 01 volume   0.88380E + 00 ppm1     0.924 ppm2   3.008
OR {22272}
    (segid "PROT" and resid 73 and name HD 2%)
    ((segid "PROT" and resid 67 and name HB1))
ASSI {22332}
    (segid "PROT" and resid 22 and name HD 2%)
    ((segid "PROT" and resid 59 and name HA))
        3.200  2.600  2.300 peak    22332 weight   0.10000E + 01 volume   0.10249E + 01 ppm1     1.047 ppm2   4.341
OR {22332}
    (segid "PROT" and resid 22 and name HD 2%)
    ((segid "PROT" and resid 35 and name HA))
OR {22332}
    (segid "PROT" and resid 22 and name HD 2%)
    ((segid "PROT" and resid 20 and name HA))
ASSI {22372}
    (segid "PROT" and resid 78 and name HD 2%)
    ((segid "PROT" and resid 25 and name HB))
        3.600  3.200  1.900 peak    22372 weight   0.10000E + 01 volume   0.49530E + 00 ppm1     0.195 ppm2   2.453
OR {22372}
    (segid "PROT" and resid 78 and name HD 2%)
    ((segid "PROT" and resid 74 and name HB2))
ASSI {22392}
    (segid "PROT" and resid 102 and name HD 2%)
    (segid "PROT" and resid 35 and name HE %)
        3.700  3.400  1.900 peak    22392 weight   0.10000E + 01 volume   0.42720E + 00 ppm1     0.760 ppm2   2.234
```

TABLE 14-continued

Ambiguous NOE Distance Restraints

```
OR {22392}
    (segid "PROT" and resid 102 and name HD 2%)
    ((segid "PROT" and resid 33 and name HD1))
OR {22392}
    (segid "PROT" and resid 102 and name HD 2%)
    ((segid "PROT" and resid 35 and name HB2))
ASSI {22412}
    (segid "PROT" and resid 78 and name HD 2%)
    ((segid "PROT" and resid 77 and name HB1))
        3.600  3.200  1.900 peak    22412 weight    0.10000E + 01 volume   0.45250E + 00 ppm1      0.190 ppm2    2.741
OR {22412}
    ((segid "PROT" and resid 50 and name HG12))
    ((segid "PROT" and resid 84 and name HB2))
ASSI {22442}
    (segid "PROT" and resid 102 and name HD 2%)
    ((segid "PROT" and resid 98 and name HB1))
        3.600  3.200  1.900 peak    22442 weight    0.10000E + 01 volume   0.48990E + 00 ppm1      0.759 ppm2    3.407
OR {22442}
    (segid "PROT" and resid 102 and name HD 2%)
    ((segid "PROT" and resid 78 and name HA))
ASSI {22452}
    (segid "PROT" and resid 78 and name HD 2%)
    ((segid "PROT" and resid 56 and name HA))
        3.400  2.900  2.100 peak    22452 weight    0.10000E + 01 volume   0.69950E + 00 ppm1      0.201 ppm2    4.065
OR {22492}
    (segid "PROT" and resid 78 and name HD 2%)
    ((segid "PROT" and resid 75 and name HA))
ASSI {22462}
    (segid "PROT" and resid 78 and name HD 2%)
    ((segid "PROT" and resid 79 and name HA))
        3.200  2.600  2.300 peak    22462 weight    0.10000E + 01 volume   0.93720E + 00 ppm1      0.203 ppm2    3.868
OR {22462}
    (segid "PROT" and resid 78 and name HD 2%)
    ((segid "PROT" and resid 25 and name HA))
ASSI {22532}
    (segid "PROT" and resid 73 and name HD 2%)
    (segid "PROT" and resid 34 and name HD %)
        3.400  2.900  2.100 peak    22532 weight    0.10000E + 01 volume   0.65350E + 00 ppm1      0 199 ppm2    7.213
OR {22532}
    (segid "PROT" and resid 78 and name HD 2%)
    (segid "PROT" and resid 34 and name HE %)
OR {22532}
    (segid "PROT" and resid 78 and name HD 2%)
    (segid "PROT" and resid 66 and name HD %)
ASSI {22562}
    (segid "PROT" and resid 102 and name HD 1%)
    ((segid "PROT" and resid 98 and name HB2))
        3.300  2.700  2.200 peak    22562 weight    0.10000E + 01 volume   0.83000E + 00 ppm1      0.757 ppm2    3.101
OR {22562}
    (segid "PROT" and resid 102 and name HD 1%)
    ((segid "PROT" and resid 106 and name HB2))
OR {22562}
    (segid "PROT" and resid 102 and name HD 1%)
    ((segid "PROT" and resid 105 and name HB2))
OR {22562}
    (segid "PROT" and resid 102 and name HD 1%)
    ((segid "PROT" and resid 32 and name HB1))
OR {22562}
    (segid "PROT" and resid 102 and name HD 1%)
    ((segid "PROT" and resid 105 and name HB1))
OR {22562}
    (segid "PROT" and resid 102 and name HD 1%)
    ((segid "PROT" and resid 85 and name HB2))
ASSI {22572}
    (segid "PROT" and resid 115 and name HD 1%)
    ((segid "PROT" and resid 114 and name HA 2))
        3.000  2.200  2.200 peak    22572 weight    0.10000E + 01 volume   0.14716E + 01 ppm1      0.759 ppm2    4.052
OR {22572}
    (segid "PROT" and resid 102 and name HD 1%)
    ((segid "PROT" and resid 28 and name HA))
OR {22572}
    (segid "PROT" and resid 115 and name HD 1%)
    ((segid "PROT" and resid 72 and name HA))
OR {22572}
    (segid "PROT" and resid 102 and name HD 1%)
    ((segid "PROT" and resid 56 and name HA))
```

TABLE 14-continued

Ambiguous NOE Distance Restraints

```
OR {22572}
    (segid "PROT" and resid 115 and name HD 1%)
    ((segid "PROT" and resid 15 and name HA))
ASSI {22692}
    (segid "PROT" and resid 63 and name HD 2%)
    ((segid "PROT" and resid 59 and name HE %))
        2.700  1.800  1.800 peak     22692 weight    0.10000E + 01 volume    0.24125E + 01 ppm1    1.080 ppm2    1.317
OR {22692}
    (segid "PROT" and resid 63 and name HD 2%)
    ((segid "PROT" and resid 19 and name HG1))
ASSI {22742}
    (segid "PROT" and resid 18 and name HD 1%)
    ((segid "PROT" and resid 17 and name HB))
        3.600  3.200  1.900 peak     22742 weight    0.10000E + 01 volume    0.48300E + 00 ppm1    0.515 ppm2    4.277
OR {22742}
    (segid "PROT" and resid 18 and name HD 1%)
    ((segid "PROT" and resid 73 and name HA))
ASSI {22822}
    (segid "PROT" and resid 73 and name HD 1%)
    ((segid "PROT" and resid 69 and name HA))
        3.100  2.400  2.400 peak     22822 weight    0.10000E + 01 volume    0.10888E + 01 ppm1    0.974 ppm2    4.103
OR {22822}
    (segid "PROT" and resid 73 and name HD 1%)
    ((segid "PROT" and resid 67 and name HA))
ASSI {22632}
    (segid "PROT" and resid 14 and name HD 1%)
    ((segid "PROT" and resid 13 and name HA))
        3.200  2.600  2.300 peak     22832 weight    0.10000E + 01 volume    0.10254E + 01 ppm1    0.851 ppm2    4.225
OR {22632}
    (segid "PROT" and resid 14 and name HD 1%)
    ((segid "PROT" and resid 115 and name HA))
OR {22832}
    (segid "PROT" and resid 14 and name HD 1%)
    ((segid "PROT" and resid 70 and name HB1))
ASSI {22852}
    (segid "PROT" and resid 78 and name HD 1%)
    (segid "PROT" and resid 109 and name HB2))
        3.400  2.900  2.100 peak     22852 weight    0.10000E + 01 volume    0.68210E + 00 ppm1    0.097 ppm2    1.581
OR {22852}
    (segid "PROT" and resid 78 and name HD 1%)
    ((segid "PROT" and resid 18 and name HB1))
OR {22852}
    (segid "PROT" and resid 78 and name HD 1%)
    ((segid "PROT" and resid 115 and name HB2))
OR {22852}
    (segid "PROT" and resid 78 and name HD 1%)
    ((segid "PROT" and resid 115 and name HG))
ASSI {22912}
    (segid "PROT" and resid 22 and name HD 1%)
    ((segid "PROT" and resid 63 and name HB2))
        2.600  1.700  1.700 peak     22912 weight    0.10000E + 01 volume    0.35385E + 01 ppm1    1.108 ppm2    1.950
OR {22912}
    ((segid "PROT" and resid 110 and name HG12))
    ((segid "PROT" and resid 111 and name HB1))
ASSI {22952}
    ((segid "PROT" and resid 110 and name HG12))
    (segid "PROT" and resid 107 and name HD %))
        3.200  2.600  2.300 peak     22952 weight    0.10000E + 01 volume    0.10158E + 01 ppm1    1.103 ppm2    7.230
OR {22952}
    (segid "PROT" and resid 22 and name HD 1%)
    (segid "PROT" and resid 68 and name HD %)
ASSI {22972}
    ((segid "PROT" and resid 98 and name HB2))
    ((segid "PROT" and resid 99 and name HA))
        3.200  2.600  2.300 peak     22972 weight    0.10000E + 01 volume    0.88740E + 00 ppm1    3.094 ppm2    3.915
OR {22972}
    ((segid "PROT" and resid 85 and name HB2))
    ((segid "PROT" and resid 99 and name HA))
ASSI {22982}
    ((segid "PROT" and resid 98 and name HB2))
    ((segid "PROT" and resid 30 and name HB1))
        3.500  3.100  2.000 peak     22982 weight    0.10000E + 01 volume    0.52590E + 00 ppm1    3.082 ppm2    4.349
OR {22982}
    ((segid "PROT" and resid 85 and name HB2))
    ((segid "PROT" and resid 64 and name HA))
```

TABLE 14-continued

| Ambiguous NOE Distance Restraints |
| --- |

```
ASSI {23002}
    ((segid "PROT" and resid 100 and name HD1))
    ((segid "PROT" and resid 112 and name HG2))
        3.300  2.700  2.200 peak    23002 weight    0.10000E + 01 volume  0.76170E + 00 ppm1    1.417 ppm2    2.231
OR {23002}
    ((segid "PROT" and resid 14 and name HG))
    ((segid "PROT" and resid 75 and name HG2))
ASSI {23062}
    ((segid "PROT" and resid 115 and name HG))
    ((segid "PROT" and resid 110 and name HD12))
        2.900  2.100  2.100 peak    23062 weight    0.10000E + 01 volume  0.18772E + 01 ppm1    1.689 ppm2    1.069
OR {23062}
    ((segid "PROT" and resid 115 and name HG))
    ((segid "PROT" and resid 21 and name HD12))
ASSI {23112}
    ((segid "PROT" and resid 78 and name HG))
    (segid "PROT" and resid 25 and name HG 2%)
        3.600  3.200  1.900 peak    23112 weight    0.10000E + 01 volume  0.49400E + 00 ppm1    0.692 ppm2    1.066
OR {23112}
    ((segid "PROT" and resid 78 and name HG))
    (segid "PROT" and resid 22 and name HD 2%)
ASSI {23352}
    ((segid "PROT" and resid 80 and name HB2))
    ((segid "PROT" and resid 54 and name HG1))
        3.000  2.200  2.200 peak    23352 weight    0.10000E + 01 volume  0.13200E + 01 ppm1    1.939 ppm2    2.743
OR {23052}
    ((segid "PROT" and resid 80 and name HB2))
    ((segid "PROT" and resid 84 and name HB2))
ASSI {23462}
    ((segid "PROT" and resid 9 and name HB1))
    ((segid "PROT" and resid 8 and name HB1))
        3.100  2.400  2.400 peak    23462 weight    0.10000E + 01 volume  0.12491E + 01 ppm1    1.884 ppm2    2.272
OR {23462}
    ((segid "PROT" and resid 54 and name HG2))
    ((segid "PROT" and resid 53 and name HB1))
OR {23462}
    ((segid "PROT" and resid 54 and name HG2))
    ((segid "PROT" and resid 53 and name HG1))
ASSI {23612}
    ((segid "PROT" and resid 19 and name HB1))
    (segid "PROT" and resid 63 and name HD 2%)
        3.300  2.700  2.200 peak    23612 weight    0.10000E + 01 volume  0.79450E + 00 ppm1    1.735 ppm2    1.082
OR {23612}
    ((segid "PROT" and resid 19 and name HB1))
    (segid "PROT" and resid 22 and name HD 1%)
ASSI {23922}
    ((segid "PROT" and resid 29 and name HG1))
    (segid "PROT" and resid 101 and name HG 2%)
        3.500  3.100  2.000 peak    23922 weight    0.10000E + 01 volume  0.51310E + 00 ppm1    2.485 ppm2    1.021
OR {23922}
    ((segid "PROT" and resid 29 and name HG1))
    (segid "PROT" and resid 101 and name HD 1%)
OR {23922}
    ((segid "PROT" and resid 23 and name HG2))
    (segid "PROT" and resid 22 and name HD 2%)
ASSI {24012}
    ((segid "PROT" and resid 42 and name HG2))
    ((segid "PROT" and resid 39 and name HG2))
        3.100  2.400  2.400 peak    24012 weight    0.10000E + 01 volume  0.10550E + 01 ppm1    2.255 ppm2    1.427
OR {24012}
    ((segid "PROT" and resid 112 and name HG2))
    ((segid "PROT" and resid 111 and name HG1))
OR {24012}
    ((segid "PROT" and resid 112 and name HD 2))
    (segid "PROT" and resid 113 and name HB %)
OR {24012}
    ((segid "PROT" and resid 112 and name HG2))
    ((segid "PROT" and resid 109 and name HD1))
ASSI {24082}
    (segid "PROT" and resid 21 and name HB))
    (segid "PROT" and resid 115 and name HD 2%)
        3.500  3.100  2.000 peak    24082 weight    0.10000E + 01 volume  0.53550E + 00 ppm1    1.950 ppm2    0.756
OR {24082}
    ((segid "PROT" and resid 21 and name HB))
    (segid "PROT" and resid 115 and name HD 1%)
```

TABLE 14-continued

Ambiguous NOE Distance Restraints

```
OR {24082}
    ((segid "PROT" and resid 21 and name HB))
    ((segid "PROT" and resid 78 and name HB1))
ASSI {24102}
    ((segid "PROT" and resid 21 and name HB))
    ((segid "PROT" and resid 24 and name HG2))
        3.600  3.200  1.900 peak    24102 weight   0.10000E + 01 volume  0.48680E + 00 ppm1   1.951 ppm2   2.487
OR {24102}
    ((segid "PROT" and resid 21 and name HB))
    ((segid "PROT" and resid 109 and name HE2))
ASSI {24162}
    ((segid "PROT" and resid 77 and name HB1))
    (segid "PROT" and resid 54 and name HE %)
        3.500  3.100  2.000 peak    24162 weight   0.10000E + 01 volume  0.51230E + 00 ppm1   2.755 ppm2   2.010
OR {24162}
    ((segid "PROT" and resid 77 and name HB1))
    ((segid "PROT" and resid 80 and name HB1))
ASSI {24282}
    ((segid "PROT" and resid 116 and name HB))
    ((segid "PROT" and resid 6 and name HE1))
        3.300  2.700  2.200 peak    24282 weight   0.10000E + 01 volume  0.80610E + ppm1      1.850 ppm2   2.995
OR {24282}
    ((segid "PROT" and resid 116 and name HB))
    ((segid "PROT" and resid 118 and name HE1))
ASSI {24302}
    ((segid "PROT" and resid 78 and name HB1))
    ((segid "PROT" and resid 82 and name HE %))
        3.600  3.200  1.900 peak    24302 weight   0.10000E + 01 volume  0.45690E + 00 ppm1   0.738 ppm2   6.484
OR {24302}
    ((segid "PROT" and resid 78 and name HB1))
    (segid "PROT" and resid 74 and name HD %)
ASSI {24332}
    ((segid "PROT" and resid 78 and name HB2))
    (segid "PROT" and resid 74 and name HE %)
        3.400  2.900  2.100 peak    24332 weight   0.10000E + 01 volume  0.89100E + 00 ppm1   0.472 ppm2   6.967
OR {24332}
    ((segid "PROT" and resid 78 and name HB2))
    (segid "PROT" and resid 106 and name HD %)
ASSI {24362}
    ((segid "PROT" and resid 56 and name HB1))
    (segid "PROT" and resid 25 and name HG 2%)
        2.800  2.000  2.000 peak    24362 weight   0.10000E + 01 volume  0.23012E + 01 ppm1   2.119 ppm2   1.058
OR {24362}
    ((segid "PROT" and resid 56 and name HB1))
    (segid "PROT" and resid 22 and name HD 2%)
ASSI {24392}
    ((segid "PROT" and resid 22 and name HB1))
    (segid "PROT" and resid 59 and name HE %)
        3.500  3.100  2.000 peak    24392 weight   0.10000E + 01 volume  0.54020E + 00 ppm1   2.130 ppm2   1.302
OR {24392}
    (segid "PROT" and resid 22 and name HB1))
    ((segid "PROT" and resid 19 and name HG1))
ASSI {24862}
    ((segid "PROT" and resid 115 and name HA))
    ((segid "PROT" and resid 6 and name HG1))
        3.400  2.900  2.100 peak    24862 weight   0.10000E + 01 volume  0.67380E + 00 ppm1   4.256 ppm2   1.408
OR {24862}
    ((segid "PROT" and resid 115 and name HA))
    (segid "PROT" and resid 113 and name HB %)
OR {24862}
    ((segid "PROT" and resid 115 and name HA))
    ((segid "PROT" and resid 6 and name HG2))
ASSI {24932}
    ((segid "PROT" and resid 34 and name HA))
    ((segid "PROT" and resid 31 and name HA))
        3.600  3.200  1.900 peak    24932 weight   0.10000E + 01 volume  0.49270E + 00 ppm1   5.003 ppm2   4.435
OR {24932}
    ((segid "PROT" and resid 34 and name HA))
    ((segid "PROT" and resid 32 and name HA))
ASSI {24952}
    ((segid "PROT" and resid 6 and name HA))
    ((segid "PROT" and resid 6 and name HE1))
        2.900  2.100  2.100 peak    24952 weight   0.10000E + 01 volume  0.18164E + 01 ppm1   4.375 ppm2   3.042
OR {24952}
    ((segid "PROT" and resid 100 and name HA))
    ((segid "PROT" and resid 104 and name HE1))
```

TABLE 14-continued

| Ambiguous NOE Distance Restraints |

```
ASSI {25012}
    ((segid "PROT" and resid 109 and name HA))
    (segid "PROT" and resid 21 and name HD 1%))
        3.000  2.200  2.200 peak    25012 weight    0.10000E + 01 volume  0.13055 + 01 ppm1    4.075 ppm2    0.676
OR {25012}
    ((segid "PROT" and resid 109 and name HA))
    ((segid "PROT" and resid 110 and name HG 2%))
ASSI {25392}
    ((segid "PROT" and resid 46 and name HA))
    ((segid "PROT" and resid 49 and name HB))
        3.400  2.900  2.100 peak    25392 weight    0.10000E + 01 volume  0.60870E + 00 ppm1    3.501 ppm2    1.933
OR {25392}
    ((segid "PROT" and resid 46 and name HA))
    ((segid "PROT" and resid 53 and name HG2))
ASSI {25412}
    ((segid "PROT" and resid 20 and name HB1))
    (segid "PROT" and resid 17 and name HD 2%)
        3.000  2.200  2.200 peak    25412 weight    0.10000E + 01 volume  0.13236E + 01 ppm1    4.097 ppm2    1.183
OR {25412}
    ((segid "PROT" and resid 49 and name HA))
    ((segid "PROT" and resid 51 and name HB2))
ASSI {25482}
    ((segid "PROT" and resid 49 and name HA))
    ((segid "PROT" and resid 87 and name HB2))
        3.300  2.700  2.200 peak    25482 weight    0.10000E + 01 volume  0.72460E + 00 ppm1    4.123 ppm2    2.071
OR {25482}
    ((segid "PROT" and resid 49 and name HA))
    ((segid "PROT" and resid 48 and name HB2))
OR (25482}
    ((segid "PROT" and resid 53 and name HA))
    ((segid "PROT" and resid 54 and name HB1))
ASSI {25492}
    ((segid "PROT" and resid 49 and name HA))
    ((segid "PROT" and resid 48 and name HG1))
        3.000  2.200  2.200 peak    25492 weight    0.10000E + 01 volume  0.14540E + 01 ppm1    4.112 ppm2    2.353
OR {25492}
    ((segid "PROT" and resid 20 and name HB1))
    ((segid "PROT" and resid 23 and name HB1))
OR {25492}
    ((segid "PROT" and resid 53 and name HA)
    ((segid "PROT" and resid 46 and name HB2))
OR {25492}
    ((segid "PROT" and resid 53 and name HA))
    ((segid "PROT" and resid 55 and name HB1))
OR {25492}
    ((segid "PROT" and resid 41 and name HA))
    ((segid "PROT" and resid 42 and name HG1))
ASSI {25642}
    ((segid "PROT" and resid 21 and name HA))
    ((segid "PROT" and resid 20 and name HB1))
        3.200  2.600  2.300 peak    25642 weight    0.10000E + 01 volume  0.90030E + 00 ppm1    3.800 ppm2    4.098
OR {25642}
    ((segid "PROT" and resid 21 and name HA))
    ((segid "PROT" and resid 109 and name HA))
ASSI {25682}
    ((segid "PROT" and resid 58 and name HA))
    ((segid "PROT" and resid 61 and name HG1))
        3.000  2.200  2.200 peak    25682 weight    0.10000E + 01 volume  0.15120E + 01 ppm1    3.883 ppm2    2.443
OR {25682}
    ((segid "PROT" and resid 83 and name HA))
    ((segid "PROT" and resid 87 and name HG1))
ASSI {25902}
    (segid "PROT" and resid 76 and name HB %)
    (segid "PROT" and resid 73 and name HD 1%)
        3.100  2.400  2.400 peak    25902 weight    0.10000E + 01 volume  0.11972E + 01 ppm1    1.533 ppm2    0.984
OR {25902}
    (segid "PROT" and resid 76 and name HB %)
    (segid "PROT" and resid 21 and name HG 2%)
ASSI {25912}
    (segid "PROT" and resid 76 and name HB %)
    ((segid "PROT" and resid 74 and name HB 2))
        3.700  3.400  1.800 peak    25912 weight    0.10000E + 01 volume  0.39640E + 00 ppm1    1.526 ppm2    2.462
OR {25912}
    (segid "PROT" and resid 76 and name HB %)
    ((segid "PROT" and resid 79 and name HG1))
```

TABLE 14-continued

| Ambiguous NOE Distance Restraints |
|---|

ASSI {26132}
    (segid "PROT" and resid 113 and name HB %)
    ((segid "PROT" and resid 111 and name HB1))
       3.500  3.100  2.000 peak    26132 weight    0.10000E + 01 volume  0.58100E + 00 ppm1    1.411 ppm2    1.932
OR {26132}
    (segid "PROT" and resid 113 and name HB %)
    ((segid "PROT" and resid 8 and name HB2))
OR {26132}
    (segid "PROT" and resid 113 and name HB %)
    ((segid "PROT" and resid 21 and name HB))
ASSI {26152}
    ((segid "PROT" and resid 93 and name HB 1))
    ((segid "PROT" and resid 94 and name HB1))
       3.300  2.700  2.200 peak    26152 weight    0.10000E + 01 volume  0.77140E + 00 ppm1    3.864 ppm2    2.109
OR {26152}
    ((segid "PROT" and resid 93 and name HB1))
    ((segid "PROT" and resid 92 and name HB1))
ASSI {26482}
    (segid "PROT" and resid 35 and name HE %)
    ((segid "PROT" and resid 27 and name HB1))
       3.400  2.900  2.100 peak    26482 weight    0.10000E + 1 volume  0.70350E + 00 ppm1    2.213 ppm2    4.052
OR {26482}
    (segid "PROT" and resid 35 and name HE %)
    ((segid "PROT" and resid 56 and name HA))
OR {26482}
    (segid "PROT" and resid 35 and name HE %)
    ((segid "PROT" and resid 28 and name HA))
OR {26482}
    (segid "PROT" and resid 35 and name HE %)
    (segid "PROT" and resid 60 and name HB2))
ASSI {26502}
    (segid "PROT" and resid 81 and name HG 1%)
    (segid "PROT" and resid 56 and name HD 2%)
       2.300  1.300  1.300 peak    26502 weight    0.10000E + 01 volume  0.62878E + 01 ppm1    0.506 ppm2    0.677
OR {26502}
    (segid "PROT" and resid 81 and name HG 1%)
    ((segid "PROT" and resid 78 and name HG))
ASSI {26512}
    (segid "PROT" and resid 116 and name HD 1%)
    ((segid "PROT" and resid 6 and name HG1))
       2.800  2.000  2.000 peak    26512 weight    0.10000E + 01 volume  0.22365E + 01 ppm1    0.828 ppm2    1.429
OR {26512}
    (segid "PROT" and resid 116 and name HD 1%)
    ((segid "PROT" and resid 6 and name HG2))
OR {26512}
    (segid "PROT" and resid 116 and name HD 1%)
    ((segid "PROT" and resid 111 and name HG1))
ASSI {26702}
    (segid "PROT" and resid 18 and name HD 2%)
    (segid "PROT" and resid 75 and name HE %))
       3.500  3.100  2.000 peak    26702 weight    0.10000E + 01 volume  0.52720E + 00 ppm1    −0.158 ppm2    2.088
OR {26702}
    (segid "PROT" and resid 18 and name HD 2%)
    ((segid "PROT" and resid 22 and name HB1))
OR {26702}
    (segid "PROT" and resid 18 and name HD 2%)
    ((segid "PROT" and resid 8 and name HG1))
ASSI {345}
    ((segid "PROT" and resid 87 and name HB2))
    ((segid "PROT" and resid 87 and name HB2))
       3.100  2.400  2.400 peak    345 weight    0.10000E + 01 volume  0.11110E + 01 ppm1    2.075 ppm2    2.246
OR {345}
    ((segid "PROT" and resid 112 and name HB1))
    ((segid "PROT" and resid 112 and name HG2))
ASSI {3685}
    ((segid "PROT" and resid 87 and name HB1))
    ((segid "PROT" and resid 86 and name HA))
       3.300  2.700  2.200 peak    365 weight    0.10000E + 01 volume  0.81740E + 00 ppm1    2.169 ppm2    4.226
OR {365}
    ((segid "PROT" and resid 87 and name HB1))
    ((segid "PROT" and resid 83 and name HB))
ASSI {395}
    ((segid "PROT" and resid 112 and name HB1))
    ((segid "PROT" and resid 108 and name HA))
       3.400  2.800  2.100 peak    395 weight    0.10000E + 01 volume  0.70760E + 00 ppm1    2.075 ppm2    4.226

TABLE 14-continued

Ambiguous NOE Distance Restraints

```
OR {395}
    ((segid "PROT" and resid 87 and name HB2))
    ((segid "PROT" and resid 86 and name HA))
ASSI {485}
    ((segid "PROT" and resid 19 and name HD1))
    ((segid "PROT" and resid 19 and name HE1))
        3.000  2.200  2.200 peak      489 weight    0.10000E + 01 volume  0.13981E + 01 ppm1     1.618 ppm2    2.941
OR {485}
    ((segid "PROT" and resid 111 and name HD1))
    ((segid "PROT" and resid 111 and name HE1))
ASSI {176}
    (segid "PROT" and resid 107 and name HD %)
    ((segid "PROT" and resid 111 and name HB1))
        2.900  2.100  2.100 peak      176 weight    0.10000E + 01 volume  0.23424E + 01 ppm1     7.234 ppm2    1.923
OR {176}
    (segid "PROT" and resid 107 and name HD %)
    ((segid "PROT" and resid 103 and name HG2))
OR {176}
    (segid "PROT" and resid 105 and name HD %)
    ((segid "PROT" and resid 104 and name HB1))
```

---

What is claimed is:

1. An isolated peptide consisting of a ZA loop of a bromodomain, and wherein said bromodomain is selected from the group consisting of SEQ ID NOs. 7, 8, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 41, and 42, and the ZA loop of SEQ ID NO: 19.

2. A fusion protein or peptide consisting of a first sequence consisting of a ZA loop of a bromodomain according to one of SEQ ID NOs. 7, 8, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 41, and 42, and a second sequence consisting of the ZA loop of SEQ ID NO: 19, and a third sequence from another protein.

* * * * *